United States Patent
Eto et al.

(10) Patent No.: US 8,134,015 B2
(45) Date of Patent: Mar. 13, 2012

(54) COMPOUND INHIBITING IN VIVO PHOSPHOROUS TRANSPORT AND MEDICINE CONTAINING THE SAME

(75) Inventors: Nobuaki Eto, Takasaki (JP); Rika Nagao, Takasaki (JP); Tetsuko Kazama, Takasaki (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 1407 days.

(21) Appl. No.: 10/550,857

(22) PCT Filed: Mar. 29, 2004

(86) PCT No.: PCT/JP2004/004427
§ 371 (c)(1),
(2), (4) Date: Apr. 10, 2006

(87) PCT Pub. No.: WO2004/085382
PCT Pub. Date: Oct. 7, 2004

(65) Prior Publication Data
US 2006/0217426 A1    Sep. 28, 2006

(30) Foreign Application Priority Data
Mar. 27, 2003    (JP) .................. 2003-089173

(51) Int. Cl.
C07D 333/36    (2006.01)
C07D 333/20    (2006.01)
(52) U.S. Cl. .......................... 549/69; 549/76
(58) Field of Classification Search .............. 546/234; 514/318; 549/69, 76
See application file for complete search history.

(56) References Cited

FOREIGN PATENT DOCUMENTS

| FR | 2 168 136 | 8/1973 |
|---|---|---|
| FR | 2168136 | 8/1973 |
| JP | 2-277073 | 11/1990 |
| WO | 00/53208 | 9/2000 |
| WO | WO 01/68142 A1 | 9/2001 |
| WO | WO 2005/037257 A2 | 4/2005 |

OTHER PUBLICATIONS

Abdel-Hamide, "Synthesis and Chemistry of some Novel 3-Heteroaryl-quinzolin-4-one Derivatives and their Antimicrobial Effects", Journal of the Indian Chemical Society, 1997, vol. 74, No. 8, pp. 619-623.*
Hcaplus 1978:546859, 1978.*
West, Anthony R., Solid State Chemistry and its Applications, Wiley, New York, 1988, pp. 358 & 365.*
Capuls 2001:713292 Abstract , "Preparation of insecticidal anthranilamides", Lahm et. al., 2001.*
Caplus 1962:436041, "Preparation and ultraviolet absorption of several 0-acetamidobenzoylhydrazones", Grammaticakis, Panos, 1962.*
Caplus 1962:436039, "Ozonization of 2,4-dinitrophenylhydrazones", Erickson et. al., 1962.*
STN Report: Referecne ED Entered STN: Feb. 27, 2001.*
Abdel-Hamid Hoda A. et al, "Synthesis of Some Biologically Active Heterocycles. Reactions of the Hydrazide of 2'-Thienoyl Anthranilic Acid and Its 3,5-Dibromo Derivative", Phosphorus, Sulfur and Silicon and the Related Elements, vol. 72 No. 1-4, pp. 237 to 247, 1982.
Vlavoic Djordie et al., "Modified Procedure for the Preparation of 5-Nitro-2-furylmethyline Diacetate and Its Use in the Synthesis of Some Novel (5-Nitro-2-furyl) azomethines via 5-Nitro-2-furaldehyde", Journal of Chemical Research, Synopses, No. 6, pp. 156 to 157, 1989.
Zaher H.A. et al, "Reactions of 2-p-Anisyl-3(4H), 1-benzoxazin-4-one with ammonia, Primary Amines, Hydrazine, Phenylhydrazine & Grignard Reagents,"Indian Journal of Chemistry, vol, 12, No. 11, pp. 1212 to 1215, 1974.
Abdel-Hamide S.G, "Synthesis and Chemistry of some Novel 3-Heteroaryl-quinazolin-4-one Derivatives and their Antimicrobial Effects", Journal of the Indian Chemical Society, vol. 74, No. 8, pp. 619 to 623, 1997.
Deshmukh M.B et al., "Synthesis and Biological Activity of some New Quinazolinyl Thazolidinones and Azetidinones", Journal of the indian Chemical Society, vol. 72, No. 12, pp. 847 to 848, 1995.

(Continued)

Primary Examiner — Nizal Chandrakumar
(74) Attorney, Agent, or Firm — Oblon, Spivak, McClelland, Maier & Neustadt, L.L.P.

(57) ABSTRACT

An objective of the present invention is to provide compounds that can effectively suppress the concentration of phosphorus in serum to effectively prevent or treat diseases induced by an increase in concentration of phosphate in serum. The compounds according to the present invention are compounds represented by formula (I) and pharmaceutically acceptable salts and solvates thereof:

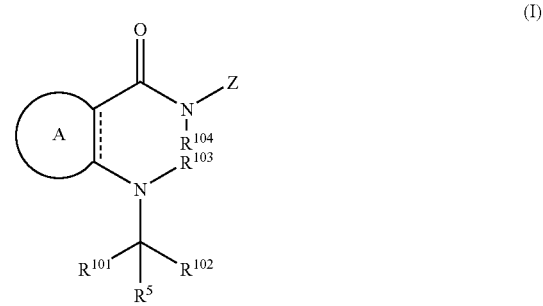

(I)

wherein A represents an optionally substituted five- to nine-membered unsaturated carbocyclic moiety or a five- to nine-membered unsaturated heterocyclic moiety, and ==== represents a single bond or a double bond, $R^5$ represents optionally substituted aryl or the like, Z represents —N=CHR$^6$R$^7$ or the like, R$^6$ and R$^7$ represent H, optionally substituted alkyl, optionally substituted aryl or the like, R$^{101}$ and R$^{102}$ together form =O, and R$^{103}$ and R$^{104}$ represent H, or R$^{101}$ and R$^{104}$ together from a bond, and R$^{102}$ and R$^{103}$ together form a bond.

12 Claims, 4 Drawing Sheets

OTHER PUBLICATIONS

Abdel-Megeed Mohamed F. et al., "Magnetic Anisotropic Effect As Demonstrated by High Resolution PMR in Some Benzoxazinones, Quina Zolinones and Their Thino Analogues", Spectro Scopy Letters, vol. 20, No. 8, pp. 583 to 390, 1987.

Reddy Padi Pratap et al.,"Reaction of 2-Amino benzohydrazides with Schiff Bases. A New Route to 3-Benzylideneamino-4 (3H)-quinazolines and 2-[2-(methylamino-phenyl)-5-aryl-1,3,4-oxadiazoles", Bulletin of the Chemical Society of Japan, vol. 59, No. 5, pp. 1575 to 1580, 1986.

Husain M.I et al., "Synthesis & Biological Activities of 3-(2'-Aryl-4'-oxothazolidin-3'-yl)-2-phenylquinazolin-4(3H)-ones", Indian Journal of Chemistry, Section B:Organic Chemistry Including Medicinal Chemistry, vol. 25B, No. 5, pp. 545 to 548, 1986.

Hayashi Eisaku et al., "Syntheses and Anti-tumor Activity of N-Heterocyclic Compounds Having the Cyclic Hydrazide Structure" Journal of the Pharmaceutical Society of Japan, vol. 98, No. 11, pp. 1560 to 1565, 1978.

Abbady A.M. et al, "2-Aryl-3-Amine-4-Quinazolinones", Acta Chimical Academiae Scientiarum Hungaricae, vol. 91, No. 3, pp. 341 to 349, 1976.

El Kerdawy M.M. et al., "Synthesis of Certain Benzoxazine and Quinazoline Derivatives as Potential Antiinflammatory Agents", Egyptian Journal of Pharmaceutical Sciences, vol. 35, No. 1-6, pp. 1 to 20, 1994.

Ismail M. Fekry et al., "Reaction of 6,8-Dibromo-2-phenyl-3,1-Benzoxazin-4-One with Hydrazines, Schiff Bases and Azines", Egyptian Journal of Chemistry, vol. 32, No. 4, pp. 433 to 444, 1991.

Verma Manjusha et al, Synthesis of Some New Benzoxazine Derivatives of Biological Interest, Heterocyclic Communications vol. 9, No. 5, pp. 499 to 502, 2003.

Database Crossfire Beilstein, Journal of Chemical Research, XP002514815, Database accession No. 6539356, vol. 6, 1989, 1 page.

A. Arques, et al., "A new synthesis of nitriles from aldehydes", Database CA, Chemical Abstracts Service, XP002514816, Database accession No. 1981 : 102983, ISSN: 0039-7881, 1980, 2 pages.

Lee C. Cheney, et al., pp. 2252-2254Database Crossfire Beilstein, Journal of the American Chemical Society, vol. 67, 1945, Database accession No. 69334, XP002514817, pp. 2252-2254.

Djordje Vlaovic, et al., "Modified Procedure for the Preparation of 5-Nitro-2-furylmethylene Diacetate and Its Use in the Synthesis of Some Novel (5-Nitro-2-furyl) azomethines via 5-Nitro-2-furaldehyde", J. Chem. Research (M), 1989, pp. 1201-1218.

A. Arques, et al., "A New Synthesis of Nitriles from Aldehydes", Communications, Synthesis, ISSN:0039-7881, Sep. 1980, pp. 702-704.

Lee C. Cheney, et al., Database Crossfire Beilstein, Journal of the American Chemical Society, vol. 67, 1945, Database accession no. 69334, XP002514817, pp. 2252-2254.

* cited by examiner

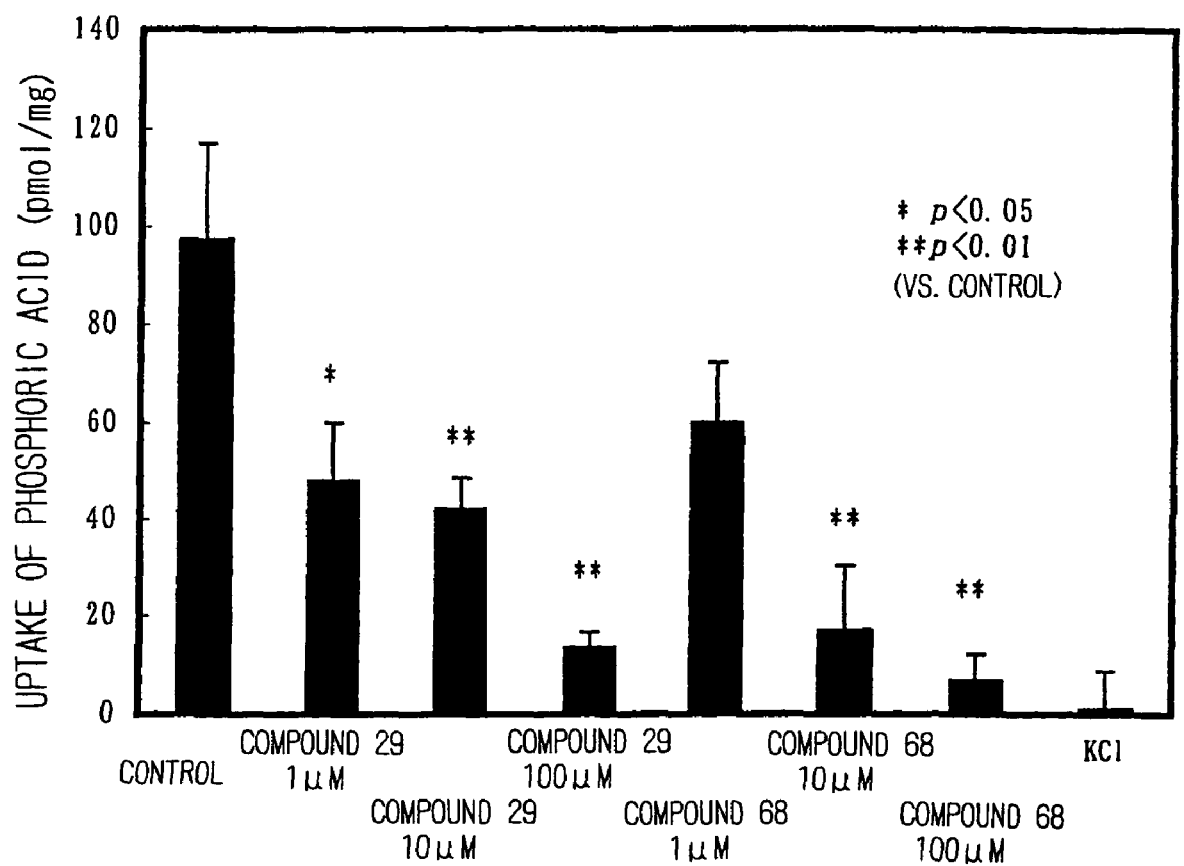
F I G. 1

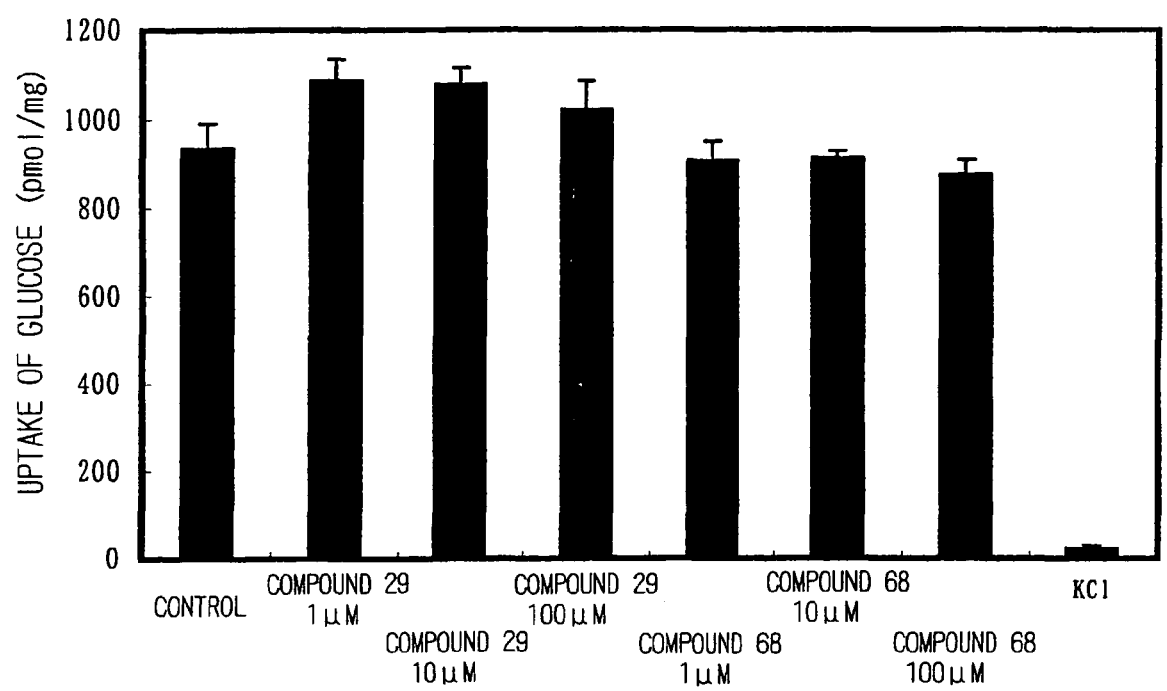
F I G. 2

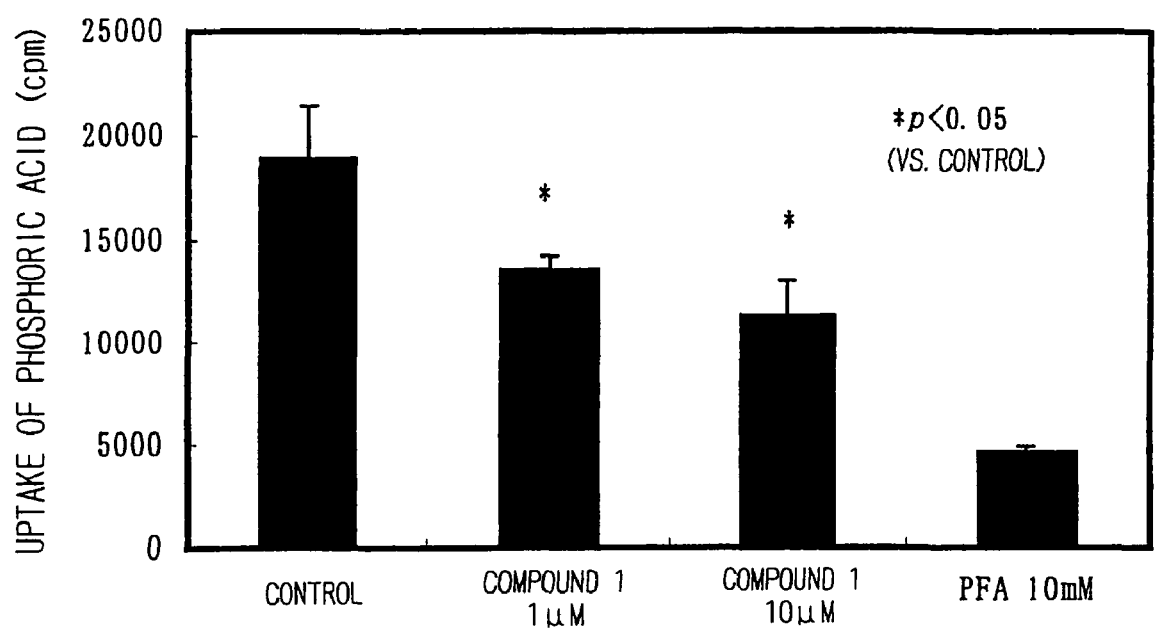
F I G. 3

COMPOUND INHIBITING IN VIVO PHOSPHOROUS TRANSPORT AND MEDICINE CONTAINING THE SAME

BACKGROUND OF THE INVENTION

1. Field of the Invention

The present invention relates to compounds capable of suppressing the phosphate concentration of serum, and more particularly to compounds useful for the prevention and treatment of hyperphosphatemia.

2. Related Art

The phosphate concentration of serum is specified by balance between absorption of phosphate from the intestine, intracellular and bone accumulation, filtration into primitive urine in the kidney, and subsequent reabsorption in uriniferous tubules. When the phosphate concentration of serum is not less than 5.0 mg/dl, this condition is called hyperphosphatemia and is a clinical condition that significantly appears mainly in end-stage renal failure and dialysis patients. This is mainly induced by deteriorated excretion of phosphate involved in elimination of renal function. It is also suggested that an increase in phosphate absorption from the intestine derived from the administration of vitamin D participates in this clinical condition. The hyperphosphatemia secondarily leads to hypocalcemia and thus induces secondary hyperparathyroidism which is in turn a principal factor for renal osteodystrophy.

In the prior art technique, to alleviate these clinical conditions, ingestion of a diet having a low phosphate content and the use of a phosphate adsorbent having the function of adsorbing phosphate in the diet have been carried out from the viewpoint of reducing the absorption of phosphate from the intestine. However, it has been pointed out that the diet having a low phosphate content is disadvantageous in that a nutritional disorder is likely to occur, for example, due to lack of ingestion of other nutriments, or observance of this dietary is difficult because the taste is not good. Representative examples of oral phosphate adsorbents include calcium preparations, magnesium preparations, and aluminum preparations. However, it has been pointed out, for example, that the calcium preparations and the magnesium preparations induce hypercalcemia and hypermagnesemia, respectively, and the aluminum preparations induce aluminum osteopathy, aluminum cerebropathy, and dialysis dementia. In recent years, various anion exchange resins have been developed as the oral phosphate adsorbent. Since, however, these anion exchange resins have lower phosphate adsorption capacity than the above group of compounds, a high level of dosage is necessary for phosphate absorption reduction purposes. Therefore, it cannot be said that the compliance for patients is good.

Despite the fact that all the conventional therapeutic agents for hyperphosphatemia suffer from the above problems, up to now, therapeutic agents for hyperphosphatemia which can solve the above problems have not been reported.

Therapeutic agents for hyperphosphatemia are disclosed, for example, in WO 98/03185 and Kidney and Metabolic Bone Diseases, Vol. 15, No. 1 pp 75-80 (2002).

SUMMARY OF THE INVENTION

The present inventors have now found compounds that can inhibit sodium-dependent phosphate transport into rabbit jejunal brush border membrane vesicle (hereinafter referred to as "rabbit BBMV") and can inhibit sodium-dependent phosphate uptake in *Xenopus oocytes*, which express sodium-dependent phosphate absorption carrier (NaPi-2a and NaPi-2b), present in the kidney and the small intestine, on cell membranes. The present inventors have also found that compounds having a hydrazine skeleton can lower blood radioactivity of normal rats to which diets containing $^{32}P$, a radioisotope, have been administered orally.

An object of the present invention is to provide compounds and pharmaceutical compositions that can effectively prevent or treat diseases induced by an increase in the phosphate concentration of serum by effectively suppressing the phosphate concentration of serum through a mechanism different from the conventional mechanism.

According to the present invention, there are provided compounds represented by formula (I) and pharmaceutically acceptable salts and solvates thereof:

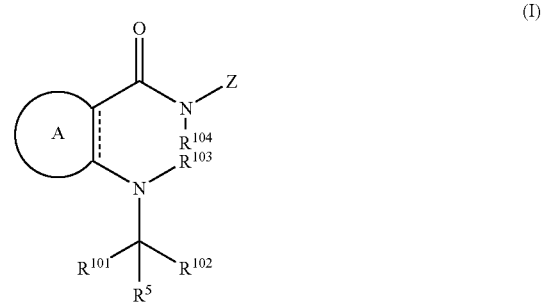

(I)

wherein

A represents a five- to nine-membered unsaturated carbocyclic moiety or a five- to nine-membered unsaturated heterocyclic moiety, and ═══ represents a single bond or a double bond, the carbocyclic moiety and heterocyclic moiety represented by A are optionally substituted by (a) a halogen atom;
(b) hydroxyl;
(c) $C_{1-6}$ alkyl;
(d) $C_{1-6}$ alkoxy;
(e) aryl;
(f) aryloxy;
(g) arylthio;
(h) alkylthio;
(i) nitro;
(j) amino;
(k) mono- or di-arylamino;
(l) mono- or di-$C_{1-6}$ alkylamino;
(m) $C_{2-6}$ alkenyl;
(n) $C_{2-6}$ alkenyloxy;
(o) $C_{2-6}$ alkenylthio;
(p) mono- or di-$C_{2-6}$ alkenylamino;
(q) carboxyl; or
(r) $C_{1-6}$ alkyl- or aryl-oxycarbonyl;
(c) the $C_{1-6}$ alkyl group, (d) the $C_{1-6}$ alkoxy group, (e) the aryl group, (f) the aryloxy group, (g) the arylthio group, (h) the alkylthio group, (m) the $C_{2-6}$ alkenyl group, (n) the $C_{2-6}$ alkenyloxy group, and (o) the $C_{2-6}$ alkenylthio group are optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, (14) arylamino in which the amino group is optionally substituted by $C_{1-6}$ alkyl, and the aryl group is optionally substituted by halogen, $C_{1-6}$ alkyl, $C_{1-6}$ alkoxy, or $C_{1-6}$ alkylamino, (15) $C_{1-6}$ alkoxy-$(CH_2CH_2O)m$ wherein m is an integer of 1 to 6, (16) carboxyl, (17) an oxygen atom (=O), or (18) $C_{3-7}$ cycloalkyl, the aryl moiety in (k) the mono- or di-arylamino group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, (14) arylamino in which the amino group is optionally substituted by $C_{1-6}$ alkyl, and the aryl group is optionally substituted by halogen, $C_{1-6}$ alkyl, $C_{1-6}$ alkoxy, or $C_{1-6}$ alkylamino, (15) $C_{1-6}$ alkoxy-$(CH_2CH_2O)m$ wherein m is an integer of 1 to 6, (16) carboxyl, (17) an oxygen atom (=O), or (18) $C_{3-7}$ cycloalkyl, and, in the case of the mono-arylamino group, the amino group is optionally substituted by $C_{1-6}$ alkyl optionally substituted by hydroxyl or a halogen atom, in (l) the mono- or di-$C_{1-6}$ alkylamino, the di-$C_{1-6}$ alkyl group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl, a halogen atom, or aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two $C_{1-6}$ alkyl groups on the amino group and the cyclic amino moiety are optionally substituted by hydroxyl or a halogen atom; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom; hydroxyl; carboxyl; $C_{1-6}$ alkoxy- or aryloxy-carbonyl; $C_{1-6}$ alkylcarbonyl; aryl optionally substituted by a halogen atom or hydroxyl; an oxygen atom (=O); or a heterocyclic group, in (p) the mono- or di-$C_{2-6}$ alkenylamino group, the amino group of the monoalkenylamino group is optionally substituted by $C_{1-6}$ alkyl optionally substituted by hydroxyl or a halogen atom, and the di-$C_{2-6}$ alkenyl together may form unsaturated cyclic amino optionally containing 1 to 3 heteroatoms, and one or two alkenyl groups on the amino group or the unsaturated cyclic amino moiety are optionally substituted by a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two $C_{1-6}$ alkyl groups on the amino group and the cyclic amino moiety are optionally substituted by hydroxyl or a halogen atom; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom; hydroxyl; carboxyl; $C_{1-6}$ alkoxy- or aryloxy-carbonyl; $C_{1-6}$ alkylcarbonyl; aryl optionally substituted by a halogen atom or hydroxyl; an oxygen atom (=O); or a heterocyclic group, when the carbocyclic moiety and hetrocyclic moiety represented by A are substituted by two (c) $C_{1-6}$ alkyl groups or (m) $C_{2-6}$ alkenyl groups, the alkyl or alkenyl groups together with the carbon atoms to which they are respectively attached may form an unsaturated five- to seven-membered carbocyclic ring, $R^5$ represents $C_{1-6}$ alkyl, aryl, $C_{1-6}$ alkoxy, aryloxy, $C_{1-6}$ alkylamino, arylamino, $C_{1-6}$ alkylthio, arylthio, $C_{3-7}$ cycloalkyl, or a heterocyclic group, and the $C_{1-6}$ alkyl, aryl, $C_{1-6}$ alkoxy, aryloxy, $C_{1-6}$ alkylamino, arylamino, $C_{1-6}$ alkylthio, arylthio, $C_{3-7}$ cycloalkyl, or heterocyclic group represented by $R^5$ may be the same or different, and is optionally substituted by (I) a halogen atom;

(II) $C_{1-6}$ alkyl optionally containing a substituent selected from the group consisting of (1) hydroxyl, (2) thiol, (3) amino, (4) $C_{1-6}$ alkoxy, (5) $C_{1-6}$ alkylthio, (6) $C_{1-6}$ alkylsulfinyl, (7) $C_{1-6}$ alkylsulfonyl, (8) mono- or di-$C_{1-6}$ alkylamino, (8') amino substituted by a heterocyclic group optionally substituted by $C_{1-6}$ alkyl, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S(=O)j- wherein Het represents a heterocyclic group, j is 0, 1, or 2, and Het is optionally substituted by alkyl optionally substituted by mono- or di-$C_{1-6}$ alkylamino in which the di-$C_{1-6}$ alkylamino group may form cyclic amino optionally containing 1 to 3 heteroatoms and one or two alkyl groups on the amino group and the cyclic amino moiety are optionally substituted by hydroxyl, (24) cyano, and (25) a halogen atom, wherein the alkyl moiety in (4) the $C_{1-6}$ alkoxy group, (5) the $C_{1-6}$ alkylthio group, (6) the $C_{1-6}$ alkylsulfinyl group, and (7) the $C_{1-6}$ alkylsulfonyl group is optionally substituted by a halogen atom; $C_{1-6}$ alkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms; aryloxy; arylthio; hydroxyl; carboxyl; —S(=O)$_2$(—OH); $C_{1-6}$ alkoxy- or aryloxy-carbonyl; $C_{1-6}$ alkylcarbonyl; aryl; or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and cyclic amino moiety are optionally substituted by hydroxy, and in (8) the mono- or di-$C_{1-6}$ alkylamino group, the di-$C_{1-6}$ alkylamino group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, preferably a five- to seven-membered saturated or unsaturated heterocyclic ring, more preferably pyridyl, pyrimidyl, or pyridazyl, and, when one carbon atom in the cyclic amino moiety is substituted by two $C_{1-6}$ alkoxy groups which may be the same or different, the two alkoxy groups together may form group —O—(CH$_2$)p-O— wherein p is an integer of 2 to 4, and the cyclic amino group may condense with a monocyclic or bicyclic aromatic carbocyclic ring, preferably phenyl or naphthyl, or a monocyclic or bicyclic aromatic heterocyclic ring, preferably pyridyl or naphthyridyl to represent a bicyclic or tricyclic heterocyclic group;

(III) $C_{1-6}$ alkoxy optionally substituted by a halogen atom;
(IV) $C_{1-6}$ alkylthio optionally substituted by a halogen atom;
(V) $C_{3-7}$ cycloalkyl;
(VI) aryl;
(VII) aryloxy;
(VIII) $C_{1-6}$ alkylcarbonylamino;
(VIX) $C_{1-6}$ alkylcarbonyloxy;
(X) hydroxyl;
(XI) nitro;
(XII) cyano;
(XIII) amino;
(XIV) mono- or di-$C_{1-6}$ alkylamino in which the di-$C_{1-6}$ alkylamino group may form cyclic amino optionally containing 1 to 3 heteroatoms;
(XV) arylamino;
(XVI) $C_{1-6}$ alkyl- or aryl-sulfonylamino;
(XVII) $C_{1-6}$ alkyl- or aryl-ureido;
(XVIII) $C_{1-6}$ alkoxy- or aryloxy-carbonylamino;
(XIX) $C_{1-6}$ alkylamino- or arylamino-carbonyloxy;
(XX) $C_{1-6}$ alkoxy- or aryloxy-carbonyl;
(XXI) acyl;
(XXII) carboxyl;
(XXIII) carbamoyl;
(XXIV) mono- or di-alkylcarbamoyl;
(XXV) a heterocyclic group;
(XXVI) alkyl- or aryl-sulfonyl;
(XXVII) $C_{2-6}$ alkenyloxy group; or
(XXVIII) $C_{2-6}$ alkynyloxy, Z represents group (A), group (B), or group (C):

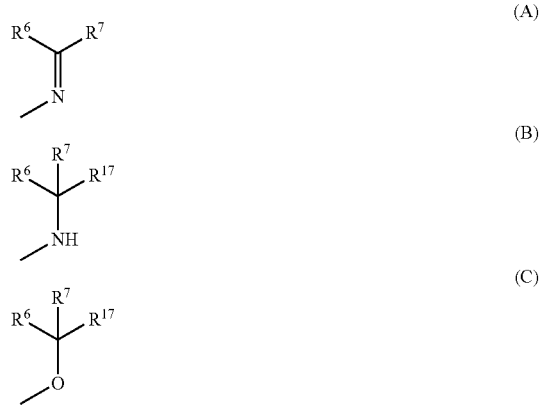

wherein
$R^6$ and $R^7$, which may be the same or different, represent a hydrogen atom, $C_{1-6}$ alkyl, $C_{2-6}$ alkenyl, $C_{2-6}$ alkynyl, aryl, aryl $C_{1-6}$ alkyl, aryl $C_{2-6}$ alkenyl, or a heterocyclic group, and the $C_{1-6}$ alkyl, aryl, aryl $C_{1-6}$ alkyl, aryl $C_{2-6}$ alkenyl, and heterocyclic groups, which may be the same or different, are optionally substituted by:
(I) a halogen atom;
(II) $C_{1-6}$ alkyl optionally having a substituent selected from a group consisting of (1) hydroxyl, (2) thiol, (3) amino, (4) $C_{1-6}$ alkoxy, (5) $C_{1-6}$ alkylthio optionally substituted by hydroxyl, (6) $C_{1-6}$ alkylsulfinyl, (7) $C_{1-6}$ alkylsulfonyl, (8) mono- or di-$C_{1-6}$ alkylamino in which the di-$C_{1-6}$ alkylamino group may form cyclic amino optionally containing 1 to 3 heteroatoms, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S— wherein Het represents a heterocyclic group, (24) cyano, (25) a halogen atom, and (26) $C_{1-6}$ alkyl- or aryl-oxycarbonyl;
(III) $C_{1-6}$ alkoxy optionally having a substituent selected from the group consisting of (1) hydroxyl, (2) thiol, (3) amino, (4) $C_{1-6}$ alkoxy, (5) $C_{1-6}$ alkylthio optionally substituted by hydroxyl, (6) $C_{1-6}$ alkylsulfinyl, (7) $C_{1-6}$ alkylsulfonyl, (8) mono- or di-$C_{1-6}$ alkylamino in which the di-$C_{1-6}$ alkylamino group may form cyclic amino optionally containing 1 to 3 heteroatoms, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S— wherein Het represents a heterocyclic group, (24) cyano, (25) a halogen atom, and (26) $C_{1-6}$ alkyl- or aryl-oxycarbonyl;
(IV) $C_{1-6}$ alkylthio optionally substituted by a halogen atom;
(V) $C_{3-7}$ cycloalkyl;
(VI) aryl;
(VII) aryloxy;
(VIII) $C_{1-6}$ alkylcarbonylamino;
(VIX) $C_{1-6}$ alkylcarbonyloxy;
(X) hydroxyl;

(XI) nitro;
(XII) cyano;
(XIII) amino;
(XIV) mono- or di-$C_{1-6}$ alkylamino in which the di-$C_{1-6}$ alkylamino may form cyclic amino optionally containing 1 to 3 heteroatoms;
(XV) arylamino;
(XVI) $C_{1-6}$ alkyl- or aryl-sulfonylamino;
(XVII) $C_{1-6}$ alkyl- or aryl-ureido;
(XVIII) $C_{1-6}$ alkoxy- or aryloxy-carbonylamino;
(XIX) $C_{1-6}$ alkylamino- or arylamino-carbonyloxy;
(XX) $C_{1-6}$ alkoxy- or aryloxy-carbonyl;
(XXI) acyl;
(XXII) carboxyl;
(XXIII) carbamoyl;
(XXIV) mono- or di-alkylcarbamoyl;
(XXV) a heterocyclic group;
(XXVI) alkyl- or aryl-sulfonyl;
(XXVII) $C_{2-6}$ alkenyloxy; or
(XXVIII) $C_{2-6}$ alkynyloxy,
$R^{17}$ represents a hydrogen atom,
$R^{101}$ and $R^{102}$ together represent =O, and $R^{103}$ and $R^{104}$ represent a hydrogen atom, or $R^{101}$ and $R^{104}$ together represent a bond, and $R^{102}$ and $R^{103}$ together represent a bond.

Compounds according to the present invention include compounds represented by formula (I-3) and pharmaceutically acceptable salts and solvates thereof:

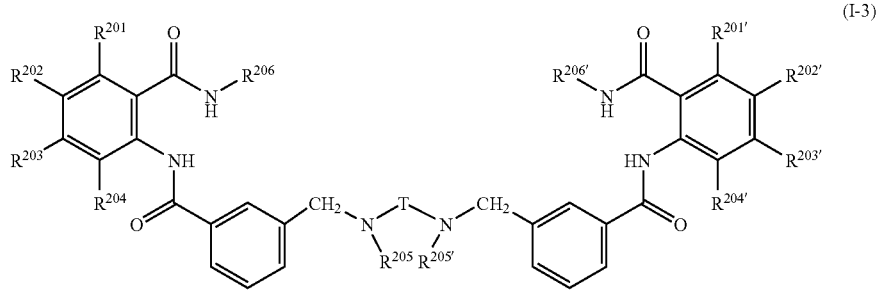

(I-3)

wherein $R^{201}$, $R^{202}$, $R^{203}$, $R^{204}$, $R^{201'}$, $R^{202'}$, $R^{203'}$, and $R^{204'}$, which may be the same or different, represent a hydrogen atom, a halogen atom, hydroxyl, $C_{1-6}$ alkyl, or $C_{1-6}$ alkoxy, $R^{205}$ and $R^{205'}$, which may be the same or different, represent a hydrogen atom or $C_{1-6}$ alkyl, $R^{206}$ and $R^{206'}$, which may be the same or different, represent group A or group B

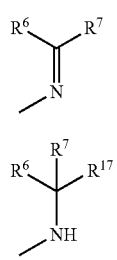

(A)

(B)

wherein $R^6$ represents a hydrogen atom or $C_{1-6}$ alkyl, $R^7$ represents aryl or a saturated or unsaturated five- or six-membered heterocyclic group in which the aryl group and heterocyclic group are optionally substituted by a halogen atom or $C_{1-6}$ alkyl optionally substituted by a halogen atom, and T represents $C_{2-8}$ alkylene chain.

The pharmaceutical composition according to the present invention comprises the compound according to the present invention.

The pharmaceutical composition according to the present invention may be used for the prevention or treatment of diseases for which serum phosphorus lowering action or phosphate transport inhibition is therapeutically effective. Further, the compounds according to the present invention may be used as a serum phosphorus concentration lowering agent and a phosphate transport inhibitor.

According to the present invention, there is provided use of the compound according to the present invention, for the manufacture of a medicament in the prevention or treatment of diseases for which serum phosphorus lowering action or phosphate transport inhibition is therapeutically effective.

Further, according to the present invention, there is provided use of the compound according to the present invention, for the manufacture of a serum phosphorus concentration lowering agent.

Furthermore, according to the present invention, there is provided use of the compound according to the present invention, for the manufacture of a phosphate transport inhibitor.

Furthermore, according to the present invention, there is provided a method for preventing or treating a disease for which serum phosphorus lowering action or phosphate transport inhibition is therapeutically effective, said method comprising the step of administering a therapeutically or prophylactically effective amount of the compound according to the present invention to a mammal.

Furthermore, according to the present invention, there is provided a method for lowering the concentration of serum phosphorus in a blood stream, said method comprising the step of administering a therapeutically or prophylactically effective amount of the compound according to the present invention to a mammal.

Furthermore, according to the present invention, there is provided a method for inhibiting phosphate transport in vivo, said method comprising the step of administering a therapeutically or prophylactically effective amount of the compound according to the present invention to a mammal.

BRIEF DESCRIPTION OF THE DRAWINGS

FIG. 1 shows the inhibition of sodium-dependent phosphate uptake of rabbit jejunal brush border membrane vesicle by compounds according to the present invention;

FIG. 2 shows the inhibition of sodium-dependent glucose uptake of rabbit jejunal brush border membrane vesicle by compounds according to the present invention;

FIG. 3 shows the inhibition of sodium-dependent phosphate uptake of *Xenopus oocytes*, which have expressed NaPi-2a by compounds according to the present invention.

DETAILED DESCRIPTION OF THE INVENTION

Compounds

Figure 4:
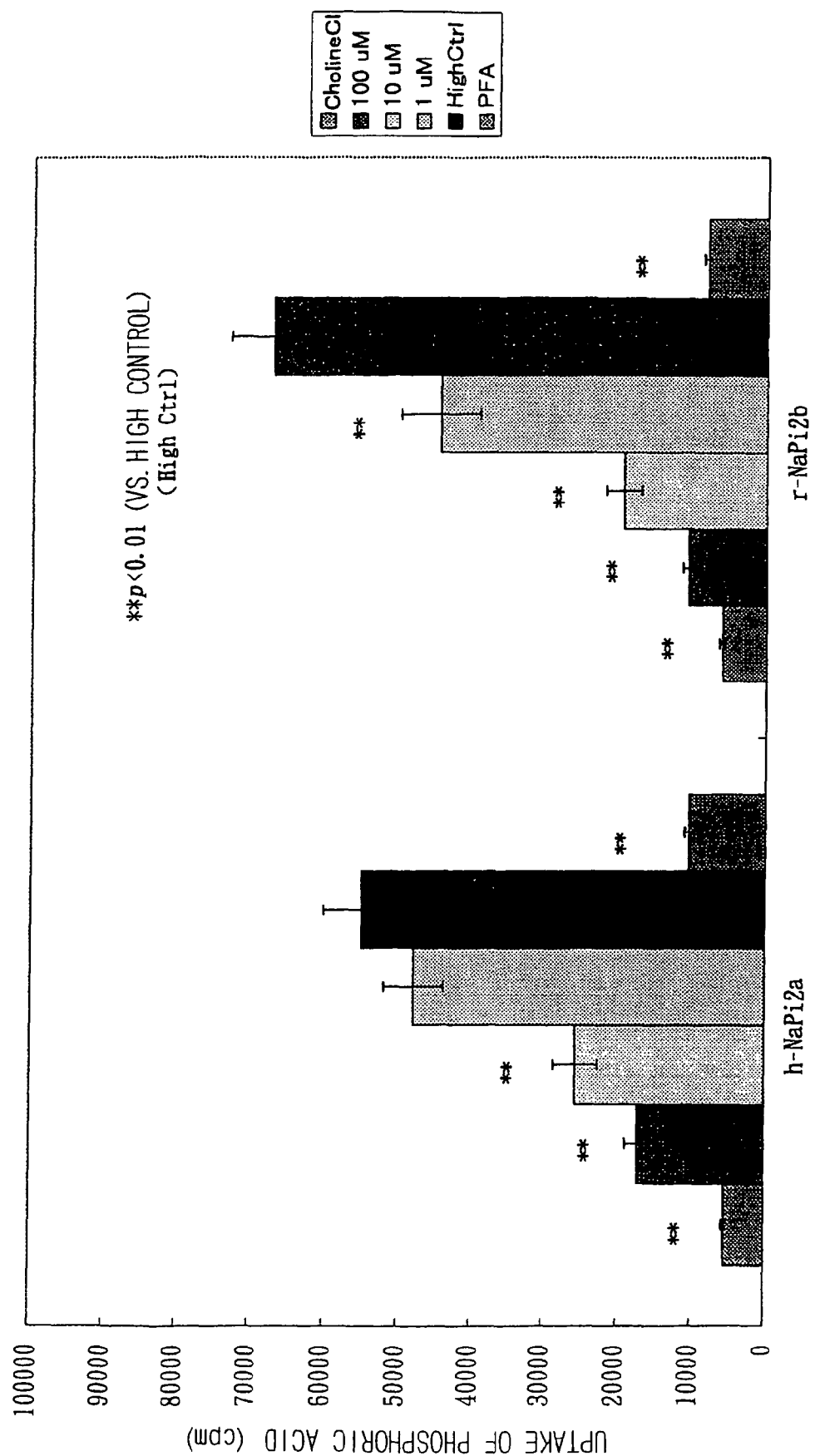
FIG. 4 shows the inhibition of sodium-dependent phosphate uptake of *Xenopus oocytes*, which have expressed NaPi-2a and NaPi-2b by compounds according to the present invention.

The terms "$C_{1-6}$ alkyl" and "$C_{1-6}$ alkoxy" as used herein as a group or a part of a group respectively mean straight chain or branched chain alkyl and alkoxy having 1 to 6 carbon atoms. Preferably, the "$C_{1-6}$ alkyl" and "$C_{1-6}$ alkoxy" may be $C_{1-4}$ alkyl and $C_{1-4}$ alkoxy, respectively.

The term "$C_{3-7}$ cycloalkyl" as used herein as a group or a part of a group means cyclic alkyl having 3 to 7 carbon atoms. Preferably, the "$C_{3-7}$ cycloalkyl" is $C_{5-7}$ cycloalkyl.

The terms "$C_{2-6}$ alkenyl" and "$C_{2-6}$ alkynyl" as used herein as a group or a part of a group respectively mean straight chain or branched chain alkenyl having 2 to 6 carbon atoms and alkynyl having 2 to 6 carbon atoms. Preferably, the "$C_{2-6}$ alkenyl" is $C_{2-4}$ alkenyl. Preferably, the "$C_{2-6}$ alkynyl" is $C_{2-4}$ alkynyl.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{3-7}$ cycloalkyl include cyclopropyl, cyclopentyl, and cyclohexyl.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

The term "halogen atom" as used herein means a fluorine, chlorine, bromine, or iodine atom.

The terms "unsaturated carbocyclic ring" and "unsaturated heterocyclic ring" as used herein respectively mean carbocyclic ring and heterocyclic ring having one or more unsaturated bonds such as a double bond.

The term "aryl" as used herein means a monocyclic, bicyclic, or tricyclic aromatic hydrocarbon group. Examples of aryl include phenyl, naphthyl, and anthryl.

The term "aryl $C_{1-6}$ alkyl" as used herein means $C_{1-6}$ alkyl substituted by a monocyclic, bicyclic, or tricyclic aromatic hydrocarbon group. Examples of aryl $C_{1-6}$ alkyl include benzyl ($C_6H_5CH_2$—) and phenethyl ($C_6H_5CH_2CH_2$—).

The term "arylamino" as used herein means amino substituted by a monocyclic, bicyclic, or tricyclic aromatic hydrocarbon group.

The term "aryl $C_{2-6}$ alkenyl" as used herein means $C_{2-6}$ alkenyl substituted by a monocyclic, bicyclic, or tricyclic aromatic hydrocarbon group. Examples of aryl $C_{2-6}$ alkenyl include phenylethenyl ($C_6H_5$—CH=CH—).

The term "heterocyclic group" as used herein means a saturated or unsaturated five- to nine-membered (preferably five- to seven-membered, more preferably five- or six-membered) monocyclic heterocyclic group and a saturated or unsaturated nine- to eleven-membered bicyclic heterocyclic group. The heterocyclic group contains one or more heteroatoms selected from oxygen, nitrogen, and sulfur atoms. Examples of the heterocyclic ring include pyridyl, furyl, thienyl, pyrrolyl, pyridazyl, pyrimidyl, pyrazyl, isoxazolyl, quinolyl, quinoxalinyl, and quinazolidyl.

In the di-$C_{1-6}$ alkylamino group as used herein, two $C_{1-6}$ alkyl groups attached to the nitrogen atom together may form "cyclic amino." The term "cyclic amino" as used herein means a saturated five- to eight-membered heterocyclic group formed by combining two $C_{1-6}$ alkyl groups attached to the nitrogen atom with each other. The cyclic amino group may contain, in addition to the nitrogen atom in the amino group, 1 to 3 heteroatoms, preferably one oxygen atom, one nitrogen atom, or one sulfur atom. Examples of the saturated cyclic amino group include pyrrolidyl, piperidyl, piperazyl, morpholyl, thiomorpholyl, homopiperidyl, and [1,4]diazepine.

In the di-$C_{2-6}$ alkenylamino group as used herein, two $C_{2-6}$ alkenyl groups attached to the nitrogen atom together may form "unsaturated cyclic amino." The term "cyclic amino" as used herein means an unsaturated five- to eight-membered heterocyclic group formed by combining two $C_{2-6}$ alkenyl groups attached to the nitrogen atom with each other. The cyclic amino group may contain, in addition to the nitrogen atom in the amino group, 1 to 3 heteroatoms, preferably one oxygen atom or one nitrogen atom. Examples of the unsaturated cyclic amino group include pyrrole, pyrazole, imidazolyl, and tetrahydropyridyl.

Compounds represented by formula (I) include hydrazine derivatives and quinazolone derivatives. When $R^{101}$ and $R^{102}$ together represent =O and $R^{103}$ and $R^{104}$ represent a hydrogen atom, formula (I) represents hydrazine derivatives. When $R^{101}$ and $R^{104}$ together represent a bond and when $R^{102}$ and $R^{103}$ together represent a bond, formula (I) represent quinazolone derivatives.

In formula (I) and formula (I-1) and formula (I-2) which will be described later, the five- to nine-membered unsaturated carbocyclic moiety or five- to nine-membered unsaturated heterocyclic moiety represented by A may represent, for example, benzene ring moiety, cyclohexene ring moiety, or pyridine ring moiety.

In formula (I) and formula (I-1) and formula (I-2) which will be described later, when the carbocyclic moiety and hetrocyclic moiety represented by A are substituted by two substituents, (c) $C_{1-6}$ alkyl groups or (m) $C_{2-6}$ alkenyl groups, these alkyl groups or these alkenyl groups together may form a $C_{3-5}$ alkylene chain or a $C_{3-5}$ alkylene chain. In this case, A may represent, for example, naphthyl, quinolyl, benzo[b]thiophene, 4,5,6,7-tetrahydrobenzo[b]thiophene, cyclopenta[b]thiophene, or quinazolyl.

In formula (I) and formulae (I-1) and (I-2) which will be described later, preferably, the five- to nine-membered unsaturated carbocyclic moiety or the five- to nine-membered unsaturated heterocyclic moiety represented by A may represent formula (IIa) or formula (IIa'):

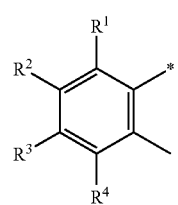

(IIa)

-continued

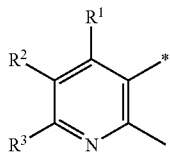

(IIa')

wherein R¹, R², R³, and R⁴, which may be the same or different, represent
(a) a halogen atom;
(b) hydroxyl;
(c) $C_{1-6}$ alkyl;
(d) $C_{1-6}$ alkoxy;
(e) aryl;
(f) aryloxy;
(g) arylthio;
(h) alkylthio;
(i) nitro;
(j) amino;
(i) nitro;
(j) amino;
(k) mono- or di-arylamino;
(l) mono- or di-$C_{1-6}$ alkylamino;
(m) $C_{2-6}$ alkenyl;
(n) $C_{2-6}$ alkenyloxy;
(o) $C_{2-6}$ alkenylthio;
(p) mono- or di-$C_{2-6}$ alkenylamino;
(q) carboxyl;
(r) $C_{1-6}$ alkyl- or aryl-oxycarbonyl; or
(s) a hydrogen atom,
(c) the $C_{1-6}$ alkyl group, (d) the $C_{1-6}$ alkoxy group, (e) the aryl group, (f) the aryloxy group, (g) the arylthio group, (h) the alkylthio group, (m) the $C_{2-6}$ alkenyl group, (n) the $C_{2-6}$ alkenyloxy group, and (o) the $C_{2-6}$ alkenylthio group are optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by halogen, $C_{1-6}$ alkyl, $C_{1-6}$ alkoxy, or $C_{1-6}$ alkylamino, (15) $C_{1-6}$ alkoxy-$(CH_2CH_2O)m$ wherein m is an integer of 1 to 6, (16) carboxyl, (17) an oxygen atom (=O), or (18) $C_{3-7}$ cycloalkyl,
the aryl moiety in (k) the mono- or di-arylamino group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, (14) arylamino in which the amino group is optionally substituted by $C_{1-6}$ alkyl, and the aryl group is optionally substituted by a halogen atom, $C_{1-6}$ alkyl, $C_{1-6}$ alkoxy, or $C_{1-6}$ alkylamino, (15) $C_{1-6}$ alkoxy-$(CH_2CH_2O)m$ wherein m is an integer of 1 to 6, (16) carboxyl, (17) an oxygen atom (=O), or (18) $C_{3-7}$ cycloalkyl, and, in the case of the mono-arylamino group, the amino group is optionally substituted by $C_{1-6}$ alkyl optionally substituted by hydroxyl or a halogen atom, in (l) the mono- or di-$C_{1-6}$ alkylamino, the di-$C_{1-6}$ alkyl group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl, a halogen atom, or aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two $C_{1-6}$ alkyl groups on the amino group and the cyclic amino moiety are optionally substituted by hydroxyl or a halogen atom; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, in (p) the mono- or di-$C_{2-6}$ alkenylamino group, the amino group of the monoalkenylamino group is optionally substituted by $C_{1-6}$ alkyl optionally substituted by hydroxyl or a halogen atom, and the di-$C_{2-6}$ alkenyl together may form unsaturated cyclic amino optionally containing 1 to 3 heteroatoms, and one or two alkenyl groups on the amino group or the unsaturated cyclic amino moiety is optionally substituted by a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two $C_{1-6}$ alkyl groups on the amino group and the cyclic amino moiety are optionally substituted by hydroxyl or a halogen atom; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic-amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, when the carbocyclic moiety and hetrocyclic moiety represented by A are substituted by two (c) $C_{1-6}$ alkyl groups or (m) $C_{2-6}$ alkenyl groups, preferably when positions of $R^2$ and $R^3$ are substituted, the alkyl or alkenyl groups together with the carbon atoms to which they are respectively attached may form an unsaturated five- to seven-membered carbocyclic ring, and

* represents a bond to —C(=O)—N(—Z)(—$R^{104}$).

In formula (I) and formula (I-1) and formula (I-2) which will be described later, A may represent formula (IIa), and, in this case, preferably $R^1$, $R^2$, $R^3$, and $R^4$ represent
- (a) a halogen atom;
- (b) hydroxyl;
- (c) $C_{1-6}$ alkyl;
- (d) $C_{1-6}$ alkoxy;
- (e) aryl;
- (f) aryloxy;
- (g) arylthio;
- (h) alkylthio;
- (i) nitro;
- (j) amino; or
- (k) a hydrogen atom, and
- (c) the $C_{1-6}$ alkyl group, (d) the $C_{1-6}$ alkoxy group, (e) the aryl group, (f) the aryloxy group, (g) the arylthio group, and (h) the alkylthio group are optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by halogen, $C_{1-6}$ alkyl, $C_{1-6}$ alkoxy, or $C_{1-6}$ alkylamino.

In formula (I) and formula (I-1) and formula (I-2) which will be described later, when A represents formula (IIa) or formula (IIa'), preferably, $R^1$, $R^3$, and $R^4$, which may be the same or different, represent a hydrogen atom;
a halogen atom;
$C_{1-6}$ alkyl in which the alkyl group is optionally substituted by $C_{1-6}$ alkoxy or a halogen atom;
aryl optionally substituted by $C_{1-6}$ alkoxy or a halogen atom;
$C_{1-6}$ alkoxy in which the alkoxy group is optionally substituted by $C_{1-6}$ alkoxy or a halogen atom; or
aryloxy optionally substituted by $C_{1-6}$ alkoxy or a halogen atom, $R^2$ may represent
a hydrogen atom;
a halogen atom;
hydroxyl;
$C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen atom, $C_{1-6}$ alkyl, $C_{1-6}$ alkoxy, or $C_{1-6}$ alkylamino; or
$C_{1-6}$ alkoxy in which the alkoxy group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, or (13) a halogen atom, more preferably,
$R^1$, $R^3$, and $R^4$ represent a hydrogen atom,
$R^2$ represents
a halogen atom;
hydroxyl;
$C_{1-6}$ alkyl optionally substituted by mono- or di-$C_{1-6}$ alkylamino; or
$C_{1-6}$ alkoxy optionally substituted by mono- or di-$C_{1-6}$ alkylamino.

In formula (I) and formula (I-1) and formula (I-2) which will be described later, when A represents formula (IIa) or formula (IIa'), preferably, $R^1$, $R^2$, $R^3$, and $R^4$, which may be the same or different, represent a hydrogen atom; a halogen atom; hydroxyl; optionally substituted $C_{1-6}$ alkyl; optionally substituted $C_{2-6}$ alkenyl; optionally substituted $C_{1-6}$ alkoxy; optionally substituted mono- or di-arylamino; optionally substituted mono- or di-$C_{1-6}$ alkylamino in which the dialkylamino together may form optionally substituted cyclic amino optionally containing 1 to 3 heteroatoms; optionally substituted mono- or di-$C_{2-6}$ alkenylamino in which the di-$C_{2-6}$ alkenylamino group together may form optionally substituted unsaturated cyclic amino optionally containing 1 to 3 heteroatoms, and, when $R^2$ and $R^3$ are optionally substituted $C_{1-6}$ alkyl or optionally substituted $C_{2-6}$ alkenyl, the alkyl or alkenyl groups together with the carbon atoms to which $R^2$ and $R^3$ are respectively attached may form an unsaturated five- to seven-membered carbocyclic ring, and, more preferably, $R^1$ and $R^4$ represent a hydrogen atom.

In formula (I) and formula (I-1) and formula (I-2) which will be described later, when A represents formula (IIa) or formula (IIa'), preferably, $R^1$, $R^2$, $R^3$, and $R^4$, which may be the same or different, represent a hydrogen atom; a halogen atom; hydroxyl; optionally substituted $C_{1-6}$ alkyl; or optionally substituted $C_{1-6}$ alkoxy, and more preferably, $R^1$ and $R^4$ represent a hydrogen atom.

In formula (I) and formula (I-1) and formula (I-2) which will be described later, when A represents formula (IIa) or formula (IIa'), $R^1$, $R^2$, $R^3$, and $R^4$ more preferably represent a hydrogen atom.

In formula (I) and formula (I-1) and formula (I-2) which will be described later, when A represents formula (IIa) or formula (IIa'), more preferably,
$R^1$ and $R^4$ represent a hydrogen atom,
any one of $R^2$ and $R^3$, preferably $R^2$, represents a halogen atom; hydroxyl; $C_{1-6}$ alkyl optionally having a substituent, preferably a halogen atom, mono- or di-alkylamino which may form cyclic amino, or hydroxyl; $C_{1-6}$ alkoxy optionally having a substituent, preferably a halogen atom, mono- or di-alkylamino which may form cyclic amino, hydroxyl, $C_{1-6}$ alkoxy-$(CH_2CH_2O)m$, wherein m is an integer of 1 to 6, or $C_{3-7}$ cycloalkyl; optionally substituted mono- or di-arylamino; mono- or di-$C_{1-6}$ alkylamino optionally having a substituent, preferably hydroxyl, $C_{1-6}$ alkyl optionally substituted by hydroxyl, an oxygen atom (=O), mono- or di-$C_{1-6}$ alkylamino which may form cyclic amino, or carboxyl, and the dialkylamino together may form cyclic amino optionally having a substituent, preferably hydroxyl, $C_{1-6}$ alkyl optionally substituted by hydroxyl, an oxygen atom (=O), mono- or di-$C_{1-6}$ alkylamino which may form cyclic amino, or carboxyl, and the cyclic amino group may contain 1 to 3 heteroatoms; optionally substituted mono- or di-$C_{2-6}$ alkenylamino, in which the di-$C_{2-6}$ alkenylamino group together may form optionally substituted unsaturated cyclic amino optionally containing 1 to 3 heteroatoms, and the other (preferably, $R^3$) represents a hydrogen atom.

In the above preferred embodiment, more preferably, the cyclic amino group may be a five- to seven-membered heterocyclic group that optionally contains one oxygen atom, one nitrogen atom, or one sulfur atom in addition to the nitrogen atom in the amino group. Particularly preferred saturated cyclic amino groups include pyrrolidyl, piperidyl, piperazyl, morpholyl, thiomorpholyl, homopiperidyl, and [1,4] diazepine.

In formula (I) and formula (I-1) and formula (I-2) which will be described later, when A represents formula (IIa) or formula (IIa'), more preferably, $R^1$ and $R^4$ represent a hydrogen atom, and any one of $R^2$ and $R^3$ represents a halogen atom; hydroxyl; optionally substituted $C_{1-6}$ alkyl; optionally substituted $C_{1-6}$ alkoxy with the other representing a hydrogen atom.

In formula (I) and formula (I-1) and formula (I-2) which will be described later, when A represents formula (IIa) or formula (IIa'), more preferably, $R^1$ and $R^4$ represent a hydrogen atom, and $R^2$ and $R^3$, which may be the same or different, represent a halogen atom; hydroxyl; $C_{1-6}$ alkyl optionally having a substituent, preferably a halogen atom, mono- or di-alkylamino group which may form cyclic amino, or hydroxyl; $C_{1-6}$ alkoxy optionally having a substituent, preferably a halogen atom, mono- or di-alkylamino which may form cyclic amino, hydroxyl, $C_{1-6}$ alkoxy-$(CH_2CH_2O)m$ wherein m is an integer of 1 to 6, or $C_{3-7}$ cycloalkyl.

In the above preferred embodiment, more preferably, the cyclic amino group may be a five- to seven-membered heterocyclic group that optionally contains one oxygen atom, one nitrogen atom, or one sulfur atom in addition to the nitrogen atom in the amino group. Particularly preferred saturated cyclic amino groups include pyrrolidyl, piperidyl, piperazyl, morpholyl, thiomorpholyl, homopiperidyl, and [1,4] diazepine.

In formula (I) and formula (I-1) and formula (I-2) which will be described later, when A represents formula (IIa) or formula (IIa'), more preferably, $R^1$ and $R^4$ represent a hydrogen atom, and $R^2$ and $R^3$ together with the carbon atoms to which they are respectively attached form an unsaturated five- to seven-membered carbocyclic ring. Particularly preferably, group A together with $R^2$ and $R^3$ forms naphthyl or quinolyl.

In formula (I) and formula (I-1) and formula (I-2) which will be described later, when A represents formula (IIa) or formula (IIa'), more preferably, $R^1$ and $R^4$ represent a hydrogen atom, and $R^2$ and $R^3$, which may be the same or different, represent $C_{1-6}$ alkoxy optionally having a substituent ($C_{1-6}$ alkoxy-$(CH_2CH_2O)m$ wherein m is an integer of 1 to 6).

In formula (I) and formula (I-1) and formula (I-2) which will be described later, when A represents formula (IIa) or formula (IIa'), more preferably, $R^1$ and $R^4$ represent a hydrogen atom; any one of $R^2$ and $R^3$ (preferably, $R^2$) represents mono- or di-$C_{1-6}$ alkylamino optionally having a substituent, preferably hydroxyl, $C_{1-6}$ alkyl optionally substituted by hydroxyl, an oxygen atom (=O), mono- or di-$C_{1-6}$ alkylamino which may form cyclic amino, or carboxyl, and the dialkylamino group together may form cyclic amino optionally having a substituent, preferably hydroxyl, $C_{1-6}$ alkyl optionally substituted by hydroxyl, an oxygen atom (=O), mono- or di-$C_{1-6}$ alkylamino which may form cyclic amino, or carboxyl, and the cyclic amino group may contain 1 to 3 heteroatoms; and the other (preferably, $R^3$) represents a hydrogen atom.

In the above preferred embodiment, more preferably, the cyclic amino group may be a five- to seven-membered heterocyclic group that optionally contains one oxygen atom, one nitrogen atom, or one sulfur atom in addition to the nitrogen atom in the amino group. Particularly preferred saturated cyclic amino groups include pyrrolidyl, piperidyl, piperazyl, morpholyl, thiomorpholyl, homopiperidyl, and [1,4] diazepine.

In formula (I) and formula (I-1) and formula (I-2) which will be described later, when A represents formula (IIa) or formula (IIa'), more preferably, $R^1$ and $R^4$ represent a hydrogen atom; any one of $R^2$ and $R^3$ (preferably, $R^2$) represents $C_{1-6}$ alkoxy optionally having a substituent, preferably a halogen atom, mono- or di-alkylamino which may form cyclic amino, hydroxyl, $C_{1-6}$ alkoxy-$(CH_2CH_2O)m$ wherein m is an integer of 1 to 6, or $C_{3-7}$ cycloalkyl; and the other (preferably, $R^3$) represents a hydrogen atom.

In the above preferred embodiment, more preferably, the cyclic amino group may be a five- to seven-membered heterocyclic group that optionally contains one oxygen atom, one nitrogen atom, or one sulfur atom in addition to the nitrogen atom in the amino group. Particularly preferred saturated cyclic amino groups include pyrrolidyl, piperidyl, piperazyl, morpholyl, thiomorpholyl, homopiperidyl, and [1,4] diazepine.

In formula (I) and formula (I-1) and formula (I-2) which will be described later, preferably, the five- to nine-membered unsaturated carbocyclic moiety or the five- to nine-membered unsaturated heterocyclic moiety represented by A represents formula (IIb):

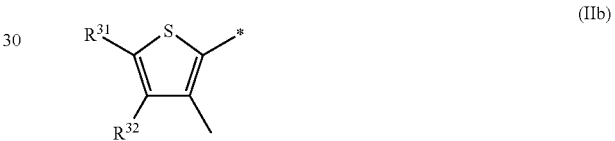

wherein $R^{31}$ and $R^{32}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, when $R^{31}$ and $R^{32}$ represent alkyl or alkenyl, the alkyl or alkenyl groups together with the carbon atoms to which they are respectively attached may form an unsaturated five- to seven-membered carbocyclic ring, and

* represents a bond to $—C(=O)—N(—Z)(—R^{104})$.

In formula (I) and formula (I-1) and formula (I-2) which will be described later, when A represents formula (IIb), preferably, $R^{31}$ and $R^{32}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino, when $R^{31}$ and $R^{32}$ represent alkyl, the alkyl groups together with the carbon atoms to which they are respectively attached may form an unsaturated five- to seven-membered carbocyclic ring, and, in this case, $R^{31}$ and $R^{32}$ together form a $C_{3-5}$ alkylene chain, and ═══ represents a double bond.

In formula (I) and formula (I-1) and formula (I-2) which will be described later, when A represents formula (IIb), more preferably,
(i) $R^{31}$ and $R^{32}$ represent a hydrogen atom, or
(ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, preferably piperidyl, morpholyl, and thiomorpholyl, or by a halogen atom, and the cyclic amino group may contain 1 to 3 heteroatoms, or
(iii) $R^{31}$ and $R^{32}$, which may be the same or different, represent $C_{1-6}$ alkyl optionally substituted by mono- or di-$C_{1-6}$ alkylamino, which may form cyclic amino, preferably piperidyl, morpholyl, and thiomorpholyl, or by a halogen atom, and the cyclic amino group may contain 1 to 3 heteroatoms, or
(iv) $R^{31}$ and $R^{32}$ together with the carbon atoms to which they are respectively attached form a saturated or unsaturated five- to seven-membered carbocyclic ring, preferably a cyclohexane ring, a benzene ring, and a cyclopentane ring.

In formula (I) and formula (I-1) and formula (I-2) which will be described later, when A represents formula (IIb), more preferably, $R^{31}$ and $R^{32}$ represent a hydrogen atom, or any one of $R^{31}$ and $R^{32}$ represents a hydrogen atom with the other representing $C_{1-6}$ alkyl optionally substituted by a halogen atom, or $R^{31}$ and $R^{32}$ together with the carbon atoms to which they are respectively attached form an unsaturated five- to seven-membered carbocyclic ring. In this case, $R^{31}$ and $R^{32}$ together may form a $C_{3-5}$ alkylene chain, and ═══ may represent a double bond.

In formula (I) and formula (I-1) and formula (I-2) which will be described later, preferably, the five- to nine-membered unsaturated carbocyclic moiety or the five- to nine-membered unsaturated heterocyclic moiety represented by A represents formula (IIc):

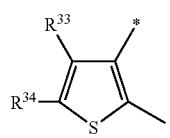

(IIc)

wherein $R^{33}$ and $R^{34}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino, when $R^{33}$ and $R^{34}$ represent alkyl, the alkyl groups together with the carbon atoms to which they are respectively attached may form an unsaturated five- to seven-membered carbocyclic ring, and
* represents a bond to —C(═O)—N(—Z)(—$R^{104}$).

In formula (I) and formula (I-1) and formula (I-2) which will be described later, when A represents formula (IIc), preferably,
$R^{33}$ and $R^{34}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino,
when $R^{33}$ and $R^{34}$ represent alkyl, the alkyl groups together with the carbon atoms to which they are respectively attached may form an unsaturated five- to seven-membered carbocyclic ring, and, in this case, $R^{33}$ and $R^{34}$ together form a $C_{3-5}$ alkylene chain, and ═══ represents a double bond.

In formula (I) and formula (I-1) and formula (I-2) which will be described later, when A represents formula (IIc), more preferably,
(i) $R^{33}$ and $R^{34}$ represent a hydrogen atom, or
(ii) any one of $R^{33}$ and $R^{34}$ represents a hydrogen atom, and the other represents $C_{1-6}$ alkyl optionally substituted by mono- or di-$C_{1-6}$ alkylamino, which may form cyclic amino, preferably piperidyl, morpholyl, and thiomorpholyl, or by a halogen atom, and the cyclic amino group may contain 1 to 3 heteroatoms, or
(iii) $R^{33}$ and $R^{34}$, which may be the same or different, represent $C_{1-6}$ alkyl optionally substituted by mono- or di-$C_{1-6}$ alkylamino, which may form cyclic amino, preferably piperidyl, morpholyl, and thiomorpholyl, or by a halogen atom, and the cyclic amino group may contain 1 to 3 heteroatoms, or
(iv) $R^{33}$ and $R^{34}$ together with the carbon atoms to which they are respectively attached form a saturated or unsaturated five- to seven-membered carbocyclic ring, preferably a cyclohexane ring, a benzene ring, and a cyclopentane ring.

In formula (I) and formula (I-1) and formula (I-2) which will be described later, when A represents formula (IIc), more preferably, $R^{33}$ and $R^{34}$ represent a hydrogen atom, or any one of $R^{33}$ and $R^{34}$ represents a hydrogen atom with the other representing $C_{1-6}$ alkyl optionally substituted by a halogen atom, or $R^{33}$ and $R^{34}$ together with the carbon atoms to which they are respectively attached form an unsaturated five- to seven-membered carbocyclic ring. In this case, $R^{33}$ and $R^{34}$ together may form a $C_{3-5}$ alkylene chain, and ═══ may represent a double bond.

In formula (I) and formula (I-1) and formula (I-2) which will be described later, preferably, the five- to nine-membered saturated or unsaturated carbocyclic moiety or the five- to nine-membered saturated or unsaturated heterocyclic moiety represented by A represents formula (IId):

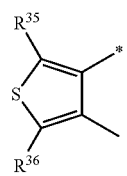

(IId)

wherein $R^{35}$ and $R^{36}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, and

* represents a bond to —C(=O)—N(—Z)(—$R^{104}$).

In formula (I) and formula (I-1) and formula (I-2) which will be described later, when A represents formula (IId), more preferably, $R^{35}$ and $R^{36}$ represent a hydrogen atom, or any one of $R^{35}$ and $R^{36}$ represents a hydrogen atom with the other representing $C_{1-6}$ alkyl optionally substituted by a halogen atom.

In formula (I) and formula (I-1) and formula (I-2) which will be described later, preferably, $R^5$ may represent optionally substituted $C_{5-7}$ cycloalkyl, optionally substituted aryl, more preferably phenyl or naphthyl, an optionally substituted saturated or unsaturated five- or six-membered heterocyclic group, more preferably pyridyl, furyl, thienyl, isoxazole, and pyrimidyl, or an optionally substituted saturated or unsaturated nine- to eleven-membered bicyclic heterocyclic group, more preferably quinoxalinyl.

In formula (I) and formula (I-1) and formula (I-2) which will be described later, particularly preferably, $R^5$ represents a cyclic group selected from $C_{5-7}$ cycloalkyl, phenyl, pyridyl, furyl, thienyl, isoxazole, pyrimidyl, and quinoxalinyl, in which the cyclic group is optionally substituted by a halogen atom; $C_{1-6}$ alkyl optionally substituted by a halogen atom; $C_{1-6}$ alkoxy optionally substituted by a halogen atom; or hydroxyl.

In formula (I) and formula (I-1) and formula (I-2) which will be described later, particularly preferably, $R^5$ represents a cyclic group selected from $C_{5-7}$ cycloalkyl, phenyl, pyridyl, furyl, thienyl, isoxazole, pyrimidyl, and quinoxalinyl, in which the cyclic group is optionally substituted by $C_{1-6}$ alkyl in which the alkyl group is optionally substituted by optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, or optionally substituted mono- or di-$C_{1-6}$ alkylamino in which the di-$C_{1-6}$ alkylamino may form cyclic amino optionally containing 1 to 3 heteroatoms.

In formula (I) and formula (I-1) and formula (I-2) which will be described later, preferably, $R^5$ represents a group of formula (IIIa), (IIIb), or (IIIc):

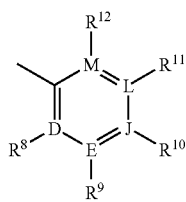

(IIIa)

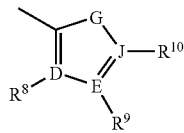

(IIIb)

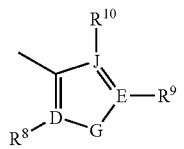

(IIIc)

wherein
D, E, J, L, and M, which may be the same or different, represent a carbon or nitrogen atom,
G represents an oxygen or sulfur atom,
$R^8$, $R^9$, $R^{10}$, $R^{11}$, and $R^{12}$, which may be the same or different, represent
(I) a halogen atom;
(II) $C_{1-6}$ alkyl optionally containing a substituent selected from the group consisting of (1) hydroxyl, (2) thiol, (3) amino, (4) $C_{1-6}$ alkoxy, (5) $C_{1-6}$ alkylthio, (6) $C_{1-6}$ alkylsulfinyl, (7) $C_{1-6}$ alkylsulfonyl, (8) mono- or di-$C_{1-6}$ alkylamino, (8') amino substituted by a heterocyclic group optionally substituted by $C_{1-6}$ alkyl, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S(=O)j- wherein Het represents a heterocyclic group, j is 0, 1, or 2, and Het is optionally substituted by alkyl optionally substituted by mono- or di-$C_{1-6}$ alkylamino in which the di-$C_{1-6}$ alkylamino group may form cyclic amino optionally containing 1 to 3 heteroatoms and one or two alkyl groups on the amino group and the cyclic amino moiety are optionally substituted by hydroxyl, (24) cyano, and (25) a halogen atom,
wherein the alkyl moiety in (4) the $C_{1-6}$ alkoxy group, (5) the $C_{1-6}$ alkylthio group, (6) the $C_{1-6}$ alkylsulfinyl group, and (7) the $C_{1-6}$ alkylsulfonyl group is optionally substituted by a hydrogen atom, a halogen atom; $C_{1-6}$ alkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms; aryloxy; arylthio; hydroxyl; carboxyl; —S(=O)$_2$(—OH); $C_{1-6}$ alkoxy- or aryloxy-carbonyl; $C_{1-6}$ alkylcarbonyl; aryl; or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxy, and
in (8) the mono- or di-$C_{1-6}$ alkylamino group, the di-$C_{1-6}$ alkylamino group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, preferably a five- to seven-membered saturated or unsaturated heterocyclic group, more preferably pyridyl, pyrimidyl, and pyridazyl, and, when one carbon atom in the cyclic amino moiety is substituted by two $C_{1-6}$ alkoxy groups which may be the same or different, the two alkoxy groups together may form group —O—$(CH_2)p$-O— wherein p is an integer of 2 to 4, and the cyclic amino group may condense with a monocyclic or bicyclic aromatic carbocyclic ring, preferably phenyl or naphthyl, or a monocyclic or bicyclic aromatic heterocyclic ring, preferably pyridyl or naphthyridyl, to represent a bicyclic or tricyclic heterocyclic group;

(III) $C_{1-6}$ alkoxy optionally substituted by a halogen atom;
(IV) $C_{1-6}$ alkylthio optionally substituted by a halogen atom;
(V) $C_{3-7}$ cycloalkyl;
(VI) aryl;
(VII) aryloxy;
(VIII) $C_{1-6}$ alkylcarbonylamino;
(VIX) $C_{1-6}$ alkylcarbonyloxy;
(X) hydroxyl;
(XI) nitro;
(XII) cyano;
(XIII) amino;
(XIV) mono- or di-$C_{1-6}$ alkylamino in which the di-$C_{1-6}$ alkylamino group may form cyclic amino optionally containing 1 to 3 heteroatoms;
(XV) arylamino;
(XVI) $C_{1-6}$ alkyl- or aryl-sulfonylamino;
(XVII) $C_{1-6}$ alkyl- or aryl-ureido;
(XVIII) $C_{1-6}$ alkoxy- or aryloxy-carbonylamino;
(XIX) $C_{1-6}$ alkylamino- or arylamino-carbonyloxy;
(XX) $C_{1-6}$ alkoxy- or aryloxy-carbonyl;
(XXI) acyl;
(XXII) carboxyl;
(XXIII) carbamoyl;
(XXIV) mono- or di-alkylcarbamoyl;
(XXV) a heterocyclic group;
(XXVI) alkyl- or aryl-sulfonyl;
(XXVII) $C_{2-6}$ alkenyloxy;
(XXVIII) $C_{2-6}$ alkynyloxy; or
(XXIX) a hydrogen atom, and
when D, E, J, L, or M represents a nitrogen atom, $R^8$, $R^9$, $R^{10}$, $R^{11}$, and $R^{12}$ each are absent, or otherwise together with a nitrogen atom may form N-oxide (N→O).

In formula (I) and formula (I-1) and formula (I-2) which will be described later, when $R^5$ represents formula (IIIa), formula (IIIb) and formula (IIIc), preferably, $R^8$, $R^9$, $R^{10}$, $R^{11}$, and $R^{12}$, which may be the same or different, represent
a hydrogen atom;
a halogen atom;
hydroxymethyl; or
$C_{1-6}$ alkyl optionally substituted by a halogen atom.

In formula (I) and formula (I-1) and formula (I-2) which will be described later, when $R^5$ represents formula (IIIa), formula (IIIb) and formula (IIIc), preferably, the substituted $C_{1-6}$ alkyl which may be represented by $R^8$, $R^9$, $R^{10}$, $R^{11}$, and $R^{12}$ represents a group of formula (IV):

$$-CH_2-Q-X1-R^{13} \qquad (IV)$$

wherein
Q represents an oxygen atom, a sulfur atom, sulfinyl, or sulfonyl,
X1 represents a bond or straight chain or branched chain alkylene having 1 to 5 carbon atoms,
$R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by $C_{1-6}$ alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl, and this heterocyclic group preferably represents a five- or six-membered saturated or unsaturated heterocyclic group;

or a group of formula (V)

$$-CH_2-N\begin{matrix}X2-R^{14}\\X3-R^{15}\end{matrix} \qquad (V)$$

wherein
X2 represents a bond or straight chain or branched chain alkylene having 1 to 5 carbon atoms,
X3 represents a bond or straight chain or branched chain alkylene having 1 to 5 carbon atoms,
$R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, preferably a five- or six-membered saturated or unsaturated heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached may form a heterocyclic group that may contain 1 to 3 heteroatoms, preferably one oxygen atom, one nitrogen atom, or one sulfur atom, in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two —$C_{1-6}$ alkoxy groups which may be the same or different, the two alkoxy groups together may form group —O—$(CH_2)$p-O— wherein p is an integer of 2 to 4, and the cyclic amino group may condense with a monocyclic or bicyclic aromatic carbocyclic ring, preferably phenyl or naphthyl, or a monocyclic or bicyclic aromatic heterocyclic ring, preferably pyridyl or naphthyridyl, to represent a bicyclic or tricyclic heterocyclic group.

Preferably, the cyclic amino group present in formula (IV) and formula (V) may be a five- to seven-membered heterocyclic group that optionally contains one oxygen atom, one nitrogen atom, or one sulfur atom in addition to the nitrogen atom in the amino group, more preferably piperidyl, piperazyl, morpholyl, and thiomorpholyl.

In formula (I) and formula (I-1) and formula (I-2) which will be described later, when $R^5$ represents formula (IIa), formula (IIIb) or formula (IIIc), preferably, D, E, J, L, and M represent a carbon atom.

In formula (I) and formula (I-1) and formula (I-2) which will be described later, when $R^5$ represents formula (IIIa), formula (IIIb) or formula (IIIc), preferably, any one or two of D, E, J, L, and M represent a nitrogen atom and the others represent a carbon atom.

In formula (I) and formula (I-1) and formula (I-2) which will be described later, when $R^5$ represents formula (IIIa), preferably, D, E, J, L, and M represent a carbon atom.

In formula (I) and formula (I-1) and formula (I-2) which will be described later, when $R^5$ represents formula (IIIa), preferably, any one or two of D, E, J, L, and M represent a nitrogen atom with the others representing a carbon atom.

In formula (I) and formula (I-1) and formula (I-2) which will be described later, when $R^5$ represents formula (IIIb), preferably, D, E, and J represent a carbon atom, and G represents an oxygen or sulfur atom.

In formula (I) and formula (I-1) and formula (I-2) which will be described later, when $R^5$ represents formula (IIIc), preferably, D, E, and J represent a carbon atom, and G represents an oxygen or sulfur atom.

In formula (I) and formula (I-1) and formula (I-2) which will be described later, when $R^5$ represents formula (IIIa), preferably, D, E, J, L, and M represent a carbon atom, any one of $R^8$, $R^9$, $R^{10}$, $R^{11}$, and $R^{12}$ represents a group other than a hydrogen atom, and the others represent a hydrogen atom.

In formula (I) and formula (I-1) and formula (I-2) which will be described later, when $R^5$ represents formula (IIIa), preferably, D, E, J, L, and M represent a carbon atom, any one of $R^8$, $R^9$, $R^{10}$, $R^{11}$, and $R^{12}$ represents a halogen atom; optionally substituted $C_{1-6}$ alkyl; or optionally substituted $C_{1-6}$ alkoxy, and the other groups represent a hydrogen atom.

In formula (I) and formula (I-1) and formula (I-2) which will be described later, when $R^5$ represents formula (IIIa), preferably, D, E, J, L, and M represent a carbon atom, $R^{10}$ represents a group other than a hydrogen atom, preferably substituted $C_{1-6}$ alkyl, more preferably a group of formula (IV) or formula (V), and $R^8$, $R^9$, $R^{11}$, and $R^{12}$ represent a hydrogen atom.

In formula (I) and formula (I-1) and formula (I-2) which will be described later, when $R^5$ represents formula (IIIa), preferably, D, E, J, L, and M represent a carbon atom, $R^{11}$ represents a group other than a hydrogen atom, preferably substituted $C_{1-6}$ alkyl, more preferably a group of formula (IV) or formula (V), and $R^8$, $R^9$, $R^{10}$, and $R^{12}$ represent a hydrogen atom.

In formula (I) and formula (I-1) and formula (I-2) which will be described later, when $R^5$ represents formula (IIIa), preferably, D, E, J, L, and M represent a carbon atom, and any two of $R^8$, $R^9$, $R^{10}$, $R^{11}$, and $R^{12}$ represent a group other than a hydrogen atom with the others representing a hydrogen atom.

In formula (I) and formula (I-1) and formula (I-2) which will be described later, when $R^5$ represents formula (IIIa), preferably, D, E, J, L, and M represent a carbon atom, $R^{10}$ and $R^{11}$ represent a group other than a hydrogen atom, preferably optionally substituted $C_{1-6}$ alkoxy, more preferably optionally substituted methoxy, and $R^8$, $R^9$, and $R^{12}$ represent a hydrogen atom.

In formula (I) and formula (I-1) and formula (I-2) which will be described later, when $R^5$ represents formula (IIIa), preferably, D, E, J, L, and M represent a carbon atom, $R^9$ and Rat represent a group other than a hydrogen atom, preferably, optionally substituted $C_{1-6}$ alkoxy, more preferably optionally substituted methoxy, and $R^8$, $R^{10}$, and $R^{12}$ represent a hydrogen atom.

In formula (I) and formula (I-1) and formula (I-2) which will be described later, when $R^5$ represents formula (IIIb) and formula (IIIc), preferably, D, E, and J represent a carbon atom.

In formula (I) and formula (I-1) and formula (I-2) which will be described later, when $R^5$ represents formula (IIIb) and formula (IIIc), preferably, any one or two of D, E, and J represent a nitrogen atom with the other(s) representing a carbon atom.

In formula (I) and formula (I-1) and formula (I-2) which will be described later, when $R^5$ represents formula (IIIa), preferably, D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom.

In formula (I) and formula (I-1) and formula (I-2) which will be described later, when $R^5$ represents formula (IIIa), preferably, any one or two of D, E, J, L, and M represent a nitrogen atom, and the others represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom, or $C_{1-6}$ alkoxy optionally substituted by a halogen atom, and the others represent a hydrogen atom.

In formula (I) and formula (I-1) and formula (I-2) which will be described later, when $R^5$ represents formula (IIIb), preferably, D, E, and J represent a carbon atom, and G represents an oxygen or sulfur atom, one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom.

In formula (I) and formula (I-1) and formula (I-2) which will be described later, when $R^5$ represents formula (IIIc), preferably, D, E, and J represent a carbon atom, and G represents an oxygen or sulfur atom, one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom.

In formula (I) and formula (I-1) and formula (I-2) which will be described later, when $R^5$ represents formula (IIIa), preferably, D, E, J, L, and M represent a carbon atom, $R^8$, $R^9$, and $R^{12}$ represent a hydrogen atom, one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above with the other groups representing a hydrogen atom.

In formula (I) and formula (I-1) and formula (I-2) which will be described later, when $R^5$ represents formula (IIIa), preferably, any one or two of D, E, J, L, and M represent a nitrogen atom, and the others represent a carbon atom, $R^8$, $R^9$, and $R^{12}$ represent a hydrogen atom, one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above with the other groups representing a hydrogen atom.

In formula (I) and formula (I-1) and formula (I-2) which will be described later, when $R^5$ represents formula (IIIb), preferably, D, E, and J represent a carbon atom, and G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above with the others representing a hydrogen atom.

In formula (I) and formula (I-1) and formula (I-2) which will be described later, when $R^5$ represents formula (IIIc), preferably, D, E, and J represent a carbon atom, and G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above with the others representing a hydrogen atom.

In formula (I) and formula (I-1) and formula (I-2) which will be described later, preferably, $R^6$ represents a hydrogen atom; optionally substituted $C_{1-6}$ alkyl; or optionally substituted aryl.

In formula (I) and formula (I-1) and formula (I-2) which will be described later, more preferably, $R^6$ represents a hydrogen atom; $C_{1-6}$ alkyl optionally substituted by a halogen atom or $C_{1-6}$ alkoxy; or aryl optionally substituted by a halogen atom, $C_{1-6}$ alkyl, or $C_{1-6}$ alkoxy, most preferably, a hydrogen atom, or $C_{1-6}$ alkyl.

In formula (I) and formula (I-1) and formula (I-2) which will be described later, preferably, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

In formula (I) and formula (I-1) and formula (I-2) which will be described later, more preferably, $R^7$ represents a cyclic group selected from phenyl, naphthyl, furyl, pyrrolyl, and thienyl, and the cyclic group is optionally substituted by a halogen atom; $C_{1-6}$ alkyl optionally substituted by a halogen atom; $C_{1-6}$ alkoxy in which the alkoxy group is optionally substituted by a halogen atom, aryloxy optionally substituted by a halogen atom and $C_{1-6}$ alkyl, $C_{1-6}$ alkoxy in which the alkoxy group is optionally substituted by mono- or di-$C_{1-6}$ alkylamine in which the di-$C_{1-6}$ alkylamino group may form cyclic amino optionally containing 1 to 3 heteroatoms, or a halogen atom, arylthio optionally substituted by a halogen atom and $C_{1-6}$ alkyl, $C_{1-6}$ alkylthio in which the alkylthio group is optionally substituted by mono- or di-$C_{1-6}$ alkylamine in which the di-$C_{1-6}$ alkylamino group may form cyclic amino optionally containing 1 to 3 heteroatoms, or a halogen atom, arylamino optionally substituted by $C_{1-6}$ alkyl, mono- or di-$C_{1-6}$ alkylamine in which the di-$C_{1-6}$ alkylamino group may form cyclic amino optionally containing 1 to 3 heteroatoms; hydroxyl; mono- or di-$C_{1-6}$ alkylamino in which the di-$C_{1-6}$ alkylamino group may form cyclic amino optionally containing 1 to 3 heteroatoms; nitro; $C_{2-6}$ alkenyloxy; or $C_{2-6}$ alkynyloxy.

In formula (I) and formula (I-1) and formula (I-2) which will be described later, preferably, $R^6$ represents a hydrogen atom or $C_{1-6}$ alkyl, $R^7$ represents optionally substituted aryl, preferably phenyl or naphthyl, optionally substituted aryl, preferably phenyl or naphthyl, $C_{1-6}$ alkyl, optionally substituted aryl, preferably phenyl or naphthyl, $C_{2-6}$ alkenyl, or optionally substituted saturated or unsaturated five- or six-membered heterocyclic group, preferably furyl, thienyl, pyrrolyl, or pyridyl.

Among the compounds of formula (I), hydrazine derivatives may be represented by formula (I-1).

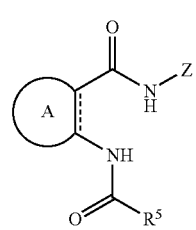

(I-1)

wherein A, $R^5$, Z, and ==== are as defined in formula (I).

In formula (I-1), preferably,

A represents formula (IIa) or formula (IIa') wherein $R^1$, $R^2$, $R^3$, and $R^4$ are as defined in formula (IIa) and formula (IIa') and are preferably the same or different and represent a hydrogen atom; a halogen atom; hydroxyl; optionally substituted $C_{1-6}$ alkyl; or optionally substituted $C_{1-6}$ alkoxy, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl and more preferably represents a group of formula (IIIa), formula (IIIb) or formula (IIIc), and Z represents group (A), group (B), or group (C) wherein $R^6$ represents a hydrogen atom or $C_{1-6}$ alkyl, $R^7$ represents optionally substituted aryl, preferably phenyl or naphthyl, optionally substituted aryl, preferably phenyl or naphthyl, $C_{1-6}$ alkyl, optionally substituted aryl, preferably phenyl or naphthyl, $C_{2-6}$ alkenyl, or optionally substituted saturated or unsaturated five- or six-membered heterocyclic group, preferably furyl, thienyl, pyrrolyl, or pyridyl, and $R^{17}$ represents a hydrogen atom.

In formula (I-1), preferably,

A represents formula (IIa) wherein $R^1$, $R^2$, $R^3$, and $R^4$ are as defined in formula (IIa), ===== represents a double bond, $R^5$ represents optionally substituted $C_{5-7}$ cycloalkyl, optionally substituted aryl, or optionally substituted saturated or unsaturated five- or six-membered heterocyclic group, preferably pyridyl, thienyl, isoxazole, or pyrimidyl and more preferably represents a group of formula (IIIa), formula (IIIb), or formula (IIIc), and Z represents group (A) or group (B) wherein $R^6$ represents a hydrogen atom or $C_{1-6}$ alkyl, $R^7$ represents optionally substituted aryl, preferably phenyl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-1), preferably,

A represents formula (IIb) wherein $R^{31}$ and $R^{32}$ are as defined in formula (IIb), preferably, $R^{31}$ and $R^{32}$ represent a hydrogen atom, or any one of $R^{31}$ and $R^{32}$ represents a hydrogen atom with the other representing $C_{1-6}$ alkyl optionally substituted by a halogen atom, or $R^{31}$ and $R^{32}$ together form a $C_{3-5}$ alkylene chain, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl, more preferably represents a group of formula (IIIa), formula (IIIb), or formula (IIIc), and Z represents group (A) or group (B) wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-1), preferably,

A represents formula (IIc) wherein $R^{33}$ and $R^{34}$ are as defined in formula (IIc), and, preferably, $R^{33}$ and $R^{34}$ represent a hydrogen atom, or any one of $R^{33}$ and $R^{34}$ represents a hydrogen atom with the other representing $C_{1-6}$ alkyl optionally substituted by a halogen atom, or $R^{33}$ and $R^{34}$ together form a $C_{3-5}$ alkylene chain, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl, and more preferably, represents a group of formula (IIIa), formula (IIIb), or formula (IIIc), and Z represents group (A) and group (B) wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-1), preferably,

A represents formula (IId) wherein $R^{35}$ and $R^{36}$ are as defined in formula (IId), and, preferably, $R^{35}$ and $R^{36}$ represent a hydrogen atom, or any one of $R^{35}$ and $R^{36}$ represents a hydrogen atom with the other representing $C_{1-6}$ alkyl optionally substituted by a halogen atom, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl, and more preferably represents a group of formula (IIIa), formula (IIIb), or formula (IIIc), Z represents group (A) or group (B) wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-1), more preferably,

A represents formula (IIa) or formula (IIa'), wherein (1) $R^1$, $R^2$, $R^3$, and $R^4$ represent a hydrogen atom, (2) $R^1$ and $R^4$ represent a hydrogen atom, any one of $R^2$ and $R^3$ represents a halogen atom; hydroxyl; optionally substituted $C_{1-6}$ alkyl; optionally substituted $C_{1-6}$ alkoxy; optionally substituted mono- or di-arylamino; optionally substituted mono- or di-$C_{1-6}$ alkylamino in which the dialkylamino together may form optionally substituted cyclic amino optionally containing 1 to 3 heteroatoms; or optionally substituted mono- or di-$C_{2-6}$ alkenylamino in which the di-$C_{2-6}$ alkenylamino group together may form optionally substituted unsaturated cyclic amino optionally containing 1 to 3 heteroatoms, and the other represents a hydrogen atom, (3) $R^1$ and $R^4$ represent a hydrogen atom, and $R^2$ and $R^3$, which may be the same or different, represent a halogen atom; hydroxyl; optionally substituted $C_{1-6}$ alkyl; or optionally substituted $C_{1-6}$ alkoxy, (4) $R^1$ and $R^4$ represent a hydrogen atom, and $R^2$ and $R^3$ together with the carbon atoms to which they are respectively attached form a saturated or unsaturated five- to seven-membered carbocyclic ring, (5) $R^1$ and $R^4$ represent a hydrogen atom, any one of $R^2$ and $R^3$ represents optionally substituted mono- or di-$C_{1-6}$ alkylamino in which the di-$C_{1-6}$ alkylamino together may form optionally substituted cyclic amino optionally containing 1 to 3 heteroatoms, and the other represents a hydrogen atom, or (6) $R^1$ and $R^4$ represent a hydrogen atom, any one of $R^2$ and $R^3$ represents optionally substituted $C_{1-6}$ alkoxy, and the other represents a hydrogen atom, $R^5$ represents formula (IIIa)

wherein (i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom, (iii) D, E, J, L, and M represent a carbon atom, $R^8$, $R^9$, and $R^{12}$ represent a hydrogen atom, any one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, or (iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, Z represents group (A), group (B), or group (C):

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-1), more preferably,

A represents formula (IIa) or formula (IIa')

wherein (1) $R^1$, $R^2$, $R^3$, and $R^4$ represent a hydrogen atom, (2) $R^1$ and $R^4$ represent a hydrogen atom, any one of $R^2$ and $R^3$ represents a halogen atom; hydroxyl; optionally substituted $C_{1-6}$ alkyl; optionally substituted $C_{1-6}$ alkoxy; optionally substituted mono- or di-arylamino; optionally substituted mono- or di-$C_{1-6}$ alkylamino in which the dialkylamino together may form optionally substituted cyclic amino optionally containing 1 to 3 heteroatoms; or optionally substituted mono- or di-$C_{2-6}$ alkenylamino in which the di-$C_{2-6}$ alkenylamino group together may form optionally substituted unsaturated cyclic amino optionally containing 1 to 3 heteroatoms, and the other represents a hydrogen atom, (3) $R^1$ and $R^4$ represent a hydrogen atom, and $R^2$ and $R^3$, which may be the same or different, represent a halogen atom; hydroxyl; optionally substituted $C_{1-6}$ alkyl; or optionally substituted $C_{1-6}$ alkoxy, (4) $R^1$ and $R^4$ represent a hydrogen atom, and $R^2$ and $R^3$ together with the carbon atoms to which they are respectively attached form a saturated or unsaturated five- to seven-membered carbocyclic ring, (5) $R^1$ and $R^4$ represent a hydrogen atom, any one of $R^2$ and $R^3$ represents optionally substituted mono- or di-$C_{1-6}$ alkylamino in which the di-$C_{1-6}$ alkylamino together may form optionally substituted cyclic amino optionally containing 1 to 3 heteroatoms, and the other represents a hydrogen atom, or (6) $R^1$ and $R^4$ represent a hydrogen atom, any one of $R^2$ and $R^3$ represents optionally substituted $C_{1-6}$ alkoxy, and the other represents a hydrogen atom, $R^5$ represents formula (IIIb) or formula (IIIc)

wherein (i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or (ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-1), more preferably,

A represents formula (IIb)

wherein (i) $R^{31}$ and $R^{32}$ represent a hydrogen atom, (ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms, (iii) $R^{31}$ and $R^{32}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or (iv) $R^{31}$ and $R^{32}$ together with the carbon atoms to which they are respectively attached form a saturated or unsaturated five- to seven-membered carbocyclic ring, $R^5$ represents formula (IIIa)

wherein (i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom, (iii) D, E, J, L, and M represent a carbon atom, $R^8$, $R^9$, and $R^{12}$ represent a hydrogen atom, any one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, or (iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.
In formula (I-1), more preferably,
A represents formula (IIb)
wherein
(i) $R^{31}$ and $R^{32}$ represent a hydrogen atom,
(ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{31}$ and $R^{32}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or
(iv) $R^{31}$ and $R^{32}$ together with the carbon atoms to which they are respectively attached form a saturated or unsaturated five- to seven-membered carbocyclic ring, $R^5$ represents formula (IIIb) or formula (IIIc)
wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or
(ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.
In formula (I-1), more preferably,
A represents formula (IIc)
wherein
(i) $R^{33}$ and $R^{34}$ represent a hydrogen atom,
(ii) any one of $R^{33}$ and $R^{34}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{33}$ and $R^{34}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or (iv) $R^{33}$ and $R^{34}$ together with the carbon atoms to which they are respectively attached form a saturated or unsaturated five- to seven-membered carbocyclic ring, $R^5$ represents formula (IIIa)
wherein
(i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom,
(ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom,
(iii) D, E, J, L, and M represent a carbon atom, $R^8$, $R^9$, and $R^{12}$ represent a hydrogen atom, any one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, or
(iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.
In formula (I-1), more preferably,
A represents formula (IIc)
wherein
(i) $R^{33}$ and $R^{34}$ represent a hydrogen atom,
(ii) any one of $R^{33}$ and $R^{34}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{33}$ and $R^{34}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or
(iv) $R^{33}$ and $R^{34}$ together with the carbon atoms to which they are respectively attached form a saturated or unsaturated five- to seven-membered carbocyclic ring, $R^5$ represents formula (IIIb) or formula (IIIc)
wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or
(ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.

In formula (I-1), more preferably,
A represents formula (IId)
wherein $R^{35}$ and $R^{36}$ represent a hydrogen atom, or any one of $R^{35}$ and $R^{36}$ represents a hydrogen atom with the other representing $C_{1-6}$ alkyl optionally substituted by a halogen atom,
$R^5$ represents formula (IIIa)
wherein
(i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom,
(ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom,
(iii) D, E, J, L, and M represent a carbon atom, $R^8$, $R^9$, and $R^{12}$ represent a hydrogen atom, any one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, or
(iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.

In formula (I-1), more preferably,
A represents formula (IId)
wherein $R^{35}$ and $R^{36}$ represent a hydrogen atom, or any one of $R^{35}$ and $R^{36}$ represents a hydrogen atom with the other representing $C_{1-6}$ alkyl optionally substituted by a halogen atom,
$R^5$ represents formula (IIIb) or formula (IIIc)
wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or (ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.

Among the compounds of formula (I), quinazolone derivatives may be represented by formula (I-2).

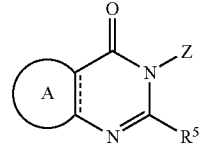

(I-2)

wherein A, $R^5$, Z, and ==== are as defined in formula (I).

In formula (I-2), preferably,
A represents formula (IIa) or formula (IIa') wherein $R^1$, $R^2$, $R^3$, and $R^4$ are as defined in formula (IIa) and formula (IIa') and are preferably the same or different and represent a hydrogen atom; a halogen atom; hydroxyl; optionally substituted $C_{1-6}$ alkyl; or optionally substituted $C_{1-6}$ alkoxy,
$R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl and more preferably represents a group of formula (IIIa), formula (IIIb) or formula (IIIc).
Z represents group (A), group (B), or group (C) wherein $R^6$ represents a hydrogen atom or $C_{1-6}$ alkyl, $R^7$ represents optionally substituted aryl, preferably, phenyl, or naphthyl, optionally substituted aryl, preferably phenyl, or naphthyl, $C_{1-6}$ alkyl, optionally substituted aryl, preferably phenyl, or naphthyl, $C_{2-6}$ alkenyl, or optionally substituted saturated or unsaturated five- or six-membered heterocyclic group, preferably furyl, thienyl, pyrrolyl, or pyridyl, and $R^{17}$ represents a hydrogen atom.

In formula (I-2), preferably,
A represents formula (IIa) wherein $R^1$, $R^2$, $R^3$, and $R^4$ are as defined in formula (IIa),
==== represents a double bond,
$R^5$ represents optionally substituted $C_{5-7}$ cycloalkyl, optionally substituted aryl, or optionally substituted saturated or unsaturated five- or six-membered heterocyclic group, preferably pyridyl, thienyl, isoxazole, or pyrimidyl and more preferably represents a group of formula (IIIa), formula (IIIb), or formula (IIIc).
Z represents group (A) or group (B) wherein $R^6$ represents a hydrogen atom or $C_{1-6}$ alkyl, $R^7$ represents optionally substituted aryl, preferably phenyl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-2), preferably,

A represents formula (IIb) wherein $R^{31}$ and $R^{32}$ are as defined in formula (IIb), preferably, $R^{31}$ and $R^{32}$ represent a hydrogen atom, or any one of $R^{31}$ and $R^{32}$ represents a hydrogen atom with the other representing $C_{1-6}$ alkyl optionally substituted by a halogen atom, or $R^{31}$ and $R^{32}$ together may form a $C_{3-5}$ alkylene chain, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl, more preferably a group of formula (IIIa), formula (IIIb), or formula (IIIc), and Z represents group (A) or group (B) wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-2), preferably,

A represents formula (IIc) wherein $R^{33}$ and $R^{34}$ are as defined in formula (IIc), and, preferably, $R^{33}$ and $R^{34}$ represent a hydrogen atom, or any one of $R^{33}$ and $R^{34}$ represents a hydrogen atom with the other representing $C_{1-6}$ alkyl optionally substituted by a halogen atom, or $R^{33}$ and $R^{34}$ together form a $C_{3-5}$ alkylene chain, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl, more preferably a group of formula (IIIa), formula (IIIb), or formula (IIIc), and Z represents group (A) and group (B) wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-2), preferably,

A represents formula (IId) wherein $R^{35}$ and $R^{36}$ are as defined in formula (IId), and $R^{35}$ and $R^{36}$ represent a hydrogen atom, or any one of $R^{35}$ and $R^{36}$ represents a hydrogen atom with the other representing $C_{1-6}$ alkyl optionally substituted by a halogen atom, $R^5$ represents optionally substituted $C_{5-7}$ cycloalkyl, optionally substituted aryl, preferably phenyl, or optionally substituted saturated or unsaturated five- or six-membered heterocyclic group, preferably pyridyl, thienyl, isoxazole, or pyrimidyl, more preferably a group of formula (IIIa), formula (IIIb), or formula (IIIc), Z represents group (A) or group (B) wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

In formula (I-2), more preferably,

A represents formula (IIa) or formula (IIa'),
wherein
(1) $R^1$, $R^2$, $R^3$, and $R^4$ represent a hydrogen atom,
(2) $R^1$ and $R^4$ represent a hydrogen atom, any one of $R^2$ and $R^3$ represents a halogen atom; hydroxyl; optionally substituted $C_{1-6}$ alkyl; optionally substituted $C_{1-6}$ alkoxy; optionally substituted mono- or di-arylamino; optionally substituted mono- or di-$C_{1-6}$ alkylamino in which the dialkylamino together may form optionally substituted cyclic amino optionally containing 1 to 3 heteroatoms; or optionally substituted mono- or di-$C_{2-6}$ alkenylamino in which the di-$C_{2-6}$ alkenylamino group together may form optionally substituted unsaturated cyclic amino optionally containing 1 to 3 heteroatoms, and the other represents a hydrogen atom, (3) $R^1$ and $R^4$ represent a hydrogen atom, and $R^2$ and $R^3$, which may be the same or different, represent a halogen atom; hydroxyl; optionally substituted $C_{1-6}$ alkyl; or optionally substituted $C_{1-6}$ alkoxy, (4) $R^1$ and $R^4$ represent a hydrogen atom, and $R^2$ and $R^3$ together with the carbon atoms to which they are respectively attached form a saturated or unsaturated five- to seven-membered carbocyclic ring, (5) $R^1$ and $R^4$ represent a hydrogen atom, any one of $R^2$ and $R^3$ represents optionally substituted mono- or di-$C_{1-6}$ alkylamino in which the di-$C_{1-6}$ alkylamino together may form optionally substituted cyclic amino optionally containing 1 to 3 heteroatoms, and the other represents a hydrogen atom, or (6) $R^1$ and $R^4$ represent a hydrogen atom, any one of $R^2$ and $R^3$ represents optionally substituted $C_{1-6}$ alkoxy, and the other represents a hydrogen atom, $R^5$ represents formula (IIIa)
wherein
(i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom, (iii) D, E, J, L, and M represent a carbon atom, $R^8$, $R^9$, and $R^{12}$ represent a hydrogen atom, any one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, (iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.

In formula (I-2), more preferably,

A represents formula (IIa) or formula (IIa')
wherein
(1) $R^1$, $R^2$, $R^3$, and $R^4$ represent a hydrogen atom,
(2) $R^1$ and $R^4$ represent a hydrogen atom, any one of $R^2$ and $R^3$ represents a halogen atom; hydroxyl; optionally substituted $C_{1-6}$ alkyl; optionally substituted $C_{1-6}$ alkoxy; optionally substituted mono- or di-arylamino; optionally substituted monoor di-$C_{1-6}$ alkylamino in which the dialkylamino together may form optionally substituted cyclic amino optionally containing 1 to 3 heteroatoms; or optionally substituted mono- or di-$C_{2-6}$ alkenylamino in which the di-$C_{2-6}$ alkenylamino group together may form optionally substituted unsaturated cyclic amino optionally containing 1 to 3 heteroatoms, and the other represents a hydrogen atom, (3) $R^1$ and $R^4$ represent a hydrogen atom, and $R^2$ and $R^3$, which may be the same or different, represent a halogen atom; hydroxyl; optionally substituted $C_{1-6}$ alkyl; or optionally substituted $C_{1-6}$ alkoxy, (4) $R^1$ and $R^4$ represent a hydrogen atom, and $R^2$ and $R^3$ together with the carbon atoms to which they are respectively attached form a saturated or unsaturated five- to seven-membered carbocyclic ring, (5) $R^1$ and $R^4$ represent a hydrogen atom, any one of $R^2$ and $R^3$ represents optionally substituted mono- or di-$C_{1-6}$ alkylamino in which the di-$C_{1-6}$ alkylamino together may form optionally substituted cyclic amino optionally containing 1 to 3 heteroatoms, and the other represents a hydrogen atom, or (6) $R^1$ and $R^4$ represent a hydrogen atom, any one of $R^2$ and $R^3$ represents optionally substituted $C_{1-6}$ alkoxy, and the other represents a hydrogen atom, $R^5$ represents formula (IIIb) or formula (IIIc)
wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or (ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.

In formula (I-2), more preferably,
A represents formula (IIb)
wherein
(i) $R^{31}$ and $R^{32}$ represent a hydrogen atom,
(ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{31}$ and $R^{32}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or
(iv) $R^{31}$ and $R^{32}$ together with the carbon atoms to which they are respectively attached form a saturated or unsaturated five- to seven-membered carbocyclic ring, $R^5$ represents formula (IIIa)
wherein
(i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom, (iii) D, E, J, L, and M represent a carbon atom, $R^8$, $R^9$, and $R^{12}$ represent a hydrogen atom, any one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined above, and the other represents a hydrogen atom, or (iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV) wherein Q, X1, and $R^{13}$ are as defined above, or a group of formula (V) wherein X2, X3, $R^{14}$, and $R^{15}$ are as defined in above, and the other represents a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
$R^{17}$ represents a hydrogen atom.

In formula (I-2), more preferably,
A represents formula (IIb)
wherein
(i) $R^{31}$ and $R^{32}$ represent a hydrogen atom,
(ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{31}$ and $R^{32}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or
(iv) $R^{31}$ and $R^{32}$ together with the carbon atoms to which they are respectively attached form a saturated or unsaturated five- to seven-membered carbocyclic ring, $R^5$ represents formula (IIIb) or formula (IIIc)
wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or (ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):
wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and
R$^{17}$ represents a hydrogen atom.

In formula (I-2), more preferably,

A represents formula (IIc)

wherein (i) R$^{33}$ and R$^{34}$ represent a hydrogen atom, (ii) any one of R$^{33}$ and R$^{34}$ represents a hydrogen atom, and the other represents C$_{1-6}$ alkyl optionally substituted by mono- or di-C$_{1-6}$ alkylamino, which may form cyclic amino, or a halogen atom, and the cyclic amino group may contain 1 to 3 heteroatoms, (iii) R$^{33}$ and R$^{34}$, which may be the same or different, represent C$_{1-6}$ alkyl optionally substituted by mono- or di-C$_{1-6}$ alkylamino, which may form cyclic amino, or a halogen atom, and the cyclic amino group may contain 1 to 3 heteroatoms, or (iv) R$^{33}$ and R$^{34}$ together with the carbon atoms to which they are respectively attached form a saturated or unsaturated five- to seven-membered carbocyclic ring, R$^5$ represents formula (IIIa)

wherein (i) D, E, J, L, and M represent a carbon atom, any one or two of R$^8$, R$^9$, R$^{10}$, R$^{11}$, and R$^{12}$, which may be the same or different, represent a halogen atom; hydroxymethyl; C$_{1-6}$ alkyl optionally substituted by a halogen atom; or C$_{1-6}$ alkoxy optionally substituted by a halogen atom, and the others represent a hydrogen atom, (ii) any one or two of D, E, J, L, and M represent a nitrogen atom, and the others represent a carbon atom, any one or two of R$^8$, R$^9$, R$^{10}$, R$^{11}$, and R$^{12}$ may be the same or different and represent a halogen atom; hydroxymethyl; C$_{1-6}$ alkyl optionally substituted by a halogen atom, or C$_{1-6}$ alkoxy optionally substituted by a halogen atom, and the others represent a hydrogen atom, (iii) D, E, J, L, and M represent a carbon atom, R$^8$, R$^9$, and R$^{12}$ represent a hydrogen atom, any one of R$^{10}$ and R$^{11}$ represents a group of formula (IV) wherein Q, X1, and R$^{13}$ are as defined above, or a group of formula (V) wherein X2, X3, R$^{14}$, and R$^{15}$ are as defined above, and the other represents a hydrogen atom, or (iv) any one or two of D, E, J, L, and M represent a nitrogen atom, and the others represent a carbon atom, R$^8$, R$^9$, and R$^{12}$ represent a hydrogen atom, and one of R$^{10}$ and R$^{11}$ represents a group of formula (IV) wherein Q, X1, and R$^{13}$ are as defined above, or a group of formula (V) wherein X2, X3, R$^{14}$, and R$^{15}$ are as defined above, and the other represents a hydrogen atom, Z represents group (A), group (B), or group (C):

wherein

R$^6$ represents a hydrogen atom or C$_{1-6}$ alkyl,

R$^7$ represents optionally substituted aryl, optionally substituted aryl C$_{1-6}$ alkyl, optionally substituted aryl C$_{2-6}$ alkenyl, or optionally substituted saturated or unsaturated five- or six-membered heterocyclic group, and R$^{17}$ represents a hydrogen atom.

In formula (I-2), more preferably,

A represents formula (IIc)

wherein (i) R$^{33}$ and R$^{34}$ represent a hydrogen atom, (ii) any one of R$^{33}$ and R$^{34}$ represents a hydrogen atom, and the other represents C$_{1-6}$ alkyl optionally substituted by mono- or di-C$_{1-6}$ alkylamino, which may form cyclic amino, or a halogen atom, and the cyclic amino group may contain 1 to 3 heteroatoms, (iii) R$^{33}$ and R$^{34}$, which may be the same or different, represent C$_{1-6}$ alkyl optionally substituted by mono- or di-C$_{1-6}$ alkylamino, which may form cyclic amino, or a halogen atom, and the cyclic amino group may contain 1 to 3 heteroatoms, or (iv) R$^{33}$ and R$^{34}$ together with the carbon atoms to which they are respectively attached form a saturated or unsaturated five- to seven-membered carbocyclic ring, R$^5$ represents formula (IIIb) or formula (IIIc)

wherein (i) D, E, and J represent a carbon atom, G represents an oxygen or sulfur atom, any one or two of R$^8$, R$^9$, and R$^{10}$, which may be the same or different, represent a halogen atom; hydroxymethyl; C$_{1-6}$ alkyl optionally substituted by a halogen atom; or C$_{1-6}$ alkoxy optionally substituted by a halogen atom, and the others represent a hydrogen atom, or (ii) D, E, and J represent a carbon atom, G represents an oxygen or sulfur atom, one of R$^8$, R$^9$, and R$^{10}$ represents a group of formula (IV) wherein Q, X1, and R$^{13}$ are as defined above, or a group of formula (V) wherein X2, X3, R$^4$, and R$^{15}$ are as defined above, and the others represent a hydrogen atom, Z represents group (A), group (B), or group (C):

wherein

R$^6$ represents a hydrogen atom or C$_{1-6}$ alkyl,

R$^7$ represents optionally substituted aryl, optionally substituted aryl C$_{1-6}$ alkyl, optionally substituted aryl C$_{2-6}$ alkenyl, or optionally substituted saturated or unsaturated five- or six-membered heterocyclic group, and R$^{17}$ represents a hydrogen atom.

In formula (I-2), more preferably,

A represents formula (IId)

wherein R$^{35}$ and R$^{36}$ represent a hydrogen atom, or any one of R$^{35}$ and R$^{36}$ represents a hydrogen atom with the other representing C$_{1-6}$ alkyl optionally substituted by a halogen atom, R$^5$ represents formula (IIIa)

wherein (i) D, E, J, L, and M represent a carbon atom, any one or two of R$^8$, R$^9$, R$^{10}$, R$^{11}$, and R$^{12}$, which may be the same or different, represent a halogen atom; hydroxymethyl; C$_{1-6}$ alkyl optionally substituted by a halogen atom; or C$_{1-6}$ alkoxy optionally substituted by a halogen atom, and the others represent a hydrogen atom, (ii) any one or two of D, E, J, L, and M represent a nitrogen atom, and the others represent a carbon atom, any one or two of R$^8$, R$^9$, R$^{10}$, R$^{11}$, and R$^{12}$ may be the same or different and represent a halogen atom; hydroxymethyl; C$_{1-6}$ alkyl optionally substituted by a halogen atom, or C$_{1-6}$ alkoxy optionally substituted by a halogen atom, and the others represent a hydrogen atom, (iii) D, E, J, L, and M represent a carbon atom, R$^8$, R$^9$, and R$^{12}$ represent a hydrogen atom, any one of R$^{10}$ and R$^{11}$ represents a group of formula (IV) wherein Q, X1, and R$^{13}$ are as defined above, or a group of formula (V) wherein X2, X3, R$^{14}$, and R$^{15}$ are as defined above, and the other represents a hydrogen atom, or (iv) any one or two of D, E, J, L, and M represent a nitrogen atom, and the others represent a carbon atom, R$^8$, R$^9$, and R$^{12}$ represent a hydrogen atom, and one of R$^{10}$ and R$^{11}$ represents a group of formula (IV) wherein Q, X1, and R$^{13}$ are as defined above, or a group of formula (V) wherein X2, X3, R$^{14}$, and R$^{15}$ are as defined above, and the other represents a hydrogen atom, Z represents group (A), group (B), or group (C):

wherein

R$^6$ represents a hydrogen atom or C$_{1-6}$ alkyl,

R$^7$ represents optionally substituted aryl, optionally substituted aryl C$_{1-6}$ alkyl, optionally substituted aryl C$_{2-6}$ alkenyl, or optionally substituted saturated or unsaturated five- or six-membered heterocyclic group, and
$R^{17}$ represents a hydrogen atom.

In formula (I-2), more preferably,

A represents formula (IId)

wherein $R^{35}$ and $R^{36}$ represent a hydrogen atom, or any one of $R^{35}$ and $R^{36}$ represents a hydrogen atom with the other representing $C_{1-6}$ alkyl optionally substituted by a halogen atom, $R^5$ represents formula (IIIb) or formula (IIIc)

wherein (i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or (ii) D, E, and J represent a carbon atom, G represents an oxygen or sulfur atom, one of $R^8$, $R^9$, and $R^{10}$ represents a group of formula (IV) wherein Q, X1, and $R^{13}$ are as defined above, or a group of formula (V) wherein X2, X3, $R^{14}$, and $R^{15}$ are as defined above, and the others represent a hydrogen atom, Z represents group (A), group (B), or group (C):

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

Examples of preferred compounds according to the present invention include compounds 1 to 1077 described in the Examples.

Compounds of formula (I) according to the present invention include compounds wherein A represents a five- to nine-membered unsaturated carbocyclic moiety or a five- to nine-membered unsaturated heterocyclic moiety, and === represents a double bond, the carbocyclic moiety and heterocyclic moiety represented by A are optionally substituted by (a) a halogen atom;
(b) hydroxyl;
(c) $C_{1-6}$ alkyl;
(d) $C_{1-6}$ alkoxy;
(e) aryl;
(f) aryloxy;
(g) arylthio;
(h) alkylthio;
(i) nitro; or
(j) amino, (c) the $C_{1-6}$ alkyl group, (d) the $C_{1-6}$ alkoxy group, (e) the aryl group, (f) the aryloxy group, (g) the arylthio group, and (h) the alkylthio group are optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino group may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen atom, $C_{1-6}$ alkyl, $C_{1-6}$ alkoxy, or $C_{1-6}$ alkylamino, when the carbocyclic moiety and the heterocyclic moiety are substituted by two (c) $C_{1-6}$ alkyl groups, they together may form a $C_{3-5}$ alkylene chain, $R^5$ represents $C_{1-6}$ alkyl, aryl, $C_{1-6}$ alkoxy, aryloxy, $C_{1-6}$ alkylamino, arylamino, $C_{1-6}$ alkylthio, arylthio, $C_{3-7}$ cycloalkyl, or a heterocyclic group, and the $C_{1-6}$ alkyl, aryl, $C_{1-6}$ alkoxy, aryloxy, $C_{1-6}$ alkylamino, arylamino, $C_{1-6}$ alkylthio, arylthio, $C_{3-7}$ cycloalkyl, or heterocyclic group represented by $R^5$ may be the same or different, and is optionally substituted by (I) a halogen atom;

(II) $C_{1-6}$ alkyl optionally containing a substituent selected from the group consisting of (1) hydroxyl, (2) thiol, (3) amino, (4) $C_{1-6}$ alkoxy, (5) $C_{1-6}$ alkylthio, (6) $C_{1-6}$ alkylsulfinyl, (7) $C_{1-6}$ alkylsulfonyl, (8) mono- or di-$C_{1-6}$ alkylamino, (8') amino substituted by a heterocyclic group optionally substituted by $C_{1-6}$ alkyl, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S(=O)j- wherein Het represents a heterocyclic group, j is 0, 1, or 2, and Het is optionally substituted by alkyl optionally substituted by mono- or di-$C_{1-6}$ alkylamino in which the di-$C_{1-6}$ alkylamino group may form cyclic amino optionally containing 1 to 3 heteroatoms and one or two alkyl groups on the amino group and the cyclic amino moiety are optionally substituted by hydroxyl, (24) cyano, and (25) a halogen atom, wherein the alkyl moiety in (4) the $C_{1-6}$ alkoxy group, (5) the $C_{1-6}$ alkylthio group, (6) the $C_{1-6}$ alkylsulfinyl group, and (7) the $C_{1-6}$ alkylsulfonyl group is optionally substituted by a halogen atom; $C_{1-6}$ alkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms; aryloxy; arylthio; hydroxyl; carboxyl; —S(=O)$_2$(—OH); $C_{1-6}$ alkoxy- or aryloxy-carbonyl; $C_{1-6}$ alkylcarbonyl; aryl; or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxy, and in (8) the mono- or di-$C_{1-6}$ alkylamino group, the di-$C_{1-6}$ alkylamino group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl; $C_{1-6}$ alkoxy; $C_{1-6}$ alkylthio; mono- or di-$C_{1-6}$ alkylamino in which one or two alkyl groups on the amino group are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom; hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group;
- (III) $C_{1-6}$ alkoxy optionally substituted by a halogen atom;
- (IV) $C_{1-6}$ alkylthio optionally substituted by a halogen atom;
- (V) $C_{3-7}$ cycloalkyl;
- (VI) aryl;
- (VII) aryloxy;
- (VIII) $C_{1-6}$ alkylcarbonylamino;
- (VIX) $C_{1-6}$ alkylcarbonyloxy;
- (X) hydroxyl;
- (XI) nitro;
- (XII) cyano;
- (XIII) amino;
- (XIV) mono- or di-$C_{1-6}$ alkylamino in which the di-$C_{1-6}$ alkylamino group may form cyclic amino optionally containing 1 to 3 heteroatoms;
- (XV) arylamino;
- (XVI) $C_{1-6}$ alkyl- or aryl-sulfonylamino;
- (XVII) $C_{1-6}$ alkyl- or aryl-ureido;
- (XVIII) $C_{1-6}$ alkoxy- or aryloxy-carbonylamino;
- (XIX) $C_{1-6}$ alkylamino- or arylamino-carbonyloxy;
- (XX) $C_{1-6}$ alkoxy- or aryloxy-carbonyl;
- (XXI) acyl;
- (XXII) carboxyl;
- (XXIII) carbamoyl;
- (XXIV) mono- or di-alkylcarbamoyl;
- (XXV) a heterocyclic group;
- (XXVI) alkyl- or aryl-sulfonyl;
- (XXVII) $C_{2-6}$ alkenyloxy; or
- (XXVIII) $C_{2-6}$ alkynyloxy, Z represents group A or group B wherein $R^6$, $R^7$, and $R^{17}$ are as defined in formula (I), $R^{101}$ and $R^{102}$ together represent =O, and $R^{103}$ and $R^{104}$ represent a hydrogen atom, or $R^{101}$ and $R^{104}$ together represent a bond, and $R^{102}$ and $R^{103}$ together represent a bond.

Compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkyl-sulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycinate salts, phenylalanine salts, glutamic acid salts, or aspartic acid salts.

Production of Compounds

Compounds of formula (I) may be produced by reacting a hydrazine compound of formula (VI-1) or (VI-2) with a suitable carbonyl compound (compound C) in a suitable solvent, for example, toluene, in the presence of a suitable acid catalyst, for example, acetic acid.

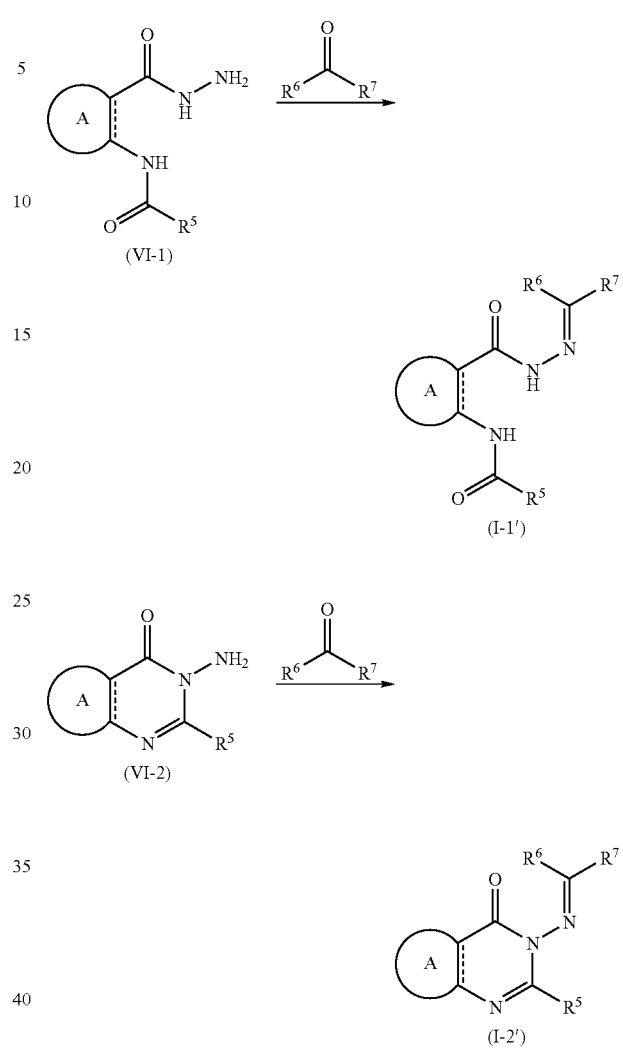

wherein A, $R^5$, $R^6$, and $R^7$ are as defined in formula (I).

The compound of formula (VI-1) and the compound of formula (VI-2) may be commercially available products, or alternatively may be produced by a production process which will be described later.

The compound of formula (VI-1) and the compound of formula (VI-2) may also be produced by reacting an amino compound of formula (VII) (compound A) with a suitable acid chloride (compound B), or by reacting an amino compound of formula (VII) (compound A) with a suitable carboxylic acid (compound B) in the presence of a suitable condensing agent, for example, 1-ethyl-3-(3-dimethylaminopropyl)carbodiimide hydrochloride, to give an amide compound of formula (VIII), then adding hydrazine to the amide compound of formula (VIII) in a suitable solvent, for example, ethanol, and heating the mixture. A reduced form of formula (VI-2) can be produced by carrying out the hydrazination at a higher temperature and prolonging the reaction time. For example, the compound of formula (VI-1) can be produced under reaction conditions of 30 to 40° C. and 12 to 24 hr, while the compound of formula (VI-2) can be produced under reaction conditions of 110 to 120° C. and 72 to 96 hr.

Scheme 2

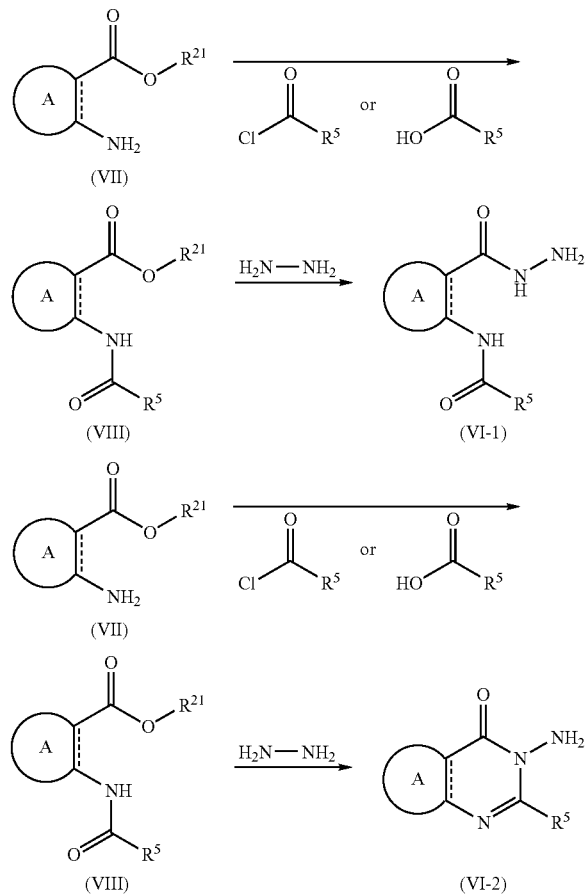

wherein A and R[5] are as defined in formula (I); and R[21] represents a hydrogen atom or a protective group of carboxyl.

The compound wherein R[5] represents phenyl substituted by formula (IV) or formula (V) can be produced by reacting a compound of formula (VIIIa) with a compound of formula (IV') or formula (V') (compound B') to give a compound of formula (VIIIb) and then subjecting the compound of formula (VIIIb) to reactions shown in scheme 1 and scheme 2.

Scheme 3

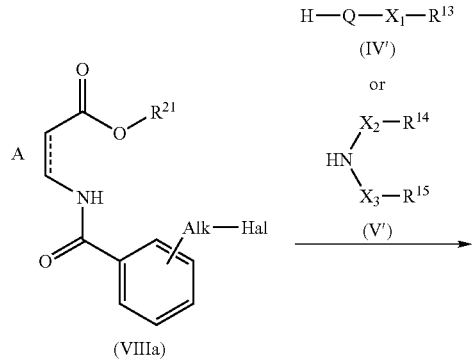

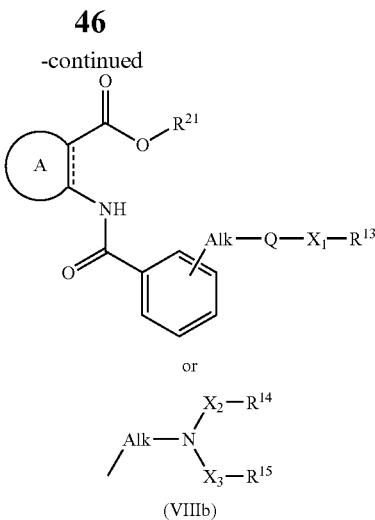

wherein A and R[5] are as defined in formula (I); Q, X1, and R[13] are as defined in formula (IV); X2, X3, R[14] and R[15] are as defined in formula (V); R[21] represents a hydrogen atom or a protective group of carboxyl; Alk represents an alkylene chain having 1 to 6 carbon atoms; and Hal represents a halogen atom.

Tandem-type compounds of formula (I-3) can also be produced according to scheme 3. Specifically, a compound to which a compound of formula (VIIIa) has been bonded in a tandem manner can be produced by reacting the compound of formula (VIIIa) with H—NR[205]-T-NR[205']—H wherein R[205], R[205'], and T are as defined in formula (I-3), instead of the compound of formula (IV') and the compound of formula (V'). The compound of formula (I-3) can be produced by subjecting this compound to reactions shown in scheme 1 and scheme 2.

An imine reduced form of formula (I) in which Z represents —NH—CR[6]R[7]R[17] can be produced by dissolving the compound produced according to scheme 1 in a suitable solvent, for example, methanol, and reducing the compound with a suitable reducing agent, for example, sodium borohydride).

Scheme 4

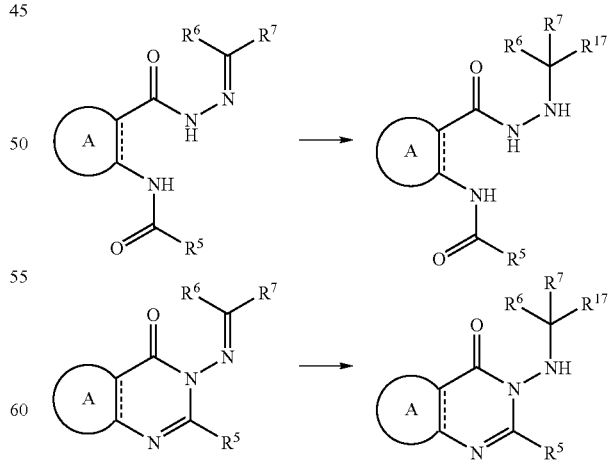

wherein A, R[5], R[6], R[7] and R[17] are as defined in formula (I).

Among amino compounds used as the starting compound in scheme 2, compounds in which ring A is a benzene ring can be synthesized by methods shown in schemes A to H.

Scheme A
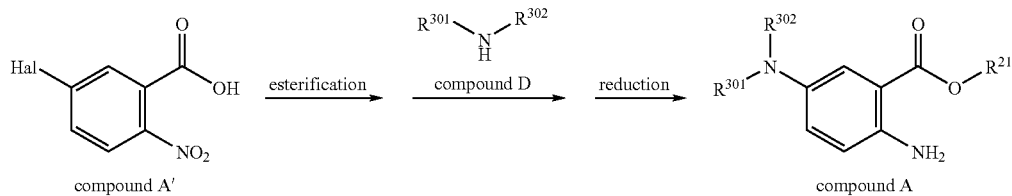
Scheme B
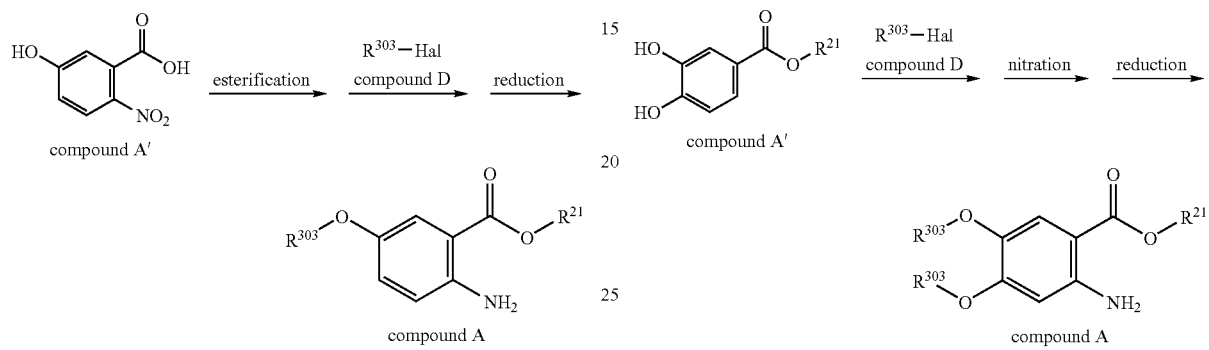
Scheme F
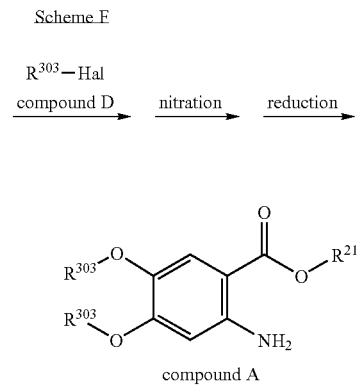
Scheme C
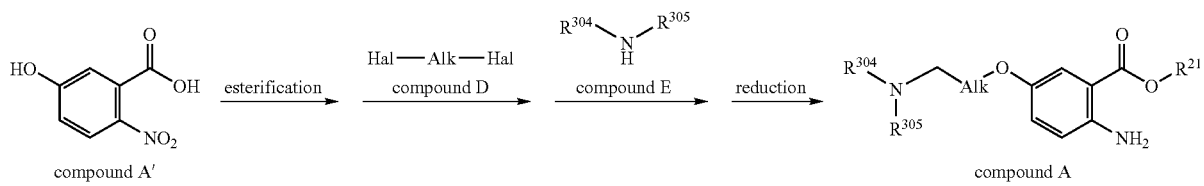
Scheme D
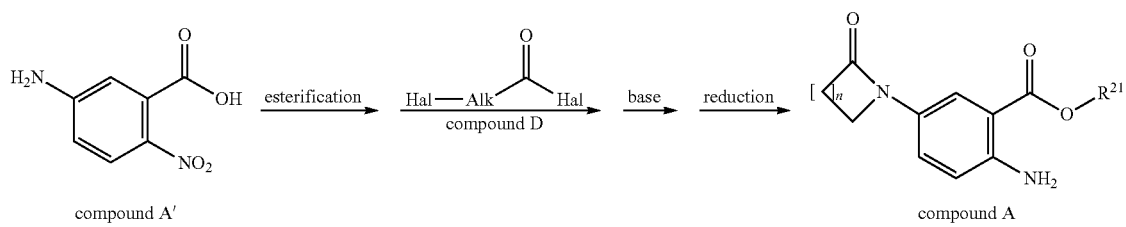
Scheme E
Scheme G
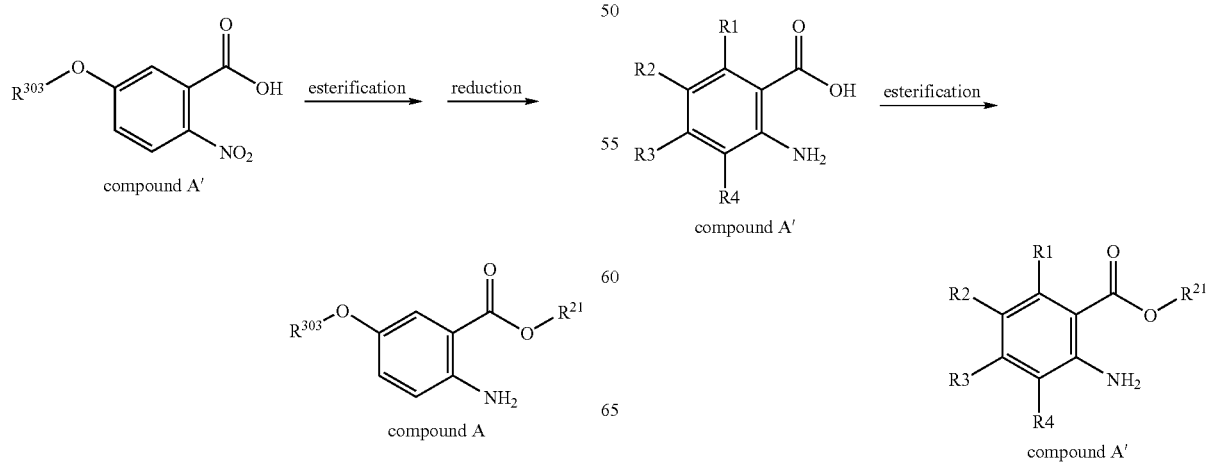

Scheme H

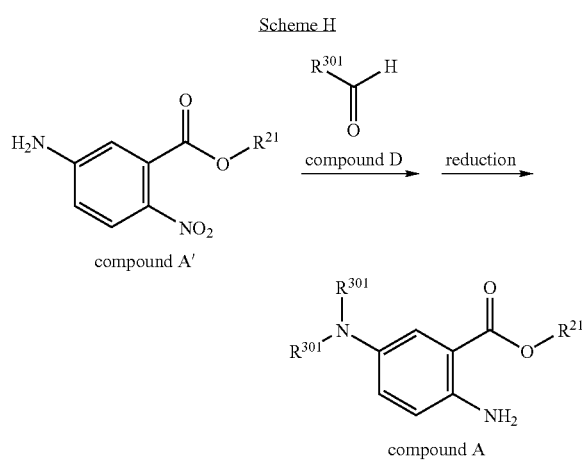

wherein $R^{21}$ represents a hydrogen atom or a protective group of carboxyl; Alk represents an alkylene chain having 2 to 7 carbon atoms; n is an integer of 1 to 6; Hal represents a halogen atom, preferably a bromine or chlorine atom; $R^{301}$, $R^{302}$, $R^{303}$, $R^{304}$, and $R^{305}$ represent optionally substituted $C_{1-6}$ alkyl, optionally substituted $C_{2-6}$ alkenyl, optionally substituted aryl, or the like; $R^1$, $R^2$, $R^3$, and $R^4$ are as defined in formula (I).

In the above schemes, the esterification can be carried out by esterifying a commercially available carboxylic acid with a suitable esterifying agent, for example, 1-ethyl-3-(3-dimethylaminopropyl)carbodiimide hydrochloride.

The introduction of the amino group can be carried out by allowing an alkylamino compound or an arylamino compound to act under basic condition, for example, potassium carbonate.

The reduction of the nitro group can be carried out using a suitable reducing agent, for example, palladium-carbon.

Use of Compounds

A group of sodium dependent phosphate transporters (NaPi) present in cells are known to be responsible for homeostasis of phosphorus in vivo. In particular, the phosphorus concentration of serum is generally regulated by phosphate absorption in intestinal epithelial cells and phosphate reabsorption in renal tubular cells, and the above phosphate transporters also participate in these mechanisms.

The compounds according to the present invention can inhibit these phosphate transporters that mainly specify phosphate absorption from the intestinal tract and phosphate reabsorption from the kidney (see Pharmacological Test Examples 1 to 3).

Further, the compounds according to the present invention can exhibit phosphate absorption inhibitory activity in the intestinal tract of rats (see Pharmacological Test Example 4).

Accordingly, the compounds according to the present invention can be used for the prevention or treatment of diseases for which serum phosphate lowering action is therapeutically effective.

The term "serum phosphate lowering action" as used herein means action that lowers phosphate concentration of serum. The phosphate concentration of serum is specified by (i) absorption from the intestinal tract and excretion into urine and feces and (ii) introduction and discharge with respect to cells in vivo and calcified tissue typified by osseous tissues. The "serum phosphate lowering action" as used herein embraces the action of lowering of the serum phosphate concentration in the case of action on a healthy living body and is not always limited to the action of lowering of serum phosphate concentration in hyperphosphatemia.

Further, the compounds according to the present invention can be used for the prevention or treatment of diseases for which phosphate transport inhibition is therapeutically effective.

The term "phosphate transport inhibition" as used herein means the inhibition of transport activity of phosphate transporters present on cell membranes of object cells. Object cells include epithelial cells of small intestine, renal epithelial cells, pulmonary epithelial cells, vascular endothelial cells, vascular smooth muscle cells, or osteoblasts.

Diseases for which the serum phosphate lowering action is effective therapeutically and diseases for which phosphate transport inhibition is therapeutically effective include (1) hyperphosphatemia, (2) renal failure and chronic renal failure, (3) secondary hyperparathyroidism and diseases related thereto, (4) metabolic osteopathy, (5) diseases for which the suppression of calcium and/or phosphorus product is effective therapeutically, and (6) other hyperphosphatemia-related diseases.

(1) Hyperphosphatemia

The compounds according to the present invention can lower the phosphate concentration of serum and can inhibit phosphate transport and thus can be used for the prevention or treatment of hyperphosphatemia. The term "hyperphosphatemia" as used herein means such a state that the phosphate concentration of serum is beyond a clinically defined normal region.

(2) Renal Failure and Chronic Renal Failure

Regarding renal failure and chronic renal failure, it has recently been suggested that an increase in serum phosphate concentration per se is an exacerbation factor of renal failure. In fact, there are a series of reports on that the progress of the renal failure can be delayed by restriction of phosphate ingestion in chronic renal failure patients (Maschio et al., Kidney Int., 22:371-376, 1982, Maschio et al., Kidney Int., 24:S273-277, 1983, Barsotti et al., Kidney Int. 24:S278-284, 1983).

Accordingly, the compounds according to the present invention which can inhibit phosphate transport and can lower phosphate concentration of serum can be used for the prevention or treatment of the renal failure and the chronic renal failure.

(3) Secondary Hyperparathyroidism and Primary Hyperparathyroidism and Diseases Related Thereto It is known that hyperphosphatemia secondarily leads to hypocalcemia and thus induces secondary hyperparathyroidism. Accordingly, the compounds according to the present invention can be used for the prevention and treatment of secondary hyperparathyroidism.

Further, in recent years, there are a report that a rise of phosphate concentration promotes the secretion of PTH (parathyroid hormone) from parathyroid cells (Almanden Y et al., J Bone Miner Res 11:970-976, 1996), a report that phosphorus restriction suppresses the secretion (Rachel K et al., J Clin Invest 96.327-333, 1995), a report that hyperplasia of parathyroids is suppressed (Slatopolsky E et al., J Clin Invest 97:2534-2540, 1996) and the like. When these reports suggesting that the serum phosphate concentration per se participates in hyperplasia of parathyroids and PTH secretion are taken into consideration, it can be said that the compounds according to the present invention can be used for the prevention and treatment of secondary hyperparathyroidism as well as primary hyperparathyroidism through a lowering in serum phosphate concentration. Further, the compounds according to the present invention can be used for the prevention and treatment of renal osteodystrophy induced by secondary hyperparathyroidism, that is, osteitis fibrosa, ostealgia and arthralgia, bone deformity, fracture and the like.

The compounds according to the present invention can prevent and treat secondary hyperparathyroidism and thus can also be used for the prevention and treatment of diseases said to be induced by PTH increase in the secondary hyperparathyroidism, for example, central or peripheral nervous system damage, anemia, myocardiopathy, hyperlipidemia, anomaly of saccharometabolism, pruritus cutaneus, tendon rupture, sexual dysfunction, muscle damage, skin ischemic ulcer, growth retardation, heart conduction disturbance, pulmonary diffusing impairment, immune deficiency, ostealgia and arthralgia, bone deformity, or fracture.

(4) Calcium and Phosphorus Metabolic Disorder

The compounds according to the present invention can remedy clinical conditions of phosphorus metabolic disorder and, at the same time, are considered to have the effect of remedying clinical conditions of metabolic disorder of minerals including calcium. Accordingly, the compounds according to the present invention can be used for the prevention and treatment of calcium and phosphorus metabolic disorders such as metabolic osteopathy.

(5) Diseases for which Suppression of Calcium and/or Phosphorus Product is Therapeutically Effective In dialysis patients, when poor control of serum phosphate concentration due to administration of a large amount of calcium preparations and administration of a large amount of vitamin D, and overconsumption of proteins is likely to cause ectopic calcification as a result of a rise of calcium and phosphorus product in blood and is in its turn causative of circulatory disorders derived from calcification of blood circulatory systems including coronary artery (Braun J et al., Am J Kidney Dis. 27:394-401, 1996, Goodman W G et al., N Engl J Med 342:1478-1483, 2000, Kimura K et al., Kidney Int. 71: S238-241, 1999). In this case, downward revision of calcium and phosphorus product is effective in remedying clinical condition (Geoffrey A B et al., Am J Kidney Dis. 31:607-617, 1998). The compounds according to the present invention are hyperphosphatemia improving drugs different from calcium preparations and thus can lower the phosphate concentration of serum without a rise of calcium concentration of serum. Thus, the compounds according to the present invention can be used for the treatment of diseases for which the suppression of calcium and/or phosphorus product in blood vessels is therapeutically effective. Such diseases include calcification of cardiovascular system in dialysis patients, age-related arterial sclerosis, diabetic vasculopathy, calcification of soft tissue, metastatic calcification, and ectopic calcification. Since a rise of calcium and phosphorus product is recognized as a risk factor of clinical conditions of red eye, arthralgia, myalgia, pruritus cutaneus, heart conduction disturbance, pulmonary diffusing impairment, angina pectoris, cardiac infarction, or heart failure induced by cardiac murmur or valvular disease (Tetsuo Tagami, Jin To Toseki (Kidney and Dialysis), Vol. 49:189-191, 2000), the compounds according to the present invention can also be used for the prevention and treatment of these diseases.

(6) Other Diseases Related to Hyperphosphatemia

In addition to the above diseases (1) to (5), hypoparathyroidism, pseudohypoparathyroidism, hypocalcemia, hypercalciuria, vitamin D toxicosis, acromegaly, overdose of phosphate, acidosis, state of hypercatabolism, rhabdomyolysis, hemolytic anemia, climacteric disturbance, malignant tumor, tumor lysis syndrome, and tumoral calcinosis involve hyperphosphatemia. Therefore, the compounds according to the present invention can also be used for the prevention and treatment of these diseases.

According to the present invention, there is provided a serum phosphate concentration lowering agent comprising the compound according to the present invention.

According to the present invention, there is provided a phosphate transport inhibitor comprising the compound according to the present invention.

According to the present invention, there is provided a method for lowering serum phosphate concentration, comprising administering the compound according to the present invention to a human or a mammal other than a human.

According to the present invention, there is provided a method for inhibiting phosphate transport, comprising administering the compound according to the present invention to a human or mammal other than a human.

Pharmaceutical Preparation

The compounds according to the present invention can be administered to human and non-human animals orally or parenterally by administration routes, for example, intraoral, nasal administration, transpulmonary administration, intrarectal administration, percutaneous administration, subcutaneous administration, or intravenous administration. Therefore, the compounds according to the present invention can be formulated into suitable dosage forms according to the administration routes. Dosage forms suitable for the above administration routes include tablets, capsules, granules, powders, ointments, poultices, aerosols, suppositories, and injections.

The compound according to the present invention per se can be administered to patients, or alternatively may be administered together with general-purpose preparation additives to patients.

The pharmaceutical composition according to the present invention can be produced according to a well-known formulation technique by using the compound according to the present invention together with the following additives.

For example, oral preparations, that is, tablets, capsules, granules, and powders, can be produced by conventional methods with the compounds according to the present invention and suitable preparation additives. Additives usable for oral preparations include excipients, binders, disintegrants, and lubricants. They may be used either solely or in a combination of two or more. Excipients include, for example, lactose, mannitol, corn starch, and calcium carbonate. Binders include, for example, gum arabic, tragacanth, gelatin, and methylcellulose. Disintegrants include, for example, corn starch, crystalline cellulose, and carboxymethylcellulose sodium. Lubricants include, for example, talc, and magnesium stearate.

Oral preparations containing the compound according to the present invention may be coated with a coating agent according to a well known method. Coating agents usable herein include, for example, hydroxypropylcellulose, hydroxypropylmethylcellulose, aminoalkylmethacrylate copolymer, hydroxypropylmethylcellulose phthalate, and carboxymethylethylcellulose.

Oral preparations can be modified for effectively drawing phosphate absorption inhibition from intestinal tracts of the compound according to the present invention.

When the compounds according to the present invention are orally administered, there is a possibility that, after the inhibition of phosphate transport carriers in small intestine epithelial cells, they are absorbed in the body and inhibit phosphate transport carriers in vascular endothelial cells, pulmonary epithelial cells, renal epithelial cells, osteoblasts and the like. Accordingly, the compounds according to the present invention have the possibility of inhibiting phosphate absorption from the intestine and further inhibiting phosphate absorption in the kidney to synergistically and effectively lower the phosphate concentration of serum. However, the possibility of exhibiting unknown toxicity upon absorption of the compounds according to the present invention in the body cannot be denied. To avoid this phenomenon, a technique may be adopted in which the compounds according to the present invention can specifically inhibit only small intestine epithelium, which is the first barrier for phosphate absorption from outside of the body, without the absorption from the intestinal tract. For example, the absorption of the compound per se from the intestinal tract can be prevented by bonding an inert water-soluble polymer to the compounds according to the present invention to increase the water solubility and molecular weight. Water soluble polymers usable herein include, for example, polyethylene glycol, dextran, and gelatin.

An enteric coating may be applied to the oral preparation according to the present invention for specific dissolution in the intestinal tract after oral administration. The enteric coating may be carried out by a well-known method using an enteric coating agent. Enteric coating agents include, for example, hydroxypropylmethylcellulose phthalate, hydroxypropylmethylcellulose acetate succinate, carboxymethylethylcellulose, and methacrylic acid copolymers.

Further, any foamable substance, which, after oral administration, can promote dissolution speed of the preparation in the intestinal tract to enhance the concentration of the effective ingredient, can be added to the oral preparation according to the present invention. Substances which are foamable upon dissolution include, for example, a combination of sodium hydrogencarbonate and citric acid.

Further, any substance, which, after oral administration, can improve the residence of the preparation in the intestinal tract, can be added to the oral preparation according to the present invention. Substances which can improve the residence include substances which become viscous upon dissolution, and examples thereof include sodium alginate, carboxymethylcellulose sodium, hydroxyethylcellulose, hydroxypropylcellulose, hydroxypropylmethylcellulose, polyvinyl alcohol, polyvinyl pyrrolidone, carboxylvinyl polymer, and chitosan.

In the oral preparation according to the present invention, the above modification methods may be properly used in combination.

The compounds according to the present invention and suitable preparation additives may be used for the manufacture of injections by a general-purpose method. Additives usable in injections include diluents, pH adjustors, tonicity adjusting agents, dissolution aids, and preservatives. They may be used either solely or in a combination of two or more. Diluents include, for example, distilled water for injections. pH adjustors include, for example, hydrochloric acid, sodium hydroxide, a combination of acetic acid with sodium acetate, and a combination of disodium hydrogenphosphate with sodium dihydrogenphosphate. Tonicity adjusting agents include, for example, sodium chloride, glucose, mannitol, and glycine. Dissolution aids include, for example, ethanol, Polysorbate 20, Polysorbate 80, sucrose fatty acid ester, and propylene glycol. Preservatives include, for example, chlorobutanol, benzalconium chloride, and benzethonium chloride.

For the compounds according to the present invention, the dose may be appropriately determined in consideration of particular conditions, for example, the age, weight, sex, type of disease, and severity of condition of patients, and the preparation may be administered, for example, in an amount of 0.1 to 1000 mg/kg, preferably 0.5 to 100 mg/kg, more preferably 1 to 20 mg/kg. This dose may be administered at a time daily or divided doses of several times daily.

EXAMPLES

The present invention is further illustrated by the following Examples that are not intended as a limitation of the scope of the invention.

Example 1

Compound 1 3,4-Dimethoxy-N-[2-(3-phenyl-allylidene-hydrazinocarbonyl)-phenyl]-benzamide Methyl 2-aminobenzoate (compound A) (2.0 g) was dissolved in anhydrous methylene chloride (40.0 ml). Subsequently, pyridine (2.0 ml) and 3,4-dimethoxybenzoyl chloride (compound B) (3.14 g) were added to the solution at room temperature, and the mixture was stirred at that temperature for 30 min. After the completion of the reaction, distilled water was added thereto, and the mixture was subjected to separatory extraction with chloroform. The organic layer was washed with a saturated aqueous sodium chloride solution, was dried over sodium sulfate, and was then concentrated to give methyl 2-[(3,4-dimethoxybenzoyl)amino] benzoate as a useful intermediate (4.17 g, yield 100%).

Methyl 2-[(3,4-dimethoxybenzoyl)amino]benzoate (4.17 g) produced by the above reaction was dissolved in ethanol (40.0 ml). Hydrazine monohydrate (20.0 ml) was added at room temperature, and the mixture was stirred with heating under reflux for 12 hr. After the completion of the reaction, the reaction solution was allowed to cool at room temperature and was cooled under ice cooling to precipitate crystals. The precipitated crystals were collected by filtration through Kiriyama Rohto (40 mm$\phi$) and were washed with ether to give N-(2-hydrazinocarbonyl-phenyl)-3,4-dimethoxybenzamide as a hydrazine compound (3.55 g, yield 91.3%).

N-(2-Hydrazinocarbonyl-phenyl)-3,4-dimethoxybenzamide (50.0 mg) was dissolved in anhydrous toluene (1.0 ml). Subsequently, a catalytic amount of acetic acid and trans-cinnamaldehyde (compound C) (40.0 µl) were added at room temperature, and the mixture was stirred with heating under reflux for 30 min. After the completion of the reaction, the reaction solution was allowed to cool at room temperature and was cooled under ice cooling to precipitate crystals. The precipitated crystals were filtered through Kiriyama Rohto (21 mm$\phi$) and were washed with toluene and hexane. The crystals were dried through a vacuum pump to give the title compound 1 (39.0 mg, yield 57.0%).

Mass spectrometric value (ESI-MS) 428 (M−1)

Compound 2 N-[2-(2-Fluoro-benzylidene-hydrazinocarbonyl)-phenyl]-3,4-dimethoxy-benzamide The title compound 2 was produced in the same manner as in Example 1.
Mass spectrometric value (ESI-MS) 420 (M−1)

Compound 3 3,4-Dimethoxy-N-[2-(2-methyl-benzylidene-hydrazinocarbonyl)-phenyl]-benzamide The title compound 3 was produced in the same manner as in Example 1.
Mass spectrometric value (ESI-MS) 416 (M−1)

Compound 4 3,4-Dimethoxy-N-[2-(2-methoxy-benzylidene-hydrazinocarbonyl)-phenyl]-benzamide The title compound 4 was produced in the same manner as in Example 1.
Mass spectrometric value (ESI-MS) 432 (M−1)

Compound 5 3,4-Dimethoxy-N-[2-(3-methoxy-benzylidene-hydrazinocarbonyl)-phenyl]-benzamide The title compound 5 was produced in the same manner as in Example 1.
Mass spectrometric value (ESI-MS) 432 (M−1)

Compound 6 N-[2-(3,5-Di-tert-butyl-4-hydroxy-benzylidene-hydrazinocarbonyl)-phenyl]-3,4-dimethoxy-benzamide The title compound 6 was produced in the same manner as in Example 1.
Mass spectrometric value (ESI-MS) 530 (M−1)

Compound 7 3,4-Dimethoxy-N-[2-(2-methyl-3-phenyl-allylidene-hydrazinocarbonyl)-phenyl]-benzamide The title compound 7 was produced in the same manner as in Example 1.
Mass spectrometric value (ESI-MS) 442 (M−1)

Compound 8 N-[2-(3,5-Bis-trifluoromethyl-benzylidene-hydrazinocarbonyl)-phenyl]-3,4-dimethoxy-benzamide The title compound 8 was produced in the same manner as in Example 1.
Mass spectrometric value (ESI-MS) 538 (M−1)

Compound 9 N-[2-(3-Cyano-benzylidene-hydrazinocarbonyl)-phenyl]-3,4-dimethoxy-benzamide The title compound 9 was produced in the same manner as in Example 1.
Mass spectrometric value (ESI-MS) 427 (M−1)

Compound 10 N-[2-(2-Bromo-benzylidene-hydrazinocarbonyl)-phenyl]-3,4-dimethoxy-benzamide The title compound 10 was produced in the same manner as in Example 1.
Mass spectrometric value (ESI-MS) 480 (M−1)

Compound 11 N-[2-(4-Hydroxy-3-methoxy-benzylidene-hydrazinocarbonyl)-phenyl]-3,4-dimethoxy-benzamide The title compound 11 was produced in the same manner as in Example 1.
Mass spectrometric value (ESI-MS) 448 (M−1)

Compound 12 3,4-Dimethoxy-N-[2-(3,4,5-trimethoxy-benzylidene-hydrazinocarbonyl)-phenyl]-benzamide The title compound 12 was produced in the same manner as in Example 1.
Mass spectrometric value (ESI-MS) 492 (M−1)

Compound 13 N-[4-Bromo-2-(3-phenyl-allylidene-hydrazinocarbonyl)-phenyl]-3,4-dimethoxy-benzamide The title compound 13 was produced in the same manner as in Example 1.
Mass spectrometric value (ESI-MS) 508 (M−1)

Compound 14 N-[4-Bromo-2-(2-bromo-benzylidene-hydrazinocarbonyl)-phenyl]-3,4-dimethoxy-benzamide The title compound 14 was produced in the same manner as in Example 1.
Mass spectrometric value (ESI-MS) 560 (M−1)

Compound 15 N-[2-(3-Fluoro-benzylidene-hydrazinocarbonyl)-phenyl]-3,4-dimethoxy-benzamide The title compound 15 was produced in the same manner as in Example 1.
Mass spectrometric value (ESI-MS) 420 (M−1)

Compound 16 N-[2-(4-Fluoro-benzylidene-hydrazinocarbonyl)-phenyl]-3,4-dimethoxy-benzamide The title compound 16 was produced in the same manner as in Example 1.
Mass spectrometric value (ESI-MS) 420 (M−1)

Compound 17 N-[2-(Benzylidene-hydrazinocarbonyl)-phenyl]-3,4-dimethoxy-benzamide The title compound 17 was produced in the same manner as in Example 1.
Mass spectrometric value (ESI-MS) 402 (M−1)

Compound 18 N-[2-(3-Hydroxy-benzylidene-hydrazinocarbonyl)-phenyl]-3,4-dimethoxy-benzamide The title compound 18 was produced in the same manner as in Example 1.
Mass spectrometric value (ESI-MS) 418 (M−1)

Compound 19 N-[2-(4-Hydroxy-benzylidene-hydrazinocarbonyl)-phenyl]-3,4-dimethoxy-benzamide The title compound 19 was produced in the same manner as in Example 1.
Mass spectrometric value (ESI-MS) 418 (M−1)

Compound 20 3,4-Dimethoxy-N-[2-(3-methyl-benzylidene-hydrazinocarbonyl)-phenyl]-benzamide The title compound 20 was produced in the same manner as in Example 1.
Mass spectrometric value (ESI-MS) 416 (M−1)

Compound 21 N-[2-(Furan-2-ylmethylene-hydrazinocarbonyl)-phenyl]-3,4-dimethoxy-benzamide The title compound 21 was produced in the same manner as in Example 1.
Mass spectrometric value (ESI-MS) 392 (M−1)

Compound 22 3,4-Dimethoxy-N-[2-(5-methyl-furan-2-ylmethylene-hydrazinocarbonyl)-phenyl]-benzamide The title compound 22 was produced in the same manner as in Example 1.
Mass spectrometric value (ESI-MS) 406 (M−1)

Compound 23 3,4-Dimethoxy-N-[2-(thiophen-2-ylmethylene-hydrazinocarbonyl)-phenyl]-benzamide The title compound 23 was produced in the same manner as in Example 1.
Mass spectrometric value (ESI-MS) 408 (M−1)

Compound 24 3,4-Dimethoxy-N-[2-(thiophen-3-ylmethylene-hydrazinocarbonyl)-phenyl]-benzamide The title compound 24 was produced in the same manner as in Example 1.
Mass spectrometric value (ESI-MS) 408 (M−1)

Compound 25 N-[2-(2,4-Dihydroxy-benzylidene-hydrazinocarbonyl)-phenyl]-3,4-dimethoxy-benzamide The title compound 25 was produced in the same manner as in Example 1.
Mass spectrometric value (ESI-MS) 434 (M−1)

Compound 26 N-[2-(3,4-Dihydroxy-benzylidene-hydrazinocarbonyl)-phenyl]-3,4-dimethoxy-benzamide The title compound 26 was produced in the same manner as in Example 1.
Mass spectrometric value (ESI-MS) 434 (M−1)

Compound 27 N-[2-(Benzylidene-hydrazinocarbonyl)-phenyl]-2-fluoro-benzamide

The title compound 27 was produced in the same manner as in Example 1.
Mass spectrometric value (ESI-MS) 360 (M−1)

Compound 28 N-[4-Bromo-2-(2-fluoro-benzylidene-hydrazinocarbonyl)-phenyl]-3,4-dimethoxy-benzamide The title compound 28 was produced in the same manner as in Example 1.
Mass spectrometric value (ESI-MS) 500 (M−1)

Compound 29 N-[4-Bromo-2-(3-fluoro-benzylidene-hydrazinocarbonyl)-phenyl]-3,4-dimethoxy-benzamide The title compound 29 was produced in the same manner as in Example 1.
$^1$H-NMR (CDCl$_3$, 400 MHz): δ 8.55 (1H, d, J=9.0 Hz), 8.32 (1H, bs), 7.49-7.67 (6H, m), 7.40 (1H, q, J=4.56 Hz), 7.13 (1H, q, J=5.53 Hz), 6.93 (1H, d, J=8.8 Hz), 3.98 (3H, s), 3.94 (3H, s)
Mass spectrometric value (ESI-MS) 500 (M−1)

Compound 30 N-[4-Bromo-2-(2-methyl-benzylidene-hydrazinocarbonyl)-phenyl]-3,4-dimethoxy-benzamide The title compound 30 was produced in the same manner as in Example 1.
Mass spectrometric value (ESI-MS) 494 (M−1)

Compound 31 N-[4-Bromo-2-(3-methyl-benzylidene-hydrazinocarbonyl)-phenyl]-3,4-dimethoxy-benzamide The title compound 31 was produced in the same manner as in Example 1.
Mass spectrometric value (ESI-MS) 494 (M−1)

Compound 32 N-[2-(3-Chloro-4-fluoro-benzylidene-hydrazinocarbonyl)-phenyl]-3,4-dimethoxy-benzamide The title compound 32 was produced in the same manner as in Example 1.
Mass spectrometric value (ESI-MS) 454 (M−1)

Compound 33 3,4-Dimethoxy-N-[2-(4-trifluoromethoxy-benzylidene-hydrazinocarbonyl)-phenyl]-benzamide The title compound 33 was produced in the same manner as in Example 1.
Mass spectrometric value (ESI-MS) 486 (M−1)

Compound 34 N-[2-(3-Bromo-4-methoxy-benzylidene-hydrazinocarbonyl)-phenyl]-3,4-dimethoxy-benzamide The title compound 34 was produced in the same manner as in Example 1.
Mass spectrometric value (ESI-MS) 512 (M−1)

Compound 35 N-[2-(3-Chloro-benzylidene-hydrazinocarbonyl)-phenyl]-3,4-dimethoxy-benzamide The title compound 35 was produced in the same manner as in Example 1.
Mass spectrometric value (ESI-MS) 436 (M−1)

Compound 36 N-[2-(4-Hydroxy-3,5-dimethyl-benzylidene-hydrazinocarbonyl)-phenyl]-3,4-dimethoxy-benzamide The title compound 36 was produced in the same manner as in Example 1.
Mass spectrometric value (ESI-MS) 446 (M−1)

Compound 37 N-[2-(3-Ethoxy-4-hydroxy-benzylidene-hydrazinocarbonyl)-phenyl]-3,4-dimethoxy-benzamide The title compound 37 was produced in the same manner as in Example 1.
Mass spectrometric value (ESI-MS) 462 (M−1)

Compound 38 2-Fluoro-N-[2-(4-fluoro-benzylidene-hydrazinocarbonyl)-phenyl]-benzamide The title compound 38 was produced in the same manner as in Example 1.
Mass spectrometric value (ESI-MS) 378 (M−1)

Compound 39 2-Fluoro-N-[2-(3-hydroxy-benzylidene-hydrazinocarbonyl)-phenyl]-benzamide The title compound 39 was produced in the same manner as in Example 1.
Mass spectrometric value (ESI-MS) 376 (M−1)

Compound 40 2-Fluoro-N-[2-(4-methyl-benzylidene-hydrazinocarbonyl)-phenyl]-benzamide The title compound 40 was produced in the same manner as in Example 1.
Mass spectrometric value (ESI-MS) 374 (M−1)

Compound 41 N-[2-(4-Chloro-3-trifluoromethyl-benzylidene-hydrazinocarbonyl)-phenyl]-3,4-dimethoxy-benzamide The title compound 41 was produced in the same manner as in Example 1.
Mass spectrometric value (ESI-MS) 504 (M−1)

Compound 42 N-[2-(4-Hydroxy-3-methyl-benzylidene-hydrazinocarbonyl)-phenyl]-3,4-dimethoxy-benzamide The title compound 42 was produced in the same manner as in Example 1.
Mass spectrometric value (ESI-MS) 432 (M−1)

Compound 43 N-[2-(2,5-Dimethyl-benzylidene-hydrazinocarbonyl)-phenyl]-3,4-dimethoxy-benzamide The title compound 43 was produced in the same manner as in Example 1.
Mass spectrometric value (ESI-MS) 430 (M−1)

Compound 44 N-[2-(2-Fluoro-5-trifluoromethyl-benzylidene-hydrazinocarbonyl)-phenyl]-3,4-dimethoxy-benzamide The title compound 44 was produced in the same manner as in Example 1.
Mass spectrometric value (ESI-MS) 488 (M−1)

Compound 45 2-Fluoro-N-[2-(4-hydroxy-3-methyl-benzylidene-hydrazinocarbonyl)-phenyl]-benzamide The title compound 45 was produced in the same manner as in Example 1.
Mass spectrometric value (ESI-MS) 390 (M−1)

Compound 46 N-[2-(2,5-Dimethyl-benzylidene-hydrazinocarbonyl)-phenyl]-2-fluoro-benzamide The title compound 46 was produced in the same manner as in Example 1.
Mass spectrometric value (ESI-MS) 388 (M−1)

Compound 47 N-[2-(3-Fluoro-benzylidene-hydrazinocarbonyl)-phenyl]-4-methoxy-benzamide The title compound 47 was produced in the same manner as in Example 1.
Mass spectrometric value (ESI-MS) 390 (M−1)

Compound 48 N-[2-(4-Fluoro-benzylidene-hydrazinocarbonyl)-phenyl]-4-methoxy-benzamide The title compound 48 was produced in the same manner as in Example 1.
Mass spectrometric value (ESI-MS) 390 (M−1)

Compound 49 4-Methoxy-N-[2-(3-methyl-benzylidene-hydrazinocarbonyl)-phenyl]-benzamide The title compound 49 was produced in the same manner as in Example 1.
Mass spectrometric value (ESI-MS) 386 (M−1)

Compound 50 N-[2-(3-Hydroxy-benzylidene-hydrazinocarbonyl)-phenyl]-4-methoxy-benzamide The title compound 50 was produced in the same manner as in Example 1.
Mass spectrometric value (ESI-MS) 388 (M−1)

Compound 51 4-Methoxy-N-[2-(4-methyl-benzylidene-hydrazinocarbonyl)-phenyl]-benzamide The title compound 51 was produced in the same manner as in Example 1.
Mass spectrometric value (ESI-MS) 386 (M−1)

Compound 52 N-[2-(4-Allyloxy-benzylidene-hydrazinocarbonyl)-phenyl]-3,4-dimethoxy-benzamide The title compound 52 was produced in the same manner as in Example 1.
Mass spectrometric value (ESI-MS) 458 (M−1)

Compound 53 N-[2-(3,5-Dimethoxy-benzylidene-hydrazinocarbonyl)-phenyl]-3,4-dimethoxy-benzamide The title compound 53 was produced in the same manner as in Example 1.
Mass spectrometric value (ESI-MS) 462 (M−1)

Compound 54 3,4-Dimethoxy-N-{2-[3-(3-trifluoromethyl-phenoxy)-benzylidene-hydrazinocarbonyl]-phenyl}-benzamide The title compound 54 was produced in the same manner as in Example 1.
Mass spectrometric value (ESI-MS) 562 (M−1)

Compound 55 N-[2-(3-Fluoro-benzylidene-hydrazinocarbonyl)-phenyl]-3,5-dimethoxy-benzamide The title compound 55 was produced in the same manner as in Example 1.
Mass spectrometric value (ESI-MS) 420 (M−1)

Compound 56 N-[2-(4-Fluoro-benzylidene-hydrazinocarbonyl)-phenyl]-3,5-dimethoxy-benzamide The title compound 56 was produced in the same manner as in Example 1.
Mass spectrometric value (ESI-MS) 420 (M−1)

Compound 57 3,5-Dimethoxy-N-[2-(4-methyl-benzylidene-hydrazinocarbonyl)-phenyl]-benzamide The title compound 57 was produced in the same manner as in Example 1.
Mass spectrometric value (ESI-MS) 416 (M−1)

Compound 58 N-[2-(3-Hydroxy-benzylidene-hydrazinocarbonyl)-phenyl]-3,5-dimethoxy-benzamide The title compound 58 was produced in the same manner as in Example 1.
Mass spectrometric value (ESI-MS) 418 (M−1)

Compound 59 N-[4-Bromo-2-(3-chloro-benzylidene-hydrazinocarbonyl)-phenyl]-3,4-dimethoxy-benzamide The title compound 59 was produced in the same manner as in Example 1.
Mass spectrometric value (ESI-MS) 516 (M−1)

Compound 60 N-[4-Bromo-2-(4-chloro-benzylidene-hydrazinocarbonyl)-phenyl]-3,4-dimethoxy-benzamide The title compound 60 was produced in the same manner as in Example 1.
Mass spectrometric value (ESI-MS) 516 (M−1)

Compound 61 N-[4-Bromo-2-(4-fluoro-benzylidene-hydrazinocarbonyl)-phenyl]-3,4-dimethoxy-benzamide The title compound 61 was produced in the same manner as in Example 1.
Mass spectrometric value (ESI-MS) 500 (M−1)

Compound 62 N-[4-Bromo-2-(4-methyl-benzylidene-hydrazinocarbonyl)-phenyl]-3,4-dimethoxy-benzamide The title compound 62 was produced in the same manner as in Example 1.
Mass spectrometric value (ESI-MS) 494 (M−1)

Compound 63 N-[4-Bromo-2-(3-hydroxy-benzylidene-hydrazinocarbonyl)-phenyl]-3,4-dimethoxy-benzamide The title compound 63 was produced in the same manner as in Example 1.
Mass spectrometric value (ESI-MS) 496 (M−1)

Compound 64 N-[4-Bromo-2-(4-hydroxy-benzylidene-hydrazinocarbonyl)-phenyl]-3,4-dimethoxy-benzamide The title compound 64 was produced in the same manner as in Example 1.
Mass spectrometric value (ESI-MS) 496 (M−1)

Compound 65 N-[4-Chloro-2-(3-fluoro-benzylidene-hydrazinocarbonyl)-phenyl]-3,4-dimethoxy-benzamide The title compound 65 was produced in the same manner as in Example 1.
Mass spectrometric value (ESI-MS) 454 (M−1)

Compound 66 N-[4-Chloro-2-(4-fluoro-benzylidene-hydrazinocarbonyl)-phenyl]-3,4-dimethoxy-benzamide The title compound 66 was produced in the same manner as in Example 1.
Mass spectrometric value (ESI-MS) 454 (M−1)

Compound 67 N-[4-Chloro-2-(3-methyl-benzylidene-hydrazinocarbonyl)-phenyl]-3,4-dimethoxy-benzamide The title compound 67 was produced in the same manner as in Example 1.
Mass spectrometric value (ESI-MS) 450 (M−1)

Compound 68 N-[4-Chloro-2-(4-methyl-benzylidene-hydrazinocarbonyl)-phenyl]-3,4-dimethoxy-benzamide The title compound 68 was produced in the same manner as in Example 1.
$^1$H-NMR (CDCl$_3$, 400 MHz): δ 9.33 (1H, s), 8.72 (1H, d, J=8.76 Hz), 8.21 (1H, s), 7.48-7.68 (6H, m), 7.20-7.25 (1H, m), 6.92 (1H, d, J=8.56 Hz), 3.97 (3H, s), 3.93 (3H, s), 2.38 (3H, s)
Mass spectrometric value (ESI-MS) 450 (M−1)

Compound 69 N-[4-Chloro-2-(3-hydroxy-benzylidene-hydrazinocarbonyl)-phenyl]-3,4-dimethoxy-benzamide The title compound 69 was produced in the same manner as in Example 1.
Mass spectrometric value (ESI-MS) 452 (M−1)

Compound 70 N-[4-Chloro-2-(4-hydroxy-benzylidene-hydrazinocarbonyl)-phenyl]-3,4-dimethoxy-benzamide The title compound 70 was produced in the same manner as in Example 1.
Mass spectrometric value (ESI-MS) 452 (M−1)

Compound 71 N-[5-Chloro-2-(3-fluoro-benzylidene-hydrazinocarbonyl)-phenyl]-3,4-dimethoxy-benzamide The title compound 71 was produced in the same manner as in Example 1.
Mass spectrometric value (ESI-MS) 454 (M−1)

Compound 72 N-[5-Chloro-2-(4-fluoro-benzylidene-hydrazinocarbonyl)-phenyl]-3,4-dimethoxy-benzamide The title compound 72 was produced in the same manner as in Example 1.
Mass spectrometric value (ESI-MS) 454 (M−1)

Compound 73 N-[5-Chloro-2-(3-methyl-benzylidene-hydrazinocarbonyl)-phenyl]-3,4-dimethoxy-benzamide The title compound 73 was produced in the same manner as in Example 1.
Mass spectrometric value (ESI-MS) 450 (M−1)

Compound 74 N-[5-Chloro-2-(4-methyl-benzylidene-hydrazinocarbonyl)-phenyl]-3,4-dimethoxy-benzamide The title compound 74 was produced in the same manner as in Example 1.
Mass spectrometric value (ESI-MS) 452 (M−1)

Compound 75 N-[5-Chloro-2-(3-hydroxy-benzylidene-hydrazinocarbonyl)-phenyl]-3,4-dimethoxy-benzamide The title compound 75 was produced in the same manner as in Example 1.
Mass spectrometric value (ESI-MS) 452 (M−1)

Compound 76 4-Fluoro-N-[2-(3-fluoro-benzylidene-hydrazinocarbonyl)-phenyl]-benzamide The title compound 76 was produced in the same manner as in Example 1.
Mass spectrometric value (ESI-MS) 379 (M−1), 757 (2M−1)

Compound 77 4-Fluoro-N-[2-(4-fluoro-benzylidene-hydrazinocarbonyl)-phenyl]-benzamide The title compound 77 was produced in the same manner as in Example 1.
Mass spectrometric value (ESI-MS) 378 (M−1)

Compound 78 4-Fluoro-N-[2-(3-methyl-benzylidene-hydrazinocarbonyl)-phenyl]-benzamide The title compound 78 was produced in the same manner as in Example 1.
Mass spectrometric value (ESI-MS) 374 (M−1)

Compound 79 4-Fluoro-N-[2-(4-methyl-benzylidene-hydrazinocarbonyl)-phenyl]-benzamide The title compound 79 was produced in the same manner as in Example 1.
Mass spectrometric value (ESI-MS) 374 (M−1)

Compound 80 4-Fluoro-N-[2-(3-hydroxy-benzylidene-hydrazinocarbonyl)-phenyl]-benzamide The title compound 80 was produced in the same manner as in Example 1.
Mass spectrometric value (ESI-MS) 376 (M−1)

Compound 81 3-Fluoro-N-[2-(3-fluoro-benzylidene-hydrazinocarbonyl)-phenyl]-benzamide The title compound 81 was produced in the same manner as in Example 1.
Mass spectrometric value (ESI-MS) 378 (M−1)

Compound 82 3-Fluoro-N-[2-(4-fluoro-benzylidene-hydrazinocarbonyl)-phenyl]-benzamide The title compound 82 was produced in the same manner as in Example 1.
Mass spectrometric value (ESI-MS) 757 (2M−1)

Compound 83 3-Fluoro-N-[2-(3-methyl-benzylidene-hydrazinocarbonyl)-phenyl]-benzamide The title compound 83 was produced in the same manner as in Example 1.
Mass spectrometric value (ESI-MS) 374 (M−1)

Compound 84 3-Fluoro-N-[2-(4-methyl-benzylidene-hydrazinocarbonyl)-phenyl]-benzamide The title compound 84 was produced in the same manner as in Example 1.
Mass spectrometric value (ESI-MS) 374 (M−1)

Compound 85 3-Fluoro-N-[2-(3-hydroxy-benzylidene-hydrazinocarbonyl)-phenyl]-benzamide The title compound 85 was produced in the same manner as in Example 1.
Mass spectrometric value (ESI-MS) 376 (M−1)

Compound 86 3-Fluoro-N-[2-(4-hydroxy-benzylidene-hydrazinocarbonyl)-phenyl]-benzamide The title compound 86 was produced in the same manner as in Example 1.
Mass spectrometric value (ESI-MS) 376 (M−1)

Compound 87 N-[4-Bromo-2-(4-chloro-3-trifluoromethyl-benzylidene-hydrazinocarbonyl)-phenyl]-3,4-dimethoxy-benzamide The title compound 87 was produced in the same manner as in Example 1.
Mass spectrometric value (ESI-MS) 582, 584 (M−1)

Compound 88 N-[4-Chloro-2-(4-chloro-3-trifluoromethyl-benzylidene-hydrazinocarbonyl)-phenyl]-3,4-dimethoxy-benzamide The title compound 88 was produced in the same manner as in Example 1.
$^1$H-NMR (CDCl$_3$, 400 MHz): δ 8.49 (1H, d, J=8.08 Hz), 8.39 (1H, s), 8.06 (1H, s), 7.96 (1H, s), 7.49-7.60 (4H, m), 7.41 (1H, d, J=9.04 Hz), 6.94 (1H, d, J=8.56 Hz), 3.98 (3H, s), 3.94 (3H, s)
Mass spectrometric value (ESI-MS) 538, 540 (M−1)

Compound 89 N-[2-(4-Chloro-3-trifluoromethyl-benzylidene-hydrazinocarbonyl)-phenyl]-3,5-dimethoxy-benzamide The title compound 89 was produced in the same manner as in Example 1.
Mass spectrometric value (ESI-MS) 504, 506 (M−1)

Compound 90 N-[2-(4-Chloro-3-trifluoromethyl-benzylidene-hydrazinocarbonyl)-phenyl]-4-methoxy-benzamide The title compound 90 was produced in the same manner as in Example 1.
Mass spectrometric value (ESI-MS) 474 (M−1)

Compound 91 N-[4-Bromo-2-(3,4-dimethyl-benzylidene-hydrazinocarbonyl)-phenyl]-3,4-dimethoxy-benzamide The title compound 91 was produced in the same manner as in Example 1.
$^1$H-NMR (CDCl$_3$, 400 MHz): δ 9.53 (1H, s), 8.61 (1H, d, J=9.04 Hz), 8.21 (1H, s), 7.69 (1H, s), 7.59-7.62 (4H, m), 7.46-7.50 (1H, m), 7.17 (1H, d, J=7.56 Hz), 6.91 (1H, d, J=8.28 Hz), 3.97 (3H, s), 3.93 (3H, s), 2.28 (3H, s), 2.28 (3H, s)
Mass spectrometric value (ESI-MS) 508 (M−1)

Compound 92 N-[4-Chloro-2-(3,4-dimethyl-benzylidene-hydrazinocarbonyl)-phenyl]-3,4-dimethoxy-benzamide The title compound 92 was produced in the same manner as in Example 1.
$^1$H-NMR (CDCl$_3$, 400 MHz): δ 9.60 (1H, s), 8.65 (1H, d, J=9.04 Hz), 8.21 (1H, s), 7.44-7.62 (6H, m), 7.17 (1H, d, J=7.80 Hz), 6.91 (1H, d, J=8.32 Hz), 3.97 (3H, s), 3.92 (3H, s), 2.28 (6H, s)
Mass spectrometric value (ESI-MS) 464 (M−1)

Compound 93 N-[2-(3,4-Dimethyl-benzylidene-hydrazinocarbonyl)-phenyl]-3,5-dimethoxy-benzamide The title compound 93 was produced in the same manner as in Example 1.
Mass spectrometric value (ESI-MS) 430 (M−1)

Compound 94 N-[2-(3,4-Dimethyl-benzylidene-hydrazinocarbonyl)-phenyl]-4-methoxy-benzamide The title compound 94 was produced in the same manner as in Example 1.
Mass spectrometric value (ESI-MS) 400 (M−1)

Compound 95 N-[2-(3,4-Dimethyl-benzylidene-hydrazinocarbonyl)-phenyl]-3-fluoro-benzamide The title compound 95 was produced in the same manner as in Example 1.
Mass spectrometric value (ESI-MS) 388 (M−1)

Compound 96 N-[2-(3,4-Dimethyl-benzylidene-hydrazinocarbonyl)-phenyl]-4-fluoro-benzamide The title compound 96 was produced in the same manner as in Example 1.
Mass spectrometric value (ESI-MS) 388 (M−1)

Compound 97 N-[4-Bromo-2-(3-bromo-4-methoxy-benzylidene-hydrazinocarbonyl)-phenyl]-3,4-dimethoxy-benzamide The title compound 97 was produced in the same manner as in Example 1.
Mass spectrometric value (ESI-MS) 590 (M−1)

Compound 98 N-[2-(3-Bromo-4-methoxy-benzylidene-hydrazinocarbonyl)-4-chloro-phenyl]-3,4-dimethoxy-benzamide The title compound 98 was produced in the same manner as in Example 1.
Mass spectrometric value (ESI-MS) 544 (M−1)

Compound 99 N-[2-(3-Bromo-4-methoxy-benzylidene-hydrazinocarbonyl)-phenyl]-3,5-dimethoxy-benzamide The title compound 99 was produced in the same manner as in Example 1.
Mass spectrometric value (ESI-MS) 510 (M−1)

Compound 100 N-[2-(3-Bromo-4-methoxy-benzylidene-hydrazinocarbonyl)-phenyl]-4-methoxy-benzamide The title compound 100 was produced in the same manner as in Example 1.
Mass spectrometric value (ESI-MS) 482 (M−1)

Compound 101 N-[2-(3-Bromo-4-methoxy-benzylidene-hydrazinocarbonyl)-phenyl]-3-fluoro-benzamide The title compound 101 was produced in the same manner as in Example 1.
Mass spectrometric value (ESI-MS) 468, 470 (M−1)

Compound 102 N-[2-(3-Bromo-4-methoxy-benzylidene-hydrazinocarbonyl)-phenyl]-4-fluoro-benzamide The title compound 102 was produced in the same manner as in Example 1.
Mass spectrometric value (ESI-MS) 468, 470 (M−1)

Compound 103 3,4-Dimethoxy-N-[2-(3-nitro-benzylidene-hydrazinocarbonyl)-phenyl]-benzamide The title compound 103 was produced in the same manner as in Example 1.
Mass spectrometric value (ESI-MS) 447 (M−1)

Compound 104 N-[2-(4-Dimethylamino-benzylidene-hydrazinocarbonyl)-phenyl]-3,4-dimethoxy-benzamide The title compound 104 was produced in the same manner as in Example 1.
Mass spectrometric value (ESI-MS) 445 (M−1)

Compound 105 N-[4-Bromo-2-(3-fluoro-benzylidene-hydrazinocarbonyl)-phenyl]-4-fluoro-benzamide The title compound 105 was produced in the same manner as in Example 1.
Mass spectrometric value (ESI-MS) 458 (M−1)

Compound 106 N-[4-Bromo-2-(4-fluoro-benzylidene-hydrazinocarbonyl)-phenyl]-4-fluoro-benzamide The title compound 106 was produced in the same manner as in Example 1.
Mass spectrometric value (ESI-MS) 456 (M−1)

Compound 107 N-[4-Bromo-2-(3-chloro-benzylidene-hydrazinocarbonyl)-phenyl]-4-fluoro-benzamide The title compound 107 was produced in the same manner as in Example 1.
Mass spectrometric value (ESI-MS) 472, 474 (M−1)

Compound 108 N-[4-Bromo-2-(4-chloro-benzylidene-hydrazinocarbonyl)-phenyl]-4-fluoro-benzamide The title compound 108 was produced in the same manner as in Example 1.
Mass spectrometric value (ESI-MS) 472, 474 (M−1)

Compound 109 N-[4-Bromo-2-(3-hydroxy-benzylidene-hydrazinocarbonyl)-phenyl]-4-fluoro-benzamide The title compound 109 was produced in the same manner as in Example 1.
Mass spectrometric value (ESI-MS) 456, 458 (M−1)

Compound 110 N-[4-Bromo-2-(pyridin-3-ylmethylene-hydrazinocarbonyl)-phenyl]-3,4-dimethoxy-benzamide The title compound 110 was produced in the same manner as in Example 1.
Mass spectrometric value (ESI-MS) 483 (M−1)

Compound 111 N-[4-Chloro-2-(pyridin-3-ylmethylene-hydrazinocarbonyl)-phenyl]-3,4-dimethoxy-benzamide The title compound 111 was produced in the same manner as in Example 1.
Mass spectrometric value (ESI-MS) 437 (M−1)

Compound 112 4-Methoxy-N-[2-(pyridin-3-ylmethylene-hydrazinocarbonyl)-phenyl]-benzamide The title compound 112 was produced in the same manner as in Example 1.
Mass spectrometric value (ESI-MS) 373 (M−1)

Compound 113 4-Fluoro-N-[2-(pyridin-3-ylmethylene-hydrazinocarbonyl)-phenyl]-benzamide The title compound 113 was produced in the same manner as in Example 1.
Mass spectrometric value (ESI-MS) 361 (M−1)

Compound 114 N-[4-Bromo-2-(3-fluoro-benzylidene-hydrazinocarbonyl)-phenyl]-3,5-dimethoxy-benzamide The title compound 114 was produced in the same manner as in Example 1.
Mass spectrometric value (ESI-MS) 498 (M−1)

Compound 115 N-[4-Bromo-2-(4-fluoro-benzylidene-hydrazinocarbonyl)-phenyl]-3,5-dimethoxy-benzamide The title compound 115 was produced in the same manner as in Example 1.
Mass spectrometric value (ESI-MS) 498, 500 (M−1)

Compound 116 N-[4-Bromo-2-(3-chloro-benzylidene-hydrazinocarbonyl)-phenyl]-3,5-dimethoxy-benzamide The title compound 116 was produced in the same manner as in Example 1.
Mass spectrometric value (ESI-MS) 516, 518 (M−1)

Compound 117 N-[4-Bromo-2-(4-chloro-benzylidene-hydrazinocarbonyl)-phenyl]-3,5-dimethoxy-benzamide The title compound 117 was produced in the same manner as in Example 1.
Mass spectrometric value (ESI-MS) 514, 516 (M−1)

Compound 118 N-[4-Bromo-2-(3-methyl-benzylidene-hydrazinocarbonyl)-phenyl]-3,5-dimethoxy-benzamide The title compound 118 was produced in the same manner as in Example 1.
Mass spectrometric value (ESI-MS) 496 (M−1)

Compound 119 N-[4-Bromo-2-(4-methyl-benzylidene-hydrazinocarbonyl)-phenyl]-3,5-dimethoxy-benzamide The title compound 119 was produced in the same manner as in Example 1.
Mass spectrometric value (ESI-MS) 494 (M−1)

Compound 120 N-[2-(3-Fluoro-benzylidene-)-hydrazinocarbonyl)-phenyl)-3-trifluoromethoxy-benzamide The title compound 120 was produced in the same manner as in Example 1.
Mass spectrometric value (ESI-MS) 444 (M−1)

Compound 121 N-[2-(4-Fluoro-benzylidene-)-hydrazinocarbonyl)-phenyl)-3-trifluoromethoxy-benzamide The title compound 121 was produced in the same manner as in Example 1.
Mass spectrometric value (ESI-MS) 444 (M−1)

Compound 122 N-[2-(3-Chloro-benzylidene-)-hydrazinocarbonyl)-phenyl)-3-trifluoromethoxy-benzamide The title compound 122 was produced in the same manner as in Example 1.
Mass spectrometric value (ESI-MS) 459, 461 (M−1)

Compound 123 N-[2-(4-Chloro-benzylidene-)-hydrazinocarbonyl)-phenyl)-3-trifluoromethoxy-benzamide The title compound 123 was produced in the same manner as in Example 1.
Mass spectrometric value (ESI-MS) 459, 461 (M−1)

Compound 124 N-[2-(4-Methyl-benzylidene-)-hydrazinocarbonyl)-phenyl)-3-trifluoromethoxy-benzamide The title compound 124 was produced in the same manner as in Example 1.
Mass spectrometric value (ESI-MS) 440 (M−1)

Compound 125 N-[4-(3-Dimethylamino-propoxy)-2-(4-fluoro-benzylidene-hydrazinocarbonyl)-phenyl]-3,4-dimethoxy-benzamide The title compound 125 was produced in the same manner as in Example 2, except that N-(2-chloroethyl)-N,N-dimethylamine hydrochloride was changed to 3-dimethylaminopropyl chloride hydrochloride.
Mass spectrometric value (ESI-MS) 521, 523 (M−1)

Compound 126 N-[4-Chloro-2-(3,4-dimethoxy-benzylidene-hydrazinocarbonyl)-phenyl]-3,4-dimethoxy-benzamide The title compound 126 was produced in the same manner as in Example 1.
Mass spectrometric value (ESI-MS) 496 (M−1)

Compound 127 N-[4-Bromo-2-(3,4-dimethoxy-benzylidene-hydrazinocarbonyl)-phenyl]-3,4-dimethoxy-benzamide The title compound 127 was produced in the same manner as in Example 1.
Mass spectrometric value (ESI-MS) 540 (M−1)

Compound 128 N-[4-Bromo-2-(3,4-dimethoxy-benzylidene-hydrazinocarbonyl)-phenyl]-3,5-dimethoxy-benzamide The title compound 128 was produced in the same manner as in Example 1.
Mass spectrometric value (ESI-MS) 542 (M−1)

Compound 129 N-[2-(3-Fluoro-benzylidene-hydrazinocarbonyl)-phenyl]-nicotinamide The title compound 129 was produced in the same manner as in Example 1.
Mass spectrometric value (ESI-MS) 361 (M−1)

Compound 130 N-[2-(4-Fluoro-benzylidene-hydrazinocarbonyl)-phenyl]-nicotinamide The title compound 130 was produced in the same manner as in Example 1.
$^1$H-NMR (CDCl$_3$, 400 MHz): δ 9.69 (1H, s), 9.28 (1H, s), 8.77 (1H, dd, J=1.44 Hz, J=4.88 Hz), 8.66 (1H, d, J=7.80 Hz), 8.25-8.33 (2H, m), 7.81 (2H, s), 7.50-7.60 (2H, m), 7.43 (1H, dd, J=4.88 Hz, J=8.04 Hz), 7.05-7.15 (3H, m)
Mass spectrometric value (ESI-MS) 361 (M−1)

Compound 131 N-[2-(3-Methyl-benzylidene-hydrazinocarbonyl)-phenyl]-nicotinamide The title compound 131 was produced in the same manner as in Example 1.
Mass spectrometric value (ESI-MS) 357 (M−1)

Compound 132 N-[2-(4-Methyl-benzylidene-hydrazinocarbonyl)-phenyl]-nicotinamide The title compound 132 was produced in the same manner as in Example 1.
Mass spectrometric value (ESI-MS) 357 (M−1)

Compound 133 N-[2-(3,4-Dimethyl-benzylidene-hydrazinocarbonyl)-phenyl]-nicotinamide The title compound 133 was produced in the same manner as in Example 1.
Mass spectrometric value (ESI-MS) 371 (M−1)

Compound 134 N-[2-(3-Fluoro-benzylidene-hydrazinocarbonyl)-phenyl]-isonicotinamide The title compound 134 was produced in the same manner as in Example 1.
Mass spectrometric value (ESI-MS) 361 (M−1)

Compound 135 N-[2-(4-Fluoro-benzylidene-hydrazinocarbonyl)-phenyl]-isonicotinamide The title compound 135 was produced in the same manner as in Example 1.
Mass spectrometric value (ESI-MS) 361 (M−1)

Compound 136 N-[2-(3-Methyl-benzylidene-hydrazinocarbonyl)-phenyl]-isonicotinamide The title compound 136 was produced in the same manner as in Example 1.
Mass spectrometric value (ESI-MS) 357 (M−1)

Compound 137 N-[2-(4-Methyl-benzylidene-hydrazinocarbonyl)-phenyl]-isonicotinamide The title compound 137 was produced in the same manner as in Example 1.
Mass spectrometric value (ESI-MS) 357 (M−1)

Compound 138 N-[2-(3,4-Dimethyl-benzylidene-hydrazinocarbonyl)-phenyl]-isonicotinamide The title compound 138 was produced in the same manner as in Example 1.
Mass spectrometric value (ESI-MS) 371 (M−1)

Example 2

Compound 139 N-[4-(2-Dimethylamino-ethoxy-)-2-(4-fluoro-benzylidene-hydrazinocarbonyl)-phenyl]-3,4-dimethoxy-benzamide N-[2-(4-Fluoro-benzylidene-hydrazinocarbonyl)-4-hydroxy-phenyl]-3,4-dimethoxy-benzamide (50 mg) synthesized in the same manner as in Example 1 was dissolved in anhydrous DMF (1.5 ml). NaH (60% in oil, 20 mg) was added to the solution at room temperature, and the mixture was stirred at that temperature for 5 min. Subsequently, N-(2-chloroethyl)-N,N-dimethylamine hydrochloride (47 mg) was added to the reaction solution at room temperature, and the mixture was stirred at that temperature for 12 hr. After the completion of the reaction, distilled water was added dropwise thereto under ice cooling and the mixture was subjected to separatory extraction with ethyl acetate. The organic layer was washed with saturated brine and was dried over sodium sulfate, and the organic layer was concentrated under the reduced pressure. The residue was purified by preparative TLC to give the title compound 139 (32 mg, yield 57.1%).
Mass spectrometric value (ESI-MS) 507 (M−1)

Compound 140 N-[4-(2-Diethylamino-ethoxy)-2-(4-fluoro-benzylidene-hydrazinocarbonyl)-phenyl]-3,4-dimethoxy-benzamide The title compound 140 was produced in the same manner as in Example 2, except that N-(2-chloroethyl)-N,N-dimethylamine hydrochloride was changed to 2-diethylaminoethyl chloride hydrochloride.
Mass spectrometric value (ESI-MS) 535 (M−1)

Compound 141 N-[2-(3-Fluoro-benzylidene-hydrazinocarbonyl)-4-methoxy-phenyl]-3,4-dimethoxy-benzamide The title compound 141 was produced in the same manner as in Example 1.
Mass spectrometric value (ESI-MS) 450 (M−1)

Compound 142 N-[2-(4-Fluoro-benzylidene-hydrazinocarbonyl)-4-methoxy-phenyl]-3,4-dimethoxy-benzamide The title compound 142 was produced in the same manner as in Example 1.
Mass spectrometric value (ESI-MS) 450 (M−1)

Compound 143 3,4-Dimethoxy-N-[4-methoxy-2-(3-methyl-benzylidene-hydrazinocarbonyl)-phenyl]-benzamide The title compound 143 was produced in the same manner as in Example 1.
Mass spectrometric value (ESI-MS) 446 (M−1)

Compound 144 3,4-Dimethoxy-N-[4-methoxy-2-(4-methyl-benzylidene-hydrazinocarbonyl)-phenyl]-benzamide The title compound 144 was produced in the same manner as in Example 1.
Mass spectrometric value (ESI-MS) 446 (M−1)

Compound 145 N-[2-(3,4-Dimethyl-benzylidene-hydrazinocarbonyl)-4-methoxy-phenyl]-3,4-dimethoxy-benzamide The title compound 145 was produced in the same manner as in Example 1.
Mass spectrometric value (ESI-MS) 460 (M−1)

Compound 146 N-[2-(3-Fluoro-benzylidene-hydrazinocarbonyl)-4-methyl-phenyl]-3,4-dimethoxy-benzamide The title compound 146 was produced in the same manner as in Example 1.
Mass spectrometric value (ESI-MS) 434 (M−1)

Compound 147 N-[2-(4-Fluoro-benzylidene-hydrazinocarbonyl)-4-methyl-phenyl]-3,4-dimethoxy-benzamide The title compound 147 was produced in the same manner as in Example 1.
Mass spectrometric value (ESI-MS) 434 (M−1)

Compound 148 3,4-Dimethoxy-N-[4-methyl-2-(3-methyl-benzylidene-hydrazinocarbonyl)-phenyl]-benzamide The title compound 148 was produced in the same manner as in Example 1.
Mass spectrometric value (ESI-MS) 430 (M−1)

Compound 149 3,4-Dimethoxy-N-[4-methyl-2-(4-methyl-benzylidene-hydrazinocarbonyl)-phenyl]-benzamide The title compound 149 was produced in the same manner as in Example 1.
Mass spectrometric value (ESI-MS) 430 (M−1)

Compound 150 N-[2-(3,4-Dimethyl-benzylidene-hydrazinocarbonyl)-4-methyl-phenyl]-3,4-dimethoxy-benzamide The title compound 150 was produced in the same manner as in Example 1.
Mass spectrometric value (ESI-MS) 444 (M−1)

Compound 151 Furan-2-carboxylic acid [4-bromo-2-(3-fluoro-benzylidene-hydrazinocarbonyl)-phenyl]-amide The title compound 151 was produced in the same manner as in Example 1.
Mass spectrometric value (ESI-MS) 428 (M−1)

Compound 152 Furan-2-carboxylic acid [4-bromo-2-(4-fluoro-benzylidene-hydrazinocarbonyl)-phenyl]-amide The title compound 152 was produced in the same manner as in Example 1.
Mass spectrometric value (ESI-MS) 428 (M−1)

Compound 153 Furan-2-carboxylic acid [4-bromo-2-(3-methyl-benzylidene-hydrazinocarbonyl)-phenyl]-amide The title compound 153 was produced in the same manner as in Example 1.
Mass spectrometric value (ESI-MS) 426 (M−1)

Compound 154 Furan-2-carboxylic acid [4-bromo-2-(4-methyl-benzylidene-hydrazinocarbonyl)-phenyl]-amide The title compound 154 was produced in the same manner as in Example 1.
Mass spectrometric value (ESI-MS) 424 (M−1)

Compound 155 Furan-2-carboxylic acid [4-bromo-2-(3,4-dimethyl-benzylidene-hydrazinocarbonyl)-phenyl]-amide The title compound 155 was produced in the same manner as in Example 1.
Mass spectrometric value (ESI-MS) 438 (M−1)

Compound 156 Furan-2-carboxylic acid [4-bromo-2-(4-chloro-3-trifluoromethyl-benzylidene-hydrazinocarbonyl)-phenyl]-amide The title compound 156 was produced in the same manner as in Example 1.
Mass spectrometric value (ESI-MS) 513, 514 (M−1)

Compound 157 Thiophene-2-carboxylic acid [4-bromo-2-(3-fluoro-benzylidene-hydrazinocarbonyl)-phenyl]-amide The title compound 157 was produced in the same manner as in Example 1.
Mass spectrometric value (ESI-MS) 446 (M−1)

Compound 158 Thiophene-2-carboxylic acid [4-bromo-2-(4-fluoro-benzylidene-hydrazinocarbonyl)-phenyl]-amide The title compound 158 was produced in the same manner as in Example 1.
Mass spectrometric value (ESI-MS) 446 (M−1)

Compound 159 Thiophene-2-carboxylic acid [4-bromo-2-(3-methyl-benzylidene-hydrazinocarbonyl)-phenyl]-amide The title compound 159 was produced in the same manner as in Example 1.
Mass spectrometric value (ESI-MS) 440 (M−1)

Compound 160 Thiophene-2-carboxylic acid [4-bromo-2-(4-methyl-benzylidene-hydrazinocarbonyl)-phenyl]-amide The title compound 160 was produced in the same manner as in Example 1.
Mass spectrometric value (ESI-MS) 440 (M−1)

Compound 161 Thiophene-2-carboxylic acid [4-bromo-2-(3,4-dimethyl-benzylidene-hydrazinocarbonyl)-phenyl]-amide The title compound 161 was produced in the same manner as in Example 1.
Mass spectrometric value (ESI-MS) 454, 456 (M−1)

Compound 162 Thiophene-2-carboxylic acid [4-bromo-2-(4-chloro-3-trifluoromethyl-benzylidene-hydrazinocarbonyl)-phenyl]-amide The title compound 162 was produced in the same manner as in Example 1.
Mass spectrometric value (ESI-MS) 530 (M−1)

Example 3

Compound 163 N-[2-(3,4-Dimethyl-benzylidene-hydrazinocarbonyl)-phenyl]-isonicotinamide hydrochloride A 10% hydrochloric acid-methanol solution (1.0 ml) was added to compound 138 (50 mg) synthesized in the same manner as in Example 1 at room temperature. Further, diethyl ether (5.0 ml) was added thereto, and the mixture was stirred for 30 sec. The reaction solution as such was filtered through Kiriyama Rohto (21 mmφ), and the crystals were washed with diethyl ether to give the title compound 163 (47 mg, yield 85.6%).
$^{1}$H-NMR (MeOH-d$_{4}$, 400 MHz): δ 8.97 (2H, d, J=6.84 Hz), 8.49 (1H, d, J=8.08 Hz), 8.41 (2H, d, J=6.56 Hz), 8.23 (1H, s), 7.84 (1H, d, J=6.56 Hz), 7.56-7.61 (2H, m), 7.44 (1H, d, J=7.80 Hz), 7.28 (1H, dd, J=7.32 Hz, J=7.32 Hz), 7.12 (1H, d, J=7.80 Hz), 2.23 (3H, s), 2.22 (3H, s)
Mass spectrometric value (ESI-MS) 371 (M−1)

Compound 164 N-[2-(4-Methyl-benzylidene-hydrazinocarbonyl)-phenyl]-nicotinamide hydrochloride The title compound 164 was produced in the same manner as in Example 3.
$^{1}$H-NMR (MeOH-d$_{4}$, 400 MHz): δ 9.22 (1H, s), 8.87 (1H, d, J=5.4 Hz), 8.83 (1H, d, J=8.04 Hz), 8.43 (1H, d, J=8.32 Hz), 8.25 (1H, s), 7.97-8.04 (1H, m), 7.81 (1H, dd, J=1.24 Hz, J=7.84 Hz), 7.64 (2H, d, J=8.04 Hz), 7.54-7.60 (1H, m), 7.23-7.29 (1H, m), 7.18 (2H, d, J=7.80 Hz), 2.29 (3H, s)
Mass spectrometric value (ESI-MS) 357 (M−1)

Compound 165 N-[2-(3,4-Dimethyl-benzylidene-hydrazinocarbonyl)-phenyl]-nicotinamide hydrochloride The title compound 165 was produced in the same manner as in Example 3.
$^{1}$H-NMR (CDCl$_{3}$, 400 MHz): δ 9.92 (1H, s), 9.29 (1H, s), 8.75-8.78 (2H, m), 8.30-8.40 (1H, m), 8.15 (1H, s), 7.55-7.65 (5H, m), 7.42-7.49 (2H, m), 7.15-7.25 (1H, m), 2.32 (3H, s), 2.29 (3H, s)
Mass spectrometric value (ESI-MS) 371 (M−1)

Compound 166 N-[4-Bromo-2-(3-fluoro-benzylidene-hydrazinocarbonyl)-phenyl]-isonicotinamide The title compound 166 was produced in the same manner as in Example 1.
Mass spectrometric value (ESI-MS) 439 (M−1)

Compound 167 N-[4-Bromo-2-(4-fluoro-benzylidene-hydrazinocarbonyl)-phenyl]-isonicotinamide The title compound 167 was produced in the same manner as in Example 1.
Mass spectrometric value (ESI-MS) 439 (M−1)

Compound 168 N-[4-Bromo-2-(3-methyl-benzylidene-hydrazinocarbonyl)-phenyl]-isonicotinamide The title compound 168 was produced in the same manner as in Example 1.
Mass spectrometric value (ESI-MS) 437 (M−1)

Compound 169 N-[4-Bromo-2-(4-methyl-benzylidene-hydrazinocarbonyl)-phenyl]-isonicotinamide The title compound 169 was produced in the same manner as in Example 1.
Mass spectrometric value (ESI-MS) 435, 437 (M−1)

Compound 170 N-[4-Bromo-2-(3,4-dimethyl-benzylidene-hydrazinocarbonyl)-phenyl]-isonicotinamide The title compound 170 was produced in the same manner as in Example 1.
Mass spectrometric value (ESI-MS) 451, 452 (M−1)

Compound 171 N-[4-Bromo-2-(4-chloro-3-trifluoromethyl-benzylidene-hydrazinocarbonyl)-phenyl]-isonicotinamide The title compound 171 was produced in the same manner as in Example 1.
Mass spectrometric value (ESI-MS) 525, 527 (M−1)

Compound 172 N-[4-Bromo-2-(3-fluoro-benzylidene-hydrazinocarbonyl)-phenyl]-nicotinamide The title compound 172 was produced in the same manner as in Example 1.
Mass spectrometric value (ESI-MS) 441, 442 (M−1)

Compound 173 N-[4-Bromo-2-(4-fluoro-benzylidene-hydrazinocarbonyl)-phenyl]-nicotinamide The title compound 173 was produced in the same manner as in Example 1.
Mass spectrometric value (ESI-MS) 439 (M−1)

Compound 174 N-[4-Bromo-2-(3-methyl-benzylidene-hydrazinocarbonyl)-phenyl]-nicotinamide The title compound 174 was produced in the same manner as in Example 1.
Mass spectrometric value (ESI-MS) 435 (M−1)

Compound 175 N-[4-Bromo-2-(4-methyl-benzylidene-hydrazinocarbonyl)-phenyl]-nicotinamide The title compound 175 was produced in the same manner as in Example 1.
Mass spectrometric value (ESI-MS) 437, 438 (M−1)

Compound 176 N-[4-Bromo-2-(3,4-dimethyl-benzylidene-hydrazinocarbonyl)-phenyl]-nicotinamide The title compound 176 was produced in the same manner as in Example 1.
Mass spectrometric value (ESI-MS) 451, 452 (M−1)

Compound 177 N-[4-Bromo-2-(4-chloro-3-trifluoromethyl-benzylidene-hydrazinocarbonyl)-phenyl]-nicotinamide The title compound 177 was produced in the same manner as in Example 1.
Mass spectrometric value (ESI-MS) 524, 525 (M−1)

Compound 178 N-[4-Bromo-2-(3-fluoro-benzylidene-hydrazinocarbonyl)-phenyl]-4-ethyl-benzamide The title compound 178 was produced in the same manner as in Example 1.
Mass spectrometric value (ESI-MS) 466, 468 (M−1)

Compound 179 N-[4-Bromo-2-(4-fluoro-benzylidene-hydrazinocarbonyl)-phenyl]-4-ethyl-benzamide The title compound 179 was produced in the same manner as in Example 1.
Mass spectrometric value (ESI-MS) 466 (M−1)

Compound 180 N-[4-Bromo-2-(3-methyl-benzylidene-hydrazinocarbonyl)-phenyl]-4-ethyl-benzamide The title compound 180 was produced in the same manner as in Example 1.
Mass spectrometric value (ESI-MS) 462 (M−1)

Compound 181 N-[4-Bromo-2-(4-methyl-benzylidene-hydrazinocarbonyl)-phenyl]-4-ethyl-benzamide The title compound 181 was produced in the same manner as in Example 1.
Mass spectrometric value (ESI-MS) 462, 464 (M−1)

Compound 182 N-[4-Bromo-2-(3,4-dimethyl-benzylidene-hydrazinocarbonyl)-phenyl]-4-ethyl-benzamide The title compound 182 was produced in the same manner as in Example 1.
Mass spectrometric value (ESI-MS) 476, 478 (M−1)

Compound 183 N-[4-Bromo-2-(4-chloro-3-trifluoromethyl-benzylidene-hydrazinocarbonyl)-phenyl]-4-ethyl-benzamide The title compound 183 was produced in the same manner as in Example 1.
Mass spectrometric value (ESI-MS) 550 (M−1)

Compound 184 N-[4-Chloro-2-(3-fluoro-benzylidene-hydrazinocarbonyl)-phenyl]-nicotinamide The title compound 184 was produced in the same manner as in Example 1.
Mass spectrometric value (ESI-MS) 395, 397 (M−1)

Compound 185 N-[4-Chloro-2-(4-fluoro-benzylidene-hydrazinocarbonyl)-phenyl]-nicotinamide The title compound 185 was produced in the same manner as in Example 1.
Mass spectrometric value (ESI-MS) 395 (M−1)

Compound 186 N-[4-Chloro-2-(3-methyl-benzylidene-hydrazinocarbonyl)-phenyl]-nicotinamide The title compound 186 was produced in the same manner as in Example 1.
Mass spectrometric value (ESI-MS) 391 (M−1)

Compound 187 N-[4-Chloro-2-(4-methyl-benzylidene-hydrazinocarbonyl)-phenyl]-nicotinamide The title compound 187 was produced in the same manner as in Example 1.
Mass spectrometric value (ESI-MS) 391 (M−1)

Compound 188 N-[4-Chloro-2-(3,4-dimethyl-benzylidene-hydrazinocarbonyl)-phenyl]-nicotinamide The title compound 188 was produced in the same manner as in Example 1.
Mass spectrometric value (ESI-MS) 405, 407 (M−1)

Compound 189 N-[4-Chloro-2-(4-chloro-3-trifluoromethyl-benzylidene-hydrazinocarbonyl)-phenyl]-nicotinamide The title compound 189 was produced in the same manner as in Example 1.
Mass spectrometric value (ESI-MS) 479, 480 (M−1)

Compound 190 N-[4-Chloro-2-(4-fluoro-benzylidene-hydrazinocarbonyl)-phenyl]-isonicotinamide The title compound 190 was produced in the same manner as in Example 1.
Mass spectrometric value (ESI-MS) 395, 397 (M−1)

Compound 191 N-[4-Chloro-2-(3-methyl-benzylidene-hydrazinocarbonyl)-phenyl]-isonicotinamide The title compound 191 was produced in the same manner as in Example 1.
Mass spectrometric value (ESI-MS) 391 (M−1)

Compound 192 N-[4-Chloro-2-(4-methyl-benzylidene-hydrazinocarbonyl)-phenyl]-isonicotinamide The title compound 192 was produced in the same manner as in Example 1.
Mass spectrometric value (ESI-MS) 391 (M−1)

Compound 193 N-[4-Chloro-2-(3,4-dimethyl-benzylidene-hydrazinocarbonyl)-phenyl]-isonicotinamide The title compound 193 was produced in the same manner as in Example 1.
Mass spectrometric value (ESI-MS) 405 (M−1)

Compound 194 N-[4-Chloro-2-(4-chloro-3-trifluoromethyl-benzylidene-hydrazinocarbonyl)-phenyl]-isonicotinamide The title compound 194 was produced in the same manner as in Example 1.
Mass spectrometric value (ESI-MS) 479 (M−1)

Example 4

Compound 195 N-[4-Bromo-2-(3-fluoro-benzylidene-hydrazinocarbonyl)-phenyl]-3-(pyridin-4-ylsulfanylmethyl)-benzamide Methyl 2-amino-5-bromobenzoate (compound A) (2.0 g) was dissolved in anhydrous methylene chloride (40.0 ml). Subsequently, pyridine (1.0 ml) and 3-(chloromethyl)benzoyl chloride (compound B) (2.0 g) were added to the solution at room temperature, and the mixture was stirred at that temperature for 3 hr. After the completion of the reaction, distilled water was added thereto, and the mixture was subjected to separatory extraction with chloroform. The organic layer was washed with a saturated aqueous sodium chloride solution, was dried over sodium sulfate and was then concentrated to give methyl 5-bromo-2-[3-(chloromethyl)benzoyl]aminobenzoate as a useful intermediate (3.32 g, yield 100%).

Subsequently, methyl 5-bromo-2-[3-(chloromethyl)benzoyl]aminobenzoate (1.5 g) was dissolved in anhydrous methylene chloride. Triethylamine (2.0 ml) and 4-mercaptopyridine (compound B') (880 mg) were added to the solution at room temperature, and the mixture was stirred at that temperature for 12 hr. After the completion of the reaction, distilled water was added thereto at room temperature, and the mixture was subjected to separatory extraction with chloroform. The organic layer was washed with a saturated aqueous sodium chloride solution, was dried over sodium sulfate, and was then concentrated. Diethyl ether was added to the residue for crystallization. The crystals were filtered through Kiriyama Rohto (21 mmφ) and were washed with diethyl ether to give methyl 5-bromo-2-(3-[(4-pyridylsulfanyl)methyl]benzoylamino)benzoate (1.20 g, yield 67%) as a useful intermediate.

Methyl 5-bromo-2-(3-[(4-pyridylsulfanyl)methyl]benzoylamino)-benzoate (1.20 g) obtained by the above reaction was dissolved in ethanol (25.0 ml). Hydrazine monohydrate (2.0 ml) was added to the solution at room temperature, and the mixture was heated under reflux with stirring for one hr. After the completion of the reaction, the reaction solution was allowed to cool at room temperature, was cooled under ice cooling to precipitate crystals. The precipitated crystals were filtered through Kiriyama Rohto (21 mmφ) and were washed with diethyl ether to give N-(4-bromo-2-hydrazinocarbonyl-phenyl)-3-(pyridin-4-ylsulfanylmethyl)-benzamide (753 mg, yield 65.4%) as a hydrazine compound.

N-(4-Bromo-2-hydrazinocarbonyl-phenyl)-3-(pyridin-4-ylsulfanylmethyl)-benzamide (50.0 mg) was dissolved in anhydrous toluene (1.0 ml). Subsequently, a catalytic amount of acetic acid and 3-fluorobenzaldehyde (compound C) (50.0 μl) were added to the solution at room temperature, and the mixture was heated under reflux with stirring for one hr. After the completion of the reaction, the reaction solution was allowed to cool at room temperature and was ice-cooled to precipitate crystals. The precipitated crystals were filtered through Kiriyama Rohto (21 mmφ), were washed with toluene and hexane, and were dried through a vacuum pump to give the title compound 195 (27.0 mg, yield 43.6%).
Mass spectrometric value (ESI-MS) 561, 563 (M−1)

Compound 196 N-[4-Bromo-2-(4-fluoro-benzylidene-hydrazinocarbonyl)-phenyl]-3-(pyridin-4-ylsulfanylmethyl)-benzamide The title compound 196 was produced in the same manner as in Example 4.
Mass spectrometric value (ESI-MS) 563 (M−1)

Compound 197 N-[4-Bromo-2-(3-methyl-benzylidene-hydrazinocarbonyl)-phenyl]-3-(pyridin-4-ylsulfanylmethyl)-benzamide The title compound 197 was produced in the same manner as in Example 4.
Mass spectrometric value (ESI-MS) 559 (M−1)

Compound 198 N-[4-Bromo-2-(4-methyl-benzylidene-hydrazinocarbonyl)-phenyl]-3-(pyridin-4-ylsulfanylmethyl)-benzamide The title compound 198 was produced in the same manner as in Example 4.
Mass spectrometric value (ESI-MS) 559 (M−1)

Compound 199 N-[4-Bromo-2-(3,4-dimethyl-benzylidene-hydrazinocarbonyl)-phenyl]-3-(pyridin-4-ylsulfanylmethyl)-benzamide The title compound 199 was produced in the same manner as in Example 4.
Mass spectrometric value (ESI-MS) 571 (M−1)

Compound 200 N-[4-Bromo-2-(4-chloro-3-trifluoromethyl-benzylidene-hydrazinocarbonyl)-phenyl]-3-(pyridin-4-ylsulfanylmethyl)-benzamide The title compound 200 was produced in the same manner as in Example 4.
Mass spectrometric value (ESI-MS) 647 (M−1)

Compound 201 N-[4-Bromo-2-(1-methyl-1H-pyrrol-2-ylmethylene-hydrazinocarbonyl)-phenyl]-3,4-dimethoxy-benzamide The title compound 201 was produced in the same manner as in Example 1.
Mass spectrometric value (ESI-MS) 484 (M−1)

Compound 202 N-[4-Bromo-2-(4,5-dimethyl-furan-2-ylmethylene-hydrazinocarbonyl)-phenyl]-3,4-dimethoxy-benzamide The title compound 202 was produced in the same manner as in Example 1.
Mass spectrometric value (ESI-MS) 499 (M−1)

Compound 203 N-[2-(4-Methyl-benzylidene-hydrazinocarbonyl)-phenyl]-isonicotinamide hydrochloride The title compound 203 was produced in the same manner as in Example 3.
$^1$H-NMR (CD$_3$OD, 400 MHz): δ 8.92-8.98 (2H, m), 8.49 (1H, d, J=8.6 Hz), 8.34-8.40 (2H, m), 8.26 (1H, s), 8.81-8.87 (1H, m), 7.64 (2H, d, J=8.0 Hz), 7.55-7.61 (1H, m), 7.25-7.31 (1H, m), 7.15-7.20 (2H, m), 2.30 (3H, s)
Mass spectrometric value (ESI-MS) 357 (M−1)

Compound 204 N-[2-(3-Fluoro-benzylidene-hydrazinocarbonyl)-4-iodo-phenyl]-3,4-dimethoxy-benzamide The title compound 204 was produced in the same manner as in Example 1.
Mass spectrometric value (ESI-MS) 546 (M−1)

Compound 205 N-[2-(4-Fluoro-benzylidene-hydrazinocarbonyl)-4-iodo-phenyl]-3,4-dimethoxy-benzamide The title compound 205 was produced in the same manner as in Example 1.
Mass spectrometric value (ESI-MS) 546 (M−1)

Compound 206 N-[4-Iodo-2-(3-methyl-benzylidene-hydrazinocarbonyl)-phenyl]-3,4-dimethoxy-benzamide The title compound 206 was produced in the same manner as in Example 1.
Mass spectrometric value (ESI-MS) 542 (M−1)

Compound 207 N-[4-Iodo-2-(4-methyl-benzylidene-hydrazinocarbonyl)-phenyl]-3,4-dimethoxy-benzamide The title compound 207 was produced in the same manner as in Example 1.
Mass spectrometric value (ESI-MS) 542 (M−1)

Compound 208 N-[2-(3,4-Dimethyl-benzylidene-hydrazinocarbonyl)-4-iodo-phenyl]-3,4-dimethoxy-benzamide The title compound 208 was produced in the same manner as in Example 1.
Mass spectrometric value (ESI-MS) 556 (M−1)

Compound 209 N-[2-(4-Chloro-3-trifluoromethyl-benzylidene-hydrazinocarbonyl)-4-iodo-phenyl]-3,4-dimethoxy-benzamide The title compound 209 was produced in the same manner as in Example 1.
Mass spectrometric value (ESI-MS) 630 (M−1)

Compound 210 N-[2-(1-Methyl-1H-pyrrol-2-ylmethylene-hydrazinocarbonyl)-phenyl]-isonicotinamide The title compound 210 was produced in the same manner as in Example 1.
Mass spectrometric value (ESI-MS) 346 (M−1)

Compound 211 N-[4-Bromo-2-(1-methyl-1H-pyrrol-2-ylmethylene-hydrazinocarbonyl)-phenyl]-nicotinamide The title compound 211 was produced in the same manner as in Example 1.
Mass spectrometric value (ESI-MS) 424 (M−1)

Compound 212 N-[4-Chloro-2-(1-methyl-1H-pyrrol-2-ylmethylene-hydrazinocarbonyl)-phenyl]-nicotinamide The title compound 212 was produced in the same manner as in Example 1.
Mass spectrometric value (ESI-MS) 380 (M−1)

Compound 213 N-{2-[1-(3-Fluoro-phenyl)-ethylidene-hydrazinocarbonyl]-phenyl}-3,4-dimethoxy-benzamide The title compound 213 was produced in the same manner as in Example 1.
Mass spectrometric value (ESI-MS) 434 (M−1)

Compound 214 N-{4-Bromo-2-[1-(3-fluoro-phenyl)-ethylidene-hydrazinocarbonyl]-phenyl}-3,4-dimethoxy-benzamide The title compound 214 was produced in the same manner as in Example 1.
Mass spectrometric value (ESI-MS) 512, 514 (M−1)

Compound 215 N-[4-Bromo-2-(1-m-toluyl-ethylidene-hydrazinocarbonyl)-phenyl]-nicotinamide The title compound 215 was produced in the same manner as in Example 1.
Mass spectrometric value (ESI-MS) 449, 451 (M−1)

Compound 216 N-[4-Bromo-2-(1-p-toluyl-ethylene-hydrazinocarbonyl)-phenyl]-nicotinamide The title compound 216 was produced in the same manner as in Example 1.
Mass spectrometric value (ESI-MS) 449 (M−1)

Compound 217 N-[4-Chloro-2-(1-p-toluyl-ethylene-hydrazinocarbonyl)-phenyl]-nicotinamide The title compound 217 was produced in the same manner as in Example 1.
Mass spectrometric value (ESI-MS) 405 (M−1)

Compound 218 N-[2-(4,5-Dimethyl-furan-2-ylmethylene-hydrazinocarbonyl)-phenyl]-nicotinamide The title compound 218 was produced in the same manner as in Example 1.
Mass spectrometric value (ESI-MS) 361 (M−1)

Compound 219 N-[2-(4,5-Dimethyl-furan-2-ylmethylene-hydrazinocarbonyl)-phenyl]-isonicotinamide The title compound 219 was produced in the same manner as in Example 1.
Mass spectrometric value (ESI-MS) 361 (M−1)

Compound 220 N-[4-Bromo-2-(4,5-dimethyl-furan-2-ylmethylene-hydrazinocarbonyl)-phenyl]-nicotinamide The title compound 220 was produced in the same manner as in Example 1.
Mass spectrometric value (ESI-MS) 439 (M−1)

Compound 221 N-[4-Bromo-2-(4,5-dimethyl-furan-2-ylmethylene-hydrazinocarbonyl)-phenyl]-isonicotinamide The title compound 221 was produced in the same manner as in Example 1.
Mass spectrometric value (ESI-MS) 439, 441 (M−1)

Compound 222 N-[4-Chloro-2-(4,5-dimethyl-furan-2-ylmethylene-hydrazinocarbonyl)-phenyl]-nicotinamide The title compound 222 was produced in the same manner as in Example 1.
Mass spectrometric value (ESI-MS) 395 (M−1)

Compound 223 N-[4-Chloro-2-(4,5-dimethyl-furan-2-ylmethylene-hydrazinocarbonyl)-phenyl]-isonicotinamide The title compound 223 was produced in the same manner as in Example 1.
Mass spectrometric value (ESI-MS) 395 (M−1)

Compound 224 N-[2-(Benzylidene-hydrazinocarbonyl)-phenyl]-benzamide

The title compound 224 was produced in the same manner as in Example 1.
Mass spectrometric value (ESI-MS) 342 (M−1)

Compound 225 N-[2-(2-Fluoro-benzylidene-hydrazinocarbonyl)-phenyl]-benzamide

The title compound 225 was produced in the same manner as in Example 1.
Mass spectrometric value (ESI-MS) 360 (M−1)

Compound 226 N-[2-(3-Fluoro-benzylidene-hydrazinocarbonyl)-phenyl]-benzamide

The title compound 226 was produced in the same manner as in Example 1.
Mass spectrometric value (ESI-MS) 360 (M−1)

Compound 227 N-[2-(Benzylidene-hydrazinocarbonyl)-4,5-dimethoxy-phenyl]-3,4-dimethoxy-benzamide The title compound 227 was produced in the same manner as in Example 1.
Mass spectrometric value (ESI-MS) 462 (M−1)

Compound 228 N-[2-(2-Bromo-benzylidene-hydrazinocarbonyl)-phenyl]-benzamide

The title compound 228 was produced in the same manner as in Example 1.
Mass spectrometric value (ESI-MS) 421 (M−1)

Compound 229 N-[2-(2-Methyl-benzylidene-hydrazinocarbonyl)-phenyl]-benzamide

The title compound 229 was produced in the same manner as in Example 1.
Mass spectrometric value (ESI-MS) 356 (M−1)

Compound 230 N-[4,5-Dimethoxy-2-(2-methyl-benzylidene-hydrazinocarbonyl)-phenyl]-3,4-dimethoxy-benzamide The title compound 230 was produced in the same manner as in Example 1.
Mass spectrometric value (ESI-MS) 476 (M−1)

Compound 231 N-[2-(2-Chloro-benzylidene-hydrazinocarbonyl)-phenyl]-3,4-dimethoxy-benzamide The title compound 231 was produced in the same manner as in Example 1.
Mass spectrometric value (ESI-MS) 436 (M−1)

Compound 232 3,4-Dimethoxy-N-[2-(6-methoxy-naphthalen-2-ylmethylene-hydrazinocarbonyl)-phenyl]-benzamide The title compound 232 was produced in the same manner as in Example 1.
Mass spectrometric value (ESI-MS) 482 (M−1)

Compound 233 N-[2-(Biphenyl-4-ylmethylene-hydrazinocarbonyl)-phenyl]-3,4-dimethoxy-benzamide The title compound 233 was produced in the same manner as in Example 1.
Mass spectrometric value (ESI-MS) 478 (M−1)

Compound 234 N-[2-(4-Bromo-benzylidene-hydrazinocarbonyl)-phenyl]-3,4-dimethoxy-benzamide The title compound 234 was produced in the same manner as in Example 1.
Mass spectrometric value (ESI-MS) 480 (M−1)

Compound 235 N-[2-(3-Phenyl-allylidene-hydrazinocarbonyl)-phenyl]-benzamide

The title compound 235 was produced in the same manner as in Example 1.
Mass spectrometric value (ESI-MS) 368 (M−1)

Compound 236 2-Fluoro-N-[2-(2-fluoro-benzylidene-hydrazinocarbonyl)-phenyl]-benzamide The title compound 236 was produced in the same manner as in Example 1.
Mass spectrometric value (ESI-MS) 378 (M−1)

Compound 237 2-Fluoro-N-[2-(3-fluoro-benzylidene-hydrazinocarbonyl)-phenyl]-benzamide The title compound 237 was produced in the same manner as in Example 1.
Mass spectrometric value (ESI-MS) 378 (M−1)

Compound 238 2-Fluoro-N-[2-(3-methyl-benzylidene-hydrazinocarbonyl)-phenyl]-benzamide The title compound 238 was produced in the same manner as in Example 1.
Mass spectrometric value (ESI-MS) 374 (M−1)

Compound 239 N-[2-(3-Tert-butyl-2-hydroxy-benzylidene-hydrazinocarbonyl)-phenyl]-2-fluoro-benzamide The title compound 239 was produced in the same manner as in Example 1.
Mass spectrometric value (ESI-MS) 432 (M−1)

Compound 240 3,4-Dimethoxy-N-[2-(4-nitro-benzylidene-hydrazinocarbonyl)-phenyl]-benzamide The title compound 240 was produced in the same manner as in Example 1.
Mass spectrometric value (ESI-MS) 447 (M−1)

Compound 241 N-[2-(4-Diethylamino-benzylidene-hydrazinocarbonyl)-phenyl]-3,4-dimethoxy-benzamide The title compound 241 was produced in the same manner as in Example 1.
Mass spectrometric value (ESI-MS) 473 (M−1)

Compound 242 N-[2-(3-Fluoro-benzylidene-hydrazinocarbonyl)-4-hydroxy-phenyl]-3,5-dimethoxy-benzamide The title compound 242 was produced in the same manner as in Example 1.
Mass spectrometric value (ESI-MS) 436, 437 (M−1)

Compound 243 N-[4-Bromo-2-(pyridin-2-ylmethylene-hydrazinocarbonyl)-phenyl]-3,4-dimethoxy-benzamide The title compound 243 was produced in the same manner as in Example 1.
Mass spectrometric value (ESI-MS) 483 (M−1)

Compound 244 N-[4-Chloro-2-(pyridin-2-ylmethylene-hydrazinocarbonyl)-phenyl]-3,4-dimethoxy-benzamide The title compound 244 was produced in the same manner as in Example 1.
Mass spectrometric value (ESI-MS) 437 (M−1)

Compound 245 3,4-Dimethoxy-N-[2-pyridin-2-ylmethylene-hydrazinocarbonyl)-phenyl]-benzamide The title compound 245 was produced in the same manner as in Example 1.
Mass spectrometric value (ESI-MS) 403 (M−1)

Compound 246 N-[4-Chloro-2-(6-methyl-pyridin-2-ylmethylene-hydrazinocarbonyl)-phenyl]-3,4-dimethoxy-benzamide The title compound 246 was produced in the same manner as in Example 1.
Mass spectrometric value (ESI-MS) 451 (M−1)

Compound 247 3,4-Dimethoxy-N-[2-(6-methyl-pyridin-2-ylmethylene-hydrazinocarbonyl)-phenyl]-benzamide The title compound 247 was produced in the same manner as in Example 1.
Mass spectrometric value (ESI-MS) 417 (M−1)

Compound 248 N-[4-Bromo-2-(3-methyl-benzylidene-hydrazinocarbonyl)-phenyl]-4-tert-butyl-benzamide The title compound 248 was produced in the same manner as in Example 1.
Mass spectrometric value (ESI-MS) 490, 492 (M−1)

Compound 249 N-[2-(1-m-Toluyl-ethylidene-hydrazinocarbonyl)-phenyl]-isonicotinamide The title compound 249 was produced in the same manner as in Example 1.
Mass spectrometric value (ESI-MS) 371 (M−1)

Compound 250 N-[4-Chloro-2-(1-m-toluyl-ethylidene-hydrazinocarbonyl)-phenyl]-nicotinamide The title compound 250 was produced in the same manner as in Example 1.
Mass spectrometric value (ESI-MS) 405 (M−1)

Compound 251 N-[2-(1-p-Toluyl-ethylidene-hydrazinocarbonyl)-phenyl]-nicotinamide The title compound 251 was produced in the same manner as in Example 1.
Mass spectrometric value (ESI-MS) 371 (M−1)

Compound 252 N-[4-Bromo-2-(4-methyl-benzylidene-hydrazinocarbonyl)-phenyl]-nicotinamide hydrochloride The title compound 252 was produced in the same manner as in Example 3.
$^1$H-NMR (MeOH-$d_4$, 400 MHz): δ 9.21-9.25 (1H, m), 8.79-8.93 (2H, m), 8.34-8.39 (1H, m), 8.25 (1H, s), 8.01 (1H, d, J=2.2 Hz), 8.00-8.15 (1H, m), 7.71 (1H, dd, J=8.08 Hz, J=2.20 Hz), 7.63 (2H, d, J=8.32 Hz), 7.18 (2H, d, J=8.08 Hz), 2.29 (3H, s)
Mass spectrometric value (ESI-MS) 437, 438 (M−1)

Compound 253 N-[2-(3-Methyl-benzylidene-hydrazinocarbonyl)-phenyl]-isonicotinamide hydrochloride The title compound 253 was produced in the same manner as in Example 3.
$^1$H-NMR (CDCl$_3$, 400 MHz): δ 8.96-8.99 (2H, m), 8.49 (1H, d, J=8.08 Hz), 8.42 (2H, dd, J=1.20 Hz, J=5.60 Hz), 8.27 (1H, s), 7.85 (1H, dd, J=1.20 Hz, J=7.80 Hz), 7.51-7.61 (3H, m), 7.18-7.31 (3H, m), 2.30 (3H, s)
Mass spectrometric value (ESI-MS) 357 (M−1)

Compound 255 N-[4-Bromo-2-(3-fluoro-benzylidene-hydrazinocarbonyl)-phenyl]-4-(pyridin-4-ylsulfanylmethyl)-benzamide The title compound 255 was produced in the same manner as in Example 4.
Mass spectrometric value (ESI-MS) 563 (M−1)

Compound 256 N-[4-Bromo-2-(4-fluoro-benzylidene-hydrazinocarbonyl)-phenyl]-4-(pyridin-4-ylsulfanylmethyl)-benzamide The title compound 256 was produced in the same manner as in Example 4.
Mass spectrometric value (ESI-MS) 563 (M−1)

Compound 257 N-[4-Bromo-2-(3-methyl-benzylidene-hydrazinocarbonyl)-phenyl]-4-(pyridin-4-ylsulfanylmethyl)-benzamide The title compound 257 was produced in the same manner as in Example 4.
Mass spectrometric value (ESI-MS) 559 (M−1)

Compound 258 N-[4-Bromo-2-(4-methyl-benzylidene-hydrazinocarbonyl)-phenyl]-4-(pyridin-4-ylsulfanylmethyl)-benzamide The title compound 258 was produced in the same manner as in Example 4.
Mass spectrometric value (ESI-MS) 559 (M−1)

Compound 259 N-[4-Bromo-2-(3,4-dimethyl-benzylidene-hydrazinocarbonyl)-phenyl]-4-(pyridin-4-ylsulfanylmethyl)-benzamide The title compound 259 was produced in the same manner as in Example 4.
Mass spectrometric value (ESI-MS) 571 (M−1)

Compound 260 N-[4-Bromo-2-(4-chloro-3-trifluoromethyl-benzylidene-hydrazinocarbonyl)-phenyl]-4-(pyridin-4-ylsulfanylmethyl)-benzamide The title compound 260 was produced in the same manner as in Example 4.
Mass spectrometric value (ESI-MS) 645, 647 (M−1)

Compound 261 N-[4-Bromo-2-(3-fluoro-benzylidene-hydrazinocarbonyl)-phenyl]-4-(2-hydroxy-ethylsulfanylmethyl)-benzamide The title compound 261 was produced in the same manner as in Example 4.
Mass spectrometric value (ESI-MS) 530 (M−1)

Compound 262 N-[4-Bromo-2-(4-fluoro-benzylidene-hydrazinocarbonyl)-phenyl]-4-(2-hydroxy-ethylsulfanylmethyl)-benzamide The title compound 262 was produced in the same manner as in Example 4.
Mass spectrometric value (ESI-MS) 530 (M−1)

Compound 263 N-[4-Bromo-2-(3-methyl-benzylidene-hydrazinocarbonyl)-phenyl]-4-(2-hydroxy-ethylsulfanylmethyl)-benzamide The title compound 263 was produced in the same manner as in Example 4.
Mass spectrometric value (ESI-MS) 524 (M−1)

Compound 264 N-[4-Bromo-2-(4-methyl-benzylidene-hydrazinocarbonyl)-phenyl]-4-(2-hydroxy-ethylsulfanylmethyl)-benzamide The title compound 264 was produced in the same manner as in Example 4.
Mass spectrometric value (ESI-MS) 526 (M−1)

Compound 265 N-[4-Bromo-2-(3,4-dimethyl-benzylidene-hydrazinocarbonyl)-phenyl]-4-(2-hydroxy-ethylsulfanylmethyl)-benzamide The title compound 265 was produced in the same manner as in Example 4.
Mass spectrometric value (ESI-MS) 540 (M−1)

Compound 266 N-[4-Bromo-2-(4-chloro-3-trifluoromethyl-benzylidene-hydrazinocarbonyl)-phenyl]-4-(2-hydroxy-ethylsulfanylmethyl)-benzamide The title compound 266 was produced in the same manner as in Example 4.
Mass spectrometric value (ESI-MS) 612, 614 (M−1)

Compound 267 N-[4-Bromo-2-(3,4-dimethyl-benzylidene-hydrazinocarbonyl)-phenyl]-3-(1H-[1,2,4]triazol-3-ylsulfanylmethyl)-benzamide The title compound 267 was produced in the same manner as in Example 4.
$^1$H-NMR (CD$_3$OD, 400 MHz): δ 8.60 (1H, d, J=9.0 Hz), 8.31 (1H, s), 8.28 (1H, bs), 8.05 (1H, d, J=2.2 Hz), 8.01 (1H, m), 7.86 (1H, m), 7.73 (1H, dd, J=9.0 Hz, J=2.2 Hz), 7.60

(2H, m), 7.52 (1H, m), 7.46 (1H, t, J=7.7 Hz), 7.19 (1H, d, J=7.8 Hz), 4.44 (2H, s), 2.30 (6H, s)
Mass spectrometric value (ESI-MS) 561 (M−1)

Compound 268 N-[4-Bromo-2-(4-methyl-benzylidene-hydrazinocarbonyl)-phenyl]-3-(1H-[1,2,4]triazol-3-ylsulfanylmethyl)-benzamide The title compound 268 was produced in the same manner as in Example 4.
$^1$H-NMR (CD$_3$OD, 400 MHz): δ 2.38 (3H, s), 4.44 (2H, s), 7.26 (1H, d, J=7.4 Hz), 7.46 (2H, m), 7.59 (1H, m), 7.66 (1H, dd, J=9.0 Hz, J=2.4 Hz), 7.72 (1H, m), 7.86 (2H, m), 7.97-8.05 (2H, m), 8.29-8.34 (2H, m), 8.57 (1H, d, J=8.8 Hz)
Mass spectrometric value (ESI-MS) 547 (M−1)

Compound 269 N-[4-Bromo-2-(3-methyl-benzylidene-hydrazinocarbonyl)-phenyl]-3-(1H-[1,2,4]triazol-3-ylsulfanylmethyl)-benzamide The title compound 269 was produced in the same manner as in Example 4.
$^1$H-NMR (DMSO-d$_6$, 400 MHz): δ 2.48-2.53 (3H, m), 4.43 (2H, s), 7.27-7.82 (9H, m), 7.96 (3H, m), 8.57 (1H, d, J=9.0 Hz)
Mass spectrometric value (ESI-MS) 549 (M−1)

Compound 270 N-[4-Bromo-2-(4-fluoro-benzylidene-hydrazinocarbonyl)-phenyl]-3-(1H-[1,2,4]triazol-3-ylsulfanylmethyl)-benzamide The title compound 270 was produced in the same manner as in Example 4.
$^1$H-NMR (CD$_3$OD, 400 MHz): δ 4.44 (2H, s), 7.20 (1H, m), 7.45 (1H, m), 7.59 (1H, m), 7.66 (1H, dd, J=9.0 Hz, J=2.3 Hz), 7.75 (1H, dd, J=9.0 Hz, J=2.3 Hz), 7.87 (2H, m), 7.99-8.06 (3H, m), 8.30 (1H, s), 8.36 (1H, s), 8.57 (1H, m)
Mass spectrometric value (ESI-MS) 553 (M−1)

Compound 271 N-[4-Bromo-2-(3-fluoro-benzylidene-hydrazinocarbonyl)-phenyl]-3-(1H-[1,2,4]triazol-3-ylsulfanylmethyl)-benzamide The title compound 271 was produced in the same manner as in Example 4.
$^1$H-NMR (CD$_3$OD, 400 MHz): δ 4.44 (2H, s), 7.19 (1H, m), 7.45 (2H, m), 7.59-7.77 (3H, m), 7.86 (2H, m), 7.97-8.01 (2H, m), 8.29-8.36 (2H, m), 8.58 (1H, m)
Mass spectrometric value (ESI-MS) 553 (M−1)

Compound 272 N-[4-Bromo-2-(4-chloro-3-trifluoromethyl-benzylidene-hydrazinocarbonyl)-phenyl]-3-(1H-[1,2,4]triazol-3-ylsulfanylmethyl)-benzamide The title compound 272 was produced in the same manner as in Example 4.
$^1$H-NMR (CD$_3$OD, 400 MHz): δ 4.44 (2H, s), 7.45 (1H, m), 7.59 (1H, m), 7.67 (1H, m), 7.76 (1H, dd, J=9.0 Hz, J=2.2 Hz), 7.85 (2H, m), 7.97-8.06 (3H, m), 8.29 (1H, s), 8.39 (1H, s), 8.57 (1H, dd, J=9.0 Hz, J=1.7 Hz)
Mass spectrometric value (ESI-MS) 635 (M−1)

Compound 273 N-[4-Bromo-2-(3,4-dimethyl-benzylidene-hydrazinocarbonyl)-phenyl]-4-(3-hydroxypropylsulfanylmethyl)-benzamide The title compound 273 was produced in the same manner as in Example 4.
$^1$H-NMR (CD$_3$OD, 400 MHz): δ 1.76 (2H, m), 2.31 (3H, s), 2.32 (3H, s), 2.50 (2H, t, J=7.0 Hz), 3.60 (2H, t, J=6.3 Hz), 3.80 (2H, s), 7.20 (1H, d, J=7.3 Hz), 7.52 (3H, m), 7.66 (1H, s), 7.74 (1H, dd, J=9.0 Hz, J=2.2 Hz), 7.96 (2H, d, J=8.3 Hz), 8.05 (1H, d, J=2.2 Hz), 8.30 (1H, s), 8.63 (1H, d, J=9.0 Hz)
Mass spectrometric value (ESI-MS) 552 (M−1)

Compound 274 N-[4-Bromo-2-(4-methyl-benzylidene-hydrazinocarbonyl)-phenyl]-4-(3-hydroxypropylsulfanylmethyl)-benzamide The title compound 274 was produced in the same manner as in Example 4.
$^1$H-NMR (CD$_3$OD, 400 MHz): δ 1.76 (2H, m), 2.39 (3H, s), 2.50 (2H, t, J=7.3 Hz), 3.60 (2H, t, J=6.1 Hz), 3.80 (2H, s), 7.27 (2H, d, J=8.1 Hz), 7.52 (2H, d, J=8.0 Hz), 7.74 (3H, m), 7.96 (2H, d, J=8.1 Hz), 8.01 (1H, m), 8.33 (1H, s), 8.63 (1H, d, J=8.8 Hz)
Mass spectrometric value (ESI-MS) 538 (M−1)

Compound 275 N-[4-Bromo-2-(3-methyl-benzylidene-hydrazinocarbonyl)-phenyl]-4-(3-hydroxypropylsulfanylmethyl)-benzamide The title compound 275 was produced in the same manner as in Example 4.
$^1$H-NMR (CD$_3$OD, 400 MHz): δ 1.76 (2H, m), 2.40 (3H, s), 2.51 (2H, t, J=7.1 Hz), 3.60 (2H, t, J=6.3 Hz), 3.81 (2H, s), 7.25-7.35 (2H, m), 7.52 (2H, m), 7.63 (1H, m), 7.71-7.77 (2H, m), 7.96 (2H, d, J=8.0 Hz), 8.06 (1H, s), 8.34 (1H, s), 8.62 (1H, m)
Mass spectrometric value (ESI-MS) 538 (M−1)

Compound 276 N-[4-Bromo-2-(4-fluoro-benzylidene-hydrazinocarbonyl)-phenyl]-4-(3-hydroxypropylsulfanylmethyl)-benzamide The title compound 276 was produced in the same manner as in Example 4.
$^1$H-NMR (CD$_3$OD, 400 MHz): δ 1.76 (2H, m), 2.51 (2H, m), 3.60 (2H, m), 3.81 (2H, m), 7.19 (2H, m), 7.51 (2H, m), 7.75-8.06 (6H, m), 8.35 (1H, m), 8.60 (1H, m)
Mass spectrometric value (ESI-MS) 542 (M−1)

Compound 277 N-[4-Bromo-2-(3-fluoro-benzylidene-hydrazinocarbonyl)-phenyl]-4-(3-hydroxypropylsulfanylmethyl)-benzamide The title compound 277 was produced in the same manner as in Example 4.
$^1$H-NMR (CD$_3$OD, 400 MHz): δ 1.76 (2H, m), 2.51 (2H, t, J=7.3 Hz), 3.60 (2H, t, J=6.4 Hz), 3.81 (2H, s), 7.19 (1H, m), 7.46-7.54 (3H, m), 7.60 (1H, m), 7.70 (1H, m), 7.77 (1H, dd, J=9.1 Hz, J=2.3 Hz), 7.96 (2H, m), 8.07 (1H, s), 8.35 (1H, s), 8.62 (1H, d, J=9.1 Hz)
Mass spectrometric value (ESI-MS) 542 (M−1)

Compound 278 N-[4-Bromo-2-(4-chloro-3-trifluoromethyl-benzylidene-hydrazinocarbonyl)-phenyl]-4-(3-hydroxy-propylsulfanylmethyl)-benzamide The title compound 278 was produced in the same manner as in Example 4.
$^1$H-NMR (CD$_3$OD, 400 MHz): δ 1.76 (2H, m), 2.50 (2H, t, J=7.3 Hz), 3.60 (2H, t, J=6.3 Hz), 3.80 (2H, s), 7.52 (2H, d, J=8.0 Hz), 7.69 (1H, d, J=8.3 Hz), 7.76 (1H, dd, J=8.8 Hz, J=2.0 Hz), 7.95 (2H, d, J=8.3 Hz), 8.05-8.07 (2H, m), 8.33 (1H, s), 8.39 (1H, s), 8.62 (1H, d, J=9.0 Hz)

Mass spectrometric value (ESI-MS) 626 (M−1)

Example 5

Compound 279 N-[4-Bromo-2-(3,4-dimethyl-benzylidene-hydrazinocarbonyl)-phenyl]-3-[(2-morpholin-4-yl-ethylamino)-methyl]-benzamide Methyl 2-amino-5-bromobenzoate (compound A) (3.0 g) was dissolved in anhydrous methylene chloride (40.0 ml). Subsequently, pyridine (2.1 ml) and 4-(chloromethyl)benzoyl chloride (compound B) (2.2 ml) were added to the solution at room temperature, and the mixture was stirred at that temperature for one hr. After the completion of the reaction, distilled water was added, followed by separatory extraction with chloroform. The organic layer was washed with saturated brine, was dried over sodium sulfate, and was then concentrated to give methyl 5-bromo-2-[3-(chloromethyl)benzoyl]aminobenzoate as a useful intermediate (4.90 g, yield 100%).

Methyl 5-bromo-2-[3-(chloromethyl)benzoyl]aminobenzoate (500 mg) obtained by the above reaction was dissolved in anhydrous methylene chloride (3.0 ml), triethylamine (545 µl) and 4-(2-aminoethyl)morpholine (compound B') (341 µl) were added to the solution at room temperature, and the mixture was stirred at room temperature for 15 hr. After the completion of the reaction, water was added at room temperature, and the mixture was subjected to separatory extraction with chloroform. The organic layer was washed with saturated brine, dried over sodium sulfate, and was then concentrated. The residue was purified by column chromatography eluted with a chloroform methanol system to give methyl 5-bromo-2-[(3{[(2-morpholinoethyl)amino]methyl}benzoyl)amino]benzoate as a useful intermediate (306 mg, yield 50%).

Methyl 5-bromo-2-[(3{[(2-morpholinoethyl)amino]methyl}benzoyl)-amino]benzoate obtained by the above reaction was dissolved in ethanol (5.0 ml), hydrazine monohydrate (650 µl) was added to the solution, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated to give N-(4-bromo-2-hydrazinocarbonyl-phenyl)-3-[(2-morpholin-4-yl-ethylamino)-methyl]-benzamide as a hydrazine compound (220 mg, crude yield 75%).

N-(4-Bromo-2-hydrazinocarbonyl-phenyl)-3-[(2-morpholin-4-yl-ethylamino)-methyl]-benzamide (25 mg) was dissolved in anhydrous toluene (1.0 ml), a catalytic amount of acetic acid and 3,4-dimethylbenzaldehyde (compound C) (10.0 µl) were added to the solution at room temperature, and the mixture was stirred at room temperature for 15 hr. After the completion of the reaction, the product was purified by column chromatography eluted with a chloroform methanol system to give the title compound 279 (21.1 mg, yield 67%).

$^1$H-NMR (CD$_3$OD, 400 MHz): δ 2.31 (3H, s), 2.32 (3H, s), 2.44 (4H, m), 2.60 (2H, t, J=6.1 Hz), 2.97 (2H, t, J=6.1 Hz), 3.65 (4H, t, J=4.6 Hz), 4.15 (2H, s), 7.20 (1H, d, J=7.8 Hz), 7.54 (1H, m), 7.59-7.70 (3H, m), 7.76 (1H, dd, J=9.0 Hz, J=2.2 Hz), 8.30 (2H, m), 8.07 (1H, d, J=2.2 Hz), 8.32 (1H, s), 8.64 (1H, d, J=9.0 Hz)

Mass spectrometric value (ESI-MS) 594 (M+1)

Compound 280 N-[4-Bromo-2-(3,4-dimethyl-benzylidene-hydrazinocarbonyl)-phenyl]-4-{[(2-diethylamino-ethyl)-methyl-amino]-methyl}-benzamide The title compound 280 was produced in the same manner as in Example 5.

$^1$H-NMR (CD$_3$OD, 400 MHz): δ 1.12 (6H, t, J=7.1 Hz), 2.27 (6H, s), 2.28 (3H, s), 2.60 (2H, t, J=7.3 Hz), 2.77 (4H, q, J=7.3 Hz), 2.88 (2H, t, J=7.3 Hz), 3.63 (2H, s), 7.16 (1H, d, J=7.8 Hz), 7.50 (3H, m), 7.61 (1H, s), 7.70 (1H, dd, J=9.0 Hz, J=2.2 Hz), 7.97 (2H, d, J=8.3 Hz), 8.02 (1H, d, J=2.2 Hz), 8.30 (1H, s), 8.61 (1H, d, J=9.0 Hz)

Mass spectrometric value (ESI-MS) 594 (M+1)

Compound 281 N-[4-Bromo-2-(3,4-dimethyl-benzylidene-hydrazinocarbonyl)-phenyl]-4-[(2-morpholin-4-yl-ethylamino)-methyl]-benzamide The title compound 281 was produced in the same manner as in Example 5.

$^1$H-NMR (CDCl$_3$, 400 MHz): δ 2.29 (3H, s), 2.30 (3H, s), 2.43 (4H, m), 2.54 (2H, t, J=6.0 Hz), 2.72 (2H, t, J=6.0 Hz), 3.70 (4H, t, J=4.6 Hz), 3.89 (2H, s), 7.18 (1H, d, J=7.8 Hz), 7.44-7.70 (6H, m), 7.99 (2H, d, J=7.8 Hz), 8.31 (1H, s), 8.55 (1H, d, J=8.3 Hz)

Mass spectrometric value (ESI-MS) 592 (M+1)

Compound 282 N-[4-Bromo-2-(4-methyl-benzylidene-hydrazinocarbonyl)-phenyl]-4-[(2-morpholin-4-yl-ethylamino)-methyl]-benzamide The title compound 282 was produced in the same manner as in Example 5.

$^1$H-NMR (CDCl$_3$, 400 MHz): δ 2.39 (3H, s), 2.43 (4H, m), 2.53 (2H, t, J=5.9 Hz), 2.72 (2H, t, J=5.9 Hz), 3.70 (4H, t, J=4.6 Hz), 3.89 (2H, s), 7.23 (2H, d, J=8.0 Hz), 7.45 (2H, d, J=8.0 Hz), 7.56 (1H, m), 7.70 (3H, m), 7.99 (2H, m), 8.34 (1H, s), 8.56 (1H, d, J=9.0 Hz)

Mass spectrometric value (ESI-MS) 576 (M−1)

Compound 283 N-[4-Bromo-2-(3-methyl-benzylidene-hydrazinocarbonyl)-phenyl]-4-[(2-morpholin-4-yl-ethylamino)-methyl]-benzamide The title compound 283 was produced in the same manner as in Example 5.

$^1$H-NMR (CDCl$_3$, 400 MHz): δ 2.38 (3H, s), 2.43 (4H, m), 2.52 (2H, t, J=6.0 Hz), 2.70 (2H, t, J=6.0 Hz), 3.70 (4H, t, J=4.4 Hz), 3.88 (2H, s), 7.22-7.32 (2H, m), 7.44 (2H, d, J=8.3 Hz), 7.52 (2H, m), 7.69 (2H, s), 8.00 (2H, d, J=7.8 Hz), 8.42 (2H, m)

Mass spectrometric value (ESI-MS) 578 (M−1)

Compound 284 N-[4-Bromo-2-(4-fluoro-benzylidene-hydrazinocarbonyl)-phenyl]-4-[(2-morpholin-4-yl-ethylamino)-methyl]-benzamide The title compound 284 was produced in the same manner as in Example 5.

$^1$H-NMR (CDCl$_3$, 400 MHz): δ 2.43 (4H, m), 2.52 (2H, t, J=6.0 Hz), 2.70 (2H, t, J=6.0 Hz), 3.70 (4H, t, J=4.5 Hz), 3.89 (2H, s), 7.12 (2H, m), 7.45 (2H, d, J=8.3 Hz), 7.54 (1H, m), 7.67 (1H, m), 7.82 (2H, m), 8.00 (2H, d, J=7.8 Hz), 8.39 (1H, s), 8.48 (1H, m)

Mass spectrometric value (ESI-MS) 582 (M−1)

Compound 285 N-[4-Bromo-2-(4-methyl-benzylidene-hydrazinocarbonyl)-phenyl]-4-{[(2-diethylamino-ethyl)-methyl-amino]-methyl}-benzamide The title compound 285 was produced in the same manner as in Example 5.
$^1$H-NMR (CDCl$_3$, 400 MHz): δ 1.04 (6H, t, J=7.2 Hz), 2.21 (3H, s), 2.33 (3H, s), 2.51-2.66 (8H, m), 3.55 (2H, s), 7.18 (2H, d, J=8.0 Hz), 7.43 (3H, m), 7.66 (2H, d, J=8.0 Hz), 7.74 (1H, m), 7.98 (2H, d, J=8.0 Hz), 8.36 (1H, d, J=9.0 Hz), 8.49 (1H, s)
Mass spectrometric value (ESI-MS) 576 (M−1)

Compound 286 N-[4-Bromo-2-(3-methyl-benzylidene-hydrazinocarbonyl)-phenyl]-4-{[(2-diethylamino-ethyl)-methyl-amino]-methyl}-benzamide The title compound 286 was produced in the same manner as in Example 5.
$^1$H-NMR (CDCl$_3$, 400 MHz): δ 1.04 (6H, t, J=7.1 Hz), 2.23 (3H, s), 2.40 (3H, s), 2.52-2.66 (8H, m), 3.59 (2H, s), 7.24-7.33 (2H, m), 7.45 (2H, d, J=8.3 Hz), 7.56 (2H, m), 7.70 (2H, m), 8.00 (2H, d, J=7.6 Hz), 8.38 (1H, s), 8.50 (1H, d, J=9.0 Hz)
Mass spectrometric value (ESI-MS) 578 (M−1)

Compound 287 N-[4-Bromo-2-(4-fluoro-benzylidene-hydrazinocarbonyl)-phenyl]-4-{[(2-diethylamino-ethyl)-methyl-amino]-methyl}-benzamide The title compound 287 was produced in the same manner as in Example 5.
$^1$H-NMR (CDCl$_3$, 400 MHz): δ 1.04 (6H, t, J=7.1 Hz), 2.23 (3H, s), 2.54-2.66 (8H, m), 3.59 (2H, s), 7.12 (2H, m), 7.45 (2H, d, J=8.3 Hz), 7.54 (1H, m), 7.68 (1H, s), 7.83 (2H, m), 7.99 (2H, d, J=7.8 Hz), 8.42 (1H, s), 8.47 (1H, d, J=9.0 Hz)
Mass spectrometric value (ESI-MS) 580 (M−1)

Compound 288 N-[4-Bromo-2-(3-fluoro-benzylidene-hydrazinocarbonyl)-phenyl]-4-{[(2-diethylamino-ethyl)-methyl-amino]-methyl}-benzamide The title compound 288 was produced in the same manner as in Example 5.
$^1$H-NMR (CDCl$_3$, 400 MHz): δ 1.04 (6H, t, J=7.1 Hz), 2.22 (3H, s), 2.52-2.66 (8H, m), 3.58 (2H, s), 7.10 (1H, m), 7.34-7.46 (4H, m), 7.55 (2H, m), 7.68 (1H, s), 7.99 (2H, d, J=7.8 Hz), 8.29 (1H, d, J=8.8 Hz), 8.52 (1H, s)
Mass spectrometric value (ESI-MS) 582 (M−1)

Compound 289 N-[4-Bromo-2-(4-chloro-3-trifluoromethyl-benzylidene-hydrazinocarbonyl)-phenyl]-4-{[(2-diethylamino-ethyl)-methyl-amino]-methyl}-benzamide The title compound 289 was produced in the same manner as in Example 5.
$^1$H-NMR (CDCl$_3$, 400 MHz): δ 1.04 (6H, t, J=7.1 Hz), 2.23 (3H, s), 2.53-2.66 (8H, m), 3.60 (2H, s), 7.48 (3H, m), 7.58 (1H, d, J=8.3 Hz), 7.67 (1H, s), 7.98-8.07 (4H, m), 8.56 (1H, m), 8.52 (1H, m)
Mass spectrometric value (ESI-MS) 664 (M−1)

Compound 290 N-[4-Bromo-2-(4-methoxy-benzylidene-hydrazinocarbonyl)-phenyl]-4-{[(2-diethylamino-ethyl)-methyl-amino]-methyl}-benzamide The title compound 290 was produced in the same manner as in Example 5.
$^1$H-NMR (CDCl$_3$, 400 MHz): δ 1.04 (6H, t, J=7.1 Hz), 2.21 (3H, s), 2.51-2.66 (8H, m), 3.56 (2H, s), 3.80 (3H, s), 6.89 (2H, d, J=8.8 Hz), 7.43 (3H, m), 7.71 (3H, m), 7.98 (2H, d, J=8.0 Hz), 8.38 (1H, d, J=9.0 Hz), 8.45 (1H, s)
Mass spectrometric value (ESI-MS) 594 (M−1)

Compound 291 N-[4-Bromo-2-(3-methoxy-benzylidene-hydrazinocarbonyl)-phenyl]-4-{[(2-diethylamino-ethyl)-methyl-amino]-methyl}-benzamide The title compound 291 was produced in the same manner as in Example 5.
$^1$H-NMR (CDCl$_3$, 400 MHz): δ 1.03 (6H, t, J=7.1 Hz), 2.21 (3H, s), 2.51-2.65 (8H, m), 3.56 (2H, s), 3.84 (3H, s), 6.94 (1H, m), 7.27-7.48 (6H, m), 7.75 (1H, s), 7.97 (2H, d, J=7.8 Hz), 8.41 (1H, d, J=9.0 Hz), 8.47 (1H, s)
Mass spectrometric value (ESI-MS) 592 (M−1)

Compound 292 N-[4-Bromo-2-(3,4-dimethyl-benzylidene-hydrazinocarbonyl)-phenyl]-4-[(2-diethylamino-ethylamino)-methyl]-benzamide The title compound 292 was produced in the same manner as in Example 5.
$^1$H-NMR (CDCl$_3$, 400 MHz): δ 1.05 (6H, t, J=7.2 Hz), 2.29 (3H, s), 2.30 (3H, s), 2.57-2.73 (8H, m), 3.87 (3H, s), 7.18 (1H, d, J=7.8 Hz), 7.43-7.73 (6H, m), 7.99 (2H, d, J=7.8 Hz), 8.31 (1H, s), 8.56 (1H, d, J=9.0 Hz)
Mass spectrometric value (ESI-MS) 576 (M−1)

Compound 293 N-[4-Bromo-2-(4-methyl-benzylidene-hydrazinocarbonyl)-phenyl]-4-[(2-diethylamino-ethylamino)-methyl]-benzamide The title compound 293 was produced in the same manner as in Example 5.
$^1$H-NMR (CDCl$_3$, 400 MHz): δ 1.05 (6H, t, J=7.1 Hz), 2.39 (3H, s), 2.56-2.73 (8H, m), 3.87 (2H, s), 7.22-7.27 (2H, m), 7.44 (2H, d, J=8.3 Hz), 7.57-7.71 (4H, m), 7.99 (2H, m), 8.34 (1H, s), 8.59 (1H, d, J=9.0 Hz)
Mass spectrometric value (ESI-MS) 562 (M−1)

Compound 294 N-[4-Bromo-2-(3-methyl-benzylidene-hydrazinocarbonyl)-phenyl]-4-[(2-diethylamino-ethylamino)-methyl]-benzamide The title compound 294 was produced in the same manner as in Example 5.
$^1$H-NMR (CDCl$_3$, 400 MHz): δ 1.03 (6H, t, J=7.1 Hz), 2.39 (3H, s), 2.52-2.70 (8H, m), 3.87 (2H, s), 7.23-7.33 (2H, m), 7.45 (2H, d, J=8.3 Hz), 7.55 (2H, m), 7.70 (2H, m), 8.00 (2H, d, J=7.8 Hz), 8.38 (1H, s), 8.51 (1H, d, J=9.0 Hz)
Mass spectrometric value (ESI-MS) 562 (M−1)

Compound 295 N-[4-Bromo-2-(4-fluoro-benzylidene-hydrazinocarbonyl)-phenyl]-4-[(2-diethylamino-ethylamino)-methyl]-benzamide The title compound 295 was produced in the same manner as in Example 5.
$^1$H-NMR (CDCl$_3$, 400 MHz): δ 1.05 (6H, t, J=7.1 Hz), 2.55-2.72 (8H, m), 3.87 (2H, s), 7.12 (2H, m), 7.45 (2H, d, J=8.1 Hz), 7.56-7.82 (4H, m), 7.99 (2H, d, J=7.6 Hz), 8.39 (1H, s), 8.55 (1H, d, J=8.6 Hz)
Mass spectrometric value (ESI-MS) 568 (M−1)

Compound 296 N-[4-Bromo-2-(3-fluoro-benzylidene-hydrazinocarbonyl)-phenyl]-4-[(2-diethylamino-ethylamino)-methyl]-benzamide The title compound 296 was produced in the same manner as in Example 5.

$^1$H-NMR (CDCl$_3$, 400 MHz): δ 1.04 (6H, t, J=7.1 Hz), 2.53-2.71 (8H, m), 3.88 (2H, s), 7.13 (1H, m), 7.37-7.71 (7H, m), 7.99 (2H, d, J=7.6 Hz), 8.42 (1H, s), 8.49 (1H, d, J=8.8 Hz)

Mass spectrometric value (ESI-MS) 568 (M−1)

Compound 297 N-[4-Bromo-2-(4-chloro-3-trifluoromethyl-benzylidene-hydrazinocarbonyl)-phenyl]-4-[(2-diethylamino-ethylamino)-methyl]-benzamide The title compound 297 was produced in the same manner as in Example 5.

$^1$H-NMR (CDCl$_3$, 400 MHz): δ 1.05 (3H, t, J=7.1 Hz), 1.24 (3H, m), 2.53-2.75 (6H, m), 3.72 (2H, m), 3.87 (2H, s), 7.46 (2H, d, J=7.8 Hz), 7.56 (3H, m), 7.73 (1H, m), 7.98 (3H, m), 8.06 (1H, s), 8.48 (1H, d, J=8.3 Hz)

Mass spectrometric value (ESI-MS) 650 (M−1)

Compound 298 N-[4-Bromo-2-(4-methoxy-benzylidene-hydrazinocarbonyl)-phenyl]-4-[(2-diethylamino-ethylamino)-methyl]-benzamide The title compound 298 was produced in the same manner as in Example 5.

$^1$H-NMR (CDCl$_3$, 400 MHz): δ 1.05 (6H, t, J=7.2 Hz), 2.55-2.72 (8H, m), 3.85 (3H, s), 3.87 (2H, s), 6.93 (2H, d, J=8.8 Hz), 7.44 (2H, d, J=8.0 Hz), 7.58 (1H, m), 7.75 (3H, m), 7.99 (2H, d, J=7.6 Hz), 8.31 (1H, s), 8.60 (1H, d, J=9.0 Hz)

Mass spectrometric value (ESI-MS) 578 (M−1)

Compound 299 N-[4-Bromo-2-(3-methoxy-benzylidene-hydrazinocarbonyl)-phenyl]-4-[(2-diethylamino-ethylamino)-methyl]-benzamide The title compound 299 was produced in the same manner as in Example 5.

$^1$H-NMR (CDCl$_3$, 400 MHz): δ 1.03 (6H, t, J=7.1 Hz), 2.52-2.70 (8H, m), 3.86 (3H, s), 3.87 (2H, s), 6.97 (1H, m), 7.29-7.45 (5H, m), 7.56 (1H, s), 7.73 (1H, m), 7.99 (2H, d, J=8.0 Hz), 8.39 (1H, s), 8.53 (1H, m)

Mass spectrometric value (ESI-MS) 578 (M−1)

Compound 300 4-({3-[Bis-(2-hydroxy-ethyl)-amino]-propylamino}-methyl)-N-[4-bromo-2-(3,4-dimethyl-benzylidene-hydrazinocarbonyl)-phenyl]-benzamide The title compound 300 was produced in the same manner as in Example 5.

$^1$H-NMR (CD$_3$OD, 400 MHz): δ 1.73 (2H, m), 2.29 (3H, s), 2.30 (3H, s), 2.61 (6H, m), 2.73 (2H, t, J=6.8 Hz), 3.60 (4H, m), 3.89 (2H, s), 7.18 (1H, d, J=7.6 Hz), 7.53 (3H, m), 7.64 (1H, s), 7.71 (1H, dd, J=8.8 Hz, J=2.4 Hz), 7.98-8.05 (3H, m), 8.29 (1H, s), 8.60 (1H, d, J=9.0 Hz)

Mass spectrometric value (ESI-MS) 626 (M+1)

Compound 301 4-({3-[Bis-(2-hydroxy-ethyl)-amino]-propylamino}-methyl)-N-[4-bromo-2-(3-fluoro-benzylidene-hydrazinocarbonyl)-phenyl]-benzamide The title compound 301 was produced in the same manner as in Example 5.

$^1$H-NMR (CD$_3$OD, 400 MHz): δ 1.74 (2H, m), 2.63 (6H, m), 2.75 (2H, m), 3.61 (4H, m), 3.90 (2H, s), 7.17 (1H, m), 7.45 (1H, m), 7.33-7.72 (5H, m), 7.89 (2H, m), 8.09 (1H, d, J=2.4 Hz), 8.35 (1H, s), 8.60 (1H, d, J=8.8 Hz)

Mass spectrometric value (ESI-MS) 612 (M−1)

Compound 302 4-({3-[Bis-(2-hydroxy-ethyl)-amino]-propylamino}-methyl)-N-[4-bromo-2-(4-chloro-3-trifluoromethyl-benzylidene-hydrazinocarbonyl)-phenyl]-benzamide The title compound 302 was produced in the same manner as in Example 5.

$^1$H-NMR (CD$_3$OD, 400 MHz): δ 1.75 (2H, m), 2.63 (6H, m), 2.78 (2H, m), 3.61 (4H, m), 3.91 (2H, s), 7.54 (2H, d, J=8.0 Hz), 7.66 (2H, m), 8.00 (3H, m), 8.11 (1H, d, J=2.4 Hz), 8.32 (1H, s), 8.38 (1H, s), 8.58 (1H, d, J=8.8 Hz)

Mass spectrometric value (ESI-MS) 696 (M−1)

Compound 303 4-{[Bis-(2-hydroxy-propyl)-amino]-methyl}-N-[4-bromo-2-(3,4-dimethyl-benzylidene-hydrazinocarbonyl)-phenyl]-benzamide The title compound 303 was produced in the same manner as in Example 5.

$^1$H-NMR (CDCl$_3$, 400 MHz): δ 1.11 (3H, s), 1.13 (3H, s), 2.29 (6H, m), 2.45-2.65 (4H, m), 3.60-3.99 (4H, m), 7.18 (1H, d, J=7.8 Hz), 7.47 (3H, m), 7.55 (1H, m), 7.64 (1H, s), 7.70 (1H, s), 8.01 (2H, d, J=7.6 Hz), 8.31 (1H, s), 8.52 (1H, d, J=8.6 Hz)

Mass spectrometric value (ESI-MS) 595 (M−1)

Compound 304 4-{[Bis-(2-hydroxy-propyl)-amino]-methyl}-N-[4-bromo-2-(4-methyl-benzylidene-hydrazinocarbonyl)-phenyl]-benzamide The title compound 304 was produced in the same manner as in Example 5.

$^1$H-NMR (CDCl$_3$, 400 MHz): δ 1.11 (6H, m), 2.34 (3H, s), 2.42-2.62 (4H, m), 3.59-3.93 (4H, m), 7.19 (2H, d, J=8.0 Hz), 7.44 (3H, m), 7.68 (3H, m), 7.98 (2H, d, J=7.8 Hz), 8.41 (2H, m)

Mass spectrometric value (ESI-MS) 579 (M−1)

Compound 305 N-[4-Bromo-2-(3,4-dimethyl-benzylidene-hydrazinocarbonyl)-phenyl]-4-[4-(2-morpholin-4-yl-2-oxo-ethyl)-piperazin-1-ylmethyl]-benzamide The title compound 305 was produced in the same manner as in Example 5.

$^1$H-NMR (CDCl$_3$, 400 MHz): δ 2.26 (3H, s), 2.28 (3H, s), 2.49 (8H, m), 3.16 (2H, s), 3.49-3.70 (10H, m), 7.15 (1H, d, J=7.8 Hz), 7.40-7.52 (4H, m), 7.62 (1H, s), 7.73 (1H, s), 7.96 (2H, d, J=7.8 Hz), 8.38 (1H, s), 8.49 (1H, d, J=8.8 Hz)

Mass spectrometric value (ESI-MS) 673 (M−1)

Compound 306 N-[4-Bromo-2-(4-chloro-3-trifluoromethyl-benzylidene-hydrazinocarbonyl)-phenyl]-4-[4-(2-morpholin-4-yl-2-oxo-ethyl)-piperazin-1-ylmethyl]-benzamide The title compound 306 was produced in the same manner as in Example 5.

$^1$H-NMR (CDCl$_3$, 400 MHz): δ 2.50 (8H, m), 3.15 (2H, s), 3.49-3.75 (10H, m), 7.42 (2H, m), 7.54 (2H, m), 7.71 (1H, s), 7.99 (4H, m), 8.44 (1H, d, J=8.5 Hz), 8.51 (1H, s)

Mass spectrometric value (ESI-MS) 747 (M−1)

Compound 307 N-[4-Bromo-2-(4-methoxy-benzylidene-hydrazinocarbonyl)-phenyl]-4-[4-(2-morpholin-4-yl-2-oxo-ethyl)-piperazin-1-ylmethyl]-benzamide The title compound 307 was produced in the same manner as in Example 5.
$^1$H-NMR (CDCl$_3$, 400 MHz): δ 2.48 (8H, m), 3.16 (2H, s), 3.48-3.75 (10H, m), 3.81 (3H, s), 6.89 (2H, d, J=8.8 Hz), 7.39 (2H, d, J=8.1 Hz), 7.50 (1H, m), 7.69-7.53 (3H, m), 7.96 (2H, d, J=8.0 Hz), 8.40 (1H, s), 8.49 (1H, d, J=9.0 Hz)
Mass spectrometric value (ESI-MS) 675 (M−1)

Compound 308 4-[1,4']Bipiperidinyl-1'-ylmethyl-N-[4-bromo-2-(3,4-dimethyl-benzylidene-hydrazinocarbonyl)-phenyl]-benzamide The title compound 308 was produced in the same manner as in Example 5.
$^1$H-NMR (CDCl$_3$, 400 MHz): δ 1.47 (2H, m), 1.65 (6H, m), 1.82 (2H, m), 1.94 (2H, t, J=11.2 Hz), 2.24 (3H, s), 2.26 (3H, s), 2.55-2.68 (5H, m), 2.87 (2H, d, J=11.5 Hz), 3.47 (2H, s), 7.13 (1H, d, J=7.8 Hz), 7.36 (2H, d, J=8.0 Hz), 7.43 (1H, d, J=7.8 Hz), 7.50 (1H, d, J=8.8 Hz), 7.59 (1H, s), 7.88 (1H, s), 7.96 (2H, d, J=8.0 Hz), 8.43 (1H, s), 8.53 (1H, d, J=9.0 Hz)
Mass spectrometric value (ESI-MS) 630 (M−1)

Compound 309 4-[1,4']Bipiperidinyl-1'-ylmethyl-N-[4-bromo-2-(4-methyl-benzylidene-hydrazinocarbonyl)-phenyl]-benzamide The title compound 309 was produced in the same manner as in Example 5.
$^1$H-NMR (CDCl$_3$, 400 MHz): δ 1.47 (2H, m), 1.59-1.73 (6H, m), 1.82 (2H, m), 1.93 (2H, m), 2.34 (3H, s), 2.57-2.69 (5H, m), 2.87 (2H, d, J=11.5 Hz), 3.47 (2H, s), 7.19 (2H, d, J=8.0 Hz), 7.36 (2H, d, J=8.0 Hz), 7.51 (1H, m), 7.66 (2H, d, J=8.0 Hz), 7.87 (1H, s), 7.96 (2H, d, J=8.0 Hz), 8.45 (1H, s), 8.53 (1H, d, J=9.0 Hz)
Mass spectrometric value (ESI-MS) 614 (M−1)

Compound 310 4-[1,4']Bipiperidinyl-1'-ylmethyl-N-[4-bromo-2-(3-methyl-benzylidene-hydrazinocarbonyl)-phenyl]-benzamide The title compound 310 was produced in the same manner as in Example 5.
$^1$H-NMR (CDCl$_3$, 400 MHz): δ 1.47 (2H, m), 1.59-1.74 (6H, m), 1.83 (2H, m), 1.94 (2H, m), 2.35 (3H, s), 2.59-2.75 (5H, m), 2.87 (2H, d, J=11.5 Hz), 3.47 (2H, s), 7.19 (1H, d, J=7.6 Hz), 7.26 (1H, m), 7.36 (2H, d, J=8.1 Hz), 7.51 (2H, m), 7.64 (1H, s), 7.90 (1H, s), 7.95 (2H, d, J=8.1 Hz), 8.46 (1H, s), 8.54 (1H, d, J=8.8 Hz)
Mass spectrometric value (ESI-MS) 614 (M−1)

Compound 311 4-[1,4']Bipiperidinyl-1'-ylmethyl-N-[4-bromo-2-(4-fluoro-benzylidene-hydrazinocarbonyl)-phenyl]-benzamide The title compound 311 was produced in the same manner as in Example 5.
$^1$H-NMR (CDCl$_3$, 400 MHz): δ 1.47 (2H, m), 1.60-1.75 (6H, m), 1.83 (2H, m), 1.93 (2H, m), 2.56-2.74 (5H, m), 2.87 (2H, d, J=11.2 Hz), 3.47 (2H, s), 7.06 (2H, t, J=8.5 Hz), 7.36 (2H, d, J=8.1 Hz), 7.50 (1H, d, J=8.3 Hz), 7.74 (2H, m), 7.87-8.00 (3H, m), 8.50 (2H, m)
Mass spectrometric value (ESI-MS) 620 (M−1)

Compound 312 4-[1,4']Bipiperidinyl-1'-ylmethyl-N-[4-bromo-2-(3-fluoro-benzylidene-hydrazinocarbonyl)-phenyl]-benzamide The title compound 312 was produced in the same manner as in Example 5.
$^1$H-NMR (CDCl$_3$, 400 MHz): δ 1.47 (2H, m), 1.59-1.75 (6H, m), 1.83 (2H, m), 1.94 (2H, m), 2.50-2.70 (5H, m), 2.87 (2H, d, J=11.2 Hz), 3.48 (2H, s), 7.08 (1H, m), 7.30-7.40 (3H, m), 7.50 (3H, m), 7.87 (1H, s), 7.95 (2H, d, J=8.1 Hz), 8.49 (2H, m)
Mass spectrometric value (ESI-MS) 620 (M−1)

Compound 313 4-[1,4']Bipiperidinyl-1'-ylmethyl-N-[4-bromo-2-(4-chloro-3-trifluoromethyl-benzylidene-hydrazinocarbonyl)-phenyl]-benzamide The title compound 313 was produced in the same manner as in Example 5.
$^1$H-NMR (CDCl$_3$, 400 MHz): δ 1.50 (2H, m), 1.60-1.80 (6H, m), 1.82-1.96 (4H, m), 2.62-2.78 (5H, m), 2.86 (2H, d, J=11.0 Hz), 3.46 (2H, s), 7.35 (2H, d, J=8.0 Hz), 7.51 (2H, d, J=8.6 Hz), 7.94 (5H, m), 8.50 (1H, d, J=9.0 Hz), 8.57 (1H, s)
Mass spectrometric value (ESI-MS) 702 (M−1)

Compound 314 4-[1,4']Bipiperidinyl-1'-ylmethyl-N-[4-bromo-2-(4-methoxy-benzylidene-hydrazinocarbonyl)-phenyl]-benzamide The title compound 314 was produced in the same manner as in Example 5.
$^1$H-NMR (CDCl$_3$, 400 MHz): δ 1.47 (2H, m), 1.59-1.75 (6H, m), 1.83 (2H, m), 1.94 (2H, m), 2.60-2.76 (5H, m), 2.87 (2H, d, J=11.5 Hz), 3.46 (2H, s), 3.79 (3H, s), 6.88 (2H, d, J=8.6 Hz), 7.35 (2H, d, J=8.0 Hz), 7.52 (1H, d, J=9.0 Hz), 7.68 (2H, d, J=8.6 Hz), 7.90 (1H, s), 7.95 (2H, d, J=8.0 Hz), 8.41 (1H, s), 8.55 (1H, d, J=9.0 Hz)
Mass spectrometric value (ESI-MS) 632 (M−1)

Compound 315 4-[1,4']Bipiperidinyl-1'-ylmethyl-N-[4-bromo-2-(3-methoxy-benzylidene-hydrazinocarbonyl)-phenyl]-benzamide The title compound 315 was produced in the same manner as in Example 5.
$^1$H-NMR (CDCl$_3$, 400 MHz): δ 1.47 (2H, m), 1.58-1.80 (6H, m), 1.83 (2H, m), 1.92 (2H, m), 2.59-2.75 (5H, m), 2.85 (2H, m), 3.45 (2H, s), 3.82 (3H, s), 6.91 (1H, d, J=6.8 Hz), 7.20-7.40 (5H, m), 7.52 (1H, d, J=9.0 Hz), 7.94 (3H, m), 8.49 (1H, s), 8.56 (1H, d, J=9.0 Hz)
Mass spectrometric value (ESI-MS) 632 (M−1)

Compound 316 N-[4-Bromo-2-(3,4-dimethyl-benzylidene-hydrazinocarbonyl)-phenyl]-4-[4-(2-hydroxy-ethyl)-piperazin-1-ylmethyl]-benzamide The title compound 316 was produced in the same manner as in Example 5.
$^1$H-NMR (CDCl$_3$, 400 MHz): δ 2.29 (3H, s), 2.30 (3H, s), 2.48-2.65 (10H, m), 3.58 (2H, s), 3.64 (2H, t, J=5.2 Hz), 7.18 (1H, d, J=7.8 Hz), 7.46 (3H, m), 7.57 (1H, d, J=9.0 Hz), 7.64 (1H, s), 7.70 (1H, s), 7.98 (2H, d, J=7.8 Hz), 8.29 (1H, s), 8.56 (1H, d, J=9.0 Hz)
Mass spectrometric value (ESI-MS) 592 (M−1)

Compound 317 N-[4-Bromo-2-(4-methyl-benzylidene-hydrazinocarbonyl)-phenyl]-4-[4-(2-hydroxy-ethyl)-piperazin-1-ylmethyl]-benzamide The title compound 317 was produced in the same manner as in Example 5.
$^1$H-NMR (CDCl$_3$, 400 MHz): δ 2.40 (3H, s), 2.54-2.75 (10H, m), 3.60 (2H, s), 3.68 (2H, m), 7.25 (2H, m), 7.45 (2H, d, J=8.0 Hz), 7.62 (1H, m), 7.70 (3H, m), 7.98 (2H, d, J=8.0 Hz), 8.28 (1H, s), 8.64 (1H, d, J=9.0 Hz)
Mass spectrometric value (ESI-MS) 576 (M−1)

Compound 318 N-[4-Bromo-2-(3-methyl-benzylidene-hydrazinocarbonyl)-phenyl]-4-[4-(2-hydroxy-ethyl)-piperazin-1-ylmethyl]-benzamide The title compound 318 was produced in the same manner as in Example 5.
$^1$H-NMR (CDCl$_3$, 400 MHz): δ 2.40 (3H, s), 2.50-2.67 (10H, m), 3.58 (2H, s), 3.64 (2H, t, J=5.3 Hz), 7.24 (1H, m), 7.32 (1H, m), 7.45 (2H, d, J=8.0 Hz), 7.56 (2H, m), 7.70 (2H, m), 7.99 (2H, d, J=8.0 Hz), 8.34 (1H, s), 8.53 (1H, d, J=9.2 Hz)
Mass spectrometric value (ESI-MS) 578 (M−1)

Compound 319 N-[4-Bromo-2-(4-fluoro-benzylidene-hydrazinocarbonyl)-phenyl]-4-[4-(2-hydroxy-ethyl)-piperazin-1-ylmethyl]-benzamide The title compound 319 was produced in the same manner as in Example 5.
$^1$H-NMR (CDCl$_3$, 400 MHz): δ 2.48-2.70 (10H, m), 3.58 (2H, s), 3.65 (2H, t, J=5.2 Hz), 7.12 (2H, m), 7.45 (2H, d, J=8.0 Hz), 7.53 (1H, m), 7.68 (1H, s), 7.82 (2H, m), 7.98 (2H, d, J=8.0 Hz), 8.40 (1H, s), 8.46 (1H, d, J=8.8 Hz)
Mass spectrometric value (ESI-MS) 580 (M−1)

Compound 320 N-[4-Bromo-2-(3-fluoro-benzylidene-hydrazinocarbonyl)-phenyl]-4-[4-(2-hydroxy-ethyl)-piperazin-1-ylmethyl]-benzamide The title compound 320 was produced in the same manner as in Example 5.
$^1$H-NMR (CDCl$_3$, 400 MHz): δ 2.50-2.75 (10H, m), 3.60 (2H, s), 3.69 (2H, t, J=5.2 Hz), 7.14 (1H, m), 7.36-7.72 (7H, m), 7.98 (2H, d, J=8.0 Hz), 8.39 (1H, s), 8.50 (1H, d, J=9.0 Hz)
Mass spectrometric value (ESI-MS) 582 (M−1)

Compound 321 N-[4-Bromo-2-(4-chloro-3-trifluoromethyl-benzylidene-hydrazinocarbonyl)-phenyl]-4-[4-(2-hydroxy-ethyl)-piperazin-1-ylmethyl]-benzamide The title compound 321 was produced in the same manner as in Example 5.
$^1$H-NMR (CDCl$_3$, 400 MHz): δ 2.50-2.72 (10H, m), 3.60 (2H, s), 3.66 (2H, t, J=5.2 Hz), 7.15 (1H, m), 7.43-7.72 (6H, m), 7.99 (2H, d, J=8.0 Hz), 8.07 (1H, s), 8.46 (1H, m)
Mass spectrometric value (ESI-MS) 664 (M−1)

Compound 322 N-[4-Bromo-2-(4-methoxy-benzylidene-hydrazinocarbonyl)-phenyl]-4-[4-(2-hydroxy-ethyl)-piperazin-1-ylmethyl]-benzamide The title compound 322 was produced in the same manner as in Example 5.
$^1$H-NMR (CDCl$_3$, 400 MHz): δ 2.50-2.70 (10H, m), 3.58 (2H, s), 3.65 (2H, t, J=5.2 Hz), 3.85 (3H, s), 6.94 (2H, d, J=8.8 Hz), 7.44 (2H, d, J=8.3 Hz), 7.59 (1H, m), 7.69-7.80 (3H, m), 7.98 (2H, d, J=7, 8 Hz), 8.28 (1H, s), 8.60 (1H, d, J=9.0 Hz)
Mass spectrometric value (ESI-MS) 594 (M−1)

Compound 323 N-[4-Bromo-2-(3-methoxy-benzylidene-hydrazinocarbonyl)-phenyl]-4-[4-(2-hydroxy-ethyl)-piperazin-1-ylmethyl]-benzamide The title compound 323 was produced in the same manner as in Example 5.
$^1$H-NMR (CDCl$_3$, 400 MHz): δ 2.45-2.65 (10H, m), 3.57 (2H, s), 3.63 (2H, t, J=5.4 Hz), 3.86 (3H, s), 6.98 (1H, m), 7.17 (1H, m), 7.22-7.58 (5H, m), 7.71 (1H, s), 7.97 (2H, d, J=7.8 Hz), 8.38 (1H, s), 8.50 (1H, d, J=8.8 Hz)
Mass spectrometric value (ESI-MS) 592 (M−1)

Compound 324 N-[4-Bromo-2-(3,4-dimethyl-benzylidene-hydrazinocarbonyl)-phenyl]-4-(4-hydroxy-piperidin-1-ylmethyl)-benzamide The title compound 324 was produced in the same manner as in Example 5.
$^1$H-NMR (CDCl$_3$, 400 MHz): δ 1.61 (2H, m), 1.86-2.24 (4H, m), 2.89 (3H, s), 2.30 (3H, s), 2.75 (2H, m), 3.57 (2H, s), 3.71 (1H, m), 7.18 (1H, d, J=7.8 Hz), 7.45 (3H, m), 7.55 (1H, m), 7.64 (1H, s), 7.69 (1H, s), 7.98 (2H, d, J=7.6 Hz), 8.30 (1H, s), 8.54 (1H, d, J=9.0 Hz)
Mass spectrometric value (ESI-MS) 563 (M−1)

Compound 325 N-[4-Bromo-2-(4-methyl-benzylidene-hydrazinocarbonyl)-phenyl]-4-(4-hydroxy-piperidin-1-ylmethyl)-benzamide The title compound 325 was produced in the same manner as in Example 5.
$^1$H-NMR (CDCl$_3$, 400 MHz): δ 1.60 (2H, m), 1.89 (2H, m), 2.17 (2H, m), 2.39 (3H, s), 2.74 (2H, m), 3.56 (2H, m), 3.71 (1H, s), 7.15-7.27 (2H, m), 7.44 (2H, d, J=8.0 Hz), 7.56 (1H, m), 7.69 (3H, m), 7.98 (2H, d, J=8.0 Hz), 8.32 (1H, s), 8.55 (1H, d, J=9.0 Hz)
Mass spectrometric value (ESI-MS) 549 (M−1)

Compound 326 N-[4-Bromo-2-(3-methyl-benzylidene-hydrazinocarbonyl)-phenyl]-4-(4-hydroxy-piperidin-1-ylmethyl)-benzamide The title compound 326 was produced in the same manner as in Example 5.
$^1$H-NMR (CDCl$_3$, 400 MHz): δ 1.60 (2H, m), 1.90 (2H, m), 2.17 (2H, m), 2.40 (3H, s), 2.74 (2H, m), 3.56 (2H, m), 3.71 (1H, m), 7.24-7.34 (2H, m), 7.45 (2H, m), 7.58 (2H, m), 7.70 (2H, m), 7.98 (2H, d, J=7.8 Hz), 8.31 (1H, s), 8.57 (1H, d, J=9.0 Hz)
Mass spectrometric value (ESI-MS) 547 (M−1)

Compound 327 N-[4-Bromo-2-(4-fluoro-benzylidene-hydrazinocarbonyl)-phenyl]-4-(4-hydroxy-piperidin-1-ylmethyl)-benzamide The title compound 327 was produced in the same manner as in Example 5.
$^1$H-NMR (CDCl$_3$, 400 MHz): δ 1.59 (2H, m), 1.89 (2H, m), 2.17 (2H, m), 2.74 (2H, m), 3.56 (2H, s), 3.72 (1H, m), 7.13 (2H, m), 7.45 (2H, d, J=8.0 Hz), 7.56 (1H, m), 7.66 (1H, s), 7.82 (2H, m), 7.98 (2H, d, J=8.0 Hz), 8.36 (1H, s), 8.51 (1H, d, J=8.0 Hz)
Mass spectrometric value (ESI-MS) 551 (M−1)

Compound 328 N-[4-Bromo-2-(3-fluoro-benzylidene-hydrazinocarbonyl)-phenyl]-4-(4-hydroxy-piperidin-1-ylmethyl)-benzamide The title compound 328 was produced in the same manner as in Example 5.
$^1$H-NMR (CDCl$_3$, 400 MHz): δ 1.65 (2H, m), 1.93 (2H, m), 2.30 (2H, m), 2.80 (2H, m), 3.65 (2H, s), 3.75 (1H, m), 7.15 (1H, m), 7.26-7.69 (7H, m), 7.99 (2H, d, J=7.8 Hz), 8.35 (1H, s), 8.54 (1H, d, J=9.0 Hz)
Mass spectrometric value (ESI-MS) 551 (M−1)

Compound 329 N-[4-Bromo-2-(4-chloro-3-trifluoromethyl-benzylidene-hydrazinocarbonyl)-phenyl]-4-(4-hydroxy-piperidin-1-ylmethyl)-benzamide The title compound 329 was produced in the same manner as in Example 5.
$^1$H-NMR (CDCl$_3$, 400 MHz): δ 1.58 (2H, m), 1.91 (2H, m), 2.38 (2H, m), 2.75 (2H, m), 3.58 (2H, s), 3.71 (1H, m), 7.16 (1H, m), 7.47 (2H, d, J=8.1 Hz), 7.52-7.75 (4H, m), 7.98 (2H, d, J=8.1 Hz), 8.24 (1H, s), 8.58 (1H, m)
Mass spectrometric value (ESI-MS) 635 (M−1)

Compound 330 N-[4-Bromo-2-(4-methoxy-benzylidene-hydrazinocarbonyl)-phenyl]-4-(4-hydroxy-piperidin-1-ylmethyl)-benzamide The title compound 330 was produced in the same manner as in Example 5.
$^1$H-NMR (CDCl$_3$, 400 MHz): δ 1.62 (2H, m), 1.90 (2H, m), 2.20 (2H, m), 2.75 (2H, m), 3.59 (2H, s), 3.72 (1H, m), 3.86 (3H, s), 6.95 (2H, d, J=8.8 Hz), 7.45 (2H, d, J=8.0 Hz), 7.62-7.80 (4H, m), 7.98 (2H, m), 8.21 (1H, s), 8.70 (1H, m)
Mass spectrometric value (ESI-MS) 565 (M−1)

Compound 331 N-[4-Bromo-2-(3-methoxy-benzylidene-hydrazinocarbonyl)-phenyl]-4-(4-hydroxy-piperidin-1-ylmethyl)-benzamide The title compound 331 was produced in the same manner as in Example 5.
$^1$H-NMR (CDCl$_3$, 400 MHz): δ 1.60 (2H, m), 1.90 (2H, m), 2.17 (2H, m), 2.75 (2H, m), 2.57 (2H, s), 2.72 (1H, m), 3.87 (3H, s), 6.99 (1H, m), 7.25-7.77 (7H, m), 7.97 (2H, d, J=7.5 Hz), 8.30 (1H, s), 8.63 (1H, d, J=8.6 Hz)
Mass spectrometric value (ESI-MS) 563 (M−1)

Compound 332 N-[4-Bromo-2-(3,4-dimethyl-benzylidene-hydrazinocarbonyl)-phenyl]-4-(4-hydroxymethyl-piperidin-1-ylmethyl)-benzamide The title compound 332 was produced in the same manner as in Example 5.
$^1$H-NMR (CDCl$_3$, 400 MHz): δ 1.25-1.76 (5H, m), 2.03 (2H, m), 2.28 (3H, s), 2.29 (3H, s), 2.91 (2H, m), 3.50 (2H, d, J=6.3 Hz), 3.58 (2H, s), 7.17 (1H, m), 7.41-7.72 (6H, m), 7.98 (2H, d, J=8.0 Hz), 8.32 (1H, s), 8.53 (1H, d, J=8.5 Hz)
Mass spectrometric value (ESI-MS) 575 (M−1)

Compound 333 N-[4-Bromo-2-(4-methyl-benzylidene-hydrazinocarbonyl)-phenyl]-4-(4-hydroxymethyl-piperidin-1-ylmethyl)-benzamide The title compound 333 was produced in the same manner as in Example 5.
$^1$H-NMR (CDCl$_3$, 400 MHz): δ 1.20-1.76 (5H, m), 2.04 (2H, m), 2.39 (3H, s), 2.93 (2H, m), 3.50 (2H, d, J=6.4 Hz), 3.60 (2H, s), 7.24 (2H, m), 7.42-7.76 (6H, m), 7.98 (2H, d, J=7.8 Hz), 8.33 (1H, s), 8.58 (1H, d, J=8.8 Hz)
Mass spectrometric value (ESI-MS) 561 (M−1)

Compound 334 N-[4-Bromo-2-(3-methyl-benzylidene-hydrazinocarbonyl)-phenyl]-4-(4-hydroxymethyl-piperidin-1-ylmethyl)-benzamide The title compound 334 was produced in the same manner as in Example 5.
$^1$H-NMR (CDCl$_3$, 400 MHz): δ 1.20-2.15 (7H, m), 2.38 (3H, s), 2.93 (2H, m), 3.40-3.65 (4H, m), 7.20-7.32 (1H, m), 7.40-7.70 (6H, m), 8.27 (1H, s), 8.65 (1H, d, J=8.8 Hz)
Mass spectrometric value (ESI-MS) 563 (M−1)

Compound 335 N-[4-Bromo-2-(4-fluoro-benzylidene-hydrazinocarbonyl)-phenyl]-4-(4-hydroxymethyl-piperidin-1-ylmethyl)-benzamide The title compound 335 was produced in the same manner as in Example 5.
$^1$H-NMR (CDCl$_3$, 400 MHz): δ 1.20-1.40 (5H, m), 1.72 (2H, m), 2.93 (2H, m), 3.47-3.65 (4H, m), 7.12 (2H, m), 7.40-7.88 (6H, m), 7.98 (2H, d, J=8.5 Hz), 8.47 (1H, s), 8.54 (1H, d, J=8.8 Hz)
Mass spectrometric value (ESI-MS) 567 (M−1)

Compound 336 N-[4-Bromo-2-(3-fluoro-benzylidene-hydrazinocarbonyl)-phenyl]-4-(4-hydroxymethyl-piperidin-1-ylmethyl)-benzamide The title compound 336 was produced in the same manner as in Example 5.
$^1$H-NMR (CDCl$_3$, 400 MHz): δ 1.20-1.80 (5H, m), 2.05 (2H, m), 2.93 (2H, m), 3.42-3.65 (4H, m), 7.12 (1H, m), 7.24-7.66 (6H, m), 7.82 (1H, s), 7.97 (2H, d, J=8.3 Hz), 8.30 (1H, s), 8.64 (1H, d, J=9.0 Hz)
Mass spectrometric value (ESI-MS) 565 (M−1)

Compound 337 N-[4-Bromo-2-(4-chloro-3-trifluoromethyl-benzylidene-hydrazinocarbonyl)-phenyl]-4-(4-hydroxymethyl-piperidin-1-ylmethyl)-benzamide The title compound 337 was produced in the same manner as in Example 5.
$^1$H-NMR (CDCl$_3$, 400 MHz): δ 1.20-2.22 (7H, m), 2.92 (2H, m), 3.39-3.65 (4H, m), 7.14-8.10 (9H, m), 8.32 (1H, s), 8.64 (1H, d, J=8.8 Hz)
Mass spectrometric value (ESI-MS) 649 (M−1)

Compound 338 N-[4-Bromo-2-(4-methoxy-benzylidene-hydrazinocarbonyl)-phenyl]-4-(4-hydroxymethyl-piperidin-1-ylmethyl)-benzamide The title compound 338 was produced in the same manner as in Example 5.
$^1$H-NMR (CDCl$_3$, 400 MHz): δ 1.20-1.76 (5H, m), 2.03 (2H, m), 2.91 (2H, m), 3.46-3.64 (4H, m), 3.84 (3H, s), 6.93 (2H, m), 7.41-7.80 (6H, m), 7.97 (2H, d, J=7.8 Hz), 8.32 (1H, s), 8.55 (1H, d, J=9.0 Hz)
Mass spectrometric value (ESI-MS) 579 (M−1)

Compound 339 N-[4-Bromo-2-(3-methoxy-benzylidene-hydrazinocarbonyl)-phenyl]-4-(4-hydroxymethyl-piperidin-1-ylmethyl)-benzamide The title compound 339 was produced in the same manner as in Example 5.
$^1$H-NMR (CDCl$_3$, 400 MHz): δ 1.20-2.25 (7H, m), 2.95 (2H, m), 3.45-3.67 (4H, m), 3.87 (3H, s), 6.80-7.80 (8H, m), 7.95 (2H, m), 8.25 (1H, s), 8.65 (1H, m)
Mass spectrometric value (ESI-MS) 577 (M−1)

Compound 340 N-[4-Bromo-2-(3,4-dimethyl-benzylidene-hydrazinocarbonyl)-phenyl]-4-[4-(2-hydroxy-ethyl)-piperidin-1-ylmethyl]-benzamide The title compound 340 was produced in the same manner as in Example 5.
$^1$H-NMR (DMSO-d$_6$, 400 MHz): δ 1.15 (2H, m), 1.35 (3H, m), 1.61 (2H, m), 1.92 (2H, m), 2.27 (3H, s), 2.29 (3H, s), 2.77 (2H, m), 3.42 (2H, m), 3.52 (2H, s), 7.24 (1H, d, J=7.8 Hz), 7.48 (3H, m), 7.55 (1H, s), 7.80 (1H, dd, J=9.0 Hz, J=2.4 Hz), 7.88 (2H, d, J=8.0 Hz), 8.09 (1H, d, J=2.4 Hz), 8.38 (1H, s), 8.52 (1H, d, J=9.0 Hz)
Mass spectrometric value (ESI-MS) 589 (M−1)

Example 6

Compound 341 N-[4-Bromo-2-(3-fluoro-benzylidene-hydrazinocarbonyl)-phenyl]-3-(1H-[1,2,4]triazole-3-sulfinylmethyl)-benzamide Compound 271: N-[4-bromo-2-(3-fluoro-benzylidene-hydrazinocarbonyl)-phenyl]-3-(1H-[1,2,4]triazol-3-ylsulfanylmethyl)-benzamide (100 mg) produced in the same manner as in Example 5 was dissolved in methylene chloride (5 ml), 3-chloro-peroxybenzoic acid (32 mg) was added to the solution, and the mixture was stirred at room temperature for 2 hr. The resultant crystals were filtered and were washed with methylene chloride and hexane to give the title compound 341 (76 mg, yield 70%).
$^1$H-NMR (DMSO-d$_6$, 400 MHz): δ 4.65 (2H, m), 7.29 (1H, m), 7.53 (4H, m), 7.83 (3H, m), 8.08 (1H, d, J=2.0 Hz), 8.43 (2H, m), 8.83 (1H, s), 11.72 (1H, s)
Mass spectrometric value (ESI-MS) 569 (M−1)

Compound 342 3-{[(2-Diethylamino-ethyl)-methyl-amino]-methyl}-N-[2-(3,4-dimethyl-benzylidene-hydrazinocarbonyl)-4-methyl-thiophen-3-yl]-benzamide The title compound 342 was produced in the same manner as in Example 5.
$^1$H-NMR (CDCl$_3$, 400 MHz): δ 1.07 (6H, m), 2.30 (12H, m), 2.56 (8H, m), 3.61 (2H, s), 7.18 (1H, d, J=7.6 Hz), 7.30-7.60 (6H, m), 7.93 (1H, d, J=7.6 Hz), 8.01 (1H, s)
Mass spectrometric value (ESI-MS) 532 (M−1)

Compound 343 3-{[(2-Diethylamino-ethyl)-methyl-amino]-methyl}-N-[4-methyl-2-(4-methyl-benzylidene-hydrazinocarbonyl)-thiophen-3-yl]-benzamide The title compound 343 was produced in the same manner as in Example 5.
$^1$H-NMR (CDCl$_3$, 400 MHz): δ 1.05 (6H, t, J=7.1 Hz), 2.26 (3H, s), 2.31 (3H, s), 2.39 (3H, s), 2.51-2.80 (8H, m), 3.60 (2H, s), 7.21 (2H, d, J=7.6 Hz), 7.30-7.80 (6H, m), 7.93 (1H, d, J=7.6 Hz), 8.00 (1H, s)
Mass spectrometric value (ESI-MS) 518 (M−1)

Compound 344 N-[2-(4-Chloro-3-trifluoromethyl-benzylidene-hydrazinocarbonyl)-4-methyl-thiophen-3-yl]-3-{[(2-diethylamino-ethyl)-methyl-amino]-methyl}-benzamide The title compound 344 was produced in the same manner as in Example 5.
$^1$H-NMR (CDCl$_3$, 400 MHz): δ 1.03 (6H, t, J=7.2 Hz), 2.25 (3H, s), 2.27 (3H, s), 2.52-2.70 (8H, m), 3.60 (2H, s), 7.35-7.60 (5H, m), 7.80 (1H, m), 7.92 (1H, d, J=7.6 Hz), 8.00 (2H, d, J=3.9 Hz)
Mass spectrometric value (ESI-MS) 606 (M−1)

Compound 345 3-[1,4']Bipiperidinyl-1'-ylmethyl-N-[2-(3,4-dimethyl-benzylidene-hydrazinocarbonyl)-4-methyl-thiophen-3-yl]-benzamide The title compound 345 was produced in the same manner as in Example 5.
$^1$H-NMR (CDCl$_3$, 400 MHz): δ 1.44 (2H, m), 1.50-2.10 (12H, m), 2.30 (10H, m), 2.57 (2H, m), 2.96 (2H, d, J=11.7 Hz), 3.56 (2H, s), 7.17 (1H, d, J=7.6 Hz), 7.30-7.55 (6H, m), 7.92 (1H, d, J=7.6 Hz), 7.99 (1H, s)
Mass spectrometric value (ESI-MS) 570 (M−1)

Compound 346 N-[4-Bromo-2-(3-phenyl-allylidene-hydrazinocarbonyl)-phenyl]-nicotinamide The title compound 346 was produced in the same manner as in Example 1.
$^1$H-NMR (CD$_3$OD, 400 MHz): δ 9.15 (1H, s), 8.73-8.78 (1H, m), 8.54 (1H, d, J=8.8 Hz), 8.26-8.42 (1H, m), 8.17 (1H, d, J=6.6 Hz), 8.06 (1H, d, J=2.2 Hz), 7.77 (1H, dd, J=8.8 Hz, J=2.2 Hz), 7.55-7.64 (3H, m), 7.30-7.42 (3H, m), 7.05-7.10 (2H, m)
Mass spectrometric value (ESI-MS) 447 (M−1)

Compound 347 N-[4-Bromo-2-(3-phenyl-allylidene-hydrazinocarbonyl)-phenyl]-isonicotinamide The title compound 347 was produced in the same manner as in Example 1.
$^1$H-NMR (CD$_3$OD, 400 MHz): δ 8.75-8.00 (2H, m), 8.57 (1H, d, J=9.0 Hz), 8.28 (1H, d, J=7.3 Hz), 8.05-8.08 (1H, m), 7.92-7.95 (2H, m), 7.78 (1H, dd, J=2.4 Hz, J=9.0 Hz), 7.57 (2H, d, J=7.8 Hz), 7.30-7.42 (3, m), 7.05-7.10 (2H, m)
Mass spectrometric value (ESI-MS) 447 (M−1)

Compound 348 N-[4-Chloro-2-(3-phenyl-allylidene-hydrazinocarbonyl)-phenyl]-nicotinamide The title compound 348 was produced in the same manner as in Example 1.
$^1$H-NMR (CD$_3$OD, 400 MHz): δ 9.14-9.18 (1H, m), 8.75 (1H, dd, J=4.9 Hz, J=1.5 Hz), 8.59 (1H, d, J=8.8 Hz), 8.39 (1H, ddd, J=1.4 Hz, J=1.4 Hz, J=8.0 Hz), 8.17 (1H, d. J=6.8 Hz), 7.92 (1H, d, J=2.4 Hz), 7.55-7.65 (4H, m), 7.30-7.42 (3H, m), 7.05-7.10 (2H, m)
Mass spectrometric value (ESI-MS) 403 (M−1)

Compound 349 N-[4-Chloro-2-(3-phenyl-allylidene-hydrazinocarbonyl)-phenyl]-isonicotinamide The title compound 349 was produced in the same manner as in Example 1.
$^1$H-NMR (CD$_3$OD, 400 MHz): δ 8.78 (2H, dd, J=1.7 Hz, J=4.4 Hz), 8.62 (1H, d, J=9.0 Hz), 8.18 (1H, dd, J=1.4 Hz, J=7.6 Hz), 7.93-7.97 (3H, m), 7.64 (1H, dd, J=2.2 Hz, J=9.0 Hz), 7.55-7.60 (2H, m), 7.31-7.43 (3H, m), 7.06-7.12 (2H, m)
Mass spectrometric value (ESI-MS) 403 (M−1)

Compound 350 N-{4-Bromo-2-[3-(2-hydroxy-ethoxy)-benzylidene-hydrazinocarbonyl]-phenyl}-isonicotinamide The title compound 350 was produced in the same manner as in Example 1.
$^1$H-NMR (CD$_3$OD, 400 MHz): δ 8.78 (2H, dd, J=1.7 Hz, J=4.4 Hz), 8.57 (1H, d, J=8.8 Hz), 8.31 (1H, s), 8.08 (1H, d, J=2.2 Hz), 7.95 (2H, dd, J=1.7 Hz, J=4.6 Hz), 7.81 (1H, s), 7.77-7.79 (1H, m), 7.76 (1H, d, J=2.2 Hz), 7.03 (2H, d, J=8.8 Hz), 4.11 (2H, t, J=9.5 Hz), 3.89 (2H, t, J=9.3 Hz)
Mass spectrometric value (ESI-MS) 481 (M−1)

Compound 351 N-{4-Chloro-2-[3-(2-hydroxy-ethoxy)-benzylidene-hydrazinocarbonyl]-phenyl}-isonicotinamide The title compound 351 was produced in the same manner as in Example 1.
$^1$H-NMR (CD$_3$OD, 400 MHz): δ 8.78 (2H, dd, J=1.7 Hz, J=4.6 Hz), 8.63 (1H, d, J=9.0 Hz), 8.31 (1H, s), 7.93-7.97 (3H, m), 7.79 (2H, d, J=8.8 Hz), 7.64 (1H, dd, J=2.4 Hz, J=9.0 Hz), 7.03 (2H, d, J=8.8 Hz), 4.11 (2H, t, J=4.8 Hz), 3.89 (2H, t, J=4.8 Hz)
Mass spectrometric value (ESI-MS) 437 (M−1)

Compound 352 N-{4-Bromo-2-[3-(2-methoxy-phenyl)-allylidene-hydrazinocarbonyl]-phenyl}-nicotinamide The title compound 352 was produced in the same manner as in Example 1.
$^1$H-NMR (CD$_3$OD, 400 MHz): δ 9.15 (1H, d, J=2.2 Hz), 8.75 (1H, dd, J=1.4 Hz, J=4.9 Hz), 8.39 (1H, ddd, J=1.8 Hz, J=1.8 Hz, J=7.8 Hz), 8.16 (1H, d, J=9.2 Hz), 8.06 (1H, d, J=2.4 Hz), 7.77 (1H, dd, J=2.4 Hz, J=9.0 Hz), 7.56-7.65 (2H, m), 7.30-7.40 (2H, m), 7.11 (1H, dd, J=9.5 Hz, J=6.1 Hz), 7.02 (1H, d, J=8.3 Hz), 6.97 (1H, dd, J=7.7 Hz), 3.90 (3H, s)
Mass spectrometric value (ESI-MS) 479, 480 (M−1)

Compound 353 N-{4-Bromo-2-[3-(2-methoxy-phenyl)-allylidene-hydrazinocarbonyl]-phenyl}-isonicotinamide The title compound 353 was produced in the same manner as in Example 1.
$^1$H-NMR (CD$_3$OD, 400 MHz): δ 8.76-8.80 (2H, m), 8.57 (1H, d, J=8.8 Hz), 8.17 (1H, d, J=9.5 Hz), 8.07 (1H, d, J=2.4 Hz), 7.94 (2H, dd, J=1.7 Hz, J=4.4 Hz), 7.78 (1H, dd, J=2.4 Hz, J=8.9 Hz), 7.59 (1H, d, J=6.4 Hz), 7.30-7.41 (2H, m), 6.95-7.24 (3H, m), 3.90 (3H, s)
Mass spectrometric value (ESI-MS) 479, 480 (M−1)

Compound 354 N-{4-Chloro-2-[3-(2-methoxy-phenyl)-allylidene-hydrazinocarbonyl]-phenyl}-nicotinamide The title compound 354 was produced in the same manner as in Example 1.
$^1$H-NMR (CD$_3$OD, 400 MHz): δ 9.16 (1H, d, J=2.4 Hz), 8.76 (1H, dd, J=2.1 Hz, J=5.3 Hz), 8.60 (1H, d, J=9.0 Hz), 8.35-8.42 (1H, m), 8.16 (1H, d, J=9.5 Hz), 7.92 (1H, d, J=2.4 Hz), 7.58-7.65 (3H, m), 7.30-7.41 (2H, m), 7.11 (1H, dd, J=9.5 Hz, J=16.1 Hz), 7.02 (1H, d, J=7.8 Hz), 6.97 (1H, dd, J=7.6 Hz, J=7.6 Hz), 3.90 (3H, s)
Mass spectrometric value (ESI-MS) 433 (M−1)

Compound 355 N-{4-Chloro-2-[3-(2-methoxy-phenyl)-allylidene-hydrazinocarbonyl]-phenyl}-isonicotinamide The title compound 355 was produced in the same manner as in Example 1.
$^1$H-NMR (CD$_3$OD, 400 MHz): δ 8.78 (2H, d, J=4.4 Hz), 8.63 (1H, d, J=8.8 Hz), 8.17 (1H, d, J=9.3 Hz), 7.92-7.98 (3H, m), 7.55-7.70 (2H, m), 7.30-7.38 (2H, m), 7.07-7.17 (1H, m), 6.95-7.05 (2H, m)
Mass spectrometric value (ESI-MS) 435 (M−1)

Compound 356 Pyridin-2-carboxylic acid [4-bromo-2-(4-methyl-benzylidene-hydrazinocarbonyl)-phenyl]-amide hydrochloride The title compound 356 was produced in the same manner as in Example 3.
Mass spectrometric value (ESI-MS) 473 (M−1)

Compound 357 N-[4-Bromo-2-(3-methyl-benzylidene-hydrazinocarbonyl)-phenyl]-4-(3-fluoro-phenylsulfanylmethyl)-benzamide The title compound 357 was produced in the same manner as in Example 4.
$^1$H-NMR (CD$_3$OD, 400 MHz): δ 8.59 (1H, d, J=8.8 Hz), 8.33 (1H, s), 8.05-8.08 (1H, m), 7.93 (2H, d, J=8.6 Hz), 7.60-7.80 (4H, m), 7.51 (2H, d, J=8.6 Hz), 6.80-7.40 (5H, m), 4.27 (2H, s), 2.40 (3H, s)
Mass spectrometric value (ESI-MS) 574 (M−1)

Compound 358 N-{2-[3-(4-Dimethylamino-phenyl)-allylidene-hydrazinocarbonyl]-phenyl}-nicotinamide The title compound 358 was produced in the same manner as in Example 1.
$^1$H-NMR (CD$_3$OD, 400 MHz): δ 9.17 (1H, s, J=1.5 Hz), 8.75 (1H, dd, J=1.5 Hz, H=4.9 Hz), 8.60 (1H, d, J=8.3 Hz), 8.38-8.44 (1H, m), 8.11 (1H, d, J=9.0 Hz), 7.85 (1H, d, J=7.8 Hz), 7.60-7.65 (2H, m), 7.42 (2H, d, J=8.8 Hz), 7.29 (1H, dd, J=7.7 Hz, J=7.7 Hz), 6.94-7.00 (1H, m), 6.80-6.88 (1H, m), 6.74 (2H, d, J=9.0 Hz), 3.00 (6H, s)
Mass spectrometric value (ESI-MS) 412 (M−1)

Compound 359 Pyridin-2-carboxylic acid [4-chloro-2-(3-fluoro-benzylidene-hydrazinocarbonyl)-phenyl]-amide The title compound 359 was produced in the same manner as in Example 1.
$^1$H-NMR (CD$_3$OD, 400 MHz): δ 8.79 (1H, d, J=9.0 Hz), 8.73 (1H, d, J=5.1 Hz), 8.33 (1H, s), 8.22 (1H, d, J=7.8 Hz), 7.98-8.04 (1H, m), 7.89 (1H, d, J=2.4 Hz), 7.73 (1H, d, J=10.0 Hz), 7.58-7.66 (3H, m), 7.42-7.50 (1H, m), 7.15-7.22 (1H, m)
Mass spectrometric value (ESI-MS) 395 (M−1)

Compound 360 Pyridin-2-carboxylic acid [4-chloro-2-(4-fluoro-benzylidene-hydrazinocarbonyl)-phenyl]-amide The title compound 360 was produced in the same manner as in Example 1.
$^1$H-NMR (CD$_3$OD, 400 MHz): δ 8.78 (1H, d, J=8.8 Hz), 8.72 (1H, d, J=4.9 Hz), 8.33 (1H, s), 8.22 (1H, d, J=7.8 Hz), 8.01 (1H, ddd, J=7.8 Hz, J=7.8 Hz, J=1.4 Hz), 7.89-7.95 (2H, m), 7.88 (1H, d, J=2.4 Hz), 7.58-7.65 (2H, m), 7.19 (2H, dd, J=8.8 Hz, J=8.8 Hz)
Mass spectrometric value (ESI-MS) 395 (M−1)

Compound 361 Pyridin-2-carboxylic acid [4-chloro-2-(3-methyl-benzylidene-hydrazinocarbonyl)-phenyl]-amide The title compound 361 was produced in the same manner as in Example 1.
$^1$H-NMR (CD$_3$OD, 400 MHz): δ 8.78 (1H, d, J=9.0 Hz), 8.73 (1H, d, J=4.6 Hz), 8.31 (1H, s), 8.22 (1H, d, J=7.8 Hz), 7.98-8.04 (1H, m), 7.88 (1H, d, J=2.4 Hz), 7.72 (1H, s), 7.56-7.66 (3H, m), 7.24-7.35 (2H, m), 2.40 (3H, s)
Mass spectrometric value (ESI-MS) 391 (M−1)

Compound 362 Pyridin-2-carboxylic acid [4-chloro-2-(4-methyl-benzylidene-hydrazinocarbonyl)-phenyl]-amide The title compound 362 was produced in the same manner as in Example 1.
$^1$H-NMR (CD$_3$OD, 400 MHz): δ 8.78 (1H, d, J=8.8 Hz), 8.73 (1H, d, J=4.9 Hz), 8.30 (1H, s), 8.22 (1H, d, J=7.8 Hz), 8.01 (1H, ddd, J=8.5 Hz, J=8.5 Hz, J=1.7 Hz), 7.87 (1H, d, J=2.4 Hz), 7.75 (2H, d, J=8.0 Hz), 7.57-7.64 (2H, m), 7.27 (2H, d, J=8.0 Hz), 2.38 (3H, s)
Mass spectrometric value (ESI-MS) 391 (M−1)

Compound 363 Pyridin-2-carboxylic acid [4-chloro-2-(3,4-dimethyl-benzylidene-hydrazinocarbonyl)-phenyl]-amide The title compound 363 was produced in the same manner as in Example 1.
$^1$H-NMR (CD$_3$OD, 400 MHz): δ 8.77 (1H, d, J=9.0 Hz), 8.73 (1H, d, J=4.4 Hz), 8.27 (1H, s), 8.22 (1H, d, J=7.8 Hz), 8.00 (1H, ddd, J=1.7 Hz, J=7.7 Hz, J=7.7 Hz), 7.87 (1H, d, J=2.4 Hz), 7.67 (1H, s), 7.53-7.64 (3H, m), 7.20 (1H, d, J=7.8 Hz), 2.32 (3H, s), 2.30 (3H, s)
Mass spectrometric value (ESI-MS) 405 (M−1)

Compound 364 Pyridin-2-carboxylic acid [4-chloro-2-(4-chloro-3-trifluoromethyl-benzylidene-hydrazinocarbonyl)-phenyl]-amide The title compound 364 was produced in the same manner as in Example 1.
$^1$H-NMR (CD$_3$OD, 400 MHz): δ 8.79 (1H, d, J=9.0 Hz), 8.71-8.75 (1H, m), 8.35-8.40 (2H, m), 8.22 (1H, d, J=7.8 Hz), 8.07 (1H, d, J=8.3 Hz), 7.98-8.04 (1H, m), 7.90 (1H, d, J=2.2 Hz), 7.70 (1H, d, J=8.6 Hz), 7.58-7.67 (2H, m)
Mass spectrometric value (ESI-MS) 479 (M−1)

Compound 366 N-{4-Chloro-2-[N'-(3,4-dimethyl-benzyl)-hydrazinocarbonyl]-phenyl}-3-(pyridin-4-ylsulfanylmethyl)-benzamide The title compound 366 was produced in the same manner as in Example 7.
Mass spectrometric value (ESI-MS) 529, 531, 532 (M−1)

Example 7

Compound 367 N-{4-Bromo-2-[N'-(4-methyl-benzyl)-hydrazinocarbonyl]-phenyl}-3,4-dimethoxy-benzamide Compound 62: N-[4-bromo-2-(4-methyl-benzylidene-hydrazinocarbonyl)-phenyl]-3,4-dimethoxy-benzamide (100 mg) produced in the same manner as in Example 1 was dissolved in a mixed solution (2.0 ml) of tetrahydrofuran/methanol=4/1, and sodium borohydride (14.0 mg) was added to the mixed solution at room temperature. The mixture was stirred at that temperature for 30 min, and, after the completion of the reaction was confirmed by TLC, distilled water (2.0 ml) was poured thereinto. The mixture was subjected to separatory extraction with chloroform, and the organic layer was dried over sodium sulfate and was then concentrated under the reduced pressure. The residue was purified by preparative TLC to give the title compound 367 (42.2 mg).
$^1$H-NMR (CD$_3$OD, 400 MHz): δ 8.66 (1H, d, J=8.8 Hz), 8.35 (1H, s), 8.06 (1H, s), 7.87-7.95 (4H, m), 7.63 (1H, d, J=8.8 Hz), 7.62 (1H, d, J=8.8 Hz), 7.50 (1H, dd, J=7.6 Hz, J=7.6 Hz), 7.19 (2H, dd, J=8.8 Hz), 3.83 (2H, s), 3.65 (4H, t, J=5.9 Hz), 2.71 (4H, t, J=5.9 Hz)
Mass spectrometric value (ESI-MS) 496, 497, 498, 499 (M−1)

Compound 368 3-[1,4']Bipiperidinyl-1'-ylmethyl-N-[4-chloro-2-(3-fluoro-benzylidene-hydrazinocarbonyl)-phenyl]-benzamide The title compound 368 was produced in the same manner as in Example 5.
$^1$H-NMR (CD$_3$OD, 400 MHz): δ 8.64 (1H, d, J=8.8 Hz), 8.35 (1H, s), 7.89-7.98 (3H, m), 7.70 (1H, d, J=9.8 Hz), 7.57-7.64 (3H, m), 7.42-7.50 (2H, m), 7.10-7.23 (1H, m), 3.62 (2H, s), 2.99 (2H, d, J=12.0 Hz), 2.59 (4H, bs), 2.29-2.39 (1H, m), 2.06 (2H, t, J=11.5 Hz), 1.86 (2H, d, J=11.7 Hz), 1.55-1.68 (6H, m), 1.40-1.50 (2H, m)
Mass spectrometric value (ESI-MS) 574, 576 (M−1)

Compound 369 3-[1,4']Bipiperidinyl-1'-ylmethyl-N-[4-chloro-2-(4-fluoro-benzylidene-hydrazinocarbonyl)-phenyl]-benzamide The title compound 369 was produced in the same manner as in Example 5.
$^1$H-NMR (CD$_3$OD, 400 MHz): δ 8.63 (1H, d, J=9.0 Hz), 8.35 (1H, s), 7.88-7.97 (5H, m), 7.56-7.64 (2H, m), 7.52 (1H, dd, J=7.7 Hz, J=7.7 Hz), 7.15-7.22 (2H, m), 3.62 (2H, s), 3.98 (2H, d, J=12.2 Hz), 2.57 (4H, bs), 2.25-2.35 (1H, m), 2.05 (2H, t, J=11.1 Hz), 1.80-1.90 (2H, m), 1.53-1.66 (7H, m), 1.40-1.50 (2H, m)
Mass spectrometric value (ESI-MS) 574, 576 (M−1)

Compound 370 3-[1,4']Bipiperidinyl-1'-ylmethyl-N-[4-chloro-2-(3-methyl-benzylidene-hydrazinocarbonyl)-phenyl]-benzamide The title compound 370 was produced in the same manner as in Example 5.
$^1$H-NMR (CD$_3$OD, 400 MHz): δ 8.53 (1H, d, J=9.0 Hz), 8.33 (1H, s), 7.88-7.98 (4H, m), 7.71 (1H, s), 7.57-7.65 (3H, m), 7.52 (1H, dd, J=7.7 Hz, J=7.7 Hz), 7.25-7.37 (2H, m), 3.63 (2H, s), 3.99 (2H, d, J=12.0 Hz), 2.56 (4H, bs), 2.39 (3H, s), 2.25-2.37 (1H, m), 2.06 (2H, t, J=11.3 Hz), 1.80-1.90 (2H, m), 1.55-1.64 (6H, m), 1.40-1.49 (2H, m)
Mass spectrometric value (ESI-MS) 570, 571 (M−1)

Compound 371 3-[1,4']Bipiperidinyl-1'-ylmethyl-N-[4-chloro-2-(4-methyl-benzylidene-hydrazinocarbonyl)-phenyl]-benzamide The title compound 371 was produced in the same manner as in Example 5.
$^1$H-NMR (CD$_3$OD, 400 MHz): δ 8.64 (1H, d, J=9.0 Hz), 8.33 (1H, s), 7.89-7.98 (3H, m), 7.74 (2H, d, J=8.3 Hz), 7.57-7.64 (2H, m), 7.52 (1H, dd, J=7.7 Hz, J=7.7 Hz), 7.27 (2H, d, J=7.8 Hz), 3.63 (2H, s), 2.95-3.05 (2H, m), 2.56 (4H, bs), 2.39 (3H, s), 2.25-2.35 (1H, m), 2.00-2.10 (2H, m), 1.80-1.90 (2H, m), 1.59 (6H, bs), 1.40-1.50 (2H, m)
Mass spectrometric value (ESI-MS) 570, 571 (M−1)

Compound 372 3-[1,4']Bipiperidinyl-1'-ylmethyl-N-[4-chloro-2-(3,4-dimethyl-benzylidene-hydrazinocarbonyl)-phenyl]-benzamide The title compound 372 was produced in the same manner as in Example 5.

$^1$H-NMR (CD$_3$OD, 400 MHz): δ 8.64 (1H, d, J=9.0 Hz), 8.30 (1H, s), 7.96 (1H, s), 7.89-7.95 (2H, m), 7.65 (1H, s), 7.49-7.68 (4H, m), 7.20 (1H, d, J=8.0 Hz), 3.62 (2H, s), 2.99 (2H, d, J=11.5 Hz), 2.55 (4H, bs), 2.32 (3H, s), 2.30 (3H, s), 2.25-2.30 (1H, m), 2.01-2.10 (2H, m), 1.80-1.88 (2H, m), 1.54-1.65 (6H, m), 1.40-1.50 (2H, m)

Mass spectrometric value (ESI-MS) 584, 585 (M−1)

Compound 373 3-[1,4']Bipiperidinyl-1'-ylmethyl-N-[4-chloro-2-(4-chloro-3-trifluoromethyl-benzylidene-hydrazinocarbonyl)-phenyl]-benzamide The title compound 373 was produced in the same manner as in Example 5.

$^1$H-NMR (CD$_3$OD, 400 MHz): δ 8.63 (1H, d, J=9.0 Hz), 8.35 (1H, s), 8.05 (1H, d, J=8.3 Hz), 7.89-7.98 (4H, m), 7.71 (1H, d, J=8.6 Hz), 7.64 (1H, dd, J=9.0 Hz, J=2.2 Hz), 7.56-7.62 (1H, m), 7.53 (1H, dd, J=7.6 Hz, J=7.6 Hz), 3.66 (2H, s), 3.00-3.10 (6H, m), 2.09-2.18 (3H, m), 1.96-2.03 (2H, m), 1.70-1.80 (6H, m), 1.55-1.65 (2H, m)

Mass spectrometric value (ESI-MS) 658, 660 (M−1)

Compound 374 3-[1,4']Bipiperidinyl-1'-ylmethyl-N-[4-chloro-2-(3-methoxy-benzylidene-hydrazinocarbonyl)-phenyl]-benzamide The title compound 374 was produced in the same manner as in Example 5.

$^1$H-NMR (CD$_3$OD, 400 MHz): δ 8.62 (1H, d, J=9.0 Hz), 8.32 (1H, s), 7.87-7.98 (4H, m), 7.47-7.65 (4H, m), 7.28-7.38 (2H, m), 6.97-7.03 (1H, m), 3.86 (3H, s), 3.61 (3H, s), 2.97 (2H, d, J=10.5 Hz), 2.55 (4H, bs), 2.25-2.35 (1H, m), 1.97-2.10 (2H, m), 1.80-1.88 (2H, m), 1.54-1.65 (6H, m), 1.44 (2H, bs)

Mass spectrometric value (ESI-MS) 586, 588 (M−1)

Compound 375 3-[1,4']Bipiperidinyl-1'-ylmethyl-N-[4-chloro-2-(4-methoxy-benzylidene-hydrazinocarbonyl)-phenyl]-benzamide The title compound 375 was produced in the same manner as in Example 5.

$^1$H-NMR (CD$_3$OD, 400 MHz): δ 8.64 (1H, d, J=9.0 Hz), 8.30 (1H, s), 7.96 (1H, s), 7.89-7.94 (2H, m), 7.79 (2H, d, J=8.8 Hz), 7.57-7.64 (2H, m), 7.52 (1H, dd, J=7.6 Hz, J=7.6 Hz), 6.99 (2H, d, J=8.8 Hz), 3.85 (3H, s), 3.62 (2H, s), 3.99 (2H, d, J=12.0 Hz), 2.56 (4H, bs), 2.25-2.35 (1H, m), 2.05 (2H, t, J=11.0 Hz), 1.80-1.90 (2H, m), 1.55-1.65 (6H, m), 1.40-1.50 (2H, m)

Mass spectrometric value (ESI-MS) 586, 587 (M−1)

Compound 376 3-[1,4']Bipiperidinyl-1'-ylmethyl-N-[4-chloro-2-(3-hydroxy-benzylidene-hydrazinocarbonyl)-phenyl]-benzamide The title compound 376 was produced in the same manner as in Example 5.

$^1$H-NMR (CD$_3$OD, 400 MHz): δ 8.64 (1H, d, J=9.0 Hz), 8.29 (1H, s), 7.89-7.98 (4H, m), 7.62 (1H, dd, J=2.4 Hz, J=9.0 Hz), 7.59 (1H, d, J=7.8 Hz), 7.52 (1H, dd, J=7.6 Hz, J=7.6 Hz), 7.32 (1H, s), 7.20-7.30 (2H, m), 6.85-6.90 (1H, m), 3.64 (2H, s), 3.02 (2H, d, J=11.7 Hz), 2.66 (4H, bs), 2.32 (1H, bs), 2.08 (2H, t, J=11.4 Hz), 1.85-1.93 (2H, m), 1.52-1.68 (6H, m), 1.40-1.51 (2H, m)

Mass spectrometric value (ESI-MS) 572, 574 (M−1)

Compound 377 3-[1,4']Bipiperidinyl-1'-ylmethyl-N-[4-chloro-2-(4-hydroxy-benzylidene-hydrazinocarbonyl)-phenyl]-benzamide The title compound 377 was produced in the same manner as in Example 5.

$^1$H-NMR (CD$_3$OD, 400 MHz): δ 8.64 (1H, d, J=9.0 Hz), 8.26 (1H, s), 7.96 (1H, s), 7.88-7.94 (2H, m), 7.70 (1H, d, J=8.8 Hz), 7.62 (2H, d, J=2.4 Hz), 7.57-7.63 (2H, m), 7.52 (1H, dd, J=7.6 Hz, J=7.6 Hz), 6.84 (2H, d, J=8.5 Hz), 3.63 (2H, s), 2.99 (2H, d, J=12.0 Hz), 2.57 (4H, bs), 2.27-2.36 (1H, m), 2.06 (2H, t, J=11.2 Hz), 1.85 (2H, d, J=12.7 Hz), 1.52-1.67 (6H, m), 1.40-1.50 (2H, m)

Mass spectrometric value (ESI-MS) 572, 574, 575 (M−1)

Compound 378 4-[1,4']Bipiperidinyl-1'-ylmethyl-N-{4-bromo-2-[N'-(3-methoxy-benzyl)-hydrazinocarbonyl]-phenyl}-benzamide The title compound 378 was produced in the same manner as in Example 7.

Mass spectrometric value (ESI-MS) 632, 634 (M−1)

Compound 379 N-[4-Chloro-2-(3-fluoro-benzylidene-hydrazinocarbonyl)-phenyl]-3-{[(2-diethylamino-ethyl)-methyl-amino]-methyl}-benzamide The title compound 379 was produced in the same manner as in Example 5.

$^1$H-NMR (CD$_3$OD, 400 MHz): δ 8.64 (1H, d, J=9.0 Hz), 8.35 (1H, s), 7.90-8.00 (2H, m), 7.89 (1H, s), 7.70 (1H, d, J=9.8 Hz), 7.56-7.63 (3H, m), 7.53 (1H, dd, J=7.7 Hz), 7.43-7.49 (1H, m), 3.67 (2H, s), 2.69-2.75 (2H, m), 2.54-2.64 (6H, m), 2.28 (3H, s), 1.03 (6H, t, J=7.2 Hz)

Mass spectrometric value (ESI-MS) 536, 538 (M−1)

Compound 380 N-[4-Chloro-2-(4-fluoro-benzylidene-hydrazinocarbonyl)-phenyl]-3-{[(2-diethylamino-ethyl)-methyl-amino]-methyl}-benzamide The title compound 380 was produced in the same manner as in Example 5.

$^1$H-NMR (CD$_3$OD, 400 MHz): δ 8.64 (1H, d, J=9.0 Hz), 8.35 (1H, s), 7.98 (1H, s), 7.94 (1H, d, J=2.2 Hz), 7.87-7.93 (3H, m), 7.58-7.64 (2H, m), 7.53 (1H, dd, J=7.4 Hz, J=7.4 Hz), 7.19 (2H, dd, J=8.8 Hz, J=8.8 Hz), 3.67 (2H, s), 2.68-2.74 (2H, m), 2.53-2.63 (6H, m), 2.28 (3H, s), 1.02 (6H, t, J=7.2 Hz)

Mass spectrometric value (ESI-MS) 536, 538 (M−1)

Compound 381 N-[4-Chloro-2-(3-methyl-benzylidene-hydrazinocarbonyl)-phenyl]-3-{[(2-diethylamino-ethyl)-methyl-amino]-methyl}-benzamide The title compound 381 was produced in the same manner as in Example 5.

$^1$H-NMR (CD$_3$OD, 400 MHz): δ 8.65 (1H, d, J=9.0 Hz), 8.33 (1H, s), 7.99 (1H, s), 7.89-7.96 (2H, m), 7.71 (2H, s), 7.58-7.65 (2H, m), 7.53 (1H, dd, J=7.6 Hz, J=7.6 Hz), 7.25-7.35 (2H, m), 3.67 (2H, s), 2.67-2.75 (2H, m), 2.51-2.62 (6H, m), 2.39 (3H, s), 2.28 (3H, s), 1.01 (6H, t, J=7.2 Hz)

Mass spectrometric value (ESI-MS) 532, 534 (M−1)

Compound 382 N-[4-Chloro-2-(4-methyl-benzylidene-hydrazinocarbonyl)-phenyl]-3-{[(2-diethylamino-ethyl)-methyl-amino]-methyl}-benzamide The title compound 382 was produced in the same manner as in Example 5.
$^1$H-NMR (CD$_3$OD, 400 MHz): δ 8.64 (1H, d, J=9.0 Hz), 8.33 (1H, s), 7.98 (1H, s), 7.88-7.94 (2H, m), 7.73 (2H, d, J=8.3 Hz), 7.58-7.63 (2H, m), 7.52 (1H, dd, J=7.6 Hz, J=7.6 Hz), 7.26 (2H, d, J=8.0 Hz), 3.67 (2H, s), 2.68-2.74 (2H, m), 2.53-2.63 (6H, m), 2.38 (3H, s), 2.28 (3H, s), 1.02 (6H, t, J=7.2 Hz)
Mass spectrometric value (ESI-MS) 532, 534 (M−1)

Compound 383 N-[4-Chloro-2-(3,4-dimethyl-benzylidene-hydrazinocarbonyl)-phenyl]-3-{[(2-diethylamino-ethyl)-methyl-amino]-methyl}-benzamide The title compound 383 was produced in the same manner as in Example 5.
$^1$H-NMR (CD$_3$OD, 400 MHz): δ 8.65 (1H, d, J=9.0 Hz), 8.30 (1H, s), 7.99 (1H, s), 7.89-7.95 (2H, m), 7.66 (1H, s), 7.58-7.64 (2H, m), 7.50-7.57 (2H, m), 7.20 (1H, d, J=8.1 Hz), 3.67 (2H, s), 2.68-2.75 (2H, m), 2.54-2.63 (6H, m), 2.32 (3H, s), 2.31 (3H, s), 2.29 (3H, s), 1.02 (6H, t, J=7.3 Hz)
Mass spectrometric value (ESI-MS) 546, 548 (M−1)

Compound 384 N-[4-Chloro-2-(4-chloro-3-trifluoromethyl-benzylidene-hydrazinocarbonyl)-phenyl]-3-{[(2-diethylamino-ethyl)-methyl-amino]-methyl}-benzamide The title compound 384 was produced in the same manner as in Example 5.
$^1$H-NMR (CD$_3$OD, 400 MHz): δ 8.63 (1H, d, J=8.8 Hz), 8.38 (1H, s), 8.33 (1H, s), 8.03 (1H, d, J=8.3 Hz), 7.95-8.00 (2H, m), 7.92 (1H, d, J=7.8 Hz), 7.68 (1H, d, J=8.3 Hz), 7.57-7.64 (2H, m), 7.53 (1H, s), 3.66 (2H, s), 2.71-2.79 (2H, m), 2.54-2.66 (6H, m), 2.28 (3H, s), 1.03 (6H, t, J=7.2 Hz)
Mass spectrometric value (ESI-MS) 620, 622 (M−1)

Compound 385 N-[4-Chloro-2-(3-methoxy-benzylidene-hydrazinocarbonyl)-phenyl]-3-{[(2-diethylamino-ethyl)-methyl-amino]-methyl}-benzamide The title compound 385 was produced in the same manner as in Example 5.
$^1$H-NMR (CD$_3$OD, 400 MHz): δ 8.64 (1H, d, J=9.0 Hz), 8.33 (1H, s), 7.98 (1H, s), 7.89-7.96 (2H, m), 7.49-7.63 (4H, m), 7.27-7.37 (2H, m), 6.95-7.05 (1H, m), 3.86 (3H, s), 3.66 (2H, s), 2.67-2.73 (2H, m), 2.53-2.62 (6H, m), 2.27 (3H, s), 1.02 (6H, t, J=7.2 Hz)
Mass spectrometric value (ESI-MS) 548, 550 (M−1)

Compound 386 N-[4-Chloro-2-(4-methoxy-benzylidene-hydrazinocarbonyl)-phenyl]-3-{[(2-diethylamino-ethyl)-methyl-amino]-methyl}-benzamide The title compound 386 was produced in the same manner as in Example 5.
$^1$H-NMR (CD$_3$OD, 400 MHz): δ 8.64 (1H, d, J=9.0 Hz), 8.30 (1H, s), 7.98 (1H, s), 7.88-7.95 (2H, m), 7.79 (2H, d, J=9.0 Hz), 7.58-7.64 (2H, m), 7.52 (1H, dd, J=7.7 Hz, J=7.7 Hz), 6.99 (2H, d, J=8.8 Hz), 3.84 (3H, s), 3.66 (2H, s), 2.67-2.73 (2H, m), 2.52-2.62 (6H, m), 2.28 (3H, s), 1.02 (6H, t, J=7.2 Hz)
Mass spectrometric value (ESI-MS) 548, 550 (M−1)

Compound 387 N-[4-Chloro-2-(3-hydroxy-benzylidene-hydrazinocarbonyl)-phenyl]-3-{[(2-diethylamino-ethyl)-methyl-amino]-methyl}-benzamide The title compound 387 was produced in the same manner as in Example 5.
$^1$H-NMR (CD$_3$OD, 400 MHz): δ 8.64 (1H, d, J=9.0 Hz), 8.29 (1H, s), 7.91 (1H, s), 7.88-7.95 (2H, m), 7.61 (2H, dd, J=2.2 Hz, J=9.0 Hz), 7.53 (1H, dd, J=7.7 Hz, J=7.7 Hz), 7.21-7.34 (3H, m), 6.85-6.90 (1H, ddd, J=2.2 Hz, J=2.2 Hz, J=6.8 Hz), 3.67 (2H, s), 2.70-2.75 (2H, m), 2.54-2.64 (6H, m), 2.28 (3H, s), 1.02 (6H, t, J=7.2 Hz)
Mass spectrometric value (ESI-MS) 534, 536 (M−1)

Compound 388 N-[4-Chloro-2-(4-hydroxy-benzylidene-hydrazinocarbonyl)-phenyl]-3-{[(2-diethylamino-ethyl)-methyl-amino]-methyl}-benzamide The title compound 388 was produced in the same manner as in Example 5.
$^1$H-NMR (CD$_3$OD, 400 MHz): δ 8.65 (1H, d, J=9.0 Hz), 8.27 (1H, s), 7.98 (1H, s), 7.88-7.95 (2H, m), 7.70 (2H, d, J=8.8 Hz), 7.61 (2H, dd, J=1.8 Hz, J=8.8 Hz), 7.53 (1H, dd, J=7.7 Hz, J=7.7 Hz), 6.84 (2H, d, J=8.8 Hz), 3.68 (2H, s), 2.76 (2H, t, J=7.3 Hz), 2.55-2.68 (6H, m), 2.29 (3H, s), 1.04 (6H, t, J=7.2 Hz)
Mass spectrometric value (ESI-MS) 534, 536 (M−1)

Compound 389 N-[4-Chloro-2-(3-fluoro-benzylidene-hydrazinocarbonyl)-phenyl]-3-(1H-[1,2,4]triazol-3-ylsulfanylmethyl)-benzamide The title compound 389 was produced in the same manner as in Example 4.
Mass spectrometric value (ESI-MS) 506 (M−1)

Compound 390 N-[4-Chloro-2-(4-fluoro-benzylidene-hydrazinocarbonyl)-phenyl]-3-(1H-[1,2,4]triazol-3-ylsulfanylmethyl)-benzamide The title compound 390 was produced in the same manner as in Example 4.
Mass spectrometric value (ESI-MS) 506 (M−1)

Compound 391 N-[4-Chloro-2-(3-methyl-benzylidene-hydrazinocarbonyl)-phenyl]-3-(1H-[1,2,4]triazol-3-ylsulfanylmethyl)-benzamide The title compound 391 was produced in the same manner as in Example 4.
Mass spectrometric value (ESI-MS) 503, 504 (M−1)

Compound 392 N-[4-Chloro-2-(4-methyl-benzylidene-hydrazinocarbonyl)-phenyl]-3-(1H-[1,2,4]triazol-3-ylsulfanylmethyl)-benzamide The title compound 392 was produced in the same manner as in Example 4.
Mass spectrometric value (ESI-MS) 503, 504 (M−1)

Compound 393 N-[4-Chloro-2-(4-chloro-3-trifluoromethyl-benzylidene-hydrazinocarbonyl)-phenyl]-3-(1H-[1,2,4]triazol-3-ylsulfanylmethyl)-benzamide The title compound 393 was produced in the same manner as in Example 4.
Mass spectrometric value (ESI-MS) 591, 593 (M−1)

Compound 394 N-[4-Chloro-2-(3-fluoro-benzylidene-hydrazinocarbonyl)-phenyl]-3-{[(2-hydroxy-ethyl)-methyl-amino]-methyl}-benzamide The title compound 394 was produced in the same manner as in Example 5.
$^1$H-NMR (CD$_3$OD, 400 MHz): δ 8.64 (1H, d, J=9.0 Hz), 8.35 (1H, s), 8.00 (1H, s), 7.88-7.95 (2H, m), 7.71 (1H, d, J=9.3 Hz), 7.58-7.67 (3H, m), 7.53 (1H, dd, J=7.7 Hz, J=7.7 Hz), 7.42-7.50 (1H, m), 7.15-7.22 (1H, m), 3.69-3.74 (4H, m), 2.62 (2H, t, J=6.0 Hz), 2.30 (3H, s)
Mass spectrometric value (ESI-MS) 481, 483 (M−1)

Compound 395 N-[4-Chloro-2-(4-fluoro-benzylidene-hydrazinocarbonyl)-phenyl]-3-{[(2-hydroxy-ethyl)-methyl-amino]-methyl}-benzamide The title compound 395 was produced in the same manner as in Example 5.
$^1$H-NMR (CD$_3$OD, 400 MHz): δ 8.63 (1H, d, J=9.0 Hz), 8.35 (1H, s), 7.95-8.02 (2H, m), 7.87-7.95 (3H, m), 7.63 (1H, d, J=9.0 Hz), 7.62 (1H, d, J=9.0 Hz), 7.52 (1H, dd, J=7.7 Hz, J=7.7 Hz), 7.19 (2H, dd, J=8.8 Hz, J=8.8 Hz), 3.69-3.75 (4H, m), 2.62 (2H, t, J=6.0 Hz), 2.30 (3H, s)
Mass spectrometric value (ESI-MS) 481, 483 (M−1)

Compound 396 N-[4-Chloro-2-(3-methyl-benzylidene-hydrazinocarbonyl)-phenyl]-3-{[(2-hydroxy-ethyl)-methyl-amino]-methyl}-benzamide The title compound 396 was produced in the same manner as in Example 5.
$^1$H-NMR (CD$_3$OD, 400 MHz): δ 8.65 (1H, d, J=8.8 Hz), 8.33 (1H, s), 7.99 (1H, s), 7.88-7.95 (3H, m), 7.71 (1H, s), 7.60-7.65 (3H, m), 7.52 (1H, dd, J=7.6 Hz, J=7.6 Hz), 7.25-7.36 (2H, m), 3.68-3.74 (4H, m), 2.61 (2H, t, J=6.0 Hz), 2.39 (3H, s), 2.29 (3H, s)
Mass spectrometric value (ESI-MS) 477 (M−1)

Compound 397 N-[4-Chloro-2-(4-methyl-benzylidene-hydrazinocarbonyl)-phenyl]-3-{[(2-hydroxy-ethyl)-methyl-amino]-methyl}-benzamide The title compound 397 was produced in the same manner as in Example 5.
$^1$H-NMR (CD$_3$OD, 400 MHz): δ 8.64 (1H, d, J=9.0 Hz), 8.33 (1H, s), 8.00 (1H, bs), 7.90-7.95 (2H, m), 7.74 (2H, d, J=7.8 Hz), 7.60-7.65 (2H, m), 7.53 (1H, dd, J=7.7 Hz, J=7.7 Hz), 7.27 (2H, d, J=7.8 Hz), 3.70-3.78 (4H, m), 2.65 (2H, t, J=6.0 Hz), 2.38 (3H, s), 2.32 (3H, s)
Mass spectrometric value (ESI-MS) 477 (M−1)

Compound 398 N-[4-Chloro-2-(3,4-dimethyl-benzylidene-hydrazinocarbonyl)-phenyl]-3-{[(2-hydroxy-ethyl)-methyl-amino]-methyl}-benzamide The title compound 398 was produced in the same manner as in Example 5.
$^1$H-NMR (CD$_3$OD, 400 MHz): δ 8.65 (1H, d, J=9.0 Hz), 8.30 (1H, s), 8.00 (1H, bs), 7.90-7.95 (2H, m), 7.66 (1H, s), 7.59-7.65 (2H, m), 7.50-7.57 (2H, m), 7.20 (1H, d, J=7.8 Hz), 3.76 (2H, s), 3.73 (2H, t, J=6.0 Hz), 2.66 (2H, t, J=6.0 Hz), 2.33 (3H, s), 2.31 (3H, s), 2.30 (3H, s)
Mass spectrometric value (ESI-MS) 491 (M−1)

Compound 399 N-[4-Chloro-2-(4-chloro-3-trifluoromethyl-benzylidene-hydrazinocarbonyl)-phenyl]-3-{[(2-hydroxy-ethyl)-methyl-amino]-methyl}-benzamide The title compound 399 was produced in the same manner as in Example 5.
$^1$H-NMR (CD$_3$OD, 400 MHz): δ 8.63 (1H, d, J=9.0 Hz), 8.39 (1H, s), 8.34 (1H, s), 8.03-8.08 (1H, m), 8.00 (1H, s), 7.94 (1H, d, J=2.4 Hz), 7.90 (1H, d, J=8.3 Hz), 7.70 (1H, d, J=8.5 Hz), 7.58-7.67 (2H, m), 7.52 (1H, dd, J=7.6 Hz, J=7.6 Hz), 3.68-3.74 (4H, m), 2.60 (2H, t, J=6.0 Hz), 2.28 (3H, s)
Mass spectrometric value (ESI-MS) 565 (M−1)

Compound 400 N-[4-Chloro-2-(3-methoxy-benzylidene-hydrazinocarbonyl)-phenyl]-3-{[(2-hydroxy-ethyl)-methyl-amino]-methyl}-benzamide The title compound 400 was produced in the same manner as in Example 5.
$^1$H-NMR (CD$_3$OD, 400 MHz): δ 8.64 (1H, d, J=9.0 Hz), 8.33 (1H, s), 7.99 (1H, s), 7.88-7.94 (2H, m), 7.58-7.64 (2H, m), 7.57 (1H, s), 7.48-7.54 (1H, m), 7.26-7.36 (2H, m), 6.97-7.02 (1H, m), 3.86 (3H, s), 3.68-3.74 (4H, m), 2.61 (2H, t, J=6.1 Hz), 2.29 (3H, s)
Mass spectrometric value (ESI-MS) 493, 495 (M−1)

Compound 401 N-[4-Chloro-2-(4-methoxy-benzylidene-hydrazinocarbonyl)-phenyl]-3-{[(2-hydroxy-ethyl)-methyl-amino]-methyl}-benzamide The title compound 401 was produced in the same manner as in Example 5.
$^1$H-NMR (CD$_3$OD, 400 MHz): δ 8.65 (1H, d, J=9.0 Hz), 8.31 (1H, s), 7.99 (1H, s), 7.75-7.93 (5H, m), 7.58-7.65 (2H, m), 7.53 (1H, dd, J=7.7 Hz, J=7.7 Hz), 7.00 (1H, d, J=8.8 Hz), 3.85 (3H, s), 3.67-3.74 (4H, m), 2.63 (2H, t, J=6.1 Hz), 2.31 (3H, s)
Mass spectrometric value (ESI-MS) 493, 494 (M−1)

Compound 402 N-[4-Chloro-2-(3-hydroxy-benzylidene-hydrazinocarbonyl)-phenyl]-3-{[(2-hydroxy-ethyl)-methyl-amino]-methyl}-benzamide The title compound 402 was produced in the same manner as in Example 5.
$^1$H-NMR (CD$_3$OD, 400 MHz): δ 8.63 (1H, d, J=9.0 Hz), 8.29 (1H, s), 7.99 (1H, s), 7.88-7.94 (3H, m), 7.62 (2H, d, J=7.8 Hz), 7.52 (1H, dd, J=7.7 Hz, J=7.7 Hz), 7.31 (1H, bs), 7.23-7.28 (2H, m), 3.68-3.74 (4H, m), 2.61 (2H, t, J=6.1 Hz), 2.29 (3H, s)
Mass spectrometric value (ESI-MS) 479 (M−1)

Compound 403 N-[4-Chloro-2-(4-hydroxy-benzylidene-hydrazinocarbonyl)-phenyl]-3-{[(2-hydroxy-ethyl)-methyl-amino]-methyl}-benzamide The title compound 403 was produced in the same manner as in Example 5.
$^1$H-NMR (CD$_3$OD, 400 MHz): δ 8.65 (1H, d, J=9.0 Hz), 8.27 (1H, s), 7.99 (1H, s), 7.89-7.94 (3H, m), 7.71 (2H, d, J=8.7 Hz), 7.58-7.65 (2H, m), 7.52 (1H, dd, J=7.7 Hz, J=7.7 Hz), 6.84 (2H, d, J=8.7 Hz), 3.71 (2H, t, J=6.1 Hz), 3.70 (2H, s), 2.61 (2H, t, J=6.1 Hz), 2.29 (3H, s)
Mass spectrometric value (ESI-MS) 479, 481 (M−1)

Compound 404 3-{[Bis-(2-hydroxy-ethyl)-amino]-methyl}-N-[4-chloro-2-(3-methyl-benzylidene-hydrazinocarbonyl)-phenyl]-benzamide The title compound 404 was produced in the same manner as in Example 5.
$^1$H-NMR (CD$_3$OD, 400 MHz): δ 8.67 (1H, d, J=9.0 Hz), 8.34 (1H, s), 8.07 (1H, s), 7.94 (1H, d, J=2.4 Hz), 7.90 (1H, d, J=7.8 Hz), 7.74 (1H, s), 7.61-7.66 (3H, m), 7.51 (1H, dd, J=7.7 Hz, J=7.7 Hz), 7.25-7.37 (2H, m), 3.83 (2H, s), 3.66 (4H, t, J=5.9 Hz), 2.71 (4H, t, J=5.9 Hz), 2.40 (3H, s)
Mass spectrometric value (ESI-MS) 507, 509 (M−1)

Compound 405 3-{[Bis-(2-hydroxy-ethyl)-amino]-methyl}-N-[4-chloro-2-(4-methyl-benzylidene-hydrazinocarbonyl)-phenyl]-benzamide The title compound 405 was produced in the same manner as in Example 5.
Mass spectrometric value (ESI-MS) 507, 508 (M−1)

Compound 406 3-{[Bis-(2-hydroxy-ethyl)-amino]-methyl}-N-[4-chloro-2-(3,4-dimethyl-benzylidene-hydrazinocarbonyl)-phenyl]-benzamide The title compound 406 was produced in the same manner as in Example 5.
$^1$H-NMR (CD$_3$OD, 400 MHz): δ 8.67 (1H, d, J=9.0 Hz), 8.30 (1H, s), 8.06 (1H, s), 7.92 (1H, d, J=2.4 Hz), 7.87-7.91 (1H, m), 7.68 (1H, s), 7.60-7.65 (2H, m), 7.47-7.58 (2H, m), 7.20 (1H, d, J=7.8 Hz), 3.83 (2H, s), 3.65 (4H, t, J=5.8 Hz), 2.71 (4H, t, J=5.8 Hz), 2.32 (3H, s), 2.30 (3H, s)
Mass spectrometric value (ESI-MS) 521, 522 (M−1)

Compound 407 3-{[Bis-(2-hydroxy-ethyl)-amino]-methyl}-N-[4-chloro-2-(4-chloro-3-trifluoromethyl-benzylidene-hydrazinocarbonyl)-phenyl]-benzamide The title compound 407 was produced in the same manner as in Example 5.
$^1$H-NMR (CD$_3$OD, 400 MHz): δ 8.66 (1H, d, J=8.8 Hz), 8.39 (1H, s), 8.37 (1H, s), 8.05-8.10 (2H, m), 7.95 (1H, d, J=2.2 Hz), 7.84-7.92 (1H, m), 7.70 (1H, d, J=8.3 Hz), 7.60-7.68 (2H, m), 7.48-7.53 (1H, dd, J=7.8 Hz, J=7.8 Hz), 3.83 (2H, s), 3.65 (4H, t, J=5.8 Hz), 2.71 (4H, t, J=5.8 Hz)
Mass spectrometric value (ESI-MS) 595, 597 (M−1)

Compound 408 3-{[Bis-(2-hydroxy-ethyl)-amino]-methyl}-N-[4-chloro-2-(3-methoxy-benzylidene-hydrazinocarbonyl)-phenyl]-benzamide The title compound 408 was produced in the same manner as in Example 5.
$^1$H-NMR (CD$_3$OD, 400 MHz): δ 8.66 (1H, d, J=9.0 Hz), 8.33 (1H, s), 8.06 (1H, s), 7.89-7.96 (2H, m), 7.58-7.66 (3H, m), 7.48-7.54 (1H, m), 7.28-7.38 (2H, m), 6.97-7.04 (1H, m), 3.87 (3H, s), 3.85 (2H, s), 3.66 (4H, t, J=5.9 Hz), 2.72 (4H, t, J=5.9 Hz)
Mass spectrometric value (ESI-MS) 523, 525 (M−1)

Compound 409 3-{[Bis-(2-hydroxy-ethyl)-amino]-methyl}-N-[4-chloro-2-(4-methoxy-benzylidene-hydrazinocarbonyl)-phenyl]-benzamide The title compound 409 was produced in the same manner as in Example 5.
$^1$H-NMR (CD$_3$OD, 400 MHz): δ 8.66 (1H, d, J=9.0 Hz), 8.31 (1H, s), 8.06 (1H, s), 7.80-7.94 (4H, m), 7.60-7.66 (2H, m), 7.50 (1H, dd, J=7.7 Hz, J=7.7 Hz), 7.00 (1H, d, J=9.0 Hz), 3.90 (3H, s), 3.85 (2H, s), 3.66 (4H, t, J=5.9 Hz), 2.71 (4H, t, J=5.9 Hz)
Mass spectrometric value (ESI-MS) 523, 525 (M−1)

Compound 410 3-{[Bis-(2-hydroxy-ethyl)-amino]-methyl}-N-[4-chloro-2-(3-hydroxy-benzylidene-hydrazinocarbonyl)-phenyl]-benzamide The title compound 410 was produced in the same manner as in Example 5.
$^1$H-NMR (CD$_3$OD, 400 MHz): δ 8.65 (1H, d, J=9.0 Hz), 8.29 (1H, s), 8.05 (1H, s), 7.93 (1H, d, J=2.4 Hz), 7.87-7.92 (1H, m), 7.60-7.66 (2H, m), 7.50 (1H, dd, J=7.7 Hz, J=7.7 Hz), 7.33 (1H, s), 7.26 (2H, d, J=4.9 Hz), 6.85-6.92 (1H, m), 3.83 (2H, s), 3.66 (4H, t, J=5.9 Hz), 2.71 (4H, t, J=5.9 Hz)
Mass spectrometric value (ESI-MS) 509 (M−1)

Compound 411 3-{[Bis-(2-hydroxy-ethyl)-amino]-methyl}-N-[4-chloro-2-(4-hydroxy-benzylidene-hydrazinocarbonyl)-phenyl]-benzamide The title compound 411 was produced in the same manner as in Example 5.
$^1$H-NMR (CD$_3$OD, 400 MHz): δ 8.67 (1H, d, J=9.0 Hz), 8.27 (1H, s), 8.06 (1H, s), 7.85-7.93 (2H, m), 7.72 (2H, d, J=8.8 Hz), 7.60-7.65 (2H, m), 7.47-7.54 (1H, m), 6.85 (2H, d, J=8.6 Hz), 3.83 (2H, s), 3.65 (4H, t, J=5.9 Hz), 2.71 (4H, t, J=5.9 Hz)
Mass spectrometric value (ESI-MS) 509, 511 (M−1)

Compound 412 N-[4-Chloro-2-(3-fluoro-benzylidene-hydrazinocarbonyl)-phenyl]-4-{[(2-hydroxy-ethyl)-methyl-amino]-methyl}-benzamide The title compound 412 was produced in the same manner as in Example 5.
$^1$H-NMR (CD$_3$OD, 400 MHz): δ 8.65 (1H, d, J=9.0 Hz), 8.36 (1H, s), 7.98 (2H, d, J=8.3 Hz), 7.94 (1H, d, J=2.4 Hz), 7.68-7.74 (1H, m), 7.58-7.65 (2H, m), 7.55 (2H, d, J=8.3 Hz), 7.43-7.50 (1H, m), 7.10-7.23 (1H, m), 3.69 (2H, t, J=6.1 Hz), 3.67 (2H, s), 2.58 (2H, t, J=6.1 Hz), 2.28 (3H, s)
Mass spectrometric value (ESI-MS) 482 (M−1)

Compound 413 N-[4-Chloro-2-(4-fluoro-benzylidene-hydrazinocarbonyl)-phenyl]-4-{[(2-hydroxy-ethyl)-methyl-amino]-methyl}-benzamide The title compound 413 was produced in the same manner as in Example 5.
$^1$H-NMR (CD$_3$OD, 400 MHz): δ 8.65 (1H, d, J=9.0 Hz), 8.36 (1H, s), 7.98 (2H, d, J=8.3 Hz), 7.87-7.95 (3H, m), 7.63 (1H, dd, J=2.4 Hz, J=9.0 Hz), 7.55 (2H, d, J=7.8 Hz), 7.19 (2H, dd, J=8.7 Hz, J=8.7 Hz), 3.69 (2H, t, J=6.0 Hz), 3.67 (2H, s), 2.58 (2H, t, J=6.0 Hz), 2.28 (3H, s)
Mass spectrometric value (ESI-MS) 481, 483 (M−1)

Compound 414 N-[4-Chloro-2-(3-methyl-benzylidene-hydrazinocarbonyl)-phenyl]-4-{[(2-hydroxy-ethyl)-methyl-amino]-methyl}-benzamide The title compound 414 was produced in the same manner as in Example 5.
$^1$H-NMR (CD$_3$OD, 400 MHz): δ 8.66 (1H, d, J=9.0 Hz), 8.34 (1H, s), 7.98 (2H, d, J=8.0 Hz), 7.93 (1H, d, J=2.4 Hz), 7.72 (1H, s), 7.60-7.65 (2H, m), 7.55 (2H, d, J=8.0 Hz), 7.26-7.36 (2H, m), 3.69 (2H, t, J=6.1 Hz), 3.67 (2H, s), 2.58 (2H, t, J=6.1 Hz), 2.40 (3H, s), 2.28 (3H, s)

Mass spectrometric value (ESI-MS) 477, 479 (M−1)

Compound 415 N-[4-Chloro-2-(4-methyl-benzylidene-hydrazinocarbonyl)-phenyl]-4-{[(2-hydroxy-ethyl)-methyl-amino]-methyl}-benzamide The title compound 415 was produced in the same manner as in Example 5.

$^1$H-NMR (CD$_3$OD, 400 MHz): δ 8.66 (1H, d, J=9.0 Hz), 8.33 (1H, s), 7.98 (2H, d, J=8.0 Hz), 7.93 (1H, d, J=2.5 Hz), 7.74 (2H, d, J=8.0 Hz), 7.62 (1H, dd, J=2.5 Hz, J=9.0 Hz), 7.55 (2H, d, J=8.0 Hz), 7.27 (2H, d, J=7.8 Hz), 3.69 (2H, t, J=6.1 Hz), 3.67 (3H, s), 2.58 (2H, t, J=6.1 Hz), 2.39 (3H, s), 2.27 (3H, s)

Mass spectrometric value (ESI-MS) 477 (M−1)

Compound 416 N-[4-Chloro-2-(3,4-dimethyl-benzylidene-hydrazinocarbonyl)-phenyl]-4-{[(2-hydroxy-ethyl)-methyl-amino]-methyl}-benzamide The title compound 416 was produced in the same manner as in Example 5.

$^1$H-NMR (CD$_3$OD, 400 MHz): δ 8.66 (1H, d, J=9.0 Hz), 8.30 (1H, s), 7.98 (2H, d, J=8.3 Hz), 7.92 (1H, d, J=2.4 Hz), 7.66 (1H, s), 7.61 (1H, dd, J=2.4 Hz, J=9.0 Hz), 7.52-7.57 (3H, m), 7.20 (1H, d, J=8.0 Hz), 3.69 (2H, d, J=8.0 Hz), 3.67 (2H, s), 2.58 (2H, t, J=6.1 Hz), 2.32 (3H, s), 2.30 (3H, s), 2.27 (3H, s)

Mass spectrometric value (ESI-MS) 491, 493 (M−1)

Compound 417 N-[4-Chloro-2-(4-chloro-3-trifluoromethyl-benzylidene-hydrazinocarbonyl)-phenyl]-4-{[(2-hydroxy-ethyl)-methyl-amino]-methyl}-benzamide The title compound 417 was produced in the same manner as in Example 5.

$^1$H-NMR (CD$_3$OD, 400 MHz): δ 8.55 (1H, d, J=9.0 Hz), 8.30 (1H, s), 8.25 (1H, s), 7.93-7.98 (1H, m), 7.83-7.90 (3H, m), 7.60 (1H, d, J=8.3 Hz), 7.54 (1H, dd, J=2.3 Hz, J=8.8 Hz), 7.46 (2H, d, J=8.3 Hz), 3.59 (2H, t, J=6.0 Hz), 3.58 (2H, s), 2.49 (2H, t, J=6.0 Hz), 2.18 (3H, s)

Mass spectrometric value (ESI-MS) 565, 567 (M−1)

Compound 418 N-[4-Chloro-2-(3-methoxy-benzylidene-hydrazinocarbonyl)-phenyl]-4-{[(2-hydroxy-ethyl)-methyl-amino]-methyl}-benzamide The title compound 418 was produced in the same manner as in Example 5.

$^1$H-NMR (CD$_3$OD, 400 MHz): δ 8.56 (1H, d, J=9.0 Hz), 8.24 (1H, s), 7.82-7.90 (3H, m), 7.42-7.55 (4H, m), 7.18-7.27 (2H, m), 6.88-6.94 (1H, m), 3.77 (3H, s), 3.56-3.61 (4H, m), 2.50 (2H, t, J=6.0 Hz), 2.18 (3H, s)

Mass spectrometric value (ESI-MS) 493, 495 (M−1)

Compound 419 N-[4-Chloro-2-(4-methoxy-benzylidene-hydrazinocarbonyl)-phenyl]-4-{[(2-hydroxy-ethyl)-methyl-amino]-methyl}-benzamide The title compound 419 was produced in the same manner as in Example 5.

$^1$H-NMR (CD$_3$OD, 400 MHz): δ 8.56 (1H, d, J=9.0 Hz), 8.21 (1H, s), 7.88 (2H, d, J=8.3 Hz), 7.81 (1H, d, J=2.2 Hz), 7.69 (2H, d, J=8.8 Hz), 7.50 (1H, dd, J=2.4 Hz, J=8.8 Hz), 7.45 (2H, d, J=8.3 Hz), 6.89 (2H, d, J=8.8 Hz), 3.75 (3H, s), 3.59 (2H, t, J=6.1 Hz), 3.59 (2H, s), 2.50 (2H, t, J=6.1 Hz), 2.19 (3H, s)

Mass spectrometric value (ESI-MS) 493, 495 (M−1)

Compound 420 N-[4-Chloro-2-(3-hydroxy-benzylidene-hydrazinocarbonyl)-phenyl]-4-{[(2-hydroxy-ethyl)-methyl-amino]-methyl}-benzamide The title compound 420 was produced in the same manner as in Example 5.

$^1$H-NMR (CD$_3$OD, 400 MHz): δ 8.55 (1H, d, J=8.8 Hz), 8.19 (1H, s), 7.88 (2H, d, J=7.8 Hz), 7.82-7.85 (1H, m), 7.50-7.55 (1H, m), 7.46 (2H, d, J=7.6 Hz), 7.22 (1H, s), 7.13-7.18 (2H, m), 6.75-6.82 (1H, m), 3.56-3.62 (4H, m), 2.49 (2H, t, J=6.1 Hz), 2.19 (3H, s)

Mass spectrometric value (ESI-MS) 479, 481 (M−1)

Compound 421 N-[4-Chloro-2-(4-hydroxy-benzylidene-hydrazinocarbonyl)-phenyl]-4-{[(2-hydroxy-ethyl)-methyl-amino]-methyl}-benzamide The title compound 421 was produced in the same manner as in Example 5.

Mass spectrometric value (ESI-MS) 479, 481 (M−1)

Compound 422 N-[4-Chloro-2-(3-fluoro-benzylidene-hydrazinocarbonyl)-phenyl]-3-{[ethyl-(2-hydroxy-ethyl)-amino]-methyl}-benzamide The title compound 422 was produced in the same manner as in Example 5.

$^1$H-NMR (CD$_3$OD, 400 MHz): δ 8.55 (1H, d, J=9.0 Hz), 8.26 (1H, s), 7.93 (1H, s), 7.84 (1H, d, J=2.4 Hz), 7.78-7.83 (1H, m), 7.33-7.70 (6H, m), 7.05-7.20 (1H, m), 3.72 (2H, s), 3.57 (2H, t, J=6.1 Hz), 2.59 (2H, t, J=6.0 Hz), 2.54 (3H, q, J=7.3 Hz), 1.02 (3H, t, J=7.1 Hz)

Mass spectrometric value (ESI-MS) 495 (M−1)

Compound 423 N-[4-Chloro-2-(4-fluoro-benzylidene-hydrazinocarbonyl)-phenyl]-3-{[ethyl-(2-hydroxy-ethyl)-amino]-methyl}-benzamide The title compound 423 was produced in the same manner as in Example 5.

$^1$H-NMR (CD$_3$OD, 400 MHz): δ 8.54 (1H, d, J=9.0 Hz), 8.26 (1H, s), 7.92 (1H, s), 7.77-7.85 (4H, m), 7.53 (2H, dd, J=2.2 Hz, J=9.0 Hz), 7.41 (1H, dd, J=7.7 Hz, J=7.7 Hz), 7.09 (2H, dd, J=8.8 Hz, J=8.8 Hz), 3.68 (2H, s), 3.57 (2H, t, J=6.2 Hz), 2.57 (2H, t, J=6.3 Hz), 2.53 (2H, q, J=7.1 Hz), 1.01 (3H, t, J=7.2 Hz)

Mass spectrometric value (ESI-MS) 495 (M−1)

Compound 424 N-[4-Chloro-2-(3-methyl-benzylidene-hydrazinocarbonyl)-phenyl]-3-{[ethyl-(2-hydroxy-ethyl)-amino]-methyl}-benzamide The title compound 424 was produced in the same manner as in Example 5.

$^1$H-NMR (CD$_3$OD, 400 MHz): δ 8.56 (1H, d, J=9.0 Hz), 8.24 (1H, s), 7.92 (1H, s), 7.83 (1H, d, J=2.4 Hz), 7.78-7.82 (1H, m), 7.62 (1H, s), 7.53 (2H, dd, J=2.2 Hz, J=9.0 Hz), 7.42 (2H, dd, J=7.4 Hz, J=7.4 Hz), 7.15-7.26 (2H, m), 3.69 (2H, s), 3.57 (2H, t, J=6.3 Hz), 2.57 (2H, t, J=6.3 Hz), 2.53 (2H, q, J=7.2 Hz), 2.30 (3H, s), 1.01 (3H, t, J=7.2 Hz)

Mass spectrometric value (ESI-MS) 491 (M−1), 515 (M+23)

Compound 425 N-[4-Chloro-2-(4-methyl-benzylidene-hydrazinocarbonyl)-phenyl]-3-{[ethyl-(2-hydroxy-ethyl)-amino]-methyl}-benzamide The title compound 425 was produced in the same manner as in Example 5.

$^1$H-NMR (CD$_3$OD, 400 MHz): δ 8.65 (1H, d, J=9.0 Hz), 8.33 (1H, s), 8.01 (1H, s), 7.88-7.94 (2H, m), 7.74 (2H, d, J=8.1 Hz), 7.60-7.65 (2H, m), 7.51 (2H, m), 7.26 (2H, d, J=8.1 Hz), 3.80 (2H, s), 3.67 (2H, t, J=6.2 Hz), 2.69 (2H, t, J=6.2 Hz), 2.64 (2H, q, J=7.1 Hz), 2.38 (3H, s), 1.11 (3H, t, J=7.2 Hz)

Mass spectrometric value (ESI-MS) 491 (M−1), 515 (M+23)

Compound 426 N-[4-Chloro-2-(3,4-dimethyl-benzylidene-hydrazinocarbonyl)-phenyl]-3-{[ethyl-(2-hydroxy-ethyl)-amino]-methyl}-benzamide The title compound 426 was produced in the same manner as in Example 5.

$^1$H-NMR (CD$_3$OD, 400 MHz): δ 8.66 (1H, d, J=9.0 Hz), 8.30 (1H, s), 8.02 (1H, s), 7.89-7.94 (2H, m), 7.60-7.69 (3H, m), 7.49-7.57 (2H, m), 7.21 (1H, d, J=7.8 Hz), 3.82 (2H, s), 3.68 (2H, t, J=6.2 Hz), 2.70 (2H, t, J=6.2 Hz), 2.66 (2H, q, J=7.1 Hz), 2.32 (3H, s), 2.30 (3H, s), 1.12 (3H, t, J=7.2 Hz)

Mass spectrometric value (ESI-MS) 505 (M−1)

Compound 427 N-[4-Chloro-2-(4-chloro-3-trifluoromethyl-benzylidene-hydrazinocarbonyl)-phenyl]-3-{[ethyl-(2-hydroxy-ethyl)-amino]-methyl}-benzamide The title compound 427 was produced in the same manner as in Example 5.

Mass spectrometric value (ESI-MS) 579 (M−1)

Compound 428 N-[4-Chloro-2-(3-methoxy-benzylidene-hydrazinocarbonyl)-phenyl]-3-{[ethyl-(2-hydroxy-ethyl)-amino]-methyl}-benzamide The title compound 428 was produced in the same manner as in Example 5.

$^1$H-NMR (CD$_3$OD, 400 MHz): δ 8.65 (1H, d, J=8.8 Hz), 8.33 (1H, s), 8.01 (1H, s), 7.93 (1H, d, J=2.2. Hz), 7.89 (1H, d, J=2.2. Hz), 7.56-7.66 (3H, m), 7.50 (1H, dd, J=7.7 Hz, J=7.7 Hz), 7.29-7.37 (2H, m), 6.97-7.04 (1H, m), 3.86 (3H, s), 3.77 (2H, s), 3.66 (2H, t, J=6.2 Hz), 2.66 (2H, t, J=6.4 Hz), 2.61 (2H, q, J=7.4 Hz), 1.10 (3H, t, J=7.2 Hz)

Mass spectrometric value (ESI-MS) 507 (M−1)

Compound 429 N-[4-Chloro-2-(4-methoxy-benzylidene-hydrazinocarbonyl)-phenyl]-3-{[ethyl-(2-hydroxy-ethyl)-amino]-methyl}-benzamide The title compound 429 was produced in the same manner as in Example 5.

$^1$H-NMR (CD$_3$OD, 400 MHz): δ 8.65 (1H, d, J=9.0 Hz), 8.30 (1H, s), 8.01 (1H, s), 7.91 (1H, d, J=2.4 Hz), 7.87-7.91 (1H, m), 7.80 (2H, d, J=8.8 Hz), 7.59-7.65 (2H, m), 7.51 (1H, dd, J=7.7 Hz, J=7.7 Hz), 6.99 (2H, d, J=8.8 Hz), 3.85 (3H, s), 3.78 (2H, s), 3.66 (2H, t, J=6.2 Hz), 2.67 (2H, t, J=6.3 Hz), 2.62 (2H, q, J=7.2 Hz), 1.10 (3H, t, J=7.1 Hz)

Mass spectrometric value (ESI-MS) 507 (M−1)

Compound 430 N-[4-Chloro-2-(3-hydroxy-benzylidene-hydrazinocarbonyl)-phenyl]-3-{[ethyl-(2-hydroxy-ethyl)-amino]-methyl}-benzamide The title compound 430 was produced in the same manner as in Example 5.

$^1$H-NMR (CD$_3$OD, 400 MHz): δ 8.65 (1H, d, J=8.8 Hz), 8.29 (1H, s), 8.01 (1H, s), 7.93 (1H, d, J=2.2 Hz), 7.89 (1H, d, J=7.6 Hz), 7.60-7.66 (2H, m), 7.51 (1H, dd, J=7.6 Hz, J=7.6 Hz), 7.22-7.40 (3H, m), 3.78 (2H, s), 3.66 (2H, t, J=6.4 Hz), 2.67 (2H, t, J=6.4 Hz), 2.62 (2H, q, J=7.3 Hz), 1.10 (3H, t, J=7.2 Hz)

Mass spectrometric value (ESI-MS) 493 (M−1)

Compound 431 N-[4-Chloro-2-(4-hydroxy-benzylidene-hydrazinocarbonyl)-phenyl]-3-{[ethyl-(2-hydroxy-ethyl)-amino]-methyl}-benzamide The title compound 431 was produced in the same manner as in Example 5.

$^1$H-NMR (CD$_3$OD, 400 MHz): δ 8.65 (1H, d, J=8.8 Hz), 8.27 (1H, s), 8.00 (1H, s), 7.86-7.94 (2H, m), 7.70 (2H, d, J=8.8 Hz), 7.58-7.65 (2H, m), 7.50 (1H, dd, J=7.7 Hz, J=7.7 Hz), 6.84 (2H, d, J=8.6 Hz), 3.77 (2H, s), 3.66 (2H, t, J=6.3 Hz), 2.66 (2H, t, J=6.3 Hz), 2.62 (2H, q, J=7.2 Hz), 1.10 (3H, t, J=7.1 Hz)

Mass spectrometric value (ESI-MS) 493 (M−1)

Compound 432 N-[4-Chloro-2-(3-fluoro-benzylidene-hydrazinocarbonyl)-phenyl]-4-{[ethyl-(2-hydroxy-ethyl)-amino]-methyl}-benzamide The title compound 432 was produced in the same manner as in Example 5.

$^1$H-NMR (CD$_3$OD, 400 MHz): δ 8.65 (1H, d, J=9.0 Hz), 8.36 (1H, s), 7.92-8.00 (3H, m), 7.71 (1H, d, J=9.5 Hz), 7.54-7.65 (4H, m), 7.43-7.51 (1H, m), 7.15-7.23 (1H, m), 3.75 (2H, s), 3.63 (2H, t, J=6.2 Hz), 2.64 (2H, t, J=6.2 Hz), 2.60 (2H, q, J=7.3 Hz), 1.09 (3H, t, J=7.1 Hz)

Mass spectrometric value (ESI-MS) 495 (M−1)

Compound 433 N-[4-Chloro-2-(4-fluoro-benzylidene-hydrazinocarbonyl)-phenyl]-4-{[ethyl-(2-hydroxy-ethyl)-amino]-methyl}-benzamide The title compound 433 was produced in the same manner as in Example 5.

$^1$H-NMR (CD$_3$OD, 400 MHz): δ 8.65 (1H, d, J=8.8 Hz), 8.35 (1H, s), 7.96 (2H, d, J=8.3 Hz), 7.87-7.94 (3H, m), 7.61 (1H, dd, J=2.4 Hz, J=9.0 Hz), 7.55 (2H, d, J=8.0 Hz), 7.19 (2H, dd, J=8.8 Hz, J=8.8 Hz), 3.74 (2H, s), 3.63 (2H, t, J=6.2 Hz), 2.64 (2H, t, J=6.3 Hz), 2.60 (2H, q, J=7.2 Hz), 1.09 (3H, t, J=7.1 Hz)

Mass spectrometric value (ESI-MS) 495 (M−1)

Compound 434 N-[4-Chloro-2-(3-methyl-benzylidene-hydrazinocarbonyl)-phenyl]-4-{[ethyl-(2-hydroxy-ethyl)-amino]-methyl}-benzamide The title compound 434 was produced in the same manner as in Example 5.

$^1$H-NMR (CD$_3$OD, 400 MHz): δ 8.66 (1H, d, J=8.8 Hz), 8.33 (1H, s), 7.97 (2H, d, J=8.3 Hz), 7.93 (1H, d, J=2.4 Hz), 7.12 (1H, s), 7.60-7.65 (2H, m), 7.56 (2H, d, J=8.3 Hz), 7.25-7.36 (2H, m), 3.74 (2H, s), 3.63 (2H, t, J=6.2 Hz), 2.64 (2H, t, J=6.3 Hz), 2.60 (2H, q, J=7.1 Hz), 2.40 (3H, s), 1.09 (3H, t, J=7.1 Hz)
Mass spectrometric value (ESI-MS) 491 (M−1)

Compound 435 N-[4-Chloro-2-(4-methyl-benzylidene-hydrazinocarbonyl)-phenyl]-4-{[ethyl-(2-hydroxy-ethyl)-amino]-methyl}-benzamide The title compound 435 was produced in the same manner as in Example 5.
$^1$H-NMR (CD$_3$OD, 400 MHz): δ 8.66 (1H, d, J=9.0 Hz), 8.33 (1H, s), 7.97 (2H, d, J=8.3 Hz), 7.92 (1H, d, J=2.2 Hz), 7.89 (1H, s), 7.74 (2H, d, J=8.0 Hz), 7.61 (1H, dd, J=2.4 Hz, J=8.8 Hz), 7.27 (1H, d, J=8.0 Hz), 3.77 (2H, s), 3.64 (2H, t, J=6.2 Hz), 2.67 (2H, t, J=6.3 Hz), 2.63 (2H, q, J=7.1 Hz), 2.38 (3H, s), 1.10 (3H, t, 7.2 Hz)
Mass spectrometric value (ESI-MS) 491 (M−1)

Compound 436 N-[4-Chloro-2-(3,4-dimethyl-benzylidene-hydrazinocarbonyl)-phenyl]-4-{[ethyl-(2-hydroxy-ethyl)-amino]-methyl}-benzamide The title compound 436 was produced in the same manner as in Example 5.
$^1$H-NMR (CD$_3$OD, 400 MHz): δ 8.66 (1H, d, J=8.8 Hz), 8.30 (1H, s), 7.97 (2H, d, J=8.3 Hz), 7.92 (1H, d, J=2.4 Hz), 7.52-7.68 (5H, m), 7.20 (1H, d, J=7.8 Hz), 3.77 (2H, s), 3.64 (2H, t, J=6.2 Hz), 2.67 (2H, t, J=6.2 Hz), 2.63 (2H, q, J=7.2 Hz), 2.32 (3H, s), 2.31 (3H, s), 1.10 (3H, t, J=7.1 Hz)
Mass spectrometric value (ESI-MS) 505 (M−1)

Compound 437 N-[4-Chloro-2-(4-chloro-3-trifluoromethyl-benzylidene-hydrazinocarbonyl)-phenyl]-4-{[ethyl-(2-hydroxy-ethyl)-amino]-methyl}-benzamide The title compound 437 was produced in the same manner as in Example 5.
$^1$H-NMR (CD$_3$OD, 400 MHz): δ 8.64 (1H, d, J=9.0 Hz), 8.39 (1H, s), 8.34 (1H, s), 8.05 (1H, d, J=8.1 Hz), 7.93-7.98 (2H, m), 7.89 (1H, s), 7.70 (1H, d, J=8.3 Hz), 7.63 (1H, dd, J=2.4 Hz, J=9.0 Hz), 7.56 (2H, d, J=8.3 Hz), 3.75 (2H, s), 3.63 (2H, t, J=6.4 Hz), 2.64 (2H, t, J=6.4 Hz), 2.60 (2H, q, J=7.1 Hz), 1.09 (3H, t, J=7.2 Hz)
Mass spectrometric value (ESI-MS) 579 (M−1)

Compound 438 N-[4-Chloro-2-(3-methoxy-benzylidene-hydrazinocarbonyl)-phenyl]-4-{[ethyl-(2-hydroxy-ethyl)-amino]-methyl}-benzamide The title compound 438 was produced in the same manner as in Example 5.
$^1$H-NMR (CD$_3$OD, 400 MHz): δ 8.66 (1H, d, J=8.8 Hz), 8.33 (1H, s), 7.92-7.99 (3H, m), 7.62 (1H, dd, J=2.2 Hz, J=8.8 Hz), 7.54-7.60 (3H, m), 7.28-7.37 (2H, m), 6.98-7.04 (1H, m), 3.87 (3H, s), 3.74 (2H, s), 3.63 (2H, t, J=6.2 Hz), 2.64 (2H, t, J=6.3 Hz), 2.60 (2H, q, J=7.2 Hz), 1.09 (3H, t, J=7.1 Hz)
Mass spectrometric value (ESI-MS) 507 (M−1)

Compound 439 N-[4-Chloro-2-(4-methoxy-benzylidene-hydrazinocarbonyl)-phenyl]-4-{[ethyl-(2-hydroxy-ethyl)-amino]-methyl}-benzamide The title compound 439 was produced in the same manner as in Example 5.
$^1$H-NMR (CD$_3$OD, 400 MHz): δ 8.66 (1H, d, J=9.0 Hz), 8.31 (1H, s), 7.96 (2H, d, J=8.3 Hz), 7.92 (1H, d, J=2.4 Hz), 7.80 (2H, d, J=8.8 Hz), 7.61 (1H, dd, J=2.4 Hz, J=9.0 Hz), 7.56 (2H, d, J=8.3 Hz), 6.99 (2H, d, J=8.8 Hz), 3.85 (3H, s), 3.74 (2H, s), 3.63 (2H, t, J=6.4 Hz), 2.65 (2H, t, J=6.4 Hz), 2.60 (2H, q, J=7.2 Hz), 1.09 (3H, t, J=7.1 Hz)
Mass spectrometric value (ESI-MS) 507 (M−1)

Compound 440 N-[4-Chloro-2-(3-hydroxy-benzylidene-hydrazinocarbonyl)-phenyl]-4-{[ethyl-(2-hydroxy-ethyl)-amino]-methyl}-benzamide The title compound 440 was produced in the same manner as in Example 5.
$^1$H-NMR (CD$_3$OD, 400 MHz): δ 8.65 (1H, d, J=8.8 Hz), 8.29 (1H, s), 7.88-7.99 (3H, m), 7.62 (1H, dd, J=2.4 Hz, J=9.0 Hz), 7.56 (2H, d, J=8.3 Hz), 7.30-7.33 (1H, m), 7.23-7.27 (2H, m), 6.85-6.91 (1H, m), 3.75 (2H, s), 3.63 (2H, t, J=6.3 Hz), 2.65 (2H, t, J=6.2 Hz), 2.61 (2H, q, J=7.1 Hz), 1.09 (3H, t, J=7.1 Hz)
Mass spectrometric value (ESI-MS) 493 (M−1)

Compound 441 N-[4-Chloro-2-(4-hydroxy-benzylidene-hydrazinocarbonyl)-phenyl]-4-{[ethyl-(2-hydroxy-ethyl)-amino]-methyl}-benzamide The title compound 441 was produced in the same manner as in Example 5.
$^1$H-NMR (CD$_3$OD, 400 MHz): δ 8.66 (1H, d, J=8.8 Hz), 8.27 (1H, s), 7.97 (2H, d, J=8.1 Hz), 7.91 (1H, d, J=2.4 Hz), 7.70 (2H, d, J=8.8 Hz), 7.61 (1H, dd, J=2.4 Hz, J=9.0 Hz), 7.56 (2H, d, J=8.3 Hz), 6.85 (2H, d, J=8.8 Hz), 3.78 (2H, s), 3.64 (2H, t, J=6.2 Hz), 2.68 (2H, t, J=6.2 Hz), 2.64 (2H, q, J=7.2 Hz), 1.10 (3H, t, J=7.1 Hz)
Mass spectrometric value (ESI-MS) 493 (M−1)

Compound 442 N-[4-Chloro-2-(3-fluoro-benzylidene-hydrazinocarbonyl)-phenyl]-4-(2-diethylamino-ethylsulfanylmethyl)-benzamide The title compound 442 was produced in the same manner as in Example 5.
$^1$H-NMR (CD$_3$OD, 400 MHz): δ 8.65 (1H, d, J=9.0 Hz), 8.36 (1H, s), 7.97 (2H, d, J=8.3 Hz), 7.94 (1H, d, J=2.4 Hz), 7.71 (1H, d, J=8.1 Hz), 7.58-7.65 (2H, m), 7.55 (2H, d, J=8.3 Hz), 7.43-7.50 (1H, m), 7.15-7.25 (1H, m), 3.85 (2H, s), 2.60-2.67 (2H, m), 2.50-2.59 (6H, m), 1.00 (6H, t, J=7.2 Hz)
Mass spectrometric value (ESI-MS) 539 (M−1)

Compound 443 N-[4-Chloro-2-(4-fluoro-benzylidene-hydrazinocarbonyl)-phenyl]-4-(2-diethylamino-ethylsulfanylmethyl)-benzamide The title compound 443 was produced in the same manner as in Example 5.
$^1$H-NMR (CD$_3$OD, 400 MHz): δ 8.65 (1H, d, J=9.0 Hz), 8.35 (1H, s), 7.97 (2H, d, J=8.3 Hz), 7.88-7.95 (3H, m), 7.62 (1H, dd, J=2.2 Hz, J=8.8 Hz), 7.55 (1H, d, J=8.3 Hz), 7.19 (2H, dd, J=8.7 Hz, J=8.7 Hz), 3.85 (1H, s), 2.49-2.67 (8H, m), 1.00 (6H, t, J=7.2 Hz)
Mass spectrometric value (ESI-MS) 539 (M−1)

Compound 444 N-[4-Chloro-2-(3-methyl-benzylidene-hydrazinocarbonyl)-phenyl]-4-(2-diethylamino-ethylsulfanylmethyl)-benzamide The title compound 444 was produced in the same manner as in Example 5.
$^1$H-NMR (CD$_3$OD, 400 MHz): δ 8.66 (1H, d, J=8.8 Hz), 8.33 (1H, s), 7.97 (2H, d, J=8.3 Hz), 7.93 (1H, d, J=2.4 Hz), 7.72 (1H, s), 7.60-7.65 (2H, m), 7.55 (2H, d, J=8.3 Hz), 7.25-7.36 (2H, m), 3.84 (2H, s), 2.48-2.66 (8H, m), 2.39 (3H, s), 1.00 (6H, t, J=7.2 Hz)
Mass spectrometric value (ESI-MS) 535 (M−1)

Compound 445 N-[4-Chloro-2-(4-methyl-benzylidene-hydrazinocarbonyl)-phenyl]-4-(2-diethylamino-ethylsulfanylmethyl)-benzamide The title compound 445 was produced in the same manner as in Example 5.
$^1$H-NMR (CD$_3$OD, 400 MHz): δ 8.66 (1H, d, J=8.8 Hz), 8.33 (1H, s), 7.97 (2H, d, J=8.3 Hz), 7.93 (1H, d, J=2.4 Hz), 7.74 (2H, d, J=7.8 Hz), 7.61 (1H, dd, J=2.2 Hz, J=9.0 Hz), 7.55 (2H, d, J=8.3 Hz), 7.27 (2H, d, J=7.8 Hz), 3.84 (2H, s), 2.47-2.66 (8H, m), 2.39 (3H, s), 1.00 (6H, t, J=7.2 Hz)
Mass spectrometric value (ESI-MS) 535 (M−1)

Compound 446 N-[4-Chloro-2-(3,4-dimethyl-benzylidene-hydrazinocarbonyl)-phenyl]-4-(2-diethylamino-ethylsulfanylmethyl)-benzamide The title compound 446 was produced in the same manner as in Example 5.
$^1$H-NMR (CD$_3$OD, 400 MHz): δ 8.66 (1H, d, J=9.0 Hz), 8.33 (1H, s), 7.96 (2H, d, J=8.3 Hz), 7.91 (1H, d, J=2.4 Hz), 7.65 (1H, s), 7.60 (1H, dd, J=2.4 Hz, J=9.0 Hz), 7.51-7.56 (3H, m), 7.19 (1H, d, J=7.8 Hz), 3.83 (2H, s), 2.58-2.65 (2H, m), 2.48-2.58 (6H, m), 2.31 (3H, s), 2.29 (3H, s), 0.99 (6H, t, J=7.2 Hz)
Mass spectrometric value (ESI-MS) 549 (M−1)

Compound 447 N-[4-Chloro-2-(4-chloro-3-trifluoromethyl-benzylidene-hydrazinocarbonyl)-phenyl]-4-(2-diethylamino-ethylsulfanylmethyl)-benzamide The title compound 447 was produced in the same manner as in Example 5.
$^1$H-NMR (CD$_3$OD, 400 MHz): δ 8.64 (1H, d, J=9.0 Hz), 8.39 (1H, s), 8.35 (1H, s), 8.05 (1H, d, J=8.3 Hz), 7.93-7.99 (3H, m), 7.70 (1H, d, J=8.3 Hz), 7.63 (1H, dd, J=2.4 Hz, J=9.0 Hz), 7.55 (2H, d, J=8.0 Hz), 3.85 (2H, s), 2.50-2.68 (8H, m), 1.00 (6H, t, J=7.2 Hz)
Mass spectrometric value (ESI-MS) 623 (M−1)

Compound 448 N-[4-Chloro-2-(3-methoxy-benzylidene-hydrazinocarbonyl)-phenyl]-4-(2-diethylamino-ethylsulfanylmethyl)-benzamide The title compound 448 was produced in the same manner as in Example 5.
$^1$H-NMR (CD$_3$OD, 400 MHz): δ 8.66 (1H, d, J=9.0 Hz), 8.33 (1H, s), 7.92-8.00 (3H, m), 7.63 (1H, dd, J=2.4 Hz, J=9.0 Hz), 7.59 (1H, s), 7.55 (2H, d, J=8.0 Hz), 7.28-7.38 (2H, m), 6.98-7.03 (1H, m), 3.88 (3H, s), 3.84 (2H, s), 2.58-2.66 (2H, m), 2.47-2.58 (6H, m), 0.99 (6H, t, J=7.2 Hz)
Mass spectrometric value (ESI-MS) 551 (M−1)

Compound 449 N-[4-Chloro-2-(4-methoxy-benzylidene-hydrazinocarbonyl)-phenyl]-4-(2-diethylamino-ethylsulfanylmethyl)-benzamide The title compound 449 was produced in the same manner as in Example 5.
$^1$H-NMR (CD$_3$OD, 400 MHz): δ 8.66 (1H, d, J=9.0 Hz), 8.31 (1H, s), 7.97 (2H, d, J=8.3 Hz), 7.92 (1H, d, J=2.4 Hz), 7.80 (2H, d, J=8.8 Hz), 7.61 (1H, dd, J=2.4 Hz, J=9.0 Hz), 7.55 (2H, d, J=8.6 Hz), 7.00 (2H, d, J=8.8 Hz), 3.85 (3H, s), 3.84 (2H, s), 2.49-2.67 (8H, m), 1.00 (6H, t, J=7.2 Hz)
Mass spectrometric value (ESI-MS) 551 (M−1)

Compound 450 N-[4-Chloro-2-(3-hydroxy-benzylidene-hydrazinocarbonyl)-phenyl]-4-(2-diethylamino-ethylsulfanylmethyl)-benzamide The title compound 450 was produced in the same manner as in Example 5.
$^1$H-NMR (CD$_3$OD, 400 MHz): δ 8.64 (1H, d, J=9.0 Hz), 8.29 (1H, s), 7.97 (2H, d, J=8.3 Hz), 7.93 (1H, d, J=2.4 Hz), 7.62 (1H, dd, J=2.4 Hz, J=8.8 Hz), 7.55 (2H, d, J=8.3 Hz), 7.31 (1H, s), 7.22-7.28 (2H, m), 6.83-6.91 (1H, m), 3.85 (2H, s), 2.57-2.66 (2H, m), 2.48-2.57 (6H, m), 1.00 (6H, t, J=7.2 Hz)
Mass spectrometric value (ESI-MS) 537 (M−1)

Compound 451 N-[4-Chloro-2-(4-hydroxy-benzylidene-hydrazinocarbonyl)-phenyl]-4-(2-diethylamino-ethylsulfanylmethyl)-benzamide The title compound 451 was produced in the same manner as in Example 5.
$^1$H-NMR (CD$_3$OD, 400 MHz): δ 8.66 (1H, d, J=8.8 Hz), 8.27 (1H, s), 7.96 (2H, d, J=8.3 Hz), 7.91 (1H, d, J=2.4 Hz), 7.71 (2H, d, J=8.6 Hz), 7.61 (1H, dd, J=2.4 Hz, J=9.0 Hz), 7.55 (2H, d, J=8.3 Hz), 6.84 (2H, d, J=8.8 Hz), 3.84 (2H, s), 2.49-2.66 (8H, m), 1.00 (6H, t, J=7.2 Hz)
Mass spectrometric value (ESI-MS) 537 (M−1)

Compound 452 N-[4-Chloro-2-(3-fluoro-benzylidene-hydrazinocarbonyl)-phenyl]-3-(2-diethylamino-ethylsulfanylmethyl)-benzamide The title compound 452 was produced in the same manner as in Example 5.
$^1$H-NMR (CD$_3$OD, 400 MHz): δ 8.65 (1H, d, J=9.0 Hz), 8.36 (1H, s), 7.93-7.99 (2H, m), 7.89 (1H, d, J=8.3 Hz), 7.70 (1H, d, J=8.5 Hz), 7.52-7.65 (3H, m), 7.41-7.56 (2H, m), 7.15-7.23 (1H, m), 3.88 (2H, s), 2.42-2.66 (8H, m), 0.96 (6H, t, J=7.2 Hz)
Mass spectrometric value (ESI-MS) 539 (M−1)

Compound 453 N-[4-Chloro-2-(4-fluoro-benzylidene-hydrazinocarbonyl)-phenyl]-3-(2-diethylamino-ethylsulfanylmethyl)-benzamide The title compound 453 was produced in the same manner as in Example 5.
$^1$H-NMR (CD$_3$OD, 400 MHz): δ 8.65 (1H, d, J=8.8 Hz), 8.36 (1H, s), 7.85-7.99 (5H, m), 7.57-7.65 (2H, m), 7.47-7.55 (1H, m), 7.12-7.23 (2H, m), 3.88 (2H, s), 2.46-2.65 (8H, m), 0.96 (6H, t, J=7.2 Hz)
Mass spectrometric value (ESI-MS) 539 (M−1)

Compound 454 N-[4-Chloro-2-(3-methyl-benzylidene-hydrazinocarbonyl)-phenyl]-3-(2-diethylamino-ethylsulfanylmethyl)-benzamide The title compound 454 was produced in the same manner as in Example 5.
$^1$H-NMR (CD$_3$OD, 400 MHz): δ 8.66 (1H, d, J=9.0 Hz), 8.34 (1H, s), 7.98 (1H, s), 7.89 (1H, d, J=7.1 Hz), 7.71 (1H, s), 7.59-7.66 (3H, m), 7.52 (1H, dd, J=7.7 Hz, J=7.7 Hz), 7.24-7.35 (2H, m), 3.88 (2H, s), 2.46-2.65 (8H, m), 2.39 (3H, s), 0.96 (6H, t, J=7.2 Hz)
Mass spectrometric value (ESI-MS) 535 (M−1)

Compound 455 N-[4-Chloro-2-(4-methyl-benzylidene-hydrazinocarbonyl)-phenyl]-3-(2-diethylamino-ethylsulfanylmethyl)-benzamide The title compound 455 was produced in the same manner as in Example 5.
$^1$H-NMR (CD$_3$OD, 400 MHz): δ 8.65 (1H, d, J=9.0 Hz), 8.33 (1H, s), 7.97 (1H, s), 7.84-7.95 (2H, m), 7.73 (2H, d, J=8.1 Hz), 7.58-7.65 (2H, m), 7.51 (1H, dd, J=7.6 Hz, J=7.6 Hz), 7.26 (2H, d, J=7.8 Hz), 3.88 (2H, s), 2.46-2.66 (8H, m), 2.38 (3H, s), 0.96 (6H, t, J=7.2 Hz)
Mass spectrometric value (ESI-MS) 535 (M−1)

Compound 456 N-[4-Chloro-2-(3,4-dimethyl-benzylidene-hydrazinocarbonyl)-phenyl]-3-(2-diethylamino-ethylsulfanylmethyl)-benzamide The title compound 456 was produced in the same manner as in Example 5.
$^1$H-NMR (CD$_3$OD, 400 MHz): δ 8.65 (1H, d, J=9.0 Hz), 8.30 (1H, s), 7.97 (1H, s), 7.87-7.94 (2H, m), 7.58-7.67 (3H, m), 7.48-7.56 (2H, m), 7.19 (1H, d, J=7.6 Hz), 3.88 (2H, s), 2.46-2.67 (8H, m), 2.31 (3H, s), 2.29 (3H, s), 0.96 (6H, q, J=7.2 Hz)
Mass spectrometric value (ESI-MS) 549 (M−1)

Compound 457 N-[4-Chloro-2-(4-chloro-3-trifluoromethyl-benzylidene-hydrazinocarbonyl)-phenyl]-3-(2-diethylamino-ethylsulfanylmethyl)-benzamide The title compound 457 was produced in the same manner as in Example 5.
$^1$H-NMR (CD$_3$OD, 400 MHz): δ 8.63 (1H, d, J=9.0 Hz), 8.40 (1H, s), 8.33 (1H, s), 8.04 (1H, d, J=7.8 Hz), 7.93-8.00 (2H, m), 7.89 (1H, d, J=7.1 Hz), 7.69 (1H, d, J=8.0 Hz), 7.60-7.65 (2H, m), 7.52 (1H, dd, J=7.6 Hz, J=7.6 Hz), 3.88 (2H, s), 2.58-2.67 (2H, m), 2.47-2.58 (6H, m), 0.97 (6H, t, J=7.1 Hz)
Mass spectrometric value (ESI-MS) 623 (M−1)

Compound 458 N-[4-Chloro-2-(3-methoxy-benzylidene-hydrazinocarbonyl)-phenyl]-3-(2-diethylamino-ethylsulfanylmethyl)-benzamide The title compound 458 was produced in the same manner as in Example 5.
$^1$H-NMR (CD$_3$OD, 400 MHz): δ 8.64 (1H, d, J=9.0 Hz), 8.34 (1H, s), 7.97 (1H, s), 7.93 (1H, d, J=2.4 Hz), 7.87-7.91 (1H, m), 7.59-7.65 (2H, m), 7.57 (1H, s), 7.51 (1H, dd, J=7.7 Hz, J=7.7 Hz), 7.28-7.37 (2H, m), 6.97-7.03 (1H, m), 3.87 (2H, s), 3.86 (3H, s), 2.46-2.65 (8H, m), 0.96 (6H, t, J=7.2 Hz)
Mass spectrometric value (ESI-MS) 551 (M−1)

Compound 459 N-[4-Chloro-2-(4-methoxy-benzylidene-hydrazinocarbonyl)-phenyl]-3-(2-diethylamino-ethylsulfanylmethyl)-benzamide The title compound 459 was produced in the same manner as in Example 5.
$^1$H-NMR (CD$_3$OD, 400 MHz): δ 8.65 (1H, d, J=9.0 Hz), 8.31 (1H, s), 7.97 (1H, s), 7.92 (1H, d, J=2.4 Hz), 7.89 (1H, d, J=9.0 Hz), 7.79 (2H, d, J=8.8 Hz), 7.59-7.65 (2H, m), 7.51 (1H, dd, J=7.7 Hz, J=7.7 Hz), 6.99 (2H, d, J=8.8 Hz), 3.88 (2H, s), 3.84 (3H, s), 2.46-2.66 (8H, m), 0.96 (6H, t, J=7.2 Hz)
Mass spectrometric value (ESI-MS) 551 (M−1)

Compound 460 N-[4-Chloro-2-(3-hydroxy-benzylidene-hydrazinocarbonyl)-phenyl]-3-(2-diethylamino-ethylsulfanylmethyl)-benzamide The title compound 460 was produced in the same manner as in Example 5.
Mass spectrometric value (ESI-MS) 537 (M−1)

Compound 461 N-[4-Chloro-2-(4-hydroxy-benzylidene-hydrazinocarbonyl)-phenyl]-3-(2-diethylamino-ethylsulfanylmethyl)-benzamide The title compound 461 was produced in the same manner as in Example 5.
$^1$H-NMR (CD$_3$OD, 400 MHz): δ 8.66 (1H, d, J=9.0 Hz), 8.27 (1H, s), 7.97 (1H, s), 7.91 (1H, d, J=2.4 Hz), 7.89 (1H, d, J=7.6 Hz), 7.70 (2H, d, J=8.5 Hz), 7.58-7.65 (2H, m), 7.52 (1H, dd, J=7.8 Hz, J=7.8 Hz), 6.84 (2H, d, J=8.6 Hz), 3.88 (2H, s), 2.46-2.65 (8H, m), 0.96 (6H, t, J=7.2 Hz)
Mass spectrometric value (ESI-MS) 537 (M−1)

Compound 462 N-[4-Chloro-2-(3-fluoro-benzylidene-hydrazinocarbonyl)-phenyl]-3-[1-(2-dimethylamino-ethyl)-1H-tetrazol-5-ylsulfanylmethyl]-benzamide The title compound 462 was produced in the same manner as in Example 5.
$^1$H-NMR (CD$_3$OD, 400 MHz): δ 8.62 (1H, d, J=9.0 Hz), 8.36 (1H, s), 8.03 (1H, s), 7.93 (1H, d, J=2.2 Hz), 7.88-7.93 (2H, m), 7.69 (1H, d, J=10.0 Hz), 7.58-7.65 (3H, m), 7.42-7.52 (2H, m), 7.19 (1H, ddd, J=2.0 Hz, J=8.4 Hz, J=8.4 Hz), 4.63 (2H, s), 4.33 (2H, t, J=6.3 Hz), 2.67 (2H, t, J=6.3 Hz), 2.18 (6H, s)
Mass spectrometric value (ESI-MS) 579, 581 (M−1)

Compound 463 N-[4-Chloro-2-(4-fluoro-benzylidene-hydrazinocarbonyl)-phenyl]-3-[1-(2-dimethylamino-ethyl)-1H-tetrazol-5-ylsulfanylmethyl]-benzamide The title compound 463 was produced in the same manner as in Example 5.
$^1$H-NMR (CD$_3$OD, 400 MHz): δ 8.62 (1H, d, J=8.8 Hz), 8.36 (1H, s), 8.04 (1H, s), 7.87-7.94 (4H, m), 7.59-7.65 (2H, m), 7.48 (1H, dd, J=7.7 Hz, J=7.7 Hz), 7.19 (2H, dd, J=8.7 Hz, J=8.7 Hz), 4.63 (2H, s), 4.32 (2H, t, J=6.3 Hz), 2.67 (2H, t, J=6.3 Hz), 2.18 (6H, s)
Mass spectrometric value (ESI-MS) 579 (M−1)

Compound 464 N-[4-Chloro-2-(3-methyl-benzylidene-hydrazinocarbonyl)-phenyl]-3-[1-(2-dimethylamino-ethyl)-1H-tetrazol-5-ylsulfanylmethyl]-benzamide The title compound 464 was produced in the same manner as in Example 5.
$^1$H-NMR (CD$_3$OD, 400 MHz): δ 8.63 (1H, d, J=9.0 Hz), 8.34 (1H, s), 8.04 (1H, s), 7.88-7.94 (2H, m), 7.70 (1H, s), 7.59-7.64 (3H, m), 7.49 (1H, dd, J=7.7 Hz, J=7.7 Hz), 7.25-7.36 (2H, m), 4.63 (2H, s), 4.32 (2H, t, J=6.4 Hz), 2.66 (2H, t, J=6.4 Hz), 2.39 (3H, s), 2.17 (6H, s)
Mass spectrometric value (ESI-MS) 575 (M−1)

Compound 465 N-[4-Chloro-2-(4-methyl-benzylidene-hydrazinocarbonyl)-phenyl]-3-[1-(2-dimethylamino-ethyl)-1H-tetrazol-5-ylsulfanylmethyl]-benzamide The title compound 465 was produced in the same manner as in Example 5.
$^1$H-NMR (CD$_3$OD, 400 MHz): δ 8.63 (1H, d, J=8.8 Hz), 8.33 (1H, s), 8.04 (1H, s), 7.88-7.94 (2H, m), 7.73 (2H, d, J=8.1 Hz), 7.61 (2H, dd, J=2.2 Hz, J=9.0 Hz), 7.48 (1H, dd, J=7.7 Hz, J=7.7 Hz), 7.27 (2H, d, J=8.1 Hz), 4.63 (2H, s), 4.32 (2H, t, J=6.3 Hz), 2.67 (2H, t, J=6.3 Hz), 2.38 (3H, s), 2.17 (6H, s)
Mass spectrometric value (ESI-MS) 575 (M−1)

Compound 466 N-[4-Chloro-2-(3,4-dimethyl-benzylidene-hydrazinocarbonyl)-phenyl]-3-[1-(2-dimethylamino-ethyl)-1H-tetrazol-5-ylsulfanylmethyl]-benzamide The title compound 466 was produced in the same manner as in Example 5.
$^1$H-NMR (CD$_3$OD, 400 MHz): δ 8.63 (1H, d, J=8.8 Hz), 8.30 (1H, s), 8.04 (1H, s), 7.89-7.95 (2H, m), 7.59-7.68 (3H, m), 7.54 (1H, d, J=8.0 Hz), 7.49 (1H, dd, J=7.7 Hz, J=7.7 Hz), 7.21 (1H, d), 4.63 (2H, s), 4.32 (2H, t, J=6.3 Hz), 2.66 (2H, t, J=6.3 Hz), 2.32 (3H, s), 2.31 (3H, s), 2.17 (6H, s)
Mass spectrometric value (ESI-MS) 589, 591 (M−1)

Compound 467 N-[4-Chloro-2-(4-chloro-3-trifluoromethyl-benzylidene-hydrazinocarbonyl)-phenyl]-3-[1-(2-dimethylamino-ethyl)-1H-tetrazol-5-ylsulfanylmethyl]-benzamide The title compound 467 was produced in the same manner as in Example 5.
$^1$H-NMR (CD$_3$OD, 400 MHz): δ 8.60 (1H, d, J=9.0 Hz), 8.39 (1H, s), 8.31 (1H, s), 8.02-8.07 (2H, m), 7.93 (1H, d, J=2.2 Hz), 7.89 (1H, d, J=7.8 Hz), 7.69 (1H, d, J=8.3 Hz), 7.62 (2H, dd, J=2.2 Hz, J=8.8 Hz), 7.49 (1H, dd, J=7.7 Hz, J=7.7 Hz), 4.63 (2H, s), 4.32 (2H, t, J=6.4 Hz), 3.44 (1H, s), 2.67 (2H, t, J=6.3 Hz), 2.18 (6H, s)
Mass spectrometric value (ESI-MS) 663 (M−1)

Compound 468 N-[4-Chloro-2-(3-methoxy-benzylidene-hydrazinocarbonyl)-phenyl]-3-[1-(2-dimethylamino-ethyl)-1H-tetrazol-5-ylsulfanylmethyl]-benzamide The title compound 468 was produced in the same manner as in Example 5.
$^1$H-NMR (CD$_3$OD, 400 MHz): δ 8.63 (1H, d, J=9.0 Hz), 8.34 (1H, s), 8.04 (1H, s), 7.94 (1H, d, J=2.4 Hz), 7.91 (1H, d, J=8.3 Hz), 7.60-7.66 (2H, m), 7.57 (1H, s), 7.49 (1H, dd, J=7.8 Hz, J=7.8 Hz), 7.28-7.38 (2H, m), 6.98-7.04 (1H, m), 4.63 (2H, s), 4.32 (2H, t, J=6.4 Hz), 3.86 (3H, s), 3.44 (1H, s), 2.67 (2H, t, J=6.3 Hz), 2.17 (6H, s)
Mass spectrometric value (ESI-MS) 591 (M−1)

Compound 469 N-[4-Chloro-2-(4-methoxy-benzylidene-hydrazinocarbonyl)-phenyl]-3-[1-(2-dimethylamino-ethyl)-1H-tetrazol-5-ylsulfanylmethyl]-benzamide The title compound 469 was produced in the same manner as in Example 5.
$^1$H-NMR (CD$_3$OD, 400 MHz): δ 8.63 (1H, d, J=9.0 Hz), 8.31 (1H, s), 8.04 (1H, s), 7.88-7.94 (2H, m), 7.79 (2H, d, J=8.8 Hz), 7.58-7.64 (2H, m), 7.48 (1H, dd, J=7.7 Hz, J=7.7 Hz), 6.99 (2H, d, J=8.8 Hz), 4.63 (2H, s), 4.32 (2H, t, J=6.3 Hz), 3.84 (3H, s), 3.45 (1H, s), 2.67 (2H, t, J=6.3 Hz), 2.18 (6H, s)
Mass spectrometric value (ESI-MS) 591 (M−1)

Compound 470 N-[4-Chloro-2-(3-hydroxy-benzylidene-hydrazinocarbonyl)-phenyl]-3-[1-(2-dimethylamino-ethyl)-1H-tetrazol-5-ylsulfanylmethyl]-benzamide The title compound 470 was produced in the same manner as in Example 5.
$^1$H-NMR (CD$_3$OD, 400 MHz): δ 8.62 (1H, d, J=8.8 Hz), 8.29 (1H, s), 8.04 (1H, s), 7.89-7.95 (2H, m), 7.55-7.65 (2H, m), 7.48 (1H, dd, J=7.8 Hz, J=7.8 Hz), 7.31 (1H, s), 7.22-7.29 (2H, m), 6.86-6.90 (1H, m), 4.63 (2H, s), 4.32 (2H, s), 2.67 (2H, t, J=6.3 Hz), 2.17 (6H, s)
Mass spectrometric value (ESI-MS) 577 (M−1)

Compound 471 N-[4-Chloro-2-(4-hydroxy-benzylidene-hydrazinocarbonyl)-phenyl]-3-[1-(2-dimethylamino-ethyl)-1H-tetrazol-5-ylsulfanylmethyl]-benzamide The title compound 471 was produced in the same manner as in Example 5.
$^1$H-NMR (CD$_3$OD, 400 MHz): δ 8.63 (1H, d, J=9.0 Hz), 8.27 (1H, s), 8.04 (1H, s), 7.87-7.93 (2H, m), 7.69 (2H, d, J=8.5 Hz), 7.57-7.63 (2H, m), 7.48 (1H, dd, J=7.7 Hz, J=7.7 Hz), 6.84 (2H, d, J=8.5 Hz), 4.63 (2H, s), 4.32 (2H, t, J=6.4 Hz), 2.67 (2H, t, J=6.4 Hz), 2.17 (6H, s)
Mass spectrometric value (ESI-MS) 577 (M−1)

Compound 472 3-{[(2-Diethylamino-ethyl)-methylamino]-methyl}-N-[2-(3-fluoro-benzylidene-hydrazinocarbonyl)-4-iodo-phenyl]-benzamide The title compound 472 was produced in the same manner as in Example 5.
$^1$H-NMR (CD$_3$OD, 400 MHz): δ 8.44 (1H, d, J=8.8 Hz), 8.36 (1H, s), 8.23 (1H, s), 7.97 (1H, s), 7.88-7.95 (2H, m), 7.68 (1H, d, J=9.5 Hz), 7.42-7.63 (5H, m), 7.18 (1H, dd, J=8.4 Hz, J=8.4 Hz), 3.67 (2H, s), 2.78 (2H, t, J=7.1 Hz), 2.65 (4H, q, J=7.2 Hz), 2.58 (2H, t, J=7.2 Hz), 2.28 (3H, s), 1.04 (6H, t, J=7.2 Hz)
Mass spectrometric value (ESI-MS) 628 (M−1)

Compound 473 3-{[(2-Diethylamino-ethyl)-methylamino]-methyl}-N-[2-(4-fluoro-benzylidene-hydrazinocarbonyl)-4-iodo-phenyl]-benzamide The title compound 473 was produced in the same manner as in Example 5.
$^1$H-NMR (CD$_3$OD, 400 MHz): δ 8.44 (1H, d, J=8.8 Hz), 8.36 (1H, s), 8.21 (1H, d, J=1.9 Hz), 7.86-7.99 (5H, m), 7.60 (1H, d, J=7.6 Hz), 7.52 (1H, dd, J=8.8 Hz, J=8.8 Hz), 7.18 (2H, dd, J=8.8 Hz, J=8.8 Hz), 3.67 (2H, s), 2.77 (2H, t, J=7.1 Hz), 2.64 (4H, q, J=7.2 Hz), 2.58 (2H, t, J=7.2 Hz), 2.28 (3H, s), 1.04 (6H, t, J=7.2 Hz)
Mass spectrometric value (ESI-MS) 628 (M−1)

Compound 474 3-{[(2-Diethylamino-ethyl)-methylamino]-methyl}-N-[4-iodo-2-(3-methyl-benzylidene-hydrazinocarbonyl)-phenyl]-benzamide The title compound 474 was produced in the same manner as in Example 5.
$^1$H-NMR (CD$_3$OD, 400 MHz): δ 8.45 (1H, d, J=8.8 Hz), 8.33 (1H, s), 8.22 (1H, d, J=1.1 Hz), 7.97 (1H, s), 7.88-7.93

(2H, m), 7.69 (1H, s), 7.58-7.63 (2H, m), 7.52 (1H, dd, J=7.7 Hz, J=7.7 Hz), 7.32 (1H, dd, J=7.6 Hz, J=7.6 Hz), 7.25 (1H, d, J=7.3 Hz), 3.66 (2H, s), 2.67-2.73 (2H, m), 2.52-2.61 (6H, m), 2.38 (3H, s), 2.27 (3H, s), 1.01 (6H, t, J=7.2 Hz)

Mass spectrometric value (ESI-MS) 624 (M−1)

Compound 475 3-{[(2-Diethylamino-ethyl)-methyl-amino]-methyl}-N-[4-iodo-2-(4-methyl-benzylidene-hydrazinocarbonyl)-phenyl]-benzamide The title compound 475 was produced in the same manner as in Example 5.

$^1$H-NMR (CD$_3$OD, 400 MHz): δ 8.44 (1H, d, J=8.8 Hz), 8.33 (1H, s), 8.21 (1H, d, J=2.0 Hz), 7.97 (1H, s), 7.89-7.94 (2H, m), 7.72 (2H, d, J=8.0 Hz), 7.60 (1H, d, J=7.6 Hz), 7.52 (1H, dd, J=7.7 Hz, J=7.7 Hz), 7.26 (2H, d, J=7.8 Hz), 3.67 (2H, s), 2.75 (2H, t, J=7.2 Hz), 2.62 (4H, q, J=7.2 Hz), 2.57 (2H, t, J=7.2 Hz), 2.37 (3H, s), 2.28 (3H, s), 1.03 (6H, t, J=7.2 Hz)

Mass spectrometric value (ESI-MS) 624 (M−1)

Compound 476 3-{[(2-Diethylamino-ethyl)-methyl-amino]-methyl}-N-[2-(3,4-dimethyl-benzylidene-hydrazinocarbonyl)-4-iodo-phenyl]-benzamide The title compound 476 was produced in the same manner as in Example 5.

$^1$H-NMR (CD$_3$OD, 400 MHz): δ 8.44 (1H, d, J=8.8 Hz), 8.30 (1H, s), 8.20 (1H, d, J=2.0 Hz), 7.97 (1H, s), 7.90 (2H, dd, J=2.0 Hz, J=8.8 Hz), 7.58-7.66 (2H, m), 7.48-7.56 (2H, m), 7.19 (1H, d, J=7.8 Hz), 3.66 (2H, s), 2.68-2.75 (2H, m), 2.53-2.64 (6H, m), 2.30 (3H, s), 2.29 (3H, s), 2.27 (3H, s), 1.02 (6H, t, J=7.2 Hz)

Mass spectrometric value (ESI-MS) 638 (M−1)

Compound 477 N-[2-(4-chloro-3-trifluoromethyl-benzylidene-hydrazinocarbonyl)-4-iodo-phenyl]-3-{[(2-diethylamino-ethyl)-methyl-amino]-methyl}-benzamide The title compound 477 was produced in the same manner as in Example 5.

$^1$H-NMR (CD$_3$OD, 400 MHz): δ 8.43 (1H, d, J=8.8 Hz), 8.38 (1H, s), 8.32 (1H, s), 8.25 (1H, s), 8.02 (1H, d, J=0.6 Hz), 7.97 (1H, s), 7.88-7.94 (2H, m), 7.67 (1H, d, J=8.5 Hz), 7.60 (1H, d, J=7.3 Hz), 7.52 (1H, dd, J=7.6 Hz, J=7.6 Hz), 3.66 (2H, s), 2.75 (2H, t, J=7.2 Hz), 2.62 (4H, q, J=7.2 Hz), 2.56 (2H, t, J=7.2 Hz), 2.27 (3H, s), 1.03 (6H, t, J=7.2 Hz)

Mass spectrometric value (ESI-MS) 712 (M−1)

Compound 478 3-{[(2-Diethylamino-ethyl)-methyl-amino]-methyl}-N-[4-iodo-2-(3-methoxy-benzylidene-hydrazinocarbonyl)-phenyl]-benzamide The title compound 478 was produced in the same manner as in Example 5.

$^1$H-NMR (CD$_3$OD, 400 MHz): δ 8.44 (1H, d, J=8.8 Hz), 8.33 (1H, s), 8.22 (1H, d, J=2.0 Hz), 7.97 (1H, s), 7.88-7.94 (2H, m), 7.60 (1H, d, J=7.6 Hz), 7.56 (1H, bs), 7.52 (1H, dd, J=7.7 Hz, J=7.7 Hz), 7.22-7.36 (2H, m), 6.97-7.03 (1H, m), 3.86 (3H, s), 3.66 (2H, s), 2.71 (2H, t, J=7.2 Hz), 2.53-2.62 (6H, m), 2.27 (3H, s), 1.02 (6H, t, J=7.2 Hz)

Mass spectrometric value (ESI-MS) 640 (M−1)

Compound 479 3-{[(2-Diethylamino-ethyl)-methyl-amino]-methyl}-N-[4-iodo-2-(4-methoxy-benzylidene-hydrazinocarbonyl)-phenyl]-benzamide The title compound 479 was produced in the same manner as in Example 5.

$^1$H-NMR (CD$_3$OD, 400 MHz): δ 8.45 (1H, d, J=8.8 Hz), 8.31 (1H, s), 8.20 (1H, d, J=2.2 Hz), 7.97 (1H, s), 7.88-7.94 (2H, m), 7.78 (2H, d, J=8.8 Hz), 7.60 (1H, d, J=7.6 Hz), 7.52 (1H, dd, J=7.7 Hz, J=7.7 Hz), 6.99 (2H, d, J=8.8 Hz), 3.84 (3H, s), 3.67 (2H, s), 2.73 (2H, t, J=7.2 Hz), 2.60 (4H, q, J=7.2 Hz), 2.54-2.60 (2H, m), 2.28 (3H, s), 1.03 (6H, t, J=7.2 Hz)

Mass spectrometric value (ESI-MS) 640 (M−1)

Compound 480 3-{[(2-Diethylamino-ethyl)-methyl-amino]-methyl}-N-[2-(3-hydroxy-benzylidene-hydrazinocarbonyl)-4-iodo-phenyl]-benzamide The title compound 480 was produced in the same manner as in Example 5.

$^1$H-NMR (CD$_3$OD, 400 MHz): δ 8.44 (1H, d, J=8.8 Hz), 8.29 (1H, s), 8.21 (1H, d, J=2.0 Hz), 7.97 (1H, s), 7.88-7.94 (2H, m), 7.60 (1H, d, J=7.6 Hz), 7.52 (1H, dd, J=7.6 Hz, J=7.6 Hz), 7.30 (1H, s), 7.20-7.28 (2H, m), 6.87 (1H, ddd, J=2.2 Hz, J=2.2 Hz, J=7.1 Hz), 3.66 (2H, s), 2.72 (2H, t, J=7.2 Hz), 2.59 (4H, q, J=7.2 Hz), 2.56 (2H, t, J=6.8 Hz), 2.27 (3H, s), 1.02 (6H, t, J=7.2 Hz)

Mass spectrometric value (ESI-MS) 626 (M−1)

Compound 481 3-{[(2-Diethylamino-ethyl)-methyl-amino]-methyl}-N-[2-(4-hydroxy-benzylidene-hydrazinocarbonyl)-4-iodo-phenyl]-benzamide The title compound 481 was produced in the same manner as in Example 5.

$^1$H-NMR (CD$_3$OD, 400 MHz): δ 8.45 (1H, d, J=8.8 Hz), 8.27 (1H, s), 8.19 (1H, d, J=2.0 Hz), 7.97 (1H, s), 7.88-7.95 (2H, m), 7.69 (1H, d, J=8.5 Hz), 7.52 (1H, dd, J=7.7 Hz, J=7.7 Hz), 6.83 (2H, d, J=8.5 Hz), 3.67 (2H, s), 2.75 (2H, t, J=7.2 Hz), 2.62 (4H, q, J=7.2 Hz), 2.75-2.64 (2H, m), 2.28 (3H, s), 1.03 (6H, t, J=7.2 Hz)

Mass spectrometric value (ESI-MS) 626 (M−1)

Compound 482 3-[1,4']Bipiperidinyl-1'-ylmethyl-N-[2-(3-fluoro-benzylidene-hydrazinocarbonyl)-4-iodo-phenyl]-benzamide The title compound 482 was produced in the same manner as in Example 5.

$^1$H-NMR (CD$_3$OD, 400 MHz): δ 8.44 (1H, d, J=8.8 Hz), 8.36 (1H, s), 8.22 (1H, d, J=2.0 Hz), 7.87-7.97 (4H, m), 7.42-7.72 (4H, m), 7.14-7.23 (1H, m), 3.61 (2H, s), 2.98 (2H, d, J=11.5 Hz), 2.60 (4H, bs), 2.30-2.40 (1H, m), 2.05 (2H, t, J=11.2 Hz), 1.82-1.91 (2H, m), 1.55-1.66 (6H, m), 1.40-1.50 (2H, m)

Mass spectrometric value (ESI-MS) 666 (M−1)

Compound 483 3-[1,4']Bipiperidinyl-1'-ylmethyl-N-[2-(4-fluoro-benzylidene-hydrazinocarbonyl)-4-iodo-phenyl]-benzamide The title compound 483 was produced in the same manner as in Example 5.

$^1$H-NMR (CD$_3$OD, 400 MHz): δ 8.43 (1H, d, J=8.8 Hz), 8.35 (1H, s), 8.21 (1H, d, J=2.0 Hz), 7.85-7.97 (5H, m), 7.58 (1H, d, J=7.8 Hz), 7.51 (1H, dd, J=7.7 Hz, J=7.7 Hz), 7.18 (2H, dd, J=8.7 Hz, J=8.7 Hz), 3.61 (2H, s), 2.98 (2H, d, J=12.0

Hz), 2.59 (4H, bs), 2.25-2.38 (1H, m), 2.05 (2H, t, J=11.5 Hz), 1.85 (2H, d, J=12.7 Hz), 1.54-1.66 (6H, m), 1.40-1.50 (2H, m)

Mass spectrometric value (ESI-MS) 666 (M−1)

Compound 484 3-[1,4']Bipiperidinyl-1'-ylmethyl-N-[4-iodo-2-(3-methyl-benzylidene-hydrazinocarbonyl)-phenyl]-benzamide The title compound 484 was produced in the same manner as in Example 5.
$^1$H-NMR (CD$_3$OD, 400 MHz): δ 8.44 (1H, d, J=8.8 Hz), 8.34 (1H, s), 8.21 (1H, d, J=1.9 Hz), 7.88-7.97 (3H, m), 7.68 (1H, s), 7.55-7.64 (2H, m), 7.50 (1H, dd, J=7.7 Hz, J=7.7 Hz), 7.21-7.34 (2H, m), 3.60 (2H, s), 2.97 (2H, d, J=10.8 Hz), 2.54 (4H, bs), 2.38 (3H, s), 2.25-2.35 (1H, m), 2.25-2.35 (1H, m), 2.03 (2H, t, J=11.7 Hz), 1.83 (2H, d, J=12.4 Hz), 1.50-1.65 (6H, m), 1.38-1.48 (2H, m)

Mass spectrometric value (ESI-MS) 662 (M−1)

Compound 485 3-[1,4']Bipiperidinyl-1'-ylmethyl-N-[4-iodo-2-(4-methyl-benzylidene-hydrazinocarbonyl)-phenyl]-benzamide The title compound 485 was produced in the same manner as in Example 5.
$^1$H-NMR (CD$_3$OD, 400 MHz): δ 8.44 (1H, d, J=8.8 Hz), 8.33 (1H, s), 8.21 (1H, d, J=2.0 Hz), 7.87-7.97 (3H, m), 7.72 (2H, d, J=8.1 Hz), 7.58 (1H, d, J=7.6 Hz), 7.51 (1H, dd, J=7.6 Hz, J=7.6 Hz), 7.26 (2H, d, J=8.1 Hz), 3.61 (2H, s), 2.98 (2H, d, J=11.0 Hz), 2.55 (4H, bs), 2.37 (3H, s), 2.23-2.35 (1H, m), 2.05 (2H, t, J=11.7 Hz), 1.84 (2H, d, J=12.0 Hz), 1.53-1.66 (6H, m), 1.40-1.50 (2H, m)

Mass spectrometric value (ESI-MS) 662 (M−1)

Compound 486 3-[1,4']Bipiperidinyl-1'-ylmethyl-N-[2-(3,4-dimethyl-benzylidene-hydrazinocarbonyl)-4-iodo-phenyl]-benzamide The title compound 486 was produced in the same manner as in Example 5.
$^1$H-NMR (CD$_3$OD, 400 MHz): δ 8.44 (1H, d, J=8.8 Hz), 8.30 (1H, s), 8.19 (1H, d, J=2.2 Hz), 7.87-7.96 (3H, m), 7.62 (1H, s), 7.57 (1H, d, J=7.6 Hz), 7.51 (2H, d, J=7.6 Hz), 7.15-7.22 (1H, m), 3.60 (2H, s), 2.92-3.02 (2H, m), 2.52 (4H, bs), 2.29 (3H, s), 2.27 (3H, s), 2.20-2.33 (1H, m), 1.98-2.09 (2H, m), 1.78-2.87 (2H, m), 1.50-1.65 (6H, m), 1.38-1.48 (2H, m)

Mass spectrometric value (ESI-MS) 676 (M−1)

Compound 487 3-[1,4']Bipiperidinyl-1'-ylmethyl-N-[2-(4-chloro-3-trifluoromethyl-benzylidene-hydrazinocarbonyl)-4-iodo-phenyl]-benzamide The title compound 487 was produced in the same manner as in Example 5.
$^1$H-NMR (CD$_3$OD, 400 MHz): δ 8.38-8.45 (2H, m), 8.24 (1H, s), 8.24 (1H, s), 8.03 (1H, d, J=8.0 Hz), 7.87-7.97 (3H, m), 7.68 (1H, d, J=8.3 Hz), 7.58 (1H, d, J=6.8 Hz), 7.51 (1H, dd, J=7.7 Hz, J=7.7 Hz), 3.61 (2H, s), 2.98 (2H, d, J=10.5 Hz), 2.59 (4H, s), 2.28-2.38 (1H, m), 2.04 (2H, t, J=11.7 Hz), 1.80-1.90 (2H, m98, 1.55-1.65 (6H, m), 1.41-1.50 (2H, m)

Mass spectrometric value (ESI-MS) 750 (M−1)

Compound 488 3-[1,4']Bipiperidinyl-1'-ylmethyl-N-[4-iodo-2-(3-methoxy-benzylidene-hydrazinocarbonyl)-phenyl]-benzamide The title compound 488 was produced in the same manner as in Example 5.
$^1$H-NMR (CD$_3$OD, 400 MHz): δ 8.44 (1H, d, J=8.8 Hz), 8.34 (1H, s), 8.21 (1H, d, J=2.0 Hz), 7.87-7.97 (3H, m), 7.48-7.60 (3H, m), 7.27-7.36 (2H, m), 6.96-7.03 (1H, m), 3.85 (3H, s), 3.60 (2H, s), 2.97 (2H, d, J=11.2 Hz), 2.55 (4H, bs), 2.23-2.33 (1H, m), 2.03 (2H, t, J=11.6 Hz), 1.83 (2H, d, J=11.2 Hz), 1.53-1.65 (6H, m), 1.40-1.50 (2H, m)

Mass spectrometric value (ESI-MS) 678 (M−1)

Compound 489 3-[1,4']Bipiperidinyl-1'-ylmethyl-N-[4-iodo-2-(4-methoxy-benzylidene-hydrazinocarbonyl)-phenyl]-benzamide The title compound 489 was produced in the same manner as in Example 5.
$^1$H-NMR (CD$_3$OD, 400 MHz): δ 8.44 (1H, d, J=8.8 Hz), 8.32 (1H, s), 8.18-8.22 (1H, m), 7.87-7.97 (3H, m), 7.75-7.82 (2H, m), 7.55-7.62 (1H, m), 7.45-7.55 (1H, m), 6.95-7.03 (2H, m), 3.84 (3H, s), 3.61 (2H, s), 2.93-3.02 (2H, m), 2.56 (4H, bs), 2.20-2.35 (1H, m), 2.00-2.10 (2H, m), 1.80-1.88 (2H, m), 1.55-1.65 (6H, m), 1.40-1.50 (2H, m)

Mass spectrometric value (ESI-MS) 678 (M−1)

Compound 490 3-[1,4']Bipiperidinyl-1'-ylmethyl-N-[2-(3-hydroxy-benzylidene-hydrazinocarbonyl)-4-iodo-phenyl]-benzamide The title compound 490 was produced in the same manner as in Example 5.
$^1$H-NMR (CD$_3$OD, 400 MHz): δ 8.43 (1H, d, J=8.8 Hz), 8.29 (1H, s), 8.19-8.22 (1H, m), 7.87-7.97 (3H, m), 7.57 (1H, d, J=7.3 Hz), 7.47-7.53 (1H, m), 7.30 (1H, s), 7.18-7.27 (2H, m), 6.83-6.89 (1H, m), 3.61 (2H, s), 2.98 (2H, d, J=10.5 Hz), 2.56 (4H, bs), 2.25-2.35 (1H, m), 2.04 (2H, t, J=12.0 Hz), 1.84 (2H, d, J=12.0 Hz), 1.53-1.66 (6H, m), 1.40-1.50 (2H, m)

Mass spectrometric value (ESI-MS) 664 (M−1)

Compound 491 3-[1,4']Bipiperidinyl-1'-ylmethyl-N-[2-(4-hydroxy-benzylidene-hydrazinocarbonyl)-4-iodo-phenyl]-benzamide The title compound 491 was produced in the same manner as in Example 5.
$^1$H-NMR (CD$_3$OD, 400 MHz): δ 8.44 (1H, dd, J=3.7 Hz, J=8.8 Hz), 8.27 (1H, s), 8.18 (1H, bs), 7.86-7.96 (3H, m), 7.65-7.72 (2H, m), 7.54-7.61 (1H, m), 7.47-7.54 (1H, m), 6.79-6.86 (2H, m), 3.59-3.64 (2H, m), 2.93-3.03 (4H, m), 2.57 (4H, bs), 2.25-2.37 (1H, m), 1.95-2.10 (2H, m), 1.80-1.90 (2H, m), 1.58 (6H, bs), 1.45 (2H, bs)

Mass spectrometric value (ESI-MS) 664 (M−1)

Compound 492 N-{4-Chloro-2-[N'-(3,4-dimethyl-benzyl)-hydrazinocarbonyl]-phenyl}-3-(2-hydroxy-ethylsulfanylmethyl)-benzamide The title compound 492 was produced in the same manner as in Example 5.
$^1$H-NMR (CD$_3$OD, 400 MHz): δ 8.60 (1H, d, J=8.8 Hz), 7.90 (1H, s), 7.78 (1H, d, J=7.6 Hz), 7.59-7.70 (2H, m), 7.45-7.55 (2H, m), 7.09-7.13 (2H, m), 7.01 (1H, d, J=7.8 Hz), 3.96 (2H, s), 3.86 (2H, s), 3.67 (2H, t, J=6.8 Hz), 2.58 (2H, t, J=6.8 Hz), 2.16 (3H, s), 2.09 (3H, s)

Mass spectrometric value (ESI-MS) 496, 498, 499 (M−1)

Compound 493 N-[4-Chloro-2-(3,4-dimethyl-benzylidene-hydrazinocarbonyl)-phenyl]-3-(2-hydroxy-ethanesulfonylmethyl)-benzamide The title compound 493 was produced in the same manner as in Example 6.
$^1$H-NMR (CD$_3$OD, 400 MHz): δ 8.67 (1H, d, J=9.0 Hz), 8.31 (1H, s), 8.11 (1H, s), 8.04 (1H, d, J=8.0 Hz), 7.94 (1H, d, J=2.4 Hz), 7.73 (1H, d, J=8.0 Hz), 7.67 (1H, s), 7.58-7.64

(2H, m), 7.54 (1H, d, J=7.3 Hz), 7.21 (1H, d, J=7.6 Hz), 4.63 (2H, s), 4.06 (2H, t, J=5.6 Hz), 3.20 (2H, t, J=5.7 Hz), 2.32 (3H, s), 2.32 (3H, s)

Mass spectrometric value (ESI-MS) 526, 528, 529 (M−1)

Compound 494 N-[4-Bromo-2-(4-methyl-benzylidene-hydrazinocarbonyl)-phenyl]-4-methyl-benzamide The title compound 494 was produced in the same manner as in Example 5.

$^1$H-NMR (CDCl$_3$, 400 MHz): δ 8.52 (1H, d, J=8.8 Hz), 8.33 (1H, s), 7.93 (2H, d, J=7.8 Hz), 7.65-7.74 (3H, m), 7.54 (1H, d, J=8.5 Hz), 7.21-7.30 (4H, m), 2.24 (3H, s), 2.38 (3H, s)

Mass spectrometric value (ESI-MS) 448, 450 (M−1)

Compound 495 Pyridin-2-carboxylic acid [4-bromo-2-(3-fluoro-benzylidene-hydrazinocarbonyl)-phenyl]-amide The title compound 495 was produced in the same manner as in Example 5.

$^1$H-NMR (CDCl$_3$, 400 MHz): δ 8.72 (1H, s), 8.67 (1H, d, J=9.0 Hz), 8.28 (1H, s), 8.22 (1H, d, J=7.8 Hz), 7.86-7.92 (2H, m), 7.66 (1H, dd, J=2.2 Hz, J=8.8 Hz), 7.51-7.60 (2H, m), 7.46-7.51 (1H, m), 7.33-7.39 (1H, m), 7.03-7.10 (1H, m)

Mass spectrometric value (ESI-MS) 439, 441 (M−1)

Compound 496 Pyridin-2-carboxylic acid [4-bromo-2-(4-fluoro-benzylidene-hydrazinocarbonyl)-phenyl]-amide The title compound 496 was produced in the same manner as in Example 5.

$^1$H-NMR (CDCl$_3$, 400 MHz): δ 8.70 (1H, d, J=4.1 Hz), 8.65 (1H, d, J=9.0 Hz), 8.29 (1H, s), 8.21 (1H, d, J=7.8 Hz), 7.84-7.91 (2H, m), 7.74-7.81 (2H, m), 7.61-7.66 (1H, m), 7.44-7.50 (1H, m), 7.06 (2H, dd, J=8.5 Hz, J=8.5 Hz)

Mass spectrometric value (ESI-MS) 439, 441 (M−1)

Compound 497 Pyridin-2-carboxylic acid [4-bromo-2-(3-methyl-benzylidene-hydrazinocarbonyl)-phenyl]-amide The title compound 497 was produced in the same manner as in Example 5.

$^1$H-NMR (CDCl$_3$, 400 MHz): δ 8.69 (1H, s), 8.65 (1H, d, J=9.0 Hz), 8.29 (1H, s), 8.22 (1H, d, J=7.8 Hz), 7.79-7.89 (2H, m), 7.57-7.66 (2H, m), 7.48-7.54 (1H, m), 7.41-7.46 (1H, m), 7.21-7.27 (1H, m), 7.11-7.17 (1H, m), 2.35 (3H, s)

Mass spectrometric value (ESI-MS) 435, 437 (M−1)

Compound 498 Pyridin-2-carboxylic acid [4-bromo-2-(4-methyl-benzylidene-hydrazinocarbonyl)-phenyl]-amide The title compound 498 was produced in the same manner as in Example 5.

$^1$H-NMR (CDCl$_3$, 400 MHz): δ 8.63 (1H, d, J=3.9 Hz), 8.58 (1H, d, J=9.0 Hz), 8.24 (1H, s), 8.16 (1H, d, J=8.1 Hz), 7.77-7.84 (2H, m), 7.52-7.62 (3H, m), 7.37-7.42 (1H, m), 7.11 (2H, d, J=8.1 Hz), 2.25 (3H, s)

Mass spectrometric value (ESI-MS) 435, 437 (M−1)

Compound 499 Pyridin-2-carboxylic acid [4-bromo-2-(3,4-dimethyl-benzylidene-hydrazinocarbonyl)-phenyl]-amide The title compound 499 was produced in the same manner as in Example 5.

$^1$H-NMR (CDCl$_3$, 400 MHz): δ 8.69 (1H, s), 8.65 (1H, d, J=9.0 Hz), 8.24 (1H, s), 8.21 (1H, d, J=7.8 Hz), 7.80-7.89 (2H, m), 7.57-7.63 (2H, m), 7.42-7.47 (2H, m), 7.12 (1H, d, J=7.6 Hz), 2.26 (3H, s), 2.21 (3H, s)

Mass spectrometric value (ESI-MS) 449, 451 (M−1)

Compound 500 Pyridin-2-carboxylic acid [4-bromo-2-(4-chloro-3-trifluoromethyl-benzylidene-hydrazinocarbonyl)-phenyl]-amide The title compound 500 was produced in the same manner as in Example 5.

$^1$H-NMR (CDCl$_3$, 400 MHz): δ 8.63 (1H, s), 8.59 (1H, d, J=8.8 Hz), 8.24 (1H, s), 8.14 (1H, d, J=7.8 Hz), 7.97 (1H, s), 7.92 (1H, d, J=7.8 Hz), 7.78-7.84 (2H, m), 7.58 (1H, dd, J=2.2 Hz, J=9.0 Hz), 7.45 (1H, d, J=8.3 Hz), 7.38-7.43 (1H, m)

Mass spectrometric value (ESI-MS) 523, 525 (M−1)

Compound 501 N-[4-Bromo-2-(3-fluoro-benzylidene-hydrazinocarbonyl)-phenyl]-4-ethoxy-benzamide The title compound 501 was produced in the same manner as in Example 5.

$^1$H-NMR (CDCl$_3$, 400 MHz): δ 8.52 (1H, d, J=8.8 Hz), 8.35 (1H, s), 7.99 (2H, d, J=8.5 Hz), 7.71 (1H, s), 7.51-7.60 (3H, m), 7.35-7.42 (1H, m), 7.09-7.15 (1H, m), 6.95-6.99 (2H, m), 4.10 (2H, q, J=7.0 Hz), 1.45 (3H, t, J=7.0 Hz)

Mass spectrometric value (ESI-MS) 482, 484 (M−1)

Compound 502 N-[4-Bromo-2-(4-fluoro-benzylidene-hydrazinocarbonyl)-phenyl]-4-ethoxy-benzamide The title compound 502 was produced in the same manner as in Example 5.

$^1$H-NMR (CDCl$_3$, 400 MHz): δ 8.53 (1H, d, J=9.0 Hz), 8.25 (1H, s), 7.92 (2H, d, J=8.8 Hz), 7.70-7.79 (3H, m), 7.55 (1H, dd, J=9.0 Hz, J=2.2 Hz), 7.00-7.09 (2H, m), 6.87-6.94 (2H, m), 4.04 (2H, q, J=7.0 Hz), 1.39 (3H, t, J=7.0 Hz)

Mass spectrometric value (ESI-MS) 482, 484 (M−1)

Compound 503 N-[4-Bromo-2-(4-methyl-benzylidene-hydrazinocarbonyl)-phenyl]-4-ethoxy-benzamide The title compound 503 was produced in the same manner as in Example 5.

$^1$H-NMR (CDCl$_3$, 400 MHz): δ 8.56 (1H, d, J=9.0 Hz), 8.31 (1H, s), 7.99 (2H, d, J=8.5 Hz), 7.71 (2H, s), 7.69 (1H, s), 7.53-7.59 (1H, m), 7.22 (2H, d, J=8.1 Hz), 6.96 (2H, d, J=8.8 Hz), 4.09 (2H, q, J=7.0 Hz), 2.38 (3H, s), 1.44 (3H, t, J=7.0 Hz)

Mass spectrometric value (ESI-MS) 478, 480 (M−1)

Compound 504 N-[4-Bromo-2-(3,4-dimethyl-benzylidene-hydrazinocarbonyl)-phenyl]-4-ethoxy-benzamide The title compound 504 was produced in the same manner as in Example 5.

$^1$H-NMR (CDCl$_3$, 400 MHz): δ 8.48 (1H, d, J=8.5 Hz), 8.33 (1H, s), 7.99 (2H, d, J=8.1 Hz), 7.69 (1H, s), 7.63 (1H, s), 7.45-7.56 (2H, m), 7.16 (1H, d, J=7.8 Hz), 6.92-6.98 (2H, m), 4.08 (2H, q, J=6.9 Hz), 2.29 (3H, s), 2.27 (3H, s), 1.44 (3H, t, J=6.8 Hz)

Mass spectrometric value (ESI-MS) 492, 494 (M−1)

Compound 505 Pyridin-2-carboxylic acid [2-(3-fluoro-benzylidene-hydrazinocarbonyl)-phenyl]-amide The title compound 505 was produced in the same manner as in Example 5.
$^1$H-NMR (CDCl$_3$, 400 MHz): δ 8.65-8.76 (2H, m), 8.20-8.28 (2H, m), 7.86-7.92 (1H, m), 7.65-7.72 (1H, m), 7.50-7.61 (3H, m), 7.43-7.50 (1H, m), 7.31-7.38 (1H, m), 7.10-7.20 (1H, m), 7.02-7.10 (1H, m)
Mass spectrometric value (ESI-MS) 361 (M−1)

Compound 506 Pyridin-2-carboxylic acid [2-(4-fluoro-benzylidene-hydrazinocarbonyl)-phenyl]-amide The title compound 506 was produced in the same manner as in Example 5.
$^1$H-NMR (CDCl$_3$, 400 MHz): δ 8.65-8.75 (2H, m), 8.20-8.28 (2H, m), 7.88 (1H, dd, J=1.7 Hz, J=7.7 Hz), 7.74-7.83 (2H, m), 7.63-7.70 (1H, m), 7.51-7.59 (1H, m), 7.43-7.49 (1H, m), 7.09-7.19 (1H, m), 7.06 (2H, dd, J=8.5 Hz, J=8.5 Hz)
Mass spectrometric value (ESI-MS) 361 (M−1)

Compound 507 Pyridin-2-carboxylic acid [2-(3,4-dimethyl-benzylidene-hydrazinocarbonyl)-phenyl]-amide The title compound 507 was produced in the same manner as in Example 5.
$^1$H-NMR (CDCl$_3$, 400 MHz): δ 8.65-8.74 (2H, m), 8.23 (1H, d, J=7.6 Hz), 8.20 (1H, s), 7.87 (1H, ddd, J=1.7 Hz, J=7.7 Hz, J=7.7 Hz), 7.63-7.69 (1H, m), 7.57-7.63 (1H, m), 7.49-7.57 (1H, m), 7.42-7.49 (2H, m), 7.07-7.15 (2H, m), 2.26 (3H, s), 2.24 (3H, s)
Mass spectrometric value (ESI-MS) 371 (M−1)

Compound 508 Pyridin-2-carboxylic acid [2-(4-chloro-3-trifluoromethyl-benzylidene-hydrazinocarbonyl)-phenyl]-amide The title compound 508 was produced in the same manner as in Example 5.
$^1$H-NMR (CDCl$_3$, 400 MHz): δ 8.67-8.73 (2H, m), 8.29 (1H, s), 8.23 (1H, d, J=7.8 Hz), 7.96-8.05 (2H, m), 7.89 (1H, ddd, J=1.7 Hz, J=7.7 Hz, J=7.7 Hz), 7.70 (1H, d, J=7.1 Hz), 7.46-7.59 (3H, m), 7.11-7.18 (1H, m)
Mass spectrometric value (ESI-MS) 445 (M−1)

Compound 509 Cyclohexanecarboxylic acid [4-bromo-2-(3-fluoro-benzylidene-hydrazinocarbonyl)-phenyl]-amide The title compound 509 was produced in the same manner as in Example 5.
$^1$H-NMR (CDCl$_3$, 400 MHz): δ 8.49 (1H, d, J=9.0 Hz), 8.22-8.29 (1H, m), 7.48-7.68 (3H, m), 7.35-7.44 (2H, m), 7.12-7.18 (1H, m), 2.27-2.36 (1H, m), 1.97-2.04 (2H, m), 1.79-1.87 (2H, m), 1.66-1.73 (1H, m), 1.45-1.52 (1H, m), 1.21-1.38 (4H, m)
Mass spectrometric value (ESI-MS) 444, 446 (M−1)

Compound 510 Isoxazole-5-carboxylic acid [4-bromo-2-(3-fluoro-benzylidene-hydrazinocarbonyl)-phenyl]-amide The title compound 510 was produced in the same manner as in Example 5.
$^1$H-NMR (CDCl$_3$, 400 MHz): δ 8.59 (1H, d, J=8.8 Hz), 8.39 (1H, d, J=2.0 Hz), 8.31 (1H, s), 7.92 (1H, s), 7.63 (1H, dd, J=2.2 Hz, J=9.0 Hz), 7.51-7.59 (2H, m), 7.34-7.41 (1H, m), 7.07-7.13 (1H, m), 7.03 (1H, d, J=1.7 Hz)
Mass spectrometric value (ESI-MS) 429, 431 (M−1)

Compound 511 Isoxazole-5-carboxylic acid [4-bromo-2-(3-methyl-benzylidene-hydrazinocarbonyl)-phenyl]-amide The title compound 511 was produced in the same manner as in Example 5.
$^1$H-NMR (CDCl$_3$, 400 MHz): δ 8.58 (1H, d, J=9.0 Hz), 8.39 (1H, d, J=2.0 Hz), 8.29 (1H, s), 7.93 (1H, d, J=1.7 Hz), 7.63-7.70 (2H, m), 7.55 (1H, d, J=7.8 Hz), 7.17-7.31 (2H, m), 7.03 (1H, d, J=1.7 Hz), 2.38 (3H, s)
Mass spectrometric value (ESI-MS) 425, 427 (M−1)

Compound 512 Isoxazole-5-carboxylic acid [4-bromo-2-(3,4-dimethyl-benzylidene-hydrazinocarbonyl)-phenyl]-amide The title compound 512 was produced in the same manner as in Example 5.
$^1$H-NMR (CDCl$_3$, 400 MHz): δ 8.59 (1H, d, J=8.8 Hz), 8.40 (1H, d, J=1.7 Hz), 8.26 (1H, s), 7.96 (1H, d, J=2.2 Hz), 7.68 (1H, dd, J=2.2 Hz, J=9.0 Hz), 7.63 (1H, s), 7.51 (1H, d, J=7.3 Hz), 7.18 (1H, d, J=7.8 Hz), 7.05 (1H, d, J=1.7 Hz), 2.30 (3H, s), 2.29 (3H, s)
Mass spectrometric value (ESI-MS) 439, 441 (M−1)

Compound 513 Isoxazole-5-carboxylic acid [4-bromo-2-(4-chloro-3-trifluoromethyl-benzylidene-hydrazinocarbonyl)-phenyl]-amide The title compound 513 was produced in the same manner as in Example 5.
$^1$H-NMR (CDCl$_3$, 400 MHz): δ 8.60 (1H, d, J=9.0 Hz), 8.42 (1H, d, J=1.7 Hz), 8.35 (1H, s), 8.10 (1H, s), 8.04 (1H, d, J=8.3 Hz), 7.97-8.01 (1H, m), 7.70 (1H, dd, J=2.3 Hz, J=8.9 Hz), 7.58 (1H, d, J=8.3 Hz), 7.06 (1H, d, J=1.7 Hz)
Mass spectrometric value (ESI-MS) 513, 515 (M−1)

Compound 514 2,5-Dimethyl-furan-3-carboxylic acid [2-(3-fluoro-benzylidene-hydrazinocarbonyl)-phenyl]-amide The title compound 514 was produced in the same manner as in Example 5.
$^1$H-NMR (CDCl$_3$, 400 MHz): δ 8.56 (1H, d, J=8.5 Hz), 8.27 (1H, s), 7.46-7.68 (4H, m), 7.35-7.42 (1H, m), 7.04-7.14 (2H, m), 6.39 (1H, s), 2.62 (3H, s), 2.29 (3H, s)
Mass spectrometric value (ESI-MS) 378 (M−1)

Compound 515 2,5-Dimethyl-furan-3-carboxylic acid [2-(4-fluoro-benzylidene-hydrazinocarbonyl)-phenyl]-amide The title compound 515 was produced in the same manner as in Example 5.
$^1$H-NMR (CDCl$_3$, 400 MHz): δ 8.54 (1H, d, J=8.3 Hz), 8.27 (1H, s), 7.76-7.85 (2H, m), 7.61 (1H, d, J=7.6 Hz), 7.48 (1H, t, J=7.8 Hz), 7.01-7.16 (3H, m), 6.38 (1H, s), 2.62 (3H, s), 2.28 (3H, s)
Mass spectrometric value (ESI-MS) 378 (M−1)

Compound 516 2,5-Dimethyl-furan-3-carboxylic acid [2-(3-methyl-benzylidene-hydrazinocarbonyl)-phenyl]-amide The title compound 516 was produced in the same manner as in Example 5.
$^1$H-NMR (CDCl$_3$, 400 MHz): δ 8.56 (1H, d, J=8.1 Hz), 8.27 (1H, s), 7.67-7.74 (1H, m), 7.40-7.60 (4H, m), 7.28-7.35 (1H, m), 6.96-7.04 (1H, m), 6.38 (1H, s), 2.64 (3H, s), 2.40 (3H, s), 2.29 (3H, s)
Mass spectrometric value (ESI-MS) 374 (M−1)

Compound 517 N-[3-(3-Fluoro-benzylidene-hydrazinocarbonyl)-4-methyl-thiophen-2-yl]-3,4-dimethoxy-benzamide The title compound 517 was produced in the same manner as in Example 5.
$^1$H-NMR (CDCl$_3$, 400 MHz): δ 8.15 (1H, s), 7.62-7.69 (2H, m), 7.58 (1H, d, J=9.3 Hz), 7.52 (1H, d, J=7.6 Hz), 7.37-7.44 (1H, m), 7.10-7.17 (1H, m), 6.93 (1H, d, J=8.3 Hz), 6.53 (1H, s), 3.98 (3H, s), 3.96 (3H, s), 2.60 (3H, s)
Mass spectrometric value (ESI-MS) 440 (M−1)

Compound 518 3,4-Dimethoxy-N-[4-methyl-3-(3-methyl-benzylidene-hydrazinocarbonyl)-thiophen-2-yl]-benzamide The title compound 518 was produced in the same manner as in Example 5.
$^1$H-NMR (CDCl$_3$, 400 MHz): δ 8.10 (1H, s), 7.63-7.72 (3H, m), 7.54 (1H, d, J=7.6 Hz), 7.24-7.35 (2H, m), 6.92 (1H, d, J=8.3 Hz), 6.53 (1H, s), 3.98 (3H, s), 3.96 (3H, s), 2.61 (3H, s), 2.40 (3H, s)
Mass spectrometric value (ESI-MS) 436 (M−1)

Compound 519 3,4-Dimethoxy-N-[4-methyl-3-(4-methyl-benzylidene-hydrazinocarbonyl)-thiophen-2-yl]-benzamide The title compound 519 was produced in the same manner as in Example 5.
$^1$H-NMR (CDCl$_3$, 400 MHz): δ 8.10 (1H, s), 7.63-7.73 (4H, m), 7.22-7.28 (2H, m), 6.92 (1H, d, J=8.1 Hz), 6.54 (1H, s), 3.98 (3H, s), 3.96 (3H, s), 2.61 (3H, s), 2.40 (3H, s)
Mass spectrometric value (ESI-MS) 436 (M−1)

Compound 521 N-[3-(3,4-Dimethyl-benzylidene-hydrazinocarbonyl)-4-methyl-thiophen-2-yl]-3,4-dimethoxy-benzamide The title compound 521 was produced in the same manner as in Example 5.
$^1$H-NMR (CDCl$_3$, 400 MHz): δ 8.07 (1H, s), 7.63-7.70 (3H, m), 7.47 (1H, d, J=8.5 Hz), 7.19 (1H, d, J=7.8 Hz), 6.92 (1H, d, J=8.5 Hz), 6.54 (1H, s), 3.98 (3H, s), 3.96 (3H, s), 2.61 (3H, s), 2.31 (6H, s)
Mass spectrometric value (ESI-MS) 450 (M−1)

Compound 522 N-[3-(4-Chloro-3-trifluoromethyl-benzylidene-hydrazinocarbonyl)-4-methyl-thiophen-2-yl]-3,4-dimethoxy-benzamide The title compound 522 was produced in the same manner as in Example 5.
$^1$H-NMR (CDCl$_3$, 400 MHz): δ 8.23 (1H, s), 8.05-8.08 (1H, m), 7.93-7.98 (1H, m), 7.62-7.68 (2H, m), 7.58 (1H, d, J=8.5 Hz), 6.92-7.68 (2H, m), 7.58 (1H, d, J=8.5 Hz), 6.92-6.97 (1H, m), 6.55 (1H, s), 3.98 (3H, s), 3.96 (3H, s), 2.61 (3H, s)
Mass spectrometric value (ESI-MS) 524 (M−1)

Compound 523 N-[2-(3,4-Dimethyl-benzylidene-hydrazinocarbonyl)-4-methyl-thiophen-3-yl]-3-(1H-[1,2,4]triazol-3-ylsulfanylmethyl)-benzamide The title compound 523 was produced in the same manner as in Example 5.
Mass spectrometric value (ESI-MS) 503 (M−1)

Compound 524 N-[2-(3-Fluoro-benzylidene-hydrazinocarbonyl)-4-methyl-thiophen-3-yl]-3-(1H-[1,2,4]triazol-3-ylsulfanylmethyl)-benzamide The title compound 524 was produced in the same manner as in Example 5.
Mass spectrometric value (ESI-MS) 493 (M−1)

Compound 525 N-[2-(3,4-Dimethyl-benzylidene-hydrazinocarbonyl)-4-methyl-thiophen-3-yl]-3-(3-hydroxy-propylsulfanylmethyl)-benzamide The title compound 525 was produced in the same manner as in Example 5.
Mass spectrometric value (ESI-MS) 494 (M−1)

Compound 526 3-(3-Hydroxy-propylsulfanylmethyl)-N-[4-methyl-2-(4-methyl-benzylidene-hydrazinocarbonyl)-thiophen-3-yl]-benzamide The title compound 526 was produced in the same manner as in Example 5.
Mass spectrometric value (ESI-MS) 480 (M−1)

Compound 527 N-[2-(3-Fluoro-benzylidene-hydrazinocarbonyl)-4-methyl-thiophen-3-yl]-3-(3-hydroxy-propylsulfanylmethyl)-benzamide The title compound 527 was produced in the same manner as in Example 5.
Mass spectrometric value (ESI-MS) 484 (M−1)

Compound 528 3-{[(2-Diethylamino-ethyl)-methyl-amino]-methyl}-N-[2-(4-fluoro-benzylidene-hydrazinocarbonyl)-4-methyl-thiophen-3-yl]-benzamide The title compound 528 was produced in the same manner as in Example 5.
Mass spectrometric value (ESI-MS) 522 (M−1)

Compound 529 3-{[(2-Diethylamino-ethyl)-methyl-amino]-methyl}-N-[2-(3-fluoro-benzylidene-hydrazinocarbonyl)-4-methyl-thiophen-3-yl]-benzamide The title compound 529 was produced in the same manner as in Example 5.
Mass spectrometric value (ESI-MS) 522 (M−1)

Compound 530 3-{[(2-Diethylamino-ethyl)-methyl-amino]-methyl}-N-[2-(4-methoxy-benzylidene-hydrazinocarbonyl)-4-methyl-thiophen-3-yl]-benzamide The title compound 530 was produced in the same manner as in Example 5.
Mass spectrometric value (ESI-MS) 534 (M−1)

Compound 531 3-[1,4']Bipiperidinyl-1'-ylmethyl-N-[2-(4-methoxy-benzylidene-hydrazinocarbonyl)-4-methyl-thiophen-3-yl]-benzamide The title compound 531 was produced in the same manner as in Example 5.
Mass spectrometric value (ESI-MS) 572 (M−1)

Compound 532 N-[2-(3,4-Dimethyl-benzylidene-hydrazinocarbonyl)-4-methyl-thiophen-3-yl]-3-[4-(2-hydroxy-ethyl)-piperazin-1-ylmethyl]-benzamide The title compound 532 was produced in the same manner as in Example 5.
Mass spectrometric value (ESI-MS) 532 (M−1)

Compound 533 3-[4-(2-Hydroxy-ethyl)-piperazin-1-ylmethyl]-N-[4-methyl-2-(4-methyl-benzylidene-hydrazinocarbonyl)-thiophen-3-yl]-benzamide The title compound 533 was produced in the same manner as in Example 5.
Mass spectrometric value (ESI-MS) 518 (M−1)

Compound 534 N-[2-(4-Fluoro-benzylidene-hydrazinocarbonyl)-4-methyl-thiophen-3-yl]-3-[4-(2-hydroxy-ethyl)-piperazin-1-ylmethyl]-benzamide The title compound 534 was produced in the same manner as in Example 5.
Mass spectrometric value (ESI-MS) 522 (M−1)

Compound 535 N-[2-(3-Fluoro-benzylidene-hydrazinocarbonyl)-4-methyl-thiophen-3-yl]-3-[4-(2-hydroxy-ethyl)-piperazin-1-ylmethyl]-benzamide The title compound 535 was produced in the same manner as in Example 5.
Mass spectrometric value (ESI-MS) 522 (M−1)

Compound 536 3-[(2-Diethylamino-ethylamino)-methyl]-N-[2-(3,4-dimethyl-benzylidene-hydrazinocarbonyl)-4-methyl-thiophen-3-yl]-benzamide The title compound 536 was produced in the same manner as in Example 5.
Mass spectrometric value (ESI-MS) 518 (M−1)

Compound 537 3-[(2-Diethylamino-ethylamino)-methyl]-N-[4-methyl-2-(4-methyl-benzylidene-hydrazinocarbonyl)-thiophen-3-yl]-benzamide The title compound 537 was produced in the same manner as in Example 5.
Mass spectrometric value (ESI-MS) 504 (M−1)

Compound 538 3-[(2-Diethylamino-ethylamino)-methyl]-N-[2-(3-fluoro-benzylidene-hydrazinocarbonyl)-4-methyl-thiophen-3-yl]-benzamide The title compound 538 was produced in the same manner as in Example 5.
Mass spectrometric value (ESI-MS) 508 (M−1)

Compound 539 N-[2-(4-Chloro-3-trifluoromethyl-benzylidene-hydrazinocarbonyl)-4-methyl-thiophen-3-yl]-3-[(2-diethylamino-ethylamino)-methyl]-benzamide The title compound 539 was produced in the same manner as in Example 5.
Mass spectrometric value (ESI-MS) 592 (M−1)

Compound 540 3-{[Bis-(2-hydroxy-propyl)-amino]-methyl}-N-[4-methyl-2-(4-methyl-benzylidene-hydrazinocarbonyl)-thiophen-3-yl]-benzamide The title compound 540 was produced in the same manner as in Example 5.
Mass spectrometric value (ESI-MS) 521 (M−1)

Compound 541 N-[2-(3,4-Dimethyl-benzylidene-hydrazinocarbonyl)-4-methyl-thiophen-3-yl]-3-(4-hydroxy-piperidin-1-ylmethyl)-benzamide The title compound 541 was produced in the same manner as in Example 5.
Mass spectrometric value (ESI-MS) 503 (M−1)

Compound 542 N-[2-(3-Fluoro-benzylidene-hydrazinocarbonyl)-4-methyl-thiophen-3-yl]-3-(4-hydroxy-piperidin-1-ylmethyl)-benzamide The title compound 542 was produced in the same manner as in Example 5.
Mass spectrometric value (ESI-MS) 493 (M−1)

Compound 543 3-(4-Hydroxy-piperidin-1-ylmethyl)-N-[2-(4-methoxy-benzylidene-hydrazinocarbonyl)-4-methyl-thiophen-3-yl]-benzamide The title compound 543 was produced in the same manner as in Example 5.
Mass spectrometric value (ESI-MS) 505 (M−1)

Compound 544 Pyridin-2-carboxylic acid {4-bromo-2-[N'-(4-methyl-benzyl)-hydrazinocarbonyl]-phenyl}-amide The title compound 544 was produced in the same manner as in Example 7.
Mass spectrometric value (ESI-MS) 439 (M−1)

Compound 545 N-{2-[N'-(4-Methyl-benzyl)-hydrazinocarbonyl]-phenyl}-isonicotinamide The title compound 545 was produced in the same manner as in Example 7.
Mass spectrometric value (ESI-MS) 359 (M−1)

Compound 546 N-{4-Bromo-2-[N'-(4-chloro-3-trifluoromethyl-benzyl)-hydrazinocarbonyl]-phenyl}-3-(2-hydroxy-ethylsulfanylmethyl)-benzamide The title compound 546 was produced in the same manner as in Example 7.
Mass spectrometric value (ESI-MS) 614, 616, 617 (M−1)

Compound 547 N-{4-Chloro-2-[N'-(4-methyl-benzyl)-hydrazinocarbonyl]-phenyl}-3-(2-hydroxy-ethylsulfanylmethyl)-benzamide The title compound 547 was produced in the same manner as in Example 7.
Mass spectrometric value (ESI-MS) 483 (M−1)

Compound 548 N-{4-Bromo-2-[N'-(3,4-dimethyl-benzyl)-hydrazinocarbonyl]-phenyl}-3,4-dimethoxy-benzamide The title compound 548 was produced in the same manner as in Example 7.
Mass spectrometric value (ESI-MS) 508, 510 (M−1)

Compound 549 3-{[Bis-(2-hydroxy-ethyl)-amino]-methyl}-N-[4-chloro-2-(3-fluoro-benzylidene-hydrazinocarbonyl)-phenyl]-benzamide The title compound 549 was produced in the same manner as in Example 5.
$^1$H-NMR (CD$_3$OD, 400 MHz): δ 8.66 (1H, d, J=9.0 Hz), 8.35 (1H, s), 8.07 (1H, s), 7.93-7.96 (1H, m), 7.85-7.96 (1H, m), 7.85-7.92 (1H, m), 7.71-7.76 (1H, m), 7.58-7.65 (3H, m), 7.40-7.54 (2H, m), 7.15-7.23 (1H, m), 3.83 (2H, s), 3.61-3.67 (4H, m), 2.67-2.74 (4H, m)
Mass spectrometric value (ESI-MS) 511, 513 (M−1)

Compound 550 3-{[Bis-(2-hydroxy-ethyl)-amino]-methyl}-N-[4-chloro-2-(4-fluoro-benzylidene-hydrazinocarbonyl)-phenyl]-benzamide The title compound 550 was produced in the same manner as in Example 5.
$^1$H-NMR (CD$_3$OD, 400 MHz): δ 8.66 (1H, d, J=8.8 Hz), 8.35 (1H, s), 8.06 (1H, s), 7.87-7.95 (4H, m), 7.63 (1H, d, J=8.8 Hz), 7.62 (1H, d, J=8.8 Hz), 7.50 (1H, dd, J=7.6 Hz, J=7.6 Hz), 7.19 (2H, dd, J=8.8 Hz), 3.83 (2H, s), 3.65 (4H, t, J=5.9 Hz), 2.71 (4H, t, J=5.9 Hz)
Mass spectrometric value (ESI-MS) 511, 513 (M−1)

Example 8

Compound 551 N-[3-(3,4-Dimethyl-benzylidene-hydrazinocarbonyl)-4-methyl-thiophen-2-yl]-3-(1H-[1,2,4]triazol-3-ylsulfanylmethyl)-benzamide Ethyl 2-amino-4-methylthiophene-3-carboxylate (compound A) (3.0 g) was dissolved in anhydrous methylene chloride (40.0 ml). Subsequently, pyridine (1.5 ml) and 3-(chloromethyl)benzoyl chloride (compound B) (2.8 ml) were added to the solution, and the mixture was stirred at 0° C. for one hr. After the completion of the reaction, distilled water was added, and the mixture was subjected to separatory extraction with chloroform. The organic layer was washed with saturated brine, was dried over sodium sulfate, and was then concentrated to give 2-(3-chloromethyl-benzoylamino-4-methyl-thiophene-3-carboxylic acid ethyl ester as a useful intermediate (3.80 g, yield 70%).

2-(3-Chloromethyl-benzoylamino-4-methyl-thiophene-3-carboxylic acid ethyl ester (700 mg) obtained by the above reaction was dissolved in anhydrous methylene chloride (5.0 ml), triethylamine (580 μl) and 3-mercapto-1,2,4-triazole (compound B') (404 mg) were added to the solution at room temperature, and the mixture was stirred at room temperature for 15 hr. After the completion of the reaction, water was added at room temperature, and the reaction mixture was extracted by liquid separation using chloroform. The organic layer was washed with saturated brine, was dried over sodium sulfate, and was then concentrated. The residue was purified by column chromatography eluted with a chloroform-methanol system to give 4-methyl-2-[3 (1H-[1,2,4]triazol-3-ylsulfanylmethyl)-benzoylamino]-thiophene-3-carboxylic acid ethyl ester as a useful intermediate (606 mg, yield 72%).

4-Methyl-2-[3 (1H-[1,2,4]triazol-3-ylsulfanylmethyl)-benzoylamino]-thiophene-3-carboxylic acid ethyl ester produced by the above reaction was dissolved in ethanol (5.0 ml), hydrazine monohydrate (650 μl) was added to the solution, and the mixture was heated under reflux with stirring for 15 hr. After the completion of the reaction, water was added thereto at room temperature, and the mixture was subjected to separatory extraction with chloroform. The organic layer was washed with saturated brine, was dried over sodium sulfate, and was then concentrated to give a hydrazine compound N-(3-hydrazinocarbonyl-4-methyl-thiophen-2-yl)-3-(1H-[1,2,4]triazol-3-ylsulfanylmethyl)-benzamide (103 mg, crude yield 20%).

N-(3-Hydrazinocarbonyl-4-methyl-thiophen-2-yl)-3-(1H-[1,2,4]triazol-3-ylsulfanylmethyl)-benzamide (20 mg) was dissolved in anhydrous toluene (1.0 ml), 3,4-dimethyl-benzaldehyde (compound C) (13.0 μl) was added to the solution at room temperature, and the mixture was heated under reflux with stirring for 15 hr. After the completion of the reaction, the reaction product was purified by column chromatography eluted with a chloroform-methanol system to give the title compound 551 (17.4 mg, yield 69%).
$^1$H-NMR (DMSO-d$_6$, 400 MHz): δ 2.25 (6H, s), 2.37 (3H, s), 4.40 (2H, s), 6.79 (1H, s), 7.15-8.00 (7H, m), 8.28 (1H, s), 8.56 (1H, s), 11.20-11.70 (2H, m), 14.05 (1H, s)
Mass spectrometric value (ESI-MS) 503 (M−1)

Compound 552 N-[4-Methyl-3-(4-methyl-benzylidene-hydrazinocarbonyl)-thiophen-2-yl]-3-(1H-[1,2,4]triazol-3-ylsulfanylmethyl)-benzamide The title compound 552 was produced in substantially the same manner as in Example 8.
$^1$H-NMR (DMSO-d$_6$, 400 MHz): δ 2.34 (3H, s), 2.37 (3H, s), 4.40 (2H, s), 6.80 (1H, s), 7.20-8.00 (8H, m), 8.30 (1H, m), 8.57 (1H, s), 11.30-11.70 (2H, m), 14.10 (1H, s)
Mass spectrometric value (ESI-MS) 489 (M−1)

Compound 553 N-[3-(4-Fluoro-benzylidene-hydrazinocarbonyl)-4-methyl-thiophen-2-yl]-3-(1H-[1,2,4]triazol-3-ylsulfanylmethyl)-benzamide The title compound 553 was produced in substantially the same manner as in Example 8.
$^1$H-NMR (DMSO-d$_6$, 400 MHz): δ 2.36 (3H, s), 4.40 (2H, s), 6.81 (1H, s), 7.25-8.00 (8H, m), 8.40 (1H, m), 8.57 (1H, s), 11.30-11.70 (2H, m), 14.05 (1H, s)
Mass spectrometric value (ESI-MS) 493 (M−1)

Compound 554 N-[3-(3-Fluoro-benzylidene-hydrazinocarbonyl)-4-methyl-thiophen-2-yl]-3-(1H-[1,2,4]triazol-3-ylsulfanylmethyl)-benzamide The title compound 554 was produced in substantially the same manner as in Example 8.
$^1$H-NMR (DMSO-d$_6$, 400 MHz): δ 2.35 (3H, s), 4.40 (2H, s), 6.81 (1H, s), 7.20-7.96 (8H, m), 8.36 (1H, s), 8.56 (1H, s), 11.40-11.75 (2H, m), 14.05 (1H, s)
Mass spectrometric value (ESI-MS) 493 (M−1)

Compound 555 N-[3-(4-Chloro-3-trifluoromethyl-benzylidene-hydrazinocarbonyl)-4-methyl-thiophen-2-yl]-3-(1H-[1,2,4]triazol-3-ylsulfanylmethyl)-benzamide The title compound 555 was produced in substantially the same manner as in Example 8.
$^1$H-NMR (DMSO-d$_6$, 400 MHz): δ 2.34 (3H, s), 4.38 (2H, s), 6.82 (1H, s), 7.40-8.58 (9H, m), 11.40-11.75 (2H, m), 14.05 (1H, s)
Mass spectrometric value (ESI-MS) 577 (M−1)

Compound 556 N-[3-(4-Methoxy-benzylidene-hydrazinocarbonyl)-4-methyl-thiophen-2-yl]-3-(1H-[1,2,4]triazol-3-ylsulfanylmethyl)-benzamide The title compound 556 was produced in substantially the same manner as in Example 8.
$^1$H-NMR (DMSO-d$_6$, 400 MHz): δ 2.37 (3H, s), 3.80 (3H, s), 4.40 (2H, s), 6.80 (1H, s), 7.01 (2H, m), 7.40-7.74 (6H, m), 8.35 (1H, s), 8.57 (1H, s), 11.20-11.75 (2H, m), 14.05 (1H, s)
Mass spectrometric value (ESI-MS) 505 (M−1)

Compound 557 N-[3-(3,4-Dimethyl-benzylidene-hydrazinocarbonyl)-4-methyl-thiophen-2-yl]-3-(3-hydroxy-propylsulfanylmethyl)-benzamide The title compound 557 was produced in substantially the same manner as in Example 8.
$^1$H-NMR (CD$_3$OD, 400 MHz): δ 1.77 (2H, m), 2.31 (6H, m), 2.50 (5H, m), 3.63 (2H, m), 3.82 (2H, s), 6.70 (1H, s), 7.19 (1H, d, J=7.8 Hz), 7.45-7.67 (4H, m), 7.80-7.95 (2H, m), 8.22 (1H, s)
Mass spectrometric value (ESI-MS) 494 (M−1)

Compound 558 3-(3-Hydroxy-propylsulfanylmethyl)-N-[4-methyl-3-(4-methyl-benzylidene-hydrazinocarbonyl)-thiophen-2-yl]-benzamide The title compound 558 was produced in substantially the same manner as in Example 8.
$^1$H-NMR (CD$_3$OD, 400 MHz): δ 1.77 (2H, m), 2.38 (3H, s), 2.50 (5H, m), 3.60 (2H, t, J=6.4 Hz), 3.82 (2H, s), 6.71 (1H, d, J=0.96 Hz), 7.26 (2H, d, J=7.6 Hz), 7.50 (1H, m), 7.60 (1H, m), 7.73 (2H, m), 7.84 (1H, m), 7.92 (1H, s), 8.26 (1H, s)
Mass spectrometric value (ESI-MS) 480 (M−1)

Compound 559 N-[3-(4-Fluoro-benzylidene-hydrazinocarbonyl)-4-methyl-thiophen-2-yl]-3-(3-hydroxy-propylsulfanylmethyl)-benzamide The title compound 559 was produced in substantially the same manner as in Example 8.
$^1$H-NMR (CD$_3$OD, 400 MHz): δ 1.77 (2H, m), 2.50 (5H, m), 3.62 (2H, m), 3.82 (2H, s), 6.71 (1H, s), 7.12 (2H, m), 7.50 (1H, m), 7.60 (1H, m), 7.87 (4H, m), 8.28 (1H, s)
Mass spectrometric value (ESI-MS) 484 (M−1)

Compound 560 N-[3-(3-Fluoro-benzylidene-hydrazinocarbonyl)-4-methyl-thiophen-2-yl]-3-(3-hydroxy-propylsulfanylmethyl)-benzamide The title compound 560 was produced in substantially the same manner as in Example 8.
$^1$H-NMR (CD$_3$OD, 400 MHz): δ 1.77 (2H, m), 2.51 (5H, m), 3.60 (2H, t, J=6.2 Hz), 3.82 (2H, s), 6.72 (1H, s), 7.18 (1H, m), 7.42-7.65 (5H, m), 7.84 (1H, s), 7.93 (1H, s), 8.29 (1H, s)
Mass spectrometric value (ESI-MS) 484 (M−1)

Compound 561 N-[3-(4-Chloro-3-trifluoromethyl-benzylidene-hydrazinocarbonyl)-4-methyl-thiophen-2-yl]-3-(3-hydroxy-propylsulfanylmethyl)-benzamide The title compound 561 was produced in substantially the same manner as in Example 8.
$^1$H-NMR (CD$_3$OD, 400 MHz): δ 1.77 (2H, m), 2.50 (5H, m), 3.60 (2H, t, J=6.1 Hz), 3.82 (2H, s), 6.72 (1H, s), 7.50 (1H, m), 7.61 (1H, d, J=7.3 Hz), 7.68 (1H, d, J=8.3 Hz), 7.84 (1H, m), 7.93 (1H, s), 8.05 (1H, m), 8.33 (2H, s)
Mass spectrometric value (ESI-MS) 568 (M−1)

Compound 562 3-(3-Hydroxy-propylsulfanylmethyl)-N-[3-(4-methoxy-benzylidene-hydrazinocarbonyl)-4-methyl-thiophen-2-yl]-benzamide The title compound 562 was produced in substantially the same manner as in Example 8.
$^1$H-NMR (CD$_3$OD, 400 MHz): δ 1.77 (2H, m), 2.50 (5H, m), 3.60 (2H, t, J=6.2 Hz), 3.81 (2H, s), 3.84 (3H, s), 6.70 (1H, d, J=1.0 Hz), 6.99 (2H, d, J=8.3 Hz), 7.50 (1H, m), 7.60 (1H, m), 7.80 (3H, m), 7.92 (1H, s), 8.23 (1H, m)
Mass spectrometric value (ESI-MS) 496 (M−1)

Compound 563 3-{[(2-Diethylamino-ethyl)-methyl-amino]-methyl}-N-[3-(3,4-dimethyl-benzylidene-hydrazinocarbonyl)-4-methyl-thiophen-2-yl]-benzamide The title compound 563 was produced in substantially the same manner as in Example 8.
$^1$H-NMR (CD$_3$OD, 400 MHz): δ 1.05 (6H, t, J=7.2 Hz), 2.26 (3H, s), 2.30 (3H, s), 2.31 (3H, s), 2.50 (2H, m), 2.57 (2H, m), 2.67 (5H, m), 2.79 (2H, m), 3.65 (2H, s), 6.64 (1H, s), 7.19 (1H, d, J=7.8 Hz), 7.46-7.65 (4H, m), 7.86-7.97 (2H, m), 8.21 (1H, s)
Mass spectrometric value (ESI-MS) 532 (M−1)

Compound 564 3-{[(2-Diethylamino-ethyl)-methyl-amino]-methyl}-N-[4-methyl-3-(4-methyl-benzylidene-hydrazinocarbonyl)-thiophen-2-yl]-benzamide The title compound 564 was produced in substantially the same manner as in Example 8.
$^1$H-NMR (CD$_3$OD, 400 MHz): δ 1.05 (6H, t, J=7.3 Hz), 2.26 (3H, s), 2.38 (3H, s), 2.50 (2H, s), 2.57 (2H, m), 2.67 (5H, m), 2.78 (2H, m), 3.65 (2H, s), 6.63 (1H, s), 7.25 (2H, d, J=7.8 Hz), 7.51 (1H, dd, J=7.6 Hz, J=7.6 Hz), 7.58 (1H, d, J=7.6 Hz), 7.72 (2H, m), 7.91 (2H, m), 8.25 (1H, s)
Mass spectrometric value (ESI-MS) 518 (M−1)

Compound 565 3-{[(2-Diethylamino-ethyl)-methyl-amino]-methyl}-N-[3-(4-fluoro-benzylidene-hydrazinocarbonyl)-4-methyl-thiophen-2-yl]-benzamide The title compound 565 was produced in substantially the same manner as in Example 8.
$^1$H-NMR (CD$_3$OD, 400 MHz): δ 1.05 (6H, m), 2.56 (3H, s), 2.49 (2H, m), 2.57 (2H, m), 2.66 (5H, m), 2.77 (2H, m), 3.64 (2H, s), 6.62 (1H, s), 7.16 (2H, dd, J=8.7 Hz, J=8.7 Hz), 7.50 (2H, m), 7.91 (4H, m), 8.27 (1H, s)
Mass spectrometric value (ESI-MS) 522 (M−1)

Compound 566 3-{[(2-Diethylamino-ethyl)-methyl-amino]-methyl}-N-[3-(3-fluoro-benzylidene-hydrazinocarbonyl)-4-methyl-thiophen-2-yl]-benzamide The title compound 566 was produced in substantially the same manner as in Example 8.
$^1$H-NMR (CD$_3$OD, 400 MHz): δ 1.07 (6H, t, J=7.2 Hz), 2.26 (3H, m), 2.50 (2H, s), 2.58 (2H, m), 2.72 (5H, m), 2.83

(2H, m), 3.65 (2H, s), 6.62 (1H, s), 7.15 (1H, ddd, J=8.3 Hz, J=8.3 Hz, J=1.7 Hz), 7.40-7.80 (5H, m), 7.87-7.90 (2H, m), 8.27 (1H, s)

Mass spectrometric value (ESI-MS) 522 (M−1)

Compound 567 N-[3-(4-Chloro-3-trifluoromethyl-benzylidene-hydrazinocarbonyl)-4-methyl-thiophen-2-yl]-3-{[(2-diethylamino-ethyl)-methyl-amino]-methyl}-benzamide The title compound 567 was produced in substantially the same manner as in Example 8.

$^1$H-NMR (CD$_3$OD, 400 MHz): δ 1.06 (6H, t, J=7.3 Hz), 2.26 (3H, m), 2.49 (2H, s), 2.57 (2H, m), 2.68 (5H, m), 2.80 (2H, m), 3.64 (2H, s), 6.60 (1H, s), 7.50 (1H, m), 7.57 (1H, d, J=7.6 Hz), 7.65 (1H, d, J=8.3 Hz), 7.94 (3H, m), 8.28 (2H, m)

Mass spectrometric value (ESI-MS) 606 (M−1)

Compound 568 3-{[(2-Diethylamino-ethyl)-methyl-amino]-methyl}-N-[3-(4-methoxy-benzylidene-hydrazinocarbonyl)-4-methyl-thiophen-2-yl]-benzamide The title compound 568 was produced in substantially the same manner as in Example 8.

$^1$H-NMR (CD$_3$OD, 400 MHz): δ 1.05 (6H, t, J=7.2 Hz), 2.25 (3H, s), 2.49 (2H, s), 2.57 (2H, m), 2.66 (5H, m), 2.77 (2H, m), 3.64 (2H, m), 3.83 (3H, s), 6.63 (1H, s), 6.97 (2H, d, J=8.5 Hz), 7.42-7.59 (2H, m), 7.76 (2H, m), 7.90 (2H, m), 8.22 (1H, s)

Mass spectrometric value (ESI-MS) 534 (M−1)

Compound 569 3-[1,4']Bipiperidinyl-1'-ylmethyl-N-[3-(3,4-dimethyl-benzylidene-hydrazinocarbonyl)-4-methyl-thiophen-2-yl]-benzamide The title compound 569 was produced in substantially the same manner as in Example 8.

$^1$H-NMR (CD$_3$OD, 400 MHz): δ 1.49 (2H, m), 1.64 (6H, m), 1.87 (2H, m), 2.03 (2H, m), 2.27 (1H, m), 2.29 (6H, m), 2.49 (3H, s), 2.71 (4H, m), 2.96 (2H, d, J=11.0 Hz), 3.59 (2H, s), 6.66 (1H, s), 7.18 (1H, d, J=7.6 Hz), 7.45-7.73 (4H, m), 7.88 (2H, s), 8.22 (1H, s)

Mass spectrometric value (ESI-MS) 570 (M−1)

Compound 570 3-[1,4']Bipiperidinyl-1'-ylmethyl-N-[4-methyl-3-(4-methyl-benzylidene-hydrazinocarbonyl)-thiophen-2-yl]-benzamide The title compound 570 was produced in substantially the same manner as in Example 8.

$^1$H-NMR (CD$_3$OD, 400 MHz): δ 1.49 (2H, m), 1.65 (6H, m), 1.88 (2H, d, J=11.0 Hz), 2.04 (2H, t, J=11.5 Hz), 2.34 (1H, s), 2.37 (3H, s), 2.49 (3H, s), 2.74 (4H, bs), 2.97 (2H, d, J=11.2 Hz), 3.58 (2H, s), 6.67 (1H, s), 7.24 (2H, d, J=7.8 Hz), 7.45-7.60 (2H, m), 7.70 (2H, m), 7.85-7.95 (2H, m), 8.26 (1H, s)

Mass spectrometric value (ESI-MS) 556 (M−1)

Compound 571 3-[1,4']Bipiperidinyl-1'-ylmethyl-N-[3-(4-fluoro-benzylidene-hydrazinocarbonyl)-4-methyl-thiophen-2-yl]-benzamide The title compound 571 was produced in substantially the same manner as in Example 8.

$^1$H-NMR (CD$_3$OD, 400 MHz): δ 1.48 (2H, m), 1.63 (6H, m), 1.86 (2H, d, J=11.4 Hz), 2.03 (2H, t, J=11.2 Hz), 2.36- 2.54 (4H, m), 2.66 (4H, m), 2.96 (2H, d, J=11.2 Hz), 3.58 (2H, s), 6.66 (1H, s), 7.17 (2H, dd, J=8.5 Hz, J=8.5 Hz), 7.45-7.60 (2H, m), 7.85-7.94 (4H, m), 8.28 (1H, s)

Mass spectrometric value (ESI-MS) 560 (M−1)

Compound 572 3-[1,4']Bipiperidinyl-1'-ylmethyl-N-[3-(3-fluoro-benzylidene-hydrazinocarbonyl)-4-methyl-thiophen-2-yl]-benzamide The title compound 572 was produced in substantially the same manner as in Example 8.

$^1$H-NMR (CD$_3$OD, 400 MHz): δ 1.49 (2H, m), 1.64 (6H, m), 1.87 (2H, d, J=11.7 Hz), 2.03 (2H, t, J=11.2 Hz), 2.49 (4H, s), 2.72 (4H, m), 2.96 (2H, d, J=11.5 Hz), 3.58 (2H, s), 6.65 (1H, s), 7.15 (1H, m), 7.40-7.75 (5H, m), 7.85-7.95 (2H, m), 8.28 (1H, s)

Mass spectrometric value (ESI-MS) 560 (M−1)

Compound 573 3-[1,4']Bipiperidinyl-1'-ylmethyl-N-[3-(4-chloro-3-trifluoromethyl-benzylidene-hydrazinocarbonyl)-4-methyl-thiophen-2-yl]-benzamide The title compound 573 was produced in substantially the same manner as in Example 8.

$^1$H-NMR (CD$_3$OD, 400 MHz): δ 1.49 (2H, m), 1.63 (6H, m), 1.87 (2H, d, J=11.2 Hz), 2.04 (2H, t, J=11.1 Hz), 2.40-2.54 (4H, m), 2.68 (4H, m), 2.97 (2H, d, J=11.5 Hz), 3.59 (2H, s), 6.65 (1H, s), 7.45-7.60 (2H, m), 7.67 (1H, d, J=8.3 Hz), 7.85-8.05 (3H, m), 8.31 (2H, m)

Mass spectrometric value (ESI-MS) 644 (M−1)

Compound 574 3-[1,4']Bipiperidinyl-1'-ylmethyl-N-[3-(4-methoxy-benzylidene-hydrazinocarbonyl)-4-methyl-thiophen-2-yl]-benzamide The title compound 574 was produced in substantially the same manner as in Example 8.

$^1$H-NMR (CD$_3$OD, 400 MHz): δ 1.49 (2H, m), 1.61 (6H, m), 1.85 (2H, d, J=11.7 Hz), 2.02 (2H, t, J=11.6 Hz), 2.30-2.52 (4H, m), 2.65 (4H, bs), 2.95 (2H, d, J=11.0 Hz), 3.58 (2H, s), 3.83 (3H, s), 6.66 (1H, s), 6.98 (2H, d, J=8.3 Hz), 7.44-7.61 (2H, m), 7.76 (2H, m), 7.90 (2H, m), 8.23 (1H, s)

Mass spectrometric value (ESI-MS) 572 (M−1)

Compound 575 N-[3-(3,4-Dimethyl-benzylidene-hydrazinocarbonyl)-4-methyl-thiophen-2-yl]-3-[4-(2-hydroxy-ethyl)-piperazin-1-ylmethyl]-benzamide The title compound 575 was produced in substantially the same manner as in Example 8.

$^1$H-NMR (CD$_3$OD, 400 MHz): δ 2.29 (6H, s), 2.48 (3H, s), 2.52-2.70 (10H, m), 3.62 (2H, s), 3.66 (2H, t, J=6.0 Hz), 6.68 (1H, d, J=1.0 Hz), 7.17 (1H, d, J=7.6 Hz), 7.50 (2H, m), 7.59 (2H, m), 7.80-7.95 (2H, m), 8.22 (1H, s)

Mass spectrometric value (ESI-MS) 532 (M−1)

Compound 576 3-[4-(2-Hydroxy-ethyl)-piperazin-1-ylmethyl]-N-[4-methyl-3-(4-methyl-benzylidene-hydrazinocarbonyl)-thiophen-2-yl]-benzamide The title compound 576 was produced in substantially the same manner as in Example 8.

$^1$H-NMR (CD$_3$OD, 400 MHz): δ 2.38 (3H, s), 2.49 (3H, s), 2.54-2.74 (10H, m), 3.60-3.70 (4H, m), 6.71 (1H, d, J=1.2 Hz), 7.25 (2H, d, J=7.6 Hz), 7.51 (1H, dd, J=7.4 Hz, J=7.4 Hz), 7.59 (1H, d, J=7.4 Hz), 7.71 (2H, bs), 7.85-7.95 (2H, m), 8.26 (1H, s)

Mass spectrometric value (ESI-MS) 518 (M−1)

Compound 577 N-[3-(4-Fluoro-benzylidene-hydrazinocarbonyl)-4-methyl-thiophen-2-yl]-3-[4-(2-hydroxy-ethyl)-piperazin-1-ylmethyl]-benzamide The title compound 577 was produced in substantially the same manner as in Example 8.
$^1$H-NMR (CD$_3$OD, 400 MHz): δ 2.49 (3H, m), 2.52-2.76 (10H, m), 3.63 (2H, s), 3.68 (2H, t, J=5.8 Hz), 6.69 (1H, d, J=1.0 Hz), 7.17 (2H, dd, J=8.6 Hz, J=8.6 Hz), 7.50 (1H, dd, J=7.6 Hz, J=7.6 Hz), 7.59 (1H, d, J=7.6 Hz), 7.82-7.94 (4H, m), 8.28 (1H, s)
Mass spectrometric value (ESI-MS) 522 (M−1)

Compound 578 N-[3-(3-Fluoro-benzylidene-hydrazinocarbonyl)-4-methyl-thiophen-2-yl]-3-[4-(2-hydroxy-ethyl)-piperazin-1-ylmethyl]-benzamide The title compound 578 was produced in substantially the same manner as in Example 8.
$^1$H-NMR (CD$_3$OD, 400 MHz): δ 2.49 (3H, s), 2.57 (4H, m), 2.64 (2H, t, J=5.9 Hz), 2.71 (4H, m), 3.63 (2H, s), 3.68 (2H, t, J=5.9 Hz), 6.68 (1H, d, J=1.0 Hz), 7.16 (1H, dd, J=8.1 Hz, J=8.1 Hz), 7.40-7.70 (5H, m), 7.82-7.95 (2H, m), 8.28 (1H, s)
Mass spectrometric value (ESI-MS) 522 (M−1)

Compound 579 N-[3-(4-Chloro-3-trifluoromethyl-benzylidene-hydrazinocarbonyl)-4-methyl-thiophen-2-yl]-3-[4-(2-hydroxy-ethyl)-piperazin-1-ylmethyl]-benzamide The title compound 579 was produced in substantially the same manner as in Example 8.
$^1$H-NMR (CD$_3$OD, 400 MHz): δ 2.49 (3H, s), 2.52-2.68 (10H, m), 3.63 (2H, s), 3.66 (2H, t, J=6.0 Hz), 6.70 (1H, d, J=1.0 Hz), 7.51 (1H, dd, J=7.3 Hz, J=7.3 Hz), 7.60 (1H, d, J=7.3 Hz), 7.67 (1H, d, J=8.3 Hz), 7.87 (1H, m), 7.93 (1H, s), 8.00 (1H, bs), 8.32 (2H, m)
Mass spectrometric value (ESI-MS) 606 (M−1)

Compound 580 3-[4-(2-Hydroxy-ethyl)-piperazin-1-ylmethyl]-N-[3-(4-methoxy-benzylidene-hydrazinocarbonyl)-4-methyl-thiophen-2-yl]-benzamide The title compound 580 was produced in substantially the same manner as in Example 8.
$^1$H-NMR (CD$_3$OD, 400 MHz): δ 2.49 (3H, s), 2.50-2.75 (10H, m), 3.63 (2H, s), 3.67 (2H, t, J=6.0 Hz), 3.83 (3H, s), 6.69 (1H, d, J=1.0 Hz), 6.98 (2H, d, J=8.3 Hz), 7.50 (1H, dd, J=7.6 Hz, J=7.6 Hz), 7.59 (1H, d, J=7.6 Hz), 7.76 (2H, m), 7.82-7.94 (2H, m), 8.23 (1H, s)
Mass spectrometric value (ESI-MS) 534 (M−1)

Compound 581 3-[(2-Diethylamino-ethylamino)-methyl]-N-[3-(3,4-dimethyl-benzylidene-hydrazinocarbonyl)-4-methyl-thiophen-2-yl]-benzamide The title compound 581 was produced in substantially the same manner as in Example 8.
$^1$H-NMR (CD$_3$OD, 400 MHz): δ 1.20 (6H, t, J=7.2 Hz), 2.31 (3H, s), 2.32 (3H, s), 2.51 (3H, s), 2.91 (2H, t, J=6.2 Hz), 3.02 (6H, m), 3.97 (2H, s), 6.71 (1H, d, J=1.0 Hz), 7.20 (1H, d, J=7.8 Hz), 7.50-7.70 (4H, m), 7.91 (1H, m), 7.99 (1H, m), 8.25 (1H, s)
Mass spectrometric value (ESI-MS) 518 (M−1)

Compound 582 3-[(2-Diethylamino-ethylamino)-methyl]-N-[4-methyl-3-(4-methyl-benzylidene-hydrazinocarbonyl)-thiophen-2-yl]-benzamide The title compound 582 was produced in substantially the same manner as in Example 8.
$^1$H-NMR (CD$_3$OD, 400 MHz): δ 1.22 (6H, t, J=7.2 Hz), 2.39 (3H, s), 2.51 (3H, s), 2.93 (2H, t, J=6.2 Hz), 3.06 (6H, m), 3.39 (2H, s), 6.72 (1H, d, J=1.0 Hz), 7.27 (2H, d, J=7.8 Hz), 7.52-7.77 (4H, m), 7.91 (1H, m), 8.01 (1H, m), 8.28 (1H, s)
Mass spectrometric value (ESI-MS) 504 (M−1)

Compound 583 3-[(2-Diethylamino-ethylamino)-methyl]-N-[3-(4-fluoro-benzylidene-hydrazinocarbonyl)-4-methyl-thiophen-2-yl]-benzamide The title compound 583 was produced in substantially the same manner as in Example 8.
$^1$H-NMR (CD$_3$OD, 400 MHz): δ 1.19 (6H, t, J=7.2 Hz), 2.52 (3H, s), 2.89 (2H, t, J=6.1 Hz), 2.98 (6H, m), 3.96 (2H, s), 6.72 (1H, d, J=1.0 Hz), 7.19 (2H, dd, J=8.7 Hz, J=8.7 Hz), 7.56 (1H, m), 7.64 (1H, d, J=7.2 Hz), 7.90 (3H, m), 7.99 (1H, s), 8.30 (1H, s)
Mass spectrometric value (ESI-MS) 509 (M−1)

Compound 584 3-[(2-Diethylamino-ethylamino)-methyl]-N-[3-(3-fluoro-benzylidene-hydrazinocarbonyl)-4-methyl-thiophen-2-yl]-benzamide The title compound 584 was produced in substantially the same manner as in Example 8.
$^1$H-NMR (CD$_3$OD, 400 MHz): δ 1.20 (6H, t, J=7.2 Hz), 2.52 (3H, s), 2.90 (2H, m), 3.00 (6H, m), 3.96 (2H, s), 6.71 (1H, d, J=1.2 Hz), 7.18 (1H, dd, J=8.3 Hz, J=8.3 Hz), 7.46 (1H, m), 7.52-7.75 (4H, m), 7.91 (1H, m), 7.99 (1H, s), 8.31 (1H, s)
Mass spectrometric value (ESI-MS) 508 (M−1)

Compound 585 N-[3-(4-Chloro-3-trifluoromethyl-benzylidene-hydrazinocarbonyl)-4-methyl-thiophen-2-yl]-3-[(2-diethylamino-ethylamino)-methyl]-benzamide The title compound 585 was produced in substantially the same manner as in Example 8.
$^1$H-NMR (CD$_3$OD, 400 MHz): δ 1.16 (6H, t, J=7.2 Hz), 2.51 (3H, s), 2.91 (8H, m), 3.95 (2H, s), 6.70 (1H, d, J=1.2 Hz), 7.55 (1H, m), 7.64 (1H, d, J=8.0 Hz), 7.69 (1H, d, J=8.3 Hz), 7.91 (1H, m), 7.98 (2H, m), 8.34 (2H, s)
Mass spectrometric value (ESI-MS) 592 (M−1)

Compound 586 3-[(2-Diethylamino-ethylamino)-methyl]-N-[3-(4-methoxy-benzylidene-hydrazinocarbonyl)-4-methyl-thiophen-2-yl]-benzamide The title compound 586 was produced in substantially the same manner as in Example 8.
$^1$H-NMR (CD$_3$OD, 400 MHz): δ 1.16 (6H, t, J=7.2 Hz), 2.51 (3H, s), 2.90 (8H, m), 3.85 (3H, s), 3.94 (2H, s), 6.70 (1H, d, J=1.0 Hz), 6.99 (2H, d, J=8.8 Hz), 7.56 (1H, m), 7.64 (1H, m), 7.79 (2H, d, J=7.3 Hz), 7.91 (1H, m), 7.98 (1H, s), 8.25 (1H, s)
Mass spectrometric value (ESI-MS) 520 (M−1)

Compound 587 3-{[Bis-(2-hydroxy-propyl)-amino]-methyl}-N-[3-(3,4-dimethyl-benzylidene-hydrazinocarbonyl)-4-methyl-thiophen-2-yl]-benzamide The title compound 587 was produced in substantially the same manner as in Example 8.
$^1$H-NMR (CD$_3$OD, 400 MHz): δ 1.09 (6H, m), 2.31 (6H, m), 2.51 (7H, m), 3.60-3.95 (4H, m), 6.70 (1H, d, J=1.0 Hz), 7.19 (1H, d, J=8.0 Hz), 7.52 (2H, m), 7.65 (2H, d, J=6.6 Hz), 7.87 (1H, m), 7.99 (1H, s), 8.22 (1H, s)
Mass spectrometric value (ESI-MS) 535 (M−1)

Compound 588 3-{[Bis-(2-hydroxy-propyl)-amino]-methyl}-N-[4-methyl-3-(4-methyl-benzylidene-hydrazinocarbonyl)-thiophen-2-yl]-benzamide The title compound 588 was produced in substantially the same manner as in Example 8.
$^1$H-NMR (CD$_3$OD, 400 MHz): δ 1.09 (6H, m), 2.38 (3H, s), 2.51 (7H, m), 3.68-3.94 (4H, m), 6.70 (1H, d, J=1.2 Hz), 7.25 (2H, m), 7, 51 (1H, m), 7.65 (1H, d, J=7.3 Hz), 7.73 (2H, m), 7.87 (1H, m), 7.99 (1H, s), 8.26 (1H, s)
Mass spectrometric value (ESI-MS) 521 (M−1)

Compound 589 3-{[Bis-(2-hydroxy-propyl)-amino]-methyl}-N-[3-(4-fluoro-benzylidene-hydrazinocarbonyl)-4-methyl-thiophen-2-yl]-benzamide The title compound 589 was produced in substantially the same manner as in Example 8.
$^1$H-NMR (CD$_3$OD, 400 MHz): δ 1.09 (6H, m), 2.49 (7H, m), 3.65-3.95 (4H, m), 6.71 (1H, m), 7.18 (2H, dd, J=8.8 Hz, J=8.8 Hz), 7.51 (1H, dd, J=7.4 Hz, J=7.4 Hz), 7.65 (1H, d, J=7.4 Hz), 7.88 (3H, m), 7.99 (1H, s), 8.29 (1H, s)
Mass spectrometric value (ESI-MS) 526 (M−1)

Compound 590 3-{[Bis-(2-hydroxy-propyl)-amino]-methyl}-N-[3-(3-fluoro-benzylidene-hydrazinocarbonyl)-4-methyl-thiophen-2-yl]-benzamide The title compound 590 was produced in substantially the same manner as in Example 8.
$^1$H-NMR (CD$_3$OD, 400 MHz): δ 1.09 (6H, m), 2.49 (7H, m), 3.87 (4H, m), 6.71 (1H, d, J=1.0 Hz), 7.17 (2H, m), 7.40-7.75 (4H, m), 7.87 (1H, d, J=7.8 Hz), 8.00 (1H, s), 8.29 (1H, s)
Mass spectrometric value (ESI-MS) 525 (M−1)

Compound 591 3-{[Bis-(2-hydroxy-propyl)-amino]-methyl}-N-[3-(4-chloro-3-trifluoromethyl-benzylidene-hydrazinocarbonyl)-4-methyl-thiophen-2-yl]-benzamide The title compound 591 was produced in substantially the same manner as in Example 8.
$^1$H-NMR (CD$_3$OD, 400 MHz): δ 1.08 (6H, m), 2.50 (7H, m), 3.65-3.95 (4H, m), 6.71 (1H, d, J=1.0 Hz), 7.51 (1H, dd, J=7.6 Hz, J=7.6 Hz), 7.66 (2H, m), 7.86 (1H, m), 8.02 (2H, m), 8.33 (2H, m)
Mass spectrometric value (ESI-MS) 609 (M−1)

Compound 592 3-{[Bis-(2-hydroxy-propyl)-amino]-methyl}-N-[3-(4-methoxy-benzylidene-hydrazinocarbonyl)-4-methyl-thiophen-2-yl]-benzamide The title compound 592 was produced in substantially the same manner as in Example 8.
$^1$H-NMR (CD$_3$OD, 400 MHz): δ 1.09 (6H, d, J=6.1 Hz), 2.49 (7H, m), 3.85 (7H, m), 6.70 (1H, d, J=1.0 Hz), 6.99 (2H, d, J=8.3 Hz), 7.51 (1H, m), 7.65 (1H, d, J=7.6 Hz), 7.84 (3H, m), 7.99 (1H, s), 8.23 (1H, s)
Mass spectrometric value (ESI-MS) 537 (M−1)

Compound 593 N-[3-(3,4-Dimethyl-benzylidene-hydrazinocarbonyl)-4-methyl-thiophen-2-yl]-3-(4-hydroxy-piperidin-1-ylmethyl)-benzamide The title compound 593 was produced in substantially the same manner as in Example 8.
$^1$H-NMR (CD$_3$OD, 400 MHz): δ 1.59 (2H, m), 1.85 (2H, m), 2.29 (8H, bs), 2.48 (3H, s), 2.84 (2H, m), 3.66 (3H, m), 6.68 (1H, d, J=1.0 Hz), 7.17 (1H, d, J=7.6 Hz), 7.52 (1H, m), 7.61 (2H, d, J=5.6 Hz), 7.89 (2H, m), 8.22 (1H, s)
Mass spectrometric value (ESI-MS) 503 (M−1)

Compound 594 3-(4-Hydroxy-piperidin-1-ylmethyl)-N-[4-methyl-3-(4-methyl-benzylidene-hydrazinocarbonyl)-thiophen-2-yl]-benzamide The title compound 594 was produced in substantially the same manner as in Example 8.
$^1$H-NMR (CD$_3$OD, 400 MHz): δ 1.59 (2H, m), 1.86 (2H, m), 2.35 (5H, m), 2.49 (3H, s), 2.87 (2H, m), 3.67 (3H, m), 6.70 (1H, d, J=1.2 Hz), 7.25 (2H, d, J=7.8 Hz), 7.53 (1H, dd, J=7.3 Hz, J=7.3 Hz), 7.63 (1H, d, J=7.3 Hz), 7.71 (2H, m), 7.91 (2H, m), 8.26 (1H, s)
Mass spectrometric value (ESI-MS) 489 (M−1)

Compound 595 N-[3-(4-Fluoro-benzylidene-hydrazinocarbonyl)-4-methyl-thiophen-2-yl]-3-(4-hydroxy-piperidin-1-ylmethyl)-benzamide The title compound 595 was produced in substantially the same manner as in Example 8.
$^1$H-NMR (CD$_3$OD, 400 MHz): δ 1.62 (2H, m), 1.87 (2H, m), 2.36 (2H, m), 2.49 (3H, s), 2.89 (2H, m), 3.66 (1H, m), 3.74 (2H, s), 6.72 (1H, d, J=1.0 Hz), 7.18 (2H, dd, J=8.6 Hz, J=8.6 Hz), 7.54 (1H, m), 7.64 (1H, d, J=7.3 Hz), 7.91 (4H, m), 8.29 (1H, s)
Mass spectrometric value (ESI-MS) 493 (M−1)

Compound 596 N-[3-(3-Fluoro-benzylidene-hydrazinocarbonyl)-4-methyl-thiophen-2-yl]-3-(4-hydroxy-piperidin-1-ylmethyl)-benzamide The title compound 596 was produced in substantially the same manner as in Example 8.
$^1$H-NMR (CD$_3$OD, 400 MHz): δ 1.60 (2H, m), 1.87 (2H, m), 2.35 (2H, m), 2.49 (3H, s), 2.88 (2H, m), 3.66 (1H, m), 3.72 (2H, s), 6.69 (1H, d, J=1.1 Hz), 7.16 (1H, dd, J=8.3 Hz, J=8.3 Hz), 7.44 (1H, m), 7.53 (2H, m), 7.63 (2H, m), 7.91 (2H, m), 8.28 (1H, s)
Mass spectrometric value (ESI-MS) 493 (M−1)

Compound 597 N-[3-(4-Chloro-3-trifluoromethyl-benzylidene-hydrazinocarbonyl)-4-methyl-thiophen-2-yl]-3-(4-hydroxy-piperidin-1-ylmethyl)-benzamide The title compound 597 was produced in substantially the same manner as in Example 8.
$^1$H-NMR (CD$_3$OD, 400 MHz): δ 1.61 (2H, m), 1.86 (2H, m), 2.37 (2H, m), 2.50 (3H, s), 2.90 (2H, m), 3.67 (1H, m), 3.74 (2H, s), 6.72 (1H, d, J=1.0 Hz), 7.55 (1H, dd, J=7.5 Hz, J=7.5 Hz), 7.66 (2H, m), 7.92 (3H, m), 8.33 (2H, m)
Mass spectrometric value (ESI-MS) 577 (M−1)

Compound 598 3-(4-Hydroxy-piperidin-1-ylmethyl)-N-[3-(4-methoxy-benzylidene-hydrazinocarbonyl)-4-methyl-thiophen-2-yl]-benzamide The title compound 598 was produced in substantially the same manner as in Example 8.

$^1$H-NMR (CD$_3$OD, 400 MHz): δ 1.61 (2H, m), 1.87 (2H, m), 2.37 (2H, m), 2.49 (3H, s), 2.89 (2H, m), 3.66 (1H, m), 3.73 (2H, s), 3.84 (3H, s), 6.69 (1H, d, J=1.0 Hz), 6.97 (2H, d, J=8.3 Hz), 7.53 (1H, m), 7.62 (1H, m), 7.76 (2H, m), 7.90 (2H, m), 8.23 (1H, s)

Mass spectrometric value (ESI-MS) 505 (M−1)

Compound 599 N-[3-(3,4-Dimethyl-benzylidene-hydrazinocarbonyl)-4-methyl-thiophen-2-yl]-3-(4-hydroxymethyl-piperidin-1-ylmethyl)-benzamide The title compound 599 was produced in substantially the same manner as in Example 8.

$^1$H-NMR (CD$_3$OD, 400 MHz): δ 1.29 (2H, m), 1.50 (1H, m), 1.75 (2H, d, J=11.5 Hz), 2.19 (2H, m), 2.30 (6H, s), 2.49 (3H, s), 2.99 (2H, d, J=10.8 Hz), 3.38 (2H, d, J=6.6 Hz), 3.73 (2H, s), 6.70 (1H, d, J=1.0 Hz), 7.19 (1H, d, J=7.6 Hz), 7.54 (2H, m), 7.62 (2H, m), 7.91 (2H, m), 8.22 (1H, s)

Mass spectrometric value (ESI-MS) 517 (M−1)

Compound 600 3-(4-Hydroxymethyl-piperidin-1-ylmethyl)-N-[4-methyl-3-(4-methyl-benzylidene-hydrazinocarbonyl)-thiophen-2-yl]-benzamide The title compound 600 was produced in substantially the same manner as in Example 8.

$^1$H-NMR (CD$_3$OD, 400 MHz): δ 1.30 (2H, m), 1.50 (1H, m), 1.75 (2H, d, J=13.2 Hz), 2.22 (2H, t, J=11.5 Hz), 2.37 (3H, s), 2.48 (3H, s), 3.00 (2H, d, J=11.0 Hz), 3.38 (2H, d, J=6.3 Hz), 3.74 (2H, s), 6.68 (1H, d, J=1.0 Hz), 7.24 (2H, d, J=7.8 Hz), 7.52 (1H, dd, J=7.4 Hz, J=7.4 Hz), 7.62 (1H, d, J=7.4 Hz), 7.69 (2H, m), 7.90 (2H, m), 8.25 (1H, s)

Mass spectrometric value (ESI-MS) 503 (M−1)

Compound 601 N-[3-(4-Fluoro-benzylidene-hydrazinocarbonyl)-4-methyl-thiophen-2-yl]-3-(4-hydroxymethyl-piperidin-1-ylmethyl)-benzamide The title compound 601 was produced in substantially the same manner as in Example 8.

$^1$H-NMR (CD$_3$OD, 400 MHz): δ 1.30 (2H, m), 1.50 (1H, m), 1.75 (2H, d, J=12.2 Hz), 2.22 (2H, t, J=11.4 Hz), 2.48 (3H, s), 3.01 (2H, d, J=11.2 Hz), 3.38 (2H, d, J=6.4 Hz), 3.73 (2H, s), 6.68 (1H, d, J=1.0 Hz), 7.16 (2H, dd, J=8.6 Hz, J=8.6 Hz), 7.52 (1H, dd, J=7.6 Hz, J=7.6 Hz), 7.62 (1H, d, J=7.6 Hz), 7.88 (4H, m), 8.28 (1H, s)

Mass spectrometric value (ESI-MS) 507 (M−1)

Compound 602 N-[3-(3-Fluoro-benzylidene-hydrazinocarbonyl)-4-methyl-thiophen-2-yl]-3-(4-hydroxymethyl-piperidin-1-ylmethyl)-benzamide The title compound 602 was produced in substantially the same manner as in Example 8.

$^1$H-NMR (CD$_3$OD, 400 MHz): δ 1.31 (2H, m), 1.51 (1H, m), 1.76 (2H, d, J=11.5 Hz), 2.23 (2H, d, J=10.8 Hz), 2.45 (3H, s), 3.02 (2H, d, J=11.2 Hz), 3.39 (2H, d, J=6.3 Hz), 3.75 (2H, s), 6.69 (1H, d, J=1.0 Hz), 7.17 (1H, m), 7.44 (1H, m), 7.53 (2H, m), 7.63 (2H, m), 7.90 (2H, m), 8.28 (1H, s)

Mass spectrometric value (ESI-MS) 507 (M−1)

Compound 603 N-[3-(4-Chloro-3-trifluoromethyl-benzylidene-hydrazinocarbonyl)-4-methyl-thiophen-2-yl]-3-(4-hydroxymethyl-piperidin-1-ylmethyl)-benzamide The title compound 603 was produced in substantially the same manner as in Example 8.

$^1$H-NMR (CD$_3$OD, 400 MHz): δ 1.31 (2H, m), 1.51 (1H, m), 1.76 (2H, d, J=11.7 Hz), 2.21 (2H, t, J=11.5 Hz), 2.49 (3H, s), 3.01 (2H, d, J=11.5 Hz), 3.38 (2H, d, J=6.3 Hz), 3.74 (2H, s), 6.70 (1H, s), 7.54 (1H, dd, J=7.4 Hz), 7.65 (2H, m), 7.94 (3H, m), 8.31 (2H, m)

Mass spectrometric value (ESI-MS) 591 (M−1)

Compound 604 3-(4-Hydroxymethyl-piperidin-1-ylmethyl)-N-[3-(4-methoxy-benzylidene-hydrazinocarbonyl)-4-methyl-thiophen-2-yl]-benzamide The title compound 604 was produced in substantially the same manner as in Example 8.

$^1$H-NMR (CD$_3$OD, 400 MHz): δ 1.29 (2H, m), 1.50 (1H, m), 1.75 (2H, d, J=12.2 Hz), 2.20 (2H, t, J=11.1 Hz), 2.47 (3H, s), 3.00 (2H, d, J=10.8 Hz), 3.38 (2H, d, J=6.4 Hz), 3.72 (2H, s), 3.83 (3H, s), 6.67 (1H, s), 6.96 (2H, d, J=8.3 Hz), 7.51 (1H, dd, J=7.4 Hz), 7.61 (1H, d, J=7.4 Hz), 7.75 (2H, d, J=6.4 Hz), 7.89 (2H, m), 8.23 (1H, m)

Mass spectrometric value (ESI-MS) 519 (M−1)

Compound 605 N-[3-(3,4-Dimethyl-benzylidene-hydrazinocarbonyl)-4,5,6,7-tetrahydro-benzo[b]thiophen-2-yl]-3-(3-hydroxy-propylsulfanyl-methyl)-benzamide The title compound 605 was produced in substantially the same manner as in Example 8.

$^1$H-NMR (CD$_3$OD, 400 MHz): δ 1.77 (2H, m), 1.89 (4H, m), 2.30 (6H, s), 2.51 (2H, t, J=7.2 Hz), 2.74 (2H, m), 2.85 (2H, m), 3.60 (2H, t, J=6.2 Hz), 3.82 (2H, s), 7.19 (1H, d, J=7.6 Hz), 7.51 (2H, m), 7.61 (2H, m), 7.87 (2H, m), 8.21 (1H, s)

Mass spectrometric value (ESI-MS) 534 (M−1)

Compound 606 N-[3-(4-Fluoro-benzylidene-hydrazinocarbonyl)-4,5,6,7-tetrahydro-benzo[b]thiophen-2-yl]-3-(3-hydroxy-propylsulfanylmethyl)-benzamide The title compound 606 was produced in substantially the same manner as in Example 8.

$^1$H-NMR (CD$_3$OD, 400 MHz): δ 1.77 (2H, m), 1.89 (4H, m), 2.51 (2H, t, J=7.3 Hz), 2.75 (2H, m), 2.86 (2H, m), 3.60 (2H, t, J=6.2 Hz), 3.82 (2H, s), 7.18 (2H, dd, J=8.8 Hz, J=8.8 Hz), 7.50 (1H, dd, J=7.6 Hz, J=7.6 Hz), 7.60 (1H, d, J=7.6 Hz), 7.87 (2H, m), 8, 06 (2H, m), 8.27 (1H, s)

Mass spectrometric value (ESI-MS) 524 (M−1)

Compound 607 N-[3-(3-Fluoro-benzylidene-hydrazinocarbonyl)-4,5,6,7-tetrahydro-benzo[b]thiophen-2-yl]-3-(3-hydroxy-propylsulfanylmethyl)-benzamide The title compound 607 was produced in substantially the same manner as in Example 8.

$^1$H-NMR (CD$_3$OD, 400 MHz): δ 1.77 (2H, m), 1.90 (4H, m), 2.51 (2H, t, J=7.3 Hz), 2.77 (2H, m), 2.86 (2H, bs), 3.63 (2H, m), 3.82 (2H, s), 7.17 (1H, dd, J=8.0 Hz, J=8.0 Hz), 7.55 (5H, m), 7.84 (1H, d, J=7.1 Hz), 7.92 (1H, s), 8.27 (1H, s)

Mass spectrometric value (ESI-MS) 524 (M−1)

Compound 608 N-[3-(4-Chloro-3-trifluoromethyl-benzylidene-hydrazinocarbonyl)-4,5,6,7-tetrahydro-benzo[b]thiophen-2-yl]-3-(3-hydroxy-propylsulfanylmethyl)-benzamide The title compound 608 was produced in substantially the same manner as in Example 8.
$^1$H-NMR (CD$_3$OD, 400 MHz): δ 1.77 (2H, m), 1.90 (4H, m), 2.51 (2H, m), 2.76 (2H, m), 2.86 (2H, m), 3.60 (2H, m), 3.83 (2H, s), 7.52 (1H, m), 7.62 (1H, m), 7.68 (1H, m), 7.75-8.08 (4H, m), 8.32 (1H, s)
Mass spectrometric value (ESI-MS) 608 (M−1)

Compound 609 3-{[(2-Diethylamino-ethyl)-methyl-amino]-methyl}-N-[3-(3,4-dimethyl-benzylidene-hydrazinocarbonyl)-4,5,6,7-tetrahydro-benzo[b]thiophen-2-yl]-benzamide The title compound 609 was produced in substantially the same manner as in Example 8.
$^1$H-NMR (CDCl$_3$, 400 MHz): δ 1.08 (6H, t, J=7.2 Hz), 1.85 (4H, m), 2.24 (3H, s), 2.29 (6H, s), 2.75 (12H, m), 3.62 (2H, s), 7.17 (1H, d, J=7.6 Hz), 7.44 (2H, dd, J=15.0 Hz, J=7.6 Hz), 7.55 (2H, d, J=7.6 Hz), 7.63 (2H, s), 7.95 (2H, m), 8.06 (1H, s)
Mass spectrometric value (ESI-MS) 572 (M−1)

Compound 610 3-{[(2-Diethylamino-ethyl)-methyl-amino]-methyl}-N-[3-(4-methyl-benzylidene-hydrazinocarbonyl)-4,5,6,7-tetrahydro-benzo-[b]thiophen-2-yl]-benzamide The title compound 610 was produced in substantially the same manner as in Example 8.
$^1$H-NMR (CDCl$_3$, 400 MHz): δ 1.08 (6H, t, J=7.1 Hz), 1.85 (4H, m), 2.24 (3H, s), 2.37 (3H, s), 2.74 (12H, m), 3.61 (2H, s), 7.20 (2H, d, J=8.0 Hz), 7.44 (1H, dd, J=15.9 Hz, J=8.1 Hz), 7.54 (1H, d, J=7.8 Hz), 7.66 (2H, d, J=8.0 Hz), 7.95 (2H, m), 8.12 (1H, s)
Mass spectrometric value (ESI-MS) 558 (M−1)

Compound 611 3-{[(2-Diethylamino-ethyl)-methyl-amino]-methyl}-N-[3-(4-fluoro-benzylidene-hydrazinocarbonyl)-4,5,6,7-tetrahydro-benzo-[b]thiophen-2-yl]-benzamide The title compound 611 was produced in substantially the same manner as in Example 8.
$^1$H-NMR (CDCl$_3$, 400 MHz): δ 1.10 (6H, t, J=7.3 Hz), 1.83 (4H, m), 2.24 (3H, s), 2.75 (12H, m), 3.61 (2H, s), 7.09 (2H, dd, J=8.6 Hz, J=8.6 Hz), 7.44 (1H, dd, J=15.1 Hz, J=7.6 Hz), 7.54 (1H, d, J=7.6 Hz), 7.76 (2H, m), 7.93 (2H, m), 8.16 (1H, s)
Mass spectrometric value (ESI-MS) 562 (M−1)

Compound 612 3-{[(2-Diethylamino-ethyl)-methyl-amino]-methyl}-N-[3-(3-fluoro-benzylidene-hydrazinocarbonyl)-4,5,6,7-tetrahydro-benzo-[b]thiophen-2-yl]-benzamide The title compound 612 was produced in substantially the same manner as in Example 8.
$^1$H-NMR (CDCl$_3$, 400 MHz): δ 1.11 (6H, t, J=7.2 Hz), 1.81 (4H, m), 2.23 (3H, s), 2.77 (12H, m), 3.61 (2H, s), 7.08 (1H, m), 7.31-7.59 (4H, m), 7.91 (2H, m), 8.21 (1H, s)
Mass spectrometric value (ESI-MS) 562 (M−1)

Compound 613 N-[3-(4-Chloro-3-trifluoromethyl-benzylidene-hydrazinocarbonyl)-4,5,6,7-tetrahydro-benzo[b]thiophen-2-yl]-3-{[(2-diethylamino-ethyl)-methyl-amino]-methyl}-benzamide The title compound 613 was produced in substantially the same manner as in Example 8.
$^1$H-NMR (CDCl$_3$, 400 MHz): δ 1.10 (6H, m), 1.91 (4H, m), 2.25 (3H, s), 2.55-2.80 (12H, m), 3.63 (2H, s), 7.46 (1H, m), 7.57 (2H, d, 8.3 Hz), 7.94 (3H, m), 8.04 (1H, m), 8.23 (1H, s)
Mass spectrometric value (ESI-MS) 646 (M−1)

Compound 614 3-{[(2-Diethylamino-ethyl)-methyl-amino]-methyl}-N-[3-(4-methoxy-benzylidene-hydrazinocarbonyl)-4,5,6,7-tetrahydro-benzo-[b]thiophen-2-yl]-benzamide The title compound 614 was produced in substantially the same manner as in Example 8.
$^1$H-NMR (CDCl$_3$, 400 MHz): δ 1.04 (6H, t, J=7.1 Hz), 1.83 (4H, m), 2.23 (3H, s), 2.68 (12H, m), 3.60 (2H, s), 3.82 (3H, s), 6.89 (2H, d, J=8.8 Hz), 7.45 (1H, dd, J=15.4 Hz, J=7.6 Hz), 7.56 (1H, d, J=7.6 Hz), 7.70 (2H, d, J=8.8 Hz), 7.82-8.02 (2H, m), 8.09 (1H, s)
Mass spectrometric value (ESI-MS) 574 (M−1)

Compound 615 3-[1,4']Bipiperidinyl-1'-ylmethyl-N-[3-(3,4-dimethyl-benzylidene-hydrazinocarbonyl)-4,5,6,7-tetrahydro-benzo[b]thiophen-2-yl]-benzamide The title compound 615 was produced in substantially the same manner as in Example 8.
$^1$H-NMR (CDCl$_3$, 400 MHz): δ 1.46 (2H, bs), 1.68-2.06 (15H, m), 2.27 (6H, s), 2.60-3.02 (10H, m), 3.54 (2H, s), 7.14 (1H, m), 7.46 (3H, m), 7.60 (1H, s), 7.94 (2H, m), 8.11 (1H, s)
Mass spectrometric value (ESI-MS) 610 (M−1)

Compound 616 3-[1,4']Bipiperidinyl-1'-ylmethyl-N-[3-(4-methyl-benzylidene-hydrazinocarbonyl)-4,5,6,7-tetrahydro-benzo[b]thiophen-2-yl]-benzamide The title compound 616 was produced in substantially the same manner as in Example 8.
$^1$H-NMR (CDCl$_3$, 400 MHz): δ 1.47 (2H, bs), 1.68-2.08 (14H, m), 2.37 (3H, s), 2.65-3.00 (11H, m), 3.54 (2H, s), 7.20 (2H, d, J=7.8 Hz), 7.45 (2H, m), 7.66 (2H, d, J=7.8 Hz), 7.90 (2H, m), 8.16 (1H, s)
Mass spectrometric value (ESI-MS) 596 (M−1)

Compound 617 3-[1,4']Bipiperidinyl-1'-ylmethyl-N-[3-(4-fluoro-benzylidene-hydrazinocarbonyl)-4,5,6,7-tetrahydro-benzo[b]thiophen-2-yl]-benzamide The title compound 617 was produced in substantially the same manner as in Example 8.
$^1$H-NMR (CDCl$_3$, 400 MHz): δ 1.48 (2H, bs), 1.65-2.10 (14H, m), 2.74 (7H, m), 2.87 (2H, m), 2.94 (2H, m), 3.55 (2H, s), 7.10 (2H, dd, J=8.6 Hz, J=8.6 Hz), 7.46 (2H, m), 7.77 (2H, m), 7.92 (1H, d, J=7.6 Hz), 7.97 (1H, s), 8.18 (1H, s)
Mass spectrometric value (ESI-MS) 600 (M−1)

Compound 618 3-[1,4']Bipiperidinyl-1'-ylmethyl-N-[3-(3-fluoro-benzylidene-hydrazinocarbonyl)-4,5,6,7-tetrahydro-benzo[b]thiophen-2-yl]-benzamide The title compound 618 was produced in substantially the same manner as in Example 8.
$^1$H-NMR (CDCl$_3$, 400 MHz): δ 1.48 (2H, bs), 1.70-2.08 (14H, m), 2.86 (11H, m), 3.55 (2H, s), 7.10 (1H, ddd, J=8.3 Hz, J=8.3 Hz, J=2.4 Hz), 7.50 (5H, m), 7.91 (1H, d, J=7.6 Hz), 7.97 (1H, s), 8.20 (1H, s)
Mass spectrometric value (ESI-MS) 600 (M−1)

Compound 619 3-[1,4']Bipiperidinyl-1'-ylmethyl-N-[3-(4-chloro-3-trifluoromethyl-benzylidene-hydrazinocarbonyl)-4,5,6,7-tetrahydro-benzo[b]thiophen-2-yl]-benzamide The title compound 619 was produced in substantially the same manner as in Example 8.
$^1$H-NMR (CDCl$_3$, 400 MHz): δ 1.47 (2H, bs), 1.86 (14H, m), 2.84 (11H, m), 3.53 (2H, s), 7.48 (3H, m), 7.91 (3H, m), 8.01 (1H, s), 8.31 (1H, s)
Mass spectrometric value (ESI-MS) 684 (M−1)

Compound 620 3-[1,4']Bipiperidinyl-1'-ylmethyl-N-[3-(4-methoxy-benzylidene-hydrazinocarbonyl)-4,5,6,7-tetrahydro-benzo[b]thiophen-2-yl]-benzamide The title compound 620 was produced in substantially the same manner as in Example 8.
$^1$H-NMR (CDCl$_3$, 400 MHz): δ 1.47 (2H, bs), 1.85 (14H, m), 2.82 (11H, m), 3.53 (2H, bs), 3.82 (3H, m), 6.90 (2H, m), 7.43 (2H, m), 7.69 (2H, d, J=7.1 Hz), 7.91 (2H, m), 8.15 (1H, s)
Mass spectrometric value (ESI-MS) 612 (M−1)

Compound 621 N-[3-(3,4-Dimethyl-benzylidene-hydrazinocarbonyl)-4,5,6,7-tetrahydro-benzo[b]thiophen-2-yl]-3-[4-(2-hydroxy-ethyl)-piperazin-1-ylmethyl]-benzamide The title compound 621 was produced in substantially the same manner as in Example 8.
$^1$H-NMR (CDCl$_3$, 400 MHz): δ 1.87 (4H, m), 2.29 (6H, s), 2.55 (10H, m), 2.72 (2H, m), 2.86 (2H, m), 3.60 (4H, m), 7.16 (1H, d, J=7.6 Hz), 7.43 (2H, m), 7.54 (1H, d, J=7.8 Hz), 7.62 (1H, s), 7.93 (1H, d, J=7.8 Hz), 8.00 (1H, s), 8.05 (1H, s)
Mass spectrometric value (ESI-MS) 572 (M−1)

Compound 622 3-[4-(2-Hydroxy-ethyl)-piperazin-1-ylmethyl]-N-[3-(4-methyl-benzylidene-hydrazinocarbonyl)-4,5,6,7-tetrahydro-benzo-[b]thiophen-2-yl]-benzamide The title compound 622 was produced in substantially the same manner as in Example 8.
$^1$H-NMR (CDCl$_3$, 400 MHz): δ 1.85 (4H, m), 2.37 (3H, s), 2.54 (10H, m), 2.71 (2H, m), 2.85 (2H, m), 3.60 (4H, m), 7.20 (2H, d, J=7.8 Hz), 7.43 (1H, dd, J=7.8 Hz, J=7.8 Hz), 7.54 (1H, d, J=7.8 Hz), 7.66 (2H, d, J=7.8 Hz), 7.92 (1H, d, J=7.8 Hz), 8.00 (1H, s), 8.10 (1H, s)
Mass spectrometric value (ESI-MS) 558 (M−1)

Compound 623 N-[3-(4-Fluoro-benzylidene-hydrazinocarbonyl)-4,5,6,7-tetrahydro-benzo[b]thiophen-2-yl]-3-[4-(2-hydroxy-ethyl)-piperazin-1-ylmethyl]-benzamide The title compound 623 was produced in substantially the same manner as in Example 8.
$^1$H-NMR (CDCl$_3$, 400 MHz): δ 1.87 (4H, m), 2.54 (10H, m), 2.73 (2H, m), 2.86 (2H, m), 3.60 (4H, m), 7.11 (2H, dd, J=8.7 Hz, J=8.7 Hz), 7.44 (1H, dd, J=7.6 Hz, J=7.6 Hz), 7.54 (1H, d, J=7.6 Hz), 7.79 (2H, m), 7.92 (1H, m), 8.00 (1H, s), 8.12 (1H, s)
Mass spectrometric value (ESI-MS) 562 (M−1)

Compound 624 N-[3-(3-Fluoro-benzylidene-hydrazinocarbonyl)-4,5,6,7-tetrahydro-benzo[b]thiophen-2-yl]-3-[4-(2-hydroxy-ethyl)-piperazin-1-ylmethyl]-benzamide The title compound 624 was produced in substantially the same manner as in Example 8.
$^1$H-NMR (CDCl$_3$, 400 MHz): δ 1.87 (4H, m), 2.54 (10H, m), 2.72 (2H, m), 2.84 (2H, m), 3.60 (4H, m), 7.11 (1H, ddd, J=8.3 Hz, J=8.3 Hz, J=2.4 Hz), 7.45 (5H, m), 7.92 (1H, d, J=7.6 Hz), 8.00 (1H, s), 8.14 (1H, s)
Mass spectrometric value (ESI-MS) 562 (M−1)

Compound 625 N-[3-(4-Chloro-3-trifluoromethyl-benzylidene-hydrazinocarbonyl)-4,5,6,7-tetrahydro-benzo[b]thiophen-2-yl]-3-[4-(2-hydroxy-ethyl)-piperazin-1-ylmethyl]-benzamide The title compound 625 was produced in substantially the same manner as in Example 8.
$^1$H-NMR (CDCl$_3$, 400 MHz): δ 1.83 (4H, m), 2.53 (10H, m), 2.69 (2H, m), 2.82 (2H, m), 3.60 (4H, m), 7.44 (1H, dd, J=7.7 Hz, J=7.7 Hz), 7.54 (2H, d, J=8.3 Hz), 7.92 (2H, m), 7.98 (1H, s), 8.01 (1H, s), 8.22 (1H, s)
Mass spectrometric value (ESI-MS) 646 (M−1)

Compound 626 3-[4-(2-Hydroxy-ethyl)-piperazin-1-ylmethyl]-N-[3-(4-methoxy-benzylidene-hydrazinocarbonyl)-4,5,6,7-tetrahydro-benzo-[b]thiophen-2-yl]-benzamide The title compound 626 was produced in substantially the same manner as in Example 8.
$^1$H-NMR (CDCl$_3$, 400 MHz): δ 1.85 (4H, m), 2.53 (10H, m), 2.70 (2H, m), 2.84 (2H, m), 3.59 (4H, m), 3.83 (3H, s), 6.90 (2H, d, J=8.8 Hz), 7.42 (1H, dd, J=7.8 Hz, J=7.8 Hz), 7.53 (1H, d, J=7.8 Hz), 7.72 (2H, d, J=8.8 Hz), 7.92 (1H, d, J=7.8 Hz), 7.99 (1H, s), 8.07 (1H, s)
Mass spectrometric value (ESI-MS) 574 (M−1)

Compound 627 3-{[Bis-(2-hydroxy-propyl)-amino]-methyl}-N-[3-(3,4-dimethyl-benzylidene-hydrazinocarbonyl)-4,5,6,7-tetrahydro-benzo-[b]thiophen-2-yl]-benzamide The title compound 627 was produced in substantially the same manner as in Example 8.
$^1$H-NMR (CDCl$_3$, 400 MHz): δ 1.14 (6H, m), 1.84 (4H, m), 2.25 (6H, m), 2.50 (2H, d, J=5.6 Hz), 2.62 (2H, m), 2.70 (2H, m), 2.83 (2H, m), 3.81-4.06 (4H, m), 7.08 (1H, m), 7.46 (3H, m), 7.60 (1H, s), 8.02 (2H, m), 8.20 (1H, bs)
Mass spectrometric value (ESI-MS) 575 (M−1)

Compound 628 3-{[Bis-(2-hydroxy-propyl)-amino]-methyl}-N-[3-(4-methyl-benzylidene-hydrazinocarbonyl)-4,5,6,7-tetrahydro-benzo-[b]thiophen-2-yl]-benzamide The title compound 628 was produced in substantially the same manner as in Example 8.
$^1$H-NMR (CDCl$_3$, 400 MHz): δ 1.13 (6H, m), 1.87 (4H, m), 2.37 (3H, m), 2.50 (2H, d, J=5.6 Hz), 2.62 (2H, m), 2.71 (2H, m), 2.84 (2H, m), 3.93 (4H, m), 7.16 (2H, m), 7.44 (2H, m), 7.70 (2H, m), 8.00 (2H, m), 8.22 (1H, bs)
Mass spectrometric value (ESI-MS) 561 (M−1)

Compound 629 3-{[Bis-(2-hydroxy-propyl)-amino]-methyl}-N-[3-(4-fluoro-benzylidene-hydrazinocarbonyl)-4,5,6,7-tetrahydro-benzo[b]thiophen-2-yl]-benzamide The title compound 629 was produced in substantially the same manner as in Example 8.
$^1$H-NMR (CDCl$_3$, 400 MHz): δ 1.12 (6H, t, J=6.1 Hz), 1.88 (4H, m), 2.50 (2H, m), 2.63 (2H, m), 2.73 (2H, m), 2.84 (2H, m), 3.94 (4H, m), 7.06 (2H, dd, J=8.6 Hz, J=8.6 Hz), 7.44 (2H, m), 7.85 (2H, m), 8.05 (2H, m), 8.25 (1H, d, J=6.8 Hz)
Mass spectrometric value (ESI-MS) 565 (M−1)

Compound 630 3-{[Bis-(2-hydroxy-propyl)-amino]-methyl}-N-[3-(3-fluoro-benzylidene-hydrazinocarbonyl)-4,5,6,7-tetrahydro-benzo[b]thiophen-2-yl]-benzamide The title compound 630 was produced in substantially the same manner as in Example 8.
$^1$H-NMR (CDCl$_3$, 400 MHz): δ 1.14 (6H, t, J=6.1 Hz), 1.84 (4H, m), 2.51 (2H, m), 2.66 (4H, m), 2.83 (2H, m), 3.95 (4H, m), 7.00 (1H, m), 7.23 (1H, m), 7.42 (3H, m), 7.72 (1H, m), 8.03 (1H, m), 8.18 (1H, s), 8.27 (1H, d, J=10.3 Hz)
Mass spectrometric value (ESI-MS) 565 (M−1)

Compound 631 3-{[Bis-(2-hydroxy-propyl)-amino]-methyl}-N-[3-(4-chloro-3-trifluoromethyl-benzylidene-hydrazinocarbonyl)-4,5,6,7-tetrahydro-benzo[b]thiophen-2-yl]-benzamide The title compound 631 was produced in substantially the same manner as in Example 8.
$^1$H-NMR (CDCl$_3$, 400 MHz): δ 1.12 (6H, m), 1.72 (4H, m), 2.52 (2H, d, J=6.1 Hz), 2.68 (6H, m), 3.97 (4H, m), 7.32 (1H, d, J=8.3 Hz), 7.43 (2H, m), 7.87 (1H, m), 8.01 (2H, m), 8.30 (1H, s), 8.33 (1H, s)
Mass spectrometric value (ESI-MS) 649 (M−1)

Compound 632 3-{[Bis-(2-hydroxy-propyl)-amino]-methyl}-N-[3-(4-methoxy-benzylidene-hydrazinocarbonyl)-4,5,6,7-tetrahydro-benzo-[b]thiophen-2-yl]-benzamide The title compound 632 was produced in substantially the same manner as in Example 8.
$^1$H-NMR (CDCl$_3$, 400 MHz): δ 1.13 (6H, m), 1.86 (4H, m), 2.49 (2H, m), 2.62 (2H, m), 2.70 (2H, m), 2.81 (2H, m), 3.75-4.05 (7H, m), 6.82 (2H, m), 7.42 (2H, m), 7.74 (2H, m), 8.01 (1H, m), 8.06 (1H, s), 8.23 (1H, m)
Mass spectrometric value (ESI-MS) 577 (M−1)

Compound 633 N-[3-(3,4-Dimethyl-benzylidene-hydrazinocarbonyl)-4,5,6,7-tetrahydro-benzo[b]thiophen-2-yl]-3-(4-hydroxy-piperidin-1-ylmethyl)-benzamide The title compound 633 was produced in substantially the same manner as in Example 8.
$^1$H-NMR (CDCl$_3$, 400 MHz): δ 1.64 (2H, m), 1.85 (6H, m), 2.25 (8H, m), 2.75 (6H, m), 3.63 (2H, s), 3.70 (1H, m), 7.15 (1H, d, J=7.8 Hz), 7.43 (2H, m), 7.56 (1H, m), 7.61 (1H, s), 7.93 (1H, d, J=7.8 Hz), 7.98 (1H, s), 8.06 (1H, s)
Mass spectrometric value (ESI-MS) 543 (M−1)

Compound 634 3-(4-Hydroxy-piperidin-1-ylmethyl)-N-[3-(4-methyl-benzylidene-hydrazinocarbonyl)-4,5,6,7-tetrahydro-benzo[b]thiophen-2-yl]-benzamide The title compound 634 was produced in substantially the same manner as in Example 8.
$^1$H-NMR (CDCl$_3$, 400 MHz): δ 1.64 (2H, m), 1.86 (6H, m), 2.26 (2H, t, J=9.5 Hz), 2.37 (3H, s), 2.71 (2H, m), 2.81 (4H, m), 3.64 (2H, s), 3.72 (1H, m), 7.19 (2H, d, J=7.9 Hz), 7.43 (1H, dd, J=7.8 Hz), 7.57 (1H, d, J=7.8 Hz), 7.66 (2H, d, J=7.9 Hz), 7.94 (2H, m), 8.09 (1H, s)
Mass spectrometric value (ESI-MS) 529 (M−1)

Compound 635 N-[3-(4-Fluoro-benzylidene-hydrazinocarbonyl)-4,5,6,7-tetrahydro-benzo[b]thiophen-2-yl]-3-(4-hydroxy-piperidin-1-ylmethyl)-benzamide The title compound 635 was produced in substantially the same manner as in Example 8.
$^1$H-NMR (CDCl$_3$, 400 MHz): δ 1.64 (2H, m), 1.90 (6H, m), 2.23 (2H, m), 2.80 (6H, m), 3.62 (2H, s), 3.73 (1H, m), 7.11 (2H, dd, J=8.6 Hz, J=8.6 Hz), 7.45 (1H, m), 7.58 (1H, m), 7.79 (2H, dd, J=8.6 Hz, J=8.6 Hz), 7.94 (1H, d, J=7.8 Hz), 7.99 (1H, s), 8.12 (1H, s)
Mass spectrometric value (ESI-MS) 533 (M−1)

Compound 636 N-[3-(3-Fluoro-benzylidene-hydrazinocarbonyl)-4,5,6,7-tetrahydro-benzo[b]thiophen-2-yl]-3-(4-hydroxy-piperidin-1-ylmethyl)-benzamide The title compound 636 was produced in substantially the same manner as in Example 8.
$^1$H-NMR (CDCl$_3$, 400 MHz): δ 1.69 (2H, m), 1.90 (6H, m), 2.42 (2H, bs), 2.78 (6H, m), 3.75 (3H, m), 7.11 (1H, m), 7.30-7.80 (5H, m), 7.98 (2H, m), 8.14 (1H, s)
Mass spectrometric value (ESI-MS) 533 (M−1)

Compound 637 N-[3-(4-Chloro-3-trifluoromethyl-benzylidene-hydrazinocarbonyl)-4,5,6,7-tetrahydro-benzo[b]thiophen-2-yl]-3-(4-hydroxy-piperidin-1-ylmethyl)-benzamide The title compound 637 was produced in substantially the same manner as in Example 8.
$^1$H-NMR (CDCl$_3$, 400 MHz): δ 1.63 (2H, m), 1.85 (6H, m), 2.19 (2H, m), 2.74 (6H, m), 3.58 (2H, s), 3.71 (1H, m), 7.44 (1H, dd, J=7.6 Hz, J=7.6 Hz), 7.54 (2H, m), 7.94 (4H, m), 8.23 (1H, s)
Mass spectrometric value (ESI-MS) 617 (M−1)

Compound 638 3-(4-Hydroxy-piperidin-1-ylmethyl)-
N-[3-(4-methoxy-benzylidene-hydrazinocarbonyl)-4,
5,6,7-tetrahydro-benzo[b]thiophen-2-yl]-benzamide The title compound 638 was produced in substantially the same manner as in Example 8.
¹H-NMR (CDCl₃, 400 MHz): δ 1.62 (2H, m), 1.87 (6H, m), 2.19 (2H, m), 2.77 (6H, m), 3.59 (2H, s), 3.70 (1H, m), 3.83 (3H, s), 6.90 (2H, d, J=8.5 Hz), 7.43 (1H, dd, J=7.6 Hz, J=7.6 Hz), 7.55 (1H, d, J=7.6 Hz), 7.72 (2H, d, J=8.5 Hz), 7.92 (1H, d, J=7.6 Hz), 7.98 (1H, s), 8.06 (1H, s)
Mass spectrometric value (ESI-MS) 545 (M−1)

Compound 639 N-[3-(3,4-Dimethyl-benzylidene-
hydrazinocarbonyl)-4,5,6,7-tetrahydro-benzo[b]
thiophen-2-yl]-3-(4-hydroxymethyl-piperidin-1-ylm-
ethyl)-benzamide The title compound 639 was produced in substantially the same manner as in Example 8.
¹H-NMR (CDCl₃, 400 MHz): δ 1.37 (2H, m), 1.49 (1H, m), 1.71 (2H, m), 1.86 (4H, m), 2.04 (2H, m), 2.29 (6H, s), 2.73 (2H, m), 2.86 (2H, m), 2.93 (2H, m), 3.49 (2H, d, J=6.3 Hz), 3.62 (2H, s), 7.16 (1H, d, J=7.8 Hz), 7.45 (2H, m), 7.58 (1H, m), 7.63 (1H, s), 7.94 (1H, d, J=7.8 Hz), 7.99 (1H, s), 8.05 (1H, s)
Mass spectrometric value (ESI-MS) 557 (M−1)

Compound 640 3-(4-Hydroxymethyl-piperidin-1-
ylmethyl)-N-[3-(4-methyl-benzylidene-hydrazi-
nocarbonyl)-4,5,6,7-tetrahydro-benzo[b]thiophen-2-
yl]-benzamide The title compound 640 was produced in substantially the same manner as in Example 8.
¹H-NMR (CDCl₃, 400 MHz): δ 1.40 (2H, m), 1.50 (1H, m), 1.71 (2H, m), 1.89 (4H, m), 2.06 (2H, m), 2.38 (3H, m), 2.73 (2H, m), 2.86 (2H, m), 2.95 (2H, m), 3.49 (2H, d, J=6.1 Hz), 3.63 (2H, s), 7.21 (2H, d, J=8.0 Hz), 7.45 (1H, dd, J=7.7 Hz, J=14.9 Hz), 7.59 (1H, d, J=7.6 Hz), 7.68 (2H, d, J=8.0 Hz), 7.97 (2H, m), 8.09 (1H, s)
Mass spectrometric value (ESI-MS) 543 (M−1)

Compound 641 N-[3-(4-Fluoro-benzylidene-hydrazi-
nocarbonyl)-4,5,6,7-tetrahydro-benzo[b]thiophen-2-
yl]-3-(4-hydroxymethyl-piperidin-1-ylmethyl)-ben-
zamide The title compound 641 was produced in substantially the same manner as in Example 8.
¹H-NMR (CDCl₃, 400 MHz): δ 1.34 (2H, m), 1.50 (1H, m), 1.69 (2H, m), 1.84 (4H, m), 2.01 (2H, m), 2.71 (2H, m), 2.87 (4H, m), 3.49 (2H, d, J=6.4 Hz), 3.58 (2H, s), 7.10 (2H, dd, J=8.5 Hz), 7.43 (1H, m), 7.55 (1H, m), 7.78 (2H, m), 7.91 (1H, m), 7.98 (1H, bs), 8.13 (1H, s)
Mass spectrometric value (ESI-MS) 547 (M−1)

Compound 642 N-[3-(3-Fluoro-benzylidene-hydrazi-
nocarbonyl)-4,5,6,7-tetrahydro-benzo[b]thiophen-2-
yl]-3-(4-hydroxymethyl-piperidin-1-ylmethyl)-ben-
zamide The title compound 642 was produced in substantially the same manner as in Example 8.
¹H-NMR (CDCl₃, 400 MHz): δ 1.35 (2H, m), 1.51 (1H, m), 1.70 (2H, m), 1.84 (4H, m), 2.01 (2H, m), 2.70 (2H, m), 2.83 (2H, m), 2.90 (2H, m), 3, 49 (2H, d, J=6.3 Hz), 3.58 (2H, s), 7.10 (1H, ddd, J=8.3 Hz, J=8.3 Hz, J=2.7 Hz), 7.45 (5H, m), 7.90 (1H, d, J=7.4 Hz), 7.98 (1H, s), 8.14 (1H, s)
Mass spectrometric value (ESI-MS) 547 (M−1)

Compound 643 N-[3-(4-Chloro-3-trifluoromethyl-
benzylidene-hydrazinocarbonyl)-4,5,6,7-tetrahydro-
benzo[b]thiophen-2-yl]-3-(4-hydroxymethyl-piperi-
din-1-ylmethyl)-benzamide The title compound 643 was produced in substantially the same manner as in Example 8.
¹H-NMR (CDCl₃, 400 MHz): δ 1.39 (2H, m), 1.52 (1H, m), 1.72 (2H, m), 1.88 (4H, m), 2.05 (2H, m), 2.66-2.98 (6H, m), 3.50 (2H, d, J=6.1 Hz), 3.61 (2H, s), 7.46 (1H, m), 7.57 (1H, m), 7.86 (1H, m), 7.96 (3H, m), 8.04 (1H, s), 8.21 (1H, s)
Mass spectrometric value (ESI-MS) 631 (M−1)

Compound 644 3-(4-Hydroxymethyl-piperidin-1-
ylmethyl)-N-[3-(4-methoxy-benzylidene-hydrazi-
nocarbonyl)-4,5,6,7-tetrahydro-benzo-[b]thiophen-2-
yl]-benzamide The title compound 644 was produced in substantially the same manner as in Example 8.
¹H-NMR (CDCl₃, 400 MHz): δ 1.34 (2H, m), 1.49 (1H, m), 1.69 (2H, m), 1.84 (4H, m), 2.00 (2H, m), 2.69 (2H, m), 2.81 (2H, m), 2.88 (2H, m), 3.48 (2H, d, J=6.4 Hz), 3.57 (2H, s), 3.83 (3H, s), 6.90 (2H, d, J=8.8 Hz), 7.43 (1H, m), 7.55 (1H, m), 7.70 (2H, d, J=8.8 Hz), 7.91 (1H, d, J=7.8 Hz), 7.97 (1H, m), 8.07 (1H, s)
Mass spectrometric value (ESI-MS) 559 (M−1)

Compound 645 N-{3-[N'-(3,4-Dimethyl-benzyl)-
hydrazinocarbonyl]-4-methyl-thiophen-2-yl}-3-(3-
hydroxy-propylsulfanylmethyl)-benzamide The title compound 645 was produced in substantially the same manner as in Example 8.
¹H-NMR (CDCl₃, 400 MHz): δ 1.87 (2H, m), 2.26 (9H, m), 2.56 (2H, m), 3.73 (2H, m), 3.82 (2H, s), 4.06 (2H, s), 6.46 (1H, s), 7.13 (1H, bs), 7.18 (1H, bs), 7.50 (1H, m), 7.57 (1H, d, J=7.8 Hz), 7.93 (2H, m), 13.00 (1H, s)
Mass spectrometric value (ESI-MS) 496 (M−1)

Compound 646 3-[(3,4-Dimethyl-benzylidene-)-
amino]-2-[3-(1H-[1,2,4]triazol-3-ylsulfanylmethyl)-
phenyl]-5,6,7,8-tetrahydro-3H-benzo[4,5]thieno[2,3-
d]pyrimidin-4-one The title compound 646 was produced in substantially the same manner as in Example 8.
¹H-NMR (CDCl₃, 400 MHz): δ 1.88 (4H, m), 2.31 (3H, s), 2.33 (3H, s), 2.80 (2H, m), 3.05 (2H, m), 4.33 (2H, s), 7.10-7.88 (7H, m), 8.03 (1H, s), 8.76 (1H, s)
Mass spectrometric value (ESI-MS) 525 (M−1)

Compound 647 3-[(4-Methyl-benzylidene-)-amino]-
2-[3-(1H-[1,2,4]triazol-3-ylsulfanylmethyl)-phenyl]-
5,6,7,8-tetrahydro-3H-benzo[4,5]thieno[2,3-d]pyri-
midin-4-one The title compound 647 was produced in substantially the same manner as in Example 8.
¹H-NMR (CDCl₃, 400 MHz): δ 1.88 (4H, m), 2.35 (3H, s), 2.80 (2H, m), 3.05 (2H, m), 4.34 (2H, s), 7.17 (2H, d, J=7.8 Hz), 7.26 (1H, m), 7.37 (1H, m), 7.56 (2H, m), 7.76 (1H, s), 8.00 (2H, m), 8.81 (1H, s)
Mass spectrometric value (ESI-MS) 511 (M−1)

Compound 648 3-[(4-Fluoro-benzylidene-)-amino]-2-[3-(1H-[1,2,4]triazol-3-ylsulfanylmethyl)-phenyl]-5,6,7,8-tetrahydro-3H-benzo[4,5]thieno[2,3-d]pyrimidin-4-one The title compound 648 was produced in substantially the same manner as in Example 8.

$^1$H-NMR (CDCl$_3$, 400 MHz): δ 1.89 (4H, m), 2.81 (2H, m), 3.05 (2H, m), 4.36 (2H, s), 7.08 (2H, dd, J=8.7 Hz), 7.31 (1H, m), 7.40 (1H, d, J=7.8 Hz), 7.56 (1H, d, J=7.8 Hz), 7.69 (2H, m), 7.76 (1H, m), 8.04 (1H, s), 8.92 (1H, s)

Mass spectrometric value (ESI-MS) 515 (M−1)

Compound 649 3-[(3-Fluoro-benzylidene)-amino]-2-[3-(1H-[1,2,4]triazol-3-ylsulfanylmethyl)-phenyl]-5,6,7,8-tetrahydro-3H-benzo[4,5]thieno[2,3-d]pyrimidin-4-one The title compound 649 was produced in substantially the same manner as in Example 8.

$^1$H-NMR (CDCl$_3$, 400 MHz): δ 1.89 (4H, m), 2.81 (2H, m), 3.05 (2H, m), 4.36 (2H, s), 7.15 (1H, m), 7.36 (5H, m), 7.55 (1H, m), 7.75 (1H, m), 8.03 (1H, s), 9.01 (1H, s)

Mass spectrometric value (ESI-MS) 515 (M−1)

Compound 650 3-[(4-Chloro-3-trifluoromethyl-benzylidene)-amino]-2-[3-(1H-[1,2,4]triazol-3-ylsulfanylmethyl)-phenyl]-5,6,7,8-tetrahydro-3H-benzo[4,5]thieno[2,3-d]pyrimidin-4-one The title compound 650 was produced in substantially the same manner as in Example 8.

$^1$H-NMR (CDCl$_3$, 400 MHz): δ 1.89 (4H, m), 2.68 (2H, m), 2.81 (2H, m), 4.37 (2H, s), 7.30-8.02 (7H, m), 8.06 (1H, m), 9.17 (1H, s)

Mass spectrometric value (ESI-MS) 599 (M−1)

Compound 651 3-[(4-Methoxy-benzylidene)-amino]-2-[3-(1H-[1,2,4]triazol-3-ylsulfanylmethyl)-phenyl]-5,6,7,8-tetrahydro-3H-benzo[4,5]thieno[2,3-d]pyrimidin-4-one The title compound 651 was produced in substantially the same manner as in Example 8.

$^1$H-NMR (CDCl$_3$, 400 MHz): δ 1.88 (4H, m), 2.80 (2H, m), 3.05 (2H, m), 3.81 (3H, s), 4.33 (2H, s), 6.87 (2H, d, J=8.8 Hz), 7.28 (1H, m), 7.55 (1H, m), 7.61 (2H, d, J=8.8 Hz), 7.76 (1H, m), 8.00 (1H, s), 8.73 (1H, s), 9.15 (1H, s)

Mass spectrometric value (ESI-MS) 527 (M−1)

Example 9

Compound 652 3-{[Acetyl-(2-diethylamino-ethyl)-amino]-methyl}-N-[3-(3,4-dimethyl-benzylidene-hydrazinocarbonyl)-4,5,6,7-tetrahydro-benzo[b]thiophen-2-yl]-benzamide 2-Amino-4,5,6,7-tetrahydrobenzothiophene-3-carboxylic acid ethyl ester (Compound A) (4.0 g) was dissolved in anhydrous methylene chloride (40.0 ml). Subsequently, pyridine (2.8 ml) and 3-(chloromethyl)benzoyl chloride (compound B) (3.0 ml) were added at 0° C., and the mixture was stirred at 0° C. for one hr. After the completion of the reaction, distilled water was added, and the mixture was subjected to separatory extraction with chloroform, and the organic layer was washed with saturated brine, was dried over sodium sulfate, and was then concentrated to give 2-(3-chloromethyl-benzoylamino)-4,5,6,7-tetrahydro-benzo[b]thiophene-3-carboxylic acid ethyl ester as a useful intermediate (7.42 g, yield 100%).

2-(3-Chloromethyl-benzoylamino)-4,5,6,7-tetrahydrobenzo[b]-thiophene-3-carboxylic acid ethyl ester (800 mg) produced by the above reaction was dissolved in anhydrous methylene chloride (5.0 ml). Triethylamine (580 μl) and N,N-diethylethylenediamine (compound B') (464 mg) were added to the solution at room temperature, and the mixture was stirred at room temperature for 15 hr. After the completion of the reaction, water was added at room temperature, and the mixture was subjected to separatory extraction with chloroform. The organic layer was washed with saturated brine, was dried over sodium sulfate, and was then concentrated to give 2-{3-[(2-diethylamino-ethylamino)-methyl]-benzoylamino}-4,5,6,7-tetrahydro-benzo[b]thiophene-3-carboxylic acid ethyl ester as a crude useful intermediate (902 mg, yield 100%).

2-{3-[(2-Diethylamino-ethylamino)-methyl]-benzoylamino}-4,5,6,7-tetrahydro-benzo[b]thiophene-3-carboxylic acid ethyl ester produced by the above reaction was dissolved in ethanol (5.0 ml). Hydrazine monohydrate (2 ml) was added to the solution, and the mixture was heated under reflux with stirring for 15 hr. After the completion of the reaction, water was added at room temperature, and the mixture was subjected to separatory extraction with chloroform. The organic layer was washed with saturated brine, was dried over sodium sulfate, and was then concentrated to give 3-[(2-diethylamino-ethylamino)-methyl]-N-(3-hydrazinocarbonyl-4,5,6,7-tetrahydro-benzo[b]thiophen-2-yl)-benzamide as a hydrazine compound (464 mg, yield 52%).

3-[(2-Diethylamino-ethylamino)-methyl]-N-(3-hydrazinocarbonyl-4,5,6,7-tetrahydro-benzo[b]thiophen-2-yl)-benzamide (77 mg) was dissolved in anhydrous toluene (1.0 ml). Acetic acid (50.0 μl) and 3,4-dimethylbenzaldehyde (compound C) (55.0 μl) were added to the solution at room temperature, and the mixture was heated under reflux with stirring for 15 hr. After the completion of the reaction, the reaction product was purified by column chromatography eluted with a chloroform-methanol system to give the title compound 652 (58.4 mg, yield 58%).

$^1$H-NMR (CDCl$_3$, 400 MHz): δ 0.98 (6H, m), 1.85 (7H, m), 2.28 (6H, m), 2.45-2.90 (12H, m), 3.76 (2H, m), 7.14 (1H, m), 7.32-8.12 (7H, m)

Mass spectrometric value (ESI-MS) 600 (M−1)

Compound 653 3-{[Acetyl-(2-diethylamino-ethyl)-amino]-methyl}-N-[3-(4-methyl-benzylidene-hydrazinocarbonyl)-4,5,6,7-tetrahydro-benzo[b]-thiophen-2-yl]-benzamide The title compound 653 was produced in substantially the same manner as in Example 9.

$^1$H-NMR (CDCl$_3$, 400 MHz): δ 0.98 (6H, m), 1.83 (7H, m), 2.38 (3H, s), 2.42-2.90 (12H, m), 3.75 (2H, m), 7.24 (2H, m), 7.40-8.15 (7H, m)

Mass spectrometric value (ESI-MS) 586 (M−1)

Compound 654 3-{[Acetyl-(2-diethylamino-ethyl)-amino]-methyl}-N-[3-(4-fluoro-benzylidene-hydrazinocarbonyl)-4,5,6,7-tetrahydro-benzo[b]-thiophen-2-yl]-benzamide The title compound 654 was produced in substantially the same manner as in Example 9.

$^1$H-NMR (CDCl$_3$, 400 MHz): δ 0.93 (6H, m), 1.83 (7H, m), 2.48 (4H, m), 2.69 (6H, m), 2.80 (2H, m), 3.75 (2H, m), 7.06 (2H, m), 7.40-7.95 (6H, m), 8.09 (1H, s)

Mass spectrometric value (ESI-MS) 590 (M−1)

Compound 655 3-{[Acetyl-(2-diethylamino-ethyl)-amino]-methyl}-N-[3-(3-fluoro-benzylidene-hydrazinocarbonyl)-4,5,6,7-tetrahydro-benzo[b]-thiophen-2-yl]-benzamide The title compound 655 was produced in substantially the same manner as in Example 9.
$^1$H-NMR (CDCl$_3$, 400 MHz): δ 0.94 (6H, m), 1.83 (7H, m), 2.62 (12H, m), 3.76 (2H, m), 7.08 (1H, m), 7.29-8.20 (8H, m)
Mass spectrometric value (ESI-MS) 590 (M−1)

Compound 656 3-{[Acetyl-(2-diethylamino-ethyl)-amino]-methyl}-N-[3-(4-chloro-3-trifluoromethyl-benzylidene-hydrazinocarbonyl)-4,5,6,7-tetrahydro-benzo[b]thiophen-2-yl]-benzamide The title compound 656 was produced in substantially the same manner as in Example 9.
$^1$H-NMR (CDCl$_3$, 400 MHz): δ 0.93 (6H, m), 1.83 (7H, m), 2.62 (12H, m), 3.77 (2H, m), 7.40-8.30 (8H, m)
Mass spectrometric value (ESI-MS) 674 (M−1)

Compound 657 3-{[Acetyl-(2-diethylamino-ethyl)-amino]-methyl}-N-[3-(4-methoxy-benzylidene-hydrazinocarbonyl)-4,5,6,7-tetrahydro-benzo[b]thiophen-2-yl]-benzamide The title compound 657 was produced in substantially the same manner as in Example 9.
$^1$H-NMR (CDCl$_3$, 400 MHz): δ 0.98 (6H, m), 1.87 (7H, m), 2.63 (12H, m), 3.77 (2H, m), 3.84 (3H, s), 6.89 (2H, m), 7.40-8.10 (7H, m)
Mass spectrometric value (ESI-MS) 602 (M−1)

Compound 658 N-[3-(3,4-Dimethyl-benzylidene-hydrazinocarbonyl)-thiophen-2-yl]-3-(3-hydroxy-propylsulfanylmethyl)-benzamide The title compound 658 was produced in substantially the same manner as in Example 8.
$^1$H-NMR (CD$_3$OD, 400 MHz): δ 1.80 (2H, m), 2.30 (3H, s), 2.31 (3H, s), 2.53 (2H, t, J=7.4 Hz), 3.62 (2H, m), 3.85 (2H, s), 7.00 (1H, d, J=6.1 Hz), 7.18 (1H, d, J=7.8 Hz), 7.52 (3H, m), 7.64 (2H, m), 7.90 (1H, s), 7.97 (1H, s), 8.28 (1H, s)
Mass spectrometric value (ESI-MS) 480 (M−1)

Compound 659 3-(3-Hydroxy-propylsulfanylmethyl)-N-[3-(4-methyl-benzylidene-hydrazinocarbonyl)-thiophen-2-yl]-benzamide The title compound 659 was produced in substantially the same manner as in Example 8.
$^1$H-NMR (CD$_3$OD, 400 MHz): δ 1.79 (2H, m), 2.35 (3H, s), 2.53 (2H, t, J=7.3 Hz), 3.62 (2H, t, J=6.2 Hz), 3.82 (2H, s), 6.97 (1H, d, J=5.8 Hz), 7.21 (2H, d, J=7.8 Hz), 7.49 (2H, m), 7.60 (1H, d, J=7.80), 7.69 (2H, d, J=7.8 Hz), 7.87 (1H, m), 7.94 (1H, s), 8.27 (1H, s)
Mass spectrometric value (ESI-MS) 466 (M−1)

Compound 660 N-[3-(4-Fluoro-benzylidene-hydrazinocarbonyl)-thiophen-2-yl]-3-(3-hydroxy-propylsulfanylmethyl)-benzamide The title compound 660 was produced in substantially the same manner as in Example 8.
$^1$H-NMR (CD$_3$OD, 400 MHz): δ 1.80 (2H, m), 2.53 (2H, t, J=7.4 Hz), 3.62 (2H, t, J=6.4 Hz), 3.82 (2H, s), 6.96 (1H, d, J=5.9 Hz), 7.14 (2H, dd, J=8.7 Hz), 7.48 (2H, m), 7.60 (1H, d, J=7.6 Hz), 7.85 (3H, m), 7.93 (1H, s), 8.29 (1H, s)
Mass spectrometric value (ESI-MS) 470 (M−1)

Compound 661 N-[3-(3-Fluoro-benzylidene-hydrazinocarbonyl)-thiophen-2-yl]-3-(3-hydroxy-propylsulfanylmethyl)-benzamide The title compound 661 was produced in substantially the same manner as in Example 8.
$^1$H-NMR (CD$_3$OD, 400 MHz): δ 1.80 (2H, m), 2.54 (2H, t, J=7.3 Hz), 3.62 (2H, t, J=9.4 Hz), 3.86 (2H, s), 7.03 (1H, d, J=5.8 Hz), 7.17 (1H, m), 7.42-7.80 (6H, m), 7.87 (1H, m), 7.98 (1H, bs), 8.35 (1H, s)
Mass spectrometric value (ESI-MS) 470 (M−1)

Compound 662 N-[3-(4-Chloro-3-trifluoromethyl-benzylidene-hydrazinocarbonyl)-thiophen-2-yl]-3-(3-hydroxy-propylsulfanylmethyl)-benzamide The title compound 662 was produced in substantially the same manner as in Example 8.
$^1$H-NMR (CD$_3$OD, 400 MHz): δ 1.80 (1H, m), 2.54 (2H, t, J=7.3 Hz), 3.62 (2H, t, J=6.2 Hz), 3.86 (2H, s), 7.03 (1H, d, J=5.8 Hz), 7.53 (2H, m), 7.66 (2H, m), 7.90 (1H, d, J=7.8 Hz), 7.98 (1H, bs), 8.04 (1H, d, J=8.8 Hz), 8.33 (1H, s), 8.38 (1H, s)
Mass spectrometric value (ESI-MS) 554 (M−1)

Compound 663 3-(3-Hydroxy-propylsulfanylmethyl)-N-[3-(4-methoxy-benzylidene-hydrazinocarbonyl)-thiophen-2-yl]-benzamide The title compound 663 was produced in substantially the same manner as in Example 8.
$^1$H-NMR (CD$_3$OD, 400 MHz): δ 1.80 (2H, m), 2.54 (2H, t, J=7.3 Hz), 3.62 (2H, t, J=6.2 Hz), 3.85 (6H, m), 6.99 (2H, d, J=8.8 Hz), 7.02 (1H, s, J=5.9 Hz), 7.53 (2H, m), 7.65 (1H, d, J=7.8 Hz), 7.79 (2H, d, J=8.5 Hz), 7.90 (1H, d, J=7.8 Hz), 8.30 (1H, s)
Mass spectrometric value (ESI-MS) 482 (M−1)

Compound 664 3-{[(2-Diethylamino-ethyl)-methyl-amino]-methyl}-N-[3-(3,4-dimethyl-benzylidene-hydrazinocarbonyl)-thiophen-2-yl]-benzamide The title compound 664 was produced in substantially the same manner as in Example 8.
$^1$H-NMR (CDCl$_3$, 400 MHz): δ 1.04 (6H, t, J=7.1 Hz), 2.22 (9H, m), 2.62 (8H, m), 3.59 (2H, s), 6.77 (1H, d, J=5.4 Hz), 7.09 (1H, m), 7.44 (5H, m), 7.94 (2H, d, J=7.6 Hz), 8.26 (1H, s)
Mass spectrometric value (ESI-MS) 518 (M−1)

Compound 665 3-{[(2-Diethylamino-ethyl)-methyl-amino]-methyl}-N-[3-(4-methyl-benzylidene-hydrazinocarbonyl)-thiophen-2-yl]-benzamide The title compound 665 was produced in substantially the same manner as in Example 8.
$^1$H-NMR (CDCl$_3$, 400 MHz): δ 1.03 (6H, t, J=7.1 Hz), 2.21 (3H, s), 2.34 (3H, s), 2.59 (8H, m), 3.58 (2H, s), 6.80 (1H, d, J=4.6 Hz), 7.16 (2H, m), 7.42 (2H, m), 7.58 (3H, m), 7.93 (1H, d, J=7.8 Hz), 7.98 (1H, s), 8.28 (1H, s)
Mass spectrometric value (ESI-MS) 504 (M−1)

Compound 666 3-{[(2-Diethylamino-ethyl)-methyl-amino]-methyl}-N-[3-(4-fluoro-benzylidene-hydrazinocarbonyl)-thiophen-2-yl]-benzamide The title compound 666 was produced in substantially the same manner as in Example 8.
$^1$H-NMR (CDCl$_3$, 400 MHz): δ 1.04 (6H, t, J=7.1 Hz), 2.21 (3H, s), 2.62 (8H, m), 3.58 (2H, s), 6.78 (1H, d, J=4.6 Hz), 7.02 (2H, m), 7.42 (2H, m), 7.55 (1H, d, J=7.6 Hz), 7.67 (2H, m), 7.91 (1H, d, J=7.8 Hz), 7.96 (1H, s), 8.36 (1H, s)
Mass spectrometric value (ESI-MS) 508 (M−1)

Compound 667 3-{[(2-Diethylamino-ethyl)-methyl-amino]-methyl}-N-[3-(3-fluoro-benzylidene-hydrazinocarbonyl)-thiophen-2-yl]-benzamide The title compound 667 was produced in substantially the same manner as in Example 8.
$^1$H-NMR (CDCl$_3$, 400 MHz): δ 1.04 (6H, t, J=7.1 Hz), 2.20 (3H, s), 2.60 (8H, m), 3.57 (2H, s), 6.76 (1H, bs), 7.02 (1H, m), 7.41 (6H, m), 7.91 (1H, d, J=7.8 Hz), 7.97 (1H, s), 8.38 (1H, bs)
Mass spectrometric value (ESI-MS) 508 (M−1)

Compound 668 N-[3-(4-Chloro-3-trifluoromethyl-benzylidene-hydrazinocarbonyl)-thiophen-2-yl]-3-{[(2-diethylamino-ethyl)-methyl-amino]-methyl}-benzamide The title compound 668 was produced in substantially the same manner as in Example 8.
$^1$H-NMR (CDCl$_3$, 400 MHz): δ 1.02 (6H, t, J=7.1 Hz), 2.20 (3H, s), 2.58 (8H, m), 3.56 (2H, s), 6.74 (1H, bs), 7.41 (2H, m), 7.54 (2H, d, J=7.6 Hz), 7.76 (1H, dd, J=8.3 Hz, J=1.4 Hz), 7.88 (2H, m), 7.96 (1H, s), 8.45 (1H, bs)
Mass spectrometric value (ESI-MS) 592 (M−1)

Compound 669 3-{[(2-Diethylamino-ethyl)-methyl-amino]-methyl}-N-[3-(4-methoxy-benzylidene-hydrazinocarbonyl)-thiophen-2-yl]-benzamide The title compound 669 was produced in substantially the same manner as in Example 8.
$^1$H-NMR (CDCl$_3$, 400 MHz): δ 1.01 (6H, t, J=7.1 Hz), 2.19 (3H, s), 2.56 (8H, m), 3.56 (2H, s), 3.75 (3H, s), 6.75 (1H, m), 6.81 (2H, m), 7.42 (2H, m), 7.87 (3H, m), 7.90 (1H, d, J=7.84), 7.97 (1H, s), 8.32 (1H, s)
Mass spectrometric value (ESI-MS) 520 (M−1)

Compound 670 3-{[Bis-(2-hydroxy-propyl)-amino]-methyl}-N-[3-(3,4-dimethyl-benzylidene-hydrazinocarbonyl)-thiophen-2-yl]-benzamide The title compound 670 was produced in substantially the same manner as in Example 8.
$^1$H-NMR (CD$_3$OD, 400 MHz): δ 1.11 (6H, m), 2.30 (3H, s), 2.32 (3H, s), 2.52 (4H, m), 3.83 (4H, m), 7.01 (1H, d, J=5.8 Hz), 7.19 (1H, d, J=7.8 Hz), 7.53 (3H, m), 7.67 (2H, m), 7.93 (1H, d, J=7.6 Hz), 8.06 (1H, m), 8.29 (1H, s)
Mass spectrometric value (ESI-MS) 521 (M−1)

Compound 671 3-{[Bis-(2-hydroxy-propyl)-amino]-methyl}-N-[3-(4-methyl-benzylidene-hydrazinocarbonyl)-thiophen-2-yl]-benzamide The title compound 671 was produced in substantially the same manner as in Example 8.
$^1$H-NMR (CD$_3$OD, 400 MHz): δ 1.11 (6H, d, J=6.1 Hz), 2.39 (3H, s), 2.52 (4H, m), 3.82 (4H, m), 7.01 (1H, m), 7.26 (2H, d, J=7.6 Hz), 7.53 (2H, m), 7.68 (1H, d, J=7.1 Hz), 7.74 (2H, d, J=7.8 Hz), 7.92 (1H, d, J=7.6 Hz), 8.06 (1H, m), 8.33 (1H, s)
Mass spectrometric value (ESI-MS) 507 (M−1)

Compound 672 3-{[Bis-(2-hydroxy-propyl)-amino]-methyl}-N-[3-(4-fluoro-benzylidene-hydrazinocarbonyl)-thiophen-2-yl]-benzamide The title compound 672 was produced in substantially the same manner as in Example 8.
$^1$H-NMR (CD$_3$OD, 400 MHz): δ 1.10 (6H, d, J=6.3 Hz), 2.51 (4H, m), 3.86 (4H, m), 7.02 (1H, d, J=5.9 Hz), 7.18 (2H, dd, J=8.4 Hz, J=8.4 Hz), 7.53 (2H, m), 7.68 (1H, dd, J=7.6 Hz), 7.91 (3H, m), 8.06 (1H, m), 8.35 (1H, s)
Mass spectrometric value (ESI-MS) 511 (M−1)

Compound 673 3-{[Bis-(2-hydroxy-propyl)-amino]-methyl}-N-[3-(3-fluoro-benzylidene-hydrazinocarbonyl)-thiophen-2-yl]-benzamide The title compound 673 was produced in substantially the same manner as in Example 8.
$^1$H-NMR (CD$_3$OD, 400 MHz): δ 1.11 (6H, m), 2.52 (4H, m), 3.87 (4H, m), 7.03 (1H, d, J=6.1 Hz), 7.15 (1H, m), 7.40-7.75 (6H, m), 7.90 (1H, m), 8.07 (1H, m), 8.36 (1H, m)
Mass spectrometric value (ESI-MS) 511 (M−1)

Compound 674 3-[(4-Chloro-3-trifluoromethyl-benzylidene)-amino]-2-(3-{[(2-diethylamino-ethyl)-methyl-amino]-methyl}-phenyl)-5,6,7,8-tetrahydro-3H-benzo[4,5]thieno[2,3-d]pyrimidin-4-one The title compound 674 was produced in substantially the same manner as in Example 8.
$^1$H-NMR (CDCl$_3$, 400 MHz): δ 0.99 (6H, t, J=7.1 Hz), 1.90 (4H, m), 2.12 (3H, s), 2.50 (8H, m), 2.82 (2H, m), 3.05 (2H, m), 3.52 (2H, s), 7.38 (2H, m), 7.54 (2H, m), 7.62 (1H, bs), 7.78 (1H, m), 7.98 (1H, m), 9.18 (1H, s)
Mass spectrometric value (ESI-MS) 630 (M+1)

Compound 675 2-(3-{[(2-Diethylamino-ethyl)-methyl-amino]-methyl}-phenyl)-3-[(4-methoxy-benzylidene-)-amino]-5,6,7,8-tetrahydro-3H-benzo[4,5]thieno[2,3-d]pyrimidin-4-one The title compound 675 was produced in substantially the same manner as in Example 8.
$^1$H-NMR (CDCl$_3$, 400 MHz): δ 1.00 (6H, t, J=7.1 Hz), 1.89 (4H, m), 2.11 (3H, s), 2.52 (8H, m), 2.81 (2H, m), 3.06 (2H, m), 3.50 (2H, s), 3.84 (3H, s), 6.89 (2H, d, J=8.8 Hz), 7.35 (2H, m), 7.58 (1H, m), 7.66 (3H, m), 8.77 (1H, s)
Mass spectrometric value (ESI-MS) 558 (M+1)

Compound 676 N-[4-Bromo-2-(4-methyl-benzylidene-hydrazinocarbonyl)-phenyl]-3-(2-hydroxy-ethanesulfonylmethyl)-benzamide The title compound 676 was produced in the same manner as in Example 6.
$^1$H-NMR (CD$_3$OD, 400 MHz): δ 8.58 (1H, d, J=8.8 Hz), 8.34 (1H, s), 8.07 (1H, d, J=2.2 Hz), 8.00 (2H, s), 7.23-7.78 (3H, m), 7.57-7.63 (2H, m), 7.27 (2H, d, J=2.0 Hz), 4.39 (1H, d, J=13.2 Hz), 4.20 (1H, d, J=13.2 Hz), 3.96-4.05 (2H, m), 3.00-3.15 (1H, m), 2.80-2.95 (1H, m), 2.39 (3H, s)
Mass spectrometric value (ESI-MS) 556, 558 (M−1)

Compound 677 N-[4-Bromo-2-(4-methyl-benzylidene-hydrazinocarbonyl)-phenyl]-3-(2-hydroxy-ethanesulfinylmethyl)-benzamide The title compound 677 was produced in the same manner as in Example 6.
$^1$H-NMR (CD$_3$OD, 400 MHz): δ 8.61 (1H, d, J=9.0 Hz), 8.34 (1H, s), 8.06-8.13 (2H, m), 8.04 (1H, d, J=8.3 Hz), 7.72-7.79 (4H, m), 7.60 (1H, dd, J=7.8 Hz, J=7.8 Hz), 7.28 (2H, d, J=8.1 Hz), 4.83 (2H, s), 4.05 (2H, t, J=5.6 Hz), 3.20 (2H, t, J=5.6 Hz), 2.39 (3H, s)
Mass spectrometric value (ESI-MS) 542, 543 (M−1)

Compound 678 N-[4-Bromo-2-(4-chloro-3-trifluoromethyl-benzylidene-hydrazinocarbonyl)-phenyl]-3-(2-hydroxy-ethanesulfonylmethyl)-benzamide The title compound 678 was produced in the same manner as in Example 6.
$^1$H-NMR (CD$_3$OD, 400 MHz): δ 8.55 (1H, d, J=9.0 Hz), 8.40 (1H, s), 8.32 (1H, s), 8.07 (1H, d, J=2.0 Hz), 8.05 (1H, s, J=8.5 Hz), 7.96-8.05 (2H, m), 7.77 (1H, dd, J=2.0 Hz, J=8.8 Hz), 7.69 (1H, d, J=8.3 Hz), 7.56-7.66 (2H, m), 4.39 (1H, d, J=12.9 Hz), 4.20 (1H, d, J=13.2 Hz), 3.96-4.03 (2H, m), 3.03-3.13 (1H, m), 2.87 (1H, dt, J=4.2 Hz, J=13.4 Hz)
Mass spectrometric value (ESI-MS) 664, 646 (M−1)

Compound 679 N-[4-Bromo-2-(4-chloro-3-trifluoromethyl-benzylidene-hydrazinocarbonyl)-phenyl]-3-(2-hydroxy-ethanesulfinylmethyl)-benzamide The title compound 679 was produced in the same manner as in Example 6.
$^1$H-NMR (CDCl$_3$, 400 MHz): δ 8.70-8.80 (1H, m), 8.20-8.27 (1H, m), 8.05-8.15 (2H, m), 7.97 (2H, s), 7.60-7.70 (3H, m), 7.49-7.60 (2H, m), 4.52 (2H, m), 4.22-4.26 (2H, m), 3.10-3.15 (2H, m)
Mass spectrometric value (ESI-MS) 628, 630 (M−1)

Compound 680 N-[4-Chloro-2-(3-fluoro-benzylidene-hydrazinocarbonyl)-phenyl]-3-(furan-2-ylmethylsulfanylmethyl)-benzamide The title compound 680 was produced in the same manner as in Example 5.
$^1$H-NMR (CD$_3$OD, 400 MHz): δ 8.64 (1H, d, J=9.0 Hz), 8.36 (1H, s), 7.93-7.97 (2H, m), 7.85-7.90 (1H, m), 7.69 (1H, d, J=10.0 Hz), 7.63 (1H, dd, J=2.4 Hz, J=9.0 Hz), 7.58 (2H, dd, J=7.6 Hz, J=7.6 Hz), 7.50 (1H, dd, J=7.6 Hz, J=7.6 Hz), 7.40-7.48 (2H, m), 7.18 (2H, m), 6.29-6.33 (1H, m), 6.21 (1H, d, J=3.2 Hz), 3.81 (2H, s), 3.64 (2H, s)
Mass spectrometric value (ESI-MS) 520, 522 (M−1)

Compound 681 N-[4-Chloro-2-(4-fluoro-benzylidene-hydrazinocarbonyl)-phenyl]-3-(furan-2-ylmethylsulfanylmethyl)-benzamide The title compound 681 was produced in the same manner as in Example 5.
$^1$H-NMR (CD$_3$OD, 400 MHz): δ 8.64 (1H, d, J=9.0 Hz), 8.35 (1H, s), 7.85-7.96 (5H, m), 7.62 (1H, dd, J=2.4 Hz, J=9.0 Hz), 7.57 (1H, d, J=7.8 Hz), 7.50 (1H, dd, J=7.7 Hz, J=7.7 Hz), 7.40-7.42 (1H, m), 7.18 (2H, dd, J=8.8 Hz, J=8.8 Hz), 7.31 (1H, dd, J=2.0 Hz, J=3.2 Hz), 6.21 (1H, d, J=3.2 Hz), 3.81 (2H, s), 3.64 (2H, s)
Mass spectrometric value (ESI-MS) 520, 522 (M−1)

Compound 682 N-[4-Chloro-2-(4-methyl-benzylidene-hydrazinocarbonyl)-phenyl]-3-(furan-2-ylmethylsulfanylmethyl)-benzamide The title compound 682 was produced in the same manner as in Example 5.
$^1$H-NMR (CD$_3$OD, 400 MHz): δ 8.65 (1H, d, J=9.0 Hz), 8.33 (1H, s), 7.91-7.96 (2H, m), 7.85-7.90 (1H, m), 7.73 (2H, d, J=8.0 Hz), 7.62 (1H, dd, J=2.4 Hz, J=9.0 Hz), 7.58 (1H, d, J=7.6 Hz), 7.50 (1H, dd, J=7.8 Hz, J=7.8 Hz), 7.40-7.42 (1H, m), 7.26 (2H, d, J=8.1 Hz), 6.29-6.33 (1H, m), 6.20-6.23 (1H, m), 3.82 (2H, s), 3.64 (2H, s), 2.38 (3H, s)
Mass spectrometric value (ESI-MS) 516, 518 (M−1)

Compound 683 N-[4-Chloro-2-(3,4-dimethyl-benzylidene-hydrazinocarbonyl)-phenyl]-3-(furan-2-ylmethylsulfanylmethyl)-benzamide The title compound 683 was produced in the same manner as in Example 5.
$^1$H-NMR (CD$_3$OD, 400 MHz): δ 8.66 (1H, d, J=8.8 Hz), 8.30 (1H, s), 7.86-7.98 (3H, m), 7.48-7.78 (5H, m), 7.41 (1H, s), 7.15-7.27 (1H, m), 6.29-6.35 (1H, m), 6.20-6.25 (1H, m), 3.82 (2H, s), 3.64 (2H, s), 2.31 (6H, s)
Mass spectrometric value (ESI-MS) 530, 532 (M−1)

Compound 684 N1-[4-Chloro-2-({2-[(E)-1-(3,4-dimethylphenyl)methylidene]hydrazino}carbonyl)phenyl}-3-{[{3-[(3-{[4-chloro-2-({2-[(E)-1-(3,4-dimethylphenyl)methylidene]hydrazino}carbonyl)anilino}carbonyl}benzyl}(methyl)amino)propyl](methyl)amino)methyl)benzamide The title compound 684 was produced in the same manner as in Example 8.
$^1$H-NMR (CDCl$_3$, 400 MHz): δ 11.57 (2H, s), 10.57 (2H, s), 8.67 (2H, d, J=9.0 Hz), 8.44 (2H, s), 7.80 (2H, s), 7.71-7.73 (2H, m), 7.64 (2H, s), 7.56 (2H, s), 7.38 (4H, dd, J=7.8 Hz, J=7.8 Hz), 7.20-7.35 (4H, m), 7.10 (2H, d, J=7.8 Hz), 3.53 (4H, s), 2.46 (4H, s), 2.23 (6H, s), 2.18 (6H, s), 2.14 (6H, s), 1.80 (2H, s), 1.61 (4H, s)
Mass spectrometric value (ESI-MS) 935 (M−1)

Compound 685 N1-[4-Chloro-2-({2-[(E)-1-(3-fluorophenyl)methylidene]hydrazino}carbonyl}phenyl}-3-{[{3-[(3-{[4-chloro-2-({2-[(E)-1-(3-fluorophenyl)methylidene]hydrazino}carbonyl}anilino}carbonyl}benzyl}(methyl)amino)propyl)(methyl)amino]methyl]-benzamide The title compound 685 was produced in the same manner as in Example 8.
$^1$H-NMR (CD$_3$OD, 400 MHz): δ 8.59 (2H, d, J=9.0 Hz), 8.40 (2H, s), 7.88-7.90 (4H, m), 7.85 (2H, s), 7.79 (2H, d, J=7.1 Hz), 7.63 (2H, d, J=10.5 Hz), 7.52-7.58 (4H, m), 7.35-7.45 (6H, m), 7.12-7.20 (2H, m), 3.62 (4H, s), 2.53 (4H, m), 2.23 (6H, s), 1.78-1.85 (2H, m)
Mass spectrometric value (ESI-MS) 915 (M−1)

Compound 686 N-[4-Chloro-2-(3,4-dimethyl-benzylidene-hydrazinocarbonyl)-phenyl]-3-(furan-2-ylmethanesulfonylmethyl)-benzamide The title compound 686 was produced in the same manner as in Example 6.
$^1$H-NMR (CDCl$_3$, 400 MHz): δ 8.64 (1H, d, J=9.0 Hz), 8.30 (1H, s), 8.01 (2H, s), 7.88-7.94 (2H, m), 7.52-7.68 (5H, m), 7.20 (1H, d, J=7.8 Hz), 6.50 (1H, d, J=3.2 Hz), 6.42-6.45 (1H, m), 4.25-4.37 (2H, m), 4.11 (1H, d, J=4.7 Hz), 4.08 (1H, d, J=4.7 Hz), 2.32 (3H, s), 2.31 (3H, s)
Mass spectrometric value (ESI-MS) 562, 564 (M−1)

Compound 687 N-[4-Chloro-2-(3,4-dimethyl-benzylidene-hydrazinocarbonyl)-phenyl]-3-(furan-2-ylmethanesulfinylmethyl)-benzamide The title compound 687 was produced in the same manner as in Example 6.
¹H-NMR (CDCl₃, 400 MHz): δ 6.37 (1H, s), 8.72 (1H, d, J=8.0 Hz), 8.00-8.22 (3H, m), 7.40-7.80 (7H, m), 6.54 (1H, d, J=3.4 Hz), 6.40-6.45 (1H, m), 4.29 (2H, s), 4.20 (2H, s), 2.29 (6H, s)
Mass spectrometric value (ESI-MS) 546, 548 (M−1)

Compound 688 N-[4-Chloro-2-(4-chloro-3-trifluoromethyl-benzylidene-hydrazinocarbonyl)-phenyl]-3-(furan-2-ylmethanesulfonylmethyl)-benzamide The title compound 688 was produced in the same manner as in Example 6.
¹H-NMR (CDCl₃, 400 MHz): δ 8.60 (1H, d, J=9.0 Hz), 8.39 (1H, s), 8.32 (1H, s), 7.89-8.07 (4H, m), 7.55-7.73 (5H, m), 6.49 (1H, m), 6.41-6.46 (1H, m), 4.31 (2H, dd, J=13.4 Hz, J=15.8 Hz), 4.09 (2H, dd, J=10.0 Hz, J=14.2 Hz)
Mass spectrometric value (ESI-MS) 636, 638 (M−1)

Compound 689 N-[4-Chloro-2-(4-chloro-3-trifluoromethyl-benzylidene-hydrazinocarbonyl)-phenyl]-3-(furan-2-ylmethanesulfinylmethyl)-benzamide The title compound 689 was produced in the same manner as in Example 6.
¹H-NMR (CDCl₃, 400 MHz): δ 8.60 (1H, d, J=9.3 Hz), 8.39 (1H, s), 8.32 (1H, s), 7.98-8.09 (3H, m), 7.94 (1H, d, J=2.2 Hz), 7.69 (2H, d, J=8.0 Hz), 7.56-7.67 (3H, m), 6.55 (1H, d, J=3.2 Hz), 6.40-6.47 (1H, m), 4.54 (2H, s), 4.51 (2H, s)
Mass spectrometric value (ESI-MS) 620 (M−1)

Compound 690 N1-[4-Chloro-2-({2-[(E)-1-(4-chloro-3-trifluoromethyl-phenyl)methylidene]hydrazino}carbonyl)phenyl]-3-{[{6-[(3-{[4-chloro-2-({2-[(E)-1-(4-chloro-3-trifluoromethyl-phenyl)methylidene]hydrazino}-carbonyl}anilino)carbonyl]benzyl}(methyl)amino)hexyl](methyl)amino]-methyl]benzamide The title compound 690 was produced in the same manner as in Example 8.
Mass spectrometric value (ESI-MS) 1125, 1127 (M−1)

Compound 691 2-{3-[4-Chloro-2-(3-fluoro-benzylidene-hydrazinocarbonyl)-phenylcarbamoyl]-benzylsulfanyl}-ethanesulfonic acid The title compound 691 was produced in the same manner as in Example 11.
¹H-NMR (CD₃OD, 400 MHz): δ 8.53 (1H, d, J=9.0 Hz), 8.34 (1H, s), 7.40-8.00 (10H, m), 4.84 (2H, s), 2.90-3.10 (2H, m), 2.70-2.86 (2H, m)
Mass spectrometric value (ESI-MS) 548 (M−1)

Compound 692 2-{3-[4-Chloro-2-(3-methyl-benzylidene-hydrazinocarbonyl)-phenylcarbamoyl]-benzylsulfanyl}-ethanesulfonic acid The title compound 692 was produced in the same manner as in Example 11.
¹H-NMR (CD₃OD, 400 MHz): δ 8.56 (1H, d, J=8.8 Hz), 7.20-8.35 (11H, m), 3.84-3.90 (2H, m), 2.92-3.04 (2H, m), 2.70-2.88 (2H, m), 2.30-2.40 (3H, m)
Mass spectrometric value (ESI-MS) 544 (M−1)

Compound 693 2-{3-[4-Chloro-2-(4-methyl-benzylidene-hydrazinocarbonyl)-phenylcarbamoyl]-benzylsulfanyl}-ethanesulfonic acid The title compound 693 was produced in the same manner as in Example 11.
¹H-NMR (CD₃OD, 400 MHz): δ 8.55 (1H, d, J=8.8 Hz), 8.32 (1H, s), 7.10-8.00 (10H, m), 3.88 (2H, s), 2.90-3.10 (2H, m), 2.68-2.86 (2H, m), 2.38 (3H, s)
Mass spectrometric value (ESI-MS) 544 (M−1)

Compound 694 2-{3-[4-Chloro-2-(3,4-dimethyl-benzylidene-hydrazinocarbonyl)-phenylcarbamoyl]-benzylsulfanyl}-ethanesulfonic acid The title compound 694 was produced in the same manner as in Example 11.
¹H-NMR (CD₃OD, 400 MHz): δ 8.56 (1H, d, J=9.0 Hz), 8.29 (1H, s), 7.46-8.00 (8H, m), 7.18-7.25 (1H, m), 3.87 (2H, s), 2.94-3.10 (2H, m), 2.75-2.86 (2H, m), 2.25-2.35 (6H, m)
Mass spectrometric value (ESI-MS) 582 (M+23)

Compound 695 6-Bromo-3-[(4-fluoro-benzylidene-)-amino]-2-[3-(2-hydroxy-ethylsulfanylmethyl)-phenyl]-3H-quinazolin-4-one The title compound 695 was produced in the same manner as in Example 10.
¹H-NMR (CDCl₃, 400 MHz): δ 8.98-9.00 (1H, m), 8.46 (1H, s), 7.85 (1H, dd, J=2.2 Hz, J=8.5 Hz), 7.65-7.72 (3H, m), 7.58 (1H, dd, J=1.7 Hz, J=7.3 Hz), 7.35-7.43 (2H, m), 7.07-7.13 (3H, m), 3.73 (2H, s), 3.56-3.64 (2H, m), 2.52-2.58 (2H, m)
Mass spectrometric value (ESI-MS) 534, 536, 537 (M+23)

Compound 696 6-Bromo-2-[3-(2-hydroxy-ethylsulfanylmethyl)-phenyl]-3-[(4-methyl-benzylidene-)-amino]-3H-quinazolin-4-one The title compound 696 was produced in the same manner as in Example 10.
¹H-NMR (CDCl₃, 400 MHz): δ 8.85 (1H, s), 8.41 (1H, d, J=2.2 Hz), 7.91 (1H, d, J=8.0 Hz), 7.79 (1H, dd, J=2.4 Hz, J=8.8 Hz), 7.59-7.64 (2H, m), 7.52-7.56 (3H, m), 7.28-7.36 (2H, m), 7.14-7.20 (1H, m), 3.67 (2H, s), 3.49 (2H, t, J=6.0 Hz), 2.46 (2H, t, J=6.0 Hz), 2.36 (1H, s), 2.33 (3H, s)
Mass spectrometric value (ESI-MS) 530, 532, 533 (M+23)

Compound 697 6-Bromo-3-[(3,4-dimethyl-benzylidene-)-amino]-2-[3-(2-hydroxy-ethylsulfanylmethyl)-phenyl]-3H-quinazolin-4-one The title compound 697 was produced in the same manner as in Example 10.
¹H-NMR (CDCl₃, 400 MHz): δ 8.78 (1H, s), 8.41 (2H, d, J=2.2 Hz), 7.79 (1H, dd, J=2.4 Hz, J=8.8 Hz), 7.64 (1H, s), 7.60 (1H, d, J=8.8 Hz), 7.53-7.57 (1H, m), 7.42 (1H, s), 7.28-7.38 (3H, m), 7.11 (1H, d, J=7.8 Hz), 3.67 (2H, s), 3.49 (2H, t, J=6.0 Hz), 2.46 (2H, t, J=6.0 Hz), 2.24 (3H, s), 2.22-2.27 (1H, m), 2.20 (3H, s)
Mass spectrometric value (ESI-MS) 546, 547 (M+23)

Compound 698 6-Bromo-3-[(4-chloro-3-trifluoromethyl-benzylidene-)-amino]-2-[3-(2-hydroxy-ethylsulfanylmethyl)-phenyl]-3H-quinazolin-4-one The title compound 698 was produced in the same manner as in Example 10.

$^1$H-NMR (CDCl$_3$, 400 MHz): δ 9.27 (1H, s), 8.46 (1H, d, J=2.2 Hz), 7.94 (1H, s), 7.86 (1H, dd, J=2.2 Hz, J=8.5 Hz), 7.75 (1H, d, J=8.3 Hz), 7.65-7.68 (2H, m), 7.54 (2H, d, J=7.8 Hz), 7.32-7.45 (2H, m), 3.75 (2H, s), 3.61 (2H, dt, J=5.9 Hz, J=5.9 Hz), 2.57 (2H, t, J=6.0 Hz), 2.03 (1H, t, J=6.1 Hz)

Mass spectrometric value (ESI-MS) 620 (M+23)

Compound 699 N-[4-Chloro-2-(3-methyl-benzylidene-hydrazinocarbonyl)-phenyl]-3-(furan-2-ylmethylsulfanylmethyl)-benzamide The title compound 699 was produced in the same manner as in Example 5.

$^1$H-NMR (CD$_3$OD, 400 MHz): δ 8.65 (1H, d, J=9.0 Hz), 8.34 (1H, s), 7.91-7.96 (2H, m), 7.85-7.90 (1H, m), 7.69 (1H, s), 7.61 (2H, dd, J=2.4 Hz, J=9.0 Hz), 7.57 (1H, d, J=7.8 Hz), 7.49 (1H, dd, J=7.6 Hz, J=7.6 Hz), 7.41 (1H, dd, J=0.8 Hz, J=2.0 Hz), 7.24-7.34 (2H, m), 6.30 (1H, dd, J=2.0 Hz, J=3.2 Hz), 6.21 (1H, d, J=3.2 Hz), 3.81 (2H, s), 3.63 (2H, s), 2.38 (3H, s)

Mass spectrometric value (ESI-MS) 516, 518 (M−1)

Compound 700 N-[4-Chloro-2-(4-chloro-3-trifluoromethyl-benzylidene-hydrazinocarbonyl)-phenyl]-3-(furan-2-ylmethylsulfanylmethyl)-benzamide The title compound 700 was produced in the same manner as in Example 5.

$^1$H-NMR (CD$_3$OD, 400 MHz): δ 8.62 (1H, d, J=9.0 Hz), 8.39 (1H, s), 8.31 (1H, s), 8.04 (1H, d, J=6.8 Hz), 7.92-7.96 (2H, m), 7.87 (1H, d, J=7.8 Hz), 7.69 (1H, d, J=8.6 Hz), 7.64 (1H, dd, J=2.4 Hz, J=9.0 Hz), 7.57 (1H, d, 7.6 Hz), 7.50 (1H, dd, J=7.7 Hz, J=7.7 Hz), 7.40 (1H, dd, J=0.8 Hz, J=2.0 Hz), 6.28-6.33 (1H, m), 6.21 (1H, d, J=7.3 Hz), 3.81 (2H, s), 3.64 (2H, s)

Mass spectrometric value (ESI-MS) 604, 606 (M−1)

Compound 701 N1-[4-Chloro-2-({2-[(E)-1-(4-fluorophenyl)methylidene]-hydrazino}carbonyl}phenyl}-3-{[{3-[(3-{[4-chloro-2-([2-[(E)-1-(4-fluorophenyl)methylidene]hydrazino}carbonyl}anilino}carbonyl}benzyl}-(methyl)amino)propyl)(methyl)amino]methyl]benzamide The title compound 701 was produced in the same manner as in Example 8.

$^1$H-NMR (CD$_3$OD, 400 MHz): δ 8.59 (2H, d, J=8.8 Hz), 8.41 (2H, s), 7.82-7.90 (8H, m), 7.79 (2H, d, J=7.1 Hz), 7.53 (2H, dd, J=2.4 Hz, J=9.0 Hz), 7.35-7.45 (4H, m), 7.14 (4H, dd, J=8.8 Hz, J=8.8 Hz), 3.59 (4H, s), 2.49 (4H, t, J=6.8 Hz), 2.20 (6H, s), 1.75-1.85 (2H, m)

Mass spectrometric value (ESI-MS) 915, 917 (M−1)

Compound 702 N1-[4-Chloro-2-({2-[(E)-1-(4-methylphenyl)methylidene]-hydrazino}carbonyl}phenyl}-3-{[{3-[(3-{[4-chloro-2-({2-[(E)-1-(4-methylphenyl)methylidene]hydrazino}carbonyl}anilino}carbonyl}benzyl}(methyl)amino)propyl)(methyl)amino]methyl]benzamide The title compound 702 was produced in the same manner as in Example 8.

$^1$H-NMR (CDCl$_3$, 400 MHz): δ 8.66 (2H, d, J=9.0 Hz), 8.46 (2H, s), 7.72-7.82 (4H, m), 7.58-7.68 (6H, m), 7.25-7.40 (4H, m), 7.12-7.16 (6H, m), 3.53 (4H, bs), 2.46 (4H, bs), 2.15 (6H, bs), 1.81 (2H, bs)

Mass spectrometric value (ESI-MS) 907, 909 (M−1)

Example 10

Compound 703 2-(3-{6-Chloro-3-[(4-chloro-3-trifluoromethyl-benzylidene)-amino]-4-oxo-3,4-dihydro-quinazolin-2-yl}-benzylsulfanyl)-ethanesulfonic acid Methyl 2-amino-5-chlorobenzoate (compound A) (4.0 g) was dissolved in anhydrous methylene chloride (80.0 ml). Subsequently, pyridine (2.8 ml) and 3-(chloromethyl)benzoyl chloride (compound B) (5.0 g) were added to the solution at room temperature, and the mixture was stirred at that temperature for 2 hr. After the completion of the reaction, distilled water was added thereto, and the mixture was subjected to separatory extraction with chloroform. The organic layer was washed with a saturated aqueous sodium chloride solution and saturated brine, was dried over sodium sulfate, and was then concentrated to give methyl 5-chloro-2-[3-(chloromethyl)benzoyl]aminobenzoate as a useful intermediate (3.32 g, yield 100%).

Subsequently, methyl 5-chloro-2-[3-(chloromethyl)benzoyl]-aminobenzoate (1.8 g) was dissolved in anhydrous methylene chloride. Triethylamine (1.5 ml) and 2-mercaptoethanesulfonic acid sodium salt (compound B') (1.3 g) were added to the solution at room temperature, and the mixture was stirred at 40° C. for 4 days. After the completion of the reaction, distilled water was added thereto at room temperature, and the mixture was subjected to separatory extraction with chloroform. The organic layer was washed with a saturated aqueous sodium chloride solution, was dried over sodium sulfate, and was then concentrated. The residue was purified by column chromatography on silica gel to give 5-chloro-2-[3-(2-sulfo-ethylsulfanylmethyl)-benzoylamino]-benzoic acid methyl ester as a useful intermediate (1.08 g, yield 46.1%).

5-Chloro-2-[3-(2-sulfo-ethylsulfanylmethyl)-benzoylamino]-benzoic acid methyl ester (1.08 g) produced by the above reaction was dissolved in ethanol (11.0 ml). Hydrazine monohydrate (1.0 ml) was added to the solution at room temperature, and the mixture was heated under reflux with stirring for 3 days. After the completion of the reaction, the reaction solution was allowed to cool at room temperature. The reaction solution as such was then concentrated, and the residue was purified by column chromatography on silica gel to give 2-[3-(3-amino-6-chloro-4-oxo-3,4-dihydroquinazolin-2-yl)-benzylsulfanyl]-ethanesulfonic acid as a quinazolone compound (542 mg, yield 52.1%).

2-[3-(3-Amino-6-chloro-4-oxo-3,4-dihydroquinazolin-2-yl)-benzylsulfanyl]-ethanesulfonic acid (50.0 mg) was dissolved in anhydrous toluene (1.0 ml). Subsequently, 4-chloro-3-trifluoromethylbenzaldehyde (compound C) (50.0 μl) was added to the solution at room temperature, and the mixture was heated under reflux with stirring for 12 hr. After the completion of the reaction, the reaction solution was allowed to cool at room temperature, distilled water was added thereto, and the mixture was subjected to separatory extraction with chloroform. The organic layer was washed with a saturated aqueous sodium chloride solution and saturated brine, was dried over sodium sulfate, and was then concentrated. The residue was purified by column chromatography on silica gel, followed by drying through a vacuum pump to give the title compound 703 (32.0 mg, yield 44.0%).

$^1$H-NMR (CDCl$_3$, 400 MHz): δ 9.16 (1H, s), 8.15-8.25 (1H, m), 7.38-7.90 (9H, m), 3.84 (2H, s), 2.97-3.05 (2H, m), 2.80-2.87 (2H, m)

Mass spectrometric value (ESI-MS) 614, 616 (M−1)

Compound 704 N1-[4-Chloro-2-({2-[(E)-1-(3-fluorophenyl)methylidene]hydrazino}carbonyl}phenyl}-3-{[{6-[(3-{[4-chloro-2-({2-[(E)-1-(3-fluorophenyl)methylidene]hydrazino}carbonyl}-anilino}carbonyl}benzyl}(methyl)amino)hexyl](methyl)amino]methyl]-benzamide The title compound 704 was produced in the same manner as in Example 8.

$^1$H-NMR (CDCl$_3$, 400 MHz): δ 8.60 (2H, d, J=9.0 Hz), 8.35 (2H, s), 7.88-7.95 (4H, m), 7.30-7.80 (14H, m), 7.10-7.20 (2H, m), 3.69 (4H, s), 2.47 (4H, t, J=7.3 Hz), 2.27 (6H, s), 1.50-1.60 (4H, m), 1.25-1.37 (4H, m)

Mass spectrometric value (ESI-MS) 957 (M−1)

Compound 705 N1-[4-Chloro-2-({2-[(E)-1-(3-methylphenyl)methylidene]hydrazino}carbonyl}phenyl}-3-{[{6-[(3-{[4-chloro-2-({2-[(E)-1-(3-methylphenyl)methylidene]hydrazino}carbonyl}-anilino}carbonyl}benzyl}(methyl)amino)hexyl](methyl)amino]methyl]-benzamide The title compound 705 was produced in the same manner as in Example 8.

$^1$H-NMR (CDCl$_3$, 400 MHz): δ 8.61 (2H, d, J=8.8 Hz), 8.35 (2H, s), 7.85-7.93 (4H, s), 7.63 (2H, s), 7.45-7.57 (10H, m), 7.14-7.30 (4H, m), 3.58 (4H, s), 2.35-2.45 (4H, m), 2.34 (6H, s), 2.18 (6H, s), 1.53 (4H, bs), 1.32 (4H, bs)

Mass spectrometric value (ESI-MS) 949 (M−1)

Compound 706 N1-[4-Chloro-2-({2-[(E)-1-(4-methylphenyl)methylidene]hydrazino}carbonyl}phenyl}-3-{[{6-[(3-{[4-chloro-2-({2-[(E)-1-(4-methylphenyl)methylidene]hydrazino}carbonyl}-anilino}carbonyl}benzyl}(methyl)amino)hexyl](methyl)amino]methyl]-benzamide The title compound 706 was produced in the same manner as in Example 8.

$^1$H-NMR (CDCl$_3$, 400 MHz): δ 8.60 (2H, d, J=8.8 Hz), 8.34 (2H, s), 7.83-7.98 (8H, m), 7.66 (2H, d, J=7.8 Hz), 7.48-7.60 (4H, m), 7.21 (6H, d, J=7.8 Hz), 3.78 (4H, s), 2.55-2.60 (4H, m), 2.30-2.35 (12H, m), 1.59 (4H, bs), 1.35 (4H, bs)

Mass spectrometric value (ESI-MS) 949 (M−1)

Compound 707 3-{[Bis-(2-hydroxy-propyl)-amino]-methyl}-N-[2-(4-chloro-3-trifluoromethyl-benzylidene-hydrazinocarbonyl)-4-methyl-thiophen-3-yl]-benzamide The title compound 707 was produced in the same manner as in Example 8.

Mass spectrometric value (ESI-MS) 609, 611, 612 (M−1)

Compound 708 2-{3-[4-Chloro-2-(4-fluoro-benzylidene-hydrazinocarbonyl)-phenylcarbamoyl]-benzylsulfanyl}-ethanesulfonic acid The title compound 708 was produced in the same manner as in Example 11.

$^1$H-NMR (CD$_3$OD, 400 MHz): δ 8.54 (1H, d, J=8.8 Hz), 8.34 (1H, s), 7.98 (1H, s), 7.35-7.92 (7H, m), 7.14-7.22 (2H, m), 3.88 (2H, s), 2.95-3.06 (2H, m), 2.70-2.86 (2H, m)

Mass spectrometric value (ESI-MS) 548 (M−1)

Example 11

Compound 709 2-{3-[4-Chloro-2-(4-chloro-3-trifluoromethyl-benzylidene-hydrazinocarbonyl)-phenylcarbamoyl]-benzylsulfanyl}-ethanesulfonic acid Methyl 2-amino-5-chlorobenzoate (compound A) (4.0 g) was dissolved in anhydrous methylene chloride (80.0 ml). Subsequently, pyridine (2.8 ml) and 3-(chloromethyl)benzoyl chloride (compound B) (5.0 g) were added to the solution at room temperature, and the mixture was stirred at that temperature for 2 hr. After the completion of the reaction, distilled water was added thereto, and the mixture was subjected to separatory extraction with chloroform. The organic layer was washed with a saturated aqueous sodium chloride solution and saturated brine, was dried over sodium sulfate, and was then concentrated to give methyl 5-chloro-2-[3-(chloromethyl)benzoyl]aminobenzoate (3.32 g, yield 100%) as a useful intermediate.

Subsequently, methyl 5-chloro-2-[3-(chloromethyl)benzoyl]aminobenzoate (1.8 g) was dissolved in anhydrous methylene chloride. Triethylamine (1.5 ml) and 2-mercaptoethanesulfonic acid sodium salt (compound B') (1.3 g) were added to the solution at room temperature, and the mixture was stirred at 40° C. for 4 days. After the completion of the reaction, distilled water was added thereto at room temperature, and the mixture was subjected to separatory extraction with chloroform. The organic layer was washed with a saturated aqueous sodium chloride solution, was dried over sodium sulfate, and was then concentrated. The residue was purified by column chromatography on silica gel to give 5-chloro-2-[3-(2-sulfo-ethylsulfanylmethyl)-benzoylamino]-benzoic acid methyl ester (1.08 g o yield 46.1%) as a useful intermediate.

5-Chloro-2-[3-(2-sulfo-ethylsulfanylmethyl)-benzoylamino]-benzoic acid methyl ester (1.27 g) produced by the above reaction was dissolved in ethanol (15.0 ml). Hydrazine monohydrate (2.0 ml) was added to the solution at room temperature, and the mixture was stirred at 40° C. for 12 hr. After the completion of the reaction, the reaction solution was allowed to cool at room temperature. The reaction solution as such was then concentrated, and the residue was purified by column chromatography on silica gel to give 2-[3-(4-chloro-2-hydrazinocarbonyl-phenylcarbamoyl)-benzylsulfanyl]-ethanesulfonic acid as a hydrazine compound (820 mg, yield 67.2%).

2-[3-(4-Chloro-2-hydrazinocarbonyl-phenylcarbamoyl)-benzylsulfanyl]-ethanesulfonic acid (50.0 mg) was dissolved in anhydrous toluene (1.0 ml). Subsequently, 4-chloro-3-trifluoromethylbenzaldehyde (compound C) (50.0 μl) was added to the solution at room temperature, and the mixture was heated under reflux with stirring for 12 hr. After the completion of the reaction, the reaction solution was allowed to cool at room temperature, distilled water was added thereto, and the mixture was subjected to separatory extraction with chloroform. The organic layer was washed with a saturated aqueous sodium chloride solution and saturated brine, was dried over sodium sulfate, and was then concentrated. The residue was purified by column chromatography on silica gel and was dried through a vacuum pump to give the title compound 709 (47.2 mg, yield 56.0%).

$^1$H-NMR (CD$_3$OD, 400 MHz): δ 8.52 (1H, d, J=9.0 Hz), 7.38-8.40 (10H, m), 3.89 (2H, s), 2.94-3.06 (2H, m), 2.70-2.88 (2H, m)

Mass spectrometric value (ESI-MS) 632 (M−1)

Compound 710 3-{[(2-Diethylamino-ethyl)-methyl-amino]-methyl}-N-[4-methyl-2-(4-methyl-benzylidene-hydrazinocarbonyl)-thiophen-3-yl]-benzamide The title compound 710 was produced in the same manner as in Example 8.

$^1$H-NMR (CD$_3$OD, 400 MHz): δ 8.18 (1H, bs), 7.88-8.03 (3H, m), 7.64-7.70 (2H, m), 7.59 (1H, d, J=7.8 Hz), 7.46-7.55 (1H, m), 7.25 (2H, bs), 3.64 (2H, s), 2.72 (2H, bs), 2.53-2.65 (6H, m), 2.37 (3H, s), 2.28 (3H, s), 2.24 (3H, s), 1.04 (6H, t, J=7.3 Hz)

Mass spectrometric value (ESI-MS) 520 (M+1)

Compound 711 3-{[(2-Diethylamino-ethyl)-methyl-amino]-methyl}-N-[2-(3,4-dimethyl-benzylidene-hydrazinocarbonyl)-4-methyl-thiophen-3-yl]-benzamide The title compound 711 was produced in the same manner as in Example 8.

$^1$H-NMR (CD$_3$OD, 400 MHz): δ 7.88-8.18 (3H, m), 7.37-7.64 (5H, m), 7.19 (1H, s), 3.63 (2H, s), 2.67-2.75 (2H, m), 2.53-2.65 (6H, m), 2.20-2.35 (12H, m), 0.98-1.10 (6H, m)

Mass spectrometric value (ESI-MS) 532 (M−1), 534 (M+1)

Compound 712 3-{[(2-Diethylamino-ethyl)-methyl-amino]-methyl}-N-[2-(4-methoxy-benzylidene-hydrazinocarbonyl)-4-methyl-thiophen-3-yl]-benzamide The title compound 712 was produced in the same manner as in Example 8.

$^1$H-NMR (CD$_3$OD, 400 MHz): δ 7.90-8.03 (3H, m), 7.72 (2H, d, J=8.1 Hz), 7.59 (1H, d, J=7.3 Hz), 7.38-7.56 (2H, m), 6.97 (2H, bs), 3.84 (2H, s), 3.64 (2H, s), 2.67-2.75 (2H, m), 2.53-2.65 (6H, m), 2.27 (3H, s), 2.24 (3H, s), 1.00-1.10 (6H, m)

Mass spectrometric value (ESI-MS) 534 (M−1), 536 (M+1)

Compound 713 N-[4-Bromo-2-(3-fluoro-benzylidene-hydrazinocarbonyl)-phenyl]-4-[(2-morpholin-4-yl-ethylamino)-methyl]-benzamide The title compound 713 was produced in the same manner as in Example 8.

$^1$H-NMR (CDCl$_3$, 400 MHz): δ 8.43 (2H, bs), 7.99 (2H, d, J=7.8 Hz), 7.68 (1H, s), 7.36-7.60 (6H, m), 7.13 (1H, ddd, J=8.3 Hz, J=8.3 Hz, J=2.0 Hz), 3.89 (2H, s), 3.68-3.73 (4H, m), 2.72 (2H, t, J=5.9 Hz), 2.53 (2H, t, J=6.0 Hz), 2.43 (4H, t, J=4.4 Hz)

Mass spectrometric value (ESI-MS) 582 (M−1)

Compound 714 N-[4-Bromo-2-(4-chloro-3-trifluoromethyl-benzylidene-hydrazinocarbonyl)-phenyl]-4-[(2-morpholin-4-yl-ethylamino)-methyl]-benzamide The title compound 714 was produced in the same manner as in Example 8.

$^1$H-NMR (CDCl$_3$, 400 MHz): δ 8.51 (1H, s), 8.31 (1H, d, J=8.3 Hz), 8.06 (1H, s), 7.99 (3H, d, J=7.6 Hz), 7.65 (1H, s), 7.58 (1H, d, J=8.3 Hz), 7.47 (3H, d, J=7.7 Hz), 3.89 (2H, s), 3.71 (4H, t, J=4.5 Hz), 2.71 (2H, t, J=6.0 Hz), 2.53 (2H, t, J=6.0 Hz), 2.43 (4H, bs)

Mass spectrometric value (ESI-MS) 664, 666 (M−1)

Compound 715 N-[4-Bromo-2-(4-methoxy-benzylidene-hydrazinocarbonyl)-phenyl]-4-[(2-morpholin-4-yl-ethylamino)-methyl]-benzamide The title compound 715 was produced in the same manner as in Example 8.

$^1$H-NMR (CDCl$_3$, 400 MHz): δ 8.43 (1H, d, J=8.8 Hz), 8.38 (1H, s), 7.98 (2H, d, J=8.1 Hz), 7.68-7.77 (3H, m), 7.48 (1H, d, J=8.8 Hz), 7.41 (2H, d, J=8.8 Hz), 6.90 (2H, d, J=8.8 Hz), 3.86 (2H, s), 3.81 (3H, s), 3.68-3.72 (4H, m), 2.69 (2H, t, J=6.0 Hz), 2.51 (2H, t, J=6.0 Hz), 2.38-2.45 (4H, m)

Mass spectrometric value (ESI-MS) 592 (M−1)

Compound 716 N-[4-Bromo-2-(3-methoxy-benzylidene-hydrazinocarbonyl)-phenyl]-4-[(2-morpholin-4-yl-ethylamino)-methyl]-benzamide The title compound 716 was produced in the same manner as in Example 8.

$^1$H-NMR (CDCl$_3$, 400 MHz): δ 8.40-8.46 (2H, m), 7.98 (2H, d, J=7.8 Hz), 7.71 (1H, s), 7.49 (1H, d, J=8.5 Hz), 7.42 (2H, d, J=8.0 Hz), 7.35 (1H, s), 7.30 (2H, d, J=5.6 Hz), 3.86 (2H, s), 3.84 (3H, s), 3.70 (4H, t, J=4.6 Hz), 2.69 (2H, t, J=4.6 Hz), 2.51 (2H, t, J=5.8 Hz), 2.40-2.47 (4H, m)

Mass spectrometric value (ESI-MS) 596 (M+1)

Compound 717 N-[4-Bromo-2-(3,4-dimethyl-benzylidene-hydrazinocarbonyl)-phenyl]-4-[4-(4-fluoro-phenyl)-piperazin-1-ylmethyl]-benzamide The title compound 717 was produced in the same manner as in Example 8.

$^1$H-NMR (CDCl$_3$, 400 MHz): δ 8.57 (1H, d, J=9.0 Hz), 8.28 (1H, s), 8.00 (2H, d, J=7.6 Hz), 7.55-7.73 (3H, m), 7.48 (3H, d, J=8.1 Hz), 7.18 (1H, d, J=7.8 Hz), 6.93-6.98 (2H, m), 6.85-6.90 (2H, m), 3.63 (2H, s), 3.13 (4H, t, J=4.6 Hz), 2.62 (4H, bs), 2.30 (3H, s), 2.29 (3H, s)

Mass spectrometric value (ESI-MS) 642 (M−1)

Compound 718 4-{[Bis-(2-hydroxy-propyl)-amino]-methyl}-N-[4-bromo-2-(3-methyl-benzylidene-hydrazinocarbonyl)-phenyl]-benzamide The title compound 718 was produced in the same manner as in Example 8.

$^1$H-NMR (CDCl$_3$, 400 MHz): δ 8.53 (1H, d, J=8.6 Hz), 8.35 (1H, s), 8.02 (2H, d, J=7.3 Hz), 7.70 (2H, s), 7.53-7.60 (2H, m), 7.45 (2H, d, J=8.1 Hz), 7.32 (1H, dd, J=7.4 Hz, J=7.4 Hz), 3.60-3.99 (4H, m), 2.42-2.66 (4H, m), 2.39 (3H, s), 1.12 (6H, d, J=6.1 Hz)

Mass spectrometric value (ESI-MS) 581 (M+1)

Compound 719 4-{[Bis-(2-hydroxy-propyl)-amino]-methyl}-N-[4-bromo-2-(4-fluoro-benzylidene-hydrazinocarbonyl)-phenyl]-benzamide The title compound 719 was produced in the same manner as in Example 8.
$^1$H-NMR (CDCl$_3$, 400 MHz): δ 8.53 (1H, bs), 8.37 (1H, bs), 8.00 (2H, bs), 7.81 (2H, bs), 7.70 (1H, bs), 7.40-7.60 (3H, m), 7.05-7.15 (2H, m), 3.83-3.98 (2H, m), 3.65-3.78 (2H, m), 2.45-2.60 (4H, m), 1.20-1.30 (3H, m), 1.06-1.16 (3H, m)
Mass spectrometric value (ESI-MS) 587 (M+1)

Compound 720 4-{[Bis-(2-hydroxy-propyl)-amino]-methyl}-N-[4-bromo-2-(3-fluoro-benzylidene-hydrazinocarbonyl)-phenyl]-benzamide The title compound 720 was produced in the same manner as in Example 8.
$^1$H-NMR (CDCl$_3$, 400 MHz): δ 8.45-8.54 (1H, m), 8.39 (1H, s), 8.00 (2H, d, J=8.3 Hz), 7.36-7.74 (7H, m), 7.10-7.20 (1H, m), 3.80-4.02 (4H, m), 2.47-2.60 (4H, m), 1.12 (6H, d, J=6.4 Hz)
Mass spectrometric value (ESI-MS) 585 (M+1)

Compound 721 4-{[Bis-(2-hydroxy-propyl)-amino]-methyl}-N-[4-bromo-2-(4-chloro-3-trifluoromethyl-benzylidene-hydrazinocarbonyl)-phenyl]-benzamide The title compound 721 was produced in the same manner as in Example 8.
$^1$H-NMR (CDCl$_3$, 400 MHz): δ 8.46 (2H, bs), 7.95-8.08 (3H, m), 7.45-7.75 (4H, m), 7.13-7.20 (2H, m), 3.60-4.03 (4H, m), 2.47-2.68 (4H, m), 1.12 (6H, d, J=6.1 Hz)
Mass spectrometric value (ESI-MS) 667, 669 (M−1)

Compound 722 4-{[Bis-(2-hydroxy-propyl)-amino]-methyl}-N-[4-bromo-2-(4-methoxy-benzylidene-hydrazinocarbonyl)-phenyl]-benzamide The title compound 722 was produced in the same manner as in Example 8.
$^1$H-NMR (CDCl$_3$, 400 MHz): δ 8.37-8.47 (2H, m), 7.98 (2H, d, J=7.8 Hz), 7.70-7.74 (3H, m), 7.38-7.53 (3H, m), 6.90 (2H, d, J=8.8 Hz), 3.77-3.95 (4H, m), 3.81 (3H, s), 2.42-2.64 (4H, m), 1.08-1.14 (6H, m)
Mass spectrometric value (ESI-MS) 597 (M+1)

Compound 723 4-{[Bis-(2-hydroxy-propyl)-amino]-methyl}-N-[4-bromo-2-(3-methoxy-benzylidene-hydrazinocarbonyl)-phenyl]-benzamide The title compound 723 was produced in the same manner as in Example 8.
$^1$H-NMR (CDCl$_3$, 400 MHz): δ 8.57 (1H, d, J=8.5 Hz), 8.34 (1H, s), 8.00 (2H, d, J=7.1 Hz), 7.72 (1H, s), 7.55-7.62 (1H, m), 7.46 (2H, d, J=8.0 Hz), 7.30-7.40 (3H, m), 6.95-7.02 (1H, m), 3.80-4.00 (4H, m), 3.86 (3H, s), 2.40-2.65 (4H, m), 1.09-1.15 (6H, m)
Mass spectrometric value (ESI-MS) 597 (M−1)

Compound 724 N-[4-Bromo-2-(3,4-dimethyl-benzylidene-hydrazinocarbonyl)-phenyl]-4-({[2-hydroxy-2-(4-hydroxy-phenyl)-ethyl]-methyl-amino}-methyl)-benzamide The title compound 724 was produced in the same manner as in Example 8.
$^1$H-NMR (CD$_3$OD, 400 MHz): δ 8.56-8.66 (1H, m), 7.96 (2H, dd, J=2.2 Hz, J=8.3 Hz), 7.87 (1H, d, J=2.4 Hz), 7.65-7.78 (3H, m), 7.46-7.56 (3H, m), 7.13-7.22 (3H, m), 6.72-6.78 (2H, m), 4.80-4.90 (1H, m), 3.75-3.90 (2H, m), 2.73-2.82 (1H, m), 2.58-2.66 (1H, m), 2.40-2.45 (3H, m), 2.28-2.32 (6H, m)
Mass spectrometric value (ESI-MS) 629 (M−1)

Compound 725 N-[4-Bromo-2-(3-fluoro-benzylidene-hydrazinocarbonyl)-phenyl]-4-({[2-hydroxy-2-(4-hydroxy-phenyl)-ethyl]-methyl-amino}-methyl)-benzamide The title compound 725 was produced in the same manner as in Example 8.
$^1$H-NMR (CD$_3$OD, 400 MHz): δ 8.61 (1H, d, J=8.0 Hz), 8.36 (1H, s), 8.07 (1H, d, J=2.2 Hz), 7.92 (2H, d, J=2.2 Hz), 7.56 (1H, dd, J=2.2 Hz, J=9.0 Hz), 7.70 (1H, d, J=9.3 Hz), 7.60 (1H, d, J=7.8 Hz), 7.42-7.49 (3H, m), 7.10-7.24 (3H, m), 6.75 (2H, d, J=8.6 Hz), 4.70-4.75 (1H, m), 3.68 (2H, d, J=4.4 Hz), 2.67 (1H, dd, J=12.7 Hz, J=8.5 Hz), 2.50 (1H, dd, J=4.9 Hz, J=12.7 Hz), 2.33 (3H, s)
Mass spectrometric value (ESI-MS) 619 (M−1)

Compound 726 N-[4-Bromo-2-(4-chloro-3-trifluoromethyl-benzylidene-hydrazinocarbonyl)-phenyl]-4-({[2-hydroxy-2-(4-hydroxy-phenyl)-ethyl]-methyl-amino}-methyl)-benzamide The title compound 726 was produced in the same manner as in Example 8.
$^1$H-NMR (CD$_3$OD, 400 MHz): δ 8.61 (1H, d, J=9.0 Hz), 8.40 (1H, s), 8.34 (1H, s), 8.04-8.10 (2H, m), 7.90-7.95 (2H, m), 7.77 (1H, dd, J=9.0 Hz, J=2.4 Hz), 7.69 (1H, d, J=8.3 Hz), 7.45 (2H, d, J=8.3 Hz), 7.13 (2H, d, J=8.6 Hz), 6.75 (2H, d, J=8.6 Hz), 4.70-4.80 (1H, m), 3.70 (2H, d, J=4.4 Hz), 2.68 (1H, dd, J=8.3 Hz, J=12.8 Hz), 2.52 (1H, dd, J=4.6 Hz, J=12.7 Hz), 2.36 (3H, s)
Mass spectrometric value (ESI-MS) 701, 703 (M−1)

Compound 727 N-[4-Bromo-2-(3-methoxy-benzylidene-hydrazinocarbonyl)-phenyl]-4-({[2-hydroxy-2-(4-hydroxy-phenyl)-ethyl]-methyl-amino}-methyl)-benzamide The title compound 727 was produced in the same manner as in Example 8.
$^1$H-NMR (CD$_3$OD, 400 MHz): δ 8.63 (1H, d, J=9.0 Hz), 8.34 (1H, s), 8.07 (1H, d, J=2.4 Hz), 7.94 (2H, d, J=8.3 Hz), 7.75 (1H, dd, J=8.8 Hz, J=2.2 Hz), 7.61 (1H, bs), 7.44 (2H, d, J=8.3 Hz), 7.26-7.36 (2H, m), 7.13 (2H, d, J=8.3 Hz), 6.97-7.03 (1H, m), 6.76 (2H, d, J=8.6 Hz), 4.72-4.82 (1H, m), 3.84 (3H, s), 3.76 (2H, d, J=5.8 Hz), 2.72 (1H, dd, J=8.6 Hz, J=13.0 Hz), 2.41 (3H, s), 2.57 (1H, dd, J=4.9 Hz, J=13.0 Hz)
Mass spectrometric value (ESI-MS) 629 (M−1)

Compound 728 N-[4-Bromo-2-(4-methyl-benzylidene-hydrazinocarbonyl)-phenyl]-4-[4-(2-morpholin-4-yl-2-oxo-ethyl)-piperazin-1-ylmethyl]-benzamide The title compound 728 was produced in the same manner as in Example 8.
$^1$H-NMR (CD$_3$OD, 400 MHz): δ 8.49 (1H, d, J=9.0 Hz), 8.41 (1H, s), 7.97 (2H, d, J=7.8 Hz), 7.73 (1H, s), 7.68 (1H, d, J=7.6 Hz), 7.51 (1H, d, J=7.8 Hz), 7.41 (2H, d, J=7.8 Hz), 7.19-7.23 (3H, m), 3.47-3.75 (10H, m), 3.16 (2H, s), 2.40-2.56 (8H, m), 2.36 (3H, s)
Mass spectrometric value (ESI-MS) 659 (M−1)

Compound 729 N-[4-Bromo-2-(3-methyl-benzylidene-hydrazinocarbonyl)-phenyl]-4-[4-(2-morpholin-4-yl-2-oxo-ethyl)-piperazin-1-ylmethyl]-benzamide The title compound 729 was produced in the same manner as in Example 8.
¹H-NMR (CD₃OD, 400 MHz): δ 8.48 (1H, d, J=8.8 Hz), 8.42 (1H, s), 7.97 (2H, d, J=7.8 Hz), 7.66-7.75 (2H, m), 7.49-7.56 (2H, m), 7.41 (2H, d, J=7.8 Hz), 7.20-7.32 (2H, m), 3.48-3.76 (10H, m), 3.16 (2H, s), 2.40-2.56 (8H, m), 2.38 (3H, s)
Mass spectrometric value (ESI-MS) 661 (M−1)

Compound 730 N-[4-Bromo-2-(4-fluoro-benzylidene-hydrazinocarbonyl)-phenyl]-4-[4-(2-morpholin-4-yl-2-oxo-ethyl)-piperazin-1-ylmethyl]-benzamide The title compound 730 was produced in the same manner as in Example 8.
¹H-NMR (CD₃OD, 400 MHz): δ 8.48 (1H, d, J=9.0 Hz), 8.43 (1H, s), 7.97 (2H, d, J=7.8 Hz), 7.76-7.87 (2H, m), 7.68-7.73 (1H, m), 7.49-7.57 (1H, m), 7.42 (2H, d, J=7.8 Hz), 7.11 (2H, dd, J=8.5 Hz, J=8.5 Hz), 3.49-3.76 (10H, m), 3.16 (2H, s), 2.40-2.65 (8H, m)
Mass spectrometric value (ESI-MS) 665 (M−1)

Compound 731 N-[4-Bromo-2-(3-fluoro-benzylidene-hydrazinocarbonyl)-phenyl]-4-[4-(2-morpholin-4-yl-2-oxo-ethyl)-piperazin-1-ylmethyl]-benzamide The title compound 731 was produced in the same manner as in Example 8.
¹H-NMR (CD₃OD, 400 MHz): δ 8.42-8.52 (2H, m), 7.96 (2H, d, J=7.8 Hz), 7.73 (1H, s), 7.46-7.60 (3H, m), 7.33-7.44 (3H, m), 7.11 (1H, ddd, J=2.4 Hz, J=8.3 Hz, J=8.3 Hz), 3.48-3.76 (10H, m), 3.15 (2H, s), 2.40-2.60 (8H, m)
Mass spectrometric value (ESI-MS) 665 (M−1)

Compound 732 N-[4-Bromo-2-(3-methoxy-benzylidene-hydrazinocarbonyl)-phenyl]-4-[4-(2-morpholin-4-yl-2-oxo-ethyl)-piperazin-1-ylmethyl]-benzamide The title compound 732 was produced in the same manner as in Example 8.
¹H-NMR (CD₃OD, 400 MHz): δ 8.50 (2H, s, J=9.0 Hz), 8.45 (1H, s), 7.95 (2H, d, J=7.8 Hz), 7.78 (1H, s), 7.51 (1H, d, J=8.8 Hz), 7.25-7.43 (3H, m), 6.90-7.00 (2H, m), 3.83 (3H, s), 3.48-3.75 (10H, m), 3.16 (2H, s), 2.40-2.60 (8H, m)
Mass spectrometric value (ESI-MS) 675, 677 (M−1)

Compound 733 4-{[Bis-(2-ethoxy-ethyl)-amino]-methyl}-N-[4-bromo-2-(3,4-dimethyl-benzylidene-hydrazinocarbonyl)-phenyl]-benzamide The title compound 733 was produced in the same manner as in Example 8.
¹H-NMR (CD₃OD, 400 MHz): δ 8.36-8.46 (2H, m), 7.98 (2H, d, J=8.0 Hz), 7.66 (2H, d, J=10.0 Hz), 7.45-7.51 (4H, m), 7.17 (1H, d, J=8.1 Hz), 3.79 (2H, s), 3.52 (4H, t, J=6.1 Hz), 3.46 (4H, q, J=7.0 Hz), 2.76 (4H, t, J=6.0 Hz), 2.29 (3H, s), 2.27 (3H, s), 1.19 (6H, t, J=7.0 Hz)
Mass spectrometric value (ESI-MS) 622, 624 (M−1)

Compound 734 4-{[Bis-(2-ethoxy-ethyl)-amino]-methyl}-N-[4-bromo-2-(4-methyl-benzylidene-hydrazinocarbonyl)-phenyl]-benzamide The title compound 734 was produced in the same manner as in Example 8.
¹H-NMR (CD₃OD, 400 MHz): δ 8.45 (1H, s), 8.36 (1H, d, J=8.8 Hz), 7.98 (2H, d, J=7.3 Hz), 7.65-7.71 (3H, m), 7.45-7.48 (3H, m), 7.20 (2H, d, J=7.8 Hz), 3.79 (2H, s), 3.53 (4H, t, J=6.2 Hz), 3.46 (4H, q, J=7.9 Hz), 2.76 (4H, t, J=6.1 Hz), 2.35 (3H, s), 1.19 (6H, t, J=7.1 Hz)
Mass spectrometric value (ESI-MS) 607, 609 (M−1)

Compound 735 4-{[Bis-(2-ethoxy-ethyl)-amino]-methyl}-N-[4-bromo-2-(3-methyl-benzylidene-hydrazinocarbonyl)-phenyl]-benzamide The title compound 735 was produced in the same manner as in Example 8.
¹H-NMR (CDCl₃, 400 MHz): δ 8.47 (1H, s), 8.34 (1H, d, J=8.8 Hz), 7.98 (2H, d, J=8.0 Hz), 7.68 (2H, d, J=8.3 Hz), 7.54 (1H, d, J=7.3 Hz), 7.42-7.50 (3H, m), 7.20-7.34 (2H, m), 3.78 (2H, s), 3.52 (4H, t, J=6.1 Hz), 3.46 (4H, q, J=7.0 Hz), 2.76 (4H, t, J=6.2 Hz), 2.38 (3H, s), 1.19 (6H, t, J=7.0 Hz)
Mass spectrometric value (ESI-MS) 609 (M−1)

Compound 736 4-{[Bis-(2-ethoxy-ethyl)-amino]-methyl}-N-[4-bromo-2-(4-fluoro-benzylidene-hydrazinocarbonyl)-phenyl]-benzamide The title compound 736 was produced in the same manner as in Example 8.
¹H-NMR (CDCl₃, 400 MHz): δ 8.48 (1H, s), 8.31 (1H, d, J=8.8 Hz), 7.98 (2H, d, J=8.0 Hz), 7.81 (2H, dd, J=6.5 Hz, J=6.5 Hz), 7.64 (1H, s), 7.42-7.51 (3H, m), 7.10 (2H, dd, J=8.7 Hz, J=8.7 Hz), 3.79 (2H, s), 3.53 (4H, t, J=6.2 Hz), 3.67 (4H, q, J=7.0 Hz), 2.76 (4H, t, J=6.1 Hz), 1.19 (6H, t, J=6.9 Hz)
Mass spectrometric value (ESI-MS) 635 (M+23)

Compound 737 4-{[Bis-(2-ethoxy-ethyl)-amino]-methyl}-N-[4-bromo-2-(3-fluoro-benzylidene-hydrazinocarbonyl)-phenyl]-benzamide The title compound 737 was produced in the same manner as in Example 8.
¹H-NMR (CDCl₃, 400 MHz): δ 8.50 (1H, s), 8.29 (1H, d, J=8.8 Hz), 7.98 (2H, d, J=8.0 Hz), 7.30-7.76 (7H, m), 7.11 (1H, ddd, J=2.0 Hz, J=8.3 Hz, J=8.3 Hz), 3.80 (2H, s), 3.53 (4H, t, J=6.2 Hz), 3.47 (4H, q, J=6.2 Hz), 2.76 (4H, t, J=6.2 Hz), 1.19 (6H, t, J=6.9 Hz)
Mass spectrometric value (ESI-MS) 635 (M+23)

Compound 738 4-{[Bis-(2-ethoxy-ethyl)-amino]-methyl}-N-[4-bromo-2-(4-chloro-3-trifluoromethyl-benzylidene-hydrazinocarbonyl)-phenyl]-benzamide The title compound 738 was produced in the same manner as in Example 8.
¹H-NMR (CDCl₃, 400 MHz): δ 8.55 (1H, s), 8.24 (1H, d, J=8.0 Hz), 8.07 (1H, s), 7.95-8.04 (3H, m), 7.62 (1H, s), 7.57 (1H, d, J=8.3 Hz), 7.50 (2H, d, J=8.3 Hz), 7.43 (1H, d, J=8.6

Hz), 3.81 (2H, s), 3.53 (4H, t, J=6.1 Hz), 3.47 (4H, q, J=7.0 Hz), 2.76 (4H, t, J=6.0 Hz), 1.19 (6H, t, J=7.1 Hz)
Mass spectrometric value (ESI-MS) 721 (M+23)

Compound 739 4-{[Bis-(2-ethoxy-ethyl)-amino]-methyl}-N-[4-bromo-2-(4-methoxy-benzylidene-hydrazinocarbonyl)-phenyl]-benzamide The title compound 739 was produced in the same manner as in Example 8.
$^1$H-NMR (CDCl$_3$, 400 MHz): δ 8.53 (1H, d, J=9.0 Hz), 8.35-8.45 (1H, m), 7.96 (2H, dd, J=7.6 Hz, 7.6 Hz), 7.75 (1H, d, J=8.5 Hz), 7.67 (1H, s), 7.53 (1H, ddd, J=1.9 Hz, J=8.8 Hz, J=8.8 Hz), 7.42-7.50 (3H, m), 5.92 (2H, d, J=8.8 Hz), 3.83 (3H, s), 3.78 (2H, s), 3.52 (4H, t, J=6.1 Hz), 3.46 (4H, q, J=7.1 Hz), 2.75 (4H, t, J=5.5 Hz), 1.19 (6H, t, J=7.1 Hz)
Mass spectrometric value (ESI-MS) 625 (M−1)

Compound 740 4-{[Bis-(2-ethoxy-ethyl)-amino]-methyl}-N-[4-bromo-2-(3-methoxy-benzylidene-hydrazinocarbonyl)-phenyl]-benzamide The title compound 740 was produced in the same manner as in Example 8.
$^1$H-NMR (CDCl$_3$, 400 MHz): δ 8.47 (1H, s), 8.36 (1H, d, J=8.8 Hz), 7.97 (2H, d, J=8.8 Hz), 7.68 (1H, s), 7.47 (3H, d, J=8.1 Hz), 7.37 (1H, s), 7.27-7.34 (2H, m), 6.92-6.98 (1H, m), 3.85 (3H, s), 3.78 (2H, s), 3.52 (4H, t, J=6.1 Hz), 3.46 (4H, q, J=7.0 Hz), 2.75 (4H, t, J=6.0 Hz), 1.18 (6H, t, J=7.0 Hz)
Mass spectrometric value (ESI-MS) 649 (M+23)

Compound 741 N-[4-Bromo-2-(4-methyl-benzylidene-hydrazinocarbonyl)-phenyl]-4-[4-(2-hydroxy-ethyl)-piperidin-1-ylmethyl]-benzamide The title compound 741 was produced in the same manner as in Example 8.
$^1$H-NMR (DMSO-d$_6$, 400 MHz): δ 8.51 (1H, d, J=9.0 Hz), 8.41 (1H, s), 8.09 (1H, d, J=2.2 Hz), 7.89 (2H, d, J=8.0 Hz), 7.81 (1H, dd, J=2.4 Hz, J=9.0 Hz), 7.65 (2H, d, J=8.3 Hz), 7.49 (2H, d, J=8.0 Hz), 7.29 (2H, d, J=7.8 Hz), 4.29 (1H, t, J=5.1 Hz), 3.52 (2H, bs), 3.38-3.46 (2H, m), 2.78 (2H, d, J=11.0 Hz), 2.36 (3H, s), 1.92 (2H, t, J=11.1 Hz), 1.61 (2H, d, J=6.1 Hz), 1.30-1.40 (3H, m), 1.10-1.20 (2H, m)
Mass spectrometric value (ESI-MS) 577 (M−1)

Compound 742 N-[4-Bromo-2-(3-methyl-benzylidene-hydrazinocarbonyl)-phenyl]-4-[4-(2-hydroxy-ethyl)-piperidin-1-ylmethyl]-benzamide The title compound 742 was produced in the same manner as in Example 8.
$^1$H-NMR (DMSO-d$_6$, 400 MHz): δ 8.51 (1H, d, J=8.8 Hz), 8.41 (1H, s), 8.10 (1H, d, J=8.3 Hz), 7.88 (2H, d, J=2.2 Hz), 7.81 (1H, dd, J=2.2 Hz, J=9.0 Hz), 7.59 (1H, s), 7.53 (1H, d, J=7.6 Hz), 7.49 (3H, d, J=7.6 Hz), 7.36 (1H, dd, J=7.6 Hz, J=7.6 Hz), 7.28 (1H, d, J=7.6 Hz), 4.29 (1H, t, J=5.1 Hz), 3.52 (2H, bs), 3.38-3.45 (2H, m), 2.77 (2H, d, J=11.2 Hz), 2.37 (3H, s), 1.92 (2H, t, J=10.6 Hz), 1.60 (2H, d, J=6.1 Hz), 1.30-1.40 (3H, m), 1.10-1.21 (2H, m)
Mass spectrometric value (ESI-MS) 575 (M−1)

Compound 743 N-[4-Bromo-2-(4-fluoro-benzylidene-hydrazinocarbonyl)-phenyl]-4-[4-(2-hydroxy-ethyl)-piperidin-1-ylmethyl]-benzamide The title compound 743 was produced in the same manner as in Example 8.
$^1$H-NMR (DMSO-d$_6$, 400 MHz): δ 8.50 (1H, d, J=9.0 Hz), 8.45 (1H, s), 8.09 (1H, d, J=2.4 Hz), 7.88 (2H, d, J=8.0 Hz), 7.78-7.85 (3H, m), 7.49 (2H, d, J=8.3 Hz), 7.32 (2H, dd, J=8.8 Hz, J=8.8 Hz), 4.29 (1H, t, J=5.1 Hz), 3.52 (2H, bs), 3.38-3.45 (2H, m), 2.77 (2H, d, J=11.2 Hz), 1.92 (2H, t, J=10.7 Hz), 1.60 (2H, d, J=6.1 Hz), 1.30-1.40 (3H, m), 1.10-1.20 (2H, m)
Mass spectrometric value (ESI-MS) 581 (M−1)

Compound 744 N-[4-Bromo-2-(3-fluoro-benzylidene-hydrazinocarbonyl)-phenyl]-4-[4-(2-hydroxy-ethyl)-piperidin-1-ylmethyl]-benzamide The title compound 744 was produced in the same manner as in Example 8.
$^1$H-NMR (DMSO-d$_6$, 400 MHz): δ 8.49 (1H, d, J=8.8 Hz), 8.44 (1H, s), 8.09 (1H, d, J=2.2 Hz), 7.88 (2H, d, J=8.0 Hz), 7.78-7.84 (1H, m), 7.47-7.63 (5H, m), 7.25-7.35 (1H, m), 4.27 (1H, t, J=5.1 Hz), 3.52 (2H, s), 3.35-3.46 (2H, m), 2.77 (2H, d, J=11.2 Hz), 1.92 (2H, dd, J=11.0 Hz, J=11.0 Hz), 1.61 (2H, d, J=11.7 Hz), 1.30-1.40 (3H, m), 1.08-1.22 (2H, m)
Mass spectrometric value (ESI-MS) 580 (M−1), 583 (M+1)

Compound 745 N-[4-Bromo-2-(4-chloro-3-trifluoromethyl-benzylidene-hydrazinocarbonyl)-phenyl]-4-[4-(2-hydroxy-ethyl)-piperidin-1-ylmethyl]-benzamide The title compound 745 was produced in the same manner as in Example 8.
$^1$H-NMR (DMSO-d$_6$, 400 MHz): δ 8.49 (1H, s), 8.44 (1H, d, J=8.8 Hz), 8.18 (1H, s), 8.05-8.10 (2H, m), 7.88 (2H, d, J=8.1 Hz), 7.79-7.85 (2H, m), 7.49 (2H, d, J=8.1 Hz), 4.29 (1H, bs), 3.52 (2H, bs), 3.38-3.45 (2H, m), 2.78 (2H, d, J=11.2 Hz), 1.86-2.00 (2H, m), 1.60 (2H, d, J=12.2 Hz), 1.30-1.40 (3H, m), 1.08-1.22 (2H, m)
Mass spectrometric value (ESI-MS) 667 (M+1)

Compound 746 N-[4-Bromo-2-(3-methoxy-benzylidene-hydrazinocarbonyl)-phenyl]-4-[4-(2-hydroxy-ethyl)-piperidin-1-ylmethyl]-benzamide The title compound 746 was produced in the same manner as in Example 8.
$^1$H-NMR (DMSO-d$_6$, 400 MHz): δ 8.48 (1H, d, J=8.8 Hz), 8.42 (1H, s), 8.09 (1H, d, J=2.0 Hz), 7.88 (2H, d, J=8.0 Hz), 7.78-7.83 (1H, m), 7.49 (2H, d, J=9.0 Hz), 7.39 (1H, dd, J=7.8 Hz, J=7.8 Hz), 7.28-7.33 (2H, m), 7.00-7.07 (1H, m), 4.29 (1H, t, J=5.0 Hz), 3.82 (3H, s), 3.52 (2H, bs), 3.37-3.46 (2H, m), 2.77 (2H, d, J=10.8 Hz), 1.86-1.98 (2H, m), 1.60 (2H, d, J=12.2 Hz), 1.30-1.40 (3H, m), 1.08-1.22 (2H, m)
Mass spectrometric value (ESI-MS) 593 (M−1)

Compound 747 N-[4-Bromo-2-(4-chloro-3-trifluoromethyl-benzylidene-hydrazinocarbonyl)-phenyl]-4-[(2-morpholin-4-yl-1-phenyl-ethylamino)-methyl]-benzamide The title compound 747 was produced in the same manner as in Example 8.
$^1$H-NMR (CDCl$_3$, 400 MHz): δ 8.51 (1H, s), 8.33 (1H, d, J=8.0 Hz), 8.06 (1H, s), 7.99 (3H, d, J=7.8 Hz), 7.65 (1H, bs), 7.58 (1H, d, J=8.3 Hz), 7.49 (1H, d, J=7.6 Hz), 7.26-7.43 (7H, m), 3.84 (1H, d, J=14.2 Hz), 3.64-3.78 (6H, m), 3.57 (1H, d, J=14.2 Hz), 2.43-2.60 (3H, m), 2.29-2.40 (3H, m)
Mass spectrometric value (ESI-MS) 742 (M−1)

Compound 748 N-[4-Bromo-2-(4-methoxy-benzylidene-hydrazinocarbonyl)-phenyl]-4-[(2-morpholin-4-yl-1-phenyl-ethylamino)-methyl]-benzamide The title compound 748 was produced in the same manner as in Example 8.

$^1$H-NMR (CDCl$_3$, 400 MHz): δ 8.44 (1H, d, J=8.8 Hz), 8.37 (1H, s), 7.99 (2H, d, J=7.8 Hz), 7.74 (2H, d, J=8.3 Hz), 7.69 (1H, s), 7.50 (1H, d, J=7.8 Hz), 7.34-7.42 (6H, m), 7.26-7.32 (1H, m), 6.91 (2H, d, J=8.8 Hz), 3.80-3.85 (1H, m), 3.82 (3H, s), 3.60-3.76 (5H, m), 3.50-3.57 (1H, m), 2.40-2.60 (3H, m), 2.28-2.34 (3H, m)

Mass spectrometric value (ESI-MS) 668 (M−1)

Compound 749 6-Bromo-2-{4-[(1,2-diethyl-pyrazolidin-4-ylamino)-methyl]-phenyl}-3-[(3,4-dimethyl-benzylidene)-amino]-3H-quinazolin-4-one The title compound 749 was produced in the same manner as in Example 8.

$^1$H-NMR (CDCl$_3$, 400 MHz): δ 8.89 (1H, d, J=8.8 Hz), 8.73 (1H, s), 8.57 (1H, s), 8.03 (2H, d, J=8.0 Hz), 7.40-7.82 (5H, m), 7.10-7.25 (1H, m), 3.91 (2H, s), 3.56-3.70 (1H, m), 3.15-3.27 (2H, m), 2.70-2.85 (6H, m), 2.34 (6H, s), 1.11 (6H, t, J=7.1 Hz)

Mass spectrometric value (ESI-MS) 589 (M+1)

Compound 750 N-[4-Bromo-2-(3,4-dimethyl-benzylidene-hydrazinocarbonyl)-phenyl]-4-[(1,2-diethyl-pyrazolidin-4-ylamino)-methyl]-benzamide The title compound 750 was produced in the same manner as in Example 8.

$^1$H-NMR (CDCl$_3$, 400 MHz): δ 8.42 (1H, d, J=9.0 Hz), 8.38 (1H, s), 7.99 (2H, d, J=8.1 Hz), 7.70 (1H, s), 7.62 (1H, s), 7.40-7.52 (4H, m), 7.15 (1H, d, J=7.8 Hz), 3.83 (2H, s), 3.56 (1H, tt, J=6.5 Hz, J=6.5 Hz), 3.12-3.20 (2H, m), 2.65-2.74 (6H, m), 2.28 (3H, s), 2.26 (3H, s), 1.09 (6H, t, J=7.2 Hz)

Mass spectrometric value (ESI-MS) 605 (M−1)

Compound 751 6-Bromo-2-{4-[(1,2-diethyl-pyrazolidin-4-ylamino)-methyl]-phenyl}-3-[(3-fluoro-benzylidene)-amino]-3H-quinazolin-4-one The title compound 751 was produced in the same manner as in Example 8.

$^1$H-NMR (CDCl$_3$, 400 MHz): δ 8.90 (1H, d, J=8.8 Hz), 8.74 (1H, s), 8.59 (1H, s), 8.02 (2H, d, J=8.3 Hz), 7.42-7.65 (6H, m), 7.21 (1H, ddd, J=1.7 Hz, J=8.3 Hz, J=8.3 Hz), 3.89 (2H, s), 3.62 (1H, tt, J=6.4 Hz, J=6.4 Hz), 3.15-3.23 (2H, m), 2.65-2.80 (6H, m), 1.10 (6H, t, J=7.2 Hz)

Compound 752 N-[4-Bromo-2-(3-fluoro-benzylidene-hydrazinocarbonyl)-phenyl]-4-[(1,2-diethyl-pyrazolidin-4-ylamino)-methyl]-benzamide The title compound 752 was produced in the same manner as in Example 8.

$^1$H-NMR (CDCl$_3$, 400 MHz): δ 8.46 (1H, s), 8.34 (1H, d, J=8.8 Hz), 7.99 (2H, d, J=7.8 Hz), 7.66 (1H, s), 7.34-7.62 (6H, m), 7.11 (1H, ddd, J=2.0 Hz, J=8.3 Hz, J=8.3 Hz), 3.85 (2H, s), 3.57 (1H, tt, J=6.5 Hz, J=6.5 Hz), 3.12-3.20 (2H, m), 2.64-2.74 (6H, m), 1.10 (6H, t, J=7.2 Hz)

Mass spectrometric value (ESI-MS) 595 (M−1)

Compound 753 6-Bromo-3-[(4-chloro-3-trifluoromethyl-benzylidene)-amino]-2-{4-[(1,2-diethyl-pyrazolidin-4-ylamino)-methyl]-phenyl}-3H-quinazolin-4-one The title compound 753 was produced in the same manner as in Example 8.

$^1$H-NMR (CDCl$_3$, 400 MHz): δ 8.88 (1H, d, J=8.8 Hz), 8.75 (1H, s), 8.58 (1H, s), 7.92-8.05 (2H, m), 7.45-7.70 (6H, m), 3.89 (2H, s), 3.54-3.65 (1H, m), 3.12-3.22 (2H, m), 2.65-2.76 (6H, m), 1.10 (6H, t, J=7.2 Hz)

Mass spectrometric value (ESI-MS) 663 (M−1)

Compound 754 N-[4-Bromo-2-(4-chloro-3-trifluoromethyl-benzylidene-hydrazinocarbonyl)-phenyl]-4-[(1,2-diethyl-pyrazolidin-4-ylamino)-methyl]-benzamide The title compound 754 was produced in the same manner as in Example 8.

$^1$H-NMR (CDCl$_3$, 400 MHz): δ 8.51 (1H, s), 8.31 (1H, d, J=8.1 Hz), 8.06 (1H, s), 7.99 (3H, d, J=7.8 Hz), 7.65 (1H, s), 7.58 (1H, d, J=8.3 Hz), 7.47 (3H, d, J=8.3 Hz), 3.86 (2H, s), 3.58 (1H, tt, J=6.3 Hz, J=6.3 Hz), 3.12-3.20 (2H, m), 2.65-2.75 (6H, m), 1.10 (6H, t, J=7.1 Hz)

Mass spectrometric value (ESI-MS) 681 (M+1)

Compound 755 6-Bromo-2-{4-[(1,2-diethyl-pyrazolidin-4-ylamino)-methyl]-phenyl}-3-[(4-methoxy-benzylidene)-amino]-3H-quinazolin-4-one The title compound 755 was produced in the same manner as in Example 8.

$^1$H-NMR (CDCl$_3$, 400 MHz): δ 8.89 (1H, d, J=8.5 Hz), 8.71 (1H, s), 8.58 (1H, s), 8.03 (2H, d, J=8.3 Hz), 7.79 (2H, d, J=8.8 Hz), 7.60 (1H, d, J=2.2 Hz), 7.57 (1H, s), 7.49 (2H, d, J=8.3 Hz), 7.00 (2H, d, J=8.8 Hz), 3.89 (5H, s), 3.62 (1H, tt, J=6.2 Hz, J=6.2 Hz), 3.15-3.25 (2H, m), 2.65-2.80 (6H, m), 1.11 (6H, t, J=7.2 Hz)

Compound 756 N-[4-Bromo-2-(4-methoxy-benzylidene-hydrazinocarbonyl)-phenyl]-4-[(1,2-diethyl-pyrazolidin-4-ylamino)-methyl]-benzamide The title compound 756 was produced in the same manner as in Example 8.

$^1$H-NMR (CDCl$_3$, 400 MHz): δ 8.46 (1H, d, J=8.8 Hz), 8.37 (1H, s), 7.98 (2H, d, J=7.8 Hz), 7.67-7.76 (3H, m), 7.49 (1H, d, J=7.6 Hz), 7.42 (2H, d, J=8.3 Hz), 6.91 (2H, d, J=8.8 Hz), 3.83 (2H, s), 3.82 (3H, s), 3.57 (1H, tt, J=6.3 Hz, J=6.3 Hz), 3.12-3.20 (2H, m), 2.65-2.75 (6H, m), 1.10 (6H, t, J=7.2 Hz)

Mass spectrometric value (ESI-MS) 607 (M−1)

Compound 757 N-[4-Bromo-2-(3,4-dimethyl-benzylidene-hydrazinocarbonyl)-phenyl]-4-{[3-(methyl-phenyl-amino)-propylamino]-methyl}-benzamide The title compound 757 was produced in the same manner as in Example 8.

$^1$H-NMR (CDCl$_3$, 400 MHz): δ 8.35-8.45 (2H, m), 7.96 (2H, d, J=7.8 Hz), 7.71 (1H, s), 7.60 (1H, s), 7.43-7.48 (2H, m), 7.40 (2H, d, J=8.3 Hz), 7.17-7.23 (2H, m), 7.14 (1H, d, J=7.8 Hz), 6.65-6.73 (3H, m), 3.83 (2H, s), 3.38 (2H, t, J=7.2

Hz), 2.89 (3H, s), 2.68 (2H, t, J=7.0 Hz), 2.26 (3H, s), 2.25 (3H, s), 1.81 (2H, tt, J=7.1 Hz, J=7.1 Hz)

Mass spectrometric value (ESI-MS) 626 (M−1), 628 (M+1)

Compound 758 N-[4-Bromo-2-(4-methyl-benzylidene-hydrazinocarbonyl)-phenyl]-4-{[3-(methyl-phenyl-amino)-propylamino]-methyl}-benzamide The title compound 758 was produced in the same manner as in Example 8.

$^1$H-NMR (CDCl$_3$, 400 MHz): δ 8.37-8.44 (2H, m), 7.92-7.79 (2H, m), 7.64-7.72 (3H, m), 7.45 (1H, d, J=8.0 Hz), 7.39 (2H, d, J=8.0 Hz), 7.16-7.23 (4H, m), 6.65-6.74 (3H, m), 3.82 (2H, s), 3.39 (2H, t, J=7.2 Hz), 2.89 (3H, s), 2.67 (2H, t, J=6.8 Hz), 2.34 (3H, s), 1.80 (2H, tt, J=7.0 Hz, J=7.0 Hz)

Mass spectrometric value (ESI-MS) 612 (M−1), 614 (M+1)

Compound 759 N-[4-Bromo-2-(4-fluoro-benzylidene-hydrazinocarbonyl)-phenyl]-4-{[3-(methyl-phenyl-amino)-propylamino]-methyl}-benzamide The title compound 759 was produced in the same manner as in Example 8.

$^1$H-NMR (CDCl$_3$, 400 MHz): δ 8.37-8.46 (2H, m), 7.98 (2H, d, J=7.8 Hz), 7.81 (2H, bs), 7.66 (1H, s), 7.50 (1H, d, J=8.6 Hz), 7.43 (2H, d, J=8.1 Hz), 7.19-7.24 (2H, m), 7.11 (2H, dd, J=8.7 Hz, J=8.7 Hz), 6.66-6.75 (3H, m), 3.84 (2H, s), 3.41 (2H, t, J=7.2 Hz), 2.92 (3H, s), 2.69 (2H, t, J=7.0 Hz), 1.81 (2H, tt, J=7.0 Hz, J=7.0 Hz)

Mass spectrometric value (ESI-MS) 616 (M−1), 618 (M+1)

Compound 760 N-[4-Bromo-2-(3-fluoro-benzylidene-hydrazinocarbonyl)-phenyl]-4-{[3-(methyl-phenyl-amino)-propylamino]-methyl}-benzamide The title compound 760 was produced in the same manner as in Example 8.

$^1$H-NMR (CDCl$_3$, 400 MHz): δ 8.45 (1H, bs), 8.34 (1H, d, J=8.5 Hz), 7.98 (2H, d, J=7.8 Hz), 7.34-7.67 (7H, m), 7.18-7.25 (2H, m), 7.11 (1H, ddd, J=1.7 Hz, J=7.6 Hz, J=7.6 Hz), 6.72 (2H, d, J=7.8 Hz), 6.68 (1H, dd, J=7.2 Hz, J=7.2 Hz), 3.84 (2H, s), 3.41 (2H, t, J=7.2 Hz), 2.91 (3H, s), 2.68 (2H, t, J=7.0 Hz), 1.80 (2H, tt, J=7.0 Hz, J=7.0 Hz)

Mass spectrometric value (ESI-MS) 614 (M−1), 618 (M+1)

Compound 761 N-[4-Bromo-2-(4-chloro-3-trifluoromethyl-benzylidene-hydrazinocarbonyl)-phenyl]-4-{[3-(methyl-phenyl-amino)-propylamino]-methyl}-benzamide The title compound 761 was produced in the same manner as in Example 8.

$^1$H-NMR (CDCl$_3$, 400 MHz): δ 8.50 (1H, s), 8.27 (1H, d, J=8.0 Hz), 8.06 (1H, s), 7.99 (2H, d, J=7.6 Hz), 7.63 (1H, bs), 7.56 (1H, d, J=8.3 Hz), 7.45 (2H, d, J=8.1 Hz), 7.19-7.25 (2H, m), 6.65-6.75 (5H, m), 3.85 (2H, s), 3.41 (2H, t, J=7.1 Hz), 2.92 (3H, s), 2.69 (2H, t, J=7.0 Hz), 1.81 (2H, tt, J=7.0 Hz, J=7.0 Hz)

Mass spectrometric value (ESI-MS) 698, 700 (M−1), 702 (M+1)

Compound 762 N-[4-Bromo-2-(4-methoxy-benzylidene-hydrazinocarbonyl)-phenyl]-4-{[3-(methyl-phenyl-amino)-propylamino]-methyl}-benzamide The title compound 762 was produced in the same manner as in Example 8.

$^1$H-NMR (CDCl$_3$, 400 MHz): δ 8.44 (1H, d, J=8.8 Hz), 8.37 (1H, s), 7.97 (2H, d, J=8.0 Hz), 7.65-7.77 (3H, m), 7.48 (1H, d, J=8.8 Hz), 7.40 (2H, d, J=8.0 Hz), 7.19-7.25 (3H, m), 6.90 (2H, d, J=8.8 Hz), 6.71 (2H, d, J=8.0 Hz), 6.68 (1H, dd, J=7.2 Hz, J=7.2 Hz), 3.81 (2H, s), 3.81 (3H, s), 3.40 (2H, t, J=7.1 Hz), 2.91 (3H, s), 2.67 (2H, t, J=7.0 Hz), 1.79 (2H, tt, J=7.0 Hz, J=7.0 Hz)

Mass spectrometric value (ESI-MS) 626 (M−1), 630 (M+1)

Compound 763 N-[4-Bromo-2-(3-methoxy-benzylidene-hydrazinocarbonyl)-phenyl]-4-{[3-(methyl-phenyl-amino)-propylamino]-methyl}-benzamide The title compound 763 was produced in the same manner as in Example 8.

$^1$H-NMR (CDCl$_3$, 400 MHz): δ 8.44 (1H, d, J=9.0 Hz), 8.40 (1H, s), 7.97 (2H, d, J=7.8 Hz), 7.71 (1H, s), 7.18-7.54 (8H, m), 6.94-7.00 (1H, m), 6.71 (2H, d, J=8.0 Hz), 6.68 (1H, dd, J=7.2 Hz, J=7.2 Hz), 3.84 (3H, s), 3.82 (2H, s), 3.40 (2H, t, J=7.1 Hz), 2.91 (3H, s), 2.67 (2H, t, J=6.8 Hz), 1.80 (2H, tt, J=7.0 Hz, J=7.0 Hz),

Mass spectrometric value (ESI-MS) 626 (M−1), 630 (M+1)

Compound 764 N-[4-Bromo-2-(3,4-dimethyl-benzylidene-hydrazinocarbonyl)-phenyl]-4-[(2-ethylsulfanyl-ethylamino)-methyl]-benzamide The title compound 764 was produced in the same manner as in Example 8.

$^1$H-NMR (CDCl$_3$, 400 MHz): δ 8.37-8.45 (2H, m), 7.98 (2H, d, J=7.8 Hz), 7.72 (1H, s), 7.60 (1H, s), 7.42-7.50 (4H, m), 7.07-7.20 (2H, m), 3.88 (2H, s), 2.83 (2H, t, J=6.2 Hz), 2.73 (2H, t, J=6.6 Hz), 2.51 (2H, q, J=7.3 Hz), 2.26 (3H, s), 2.25 (3H, s), 1.24 (3H, t, J=7.4 Hz)

Mass spectrometric value (ESI-MS) 565 (M−1)

Compound 765 N-[4-Bromo-2-(4-methyl-benzylidene-hydrazinocarbonyl)-phenyl]-4-[(2-ethylsulfanyl-ethylamino)-methyl]-benzamide The title compound 765 was produced in the same manner as in Example 8.

$^1$H-NMR (CDCl$_3$, 400 MHz): δ 8.39-8.45 (2H, m), 7.84-8.02 (2H, m), 7.68 (2H, d, J=8.5 Hz), 7.42-7.50 (3H, m), 7.15-7.25 (3H, m), 3.88 (2H, s), 2.83 (2H, t, J=6.3 Hz), 2.73 (2H, t, J=6.3 Hz), 2.52 (2H, q, J=7.4 Hz), 2.36 (3H, s), 1.25 (3H, t, J=7.4 Hz)

Mass spectrometric value (ESI-MS) 551 (M−1)

Compound 766 N-[4-Bromo-2-(3-methyl-benzylidene-hydrazinocarbonyl)-phenyl]-4-[(2-ethylsulfanyl-ethylamino)-methyl]-benzamide The title compound 766 was produced in the same manner as in Example 8.

$^1$H-NMR (CDCl$_3$, 400 MHz): δ 8.44 (1H, s), 8.37 (1H, d, J=8.8 Hz), 7.99 (2H, d, J=8.1 Hz), 7.68 (2H, s), 7.54 (1H, d, J=7.3 Hz), 7.42-7.50 (3H, m), 7.29 (1H, dd, J=7.6 Hz, J=7.6 Hz), 7.22 (1H, d, J=7.6 Hz), 3.87 (2H, s), 2.81 (2H, t, J=6.5 Hz), 2.72 (2H, t, J=6.2 Hz), 2.53 (2H, q, J=7.4 Hz), 2.37 (3H, s), 1.26 (3H, t, J=7.3 Hz)

Mass spectrometric value (ESI-MS) 551 (M−1)

Compound 767 N-[4-Bromo-2-(4-fluoro-benzylidene-hydrazinocarbonyl)-phenyl]-4-[(2-ethylsulfanyl-ethylamino)-methyl]-benzamide The title compound 767 was produced in the same manner as in Example 8.
$^1$H-NMR (CDCl$_3$, 400 MHz): δ 8.46 (1H, s), 8.33 (1H, d, J=8.3 Hz), 7.98 (2H, d, J=7.8 Hz), 7.80 (2H, bs), 7.65 (1H, s), 7.45 (3H, d, J=8.0 Hz), 7.10 (2H, dd, J=8.5 Hz, J=8.5 Hz), 3.87 (2H, s), 2.82 (2H, t, J=6.3 Hz), 2.72 (2H, t, J=6.5 Hz), 2.53 (2H, q, J=7.4 Hz), 1.26 (3H, t, J=7.3 Hz)
Mass spectrometric value (ESI-MS) 557 (M−1)

Compound 768 N-[4-Bromo-2-(3-fluoro-benzylidene-hydrazinocarbonyl)-phenyl]-4-[(2-ethylsulfanyl-ethylamino)-methyl]-benzamide The title compound 768 was produced in the same manner as in Example 8.
$^1$H-NMR (CDCl$_3$, 400 MHz): δ 8.46 (1H, bs), 8.34 (1H, d, J=7.8 Hz), 7.99 (2H, d, J=7.6 Hz), 7.66 (1H, bs), 7.34-7.60 (6H, m), 7.11 (1H, ddd, J=2.4 Hz, J=8.3 Hz, J=8.3 Hz), 3.89 (2H, s), 2.83 (2H, t, J=6.4 Hz), 2.73 (2H, t, J=6.3 Hz), 2.54 (2H, q, J=7.4 Hz), 1.26 (3H, t, J=7.2 Hz)
Mass spectrometric value (ESI-MS) 555 (M−1)

Compound 769 N-[4-Bromo-2-(4-chloro-3-trifluoromethyl-benzylidene-hydrazinocarbonyl)-phenyl]-4-[(2-ethylsulfanyl-ethylamino)-methyl]-benzamide The title compound 769 was produced in the same manner as in Example 8.
$^1$H-NMR (CDCl$_3$, 400 MHz): δ 8.53 (1H, s), 8.27 (1H, d, J=6.8 Hz), 8.06 (1H, s), 7.99 (3H, d, J=7.8 Hz), 7.63 (1H, bs), 7.57 (1H, d, J=8.3 Hz), 7.40-7.50 (3H, m), 3.90 (2H, s), 2.84 (2H, t, J=6.2 Hz), 2.73 (2H, t, J=6.5 Hz), 2.54 (2H, q, J=7.4 Hz), 1.27 (3H, t, J=7.5 Hz)
Mass spectrometric value (ESI-MS) 643 (M−1)

Compound 770 N-[4-Bromo-2-(4-methoxy-benzylidene-hydrazinocarbonyl)-phenyl]-4-[(2-ethylsulfanyl-ethylamino)-methyl]-benzamide The title compound 770 was produced in the same manner as in Example 8.
$^1$H-NMR (CDCl$_3$, 400 MHz): δ 8.37-8.45 (2H, m), 7.98 (2H, d, J=7.8 Hz), 7.68-7.74 (3H, m), 7.47 (1H, d, J=8.3 Hz), 7.42 (2H, d, J=8.0 Hz), 6.90 (2H, d, J=8.8 Hz), 3.86 (2H, s), 3.81 (3H, s), 2.81 (2H, t, J=6.5 Hz), 2.72 (2H, t, J=6.2 Hz), 2.52 (2H, q, J=7.4 Hz), 1.25 (3H, t, J=7.5 Hz)
Mass spectrometric value (ESI-MS) 569 (M−1)

Compound 771 N-[4-Bromo-2-(3-methoxy-benzylidene-hydrazinocarbonyl)-phenyl]-4-[(2-ethylsulfanyl-ethylamino)-methyl]-benzamide The title compound 771 was produced in the same manner as in Example 8.
$^1$H-NMR (CDCl$_3$, 400 MHz): δ 8.45 (1H, s), 8.39 (1H, d, J=9.0 Hz), 7.97 (2H, d, J=7.8 Hz), 7.73 (1H, bs), 7.40-7.50 (3H, m), 7.34 (1H, s), 7.26-7.30 (2H, m), 6.90-7.00 (1H, m), 3.85 (2H, s), 3.83 (3H, s), 2.81 (2H, t, J=6.4 Hz), 2.71 (2H, t, J=6.2 Hz), 2.53 (2H, q, J=7.4 Hz), 1.25 (3H, t, J=7.4 Hz)
Mass spectrometric value (ESI-MS) 567 (M−1)

Compound 772 N-[4-Bromo-2-(3,4-dimethyl-benzylidene-hydrazinocarbonyl)-phenyl]-4-(4-pyridin-2-yl-piperazin-1-ylmethyl)-benzamide The title compound 772 was produced in substantially the same manner as in Example 8.
$^1$H-NMR (CDCl$_3$, 400 MHz): δ 2.29 (3H, s), 2.30 (3H, s), 2.59 (4H, bs), 3.58 (4H, bs), 3.64 (2H, bs), 6.62 (2H, m), 7.18 (1H, d, J=7.8 Hz), 7.59 (7H, m), 8.00 (2H, d, J=8.1 Hz), 8.18 (1H, m), 8.31 (1H, s), 8.56 (1H, m), 10.08 (1H, bs), 11.68 (1H, s)
Mass spectrometric value (ESI-MS) 623 (M−1)

Compound 773 N-[4-Bromo-2-(4-methyl-benzylidene-hydrazinocarbonyl)-phenyl]-4-(4-pyridin-2-yl-piperazin-1-ylmethyl)-benzamide The title compound 773 was produced in substantially the same manner as in Example 8.
$^1$H-NMR (CDCl$_3$, 400 MHz): δ 2.39 (3H, s), 2.59 (4H, bs), 3.58 (4H, bs), 3.64 (2H, bs), 6.63 (2H, m), 7.23 (2H, d, J=7.8 Hz), 7.59 (7H, m), 8.00 (2H, d, J=7.6 Hz), 8.18 (1H, m), 8.32 (1H, s), 8.60 (1H, d, J=8.8 Hz), 9.90 (1H, bs), 11.70 (1H, bs)
Mass spectrometric value (ESI-MS) 611 (M−1)

Compound 774 N-[4-Bromo-2-(4-fluoro-benzylidene-hydrazinocarbonyl)-phenyl]-4-(4-pyridin-2-yl-piperazin-1-ylmethyl)-benzamide The title compound 774 was produced in substantially the same manner as in Example 8.
$^1$H-NMR (CDCl$_3$, 400 MHz): δ 2.59 (4H, bs), 3.59 (4H, bs), 3.65 (2H, bs), 6.63 (2H, m), 7.12 (2H, m), 7.64 (7H, m), 8.00 (2H, d, J=7.8 Hz), 8.18 (1H, m), 8.37 (1H, bs), 8.60 (1H, m), 10.20 (1H, bs), 11.70 (1H, bs)
Mass spectrometric value (ESI-MS) 613 (M−1)

Compound 775 N-[4-Bromo-2-(3-fluoro-benzylidene-hydrazinocarbonyl)-phenyl]-4-(4-pyridin-2-yl-piperazin-1-ylmethyl)-benzamide The title compound 775 was produced in substantially the same manner as in Example 8.
$^1$H-NMR (CDCl$_3$, 400 MHz): δ 2.59 (4H, bs), 3.58 (4H, bs), 3.65 (2H, bs), 6.63 (2H, m), 7.14 (1H, m), 7.50 (8H, m), 8.00 (2H, d, J=7.8 Hz), 8.18 (1H, m), 8.40 (1H, s), 8.55 (1H, bs), 10.30 (1H, bs), 11.60 (1H, bs)
Mass spectrometric value (ESI-MS) 613 (M−1)

Compound 776 N-[4-Bromo-2-(4-chloro-3-trifluoromethyl-benzylidene-hydrazinocarbonyl)-phenyl]-4-(4-pyridin-2-yl-piperazin-1-ylmethyl)-benzamide The title compound 776 was produced in substantially the same manner as in Example 8.
$^1$H-NMR (CDCl$_3$, 400 MHz): δ 2.60 (4H, bs), 3.58 (4H, bs), 3.65 (2H, bs), 6.63 (2H, m), 7.54 (6H, m), 8.02 (4H, m), 8.18 (1H, m), 8.47 (2H, bs), 10.45 (1H, bs), 11.50 (1H, bs)
Mass spectrometric value (ESI-MS) 697 (M−1)

Compound 777 N-[4-Bromo-2-(4-methoxy-benzylidene-hydrazinocarbonyl)-phenyl]-4-(4-pyridin-2-yl-piperazin-1-ylmethyl)-benzamide The title compound 777 was produced in substantially the same manner as in Example 8.
$^1$H-NMR (CDCl$_3$, 400 MHz): δ 2.59 (4H, bs), 3.61 (6H, m), 3.84 (3H, s), 6.62 (2H, m), 6.93 (2H, d, J=8.8 Hz), 7.49 (4H, m), 7.72 (3H, m), 7.80 (2H, d, J=7.6 Hz), 8.18 (1H, m), 8.31 (1H, bs), 8.58 (1H, m), 9.99 (1H, bs), 11.69 (1H, bs)
Mass spectrometric value (ESI-MS) 625 (M−1)

Compound 778 N-[4-Bromo-2-(3-methoxy-benzylidene-hydrazinocarbonyl)-phenyl]-4-(4-pyridin-2-yl-piperazin-1-ylmethyl)-benzamide The title compound 778 was produced in substantially the same manner as in Example 8.
$^1$H-NMR (CDCl$_3$, 400 MHz): δ 2.59 (4H, bs), 3.59 (6H, m), 3.86 (3H, s), 6.63 (2H, m), 6.98 (1H, m), 7.32 (3H, m), 7.54 (4H, m), 7.72 (1H, m), 8.00 (2H, d, J=7.3 Hz), 8.18 (1H, m), 8.34 (1H, bs), 8.60 (1H, d, J=8.8 Hz)
Mass spectrometric value (ESI-MS) 625 (M−1)

Compound 779 3-{[Bis-(2-hydroxy-propyl)-amino]-methyl}-N-[3-(4-chloro-3-trifluoromethyl-benzylidene-hydrazinocarbonyl)-thiophen-2-yl]-benzamide The title compound 779 was produced in substantially the same manner as in Example 8.
$^1$H-NMR (CD$_3$OD, 400 MHz): δ 1.10 (6H, m), 2.51 (4H, m), 3.88 (4H, m), 7.03 (1H, d, J=6.1 Hz), 7.53 (2H, m), 7.68 (2H, d, J=8.0 Hz), 7.92 (1H, d, J=7.8 Hz), 8.06 (2H, m), 8.32 (1H, bs), 8.39 (1H, s)
Mass spectrometric value (ESI-MS) 595 (M−1)

Compound 780 3-{[Bis-(2-hydroxy-propyl)-amino]-methyl}-N-[3-(4-methoxy-benzylidene-hydrazinocarbonyl)-thiophen-2-yl]-benzamide The title compound 780 was produced in substantially the same manner as in Example 8.
$^1$H-NMR (CD$_3$OD, 400 MHz): δ 1.10 (6H, m), 2.51 (4H, m), 3.88 (7H, m), 7.00 (3H, m), 7.53 (2H, m), 7.68 (1H, m), 7.80 (2H, d, J=8.3 Hz), 7.93 (1H, d, J=7.1 Hz), 8.06 (1H, m), 8.31 (1H, s)
Mass spectrometric value (ESI-MS) 523 (M−1)

Compound 781 2-{3-[3-(3,4-Dimethyl-benzylidene-hydrazinocarbonyl)-4-methyl-thiophen-2-ylcarbamoyl]-benzylsulfanyl}-ethanesulfonic acid The title compound 781 was produced in substantially the same manner as in Example 8.
$^1$H-NMR (CD$_3$OD, 400 MHz): δ 2.30 (6H, m), 2.47 (3H, s), 2.79 (2H, m), 2.98 (2H, m), 3.85 (2H, bs), 6.71 (1H, m), 7.18 (1H, d, J=7.6 Hz), 7.20-8.00 (6H, m), 8.23 (1H, bs)
Mass spectrometric value (ESI-MS) 544 (M−1)

Compound 782 2-{3-[4-Methyl-3-(4-methyl-benzylidene-hydrazinocarbonyl)-thiophen-2-ylcarbamoyl]-benzylsulfanyl}-ethanesulfonic acid The title compound 782 was produced in substantially the same manner as in Example 8.
$^1$H-NMR (CD$_3$OD, 400 MHz): δ 2.39 (3H, s), 2.47 (3H, s), 2.79 (2H, m), 2.99 (2H, m), 3.84 (2H, s), 6.72 (1H, m), 7.20-7.94 (8H, m), 8.26 (1H, bs)
Mass spectrometric value (ESI-MS) 530 (M−1)

Compound 783 2-{3-[3-(4-Fluoro-benzylidene-hydrazinocarbonyl)-4-methyl-thiophen-2-ylcarbamoyl]-benzylsulfanyl}-ethanesulfonic acid The title compound 783 was produced in substantially the same manner as in Example 8.
$^1$H-NMR (CD$_3$OD, 400 MHz): δ 2.47 (3H, bs), 2.80 (2H, m), 2.99 (2H, m), 3.84 (2H, bs), 6.72 (1H, m), 7.14 (2H, m), 7.49 (1H, m), 7.61 (1H, m), 7.92 (4H, m), 8.29 (1H, bs)
Mass spectrometric value (ESI-MS) 534 (M−1)

Compound 784 2-{3-[3-(4-Chloro-3-trifluoromethyl-benzylidene-hydrazinocarbonyl)-4-methyl-thiophen-2-ylcarbamoyl]-benzylsulfanyl}-ethanesulfonic acid The title compound 784 was produced in substantially the same manner as in Example 8.
$^1$H-NMR (CD$_3$OD, 400 MHz): δ 2.47 (3H, bs), 2.79 (2H, m), 2.98 (2H, m), 3.84 (2H, bs), 6.70 (1H, m), 7.40-8.02 (6H, m), 8.31 (2H, m)
Mass spectrometric value (ESI-MS) 618 (M−1)

Compound 785 2-{3-[3-(4-Methoxy-benzylidene-hydrazinocarbonyl)-4-methyl-thiophen-2-ylcarbamoyl]-benzylsulfanyl}-ethanesulfonic acid The title compound 785 was produced in substantially the same manner as in Example 8.
$^1$H-NMR (CD$_3$OD, 400 MHz): δ 2.47 (3H, bs), 2.81 (2H, m), 2.98 (2H, m), 3.84 (5H, m), 6.71 (1H, m), 6.97 (2H, m), 7.44-7.98 (6H, m), 8.24 (1H, bs)
Mass spectrometric value (ESI-MS) 546 (M−1)

Compound 786 3-{[Bis-(2-hydroxy-ethyl)-amino]-methyl}-N-[3-(3,4-dimethyl-benzylidene-hydrazinocarbonyl)-4-methyl-thiophen-2-yl]-benzamide The title compound 786 was produced in substantially the same manner as in Example 8.
$^1$H-NMR (CD$_3$OD, 400 MHz): δ 2.30 (6H, m), 2.50 (3H, s), 2.69 (4H, t, J=5.9 Hz), 3.63 (4H, t, J=5.5 Hz), 3.81 (2H, s), 6.69 (1H, m), 7.19 (1H, m), 7.51 (2H, m), 7.65 (2H, m), 7.87 (1H, m), 7.98 (1H, s), 8.22 (1H, s)
Mass spectrometric value (ESI-MS) 507 (M−1)

Compound 787 3-{[Bis-(2-hydroxy-ethyl)-amino]-methyl}-N-[4-methyl-3-(4-methyl-benzylidene-hydrazinocarbonyl)-thiophen-2-yl]-benzamide The title compound 787 was produced in substantially the same manner as in Example 8.
$^1$H-NMR (CDCl$_3$, 400 MHz): δ 2.38 (3H, s), 2.57 (3H, s), 2.78 (4H, t, J=5.1 Hz), 3.74 (4H, t, J=5.1 Hz), 3.84 (2H, s), 6.50 (1H, s), 7.19 (2H, d, J=8.0 Hz), 7.45 (2H, m), 7.70 (2H, d, J=7.8 Hz), 8.00 (1H, m), 8.08 (1H, s), 8.25 (1H, s), 9.16 (1H, s)
Mass spectrometric value (ESI-MS) 493 (M−1)

Compound 788 3-{[Bis-(2-hydroxy-ethyl)-amino]-methyl}-N-[3-(4-fluoro-benzylidene-hydrazinocarbonyl)-4-methyl-thiophen-2-yl]-benzamide The title compound 788 was produced in substantially the same manner as in Example 8.
$^1$H-NMR (CDCl$_3$, 400 MHz): δ 2.54 (3H, s), 2.79 (4H, t, J=5.2 Hz), 3.74 (4H, t, J=5.1 Hz), 3.83 (2H, s), 6.48 (1H, s), 7.04 (2H, m), 7.45 (2H, m), 7.80 (2H, m), 8.00 (1H, m), 8.13 (1H, s), 8.26 (1H, s), 9.28 (1H, s), 13.16 (1H, bs)
Mass spectrometric value (ESI-MS) 497 (M−1)

Compound 789 3-{[Bis-(2-hydroxy-ethyl)-amino]-methyl}-N-[3-(3-fluoro-benzylidene-hydrazinocarbonyl)-4-methyl-thiophen-2-yl]-benzamide The title compound 789 was produced in substantially the same manner as in Example 8.
$^1$H-NMR (CDCl$_3$, 400 MHz): δ 2.56 (3H, s), 2.79 (4H, t, J=5.0 Hz), 3.75 (4H, m), 3.84 (2H, s), 6.47 (1H, s), 7.04 (1H, m), 7.17-7.70 (5H, m), 8.01 (1H, m), 8.16 (1H, s), 8.29 (1H, s), 9.35 (1H, s), 13.20 (1H, bs)
Mass spectrometric value (ESI-MS) 497 (M−1)

Compound 790 3-{[Bis-(2-hydroxy-ethyl)-amino]-methyl}-N-[3-(4-chloro-3-trifluoromethyl-benzylidene-hydrazinocarbonyl)-4-methyl-thiophen-2-yl]-benzamide The title compound 790 was produced in substantially the same manner as in Example 8.
¹H-NMR (CD₃OD, 400 MHz): δ 2.50 (3H, s), 2.72 (4H, t, J=5.8 Hz), 3.65 (4H, t, J=5.8 Hz), 3.84 (2H, s), 6.71 (1H, d, J=1.0 Hz), 7.51 (1H, m), 7.67 (2H, m), 7.85 (1H, m), 8.00 (2H, m), 8.33 (2H, m)
Mass spectrometric value (ESI-MS) 581 (M−1)

Compound 791 3-{[Bis-(2-hydroxy-ethyl)-amino]-methyl}-N-[3-(4-methoxy-benzylidene-hydrazinocarbonyl)-4-methyl-thiophen-2-yl]-benzamide The title compound 791 was produced in substantially the same manner as in Example 8.
¹H-NMR (CDCl₃, 400 MHz): δ 2.55 (3H, s), 2.79 (4H, t, J=5.2 Hz), 3.74 (4H, m), 3.85 (5H, m), 6.51 (1H, s), 6.92 (2H, m), 7.45 (2H, m), 7.67 (1H, m), 7.77 (1H, m), 8.01 (1H, m), 8.05 (1H, s), 8.26 (1H, s), 9.09 (1H, s), 13.27 (1H, bs)
Mass spectrometric value (ESI-MS) 509 (M−1)

Compound 792 3-{[Bis-(2-hydroxy-propyl)-amino]-methyl}-N-[3-(3,4-dimethyl-benzylidene-hydrazinocarbonyl)-benzo[b]thiophen-2-yl]-benzamide The title compound 792 was produced in substantially the same manner as in Example 8.
¹H-NMR (CDCl₃, 400 MHz): δ 1.13 (3H, d, J=2.2 Hz), 1.15 (3H, d, J=2.2 Hz), 2.26 (6H, m), 2.51 (2H, d, J=6.1 Hz), 2.63 (2H, m), 3.65-4.05 (4H, m), 7.12 (1H, m), 7.30 (1H, m), 7.40-7.51 (4H, m), 7.67 (1H, m), 7.86 (2H, m), 8.03 (1H, m), 8.18 (1H, s), 8.25 (1H, d, J=5.6 Hz), 9.44 (1H, s), 13.13 (1H, m)
Mass spectrometric value (ESI-MS) 571 (M−1)

Compound 793 3-{[Bis-(2-hydroxy-propyl)-amino]-methyl}-N-[3-(4-methyl-benzylidene-hydrazinocarbonyl)-benzo[b]thiophen-2-yl]-benzamide The title compound 793 was produced in substantially the same manner as in Example 8.
¹H-NMR (CDCl₃, 400 MHz): δ 1.13 (6H, m), 2.39 (3H, s), 2.51 (2H, d, J=6.1 Hz), 2.64 (2H, m), 3.65-4.05 (4H, m), 7.19 (2H, d, J=8.0 Hz), 7.32 (1H, m), 7.42-7.50 (3H, m), 7.75 (2H, m), 7.86 (2H, m), 8.04 (1H, m), 8.19 (1H, m), 8.28 (1H, d, J=6.1 Hz), 9.40 (1H, s), 13.14 (1H, bs)
Mass spectrometric value (ESI-MS) 557 (M−1)

Compound 794 3-{[Bis-(2-hydroxy-propyl)-amino]-methyl}-N-[3-(4-fluoro-benzylidene-hydrazinocarbonyl)-benzo[b]thiophen-2-yl]-benzamide The title compound 794 was produced in substantially the same manner as in Example 8.
¹H-NMR (CDCl₃, 400 MHz): δ 1.13 (6H, m), 2.51 (2H, d, J=6.1 Hz), 2.65 (2H, m), 3.63-4.08 (4H, m), 7.07 (2H, m), 7.29 (1H, m), 7.36-7.50 (3H, m), 7.85 (4H, m), 8.03 (1H, m), 8.26 (2H, m), 9.50 (1H, d, J=4.4 Hz), 13.13 (1H, bs)
Mass spectrometric value (ESI-MS) 561 (M−1)

Compound 795 3-{[Bis-(2-hydroxy-propyl)-amino]-methyl}-N-[3-(3-fluoro-benzylidene-hydrazinocarbonyl)-benzo[b]thiophen-2-yl]-benzamide The title compound 795 was produced in substantially the same manner as in Example 8.
¹H-NMR (CDCl₃, 400 MHz): δ 1.15 (6H, m), 2.53 (2H, m), 2.67 (2H, m), 3.61-4.14 (4H, m), 7.01 (1H, m), 7.11-7.30 (3H, m), 7.45 (3H, m), 7.62-7.90 (3H, m), 7.99 (1H, m), 8.23 (1H, d, J=12.7 Hz), 8.35 (1H, d, J=6.1 Hz), 9.82 (1H, d, J=13.9 Hz), 13.10 (1H, s)
Mass spectrometric value (ESI-MS) 561 (M−1)

Compound 796 3-{[Bis-(2-hydroxy-propyl)-amino]-methyl}-N-[3-(4-chloro-3-trifluoromethyl-benzylidene-hydrazinocarbonyl)-benzo[b]thiophen-2-yl]-benzamide The title compound 796 was produced in substantially the same manner as in Example 8.
¹H-NMR (CDCl₃, 400 MHz): δ 1.14 (3H, d, J=6.1 Hz), 1.17 (3H, d, J=6.1 Hz), 2.50-2.80 (4H, m), 3.63-4.16 (4H, m), 7.06 (2H, m), 7.30 (1H, m), 7.44 (2H, m), 7.70 (1H, m), 7.80-8.07 (4H, m), 8.16 (1H, s), 8.53 (1H, s), 10.08 (1H, d, J=6.1 Hz), 13.10 (1H, d, J=1.0 Hz)
Mass spectrometric value (ESI-MS) 645 (M−1)

Compound 797 3-{[Bis-(2-hydroxy-propyl)-amino]-methyl}-N-[3-(4-methoxy-benzylidene-hydrazinocarbonyl)-benzo[b]thiophen-2-yl]-benzamide The title compound 797 was produced in substantially the same manner as in Example 8.
¹H-NMR (CDCl₃, 400 MHz): δ 1.13 (6H, m), 2.51 (2H, d, J=6.1 Hz), 2.63 (2H, m), 3.64-4.06 (7H, m), 6.90 (2H, d, J=8.8 Hz), 7.31 (1H, m), 7.48 (3H, m), 7.83 (4H, m), 8.03 (1H, m), 8.18 (1H, m), 8.28 (1H, d, J=6.4 Hz), 9.38 (1H, s), 13.16 (1H, bs)
Mass spectrometric value (ESI-MS) 573 (M−1)

Compound 798 N-[3-(3,4-Dimethyl-benzylidene-hydrazinocarbonyl)-benzo[b]thiophen-2-yl]-3-(4-hydroxymethyl-piperidin-1-ylmethyl)-benzamide The title compound 798 was produced in substantially the same manner as in Example 8.
¹H-NMR (CDCl₃, 400 MHz): δ 1.35 (2H, m), 1.51 (1H, m), 1.72 (2H, m), 2.05 (2H, m), 2.29 (3H, s), 2.30 (3H, s), 2.93 (2H, m), 3.50 (2H, d, J=6.1 Hz), 3.62 (2H, s), 7.18 (1H, d, J=7.8 Hz), 7.32 (1H, m), 7.47 (3H, m), 7.61 (1H, d, J=7.6 Hz), 7.66 (1H, s), 7.87 (2H, m), 7.97 (1H, m), 8.04 (1H, m), 8.17 (1H, m), 9.34 (1H, bs), 12.85 (1H, bs)
Mass spectrometric value (ESI-MS) 553 (M−1)

Compound 799 3-(4-Hydroxymethyl-piperidin-1-ylmethyl)-N-[3-(4-methyl-benzylidene-hydrazinocarbonyl)-benzo[b]thiophen-2-yl]-benzamide The title compound 799 was produced in substantially the same manner as in Example 8.
¹H-NMR (CDCl₃, 400 MHz): δ 1.42 (2H, m), 1.52 (1H, m), 1.73 (2H, m), 2.12 (2H, m), 2.38 (3H, s), 3.00 (2H, m), 3.50 (2H, d, J=6.1 Hz), 3.70 (2H, s), 7.23 (2H, m), 7.32 (1H, m), 7.45 (2H, m), 7.64 (1H, d, J=7.8 Hz), 7.71 (2H, m), 8.86 (2H, m), 7.97 (1H, d, J=8.0 Hz), 8.03 (1H, m), 8.21 (1H, s), 9.40 (1H, bs), 12.84 (1H, bs)
Mass spectrometric value (ESI-MS) 539 (M−1)

Compound 800 N-[3-(4-Fluoro-benzylidene-hydrazinocarbonyl)-benzo[b]thiophen-2-yl]-3-(4-hydroxymethyl-piperidin-1-ylmethyl)-benzamide The title compound 800 was produced in substantially the same manner as in Example 8.
¹H-NMR (CDCl₃, 400 MHz): δ 1.40-1.60 (3H, m), 1.73 (2H, m), 2.17 (2H, m), 3.05 (2H, m), 3.50 (2H, d, J=5.9 Hz), 3.75 (2H, s), 7.04 (1H, m), 7.11 (2H, m), 7.28 (1H, m), 7.37-7.50 (2H, m), 7.64 (1H, d, J=7.6 Hz), 7.83 (2H, m), 7.94 (1H, m), 8.01 (1H, s), 8.07 (1H, m), 8.26 (1H, s), 9.50 (1H, bs), 12.73 (1H, bs)
Mass spectrometric value (ESI-MS) 543 (M−1)

Compound 801 N-[3-(3-Fluoro-benzylidene-hydrazinocarbonyl)-benzo[b]thiophen-2-yl]-3-(4-hydroxymethyl-piperidin-1-ylmethyl)-benzamide The title compound 801 was produced in substantially the same manner as in Example 8.

$^1$H-NMR (CDCl$_3$, 400 MHz): δ 1.40 (2H, m), 1.53 (1H, m), 1.72 (2H, m), 2.09 (2H, m), 2.96 (2H, m), 3.50 (2H, d, J=6.1 Hz), 3.66 (2H, s), 7.13 (1H, m), 7.31 (1H, dd, J=7.6 Hz, J=7.6 Hz), 7.35-7.66 (6H, m), 7.85 (2H, m), 7.94 (1H, d, J=7.8 Hz), 8.02 (1H, s), 8.23 (1H, s), 9.52 (1H, bs), 12.73 (1H, bs)

Mass spectrometric value (ESI-MS) 543 (M−1)

Compound 802 N-[3-(4-Chloro-3-trifluoromethyl-benzylidene-hydrazinocarbonyl)-benzo[b]thiophen-2-yl]-3-(4-hydroxymethyl-piperidin-1-ylmethyl)-benzamide The title compound 802 was produced in substantially the same manner as in Example 8.

$^1$H-NMR (CDCl$_3$, 400 MHz): δ 1.40 (2H, m), 1.15 (1H, m), 1.72 (2H, m), 2.09 (2H, m), 2.95 (2H, m), 3.50 (2H, d, J=6.1 Hz), 3.65 (2H, s), 7.27 (1H, m), 7.40 (1H, dd, J=7.6 Hz, J=7.6 Hz), 7.47 (1H, dd, J=7.6 Hz, J=7.6 Hz), 7.55 (1H, d, J=8.0 Hz), 7.60 (1H, d, J=7.6 Hz), 7.82 (2H, m), 7.90 (1H, m), 7.95 (1H, d, J=8.0 Hz), 8.00 (1H, s), 8.06 (1H, s), 8.35 (1H, s), 9.69 (1H, bs), 12.63 (1H, bs)

Mass spectrometric value (ESI-MS) 627 (M−1)

Compound 803 3-(4-Hydroxymethyl-piperidin-1-ylmethyl)-N-[3-(4-methoxy-benzylidene-hydrazinocarbonyl)-benzo[b]thiophen-2-yl]-benzamide The title compound 803 was produced in substantially the same manner as in Example 8.

$^1$H-NMR (CDCl$_3$, 400 MHz): δ 1.39 (2H, m), 1.52 (1H, m), 1.71 (2H, m), 2.07 (2H, m), 2.95 (2H, m), 3.49 (2H, d, J=6.1 Hz), 3.64 (2H, s), 3.83 (3H, s), 6.93 (2H, d, J=8.8 Hz), 7.29 (1H, m), 7.38-7.48 (2H, m), 7.60 (1H, d, J=7.6 Hz), 7.75 (1H, m), 7.84 (2H, dd, J=8.7 Hz, J=8.7 Hz), 7.95 (2H, m), 8.01 (1H, s), 8.20 (1H, s), 9.42 (1H, bs), 12.81 (1H, bs)

Mass spectrometric value (ESI-MS) 555 (M−1)

Example A

Compound 804 3-{[Bis-(2-hydroxy-propyl)-amino]-methyl}-N-[3-(3,4-dimethyl-benzylidene-hydrazinocarbonyl)-5,6-dihydro-4H-cyclopenta[b]thiophen-2-yl]-benzamide Ethyl-2-aminocyclopenta(B)thiophene-3-carboxylate (compound A) (1.0 g) was dissolved in anhydrous methylene chloride (20.0 ml). Subsequently, pyridine (760 μl) and 3-(chloromethyl)benzoyl chloride (compound B) (880 μl) were added to the solution at 0° C., and the mixture was stirred at 0° C. for one hr. After the completion of the reaction, distilled water was added thereto, and the mixture was subjected to separatory extraction with chloroform. The organic layer was washed with saturated brine, was dried over sodium sulfate, and was then concentrated to give 2-(3-chloromethyl-benzoylamino)-5,6-dihydro-4H-cyclopenta[b]thiophene-3-carboxylic acid ethyl ester as a useful intermediate (800 mg, crude yield 100%).

2-(3-Chloromethyl-benzoylamino)-5,6-dihydro-4H-cyclopenta[b]-thiophene-3-carboxylic acid ethyl ester (800 mg) produced by the above reaction was dissolved in anhydrous methylene chloride (10.0 ml). Triethylamine (420 μl) and diisopropanolamine (compound B') (585 mg) were added to the solution at room temperature, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 2-(3-{[bis-(2-hydroxy-propyl)-amino]-methyl}-benzoylamino)-5,6-dihydro-4H-cyclopenta[b]thiophene-3-carboxylic acid ethyl ester as a useful intermediate (616 mg, yield 61%).

2-(3-{[Bis-(2-hydroxy-propyl)-amino]-methyl}-benzoylamino)-5,6-dihydro-4H-cyclopenta[b]thiophene-3-carboxylic acid ethyl ester (616 mg) produced by the above reaction was dissolved in ethanol (10.0 ml). Hydrazine monohydrate (700 μl) was added to the solution, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 3-{[bis-(2-hydroxy-propyl)-amino]-methyl}-N-(3-hydrazinocarbonyl-5,6-dihydro-4H-cyclopenta[b]thiophen-2-yl)-benzamide as a hydrazine compound (372 mg, yield 60%).

3-{[Bis-(2-hydroxy-propyl)-amino]-methyl}-N-(3-hydrazino-carbonyl-5,6-dihydro-4H-cyclopenta[b]thiophen-2-yl)benzamide (60.0 mg) produced by the above reaction was dissolved in anhydrous toluene (1.0 ml). 3,4-Dimethylbenzaldehyde (compound C) (70.0 μl) was added to the solution at room temperature, and the mixture was heated under reflux with stirring for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give the title compound 804 (70.0 mg, yield 100%).

$^1$H-NMR (CDCl$_3$, 400 MHz): δ 1.13 (6H, m), 2.28 (6H, m), 2.46-2.66 (6H, m), 2.92 (2H, m), 3.05 (2H, m), 3.58-4.05 (4H, m), 7.12 (1H, m), 7.46 (3H, m), 7.64 (1H, d, J=5.1 Hz), 8.00 (2H, m), 8.22 (1H, m), 8.95 (1H, s), 13.16 (1H, m)

Mass spectrometric value (ESI-MS) 561 (M−1)

Compound 805 3-{[Bis-(2-hydroxy-propyl)-amino]-methyl}-N-[3-(4-methyl-benzylidene-hydrazinocarbonyl)-5,6-dihydro-4H-cyclopenta[b]-thiophen-2-yl]-benzamide The title compound 805 was produced in substantially the same manner as in Example A.

$^1$H-NMR (CDCl$_3$, 400 MHz): δ 1.13 (6H, m), 2.36 (3H, m), 2.49 (4H, m), 2.62 (2H, m), 2.89 (2H, m), 3.02 (2H, m), 3.60-4.06 (4H, m), 7.13 (2H, m), 7.44 (2H, m), 7.67 (2H, dd, J=8.2 Hz, J=2.6 Hz), 8.01 (2H, m), 8.23 (1H, m), 8.97 (1H, s), 13.16 (1H, m)

Mass spectrometric value (ESI-MS) 547 (M−1)

Compound 806 3-{[Bis-(2-hydroxy-propyl)-amino]-methyl}-N-[3-(3-fluoro-benzylidene-hydrazinocarbonyl)-5,6-dihydro-4H-cyclopenta[b]thiophen-2-yl]-benzamide The title compound 806 was produced in substantially the same manner as in Example A.

$^1$H-NMR (CDCl$_3$, 400 MHz): δ 1.14 (6H, m), 2.50 (4H, m), 2.65 (2H, m), 2.89 (2H, m), 3.03 (2H, m), 3.68-4.10 (4H, m), 7.02 (1H, m), 7.27 (1H, m), 7.45 (3H, m), 7.67 (1H, m), 8.03 (1H, m), 8.15 (1H, d, J=2.7 Hz), 8.29 (1H, d, J=10.0 Hz), 9.11 (1H, s), 13.17 (1H, m)

Mass spectrometric value (ESI-MS) 551 (M−1)

Compound 807 3-{[Bis-(2-hydroxy-propyl)-amino]-methyl}-N-[3-(4-fluoro-benzylidene-hydrazinocarbonyl)-5,6-dihydro-4H-cyclopenta[b]thiophen-2-yl]-benzamide The title compound 807 was produced in substantially the same manner as in Example A.
$^1$H-NMR (CDCl$_3$, 400 MHz): δ 1.12 (6H, m), 2.49 (4H, m), 2.64 (2H, m), 2.88 (2H, m), 3.02 (2H, m), 3.02-4.06 (4H, m), 7.01 (2H, m), 7.45 (2H, m), 7.79 (2H, m), 8.02 (1H, m), 8.10 (1H, s), 8.27 (1H, d, J=5.9 Hz), 9.04 (1H, s), 13.18 (1H, m)
Mass spectrometric value (ESI-MS) 551 (M−1)

Compound 808 3-{[Bis-(2-hydroxy-propyl)-amino]-methyl}-N-[3-(4-chloro-3-trifluoromethyl-benzylidene-hydrazinocarbonyl)-5,6-dihydro-4H-cyclopenta[b]thiophen-2-yl]-benzamide The title compound 808 was produced in substantially the same manner as in Example A.
$^1$H-NMR (CDCl$_3$, 400 MHz): δ 1.12 (6H, m), 2.25-3.07 (10H, m), 3.58-4.10 (4H, m), 7.31 (1H, m), 7.46 (2H, m), 7.86 (1H, m), 7.98 (1H, s), 8.05 (1H, m), 8.33 (2H, m), 9.28 (1H, m), 13.18 (1H, m)
Mass spectrometric value (ESI-MS) 635 (M−1)

Compound 809 3-{[Bis-(2-hydroxy-propyl)-amino]-methyl}-N-[3-(4-methoxy-benzylidene-hydrazinocarbonyl)-5,6-dihydro-4H-cyclopenta[b]thiophen-2-yl]-benzamide The title compound 809 was produced in substantially the same manner as in Example A.
$^1$H-NMR (CDCl$_3$, 400 MHz): δ 1.13 (6H, m), 2.35-2.65 (6H, m), 2.91 (2H, m), 3.04 (2H, m), 3.59-4.04 (7H, m), 6.88 (2H, d, J=8.8 Hz), 7.46 (2H, m), 7.76 (2H, dd, J=9.1 Hz, J=2.1 Hz), 8.02 (2H, m), 8.24 (1H, m), 8.92 (1H, s), 13.20 (1H, m)
Mass spectrometric value (ESI-MS) 563 (M−1)

Example B

Compound 810 3-[(2-Diethylamino-ethylamino)-methyl]-N-[3-(3,4-dimethyl-benzylidene-hydrazinocarbonyl)-5,6-dihydro-4H-cyclopenta[b]-thiophen-2-yl]-benzamide Ethyl-2-aminocyclopenta(B)thiophene-3-carboxylate (compound A) (1.0 g) was dissolved in anhydrous methylene chloride (20.0 ml). Subsequently, pyridine (760 μl) and 3-(chloromethyl)benzoyl chloride (compound B) (880 μl) were added to the solution at 0° C., and the mixture was stirred at 0° C. for one hr. After the completion of the reaction, distilled water was added thereto, and the mixture was subjected to separatory extraction with chloroform. The organic layer was washed with saturated brine, was dried over sodium sulfate, and was then concentrated to give 2-(3-chloromethyl-benzoylamino)-5,6-dihydro-4H-cyclopenta[b]thiophene-3-carboxylic acid ethyl ester as a useful intermediate (800 mg, crude yield 100%).
2-(3-Chloromethyl-benzoylamino)-5,6-dihydro-4H-cyclopenta[b]-thiophene-3-carboxylic acid ethyl ester (800 mg) produced by the above reaction was dissolved in anhydrous methylene chloride (10.0 ml). Triethylamine (420 μl) and N,N-diethylethylenediamine (compound B') (510 mg) were added to the solution at room temperature, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 2-{3-[(2-diethylamino-ethylamino)-methyl]-benzoylamino}-5,6-dihydro-4H-cyclopenta[b]thiophene-3-carboxylic acid ethyl ester as a useful intermediate (671 mg, yield 68%).
2-{3-[(2-Diethylamino-ethylamino)-methyl]-benzoylamino}-5,6-dihydro-4H-cyclopenta[b]thiophene-3-carboxylic acid ethyl ester (671 mg) produced by the above reaction was dissolved in ethanol (10.0 ml), hydrazine monohydrate (700 μl) was added to the solution, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 3-[(2-diethylamino-ethylamino)-methyl-N-(3-hydrazinocarbonyl-5,6-dihydro-4H-cyclopenta[b]thiophen-2-yl)-benzamide (438 mg, yield 65%) as a hydrazine compound.
The hydrazine compound 3-[(2-diethylamino-ethylamino)-methyl-N-(3-hydrazinocarbonyl-5,6-dihydro-4H-cyclopenta[b]thiophen-2-yl)-benzamide (50 mg) produced by the above reaction was dissolved in anhydrous toluene (1.0 ml). 3,4-Dimethylbenzaldehyde (compound C) (70.0 μl) was added to the solution at room temperature, and the mixture was stirred at room temperature for 15 hr. After the completion of the reaction, the reaction product was purified by column chromatography eluted with a chloroform-methanol system to give the title compound 810 (43.0 mg, yield 66%).
$^1$H-NMR (CDCl$_3$, 400 MHz): δ 1.04 (6H, t, J=7.1 Hz), 2.28 (6H, s), 2.47-2.67 (8H, m), 2.74 (2H, m), 2.90 (2H, m), 3.05 (2H, m), 3.90 (2H, s), 7.14 (1H, d, J=7.8 Hz), 7.43 (2H, m), 7.57 (1H, d, J=7.8 Hz), 7.61 (1H, s), 7.94 (1H, d, J=7.8 Hz), 7.99 (2H, s), 8.96 (1H, bs), 12.95 (1H, bs)
Mass spectrometric value (ESI-MS) 544 (M−1)

Compound 811 3-[(2-Diethylamino-ethylamino)-methyl]-N-[3-(4-methyl-benzylidene-hydrazinocarbonyl)-5,6-dihydro-4H-cyclopenta[b]thiophen-2-yl]-benzamide The title compound 811 was produced in substantially the same manner as in Example B.
$^1$H-NMR (CDCl$_3$, 400 MHz): δ 1.06 (6H, t, J=7.1 Hz), 2.38 (3H, s), 2.51-2.80 (10H, m), 2.93 (2H, m), 3.06 (2H, m), 3.91 (2H, s), 7.21 (2H, d, J=8.0 Hz), 7.45 (1H, dd, J=7.7 Hz, J=7.7 Hz), 7.58 (1H, d, J=7.6 Hz), 7.67 (2H, d, J=7.8 Hz), 7.95 (1H, d, J=7.8 Hz), 8.00 (1H, s), 8.04 (1H, s), 8.98 (1H, bs), 12.95 (1H, bs)
Mass spectrometric value (ESI-MS) 530 (M−1)

Compound 812 3-[(2-Diethylamino-ethylamino)-methyl]-N-[3-(3-fluoro-benzylidene-hydrazinocarbonyl)-5,6-dihydro-4H-cyclopenta[b]thiophen-2-yl]-benzamide The title compound 812 was produced in substantially the same manner as in Example B.
$^1$H-NMR (CDCl$_3$, 400 MHz): δ 1.07 (6H, t, J=7.2 Hz), 2.51 (2H, m), 2.66 (4H, m), 2.73 (2H, m), 2.78 (2H, m), 2.89 (2H, m), 3.04 (2H, m), 3.90 (2H, s), 7.09 (1H, m), 7.35 (1H, m), 7.40-7.60 (4H, m), 7.92 (1H, d, J=7.8 Hz), 7.98 (1H, s), 8.09 (1H, s), 9.09 (1H, bs), 12.83 (1H, bs)

Mass spectrometric value (ESI-MS) 534 (M−1)

Compound 813 3-[(2-Diethylamino-ethylamino)-methyl]-N-[3-(4-fluoro-benzylidene-hydrazinocarbonyl)-5,6-dihydro-4H-cyclopenta[b]thiophen-2-yl]-benzamide The title compound 813 was produced in substantially the same manner as in Example B.

$^1$H-NMR (CDCl$_3$, 400 MHz): δ 1.05 (6H, t, J=7.1 Hz), 2.49-2.70 (8H, m), 2.75 (2H, m), 2.91 (2H, t, J=7.3 Hz), 3.05 (2H, t, J=7.0 Hz), 3.90 (2H, s), 7.09 (2H, dd, J=8.6 Hz, J=8.6 Hz), 7.44 (1H, dd, J=7.7 Hz, J=7.7 Hz), 7.57 (1H, d, J=7.6 Hz), 7.76 (2H, m), 7.93 (1H, d, J=7.8 Hz), 7.99 (1H, s), 8.08 (1H, s), 9.02 (1H, bs), 12.88 (1H, bs)

Mass spectrometric value (ESI-MS) 534 (M−1)

Compound 814 N-[3-(4-Chloro-3-trifluoromethyl-benzylidene-hydrazinocarbonyl)-5,6-dihydro-4H-cyclopenta[b]thiophen-2-yl]-3-[(2-diethylamino-ethylamino)-methyl]-benzamide The title compound 814 was produced in substantially the same manner as in Example B.

$^1$H-NMR (CDCl$_3$, 400 MHz): δ 1.03 (6H, t, J=7.2 Hz), 2.46-2.65 (8H, m), 2.71 (2H, m), 2.88 (2H, t, J=7.1 Hz), 3.03 (2H, t, J=6.8 Hz), 3.88 (2H, s), 7.45 (1H, dd, J=7.7 Hz, J=7.7 Hz), 7.54 (2H, m), 7.90 (2H, m), 7.98 (2H, m), 8.17 (1H, s), 9.13 (1H, bs), 12.78 (1H, bs)

Mass spectrometric value (ESI-MS) 618 (M−1)

Compound 815 3-[(2-Diethylamino-ethylamino)-methyl]-N-[3-(4-methoxy-benzylidene-hydrazinocarbonyl)-5,6-dihydro-4H-cyclopenta[b]thiophen-2-yl]-benzamide The title compound 815 was produced in substantially the same manner as in Example B.

$^1$H-NMR (CDCl$_3$, 400 MHz): δ 1.03 (6H, t, J=7.1 Hz), 2.45-2.65 (8H, m), 2.71 (2H, m), 2.89 (2H, t, J=7.2 Hz), 3.03 (2H, t, J=7.1 Hz), 3.83 (3H, s), 3.89 (2H, s), 6.89 (2H, d, J=8.8 Hz), 7.44 (1H, dd, J=7.7 Hz, J=7.7 Hz), 7.56 (1H, d, J=7.6 Hz), 7.69 (2H, d, J=8.8 Hz), 7.93 (1H, d, J=8.1 Hz), 7.99 (2H, m), 8.93 (1H, bs), 12.94 (1H, bs)

Mass spectrometric value (ESI-MS) 546 (M−1)

Compound 816 N-[3-(3,4-Dimethyl-benzylidene-hydrazinocarbonyl)-5,6-dihydro-4H-cyclopenta[b]thiophen-2-yl]-3-(4-hydroxymethyl-piperidin-1-ylmethyl)-benzamide The title compound 816 was produced in substantially the same manner as in Example A.

$^1$H-NMR (CDCl$_3$, 400 MHz): δ 1.38 (2H, m), 1.50 (1H, m), 1.73 (2H, d, J=12.0 Hz), 2.07 (2H, m), 2.30 (6H, s), 2.56 (2H, m), 2.94 (4H, m), 3.07 (2H, m), 3.50 (2H, d, J=6.1 Hz), 3.65 (2H, s), 7.17 (1H, d, J=7.8 Hz), 7.46 (2H, m), 7.60 (1H, d, J=7.8 Hz), 7.64 (1H, s), 7.97 (1H, d, J=7.6 Hz), 8.01 (2H, m), 8.96 (1H, s), 12.97 (1H, s)

Mass spectrometric value (ESI-MS) 543 (M−1)

Compound 817 3-(4-Hydroxymethyl-piperidin-1-ylmethyl)-N-[3-(4-methyl-benzylidene-hydrazinocarbonyl)-5,6-dihydro-4H-cyclopenta[b]thiophen-2-yl]-benzamide The title compound 817 was produced in substantially the same manner as in Example A.

$^1$H-NMR (CDCl$_3$, 400 MHz): δ 1.39 (2H, m), 1.52 (1H, m), 1.72 (2H, d, J=11.5 Hz), 2.11 (2H, m), 2.39 (3H, s), 2.55 (2H, m), 2.90-3.02 (4H, m), 3.07 (2H, t, J=7.1 Hz), 3.49 (2H, d, J=6.1 Hz), 3.69 (2H, s), 7.21 (2H, d, J=8.1 Hz), 7.45 (1H, dd, J=7.5 Hz, J=7.5 Hz), 7.61 (1H, d, J=7.6 Hz), 7.67 (2H, d, J=8.0 Hz), 7.94-8.02 (2H, m), 8.05 (1H, s), 8.97 (1H, s), 12.95 (1H, s)

Mass spectrometric value (ESI-MS) 529 (M−1)

Compound 818 N-[3-(4-Fluoro-benzylidene-hydrazinocarbonyl)-5,6-dihydro-4H-cyclopenta[b]thiophen-2-yl]-3-(4-hydroxymethyl-piperidin-1-ylmethyl)-benzamide The title compound 818 was produced in substantially the same manner as in Example A.

$^1$H-NMR (CDCl$_3$, 400 MHz): δ 1.35 (2H, m), 1.45-1.75 (3H, m), 2.03 (2H, m), 2.57 (2H, m), 2.94 (4H, m), 3.08 (2H, d, J=7.1 Hz), 3.50 (2H, d, J=6.1 Hz), 3.60 (2H, s), 7.12 (2H, dd, J=8.6 Hz, J=8.6 Hz), 7.45 (1H, dd, J=7.7 Hz, J=7.7 Hz), 7.58 (1H, d, J=7.6 Hz), 7.80 (2H, m), 7.95 (1H, d, J=7.8 Hz), 8.01 (1H, s), 8.09 (1H, s), 8.99 (1H, s), 12.90 (1H, s)

Mass spectrometric value (ESI-MS) 533 (M−1)

Compound 819 N-[3-(3-Fluoro-benzylidene-hydrazinocarbonyl)-5,6-dihydro-4H-cyclopenta[b]thiophen-2-yl]-3-(4-hydroxymethyl-piperidin-1-ylmethyl)-benzamide The title compound 819 was produced in substantially the same manner as in Example A.

$^1$H-NMR (CDCl$_3$, 400 MHz): δ 1.36-1.62 (3H, m), 1.74 (2H, m), 2.14 (2H, m), 2.56 (2H, m), 2.90-3.14 (6H, m), 3.50 (2H, d, J=6.1 Hz), 3.72 (2H, s), 7.11 (1H, m), 7.38 (1H, m), 7.44-7.59 (3H, m), 7.62 (1H, m), 7.90-8.03 (2H, m), 8.10 (1H, s), 9.06 (1H, s), 12.88 (1H, s)

Mass spectrometric value (ESI-MS) 533 (M−1)

Compound 820 N-[3-(4-Chloro-3-trifluoromethyl-benzylidene-hydrazinocarbonyl)-5,6-dihydro-4H-cyclopenta[b]thiophen-2-yl]-3-(4-hydroxymethyl-piperidin-1-ylmethyl)-benzamide The title compound 820 was produced in substantially the same manner as in Example A.

$^1$H-NMR (CDCl$_3$, 400 MHz): δ 1.30-1.77 (5H, m), 2.03 (2H, m), 2.58 (2H, m), 2.93 (4H, m), 3.08 (2H, d, J=7.1 Hz), 3.50 (2H, d, J=6.3 Hz), 3.60 (2H, s), 7.46 (1H, dd, J=7.6 Hz, J=7.6 Hz), 7.58 (2H, m), 7.90-8.06 (4H, m), 8.19 (1H, s), 9.09 (1H, s), 12.81 (1H, s)

Mass spectrometric value (ESI-MS) 617 (M−1)

Compound 821 3-(4-Hydroxymethyl-piperidin-1-ylmethyl)-N-[3-(4-methoxy-benzylidene-hydrazinocarbonyl)-5,6-dihydro-4H-cyclopenta[b]thiophen-2-yl]-benzamide The title compound 821 was produced in substantially the same manner as in Example A.

$^1$H-NMR (CDCl$_3$, 400 MHz): δ 1.34 (2H, m), 1.50 (1H, m), 1.70 (2H, m), 2.02 (2H, m), 2.54 (2H, m), 2.91 (4H, m), 3.59 (2H, m), 3.49 (2H, d, J=6.3 Hz), 3.58 (2H, s), 3.85 (3H, s), 6.92 (2H, m), 7.44 (1H, dd, J=7.7 Hz, J=7.7 Hz), 7.57 (1H, d, J=7.6 Hz), 7.72 (2H, m), 7.94 (1H, d, J=7.8 Hz), 8.01 (2H, m), 8.92 (1H, s), 12.96 (1H, s)

Mass spectrometric value (ESI-MS) 545 (M−1)

Compound 822 3-Dimethylaminomethyl-N-[3-(3,4-dimethyl-benzylidene-hydrazinocarbonyl)-4-methyl-thiophen-2-yl]-benzamide The title compound 822 was produced in substantially the same manner as in Example A.

$^1$H-NMR (CDCl$_3$, 400 MHz): δ 2.26 (6H, s), 2.29 (6H, s), 2.58 (3H, s), 3.53 (2H, s), 6.51 (1H, d, J=1.0 Hz), 7.17 (1H, d, J=7.8 Hz), 7.46 (2H, m), 7.57 (1H, d, J=7.6 Hz), 7.64 (1H, s), 7.95 (2H, m), 8.08 (1H, s), 9.11 (1H, s), 12.93 (1H, bs)

Mass spectrometric value (ESI-MS) 447 (M−1)

Compound 823 3-Dimethylaminomethyl-N-[4-methyl-3-(4-methyl-benzylidene-hydrazinocarbonyl)-thiophen-2-yl]-benzamide The title compound 823 was produced in substantially the same manner as in Example A.

$^1$H-NMR (CDCl$_3$, 400 MHz): δ 2.26 (6H, s), 2.39 (3H, s), 2.58 (3H, s), 3.53 (2H, s), 6.52 (1H, d, J=1.0 Hz), 7.23 (2H, d, J=7.8 Hz), 7.46 (1H, dd, J=8.3 Hz, J=8.3 Hz), 7.57 (1H, d, J=7.8 Hz), 7.69 (2H, d, J=7.6 Hz), 7.95 (2H, m), 8.12 (1H, s), 9.12 (1H, s), 12.91 (1H, bs)

Mass spectrometric value (ESI-MS) 433 (M−1)

Compound 824 N-[3-(4-Chloro-3-trifluoromethyl-benzylidene-hydrazinocarbonyl)-4-methyl-thiophen-2-yl]-3-dimethylaminomethyl-benzamide The title compound 824 was produced in substantially the same manner as in Example A.

$^1$H-NMR (CDCl$_3$, 400 MHz): δ 2.26 (6H, s), 2.52 (3H, s), 3.53 (2H, s), 6.49 (1H, s), 7.47 (1H, dd, J=7.7 Hz, J=7.7 Hz), 7.57 (2H, m), 7.94 (3H, m), 8.04 (1H, m), 8.27 (1H, s), 9.36 (1H, bs), 12.66 (1H, bs)

Mass spectrometric value (ESI-MS) 521 (M−1)

Compound 825 3-Dimethylaminomethyl-N-[3-(4-methoxy-benzylidene-hydrazinocarbonyl)-4-methyl-thiophen-2-yl]-benzamide The title compound 825 was produced in substantially the same manner as in Example A.

$^1$H-NMR (CDCl$_3$, 400 MHz): δ 2.26 (6H, s), 2.57 (3H, s), 3.53 (2H, s), 3.85 (3H, s), 6.51 (1H, d, J=1.0 Hz), 6.93 (2H, m), 7.46 (1H, dd, J=7.6 Hz, J=7.6 Hz), 7.57 (1H, d, J=7.8 Hz), 7.74 (2H, d, J=8.8 Hz), 7.95 (2H, m), 8.09 (1H, s), 9.09 (1H, s), 12.93 (1H, bs)

Mass spectrometric value (ESI-MS) 449 (M−1)

Compound 826 N-[3-(3,4-Dimethyl-benzylidene-hydrazinocarbonyl)-4-methyl-thiophen-2-yl]-3-(4-pyrimidin-2-yl-piperazin-1-ylmethyl)-benzamide The title compound 826 was produced in substantially the same manner as in Example A.

$^1$H-NMR (CDCl$_3$, 400 MHz): δ 2.29 (6H, s), 2.53 (4H, t, J=5.0 Hz), 2.59 (3H, s), 3.63 (2H, s), 3.84 (4H, t, J=5.0 Hz), 6.45 (1H, dd, J=4.6 Hz, J=4.6 Hz), 6.54 (1H, s), 7.17 (1H, d, J=7.6 Hz), 7.47 (2H, m), 7.60 (1H, d, J=7.6 Hz), 7.64 (1H, s), 7.96 (1H, d, J=7.8 Hz), 8.05 (1H, s), 8.07 (1H, s), 8.28 (2H, d, J=4.6 Hz), 9.07 (1H, s), 12.99 (1H, bs)

Mass spectrometric value (ESI-MS) 566 (M−1)

Compound 827 N-[4-Methyl-3-(4-methyl-benzylidene-hydrazinocarbonyl)-thiophen-2-yl]-3-(4-pyrimidin-2-yl-piperazin-1-ylmethyl)-benzamide The title compound 827 was produced in substantially the same manner as in Example A.

$^1$H-NMR (CDCl$_3$, 400 MHz): δ 2.39 (3H, s), 2.53 (4H, t, J=5.0 Hz), 2.59 (3H, s), 3.64 (2H, s), 3.85 (4H, t, J=4.7 Hz), 6.46 (1H, dd, J=4.7 Hz, J=4.7 Hz), 6.53 (1H, s), 7.21 (2H, d, J=8.0 Hz), 7.47 (1H, dd, J=7.7 Hz, J=7.7 Hz), 7.60 (1H, d, J=7.6 Hz), 7.68 (2H, d, J=8.1 Hz), 7.96 (1H, d, J=7.8 Hz), 8.05 (1H, s), 8.11 (1H, s), 8.29 (2H, d, J=4.6 Hz), 9.09 (1H, s), 12.97 (1H, bs)

Mass spectrometric value (ESI-MS) 552 (M−1)

Compound 828 N-[3-(4-Fluoro-benzylidene-hydrazinocarbonyl)-4-methyl-thiophen-2-yl]-3-(4-pyrimidin-2-yl-piperazin-1-ylmethyl)-benzamide The title compound 828 was produced in substantially the same manner as in Example A.

$^1$H-NMR (CDCl$_3$, 400 MHz): δ 2.54 (4H, t, J=5.0 Hz), 2.59 (3H, s), 3.64 (2H, s), 3.85 (4H, t, J=5.1 Hz), 6.46 (1H, dd, J=4.9 Hz, J=4.9 Hz), 6.54 (1H, s), 7.10 (2H, m), 7.46 (1H, dd, J=7.6 Hz, J=7.6 Hz), 7.60 (1H, d, J=7.6 Hz), 7.79 (2H, m), 7.95 (1H, d, J=7.8 Hz), 8.05 (1H, s), 8.15 (1H, s), 8.29 (2H, d, J=4.9 Hz), 9.12 (1H, s), 12.92 (1H, bs)

Mass spectrometric value (ESI-MS) 556 (M−1)

Compound 829 N-[3-(3-Fluoro-benzylidene-hydrazinocarbonyl)-4-methyl-thiophen-2-yl]-3-(4-pyrimidin-2-yl-piperazin-1-ylmethyl)-benzamide The title compound 829 was produced in substantially the same manner as in Example A.

$^1$H-NMR (CDCl$_3$, 400 MHz): δ 2.53 (4H, t, J=5.0 Hz), 2.59 (3H, s), 3.64 (2H, s), 3.85 (4H, t, J=5.0 Hz), 6.46 (1H, dd, J=4.7 Hz, J=4.7 Hz), 6.55 (1H, s), 7.12 (1H, m), 7.38 (1H, m), 7.46-7.64 (4H, m), 7.95 (1H, m), 8.05 (1H, m), 8.17 (1H, s), 8.28 (2H, d, J=4.6 Hz), 9.17 (1H, s), 12.87 (1H, bs)

Mass spectrometric value (ESI-MS) 556 (M−1)

Compound 830 N-[3-(4-Chloro-3-trifluoromethyl-benzylidene-hydrazinocarbonyl)-4-methyl-thiophen-2-yl]-3-(4-pyrimidin-2-yl-piperazin-1-ylmethyl)-benzamide The title compound 830 was produced in substantially the same manner as in Example A.

$^1$H-NMR (CDCl$_3$, 400 MHz): δ 2.53 (4H, t, J=5.0 Hz), 2.59 (3H, s), 3.65 (2H, s), 3.85 (4H, t, J=5.0 Hz), 6.46 (1H, dd, J=4.8 Hz, J=4.8 Hz), 6.55 (1H, s), 7.49 (1H, dd, J=7.7 Hz, J=7.7 Hz), 7.55 (1H, d, J=8.3 Hz), 7.61 (1H, d, J=7.6 Hz), 7.96 (2H, m), 8.05 (2H, m), 8.26 (1H, s), 8.28 (2H, d, J=4.6 Hz), 9.21 (1H, s), 12.84 (1H, bs)

Mass spectrometric value (ESI-MS) 640 (M−1)

Compound 831 N-[3-(4-Methoxy-benzylidene-hydrazinocarbonyl)-4-methyl-thiophen-2-yl]-3-(4-pyrimidin-2-yl-piperazin-1-ylmethyl)-benzamide The title compound 831 was produced in substantially the same manner as in Example A.

$^1$H-NMR (CDCl$_3$, 400 MHz): δ 2.53 (4H, t, J=4.8 Hz), 2.60 (3H, s), 3.64 (2H, s), 3.84 (7H, m), 6.45 (1H, d, J=4.8 Hz), 6.55 (1H, s), 6.93 (2H, d, J=8.8 Hz), 7.47 (1H, dd, J=7.7 Hz, J=7.7 Hz), 7.61 (1H, d, J=7.6 Hz), 7.74 (2H, d, J=8.8 Hz), 7.97 (1H, d, J=7.8 Hz), 8.05 (1H, s), 8.08 (1H, s), 8.29 (2H, d, J=4.4 Hz), 9.02 (1H, s), 13.04 (1H, bs)
Mass spectrometric value (ESI-MS) 568 (M−1)

Compound 832 N-[3-(3,4-Dimethyl-benzylidene-hydrazinocarbonyl)-4-methyl-thiophen-2-yl]-3-(1,4-dioxa-8-aza-spiro[4,5]dec-8-ylmethyl)-benzamide The title compound 832 was produced in substantially the same manner as in Example A.
¹H-NMR (CDCl₃, 400 MHz): δ 1.76 (4H, m), 2.31 (6H, s), 2.55 (4H, m), 2.62 (3H, s), 3.62 (2H, s), 3.94 (4H, s), 6.55 (1H, s), 7.26 (1H, m), 7.47 (2H, m), 7.53 (1H, m), 7.66 (1H, s), 7.95 (1H, d, J=7.8 Hz), 8.01 (1H, s), 8.07 (1H, s), 9.03 (1H, s), 13.03 (1H, bs)
Mass spectrometric value (ESI-MS) 545 (M−1)

Compound 833 3-(1,4-Dioxa-8-aza-spiro[4,5]dec-8-yl methyl]-N-[4-methyl-3-(4-methyl-benzylidene-hydrazinocarbonyl)-thiophen-2-yl]-benzamide The title compound 833 was produced in substantially the same manner as in Example A.
¹H-NMR (CDCl₃, 400 MHz): δ 1.76 (4H, t, J=5.5 Hz), 2.40 (3H, s), 2.55 (4H, m), 2.60 (3H, s), 3.62 (2H, s), 3.94 (4H, s), 6.54 (1H, s), 7.23 (2H, d, J=8.0 Hz), 7.45 (1H, dd, J=7.7 Hz, J=7.7 Hz), 7.58 (1H, d, J=7.8 Hz), 7.70 (2H, d, J=8.0 Hz), 7.93 (1H, d, J=7.8 Hz), 8.01 (1H, s), 8.11 (1H, s), 9.06 (1H, s), 12.97 (1H, bs)
Mass spectrometric value (ESI-MS) 531 (M−1)

Compound 834 3-(1,4-Dioxa-8-aza-spiro[4,5]dec-8-ylmethyl]-N-[3-(4-fluoro-benzylidene-hydrazinocarbonyl)-4-methyl-thiophen-2-yl]-benzamide The title compound 834 was produced in substantially the same manner as in Example A.
¹H-NMR (CDCl₃, 400 MHz): δ 1.76 (4H, t, J=5.4 Hz), 2.56 (4H, m), 2.59 (3H, s), 3.62 (2H, s), 3.94 (4H, s), 6.55 (1H, s), 7.12 (2H, dd, J=8.6 Hz, J=8.6 Hz), 7.45 (1H, dd, J=7.7 Hz, J=7.7 Hz), 7.58 (1H, d, J=7.8 Hz), 7.81 (2H, m), 7.93 (1H, d, J=7.6 Hz), 8.01 (1H, s), 8.15 (1H, s), 9.10 (1H, s), 12.91 (1H, bs)
Mass spectrometric value (ESI-MS) 535 (M−1)

Compound 835 3-(1,4-Dioxa-8-aza-spiro[4,5]dec-8-ylmethyl]-N-[3-(3-fluoro-benzylidene-hydrazinocarbonyl)-4-methyl-thiophen-2-yl]-benzamide The title compound 835 was produced in substantially the same manner as in Example A.
¹H-NMR (CDCl₃, 400 MHz): δ 1.76 (4H, t, J=5.4 Hz), 2.55 (7H, m), 3.62 (2H, s), 3.94 (4H, s), 6.51 (1H, s), 7.11 (1H, m), 7.34-7.60 (5H, m), 7.91 (1H, d, J=7.6 Hz), 8.01 (1H, s), 8.18 (1H, s), 9.22 (1H, s), 12.78 (1H, bs)
Mass spectrometric value (ESI-MS) 535 (M−1)

Compound 836 N-[3-(4-Chloro-3-trifluoromethyl-benzylidene-hydrazinocarbonyl)-4-methyl-thiophen-2-yl]-3-(1,4-dioxa-8-aza-spiro[4,5]dec-8-ylmethyl]-benzamide The title compound 836 was produced in substantially the same manner as in Example A.
¹H-NMR (CDCl₃, 400 MHz): δ 1.76 (4H, t, J=5.5 Hz), 2.57 (7H, m), 3.62 (2H, s), 3.94 (4H, s), 6.53 (1H, d, J=1.0 Hz), 7.46 (1H, dd, J=7.7 Hz, J=7.7 Hz), 7.57 (2H, m), 7.91 (1H, m), 7.96-8.02 (2H, m), 8.05 (1H, d, J=1.7 Hz), 8.27 (1H, s), 9.25 (1H, s), 12.76 (1H, bs)
Mass spectrometric value (ESI-MS) 619 (M−1)

Compound 837 3-(1,4-Dioxa-8-aza-spiro[4,5]dec-8-ylmethyl]-N-[3-(4-methoxy-benzylidene-hydrazinocarbonyl)-4-methyl-thiophen-2-yl]-benzamide The title compound 837 was produced in substantially the same manner as in Example A.
¹H-NMR (CDCl₃, 400 MHz): δ 1.76 (4H, m), 2.56 (4H, m), 2.61 (3H, s), 3.63 (2H, s), 3.86 (3H, s), 3.94 (4H, s), 6.55 (1H, s), 6.95 (2H, m), 7.46 (1H, dd, J=7.6 Hz, J=7.6 Hz), 7.58 (1H, m), 7.76 (2H, d, J=8.5 Hz), 7.95 (1H, d, J=7.6 Hz), 8.01 (1H, s), 8.08 (1H, s), 9.00 (1H, s), 13.03 (1H, bs)
Mass spectrometric value (ESI-MS) 547 (M−1)

Compound 838 3-{[Bis-(2-diethylamino-ethyl)-amino]-methyl}-N-[3-(3,4-dimethyl-benzylidene-hydrazinocarbonyl)-4-methyl-thiophen-2-yl]-benzamide The title compound 838 was produced in substantially the same manner as in Example B.
¹H-NMR (CDCl₃, 400 MHz): δ 0.98 (12H, t, J=7.1 Hz), 2.29 (6H, m), 2.43-2.66 (19H, m), 3.73 (2H, s), 6.52 (1H, d, J=1.0 Hz), 7.17 (1H, d, J=7.8 Hz), 7.44 (2H, m), 7.62 (2H, m), 7.92 (1H, d, J=7.8 Hz), 8.01 (1H, s), 8.09 (1H, s)
Mass spectrometric value (ESI-MS) 617 (M−1)

Compound 839 3-{[Bis-(2-diethylamino-ethyl)-amino]-methyl}-N-[4-methyl-3-(4-methyl-benzylidene-hydrazinocarbonyl)-thiophen-2-yl]-benzamide The title compound 839 was produced in substantially the same manner as in Example B.
¹H-NMR (CDCl₃, 400 MHz): δ 0.98 (12H, t, J=7.1 Hz), 2.38 (3H, s), 2.45-2.65 (19H, m), 3.72 (2H, s), 6.51 (1H, d, J=1.2 Hz), 7.22 (2H, d, J=7.8 Hz), 7.43 (1H, m), 7.60 (1H, m), 7.68 (2H, d, J=7.8 Hz), 7.91 (1H, d, J=7.8 Hz), 8.00 (1H, s), 8.13 (1H, s)
Mass spectrometric value (ESI-MS) 603 (M−1)

Compound 840 3-{[Bis-(2-diethylamino-ethyl)-amino]-methyl}-N-[3-(4-fluoro-benzylidene-hydrazinocarbonyl)-4-methyl-thiophen-2-yl]-benzamide The title compound 840 was produced in substantially the same manner as in Example B.
¹H-NMR (CDCl₃, 400 MHz): δ 0.98 (12H, t, J=7.1 Hz), 2.43-2.66 (19H, m), 3.72 (2H, s), 6.50 (1H, d, J=1.0 Hz), 7.10 (2H, dd, J=8.5 Hz, J=8.5 Hz), 7.44 (1H, m), 7.62 (1H, d, J=7.6 Hz), 7.79 (2H, m), 7.89 (1H, d, J=7.8 Hz), 8.00 (1H, s), 8.18 (1H, s)
Mass spectrometric value (ESI-MS) 607 (M−1)

Compound 841 3-{[Bis-(2-diethylamino-ethyl)-amino]-methyl}-N-[3-(3-fluoro-benzylidene-hydrazinocarbonyl)-4-methyl-thiophen-2-yl]-benzamide The title compound 841 was produced in substantially the same manner as in Example B.
¹H-NMR (CDCl₃, 400 MHz): δ 0.98 (12H, t, J=7.1 Hz), 2.44-2.64 (19H, m), 3.73 (2H, s), 6.51 (1H, s), 7.11 (1H, s), 7.34-7.64 (5H, m), 7.90 (1H, d, J=7.8 Hz), 8.01 (1H, s), 8.19 (1H, s)

Mass spectrometric value (ESI-MS) 607 (M−1)

Compound 842 3-{[Bis-(2-diethylamino-ethyl)-amino]-methyl}-N-[3-(4-chloro-3-trifluoromethyl-benzylidene-hydrazinocarbonyl)-4-methyl-thiophen-2-yl]-benzamide The title compound 842 was produced in substantially the same manner as in Example B.

$^1$H-NMR (CDCl$_3$, 400 MHz): δ 0.97 (12H, m), 2.42-2.64 (19H, m), 3.72 (2H, m), 6.47 (1H, d, J=1.0 Hz), 7.30-7.68 (4H, m), 7.77-8.05 (3H, m), 8.27 (1H, s)

Mass spectrometric value (ESI-MS) 691 (M−1)

Compound 843 3-{[Bis-(2-diethylamino-ethyl)-amino]-methyl}-N-[3-(4-methoxy-benzylidene-hydrazinocarbonyl)-4-methyl-thiophen-2-yl]-benzamide The title compound 843 was produced in substantially the same manner as in Example B.

$^1$H-NMR (CDCl$_3$, 400 MHz): δ 0.98 (12H, t, J=7.2 Hz), 2.45-2.66 (19H, m), 3.72 (2H, s), 3.85 (3H, s), 6.52 (1H, d, J=1.0 Hz), 6.93 (2H, d, J=8.8 Hz), 7.44 (1H, m), 7.62 (1H, d, J=7.8 Hz), 7.74 (2H, d, J=8.6 Hz), 7.92 (1H, d, J=7.8 Hz), 8.01 (1H, s), 8.10 (1H, s)

Mass spectrometric value (ESI-MS) 619 (M−1)

Compound 844 3-{[Bis-(2-hydroxy-propyl)-amino]-methyl}-N-[3-(3,4-dimethyl-benzylidene-hydrazinocarbonyl)-4,5-dimethyl-thiophen-2-yl]-benzamide The title compound 844 was produced in substantially the same manner as in Example B.

$^1$H-NMR (CDCl$_3$, 400 MHz): δ 1.12 (6H, m), 2.26-2.64 (16H, m), 3.62-4.05 (4H, m), 7.13 (1H, m), 7.40-7.56 (3H, m), 7.65 (1H, m), 7.99 (1H, m), 8.04 (1H, s), 8.19 (1H, s), 9.10 (1H, s), 13.02 (1H, bs)

Mass spectrometric value (ESI-MS) 549 (M−1)

Compound 845 3-{[Bis-(2-hydroxy-propyl)-amino]-methyl}-N-[4,5-dimethyl-3-(4-methyl-benzylidene-hydrazinocarbonyl)-thiophen-2-yl]-benzamide The title compound 845 was produced in substantially the same manner as in Example B.

$^1$H-NMR (CDCl$_3$, 400 MHz): δ 1.11 (6H, m), 2.28-2.64 (13H, m), 3.60-4.04 (4H, m), 7.21 (2H, m), 7.43 (2H, m), 7.73 (2H, m), 7.99 (1H, m), 8.07 (1H, s), 8.21 (1H, s), 9.09 (1H, bs), 13.01 (1H, bs)

Mass spectrometric value (ESI-MS) 535 (M−1)

Compound 846 3-{[Bis-(2-hydroxy-propyl)-amino]-methyl}-N-[3-(4-fluoro-benzylidene-hydrazinocarbonyl)-4,5-dimethyl-thiophen-2-yl]-benzamide The title compound 846 was produced in substantially the same manner as in Example B.

$^1$H-NMR (CDCl$_3$, 400 MHz): δ 1.11 (6H, m), 2.24-2.52 (8H, m), 2.63 (2H, m), 3.60-4.06 (4H, m), 7.04 (2H, m), 7.43 (2H, m), 7.83 (2H, m), 7.99 (1H, m), 8.13 (1H, s), 8.24 (1H, m), 9.24 (1H, s), 12.98 (1H, bs)

Mass spectrometric value (ESI-MS) 539 (M−1)

Compound 847 3-{[Bis-(2-hydroxy-propyl)-amino]-methyl}-N-[3-(4-chloro-3-trifluoromethyl-benzylidene-hydrazinocarbonyl)-4,5-dimethyl-thiophen-2-yl]-benzamide The title compound 847 was produced in substantially the same manner as in Example B.

$^1$H-NMR (CDCl$_3$, 400 MHz): δ 1.11 (6H, m), 2.19 (3H, m), 2.28 (3H, m), 2.52 (2H, m), 2.67 (2H, m), 3.60-4.10 (4H, m), 7.33 (1H, d, J=8.3 Hz), 7.38-7.50 (2H, m), 7.86 (1H, m), 7.98-8.10 (2H, m), 8.28 (1H, s), 8.36 (1H, s), 9.57 (1H, s), 13.03 (1H, s)

Mass spectrometric value (ESI-MS) 623 (M−1)

Compound 848 3-{[Bis-(2-hydroxy-propyl)-amino]-methyl}-N-[3-(4-methoxy-benzylidene-hydrazinocarbonyl)-4,5-dimethyl-thiophen-2-yl]-benzamide The title compound 848 was produced in substantially the same manner as in Example B.

$^1$H-NMR (CDCl$_3$, 400 MHz): δ 1.11 (6H, m), 2.24-2.64 (10H, m), 3.60-4.04 (7H, m), 6.91 (2H, m), 7.43 (2H, m), 7.79 (2H, m), 8.02 (2H, m), 8.23 (1H, s), 9.04 (1H, s), 13.02 (1H, bs)

Mass spectrometric value (ESI-MS) 551 (M−1)

Compound 849 3-{[Bis-(2-diethylamino-ethyl)-amino]-methyl}-N-[3-(4-chloro-3-trifluoromethyl-benzylidene-hydrazinocarbonyl)-4,5,6,7-tetrahydro-benzo[b]thiophen-2-yl]-benzamide The title compound 849 was produced in substantially the same manner as in Example B.

$^1$H-NMR (CDCl$_3$, 400 MHz): δ 0.98 (12H, t, J=7.1 Hz), 1.91 (4H, m), 2.48 (8H, m), 2.58 (8H, m), 2.76 (2H, m), 2.87 (2H, m), 3.73 (2H, s), 7.44 (1H, dd, J=7.7 Hz, J=7.7 Hz), 7.57 (1H, d, J=8.3 Hz), 7.62 (1H, d, J=7.6 Hz), 7.90 (1H, d, J=8.1 Hz), 7.97 (1H, dd, J=8.3 Hz, J=2.0 Hz), 8.00 (1H, s), 8.04 (1H, d, J=1.7 Hz), 8.22 (1H, s)

Mass spectrometric value (ESI-MS) 731 (M−1)

Compound 850 3-{[Bis-(2-diethylamino-ethyl)-amino]-methyl}-N-[3-(4-methoxy-benzylidene-hydrazinocarbonyl)-4,5,6,7-tetrahydro-benzo[b]-thiophen-2-yl]-benzamide The title compound 850 was produced in substantially the same manner as in Example B.

$^1$H-NMR (CDCl$_3$, 400 MHz): δ 0.98 (12H, t, J=7.2 Hz), 1.92 (4H, m), 2.49 (8H, m), 2.58 (8H, m), 2.76 (2H, m), 2.89 (2H, m), 3.72 (2H, s), 3.88 (3H, s), 6.97 (2H, m), 7.27-7.46 (3H, m), 7.61 (1H, d, J=7.8 Hz), 7.92 (1H, d, J=7.3 Hz), 8.00 (1H, s), 8.10 (1H, s)

Mass spectrometric value (ESI-MS) 659 (M−1)

Example C

Compound 851 3-{[Bis-(2-hydroxy-propyl)-amino]-methyl}-N-[3-(4-chloro-3-trifluoromethyl-benzylidene-hydrazinocarbonyl)-4-methyl-thiophen-2-yl]-benzamide; hydrochloride Diethyl ether (200 μl) was added to compound 591: 3-{[bis-(2-hydroxy-propyl)-amino]-methyl}-N-[3-(4-chloro-3-trifluoromethyl-benzylidene-hydrazinocarbonyl)-4-methyl-thiophen-2-yl]-benzamide (30 mg) produced by the process described in Example 8 at room temperature. Further, a few drops of 10% hydrochloric acid-methanol were added thereto, and the mixture was stirred for a few minutes. The reaction solution was then filtered through Kiriyama Rohto, and the crystals were washed with diethyl ether to give the title compound 851 (25 mg, yield 80%).

$^1$H-NMR (CDCl$_3$, 400 MHz): δ 1.14-1.27 (6H, m), 2.56 (3H, s), 2.90 (4H, m), 4.22 (4H, m), 6.53 (1H, m), 7.53 (2H, m), 7.70 (1H, m), 7.95 (1H, m), 8.03 (1H, d, J=8.0 Hz), 8.07 (1H, s), 8.20 (1H, d, J=7.3 Hz), 8.36 (1H, m)

Mass spectrometric value (ESI-MS) 609 (M−1)

Compound 852 3-{[Bis-(2-hydroxy-propyl)-amino]-methyl}-N-[3-(4-methoxy-benzylidene-hydrazinocarbonyl)-4-methyl-thiophen-2-yl]-benzamide; hydrochloride The title compound 852 was produced in substantially the same manner as in Example C.

$^1$H-NMR (CD$_3$OD, 400 MHz): δ 1.22 (6H, d, J=6.1 Hz), 2.53 (3H, s), 3.30 (4H, m), 3.85 (3H, s), 4.20 (4H, m), 6.73 (1H, d, J=1.0 Hz), 6.99 (2H, d, J=8.5 Hz), 7.60-7.85 (4H, m), 8.00-8.29 (3H, m)

Mass spectrometric value (ESI-MS) 538 (M−1)

Example D

Compound 853 3-{[Bis-(2-hydroxy-propyl)-amino]-methyl}-N-[2-(4-chloro-3-trifluoromethyl-benzylidene-hydrazinocarbonyl)-4-fluoro-phenyl]-benzamide; hydrochloride Diethyl ether (200 μl) was added to compound 857: 3-{[bis-(2-hydroxy-propyl)-amino]-methyl}-N-[2-(4-chloro-3-trifluoromethyl-benzylidene-hydrazinocarbonyl)-4-fluoro-phenyl]-benzamide (30 mg) produced by the process described in Example A at room temperature, a few drops of 10% hydrochloric acid-methanol were further added thereto, and the mixture was stirred for a few minutes. The reaction solution was then filtered through Kiriyama Rohto, and the crystals were washed with diethyl ether to give the title compound 853 (25 mg, yield 80%).

$^1$H-NMR (CD$_3$OD, 400 MHz): δ 1.15-1.32 (6H, m), 3.00-3.40 (4H$_3$ m), 4.10-4.86 (4H, m), 7.44 (1H, m), 7.68-7.85 (4H, m), 8.03 (1H, d, J=7.8 Hz), 8.14 (2H, m), 8.36 (1H, m), 8.41 (1H, s), 8.62 (1H, m)

Mass spectrometric value (ESI-MS) 608 (M−1)

Compound 854 3-{[Bis-(2-hydroxy-propyl)-amino]-methyl}-N-[4-fluoro-2-(4-methoxy-benzylidene-hydrazinocarbonyl)-phenyl]-benzamide; hydrochloride The title compound 854 was produced in substantially the same manner as in Example D.

$^1$H-NMR (CD$_3$OD, 400 MHz): δ 1.18 (6H, m), 3.30 (4H, m), 3.85 (3H, s), 4.00-4.30 (4H, m), 6.98 (2H, d, J=8.5 Hz), 7.35 (1H, m), 7.65-7.83 (5H, m), 8.00-8.17 (2H, m), 8.31 (1H, s), 8.70 (1H, m)

Mass spectrometric value (ESI-MS) 536 (M−1)

Example E

Compound 855 3-{[Bis-(2-diethylamino-ethyl)-amino]-methyl}-N-[3-(4-chloro-3-trifluoromethyl-benzylidene-hydrazinocarbonyl)-4,5,6,7-tetrahydro-benzo[b]thiophen-2-yl]-benzamide; hydrochloride Diethyl ether (200 μl) was added to compound 849: 3-{[bis-(2-diethylamino-ethyl)-amino]-methyl}-N-[3-(4-chloro-3-trifluoromethyl-benzylidene-hydrazinocarbonyl)-4,5,6,7-tetrahydro-benzo[b]thiophen-2-yl]-benzamide (30 mg) produced by the process described in Example B at room temperature, a few drops of 10% hydrochloric acid-methanol were further added thereto, and the mixture was stirred for a few minutes. The reaction solution was then filtered through Kiriyama Rohto, and the crystals were washed with diethyl ether to give the title compound 855 (25 mg, yield 80%).

$^1$H-NMR (CD$_3$OD, 400 MHz): δ 1.28 (12H, m), 1.91 (4H, m), 2.77 (2H, m), 2.87 (2H, m), 3.04 (4H, m), 3.18 (8H, m), 3.40 (4H, m), 3.92 (2H, s), 7.62 (1H, m), 7.70 (1H, m), 7.77 (1H, m), 7.95 (1H, m), 8.01 (2H, m), 8.32 (2H, m)

Mass spectrometric value (ESI-MS) 732 (M−1)

Compound 856 3-{[Bis-(2-diethylamino-ethyl)-amino]-methyl}-N-[3-(4-methoxy-benzylidene-hydrazinocarbonyl)-4,5,6,7-tetrahydro-benzo[b]thiophen-2-yl]-benzamide; hydrochloride The title compound 856 was produced in substantially the same manner as in Example E.

$^1$H-NMR (CD$_3$OD, 400 MHz): δ 1.29 (12H, m), 1.89 (4H, m), 2.70-2.92 (4H, m), 3.00-3.28 (12H, m), 3.43 (4H, m), 3.87 (3H, s), 3.97 (2H, s), 7.20 (1H, m), 7.30-7.40 (2H, m), 7.52 (1H, m), 7.63 (1H, m), 7.77 (1H, m), 7.98 (1H, m), 8.04 (1H, s), 8.27 (1H, s)

Mass spectrometric value (ESI-MS) 660 (M−1)

Compound 857 3-{[Bis-(2-hydroxy-propyl)-amino]-methyl}-N-[2-(4-chloro-3-trifluoromethyl-benzylidene-hydrazinocarbonyl)-4-fluoro-phenyl]-benzamide The title compound 857 was produced in substantially the same manner as in Example A.

$^1$H-NMR (CD$_3$OD, 400 MHz): δ 1.08 (6H, m), 2.43-2.60 (4H, m), 3.60-3.95 (4H, m), 7.40 (1H, m), 7.50 (1H, m), 7.60 (1H, m), 7.69 (2H, d, J=7.6 Hz), 7.85 (1H, m), 8.07 (2H, m), 8.34 (1H, m), 8.38 (1H, s), 8.65 (1H, m),

Mass spectrometric value (ESI-MS) 608 (M−1)

Example F

Compound 858 3-{[(2-Diethylamino-ethyl)-methyl-amino]-methyl}-N-[2-(3,4-dimethyl-benzylidene-hydrazinocarbonyl)-4-piperidin-1-ylphenyl]-benzamide 5-Chloro-2-nitro-benzoic acid (compound A') (5.0 g) was dissolved in methanol (150 ml). Thionyl chloride (9.5 ml) was added to the solution at 0° C., and the mixture was heated under reflux with stirring for 15 hr. After the completion of the reaction, distilled water was added thereto at 0° C., and the mixture was subjected to separatory extraction with chloroform. The organic layer was washed with distilled water and saturated brine, was dried over sodium sulfate, and was then concentrated to give 5-chloro-2-nitro-benzoic acid methyl ester as a useful intermediate (12.9 g, yield 92%).

5-Chloro-2-nitro-benzoic acid methyl ester (2.2 g) produced by the above reaction was dissolved in N,N-dimethylformamide (20 ml). Piperidine (compound D) (1.5 g) and potassium carbonate (1.5 g) were added to the solution at room temperature, and the mixture was stirred at 75° C. for 15 hr. After the completion of the reaction, distilled water was added thereto at room temperature, and the mixture was subjected to separatory extraction with chloroform. The organic layer was washed with distilled water and saturated brine, was dried over sodium sulfate, and was then concentrated to give 2-nitro-5-piperidin-1-yl-benzoic acid methyl ester as a useful intermediate (1.86 g, crude yield 69%).

2-Nitro-5-piperidin-1-yl-benzoic acid methyl ester (4.8 g) produced by the above reaction was dissolved in ethanol (5.0 ml), and 10% palladium-carbon (500 mg) was added to the solution. The air in the reaction system was then replaced by hydrogen, and the reaction solution was stirred at room temperature for 15 hr. After the completion of the reaction, the atmosphere in the reaction system was replaced by nitrogen, followed by filtration through Celite. The filtrate was concentrated, and the residue was purified by column chromatography using a hexane-acetone system to give 2-amino-5-piperidin-1-yl-benzoic acid methyl ester (compound A) as a useful intermediate (3.7 g, yield 87%).

2-Amino-5-piperidin-1-yl-benzoic acid methyl ester (compound A) (2.1 g) produced by the above reaction was dissolved in anhydrous methylene chloride (20.0 ml). Subsequently, pyridine (900 µl) and 3-(chloromethyl)benzoyl chloride (compound B) (740 µl) were added to the solution at 0° C., and the mixture was stirred at 0° C. for one hr. After the completion of the reaction, distilled water was added thereto, and the mixture was subjected to separatory extraction with chloroform. The organic layer was washed with saturated brine, was dried over sodium sulfate and was then concentrated. The residue was purified by column chromatography using a chloroform-acetone system to give 2-(3-chloromethyl-benzoylamino)-5-piperidin-1-yl-benzoic acid methyl ester as a useful intermediate (1.8 g, yield 50%).

2-(3-Chloromethyl-benzoylamino)-5-piperidin-1-yl-benzoic acid methyl ester (500 mg) produced by the above reaction was dissolved in anhydrous methylene chloride (5.0 ml). Triethylamine (400 µl) and N,N-diethyl-N'-methylethylenediamine (compound B') (325 mg) were added to the solution at room temperature, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 2-(3-{[(2-diethylamino-ethyl)-methyl-amino]-methyl}-benzoylamino)-5-piperidin-1-yl-benzoic acid methyl ester as a useful intermediate (612 mg, yield 98%).

2-(3-{[(2-Diethylamino-ethyl)-methyl-amino]-methyl}-benzoylamino)-5-piperidin-1-yl-benzoic acid methyl ester (612 mg) produced by the above reaction was dissolved in ethanol (10.0 ml). Hydrazine monohydrate (700 µl) was added to the solution, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 3-{[(2-diethylamino-ethyl)-methyl-amino]-methyl}-N-(2-hydrazinocarbonyl-4-piperidin-1-yl-phenyl)-benzamide as a hydrazine compound (612 mg, yield 100%).

3-{[(2-Diethylamino-ethyl)-methyl-amino]-methyl}-N-(2-hydrazinocarbonyl-4-piperidin-1-yl-phenyl)-benzamide as a hydrazine compound (70 mg) produced by the above reaction was dissolved in anhydrous toluene (1.0 ml). 3,4-Dimethylbenzaldehyde (compound C) (40 µl) was added to the solution at room temperature, and the mixture was stirred at 70° C. for 15 hr. After the completion of the reaction, the reaction product was purified by column chromatography eluted with a chloroform-methanol system to give the title compound 858 (62 mg, yield 70%).

$^1$H-NMR (CDCl$_3$, 400 MHz): δ 1.04 (6H, t, J=7.2 Hz), 1.26 (2H, m), 1.37 (4H, m), 2.26 (9H, m), 2.60 (6H, m), 2.69 (2H, m), 2.84 (4H, m), 3.62 (2H, s), 6.86 (1H, d, J=8.8 Hz), 7.00 (1H, s), 7.15 (1H, d, J=7.6 Hz), 7.44 (1H, dd, J=7.6 Hz, J=7.6 Hz), 7.53 (2H, m), 7.65 (1H, s), 7.89 (1H, d, J=7.6 Hz), 7.98 (1H, s), 8.10 (1H, d, J=8.8 Hz), 8.51 (1H, s), 11.23 (2H, m)

Mass spectrometric value (ESI-MS) 595 (M−1)

Compound 859 3-{[(2-Diethylamino-ethyl)-methyl-amino]-methyl}-N-[2-(4-methyl-benzylidene-hydrazinocarbonyl)-4-piperidin-1-yl-phenyl]-benzamide The title compound 859 was produced in substantially the same manner as in Example F.

$^1$H-NMR (CDCl$_3$, 400 MHz): δ 1.05 (6H, t, J=7.2 Hz), 1.29 (2H, m), 1.40 (4H, m), 2.25 (3H, s), 2.37 (3H, s), 2.62 (6H, m), 2.72 (2H, m), 2.87 (4H, m), 3.62 (2H, s), 6.89 (1H, d, J=8.8 Hz), 7.02 (1H, s), 7.20 (2H, d, J=7.8 Hz), 7.43 (1H, dd, J=7.7 Hz, J=7.7 Hz), 7.53 (1H, d, J=7.3 Hz), 7.72 (2H, d, J=7.6 Hz), 7.88 (1H, d, J=7.6 Hz), 7.97 (1H, s), 8.13 (1H, d, J=9.0 Hz), 8.51 (1H, s), 11.23 (2H, m)

Mass spectrometric value (ESI-MS) 581 (M−1)

Compound 860 3-{[(2-Diethylamino-ethyl)-methyl-amino]-methyl}-N-[2-(4-fluoro-benzylidene-hydrazinocarbonyl)-4-piperidin-1-yl-phenyl]-benzamide The title compound 860 was produced in substantially the same manner as in Example F.

$^1$H-NMR (CDCl$_3$, 400 MHz): δ 1.05 (6H, t, J=7.1 Hz), 1.28 (2H, m), 1.37 (4H, m), 2.25 (3H, s), 2.62 (6H, m), 2.72 (2H, m), 2.84 (4H, m), 3.63 (2H, s), 6.87 (1H, d, J=8.5 Hz), 6.99 (1H, m), 7.09 (2H, dd, J=8.5 Hz, J=8.5 Hz), 7.44 (1H, dd, J=7.6 Hz, J=7.6 Hz), 7.54 (1H, d, J=7.3 Hz), 7.83 (2H, m), 7.88 (1H, d, J=7.4 Hz), 7.98 (1H, s), 8.07 (1H, d, J=9.0 Hz), 8.56 (1H, s), 11.19 (1H, s)

Mass spectrometric value (ESI-MS) 585 (M−1)

Compound 861 3-{[(2-Diethylamino-ethyl)-methyl-amino]-methyl}-N-[2-(3-fluoro-benzylidene-hydrazinocarbonyl)-4-piperidin-1-yl-phenyl]-benzamide The title compound 861 was produced in substantially the same manner as in Example F.

$^1$H-NMR (CDCl$_3$, 400 MHz): δ 1.10 (6H, t, J=7.0 Hz), 1.30 (2H, m), 1.39 (4H, m), 2.25 (3H, s), 2.64-2.90 (12H, m), 3.62 (2H, s), 6.89 (1H, d, J=8.5 Hz), 7.07 (2H, m), 7.27-7.65 (4H, m), 7.68-8.00 (3H, m), 8.11 (1H, d, J=9.0 Hz), 8.53 (1H, s), 11.23 (1H, s)

Mass spectrometric value (ESI-MS) 585 (M−1)

Compound 862 N-[2-(4-Chloro-3-trifluoromethyl-benzylidene-hydrazinocarbonyl)-4-piperidin-1-yl-phenyl]-3-{[(2-diethylamino-ethyl)-methyl-amino]-methyl}-benzamide The title compound 862 was produced in substantially the same manner as in Example F.

$^1$H-NMR (CDCl$_3$, 400 MHz): δ 1.03 (6H, t, J=7.2 Hz), 1.23 (2H, m), 1.32 (4H, m), 2.27 (3H, s), 2.58 (6H, m), 2.67 (2H, m), 2.79 (4H, m), 3.64 (2H, s), 6.81 (1H, d, J=8.5 Hz), 6.92 (1H, s), 7.47 (1H, dd, J=7.7 Hz, J=7.7 Hz), 7.57 (2H, m), 7.88 (1H, d, J=7.8 Hz), 7.95 (1H, d, J=9.0 Hz), 8.01 (1H, s), 8.06 (1H, d, J=8.1 Hz), 8.10 (1H, s), 8.64 (1H, s), 11.08 (1H, s)

Mass spectrometric value (ESI-MS) 669 (M−1)

Compound 863 3-{[(2-Diethylamino-ethyl)-methyl-amino]-methyl}-N-[2-(4-methoxy-benzylidene-hydrazinocarbonyl)-4-piperidin-1-yl-phenyl]-benzamide The title compound 863 was produced in substantially the same manner as in Example F.
$^{1}$H-NMR (CDCl$_{3}$, 400 MHz): δ 1.06 (6H, t, J=7.1 Hz), 1.32 (2H, m), 1.43 (4H, m), 2.24 (3H, s), 2.62 (6H, m), 2.72 (2H, m), 2.90 (4H, m), 3.62 (2H, s), 3.82 (3H, s), 6.83-6.95 (3H, m), 7.05 (1H, s), 7.42 (1H, m), 7.52 (1H, m), 7.74 (2H, d, J=8.6 Hz), 7.88 (1H, d, J=7.6 Hz), 7.96 (1H, s), 8.18 (1H, d, J=9.0 Hz), 8.48 (1H, s)
Mass spectrometric value (ESI-MS) 597 (M−1)

Compound 864 N-[2-(3,4-Dimethyl-benzylidene-hydrazinocarbonyl)-4-piperidin-1-yl-phenyl]-3-[4-(2-hydroxy-ethyl)-piperazin-1-ylmethyl]-benzamide The title compound 864 was produced in substantially the same manner as in Example F.
$^{1}$H-NMR (CDCl$_{3}$, 400 MHz): δ 1.42 (4H, m), 1.32 (2H, m), 2.28 (3H, s), 2.29 (3H, s), 2.48-2.72 (10H, m), 2.88 (4H, m), 3.61 (4H, m), 6.92 (1H, m), 6.99 (1H, m), 7.16 (1H, d, J=7.8 Hz), 7.44 (1H, dd, J=7.7 Hz, J=7.7 Hz), 7.51 (2H, m), 7.65 (1H, s), 7.90 (1H, d, J=7.8 Hz), 7.99 (1H, s), 8.17 (1H, d, J=9.2 Hz), 8.43 (1H, s), 10.71 (1H, s), 11.21 (1H, s)
Mass spectrometric value (ESI-MS) 595 (M−1)

Compound 865 3-[4-(2-Hydroxy-ethyl)-piperazin-1-ylmethyl]-N-[2-(4-methyl-benzylidene-hydrazinocarbonyl)-4-piperidin-1-yl-phenyl]-benzamide The title compound 865 was produced in substantially the same manner as in Example F.
$^{1}$H-NMR (CDCl$_{3}$, 400 MHz): δ 1.28 (2H, m), 1.39 (4H, m), 2.36 (3H, s), 2.48-2.90 (14H, m), 3.60 (4H, m), 6.88 (1H, d, J=9.0 Hz), 6.99 (1H, s), 7.20 (2H, d, J=8.0 Hz), 7.44 (1H, dd, J=7.6 Hz, J=7.6 Hz), 7.51 (1H, d, J=7.3 Hz), 7.72 (2H, d, J=7.8 Hz), 7.90 (1H, d, J=7.6 Hz), 7.99 (1H, s), 8.13 (1H, d, J=9.0 Hz), 8.49 (1H, s), 10.95 (1H, s), 11.23 (1H, s)
Mass spectrometric value (ESI-MS) 581 (M−1)

Compound 866 N-[2-(4-Fluoro-benzylidene-hydrazinocarbonyl)-4-piperidin-1-yl-phenyl]-3-[4-(2-hydroxy-ethyl)-piperazin-1-ylmethyl]-benzamide The title compound 866 was produced in substantially the same manner as in Example F.
$^{1}$H-NMR (CDCl$_{3}$, 400 MHz): δ 1.27 (2H, m), 1.37 (4H, m), 2.55-2.90 (14H, m), 3.62 (2H, s), 3.68 (2H, t, J=5.2 Hz), 6.88 (1H, d, J=8.8 Hz), 7.00-7.16 (2H, m), 7.31-7.60 (4H, m), 7.70-8.03 (3H, m), 8.11 (1H, d, J=9.0 Hz), 8.52 (1H, s), 11.21 (1H, s), 11.35 (1H, s)
Mass spectrometric value (ESI-MS) 585 (M−1)

Compound 867 N-[2-(3-Fluoro-benzylidene-hydrazinocarbonyl)-4-piperidin-1-yl-phenyl]-3-[4-(2-hydroxy-ethyl)-piperazin-1-ylmethyl]-benzamide The title compound 867 was produced in substantially the same manner as in Example F.
$^{1}$H-NMR (CDCl$_{3}$, 400 MHz): δ 1.26 (2H, m), 1.36 (4H, m), 2.58 (10H, m), 2.83 (4H, m), 3.62 (4H, m), 6.87 (1H, d, J=8.8 Hz), 6.98 (1H, s), 7.08 (2H, dd, J=8.4 Hz, J=8.4 Hz), 7.44 (1H, dd, J=7.6 Hz, J=7.6 Hz), 7.52 (1H, d, J=7.8 Hz), 7.81 (2H, m), 7.89 (1H, d, J=7.6 Hz), 7.98 (1H, s), 8.09 (1H, d, J=9.0 Hz), 8.53 (1H, s), 11.20 (1H, s)
Mass spectrometric value (ESI-MS) 585 (M−1)

Compound 868 N-[2-(4-Chloro-3-trifluoromethyl-benzylidene-hydrazinocarbonyl)-4-piperidin-1-yl-phenyl]-3-[4-(2-hydroxy-ethyl)-piperazin-1-ylmethyl]-benzamide The title compound 868 was produced in substantially the same manner as in Example F.
$^{1}$H-NMR (CD$_{3}$OD, 400 MHz): δ 1.61 (2H, m), 1.72 (4H, m), 2.46-2.65 (10H, m), 3.22 (4H, m), 3.63 (4H, m), 7.20 (1H, dd, J=9.3 Hz, J=2.7 Hz), 7.36 (1H, d, J=2.7 Hz), 7.48 (1H, dd, J=7.7 Hz, J=7.7 Hz), 7.55 (1H, d, J=7.8 Hz), 7.65 (1H, d, J=8.3 Hz), 7.86 (1H, m), 7.93 (1H, m), 8.00 (1H, d, J=8.3 Hz), 8.26 (1H, s), 8.32 (1H, d, J=9.3 Hz), 8.36 (1H, s)
Mass spectrometric value (ESI-MS) 669 (M−1)

Compound 869 3-[4-(2-Hydroxy-ethyl)-piperazin-1-ylmethyl]-N-[2-(4-methoxy-benzylidene-hydrazinocarbonyl)-4-piperidin-1-yl-phenyl]-benzamide The title compound 869 was produced in substantially the same manner as in Example F.
$^{1}$H-NMR (CDCl$_{3}$, 400 MHz): δ 1.37 (2H, m), 1.48 (4H, m), 2.56 (10H, m), 2.93 (4H, m), 3.61 (4H, m), 3.84 (3H, s), 6.90-7.04 (4H, m), 7.44 (1H, dd, J=7.4 Hz, J=7.4 Hz), 7.51 (1H, d, J=7.4 Hz), 7.76 (2H, d, J=8.3 Hz), 7.89 (1H, d, J=7.6 Hz), 7.98 (1H, s), 8.23 (1H, m), 8.38 (1H, m), 11.21 (1H, s)
Mass spectrometric value (ESI-MS) 597 (M−1)

Compound 870 N-[2-(3,4-Dimethyl-benzylidene-hydrazinocarbonyl)-4-piperidin-1-yl-phenyl]-3-(4-hydroxy-piperidin-1-ylmethyl)-benzamide The title compound 870 was produced in substantially the same manner as in Example F.
$^{1}$H-NMR (CDCl$_{3}$, 400 MHz): δ 1.32 (2H, m), 1.43 (4H, m), 1.63 (2H, m), 1.90 (2H, m), 2.29 (8H, m), 2.80 (2H, m), 2.88 (4H, m), 3.63 (2H, s), 3.72 (1H, m), 6.91 (1H, d, J=8.8 Hz), 7.02 (1H, s), 7.15 (1H, d, J=7.8 Hz), 7.35-7.55 (3H, m), 7.65 (1H, m), 7.90 (1H, d, J=7.3 Hz), 7.97 (1H, s), 8.18 (1H, d, J=9.3 Hz), 8.44 (1H, s), 10.79 (1H, s), 11.24 (1H, s)
Mass spectrometric value (ESI-MS) 566 (M−1)

Compound 871 3-(4-Hydroxy-piperidin-1-ylmethyl)-N-[2-(4-methyl-benzylidene-hydrazinocarbonyl)-4-piperidin-1-yl-phenyl]-benzamide The title compound 871 was produced in substantially the same manner as in Example F.
$^{1}$H-NMR (CDCl$_{3}$, 400 MHz): δ 1.26 (2H, m), 1.40 (4H, m), 1.64 (2H, m), 1.89 (2H, m), 2.26 (2H, m), 2.35 (3H, s), 2.82 (6H, m), 3.63 (2H, s), 3.71 (1H, m), 6.89 (1H, d, J=8.6 Hz), 7.04 (1H, s), 7.18 (2H, d, J=7.8 Hz), 7.43 (1H, m), 7.53 (1H, m), 7.69 (2H, d, J=7.6 Hz), 7.90 (1H, d, J=7.3 Hz), 7.97 (1H, s), 8.17 (1H, d, J=8.6 Hz), 8.47 (1H, s), 10.98 (1H, s), 11.26 (1H, s)
Mass spectrometric value (ESI-MS) 552 (M−1)

Compound 872 N-[2-(4-Fluoro-benzylidene-hydrazinocarbonyl)-4-piperidin-1-yl-phenyl]-3-(4-hydroxy-piperidin-1-ylmethyl)-benzamide The title compound 872 was produced in substantially the same manner as in Example F.
$^{1}$H-NMR (CDCl$_{3}$, 400 MHz): δ 1.32 (2H, m), 1.42 (4H, m), 1.66 (2H, m), 1.92 (2H, m), 2.40 (2H, m), 2.88 (6H, m), 3.71 (2H, s), 3.76 (1H, m), 6.90 (1H, d, J=8.8 Hz), 6.98-7.11 (2H, m), 7.43 (1H, m), 7.54 (1H, m), 7.77 (2H, m), 7.89 (1H, d, J=7.6 Hz), 7.96 (1H, s), 8.05 (1H, m), 8.15 (1H, d, J=9.0 Hz), 8.47 (1H, s), 11.10-11.30 (2H, m)

Mass spectrometric value (ESI-MS) 556 (M−1)

Compound 873 N-[2-(3-Fluoro-benzylidene-hydrazinocarbonyl)-4-piperidin-1-yl-phenyl]-3-(4-hydroxy-piperidin-1-ylmethyl)-benzamide The title compound 873 was produced in substantially the same manner as in Example F.

$^1$H-NMR (CDCl$_3$, 400 MHz): δ 1.34 (2H, m), 1.44 (4H, m), 1.67 (2H, m), 1.94 (2H, m), 2.34 (2H, m), 2.88 (6H, m), 3.70 (2H, s), 3.77 (1H, m), 6.92 (1H, d, J=8.3 Hz), 7.09 (3H, m), 7.29-7.67 (4H, m), 7.90 (1H, d, J=7.8 Hz), 7.97 (1H, s), 8.14 (1H, d, J=9.0 Hz), 8.49 (1H, s), 11.02 (1H, s), 11.17 (1H, s)

Mass spectrometric value (ESI-MS) 556 (M−1)

Compound 874 N-[2-(4-Chloro-3-trifluoromethyl-benzylidene-hydrazinocarbonyl)-4-piperidin-1-yl-phenyl]-3-(4-hydroxy-piperidin-1-ylmethyl)-benzamide The title compound 874 was produced in substantially the same manner as in Example F.

$^1$H-NMR (CD$_3$OD, 400 MHz): δ 1.50-1.68 (4H, m), 1.75 (4H, m), 1.84 (2H, m), 2.22 (2H, m), 2.81 (2H, m), 3.24 (4H, t, J=5.2 Hz), 3.61 (3H, m), 7.22 (1H, dd, J=9.0 Hz, J=2.7 Hz), 7.37 (1H, d, J=2.7 Hz), 7.50 (1H, m), 7.57 (1H, m), 7.67 (1H, d, J=8.3 Hz), 7.87 (1H, d, J=7.8 Hz), 7.92 (1H, s), 8.03 (1H, d, J=8.3 Hz), 8.29 (1H, s), 8.33 (1H, d, J=9.0 Hz), 8.37 (1H, s)

Mass spectrometric value (ESI-MS) 640 (M−1)

Compound 875 3-(4-Hydroxy-piperidin-1-ylmethyl)-N-[2-(4-methoxy-benzylidene-hydrazinocarbonyl)-4-piperidin-1-yl-phenyl]-benzamide The title compound 875 was produced in substantially the same manner as in Example F.

$^1$H-NMR (CDCl$_3$, 400 MHz): δ 1.34 (2H, m), 1.45 (4H, m), 1.64 (2H, m), 1.90 (2H, m), 2.25 (2H, m), 2.79 (2H, m), 2.91 (4H, m), 3.63 (2H, s), 3.72 (1H, m), 3.83 (3H, m), 6.92 (3H, m), 7.64 (1H, s), 7.33-7.50 (1H, m), 7.53 (1H, d, J=7.6 Hz), 7.75 (2H, d, J=8.3 Hz), 7.89 (1H, d, J=7.6 Hz), 7.96 (1H, s), 8.22 (1H, d, J=8.8 Hz), 8.42 (1H, s), 10.68 (1H, bs), 11.25 (1H, s)

Mass spectrometric value (ESI-MS) 568 (M−1)

Compound 876 3-(2-Diethylamino-ethylsulfanylmethyl)-N-[2-(3,4-dimethyl-benzylidene-hydrazinocarbonyl)-4-piperidin-1-yl-phenyl]-benzamide The title compound 876 was produced in substantially the same manner as in Example F.

$^1$H-NMR (CDCl$_3$, 400 MHz): δ 1.03 (6H, t, J=7.1 Hz), 1.33 (2H, m), 1.44 (4H, m), 2.29 (6H, m), 2.59 (6H, m), 2.71 (2H, m), 2.90 (4H, m), 3.84 (2H, s), 6.92 (1H, d, J=8.8 Hz), 7.10 (1H, s), 7.16 (1H, d, J=7.6 Hz), 7.44 (1H, dd, J=7.6 Hz, J=7.6 Hz), 7.53 (2H, m), 7.66 (1H, m), 7.89 (1H, d, J=7.6 Hz), 8.00 (1H, s), 8.18 (1H, d, J=8.8 Hz), 8.44 (1H, s), 10.73 (1H, bs), 11.26 (1H, s)

Mass spectrometric value (ESI-MS) 598 (M−1)

Compound 877 3-(2-Diethylamino-ethylsulfanylmethyl)-N-[2-(4-fluoro-benzylidene-hydrazinocarbonyl)-4-piperidin-1-yl-phenyl]-benzamide The title compound 877 was produced in substantially the same manner as in Example F.

$^1$H-NMR (CDCl$_3$, 400 MHz): δ 1.08 (6H, t, J=7.0 Hz), 1.36 (2H, m), 1.46 (4H, m), 2.74 (6H, m), 2.84 (2H, m), 2.92 (4H, m), 3.83 (2H, s), 6.94 (1H, d, J=8.3 Hz), 7.05 (2H, m), 7.42 (1H, d, J=7.7 Hz, J=7.7 Hz), 7.52 (1H, m), 7.79 (2H, m), 7.88 (1H, d, J=7.6 Hz), 7.98 (1H, s), 8.03 (1H, m), 8.17 (1H, d, J=8.8 Hz), 8.47 (1H, s), 11.02 (1H, bs), 11.27 (1H, s)

Mass spectrometric value (ESI-MS) 588 (M−1)

Compound 878 N-[2-(4-Chloro-3-trifluoromethyl-benzylidene-hydrazinocarbonyl)-4-piperidin-1-yl-phenyl]-3-(2-diethylamino-ethylsulfanylmethyl)-benzamide The title compound 878 was produced in substantially the same manner as in Example F.

$^1$H-NMR (CDCl$_3$, 400 MHz): δ 1.03 (6H, m), 1.29 (2H, m), 1.38 (4H, m), 2.48-2.75 (8H, m), 2.84 (4H, m), 3.85 (2H, s), 6.90 (2H, m), 7.47 (1H, dd, J=7.6 Hz, J=7.6 Hz), 7.56 (2H, m), 7.88 (1H, d, J=7.8 Hz), 8.00-8.12 (4H, m), 8.60 (1H, s), 11.07 (2H, m)

Mass spectrometric value (ESI-MS) 672 (M−1)

Compound 879 3-(2-Diethylamino-ethylsulfanylmethyl)-N-[2-(4-methoxy-benzylidene-hydrazinocarbonyl)-4-piperidin-1-yl-phenyl]-benzamide The title compound 879 was produced in substantially the same manner as in Example F.

$^1$H-NMR (CDCl$_3$, 400 MHz): δ 1.02 (6H, t, J=7.1 Hz), 1.26 (2H, m), 1.67 (4H, m), 2.59 (6H, m), 2.70 (2H, m), 2.92 (4H, m), 3.83 (5H, m), 6.92 (3H, m), 7.02 (1H, s), 7.44 (1H, dd, J=7.6 Hz, J=7.6 Hz), 7.53 (1H, d, J=7.6 Hz), 7.77 (2H, d, J=8.3 Hz), 7.88 (1H, d, J=7.6 Hz), 7.99 (1H, m), 8.22 (1H, d, J=8.8 Hz), 8.42 (1H, s), 10.59 (1H, bs), 11.27 (1H, s)

Mass spectrometric value (ESI-MS) 600 (M−1)

Compound 880 N-[2-(3,4-Dimethyl-benzylidene-hydrazinocarbonyl)-4-piperidin-1-yl-phenyl]-3-(2-hydroxy-ethylsulfanylmethyl)-benzamide The title compound 880 was produced in substantially the same manner as in Example F.

$^1$H-NMR (CDCl$_3$, 400 MHz): δ 1.41 (2H, m), 1.51 (4H, m), 2.24 (3H, s), 2.67 (3H, s), 2.65 (2H, t, J=6.9 Hz), 2.94 (4H, m), 3.82 (2H, s), 3.93 (1H, t, J=6.8 Hz), 6.93 (1H, d, J=9.0 Hz), 7.04 (1H, s), 7.14 (1H, d, J=7.8 Hz), 7.52 (3H, m), 7.63 (1H, s), 7.80 (1H, s), 8.01 (1H, d, J=6.8 Hz), 8.25 (1H, s), 8.28 (2H, d, J=9.0 Hz), 10.56 (1H, s), 11.50 (1H, s)

Mass spectrometric value (ESI-MS) 543 (M−1)

Compound 881 3-(2-Hydroxy-ethylsulfanylmethyl)-N-[2-(4-methyl-benzylidene-hydrazinocarbonyl)-4-piperidin-1-yl-phenyl]-benzamide The title compound 881 was produced in substantially the same manner as in Example F.

$^1$H-NMR (CDCl$_3$, 400 MHz): δ 1.43 (2H, m), 1.54 (4H, m), 2.33 (3H, s), 2.64 (2H, t, J=7.1 Hz), 2.97 (4H, m), 3.82 (2H, s), 3.92 (2H, m), 6.95 (1H, m), 7.08 (1H, s), 7.19 (2H, d, J=7.8 Hz), 7.54 (2H, m), 7.69 (2H, d, J=7.8 Hz), 7.79 (1H, s), 8.00 (1H, d, J=7.1 Hz), 8.26 (1H, s), 8.30 (1H, d, J=9.3 Hz), 10.52 (1H, s), 11.49 (1H, s)

Mass spectrometric value (ESI-MS) 529 (M−1)

Compound 882 N-[2-(4-Fluoro-benzylidene-hydrazinocarbonyl)-4-piperidin-1-yl-phenyl]-3-(2-hydroxy-ethylsulfanylmethyl)-benzamide The title compound 882 was produced in substantially the same manner as in Example F.
$^1$H-NMR (CDCl$_3$, 400 MHz): δ 1.44 (2H, m), 1.57 (4H, m), 2.64 (2H, t, J=7.0 Hz), 2.99 (4H, m), 3.81 (2H, s), 3.91 (2H, m), 7.00 (1H, d, J=8.8 Hz), 7.10 (2H, dd, J=8.7 Hz, J=8.7 Hz), 7.15 (1H, s), 7.54 (2H, m), 7.78 (1H, s), 7.86 (2H, m), 8.06 (1H, d, J=7.1 Hz), 8.33 (2H, m), 10.59 (1H, s), 11.48 (1H, s)
Mass spectrometric value (ESI-MS) 533 (M−1)

Compound 883 N-[2-(3-Fluoro-benzylidene-hydrazinocarbonyl)-4-piperidin-1-yl-phenyl]-3-(2-hydroxy-ethylsulfanylmethyl)-benzamide The title compound 883 was produced in substantially the same manner as in Example F.
$^1$H-NMR (CDCl$_3$, 400 MHz): δ 1.44 (2H, m), 1.57 (4H, m), 2.65 (2H, t, J=6.9 Hz), 2.99 (4H, m), 3.82 (2H, s), 3.92 (2H, m), 6.80-7.22 (3H, m), 7.36 (1H, m), 7.53 (3H, m), 7.66 (1H, m), 7.80 (1H, s), 8.00 (1H, d, J=6.6 Hz), 8.30 (2H, m), 10.65 (1H, s), 11.46 (1H, s)
Mass spectrometric value (ESI-MS) 533 (M−1)

Compound 884 N-[2-(4-Chloro-3-trifluoromethyl-benzylidene-hydrazinocarbonyl)-4-piperidin-1-yl-phenyl]-3-(2-hydroxy-ethylsulfanylmethyl)-benzamide The title compound 884 was produced in substantially the same manner as in Example F.
$^1$H-NMR (CDCl$_3$, 400 MHz): δ 1.36 (2H, m), 1.44 (4H, m), 2.65 (2H, t, J=7.2 Hz), 2.86 (4H, m), 3.82 (2H, s), 3.92 (2H, t, J=7.1 Hz), 6.90 (1H, d, J=8.0 Hz), 6.97 (1H, s), 7.57 (3H, m), 7.76 (1H, s), 8.04 (2H, d, J=6.8 Hz), 8.14 (1H, d, J=9.8 Hz), 8.23 (1H, s), 8.43 (1H, s), 11.09 (1H, s), 11.38 (1H, s)
Mass spectrometric value (ESI-MS) 617 (M−1)

Compound 885 3-(2-Hydroxy-ethylsulfanylmethyl)-N-[2-(4-methoxy-benzylidene-hydrazinocarbonyl)-4-piperidin-1-yl-phenyl]-benzamide The title compound 885 was produced in substantially the same manner as in Example F.
$^1$H-NMR (CDCl$_3$, 400 MHz): δ 1.47 (2H, m), 1.62 (4H, m), 2.64 (2H, t, J=7.1 Hz), 3.04 (4H, m), 3.80 (3H, s), 3.81 (2H, s), 3.92 (2H, m), 6.89 (2H, d, J=8.8 Hz), 7.02 (1H, m), 7.24 (1H, m), 7.52 (2H, m), 7.76 (3H, m), 7.99 (1H, d, J=7.3 Hz), 8.25 (1H, s), 8.40 (1H, d, J=9.0 Hz), 10.50 (1H, s), 11.59 (1H, s)
Mass spectrometric value (ESI-MS) 545 (M−1)

Compound 886 3-{3-[2-(3,4-Dimethyl-benzylidene-hydrazinocarbonyl)-4-piperidin-1-yl-phenylcarbamoyl]-benzylsulfanyl}-propionic acid The title compound 886 was produced in substantially the same manner as in Example F.
$^1$H-NMR (CDCl$_3$, 400 MHz): δ 1.37 (2H, m), 1.52 (4H, m), 2.20 (6H, s), 2.75 (2H, m), 2.84 (2H, m), 2.94 (4H, m), 3.94 (2H, s), 6.93 (1H, d, J=7.8 Hz), 7.06 (1H, d, J=7.6 Hz), 7.11 (1H, s), 7.38-7.52 (3H, m), 7.55 (1H, s), 7.94 (1H, s), 8.02 (1H, d, J=6.8 Hz), 8.25 (1H, d, J=9.0 Hz), 8.28 (1H, s), 10.85 (1H, s), 11.36 (1H, s)
Mass spectrometric value (ESI-MS) 571 (M−1)

Compound 887 3-{3-[2-(4-Methyl-benzylidene-hydrazinocarbonyl)-4-piperidin-1-yl-phenylcarbamoyl]-benzylsulfanyl}-propionic acid The title compound 887 was produced in substantially the same manner as in Example F.
$^1$H-NMR (CDCl$_3$, 400 MHz): δ 1.33 (2H, m), 1.47 (4H, m), 2.29 (3H, s), 2.70 (2H, t, J=6.4 Hz), 2.80 (2H, t, J=6.3 Hz), 2.90 (4H, m), 3.89 (2H, s), 6.91 (1H, d, J=8.8 Hz), 7.12 (3H, m), 7.40-7.50 (2H, m), 7.61 (2H, d, J=7.8 Hz), 7.93 (1H, s), 7.97 (1H, d, J=7.3 Hz), 8.20 (1H, d, J=9.0 Hz), 8.35 (1H, s), 11.03 (1H, s), 11.32 (1H, s)
Mass spectrometric value (ESI-MS) 557 (M−1)

Compound 888 3-{3-[2-(4-Fluoro-benzylidene-hydrazinocarbonyl)-4-piperidin-1-yl-phenylcarbamoyl]-benzylsulfanyl}-propionic acid The title compound 888 was produced in substantially the same manner as in Example F.
$^1$H-NMR (CD$_3$OD, 400 MHz): δ 1.62 (2H, m), 1.74 (4H, m), 2.55 (2H, t, J=6.8 Hz), 2.68 (2H, t, J=7.0 Hz), 3.23 (4H, m), 3.86 (2H, s), 7.10-7.25 (3H, m), 7.36 (1H, d, J=2.9 Hz), 7.47 (1H, dd, J=7.1 Hz, J=7.1 Hz), 7.57 (1H, d, J=7.3 Hz), 7.85 (3H, m), 7.93 (1H, m), 8.32 (2H, m)
Mass spectrometric value (ESI-MS) 561 (M−1)

Compound 889 3-{3-[2-(4-Chloro-3-trifluoromethyl-benzylidene-hydrazinocarbonyl)-4-piperidin-1-yl-phenylcarbamoyl]-benzylsulfanyl}-propionic acid The title compound 889 was produced in substantially the same manner as in Example F.
$^1$H-NMR (CD$_3$OD, 400 MHz): δ 1.62 (2H, m), 1.74 (4H, m), 2.54 (2H, t, J=7.0 Hz), 2.68 (2H, t, J=7.0 Hz), 3.22 (4H, m), 3.86 (2H, s), 7.22 (1H, m), 7.36 (1H, m), 7.48 (1H, dd, J=7.6 Hz, J=7.6 Hz), 7.57 (1H, m), 7.67 (1H, m), 7.83 (1H, d, J=7.3 Hz), 7.93 (1H, s), 8.03 (1H, d, J=9.0 Hz), 8.29 (2H, m), 8.36 (1H, m)
Mass spectrometric value (ESI-MS) 646 (M−1)

Compound 890 3-{3-[2-(4-Methoxy-benzylidene-hydrazinocarbonyl)-4-piperidin-1-yl-phenylcarbamoyl]-benzylsulfanyl}-propionic acid The title compound 890 was produced in substantially the same manner as in Example F.
$^1$H-NMR (CDCl$_3$, 400 MHz): δ 1.35 (2H, m), 1.49 (4H, m), 2.71 (2H, m), 2.80 (2H, m), 2.92 (4H, m), 3.76 (3H, s), 3.89 (2H, s), 6.80 (2H, d, J=8.8 Hz), 6.92 (1H, d, J=7.3 Hz), 7.15 (1H, s), 7.45 (2H, m), 7.64 (2H, d, J=8.6 Hz), 7.95 (2H, m), 8.24 (1H, d, J=9.0 Hz), 8.31 (1H, s), 10.97 (1H, bs), 11.37 (1H, s)
Mass spectrometric value (ESI-MS) 573 (M−1)

Compound 891 {3-[2-(4-Chloro-3-trifluoromethyl-benzylidene-hydrazinocarbonyl)-4-piperidin-1-yl-phenylcarbamoyl]-benzylsulfanyl}-acetic acid The title compound 891 was produced in substantially the same manner as in Example F.
$^1$H-NMR (CD$_3$OD, 400 MHz): δ 1.63 (2H, m), 1.75 (4H, m), 3.11 (2H, s), 3.24 (4H, m), 3.94 (2H, s), 7.22 (1H, dd, J=9.2 Hz, J=2.8 Hz), 7.37 (1H, d, J=2.7 Hz), 7.48 (1H, dd, J=7.7 Hz, J=7.7 Hz), 7.58 (1H, d, J=8.0 Hz), 7.67 (1H, d, J=8.3 Hz), 7.84 (1H, d, J=8.0 Hz), 7.95 (1H, s), 8.03 (1H, d, J=8.6 Hz), 8.28 (2H, m), 8.37 (1H, s)
Mass spectrometric value (ESI-MS) 631 (M−1)

Compound 892 {3-[2-(4-Methoxy-benzylidene-hydrazinocarbonyl)-4-piperidin-1-yl-phenylcarbamoyl]-benzylsulfanyl}-acetic acid The title compound 892 was produced in substantially the same manner as in Example F.
$^1$H-NMR (CDCl$_3$, 400 MHz): δ 1.39 (2H, m), 1.53 (4H, m), 2.93 (4H, m), 3.21 (2H, s), 3.77 (3H, s), 3.98 (2H, s), 6.82 (2H, d, J=8.6 Hz), 6.93 (1H, d, J=9.3 Hz), 7.22 (1H, s), 7.48 (2H, m), 7.63 (2H, d, J=8.3 Hz), 7.82 (1H, s), 7.98 (1H, d, J=7.1 Hz), 8.25 (1H, d, J=8.8 Hz), 8.32 (1H, s), 10.93 (1H, s), 11.43 (1H, s)
Mass spectrometric value (ESI-MS) 559 (M−1)

Compound 893 3-(7,8-Dihydro-5H-1,6,9-triaza-anthracen-6-ylmethyl)-N-[2-(3,4-dimethyl-benzylidene-hydrazinocarbonyl)-4-piperidin-1-yl-phenyl]-benzamide The title compound 893 was produced in substantially the same manner as in Example F.
$^1$H-NMR (CDCl$_3$, 400 MHz): δ 1.32 (2H, m), 1.40 (4H, m), 2.22 (6H, s), 2.83 (4H, m), 2.97 (2H, t, J=5.7 Hz), 3.31 (2H, t, J=6.0 Hz), 3.84 (4H, s), 6.92 (1H, d, J=9.0 Hz), 7.09 (2H, m), 7.35 (1H, m), 7.45 (2H, m), 7.61 (2H, m), 7.77 (1H, s), 7.95 (1H, d, J=7.3 Hz), 8.02 (2H, m), 8.26 (1H, d, J=9.0 Hz), 8.49 (1H, s), 8.97 (1H, dd, J=4.3 Hz, J=1.8 Hz), 11.05 (1H, s), 11.41 (1H, s)
Mass spectrometric value (ESI-MS) 650 (M−1)

Compound 894 3-(7,8-Dihydro-5H-1,6,9-triaza-anthracen-6-ylmethyl)-N-[2-(4-methyl-benzylidene-hydrazinocarbonyl)-4-piperidin-1-yl-phenyl]-benzamide The title compound 894 was produced in substantially the same manner as in Example F.
$^1$H-NMR (CDCl$_3$, 400 MHz): δ 1.31 (2H, m), 1.39 (4H, m), 2.33 (3H, s), 2.82 (4H, m), 2.97 (2H, m), 3.31 (2H, t, J=6.0 Hz), 3.84 (4H, m), 6.92 (1H, d, J=8.1 Hz), 7.07 (1H, s), 7.15 (2H, d, J=8.1 Hz), 7.35 (1H, m), 7.47 (1H, dd, J=7.6 Hz, J=7.6 Hz), 7.60 (1H, d, J=7.3 Hz), 7.65 (2H, d, J=7.1 Hz), 7.77 (1H, s), 7.94 (1H, d, J=7.3 Hz), 8.02 (2H, m), 8.26 (1H, d, J=9.0 Hz), 8.52 (1H, s), 8.97 (1H, dd, J=4.3 Hz, J=1.8 Hz), 11.08 (1H, s), 11.39 (1H, s)
Mass spectrometric value (ESI-MS) 636 (M−1)

Compound 895 3-(7,8-Dihydro-5H-1,6,9-triaza-anthracen-6-ylmethyl)-N-[2-(4-fluoro-benzylidene-hydrazinocarbonyl)-4-piperidin-1-yl-phenyl]-benzamide The title compound 895 was produced in substantially the same manner as in Example F.
$^1$H-NMR (CDCl$_3$, 400 MHz): δ 1.20-1.40 (6H, m), 2.75 (4H, m), 2.94 (2H, m), 3.25 (2H, m), 3.82 (2H, s), 3.83 (2H, s), 6.89 (1H, d, J=8.8 Hz), 7.00 (2H, m), 7.10 (1H, s), 7.37 (1H, m), 7.46 (1H, dd, J=7.7 Hz, J=7.7 Hz), 7.59 (1H, d, J=7.3 Hz), 7.70 (2H, m), 7.77 (1H, s), 7.94 (1H, d, J=7.8 Hz), 8.04 (2H, m), 8.26 (1H, d, J=9.0 Hz), 8.61 (1H, s), 8.94 (1H, m), 11.45-11.75 (2H, m)
Mass spectrometric value (ESI-MS) 640 (M−1)

Compound 896 3-(7,8-Dihydro-5H-1,6,9-triaza-anthracen-6-ylmethyl)-N-[2-(3-fluoro-benzylidene-hydrazinocarbonyl)-4-piperidin-1-yl-phenyl]-benzamide The title compound 896 was produced in substantially the same manner as in Example F.
$^1$H-NMR (CDCl$_3$, 400 MHz): δ 1.29 (2H, m), 1.36 (4H, m), 2.79 (4H, m), 2.97 (2H, m), 3.28 (2H, t, J=6.0 Hz), 3.84 (2H, s), 3.85 (2H, s), 6.90 (1H, d, J=8.3 Hz), 7.03 (1H, m), 7.09 (1H, s), 7.28-8.00 (5H, m), 7.61 (1H, d, J=7.3 Hz), 7.77 (1H, s), 7.94 (1H, d, J=7.6 Hz), 8.05 (2H, m), 8.22 (1H, d, J=9.0 Hz), 8.60 (1H, s), 8.97 (1H, dd, J=4.1 Hz, J=2.0 Hz), 11.38 (1H, s), 11.55 (1H, s)
Mass spectrometric value (ESI-MS) 640 (M−1)

Compound 897 N-[2-(4-Chloro-3-trifluoromethyl-benzylidene-hydrazinocarbonyl)-4-piperidin-1-yl-phenyl]-3-(7,8-dihydro-5H-1,6,9-triaza-anthracen-6-ylmethyl)-benzamide The title compound 897 was produced in substantially the same manner as in Example F.
$^1$H-NMR (CDCl$_3$, 400 MHz): δ 1.30 (2H, m), 1.37 (4H, m), 2.80 (4H, m), 2.97 (2H, t, J=5.9 Hz), 3.30 (2H, t, J=5.9 Hz), 3.86 (4H, m), 6.90 (1H, d, J=8.3 Hz), 7.02 (1H, s), 7.38 (1H, m), 7.51 (2H, d, J=8.3 Hz), 7.62 (1H, d, J=8.3 Hz), 7.78 (1H, s), 7.94 (2H, d, J=7.3 Hz), 8.00 (1H, s), 8.06 (2H, m), 8.17 (1H, d, J=8.3 Hz), 8.61 (1H, s), 8.98 (1H, m), 11.25 (1H, s), 11.46 (1H, s)
Mass spectrometric value (ESI-MS) 724 (M−1)

Compound 898 3-(7,8-Dihydro-5H-1,6,9-triaza-anthracen-6-ylmethyl)-N-[2-(4-methoxy-benzylidene-hydrazinocarbonyl)-4-piperidin-1-yl-phenyl]-benzamide The title compound 898 was produced in substantially the same manner as in Example F.
$^1$H-NMR (CDCl$_3$, 400 MHz): δ 1.31 (2H, m), 1.39 (4H, m), 2.83 (4H, m), 2.97 (2H, m), 3.30 (2H, t, J=5.6 Hz), 3.78 (5H, m), 3.83 (2H, s), 6.85 (2H, d, J=8.0 Hz), 6.92 (1H, d, J=7.1 Hz), 7.09 (1H, s), 7.35 (1H, m), 7.46 (1H, t, J=7.7 Hz), 7.59 (1H, d, J=7.6 Hz), 7.67 (2H, d, J=7.8 Hz), 7.76 (1H, s), 7.94 (1H, d, J=7.6 Hz), 8.02 (2H, m), 8.28 (1H, d, J=9.0 Hz), 8.49 (1H, s), 8.96 (1H, m), 11.08 (1H, bs), 11.44 (1H, s)
Mass spectrometric value (ESI-MS) 652 (M−1)

Compound 899 3-(2,3-Dihydroxy-propylsulfanylmethyl)-N-[2-(3,4-dimethyl-benzylidene-hydrazinocarbonyl)-4-piperidin-1-yl-phenyl]-benzamide The title compound 899 was produced in substantially the same manner as in Example F.
$^1$H-NMR (CD$_3$OD, 400 MHz): δ 1.62 (2H, m), 1.75 (4H, m), 2.29 (3H, s), 2.31 (3H, s), 2.50 (1H, m), 2.63 (1H, m), 3.23 (4H, m), 3.56 (2H, m), 3.74 (1H, m), 3.88 (2H, s), 7.21 (2H, m), 7.37 (1H, d, J=2.9 Hz), 7.48 (1H, dd, J=7.7 Hz, J=7.7 Hz), 7.53 (1H, d, J=7.8 Hz), 7.59 (1H, d, J=7.6 Hz), 7.65 (1H, s), 7.85 (1H, m), 7.93 (1H, m), 8.29 (1H, s), 8.37 (1H, d, J=9.2 Hz)
Mass spectrometric value (ESI-MS) 573 (M−1)

Compound 900 3-(2,3-Dihydroxy-propylsulfanylmethyl)-N-[2-(4-methyl-benzylidene-hydrazinocarbonyl)-4-piperidin-1-yl-phenyl]-benzamide The title compound 900 was produced in substantially the same manner as in Example F.

$^1$H-NMR (DMSO-$d_6$, 400 MHz): δ 1.57 (2H, m), 1.67 (4H, m), 2.35 (3H, s), 2.40 (1H, m), 2.58 (1H, m), 3.15-3.36 (6H, m), 3.60 (1H, m), 3.86 (2H, s), 4.55 (1H, m), 4.81 (1H, m), 7.19 (1H, m), 7.28 (2H, d, J=8.1 Hz), 7.32 (1H, d, J=2.4 Hz), 7.53 (2H, m), 7.65 (2H, d, J=8.1 Hz), 7.77 (1H, m), 7.87 (1H, s), 8.29 (1H, d, J=8.3 Hz), 8.41 (1H, s), 11.42 (1H, bs), 11.95 (1H, bs)

Mass spectrometric value (ESI-MS) 559 (M−1)

Compound 901 3-(2,3-Dihydroxy-propylsulfanylmethyl)-N-[2-(4-fluoro-benzylidene-hydrazinocarbonyl)-4-piperidin-1-yl-phenyl]-benzamide The title compound 901 was produced in substantially the same manner as in Example F.

$^1$H-NMR (CD$_3$OD, 400 MHz): δ 1.62 (2H, m), 1.74 (4H, m), 2.50 (1H, m), 2.62 (1H, m), 3.23 (4H, m), 3.55 (2H, m), 3.75 (1H, m), 3.88 (2H, s), 7.17 (2H, dd, J=8.7 Hz, J=8.7 Hz), 7.22 (1H, dd, J=9.0 Hz, J=2.7 Hz), 7.37 (1H, d, J=2.7 Hz), 7.48 (1H, dd, J=7.5 Hz, J=7.5 Hz), 7.58 (1H, d, J=7.6 Hz), 7.80-7.95 (4H, m), 8.34 (1H, s), 8.37 (1H, d, J=9.3 Hz)

Mass spectrometric value (ESI-MS) 563 (M−1)

Compound 902 3-(2,3-Dihydroxy-propylsulfanylmethyl)-N-[2-(3-fluoro-benzylidene-hydrazinocarbonyl)-4-piperidin-1-yl-phenyl]-benzamide The title compound 902 was produced in substantially the same manner as in Example F.

$^1$H-NMR (DMSO-$d_6$, 400 MHz): δ 1.57 (2H, m), 1.67 (4H, m), 2.04 (1H, m), 2.58 (1H, m), 3.19-3.40 (6H, m), 3.60 (1H, m), 3.86 (2H, s), 4.54 (1H, t, J=5.7 Hz), 4.80 (1H, d, J=3.5 Hz), 7.20 (1H, m), 7.29 (2H, m), 7.44-7.64 (5H, m), 7.76 (1H, d, J=7.6 Hz), 7.87 (1H, s), 8.25 (1H, d, J=9.0 Hz), 8.44 (1H, s), 11.30 (1H, s), 12.10 (1H, s)

Mass spectrometric value (ESI-MS) 563 (M−1)

Compound 903 N-[2-(4-Chloro-3-trifluoromethyl-benzylidene-hydrazinocarbonyl)-4-piperidin-1-yl-phenyl]-3-(2,3-dihydroxy-propyl-sulfanylmethyl)-benzamide The title compound 903 was produced in substantially the same manner as in Example F.

$^1$H-NMR (CD$_3$OD, 400 MHz): δ 1.63 (2H, m), 1.75 (4H, m), 2.50 (1H, m), 2.62 (1H, m), 3.24 (4H, m), 3.54 (2H, m), 3.74 (1H, m), 3.88 (2H, s), 7.23 (1H, dd, J=9.1 Hz, J=2.8 Hz), 7.38 (1H, d, J=2.7 Hz), 7.48 (1H, dd, J=7.7 Hz, J=7.7 Hz), 7.58 (1H, d, J=7.8 Hz), 7.68 (1H, d, J=8.3 Hz), 7.84 (1H, d, J=7.8 Hz), 7.93 (1H, s), 8.06 (1H, d, J=8.3 Hz), 8.29 (1H, s), 8.34 (1H, d, J=9.0 Hz), 8.37 (1H, s)

Mass spectrometric value (ESI-MS) 647 (M−1)

Compound 904 3-(2,3-Dihydroxy-propylsulfanylmethyl)-N-[2-(4-methoxy-benzylidene-hydrazinocarbonyl)-4-piperidin-1-yl-phenyl]-benzamide The title compound 904 was produced in substantially the same manner as in Example F.

$^1$H-NMR (DMSO-$d_6$, 400 MHz): δ 1.57 (2H, m), 1.68 (4H, m), 2.40 (1H, m), 2.58 (1H, m), 3.15-3.40 (6H, m), 3.61 (1H, m), 3.82 (3H, s), 3.86 (2H, s), 7.02 (2H, d, J=8.8 Hz), 7.21 (1H, m), 7.33 (1H, m), 7.53 (2H, m), 7.70 (2H, d, J=8.8 Hz), 7.77 (1H, d, J=7.6 Hz), 7.87 (1H, s), 8.31 (1H, d, J=9.0 Hz), 8.39 (1H, s), 11.44 (1H, s), 11.87 (1H, s)

Mass spectrometric value (ESI-MS) 575 (M−1)

Compound 905 3-{[Bis-(2-diethylamino-ethyl)-amino]-methyl}-N-[2-(3,4-dimethyl-benzylidene-hydrazinocarbonyl)-4-piperidin-1-yl-phenyl]-benzamide The title compound 905 was produced in substantially the same manner as in Example F.

$^1$H-NMR (CDCl$_3$, 400 MHz): δ 0.99 (12H, t, J=7.1 Hz), 1.44 (2H, m), 1.57 (4H, m), 2.30 (6H, s), 2.50 (8H, m), 2.61 (8H, m), 3.00 (4H, m), 3.73 (2H, s), 7.02 (2H, m), 7.18 (1H, d, J=7.3 Hz), 7.42 (1H, dd, J=7.6 Hz, J=7.6 Hz), 7.51 (1H, m), 7.57 (1H, m), 7.67 (1H, s), 7.87 (1H, d, J=7.8 Hz), 7.97 (1H, s), 8.32 (2H, m), 11.14 (1H, s)

Mass spectrometric value (ESI-MS) 681 (M−1)

Compound 906 3-{[Bis-(2-diethylamino-ethyl)-amino]-methyl}-N-[2-(4-methyl-benzylidene-hydrazinocarbonyl)-4-piperidin-1-yl-phenyl]-benzamide The title compound 906 was produced in substantially the same manner as in Example F.

$^1$H-NMR (CDCl$_3$, 400 MHz): δ 1.00 (12H, t, J=7.2 Hz), 1.25 (2H, m), 1.34 (4H, m), 2.37 (3H, s), 2.51 (8H, m), 2.62 (8H, m), 2.80 (4H, m), 3.75 (2H, s), 6.85 (1H, m), 6.97 (1H, m), 7.20 (2H, d, J=8.0 Hz), 7.43 (1H, d, J=7.6 Hz), 7.59 (1H, d, J=7.3 Hz), 7.75 (2H, d, J=7.8 Hz), 7.86 (1H, d, J=7.8 Hz), 8.00 (1H, s), 8.08 (1H, d, J=9.0 Hz), 8.59 (1H, s), 11.20 (1H, s)

Mass spectrometric value (ESI-MS) 667 (M−1)

Compound 907 3-{[Bis-(2-diethylamino-ethyl)-amino]-methyl}-N-[2-(4-fluoro-benzylidene-hydrazinocarbonyl)-4-piperidin-1-yl-phenyl]-benzamide The title compound 907 was produced in substantially the same manner as in Example F.

$^1$H-NMR (CDCl$_3$, 400 MHz): δ 1.00 (12H, t, J=7.1 Hz), 1.26 (2H, m), 1.35 (4H, m), 2.51 (8H, m), 2.62 (8H, m), 2.81 (4H, m), 3.75 (2H, s), 6.85 (1H, d, J=9.0 Hz), 6.94 (1H, s), 7.10 (2H, dd, J=8.5 Hz, J=8.5 Hz), 7.44 (1H, d, J=7.6 Hz, J=7.6 Hz), 7.60 (1H, d, J=7.3 Hz), 7.85 (3H, m), 8.00 (1H, s), 8.03 (1H, d, J=9.0 Hz), 8.61 (1H, s), 11.14 (2H, m)

Mass spectrometric value (ESI-MS) 671 (M−1)

Compound 908 3-{[Bis-(2-diethylamino-ethyl)-amino]-methyl}-N-[2-(3-fluoro-benzylidene-hydrazinocarbonyl)-4-piperidin-1-yl-phenyl]-benzamide The title compound 908 was produced in substantially the same manner as in Example F.

$^1$H-NMR (CDCl$_3$, 400 MHz): δ 1.00 (12H, t, J=7.1 Hz), 1.24 (2H, m), 1.33 (4H, m), 2.51 (8H, m), 2.62 (8H, m), 2.78 (4H, m), 3.76 (2H, s), 6.84 (1H, d, J=9.3 Hz), 6.91 (1H, s), 7.11 (1H, m), 7.34-7.48 (2H, m), 7.58-7.68 (3H, m), 7.87 (1H, d, J=7.8 Hz), 8.00 (2H, m), 8.61 (1H, s)

Mass spectrometric value (ESI-MS) 671 (M−1)

Compound 909 3-{[Bis-(2-diethylamino-ethyl)-amino]-methyl}-N-[2-(4-chloro-3-trifluoromethyl-benzylidene-hydrazinocarbonyl)-4-piperidin-1-yl-phenyl]-benzamide The title compound 909 was produced in substantially the same manner as in Example F.

¹H-NMR (CDCl₃, 400 MHz): δ 1.00 (12H, t, J=7.1 Hz), 1.21 (2H, m), 1.30 (4H, m), 2.51 (8H, m), 2.62 (8H, m), 2.75 (4H, m), 3.77 (2H, s), 6.80 (1H, d, J=8.8 Hz), 6.88 (1H, s), 7.47 (1H, dd, J=7.7 Hz, J=7.7 Hz), 7.57 (1H, d, J=8.5 Hz), 7.64 (1H, d, J=7.6 Hz), 7.86 (1H, d, J=7.6 Hz), 7.91 (1H, d, J=9.0 Hz), 8.02 (1H, s), 8.08 (1H, d, J=8.0 Hz), 8.12 (1H, s), 8.67 (1H, s)

Mass spectrometric value (ESI-MS) 754 (M−1)

Compound 910 3-{[Bis-(2-diethylamino-ethyl)-amino]-methyl}-N-[2-(4-methoxy-benzylidene-hydrazinocarbonyl)-4-piperidin-1-yl-phenyl]-benzamide The title compound 910 was produced in substantially the same manner as in Example F.

¹H-NMR (CDCl₃, 400 MHz): δ 1.00 (12H, t, J=7.1 Hz), 1.28 (2H, m), 1.38 (4H, m), 2.51 (8H, m), 2.61 (8H, m), 2.83 (4H, m), 3.75 (2H, s), 3.84 (3H, s), 6.85-7.00 (4H, m), 7.43 (1H, dd, J=7.6 Hz, J=7.6 Hz), 7.59 (1H, d, J=7.6 Hz), 7.79 (2H, d, J=8.5 Hz), 7.86 (1H, d, J=7.6 Hz), 7.99 (1H, s), 8.12 (1H, d, J=9.3 Hz), 8.51 (1H, s), 11.19 (1H, s)

Mass spectrometric value (ESI-MS) 682 (M−1)

Example G

Compound 911 N-[2-(4-Chloro-3-trifluoromethyl-benzylidene-hydrazinocarbonyl)-4-dipropylamino-phenyl]-3-{[(2-diethylamino-ethyl)-methyl-amino]-methyl}-benzamide 5-Amino-2-nitro-benzoic acid methyl ester (compound A') (800 mg) was dissolved in dry THF (15 ml). Propionaldehyde (compound D) (870 μl) dissolved in a mixed liquid composed of 3 M sulfuric acid (4 ml) and THF (1 ml) was added to the solution at room temperature. Subsequently, sodium borohydride (231 mg) was added thereto at 0° C., and the mixture was stirred at room temperature for 3 hr. Thereafter, distilled water was added thereto, and the mixture was subjected to separatory extraction with chloroform. The organic layer was washed with saturated brine, was dried over sodium sulfate and was then concentrated. The residue was purified by column chromatography using a hexane-acetone system to give 2-nitro-5-propylamino-benzoic acid methyl ester as a useful intermediate (608 mg, yield 63%).

2-Nitro-5-propylamino-benzoic acid methyl ester (608 mg) produced by the above reaction was dissolved in dry THF (15 ml). Propionaldehyde (compound D) (461 μl) dissolved in a mixed liquid composed of 3 M sulfuric acid (2.1 ml) and THF (1 ml) was added to the solution at room temperature. Subsequently, sodium borohydride (145 mg) was added thereto at 0° C., and the mixture was stirred at room temperature for 3 hr. Thereafter, distilled water was added thereto, and the mixture was subjected to separatory extraction with chloroform. The organic layer was washed with saturated brine, was dried over sodium sulfate, and was then concentrated. The residue was purified by column chromatography using a hexane-acetone system to give 5-dipropylamino-2-nitro-benzoic acid methyl ester as a useful intermediate (149 mg, yield 21%).

5-Dipropylamino-2-nitro-benzoic acid methyl ester (467 mg) produced by the above reaction was dissolved in ethanol (5 ml), and 10% palladium-carbon (45 mg) was added to the solution. The air in the reaction system was then replaced by hydrogen, and the reaction solution was stirred at room temperature for 15 hr. After the completion of the reaction, the reaction solution was filtered through Celite. The filtrate was concentrated, and the residue was purified by column chromatography using a hexane-acetone system to give 2-amino-5-dipropylamino-benzoic acid methyl ester (compound A) (243 mg, yield 58%) as a useful intermediate.

2-Amino-5-dipropylamino-benzoic acid methyl ester (compound A) (243 mg) produced by the above reaction was dissolved in anhydrous methylene chloride (3.0 ml). Subsequently, pyridine (170 μl) and 3-(chloromethyl)benzoyl chloride (compound B) (166 μl) were added to the solution at 0° C., and the mixture was stirred at 0° C. for one hr. After the completion of the reaction, distilled water was added thereto, and the mixture was subjected to separatory extraction with chloroform. The organic layer was washed with saturated brine, was dried over sodium sulfate, and was then concentrated. The residue was purified by column chromatography using a hexane-acetone system to give 2-(3-chloromethyl-benzoylamino)-5-dipropylamino-benzoic acid methyl ester as a useful intermediate (280 mg, yield 64%).

2-(3-Chloromethyl-benzoylamino)-5-dipropylamino-benzoic acid methyl ester (280 mg) produced by the above reaction was dissolved in anhydrous methylene chloride (2.0 ml). Triethylamine (45 μl) and N,N-diethyl-N'-methylethylenediamine (compound B') (50 μl) were added to the solution at room temperature, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated, and the residue was purified by column chromatography using a hexane-acetone system to give 2-(3-{[(2-diethylamino-ethyl)-methyl-amino]-methyl}-benzoylamino)-5-dipropylamino-benzoic acid methyl ester as a useful intermediate (164 mg, yield 50%).

2-(3-{[(2-Diethylamino-ethyl)-methyl-amino]-methyl}-benzoylamino)-5-dipropylamino-benzoic acid methyl ester (164 mg) produced by the above reaction was dissolved in ethanol (5.0 ml). Hydrazine monohydrate (200 μl) was added to the solution, and the mixture was heated under reflux with stirring for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give 3-{[(2-diethylamino-ethyl)-methyl-amino]-methyl}-N-(4-dipropylamino-2-hydrazinocarbonyl-phenyl)-benzamide as a hydrazine compound (96 mg, yield 58%).

3-{[(2-Diethylamino-ethyl)-methyl-amino]-methyl}-N-(4-dipropylamino-2-hydrazinocarbonyl-phenyl)-benzamide (47 mg) as the hydrazine compound produced by the above reaction was dissolved in anhydrous toluene (1.0 ml). 3-Trifluoromethyl-4-chlorobenzaldehyde (compound C) (40 μl) was added to the solution at room temperature, and the mixture was stirred at room temperature for 15 hr. After the completion of the reaction, the reaction product was purified by column chromatography eluted with a chloroform-methanol system to give the title compound 911 (57 mg, yield 88%).

$^1$H-NMR (CDCl$_3$, 400 MHz): δ 0.78 (6H, t, J=7.1 Hz), 1.04 (6H, t, J=7.1 Hz), 1.37 (4H, m), 2.26 (3H, s), 2.50-2.75 (8H, m), 2.85 (4H, m), 3.62 (2H, s), 6.49 (1H, d, J=7.8 Hz), 6.65 (1H, s), 7.44 (1H, dd, J=7.6 Hz, J=7.6 Hz), 7.55 (2H, m), 7.80-8.15 (5H, m), 8.63 (1H, s), 10.83 (1H, s)

Mass spectrometric value (ESI-MS) 685 (M−1)

Compound 912 3-{[(2-Diethylamino-ethyl)-methyl-amino]-methyl}-N-[4-dipropylamino-2-(4-methoxy-benzylidene-hydrazinocarbonyl)-phenyl]-benzamide The title compound 912 was produced in substantially the same manner as in Example G.

$^1$H-NMR (CDCl$_3$, 400 MHz): δ 0.81 (6H, t, J=7.1 Hz), 1.05 (6H, t, J=7.1 Hz), 1.42 (4H, m), 2.24 (3H, s), 2.50-2.70 (8H, m), 2.95 (4H, m), 3.61 (2H, s), 3.83 (3H, s), 6.57 (1H, d, J=9.0 Hz), 6.72 (1H, s), 6.91 (2H, d, J=8.6 Hz), 7.41 (1H, dd, J=7.6 Hz, J=7.6 Hz), 7.52 (1H, d, J=7.3 Hz), 7.76 (2H, d, J=8.3 Hz), 7.85 (1H, d, J=7.6 Hz), 7.95 (1H, s), 8.05 (1H, d, J=9.0 Hz), 8.45 (1H, s), 10.93 (1H, s)

Mass spectrometric value (ESI-MS) 614 (M−1)

Compound 913 3-({2-[Bis-(2-hydroxy-ethyl)-amino]-ethylamino}-methyl)-N-[2-(3,4-dimethyl-benzylidene-hydrazinocarbonyl)-4-piperidin-1-yl-phenyl]-benzamide The title compound 913 was produced in substantially the same manner as in Example F.

$^1$H-NMR (CDCl$_3$, 400 MHz): δ 1.41 (2H, m), 1.52 (4H, m), 2.25 (6H, s), 2.61 (4H, m), 2.71 (2H, m), 2.77 (2H, m), 2.97 (4H, m), 3.58 (4H, t, J=4.8 Hz), 3.92 (2H, s), 6.94 (1H, m), 7.07 (1H, s), 7.13 (1H, d, J=7.8 Hz), 7.40-7.55 (3H, m), 7.60 (1H, s), 7.93 (2H, m), 8.22 (1H, d, J=8.3 Hz), 8.38 (1H, s), 11.20 (1H, s)

Mass spectrometric value (ESI-MS) 613 (M−1)

Compound 914 3-({2-[Bis-(2-hydroxy-ethyl)-amino]-ethylamino}-methyl)-N-[2-(4-chloro-3-trifluoromethyl-benzylidene-hydrazinocarbonyl)-4-piperidin-1-yl-phenyl]-benzamide The title compound 914 was produced in substantially the same manner as in Example F.

$^1$H-NMR (CDCl$_3$, 400 MHz): δ 1.44 (2H, m), 1.54 (4H, m), 2.60 (4H, m), 2.73 (2H, m), 2.86 (2H, m), 3.00 (4H, m), 3.56 (4H, m), 3.97 (2H, s), 6.90 (1H, m), 7.10 (1H, m), 7.73-7.55 (4H, m), 7.92 (1H, m), 8.02 (1H, m), 8.15 (1H, m), 8.60 (1H, s)

Mass spectrometric value (ESI-MS) 687 (M−1)

Compound 915 3-({2-[Bis-(2-hydroxy-ethyl)-amino]-ethylamino}-methyl)-N-[2-(4-methoxy-benzylidene-hydrazinocarbonyl)-4-piperidin-1-yl-phenyl]-benzamide The title compound 915 was produced in substantially the same manner as in Example F.

$^1$H-NMR (CDCl$_3$, 400 MHz): δ 1.40 (2H, m), 1.51 (4H, m), 2.61 (4H, m), 2.70 (2H, m), 2.76 (2H, m), 2.96 (4H, m), 3.58 (4H, m), 3.81 (3H, s), 3.90 (2H, s), 6.88 (2H, d, J=8.1 Hz), 6.93 (1H, m), 7.07 (1H, s), 7.43 (1H, m), 7.50 (1H, m), 7.72 (2H, d, J=8.3 Hz), 7.92 (2H, m), 8.22 (1H, m), 8.36 (1H, s), 11.22 (1H, bs)

Mass spectrometric value (ESI-MS) 615 (M−1)

Compound 916 3-{[(2-Diethylamino-ethyl)-methyl-amino]-methyl}-N-[2-(3,4-dimethyl-benzylidene-hydrazinocarbonyl)-4-pyrrolidin-1-yl-phenyl]-benzamide The title compound 916 was produced in substantially the same manner as in Example F.

$^1$H-NMR (CD$_3$OD, 400 MHz): δ 1.06 (6H, t, J=7.1 Hz), 1.99 (4H, m), 2.26 (9H, m), 2.58 (2H, m), 2.70 (4H, m), 2.82 (2H, m), 3.30 (4H, m), 3.63 (2H, s), 6.75 (1H, dd, J=9.2 Hz, J=2.8 Hz), 6.90 (1H, d, J=2.7 Hz), 7.14 (1H, d, J=7.8 Hz), 7.47 (2H, m), 7.54 (1H, d, J=7.8 Hz), 7.57 (1H, s), 7.85 (1H, d, J=7.8 Hz), 7.92 (1H, s), 8.24 (1H, d, J=9.0 Hz), 8.28 (1H, s)

Mass spectrometric value (ESI-MS) 581 (M−1)

Compound 917 N-[2-(4-Chloro-3-trifluoromethyl-benzylidene-hydrazinocarbonyl)-4-pyrrolidin-1-yl-phenyl]-3-{[(2-diethylamino-ethyl)-methyl-amino]-methyl}-benzamide The title compound 917 was produced in substantially the same manner as in Example F.

$^1$H-NMR (CD$_3$OD, 400 MHz): δ 1.02 (6H, t, J=7.2 Hz), 1.99 (4H, m), 2.25 (3H, s), 2.57 (6H, m), 2.70 (2H, m), 3.30 (4H, m), 3.62 (2H, s), 6.74 (1H, dd, J=9.0 Hz, J=2.7 Hz), 6.89 (1H, d, J=2.7 Hz), 7.47 (1H, dd, J=7.6 Hz, J=7.6 Hz), 7.54 (1H, d, J=7.6 Hz), 7.60 (1H, d, J=8.3 Hz), 7.84 (1H, d, J=7.6 Hz), 7.93 (2H, m), 8.18 (1H, d, J=9.0 Hz), 8.23 (1H, m), 8.35 (1H, s)

Mass spectrometric value (ESI-MS) 655 (M−1)

Compound 918 3-{[(2-Diethylamino-ethyl)-methyl-amino]-methyl}-N-[2-(4-methoxy-benzylidene-hydrazinocarbonyl)-4-pyrrolidin-1-yl-phenyl]-benzamide The title compound 918 was produced in substantially the same manner as in Example F.

$^1$H-NMR (CD$_3$OD, 400 MHz): δ 1.04 (6H, t, J=7.2 Hz), 2.00 (4H, m), 2.26 (3H, s), 2.52-2.68 (6H, m), 2.75 (2H, m), 3.31 (4H, m), 3.64 (2H, s), 3.81 (3H, s), 6.75 (1H, dd, J=9.0 Hz, J=2.7 Hz), 6.89 (1H, d, J=2.7 Hz), 6.93 (2H, d, J=8.8 Hz), 7.47 (1H, t, J=7.7 Hz), 7.54 (1H, d, J=7.3 Hz), 7.73 (2H, d, J=9.0 Hz), 7.85 (1H, m), 7.91 (1H, s), 8.25 (1H, d, J=9.0 Hz), 8.28 (1H, s)

Mass spectrometric value (ESI-MS) 583 (M−1)

Compound 919 N-[2-(3,4-Dimethyl-benzylidene-hydrazinocarbonyl)-4-pyrrolidin-1-yl-phenyl]-3-(2-hydroxy-ethylsulfanylmethyl)-benzamide The title compound 919 was produced in substantially the same manner as in Example F.

$^1$H-NMR (CD$_3$OD, 400 MHz): δ 2.06 (4H, m), 2.29 (3H, s), 2.31 (3H, s), 2.57 (2H, t, J=7.0 Hz), 3.37 (4H, m), 3.68 (2H, t, J=6.8 Hz), 3.85 (2H, s), 6.81 (1H, d, J=8.1 Hz), 6.93 (1H, s), 7.02-7.23 (2H, m), 7.45-7.59 (2H, m), 7.64 (1H, s), 7.84 (1H, d, J=7.3 Hz), 7.90 (1H, s), 8.26 (2H, m)

Mass spectrometric value (ESI-MS) 529 (M−1)

Compound 920 N-[2-(4-Chloro-3-trifluoromethyl-benzylidene-hydrazinocarbonyl)-4-pyrrolidin-1-yl-phenyl]-3-(2-hydroxy-ethylsulfanylmethyl)-benzamide The title compound 920 was produced in substantially the same manner as in Example F.

$^1$H-NMR (CD$_3$OD, 400 MHz): δ 2.07 (4H, m), 2.57 (2H, t, J=7.0 Hz), 3.38 (4H, m), 3.68 (2H, t, J=6.8 Hz), 3.85 (2H, s), 6.83 (1H, m), 6.94 (1H, m), 7.48 (1H, dd, J=7.7 Hz, J=7.7 Hz), 7.57 (1H, d, J=7.3 Hz), 7.67 (1H, d, J=8.3 Hz), 7.83 (1H, d, J=7.6 Hz), 7.90 (1H, s), 8.04 (1H, d, J=8.0 Hz), 8.22 (1H, d, J=9.0 Hz), 8.32 (1H, s), 8.36 (1H, s)

Mass spectrometric value (ESI-MS) 603 (M−1)

Compound 921 3-(2-Hydroxy-ethylsulfanylmethyl)-N-[2-(4-methoxy-benzylidene-hydrazinocarbonyl)-4-pyrrolidin-1-yl-phenyl]-benzamide The title compound 921 was produced in substantially the same manner as in Example F.

$^1$H-NMR (CD$_3$OD, 400 MHz): δ 2.05 (4H, m), 2.57 (2H, t, J=7.0 Hz), 3.36 (4H, m), 3.68 (2H, t, J=6.8 Hz), 3.84 (5H, m), 6.81 (1H, d, J=8.8 Hz), 6.93 (1H, s), 6.97 (2H, d, J=9.0 Hz), 7.47 (1H, dd, J=7.7 Hz, J=7.7 Hz), 7.57 (1H, d, J=7.3 Hz), 7.77 (2H, d, J=8.8 Hz), 7.83 (1H, d, J=7.2 Hz), 7.90 (1H, s), 8.24 (1H, d, J=9.0 Hz), 8.27 (1H, s)

Mass spectrometric value (ESI-MS) 531 (M−1)

Compound 922 N-[2-(4-Chloro-3-trifluoromethyl-benzylidene-hydrazinocarbonyl)-4-(4-methyl-[1,4]diazepan-1-yl)-phenyl]-3-{[(2-diethylamino-ethyl)-methyl-amino]-methyl}-benzamide The title compound 922 was produced in substantially the same manner as in Example F.

$^1$H-NMR (CDCl$_3$, 400 MHz): δ 1.03 (6H, t, J=7.1 Hz), 1.67 (2H, m), 2.20-2.80 (18H, m), 3.04 (2H, m), 3.11 (2H, m), 3.63 (2H, s), 6.57 (1H, d, J=8.6 Hz), 6.64 (1H, s), 7.46 (1H, m), 7.57 (2H, m), 7.78 (1H, d, J=7.8 Hz), 7.94 (1H, d, J=8.8 Hz), 8.00 (1H, s), 8.08 (1H, d, J=7.8 Hz), 8.13 (1H, s), 8.64 (1H, s), 10.87 (1H, s)

Mass spectrometric value (ESI-MS) 698, 699 (M−1)

Compound 923 N-{2-(4-Chloro-3-trifluoromethyl-benzylidene-hydrazinocarbonyl)-4-[4-(2-hydroxy-ethyl)-piperazin-1-yl]-phenyl}-3-(2-hydroxy-ethyl-sulfanylmethyl)-benzamide The title compound 923 was produced in substantially the same manner as in Example F.

$^1$H-NMR (CD$_3$OD, 400 MHz): δ 2.57 (2H, t, J=7.0 Hz), 2.60 (2H, t, J=6.0 Hz), 2.72 (4H, m), 3.31 (4H, m), 3.68 (2H, t, J=7.0 Hz), 3.73 (2H, t, J=6.0 Hz), 3.85 (2H, s), 7.23 (1H, dd, J=9.0 Hz, J=2.7 Hz), 7.38 (1H, d, J=2.7 Hz), 7.48 (1H, dd, J=7.6 Hz, J=7.6 Hz), 7.58 (1H, d, J=7.8 Hz), 7.67 (1H, d, J=8.6 Hz), 7.84 (1H, d, J=7.6 Hz), 7.91 (1H, s), 8.02 (1H, d, J=8.6 Hz), 8.31 (1H, m), 8.37 (2H, m)

Mass spectrometric value (ESI-MS) 662 (M−1)

Compound 924 N-{2-(4-Chloro-3-trifluoromethyl-benzylidene-hydrazinocarbonyl)-4-[4-(2-hydroxy-ethyl)-piperazin-1-yl]-phenyl}-3-{[(2-diethylamino-ethyl)-methyl-amino]-methyl}-benzamide The title compound 924 was produced in substantially the same manner as in Example F.

$^1$H-NMR (CD$_3$OD, 400 MHz): δ 1.01 (6H, t, J=7.2 Hz), 2.26 (3H, s), 2.58 (8H, m), 2.70 (6H, m), 3.32 (4H, m), 3.64 (2H, s), 3.73 (2H, t, J=5.9 Hz), 7.22 (1H, dd, J=9.0 Hz, J=2.7 Hz), 7.39 (1H, d, J=2.7 Hz), 7.49 (1H, dd, J=7.7 Hz, J=7.7 Hz), 7.57 (1H, d, J=7.6 Hz), 7.65 (1H, d, J=8.5 Hz), 7.87 (1H, m), 7.93 (1H, s), 7.99 (1H, d, J=8.3 Hz), 8.28 (1H, m), 8.36 (2H, m)

Mass spectrometric value (ESI-MS) 714 (M−1)

Compound 925 1-{3-(4-Chloro-3-trifluoromethyl-benzylidene-hydrazinocarbonyl)-4-[3-(2-hydroxy-ethylsulfanylmethyl)-benzoylamino]-phenyl}-piperidine-3-carboxylic acid The title compound 925 was produced in substantially the same manner as in Example F.

$^1$H-NMR (DMSO-d$_6$, 400 MHz): δ 1.54-3.90 (15H, m), 7.24 (1H, m), 7.37 (1H, s), 7.54 (2H, m), 7.77 (1H, d, J=7.3 Hz), 7.82 (1H, d, J=8.3 Hz), 7.87 (1H, s), 8.05 (1H, d, J=8.1 Hz), 8.22 (2H, m), 8.54 (1H, s), 11.23 (1H, s), 12.34 (1H, s)

Mass spectrometric value (ESI-MS) 684 (M+23)

Compound 926 N-[2-(3,4-Dimethyl-benzylidene-hydrazinocarbonyl)-4-thiomorpholin-4-yl-phenyl]-3-(2-hydroxy-ethylsulfanylmethyl)-benzamide The title compound 926 was produced in substantially the same manner as in Example F.

$^1$H-NMR (DMSO-d$_6$, 400 MHz): δ 2.27 (3H, s), 2.28 (3H, s), 2.73 (4H, m), 3.32-3.60 (8H, m), 3.85 (2H, s), 7.22 (2H, m), 7.31 (1H, d, J=2.9 Hz), 7.43-7.59 (4H, m), 7.77 (1H, d, J=7.1 Hz), 7.87 (1H, s), 8.30 (1H, m), 8.36 (1H, s), 11.38 (1H, s), 11.91 (1H, s)

Mass spectrometric value (ESI-MS) 561 (M−1)

Compound 927 N-[2-(4-Chloro-3-trifluoromethyl-benzylidene-hydrazinocarbonyl)-4-thiomorpholin-4-yl-phenyl]-3-(2-hydroxy-ethylsulfanylmethyl)-benzamide The title compound 927 was produced in substantially the same manner as in Example F.

$^1$H-NMR (DMSO-d$_6$, 400 MHz): δ 2.72 (4H, m), 3.31 (2H, m), 3.56 (6H, m), 3.84 (2H, s), 4.79 (1H, m), 7.20 (1H, m), 7.29 (1H, m), 7.53 (2H, m), 7.77 (1H, d, J=7.6 Hz), 7.80 (1H, d, J=8.5 Hz), 7.86 (1H, s), 8.05 (1H, m), 8.21 (1H, s), 8.25 (1H, m), 8.48 (1H, s), 11.20 (1H, s), 12.21 (1H, s)

Mass spectrometric value (ESI-MS) 635 (M−1)

Compound 928 3-(2-Hydroxy-ethylsulfanylmethyl)-N-[2-(4-methoxy-benzylidene-hydrazinocarbonyl)-4-thiomorpholin-4-yl-phenyl]-benzamide The title compound 928 was produced in substantially the same manner as in Example F.

$^1$H-NMR (DMSO-d$_6$, 400 MHz): δ 2.73 (4H, m), 3.35 (2H, m), 3.50-3.60 (6H, m), 3.82 (3H, s), 3.85 (2H, s), 7.03 (2H, d, J=8.8 Hz), 7.20 (1H, dd, J=9.1 Hz, J=2.8 Hz), 7.31 (1H, d, J=2.7 Hz), 7.54 (2H, m), 7.71 (2H, d, J=8.6 Hz), 7.77 (1H, d, J=7.3 Hz), 7.87 (1H, s), 8.31 (1H, d, J=9.3 Hz), 8.38 (1H, s), 11.42 (1H, s), 11.87 (1H, s)

Mass spectrometric value (ESI-MS) 563 (M−1)

Compound 929 N-[2-(4-Chloro-3-trifluoromethyl-benzylidene-hydrazinocarbonyl)-4-thiomorpholin-4-yl-phenyl]-3-{[(2-diethylamino-ethyl)-methyl-amino]-methyl}-benzamide The title compound 929 was produced in substantially the same manner as in Example F.

$^1$H-NMR (CDCl$_3$, 400 MHz): δ 1.25 (6H, s), 2.28 (3H, s), 2.44 (4H, m), 2.56-2.76 (8H, m), 3.25 (4H, m), 3.65 (2H, s), 6.84 (1H, m), 7.00 (1H, s), 7.43-7.60 (3H, m), 7.88 (1H, m), 7.95-8.11 (4H, m), 8.60 (1H, s), 11.10 (1H, s)

Mass spectrometric value (ESI-MS) 687 (M−1)

Example H

Compound 930 N-[5-Bromo-3-(4-methoxy-benzylidene-hydrazinocarbonyl)-thiophen-2-yl]-3-dimethylaminomethyl-benzamide 2-Amino-thiophene-3-carboxylic acid methyl ester (compound A) (3.0 g) was dissolved in anhydrous methylene chloride (100 ml). Subsequently, pyridine (2.4 ml) and 3-(chloromethyl)benzoyl chloride (compound B) (2.8 ml) were added to the solution at 0° C., and the mixture was stirred at 0° C. for one hr. After the completion of the reaction, distilled water was added thereto, and the mixture was subjected to separatory extraction with chloroform. The organic layer was washed with saturated brine, was dried over sodium sulfate and was then concentrated. The residue was purified by column chromatography using a hexane-acetone system to give 2-(3-chloromethyl-benzoylamino)-thiophene-3-carboxylic acid methyl ester as a useful intermediate (4.7 g, yield 100%).

2-(3-Chloromethyl-benzoylamino)-thiophene-3-carboxylic acid methyl ester (2.0 g) produced by the above reaction was dissolved in anhydrous methylene chloride (60 ml). Triethylamine (3 ml) and dimethylamine hydrochloride (compound B') (1.1 g) were added to the solution at room temperature, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography using a hexane-acetone system to give 2-(3-dimethylaminomethyl-benzoylamino)-thiophene-3-carboxylic acid methyl ester as a useful intermediate (1.14 g, yield 52%).

2-(3-dimethylaminomethyl-benzoylamino)-thiophene-3-carboxylic acid methyl ester (1.14 g) produced by the above reaction was dissolved in monochlorobenzene. N-bromosuccinimide (877 mg) and 2,2'-azobisisobutyronitrile (81 mg) were added to the solution, and the mixture was stirred at 90° C. for 2 hr. After the completion of the reaction, the reaction solution was concentrated, and the residue was purified by column chromatography using a hexane-acetone system to give 5-bromo-2-(3-dimethylaminomethyl-benzoylamino)-thiophene-3-carboxylic acid methyl ester as a useful intermediate (706 mg, yield 54%).

5-Bromo-2-(3-dimethylaminomethyl-benzoylamino)-thiophene-3-carboxylic acid methyl ester (706 mg) produced by the above reaction was dissolved in ethanol (10 ml). Hydrazine monohydrate (1 ml) was added to the solution, and the mixture was stirred at room temperature for 15 hr. After the completion of the reaction, water was added thereto at room temperature, and the mixture was subjected to separatory extraction with chloroform. The organic layer was washed with saturated brine, was dried over sodium sulfate, and was then concentrated. The residue was purified by column chromatography eluted with a chloroform-methanol system to give N-(5-bromo-3-hydrazinocarbonyl-thiophen-2-yl)-3-dimethylaminomethyl-benzamide as a hydrazine compound (448 mg, yield 64%).

N-(5-bromo-3-hydrazinocarbonyl-thiophen-2-yl)-3-dimethylamino-methyl-benzamide (50 mg) as the hydrazine compound produced by the above reaction was dissolved in anhydrous toluene (1.0 ml). p-Methoxybenzaldehyde (compound C) (60 µl) was added to the solution at room temperature, and the mixture was stirred at room temperature for 15 hr. After the completion of the reaction, the reaction product was purified by column chromatography eluted with a chloroform-methanol system to give the title compound 930 (29 mg, yield 45%).

$^1$H-NMR (CDCl$_3$, 400 MHz): δ 2.22 (6H, s), 3.67 (2H, s), 3.78 (3H, s), 6.84 (2H, m), 7.42 (1H, dd, J=7.6 Hz, J=7.6 Hz), 7.54-7.61 (3H, m), 7.89 (1H, d, J=7.6 Hz), 7.93 (1H, s), 8.22 (1H, s), 9.87 (1H, bs), 12.93 (1H, bs)

Mass spectrometric value (ESI-MS) 515 (M−1)

Compound 931 3-{[(2-Diethylamino-ethyl)-methyl-amino]-methyl}-N-[2-(4-methoxy-benzylidene-hydrazinocarbonyl)-4-(4-methyl-[1,4]diazepan-1-yl)-phenyl]-benzamide The title compound 931 was produced in substantially the same manner as in Example F.

$^1$H-NMR (CDCl$_3$, 400 MHz): δ 1.03 (6H, t, J=7.2 Hz), 1.73 (2H, m), 2.24 (5H, m), 2.37 (2H, m), 2.44-2.60 (9H, m), 2.65 (2H, m), 3.12 (2H, m), 3.20 (2H, m), 3.61 (2H, s), 3.84 (3H, s), 6.62 (1H, m), 6.69-6.78 (2H, m), 6.92 (2H, d, J=8.5 Hz), 7.41 (1H, dd, J=7.6 Hz, J=7.6 Hz), 7.52 (1H, d, J=7.6 Hz), 7.80 (2H, d, J=8.1 Hz), 7.96 (1H, s), 8.08 (1H, d, J=9.0 Hz), 8.49 (1H, s), 11.01 (1H, s)

Mass spectrometric value (ESI-MS) 626 (M−1)

Compound 932 3-[(4-Chloro-3-trifluoromethyl-benzylidene)-amino]-2-[3-(2-hydroxy-ethylsulfanylmethyl)-phenyl]-6-(4-methyl-[1,4]diazepan-1-yl)-3H-quinazolin-4-one The title compound 932 was produced in substantially the same manner as in Example F. $^1$H-NMR (CDCl$_3$, 400 MHz): δ 2.10 (2H, m), 2.42 (3H, s), 2.55-2.68 (4H, m), 2.80 (2H, m), 3.58-3.84 (8H, m), 7.23 (1H, m), 7.34-7.44 (3H, m), 7.54 (2H, m), 7.68 (2H, m), 7.76 (1H, m), 7.95 (1H, d, J=1.7 Hz), 9.36 (1H, s)

Mass spectrometric value (ESI-MS) 652 (M+23)

Compound 933 2-(3-{[(2-Diethylamino-ethyl)-methyl-amino]-methyl}-phenyl)-3-[(4-methoxy-benzylidene)-amino]-6-(4-methyl-[1,4]diazepan-1-yl)-3H-quinazolin-4-one The title compound 933 was produced in substantially the same manner as in Example F.

$^1$H-NMR (CDCl$_3$, 400 MHz): δ 0.99 (6H, t, J=7.2 Hz), 2.06 (2H, m), 2.11 (3H, s), 2.39 (3H, s), 2.45-2.60 (10H, m), 2.76 (2H, m), 3.51 (2H, s), 3.62 (2H, t, J=6.3 Hz), 3.70 (2H, m), 3.84 (3H, s), 6.90 (2H, d, J=8.8 Hz), 7.22 (1H, dd, J=9.0 Hz, J=3.2 Hz), 7.35 (1H, m), 7.44 (1H, d, J=3.2 Hz), 7.57 (1H, m), 7.60-7.70 (4H, m), 8.88 (1H, s)

Mass spectrometric value (ESI-MS) 632 (M+23)

Compound 934 1-{3-(3,4-Dimethyl-benzylidene-hydrazinocarbonyl)-4-[3-(2-hydroxy-ethylsulfanylmethyl)-benzoylamino]-phenyl}-piperidine-3-carboxylic acid The title compound 934 was produced in substantially the same manner as in Example F.

$^1$H-NMR (DMSO-d$_6$, 400 MHz): δ 1.50-3.88 (21H, m), 7.14-7.60 (7H, m), 7.77 (1H, d, J=7.3 Hz), 7.87 (1H, s), 8.32 (1H, d, J=9.0 Hz), 8.40 (1H, s), 11.44 (1H, s), 12.01 (1H, s)

Mass spectrometric value (ESI-MS) 609 (M+23)

Example I

Compound 935 N-[2-(3,4-Dimethyl-benzylidene-hydrazinocarbonyl)-4-piperidin-1-yl-phenyl]-3,4-dimethoxy-benzamide 5-Chloro-2-nitro-benzoic acid (compound A') (10.0 g) was dissolved in ethanol (100 ml). Thionyl chloride (20 ml) was added dropwise to the solution at 0° C., and the mixture was then heated under reflux with stirring for 48 hr. After the completion of the reaction, the reaction solution was concentrated under the reduced pressure. Distilled water was added to the residue, and the mixture was neutralized with a saturated aqueous sodium hydrogencarbonate solution under ice cooling. The cooled solution was subjected to separatory extraction with ethyl acetate. The organic layer was dried over sodium sulfate and was then concentrated under the reduced pressure. The residue was purified by column chromatography eluted with a chloroform-methanol system to give 5-chloro-2-nitro-benzoic acid ethyl ester as a useful intermediate (11.0 g, yield 97%).

5-Chloro-2-nitro-benzoic acid ethyl ester (3.1 g) produced by the above production process was dissolved in N,N-dimethylformamide (30 ml). Potassium carbonate (3.8 g) and piperidine (compound D) (2.8 ml) were added to the solution at room temperature, and the mixture was then heated under reflux with stirring for 12 hr. After the completion of the reaction, distilled water was added thereto at room temperature, and the mixture was subjected to separatory extraction with ethyl acetate. The organic layer was washed with saturated brine, was dried over sodium sulfate, and was then concentrated under the reduced pressure to give crude 2-nitro-5-piperidin-1-yl-benzoic acid ethyl ester (3.81 g, crude yield 100%).

Subsequently, the crude 2-nitro-5-piperidin-1-yl-benzoic acid ethyl ester (3.8 g) was dissolved in methanol (35 ml). Platinum oxide (300 mg) was added to the solution at room temperature, the air in the reaction system was replaced by hydrogen, and the mixture was then stirred for 12 hr. After the completion of the reaction, the atmosphere in the reaction system was replaced by nitrogen, and the reaction solution was then filtered through Celite to remove platinum oxide and was then concentrated under the reduced pressure to give crude 2-amino-5-piperidin-1-yl-benzoic acid ethyl ester (compound A) as a useful intermediate (3.4 g, crude yield 100%).

Subsequently, crude 2-amino-5-piperidin-1-yl-benzoic acid ethyl ester (compound A) (1.3 g) was dissolved in anhydrous methylene chloride (100 ml). Triethylamine (5.6 ml) and 3,4-dimethoxy-benzoyl chloride (compound B) (1.8 g) were added at 0° C., and the mixture was stirred at room temperature for 24 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a hexane-chloroform system to give 2-(3,4-dimethoxy-benzoylamino)-5-piperidin-1-yl-benzoic acid ethyl ester (960 mg, yield 52%).

2-(3,4-Dimethoxy-benzoylamino)-5-piperidin-1-yl-benzoic acid ethyl ester (380 mg) produced by the above process was dissolved in ethanol (10 ml). Hydrazine monohydrate (3 ml) was added dropwise to the solution at room temperature, and the mixture was stirred at 90° C. for 1.5 hr. After the completion of the reaction, the reaction solution was allowed to stand for cooling, and the precipitated crystals were filtered through Kiriyama Rohto to give N-(2-hydrazinocarbonyl-4-piperidin-1-yl-phenyl)-3,4-dimethoxy-benzamide as a useful intermediate (270 mg, yield 71%).

Subsequently, N-(2-hydrazinocarbonyl-4-piperidin-1-yl-phenyl)-3,4-dimethoxy-benzamide (56 mg) produced by the above process was dissolved in anhydrous toluene (5 ml). 3,4-Dimethylbenzaldehyde (compound C) (40 mg) and a catalytic amount of acetic acid were added dropwise to the solution at room temperature, and the mixture was stirred at 90° C. for 16 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give the title compound 935 (74 mg, yield 96%).

$^1$H-NMR (CD$_3$OD, 400 MHz): δ 8.32 (1H, d, J=9.2 Hz), 8.28 (1H, s), 7.63 (1H, s), 7.59 (1H, dd, J=2.2 Hz, J=8.3 Hz), 7.54 (1H, d, J=1.9 Hz), 7.52 (1H, d, J=7.8 Hz), 7.36 (1H, d, J=2.7 Hz), 7.17-7.24 (2H, m), 7.06 (1H, d, J=8.6 Hz), 3.92 (3H, s), 3.90 (3H, s), 3.20-3.25 (4H, m), 2.30 (3H, s), 2.29 (3H, s), 1.70-1.80 (4H, m), 1.57-1.66 (2H, m)

Mass spectrometric value (ESI-MS) 513, 514 (M−1) 537, 538 (M+23)

Compound 936 3,4-Dimethoxy-N-[4-piperidin-1-yl-2-(pyridin-3-ylmethylene-hydrazinocarbonyl)-phenyl]-benzamide The title compound 936 was produced in substantially the same manner as in Example I.

$^1$H-NMR (CD$_3$OD, 400 MHz): δ 8.89 (1H, s), 8.55-8.60 (1H, m), 8.39 (1H, s), 8.34-8.39 (1H, m), 8.28 (1H, d, J=9.0 Hz), 7.48-7.61 (3H, m), 7.37 (1H, d, J=2.9 Hz), 7.22 (1H, dd, J=2.9 Hz, J=9.3 Hz), 7.06 (1H, d, J=8.3 Hz), 3.91 (3H, s), 3.90 (3H, s), 3.20-3.25 (4H, m), 1.70-1.80 (4H, m), 1.57-1.66 (2H, m)

Mass spectrometric value (ESI-MS) 486 (M−1)

Compound 937 N-[2-(1H-Imidazol-2-ylmethylene-hydrazinocarbonyl)-4-piperidin-1-yl-phenyl]-3,4-dimethoxy-benzamide The title compound 937 was produced in substantially the same manner as in Example I.

$^1$H-NMR (CD$_3$OD, 400 MHz): δ 8.34 (1H, d, J=9.0 Hz), 7.03-7.62 (8H, m), 3.93 (3H, s), 3.90 (3H, s), 3.15-3.19 (4H, m), 1.55-1.84 (6H, m)

Mass spectrometric value (ESI-MS) 475 (M−1)

Compound 938 N-[2-(4-Hydroxy-3-methoxy-benzylidene-hydrazinocarbonyl)-4-piperidin-1-yl-phenyl]-3,4-dimethoxy-benzamide The title compound 938 was produced in substantially the same manner as in Example I.

$^1$H-NMR (CD$_3$OD, 400 MHz): δ 8.32 (1H, d, J=9.3 Hz), 8.24 (1H, s), 7.71 (1H, d, J=1.7 Hz), 7.59 (1H, dd, J=1.9 Hz, J=8.3 Hz), 7.56 (1H, d, J=2.0 Hz), 7.36 (1H, d, J=2.9 Hz), 7.22 (1H, dd, J=2.9 Hz, J=9.3 Hz), 7.05-7.11 (2H, m), 6.82 (1H, d, J=8.0 Hz), 3.94 (3H, s), 3.92 (3H, s), 3.90 (3H, s), 3.21-3.25 (4H, m), 1.71-1.80 (4H, m), 1.58-1.67 (2H, m)

Mass spectrometric value (ESI-MS) 529, 531, 532 (M−1) 555 (M+23)

Compound 939 N-[2-(3,4-Dimethyl-benzylidene-hydrazinocarbonyl)-4-morpholin-4-yl-phenyl]-3,4-dimethoxy-benzamide The title compound 939 was produced in substantially the same manner as in Example I.

$^1$H-NMR (CD$_3$OD, 400 MHz): δ 8.37 (1H, d, J=9.3 Hz), 8.28 (1H, s), 7.65 (1H, s), 7.60 (1H, dd, J=2.2 Hz, J=8.3 Hz), 7.56 (1H, d, J=2.2 Hz), 7.50-7.55 (1H, m), 7.37 (1H, d, J=2.7 Hz), 7.21-7.26 (1H, m), 7.20 (1H, d, J=7.8 Hz), 7.08 (1H, d, J=8.3 Hz), 3.92 (3H, s), 3.91 (3H, s), 3.85-3.89 (4H, m), 3.20-3.29 (4H, m), 2.32 (3H, s), 2.30 (3H, s)

Mass spectrometric value (ESI-MS) 515 (M−1)

Compound 940 N-[2-(4-Hydroxy-3-methoxy-benzylidene-hydrazinocarbonyl)-4-morpholin-4-yl-phenyl]-3,4-dimethoxy-benzamide The title compound 940 was produced in substantially the same manner as in Example I.

$^1$H-NMR (CDCL$_3$, 400 MHz): δ 11.6 (1H, bs), 8.27-8.40 (2H, m), 7.55-7.62 (2H, m), 7.47-7.53 (1H, m), 7.40-7.44 (1H, m), 6.88-7.16 (4H, m), 3.98 (3H, s), 3.97 (3H, s), 3.94 (3H, s), 3.60-3.72 (4H, m), 2.97-3.05 (4H, m)

Mass spectrometric value (ESI-MS) 533, 534, 535 (M−1) 1067 (2M−1)

Compound 941 3,4-Dimethoxy-N-[2-(4-methoxy-benzylidene-hydrazinocarbonyl)-4-morpholin-4-yl-phenyl]-benzamide The title compound 941 was produced in substantially the same manner as in Example I.

$^1$H-NMR (CD$_3$OD, 400 MHz): δ 8.28-8.32 (1H, m), 7.83-7.89 (1H, m), 7.73-7.82 (2H, m), 7.53-7.66 (3H, m), 7.20-7.30 (1H, m), 7.05-7.12 (1H, m), 6.96-7.04 (2H, m), 3.83-3.95 (13H, m), 3.29-3.35 (4H, m)

Mass spectrometric value (ESI-MS) 519, 520 (M+1)

Example J

Compound 942 3-{[Bis-(2-hydroxy-propyl)-amino]-methyl}-N-[2-(4-chloro-3-trifluoromethyl-benzylidene-hydrazinocarbonyl)-4-piperidin-1-yl-phenyl]-benzamide 5-Chloro-2-nitro-benzoic acid (compound A') (10.0 g) was dissolved in ethanol (100 ml). Thionyl chloride (20 ml) was added dropwise to the solution at 0° C., and the mixture was then heated under reflux with stirring for 48 hr. After the completion of the reaction, the reaction solution was concentrated under the reduced pressure. Distilled water was added to the residue, and the mixture was neutralized with a saturated aqueous sodium hydrogencarbonate solution under ice cooling, and was then subjected to separatory extraction with ethyl acetate. The organic layer was dried over sodium sulfate and was then concentrated under the reduced pressure. The residue was purified by column chromatography eluted with a chloroform-methanol system to give 5-chloro-2-nitro-benzoic acid ethyl ester as a useful intermediate (11.0 g, yield 97%).

5-Chloro-2-nitro-benzoic acid ethyl ester (3.1 g) produced by the above process was dissolved in N,N-dimethylformamide (30 ml), potassium carbonate (3.8 g) and piperidine (compound D) (2.8 ml) were added to the solution at room temperature, and was then heated under reflux with stirring for 12 hr. After the completion of the reaction, distilled water was added thereto at room temperature, and the mixture was subjected to separatory extraction with ethyl acetate. The organic layer was washed with saturated brine, was dried over sodium sulfate, and was then concentrated under the reduced pressure to give crude 2-nitro-5-piperidin-1-yl-benzoic acid ethyl ester (3.8 g, crude yield 100%).

Subsequently, crude 2-nitro-5-piperidin-1-yl-benzoic acid ethyl ester (3.8 g) was dissolved in methanol (35 ml), and platinum oxide (300 mg) was added to the solution at room temperature. The air in the reaction system was replaced by hydrogen, and the mixture was then stirred for 12 hr. After the completion of the reaction, the atmosphere in the reaction system was replaced by nitrogen, and the reaction solution was then filtered through Celite to remove platinum oxide, and was then concentrated under the reduced pressure to give crude 2-amino-5-piperidin-1-yl-benzoic acid ethyl ester (compound A) as a useful intermediate (3.4 g, crude yield 100%).

2-Amino-5-piperidin-1-yl-benzoic acid ethyl ester (compound A) (1.6 g) synthesized by the above process was dissolved in anhydrous methylene chloride (20 ml). Pyridine (1.0 ml) and 3-(chloromethyl)benzoyl chloride (compound B) (1.2 ml) were added dropwise to the solution at 0° C., and the mixture was then stirred at room temperature for one hr. After the completion of the reaction, the reaction solution was concentrated under the reduced pressure. Distilled water was added to the residue, and the mixture was subjected to separatory extraction with ethyl acetate. The organic layer was dried over sodium sulfate and was then concentrated under the reduced pressure. The residue was purified by column chromatography eluted with a chloroform-methanol system to give 2-(3-chloromethyl-benzoylamino)-5-piperidin-1-yl-benzoic acid ethyl ester as a useful intermediate (1.7 g, yield 63%).

2-(3-Chloromethyl-benzoylamino)-5-piperidin-1-yl-benzoic acid ethyl ester (200 mg) produced by the above reaction was dissolved in anhydrous methylene chloride (2 ml). Triethylamine (150 μl) and diisopropanolamine (compound B') (150 mg) were added to the solution at room temperature, and the mixture was then stirred at that temperature for 36 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-{[bis-(2-hydroxy-propyl)-amino]-methyl}-benzoylamino)-5-piperidin-1-yl-benzoic acid ethyl ester as a useful intermediate (200 mg, yield 82%).

Subsequently, 2-(3-{[bis-(2-hydroxy-propyl)amino]-methyl}-benzoylamino)-5-piperidin-1-yl-benzoic acid ethyl ester (200 mg) was dissolved in ethanol (2 ml). Hydrazine monohydrate (200 μl) was added dropwise to the solution at room temperature, and the mixture was then stirred at that temperature for 12 hr. After the completion of the reaction, the reaction solution was concentrated under the reduced pressure. The residue was purified by column chromatography eluted with a chloroform-methanol system to give 3-{[bis-(2-hydroxy-propyl)-amino]-methyl}-N-(2-hydrazinocarbonyl-4-piperidin-1-yl-phenyl)benzamide as a useful intermediate (200 mg, yield 100%).

3-{[Bis-(2-hydroxy-propyl)-amino]-methyl}-N-(2-hydrazino-carbonyl-4-piperidin-1-ylphenyl)benzamide (53 mg) produced by the above process was dissolved in anhydrous toluene (5 ml). 4-Chloro-3-(trifluoromethyl)benzaldehyde (compound C) (69 mg) and a catalytic amount of acetic acid were added dropwise to the solution at room temperature, and the mixture was then stirred at 90° C. for 3 hr. After the completion of the reaction, the reaction solution was allowed to stand for cooling, and the resultant crystals were collected by Kiriyama Rohto to give the title compound 942 (15 mg, yield 20%). The filtrate obtained by the filtration through Kiriyama Rohto was concentrated under the reduced pressure, and the residue was purified by column chromatography eluted with a chloroform-methanol system to again give the title compound 942 (37 mg, yield 50%) (final step: total yield 70%).

$^1$H-NMR (CD$_3$OD, 400 MHz): δ 8.31-8.38 (3H, m), 8.00-8.07 (2H, m), 7.86 (1H, d, J=8.0 Hz), 7.67 (1H, d, J=8.6 Hz), 7.58 (1H, d, J=7.8 Hz), 7.48 (1H, dd, J=7.6 Hz, J=7.6 Hz), 7.38 (1H, d, J=2.7 Hz), 7.23 (1H, dd, J=2.7 Hz, J=9.0 Hz), 3.83-3.95 (4H, m), 3.20-3.25 (4H, m), 2.38-2.55 (4H, m), 1.70-1.78 (4H, m), 1.58-1.66 (2H, m), 1.07 (3H, s), 1.06 (3H, s)

Mass spectrometric value (ESI-MS) 672, 674 (M−1)

Example K

Compound 943 3-{[Bis-(2-hydroxy-propyl)-amino]-methyl}-N-[4-(2-diethylamino-ethoxy)-2-(3,4-dimethyl-benzylidene-hydrazinocarbonyl)-phenyl]-benzamide 3-{[Bis-(2-hydroxy-propyl)-amino]-methyl}-N-[2-(3,4-dimethyl-benzylidene-hydrazinocarbonyl)-4-hydroxyphenyl]-benzamide (45 mg) produced in substantially the same manner as in Example 8 was dissolved in N,N-dimethylformamide (10 ml). 60% Sodium hydride (4.0 mg) was added to the solution at room temperature, and the mixture was stirred at that temperature for 10 min. Subsequently, (2-bromoethyl) diethylamine hydrobromide (44 mg) was added thereto, and the mixture was stirred for 12 hr. After the completion of the reaction, distilled water was added thereto, and the mixture was subjected to separatory extraction with ethyl acetate. The organic layer was washed with saturated brine and was dried over sodium sulfate. The organic layer was concentrated under the reduced pressure, and the residue was purified by column chromatography eluted with a chloroform system to give the title compound 943 (7 mg, yield 13%).

$^1$H-NMR (CDCL$_3$, 400 MHz): δ 10.02 (1H, bs), 8.20-8.25 (1H, m), 7.75-8.00 (3H, m), 7.35-7.50 (2H, m), 7.30 (1H, s), 7.23 (1H, s), 6.96-7.10 (3H, m), 4.25-4.45 (2H, m), 3.70-4.00 (4H, m), 2.30-2.80 (10H, m), 2.20-2.30 (6H, m), 1.00-1.20 (12H, m)

Mass spectrometric value (ESI-MS) 630 (M−1) 654 (M+23)

Example L

Compound 944 3-{[Bis-(2-hydroxy-propyl)-amino]-methyl}-N-[2-(3,4-dimethyl-benzylidene-hydrazinocarbonyl)-4-(2-oxo-pyrrolidin-1-yl)-phenyl]-benzamide 5-Amino-2-nitro-benzoic acid (compound A') (910 mg) was dissolved in methanol (50 ml). Thionyl chloride (0.74 ml) was added dropwise to the solution on an ice bath, and a reaction was allowed to proceed under reflux with heating for 12 hr. After the completion of the reaction, the reaction solution was allowed to stand for cooling to room temperature and was then concentrated under the reduced pressure. The residue was purified by column chromatography eluted with a chloroform-methanol system to give 5-amino-2-nitro-benzoic acid methyl ester (410 mg, yield 42%).

Subsequently, 5-amino-2-nitro-benzoic acid methyl ester (750 mg) was dissolved in anhydrous methylene chloride (30 ml). Pyridine (360 mg: dissolved in 2 ml of anhydrous methylene chloride) and 4-chloro-butyryl chloride (compound D) (630 mg: dissolved in 2 ml of anhydrous methylene chloride) were added dropwise at room temperature, and the mixture was then stirred at that temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 5-(4-chloro-butyrylamino)-2-nitro-benzoic acid methyl ester as a useful intermediate (1.2 g, yield 100%).

Subsequently, 5-(4-chloro-butyrylamino)-2-nitro-benzoic acid methyl ester (50 mg) was dissolved in N,N-dimethylformamide (5 ml). Morpholine (70 mg) and potassium carbonate (44 mg) were added to the solution at room temperature, and the mixture was stirred at room temperature for 3 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-nitro-5-(2-oxo-pyrrolidin-1-yl)-benzoic acid methyl ester (45 mg, yield 100%).

2-Nitro-5-(2-oxo-pyrrolidin-1-yl)-benzoic acid methyl ester (24 mg) was dissolved in ethanol (5 ml), and 10% palladium-carbon (3 mg) was added to the solution at room temperature. The air in the reaction system was replaced by hydrogen, and the reaction solution was then stirred at that temperature for 4 hr. After the completion of the reaction, the reaction solution was filtered through Celite to remove 10% palladium-carbon and was then concentrated under the reduced pressure. The residue was purified by column chromatography eluted with a chloroform-methanol system to give 2-amino-5-(2-oxo-pyrrolidin-1-yl)benzoic acid methyl ester (compound A) (10 mg, yield 83%).

2-Amino-5-(2-oxo-pyrrolidin-1-yl)benzoic acid methyl ester (compound A) (10 mg) produced by the above process was dissolved in anhydrous methylene chloride. Pyridine (5 mg: dissolved in 1 ml of anhydrous methylene chloride) and 3-(chloromethyl)benzoyl chloride (compound B) (11 mg: dissolved in 1 ml of anhydrous methylene chloride) were added dropwise to the solution at 0° C., and the mixture was stirred at room temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-chloromethyl-benzoylamino)-5-(2-oxo-pyrrolidin-1-yl)benzoic acid methyl ester (14 mg, yield 93%).

Subsequently, 2-(3-chloromethyl-benzoylamino)-5-(2-oxo-pyrrolidin-1-yl)benzoic acid methyl ester (14 mg) was dissolved in anhydrous methylene chloride (5 ml). Triethylamine (7 mg: dissolved in 2 ml of anhydrous methylene chloride) and diisopropanolamine (compound B') (10 mg: dissolved in 2 ml of anhydrous methylene chloride) were added dropwise to the solution at 0° C., and the mixture was stirred at room temperature for 24 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-{[bis-(2-hydroxy-propyl)-amino]-methyl}-benzoylamino)-5-(2-oxo-pyrrolidin-1-yl)-benzoic acid methyl ester (8.0 mg, yield 47%).

2-(3-{[Bis-(2-hydroxy-propyl)-amino]-methyl}-benzoylamino)-5-(2-oxo-pyrrolidin-1-yl)-benzoic acid methyl ester (8.0 mg) produced by the above reaction was dissolved in ethanol (5 ml). Hydrazine monohydrate (1 ml) was added dropwise to the solution at room temperature, and the mixture was stirred at that temperature for one hr. After the completion of the reaction, the reaction solution was concentrated under the reduced pressure, and the residue was purified by column chromatography eluted with a chloroform-methanol system to give 3-{[bis-(2-hydroxy-propyl)-amino]-methyl}-N-[2-hydrazinocarbonyl-4-(2-oxo-pyrrolidin-1-yl)-phenyl]-benzamide (8.0 mg, yield 100%).

Subsequently, 3-{[bis-(2-hydroxy-propyl)-amino]-methyl}-N-[2-hydrazinocarbonyl-4-(2-oxo-pyrrolidin-1-yl)-phenyl]-benzamide (8.0 mg) produced by the above reaction was dissolved in anhydrous toluene (5 ml). 3,4-Dimethylbenzaldehyde (compound C) (4.6 mg: dissolved in 2 ml of anhydrous toluene) and a catalytic amount of acetic acid were added dropwise to the solution at room temperature, and the mixture was stirred at that temperature for 4 hr. After the completion of the reaction, the reaction solution was neutralized with a saturated aqueous sodium hydrogencarbonate solution, and was then subjected to separatory extraction with ethyl acetate. The organic layer was washed with saturated brine, was dried over sodium sulfate, and was then concentrated under the reduced pressure. The residue was purified by column chromatography eluted with a chloroform-methanol system to give the title compound 944 (6.5 mg, yield 65%).

$^1$H-NMR (CDCL$_3$, 400 MHz): δ 12.11 (1H, d, J=8.3 Hz), 10.88 (1H, d, J=9.8 Hz), 8.74 (1H, dd, J=17.1 Hz, J=9.0 Hz), 8.20-8.30 (3H, m), 7.95-8.05 (1H, m), 7.28-7.60 (5H, m), 7.08 (1H, dd, J=3.4 Hz, J=8.0 Hz), 3.75-4.10 (5H, m), 2.40-2.61 (5H, m), 2.25 (3H, s), 2.23 (3H, s), 1.95-2.15 (2H, m), 1.25 (2H, s), 1.11 (6H, d, J=6.4 Hz)

Mass spectrometric value (ESI-MS) 598 (M−1) 622 (M+23)

Compound 945 3-{[Bis-(2-hydroxy-propyl)-amino]-methyl}-N-[2-(4-chloro-3-trifluoromethyl-benzylidene-hydrazinocarbonyl)-4-(2-oxo-pyrrolidin-1-yl)-phenyl]-benzamide The title compound 945 was produced in substantially the same manner as in Example L.

$^1$H-NMR (CDCL$_3$, 400 MHz): δ 12.33 (1H, d, J=9.0 Hz), 11.94 (1H, bs), 8.71 (1H, dd, J=9.0 Hz, J=9.0 Hz), 8.07-8.40 (3H, m), 8.11 (1H, d, J=21.0 Hz), 7.99 (1H, d, J=7.3 Hz), 7.78 (1H, dd, J=8.3 Hz, J=29.0 Hz), 7.20-7.50 (4H, m), 3.55-4.20 (6H, m), 2.45-2.74 (4H, m), 2.25-2.42 (2H, m), 1.78-1.87 (2H, m), 1.50-1.72 (6H, m)

Mass spectrometric value (ESI-MS) 672 (M−1)

Compound 946 3-{[Bis-(2-hydroxy-propyl)-amino]-methyl}-N-[2-(4-methoxy-benzylidene-hydrazinocarbonyl)-4-(2-oxo-pyrrolidin-1-yl)-phenyl]-benzamide The title compound 946 was produced in substantially the same manner as in Example L.

$^1$H-NMR (CDCL$_3$, 400 MHz): δ 12.17 (1H, d, J=8.8 Hz), 12.23 (1H, d, J=12.4 Hz), 8.70 (1H, dd, J=9.3 Hz, J=20.7 Hz), 8.14-8.27 (3H, m), 7.95-8.01 (1H, m), 7.68-7.74 (2H, m), 7.26-7.46 (3H, m), 6.78-6.82 (2H, m), 3.50-4.20 (9H, m), 2.35-2.63 (6H, m), 1.92-2.05 (2H, m), 1.00-1.30 (6H, m)

Mass spectrometric value (ESI-MS) 600 (M−1)

Compound 947 3-{[Bis-(2-hydroxy-propyl)-amino]-methyl}-N-[2-(4-fluoro-benzylidene-hydrazinocarbonyl)-4-(2-oxo-pyrrolidin-1-yl)-phenyl]-benzamide The title compound 947 was produced in substantially the same manner as in Example L.

$^1$H-NMR (CDCL$_3$, 400 MHz): δ 12.21 (1H, d, J=5.4 Hz), 11.44 (1H, d, J=12.4 Hz), 8.70 (1H, dd, J=9.0 Hz, J=26.1 Hz), 8.20-8.35 (3H, m), 7.96-7.99 (1H, m), 7.72-7.82 (2H, m), 7.38-7.46 (2H, m), 7.25-7.32 (1H, m), 6.93-6.99 (2H, m), 3.50-4.10 (6H, m), 2.35-2.64 (6H, m), 1.87-1.97 (2H, m), 1.07-1.14 (6H, m)

Mass spectrometric value (ESI-MS) 588 (M−1)

Compound 948 3-{[Bis-(2-hydroxy-propyl)-amino]-methyl}-N-[2-(4-methyl-benzylidene-hydrazinocarbonyl)-4-(2-oxo-pyrrolidin-1-yl)-phenyl]-benzamide The title compound 948 was produced in substantially the same manner as in Example L.

$^1$H-NMR (CDCL$_3$, 400 MHz): δ 12.13 (1H, d, J=3.0 Hz), 11.28 (1H, d, J=11.4 Hz), 8.68 (1H, dd, J=9.2 Hz, J=20.5 Hz), 8.16-8.29 (3H, m), 7.94-8.00 (1H, m), 7.60-7.70 (2H, m), 7.25-7.45 (3H, m), 7.06-7.11 (2H, m), 3.52-4.07 (6H, m), 2.20-2.61 (9H, m), 1.90-2.00 (2H, m), 1.09-1.30 (6H, m)

Mass spectrometric value (ESI-MS) 584 (M−1)

Example M

Compound 949 3-{[Bis-(2-hydroxy-propyl)-amino]-methyl}-N-[2-(3,4-dimethyl-benzylidene-hydrazinocarbonyl)-4-(2-hydroxy-3-piperidin-1-yl-propoxy)-phenyl]-benzamide 2-Amino-5-hydroxy-benzoic acid methyl ester (compound A) (350 mg) was dissolved in anhydrous methylene chloride (20 ml). Pyridine (230 mg) and 3-(chloromethyl) benzoic acid (compound B) (540 mg) were added dropwise to the solution at 0° C., and the mixture was stirred at room temperature for 10 min. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-chloromethyl-benzoylamino)-5-hydroxy-benzoic acid methyl ester as a useful intermediate (280 mg, yield 42%).

Subsequently, 2-(3-chloromethyl-benzoylamino)-5-hydroxy-benzoic acid methyl ester (280 mg) produced by the above reaction was dissolved in anhydrous methylene chloride (20 ml). Triethylamine (180 mg) and diisopropanolamine (compound B') (230 mg) were added dropwise to the solution at room temperature, and the mixture was stirred at that temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-{[bis-(2-hydroxy-propyl)-amino]-methyl}-benzoylamino)-5-hydroxy-benzoic acid methyl ester (58 mg, yield 16%).

2-(3-{[Bis-(2-hydroxy-propyl)-amino]-methyl}-benzoylamino)-5-hydroxy-benzoic acid methyl ester (60 mg) produced by the above process was dissolved in N,N-dimethylformamide (5 ml). Potassium carbonate (58 mg) and epibromohydrin (58 mg: dissolved in 2 ml of N,N-dimethylformamide) were added to the solution at room temperature, and the mixture was stirred at that temperature for 12 hr. After the completion of the reaction, distilled water was added thereto at room temperature, and the mixture was subjected to separatory extraction with ethyl acetate. The organic layer was washed with saturated brine, was dried over sodium sulfate, and was then concentrated under the reduced pressure. The residue was purified by column chromatography eluted with a chloroform-methanol system to give 2-(3-{[bis-(2-hydroxy-propyl)-amino]-methyl}-benzoylamino)-5-oxilanylmethoxy-benzoic acid methyl ester as a useful intermediate (68 mg, yield 66%).

2-(3-{[Bis-(2-hydroxy-propyl)-amino]-methyl}-benzoylamino)-5-oxilanylmethoxy-benzoic acid methyl ester (12 mg) produced by the above process was dissolved in anhydrous methylene chloride (5 ml). Piperidine (6.5 mg: dissolved in 1 ml of anhydrous methylene chloride) and a catalytic amount of ytterbium (III) trifluoromethanesulfonate were added to the solution at room temperature, and the mixture was stirred at that temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-{[bis-(2-hydroxy-propyl)amino]methyl}benzoylamino)-5-(2-hydroxy-3-piperidin-1-yl-propoxy)-benzoic acid methyl ester (10 mg, yield 71%).

Subsequently, 2-(3-{[bis-(2-hydroxy-propyl)-amino]-methyl}-benzoylamino)-5-(2-hydroxy-3-piperidin-1-yl-propoxy)-benzoic acid methyl ester (13 mg) produced by the above process was dissolved in ethanol (5 ml). Hydrazine monohydrate (1 ml) was added dropwise to the solution at room temperature, and the mixture was stirred at that temperature for 12 hr. After the completion of the reaction, the reaction solution was concentrated under the reduced pressure, and the residue was purified by column chromatography eluted with a chloroform-methanol system to give 3-{[bis-(2-hydroxy-propyl)-amino]-methyl}-N-[2-hydrazinocarbonyl-4-(2-hydroxy-3-piperidin-1-yl-propoxy)-phenyl]-benzamide (5.8 mg, yield 45%).

3-{[Bis-(2-hydroxy-propyl)-amino]-methyl}-N-[2-hydrazinocarbonyl-4-(2-hydroxy-3-piperidin-1-yl-propoxy)-phenyl]-benzamide (5.8 mg) produced by the above process was dissolved in anhydrous toluene (5 ml). 3,4-Dimethylbenzaldehyde (compound C) (3 mg: dissolved in 1 ml of anhydrous toluene) and a catalytic amount of acetic acid were added dropwise to the solution at room temperature, and the mixture was stirred at that temperature for 6 hr. After the completion of the reaction, the reaction solution was neutralized with a saturated aqueous sodium hydrogencarbonate solution, and was then subjected to separatory extraction with ethyl acetate. The organic layer was washed with saturated brine, was dried over sodium sulfate, and was then concentrated under the reduced pressure. The residue was purified by column chromatography eluted with a chloroform-methanol system to give the title compound 949 (4.0 mg, yield 60%).

$^1$H-NMR (CDCL$_3$, 400 MHz): δ 11.97 (1H, bs), 7.94-8.65 (4H, m), 6.98-7.65 (7H, m), 3.52-4.45 (7H, m), 1.50-2.90 (16H, m), 1.20-1.30 (6H, m), 1.00-1.18 (6H, m)

Mass spectrometric value (ESI-MS) 672 (M−1)

Compound 950 3-{[Bis-(2-hydroxy-propyl)-amino]-methyl}-N-[2-(4-chloro-3-trifluoromethyl-benzylidene-hydrazinocarbonyl)-4-(2-hydroxy-3-piperidin-1-yl-propoxy)-phenyl]-benzamide The title compound 950 was produced in substantially the same manner as in Example M.

$^1$H-NMR (CDCL$_3$, 400 MHz): δ 12.10-12.20 (1H, m), 7.20-8.70 (10H, m), 6.95-7.05 (1H, m), 1.50-4.25 (17H, m), 1.20-1.30 (6H, m), 0.85-1.18 (6H, m)

Mass spectrometric value (ESI-MS) 746 (M−1)

Compound 951 3-{[Bis-(2-hydroxy-propyl)-amino]-methyl}-N-[4-(3-diethylamino-2-hydroxy-propoxy)-2-(3,4-dimethyl-benzylidene-hydrazinocarbonyl)-phenyl]-benzamide The title compound 951 was produced in substantially the same manner as in Example M.

$^1$H-NMR (CDCL$_3$, 400 MHz): δ 12.02 (1H, bs), 8.58-8.65 (1H, m), 8.47 (1H, s), 8.17-8.24 (1H, m), 7.80-8.00 (1H, m), 7.27-7.60 (5H, m), 6.98-7.10 (2H, m), 1.50-4.12 (23H, m), 1.20-1.28 (6H, m), 1.08-1.16 (6H, m)

Mass spectrometric value (ESI-MS) 660 (M−1)

Compound 952 3-{[Bis-(2-hydroxy-propyl)-amino]-methyl}-N-[2-(4-chloro-3-trifluoromethyl-benzylidene-hydrazinocarbonyl)-4-(3-diethylamino-2-hydroxy-propoxy)-phenyl]-benzamide The title compound 952 was produced in substantially the same manner as in Example M.

$^1$H-NMR (CDCL$_3$, 400 MHz): δ 12.21 (1H, d, J=16.1 Hz), 8.64-8.67 (1H, m), 8.50-8.58 (1H, m), 8.30-8.38 (1H, m), 7.80-8.12 (3H, m), 7.35-7.50 (4H, m), 6.97-7.00 (1H, m), 1.50-4.50 (17H, m), 1.20-1.35 (6H, m), 1.08-1.17 (6H, m)

Mass spectrometric value (ESI-MS) 734 (M−1)

Compound 953 3-{[Bis-(2-hydroxy-propyl)-amino]-methyl}-N-[2-(3,4-dimethyl-benzylidene-hydrazinocarbonyl)-4-(2-hydroxy-3-morpholin-4-yl-propoxy)-phenyl]-benzamide The title compound 953 was produced in substantially the same manner as in Example M.

Mass spectrometric value (ESI-MS) 674 (M−1)

Compound 954 3-{[Bis-(2-hydroxy-propyl)-amino]-methyl}-N-[2-(4-chloro-3-trifluoromethyl-benzylidene-hydrazinocarbonyl)-4-(2-hydroxy-3-morpholin-4-yl-propoxy)-phenyl]-benzamide The title compound 954 was produced in substantially the same manner as in Example M.

Mass spectrometric value (ESI-MS) 748 (M−1)

Example N

Compound 955 N-[3-(4-Chloro-3-trifluoromethyl-benzylidene-hydrazinocarbonyl)-5-methyl-thiophen-2-yl]-3,4-dimethoxy-benzamide Methyl 2-aminothiophene-3-carboxylate (compound A) (160 mg) was dissolved in anhydrous methylene chloride (5 ml). Pyridine (120 mg: dissolved in 2 ml of anhydrous methylene chloride) and 3,4-dimethoxybenzoyl chloride (compound B) (300 mg) were added to the solution at 0° C., and the mixture was stirred at room temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography using a hexane-acetone system to give 2-(3,4-dimethoxy-benzoylamino)-thiophene-3-carboxylic acid methyl ester (320 mg, yield 100%).

Separately, phosphorus oxychloride (100 µl) was added dropwise to N,N-dimethylformamide (29 mg) at 0° C., and the mixture was stirred at that temperature for 5 min. Subsequently, the reaction system was heated to 80° C., 2-(3,4-dimethoxy-benzoylamino)-thiophene-3-carboxylic acid methyl ester (64 mg: dissolved in 1 ml of N,N-dimethylformamide) produced by the above reaction was then added dropwise thereto, and the mixture was stirred at that temperature for 2 hr. After the completion of the reaction, the reaction solution was neutralized with a saturated sodium hydrogencarbonate solution, and was then subjected to separatory extraction with chloroform. The organic layer was washed with saturated brine, was dried over sodium sulfate, and was then concentrated under the reduced pressure to give crude 2-(3,4-dimethoxy-benzoylamino)-5-formylthiophene-3-carboxylic acid methyl ester (70 mg, crude yield 100%).

Crude 2-(3,4-dimethoxy-benzoylamino)-5-formylthiophene-3-carboxylic acid methyl ester (35 mg) synthesized by the above process was dissolved in tetrahydrofuran/N,N-dimethylformamide=1/1 (10 ml). Sodium borohydride (22 mg) was added to the solution at room temperature, and the mixture was stirred at that temperature for 20 min. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure to give crude 2-(3,4-dimethoxy-benzoylamino)-5-hydroxymethyl-thiophene-3-carboxylic acid methyl ester (35 mg, crude yield 100%).

Subsequently, crude 2-(3,4-dimethoxy-benzoylamino)-5-hydroxy-methyl-thiophene-3-carboxylic acid methyl ester (crude 35 mg) synthesized by the above process was dissolved in anhydrous methylene chloride (5 ml). Pyridine (24 mg: dissolved in 1 ml of anhydrous methylene chloride) and acetic anhydride (31 mg: dissolved in 1 ml of anhydrous methylene chloride) were added dropwise to the solution at room temperature, and the mixture was stirred at that temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a chloroform-methanol system to give 5-acetoxymethyl-2-(3,4-dimethoxy-benzoylamino)-thiophene-3-carboxylic acid methyl ester as a useful intermediate (26 mg, 3 steps, yield 67%).

5-Acetoxymethyl-2-(3,4-dimethoxy-benzoylamino)-thiophene-3-carboxylic acid methyl ester (26 mg) produced by the above process was dissolved in ethanol/tetrahydrofuran=5/2 (7 ml), and 10% palladium-carbon (10 mg) was added to the solution at room temperature. The air in the reaction system was replaced by hydrogen, and the mixture was then stirred at that temperature for 12 hr. After the completion of the reaction, the atmosphere in the reaction system was replaced by nitrogen, and the reaction solution was then filtered through Celite to remove 10% palladium-carbon and was then concentrated under the reduced pressure. The residue was purified by column chromatography using a hexane-acetone system to give 2-(3,4-dimethoxy-benzoylamino)-5-methyl-thiophene-3-carboxylic acid methyl ester (13 mg, yield 59%).

Subsequently, 2-(3,4-dimethoxy-benzoylamino)-5-methyl-thiophene-3-carboxylic acid methyl ester (16 mg) synthesized by the above process was dissolved in ethanol (5 ml). Hydrazine (1 ml) was then added to the solution at room temperature, and the mixture was stirred at that temperature for 12 hr. After the completion of the reaction, the reaction system was concentrated under the reduced pressure, and the residue was purified by column chromatography eluted with a chloroform-methanol system to give N-(3-hydrazinocarbonyl)-5-methylthiophen-2-yl)-3,4-dimethoxy-benzamide (8.0 mg, yield 50%).

Subsequently, N-(3-hydrazinocarbonyl)-5-methylthiophen-2-yl)-3,4-dimethoxy-benzamide (8.0 mg) was dissolved in anhydrous toluene (5 ml), 4-chloro-3-(trifluoromethyl)benzaldehyde (compound C) (15 mg: dissolved in 1 ml of anhydrous toluene) and a catalytic amount of acetic acid were added dropwise to the solution at room temperature, and the mixture was stirred at that temperature for 3 hr. After the completion of the reaction, the reaction solution was neutralized with a saturated sodium hydrogencarbonate solution and was then subjected to separatory extraction with ethyl acetate. The organic layer was washed with saturated brine, was dried over sodium sulfate, and was then concentrated under the reduced pressure. The residue was purified by column chromatography eluted with a chloroform-methanol system to give the title compound 955 (5.0 mg, yield 38%).

$^1$H-NMR (CDCL$_3$, 400 MHz): δ 12.66 (1H, bs), 9.19 (1H, bs), 8.19 (1H, bs), 8.02 (1H, s), 7.80-7.92 (1H, m), 7.62-7.65 (2H, m), 7.56 (1H, d, J=8.3 Hz), 6.92 (1H, d, J=8.8 Hz), 3.97 (3H, s), 3.95 (3H, s), 2.44 (3H, s)

Mass spectrometric value (ESI-MS) 524 (M−1)

Example O

Compound 956 N-[3-(4-Chloro-3-trifluoromethyl-benzylidene-hydrazinocarbonyl)-4-methyl-5-piperidin-1-ylmethyl-thiophen-2-yl]-3-diethylaminomethyl-benzamide Ethyl-2-amino-4-methylthiophene-3-carboxylate (compound A) (370 mg) was dissolved in anhydrous methylene chloride (10 ml). Pyridine (240 mg: dissolved in 2 ml of anhydrous methylene chloride) and 3-(chloromethyl)benzoyl chloride (compound B) (570 mg: dissolved in 2 ml of anhydrous methylene chloride) were added dropwise to the solution at 0° C., and the mixture was stirred at room temperature for 12 hr. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-chloromethylbenzoylamino)-4-methyl-thiophene-3-carboxylic acid ethyl ester (670 mg, yield 99%).

Subsequently, 2-(3-diethylaminomethyl-benzoylamino)-4-methyl-thiophene-3-carboxylic acid ethyl ester (700 mg) synthesized by the above process was dissolved in anhydrous methylene chloride (10 ml). Triethylamine (425 mg: dissolved in 2 ml of anhydrous methylene chloride) and diethylamine (compound B') (310 mg: dissolved in 2 ml of anhydrous methylene chloride) were added dropwise to the solution at 0° C., and the mixture was stirred at room temperature for 2 hr. After the completion of the reaction, distilled water was added thereto at room temperature, and the mixture was then subjected to separatory extraction with chloroform, and the organic layer was washed with saturated brine, was dried over sodium sulfate, and was then concentrated under the reduced pressure. The residue was purified by column chromatography eluted with a chloroform-methanol system to give 2-(3-diethylaminomethyl-benzoylamino)-4-methylthiophene-3-carboxylic acid ethyl ester (690 mg, yield 88%).

Separately, phosphorus oxychloride (200 µl) was added dropwise to N,N-dimethylformamide (73 mg) at 0° C., and the mixture was stirred at that temperature for 5 min. The reaction system was heated to 80° C., 2-(3-diethylaminomethyl-benzoylamino)-4-methyl-thiophene-3-carboxylic acid ethyl ester (187 mg) synthesized by the above process was then added thereto, and the mixture was stirred at that temperature for 3 hr. After the completion of the reaction, the reaction solution was neutralized with a saturated sodium hydrogencarbonate solution, and was then subjected to separatory extraction with chloroform, and the organic layer was washed with saturated brine, was dried over sodium sulfate, and was then concentrated under the reduced pressure. The residue was purified by column chromatography eluted with a chloroform-methanol system to give 2-(3-diethylaminomethyl-benzoylamino)-5-formyl-4-methylthiophene-3-carboxylic acid ethyl ester as a useful intermediate (110 mg, yield 53%).

2-(3-diethylaminomethyl-benzoylamino)-5-formyl-4-methyl-thiophene-3-carboxylic acid ethyl ester (110 mg) synthesized by the above process was dissolved in N,N-dimethylformamide (10 ml), acetic acid (100 µl) and sodium triacetoxyborohydride (66 mg) were added to the solution at room temperature, and the mixture was stirred at that temperature for one hr. After the completion of the reaction, the reaction solution was neutralized with a saturated sodium hydrogencarbonate solution, and was then subjected to separatory extraction with ethyl acetate. The organic layer was washed with saturated brine, was dried over sodium sulfate, and was then concentrated under the reduced pressure. The residue was purified by column chromatography eluted with a chloroform-methanol system to give 2-(3-diethylaminomethyl-benzoylamino)-4-methyl-5-piperidin-1-ylmethylthiophene-3-carboxylic acid ethyl ester (79 mg, yield 64%).

Subsequently, 2-(3-diethylaminomethyl-benzoylamino)-4-methyl-5-piperidin-1-ylmethylthiophene-3-carboxylic acid ethyl ester (79 mg) was dissolved in ethanol (10 ml), hydrazine monohydrate (2 ml) was added dropwise to the solution at room temperature, and a reaction was then allowed to proceed at that temperature for 12 hr. After the completion of the reaction, the reaction system was concentrated under the reduced pressure. The residue was purified by column chromatography eluted with a chloroform-methanol system to give 3-diethylaminomethyl-N-(3-hydrazinocarbonyl-4-methyl-5-piperidin-1-ylmethylthiophen-2-yl)-benzamide as a useful intermediate (30 mg, yield 38%).

Subsequently, 3-diethylaminomethyl-N-(3-hydrazinocarbonyl-4-methyl-5-piperidin-1-ylmethylthiophen-2-yl)-benzamide (15 mg) produced by the above process was dissolved in anhydrous toluene. 4-Chloro-3-(trifluoromethyl)benzaldehyde (compound C) (21 mg: dissolved in 1 ml of anhydrous toluene) and a catalytic amount of acetic acid were added dropwise to the solution at room temperature, and the mixture was then stirred at that temperature for 3 hr. After the completion of the reaction, the reaction solution was neutralized with a saturated sodium hydrogencarbonate solution, and was then subjected to separatory extraction with ethyl acetate, and the organic layer was washed with saturated brine, was dried over sodium sulfate, and was then concentrated under the reduced pressure. The residue was purified by column chromatography eluted with a chloroform-methanol system to give the title compound 956 (6.0 mg, yield 29%).

$^1$H-NMR (CDCL$_3$, 400 MHz): δ 8.26 (1H, bs), 8.05 (1H, s), 8.00 (1H, s), 7.95 (1H, d, J=8.0 Hz), 7.88 (1H, d, J=7.6 Hz), 7.55-7.62 (2H, m), 7.42-7.48 (1H, m), 3.67 (2H, s), 2.48-2.60 (10H, m), 1.24-2.00 (9H, m), 1.07 (6H, t, J=7.1 Hz)

Mass spectrometric value (ESI-MS) 646 (M−1)

Compound 957 3-Diethylaminomethyl-N-[3-(4-methoxy-benzylidene-hydrazinocarbonyl)-4-methyl-5-piperidin-1-ylmethyl-thiophen-2-yl]-benzamide The title compound 957 was produced in substantially the same manner as in Example O.

$^1$H-NMR (CDCL$_3$, 400 MHz): δ 8.08 (1H, bs), 7.99 (1H, bs), 7.90 (1H, d, J=7.8 Hz), 7.74 (2H, d, J=8.3 Hz), 7.60 (1H, d, J=7.6 Hz), 7.40-7.45 (1H, m), 6.94 (2H, d, J=8.8 Hz), 3.86 (3H, s), 3.67 (2H, s), 2.40-2.60 (10H, m), 1.25-1.62 (9H, m), 1.06 (6H, t, J=7.1 Hz)

Mass spectrometric value (ESI-MS) 574 (M−1) 598 (M+23)

Compound 958 3-{[Bis-(2-hydroxy-propyl)-amino]-methyl}-N-[2-(4-methoxy-benzylidene-hydrazinocarbonyl)-4-piperidin-1-yl-phenyl]-benzamide The title compound 958 was produced in substantially the same manner as in Example J.

$^1$H-NMR (CD$_3$OD, 400 MHz): δ 8.38 (1H, dd, J=6.1 Hz, J=9.0 Hz), 8.29 (1H, s), 8.01 (1H, bs), 7.86 (1H, d, J=7.4 Hz), 7.75-7.85 (2H, m), 7.59 (1H, d, J=7.3 Hz), 7.48 (1H, dd, J=7.6 Hz, J=7.8 Hz), 7.37 (1H, d, J=2.7 Hz), 7.22 (1H, dd, J=3.0 Hz, J=9.0 Hz), 6.90-7.03 (2H, m), 3.80-3.90 (7H, m), 3.22-3.30 (4H, m), 2.40-2.60 (4H, m), 1.70-1.89 (4H, m), 1.62-1.64 (2H, m), 1.08 (3H, d, J=6.3 Hz), 1.07 (3H, d, J=6.1 Hz)

Mass spectrometric value (ESI-MS) 600, 601 (M−1) 622 (M−1+23)

Example P

Compound 959 3-{[Bis-(2-hydroxy-propyl)-amino]-methyl}-N-[3-(3-fluoro-benzylidene-hydrazinocarbonyl)-naphthalen-2-yl]-benzamide 3-Amino-naphthalene-2-carboxylic acid (compound A') (1.2 g) was dissolved in anhydrous methylene chloride (12 ml). 1-(3-Dimethylaminopropyl)-3-ethylcarbodiimide hydrochloride (2.5 g), 1-hydroxybenzotriazole monohydrate (1.5 g), and triethylamine (1 ml) were added to the solution at room temperature, and the mixture was then stirred at that temperature for 12 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography using a hexane-acetone system to give 3-amino-naphthalene-2-carboxylic acid methyl ester as a useful intermediate (compound A) (530 mg, yield 41%).

3-Amino-naphthalene-2-carboxylic acid methyl ester (compound A) (530 mg) produced by the above process was dissolved in anhydrous methylene chloride (10 ml). Pyridine (0.5 ml) and 3-(chloromethyl)benzoyl chloride (compound B) (0.6 ml) was added dropwise to the solution at room temperature, and the mixture was then stirred at that temperature for 30 min. After the completion of the reaction, distilled water was added thereto at room temperature, and the mixture was subjected to separatory extraction with chloroform. The organic layer was washed with saturated brine, was dried over sodium sulfate, and was concentrated under the reduced pressure to precipitate crystals. The crystals were collected by Kiriyama Rohto and were washed with a hexane-ether solvent to give 3-(3-chloromethylbenzoylamino)-naphthalene-2-carboxylic acid methyl ester (870 mg, yield 93%).

Subsequently, 3-(3-chloromethyl-benzoylamino)-naphthalene-2-carboxylic acid methyl ester (870 mg) was dissolved in anhydrous methylene chloride (15 ml). Pyridine (400 µl) and diisopropanolamine (compound B') (1.0 g) were added to the solution at room temperature, and the mixture was then stirred at that temperature for 48 hr. After the completion of the reaction, distilled water was added thereto at room temperature, and the mixture was subjected to separatory extraction with chloroform. The organic layer was washed with saturated brine, was dried over sodium sulfate, and was then concentrated under the reduced pressure. The residue was purified by column chromatography eluted with a hexane-acetone system to give 3-(3-{[bis-(2-hydroxy-propyl)-amino]-methyl}-benzoylamino)-naphthalene-2-carboxylic acid methyl ester as a useful intermediate (640 mg).

3-(3-{[Bis-(2-hydroxy-propyl)-amino]-methyl}-benzoylamino)-naphthalene-2-carboxylic acid methyl ester (640 mg) produced by the above reaction was dissolved in ethanol (7 ml). Hydrazine monohydrate (1 ml) was added dropwise to the solution at room temperature, and the mixture was then stirred at that temperature for 2 hr. After the completion of the reaction, the reaction solution was concentrated under the reduced pressure, and the residue was purified by column chromatography eluted with a chloroform-methanol system to give 3-{[bis-(2-hydroxy-propyl)amino]-methyl}-N-(3-hydrazinocarbonylnaphthalen-2-yl)-benzamide (350 mg, yield 54%).

Subsequently, 3-{[bis-(2-hydroxy-propyl)amino]-methyl}-N-(3-hydrazinocarbonylnaphthalen-2-yl)-benzamide (50 mg) was dissolved in anhydrous toluene (1 ml). 3-Fluorobenzaldehyde (compound C) (50 µl) was added dropwise to the solution at room temperature, and the mixture was then stirred at 120° C. for 12 hr. After the completion of the reaction, the reaction solution was allowed to stand for cooling at room temperature and the reaction system was then concentrated under the reduced pressure. The residue was purified by column chromatography eluted with a hexane-acetone system to give the title compound 959 (32 mg, yield 51%).

$^1$H-NMR (CDCL$_3$, 400 MHz): δ 12.05 (1H, bs), 11.40-11.55 (1H, m), 8.86 (1H, d, J=18.6 Hz), 8.10-8.40 (3H, m), 7.88 (1H, dd, J=7.3 Hz, J=17.8 Hz), 7.66 (2H, d, J=8.3 Hz), 7.25-7.50 (5H, m), 7.05-7.15 (2H, m), 6.80-6.95 (1H, m), 4.15-4.25 (2H, m), 3.95-4.05 (2H, m), 3.89 (1H, s), 3.60 (1H, d, J=1.4 Hz), 2.48-2.83 (4H, m), 1.20 (3H, d, J=6.1 Hz), 1.14 (3H, d, J=6.3 Hz)

Mass spectrometric value (ESI-MS) 555 (M−1)

Compound 960 3-{[Bis-(2-hydroxy-propyl)-amino]-methyl}-N-[3-(4-methyl-benzylidene-hydrazinocarbonyl)-naphthalen-2-yl]-benzamide The title compound 960 was produced in substantially the same manner as in Example P.

$^1$H-NMR (CDCL$_3$, 400 MHz): δ 11.90 (1H, bs), 10.90-11.00 (1H, m), 8.85 (1H, bs), 8.30 (1H, d, J=3.9 Hz), 7.86-8.20 (3H, m), 7.52-7.64 (3H, m), 7.28-7.46 (4H, m), 7.06-7.18 (1H, m), 6.88 (2H, d, J=7.8 Hz), 3.80-3.96 (4H, m), 3.55-3.60 (1H, m), 2.40-2.70 (4H, m), 2.18-2.23 (3H, m), 1.10 (3H, d, J=6.1 Hz), 1.06 (3H, d, J=6.1 Hz)

Mass spectrometric value (ESI-MS) 551 (M−1)

Compound 961 3-{[Bis-(2-hydroxy-propyl)-amino]-methyl}-N-[3-(3,4-dimethyl-benzylidene-hydrazinocarbonyl)-naphthalen-2-yl]-benzamide The title compound 961 was produced in substantially the same manner as in Example P.

$^1$H-NMR (CDCL$_3$, 400 MHz): δ 11.95-12.05 (1H, m), 10.80-10.95 (1H, m), 8.95-9.02 (1H, m), 8.15-8.32 (3H, m), 7.95-8.05 (1H, m), 7.20-7.80 (8H, m), 6.87 (1H, d, J=7.3 Hz), 3.60-4.20 (4H, m), 2.28-2.75 (4H, m), 2.00-2.15 (6H, m), 1.10-1.17 (6H, m)

Mass spectrometric value (ESI-MS) 565 (M−1)

Compound 962 3-{[Bis-(2-hydroxy-propyl)-amino]-methyl}-N-[3-(4-chloro-3-trifluoromethyl-benzylidene-hydrazinocarbonyl)-naphthalen-2-yl]-benzamide The title compound 962 was produced in substantially the same manner as in Example P.

$^1$H-NMR (CDCL$_3$, 400 MHz): δ 11.96-12.05 (1H, m), 11.71 (1H, d, J=15.1 Hz), 8.80 (1H, s), 8.32 (2H, bs), 8.13 (1H, d, J=7.8 Hz), 7.57-7.94 (4H, m), 7.25-7.46 (5H, m), 7.08 (2H, d, J=8.0 Hz), 3.50-4.20 (5H, m), 2.30-2.86 (4H, m), 1.13 (3H, d, J=6.1 Hz), 1.09 (3H, d, J=6.3 Hz)

Mass spectrometric value (ESI-MS) 639, 641, 642 (M−1)

Compound 963 3-{[Bis-(2-hydroxy-propyl)-amino]-methyl}-N-[3-(4-methoxy-benzylidene-hydrazinocarbonyl)-naphthalen-2-yl]-benzamide The title compound 963 was produced in substantially the same manner as in Example P.

$^1$H-NMR (CDCL$_3$, 400 MHz): δ 11.95 (1H, bs), 10.86-11.00 (1H, m), 8.80-8.90 (1H, m), 8.05-8.30 (3H, m), 7.85-7.95 (1H, m), 7.60-7.65 (3H, m), 7.22-7.48 (4H, m), 7.06-7.18 (1H, m), 6.59 (1H, d, J=8.5 Hz), 3.50-3.96 (8H, m), 2.40-2.70 (4H, m), 1.10 (3H, d, J=6.1 Hz), 1.06 (3H, d, J=6.1 Hz)

Mass spectrometric value (ESI-MS) 567 (M−1) 591 (M+23)

Compound 964 3-{[Bis-(2-hydroxy-propyl)-amino]-methyl}-N-[3-(3-fluoro-benzylidene-hydrazinocarbonyl)-pyridin-2-yl]-benzamide The title compound 964 was produced in substantially the same manner as in Example P.

$^1$H-NMR (CD$_3$OD, 400 MHz): δ 8.55-8.60 (1H, m), 8.29 (1H, s), 8.25 (1H, d, J=7.8 Hz), 8.07 (1H, s), 7.89-7.96 (1H, m), 7.70 (1H, d, J=10.0 Hz), 7.62 (1H, d, J=7.6 Hz), 7.57 (1H, d, J=7.3 Hz), 7.40-7.52 (2H, m), 7.32-7.40 (1H, m), 7.13-7.20 (1H, m), 3.60-3.95 (4H, m), 2.35-2.60 (4H, m), 1.08 (3H, d, J=6.1 Hz), 1.07 (3H, d, J=6.3 Hz)

Mass spectrometric value (ESI-MS) 506, 507, 508 (M−1)

Compound 965 3-{[Bis-(2-hydroxy-propyl)-amino]-methyl}-N-[3-(4-methyl-benzylidene-hydrazinocarbonyl)-pyridin-2-yl]-benzamide The title compound 965 was produced in substantially the same manner as in Example P.

$^1$H-NMR (CD$_3$OD, 400 MHz): δ 8.54-8.59 (1H, m), 8.21-8.28 (2H, m), 8.05-8.09 (1H, m), 7.86-7.95 (1H, m), 7.72 (2H, d, J=7.8 Hz), 7.62 (1H, d, J=7.8 Hz), 7.49 (1H, ddd, J=1.7 Hz, J=7.6 Hz, J=7.6 Hz), 7.32-7.37 (1H, m), 7.25 (2H, d, J=7.8 Hz), 3.81-3.93 (4H, m), 2.39-2.60 (4H, m), 2.37 (3H, s), 1.08 (3H, d, J=6.1 Hz), 1.07 (3H, d, J=6.4 Hz)

Mass spectrometric value (ESI-MS) 502, 503, 504 (M−1) 526, 527 (M+23)

Compound 966 3-{[Bis-(2-hydroxy-propyl)-amino]-methyl}-N-[3-(3,4-dimethyl-benzylidene-hydrazinocarbonyl)-pyridin-2-yl]-benzamide The title compound 966 was produced in substantially the same manner as in Example P.

$^1$H-NMR (CD$_3$OD, 400 MHz): δ 8.50-8.60 (1H, m), 8.23-8.28 (2H, m), 8.05-8.08 (1H, m), 7.88-7.98 (1H, m), 7.60-7.66 (2H, m), 7.46-7.56 (2H, m), 7.25-7.40 (1H, m), 7.18-7.22 (1H, m), 3.75-3.94 (4H, m), 2.38-2.60 (4H, m), 2.31 (3H, s), 2.30 (3H, s), 1.08 (3H, d, J=6.1 Hz), 1.07 (3H, d, J=6.1 Hz)

Mass spectrometric value (ESI-MS) 516, 517 (M−1) 540, 541 (M+23)

Compound 967 3-{[Bis-(2-hydroxy-propyl)-amino]-methyl}-N-[3-(4-chloro-3-trifluoromethyl-benzylidene-hydrazinocarbonyl)-pyridin-2-yl]-benzamide The title compound 967 was produced in substantially the same manner as in Example P.

$^1$H-NMR (CDCL$_3$, 400 MHz): δ 11.70-11.85 (1H, m), 11.61 (1H, s), 8.58 (1H, s), 8.36 (1H, s), 8.24 (1H, s), 8.00-8.10 (2H, m), 7.80-7.90 (1H, m), 7.40-7.55 (4H, m), 6.75-6.85 (1H, m), 3.86-4.10 (4H, m), 2.45-2.75 (4H, m), 1.10 (6H, d, J=6.1 Hz)

Mass spectrometric value (ESI-MS) 592 (M−1) 614 (M+23)

Compound 968 3-{[Bis-(2-hydroxy-propyl)-amino]-methyl}-N-[3-(4-methoxy-benzylidene-hydrazinocarbonyl)-pyridin-2-yl]-benzamide The title compound 968 was produced in substantially the same manner as in Example P.

$^1$H-NMR (CDCL$_3$, 400 MHz): δ 11.74 (1H, s), 11.00-11.20 (1H, m), 8.40-8.45 (1H, m), 8.22 (1H, d, J=12.4 Hz), 8.06 (1H, s), 7.80-7.90 (3H, m), 7.35-7.50 (3H, m), 6.80-7.00 (3H, m), 3.80-3.90 (7H, m), 2.40-2.75 (4H, m), 1.05-1.14 (6H, m)

Mass spectrometric value (ESI-MS) 518 (M−1) 542 (M+23)

Compound 969 N-[3-(3-Fluoro-benzylidene-hydrazinocarbonyl)-naphthalen-2-yl]-3-[4-(2-hydroxy-ethyl)-piperazin-1-ylmethyl]-benzamide The title compound 969 was produced in substantially the same manner as in Example P.

$^1$H-NMR (CDCL$_3$, 400 MHz): δ 11.15 (1H, s), 10.91 (1H, bs), 7.10-8.90 (15H, m), 3.60-3.75 (4H, m), 2.00-2.85 (11H, m)

Mass spectrometric value (ESI-MS) 552, 553 (M−1)

Compound 970 3-[4-(2-Hydroxy-ethyl)-piperazin-1-ylmethyl]-N-[3-(4-methyl-benzylidene-hydrazinocarbonyl)-naphthalen-2-yl]-benzamide The title compound 970 was produced in substantially the same manner as in Example P.

$^1$H-NMR (CDCL$_3$, 400 MHz): δ 11.19 (1H, s), 7.00-8.95 (15H, m), 3.63 (2H, s), 3.59 (2H, t, J=5.4 Hz), 2.50-2.65 (10H, m), 2.40 (3H, s)

Mass spectrometric value (ESI-MS) 548, 549, 550 (M−1)

Compound 971 N-[3-(3,4-Dimethyl-benzylidene-hydrazinocarbonyl)-naphthalen-2-yl]-3-[4-(2-hydroxy-ethyl)-piperazin-1-ylmethyl]-benzamide The title compound 971 was produced in substantially the same manner as in Example P.

$^1$H-NMR (CDCL$_3$, 400 MHz): δ 11.19 (1H, s), 7.00-9.00 (14H, m), 3.63 (2H, s), 3.59 (2H, t, J=5.4 Hz), 2.50-2.75 (10H, m), 2.32 (3H, s), 2.30 (3H, s)

Mass spectrometric value (ESI-MS) 562, 563 (M−1)

Compound 972 N-[3-(4-Chloro-3-trifluoromethyl-benzylidene-hydrazinocarbonyl)-naphthalen-2-yl]-3-[4-(2-hydroxy-ethyl)-piperazin-1-ylmethyl]-benzamide The title compound 972 was produced in substantially the same manner as in Example P.

$^1$H-NMR (CDCL$_3$, 400 MHz): δ 11.19 (1H, s), 8.97 (1H, s), 7.20-8.60 (13H, m), 3.64 (2H, s), 3.57-3.63 (2H, m), 2.50-2.60 (10H, m)

Mass spectrometric value (ESI-MS) 636, 637 (M−1)

Compound 973 3-[4-(2-Hydroxy-ethyl)-piperazin-1-ylmethyl]-N-[3-(4-methoxy-benzylidene-hydrazinocarbonyl)-naphthalen-2-yl]-benzamide The title compound 973 was produced in substantially the same manner as in Example P.

$^1$H-NMR (CDCL$_3$, 400 MHz): δ 11.25 (1H, s), 10.47 (1H, s), 8.88 (1H, s), 8.48 (1H, s), 7.97 (2H, bs), 7.82 (2H, d, J=8.3 Hz), 7.74 (1H, d, J=7.3 Hz), 7.63 (1H, d, J=8.5 Hz), 7.53 (1H, d, J=7.6 Hz), 7.38-7.43 (3H, m), 7.10-7.20 (1H, m), 6.96 (2H, d, J=8.3 Hz), 3.86 (3H, s), 3.62 (2H, s), 3.59 (2H, t, J=5.4 Hz), 2.50-2.60 (10H, m)

Mass spectrometric value (ESI-MS) 564, 565 (M−1)

Compound 974 3-{[Bis-(2-hydroxy-propyl)-amino]-methyl}-N-[4-(3-fluoro-benzylidene-hydrazinocarbonyl)-thiophen-3-yl]-benzamide The title compound 974 was produced in substantially the same manner as in Example 8.

$^1$H-NMR (CDCL$_3$, 400 MHz): δ 8.91 (1H, s), 7.95-8.27 (5H, m), 7.00-7.70 (6H, m), 3.82-4.08 (4H, m), 2.40-2.75 (4H, m), 1.10-1.17 (6H, m)

Mass spectrometric value (ESI-MS) 511, 512 (M−1) 534 (M+23)

Compound 975 3-{[Bis-(2-hydroxy-propyl)-amino]-methyl}-N-[4-(3-methyl-benzylidene-hydrazinocarbonyl)-thiophen-3-yl]-benzamide The title compound 975 was produced in substantially the same manner as in Example 8.

$^1$H-NMR (CDCL$_3$, 400 MHz): δ 11.99 (1H, s), 11.28-11.38 (1H, m), 8.36 (1H, s), 7.95-8.20 (4H, m), 7.68-7.73 (1H, m), 7.35-7.45 (1H, m), 7.15-7.34 (2H, m), 6.87-6.97 (2H, m), 4.10-4.20 (1H, m), 3.85-4.00 (3H, m), 3.65-3.75 (1H, m), 2.62-2.85 (1H, m), 2.30-2.58 (4H, m), 2.15 (3H, s), 1.14 (3H, d, J=6.1 Hz), 1.08 (3H, d, J=6.3 Hz)

Mass spectrometric value (ESI-MS) 507, 508 (M−1) 531 (M+23)

Compound 976 3-{[Bis-(2-hydroxy-propyl)-amino]-methyl}-N-[4-(4-methyl-benzylidene-hydrazinocarbonyl)-thiophen-3-yl]-benzamide The title compound 976 was produced in substantially the same manner as in Example 8.

$^1$H-NMR (CDCL$_3$, 400 MHz): δ 8.99 (1H, s), 7.95-8.30 (4H, m), 7.30-7.70 (4H, m), 7.26 (1H, d, J=6.1 Hz), 7.13 (2H, d, J=7.1 Hz), 3.38-4.05 (4H, m), 2.34-2.70 (7H, m), 1.08-1.15 (6H, m)

Mass spectrometric value (ESI-MS) 507, 508 (M−1) 531 (M+23)

Compound 977 3-{[Bis-(2-hydroxy-propyl)-amino]-methyl}-N-[4-(3,4-dimethyl-benzylidene-hydrazinocarbonyl)-thiophen-3-yl]-benzamide The title compound 977 was produced in substantially the same manner as in Example 8.

$^1$H-NMR (CDCL$_3$, 400 MHz): δ 11.98 (1H, s), 11.12-11.25 (1H, m), 8.30-8.40 (1H, m), 7.96-8.18 (4H, m), 7.70-7.80 (1H, m), 7.20-7.50 (3H, m), 6.75-6.85 (1H, m), 3.65-4.20 (4H, m), 2.45-2.55 (2H, m), 2.20-2.30 (3H, m), 2.10-2.14 (3H, m), 2.02-2.08 (3H, m), 1.14 (3H, d, J=6.1 Hz), 1.08 (3H, d, J=6.3 Hz)

Mass spectrometric value (ESI-MS) 521, 522 (M−1) 545 (M+23)

Compound 978 3-{[Bis-(2-hydroxy-propyl)-amino]-methyl}-N-[4-(4-chloro-3-trifluoromethyl-benzylidene-hydrazinocarbonyl)-thiophen-3-yl]-benzamide The title compound 978 was produced in substantially the same manner as in Example 8.

$^1$H-NMR (CDCL$_3$, 400 MHz): δ 11.85 (1H, d, J=5.1 Hz), 11.65-11.80 (1H, m), 8.28-8.35 (1H, m), 7.98-8.20 (3H, m), 7.65-7.85 (2H, m), 7.02-7.52 (4H, m), 3.60-4.20 (4H, m), 2.46-2.90 (4H, m), 1.14 (3H, d, J=6.1 Hz), 1.09 (3H, d, J=6.1 Hz)

Mass spectrometric value (ESI-MS) 595, 597 (M−1) 619, 621 (M+23)

Compound 979 3-{[Bis-(2-hydroxy-propyl)-amino]-methyl}-N-[4-(4-methoxy-benzylidene-hydrazinocarbonyl)-thiophen-3-yl]-benzamide The title compound 979 was produced in substantially the same manner as in Example 8.

$^1$H-NMR (CDCL$_3$, 400 MHz): δ 12.03 (1H, d, J=10.5 Hz), 11.16-11.30 (1H, m), 8.30-8.40 (1H, m), 7.95-8.15 (3H, m), 7.75 (1H, dd, J=3.2 Hz, J=7.6 Hz), 7.36-7.44 (3H, m), 7.28-7.32 (1H, m), 6.45-6.57 (2H, m), 3.65-4.20 (7H, m), 2.44-2.84 (4H, m), 1.13 (3H, d, J=6.1 Hz), 1.07 (3H, d, J=6.4 Hz)

Mass spectrometric value (ESI-MS) 523, 524 (M−1) 547 (M+23)

Compound 980 N-[4-(3-Fluoro-benzylidene-hydrazinocarbonyl)-thiophen-3-yl]-3-[4-(2-hydroxy-ethyl)-piperazin-1-ylmethyl]-benzamide The title compound 980 was produced in substantially the same manner as in Example 8.

$^1$H-NMR (CDCL$_3$, 400 MHz): δ 8.26 (1H, s), 7.97 (1H, s), 7.87 (1H, d, J=7.8 Hz), 7.00-7.54 (8H, m), 3.59-3.66 (4H, m), 2.50-2.75 (10H, m)

Mass spectrometric value (ESI-MS) 508, 509 (M−1) 532 (M+23)

Compound 981 3-[4-(2-Hydroxy-ethyl)-piperazin-1-ylmethyl]-N-[4-(4-methyl-benzylidene-hydrazinocarbonyl)-thiophen-3-yl]-benzamide The title compound 981 was produced in substantially the same manner as in Example 8.

$^1$H-NMR (CDCL$_3$, 400 MHz): δ 11.81 (1H, bs), 11.50 (1H, bs), 8.24 (1H, s), 7.95 (1H, s), 7.87 (2H, d, J=7.6 Hz), 7.37-7.70 (5H, m), 7.18-7.25 (2H, m), 3.58 (4H, s), 2.37 (3H, s), 2.40-2.55 (10H, m)

Mass spectrometric value (ESI-MS) 504, 505 (M−1) 528 (M+23)

Compound 982 N-[4-(3,4-Dimethyl-benzylidene-hydrazinocarbonyl)-thiophen-3-yl]-3-[4-(2-hydroxy-ethyl)-piperazin-1-ylmethyl]-benzamide The title compound 982 was produced in substantially the same manner as in Example 8.

$^1$H-NMR (CDCL$_3$, 400 MHz): δ 8.22-8.28 (1H, m), 7.95 (1H, s), 7.87 (1H, d, J=7.6 Hz), 7.30-7.56 (6H, m), 7.10-7.20 (1H, m), 3.57 (4H, s), 2.40-2.60 (10H, m), 2.28 (6H, s)

Mass spectrometric value (ESI-MS) 518, 519 (M−1) 542 (M+23)

Compound 983 N-[4-(4-Chloro-3-trifluoromethyl-benzylidene-hydrazinocarbonyl)-thiophen-3-yl]-3-[4-(2-hydroxy-ethyl)-piperazin-1-ylmethyl]-benzamide The title compound 983 was produced in substantially the same manner as in Example 8.

$^1$H-NMR (CDCL$_3$, 400 MHz): δ 11.39 (1H, bs), 8.22 (1H, s), 7.82-8.00 (5H, m), 7.40-7.60 (4H, m), 3.55-3.62 (4H, m), 2.45-2.60 (10H, m)

Mass spectrometric value (ESI-MS) 592, 594 (M−1) 616 (M+23)

Compound 984 3-[4-(2-Hydroxy-ethyl)-piperazin-1-ylmethyl]-N-[4-(4-methoxy-benzylidene-hydrazinocarbonyl)-thiophen-3-yl]-benzamide The title compound 984 was produced in substantially the same manner as in Example 8.

$^1$H-NMR (CDCL$_3$, 400 MHz): δ 11.86 (1H, bs), 11.51 (1H, bs), 8.25 (1H, d, J=3.4 Hz), 7.95 (1H, s), 7.87 (2H, d, J=7.3 Hz), 7.55-7.75 (2H, m), 7.49 (1H, d, J=7.3 Hz), 7.41 (1H, dd, J=7.7 Hz, J=7.7 Hz), 7.20-7.28 (1H, m), 6.85-7.30 (2H, m), 3.83 (3H, s), 3.58 (4H, s), 2.45-2.60 (10H, m)

Mass spectrometric value (ESI-MS) 520, 521 (M−1)

Compound 985 3-{[Bis-(2-hydroxy-propyl)-amino]-methyl}-N-[2-(3,4-dimethyl-benzylidene-hydrazinocarbonyl)-4-fluoro-phenyl]-benzamide The title compound 985 was produced in substantially the same manner as in Example P.
$^1$H-NMR (CDCL$_3$, 400 MHz): δ 12.30-12.40 (1H, m), 8.55-8.65 (1H, m), 8.24-8.32 (1H, m), 8.14 (1H, s), 7.92-8.00 (1H, m), 7.56 (1H, s), 7.39 (1H, dd, J=7.3 Hz, J=7.3 Hz), 7.31 (1H, s), 7.16-7.28 (2H, m), 6.92-7.02 (1H, m), 6.76-6.86 (1H, m), 3.80-4.15 (4H, m), 3.55-3.65 (1H, m), 2.40-2.75 (4H, m), 2.14 (3H, s), 2.06 (3H, s), 1.10 (3H, d, J=6.4 Hz), 1.06 (3H, d, J=6.1 Hz)
Mass spectrometric value (ESI-MS) 533, 534 (M−1)

Compound 986 2-(3-{[Bis-(2-hydroxy-propyl)-amino]-methyl}-benzoylamino)-N-[2-(3,4-dimethyl-benzylidene-hydrazinocarbonyl)-4-fluoro-phenyl]-5-fluoro-benzamide The title compound 986 was produced in substantially the same manner as in Example P.
$^1$H-NMR (CDCL$_3$, 400 MHz): δ 11.95-12.05 (1H, m), 11.16 (1H, bs), 10.93 (1H, bs), 8.75-8.85 (1H, m), 8.20-8.40 (1H, m), 7.20-8.10 (11H, m), 6.92-7.05 (1H, m), 3.70-3.95 (4H, m), 2.35-2.60 (4H, m), 2.12-2.21 (6H, m), 0.96-1.02 (6H, m)
Mass spectrometric value (ESI-MS) 670 (M−1)

Compound 987 3-{[Bis-(2-hydroxy-propyl)-amino]-methyl}-N-[4-fluoro-2-(3-fluoro-benzylidene-hydrazinocarbonyl)-phenyl]-benzamide The title compound 987 was produced in substantially the same manner as in Example P.
$^1$H-NMR (CD$_3$OD, 400 MHz): δ 8.60-8.66 (1H, m), 8.35 (1H, s), 8.09 (1H, d, J=5.9 Hz), 7.95 (1H, d, J=8.0 Hz), 7.38-7.83 (7H, m), 7.15-7.28 (1H, m), 3.80-4.10 (4H, m), 2.58-2.75 (4H, m), 1.12 (3H, d, J=6.1 Hz), 1.11 (3H, d, J=6.4 Hz)
Mass spectrometric value (ESI-MS) 523, 524 (M−1) 547 (M+23)

Compound 988 2-(3-{[Bis-(2-hydroxy-propyl)-amino]-methyl}-benzoylamino)-5-fluoro-N-[4-fluoro-2-(3-fluoro-benzylidene-hydrazinocarbonyl)-phenyl]-benzamide The title compound 988 was produced in substantially the same manner as in Example P.
$^1$H-NMR (CD$_3$OD, 400 MHz): δ 8.52-8.67 (1H, m), 8.32-8.40 (1H, m), 8.27 (1H, s), 7.36-8.08 (11H, m), 7.13-7.20 (1H, m), 3.60-3.95 (4H, m), 2.38-2.57 (4H, m), 1.02-1.10 (6H, m)
Mass spectrometric value (ESI-MS) 660, 661 (M−1) 684 (M+23)

Compound 989 3-{[Bis-(2-hydroxy-propyl)-amino]-methyl}-N-[4-fluoro-2-(4-methyl-benzylidene-hydrazinocarbonyl)-phenyl]-benzamide The title compound 989 was produced in substantially the same manner as in Example P.
$^1$H-NMR (CD$_3$OD, 400 MHz): δ 8.60-8.67 (1H, m), 8.31 (1H, s), 8.02-8.07 (1H, m), 7.87-7.92 (1H, m), 7.75 (2H, d, J=7.8 Hz), 7.67 (1H, dd, J=2.7 Hz, J=9.0 Hz), 7.61 (1H, d, J=7.3 Hz), 7.50 (1H, dd, J=7.6 Hz, J=7.6 Hz), 7.36-7.43 (1H, m), 7.26 (2H, d, J=7.8 Hz), 3.65-3.95 (4H, m), 2.40-2.60 (4H, m), 2.38 (3H, s), 1.09 (3H, d, J=6.1 Hz), 1.08 (3H, d, J=6.1 Hz)
Mass spectrometric value (ESI-MS) 519, 520 (M−1) 543 (M+23)

Compound 990 3-{[Bis-(2-hydroxy-propyl)-amino]-methyl}-N-[4-fluoro-2-(4-methoxy-benzylidene-hydrazinocarbonyl)-phenyl]-benzamide The title compound 990 was produced in substantially the same manner as in Example P.
$^1$H-NMR (CD$_3$OD, 400 MHz): δ 8.61-8.67 (1H, m), 8.29 (1H, s), 8.03-8.07 (1H, m), 7.87-7.92 (1H, m), 7.81 (2H, d, J=8.5 Hz), 7.66 (1H, dd, J=2.7 Hz, J=9.3 Hz), 7.61 (1H, d, J=7.1 Hz), 7.50 (1H, dd, J=7.6 Hz, J=7.6 Hz), 7.38-7.42 (1H, m), 6.99 (2H, d, J=8.8 Hz), 3.82-3.93 (4H, m), 3.84 (3H, s), 2.40-2.60 (4H, m), 1.09 (3H, d, J=6.4 Hz), 1.08 (3H, d, J=6.1 Hz)
Mass spectrometric value (ESI-MS) 535, 536, 537 (M−1) 559 (M+23)

Compound 991 N-[5-Tert-butyl-2-(3,4-dimethyl-benzylidene-hydrazinocarbonyl)-thiophen-3-yl]-3-[4-(2-hydroxy-ethyl)-piperazin-1-ylmethyl]-benzamide The title compound 991 was produced in substantially the same manner as in Example 8.
$^1$H-NMR (CD$_3$OD, 400 MHz): δ 8.15 (1H, s), 7.99 (1H, s), 7.88-7.97 (2H, m), 7.70 (1H, s), 7.60 (1H, d, J=7.3 Hz), 7.44-7.55 (2H, m), 7.20 (1H, d, J=7.8 Hz), 3.64-3.70 (4H, m), 2.53-2.70 (10H, m), 2.32 (3H, s), 2.31 (3H, s), 1.50 (9H, s)
Mass spectrometric value (ESI-MS) 574, 575, 576 (M−1)

Compound 992 3-{[Bis-(2-hydroxy-propyl)-amino]-methyl}-N-[2-(3-fluoro-benzylidene-hydrazinocarbonyl)-thiophen-3-yl]-benzamide The title compound 992 was produced in substantially the same manner as in Example 8.
$^1$H-NMR (CD$_3$OD, 400 MHz): δ 8.26-8.34 (1H, m), 7.15-8.13 (10H, m), 3.80-4.08 (4H, m), 2.55-2.70 (4H, m), 1.13 (3H, d, J=6.1 Hz), 1.12 (3H, d, J=6.1 Hz)
Mass spectrometric value (ESI-MS) 511, 512, 513 (M−1)

Compound 993 3-{[Bis-(2-hydroxy-propyl)-amino]-methyl}-N-[2-(4-chloro-3-trifluoromethyl-benzylidene-hydrazinocarbonyl)-thiophen-3-yl]-benzamide The title compound 993 was produced in substantially the same manner as in Example 8.
$^1$H-NMR (CD$_3$OD, 400 MHz): δ 8.19-8.35 (2H, m), 8.00-8.09 (3H, m), 7.83-7.94 (2H, m), 7.68 (1H, d, J=8.5 Hz), 7.58-7.65 (1H, m), 7.47-7.55 (1H, m), 3.65-3.98 (4H, m), 2.45-2.65 (4H, m), 1.03-1.14 (6H, m)
Mass spectrometric value (ESI-MS) 595, 597, 598 (M−1)

Compound 995 3-Diethylaminomethyl-N-[2-(3-fluoro-benzylidene-hydrazinocarbonyl)-thiophen-3-yl]-benzamide The title compound 995 was produced in substantially the same manner as in Example 8.
$^1$H-NMR (CDCL$_3$, 400 MHz): δ 12.38 (1H, bs), 9.08 (1H, s), 8.39 (1H, d, J=5.6 Hz), 7.95 (1H, s), 7.84 (1H, d, J=8.1 Hz), 7.74 (1H, bs), 7.65 (1H, bs), 7.51 (1H, d, J=7.6 Hz), 7.30-7.46 (4H, m), 7.02-7.10 (1H, m), 3.59 (2H, s), 2.48 (4H, q, J=7.1 Hz), 0.99 (6H, t, J=7.1 Hz)
Mass spectrometric value (ESI-MS) 451, 452, 453 (M−1)

Compound 996 3-{[Bis-(2-hydroxy-propyl)-amino]-methyl}-N-{4-bromo-2-[1-(3-fluoro-phenyl)-ethylidene-hydrazinocarbonyl]-phenyl}-benzamide The title compound 996 was produced in substantially the same manner as in Example 8.
Mass spectrometric value (ESI-MS) 599 (M−1)

Compound 997 3-{[Bis-(2-hydroxy-propyl)-amino]-methyl}-N-{4-bromo-2-[1-(4-methoxy-phenyl)-ethylidene-hydrazinocarbonyl]-phenyl}-benzamide The title compound 997 was produced in substantially the same manner as in Example 8.
Mass spectrometric value (ESI-MS) 609, 611 (M−1)

Compound 998 3-{[Bis-(2-hydroxy-propyl)-amino]-methyl}-N-{4-chloro-2-[4-(3-dimethylamino-propoxy)-benzylidene-hydrazinocarbonyl]-phenyl}-benzamide The title compound 998 was produced in substantially the same manner as in Example 8.
$^1$H-NMR (CD$_3$OD, 400 MHz): δ 8.67-8.70 (1H, m), 8.30 (1H, s), 8.06 (1H, s), 7.88-7.94 (2H, m), 7.79-7.84 (2H, m), 7.59-7.64 (2H, m), 7.47-7.54 (1H, m), 6.96-7.02 (2H, m), 4.08 (2H, t, J=6.1 Hz), 3.82-3.95 (4H, m), 2.40-2.60 (6H, m), 2.30-2.34 (6H, s), 1.95-2.05 (2H, m), 1.09 (3H, d, J=6.4 Hz), 1.08 (3H, d, J=6.1 Hz)
Mass spectrometric value (ESI-MS) 622 (M−1)

Compound 999 N-{4-Chloro-2-[4-(3-dimethylamino-propoxy)-benzylidene-hydrazinocarbonyl]-phenyl}-3-{[(2-diethylamino-ethyl)-methyl-amino]-methyl}-benzamide The title compound 999 was produced in substantially the same manner as in Example 8.
$^1$H-NMR (CDCL$_3$, 400 MHz): δ 11.58 (1H, bs), 8.54 (1H, d, J=9.3 Hz), 8.26 (1H, s), 7.95 (1H, s), 7.86 (1H, d, J=7.8 Hz), 7.72 (2H, d, J=7.6 Hz), 7.50-7.56 (2H, m), 7.38-7.45 (2H, m), 6.91 (2H, d, J=8.8 Hz), 4.03 (2H, t, J=6.5 Hz), 3.60 (2H, s), 2.47-2.65 (8H, m), 2.43 (2H, t, J=7.2 Hz), 2.23 (6H, s), 2.22 (3H, s), 1.94 (2H, tt, J=6.8 Hz, J=6.8 Hz), 0.99 (6H, t, J=7.2 Hz)
Mass spectrometric value (ESI-MS) 619, 620 (M−1)

Compound 1000 (4-{[5-Chloro-2-(3-{[(2-diethylamino-ethyl)-methyl-amino]-methyl}-benzoylamino)-benzoyl]-hydrazinomethyl}-phenoxy)-acetic acid The title compound 1000 was produced in substantially the same manner as in Example 8.
$^1$H-NMR (CD$_3$OD, 400 MHz): δ 8.62 (1H, d, J=9.0 Hz), 8.29 (1H, s), 7.89-8.00 (3H, m), 7.74 (2H, d, J=8.8 Hz), 7.51-7.65 (3H, m), 6.98 (2H, d, J=8.8 Hz), 4.44 (2H, s), 3.72 (2H, s), 3.21 (2H, t, J=6.1 Hz), 3.07 (4H, q, J=7.3 Hz), 2.74 (2H, t, J=6.1 Hz), 2.32 (3H, s), 1.20 (6H, t, J=7.3 Hz)
Mass spectrometric value (ESI-MS) 592, 594 (M−1) 618, 619 (M+23)

Compound 1001 3-{[(2-Diethylamino-ethyl)-methyl-amino]-methyl}-N-{3-(4-trifluoromethoxy-benzylidene-hydrazinocarbonyl)-4,5,6,7-tetrahydro-benzo[b]thiophen-2-yl}-benzamide The title compound 1001 was produced in substantially the same manner as in Example 8.
$^1$H-NMR (CD$_3$OD, 400 MHz): δ 8.30 (1H, s), 7.90-8.03 (4H, m), 7.58-7.64 (1H, m), 7.50-7.57 (1H, m), 7.32-7.38 (2H, m), 3.67 (2H, s), 2.88 (4H, bs), 2.72-2.82 (6H, m), 2.58-2.66 (2H, m), 2.29 (3H, s), 1.83-1.95 (4H, m), 1.09 (6H, t, J=7.2 Hz)
Mass spectrometric value (ESI-MS) 628, 629, 630 (M−1)

Compound 1002 3-{[(2-Diethylamino-ethyl)-methyl-amino]-methyl}-N-{3-[4-(2-hydroxy-ethoxy)-benzylidene-hydrazinocarbonyl]-4,5,6,7-tetrahydro-benzo[b]thiophen-2-yl}-benzamide The title compound 1002 was produced in substantially the same manner as in Example 8.
$^1$H-NMR (CD$_3$OD, 400 MHz): δ 8.22 (1H, s), 7.70-8.00 (4H, m), 7.58-7.69 (1H, m), 7.50-7.57 (1H, m), 7.02 (2H, d, J=8.8 Hz), 4.10 (2H, t, J=4.6 Hz), 3.89 (2H, t, J=4.8 Hz), 3.67 (2H, s), 2.80-2.90 (4H, m), 2.66-2.78 (6H, m), 2.60 (2H, t, J=7.0 Hz), 2.28 (3H, s), 1.80-1.95 (4H, m), 1.08 (6H, t, J=7.2 Hz)
Mass spectrometric value (ESI-MS) 604, 605, 606 (M−1)

Compound 1003 3-{[(2-Diethylamino-ethyl)-methyl-amino]-methyl}-N-{3-[1-(3-fluoro-phenyl)-ethylidene-hydrazinocarbonyl]-4,5,6,7-tetrahydro-benzo[b]thiophen-2-yl}-benzamide The title compound 1003 was produced in substantially the same manner as in Example 8.
$^1$H-NMR (CD$_3$OD, 400 MHz): δ 7.85-7.98 (2H, m), 7.68-7.80 (2H, m), 7.47-7.62 (2H, m), 7.40-7.47 (1H, m), 7.10-7.20 (1H, m), 3.66 (2H, s), 2.95 (2H, bs), 2.55-2.85 (10H, m), 2.35 (3H, s), 2.28 (3H, s), 1.87-1.93 (4H, m), 1.05 (6H, t, J=7.2 Hz)
Mass spectrometric value (ESI-MS) 576, 577, 578 (M−1) 600, 601 (M+23)

Compound 1004 Quinoxaline-2-carboxylic acid [4-chloro-2-(3-fluoro-benzylidene-hydrazinocarbonyl)-phenyl]-amide The title compound 1004 was produced in substantially the same manner as in Example 1).
$^1$H-NMR (DMSO-d$_6$, 400 MHz): δ 12.65 (1H, s), 12.30 (1H, s), 9.61 (1H, s), 8.75 (1H, d, J=8.8 Hz), 8.47 (1H, s), 8.20-8.33 (2H, m), 8.00-8.10 (3H, m), 7.79 (1H, d, J=8.6 Hz), 7.50-7.67 (3H, m), 7.28-7.38 (1H, m)
Mass spectrometric value (ESI-MS) 446, 448 (M−1)

Compound 1005 Quinoxaline-2-carboxylic acid [4-chloro-2-(3,4-dimethyl-benzylidene-hydrazinocarbonyl)-phenyl]-amide The title compound 1005 was produced in substantially the same manner as in Example 1).
$^1$H-NMR (CDCL$_3$, 400 MHz): δ 12.52 (1H, bs), 9.68 (1H, s), 9.46 (1H, bs), 8.70-8.80 (1H, bs), 8.12-8.20 (2H, m), 7.82-7.88 (3H, m), 7.40-7.70 (3H, m), 7.12 (1H, d, J=7.8 Hz), 2.26 (3H, s), 2.20 (3H, s)
Mass spectrometric value (ESI-MS) 456, 458 (M−1)

Compound 1006 Quinoxaline-2-carboxylic acid[4-chloro-2-(4-chloro-3-trifluoromethyl-benzylidene-hydrazinocarbonyl)-phenyl]-amide The title compound 1006 was produced in substantially the same manner as in Example 1).
$^1$H-NMR (DMSO-d$_6$, 400 MHz): δ 12.57 (1H, s), 12.44 (1H, s), 9.61 (1H, s), 8.73 (1H, d, J=8.8 Hz), 8.51 (1H, s), 8.20-8.32 (3H, m), 7.98-8.14 (4H, m), 7.85 (1H, d, J=8.5 Hz), 7.79 (1H, d, J=9.0 Hz)
Mass spectrometric value (ESI-MS) 530, 532 (M−1)

Compound 1007 N-[4-Chloro-2-(3-fluoro-benzylidene-hydrazinocarbonyl)-phenyl]-3-(2,3-dihydroxy-propylsulfanylmethyl)-benzamide The title compound 1007 was produced in substantially the same manner as in Example 8.

$^1$H-NMR (CD$_3$OD, 400 MHz): δ 8.64 (1H, d, J=8.8 Hz), 8.36 (1H, s), 7.97 (1H, s), 7.94 (1H, d, J=2.4 Hz), 7.87 (1H, d, J=7.8 Hz), 7.71 (1H, d, J=9.5 Hz), 7.60-7.66 (3H, m), 7.40-7.54 (2H, m), 7.15-7.25 (1H, m), 3.90 (2H, s), 3.70-3.80 (1H, m), 3.48-3.60 (2H, m), 2.64 (1H, dd, J=5.6 Hz, J=13.7 Hz), 2.51 (1H, dd, J=6.8 Hz, J=13.4 Hz)

Mass spectrometric value (ESI-MS) 514, 516 (M−1)

Compound 1008 N-[4-Chloro-2-(4-methyl-benzylidene-hydrazinocarbonyl)-phenyl]-3-(2,3-dihydroxy-propylsulfanylmethyl)-benzamide The title compound 1008 was produced in substantially the same manner as in Example 8.

$^1$H-NMR (CD$_3$OD, 400 MHz): δ 8.65 (1H, d, J=9.0 Hz), 8.36 (1H, s), 7.97 (1H, s), 7.93 (1H, d, J=2.5 Hz), 7.87 (1H, d, J=7.6 Hz), 7.74 (2H, d, J=8.3 Hz), 7.62 (2H, dd, J=2.4 Hz, J=9.0 Hz), 7.51 (1H, dd, J=7.6 Hz, J=7.6 Hz), 7.27 (2H, d, J=8.1 Hz), 3.90 (2H, s), 3.70-3.80 (1H, m), 3.50-3.61 (2H, m), 2.63 (1H, dd, J=5.6 Hz, J=13.6 Hz), 2.50 (1H, dd, J=6.8 Hz, 13.6 Hz), 2.38 (3H, s)

Mass spectrometric value (ESI-MS) 510, 512, 513 (M−1)

Compound 1009 N-[4-Chloro-2-(3,4-dimethyl-benzylidene-hydrazinocarbonyl)-phenyl]-3-(2,3-dihydroxy-propylsulfanylmethyl)-benzamide The title compound 1009 was produced in substantially the same manner as in Example 8.

$^1$H-NMR (CD$_3$OD, 400 MHz): δ 8.66 (1H, d, J=9.0 Hz), 8.31 (1H, s), 7.97 (1H, bs), 7.93 (1H, d, J=2.4 Hz), 7.87 (1H, bs), 7.60-7.69 (3H, m), 7.48-7.58 (2H, m), 7.15-7.25 (1H, m), 3.90 (2H, s), 3.70-3.80 (1H, m), 3.50-3.61 (2H, m), 2.63 (1H, dd, J=5.4 Hz, J=13.7 Hz), 2.50 (1H, dd, J=6.8 Hz, J=13.6 Hz), 2.32 (3H, s), 2.31 (3H, s)

Mass spectrometric value (ESI-MS) 524, 526, 529 (M−1)

Compound 1010 N-[4-Chloro-2-(4-chloro-3-trifluoromethyl-benzylidene-hydrazinocarbonyl)-phenyl]-3-(2,3-dihydroxy-propylsulfanylmethyl)-benzamide The title compound 1010 was produced in substantially the same manner as in Example 8.

$^1$H-NMR (CD$_3$OD, 400 MHz): δ 8.63 (1H, d, J=8.8 Hz), 8.39 (1H, s), 8.30-8.34 (1H, m), 8.08 (1H, d, J=8.3 Hz), 7.96 (1H, bs), 7.94 (1H, d, J=2.4 Hz), 7.85-7.90 (1H, m), 7.70 (1H, d, J=8.3 Hz), 7.60-7.67 (2H, m), 7.68-7.55 (1H, m), 3.89 (2H, s), 3.70-3.80 (1H, m), 3.48-3.60 (2H, m), 2.64 (1H, dd, J=5.6 Hz, J=13.7 Hz), 2.50 (1H, dd, J=7.1 Hz, J=13.7 Hz)

Mass spectrometric value (ESI-MS) 598, 600, 601, 603 (M−1)

Compound 1011 N-[4-Chloro-2-(4-methoxy-benzylidene-hydrazinocarbonyl)-phenyl]-3-(2,3-dihydroxy-propylsulfanylmethyl)-benzamide The title compound 1011 was produced in substantially the same manner as in Example 8.

$^1$H-NMR (CD$_3$OD, 400 MHz): δ 8.66 (1H, d, J=9.0 Hz), 8.31 (1H, s), 7.95-7.98 (1H, m), 7.92 (1H, d, J=2.4 Hz), 7.86-7.90 (1H, m), 7.81 (2H, d, J=8.8 Hz), 7.60-7.65 (2H, m), 7.51 (1H, dd, J=7.7 Hz, J=7.7 Hz), 7.00 (2H, d, J=8.8 Hz), 3.90 (2H, s), 3.85 (3H, s), 3.70-3.80 (1H, m), 3.50-3.61 (2H, m), 2.63 (1H, dd, J=5.6 Hz, J=13.6 Hz), 2.51 (1H, dd, J=6.8 Hz, J=13.6 Hz)

Mass spectrometric value (ESI-MS) 529, 530, 531 (M−1)

Compound 1012 N-[4-Chloro-2-(4-trifluoromethoxy-benzylidene-hydrazinocarbonyl)-phenyl]-3-(2,3-dihydroxy-propylsulfanylmethyl)-benzamide The title compound 1012 was produced in substantially the same manner as in Example 8.

$^1$H-NMR (CD$_3$OD, 400 MHz): δ 8.64 (1H, d, J=9.0 Hz), 8.39 (1H, s), 7.93-8.01 (4H, m), 7.85-7.90 (1H, m), 7.60-7.67 (2H, m), 7.51 (1H, dd, J=7.7 Hz, J=7.7 Hz), 7.36 (2H, d, J=8.1 Hz), 3.90 (2H, s), 3.70-3.80 (1H, m), 3.50-3.60 (2H, m), 2.63 (1H, dd, J=5.8 Hz, J=13.6 Hz), 2.51 (1H, dd, J=6.8 Hz, J=13.6 Hz)

Mass spectrometric value (ESI-MS) 580, 582, 583 (M−1)

Example Q

Compound 1013 3-(2,3-Dihydroxy-propylsulfanylmethyl)-N-[2-(3-fluoro-benzylidene-hydrazinocarbonyl)-4,5-bis-(2-methoxy-ethoxy)-phenyl]-benzamide 3,4-Dihydroxy-benzoic acid ethyl ester (compound A') (2.0 g) was dissolved in acetone (20 ml). Potassium carbonate (4.3 g) and 1-bromo-2-methoxy-ethane (compound D) (5 ml) were added to the solution at room temperature, and the mixture was then stirred at 70° C. for 24 hr. After the completion of the reaction, the reaction solution was allowed to stand for cooling at room temperature, and the reaction system was concentrated under the reduced pressure. Distilled water was added to the residue, and the mixture was then subjected to separatory extraction with chloroform. The organic layer was washed with saturated brine, was dried over sodium sulfate, and was then concentrated under the reduced pressure. The residue was purified by column chromatography using a hexane-acetone system to give 3,4-bis-(2-methoxy-ethoxy)-benzoic acid ethyl ester (3.06 g, yield 93%).

3,4-Bis-(2-methoxy-ethoxy)-benzoic acid ethyl ester (200 mg) produced by the above process was dissolved in acetic acid (200 μl). Fuming nitric acid (200 μl) was added dropwise to the solution at 0° C., and the mixture was then stirred at room temperature for one hr. After the completion of the reaction, the reaction system was added dropwise to distilled water (500 μl) cooled to 0° C., and the mixture was then neutralized with a saturated aqueous sodium hydrogencarbonate solution, and was further subjected to separatory extraction with ethyl acetate. The organic layer was washed with saturated brine, was dried over sodium sulfate, and was then concentrated under the reduced pressure. The residue was purified by column chromatography eluted with a hexane-acetone system to give 4,5-bis-(2-methoxy-ethoxy)-2-nitro-benzoic acid ethyl ester as a useful intermediate (220 mg, yield 96%).

Subsequently, 4,5-bis-(2-methoxy-ethoxy)-2-nitro-benzoic acid ethyl ester (3.0 mg) produced by the above process was dissolved in methanol, and platinum oxide (250 mg) was added to the solution at room temperature. The air in the reaction system was replaced by hydrogen, and the mixture was then stirred for one hr. After the completion of the reaction, the atmosphere in the reaction system was replaced by nitrogen. The reaction solution was filtered through Celite to remove platinum oxide. The filtrate was then concentrated under the reduced pressure. The residue was purified by column chromatography eluted with a hexane-acetone system to give 2-amino-4,5-bis-(2-methoxy-ethoxy)-benzoic acid ethyl ester (compound A) (2.5 g, yield 92%).

2-Amino-4,5-bis-(2-methoxy-ethoxy)-benzoic acid ethyl ester (compound A) (2.5 g) produced by the above process was dissolved in anhydrous methylene chloride (40 ml). Pyridine (1.4 ml) and 3-(chloromethyl)-benzoyl chloride (compound B) (1.3 ml) were added dropwise to the solution at 0° C., and the mixture was stirred at room temperature for 30 min. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure. The residue was purified by column chromatography using a hexane-acetone system to give 2-(3-chloromethylbenzoylamino)-4,5-bis-(2-methoxy-ethoxy)-benzoic acid ethyl ester (2.3 g, yield 62%).

Subsequently, 2-(3-chloromethyl-benzoylamino)-4,5-bis-(2-methoxy-ethoxy)-benzoic acid ethyl ester (1.1 g) was dissolved in anhydrous methylene chloride (20 ml). Triethylamine (800 µl) and 3-mercapto-1,2-propanediol (compound B') (600 µl) were added dropwise to the solution at room temperature, and the mixture was stirred at that temperature for 36 hr. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-[3-(2,3-dihydroxy-propylsulfanylmethyl)-benzoylamino]-4,5-bis-(2-methoxy-ethoxy)-benzoic acid ethyl ester (970 mg, yield 77%).

2-[3-(2,3-Dihydroxy-propylsulfanylmethyl)-benzoylamino]-4,5-bis-(2-methoxy-ethoxy)-benzoic acid ethyl ester (970 mg) produced by the above process was dissolved in ethanol (10 ml). Hydrazine monohydrate (1 ml) was added dropwise to the solution at room temperature, and the mixture was then stirred at that temperature for 36 hr. After the completion of the reaction, the reaction system was then concentrated under the reduced pressure, and the residue was purified by column chromatography eluted with a chloroform-methanol system to give 3-(2,3-dihydroxy-propylsulfanylmethyl)-N-[2-hydrazinocarbonyl-4,5-bis-(2-methoxy-ethoxy)-phenyl]-benzamide (780 mg, yield 83%).

Subsequently, 3-(2,3-dihydroxy-propylsulfanylmethyl)-N-[2-hydrazinocarbonyl-4,5-bis-(2-methoxy-ethoxy)-phenyl]-benzamide (55 mg) produced by the above process was dissolved in anhydrous toluene (1 ml), 3-fluorobenzaldehyde (compound C) (50 µl) was added dropwise to the solution at room temperature, and the mixture was then stirred at that temperature for one hr. After the completion of the reaction, the reaction system was concentrated under the reduced pressure, and the residue was purified by column chromatography eluted with a chloroform-methanol system to give the title compound 1013 (66 mg, yield 100%).

$^1$H-NMR (CDCL$_3$, 400 MHz): δ 12.00 (1H, bs), 10.14 (1H, bs), 8.50 (1H, s), 8.16 (1H, s), 7.93 (1H, d, J=7.6 Hz), 7.60-7.78 (2H, m), 7.24-7.57 (5H, m), 7.00-7.10 (1H, m), 4.20-4.28 (2H, m), 4.00-4.10 (3H, m), 3.80-3.88 (3H, m), 3.75-3.80 (2H, m), 3.60-3.72 (3H, m), 3.41 (3H, s), 3.38 (3H, s), 2.60 (2H, d, J=6.6 Hz)

Mass spectrometric value (ESI-MS) 628, 629 (M−1)

Compound 1014 N-[4,5-Bis-(2-methoxy-ethoxy)-2-(4-methyl-benzylidene-hydrazinocarbonyl)-phenyl]-3-(2,3-dihydroxy-propylsulfanylmethyl)-benzamide The title compound 1014 was produced in substantially the same manner as in Example Q.

$^1$H-NMR (CDCL$_3$, 400 MHz): δ 12.06 (1H, bs), 9.84 (1H, bs), 8.54 (1H, s), 8.13 (1H, bs), 7.90-7.96 (2H, m), 7.77 (1H, s), 7.65-7.74 (2H, m), 7.45-7.55 (3H, m), 7.18 (1H, d, J=7.8 Hz), 4.22-4.28 (2H, m), 4.00-4.14 (3H, m), 3.80-3.85 (3H, m), 3.75-3.80 (2H, m), 3.62-3.70 (3H, m), 3.41 (3H, s), 3.40 (3H, s), 2.58 (2H, d, J=6.4 Hz), 2.34 (3H, s)

Mass spectrometric value (ESI-MS) 624, 625 (M−1)

Compound 1015 3-(2,3-Dihydroxy-propylsulfanylmethyl)-N-[2-(3,4-dimethyl-benzylidene-hydrazinocarbonyl)-4,5-bis-(2-methoxy-ethoxy)-phenyl]-benzamide The title compound 1015 was produced in substantially the same manner as in Example Q.

$^1$H-NMR (CDCL$_3$, 400 MHz): δ 12.08 (1H, bs), 9.95 (1H, bs), 8.53 (1H, s), 8.11 (1H, bs), 7.93 (1H, d, J=7.6 Hz), 7.76-7.83 (2H, m), 7.60 (1H, bs), 7.45-7.57 (3H, m), 7.11 (1H, d, J=7.8 Hz), 4.23-4.28 (2H, m), 4.07-4.12 (1H, m), 3.82-3.90 (3H, m), 3.75-3.80 (2H, m), 3.60-3.70 (3H, m), 3.41 (3H, s), 3.39 (3H, s), 2.59 (2H, d, J=6.6 Hz), 2.29 (2H, d, J=7.4 Hz), 2.24 (3H, s), 2.23 (3H, s)

Mass spectrometric value (ESI-MS) 638 (M−1)

Compound 1016 N-[2-(4-Chloro-3-trifluoromethyl-benzylidene-hydrazinocarbonyl)-4,5-bis-(2-methoxy-ethoxy)-phenyl]-3-(2,3-dihydroxy-propylsulfanylmethyl)-benzamide The title compound 1016 was produced in substantially the same manner as in Example Q.

$^1$H-NMR (CDCL$_3$, 400 MHz): δ 12.07 (1H, s), 10.69 (1H, s), 8.40 (1H, s), 8.15 (1H, s), 8.07 (1H, s), 7.93 (1H, d, J=7.1 Hz), 7.73-7.77 (1H, m), 7.71 (1H, s), 7.46-7.56 (2H, m), 7.38 (1H, d, J=8.3 Hz), 7.33 (1H, s), 4.60 (1H, bs), 4.18-4.23 (2H, m), 3.97-4.08 (3H, m), 3.74-3.95 (5H, m), 3.62-3.72 (1H, m), 3.58 (2H, t, J=9.0 Hz), 3.40 (3H, s), 3.37 (3H, s), 2.58-2.72 (2H, m)

Mass spectrometric value (ESI-MS) 712, 715 (M−1)

Example R

Compound 1017 3-(2,3-Dihydroxy-propylsulfanylmethyl)-N-[2-(3-fluoro-benzylidene-hydrazinocarbonyl)-4-methoxy-phenyl]-benzamide 5-Methoxy-2-nitro-benzoic acid (2.5 g) was dissolved in N,N-dimethylformamide (compound A') (40 ml). Potassium carbonate (4.5 g) and methyl iodide (2.5 ml) were added to the solution at room temperature, and the mixture was then stirred at that temperature for 30 min. After the completion of the reaction, distilled water was added thereto at room temperature, and the mixture was then subjected to separatory extraction with ethyl acetate. The organic layer was washed with saturated brine, was dried over sodium sulfate, and was then concentrated under the reduced pressure. The residue was purified by column chromatography eluted with a hexane-acetone system to give 5-methoxy-2-nitrobenzoic acid methyl ester (2.7 g, yield 100%).

Subsequently, 5-methoxy-2-nitro-benzoic acid methyl ester (2.7 g) produced by the above process was dissolved in methanol (20 ml), and platinum oxide (180 mg) was added to the solution at room temperature. The air in the reaction system was replaced by hydrogen, the mixture was then stirred at that temperature for 5 hr. After the completion of the reaction, the atmosphere in the reaction system was replaced by nitrogen, and the reaction solution was then filtered through Celite to remove platinum oxide. The filtrate was then concentrated under the reduced pressure. The residue was purified by column chromatography eluted with a hexane-acetone system to give 2-amino-5-methoxy-benzoic acid methyl ester (compound A) (2.2 g, yield 96%).

2-Amino-5-methoxy-benzoic acid methyl ester (compound A) (2.2 g) produced by the above process was dissolved in anhydrous methylene chloride (40 ml), pyridine (1.5 ml) and 3-(chloromethyl)benzoyl chloride (compound B) (2.1 ml) was added dropwise to the solution at 0° C., and the mixture was then stirred at room temperature for 15 min. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure to precipitate crystals. The crude crystals were collected by Kiriyama Rohto and was washed with ether to give 2-(3-chloromethyl-benzoylamino)-5-methoxybenzoic acid methyl ester (3.0 g, yield 75%).

Subsequently, 2-(3-chloromethyl-benzoylamino)-5-methoxy-benzoic acid methyl ester (1.0 g) produced by the above process was dissolved in anhydrous methylene chloride (10 ml). Triethylamine (1 ml) and 3-mercapto-1,2-propanediol (compound B') (1 ml) were added dropwise to the solution at room temperature, and the mixture was then stirred at that temperature for 36 hr. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-[3-(2,3-dihydroxy-propanesulfanylmethyl)-benzoylamino]-5-methoxy-benzoic acid methyl ester as a useful intermediate (1.2 g, yield 100%).

2-[3-(2,3-Dihydroxy-propanesulfanylmethyl)-benzoylamino]-5-methoxybenzoic acid methyl ester (1.2 g) produced by the above process was dissolved in ethanol (20 ml). Hydrazine monohydrate (1.3 ml) was added dropwise to the solution at room temperature, and the mixture was then stirred at that temperature for 12 hr. After the completion of the reaction, the reaction system was then concentrated under the reduced pressure, and the residue was purified by column chromatography eluted with a chloroform-methanol system to give 3-(2,3-dihydroxy-propylsulfanylmethyl)-N-(2-hydrazinocarbonyl-4-methoxyphenyl)benzamide (840 mg, yield 65%).

Subsequently, 3-(2,3-dihydroxy-propylsulfanylmethyl)-N-(2-hydrazinocarbonyl-4-methoxy-phenyl)benzamide (61 mg) produced by the above process was dissolved in anhydrous toluene (1.5 ml). 3-Fluorobenzaldehyde (compound C) (50 µl) was added dropwise to the solution at room temperature, and the mixture was then stirred at 40° C. for 12 hr. After the completion of the reaction, the reaction system was concentrated under the reduced pressure, and the residue was purified by column chromatography eluted with a chloroform-methanol system to give the title compound 1017 (59 mg, 77%).

$^1$H-NMR (CD$_3$OD, 400 MHz): δ 8.42 (1H, d, J=9.3 Hz), 8.34 (1H, s), 7.95 (1H, s), 7.85 (1H, d, J=7.8 Hz), 7.70 (1H, d, J=10.2 Hz), 7.58-7.62 (2H, m), 7.40-7.52 (3H, m), 7.12-7.25 (2H, m), 3.90 (3H, s), 3.89 (2H, s), 3.70-3.78 (1H, m), 3.48-3.60 (2H, m), 2.63 (1H, dd, J=5.6 Hz, J=13.7 Hz), 2.50 (1H, dd, J=6.8 Hz, J=13.4 Hz)

Mass spectrometric value (ESI-MS) 510, 511 (M−1) 534 (M+23)

Compound 1018 3-(2,3-Dihydroxy-propylsulfanylmethyl)-N-[4-methoxy-2-(4-methyl-benzylidene-hydrazinocarbonyl)-phenyl]-benzamide The title compound 1018 was produced in substantially the same manner as in Example R.

$^1$H-NMR (CD$_3$OD, 400 MHz): δ 8.44 (1H, d, J=9.0 Hz), 8.32 (1H, s), 7.95 (1H, s), 7.83-7.89 (1H, m), 7.74 (2H, d, J=8.1 Hz), 7.60 (1H, d, J=7.8 Hz), 7.49 (1H, dd, J=7.6 Hz, J=7.6 Hz), 7.41 (1H, d, J=2.9 Hz), 7.19-7.29 (3H, m), 3.90 (3H, s), 3.89 (2H, s), 3.70-3.78 (1H, m), 3.48-3.61 (2H, m), 2.63 (1H, dd, J=5.9 Hz, J=13.7 Hz), 2.50 (1H, dd, J=6.8 Hz, J=13.7 Hz), 2.38 (3H, s)

Mass spectrometric value (ESI-MS) 506, 507 (M−1)

Compound 1019 3-(2,3-Dihydroxy-propylsulfanylmethyl)-N-[2-(3,4-dimethyl-benzylidene-hydrazinocarbonyl)-4-methoxy-phenyl]-benzamide The title compound 1019 was produced in substantially the same manner as in Example R.

$^1$H-NMR (CD$_3$OD, 400 MHz): δ 8.44 (1H, d, J=9.0 Hz), 8.29 (1H, s), 7.95 (1H, s), 7.86 (1H, d, J=7.6 Hz), 7.66 (1H, s), 7.60 (1H, d, J=7.8 Hz), 7.54 (1H, d, J=7.3 Hz), 7.49 (1H, dd, J=7.9 Hz, J=7.9 Hz), 7.41 (1H, d, J=2.9 Hz), 7.15-7.25 (2H, m), 3.90 (3H, s), 3.89 (2H, s), 3.70-3.80 (1H, m), 3.49-3.60 (2H, m), 2.63 (1H, dd, J=5.6 Hz, J=13.7 Hz), 2.50 (1H, dd, J=7.1 Hz, J=13.7 Hz), 2.31 (3H, s), 2.30 (3H, s)

Mass spectrometric value (ESI-MS) 520 (M−1)

Compound 1020 N-[2-(4-Chloro-3-trifluoromethyl-benzylidene-hydrazinocarbonyl)-4-methoxy-phenyl]-3-(2,3-dihydroxy-propylsulfanyl-methyl)-benzamide The title compound 1020 was produced in substantially the same manner as in Example R.

$^1$H-NMR (CD$_3$OD, 400 MHz): δ 8.41 (1H, d, J=9.3 Hz), 8.38 (1H, s), 8.32 (1H, bs), 8.05-8.15 (1H, m), 7.94 (1H, bs), 7.83-7.88 (1H, m), 7.69 (1H, d, J=8.3 Hz), 7.58-7.63 (1H, m), 7.47-7.52 (1H, m), 7.42 (1H, d, J=2.9 Hz), 7.20-7.25 (1H, m), 3.90 (3H, s), 3.89 (2H, s), 3.75-3.82 (1H, m), 3.45-3.60 (2H, m), 2.60-2.67 (1H, m), 2.45-2.54 (1H, m)

Mass spectrometric value (ESI-MS) 594, 596, 597 (M−1)

Compound 1021 3-(2,3-Dihydroxy-propylsulfanylmethyl)-N-[4-methoxy-2-(4-methoxy-benzylidene-hydrazinocarbonyl)-phenyl]-benzamide The title compound 1021 was produced in substantially the same manner as in Example R.

$^1$H-NMR (CD$_3$OD, 400 MHz): δ 8.44 (1H, d, J=9.3 Hz), 8.29 (1H, s), 7.95 (1H, bs), 7.86 (1H, d, J=7.6 Hz), 7.80 (2H, d, J=8.8 Hz), 7.60 (1H, d, J=7.8 Hz), 7.49 (1H, dd, J=7.7 Hz, J=7.7 Hz), 7.40 (1H, d, J=2.9 Hz), 7.21 (1H, dd, J=2.9 Hz, J=9.3 Hz), 6.99 (2H, d, J=8.8 Hz), 3.90 (3H, s), 3.89 (2H, s), 3.85 (3H, s), 3.70-3.80 (1H, m), 3.49-3.60 (2H, m), 2.63 (1H, dd, J=5.6 Hz, J=13.7 Hz), 2.50 (1H, dd, J=7.1 Hz, J=13.4 Hz)

Mass spectrometric value (ESI-MS) 522, 523 (M−1)

Compound 1022 3-{[(2-Diethylamino-ethyl)-methyl-amino]-methyl}-N-[2-(3-fluoro-benzylidene-hydrazinocarbonyl)-4-methoxy-phenyl]-benzamide The title compound 1022 was produced in substantially the same manner as in Example R.
$^1$H-NMR (CD$_3$OD, 400 MHz): δ 8.42 (1H, d, J=9.0 Hz), 8.36 (1H, s), 7.14-8.00 (10H, m), 3.90 (3H, s), 3.73 (2H, s), 3.25 (2H, t, J=6.0 Hz), 3.11 (4H, q, J=7.2 Hz), 2.75 (2H, t, J=5.9 Hz), 2.35 (3H, s), 1.23 (6H, t, J=7.3 Hz)
Mass spectrometric value (ESI-MS) 532, 533, 534 (M−1)

Compound 1023 N-[2-(4-Chloro-3-trifluoromethyl-benzylidene-hydrazinocarbonyl)-4-methoxy-phenyl]-3-{[(2-diethylamino-ethyl)-methyl-amino]-methyl}-benzamide The title compound 1023 was produced in substantially the same manner as in Example R.
$^1$H-NMR (CD$_3$OD, 400 MHz): δ 8.36-8.42 (2H, m), 8.33 (1H, s), 8.03 (1H, d, J=8.5 Hz), 7.96 (1H, s), 7.89 (1H, d, J=7.8 Hz), 7.69 (1H, d, J=8.3 Hz), 7.59 (1H, d, J=7.8 Hz), 7.51 (1H, dd, J=7.7 Hz, J=7.7 Hz), 7.42 (1H, d, J=2.9 Hz), 7.22 (1H, dd, J=2.9 Hz, J=9.0 Hz), 3.90 (3H, s), 3.66 (2H, s), 2.70-2.77 (2H, m), 2.53-2.65 (6H, m), 2.28 (3H, s), 1.03 (6H, t, J=7.2 Hz)
Mass spectrometric value (ESI-MS) 616, 618, 619 (M−1)

Compound 1024 3-{[(2-Diethylamino-ethyl)-methyl-amino]-methyl}-N-[4-methoxy-2-(4-methoxy-benzylidene-hydrazinocarbonyl)-phenyl]-benzamide The title compound 1024 was produced in substantially the same manner as in Example R.
$^1$H-NMR (CD$_3$OD, 400 MHz): δ 8.43 (1H, d, J=9.3 Hz), 8.30 (1H, s), 7.97 (1H, bs), 7.90 (1H, d, J=8.6 Hz), 7.78 (2H, d, J=8.8 Hz), 7.58 (1H, d, J=7.8 Hz), 7.52 (1H, dd, J=7.6 Hz, J=7.6 Hz), 7.40 (1H, d, J=2.9 Hz), 7.20 (1H, dd, J=2.9 Hz, J=9.2 Hz), 6.99 (2H, d, J=8.8 Hz), 3.89 (3H, s), 3.84 (3H, s), 3.68 (2H, s), 2.85-2.92 (2H, m), 2.75 (4H, q, J=7.1 Hz), 2.62 (2H, t, J=7.0 Hz), 2.30 (3H, s), 1.08 (6H, t, J=7.2 Hz)
Mass spectrometric value (ESI-MS) 544, 545, 546 (M−1)

Example S

Compound 1025 3-{[(2-Diethylamino-ethyl)-methyl-amino]-methyl}-N-[2-(3-fluoro-benzylidene-hydrazinocarbonyl)-4-(2-methoxy-ethoxy)-phenyl]-benzamide 5-Hydroxy-2-nitro-benzoic acid (compound A') (1.5 g) was dissolved in methanol (15 ml). Thionyl chloride (1.5 ml) was added dropwise to the solution on an ice bath, and the mixture was then stirred at 80° C. for 12 hr. After the completion of the reaction, the reaction solution was neutralized with a saturated aqueous sodium hydrogencarbonate solution, and was then subjected to separatory extraction with ethyl acetate. The organic layer was washed with saturated brine, was dried over sodium sulfate, and was then concentrated under the reduced pressure to give crude 5-hydroxy-2-nitro-benzoic acid methyl ester (1.1 g, crude yield 70%).
Crude 5-hydroxy-2-nitro-benzoic acid methyl ester (1.1 g) produced by the above process was dissolved in acetone (12 ml). Potassium carbonate (1.5 g) and 1-bromo-2-methoxy-ethane (compound D) (1.5 ml) were added to the solution at room temperature, and the mixture was then stirred at 70° C. for 20 hr. After the completion of the reaction, the reaction system was concentrated under the reduced pressure. Distilled water was then added to the residue, and the mixture was then subjected to separatory extraction with ethyl acetate. The organic layer was washed with saturated brine, was dried over sodium sulfate, and was then concentrated under the reduced pressure. The residue was purified by column chromatography eluted with a hexane-acetone system to give 5-methoxy-ethoxy-2-nitro-benzoic acid methyl ester (1.0 g, yield 73%).
Subsequently, 5-methoxy-ethoxy-2-nitro-benzoic acid methyl ester (1.0 g) produced by the above process was dissolved in methanol (10 ml), and platinum oxide (90 mg) was added to the solution at room temperature. The air in the reaction system was replaced by hydrogen, and the mixture was then stirred at that temperature for 5 hr. After the completion of the reaction, the atmosphere in the reaction system was replaced by nitrogen, and the reaction solution was filtered through Celite to remove platinum oxide. The filtrate was then concentrated under the reduced pressure, and the residue was purified by column chromatography eluted with a hexane-ethyl acetate system to give 2-amino-5-methoxy-ethoxy-benzoic acid methyl ester (compound A) as a useful intermediate (770 mg, yield 83%)
2-Amino-5-methoxy-ethoxybenzoic acid methyl ester (compound A) (770 mg) produced by the above process was dissolved in anhydrous methylene chloride (10 ml). Pyridine (500 μl) and 3-(chloromethyl)benzoyl chloride (compound B) (600 μl) were added dropwise to the solution at 0° C., and the mixture was then stirred at room temperature for 3 hr. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure to precipitate crystals. The crude crystals were collected by Kiriyama Rohto and was washed with ether to give 2-(3-chloromethylbenzoylamino)-5-methoxy-ethoxybenzoic acid methyl ester (1.1 g, yield 89%).
Subsequently, 2-(3-chloromethylbenzoylamino)-5-methoxy-ethoxybenzoic acid methyl ester (1.1 g) produced by the above process was dissolved in anhydrous methylene chloride (15 ml). Triethylamine (1 ml) and N,N-diethyl-N'-methyl-ethylenediamine (compound B') (900 μl) were added dropwise to the solution at room temperature, and the mixture was then stirred at that temperature for 12 hr. After the completion of the reaction, the reaction system was concentrated under the reduced pressure, and the residue was purified by column chromatography eluted with a chloroform-methanol system to give 2-(3-{[(2-diethylaminoethyl)-methylamino]-methyl}-benzoylamino)-5-(2-methoxy-ethoxy)-benzoic acid methyl ester as a useful intermediate (1.4 g, yield 100%).
2-(3-{[(2-Diethylamino-ethyl)-methylamino]-methyl}-benzoylamino)-5-(2-methoxy-ethoxy)-benzoic acid methyl ester (1.4 g) produced by the above process was dissolved in ethanol (15 ml). Hydrazine monohydrate (1.5 ml) was added dropwise to the solution at room temperature, and the mixture was then stirred at that temperature for 12 hr. After the completion of the reaction, the reaction system was concentrated under the reduced pressure, and the residue was purified by column chromatography eluted with a chloroform-methanol system to give 3-{[(2-dimethoxyamino-ethyl)-methyl-amino]-methyl}-N-[2-hydrazinocarbonyl-4-(2-methoxy-ethoxy)-phenyl]-benzamide (1.3 g, yield 89%).

Subsequently, 3-{[(2-dimethoxyamino-ethyl)-methyl-amino]-methyl}-N-[2-hydrazinocarbonyl-4-(2-methoxy-ethoxy)-phenyl]-benzamide (52 mg) produced by the above process was dissolved in anhydrous toluene (1 ml). 3-Fluorobenzaldehyde (compound C) (50 µl) was added dropwise to the solution at room temperature, and the mixture was then stirred at 40° C. for 3 hr. After the completion of the reaction, the reaction solution was allowed to cool at room temperature and was then purified by column chromatography eluted with a chloroform-methanol system to give the title compound 1025 (50 mg, yield 78%).

$^1$H-NMR (CD$_3$OD, 400 MHz): δ 8.43 (1H, d, J=9.0 Hz), 8.36 (1H, s), 7.99 (1H, s), 7.90-7.95 (1H, m), 7.68-7.76 (2H, m), 7.08-7.64 (6H, m), 4.20-4.25 (2H, m), 3.77-3.82 (2H, m), 3.73 (2H, s), 3.45 (3H, s), 3.18 (2H, t, J=6.1 Hz), 3.04 (4H, q, J=7.2 Hz), 2.73 (2H, t, J=6.1 Hz), 2.34 (3H, s), 1.20 (6H, t, J=7.2 Hz)

Mass spectrometric value (ESI-MS) 576, 577, 578 (M−1)

Compound 1026 3-{[(2-Diethylamino-ethyl)-methyl-amino]-methyl}-N-[4-(2-methoxy-ethoxy)-2-(4-methyl-benzylidene-hydrazinocarbonyl)-phenyl]-benzamide The title compound 1026 was produced in substantially the same manner as in Example S.

$^1$H-NMR (CD$_3$OD, 400 MHz): δ 8.43 (1H, d, J=9.0 Hz), 8.32 (1H, s), 7.97 (1H, s), 7.89-7.94 (1H, m), 7.73 (2H, d, J=8.0 Hz), 7.59 (1H, d, J=7.3 Hz), 7.52 (1H, dd, J=7.6 Hz, J=7.6 Hz), 7.43 (1H, d, J=2.9 Hz), 7.21-7.30 (3H, m), 4.20-4.25 (2H, m), 3.76-3.81 (2H, m), 3.68 (2H, s), 3.45 (3H, s), 2.58-2.90 (8H, m), 2.38 (3H, s), 2.30 (3H, s), 1.07 (6H, t, J=7.2 Hz)

Mass spectrometric value (ESI-MS) 572, 573, 574 (M−1)

Compound 1027 N-[2-(4-Chloro-3-trifluoromethyl-benzylidene-hydrazinocarbonyl)-4-(2-methoxy-ethoxy)-phenyl]-3-{[(2-diethylamino-ethyl)-methyl-amino]-methyl}-benzamide The title compound 1027 was produced in substantially the same manner as in Example S.

$^1$H-NMR (CD$_3$OD, 400 MHz): δ 8.41 (1H, d, J=9.3 Hz), 8.38 (1H, s), 8.33 (1H, s), 8.03 (1H, d, J=8.3 Hz), 7.96 (1H, s), 7.88-7.92 (1H, m), 7.68 (1H, d, J=8.3 Hz), 7.59 (1H, d, J=7.8 Hz), 7.52 (1H, dd, J=7.6 Hz, J=7.6 Hz), 7.44 (1H, d, J=2.9 Hz), 7.24 (1H, dd, J=2.9 Hz, J=9.0 Hz), 4.20-4.25 (2H, m), 3.76-3.80 (2H, m), 3.67 (2H, s), 3.44 (3H, s), 2.81 (2H, t, J=6.8 Hz), 2.68 (4H, q, J=7.2 Hz), 2.59 (2H, t, J=7.1 Hz), 2.29 (3H, s), 1.06 (6H, t, J=7.3 Hz)

Mass spectrometric value (ESI-MS) 660, 662, 663 (M−1) 684 (M+23)

Compound 1028 3-{[(2-Diethylamino-ethyl)-methyl-amino]-methyl}-N-[2-(3-fluoro-benzylidene-hydrazinocarbonyl)-4,5-bis-(2-methoxy-ethoxy)-phenyl]-benzamide The title compound 1028 was produced in substantially the same manner as in Example Q.

$^1$H-NMR (CD$_3$OD, 400 MHz): δ 8.49 (1H, bs), 8.37 (1H, bs), 8.00 (1H, bs), 7.95 (1H, d, J=7.3 Hz), 7.85-7.90 (1H, m), 7.40-7.76 (5H, m), 7.12-7.24 (1H, m), 4.22-4.32 (4H, m), 3.76-3.86 (4H, m), 3.72 (2H, s), 3.46 (3H, s), 3.46 (3H, s), 3.00-3.08 (2H, m), 2.82-2.96 (4H, m), 2.65-2.73 (2H, m), 2.33 (3H, s), 1.12-1.20 (6H, m)

Mass spectrometric value (ESI-MS) 650, 651, 652 (M−1) 672, 675 (M+23)

Compound 1029 N-[4,5-Bis-(2-methoxy-ethoxy)-2-(4-methyl-benzylidene-hydrazinocarbonyl)-phenyl]-3-{[(2-diethylamino-ethyl)-methyl-amino]-methyl}-benzamide The title compound 1029 was produced in substantially the same manner as in Example Q.

$^1$H-NMR (CD$_3$OD, 400 MHz): δ 8.49 (1H, s), 8.34 (1H, s), 8.00 (1H, s), 7.92-7.98 (1H, m), 7.74 (2H, d, J=8.0 Hz), 7.51-7.65 (3H, m), 7.27 (2H, d, J=8.3 Hz), 4.23-4.33 (4H, m), 3.77-3.87 (4H, m), 3.71 (2H, s), 3.46 (3H, s), 3.46 (3H, s), 2.60-3.00 (8H, m), 2.39 (3H, s), 2.32 (3H, s), 1.10 (6H, t, J=7.2 Hz)

Mass spectrometric value (ESI-MS) 646, 647, 648 (M−1)

Compound 1030 3-{[(2-Diethylamino-ethyl)-methyl-amino]-methyl}-N-[2-(3,4-dimethyl-benzylidene-hydrazinocarbonyl)-4,5-bis-(2-methoxy-ethoxy)-phenyl]-benzamide The title compound 1030 was produced in substantially the same manner as in Example Q.

$^1$H-NMR (CD$_3$OD, 400 MHz): δ 8.48 (1H, s), 8.31 (1H, s), 8.01 (1H, s), 7.95 (1H, d, J=7.3 Hz), 7.40-7.70 (5H, m), 7.18-7.23 (1H, m), 4.23-4.32 (4H, m), 3.76-3.86 (4H, m), 3.72 (2H, s), 3.45-3.80 (6H, m), 2.95-3.05 (2H, m), 2.80-2.90 (4H, m), 2.67 (2H, t, J=6.7 Hz), 2.26-2.34 (9H, m), 1.12 (6H, t, J=7.3 Hz)

Mass spectrometric value (ESI-MS) 660, 661, 662 (M−1)

Compound 1031 N-[2-(4-Chloro-3-trifluoromethyl-benzylidene-hydrazinocarbonyl)-4,5-bis-(2-methoxy-ethoxy)-phenyl]-3-{[(2-diethylamino-ethyl)-methyl-amino]-methyl}-benzamide The title compound 1031 was produced in substantially the same manner as in Example Q.

$^1$H-NMR (CD$_3$OD, 400 MHz): δ 7.40-8.50 (10H, m), 4.23-4.33 (4H, m), 3.77-3.88 (4H, m), 3.74 (2H, s), 3.45-3.48 (6H, m), 2.65-3.30 (8H, m), 2.35 (3H, s), 1.21 (6H, t, J=7.2 Hz)

Mass spectrometric value (ESI-MS) 734, 736, 737 (M−1)

Compound 1032 3-{[(2-Diethylamino-ethyl)-methyl-amino]-methyl}-N-[2-(4-methoxy-benzylidene-hydrazinocarbonyl)-4,5-bis-(2-methoxy-ethoxy)-phenyl]-benzamide The title compound 1032 was produced in substantially the same manner as in Example Q.

$^1$H-NMR (CD$_3$OD, 400 MHz): δ 8.48 (1H, s), 8.32 (1H, s), 8.01 (1H, s), 7.95 (1H, d, J=7.3 Hz), 7.79 (2H, d, J=8.8 Hz), 7.50-7.70 (3H, m), 7.00 (2H, d, J=8.8 Hz), 4.23-4.33 (4H, m), 3.76-3.88 (7H, m), 3.72 (2H, s), 3.45-3.48 (6H, m), 3.05-3.10 (2H, m), 2.90-3.00 (4H, m), 2.65-2.73 (2H, m), 2.33 (3H, s), 1.16 (6H, t, J=7.2 Hz)

Mass spectrometric value (ESI-MS) 662, 663, 664 (M−1)

Compound 1033 3-{[(2-Diethylamino-ethyl)-methyl-amino]-methyl}-N-{2-(3-fluoro-benzylidene-hydrazinocarbonyl)-4-[2-(2-methoxy-ethoxy)-ethoxy]-phenyl}-benzamide The title compound 1033 was produced in substantially the same manner as in Example S.

$^1$H-NMR (CDCL$_3$, 400 MHz): δ 11.36 (1H, bs), 8.48 (1H, bs), 8.21 (1H, s), 7.65-7.93 (6H, m), 7.10-7.38 (5H, m), 4.12 (2H, bs), 3.78 (2H, bs), 3.63-3.67 (4H, m), 3.56-3.62 (2H, m), 3.50-3.55 (2H, m), 3.28 (3H, s), 3.05 (4H, bs), 2.75-2.80 (2H, m), 2.20-2.40 (3H, m), 1.15-1.25 (6H, m)

Mass spectrometric value (ESI-MS) 620, 621, 622 (M−1)

Compound 1034 3-{[(2-Diethylamino-ethyl)-methyl-amino]-methyl}-N-[4-[2-(2-methoxy-ethoxy)-ethoxy]-2-(4-methyl-benzylidene-hydrazinocarbonyl)-phenyl]-benzamide The title compound 1034 was produced in substantially the same manner as in Example S.

$^1$H-NMR (CDCL$_3$, 400 MHz): δ 11.37 (1H, bs), 8.49 (1H, d, J=9.0 Hz), 8.20 (1H, s), 7.84-7.90 (2H, m), 7.80 (1H, d, J=7.6 Hz), 7.60 (2H, d, J=7.8 Hz), 7.20-7.46 (3H, m), 6.98-7.20 (3H, m), 4.05-4.10 (2H, m), 3.68-3.74 (2H, m), 3.61-3.65 (2H, m), 3.50-3.55 (4H, m), 3.28 (3H, s), 2.50-2.70 (8H, m), 2.30 (3H, s), 2.17 (3H, s), 0.95-1.04 (6H, m)

Mass spectrometric value (ESI-MS) 616, 617, 618 (M−1)

Compound 1035 3-{[(2-Diethylamino-ethyl)-methyl-amino]-methyl}-N-{2-(3,4-dimethyl-benzylidene-hydrazinocarbonyl)-4-[2-(2-methoxy-ethoxy)-ethoxy]-phenyl}-benzamide The title compound 1035 was produced in substantially the same manner as in Example S.

$^1$H-NMR (CDCL$_3$, 400 MHz): δ 11.37 (1H, bs), 8.48 (1H, d, J=9.0 Hz), 8.19 (1H, s), 7.86 (1H, s), 7.80 (1H, d, J=7.6 Hz), 7.54 (1H, s), 7.20-7.46 (4H, m), 6.96-7.12 (3H, m), 4.03-4.10 (2H, m), 3.69 (2H, bs), 3.60-3.65 (2H, m), 3.50-3.55 (4H, m), 3.27 (3H, s), 2.47-2.70 (8H, m), 2.21 (6H, s), 2.16 (3H, s), 0.98 (6H, t, J=7.0 Hz)

Mass spectrometric value (ESI-MS) 630, 631, 632 (M−1)

Compound 1036 N-{2-(4-Chloro-3-trifluoromethyl-benzylidene-hydrazinocarbonyl)-4-[2-(2-methoxy-ethoxy)-ethoxy]-phenyl}-3-{[(2-diethylamino-ethyl)-methyl-amino]-methyl}-benzamide The title compound 1036 was produced in substantially the same manner as in Example S.

$^1$H-NMR (CD$_3$OD, 400 MHz): δ 8.41 (1H, d, J=9.0 Hz), 8.38 (1H, s), 8.32 (1H, s), 8.03 (1H, d, J=8.3 Hz), 7.96 (1H, s), 7.87-7.92 (1H, m), 7.68 (1H, d, J=8.3 Hz), 7.59 (1H, d, J=7.8 Hz), 7.44-7.54 (2H, m), 7.24 (1H, dd, J=2.9 Hz, J=9.0 Hz), 4.20-4.26 (2H, m), 3.84-3.90 (2H, m), 3.68-3.74 (2H, m), 3.66 (2H, s), 3.55-3.60 (2H, m), 3.37 (3H, s), 2.53-2.75 (8H, m), 2.28 (3H, s), 1.03 (6H, t, J=7.2 Hz)

Mass spectrometric value (ESI-MS) 704, 706, 707 (M−1)

Compound 1037 3-{[(2-Diethylamino-ethyl)-methyl-amino]-methyl}-N-{2-(4-methoxy-benzylidene-hydrazinocarbonyl)-4-[2-(2-methoxy-ethoxy)-ethoxy]-phenyl}-benzamide The title compound 1037 was produced in substantially the same manner as in Example S.

$^1$H-NMR (CD$_3$OD, 400 MHz): δ 8.44 (1H, d, J=9.3 Hz), 8.29 (1H, s), 7.96 (1H, bs), 7.87-7.92 (1H, m), 7.78 (2H, d, J=8.8 Hz), 7.58 (1H, d, J=7.6 Hz), 7.51 (1H, dd, J=7.6 Hz, J=7.6 Hz), 7.43 (1H, d, J=2.9 Hz), 7.22 (1H, dd, J=2.9 Hz, J=9.0 Hz), 6.99 (2H, d, J=9.0 Hz), 4.21-4.25 (2H, m), 3.85-3.88 (2H, m), 3.84 (3H, s), 3.69-3.72 (2H, m), 3.67 (2H, s), 3.56-3.59 (2H, m), 3.37 (3H, s), 2.55-2.80 (8H, m), 2.28 (3H, s), 1.04 (6H, t, J=7.2 Hz)

Mass spectrometric value (ESI-MS) 632, 633, 634 (M−1)

Example T

Compound 1038 N-[2-(4-Chloro-3-trifluoromethyl-benzylidene-hydrazinocarbonyl)-4-(3-piperidin-1-yl-propoxy)-phenyl]-3-{[(2-diethylamino-ethyl)-methyl-amino]-methyl}-benzamide 5-Hydroxy-2-nitro-benzoic acid (compound A') (2.0 g) was dissolved in methanol (30 ml). Thionyl chloride (3.0 ml) was added dropwise to the solution on an ice bath, and the mixture was then stirred at 75° C. for 96 hr. After the completion of the reaction, the reaction solution was neutralized with a saturated aqueous sodium hydrogencarbonate solution and was then subjected to separatory extraction with ethyl acetate. The organic layer was washed with saturated brine, was dried over sodium sulfate, and was then concentrated under the reduced pressure to give crude 5-hydroxy-2-nitro-benzoic acid methyl ester (2.2 g, crude yield 100%).

Subsequently, crude 5-hydroxy-2-nitro-benzoic acid methyl ester (2.2 g) produced by the above process was dissolved in acetone (15 ml). Potassium carbonate (3.0 g) and 1-bromo-3-chloro-propane (compound D) (3.1 ml) were added to the solution at room temperature, and the mixture was then stirred at that temperature for 2 hr. After the completion of the reaction, the reaction system was concentrated under the reduced pressure. Distilled water was then added to the residue, the mixture was subjected to separatory extraction with chloroform, and the organic layer was washed with saturated brine, was dried over sodium sulfate, and was then concentrated under the reduced pressure. The residue was purified by column chromatography eluted with a hexane-acetone system to give 5-(3-chloro-propoxy)-2-nitro-benzoic acid methyl ester (2.9 g, yield 96%).

5-(3-Chloro-propoxy)-2-nitro-benzoic acid methyl ester (2.9 g) produced by the above process was dissolved in acetone (30 ml). Potassium carbonate (3.0 g) and piperidine (compound E) (2.0 ml) were added to the solution at room temperature, and the mixture was then stirred at 70° C. for 24 hr. After the completion of the reaction, the reaction system was concentrated under the reduced pressure. Distilled water was then added to the residue, the mixture was subjected to separatory extraction with chloroform, and the organic layer was washed with saturated brine, was dried over sodium sulfate, and was then concentrated under the reduced pressure. The residue was purified by column chromatography eluted with a chloroform-methanol system to give 2-nitro-5-(3-piperidin-1-yl-propoxy)-benzoic acid methyl ester (2.4 g, yield 69%).

Subsequently, 2-nitro-5-(3-piperidin-1-yl-propoxy)-benzoic acid methyl ester (2.4 g) produced by the above process was dissolved in methanol (24 ml), and platinum oxide (220 mg) was added to the solution at room temperature. The air in the reaction system was replaced by hydrogen, and the mixture was then stirred at that temperature for 12 hr. After the completion of the reaction, the atmosphere in the reaction system was replaced by nitrogen, and the reaction solution was filtered through Celite to remove platinum oxide. The filtrate was then concentrated under the reduced pressure, and the residue was purified by column chromatography eluted with a chloroform-methanol system to give 2-amino-5-(3-piperidin-1-yl-propoxy)-benzoic acid methyl ester (compound A) as a useful intermediate (1.1 g, yield 50%).

2-Amino-5-(3-piperidin-1-yl-propoxy)-benzoic acid methyl ester (compound A) (1.1 g) produced by the above process was dissolved in anhydrous methylene chloride (12 ml). Pyridine (600 μl) and 3-(chloromethyl)benzoyl chloride (compound B) (600 μl) were added dropwise to the solution at 0° C., and the mixture was stirred at room temperature for one hr. After the completion of the reaction, distilled water was added thereto at room temperature, and the mixture was then subjected to separatory extraction with chloroform. The organic layer was washed with saturated brine, was dried over sodium sulfate, and was then concentrated under the reduced pressure. The residue was purified by column chromatography eluted with a chloroform-methanol system to give 2-(3-chloromethyl-benzoylamino)-5-(3-piperidin-1-yl-propoxy)-benzoic acid methyl ester (1.5 g, yield 93%).

Subsequently, 2-(3-chloromethyl-benzoylamino)-5-(3-piperidin-1-yl-propoxy)-benzoic acid methyl ester (1.5 g) produced by the above process was dissolved in anhydrous methylene chloride (11 ml). Triethylamine (450 μl) and N,N-diethyl-N'-methyl-ethylenediamine (compound B') (480 μl) was added dropwise to the solution at room temperature, and the mixture was then stirred at that temperature for 12 hr. After the completion of the reaction, the reaction system was concentrated under the reduced pressure, and the residue was purified by column chromatography eluted with a chloroform-methanol system to give 2-(3-{[(2-diethylamino-ethyl)-methyl-amino]-methyl}benzoylamino)-5-(3-piperidin-1-yl-propoxy)-benzoic acid methyl ester as a useful intermediate (290 mg, yield 34%).

2-(3-{[(2-Diethylamino-ethyl)-methyl-amino]-methyl}benzoyl-amino)-5-(3-piperidin-1-yl-propoxy)-benzoic acid methyl ester (290 mg) produced by the above process was dissolved in ethanol (4 ml). Hydrazine monohydrate (300 μl) was added dropwise to the solution at room temperature, and the mixture was then stirred at that temperature for 6 hr. After the completion of the reaction, the reaction system was concentrated under the reduced pressure, and the residue was purified by column chromatography eluted with a chloroform-methanol system to give 3-{[(2-diethylamino-ethyl)-methyl-amino]-methyl}-N-[2-hydrazinocarbonyl-4-(3-piperidin-1-yl-propoxy)-phenyl]-benzamide (140 mg, yield 49%).

Subsequently, 3-{[(2-diethylamino-ethyl)-methyl-amino]-methyl}-N-[2-hydrazinocarbonyl-4-(3-piperidin-1-yl-propoxy)-phenyl]-benzamide (50 mg) produced by the above process was dissolved in anhydrous toluene (1.2 ml). 4-Chloro-3-(trifluoromethyl)benzaldehyde (compound C) (50 μl) was added dropwise to the solution at room temperature, and the mixture was then stirred at that temperature for 12 hr. After the completion of the reaction, the reaction system was concentrated. The residue was purified by column chromatography eluted with a chloroform-methanol system to give the title compound 1038 (67 mg, yield 100%).

$^1$H-NMR (CD$_3$OD, 400 MHz): δ 8.40 (1H, d, J=9.0 Hz), 8.37 (1H, s), 8.32 (1H, s), 8.03 (1H, d, J=8.5 Hz), 7.95 (1H, s), 7.85-7.94 (1H, m), 7.68 (1H, d, J=8.3 Hz), 7.56-7.63 (1H, m), 7.51 (1H, dd, J=7.7 Hz, J=7.7 Hz), 7.44 (1H, d, J=2.7 Hz), 7.20 (1H, dd, J=2.7 Hz, J=9.0 Hz), 4.08-4.15 (2H, m), 3.62-3.70 (2H, m), 2.45-2.72 (14H, m), 2.27 (3H, s), 1.98-2.07 (2H, m), 1.60-1.70 (4H, m), 1.45-1.54 (2H, m), 1.01 (6H, t, J=7.2 Hz)

Mass spectrometric value (ESI-MS) 727, 728, 730 (M−1)

Compound 1039 N-[2-(4-Chloro-3-trifluoromethyl-benzylidene-hydrazinocarbonyl)-4-(3-piperidin-1-yl-propoxy)-phenyl]-3-(2-hydroxy-ethylsulfanylmethyl)-benzamide The title compound 1039 was produced in substantially the same manner as in Example T.

$^1$H-NMR (CD$_3$OD, 400 MHz): δ 8.41 (1H, d, J=9.0 Hz), 8.37 (1H, s), 8.30-8.34 (1H, m), 8.04 (1H, d, J=7.1 Hz), 7.83-7.94 (2H, m), 7.68 (1H, d, J=8.3 Hz), 7.59 (1H, d, J=7.6 Hz), 7.50 (1H, dd, J=7.8 Hz, J=7.8 Hz), 7.42 (1H, d, J=2.7 Hz), 7.22 (1H, dd, J=2.7 Hz, J=9.2 Hz), 4.14 (2H, t, J=6.1 Hz), 3.86 (2H, s), 3.68 (2H, t, J=6.8 Hz), 2.65-2.80 (6H, m), 2.57 (2H, t, J=6.8 Hz), 2.05-2.15 (2H, m), 1.67-1.75 (4H, m), 1.50-1.60 (2H, m)

Mass spectrometric value (ESI-MS) 675, 677, 678 (M−1)

Compound 1040 3-(2-Hydroxy-ethylsulfanylmethyl)-N-[2-(4-methoxy-benzylidene-hydrazinocarbonyl)-4-(3-piperidin-1-yl-propoxy)-phenyl]-benzamide The title compound 1040 was produced in substantially the same manner as in Example T.

$^1$H-NMR (CD$_3$OD, 400 MHz): δ 8.45 (1H, d, J=9.0 Hz), 8.28 (1H, s), 7.92 (1H, bs), 7.85 (1H, d, J=8.0 Hz), 7.78 (2H, d, J=8.3 Hz), 7.58 (1H, d, J=7.8 Hz), 7.49 (1H, dd, J=7.7 Hz, J=7.7 Hz), 7.39 (1H, d, J=2.4 Hz), 7.18 (1H, d, J=9.3 Hz), 6.98 (2H, d, J=8.3 Hz), 4.11 (2H, t, J=5.7 Hz), 3.86 (2H, s), 3.83 (3H, s), 3.68 (2H, t, J=6.8 Hz), 2.54-2.68 (8H, m), 2.00-2.09 (2H, m), 1.62-1.70 (4H, m), 1.47-1.57 (2H, m)

Mass spectrometric value (ESI-MS) 603, 604, 605 (M−1)

Compound 1041 N-[2-(3,4-Dimethyl-benzylidene-hydrazinocarbonyl)-4-(3-piperidin-1-yl-propoxy)-phenyl]-3-(2-hydroxy-ethylsulfanylmethyl)-benzamide The title compound 1041 was produced in substantially the same manner as in Example T.

$^1$H-NMR (CD$_3$OD, 400 MHz): δ 8.45 (1H, d, J=9.3 Hz), 8.28 (1H, s), 7.93 (1H, bs), 7.86 (1H, d, J=7.8 Hz), 7.65 (1H, s), 7.59 (1H, d, J=7.8 Hz), 7.53 (1H, d, J=8.1 Hz), 7.49 (1H, dd, J=7.7 Hz, J=7.7 Hz), 7.41 (1H, d, J=2.7 Hz), 7.16-7.23 (2H, m), 4.13 (2H, t, J=6.1 Hz), 3.87 (2H, s), 3.68 (2H, t, J=6.8 Hz), 2.55-2.73 (8H, m), 2.31 (3H, s), 2.30 (3H, s), 2.00-2.10 (2H, m), 1.65-1.75 (4H, m), 1.50-1.58 (2H, m)

Mass spectrometric value (ESI-MS) 601, 602, 603 (M−1)

Compound 1042 3-(2-Hydroxy-ethylsulfanylmethyl)-N-[2-(4-methyl-benzylidene-hydrazinocarbonyl)-4-(2-piperidin-1-yl-ethoxy)-phenyl]-benzamide The title compound 1042 was produced in substantially the same manner as in Example T.

$^1$H-NMR (CD$_3$OD, 400 MHz): δ 8.46 (1H, d, J=9.0 Hz), 8.32 (1H, s), 7.93 (1H, bs), 7.86 (1H, d, J=7.8 Hz), 7.73 (2H, d, J=8.3 Hz), 7.59 (1H, d, J=7.8 Hz), 7.49 (1H, dd, J=7.7 Hz, J=7.7 Hz), 7.42 (1H, d, J=2.9 Hz), 7.25 (2H, d, J=7.8 Hz), 7.22 (1H, dd, J=2.9 Hz, J=9.3 Hz), 4.23 (2H, t, J=5.6 Hz), 3.87 (2H, s), 3.68 (2H, t, J=6.8 Hz), 2.83 (2H, t, J=5.7 Hz), 2.55-2.65 (6H, m), 2.38 (3H, s), 1.62-1.70 (4H, m), 1.46-1.55 (2H, m)

Mass spectrometric value (ESI-MS) 573, 574, 575 (M−1)

Compound 1043 N-[2-(3,4-Dimethyl-benzylidene-hydrazinocarbonyl)-4-(2-piperidin-1-yl-ethoxy)-phenyl]-3-(2-hydroxy-ethylsulfanylmethyl)-benzamide The title compound 1043 was produced in substantially the same manner as in Example T.

$^1$H-NMR (CD$_3$OD, 400 MHz): δ 8.46 (1H, d, J=9.0 Hz), 8.29 (1H, s), 7.93 (1H, s), 7.86 (1H, d, J=7.6 Hz), 7.66 (1H, s), 7.60 (1H, d, J=7.6 Hz), 7.54 (1H, d, J=8.0 Hz), 7.50 (1H, dd, J=7.7 Hz, J=7.7 Hz), 7.43 (1H, d, J=3.0 Hz), 7.17-7.25 (2H, m), 4.23 (2H, t, J=5.6 Hz), 3.87 (2H, s), 3.68 (2H, t, J=6.7 Hz), 2.83 (2H, t, J=5.5 Hz), 2.55-2.65 (6H, m), 2.32 (3H, s), 2.30 (3H, s), 1.61-1.70 (4H, m), 1.45-1.55 (2H, m)

Mass spectrometric value (ESI-MS) 587, 588 (M−1)

Compound 1044 N-[2-(4-Chloro-3-trifluoromethyl-benzylidene-hydrazinocarbonyl)-4-(2-piperidin-1-yl-ethoxy)-phenyl]-3-(2-hydroxy-ethylsulfanylmethyl)-benzamide The title compound 1044 was produced in substantially the same manner as in Example T.

$^1$H-NMR (CD$_3$OD, 400 MHz): δ 8.44 (1H, d, J=9.0 Hz), 8.38 (1H, s), 8.34 (1H, bs), 8.03-8.08 (1H, m), 7.93 (1H, bs), 7.86 (1H, d, J=7.8 Hz), 7.69 (1H, d, J=8.3 Hz), 7.60 (1H, d, J=8.6 Hz), 7.50 (1H, dd, J=7.8 Hz, J=7.8 Hz), 7.44 (1H, d, J=2.7 Hz), 7.24 (1H, dd, J=2.9 Hz, J=9.3 Hz), 4.23 (2H, t, J=5.6 Hz), 3.86 (2H, s), 3.68 (2H, t, J=7.0 Hz), 2.83 (2H, t, J=5.6 Hz), 2.55-2.63 (6H, m), 1.62-1.70 (4H, m), 1.45-1.55 (2H, m)

Mass spectrometric value (ESI-MS) 661, 663, 664 (M−1)

Compound 1045 3-(2-Hydroxy-ethylsulfanylmethyl)-N-[2-(4-methoxy-benzylidene-hydrazinocarbonyl)-4-(2-piperidin-1-yl-ethoxy)-phenyl]-benzamide The title compound 1045 was produced in substantially the same manner as in Example T.

$^1$H-NMR (CD$_3$OD, 400 MHz): δ 8.47 (1H, d, J=9.3 Hz), 8.30 (1H, s), 7.93 (1H, bs), 7.86 (1H, d, J=8.1 Hz), 7.80 (2H, d, J=8.8 Hz), 7.60 (1H, d, J=7.8 Hz), 7.50 (1H, dd, J=7.7 Hz, J=7.7 Hz), 7.42 (1H, d, J=2.9 Hz), 7.22 (1H, dd, J=2.9 Hz, J=9.0 Hz), 6.99 (2H, d, J=8.8 Hz), 4.23 (2H, t, J=5.6 Hz), 3.87 (2H, s), 3.84 (3H, s), 3.68 (2H, t, J=6.8 Hz), 2.82 (2H, t, J=5.6 Hz), 2.55-2.63 (6H, m), 1.62-1.70 (4H, m), 1.45-1.55 (2H, m)

Mass spectrometric value (ESI-MS) 589, 590 (M−1)

Compound 1046 N-[4-Cyclohexylmethoxy-2-(3-fluoro-benzylidene-hydrazinocarbonyl)-phenyl]-3-{[(2-diethylamino-ethyl)-methyl-amino]-methyl}-benzamide The title compound 1046 was produced in substantially the same manner as in Example S.

$^1$H-NMR (CD$_3$OD, 400 MHz): δ 8.41 (1H, d, J=9.0 Hz), 8.34 (1H, s), 7.97 (1H, s), 7.88-7.93 (1H, m), 7.68-7.78 (1H, m), 7.30-7.64 (5H, m), 7.08-7.22 (2H, m), 3.88 (2H, d, J=6.1 Hz), 3.69 (2H, s), 2.80-2.93 (2H, m), 2.68-2.80 (4H, m), 2.55-2.65 (2H, m), 2.30 (3H, s), 1.68-1.95 (5H, m), 1.10-1.42 (6H, m), 1.08 (6H, t, J=7.2 Hz)

Mass spectrometric value (ESI-MS) 614, 615, 616 (M−1) 638 (M+23)

Compound 1047 N-[4-Cyclohexylmethoxy-2-(4-methyl-benzylidene-hydrazinocarbonyl)-phenyl]-3-{[(2-diethylamino-ethyl)-methyl-amino]-methyl}-benzamide The title compound 1047 was produced in substantially the same manner as in Example S.

$^1$H-NMR (CD$_3$OD, 400 MHz): δ 8.41 (1H, d, J=9.0 Hz), 8.32 (1H, s), 7.96 (1H, bs), 7.88-7.92 (1H, m), 7.73 (2H, d, J=8.0 Hz), 7.58 (1H, d, J=7.6 Hz), 7.52 (1H, dd, J=7.6 Hz, J=7.6 Hz), 7.39 (1H, d, J=2.8 Hz), 7.26 (2H, d, J=8.1 Hz), 7.19 (1H, dd, J=2.9 Hz, J=9.0 Hz), 3.88 (2H, d, J=6.4 Hz), 3.68 (2H, s), 2.55-2.85 (8H, m), 2.38 (3H, s), 2.29 (3H, s), 1.70-1.95 (5H, m), 1.10-1.42 (6H, m), 1.05 (6H, t, J=7.2 Hz)

Mass spectrometric value (ESI-MS) 610, 611, 612 (M−1)

Compound 1048 N-[4-Cyclohexylmethoxy-2-(3,4-dimethyl-benzylidene-hydrazinocarbonyl)-phenyl]-3-{[(2-diethylamino-ethyl)-methyl-amino]-methyl}-benzamide The title compound 1048 was produced in substantially the same manner as in Example S.

$^1$H-NMR (CD$_3$OD, 400 MHz): δ 8.42 (1H, d, J=9.3 Hz), 8.28 (1H, s), 7.96 (1H, bs), 7.88-7.93 (1H, m), 7.64 (1H, s), 7.58 (1H, d, J=7.6 Hz), 7.49-7.55 (2H, m), 7.39 (1H, d, J=2.9 Hz), 7.16-7.23 (2H, m), 3.87 (2H, d, J=6.4 Hz), 3.67 (2H, s), 2.55-2.80 (8H, m), 2.31 (3H, s), 2.30 (3H, s), 2.29 (3H, s), 1.70-1.95 (5H, m), 1.10-1.42 (6H, m), 1.04 (6H, t, J=7.2 Hz)

Mass spectrometric value (ESI-MS) 624, 625, 626 (M−1) 670, 671 (M+23×2)

Compound 1049 N-[2-(4-Chloro-3-trifluoromethyl-benzylidene-hydrazinocarbonyl)-4-cyclohexyl-methoxy-phenyl]-3-{[(2-diethylamino-ethyl)-methyl-amino]-methyl}-benzamide The title compound 1049 was produced in substantially the same manner as in Example S.

$^1$H-NMR (CD$_3$OD, 400 MHz): δ 8.30-8.42 (2H, m), 8.03 (1H, d, J=8.3 Hz), 7.96 (1H, s), 7.87-7.92 (1H, m), 7.69 (1H, d, J=8.6 Hz), 7.59 (1H, d, J=7.6 Hz), 7.48-7.54 (2H, m), 7.41 (1H, d, J=2.7 Hz), 7.20 (1H, dd, J=2.7 Hz, J=9.0 Hz), 3.88 (2H, d, J=6.3 Hz), 3.67 (2H, s), 2.54-2.78 (8H, m), 2.28 (3H, s), 1.70-1.95 (5H, m), 1.08-1.42 (6H, m), 1.04 (6H, t, J=7.2 Hz)

Mass spectrometric value (ESI-MS) 698, 700, 701 (M−1)

Compound 1050 N-[4-Cyclohexylmethoxy-2-(4-methoxy-benzylidene-hydrazinocarbonyl)-phenyl]-3-{[(2-diethylamino-ethyl)-methyl-amino]-methyl}-benzamide The title compound 1050 was produced in substantially the same manner as in Example S.

$^1$H-NMR (CD$_3$OD, 400 MHz): δ 8.42 (1H, d, J=9.0 Hz), 8.29 (1H, s), 7.96 (1H, bs), 7.87-7.93 (1H, m), 7.78 (2H, d, J=8.8 Hz), 7.59 (1H, d, J=7.3 Hz), 7.51 (1H, dd, J=7.7 Hz, J=7.7 Hz), 7.38 (1H, d, J=3.0 Hz), 7.18 (1H, dd, J=3.0 Hz, J=9.3 Hz), 6.99 (2H, d, J=8.8 Hz), 3.87 (2H, d, J=6.4 Hz), 3.84 (3H, s), 3.67 (2H, s), 2.54-2.80 (8H, m), 2.28 (3H, s), 1.70-1.95 (5H, m), 1.10-1.42 (6H, m), 1.03 (6H, t, J=7.2 Hz)

Mass spectrometric value (ESI-MS) 626, 627, 628 (M−1) 650 (M+23)

Compound 1051 N-[2-(3-Fluoro-benzylidene-hydrazinocarbonyl)-4-(4-fluoro-butoxy)-phenyl]-3-(2-hydroxy-ethylsulfanylmethyl)-benzamide The title compound 1051 was produced in substantially the same manner as in Example S.

$^1$H-NMR (CD$_3$OD, 400 MHz): δ 8.43 (1H, d, J=9.0 Hz), 8.34 (1H, s), 7.93 (1H, s), 7.86 (1H, d, J=7.8 Hz), 7.70 (1H, d, J=9.0 Hz), 7.59 (2H, d, J=7.6 Hz), 7.40-7.52 (3H, m), 7.13-7.25 (2H, m), 4.55-4.60 (1H, m), 4.46 (1H, t, J=5.7 Hz), 4.13 (2H, t, J=5.9 Hz), 3.87 (2H, s), 3.68 (2H, t, J=6.8 Hz), 2.58 (2H, t, J=6.8 Hz), 1.80-1.95 (4H, m)

Mass spectrometric value (ESI-MS) 540, 541 (M−1) 564 (M+23)

Compound 1052 N-[4-(4-Fluoro-butoxy)-2-(4-methyl-benzylidene-hydrazinocarbonyl)-phenyl]-3-(2-hydroxy-ethylsulfanylmethyl)-benzamide The title compound 1052 was produced in substantially the same manner as in Example S.
$^1$H-NMR (CD$_3$OD, 400 MHz): δ 8.45 (1H, d, J=9.0 Hz), 8.31 (1H, s), 7.93 (1H, bs), 7.86 (1H, d, J=8.0 Hz), 7.73 (2H, d, J=8.0 Hz), 7.59 (1H, d, J=8.1 Hz), 7.49 (1H, dd, J=7.6 Hz, J=7.6 Hz), 7.42 (1H, d, J=2.9 Hz), 7.26 (2H, d, J=7.8 Hz), 7.21 (1H, dd, J=2.9 Hz, J=9.3 Hz), 4.55-4.60 (1H, m), 4.46 (1H, t, J=5.7 Hz), 4.13 (2H, t, J=6.0 Hz), 3.87 (2H, s), 3.68 (2H, t, J=6.8 Hz), 2.57 (2H, t, J=6.8 Hz), 2.38 (3H, s), 1.80-1.96 (4H, m)
Mass spectrometric value (ESI-MS) 536, 537 (M−1)

Compound 1053 N-[2-(3,4-Dimethyl-benzylidene-hydrazinocarbonyl)-4-(4-fluoro-butoxy)-phenyl]-3-(2-hydroxy-ethylsulfanylmethyl)-benzamide The title compound 1053 was produced in substantially the same manner as in Example S.
$^1$H-NMR (CD$_3$OD, 400 MHz): δ 8.45 (1H, d, J=9.3 Hz), 8.28 (1H, s), 7.93 (1H, s), 7.86 (1H, d, J=8.0 Hz), 7.65 (1H, s), 7.59 (1H, d, J=7.6 Hz), 7.53 (1H, d, J=8.8 Hz), 7.49 (1H, dd, J=7.7 Hz, J=7.7 Hz), 7.41 (1H, d, J=2.7 Hz), 7.17-7.24 (2H, m), 4.55-4.60 (1H, m), 4.46 (1H, t, J=5.7 Hz), 4.12 (2H, t, J=6.0 Hz), 3.87 (2H, s), 3.68 (2H, t, J=6.8 Hz), 2.57 (2H, t, J=6.8 Hz), 2.31 (3H, s), 2.30 (3H, s), 1.83-1.95 (4H, m)
Mass spectrometric value (ESI-MS) 550, 551 (M−1)

Compound 1054 N-[2-(4-Chloro-3-trifluoromethyl-benzylidene-hydrazinocarbonyl)-4-(4-fluoro-butoxy)-phenyl]-3-(2-hydroxy-ethylsulfanylmethyl)-benzamide The title compound 1054 was produced in substantially the same manner as in Example S.
$^1$H-NMR (CD$_3$OD, 400 MHz): δ 8.42 (1H, d, J=9.2 Hz), 8.37 (1H, s), 8.32 (1H, s), 8.01-8.05 (1H, m), 7.92 (1H, s), 7.85 (1H, d, J=7.8 Hz), 7.67 (1H, d, J=8.3 Hz), 7.59 (1H, d, J=7.6 Hz), 7.49 (1H, dd, J=7.7 Hz, J=7.7 Hz), 7.42 (1H, d, J=2.7 Hz), 7.22 (1H, dd, J=2.7 Hz, J=9.2 Hz), 4.55-4.60 (1H, m), 4.46 (1H, t, J=5.7 Hz), 4.12 (2H, t, J=5.8 Hz), 3.86 (2H, s), 3.68 (2H, t, J=6.8 Hz), 2.57 (2H, t, J=7.0 Hz), 1.80-1.95 (4H, m)
Mass spectrometric value (ESI-MS) 624, 626, 627 (M−1)

Compound 1055 N-[4-(4-Fluoro-butoxy)-2-(4-methoxy-benzylidene-hydrazinocarbonyl)-phenyl]-3-(2-hydroxy-ethylsulfanylmethyl)-benzamide The title compound 1055 was produced in substantially the same manner as in Example S.
$^1$H-NMR (CD$_3$OD, 400 MHz): δ 6.95-8.60 (12H, m), 4.55-4.62 (1H, m), 4.46 (1H, t, J=5.7 Hz), 4.12 (2H, t, J=6.0 Hz), 3.83-3.88 (3H, m), 3.79 (2H, s), 3.68 (2H, t, J=6.8 Hz), 2.57 (2H, t, J=6.8 Hz), 1.80-1.95 (4H, m)
Mass spectrometric value (ESI-MS) 552, 553 (M−1)

Compound 1056 3-{[Bis-(2-diethylamino-ethyl)-amino]-methyl}-N-[3-(4-methyl-benzylidene-hydrazinocarbonyl)-4,5,6,7-tetrahydro-benzo[b]thiophen-2-yl]-benzamide The title compound 1056 was produced in substantially the same manner as in Example B.
$^1$H-NMR (CDCl$_3$, 400 MHz): δ 0.98 (12H, t, J=7.1 Hz), 1.92 (4H, m), 2.40 (3H, s), 2.45-2.65 (16H, m), 2.76 (2H, m), 2.89 (2H, m), 3.72 (2H, s), 7.24 (2H, m), 7.43 (1H, dd, J=7.7 Hz, J=7.7 Hz), 7.60 (1H, d, J=7.3 Hz), 7.69 (2H, d, J=8.0 Hz), 7.92 (1H, m), 8.00 (1H, s), 8.08 (1H, s)
Mass spectrometric value (ESI-MS) 644 (M−1)

Compound 1057 3-{[(2-Diethylamino-ethyl)-methyl-amino]-methyl}-N-[2-(3-fluoro-benzylidene-hydrazinocarbonyl)-4-(4-fluoro-butoxy)-phenyl]-benzamide The title compound 1057 was produced in substantially the same manner as in Example S.
$^1$H-NMR (CD$_3$OD, 400 MHz): δ 8.41 (1H, d, J=9.0 Hz), 8.34 (1H, s), 7.88-7.98 (2H, m), 7.40-7.78 (6H, m), 7.14-7.26 (2H, m), 4.55-4.60 (1H, m), 4.46 (1H, t, J=5.7 Hz), 4.13 (2H, t, J=5.9 Hz), 3.68 (2H, s), 2.81 (2H, t, J=6.8 Hz), 2.68 (4H, q, J=7.1 Hz), 2.60 (2H, t, J=7.0 Hz), 2.29 (3H, s), 1.83-1.97 (4H, m), 1.06 (6H, t, J=7.2 Hz)
Mass spectrometric value (ESI-MS) 592, 593, 594 (M−1) 638 (M+2×23)

Compound 1058 3-{[(2-Diethylamino-ethyl)-methyl-amino]-methyl}-N-[4-(4-fluoro-butoxy)-2-(4-methyl-benzylidene-hydrazinocarbonyl)-phenyl]-benzamide The title compound 1058 was produced in substantially the same manner as in Example S.
$^1$H-NMR (CD$_3$OD, 400 MHz): δ 8.42 (1H, d, J=9.0 Hz), 8.32 (1H, s), 7.95 (1H, s), 7.86-7.92 (1H, m), 7.71 (2H, d, J=8.1 Hz), 7.58 (1H, d, J=7.6 Hz), 7.51 (1H, dd, J=7.7 Hz, J=7.7 Hz), 7.41 (1H, d, J=2.7 Hz), 7.25 (2H, d, J=7.8 Hz), 7.19 (1H, dd, J=2.9 Hz, J=9.0 Hz), 4.55-4.60 (1H, m), 4.45 (1H, t, J=5.6 Hz), 4.11 (2H, t, J=5.7 Hz), 3.66 (2H, s), 2.72-2.79 (2H, m), 2.54-2.68 (6H, m), 2.37 (3H, s), 2.28 (3H, s), 1.80-1.95 (4H, m), 1.04 (6H, t, J=7.2 Hz)
Mass spectrometric value (ESI-MS) 588, 589, 590 (M−1) 634, 635 (M+2×23)

Compound 1059 3-{[(2-Diethylamino-ethyl)-methyl-amino]-methyl}-N-[2-(3,4-dimethyl-benzylidene-hydrazinocarbonyl)-4-(4-fluoro-butoxy)-phenyl]-benzamide The title compound 1059 was produced in substantially the same manner as in Example S.
$^1$H-NMR (CD$_3$OD, 400 MHz): δ 8.43 (1H, d, J=9.0 Hz), 8.28 (1H, s), 7.96 (1H, bs), 7.88-7.92 (1H, m), 7.63 (1H, s), 7.48-7.62 (3H, m), 7.40 (1H, d, J=2.7 Hz), 7.17-7.23 (2H, m), 4.55-4.60 (1H, m), 4.45 (1H, t, J=5.7 Hz), 4.12 (2H, t, J=5.9 Hz), 3.67 (2H, s), 2.72-2.80 (2H, m), 2.55-2.68 (6H, m), 2.30 (3H, s), 2.29 (3H, s), 2.28 (3H, s), 1.80-1.95 (4H, m), 1.03 (6H, t, J=7.2 Hz)
Mass spectrometric value (ESI-MS) 602, 603 (M−1) 642, 648 (M+2×23)

Compound 1060 N-[2-(4-Chloro-3-trifluoromethyl-benzylidene-hydrazinocarbonyl)-4-(4-fluoro-butoxy)-phenyl]-3-{[(2-diethylamino-ethyl)-methyl-amino]-methyl}-benzamide The title compound 1060 was produced in substantially the same manner as in Example S.
$^1$H-NMR (CD$_3$OD, 400 MHz): δ 8.36-8.42 (2H, m), 8.31 (1H, s), 7.98-8.03 (1H, m), 7.95 (1H, s), 7.86-7.91 (1H, m), 7.67 (1H, d, J=8.3 Hz), 7.58 (1H, d, J=7.6 Hz), 7.51 (1H, dd, J=7.6 Hz, J=7.6 Hz), 7.42 (1H, d, J=2.9 Hz), 7.20 (1H, dd, J=2.9 Hz, J=9.0 Hz), 4.55-4.60 (1H, m), 4.45 (1H, t, J=5.7 Hz), 4.12 (2H, t, J=5.9 Hz), 3.66 (2H, s), 2.54-2.78 (8H, m), 2.27 (3H, s), 1.80-1.95 (4H, m), 1.03 (6H, t, J=7.2 Hz)

Mass spectrometric value (ESI-MS) 676, 677, 679 (M−1)

Compound 1061 3-{[(2-Diethylamino-ethyl)-methyl-amino]-methyl}-N-[4-(4-fluoro-butoxy)-2-(4-methoxy-benzylidene-hydrazinocarbonyl)-phenyl]-benzamide The title compound 1061 was produced in substantially the same manner as in Example S.

$^1$H-NMR (CD$_3$OD, 400 MHz): δ 8.43 (1H, d, J=9.3 Hz), 8.29 (1H, s), 7.95 (1H, bs), 7.87-7.92 (1H, m), 7.77 (2H, d, J=8.8 Hz), 7.56-7.61 (1H, m), 7.50 (1H, dd, J=7.6 Hz, J=7.6 Hz), 7.40 (1H, d, J=2.9 Hz), 7.19 (1H, dd, J=2.7 Hz, J=9.0 Hz), 6.97 (2H, d, J=8.8 Hz), 4.55-4.59 (1H, m), 4.45 (1H, t, J=5.7 Hz), 4.11 (2H, t, J=6.0 Hz), 3.83 (3H, s), 3.66 (2H, s), 2.54-2.77 (8H, m), 2.28 (3H, s), 1.80-1.97 (4H, m), 1.03 (6H, t, J=7.2 Hz)

Mass spectrometric value (ESI-MS) 604, 605, 606 (M−1) 606 (M+1) 628, 629 (M+23)

Compound 1062 N-[2-(4-Chloro-3-trifluoromethyl-benzylidene-hydrazinocarbonyl)-4-(4-hydroxy-piperidin-1-yl)-phenyl]-3-(2-hydroxy-ethylsulfanylmethyl)-benzamide The title compound 1062 was produced in substantially the same manner as in Example F.

$^1$H-NMR (CD$_3$OD, 400 MHz): δ 1.67 (2H, m), 2.00 (2H, m), 2.57 (2H, m), 2.99 (2H, m), 3.68 (4H, m), 3.80 (1H, m), 3.86 (2H, s), 7.25 (1H, m), 7.41 (1H, d, J=3.0 Hz), 7.49 (1H, m), 7.59 (1H, m), 7.69 (1H, d, J=8.6 Hz), 7.85 (1H, m), 7.92 (1H, m), 8.05 (1H, m), 8.34 (2H, m), 8.38 (1H, s)

Mass spectrometric value (ESI-MS) 633 (M−1)

Compound 1063 N-[2-(4-Chloro-3-trifluoromethyl-benzylidene-hydrazinocarbonyl)-4-(4-hydroxymethyl-piperidin-1-yl)-phenyl]-3-(2-hydroxy-ethylsulfanylmethyl)-benzamide The title compound 1063 was produced in substantially the same manner as in Example F.

$^1$H-NMR (CD$_3$OD, 400 MHz): δ 1.39 (2H, m), 1.63 (1H, m), 1.88 (2H, m), 2.57 (2H, t, J=6.8 Hz), 2.76 (2H, m), 3.47 (2H, d, J=6.3 Hz), 3.68 (2H, t, J=6.8 Hz), 3.81 (2H, m), 3.86 (2H, s), 7.24 (1H, dd, J=9.2 Hz, J=2.8 Hz), 7.39 (1H, d, J=2.7 Hz), 7.49 (1H, dd, J=7.7 Hz, J=7.7 Hz), 7.58 (1H, d, J=7.6 Hz), 7.67 (1H, d, J=8.3 Hz), 7.84 (1H, d, J=7.6 Hz), 7.91 (1H, s), 8.03 (1H, m), 8.33 (2H, m), 8.37 (1H, s)

Mass spectrometric value (ESI-MS) 647 (M−1)

Compound 1064 N-[2-(3,4-Dimethyl-benzylidene-hydrazinocarbonyl)-4-morpholin-4-yl-phenyl]-3-(2-hydroxy-ethylsulfanylmethyl)-benzamide The title compound 1064 was produced in substantially the same manner as in Example F.

$^1$H-NMR (CD$_3$OD, 400 MHz): δ 2.30 (3H, s), 2.31 (3H, s), 2.57 (2H, m), 3.24 (4H, m), 3.68 (2H, m), 3.87 (6H, m), 7.21 (2H, m), 7.38 (1H, s), 7.45-7.62 (3H, m), 7.66 (1H, m), 7.83-7.96 (2H, m), 8.28 (1H, s), 8.40 (1H, m)

Mass spectrometric value (ESI-MS) 545 (M−1)

Compound 1065 N-[2-(4-Chloro-3-trifluoromethyl-benzylidene-hydrazinocarbonyl)-4-morpholin-4-yl-phenyl]-3-(2-hydroxy-ethylsulfanylmethyl)-benzamide The title compound 1065 was produced in substantially the same manner as in Example F.

$^1$H-NMR (DMSO-d$_6$, 400 MHz): δ 2.50 (2H, m), 3.20 (4H, m), 3.54 (2H, m), 3.78 (4H, m), 3.84 (2H, s), 7.24 (1H, d, J=8.1 Hz), 7.32 (1H, s), 7.53 (2H, m), 7.75-7.84 (2H, m), 7.87 (1H, s), 8.05 (1H, d, J=7.8 Hz), 8.20 (1H, s), 8.25 (1H, d, J=9.0 Hz), 8.48 (1H, s), 11.25 (1H, bs), 12.24 (1H, s)

Mass spectrometric value (ESI-MS) 619 (M−1)

Compound 1066 3-(2-Hydroxy-ethylsulfanylmethyl)-N-[2-(4-methoxy-benzylidene-hydrazinocarbonyl)-4-morpholin-4-yl-phenyl]-benzamide The title compound 1066 was produced in substantially the same manner as in Example F.

$^1$H-NMR (CD$_3$OD, 400 MHz): δ 2.57 (2H, m), 3.30 (4H, m), 3.68 (2H, m), 3.86 (9H, m), 7.00 (2H, m), 7.24 (1H, m), 7.38 (1H, m), 7.49 (1H, m), 7.60 (1H, m), 7.75-7.95 (4H, m), 8.29 (1H, s), 8.42 (1H, m)

Mass spectrometric value (ESI-MS) 547 (M−1)

Compound 1067 N-[4-[1,4']Bipiperazinyl-1'-yl-2-(4-chloro-3-trifluoromethyl-benzylidene-hydrazinocarbonyl)-phenyl]-3-(2-hydroxy-ethylsulfanylmethyl)-benzamide The title compound 1067 was produced in substantially the same manner as in Example F.

$^1$H-NMR (CD$_3$OD, 400 MHz): δ 1.60 (2H, m), 1.77 (6H, m), 2.11 (2H, m), 2.57 (2H, t, J=6.8 Hz), 2.75-3.02 (7H, m), 3.68 (2H, t, J=6.7 Hz), 3.86 (2H, s), 3.93 (2H, m), 7.26 (1H, m), 7.40 (1H, m), 7.49 (1H, m), 7.59 (1H, m), 7.68 (1H, d, J=8.1 Hz), 7.84 (1H, d, J=8.0 Hz), 7.92 (1H, s), 8.04 (1H, d, J=9.3 Hz), 8.30-8.40 (3H, m),

Mass spectrometric value (ESI-MS) 700 (M−1)

Compound 1068 N-[4-[1,4']Bipiperazinyl-1'-yl-2-(4-methoxy-benzylidene-hydrazinocarbonyl)-phenyl]-3-(2-hydroxy-ethylsulfanyl-methyl)-benzamide The title compound 1068 was produced in substantially the same manner as in Example F.

$^1$H-NMR (DMSO-d$_6$, 400 MHz): δ 1.39 (2H, m), 1.45-1.65 (6H, m), 1.84 (2H, m), 2.50 (7H, m), 2.70 (2H, m), 3.54 (2H, m), 3.83 (7H, m), 4.78 (1H, t, J=5.6 Hz), 7.02 (2H, d, J=8.8 Hz), 7.19 (1H, m), 7.31 (1H, m), 7.53 (2H, m), 7.70 (2H, d, J=7.8 Hz), 7.76 (1H, d, J=7.3 Hz), 7.86 (1H, s), 8.31 (1H, d, J=9.0 Hz), 8.39 (1H, s), 11.67 (1H, s), 11.88 (1H, s)

Mass spectrometric value (ESI-MS) 628 (M−1)

Compound 1069 N-[2-(3,4-Dimethyl-benzylidene-hydrazinocarbonyl)-4-(4-methyl-piperidin-1-yl)-phenyl]-3-(2-hydroxy-ethylsulfanylmethyl)-benzamide The title compound 1069 was produced in substantially the same manner as in Example F.

$^1$H-NMR (DMSO-d$_6$, 400 MHz): δ 0.97 (3H, d, J=6.6 Hz), 1.27 (2H, m), 1.53 (1H, m), 1.74 (2H, m), 2.27 (3H, s), 2.28 (3H, s), 2.50 (2H, m), 2.70 (2H, m), 3.54 (2H, m), 3.75 (2H, m), 3.85 (2H, s), 4.77 (1H, t, J=5.7 Hz), 7.21 (2H, m), 7.31 (1H, m), 7.45 (1H, d, J=7.6 Hz), 7.52 (3H, m), 7.76 (1H, d, J=7.3 Hz), 7.87 (1H, s), 8.29 (1H, m), 8.37 (1H, s), 11.41 (1H, s), 11.90 (1H, s)

Mass spectrometric value (ESI-MS) 557 (M−1)

Compound 1070 N-[2-(4-Chloro-3-trifluoromethyl-benzylidene-hydrazinocarbonyl)-4-(4-methyl-piperidin-1-yl)-phenyl]-3-(2-hydroxy-ethylsulfanylmethyl)-benzamide The title compound 1070 was produced in substantially the same manner as in Example F.

$^1$H-NMR (DMSO-$d_6$, 400 MHz): δ 0.96 (3H, d, J=6.3 Hz), 1.27 (2H, m), 1.53 (1H, m), 1.74 (2H, m), 2.50 (2H, m), 2.70 (2H, m), 3.54 (2H, m), 3.74 (2H, m), 3.84 (2H, s), 4.83 (1H, m), 7.19 (1H, d, J=8.6 Hz), 7.33 (1H, s), 7.52 (2H, m), 7.79 (2H, m), 7.86 (1H, s), 8.04 (1H, d, J=7.6 Hz), 8.23 (2H, m), 8.49 (1H, s), 12.24 (1H, s)

Mass spectrometric value (ESI-MS) 631 (M−1)

Compound 1071 3-(2-Hydroxy-ethylsulfanylmethyl)-N-[2-(4-methoxy-benzylidene-hydrazinocarbonyl)-4-(4-methyl-piperidin-1-yl)-phenyl]-benzamide The title compound 1071 was produced in substantially the same manner as in Example F.

$^1$H-NMR (CD$_3$OD, 400 MHz): δ 1.01 (3H, d, J=6.1 Hz), 1.37 (2H, m), 1.55 (1H, m), 1.80 (2H, m), 2.57 (2H, t, J=6.7 Hz), 2.76 (2H, m), 3.68 (2H, m), 3.76 (2H, m), 3.84 (3H, s), 3.86 (2H, s), 6.99 (2H, d, J=8.8 Hz), 7.22 (1H, m), 7.38 (1H, m), 7.49 (1H, m), 7.58 (1H, m), 7.79 (2H, d, J=8.5 Hz), 7.85 (1H, d, J=7.6 Hz), 7.92 (1H, s), 8.30 (1H, s), 8.36 (1H, d, J=9.3 Hz)

Mass spectrometric value (ESI-MS) 559 (M−1)

Compound 1072 N-[2-(4-Chloro-3-trifluoromethyl-benzylidene-hydrazinocarbonyl)-4-(4-methyl-piperazin-1-yl)-phenyl]-3-(2-hydroxy-ethylsulfanylmethyl)-benzamide The title compound 1072 was produced in substantially the same manner as in Example F.

$^1$H-NMR (CD$_3$OD, 400 MHz): δ 2.44 (3H, m), 2.56 (2H, m), 2.74 (4H, m), 3.30 (4H, m), 3.66 (2H, m), 3.85 (2H, m), 7.26 (1H, m), 7.40 (1H, s), 7.49 (1H, m), 7.58 (1H, m), 7.68 (1H, m), 7.83 (1H, m), 7.91 (1H, s), 8.02 (1H, m), 8.35 (3H, m)

Mass spectrometric value (ESI-MS) 632 (M−1)

Compound 1073 3-(2-Hydroxy-ethylsulfanylmethyl)-N-[2-(4-methoxy-benzylidene-hydrazinocarbonyl)-4-(4-methyl-piperazin-1-yl)-phenyl]-benzamide The title compound 1073 was produced in substantially the same manner as in Example F.

$^1$H-NMR (CD$_3$OD, 400 MHz): δ 2.34 (3H, s), 2.57 (2H, t, J=6.8 Hz), 2.66 (4H, m), 3.31 (4H, m), 3.68 (2H, t, J=6.8 Hz), 3.84 (3H, s), 3.86 (2H, s), 6.99 (2H, d, J=8.8 Hz), 7.24 (1H, dd, J=9.1 Hz, J=2.7 Hz), 7.38 (1H, d, J=2.9 Hz), 7.49 (1H, d, J=7.7 Hz), 7.59 (1H, d, J=7.6 Hz), 7.79 (2H, d, J=8.8 Hz), 7.85 (1H, d, J=7.8 Hz), 7.92 (1H, s), 8.29 (1H, s), 8.40 (1H, d, J=9.0 Hz)

Mass spectrometric value (ESI-MS) 560 (M−1)

Compound 1074 3-{[(2-Diethylamino-ethyl)-methyl-amino]-methyl}-N-[2-(3,4-dimethyl-benzylidene-hydrazinocarbonyl)-4-morpholin-4-yl-phenyl]-benzamide The title compound 1074 was produced in substantially the same manner as in Example F.

$^1$H-NMR (CDCl$_3$, 400 MHz): δ 1.04 (6H, t, J=7.1 Hz), 2.28 (9H, m), 2.59 (6H, m), 2.68 (2H, m), 2.85 (4H, m), 3.41 (4H, m), 3.64 (2H, s), 6.83 (1H, d, J=9.0 Hz), 6.97 (1H, s), 7.18 (1H, d, J=7.6 Hz), 7.47 (1H, dd, J=7.6 Hz, J=7.6 Hz), 7.56 (2H, m), 7.69 (1H, s), 7.89 (1H, d, J=7.6 Hz), 8.00 (1H, s), 8.09 (1H, d, J=9.0 Hz), 8.55 (1H, s), 11.22 (1H, s)

Mass spectrometric value (ESI-MS) 597 (M−1)

Compound 1075 N-[2-(4-Chloro-3-trifluoromethyl-benzylidene-hydrazinocarbonyl)-4-morpholin-4-yl-phenyl]-3-{[(2-diethylamino-ethyl)-methyl-amino]-methyl}-benzamide The title compound 1075 was produced in substantially the same manner as in Example F.

$^1$H-NMR (CDCl$_3$, 400 MHz): δ 1.03 (6H, t, J=7.1 Hz), 2.28 (3H, s), 2.57 (6H, m), 2.66 (2H, m), 2.80 (4H, m), 3.34 (4H, m), 3.65 (2H, s), 6.80 (1H, d, J=8.6 Hz), 6.89 (1H, s), 7.50 (1H, m), 7.60 (2H, m), 7.89 (1H, d, J=7.6 Hz), 7.97 (1H, m), 8.03 (1H, s), 8.08 (1H, d, J=8.3 Hz), 8.13 (1H, s), 8.66 (1H, s), 11.08 (1H, s)

Mass spectrometric value (ESI-MS) 671 (M−1)

Compound 1076 3-{[(2-Diethylamino-ethyl)-methyl-amino]-methyl}-N-[2-(4-methoxy-benzylidene-hydrazinocarbonyl)-4-morpholin-4-yl-phenyl]-benzamide The title compound 1076 was produced in substantially the same manner as in Example F.

$^1$H-NMR (CDCl$_3$, 400 MHz): δ 1.06 (6H, t, J=7.1 Hz), 2.25 (3H, s), 2.62 (6H, m), 2.72 (2H, m), 2.91 (4H, m), 3.46 (4H, m), 3.62 (2H, s), 3.82 (3H, s), 6.84-6.92 (3H, m), 7.07 (1H, s), 7.44 (1H, dd, J=7.7 Hz, J=7.7 Hz), 7.53 (1H, m), 7.75 (2H, d, J=8.5 Hz), 7.88 (1H, d, J=7.8 Hz), 7.97 (1H, s), 8.17 (1H, d, J=9.0 Hz), 8.57 (1H, s), 11.34 (1H, s)

Mass spectrometric value (ESI-MS) 599 (M−1)

Example U

Compound 1077 N-Benzoyloxy-5-chloro-2-(3-diethylaminomethyl-benzoylamino)-benzamide 2-Amino-5-chloro-benzoic acid methyl ester (1.5 g) was dissolved in anhydrous methylene chloride (25 ml). Pyridine (1.4 ml) and 3-(chloromethyl)benzoyl chloride (1.4 ml) were added dropwise to the solution at 0° C., and the mixture was then stirred at room temperature for 30 min. After the completion of the reaction, distilled water was added thereto at room temperature, and the mixture was subjected to separatory extraction with chloroform. The organic layer was then washed with saturated brine, was dried over sodium sulfate, and was then concentrated under the reduced pressure to precipitate crystals. The precipitated crystals were collected by filtration through Kiriyama Rohto and were washed with ether to give 5-chloro-2-(3-chloromethyl-benzoylamino)-benzoic acid methyl ester as a useful intermediate (2.4 g, yield 90%).

5-Chloro-2-(3-chloromethyl-benzoylamino)-benzoic acid methyl ester (2.4 g) produced by the above process was dissolved in anhydrous methylene chloride (30 ml). Triethylamine (1.5 ml) and diethylamine (2.0 ml) were added dropwise to the solution at room temperature, and the mixture was then stirred at that temperature for 48 hr. After the completion of the reaction, the reaction system was concentrated under the reduced pressure, and the residue was purified by column chromatography eluted with a chloroform-methanol system to give 5-chloro-2-(3-diethylaminomethyl-benzoylamino)-benzoic acid methyl ester as a useful intermediate (1.9 g, yield 71%).

Subsequently, 5-chloro-2-(3-diethylaminomethyl-benzoylamino)-benzoic acid methyl ester (1.9 g) produced by the above process was dissolved in tetrahydrofuran/distilled water=4/1 (20 ml). Lithium hydroxide monohydrate (420 mg) was added to the solution at room temperature, and the mixture was then stirred at that temperature for 2.5 hr. After the completion of the reaction, the reaction system was concentrated under the reduced pressure, and the residue was purified by column chromatography eluted with a chloroform-methanol system to give 5-chloro-2-(3-diethylaminomethyl-benzoylamino)-benzoic acid (1.0 g, yield 56%).

5-Chloro-2-(3-diethylaminomethyl-benzoylamino)-benzoic acid (50 mg) produced by the above process was dissolved in N,N-dimethylformamide (1.0 ml). 1-(3-Dimethylaminopropyl)-3-ethylcarbodiimide hydrochloride (38 mg), 1-hydroxy-benzotriazole monohydrate (28 mg), triethylamine (50 µl) and o-benzyl-hydroxylamine hydrochloride (40 mg) were added to the solution at room temperature, and the mixture was then stirred at that temperature for 24 hr. After the completion of the reaction, distilled water was added thereto at room temperature, and the mixture was subjected to separatory extraction with ethyl acetate. The organic layer was washed with saturated brine, was dried over sodium sulfate, and was then concentrated under the reduced pressure. The residue was purified by column chromatography eluted with a chloroform-methanol system to give the title compound 1077 (29 mg, yield 45%).

$^1$H-NMR (CD$_3$OD, 400 MHz): δ 8.55 (1H, d, J=9.0 Hz), 7.98 (1H, s), 7.87-7.91 (1H, m), 7.61-7.65 (2H, m), 7.40-7.56 (4H, m), 7.23-7.38 (3H, m), 4.99 (2H, s), 3.89 (2H, s), 2.73 (4H, q, J=7.2 Hz), 1.15 (6H, t, J=7.2 Hz)

Mass spectrometric value (ESI-MS) 463, 465, 466 (M−1) 465, 467 (M+1) 489 (M+23)

Starting compounds for compounds 1 to 1076 are shown in Table 1. In the table, compounds A, B, C, and B' correspond to compounds described in Examples 1 to 11 and Examples A to T and schemes 1 and 2.

TABLE 1

| | A | B | C | B' |
|---|---|---|---|---|
| Compound 1 | Methyl 2-aminobenzoate | 3,4-Dimethoxybenzoyl chloride | Trans-cinnamaldehyde | |
| Compound 2 | Methyl 2-aminobenzoate | 3,4-Dimethoxybenzoyl chloride | 2-Fluorobenzaldehyde | |
| Compound 3 | Methyl 2-aminobenzoate | 3,4-Dimethoxybenzoyl chloride | o-Tolualdehyde | |
| Compound 4 | Methyl 2-aminobenzoate | 3,4-Dimethoxybenzoyl chloride | o-Methoxybenzaldehyde | |
| Compound 5 | Methyl 2-aminobenzoate | 3,4-Dimethoxybenzoyl chloride | m-Methoxybenzaldehyde | |
| Compound 6 | Methyl 2-aminobenzoate | 3,4-Dimethoxybenzoyl chloride | 3,5-Ditert-butyl-4-hydroxybenzaldehyde | |
| Compound 7 | Methyl 2-aminobenzoate | 3,4-Dimethoxybenzoyl chloride | α-Methyl-cinnamaldehyde | |
| Compound 8 | Methyl 2-aminobenzoate | 3,4-Dimethoxybenzoyl chloride | 3,5-Ditrifluoromethylbenzaldehyde | |
| Compound 9 | Methyl 2-aminobenzoate | 3,4-Dimethoxybenzoyl chloride | 3-Cyanobenzaldehyde | |
| Compound 10 | Methyl 2-aminobenzoate | 3,4-Dimethoxybenzoyl chloride | 2-Bromobenzaldehyde | |
| Compound 11 | Methyl 2-aminobenzoate | 3,4-Dimethoxybenzoyl chloride | Vanillin | |
| Compound 12 | Methyl 2-aminobenzoate | 3,4-Dimethoxybenzoyl chloride | 3,4,5-Trimethoxybenzaldehyde | |
| Compound 13 | Methyl 2-amino-5-bromobenzoate | 3,4-Dimethoxybenzoyl chloride | Trans-cinnamaldehyde | |
| Compound 14 | Methyl 2-amino-5-bromobenzoate | 3,4-Dimethoxybenzoyl chloride | 2-Bromobenzaldehyde | |
| Compound 15 | Methyl 2-aminobenzoate | 3,4-Dimethoxybenzoyl chloride | 3-Fluorobenzaldehyde | |
| Compound 16 | Methyl 2-aminobenzoate | 3,4-Dimethoxybenzoyl chloride | 4-Fluorobenzaldehyde | |
| Compound 17 | Methyl 2-aminobenzoate | 3,4-Dimethoxybenzoyl chloride | Benzaldehyde | |
| Compound 18 | Methyl 2-aminobenzoate | 3,4-Dimethoxybenzoyl chloride | 3-Hydroxybenzaldehyde | |
| Compound 19 | Methyl 2-aminobenzoate | 3,4-Dimethoxybenzoyl chloride | 4-Hydroxybenzaldehyde | |
| Compound 20 | Methyl 2-aminobenzoate | 3,4-Dimethoxybenzoyl chloride | m-Tolualdehyde | |
| Compound 21 | Methyl 2-aminobenzoate | 3,4-Dimethoxybenzoyl chloride | Furfural | |
| Compound 22 | Methyl 2-aminobenzoate | 3,4-Dimethoxybenzoyl chloride | 5-Methylfurfural | |

TABLE 1-continued

| | A | B | C | B' |
|---|---|---|---|---|
| Compound 23 | Methyl 2-aminobenzoate | 3,4-Dimethoxybenzoyl chloride | 2-Thiophene-carboxyaldehyde | |
| Compound 24 | Methyl 2-aminobenzoate | 3,4-Dimethoxybenzoyl chloride | 3-Thiophene-carboxyaldehyde | |
| Compound 25 | Methyl 2-aminobenzoate | 3,4-Dimethoxybenzoyl chloride | 2,4-Dihydroxybenzaldehyde | |
| Compound 26 | Methyl 2-aminobenzoate | 3,4-Dimethoxybenzoyl chloride | 3,4-Dihydroxybenzaldehyde | |
| Compound 27 | Methyl 2-aminobenzoate | 2-Fluorobenzoyl chloride | Benzaldehyde | |
| Compound 28 | Methyl 2-amino-5-bromobenzoate | 3,4-Dimethoxybenzoyl chloride | 2-Fluorobenzaldehyde | |
| Compound 29 | Methyl 2-amino-5-bromobenzoate | 3,4-Dimethoxybenzoyl chloride | 3-Fluorobenzaldehyde | |
| Compound 30 | Methyl 2-amino-5-bromobenzoate | 3,4-Dimethoxybenzoyl chloride | o-Tolualdehyde | |
| Compound 31 | Methyl 2-amino-5-bromobenzoate | 3,4-Dimethoxybenzoyl chloride | m-Tolualdehyde | |
| Compound 32 | Methyl 2-aminobenzoate | 3,4-Dimethoxybenzoyl chloride | 3-Chloro-4-fluorobenzaldehyde | |
| Compound 33 | Methyl 2-aminobenzoate | 3,4-Dimethoxybenzoyl chloride | 4-Trifluoromethoxybenzaldehyde | |
| Compound 34 | Methyl 2-aminobenzoate | 3,4-Dimethoxybenzoyl chloride | 3-Bromo-4-methoxybenzaldehyde | |
| Compound 35 | Methyl 2-aminobenzoate | 3,4-Dimethoxybenzoyl chloride | 3-Chlorobenzaldehyde | |
| Compound 36 | Methyl 2-aminobenzoate | 3,4-Dimethoxybenzoyl chloride | 3,5-Dimethyl-4-hydroxybenzaldehyde | |
| Compound 37 | Methyl 2-aminobenzoate | 3,4-Dimethoxybenzoyl chloride | 3-Ethoxy-4-hydroxybenzaldehyde | |
| Compound 38 | Methyl 2-aminobenzoate | 2-Fluorobenzoyl chloride | 4-Fluorobenzaldehyde | |
| Compound 39 | Methyl 2-aminobenzoate | 2-Fluorobenzoyl chloride | 3-Hydroxybenzaldehyde | |
| Compound 40 | Methyl 2-aminobenzoate | 2-Fluorobenzoyl chloride | p-Tolualdehyde | |
| Compound 41 | Methyl 2-aminobenzoate | 3,4-Dimethoxybenzoyl chloride | 4-Chloro-3-trifluoromethylbenzaldehyde | |
| Compound 42 | Methyl 2-aminobenzoate | 3,4-Dimethoxybenzoyl chloride | 4-Hydroxy-3-methylbenzaldehyde | |
| Compound 43 | Methyl 2-aminobenzoate | 3,4-Dimethoxybenzoyl chloride | 2,5-Dimethylbenzaldehyde | |
| Compound 44 | Methyl 2-aminobenzoate | 3,4-Dimethoxybenzoyl chloride | 2-Fluoro-5-trifluoromethylbenzaldehyde | |
| Compound 45 | Methyl 2-aminobenzoate | 2-Fluorobenzoyl chloride | 4-Hydroxy-3-methylbenzaldehyde | |
| Compound 46 | Methyl 2-aminobenzoate | 2-Fluorobenzoyl chloride | 2,5-Dimethylbenzaldehyde | |
| Compound 47 | Methyl 2-aminobenzoate | 4-Methoxybenzoyl chloride | 3-Fluorobenzaldehyde | |
| Compound 48 | Methyl 2-aminobenzoate | 4-Methoxybenzoyl chloride | 4-Fluorobenzaldehyde | |
| Compound 49 | Methyl 2-aminobenzoate | 4-Methoxybenzoyl chloride | m-Tolualdehyde | |
| Compound 50 | Methyl 2-aminobenzoate | 4-Methoxybenzoyl chloride | 3-Hydroxybenzaldehyde | |
| Compound 51 | Methyl 2-aminobenzoate | 4-Methoxybenzoyl chloride | p-Tolualdehyde | |
| Compound 52 | Methyl 2-aminobenzoate | 3,4-Dimethoxybenzoyl chloride | 4-Allyloxybenzaldehyde | |
| Compound 53 | Methyl 2-aminobenzoate | 3,4-Dimethoxybenzoyl chloride | 3,5-Dimethoxybenzaldehyde | |
| Compound 54 | Methyl 2-aminobenzoate | 3,4-Dimethoxybenzoyl chloride | 3-[3-(Trifluoromethyl)phenoxy]-benzaldehyde | |
| Compound 55 | Methyl 2-aminobenzoate | 3,5-Dimethoxybenzoyl chloride | 3-Fluorobenzaldehyde | |
| Compound 56 | Methyl 2-aminobenzoate | 3,5-Dimethoxybenzoyl chloride | 4-Fluorobenzaldehyde | |
| Compound 57 | Methyl 2-aminobenzoate | 3,5-Dimethoxybenzoyl chloride | p-Tolualdehyde | |
| Compound 58 | Methyl 2-aminobenzoate | 3,5-Dimethoxybenzoyl chloride | 3-Hydroxybenzaldehyde | |
| Compound 59 | Methyl 2-amino-5-bromobenzoate | 3,4-Dimethoxybenzoyl chloride | 3-Chlorobenzaldehyde | |
| Compound 60 | Methyl 2-amino-5-bromobenzoate | 3,4-Dimethoxybenzoyl chloride | 4-Chlorobenzaldehyde | |

TABLE 1-continued

| | A | B | C | B' |
|---|---|---|---|---|
| Compound 61 | Methyl 2-amino-5-bromobenzoate | 3,4-Dimethoxybenzoyl chloride | 4-Fluorobenzaldehyde | |
| Compound 62 | Methyl 2-amino-5-bromobenzoate | 3,4-Dimethoxybenzoyl chloride | p-Tolualdehyde | |
| Compound 63 | Methyl 2-amino-5-bromobenzoate | 3,4-Dimethoxybenzoyl chloride | 3-Hydroxybenzaldehyde | |
| Compound 64 | Methyl 2-amino-5-bromobenzoate | 3,4-Dimethoxybenzoyl chloride | 4-Hydroxybenzaldehyde | |
| Compound 65 | Methyl 2-amino-5-chlorobenzoate | 3,4-Dimethoxybenzoyl chloride | 3-Fluorobenzaldehyde | |
| Compound 66 | Methyl 2-amino-5-chlorobenzoate | 3,4-Dimethoxybenzoyl chloride | 4-Fluorobenzaldehyde | |
| Compound 67 | Methyl 2-amino-5-chlorobenzoate | 3,4-Dimethoxybenzoyl chloride | m-Tolualdehyde | |
| Compound 68 | Methyl 2-amino-5-chlorobenzoate | 3,4-Dimethoxybenzoyl chloride | p-Tolualdehyde | |
| Compound 69 | Methyl 2-amino-5-chlorobenzoate | 3,4-Dimethoxybenzoyl chloride | 3-Hydroxybenzaldehyde | |
| Compound 70 | Methyl 2-amino-5-chlorobenzoate | 3,4-Dimethoxybenzoyl chloride | 4-Hydroxybenzaldehyde | |
| Compound 71 | Methyl 2-amino-4-chlorobenzoate | 3,4-Dimethoxybenzoyl chloride | 3-Fluorobenzaldehyde | |
| Compound 72 | Methyl 2-amino-4-chlorobenzoate | 3,4-Dimethoxybenzoyl chloride | 4-Fluorobenzaldehyde | |
| Compound 73 | Methyl 2-amino-4-chlorobenzoate | 3,4-Dimethoxybenzoyl chloride | m-Tolualdehyde | |
| Compound 74 | Methyl 2-amino-4-chlorobenzoate | 3,4-Dimethoxybenzoyl chloride | p-Tolualdehyde | |
| Compound 75 | Methyl 2-amino-4-chlorobenzoate | 3,4-Dimethoxybenzoyl chloride | 3-Hydroxybenzaldehyde | |
| Compound 76 | Methyl 2-aminobenzoate | 4-Fluorobenzoyl chloride | 3-Fluorobenzaldehyde | |
| Compound 77 | Methyl 2-aminobenzoate | 4-Fluorobenzoyl chloride | 4-Fluorobenzaldehyde | |
| Compound 78 | Methyl 2-aminobenzoate | 4-Fluorobenzoyl chloride | m-Tolualdehyde | |
| Compound 79 | Methyl 2-aminobenzoate | 4-Fluorobenzoyl chloride | p-Tolualdehyde | |
| Compound 80 | Methyl 2-aminobenzoate | 4-Fluorobenzoyl chloride | 3-Hydroxybenzaldehyde | |
| Compound 81 | Methyl 2-aminobenzoate | 3-Fluorobenzoyl chloride | 3-Fluorobenzaldehyde | |
| Compound 82 | Methyl 2-aminobenzoate | 3-Fluorobenzoyl chloride | 4-Fluorobenzaldehyde | |
| Compound 83 | Methyl 2-aminobenzoate | 3-Fluorobenzoyl chloride | m-Tolualdehyde | |
| Compound 84 | Methyl 2-aminobenzoate | 3-Fluorobenzoyl chloride | p-Tolualdehyde | |
| Compound 85 | Methyl 2-aminobenzoate | 3-Fluorobenzoyl chloride | 3-Hydroxybenzaldehyde | |
| Compound 86 | Methyl 2-aminobenzoate | 3-Fluorobenzoyl chloride | 4-Hydroxybenzaldehyde | |
| Compound 87 | Methyl 2-amino-5-bromobenzoate | 3,4-Dimethoxybenzoyl chloride | 4-Chloro-3-trifluoromethylbenzaldehyde | |
| Compound 88 | Methyl 2-amino-5-chlorobenzoate | 3,4-Dimethoxybenzoyl chloride | 4-Chloro-3-trifluoromethylbenzaldehyde | |
| Compound 89 | Methyl 2-aminobenzoate | 3,5-Dimethoxybenzoyl chloride | 4-Chloro-3-trifluoromethylbenzaldehyde | |
| Compound 90 | Methyl 2-aminobenzoate | 4-Methoxybenzoyl chloride | 4-Chloro-3-trifluoromethylbenzaldehyde | |
| Compound 91 | Methyl 2-amino-5-bromobenzoate | 3,4-Dimethoxybenzoyl chloride | 3,4-Dimethylbenzaldehyde | |
| Compound 92 | Methyl 2-amino-5-chlorobenzoate | 3,4-Dimethoxybenzoyl chloride | 3,4-Dimethylbenzaldehyde | |
| Compound 93 | Methyl 2-aminobenzoate | 3,5-Dimethoxybenzoyl chloride | 3,4-Dimethylbenzaldehyde | |
| Compound 94 | Methyl 2-aminobenzoate | 4-Methoxybenzoyl chloride | 3,4-Dimethylbenzaldehyde | |
| Compound 95 | Methyl 2-aminobenzoate | 3-Fluorobenzoyl chloride | 3,4-Dimethylbenzaldehyde | |
| Compound 96 | Methyl 2-aminobenzoate | 4-Fluorobenzoyl chloride | 3,4-Dimethylbenzaldehyde | |
| Compound 97 | Methyl 2-amino-5-bromobenzoate | 3,4-Dimethoxybenzoyl chloride | 3-Bromo-4-methoxybenzaldehyde | |
| Compound 98 | Methyl 2-amino-5-chlorobenzoate | 3,4-Dimethoxybenzoyl chloride | 3-Bromo-4-methoxybenzaldehyde | |
| Compound 99 | Methyl 2-aminobenzoate | 3,5-Dimethoxybenzoyl chloride | 3-Bromo-4-methoxybenzaldehyde | |

TABLE 1-continued

| | A | B | C | B' |
|---|---|---|---|---|
| Compound 100 | Methyl 2-aminobenzoate | 4-Methoxybenzoyl chloride | 3-Bromo-4-methoxybenzaldehyde | |
| Compound 101 | Methyl 2-aminobenzoate | 3-Fluorobenzoyl chloride | 3-Bromo-4-methoxybenzaldehyde | |
| Compound 102 | Methyl 2-aminobenzoate | 4-Fluorobenzoyl chloride | 3-Bromo-4-methoxybenzaldehyde | |
| Compound 103 | Methyl 2-aminobenzoate | 3,4-Dimethoxybenzoyl chloride | 3-Nitrobenzaldehyde | |
| Compound 104 | Methyl 2-aminobenzoate | 3,4-Dimethoxybenzoyl chloride | 4-Dimethylaminobenzaldehyde | |
| Compound 105 | Methyl 2-amino-5-bromobenzoate | 4-Fluorobenzoyl chloride | 3-Fluorobenzaldehyde | |
| Compound 106 | Methyl 2-amino-5-bromobenzoate | 4-Fluorobenzoyl chloride | 4-Fluorobenzaldehyde | |
| Compound 107 | Methyl 2-amino-5-bromobenzoate | 4-Fluorobenzoyl chloride | 3-Chlorobenzaldehyde | |
| Compound 108 | Methyl 2-amino-5-bromobenzoate | 4-Fluorobenzoyl chloride | 4-Chlorobenzaldehyde | |
| Compound 109 | Methyl 2-amino-5-bromobenzoate | 4-Fluorobenzoyl chloride | 3-Hydroxybenzaldehyde | |
| Compound 110 | Methyl 2-amino-5-bromobenzoate | 3,4-Dimethoxybenzoyl chloride | 3-Pyridine-carboxyaldehyde | |
| Compound 111 | Methyl 2-amino-5-chlorobenzoate | 3,4-Dimethoxybenzoyl chloride | 3-Pyridine-carboxyaldehyde | |
| Compound 112 | Methyl 2-aminobenzoate | 4-Methoxybenzoyl chloride | 3-Pyridine-carboxyaldehyde | |
| Compound 113 | Methyl 2-aminobenzoate | 4-Fluorobenzoyl chloride | 3-Pyridine-carboxyaldehyde | |
| Compound 114 | Methyl 2-amino-5-bromobenzoate | 3,5-Dimethoxybenzoyl chloride | 3-Fluorobenzaldehyde | |
| Compound 115 | Methyl 2-amino-5-bromobenzoate | 3,5-Dimethoxybenzoyl chloride | 4-Fluorobenzaldehyde | |
| Compound 116 | Methyl 2-amino-5-bromobenzoate | 3,5-Dimethoxybenzoyl chloride | 3-Chlorobenzaldehyde | |
| Compound 117 | Methyl 2-amino-5-bromobenzoate | 3,5-Dimethoxybenzoyl chloride | 4-Chlorobenzaldehyde | |
| Compound 118 | Methyl 2-amino-5-bromobenzoate | 3,5-Dimethoxybenzoyl chloride | m-Tolualdehyde | |
| Compound 119 | Methyl 2-amino-5-bromobenzoate | 3,5-Dimethoxybenzoyl chloride | p-Tolualdehyde | |
| Compound 120 | Methyl 2-aminobenzoate | 3-Trifluoromethoxybenzoyl chloride | 3-Fluorobenzaldehyde | |
| Compound 121 | Methyl 2-aminobenzoate | 3-Trifluoromethoxybenzoyl chloride | 4-Fluorobenzaldehyde | |
| Compound 122 | Methyl 2-aminobenzoate | 3-Trifluoromethoxybenzoyl chloride | 3-Chlorobenzaldehyde | |
| Compound 123 | Methyl 2-aminobenzoate | 3-Trifluoromethoxybenzoyl chloride | 4-Chlorobenzaldehyde | |
| Compound 124 | Methyl 2-aminobenzoate | 3-Trifluoromethoxybenzoyl chloride | p-Tolualdehyde | |
| Compound 125 | Methyl 2-amino-5-hydroxy-benzoate | 3,4-Dimethoxybenzoyl chloride | 4-Fluorobenzaldehyde | |
| Compound 126 | Methyl 2-amino-5-chlorobenzoate | 3,4-Dimethoxybenzoyl chloride | 3,4-Dimethoxybenzaldehyde | |
| Compound 127 | Methyl 2-amino-5-bromobenzoate | 3,4-Dimethoxybenzoyl chloride | 3,4-Dimethoxybenzaldehyde | |
| Compound 128 | Methyl 2-amino-5-bromobenzoate | 3,5-Dimethoxybenzoyl chloride | 3,4-Dimethoxybenzaldehyde | |
| Compound 129 | Methyl 2-aminobenzoate | Nicotinoyl chloride hydrochloride | 3-Fluorobenzaldehyde | |
| Compound 130 | Methyl 2-aminobenzoate | Nicotinoyl chloride hydrochloride | 4-Fluorobenzaldehyde | |
| Compound 131 | Methyl 2-aminobenzoate | Nicotinoyl chloride hydrochloride | m-Tolualdehyde | |
| Compound 132 | Methyl 2-aminobenzoate | Nicotinoyl chloride hydrochloride | p-Tolualdehyde | |
| Compound 133 | Methyl 2-aminobenzoate | Nicotinoyl chloride hydrochloride | 3,4-Dimethylbenzaldehyde | |
| Compound 134 | Methyl 2-aminobenzoate | Isonicotinoyl chloride hydrochloride | 3-Fluorobenzaldehyde | |
| Compound 135 | Methyl 2-aminobenzoate | Isonicotinoyl chloride hydrochloride | 4-Fluorobenzaldehyde | |
| Compound 136 | Methyl 2-aminobenzoate | Isonicotinoyl chloride hydrochloride | m-Tolualdehyde | |

TABLE 1-continued

| | A | B | C | B' |
|---|---|---|---|---|
| Compound 137 | Methyl 2-aminobenzoate | Isonicotinoyl chloride hydrochloride | p-Tolualdehyde | |
| Compound 138 | Methyl 2-aminobenzoate | Isonicotinoyl chloride hydrochloride | 3,4-Dimethylbenzaldehyde | |
| Compound 139 | Methyl 2-amino-5-hydroxybenzoate | 3,4-Dimethoxybenzoyl chloride | 4-Fluorobenzaldehyde | |
| Compound 140 | Methyl 2-amino-5-hydroxybenzoate | 3,4-Dimethoxybenzoyl chloride | 4-Fluorobenzaldehyde | |
| Compound 141 | Methyl 2-amino-5-methoxybenzoate | 3,4-Dimethoxybenzoyl chloride | 3-Fluorobenzaldehyde | |
| Compound 142 | Methyl 2-amino-5-methoxybenzoate | 3,4-Dimethoxybenzoyl chloride | 4-Fluorobenzaldehyde | |
| Compound 143 | Methyl 2-amino-5-methoxybenzoate | 3,4-Dimethoxybenzoyl chloride | m-Tolualdehyde | |
| Compound 144 | Methyl 2-amino-5-methoxybenzoate | 3,4-Dimethoxybenzoyl chloride | p-Tolualdehyde | |
| Compound 145 | Methyl 2-amino-5-methoxybenzoate | 3,4-Dimethoxybenzoyl chloride | 3,4-Dimethylbenzaldehyde | |
| Compound 146 | Methyl 2-amino-5-methylbenzoate | 3,4-Dimethoxybenzoyl chloride | 3-Fluorobenzaldehyde | |
| Compound 147 | Methyl 2-amino-5-methylbenzoate | 3,4-Dimethoxybenzoyl chloride | 4-Fluorobenzaldehyde | |
| Compound 148 | Methyl 2-amino-5-methylbenzoate | 3,4-Dimethoxybenzoyl chloride | m-Tolualdehyde | |
| Compound 149 | Methyl 2-amino-5-methylbenzoate | 3,4-Dimethoxybenzoyl chloride | p-Tolualdehyde | |
| Compound 150 | Methyl 2-amino-5-methylbenzoate | 3,4-Dimethoxybenzoyl chloride | 3,4-Dimethylbenzaldehyde | |
| Compound 151 | Methyl 2-amino-5-bromobenzoate | 2-Furoyl chloride | 3-Fluorobenzaldehyde | |
| Compound 152 | Methyl 2-amino-5-bromobenzoate | 2-Furoyl chloride | 4-Fluorobenzaldehyde | |
| Compound 153 | Methyl 2-amino-5-bromobenzoate | 2-Furoyl chloride | m-Tolualdehyde | |
| Compound 154 | Methyl 2-amino-5-bromobenzoate | 2-Furoyl chloride | p-Tolualdehyde | |
| Compound 155 | Methyl 2-amino-5-bromobenzoate | 2-Furoyl chloride | 3,4-Dimethylbenzaldehyde | |
| Compound 156 | Methyl 2-amino-5-bromobenzoate | 2-Furoyl chloride | 4-Chloro-3-trifluoromethylbenzaldehyde | |
| Compound 157 | Methyl 2-amino-5-bromobenzoate | Thiophene-2-carbonyl chloride | 3-Fluorobenzaldehyde | |
| Compound 158 | Methyl 2-amino-5-bromobenzoate | Thiophene-2-carbonyl chloride | 4-Fluorobenzaldehyde | |
| Compound 159 | Methyl 2-amino-5-bromobenzoate | Thiophene-2-carbonyl chloride | m-Tolualdehyde | |
| Compound 160 | Methyl 2-amino-5-bromobenzoate | Thiophene-2-carbonyl chloride | p-Tolualdehyde | |
| Compound 161 | Methyl 2-amino-5-bromobenzoate | Thiophene-2-carbonyl chloride | 3,4-Dimethylbenzaldehyde | |
| Compound 162 | Methyl 2-amino-5-bromobenzoate | Thiophene-2-carbonyl chloride | 4-Chloro-3-trifluoromethylbenzaldehyde | |
| Compound 163 | Methyl 2-aminobenzoate | Isonicotinoyl chloride hydrochloride | 3,4-Dimethylbenzaldehyde | |
| Compound 164 | Methyl 2-aminobenzoate | Nicotinoyl chloride hydrochloride | p-Tolualdehyde | |
| Compound 165 | Methyl 2-aminobenzoate | Nicotinoyl chloride hydrochloride | 3,4-Dimethylbenzaldehyde | |
| Compound 166 | Methyl 2-amino-5-bromobenzoate | Isonicotinoyl chloride hydrochloride | 3-Fluorobenzaldehyde | |
| Compound 167 | Methyl 2-amino-5-bromobenzoate | Isonicotinoyl chloride hydrochloride | 4-Fluorobenzaldehyde | |
| Compound 168 | Methyl 2-amino-5-bromobenzoate | Isonicotinoyl chloride hydrochloride | m-Tolualdehyde | |
| Compound 169 | Methyl 2-amino-5-bromobenzoate | Isonicotinoyl chloride hydrochloride | p-Tolualdehyde | |
| Compound 170 | Methyl 2-amino-5-bromobenzoate | Isonicotinoyl chloride hydrochloride | 3,4-Dimethylbenzaldehyde | |

TABLE 1-continued

| | A | B | C | B' |
|---|---|---|---|---|
| Compound 171 | Methyl 2-amino-5-bromobenzoate | Isonicotinoyl chloride hydrochloride | 4-Chloro-3-trifluoromethylbenzaldehyde | |
| Compound 172 | Methyl 2-amino-5-bromobenzoate | Nicotinoyl chloride hydrochloride | 3-Fluorobenzaldehyde | |
| Compound 173 | Methyl 2-amino-5-bromobenzoate | Nicotinoyl chloride hydrochloride | 4-Fluorobenzaldehyde | |
| Compound 174 | Methyl 2-amino-5-bromobenzoate | Nicotinoyl chloride hydrochloride | m-Tolualdehyde | |
| Compound 175 | Methyl 2-amino-5-bromobenzoate | Nicotinoyl chloride hydrochloride | p-Tolualdehyde | |
| Compound 176 | Methyl 2-amino-5-bromobenzoate | Nicotinoyl chloride hydrochloride | 3,4-Dimethylbenzaldehyde | |
| Compound 177 | Methyl 2-amino-5-bromobenzoate | Nicotinoyl chloride hydrochloride | 4-Chloro-3-trifluoromethylbenzaldehyde | |
| Compound 178 | Methyl 2-amino-5-bromobenzoate | 4-Ethyl benzoyl chloride | 3-Fluorobenzaldehyde | |
| Compound 179 | Methyl 2-amino-5-bromobenzoate | 4-Ethyl benzoyl chloride | 4-Fluorobenzaldehyde | |
| Compound 180 | Methyl 2-amino-5-bromobenzoate | 4-Ethyl benzoyl chloride | m-Tolualdehyde | |
| Compound 181 | Methyl 2-amino-5-bromobenzoate | 4-Ethyl benzoyl chloride | p-Tolualdehyde | |
| Compound 182 | Methyl 2-amino-5-bromobenzoate | 4-Ethyl benzoyl chloride | 3,4-Dimethylbenzaldehyde | |
| Compound 183 | Methyl 2-amino-5-bromobenzoate | 4-Ethyl benzoyl chloride | 4-Chloro-3-trifluoromethylbenzaldehyde | |
| Compound 184 | Methyl 2-amino-5-chlorobenzoate | Nicotinoyl chloride hydrochloride | 3-Fluorobenzaldehyde | |
| Compound 185 | Methyl 2-amino-5-chlorobenzoate | Nicotinoyl chloride hydrochloride | 4-Fluorobenzaldehyde | |
| Compound 186 | Methyl 2-amino-5-chlorobenzoate | Nicotinoyl chloride hydrochloride | m-Tolualdehyde | |
| Compound 187 | Methyl 2-amino-5-chlorobenzoate | Nicotinoyl chloride hydrochloride | p-Tolualdehyde | |
| Compound 188 | Methyl 2-amino-5-chlorobenzoate | Nicotinoyl chloride hydrochloride | 3,4-Dimethylbenzaldehyde | |
| Compound 189 | Methyl 2-amino-5-chlorobenzoate | Nicotinoyl chloride hydrochloride | 4-Chloro-3-trifluoromethylbenzaldehyde | |
| Compound 190 | Methyl 2-amino-5-chlorobenzoate | Isonicotinoyl chloride hydrochloride | 4-Fluorobenzaldehyde | |
| Compound 191 | Methyl 2-amino-5-chlorobenzoate | Isonicotinoyl chloride hydrochloride | m-Tolualdehyde | |
| Compound 192 | Methyl 2-amino-5-chlorobenzoate | Isonicotinoyl chloride hydrochloride | p-Tolualdehyde | |
| Compound 193 | Methyl 2-amino-5-chlorobenzoate | Isonicotinoyl chloride hydrochloride | 3,4-Dimethylbenzaldehyde | |
| Compound 194 | Methyl 2-amino-5-chlorobenzoate | Isonicotinoyl chloride hydrochloride | 4-Chloro-3-trifluoromethylbenzaldehyde | |
| Compound 195 | Methyl 2-amino-5-bromobenzoate | 3-(Chloromethyl)-benzoyl chloride | 3-Fluorobenzaldehyde | 4-Mercapto-pyridine |
| Compound 196 | Methyl 2-amino-5-bromobenzoate | 3-(Chloromethyl)-benzoyl chloride | 4-Fluorobenzaldehyde | 4-Mercapto-pyridine |
| Compound 197 | Methyl 2-amino-5-bromobenzoate | 3-(Chloromethyl)-benzoyl chloride | m-Tolualdehyde | 4-Mercapto-pyridine |
| Compound 198 | Methyl 2-amino-5-bromobenzoate | 3-(Chloromethyl)-benzoyl chloride | p-Tolualdehyde | 4-Mercapto-pyridine |
| Compound 199 | Methyl 2-amino-5-bromobenzoate | 3-(Chloromethyl)-benzoyl chloride | 3,4-Dimethylbenzaldehyde | 4-Mercapto-pyridine |
| Compound 200 | Methyl 2-amino-5-bromobenzoate | 3-(Chloromethyl)-benzoyl chloride | 4-Chloro-3-trifluoromethylbenzaldehyde | 4-Mercapto-pyridine |
| Compound 201 | Methyl 2-amino-5-bromobenzoate | 3,4-Dimethoxybenzoyl chloride | 1-Methylpyrrole-2-carboxaldehyde | |
| Compound 202 | Methyl 2-amino-5-bromobenzoate | 3,4-Dimethoxybenzoyl chloride | 4,5-Dimethyl-2-furancarboxaldehyde | |
| Compound 203 | Methyl 2-aminobenzoate | Isonicotinoyl chloride hydrochloride | p-Tolualdehyde | |
| Compound 204 | Methyl 2-amino-5-iodobenzoate | 3,4-Dimethoxybenzoyl chloride | 3-Fluorobenzaldehyde | |
| Compound 205 | Methyl 2-amino-5-iodobenzoate | 3,4-Dimethoxybenzoyl chloride | 4-Fluorobenzaldehyde | |

TABLE 1-continued

| | A | B | C | B' |
|---|---|---|---|---|
| Compound 206 | Methyl 2-amino-5-iodobenzoate | 3,4-Dimethoxybenzoyl chloride | m-Tolualdehyde | |
| Compound 207 | Methyl 2-amino-5-iodobenzoate | 3,4-Dimethoxybenzoyl chloride | p-Tolualdehyde | |
| Compound 208 | Methyl 2-amino-5-iodobenzoate | 3,4-Dimethoxybenzoyl chloride | 3,4-Dimethylbenzaldehyde | |
| Compound 209 | Methyl 2-amino-5-iodobenzoate | 3,4-Dimethoxybenzoyl chloride | 4-Chloro-3-trifluoromethylbenzaldehyde | |
| Compound 210 | Methyl 2-aminobenzoate | Isonicotinoyl chloride hydrochloride | 1-Methylpyrrole-2-carboxaldehyde | |
| Compound 211 | Methyl 2-amino-5-bromobenzoate | Nicotinoyl chloride hydrochloride | 1-Methylpyrrole-2-carboxaldehyde | |
| Compound 212 | Methyl 2-amino-5-chlorobenzoate | Nicotinoyl chloride hydrochloride | 1-Methylpyrrole-2-carboxaldehyde | |
| Compound 213 | Methyl 2-aminobenzoate | 3,4-Dimethoxybenzoyl chloride | 3-Fluoro-acetophenone | |
| Compound 214 | Methyl 2-amino-5-bromobenzoate | 3,4-Dimethoxybenzoyl chloride | 3-Fluoro-acetophenone | |
| Compound 215 | Methyl 2-amino-5-bromobenzoate | Nicotinoyl chloride hydrochloride | 3-Methyl-acetophenone | |
| Compound 216 | Methyl 2-amino-5-bromobenzoate | Nicotinoyl chloride hydrochloride | 4-Methyl-acetophenone | |
| Compound 217 | Methyl 2-amino-5-chlorobenzoate | Nicotinoyl chloride hydrochloride | 4-Methyl-acetophenone | |
| Compound 218 | Methyl 2-aminobenzoate | Nicotinoyl chloride hydrochloride | 4,5-Dimethyl-2-furancarboxaldehyde | |
| Compound 219 | Methyl 2-aminobenzoate | Isonicotinoyl chloride hydrochloride | 4,5-Dimethyl-2-furancarboxaldehyde | |
| Compound 220 | Methyl 2-amino-5-bromobenzoate | Nicotinoyl chloride hydrochloride | 4,5-Dimethyl-2-furancarboxaldehyde | |
| Compound 221 | Methyl 2-amino-5-bromobenzoate | Isonicotinoyl chloride hydrochloride | 4,5-Dimethyl-2-furancarboxaldehyde | |
| Compound 222 | Methyl 2-amino-5-chlorobenzoate | Nicotinoyl chloride hydrochloride | 4,5-Dimethyl-2-furancarboxaldehyde | |
| Compound 223 | Methyl 2-amino-5-chlorobenzoate | Isonicotinoyl chloride hydrochloride | 4,5-Dimethyl-2-furancarboxaldehyde | |
| Compound 224 | Methyl 2-aminobenzoate | Benzoyl chloride | Benzaldehyde | |
| Compound 225 | Methyl 2-aminobenzoate | Benzoyl chloride | 2-Fluorobenzaldehyde | |
| Compound 226 | Methyl 2-aminobenzoate | Benzoyl chloride | 3-Fluorobenzaldehyde | |
| Compound 227 | Methyl 2-amino-3,4-dimethoxybenzoate | 3,4-Dimethoxybenzoyl chloride | Benzaldehyde | |
| Compound 228 | Methyl 2-aminobenzoate | Benzoyl chloride | 2-Bromobenzaldehyde | |
| Compound 229 | Methyl 2-aminobenzoate | Benzoyl chloride | o-Tolualdehyde | |
| Compound 230 | Methyl 2-amino-3,4-dimethoxybenzoate | 3,4-Dimethoxybenzoyl chloride | o-Tolualdehyde | |
| Compound 231 | Methyl 2-aminobenzoate | 3,4-Dimethoxybenzoyl chloride | 2-Chlorobenzaldehyde | |
| Compound 232 | Methyl 2-aminobenzoate | 3,4-Dimethoxybenzoyl chloride | 6-Methoxy-2-naphthaldehyde | |
| Compound 233 | Methyl 2-aminobenzoate | 3,4-Dimethoxybenzoyl chloride | 4-Biphenyl-carboxaldehyde | |
| Compound 234 | Methyl 2-aminobenzoate | 3,4-Dimethoxybenzoyl chloride | 4-Bromobenzaldehyde | |
| Compound 235 | Methyl 2-aminobenzoate | Benzoyl chloride | Trans-cinnamaldehyde | |
| Compound 236 | Methyl 2-aminobenzoate | 2-Fluorobenzoyl chloride | 2-Fluorobenzaldehyde | |
| Compound 237 | Methyl 2-aminobenzoate | 2-Fluorobenzoyl chloride | 3-Fluorobenzaldehyde | |
| Compound 238 | Methyl 2-aminobenzoate | 2-Fluorobenzoyl chloride | m-Tolualdehyde | |
| Compound 239 | Methyl 2-aminobenzoate | 2-Fluorobenzoyl chloride | 2-Hydroxy-3-tert-butylbenzaldehyde | |
| Compound 240 | Methyl 2-aminobenzoate | 3,4-Dimethoxybenzoyl chloride | 4-Nitrobenzaldehyde | |
| Compound 241 | Methyl 2-aminobenzoate | 3,4-Dimethoxybenzoyl chloride | 4-Diethylaminobenzaldehyde | |
| Compound 242 | Methyl 2-amino-5-hydroxybenzoate | 3,5-Dimethoxybenzoyl chloride | 3-Fluorobenzaldehyde | |
| Compound 243 | Methyl 2-amino-5-bromobenzoate | 3,4-Dimethoxybenzoyl chloride | 2-Pyridyl-carboxaldehyde | |

TABLE 1-continued

| | A | B | C | B' |
|---|---|---|---|---|
| Compound 244 | Methyl 2-amino-5-chlorobenzoate | 3,4-Dimethoxybenzoyl chloride | 2-Pyridyl-carboxaldehyde | |
| Compound 245 | Methyl 2-aminobenzoate | 3,4-Dimethoxybenzoyl chloride | 2-Pyridyl-carboxaldehyde | |
| Compound 246 | Methyl 2-amino-5-chlorobenzoate | 3,4-Dimethoxybenzoyl chloride | 6-Methyl-2-pyridine-carboxaldehyde | |
| Compound 247 | Methyl 2-aminobenzoate | 3,4-Dimethoxybenzoyl chloride | 6-Methyl-2-pyridine-carboxaldehyde | |
| Compound 248 | Methyl 2-amino-5-bromobenzoate | 4-tert-butylbenzoyl chloride | m-Tolualdehyde | |
| Compound 249 | Methyl 2-aminobenzoate | Isonicotinoyl chloride hydrochloride | 3-Methylacetophenone | |
| Compound 250 | Methyl 2-amino-5-chlorobenzoate | Nicotinoyl chloride hydrochloride | 3-Methylacetophenone | |
| Compound 251 | Methyl 2-aminobenzoate | Nicotinoyl chloride hydrochloride | 4-Methylacetophenone | |
| Compound 252 | Methyl 2-amino-5-bromobenzoate | Nicotinoyl chloride hydrochloride | p-Tolualdehyde | |
| Compound 253 | Methyl 2-aminobenzoate | Isonicotinoyl chloride hydrochloride | m-Tolualdehyde | |
| Vacant number | | | | |
| Compound 255 | Methyl 2-amino-5-bromobenzoate | 4-(Chloromethyl)-benzoyl chloride | 3-Fluorobenzaldehyde | 4-Mercapto-pyridine |
| Compound 256 | Methyl 2-amino-5-bromobenzoate | 4-(Chloromethyl)-benzoyl chloride | 4-Fluorobenzaldehyde | 4-Mercapto-pyridine |
| Compound 257 | Methyl 2-amino-5-bromobenzoate | 4-(Chloromethyl)-benzoyl chloride | m-Tolualdehyde | 4-Mercapto-pyridine |
| Compound 258 | Methyl 2-amino-5-bromobenzoate | 4-(Chloromethyl)-benzoyl chloride | p-Tolualdehyde | 4-Mercapto-pyridine |
| Compound 259 | Methyl 2-amino-5-bromobenzoate | 4-(Chloromethyl)-benzoyl chloride | 3,4-Dimethylbenzaldehyde | 4-Mercapto-pyridine |
| Compound 260 | Methyl 2-amino-5-bromobenzoate | 4-(Chloromethyl)-benzoyl chloride | 4-Chloro-3-trifluoromethylbenzaldehyde | 4-Mercapto-pyridine |
| Compound 261 | Methyl 2-amino-5-bromobenzoate | 4-(Chloromethyl)-benzoyl chloride | 3-Fluorobenzaldehyde | 2-Mercapto-ethanol |
| Compound 262 | Methyl 2-amino-5-bromobenzoate | 4-(Chloromethyl)-benzoyl chloride | 4-Fluorobenzaldehyde | 2-Mercapto-ethanol |
| Compound 263 | Methyl 2-amino-5-bromobenzoate | 4-(Chloromethyl)-benzoyl chloride | m-Tolualdehyde | 2-Mercapto-ethanol |
| Compound 264 | Methyl 2-amino-5-bromobenzoate | 4-(Chloromethyl)-benzoyl chloride | p-Tolualdehyde | 2-Mercapto-ethanol |
| Compound 265 | Methyl 2-amino-5-bromobenzoate | 4-(Chloromethyl)-benzoyl chloride | 3,4-Dimethylbenzaldehyde | 2-Mercapto-ethanol |
| Compound 266 | Methyl 2-amino-5-bromobenzoate | 4-(Chloromethyl)-benzoyl chloride | 4-Chloro-3-trifluoromethylbenzaldehyde | 2-Mercapto-ethanol |
| Compound 267 | Methyl 2-amino-5-bromobenzoate | 3-(Chloromethyl)-benzoyl chloride | 3,4-Dimethylbenzaldehyde | 3-Mercapto-1,2,4-triazole |
| Compound 268 | Methyl 2-amino-5-bromobenzoate | 3-(Chloromethyl)-benzoyl chloride | p-Tolualdehyde | 3-Mercapto-1,2,4-triazole |
| Compound 269 | Methyl 2-amino-5-bromobenzoate | 3-(Chloromethyl)-benzoyl chloride | m-Tolualdehyde | 3-Mercapto-1,2,4-triazole |
| Compound 270 | Methyl 2-amino-5-bromobenzoate | 3-(Chloromethyl)-benzoyl chloride | 4-Fluorobenzaldehyde | 3-Mercapto-1,2,4-triazole |
| Compound 271 | Methyl 2-amino-5-bromobenzoate | 3-(Chloromethyl)-benzoyl chloride | 3-Fluorobenzaldehyde | 3-Mercapto-1,2,4-triazole |
| Compound 272 | Methyl 2-amino-5-bromobenzoate | 3-(Chloromethyl)-benzoyl chloride | 4-Chloro-3-trifluoromethylbenzaldehyde | 3-Mercapto-1,2,4-triazole |
| Compound 273 | Methyl 2-amino-5-bromobenzoate | 4-(Chloromethyl)-benzoyl chloride | 3,4-Dimethylbenzaldehyde | 3-Mercapto-1-propanol |
| Compound 274 | Methyl 2-amino-5-bromobenzoate | 4-(Chloromethyl)-benzoyl chloride | p-Tolualdehyde | 3-Mercapto-1-propanol |
| Compound 275 | Methyl 2-amino-5-bromobenzoate | 4-(Chloromethyl)-benzoyl chloride | m-Tolualdehyde | 3-Mercapto-1-propanol |
| Compound 276 | Methyl 2-amino-5-bromobenzoate | 4-(Chloromethyl)-benzoyl chloride | 4-Fluorobenzaldehyde | 3-Mercapto-1-propanol |
| Compound 277 | Methyl 2-amino-5-bromobenzoate | 4-(Chloromethyl)-benzoyl chloride | 3-Fluorobenzaldehyde | 3-Mercapto-1-propanol |
| Compound 278 | Methyl 2-amino-5-bromobenzoate | 4-(Chloromethyl)-benzoyl chloride | 4-Chloro-3-trifluoromethylbenzaldehyde | 3-Mercapto-1-propanol |
| Compound 279 | Methyl 2-amino-5-bromobenzoate | 3-(Chloromethyl)-benzoyl chloride | 3,4-Dimethylbenzaldehyde | 4-(2-Aminoethyl)-morpholine |
| Compound 280 | Methyl 2-amino-5-bromobenzoate | 4-(Chloromethyl)-benzoyl chloride | 3,4-Dimethylbenzaldehyde | N,N-Diethyl-N'-methyl-ethylenediamine |

TABLE 1-continued

|  | A | B | C | B' |
|---|---|---|---|---|
| Compound 281 | Methyl 2-amino-5-bromobenzoate | 4-(Chloromethyl)-benzoyl chloride | 3,4-Dimethylbenzaldehyde | 4-(2-Aminoethyl)-morpholine |
| Compound 282 | Methyl 2-amino-5-bromobenzoate | 4-(Chloromethyl)-benzoyl chloride | p-Tolualdehyde | 4-(2-Aminoethyl)-morpholine |
| Compound 283 | Methyl 2-amino-5-bromobenzoate | 4-(Chloromethyl)-benzoyl chloride | m-Tolualdehyde | 4-(2-Aminoethyl)-morpholine |
| Compound 284 | Methyl 2-amino-5-bromobenzoate | 4-(Chloromethyl)-benzoyl chloride | 4-Fluorobenzaldehyde | 4-(2-Aminoethyl)-morpholine |
| Compound 285 | Methyl 2-amino-5-bromobenzoate | 4-(Chloromethyl)-benzoyl chloride | p-Tolualdehyde | N,N-Diethyl-N'-methyl-ethylenediamine |
| Compound 286 | Methyl 2-amino-5-bromobenzoate | 4-(Chloromethyl)-benzoyl chloride | m-Tolualdehyde | N,N-Diethyl-N'-methyl-ethylenediamine |
| Compound 287 | Methyl 2-amino-5-bromobenzoate | 4-(Chloromethyl)-benzoyl chloride | 4-Fluorobenzaldehyde | N,N-Diethyl-N'-methyl-ethylenediamine |
| Compound 288 | Methyl 2-amino-5-bromobenzoate | 4-(Chloromethyl)-benzoyl chloride | 3-Fluorobenzaldehyde | N,N-Diethyl-N'-methyl-ethylenediamine |
| Compound 289 | Methyl 2-amino-5-bromobenzoate | 4-(Chloromethyl)-benzoyl chloride | 4-Chloro-3-trifluoromethylbenzaldehyde | N,N-Diethyl-N'-methyl-ethylenediamine |
| Compound 290 | Methyl 2-amino-5-bromobenzoate | 4-(Chloromethyl)-benzoyl chloride | p-Methoxybenzaldehyde | N,N-Diethyl-N'-methyl-ethylenediamine |
| Compound 291 | Methyl 2-amino-5-bromobenzoate | 4-(Chloromethyl)-benzoyl chloride | m-Methoxybenzaldehyde | N,N-Diethyl-N'-methyl-ethylenediamine |
| Compound 292 | Methyl 2-amino-5-bromobenzoate | 4-(Chloromethyl)-benzoyl chloride | 3,4-Dimethylbenzaldehyde | N,N-Diethyl-ethylenediamine |
| Compound 293 | Methyl 2-amino-5-bromobenzoate | 4-(Chloromethyl)-benzoyl chloride | p-Tolualdehyde | N,N-Diethyl-ethylenediamine |
| Compound 294 | Methyl 2-amino-5-bromobenzoate | 4-(Chloromethyl)-benzoyl chloride | m-Tolualdehyde | N,N-Diethyl-ethylenediamine |
| Compound 295 | Methyl 2-amino-5-bromobenzoate | 4-(Chloromethyl)-benzoyl chloride | 4-Fluorobenzaldehyde | N,N-Diethyl-ethylenediamine |
| Compound 296 | Methyl 2-amino-5-bromobenzoate | 4-(Chloromethyl)-benzoyl chloride | 3-Fluorobenzaldehyde | N,N-Diethyl-ethylenediamine |
| Compound 297 | Methyl 2-amino-5-bromobenzoate | 4-(Chloromethyl)-benzoyl chloride | 4-Chloro-3-trifluoromethylbenzaldehyde | N,N-Diethyl-ethylenediamine |
| Compound 298 | Methyl 2-amino-5-bromobenzoate | 4-(Chloromethyl)-benzoyl chloride | p-Methoxybenzaldehyde | N,N-Diethyl-ethylenediamine |
| Compound 299 | Methyl 2-amino-5-bromobenzoate | 4-(Chloromethyl)-benzoyl chloride | m-Methoxybenzaldehyde | N,N-Diethyl-ethylenediamine |
| Compound 300 | Methyl 2-amino-5-bromobenzoate | 4-(Chloromethyl)-benzoyl chloride | 3,4-Dimethylbenzaldehyde | N-(3-Amino-propyl)di-ethanolamine |
| Compound 301 | Methyl 2-amino-5-bromobenzoate | 4-(Chloromethyl)-benzoyl chloride | 3-Fluorobenzaldehyde | N-(3-Amino-propyl)di-ethanolamine |
| Compound 302 | Methyl 2-amino-5-bromobenzoate | 4-(Chloromethyl)-benzoyl chloride | 4-Chloro-3-trifluoromethylbenzaldehyde | N-(3-Amino-propyl)di-ethanolamine |
| Compound 303 | Methyl 2-amino-5-bromobenzoate | 4-(Chloromethyl)-benzoyl chloride | 3,4-Dimethylbenzaldehyde | Diisopropanol-amine |
| Compound 304 | Methyl 2-amino-5-bromobenzoate | 4-(Chloromethyl)-benzoyl chloride | p-Tolualdehyde | Diisopropanol-amine |
| Compound 305 | Methyl 2-amino-5-bromobenzoate | 4-(Chloromethyl)-benzoyl chloride | 3,4-Dimethylbenzaldehyde | N-(2-(1-Piperazino)-acetyl)-morpholine |
| Compound 306 | Methyl 2-amino-5-bromobenzoate | 4-(Chloromethyl)-benzoyl chloride | 4-Chloro-3-trifluoromethylbenzaldehyde | N-(2-(1-Piperazino)-acetyl)-morpholine |
| Compound 307 | Methyl 2-amino-5-bromobenzoate | 4-(Chloromethyl)-benzoyl chloride | p-Methoxybenzaldehyde | N-(2-(1-Piperazino)-acetyl)-morpholine |
| Compound 308 | Methyl 2-amino-5-bromobenzoate | 4-(Chloromethyl)-benzoyl chloride | 3,4-Dimethylbenzaldehyde | 4-Piperidino-piperidine |
| Compound 309 | Methyl 2-amino-5-bromobenzoate | 4-(Chloromethyl)-benzoyl chloride | p-Tolualdehyde | 4-Piperidino-piperidine |
| Compound 310 | Methyl 2-amino-5-bromobenzoate | 4-(Chloromethyl)-benzoyl chloride | m-Tolualdehyde | 4-Piperidino-piperidine |
| Compound 311 | Methyl 2-amino-5-bromobenzoate | 4-(Chloromethyl)-benzoyl chloride | 4-Fluorobenzaldehyde | 4-Piperidino-piperidine |

TABLE 1-continued

| | A | B | C | B' |
|---|---|---|---|---|
| Compound 312 | Methyl 2-amino-5-bromobenzoate | 4-(Chloromethyl)-benzoyl chloride | 3-Fluorobenzaldehyde | 4-Piperidino-piperidine |
| Compound 313 | Methyl 2-amino-5-bromobenzoate | 4-(Chloromethyl)-benzoyl chloride | 4-Chloro-3-trifluoromethylbenzaldehyde | 4-Piperidino-piperidine |
| Compound 314 | Methyl 2-amino-5-bromobenzoate | 4-(Chloromethyl)-benzoyl chloride | p-Methoxybenzaldehyde | 4-Piperidino-piperidine |
| Compound 315 | Methyl 2-amino-5-bromobenzoate | 4-(Chloromethyl)-benzoyl chloride | m-Methoxybenzaldehyde | 4-Piperidino-piperidine |
| Compound 316 | Methyl 2-amino-5-bromobenzoate | 4-(Chloromethyl)-benzoyl chloride | 3,4-Dimethylbenzaldehyde | 1-(2-Hydroxyethyl)-piperazine |
| Compound 317 | Methyl 2-amino-5-bromobenzoate | 4-(Chloromethyl)-benzoyl chloride | p-Tolualdehyde | 1-(2-Hydroxyethyl)-piperazine |
| Compound 318 | Methyl 2-amino-5-bromobenzoate | 4-(Chloromethyl)-benzoyl chloride | m-Tolualdehyde | 1-(2-Hydroxyethyl)-piperazine |
| Compound 319 | Methyl 2-amino-5-bromobenzoate | 4-(Chloromethyl)-benzoyl chloride | 4-Fluorobenzaldehyde | 1-(2-Hydroxyethyl)-piperazine |
| Compound 320 | Methyl 2-amino-5-bromobenzoate | 4-(Chloromethyl)-benzoyl chloride | 3-Fluorobenzaldehyde | 1-(2-Hydroxyethyl)-piperazine |
| Compound 321 | Methyl 2-amino-5-bromobenzoate | 4-(Chloromethyl)-benzoyl chloride | 4-Chloro-3-trifluoromethylbenzaldehyde | 1-(2-Hydroxyethyl)-piperazine |
| Compound 322 | Methyl 2-amino-5-bromobenzoate | 4-(Chloromethyl)-benzoyl chloride | p-Methoxybenzaldehyde | 1-(2-Hydroxyethyl)-piperazine |
| Compound 323 | Methyl 2-amino-5-bromobenzoate | 4-(Chloromethyl)-benzoyl chloride | m-Methoxybenzaldehyde | 1-(2-Hydroxyethyl)- |
| Compound 324 | Methyl 2-amino-5-bromobenzoate | 4-(Chloromethyl)-benzoyl chloride | 3,4-Dimethylbenzaldehyde | 4-Hydroxypiperidine |
| Compound 325 | Methyl 2-amino-5-bromobenzoate | 4-(Chloromethyl)-benzoyl chloride | p-Tolualdehyde | 4-Hydroxypiperidine |
| Compound 326 | Methyl 2-amino-5-bromobenzoate | 4-(Chloromethyl)-benzoyl chloride | m-Tolualdehyde | 4-Hydroxypiperidine |
| Compound 327 | Methyl 2-amino-5-bromobenzoate | 4-(Chloromethyl)-benzoyl chloride | 4-Fluorobenzaldehyde | 4-Hydroxypiperidine |
| Compound 328 | Methyl 2-amino-5-bromobenzoate | 4-(Chloromethyl)-benzoyl chloride | 3-Fluorobenzaldehyde | 4-Hydroxypiperidine |
| Compound 329 | Methyl 2-amino-5-bromobenzoate | 4-(Chloromethyl)-benzoyl chloride | 4-Chloro-3-trifluoromethylbenzaldehyde | 4-Hydroxypiperidine |
| Compound 330 | Methyl 2-amino-5-bromobenzoate | 4-(Chloromethyl)-benzoyl chloride | p-Methoxybenzaldehyde | 4-Hydroxypiperidine |
| Compound 331 | Methyl 2-amino-5-bromobenzoate | 4-(Chloromethyl)-benzoyl chloride | m-Methoxybenzaldehyde | 4-Hydroxypiperidine |
| Compound 332 | Methyl 2-amino-5-bromobenzoate | 4-(Chloromethyl)-benzoyl chloride | 3,4-Dimethylbenzaldehyde | 4-Piperidine-methanol |
| Compound 333 | Methyl 2-amino-5-bromobenzoate | 4-(Chloromethyl)-benzoyl chloride | p-Tolualdehyde | 4-Piperidine-methanol |
| Compound 334 | Methyl 2-amino-5-bromobenzoate | 4-(Chloromethyl)-benzoyl chloride | m-Tolualdehyde | 4-Piperidine-methanol |
| Compound 335 | Methyl 2-amino-5-bromobenzoate | 4-(Chloromethyl)-benzoyl chloride | 4-Fluorobenzaldehyde | 4-Piperidine-methanol |
| Compound 336 | Methyl 2-amino-5-bromobenzoate | 4-(Chloromethyl)-benzoyl chloride | 3-Fluorobenzaldehyde | 4-Piperidine-methanol |
| Compound 337 | Methyl 2-amino-5-bromobenzoate | 4-(Chloromethyl)-benzoyl chloride | 4-Chloro-3-trifluoromethylbenzaldehyde | 4-Piperidine-methanol |
| Compound 338 | Methyl 2-amino-5-bromobenzoate | 4-(Chloromethyl)-benzoyl chloride | p-Methoxybenzaldehyde | 4-Piperidine-methanol |
| Compound 339 | Methyl 2-amino-5-bromobenzoate | 4-(Chloromethyl)-benzoyl chloride | m-Methoxybenzaldehyde | 4-Piperidine-methanol |
| Compound 340 | Methyl 2-amino-5-bromobenzoate | 4-(Chloromethyl)-benzoyl chloride | 3,4-Dimethylbenzaldehyde | 4-Piperidine-ethanol |
| Compound 341 | Methyl 2-amino-5-bromobenzoate | 3-(Chloromethyl)-benzoyl chloride | 3-Fluorobenzaldehyde | 3-Mercapto-1,2,4-triazole |
| Compound 342 | Methyl 3-amino-4-methylthiophene-2-carboxylate | 3-(Chloromethyl)-benzoyl chloride | 3,4-Dimethylbenzaldehyde | N,N-Diethyl-N'-methyl-ethylenediamine |
| Compound 343 | Methyl 3-amino-4-methylthiophene-2-carboxylate | 3-(Chloromethyl)-benzoyl chloride | p-Tolualdehyde | N,N-Diethyl-N'-methyl-ethylenediamine |
| Compound 344 | Methyl 3-amino-4-methylthiophene-2-carboxylate | 3-(Chloromethyl)-benzoyl chloride | 4-Chloro-3-trifluoromethylbenzaldehyde | N,N-Diethyl-N'-methyl-ethylenediamine |
| Compound 345 | Methyl 3-amino-4-methylthiophene-2-carboxylate | 3-(Chloromethyl)-benzoyl chloride | 3,4-Dimethylbenzaldehyde | 4-Piperidino-piperidine |
| Compound 346 | Methyl 2-amino-5-bromobenzoate | Nicotinoyl chloride hydrochloride | Trans-cinnamaldehyde | |
| Compound 347 | Methyl 2-amino-5-bromobenzoate | Isonicotinoyl chloride hydrochloride | Trans-cinnamaldehyde | |

TABLE 1-continued

| | A | B | C | B' |
|---|---|---|---|---|
| Compound 348 | Methyl 2-amino-5-chlorobenzoate | Nicotinoyl chloride hydrochloride | Trans-cinnamaldehyde | |
| Compound 349 | Methyl 2-amino-5-chlorobenzoate | Isonicotinoyl chloride hydrochloride | Trans-cinnamaldehyde | |
| Compound 350 | Methyl 2-amino-5-bromobenzoate | Isonicotinoyl chloride hydrochloride | 3-(2-Hydroxy-ethoxy)-benzaldehyde | |
| Compound 351 | Methyl 2-amino-5-chlorobenzoate | Isonicotinoyl chloride hydrochloride | 3-(2-Hydroxy-ethoxy)-benzaldehyde | |
| Compound 352 | Methyl 2-amino-5-bromobenzoate | Nicotinoyl chloride hydrochloride | 2-Methoxy-cinnamaldehyde | |
| Compound 353 | Methyl 2-amino-5-bromobenzoate | Isonicotinoyl chloride hydrochloride | 2-Methoxy-cinnamaldehyde | |
| Compound 354 | Methyl 2-amino-5-chlorobenzoate | Nicotinoyl chloride hydrochloride | 2-Methoxy-cinnamaldehyde | |
| Compound 355 | Methyl 2-amino-5-chlorobenzoate | Isonicotinoyl chloride hydrochloride | 2-Methoxy-cinnamaldehyde | |
| Compound 356 | Methyl 2-amino-5-bromobenzoate | Picolinoyl chloride hydrochloride | p-Tolualdehyde | |
| Compound 357 | Methyl 2-amino-5-bromobenzoate | 4-(Chloromethyl)-benzoyl chloride | m-Tolualdehyde | 3-Fluoro-benzenethiol |
| Compound 358 | Methyl 2-aminobenzoate | Nicotinoyl chloride hydrochloride | 4-Dimethyl-amino-cinnamaldehyde | |
| Compound 359 | Methyl 2-amino-5-chlorobenzoate | Picolinoyl chloride hydrochloride | 3-Fluorobenzaldehyde | |
| Compound 360 | Methyl 2-amino-5-chlorobenzoate | Picolinoyl chloride hydrochloride | 4-Fluorobenzaldehyde | |
| Compound 361 | Methyl 2-amino-5-chlorobenzoate | Picolinoyl chloride hydrochloride | m-Tolualdehyde | |
| Compound 362 | Methyl 2-amino-5-chlorobenzoate | Picolinoyl chloride hydrochloride | p-Tolualdehyde | |
| Compound 363 | Methyl 2-amino-5-chlorobenzoate | Picolinoyl chloride hydrochloride | 3,4-Dimethylbenzaldehyde | |
| Compound 364 | Methyl 2-amino-5-chlorobenzoate | Picolinoyl chloride hydrochloride | 4-Chloro-3-trifluoromethylbenzaldehyde | |
| Vacant number | | | | |
| Compound 366 | Methyl 2-amino-5-chlorobenzoate | 3-(Chloromethyl)-benzoyl chloride | 3,4-Dimethylbenzaldehyde | 4-Mercapto-pyridine |
| Compound 367 | Methyl 2-amino-5-bromobenzoate | 3,4-Dimethoxybenzoyl chloride | p-Tolualdehyde | |
| Compound 368 | Methyl 2-amino-5-chlorobenzoate | 3-(Chloromethyl)-benzoyl chloride | 3-Fluorobenzaldehyde | 4-Piperidino-piperidine |
| Compound 369 | Methyl 2-amino-5-chlorobenzoate | 3-(Chloromethyl)-benzoyl chloride | 4-Fluorobenzaldehyde | 4-Piperidino-piperidine |
| Compound 370 | Methyl 2-amino-5-chlorobenzoate | 3-(Chloromethyl)-benzoyl chloride | m-Tolualdehyde | 4-Piperidino-piperidine |
| Compound 371 | Methyl 2-amino-5-chlorobenzoate | 3-(Chloromethyl)-benzoyl chloride | p-Tolualdehyde | 4-Piperidino-piperidine |
| Compound 372 | Methyl 2-amino-5-chlorobenzoate | 3-(Chloromethyl)-benzoyl chloride | 3,4-Dimethylbenzaldehyde | 4-Piperidino-piperidine |
| Compound 373 | Methyl 2-amino-5-chlorobenzoate | 3-(Chloromethyl)-benzoyl chloride | 4-Chloro-3-trifluoromethylbenzaldehyde | 4-Piperidino-piperidine |
| Compound 374 | Methyl 2-amino-5-chlorobenzoate | 3-(Chloromethyl)-benzoyl chloride | 3-Methoxybenzaldehyde | 4-Piperidino-piperidine |
| Compound 375 | Methyl 2-amino-5-chlorobenzoate | 3-(Chloromethyl)-benzoyl chloride | 4-Methoxybenzaldehyde | 4-Piperidino-piperidine |
| Compound 376 | Methyl 2-amino-5-chlorobenzoate | 3-(Chloromethyl)-benzoyl chloride | 3-Hydroxybenzaldehyde | 4-Piperidino-piperidine |
| Compound 377 | Methyl 2-amino-5-chlorobenzoate | 3-(Chloromethyl)-benzoyl chloride | 4-Hydroxybenzaldehyde | 4-Piperidino-piperidine |
| Compound 378 | Methyl 2-amino-5-bromobenzoate | 4-(Chloromethyl)-benzoyl chloride | 3-Methoxybenzaldehyde | 4-Piperidino-piperidine |
| Compound 379 | Methyl 2-amino-5-chlorobenzoate | 3-(Chloromethyl)-benzoyl chloride | 3-Fluorobenzaldehyde | N,N-Diethyl-N'-methyl-ethylenediamine |
| Compound 380 | Methyl 2-amino-5-chlorobenzoate | 3-(Chloromethyl)-benzoyl chloride | 4-Fluorobenzaldehyde | N,N-Diethyl N'-methyl-ethylenediamine |
| Compound 381 | Methyl 2-amino-5-chlorobenzoate | 3-(Chloromethyl)-benzoyl chloride | m-Tolualdehyde | N,N-Diethyl-N'-methyl-ethylenediamine |

TABLE 1-continued

| | A | B | C | B' |
|---|---|---|---|---|
| Compound 382 | Methyl 2-amino-5-chlorobenzoate | 3-(Chloromethyl)-benzoyl chloride | p-Tolualdehyde | N,N-Diethyl-N'-methyl-ethylenediamine |
| Compound 383 | Methyl 2-amino-5-chlorobenzoate | 3-(Chloromethyl)-benzoyl chloride | 3,4-Dimethylbenzaldehyde | N,N-Diethyl-N'-methyl-ethylenediamine |
| Compound 384 | Methyl 2-amino-5-chlorobenzoate | 3-(Chloromethyl)-benzoyl chloride | 4-Chloro-3-trifluoromethylbenzaldehyde | N,N-Diethyl-N'-methyl-ethylenediamine |
| Compound 385 | Methyl 2-amino-5-chlorobenzoate | 3-(Chloromethyl)-benzoyl chloride | 3-Methoxybenzaldehyde | N,N-Diethyl-N'-methyl-ethylenediamine |
| Compound 386 | Methyl 2-amino-5-chlorobenzoate | 3-(Chloromethyl)-benzoyl chloride | 4-Methoxybenzaldehyde | N,N-Diethyl-N'-methyl-ethylenediamine |
| Compound 387 | Methyl 2-amino-5-chlorobenzoate | 3-(Chloromethyl)-benzoyl chloride | 3-Hydroxybenzaldehyde | N,N-Diethyl-N'-methyl-ethylenediamine |
| Compound 388 | Methyl 2-amino-5-chlorobenzoate | 3-(Chloromethyl)-benzoyl chloride | 4-Hydroxybenzaldehyde | N,N-Diethyl-N'-methyl-ethylenediamine |
| Compound 389 | Methyl 2-amino-5-chlorobenzoate | 3-(Chloromethyl)-benzoyl chloride | 3-Fluorobenzaldehyde | 3-Mercapto-1,2,4-triazole |
| Compound 390 | Methyl 2-amino-5-chlorobenzoate | 3-(Chloromethyl)-benzoyl chloride | 4-Fluorobenzaldehyde | 3-Mercapto-1,2,4-triazole |
| Compound 391 | Methyl 2-amino-5-chlorobenzoate | 3-(Chloromethyl)-benzoyl chloride | m-Tolualdehyde | 3-Mercapto-1,2,4-triazole |
| Compound 392 | Methyl 2-amino-5-chlorobenzoate | 3-(Chloromethyl)-benzoyl chloride | p-Tolualdehyde | 3-Mercapto-1,2,4-triazole |
| Compound 393 | Methyl 2-amino-5-chlorobenzoate | 3-(Chloromethyl)-benzoyl chloride | 4-Chloro-3-trifluoromethylbenzaldehyde | 3-Mercapto-1,2,4-triazole |
| Compound 394 | Methyl 2-amino-5-chlorobenzoate | 3-(Chloromethyl)-benzoyl chloride | 3-Fluorobenzaldehyde | 2-(Methylamino)ethanol |
| Compound 395 | Methyl 2-amino-5-chlorobenzoate | 3-(Chloromethyl)-benzoyl chloride | 4-Fluorobenzaldehyde | 2-(Methylamino)ethanol |
| Compound 396 | Methyl 2-amino-5-chlorobenzoate | 3-(Chloromethyl)-benzoyl chloride | m-Tolualdehyde | 2-(Methylamino)ethanol |
| Compound 397 | Methyl 2-amino-5-chlorobenzoate | 3-(Chloromethyl)-benzoyl chloride | p-Tolualdehyde | 2-(Methylamino)ethanol |
| Compound 398 | Methyl 2-amino-5-chlorobenzoate | 3-(Chloromethyl)-benzoyl chloride | 3,4-Dimethylbenzaldehyde | 2-(Methylamino)ethanol |
| Compound 399 | Methyl 2-amino-5-chlorobenzoate | 3-(Chloromethyl)-benzoyl chloride | 4-Chloro-3-trifluoromethylbenzaldehyde | 2-(Methylamino)ethanol |
| Compound 400 | Methyl 2-amino-5-chlorobenzoate | 3-(Chloromethyl)-benzoyl chloride | 3-Methoxybenzaldehyde | 2-(Methylamino)ethanol |
| Compound 401 | Methyl 2-amino-5-chlorobenzoate | 3-(Chloromethyl)-benzoyl chloride | 4-Methoxybenzaldehyde | 2-(Methylamino)ethanol |
| Compound 402 | Methyl 2-amino-5-chlorobenzoate | 3-(Chloromethyl)-benzoyl chloride | 3-Hydroxybenzaldehyde | 2-(Methylamino)ethanol |
| Compound 403 | Methyl 2-amino-5-chlorobenzoate | 3-(Chloromethyl)-benzoyl chloride | 4-Hydroxybenzaldehyde | 2-(Methylamino)ethanol |
| Compound 404 | Methyl 2-amino-5-chlorobenzoate | 3-(Chloromethyl)-benzoyl chloride | m-Tolualdehyde | Diethanolamine |
| Compound 405 | Methyl 2-amino-5-chlorobenzoate | 3-(Chloromethyl)-benzoyl chloride | p-Tolualdehyde | Diethanolamine |
| Compound 406 | Methyl 2-amino-5-chlorobenzoate | 3-(Chloromethyl)-benzoyl chloride | 3,4-Dimethylbenzaldehyde | Diethanolamine |
| Compound 407 | Methyl 2-amino-5-chlorobenzoate | 3-(Chloromethyl)-benzoyl chloride | 4-Chloro-3-trifluoromethylbenzaldehyde | Diethanolamine |
| Compound 408 | Methyl 2-amino-5-chlorobenzoate | 3-(Chloromethyl)-benzoyl chloride | 3-Methoxybenzaldehyde | Diethanolamine |
| Compound 409 | Methyl 2-amino-5-chlorobenzoate | 3-(Chloromethyl)-benzoyl chloride | 4-Methoxybenzaldehyde | Diethanolamine |
| Compound 410 | Methyl 2-amino-5-chlorobenzoate | 3-(Chloromethyl)-benzoyl chloride | 3-Hydroxybenzaldehyde | Diethanolamine |
| Compound 411 | Methyl 2-amino-5-chlorobenzoate | 3-(Chloromethyl)-benzoyl chloride | 4-Hydroxybenzaldehyde | Diethanolamine |
| Compound 412 | Methyl 2-amino-5-chlorobenzoate | 4-(Chloromethyl)-benzoyl chloride | 3-Fluorobenzaldehyde | 2-(Methylamino)ethanol |
| Compound 413 | Methyl 2-amino-5-chlorobenzoate | 4-(Chloromethyl)-benzoyl chloride | 4-Fluorobenzaldehyde | 2-(Methylamino)ethanol |
| Compound 414 | Methyl 2-amino-5-chlorobenzoate | 4-(Chloromethyl)-benzoyl chloride | m-Tolualdehyde | 2-(Methylamino)ethanol |
| Compound 415 | Methyl 2-amino-5-chlorobenzoate | 4-(Chloromethyl)-benzoyl chloride | p-Tolualdehyde | 2-(Methylamino)ethanol |
| Compound 416 | Methyl 2-amino-5-chlorobenzoate | 4-(Chloromethyl)-benzoyl chloride | 3,4-Dimethylbenzaldehyde | 2-(Methylamino)ethanol |

TABLE 1-continued

| | A | B | C | B' |
|---|---|---|---|---|
| Compound 417 | Methyl 2-amino-5-chlorobenzoate | 4-(Chloromethyl)-benzoyl chloride | 4-Chloro-3-trifluoromethylbenzaldehyde | 2-(Methylamino) ethanol |
| Compound 418 | Methyl 2-amino-5-chlorobenzoate | 4-(Chloromethyl)-benzoyl chloride | 3-Methoxybenzaldehyde | 2-(Methylamino) ethanol |
| Compound 419 | Methyl 2-amino-5-chlorobenzoate | 4-(Chloromethyl)-benzoyl chloride | 4-Methoxybenzaldehyde | 2-(Methylamino) ethanol |
| Compound 420 | Methyl 2-amino-5-chlorobenzoate | 4-(Chloromethyl)-benzoyl chloride | 3-Hydroxybenzaldehyde | 2-(Methylamino) ethanol |
| Compound 421 | Methyl 2-amino-5-chlorobenzoate | 4-(Chloromethyl)-benzoyl chloride | 4-Hydroxybenzaldehyde | 2-(Methylamino) ethanol |
| Compound 422 | Methyl 2-amino-5-chlorobenzoate | 3-(Chloromethyl)-benzoyl chloride | 3-Fluorobenzaldehyde | 2-(Ethylamino) ethanol |
| Compound 423 | Methyl 2-amino-5-chlorobenzoate | 3-(Chloromethyl)-benzoyl chloride | 4-Fluorobenzaldehyde | 2-(Ethylamino) ethanol |
| Compound 424 | Methyl 2-amino-5-chlorobenzoate | 3-(Chloromethyl)-benzoyl chloride | m-Tolualdehyde | 2-(Ethylamino) ethanol |
| Compound 425 | Methyl 2-amino-5-chlorobenzoate | 3-(Chloromethyl)-benzoyl chloride | p-Tolualdehyde | 2-(Ethylamino) ethanol |
| Compound 426 | Methyl 2-amino-5-chlorobenzoate | 3-(Chloromethyl)-benzoyl chloride | 3,4-Dimethylbenzaldehyde | 2-(Ethylamino) ethanol |
| Compound 427 | Methyl 2-amino-5-chlorobenzoate | 3-(Chloromethyl)-benzoyl chloride | 4-Chloro-3-trifluoromethylbenzaldehyde | 2-(Ethylamino) ethanol |
| Compound 428 | Methyl 2-amino-5-chlorobenzoate | 3-(Chloromethyl)-benzoyl chloride | 3-Methoxybenzaldehyde | 2-(Ethylamino) ethanol |
| Compound 429 | Methyl 2-amino-5-chlorobenzoate | 3-(Chloromethyl)-benzoyl chloride | 4-Methoxybenzaldehyde | 2-(Ethylamino) ethanol |
| Compound 430 | Methyl 2-amino-5-chlorobenzoate | 3-(Chloromethyl)-benzoyl chloride | 3-Hydroxybenzaldehyde | 2-(Ethylamino) ethanol |
| Compound 431 | Methyl 2-amino-5-chlorobenzoate | 3-(Chloromethyl)-benzoyl chloride | 4-Hydroxybenzaldehyde | 2-(Ethylamino) ethanol |
| Compound 432 | Methyl 2-amino-5-chlorobenzoate | 4-(Chloromethyl)-benzoyl chloride | 3-Fluorobenzaldehyde | 2-(Ethylamino) ethanol |
| Compound 433 | Methyl 2-amino-5-chlorobenzoate | 4-(Chloromethyl)-benzoyl chloride | 4-Fluorobenzaldehyde | 2-(Ethylamino) ethanol |
| Compound 434 | Methyl 2-amino-5-chlorobenzoate | 4-(Chloromethyl)-benzoyl chloride | m-Tolualdehyde | 2-(Ethylamino) ethanol |
| Compound 435 | Methyl 2-amino-5-chlorobenzoate | 4-(Chloromethyl)-benzoyl chloride | p-Tolualdehyde | 2-(Ethylamino) ethanol |
| Compound 436 | Methyl 2-amino-5-chlorobenzoate | 4-(Chloromethyl)-benzoyl chloride | 3,4-Dimethylbenzaldehyde | 2-(Ethylamino) ethanol |
| Compound 437 | Methyl 2-amino-5-chlorobenzoate | 4-(Chloromethyl)-benzoyl chloride | 4-Chloro-3-trifluoromethylbenzaldehyde | 2-(Ethylamino) ethanol |
| Compound 438 | Methyl 2-amino-5-chlorobenzoate | 4-(Chloromethyl)-benzoyl chloride | 3-Methoxybenzaldehyde | 2-(Ethylamino) ethanol |
| Compound 439 | Methyl 2-amino-5-chlorobenzoate | 4-(Chloromethyl)-benzoyl chloride | 4-Methoxybenzaldehyde | 2-(Ethylamino) ethanol |
| Compound 440 | Methyl 2-amino-5-chlorobenzoate | 4-(Chloromethyl)-benzoyl chloride | 3-Hydroxybenzaldehyde | 2-(Ethylamino) ethanol |
| Compound 441 | Methyl 2-amino-5-chlorobenzoate | 4-(Chloromethyl)-benzoyl chloride | 4-Hydroxybenzaldehyde | 2-(Ethylamino) ethanol |
| Compound 442 | Methyl 2-amino-5-chlorobenzoate | 4-(Chloromethyl)-benzoyl chloride | 3-Fluorobenzaldehyde | 2-Diethylamino-ethanethiol hydrochloride |
| Compound 443 | Methyl 2-amino-5-chlorobenzoate | 4-(Chloromethyl)-benzoyl chloride | 4-Fluorobenzaldehyde | 2-Diethylamino-ethanethiol hydrochloride |
| Compound 444 | Methyl 2-amino-5-chlorobenzoate | 4-(Chloromethyl)-benzoyl chloride | m-Tolualdehyde | 2-Diethylamino-ethanethiol hydrochloride |
| Compound 445 | Methyl 2-amino-5-chlorobenzoate | 4-(Chloromethyl)-benzoyl chloride | p-Tolualdehyde | 2-Diethylamino-ethanethiol hydrochloride |
| Compound 446 | Methyl 2-amino-5-chlorobenzoate | 4-(Chloromethyl)-benzoyl chloride | 3,4-Dimethylbenzaldehyde | 2-Diethylamino-ethanethiol hydrochloride |
| Compound 447 | Methyl 2-amino-5-chlorobenzoate | 4-(Chloromethyl)-benzoyl chloride | 4-Chloro-3-trifluoromethylbenzaldehyde | 2-Diethylamino-ethanethiol hydrochloride |
| Compound 448 | Methyl 2-amino-5-chlorobenzoate | 4-(Chloromethyl)-benzoyl chloride | 3-Methoxybenzaldehyde | 2-Diethylamino-ethanethiol hydrochloride |
| Compound 449 | Methyl 2-amino-5-chlorobenzoate | 4-(Chloromethyl)-benzoyl chloride | 4-Methoxybenzaldehyde | 2-Diethylamino-ethanethiol hydrochloride |
| Compound 450 | Methyl 2-amino-5-chlorobenzoate | 4-(Chloromethyl)-benzoyl chloride | 3-Hydroxybenzaldehyde | 2-Diethylamino-ethanethiol hydrochloride |

TABLE 1-continued

| | A | B | C | B' |
|---|---|---|---|---|
| Compound 451 | Methyl 2-amino-5-chlorobenzoate | 4-(Chloromethyl)-benzoyl chloride | 4-Hydroxybenzaldehyde | 2-Diethylamino-ethanethiol hydrochloride |
| Compound 452 | Methyl 2-amino-5-chlorobenzoate | 3-(Chloromethyl)-benzoyl chloride | 3-Fluorobenzaldehyde | 2-Diethylamino-ethanethiol hydrochloride |
| Compound 453 | Methyl 2-amino-5-chlorobenzoate | 3-(Chloromethyl)-benzoyl chloride | 4-Fluorobenzaldehyde | 2-Diethylamino-ethanethiol hydrochloride |
| Compound 454 | Methyl 2-amino-5-chlorobenzoate | 3-(Chloromethyl)-benzoyl chloride | m-Tolualdehyde | 2-Diethylamino-ethanethiol hydrochloride |
| Compound 455 | Methyl 2-amino-5-chlorobenzoate | 3-(Chloromethyl)-benzoyl chloride | p-Tolualdehyde | 2-Diethylamino-ethanethiol hydrochloride |
| Compound 456 | Methyl 2-amino-5 chlorobenzoate | 3-(Chloromethyl)-benzoyl chloride | 3,4-Dimethylbenzaldehyde | 2-Diethylamino-ethanethiol hydrochloride |
| Compound 457 | Methyl 2-amino-5-chlorobenzoate | 3-(Chloromethyl)-benzoyl chloride | 4-Chloro-3-trifluoromethylbenzaldehyde | 2-Diethylamino-ethanethiol hydrochloride |
| Compound 458 | Methyl 2-amino-5-chlorobenzoate | 3-(Chloromethyl)-benzoyl chloride | 3-Methoxybenzaldehyde | 2-Diethylamino-ethanethiol hydrochloride |
| Compound 459 | Methyl 2-amino-5-chlorobenzoate | 3-(Chloromethyl)-benzoyl chloride | 4-Methoxybenzaldehyde | 2-Diethylamino-ethanethiol hydrochloride |
| Compound 460 | Methyl 2-amino-5-chlorobenzoate | 3-(Chloromethyl)-benzoyl chloride | 3-Hydroxybenzaldehyde | 2-Diethylamino-ethanethiol hydrochloride |
| Compound 461 | Methyl 2-amino-5-chlorobenzoate | 3-(Chloromethyl)-benzoyl chloride | 4-Hydroxybenzaldehyde | 2-Diethylamino-ethanethiol hydrochloride |
| Compound 462 | Methyl 2-amino-5-chlorobenzoate | 3-(Chloromethyl)-benzoyl chloride | 3-Fluorobenzaldehyde | 1-(2-Dimethylaminoethyl)-5-mercapto-tetrazole |
| Compound 463 | Methyl 2-amino-5-chlorobenzoate | 3-(Chloromethyl)-benzoyl chloride | 4-Fluorobenzaldehyde | 1-(2-Dimethylaminoethyl)-5-mercapto-tetrazole |
| Compound 464 | Methyl 2-amino-5-chlorobenzoate | 3-(Chloromethyl)-benzoyl chloride | m-Tolualdehyde | 1-(2-Dimethyl aminoethyl)-5-mercapto-tetrazole |
| Compound 465 | Methyl 2-amino-5-chlorobenzoate | 3-(Chloromethyl)-benzoyl chloride | p-Tolualdehyde | 1-(2-Dimethylaminoethyl)-5-mercapto-tetrazole |
| Compound 466 | Methyl 2-amino-5-chlorobenzoate | 3-(Chloromethyl)-benzoyl chloride | 3,4-Dimethylbenzaldehyde | 1-(2-Dimethylaminoethyl)-5-mercapto-tetrazole |
| Compound 467 | Methyl 2-amino-5-chlorobenzoate | 3-(Chloromethyl)-benzoyl chloride | 4-Chloro-3-trifluoromethylbenzaldehyde | 1-(2-Dimethylaminoethyl)-5-mercapto-tetrazole |
| Compound 468 | Methyl 2-amino-5-chlorobenzoate | 3-(Chloromethyl)-benzoyl chloride | 3-Methoxybenzaldehyde | 1(2-Dimethylaminoethyl)-5-mercapto-tetrazole |
| Compound 469 | Methyl 2-amino-5-chlorobenzoate | 3-(Chloromethyl)-benzoyl chloride | 4-Methoxybenzaldehyde | 1-(2-Dimethylaminoethyl)-5-mercapto-tetrazole |
| Compound 470 | Methyl 2-amino-5-chlorobenzoate | 3-(Chloromethyl)-benzoyl chloride | 3-Hydroxybenzaldehyde | 1-(2-Dimethylaminoethyl)-5-mercapto-tetrazole |
| Compound 471 | Methyl 2-amino-5-chlorobenzoate | 3-(Chloromethyl)-benzoyl chloride | 4-Hydroxybenzaldehyde | 1-(2-Dimethylaminoethyl)-5-mercapto-tetrazole |
| Compound 472 | Methyl 2-amino-5-iodobenzoate | 3-(Chloromethyl)-benzoyl chloride | 3-Fluorobenzaldehyde | N,N-Diethyl-N'-methyl-ethylenediamine |
| Compound 473 | Methyl 2-amino-5-iodobenzoate | 3-(Chloromethyl)-benzoyl chloride | 4-Fluorobenzaldehyde | N,N-Diethyl-N'-methyl-ethylenediamine |
| Compound 474 | Methyl 2-amino-5-iodobenzoate | 3-(Chloromethyl)-benzoyl chloride | m-Tolualdehyde | N,N-Diethyl-N'-methyl-ethylenediamine |
| Compound 475 | Methyl 2-amino-5-iodobenzoate | 3-(Chloromethyl)-benzoyl chloride | p-Tolualdehyde | N,N-Diethyl-N'-methyl-ethylenediamine |
| Compound 476 | Methyl 2-amino-5-iodobenzoate | 3-(Chloromethyl)-benzoyl chloride | 3,4-Dimethylbenzaldehyde | N,N-Diethyl-N'-methyl-ethylenediamine |

TABLE 1-continued

| | A | B | C | B' |
|---|---|---|---|---|
| Compound 477 | Methyl 2-amino-5-iodobenzoate | 3-(Chloromethyl)-benzoyl chloride | 4-Chloro-3-trifluoromethylbenzaldehyde | N,N-Diethyl-N'-methyl-ethylenediamine |
| Compound 478 | Methyl 2-amino-5-iodobenzoate | 3-(Chloromethyl)-benzoyl chloride | 3-Methoxybenzaldehyde | N,N-Diethyl-N'-methyl-ethylenediamine |
| Compound 479 | Methyl 2-amino-5-iodobenzoate | 3-(Chloromethyl)-benzoyl chloride | 4-Methoxybenzaldehyde | N,N-Diethyl N'-methyl-ethylenediamine |
| Compound 480 | Methyl 2-amino-5-iodobenzoate | 3-(Chloromethyl)-benzoyl chloride | 3-Hydroxybenzaldehyde | N,N-Diethyl-N'-methyl-ethylenediamine |
| Compound 481 | Methyl 2-amino-5-iodobenzoate | 3-(Chloromethyl)-benzoyl chloride | 4-Hydroxybenzaldehyde | N,N-Diethyl-N'-methyl-ethylenediamine |
| Compound 482 | Methyl 2-amino-5-iodobenzoate | 3-(Chloromethyl)-benzoyl chloride | 3-Fluorobenzaldehyde | 4-Piperidino-piperidine |
| Compound 483 | Methyl 2-amino-5-iodobenzoate | 3-(Chloromethyl)-benzoyl chloride | 4-Fluorobenzaldehyde | 4-Piperidino-piperidine |
| Compound 484 | Methyl 2-amino-5-iodobenzoate | 3-(Chloromethyl)-benzoyl chloride | m-Tolualdehyde | 4-Piperidino-piperidine |
| Compound 485 | Methyl 2-amino-5-iodobenzoate | 3-(Chloromethyl)-benzoyl chloride | p-Tolualdehyde | 4-Piperidino-piperidine |
| Compound 486 | Methyl 2-amino-5-iodobenzoate | 3-(Chloromethyl)-benzoyl chloride | 3,4-Dimethylbenzaldehyde | 4-Piperidino-piperidine |
| Compound 487 | Methyl 2-amino-5-iodobenzoate | 3-(Chloromethyl)-benzoyl chloride | 4-Chloro-3-trifluoromethylbenzaldehyde | 4-Piperidino-piperidine |
| Compound 488 | Methyl 2-amino-5-iodobenzoate | 3-(Chloromethyl)-benzoyl chloride | 3-Methoxybenzaldehyde | 4-Piperidino-piperidine |
| Compound 489 | Methyl 2-amino-5-iodobenzoate | 3-(Chloromethyl)-benzoyl chloride | 4-Methoxybenzaldehyde | 4-Piperidino-piperidine |
| Compound 490 | Methyl 2-amino-5-iodobenzoate | 3-(Chloromethyl)-benzoyl chloride | 3-Hydroxybenzaldehyde | 4-Piperidino-piperidine |
| Compound 491 | Methyl 2-amino-5-iodobenzoate | 3-(Chloromethyl)-benzoyl chloride | 4-Hydroxybenzaldehyde | 4-Piperidino-piperidine |
| Compound 492 | Methyl 2-amino-5-chlorobenzoate | 3-(Chloromethyl)-benzoyl chloride | 3,4-Dimethylbenzaldehyde | 2-Mercapto-ethanol |
| Compound 493 | Methyl 2-amino-5-chlorobenzoate | 3-(Chloromethyl)-benzoyl chloride | 3,4-Dimethylbenzaldehyde | 2-Mercapto-ethanol |
| Compound 494 | Methyl 2-amino-5-bromobenzoate | 4-Methylbenzoyl chloride | p-Tolualdehyde | |
| Compound 495 | Methyl 2-amino-5-bromobenzoate | Picolinoyl chloride hydrochloride | 3-Fluorobenzaldehyde | |
| Compound 496 | Methyl 2-amino-5-bromobenzoate | Picolinoyl chloride hydrochloride | 4-Fluorobenzaldehyde | |
| Compound 497 | Methyl 2-amino-5-bromobenzoate | Picolinoyl chloride hydrochloride | m-Tolualdehyde | |
| Compound 498 | Methyl 2-amino-5-bromobenzoate | Picolinoyl chloride hydrochloride | p-Tolualdehyde | |
| Compound 499 | Methyl 2-amino-5-bromobenzoate | Picolinoyl chloride hydrochloride | 3,4-Dimethylbenzaldehyde | |
| Compound 500 | Methyl 2-amino-5-bromobenzoate | Picolinoyl chloride hydrochloride | 4-Chloro-3-trifluoromethylbenzaldehyde | |
| Compound 501 | Methyl 2-amino-5-bromobenzoate | 4-Ethoxybenzoyl chloride | 3-Fluorobenzaldehyde | |
| Compound 502 | Methyl 2-amino-5-bromobenzoate | 4-Ethoxybenzoyl chloride | 4-Fluorobenzaldehyde | |
| Compound 503 | Methyl 2-amino-5-bromobenzoate | 4-Ethoxybenzoyl chloride | p-Tolualdehyde | |
| Compound 504 | Methyl 2-amino-5-bromobenzoate | 4-Ethoxybenzoyl chloride | 3,4-Dimethylbenzaldehyde | |
| Compound 505 | Methyl 2-aminobenzoate | Picolinoyl chloride hydrochloride | 3-Fluorobenzaldehyde | |
| Compound 506 | Methyl 2-aminobenzoate | Picolinoyl chloride hydrochloride | 4-Fluorobenzaldehyde | |
| Compound 507 | Methyl 2-aminobenzoate | Picolinoyl chloride hydrochloride | 3,4-Dimethylbenzaldehyde | |
| Compound 508 | Methyl 2-aminobenzoate | Picolinoyl chloride hydrochloride | 4-Chloro-3-trifluoromethylbenzaldehyde | |
| Compound 509 | Methyl 2-amino-5-bromobenzoate | Cyclohexane-carbonyl chloride | 3-Fluorobenzaldehyde | |
| Compound 510 | Methyl 2-amino-5-bromobenzoate | Isoxazole-5-carbonyl chloride | 3-Fluorobenzaldehyde | |
| Compound 511 | Methyl 2-amino-5-bromobenzoate | Isoxazole-5-carbonyl chloride | m-Tolualdehyde | |
| Compound 512 | Methyl 2-amino-5-bromobenzoate | Isoxazole-5-carbonyl chloride | 3,4-Dimethylbenzaldehyde | |

TABLE 1-continued

| | A | B | C | B' |
|---|---|---|---|---|
| Compound 513 | Methyl 2-amino-5-bromobenzoate | Isoxazole-5-carbonyl chloride | 4-Chloro-3-trifluoromethylbenzaldehyde | |
| Compound 514 | Methyl 2-aminobenzoate | 2,5-Dimethylfuran-3-carbonyl chloride | 3-Fluorobenzaldehyde | |
| Compound 515 | Methyl 2-aminobenzoate | 2,5-Dimethylfuran-3-carbonyl chloride | 4-Fluorobenzaldehyde | |
| Compound 516 | Methyl 2-aminobenzoate | 2,5-Dimethylfuran-3-carbonyl chloride | m-Tolualdehyde | |
| Compound 517 | Ethyl 2-amino-4-methylthiophene-3-carboxylate | 3,4-Dimethoxybenzoyl chloride | 3-Fluorobenzaldehyde | |
| Compound 518 | Ethyl 2-amino-4-methylthiophene-3-carboxylate | 3,4-Dimethoxybenzoyl chloride | m-Tolualdehyde | |
| Compound 519 | Ethyl 2-amino-4-methylthiophene-3-carboxylate | 3,4-Dimethoxybenzoyl chloride | p-Tolualdehyde | |
| Vacant number Compound 521 | Ethyl 2-amino-4-methylthiophene-3-carboxylate | 3,4-Dimethoxybenzoyl chloride | 3,4-Dimethylbenzaldehyde | |
| Compound 522 | Ethyl 2-amino-4-methylthiophene-3-carboxylate | 3,4-Dimethoxybenzoyl chloride | 4-Chloro-3-trifluoromethylbenzaldehyde | |
| Compound 523 | Methyl 3-amino-4-methylthiophene-2-carboxylate | 3-(Chloromethyl)-benzoyl chloride | 3,4-Dimethylbenzaldehyde | 3-Mercapto-1,2,4-triazole |
| Compound 524 | Methyl 3-amino-4-methylthiophene-2-carboxylate | 3-(Chloromethyl)-benzoyl chloride | 3-Fluorobenzaldehyde | 3-Mercapto-1,2,4-triazole |
| Compound 525 | Methyl 3-amino-4-methylthiophene-2-carboxylate | 3-(Chloromethyl)-benzoyl chloride | 3,4-Dimethylbenzaldehyde | 3-Mercapto-1-propanol |
| Compound 526 | Methyl 3-amino-4-methylthiophene-2-carboxylate | 3-(chloromethyl)-benzoyl chloride | p-Tolualdehyde | 3-Mercapto-1-propanol |
| Compound 527 | Methyl 3-amino-4-methylthiophene-2-carboxylate | 3-(Chloromethyl)-benzoyl chloride | 3-Fluorobenzaldehyde | 3-Mercapto-1-propanol |
| Compound 528 | Methyl 3-amino-4-methylthiophene-2-carboxylate | 3-(Chloromethyl)-benzoyl chloride | 3-Fluorobenzaldehyde | N,N-Diethyl-N'-methyl-ethylenediamine |
| Compound 529 | Methyl 3-amino-4-methylthiophene-2-carboxylate | 3-(Chloromethyl)-benzoyl chloride | 3-Fluorobenzaldehyde | N,N-Diethyl-N'-methyl-ethylenediamine |
| Compound 530 | Methyl 3-amino-4-methylthiophene-2-carboxylate | 3-(Chloromethyl)-benzoyl chloride | p-Methoxybenzaldehyde | N,N-Diethyl-N'-methyl-ethylenediamine |
| Compound 531 | Methyl 3-amino-4-methylthiophene-2-carboxylate | 3-(Chloromethyl)-benzoyl chloride | p-Methoxybenzaldehyde | 4-Piperidino-piperidine |
| Compound 532 | Methyl 3-amino-4-methylthiophene-2-carboxylate | 3-(Chloromethyl)-benzoyl chloride | 3,4-Dimethylbenzaldehyde | 1-(2-Hydroxyethyl)-piperazine |
| Compound 533 | Methyl 3-amino-4-methylthiophene-2-carboxylate | 3-(Chloromethyl)-benzoyl chloride | p-Tolualdehyde | 1-(2-Hydroxyethyl)-piperazine |
| Compound 534 | Methyl 3-amino-4-methylthiophene-2-carboxylate | 3-(Chloromethyl)-benzoyl chloride | 4-Fluorobenzaldehyde | 1-(2-Hydroxyethyl) piperazine |
| Compound 535 | Methyl 3-amino-4-methylthiophene-2-carboxylate | 3-(Chloromethyl)-benzoyl chloride | 3-Fluorobenzaldehyde | 1-(2-Hydroxyethyl) piperazine |
| Compound 536 | Methyl 3-amino-4-methylthiophene-2-carboxylate | 3-(Chloromethyl)-benzoyl chloride | 3,4-Dimethylbenzaldehyde | N,N-Diethyl-ethylenediamine |
| Compound 537 | Methyl 3-amino-4-methylthiophene-2-carboxylate | 3-(Chloromethyl)-benzoyl chloride | p-Tolualdehyde | N,N-Diethyl-ethylenediamine |
| Compound 538 | Methyl 3-amino-4-methylthiophene-2-carboxylate | 3-(Chloromethyl)-benzoyl chloride | 3-Fluorobenzaldehyde | N,N-Diethyl-ethylenediamine |
| Compound 539 | Methyl 3-amino-4-methylthiophene-2-carboxylate | 3-(Chloromethyl)-benzoyl chloride | 4-Chloro-3-trifluoromethylbenzaldehyde | N,N-Diethyl-ethylenediamine |

TABLE 1-continued

| | A | B | C | B' |
|---|---|---|---|---|
| Compound 540 | Methyl 3-amino-4-methylthiophene-2-carboxylate | 3-(Chloromethyl)-benzoyl chloride | p-Tolualdehyde | Diisopropanolamine |
| Compound 541 | Methyl 3-amino-4-methylthiophene-2-carboxylate | 3-(Chloromethyl)-benzoyl chloride | 3,4-Dimethylbenzaldehyde | 4-Hydroxypiperidine |
| Compound 542 | Methyl 3-amino-4-methylthiophene-2-carboxylate | 3-(Chloromethyl)-benzoyl chloride | 3-Fluorobenzaldehyde | 4-Hydroxypiperidine |
| Compound 543 | Methyl 3-amino-4-methylthiophene-2-carboxylate | 3-(Chloromethyl)-benzoyl chloride | p-Methoxybenzaldehyde | 4-Hydroxypiperidine |
| Compound 544 | Methyl 2-amino-5-bromobenzoate | Picolinoyl chloride hydrochloride | p-Tolualdehyde | |
| Compound 545 | Methyl 2-aminobenzoate | Isonicotinoyl chloride hydrochloride | p-Tolualdehyde | |
| Compound 546 | Methyl 2-amino-5-bromobenzoate | 3-(Chloromethyl)-benzoyl chloride | 4-Chloro-3-trifluoromethylbenzaldehyde | 2-Mercapto-ethanol |
| Compound 547 | Methyl 2-amino-5-chlorobenzoate | 3-(Chloromethyl)-benzoyl chloride | p-Tolualdehyde | 2-Mercapto-ethanol |
| Compound 548 | Methyl 2-amino-5-bromobenzoate | 3,4-Dimethoxybenzoyl chloride | 3,4-Dimethylbenzaldehyde | |
| Compound 549 | Methyl 2-amino-5-chlorobenzoate | 3-(Chloromethyl)-benzoyl chloride | 3-Fluorobenzaldehyde | Diethanolamine |
| Compound 550 | Methyl 2-amino-5-chlorobenzoate | 3-(Chloromethyl)-benzoyl chloride | 4-Fluorobenaldehyde | Diethanolamine |
| Compound 551 | Ethyl 2-amino-4-methylthiophene-3-carboxylate | 3-(Chloromethyl)-benzoyl chloride | 3,4-Dimethylbenzaldehyde | 3-Mercapto-1,2,4-triazole |
| Compound 552 | Ethyl 2-amino-4-methylthiophene-3-carboxylate | 3-(Chloromethyl)-benzoyl chloride | p-Tolualdehyde | 3-Mercapto-1,2,4-triazole |
| Compound 553 | Ethyl 2-amino-4-methylthiophene-3-carboxylate | 3-(Chloromethyl)-benzoyl chloride | 4-Fluorobenzaldehyde | 3-Mercapto-1,2,4-triazole |
| Compound 554 | Ethyl 2-amino-4-methylthiophene-3-carboxylate | 3-(Chloromethyl)-benzoyl chloride | 3-Fluorobenzaldehyde | 3-Mercapto-1,2,4-triazole |
| Compound 555 | Ethyl 2-amino-4-methylthiophene-3-carboxylate | 3-(Chloromethyl)-benzoyl chloride | 4-Chloro-3-trifluoromethylbenzaldehyde | 3-Mercapto-1,2,4-triazole |
| Compound 556 | Ethyl 2-amino-4-methylthiophene-3-carboxylate | 3-(Chloromethyl)-benzoyl chloride | p-Methoxybenzaldehyde | 3-Mercapto-1,2,4-triazole |
| Compound 557 | Ethyl 2-amino-4-methylthiophene-3-carboxylate | 3-(Chloromethyl)-benzoyl chloride | 3,4-Dimethylbenzaldehyde | 3-Mercapto-1-propanol |
| Compound 558 | Ethyl 2-amino-4-methylthiophene-3-carboxylate | 3-(Chloromethyl)-benzoyl chloride | p-Tolualdehyde | 3-Mercapto-1-propanol |
| Compound 559 | Ethyl 2-amino-4-methylthiophene-3-carboxylate | 3-(Chloromethyl)-benzoyl chloride | 4-Fluorobenzaldehyde | 3-Mercapto-1-propanol |
| Compound 560 | Ethyl 2-amino-4-methylthiophene-3-carboxylate | 3-(Chloromethyl)-benzoyl chloride | 3-Fluorobenzaldehyde | 3-Mercapto-1-propanol |
| Compound 561 | Ethyl 2-amino-4-methylthiophene-3-carboxylate | 3-(Chloromethyl)-benzoyl chloride | 4-Chloro-3-trifluoromethylbenzaldehyde | 3-Mercapto-1-propanol |
| Compound 562 | Ethyl 2-amino-4-methylthiophene-3-carboxylate | 3-(Chloromethyl)-benzoyl chloride | p-Methoxybenzaldehyde | 3-Mercapto-1-propanol |
| Compound 563 | Ethyl 2-amino-4-methylthiophene-3-carboxylate | 3-(Chloromethyl)-benzoyl chloride | 3,4-Dimethylbenzaldehyde | N,N-Diethyl-N'-methylethylenediamine |
| Compound 564 | Ethyl 2-amino-4-methylthiophene-3-carboxylate | 3-(Chloromethyl)-benzoyl chloride | p-Tolualdehyde | N,N-Diethyl-N'-methylethylenediamine |
| Compound 565 | Ethyl 2-amino-4-methylthiophene-3-carboxylate | 3-(Chloromethyl)-benzoyl chloride | 4-Fluorobenzaldehyde | N,N-Diethyl-N'-methylethylenediamine |
| Compound 566 | Ethyl 2-amino-4-methylthiophene-3-carboxylate | 3-(Chloromethyl)-benzoyl chloride | 3-Fluorobenzaldehyde | N,N-Diethyl-N'-methylethylenediamine |
| Compound 567 | Ethyl 2-amino-4-methylthiophene-3-carboxylate | 3-(Chloromethyl)-benzoyl chloride | 4-Chloro-3-trifluoromethylbenzaldehyde | N,N-Diethyl-N'-methylethylenediamine |

TABLE 1-continued

| | A | B | C | B' |
|---|---|---|---|---|
| Compound 568 | Ethyl 2-amino-4-methylthiophene-3-carboxylate | 3-(Chloromethyl)-benzoyl chloride | p-Methoxybenzaldehyde | N,N-Diethyl-N'-methylethylenediamine |
| Compound 569 | Ethyl 2-amino-4-methylthiophene-3-carboxylate | 3-(Chloromethyl)-benzoyl chloride | 3,4-Dimethylbenzaldehyde | 4-Piperidino-piperidine |
| Compound 570 | Ethyl 2-amino-4-methylthiophene-3-carboxylate | 3-(Chloromethyl)-benzoyl chloride | p-Tolualdehyde | 4-Piperidino-piperidine |
| Compound 571 | Ethyl 2-amino-4-methylthiophene-3-carboxylate | 3-(Chloromethyl)-benzoyl chloride | 4-Fluorobenzaldehyde | 4-Piperidino-piperidine |
| Compound 572 | Ethyl 2-amino-4-methylthiophene-3-carboxylate | 3-(Chloromethyl)-benzoyl chloride | 3-Fluorobenzaldehyde | 4-Pipendino-piperidine |
| Compound 573 | Ethyl 2-amino-4-methylthiophene-3-carboxylate | 3-(Chloromethyl)-benzoyl chloride | 4-Chloro-3-trifluoromethylbenzaldehyde | 4-Piperidino-piperidine |
| Compound 574 | Ethyl 2-amino-4-methylthiophene-3-carboxylate | 3-(Chloromethyl)-benzoyl chloride | p-Methoxybenzaldehyde | 4-Piperidino-piperidine |
| Compound 575 | Ethyl 2-amino-4-methylthiophene-3-carboxylate | 3-(Chloromethyl)-benzoyl chloride | 3,4-Dimethylbenzaldehyde | 1-(2-Hydroxyethyl)-piperazine |
| Compound 576 | Ethyl 2-amino-4-methylthiophene-3-carboxylate | 3-(Chloromethyl)-benzoyl chloride | p-Tolualdehyde | 1-(2-Hydroxyethyl)-piperazine |
| Compound 577 | Ethyl 2-amino-4-methylthiophene-3-carboxylate | 3-(Chloromethyl)-benzoyl chloride | 4-Fluorobenzaldehyde | 1-(2-Hydroxyethyl)-piperazine |
| Compound 578 | Ethyl 2-amino-4-methylthiophene-3-carboxylate | 3-(Chloromethyl)-benzoyl chloride | 3-Fluorobenzaldehyde | 1-(2-Hydroxyethyl)-piperazine |
| Compound 579 | Ethyl 2-amino-4-methylthiophene-3-carboxylate | 3-(Chloromethyl)-benzoyl chloride | 4-Chloro-3-trifluoromethylbenzaldehyde | 1-(2-Hydroxyethyl)-piperazine |
| Compound 580 | Ethyl 2-amino-4-methylthiophene-3-carboxylate | 3-(Chloromethyl)-benzoyl chloride | p-Methoxybenzaldehyde | 1-(2-Hydroxyethyl)-piperazine |
| Compound 581 | Ethyl 2-amino-4-methylthiophene-3-carboxylate | 3-(Chloromethyl)-benzoyl chloride | 3,4-Dimethylbenzaldehyde | N,N-Diethylethylenediamine |
| Compound 582 | Ethyl 2-amino-4-methylthiophene-3-carboxylate | 3-(Chloromethyl)-benzoyl chloride | p-Tolualdehyde | N,N-Diethylethylenediamine |
| Compound 583 | Ethyl 2-amino-4-methylthiophene-3-carboxylate | 3-(Chloromethyl)-benzoyl chloride | 4-Fluorobenzaldehyde | N,N-Diethylethylenediamine |
| Compound 584 | Ethyl 2-amino-4-methylthiophene-3-carboxylate | 3-(Chloromethyl)-benzoyl chloride | 3-Fluorobenzaldehyde | N,N-Diethylethylenediamine |
| Compound 585 | Ethyl 2-amino-4-methylthiophene-3-carboxylate | 3-(Chloromethyl)-benzoyl chloride | 4-Chloro-3-trifluoromethylbenzaldehyde | N,N-Diethyl-ethylenediamine |
| Compound 586 | Ethyl 2-amino-4-methylthiophene-3-carboxylate | 3-(Chloromethyl)-benzoyl chloride | p-Methoxybenzaldehyde | N,N-Diethyl-ethylenediamine |
| Compound 587 | Ethyl 2-amino-4-methylthiophene-3-carboxylate | 3-(Chloromethyl)-benzoyl chloride | 3,4-Dimethylbenzaldehyde | Diisopropanolamine |
| Compound 588 | Ethyl 2-amino-4-methylthiophene-3-carboxylate | 3-(Chloromethyl)-benzoyl chloride | p-Tolualdehyde | Diisopropanolamine |
| Compound 589 | Ethyl 2-amino-4-methylthiophene-3-carboxylate | 3-(Chloromethyl)-benzoyl chloride | 4-Fluorobenzaldehyde | Diisopropanolamine |
| Compound 590 | Ethyl 2-amino-4-methylthiophene-3-carboxylate | 3-(Chloromethyl)-benzoyl chloride | 3-Fluorobenzaldehyde | Diisopropanolamine |
| Compound 591 | Ethyl 2-amino-4-methylthiophene-3-carboxylate | 3-(Chloromethyl)-benzoyl chloride | 4-Chloro-3-trifluoromethylbenzaldehyde | Diisopropanolamine |
| Compound 592 | Ethyl 2-amino-4-methylthiophene-3-carboxylate | 3-(Chloromethyl)-benzoyl chloride | p-Methoxybenzaldehyde | Diisopropanolamine |
| Compound 593 | Ethyl 2-amino-4-methylthiophene-3-carboxylate | 3-(Chloromethyl)-benzoyl chloride | 3,4-Dimethylbenzaldehyde | 4-Hydroxypiperidine |

TABLE 1-continued

| | A | B | C | B' |
|---|---|---|---|---|
| Compound 594 | Ethyl 2-amino-4-methylthiophene-3-carboxylate | 3-(Chloromethyl)-benzoyl chloride | p-Tolualdehyde | 4-Hydroxypiperidine |
| Compound 595 | Ethyl 2-amino-4-methylthiophene-3-carboxylate | 3-(Chloromethyl)-benzoyl chloride | 4-Fluorobenzaldehyde | 4-Hydroxypiperidine |
| Compound 596 | Ethyl 2-amino-4-methylthiophene-3-carboxylate | 3-(Chloromethyl)-benzoyl chloride | 3-Fluorobenzaldehyde | 4-Hydroxypiperidine |
| Compound 597 | Ethyl 2-amino-4-methylthiophene-3-carboxylate | 3-(Chloromethyl)-benzoyl chloride | 4-Chloro-3-trifluoromethylbenzaldehyde | 4-Hydroxypiperidine |
| Compound 598 | Ethyl 2-amino-4-methylthiophene-3-carboxylate | 3-(Chloromethyl)-benzoyl chloride | p-Methoxybenzaldehyde | 4-Hydroxypiperidine |
| Compound 599 | Ethyl 2-amino-4-methylthiophene-3-carboxylate | 3-(Chloromethyl)-benzoyl chloride | 3,4-Dimethylbenzaldehyde | 4-Piperidine-methanol |
| Compound 600 | Ethyl 2-amino-4-methylthiophene-3-carboxylate | 3-(Chloromethyl)-benzoyl chloride | p-Tolualdehyde | 4-Piperidine-methanol |
| Compound 601 | Ethyl 2-amino-4-methylthiophene-3-carboxylate | 3-(Chloromethyl)-benzoyl chloride | 4-Fluorobenzaldehyde | 4-Piperidine-methanol |
| Compound 602 | Ethyl 2-amino-4-methylthiophene-3-carboxylate | 3-(Chloromethyl)-benzoyl chloride | 3-Fluorobenzaldehyde | 4-Piperidine-methanol |
| Compound 603 | Ethyl 2-amino-4-methylthiophene-3-carboxylate | 3-(Chloromethyl)-benzoyl chloride | 4-Chloro-3-trifluoromethylbenzaldehyde | 4-Piperidine-methanol |
| Compound 604 | Ethyl 2-amino-4-methylthiophene-3-carboxylate | 3-(Chloromethyl)-benzoyl chloride | p-Methoxybenzaldehyde | 4-Piperidine-methanol |
| Compound 605 | 2-Amino-4,5,6,7-tetra-hydrobenzothiophene-3-carboxylic acid ethyl ester | 3-(Chloromethyl)-benzoyl chloride | 3,4-Dimethylbenzaldehyde | 3-Mercapto-1-propanol |
| Compound 606 | 2-Amino-4,5,6,7-tetra-hydrobenzothiophene-3-carboxylic acid ethyl ester | 3-(Chloromethyl)-benzoyl chloride | 4-Fluorobenzaldehyde | 3-Mercapto-1-propanol |
| Compound 607 | 2-Amino-4,5,6,7-tetra-hydrobenzothiophene-3-carboxylic acid ethyl ester | 3-(Chloromethyl)-benzoyl chloride | 3-Fluorobenzaldehyde | 3-Mercapto-1-propanol |
| Compound 608 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | 3-Mercapto-1-propanol |
| Compound 609 | 2-Amino-4,5,6,7-tetra-hydrobenzothiophene-3-carboxylic acid ethyl ester | 3-(Chloromethyl)-benzoyl chloride | 3,4-Dimethylbenzaldehyde | N,N-Diethyl-N'-methylethylenediamine |
| Compound 610 | 2-Amino-4,5,6,7-tetra-hydrobenzothiophene-3-carboxylic acid ethyl ester | 3-(Chloromethyl)-benzoyl chloride | p-Tolualdehyde | N,N-Diethyl-N'-methylethylenediamine |
| Compound 611 | 2-Amino-4,5,6,7-tetra-hydrobenzothiophene-3-carboxylic acid ethyl ester | 3-(Chloromethyl)-benzoyl chloride | 4-Fluorobenzaldehyde | N,N-Diethyl-N'-methylethylenediamine |
| Compound 612 | 2-Amino-4,5,6,7-tetra-hydrobenzothiophene-3-carboxylic acid ethyl ester | 3-(Chloromethyl)-benzoyl chloride | 3-Fluorobenzaldehyde | N,N-Diethyl-N'-methylethylenediamine |
| Compound 613 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | N,N-Diethyl-N'-methylethylenediamine |
| Compound 614 | 2-Amino-4,5,6,7-tetra-hydrobenzothiophene-3-carboxylic acid ethyl ester | 3-(Chloromethyl)-benzoyl chloride | p-Methoxybenzaldehyde | N,N-Diethyl-N'-methylethylenediamine |
| Compound 615 | 2-Amino-4,5,6,7-tetra-hydrobenzothiophene-3-carboxylic acid ethyl ester | 3-(Chloromethyl)-benzoyl chloride | 3,4-Dimethylbenzaldehyde | 4-Piperidino-piperidine |

TABLE 1-continued

| | A | B | C | B' |
|---|---|---|---|---|
| Compound 616 | 2-Amino-4,5,6,7-tetra-hydrobenzothiophene-3-carboxylic acid ethyl ester | 3-(Chloromethyl)-benzoyl chloride | p-Tolualdehyde | 4-Piperidino-piperidine |
| Compound 617 | 2-Amino-4,5,6,7-tetra-hydrobenzothiophene-3-carboxylic acid ethyl ester | 3-(Chloromethyl)-benzoyl chloride | 4-Fluorobenzaldehyde | 4-Piperidino-piperidine |
| Compound 618 | 2-Amino-4,5,6,7-tetra-hydrobenzothiophene-3-carboxylic acid ethyl ester | 3-(Chloromethyl)-benzoyl chloride | 3-Fluorobenzaldehyde | 4-Piperidino-piperidine |
| Compound 619 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | 4-Piperidino-piperidine |
| Compound 620 | 2-Amino-4,5,6,7-tetra-hydrobenzothiophene-3-carboxlic acid ethyl ester | 3-(Chloromethyl)-benzoyl chloride | p-Methoxybenzaldehyde | 4-Piperidino-piperidine |
| Compound 621 | 2-Amino-4,5,6,7-tetra-hydrobenzothiophene-3-carboxylic acid ethyl ester | 3-(Chloromethyl)-benzoyl chloride | 3,4-Dimethylbenzaldehyde | 4-Piperazine-ethanol |
| Compound 622 | 2-Amino-4,5,6,7-tetra-hydrobenzothiophene-3-carboxylic acid ethyl ester | 3-(Chloromethyl)-benzoyl chloride | p-Tolualdehyde | 4-Piperazine-ethanol |
| Compound 623 | 2-Amino-4,5,6,7-tetra-hydrobenzothiophene-3-carboxylic acid ethyl ester | 3-(Chloromethyl)-benzoyl chloride | 4-Fluorobenzaldehyde | 4-Piperazine-ethanol |
| Compound 624 | 2-Amino-4,5,6,7-tetra-hydrobenzothiophene-3-carboxylic acid ethyl ester | 3-(Chloromethyl)-benzoyl chloride | 3-Fluorobenzaldehyde | 4-Piperazine-ethanol |
| Compound 625 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | 4-Piperazine-ethanol |
| Compound 626 | 2-Amino-4,5,6,7-tetra-hydrobenzothiophene-3-carboxylic acid ethyl ester | 3-(Chloromethyl)-benzoyl chloride | p-Methoxybenzaldehyde | 4-Piperazine-ethanol |
| Compound 627 | 2-Amino-4,5,6,7-tetra-hydrobenzothiophene-3-carboxylic acid ethyl ester | 3-(Chloromethyl)-benzoyl chloride | 3,4-Dimethylbenzaldehyde | Diisopropanolamine |
| Compound 628 | 2-Amino-4,5,6,7-tetra-hydrobenzothiophene-3-carboxylic acid ethyl ester | 3-(Chloromethyl)-benzoyl chloride | p-Tolualdehyde | Diisopropanolamine |
| Compound 629 | 2-Amino-4,5,6,7-tetra-hydrobenzothiophene-3-carboxylic acid ethyl ester | 3-(Chloromethyl)-benzoyl chloride | 4-Fluorobenzaldehyde | Diisopropanolamine |
| Compound 630 | 2-Amino-4,5,6,7-tetra-hydrobenzothiophene-3-carboxylic acid ethyl ester | 3-(Chloromethyl)-benzoyl chloride | 3-Fluorobenzaldehyde | Diisopropanolamine |
| Compound 631 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | Diisopropanolamine |
| Compound 632 | 2-Amino-4,5,6,7-tetra-hydrobenzothiophene-3-carboxylic acid ethyl ester | 3-(Chloromethyl)-benzoyl chloride | p-Methoxybenzaldehyde | Diisopropanolamine |
| Compound 633 | 2-Amino-4,5,6,7-tetra-hydrobenzothiophene-3-carboxylic acid ethyl ester | 3-(Chloromethyl)-benzoyl chloride | 3,4-Dimethylbenzaldehyde | 4-Hydroxypiperidine |
| Compound 634 | 2-Amino-4,5,6,7-tetra-hydrobenzothiophene-3-carboxylic acid ethyl ester | 3-(Chloromethyl)-benzoyl chloride | p-Tolualdehyde | 4-Hydroxypiperidine |

TABLE 1-continued

| | A | B | C | B' |
|---|---|---|---|---|
| Compound 635 | 2-Amino-4,5,6,7-tetra-hydrobenzothiophene-3-carboxylic acid ethyl ester | 3-(Chloromethyl)-benzoyl chloride | 4-Fluorobenzaldehyde | 4-Hydroxypiperidine |
| Compound 636 | 2-Amino-4,5,6,7-tetra-hydrobenzothiophene-3-carboxylic acid ethyl ester | 3-(Chloromethyl)-benzoyl chloride | 3-Fluorobenzaldehyde | 4-Hydroxypiperidine |
| Compound 637 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | 4-Hydroxypiperidine |
| Compound 638 | 2-Amino-4,5,6,7-tetra-hydrobenzothiophene-3-carboxylic acid ethyl ester | 3-(Chloromethyl)-benzoyl chloride | p-Methoxybenzaldehyde | 4-Hydroxypiperidine |
| Compound 639 | 2-Amino-4,5,6,7-tetra-hydrobenzothiophene-3-carboxylic acid ethyl ester | 3-(Chloromethyl)-benzoyl chloride | 3,4-Dimethylbenzaldehyde | 4-Piperidine-methanol |
| Compound 640 | 2-Amino-4,5,6,7-tetra-hydrobenzothiophene-3-carboxylic acid ethyl ester | 3-(Chloromethyl)-benzoyl chloride | p-Tolualdehyde | 4-Piperidine-methanol |
| Compound 641 | 2-Amino-4,5,6,7-tetra-hydrobenzothiophene-3-carboxylic acid ethyl ester | 3-(Chloromethyl)-benzoyl chloride | 4-Fluorobenzaldehyde | 4-Piperidine-methanol |
| Compound 642 | 2-Amino-4,5,6,7-tetra-hydrobenzothiophene-3-carboxylic acid ethyl ester | 3-(Chloromethyl)-benzoyl chloride | 3-Fluorobenzaldehyde | 4-Piperidine-methanol |
| Compound 643 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | 4-Piperidine-methanol |
| Compound 644 | 2-Amino-4,5,6,7-tetra-hydrobenzothiophene-3-carboxylic acid ethyl ester | 3-(Chloromethyl)-benzoyl chloride | p-Methoxybenzaldehyde | 4-Piperidine-methanol |
| Compound 645 | Ethyl 2-amino-4-methylthiophene-3-carboxylate | 3-(Chloromethyl)-benzoyl chloride | 3,4-Dimethylbenzaldehyde | 3-Mercapto-1-propanol |
| Compound 646 | 2-Amino-4,5,6,7-tetra-hydrobenzothiophene-3-carboxylic acid ethyl ester | 3-(Chloromethyl)-benzoyl chloride | 3,4-Dimethylbenzaldehyde | 3-Mercapto-1,2,4-triazole |
| Compound 647 | 2-Amino-4,5,6,7-tetra-hydrobenzothiophene-3-carboxylic acid ethyl ester | 3-(Chloromethyl)-benzoyl chloride | p-Tolualdehyde | 3-Mercapto-1,2,4-triazole |
| Compound 648 | 2-Amino-4,5,6,7-tetra-hydrobenzothiophene-3-carboxylic acid ethyl ester | 3-(Chloromethyl)-benzoyl chloride | 4-Fluorobenzaldehyde | 3-Mercapto-1,2,4-triazole |
| Compound 649 | 2-Amino-4,5,6,7-tetra-hydrobenzothiophene-3-carboxylic acid ethyl ester | 3-(Chloromethyl)-benzoyl chloride | 3-Fluorobenzaldehyde | 3-Mercapto-1,2,4-triazole |
| Compound 650 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | 3-Mercapto-1,2,4-triazole |
| Compound 651 | 2-Amino-4,5,6,7-tetra-hydrobenzothiophene-3-carboxylic acid ethyl ester | 3-(Chloromethyl)-benzoyl chloride | p-Methoxybenzaldehyde | 3-Mercapto-1,2,4-triazole |
| Compound 652 | 2-Amino-4,5,6,7-tetra-hydrobenzothiophene-3-carboxylic acid ethyl ester | 3-(Chloromethyl)-benzoyl chloride | 3,4-Dimethylbenzaldehyde | N,N-Diethyl ethylenediamine |
| Compound 653 | 2-Amino-4,5,6,7-tetra-hydrobenzothiophene-3-carboxylic acid ethyl ester | 3-(Chloromethyl)-benzoyl chloride | p-Tolualdehyde | N,N-Diethyl ethylenediamine |

TABLE 1-continued

| | A | B | C | B' |
|---|---|---|---|---|
| Compound 654 | 2-Amino-4,5,6,7-tetra-hydrobenzothiophene-3-carboxylic acid ethyl ester | 3-(Chloromethyl)-benzoyl chloride | 4-Fluorobenzaldehyde | N,N-Diethyl-ethylenediamine |
| Compound 655 | 2-Amino-4,5,6,7-tetra-hydrobenzothiophene-3-carboxylic acid ethyl ester | 3-(Chloromethyl)-benzoyl chloride | 3-Fluorobenzaldehyde | N,N-Diethyl-ethylenediamine |
| Compound 656 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | N,N-Diethyl ethylenediamine |
| Compound 657 | 2-Amino-4,5,6,7-tetra-hydrobenzothiophene-3-carboxylic acid ethyl ester | 3-(Chloromethyl)-benzoyl chloride | p-Methoxybenzaldehyde | N,N-Diethyl-ethylenediamine |
| Compound 658 | Ethyl 2-aminothiophene-3-carboxylate | 3-(Chloromethyl)-benzoyl chloride | 3,4-Dimethylbenzaldehyde | 3-Mercapto-1-propanol |
| Compound 659 | Ethyl 2-aminothiophene-3-carboxylate | 3-(Chloromethyl)-benzoyl chloride | p-Tolualdehyde | 3-Mercapto-1-propanol |
| Compound 660 | Ethyl 2-aminothiophene-3-carboxylate | 3-(Chloromethyl)-benzoyl chloride | 4-Fluorobenzaldehyde | 3-Mercapto-1-propanol |
| Compound 661 | Ethyl 2-aminothiophene-3-carboxylate | 3-(Chloromethyl)-benzoyl chloride | 3-Fluorobenzaldehyde | 3-Mercapto-1-propanol |
| Compound 662 | Ethyl 2-aminothiophene-3-carboxylate | 3-(Chloromethyl)-benzoyl chloride | 4-Chloro-3-trifluoromethylbenzaldehyde | 3-Mercapto-1-propanol |
| Compound 663 | Ethyl 2-aminothiophene-3-carboxylate | 3-(Chloromethyl)-benzoyl chloride | p-Methoxybenzaldehyde | 3-Mercapto-1-propanol |
| Compound 664 | Ethyl 2-aminothiophene-3-carboxylate | 3-(Chloromethyl)-benzoyl chloride | 3,4-Dimethylbenzaldehyde | N,N-Diethyl-N'-methyl-ethylenediamine |
| Compound 665 | Ethyl 2-aminothiophene-3-carboxylate | 3-(Chloromethyl)-benzoyl chloride | p-Tolualdehyde | N,N-Diethyl N'-methyl-ethylenediamine |
| Compound 666 | Ethyl 2-aminothiophene-3-carboxylate | 3-(Chloromethyl)-benzoyl chloride | 4-Fluorobenzaldehyde | N,N-Diethyl-N'-methyl-ethylenediamine |
| Compound 667 | Ethyl 2-aminothiophene-3-carboxylate | 3-(Chloromethyl)-benzoyl chloride | 3-Fluorobenzaldehyde | N,N-Diethyl-N'-methyl-ethylenediamine |
| Compound 668 | Ethyl 2-aminothiophene-3-carboxylate | 3-(Chloromethyl)-benzoyl chloride | 4-Chloro-3-trifluoromethylbenzaldehyde | N,N-Diethyl-N'-methyl-ethylenediamine |
| Compound 669 | Ethyl 2-aminothiophene-3-carboxylate | 3-(Chloromethyl)-benzoyl chloride | p-Methoxybenzaldehyde | N,N-Diethyl N'-methyl-ethylenediamine |
| Compound 670 | Ethyl 2-aminothiophene-3-carboxylate | 3-(Chloromethyl)-benzoyl chloride | 3,4-Dimethylbenzaldehyde | Diisopropanolamine |
| Compound 671 | Ethyl 2-aminothiophene-3-carboxylate | 3-(Chloromethyl)-benzoyl chloride | p-Tolualdehyde | Diisopropanolamine |
| Compound 672 | Ethyl 2-aminothiophene-3-carboxylate | 3-(Chloromethyl)-benzoyl chloride | 4-Fluorobenzaldehyde | Diisopropanolamine |
| Compound 673 | Ethyl 2-aminothiophene-3-carboxylate | 3-(Chloromethyl)-benzoyl chloride | 3-Fluorobenzaldehyde | Diisopropanolamine |
| Compound 674 | 2-Amino-4,5,6,7-tetra-hydrobenzothiophene-3-carboxylic acid ethyl ester | 3-(Chloromethyl)-benzoyl chloride | 4-Chloro-3-trifluoromethylbenzaldehyde | N,N-Diethyl-N'-methyl-ethylenediamine |
| Compound 675 | 2-Amino-4,5,6,7-tetra-hydrobenzothiophene-3-carboxylic acid ethyl ester | 3-(Chloromethyl)-benzoyl chloride | p-Methoxybenzaldehyde | N,N-Diethyl-N'-methyl-ethylenediamine |
| Compound 676 | Methyl 2-amino-5-bromobenzoate | 3-(Chloromethyl)-benzoyl chloride | p-Tolualdehyde | 2-Mercapto-ethanol |
| Compound 677 | Methyl 2-amino-5-bromobenzoate | 3-(Chloromethyl)-benzoyl chloride | p-Tolualdehyde | 2-Mercapto-ethanol |

TABLE 1-continued

| | A | B | C | B' |
|---|---|---|---|---|
| Compound 678 | Methyl 2-amino-5-bromobenzoate | 3-(Chloromethyl)-benzoyl chloride | 4-Chloro-3-trifluoromethylbenzaldehyde | 2-Mercapto-ethanol |
| Compound 679 | Methyl 2-amino-5-bromobenzoate | 3-(Chloromethyl)-benzoyl chloride | 4-Chloro-3-trifluoromethylbenzaldehyde | 2-Mercapto-ethanol |
| Compound 680 | Methyl 2-amino-5-chlorobenzoate | 3-(Chloromethyl)-benzoyl chloride | 3-Fluorobenzaldehyde | Furfuryl mercaptan |
| Compound 681 | Methyl 2-amino-5-chlorobenzoate | 3-(Chloromethyl)-benzoyl chloride | 4-Fluorobenzaldehyde | Furfuryl mercaptan |
| Compound 682 | Methyl 2-amino-5-chlorobenzoate | 3-(Chloromethyl)-benzoyl chloride | p-Tolualdehyde | Furfuryl mercaptan |
| Compound 683 | Methyl 2-amino-5-chlorobenzoate | 3-(Chloromethyl)-benzoyl chloride | 3,4-Dimethylbenzaldehyde | Furfuryl mercaptan |
| Compound 684 | Methyl 2-amino-5-chlorobenzoate | 3-(Chloromethyl)-benzoyl chloride | 3,4-Dimethylbenzaldehyde | N,N'-Dimethyl-1,3-propane-diamine |
| Compound 685 | Methyl 2-amino-5-chlorobenzoate | 3-(Chloromethyl)-benzoyl chloride | 3-Fluorobenzaldehyde | N,N'-Dimethyl-1,3-propane-diamine |
| Compound 686 | Methyl 2-amino-5-chlorobenzoate | 3-(Chloromethyl)-benzoyl chloride | 3,4-Dimethylbenzaldehyde | Furfuryl mercaptan |
| Compound 687 | Methyl 2-amino-5-chlorobenzoate | 3-(Chloromethyl)-benzoyl chloride | 3,4-Dimethylbenzaldehyde | Furfuryl mercaptan |
| Compound 688 | Methyl 2-amino-5-chlorobenzoate | 3-(Chloromethyl)-benzoyl chloride | 4-Chloro-3-trifluoromethylbenzaldehyde | Furfuryl mercaptan |
| Compound 689 | Methyl 2-amino-5-chlorobenzoate | 3-(Chloromethyl)-benzoyl chloride | 4-Chloro-3-trifluoromethylbenzaldehyde | Furfuryl mercaptan |
| Compound 690 | Methyl 2-amino-5-chlorobenzoate | 3-(Chloromethyl)-benzoyl chloride | 4-Chloro-3-trifluoromethylbenzaldehyde | N,N'-Dimethyl-1,6-hexane-diamine |
| Compound 691 | Methyl 2-amino-5-chlorobenzoate | 3-(Chloromethyl)-benzoyl chloride | 3-Fluorobenzaldehyde | 2-Mercapto-ethane-sulfonic acid sodium salt |
| Compound 692 | Methyl 2-amino-5-chlorobenzoate | 3-(Chloromethyl)-benzoyl chloride | m-Tolualdehyde | 2-Mercapto-ethane-sulfonic acid sodium salt |
| Compound 693 | Methyl 2-amino-5-chlorobenzoate | 3-(Chloromethyl)-benzoyl chloride | p-Tolualdehyde | 2-Mercapto-ethane-sulfonic acid sodium salt |
| Compound 694 | Methyl 2-amino-5-chlorobenzoate | 3-(Chloromethyl)-benzoyl chloride | 3,4-Dimethylbenzaldehyde | 2-Mercapto-ethane-sulfonic acid sodium salt |
| Compound 695 | Methyl 2-amino-5-bromobenzoate | 3-(Chloromethyl)-benzoyl chloride | 4-Fluorobenzaldehyde | 2-Mercapto-ethanol |
| Compound 696 | Methyl 2-amino-5-bromobenzoate | 3-(Chloromethyl)-benzoyl chloride | p-Tolualdehyde | 2-Mercapto-ethanol |
| Compound 697 | Methyl 2-amino-5-bromobenzoate | 3-(Chloromethyl)-benzoyl chloride | 3,4-Dimethylbenzaldehyde | 2-Mercapto-ethanol |
| Compound 698 | Methyl 2-amino-5-bromobenzoate | 3-(Chloromethyl)-benzoyl chloride | 4-Chloro-3-trifluoromethylbenzaldehyde | 2-Mercapto-ethanol |
| Compound 699 | Methyl 2-amino-5-chlorobenzoate | 3-(Chloromethyl)-benzoyl chloride | m-Tolualdehyde | Furfuryl mercaptan |
| Compound 700 | Methyl 2-amino-5-chlorobenzoate | 3-(Chloromethyl)-benzoyl chloride | 4-Chloro-3-trifluoromethylbenzaldehyde | Furfuryl mercaptan |
| Compound 701 | Methyl 2-amino-5-chlorobenzoate | 3-(Chloromethyl)-benzoyl chloride | 4-Fluorobenzaldehyde | N,N'-Dimethyl-1,3-propane-diamine |
| Compound 702 | Methyl 2-amino-5-chlorobenzoate | 3-(Chloromethyl)-benzoyl chloride | p-Tolualdehyde | N,N'-Dimethyl-1,3-propane-diamine |
| Compound 703 | Methyl 2-amino-5-chlorobenzoate | 3-(Chloromethyl)-benzoyl chloride | 4-Chloro-3-trifluoromethylbenzaldehyde | 2-Mercapto-ethane-sulfonic acid sodium salt |
| Compound 704 | Methyl 2-amino-5-chlorobenzoate | 3-(Chloromethyl)-benzoyl chloride | 3-Fluorobenzaldehyde | N,N'-Dimethyl-1,6-hexane-diamine |

TABLE 1-continued

| | A | B | C | B' |
|---|---|---|---|---|
| Compound 705 | Methyl 2-amino-5-chlorobenzoate | 3-(Chloromethyl)-benzoyl chloride | m-Tolualdehyde | N,N'-Dimethyl-1,6-hexane-diamine |
| Compound 706 | Methyl 2-amino-5-chlorobenzoate | 3-(Chloromethyl)-benzoyl chloride | p-Tolualdehyde | N,N'-Dimethyl-1,6-hexane-diamine |
| Compound 707 | Methyl 3-amino-4-methylthiophene-2-carboxylate | 3-(Chloromethyl)-benzoyl chloride | 4-Chloro-3-trifluoromethylbenzaldehyde | Diisopropanolamine |
| Compound 708 | Methyl 2-amino-5-chlorobenzoate | 3-(Chloromethyl)-benzoyl chloride | 4-Fluorobenzaldehyde | 2-Mercapto-ethane-sulfonic acid sodium salt |
| Compound 709 | Methyl 2-amino-5-chlorobenzoate | 3-(Chloromethyl)-benzoyl chloride | 4-Chloro-3-trifluoromethylbenzaldehyde | 2-Mercapto-ethane-sulfonic acid sodium salt |
| Compound 710 | Methyl 3-amino-4-methylthiophene-2-carboxylate | 3-(Chloromethyl)-benzoyl chloride | p-Tolualdehyde | N,N-Diethyl N'-methyl-ethylenediamine |
| Compound 711 | Methyl 3-amino-4-methylthiophene-2-carboxylate | 3-(Chloromethyl)-benzoyl chloride | 3,4-Dimethylbenzaldehyde | N,N-Diethyl-N'-methyl-ethylenediamine |
| Compound 712 | Methyl 3-amino-4-methylthiophene-2-carboxylate | 3-(Chloromethyl)-benzoyl chloride | p-Methoxybenzaldehyde | N,N-Diethyl-N'-methyl-ethylenediamine |
| Compound 713 | Methyl 2-amino-5-bromobenzoate | 4-(Chloromethyl)-benzoyl chloride | 3-Fluorobenzaldehyde | 4-(2-Aminoethyl)-morpholine |
| Compound 714 | Methyl 2-amino-5-bromobenzoate | 4-(Chloromethyl)-benzoyl chloride | 4-Chloro-3-trifluoromethylbenzaldehyde | 4-(2-Aminoethyl)-morpholine |
| Compound 715 | Methyl 2-amino-5-bromobenzoate | 4-(Chloromethyl)-benzoyl chloride | p-Methoxybenzaldehyde | 4-(2-Aminoethyl)-morpholine |
| Compound 716 | Methyl 2-amino-5-bromobenzoate | 4-(Chloromethyl)-benzoyl chloride | m-Methoxybenzaldehyde | 4-(2-Aminoethyl)-morpholine |
| Compound 717 | Methyl 2-amino-5-bromobenzoate | 4-(Chloromethyl)-benzoyl chloride | 3,4-Dimethylbenzaldehyde | 1-(4-Fluoro-phenyl)-piperazine |
| Compound 718 | Methyl 2-amino-5-bromobenzoate | 4-(Chloromethyl)-benzoyl chloride | m-Tolualdehyde | Diisopropanolamine |
| Compound 719 | Methyl 2-amino-5-bromobenzoate | 4-(Chloromethyl)-benzoyl chloride | 4-Fluorobenzaldehyde | Diisopropanolamine |
| Compound 720 | Methyl 2-amino-5-bromobenzoate | 4-(Chloromethyl)-benzoyl chloride | 3-Fluorobenzaldehyde | Diisopropanolamine |
| Compound 721 | Methyl 2-amino-5-bromobenzoate | 4-(Chloromethyl)-benzoyl chloride | 4-Chloro-3-trifluoromethylbenzaldehyde | Diisopropanolamine |
| Compound 722 | Methyl 2-amino-5-bromobenzoate | 4-(Chloromethyl)-benzoyl chloride | p-Methoxybenzaldehyde | Diisopropanolamine |
| Compound 723 | Methyl 2-amino-5-bromobenzoate | 4-(Chloromethyl)-benzoyl chloride | m-Methoxybenzaldehyde | Diisopropanolamine |
| Compound 724 | Methyl 2-amino-5-bromobenzoate | 4-(Chloromethyl)-benzoyl chloride | 3,4-Dimethylbenzaldehyde | Cineferin |
| Compound 725 | Methyl 2-amino-5-bromobenzoate | 4-(Chloromethyl)-benzoyl chloride | 3-Fluorobenzaldehyde | Cineferin |
| Compound 726 | Methyl 2-amino-5-bromobenzoate | 4-(Chloromethyl)-benzoyl chloride | 4-Chloro-3-trifluoromethylbenzaldehyde | Cineferin |
| Compound 727 | Methyl 2-amino-5-bromobenzoate | 4-(Chloromethyl)-benzoyl chloride | m-Methoxybenzaldehyde | Cineferin |
| Compound 728 | Methyl 2-amino-5-bromobenzoate | 4-(Chloromethyl)-benzoyl chloride | p-Tolualdehyde | N-(2-(1-Piperazino)acetyl)-morpholine |
| Compound 729 | Methyl 2-amino-5-bromobenzoate | 4-(Chloromethyl)-benzoyl chloride | m-Tolualdehyde | N-(2-(1-Piperazino)-acetyl)-morpholine |
| Compound 730 | Methyl 2-amino-5-bromobenzoate | 4-(Chloromethyl)-benzoyl chloride | 4-Fluorobenzaldehyde | N-(2-(1-Piperazino)-acetyl)-morpholine |
| Compound 731 | Methyl 2-amino-5-bromobenzoate | 4-(Chloromethyl)-benzoyl chloride | 3-Fluorobenzaldehyde | N-(2-(1-Piperazino)-acetyl)-morpholine |

TABLE 1-continued

| | A | B | C | B' |
|---|---|---|---|---|
| Compound 732 | Methyl 2-amino-5-bromobenzoate | 4-(Chloromethyl)-benzoyl chloride | m-Methoxybenzaldehyde | N-(2-(1-Piperazino)-acetyl) morpholine |
| Compound 733 | Methyl 2-amino-5-bromobenzoate | 4-(Chloromethyl)-benzoyl chloride | 3,4-Dimethylbenzaldehyde | Bis(2-ethoxy-ethyl)-amine |
| Compound 734 | Methyl 2-amino-5-bromobenzoate | 4-(Chloromethyl)-benzoyl chloride | p-Tolualdehyde | Bis(2-ethoxy-ethyl)-amine |
| Compound 735 | Methyl 2-amino-5-bromobenzoate | 4-(Chloromethyl)-benzoyl chloride | m-Tolualdehyde | Bis(2-ethoxy-ethyl)-amine |
| Compound 736 | Methyl 2-amino-5-bromobenzoate | 4-(Chloromethyl)-benzoyl chloride | 4-Fluorobenzaldehyde | Bis(2-ethoxy-ethyl)amine |
| Compound 737 | Methyl 2-amino-5-bromobenzoate | 4-(Chloromethyl)-benzoyl chloride | 3-Fluorobenzaldehyde | Bis(2-ethoxy-ethyl)amine |
| Compound 738 | Methyl 2-amino-5-bromobenzoate | 4-(Chloromethyl)-benzoyl chloride | 4-Chloro-3-trifluoromethylbenzaldehyde | Bis(2-ethoxy-ethyl)amine |
| Compound 739 | Methyl 2-amino-5-bromobenzoate | 4-(Chloromethyl)-benzoyl chloride | p-Methoxybenzaldehyde | Bis(2-ethoxy-ethyl)amine |
| Compound 740 | Methyl 2-amino-5-bromobenzoate | 4-(Chloromethyl)-benzoyl chloride | m-Methoxybenzaldehyde | Bis(2-ethoxy-ethyl)amine |
| Compound 741 | Methyl 2-amino-5-bromobenzoate | 4-(Chloromethyl)-benzoyl chloride | p-Tolualdehyde ethanol | 4-Piperidine-ethanol |
| Compound 742 | Methyl 2-amino-5-bromobenzoate | 4-(Chloromethyl)-benzoyl chloride | m-Tolualdehyde | 4-Piperidine-ethanol |
| Compound 743 | Methyl 2-amino-5-bromobenzoate | 4-(Chloromethyl)-benzoyl chloride | 4-Fluorobenzaldehyde | 4-Piperidine-ethanol |
| Compound 744 | Methyl 2-amino-5-bromobenzoate | 4-(Chloromethyl)-benzoyl chloride | 3-Fluorobenzaldehyde | 4-Piperidine-ethanol |
| Compound 745 | Methyl 2-amino-5-bromobenzoate | 4-(Chloromethyl)-benzoyl chloride | 4-Chloro-3-trifluoromethylbenzaldehyde | 4-Piperidine-ethanol |
| Compound 746 | Methyl 2-amino-5-bromobenzoate | 4-(Chloromethyl)-benzoyl chloride | m-Methoxybenzaldehyde | 4-Piperidine-ethanol |
| Compound 747 | Methyl 2-amino-5-bromobenzoate | 4-(Chloromethyl)-benzoyl chloride | 4-Chloro-3-trifluoromethylbenzaldehyde | 2-Morpholine-4-yl-1-phenyl-ethylamine |
| Compound 748 | Methyl 2-amino-5-bromobenzoate | 4-(Chloromethyl)-benzoyl chloride | p-Methoxybenzaldehyde | 2-Morpholine-4-yl-1-phenyl-ethylamine |
| Compound 749 | Methyl 2-amino-5-bromobenzoate | 4-(Chloromethyl)-benzoyl chloride | 3,4-Dimethylbenzaldehyde | 4-Amino-1,2-diethyl-pyrazolidine |
| Compound 750 | Methyl 2-amino-5-bromobenzoate | 4-(Chloromethyl)-benzoyl chloride | 3,4-Dimethylbenzaldehyde | 4-Amino-1,2-diethyl-pyrazolidine |
| Compound 751 | Methyl 2-amino-5-bromobenzoate | 4-(Chloromethyl)-benzoyl chloride | 3-Fluorobenzaldehyde | 4-Amino-1,2-diethyl-pyrazolidine |
| Compound 752 | Methyl 2-amino-5-bromobenzoate | 4-(Chloromethyl)-benzoyl chloride | 3-Fluorobenzaldehyde | 4-Amino-1,2-diethyl-pyrazolidine |
| Compound 753 | Methyl 2-amino-5-bromobenzoate | 4-(Chloromethyl)-benzoyl chloride | 4-Chloro-3-trifluoromethylbenzaldehyde | 4-Amino-1,2-diethyl-pyrazolidine |
| Compound 754 | Methyl 2-amino-5-bromobenzoate | 4-(Chloromethyl)-benzoyl chloride | 4-Chloro-3-trifluoromethylbenzaldehyde | 4-Amino-1,2-diethyl-pyrazolidine |
| Compound 755 | Methyl 2-amino-5-bromobenzoate | 4-(Chloromethyl)-benzoyl chloride | p-Methoxybenzaldehyde | 4-Amino-1,2-diethyl-pyrazolidine |
| Compound 756 | Methyl 2-amino-5-bromobenzoate | 4-(Chloromethyl)-benzoyl chloride | p-Methoxybenzaldehyde | 4-Amino-1,2-diethyl-pyrazolidine |
| Compound 757 | Methyl 2-amino-5-bromobenzoate | 4-(Chloromethyl)-benzoyl chloride | 3,4-Dimethylbenzaldehyde | N-(3-Amino-propyl)-N-methylaniline |
| Compound 758 | Methyl 2-amino-5-bromobenzoate | 4-(Chloromethyl)-benzoyl chloride | p-Tolualdehyde | N-(3-Amino-propyl)-N-methylaniline |
| Compound 759 | Methyl 2-amino-5-bromobenzoate | 4-(Chloromethyl)-benzoyl chloride | 4-Fluorobenzaldehyde | N-(3-Amino-propyl)-N-methylaniline |
| Compound 760 | Methyl 2-amino-5-bromobenzoate | 4-(Chloromethyl)-benzoyl chloride | 3-Fluorobenzaldehyde | N-(3-Amino-propyl)-N-methylaniline |
| Compound 761 | Methyl 2-amino-5-bromobenzoate | 4-(Chloromethyl)-benzoyl chloride | 4-Chloro-3-trifluoromethylbenzaldehyde | N-(3-Amino-propyl)-N-methylaniline |

TABLE 1-continued

| | A | B | C | B' |
|---|---|---|---|---|
| Compound 762 | Methyl 2-amino-5-bromobenzoate | 4-(Chloromethyl)-benzoyl chloride | p-Methoxybenzaldehyde | N-(3-Amino-propyl)-N-methylaniline |
| Compound 763 | Methyl 2-amino-5-bromobenzoate | 4-(Chloromethyl)-benzoyl chloride | m-Methoxybenzaldehyde | N-(3-Amino-propyl)-N-methylaniline |
| Compound 764 | Methyl 2-amino-5-bromobenzoate | 4-(Chloromethyl)-benzoyl chloride | 3,4-Dimethylbenzaldehyde | 2-(Ethylthio)-ethylamine |
| Compound 765 | Methyl 2-amino-5-bromobenzoate | 4-(Chloromethyl)-benzoyl chloride | p-Tolualdehyde | 2-(Ethylthio)-ethylamine |
| Compound 766 | Methyl 2-amino-5-bromobenzoate | 4-(Chloromethyl)-benzoyl chloride | m-Tolualdehyde | 2-(Ethylthio)-ethylamine |
| Compound 767 | Methyl 2-amino-5-bromobenzoate | 4-(Chloromethyl)-benzoyl chloride | 4-Fluorobenzaldehyde | 2-(Ethylthio)-ethylamine |
| Compound 768 | Methyl 2-amino-5-bromobenzoate | 4-(Chloromethyl)-benzoyl chloride | 3-Fluorobenzaldehyde | 2-(Ethylthio)-ethylamine |
| Compound 769 | Methyl 2-amino-5-bromobenzoate | 4-(Chloromethyl)-benzoyl chloride | 4-Chloro-3-trifluoromethylbenzaldehyde | 2-(Ethylthio)-ethylamine |
| Compound 770 | Methyl 2-amino-5-bromobenzoate | 4-(Chloromethyl)-benzoyl chloride | p-Methoxybenzaldehyde | 2-(Ethylthio)-ethylamine |
| Compound 771 | Methyl 2-amino-5-bromobenzoate | 4-(Chloromethyl)-benzoyl chloride | m-Methoxybenzaldehyde | 2-(Ethylthio)-ethylamine |
| Compound 772 | Methyl 2-amino-5-bromobenzoate | 4-(Chloromethyl)-benzoyl chloride | 3,4-Dimethylbenzaldehyde | 1-(2-Pyridyl)-piperazine |
| Compound 773 | Methyl 2-amino-5-bromobenzoate | 4-(Chloromethyl)-benzoyl chloride | pTolualdehyde | 1-(2-Pyridyl)-piperazine |
| Compound 774 | Methyl 2-amino-5-bromobenzoate | 4-(Chloromethyl)-benzoyl chloride | 4-Fluorobenzaldehyde | 1-(2-Pyridyl)-piperazine |
| Compound 775 | Methyl 2-amino-5-bromobenzoate | 4-(Chloromethyl)-benzoyl chloride | 3-Fluorobenzaldehyde | 1-(2-Pyridyl)-piperazine |
| Compound 776 | Methyl 2-amino-5-bromobenzoate | 4-(Chloromethyl)-benzoyl chloride | 4-Chloro-3-trifluoromethylbenzaldehyde | 1-(2-Pyridyl)-piperazine |
| Compound 777 | Methyl 2-amino-5-bromobenzoate | 4-(Chloromethyl)-benzoyl chloride | p-Methoxybenzaldehyde | 1-(2-Pyridyl)-piperazine |
| Compound 778 | Methyl 2-amino-5-bromobenzoate | 4-(Chloromethyl)-benzoyl chloride | m-Methoxybenzaldehyde | 1-(2-Pyridyl)-piperazine |
| Compound 779 | Ethyl 2-aminothiophene-3-carboxylate | 3-(Chloromethyl)-benzoyl chloride | 4-Chloro-3-trifluoromethylbenzaldehyde | Diisopropanolamine |
| Compound 780 | Ethyl 2-aminothiophene-3-carboxylate | 3-(Chloromethyl)-benzoyl chloride | p-Methoxybenzaldehyde | Diisopropanolamine |
| Compound 781 | Methyl 2-amino-4-methylthiophene-3-carboxylate | 3-(Chloromethyl)-benzoyl chloride | 3,4-Dimethylbenzaldehyde | 2-Mercapto-ethane-sulfonic acid |
| Compound 782 | Methyl 2-amino-4-methylthiophene-3-carboxylate | 3-(Chloromethyl)-benzoyl chloride | p-Tolualdehyde | 2-Mercapto-ethane-sulfonic acid |
| Compound 783 | Methyl 2-amino-4-methylthiophene-3-carboxylate | 3-(Chloromethyl)-benzoyl chloride | 4-Fluorobenzaldehyde | 2-Mercapto-ethane-sulfonic acid |
| Compound 784 | Methyl 2-amino-4-methylthiophene-3-carboxylate | 3-(Chloromethyl)-benzoyl chloride | 4-Chloro-3-trifluoromethylbenzaldehyde | 2-Mercapto-ethane-sulfonic acid |
| Compound 785 | Methyl 2-amino-4-methylthiophene-3-carboxylate | 3-(Chloromethyl)-benzoyl chloride | p-Methoxybenzaldehyde | 2-Mercapto-ethane-sulfonic acid |
| Compound 786 | Methyl 2-amino-4-methylthiophene-3-carboxylate | 3-(Chloromethyl)-benzoyl chloride | 3,4-Dimethylbenzaldehyde | Diethanolamine |
| Compound 787 | Methyl 2-amino-4-methylthiophene-3-carboxylate | 3-(Chloromethyl)-benzoyl chloride | p-Tolualdehyde | Diethanolamine |
| Compound 788 | Methyl 2-amino-4-methylthiophene-3-carboxylate | 3-(Chloromethyl)-benzoyl chloride | 4-Fluorobenzaldehyde | Diethanolamine |
| Compound 789 | Methyl 2-amino-4-methylthiophene-3-carboxylate | 3-(Chloromethyl)-benzoyl chloride | 3-Fluorobenzaldehyde | Diethanolamine |
| Compound 790 | Methyl 2-amino-4-methylthiophene-3-carboxylate | 3-(Chloromethyl)-benzoyl chloride | 4-Chloro-3-trifluoromethylbenzaldehyde | Diethanolamine |
| Compound 791 | Methyl 2-amino-4-methylthiophene-3-carboxylate | 3-(Chloromethyl)-benzoyl chloride | p-Methoxybenzaldehyde | Diethanolamine |
| Compound 792 | Ethyl-2-amino-benzo(B)thiophene-3-carboxylate | 3-(Chloromethyl)-benzoyl chloride | 3,4-Dimethylbenzaldehyde | Diisopropanolamine |

TABLE 1-continued

| | A | B | C | B' |
|---|---|---|---|---|
| Compound 793 | Ethyl-2-amino-benzo(B)thiophene-3-carboxylate | 3-(Chloromethyl)-benzoyl chloride | p-Tolualdehyde | Diisopropanolamine |
| Compound 794 | Ethyl-2-amino-benzo(B)thiophene-3-carboxylate | 3-(Chloromethyl)-benzoyl chloride | 4-Fluorobenzaldehyde | Diisopropanolamine |
| Compound 795 | Ethyl-2-amino-benzo(B)thiophene-3-carboxylate | 3-(Chloromethyl)-benzoyl chloride | 3-Fluorobenzaldehyde | Diisopropanolamine |
| Compound 796 | Ethyl-2-amino-benzo(B)thiophene-3-carboxylate | 3-(Chloromethyl)-benzoyl chloride | 4-Chloro-3-trifluoromethylbenzaldehyde | Diisopropanolamine |
| Compound 797 | Ethyl-2-amino-benzo(B)thiophene-3-carboxylate | 3-(Chloromethyl)-benzoyl chloride | p-Methoxybenzaldehyde | Diisopropanolamine |
| Compound 798 | Ethyl-2-amino-benzo(B)thiophene-3-carboxylate | 3-(Chloromethyl)-benzoyl chloride | 3,4-Dimethylbenzaldehyde | 4-Piperidine-methanol |
| Compound 799 | Ethyl-2-amino-benzo(B)thiophene-3-carboxylate | 3-(Chloromethyl)-benzoyl chloride | p-Tolualdehyde | 4-Piperidine-methanol |
| Compound 800 | Ethyl-2-amino-benzo(B)thiophene-3-carboxylate | 3-(Chloromethyl)-benzoyl chloride | 4-Fluorobenzaldehyde | 4-Piperidine-methanol |
| Compound 801 | Ethyl-2-amino-benzo(B)thiophene-3-carboxylate | 3-(Chloromethyl)-benzoyl chloride | 3-Fluorobenzaldehyde | 4-Piperidine-methanol |
| Compound 802 | Ethyl-2-amino-benzo(B)thiophene-3-carboxylate | 3-(Chloromethyl)-benzoyl chloride | 4-Chloro-3-trifluoromethylbenzaldehyde | 4-Piperidine-methanol |
| Compound 803 | Ethyl-2-amino-benzo(B)thiophene-3-carboxylate | 3-(Chloromethyl)-benzoyl chloride | p-Methoxybenzaldehyde | 4-Piperidine-methanol |
| Compound 804 | Ethyl-2-aminocyclopenta(B)-thiophene-3-carboxylate | 3-(Chloromethyl)-benzoyl chloride | 3,4-Dimethylbenzaldehyde | Diisopropanolamine |
| Compound 805 | Ethyl-2-aminocyclopenta(B)-thiophene-3-carboxylate | 3-(Chloromethyl)-benzoyl chloride | p-Tolualdehyde | Diisopropanolamine |
| Compound 806 | Ethyl-2-aminocyclopenta(B)-thiophene-3-carboxylate | 3-(Chloromethyl)-benzoyl chloride | 3-Fluorobenzaldehyde | Diisopropanolamine |
| Compound 807 | Ethyl-2-aminocyclopenta(B)-thiophene-3-carboxylate | 3-(Chloromethyl)-benzoyl chloride | 4-Fluorobenzaldehyde | Diisopropanolamine |
| Compound 808 | Ethyl-2-aminocyclopenta(B)-thiophene-3-carboxylate | 3-(Chloromethyl)-benzoyl chloride | 4-Chloro-3-trifluoromethylbenzaldehyde | Diisopropanolamine |
| Compound 809 | Ethyl-2-aminocyclopenta(B)-thiophene-3-carboxylate | 3-(Chloromethyl)-benzoyl chloride | p-Methoxybenzaldehyde | Diisopropanolamine |
| Compound 810 | Ethyl-2-aminocyclopenta(B)-thiophene-3-carboxylate | 3-(Chloromethyl)-benzoyl chloride | 3,4-Dimethylbenzaldehyde | N,N-Diethyl-ethylenediamine |
| Compound 811 | Ethyl-2-aminocyclopenta(B)-thiophene-3-carboxylate | 3-(Chloromethyl)-benzoyl chloride | p-Tolualdenhyde | N,N-Diethyl-ethylenediamine |
| Compound 812 | Ethyl-2-aminocyclopenta(B)-thiophene-3-carboxylate | 3-(Chloromethyl)-benzoyl chloride | 3-Fluorobenzaldehyde | N,N-Diethyl-ethylenediamine |
| Compound 813 | Ethyl-2-aminocyclopenta(B)-thiophene-3-carboxylate | 3-(Chloromethyl)-benzoyl chloride | 4-Fluorobenzaldehyde | N,N-Diethyl-ethylenediamine |
| Compound 814 | Ethyl-2-aminocyclopenta(B)-thiophene-3-carboxylate | 3-(Chloromethyl)-benzoyl chloride | 4-Chloro-3-trifluoromethylbenzaldehyde | N,N-Diethyl-ethylenediamine |

TABLE 1-continued

| | A | B | C | B' |
|---|---|---|---|---|
| Compound 815 | Ethyl-2-aminocyclopenta(B)-thiophene-3-carboxylate | 3-(Chloromethyl)-benzoyl chloride | p-Methoxybenzaldehyde | N,N-Diethyl-ethylenediamine |
| Compound 816 | Ethyl-2-aminocyclopenta(B)-thiophene-3-carboxylate | 3-(Chloromethyl)-benzoyl chloride | 3,4-Dimethylbenzaldehyde | 4-Piperidine-methanol |
| Compound 817 | Ethyl-2-aminocyclopenta(B)-thiophene-3-carboxylate | 3-(Chloromethyl)-benzoyl chloride | p-Tolualdehyde | 4-Piperidine-methanol |
| Compound 818 | Ethyl-2-aminocyclopenta(B)-thiophene-3-carboxylate | 3-(Chloromethyl)-benzoyl chloride | 4-Fluorobenzaldehyde | 4-Piperidine-methanol |
| Compound 819 | Ethyl-2-aminocyclopenta(B)-thiophene-3-carboxylate | 3-(Chloromethyl)-benzoyl chloride | 3-Fluorobenzaldehyde | 4-Piperidine-methanol |
| Compound 820 | Ethyl-2-aminocyclopenta(B)-thiophene-3-carboxylate | 3-(Chloromethyl)-benzoyl chloride | 4-Chloro-3-trifluoromethylbenzaldehyde | 4-Piperidine-methanol |
| Compound 821 | Ethyl-2-aminocyclopenta(B)-thiophene-3-carboxylate | 3-(Chloromethyl)-benzoyl chloride | p-Methoxybenzaldehyde | 4-Piperidine-methanol |
| Compound 822 | Methyl 2-amino-4-methylthiophene-3-carboxylate | 3-(Chloromethyl)-benzoyl chloride | 3,4-Dimethylbenzaldehyde | Dimethylamine hydrochloride |
| Compound 823 | Methyl 2-amino-4-methylthiophene-3-carboxylate | 3-(Chloromethyl)-benzoyl chloride | p-Tolualdehyde | Dimethylamine hydrochloride |
| Compound 824 | Methyl 2-amino-4-methylthiophene-3-carboxylate | 3-(Chloromethyl)-benzoyl chloride | 4-Chloro-3-trifluoromethylbenzaldehyde | Dimethylamine hydrochloride |
| Compound 825 | Methyl 2-amino-4-methylthiophene-3-carboxylate | 3-(Chloromethyl)-benzoyl chloride | p-Methoxybenzaldehyde | Dimethylamine hydrochloride |
| Compound 826 | Methyl 2-amino-4-methylthiophene-3-carboxylate | 3-(Chloromethyl)-benzoyl chloride | 3,4-Dimethylbenzaldehyde | 1-(2-Pyrimidyl)-piperazine |
| Compound 827 | Methyl 2-amino-4-methylthiophene-3-carboxylate | 3-(Chloromethyl)-benzoyl chloride | p-Tolualdehyde | 1-(2-Pyrimidyl)-piperazine |
| Compound 828 | Methyl 2-amino-4-methylthiophene-3-carboxylate | 3-(Chloromethyl)-benzoyl chloride | 4-Fluorobenzaldehyde | 1-(2-Pyrimidyl)-piperazine |
| Compound 829 | Methyl 2-amino-4-methylthiophene-3-carboxylate | 3-(Chloromethyl)-benzoyl chloride | 3-Fluorobenzaldehyde | 1-(2-Pyrimidyl)-piperazine |
| Compound 830 | Methyl 2-amino-4-methylthiophene-3-carboxylate | 3-(Chloromethyl)-benzoyl chloride | 4-Chloro-3-trifluoromethylbenzaldehyde | 1-(2-Pyrimidyl)-piperazine |
| Compound 831 | Methyl 2-amino-4-methylthiophene-3-carboxylate | 3-(Chloromethyl)-benzoyl chloride | p-Methoxybenzaldehyde | 1-(2-Pyrimidyl)-piperazine |
| Compound 832 | Methyl 2-amino-4-methylthiophene-3-carboxylate | 3-(Chloromethyl)-benzoyl chloride | 3,4-Dimethylbenzaldehyde | 1,4-Dioxa-8-azaspiro[4,5]decane |
| Compound 833 | Methyl 2-amino-4-methylthiophene-3-carboxylate | 3-(Chloromethyl)-benzoyl chloride | p-Tolualdehyde | 1,4-Dioxa-8-azaspiro[4,5]decane |
| Compound 834 | Methyl 2-amino-4-methylthiophene-3-carboxylate | 3-(Chloromethyl)-benzoyl chloride | 4-Fluorobenzaldehyde | 1,4-Dioxa-8-azaspiro[4,5]decane |
| Compound 835 | Methyl 2-amino-4-methylthiophene-3-carboxylate | 3-(Chloromethyl)-benzoyl chloride | 3-Fluorobenzaldehyde | 1,4-Dioxa-8-azaspiro[4,5]decane |
| Compound 836 | Methyl 2-amino-4-methylthiophene-3-carboxylate | 3-(Chloromethyl)-benzoyl chloride | 4-Chloro-3-trifluoromethylbenzaldehyde | 1,4-Dioxa-8-azaspiro[4,5]decane |
| Compound 837 | Methyl 2-amino-4-methylthiophene-3-carboxylate | 3-(Chloromethyl)-benzoyl chloride | p-Methoxybenzaldehyde | 1,4-Dioxa-8-azaspiro[4,5]decane |

TABLE 1-continued

| | A | B | C | B' |
|---|---|---|---|---|
| Compound 838 | Methyl 2-amino-4-methylthiophene-3-carboxylate | 3-(Chloromethyl)-benzoyl chloride | 3,4-Dimethylbenzaldehyde | 1,1,7,7-Tetraethyldiethylenetriamine |
| Compound 839 | Methyl 2-amino-4-methylthiophene-3 carboxylate | 3-(Chloromethyl)-benzoyl chloride | p-Tolualdehyde | 1,1,7,7-Tetraethyldiethylenetriamine |
| Compound 840 | Methyl 2-amino-4-methylthiophene-3-carboxylate | 3-(Chloromethyl)-benzoyl chloride | 4-Fluorobenzaldehyde | 1,1,7,7-Tetraethyldiethylenetriamine |
| Compound 841 | Methyl 2-amino-4-methylthiophene-3-carboxylate | 3-(Chloromethyl)-benzoyl chloride | 3-Fluorobenzaldehyde | 1,1,7,7-Tetraethyldiethylenetriamine |
| Compound 842 | Methyl 2-amino-4-methylthiophene-3-carboxylate | 3-(Chloromethyl)-benzoyl chloride | 4-Chloro-3-trifluoromethylbenzaldehyde | 1,1,7,7-Tetraethyldiethylenetriamine |
| Compound 843 | Methyl 2-amino-4-methylthiophene-3-carboxylate | 3-(Chloromethyl)-benzoyl chloride | p-Methoxybenzaldehyde | 1,1,7,7-Tetraethyldiethylenetriamine |
| Compound 844 | Ethyl 2-amino-4,5-dimethylthiophene-3-carboxylate | 3-(Chloromethyl)-benzoyl chloride | 3,4-Dimethylbenzaldehyde | Diisopropanolamine |
| Compound 845 | Ethyl 2-amino-4,5-dimethylthiophene-3-carboxylate | 3-(Chloromethyl)-benzoyl chloride | p-Tolualdehyde | Diisopropanolamine |
| Compound 846 | Ethyl 2-amino-4,5-dimethylthiophene-3-carboxylate | 3-(Chloromethyl)-benzoyl chloride | 4-Fluorobenzaldehyde | Diisopropanolamine |
| Compound 847 | Ethyl 2-amino-4,5-dimethylthiophene-3-carboxylate | 3-(Chloromethyl)-benzoyl chloride | 4-Chloro-3-trifluoromethylbenzaldehyde | Diisopropanolamine |
| Compound 848 | Ethyl 2-amino-4,5-dimethylthiophene-3-carboxylate | 3-(Chloromethyl)-benzoyl chloride | p-Methoxybenzaldehyde | Diisopropanolamine |
| Compound 849 | Ethyl 2-amino-4,5,6,7-tetrahydrobenzo(B)thiophene-3-carboxylate | 3-(Chloromethyl)-benzoyl chloride | 4-Chloro-3 trifluoromethylbenzaldehyde | 1,1,7,7-Tetraethyldiethylenetriamine |
| Compound 850 | Ethyl 2-amino-4,5,6,7-tetrahydrobenzo(B)thiophene-3-carboxylate | 3-(Chloromethyl)-benzoyl chloride | p-Methoxybenzaldehyde | 1,1,7,7-Tetraethyldiethylenetriamine |
| Compound 851 | Methyl 2-amino-4-methylthiophene-3-carboxylate | 3-(Chloromethyl)-benzoyl chloride | 4-Chloro-3-trifluoromethylbenzaldehyde | Diisopropanolamine |
| Compound 852 | Methyl 2-amino-4-methylthiophene-3-carboxylate | 3-(Chloromethyl)-benzoyl chloride | p-Methoxybenzaldehyde | Diisopropanolamine |
| Compound 853 | 2-Amino-5-fluorobenzoic acid methyl ester | 3-(Chloromethyl)-benzoyl chloride | 4-Chloro-3-trifluoromethylbenzaldehyde | Diisopropanolamine |
| Compound 854 | 2-Amino-5-fluorobenzoic acid methyl ester | 3-(Chloromethyl)-benzoyl chloride | p-Methoxybenzaldehyde | Diisopropanolamine |
| Compound 855 | Ethyl 2-amino-4,5,6,7-tetrahydrobenzo(B)thiophene-3-carboxylate | 3-(Chloromethyl)-benzoyl chloride | 4-Chloro-3-trifluoromethylbenzaldehyde | 1,1,7,7-Tetraethyldiethylenetriamine |
| Compound 856 | Ethyl 2-amino-4,5,6,7-tetrahydrobenzo(B)thiophene-3-carboxylate | 3-(Chloromethyl)-benzoyl chloride | p-Methoxybenzaldehyde | 1,1,7,7-Tetraethyldiethylenetriamine |
| Compound 857 | 2-Amino-5-fluorobenzoic acid methyl ester | 3-(Chloromethyl)-benzoyl chloride | 4-Chloro-3-trifluoromethylbenzaldehyde | Diisopropanolamine |
| Compound 858 | 2-Amino-5-piperidine-1-yl-benzoic acid methyl ester | 3-(Chloromethyl)-benzoyl chloride | 3,4-Dimethylbenzaldehyde | N,N-Diethyl-N'-methyl-ethylenediamine |
| Compound 859 | 2-Amino-5-piperidine-1-yl-benzoic acid methyl ester | 3-(Chloromethyl)-benzoyl chloride | p-Tolualdehyde | N,N-Diethyl-N'-methyl-ethylenediamine |
| Compound 860 | 2-Amino-5-piperidine-1-yl-benzoic acid methyl ester | 3-(Chloromethyl)-benzoyl chloride | 4-Fluorobenzaldehyde | N,N-Diethyl-N'-methyl-ethylenediamine |

TABLE 1-continued

| | A | B | C | B' |
|---|---|---|---|---|
| Compound 861 | 2-Amino-5-piperidine-1-yl-benzoic acid methyl ester | 3-(Chloromethyl)-benzoyl chloride | 3-Fluorobenzaldehyde | N,N-Diethyl-N'-methyl-ethylenediamine |
| Compound 862 | 2-Amino-5-piperidine-1-yl-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 863 | 2-Amino-5-piperidine-1-yl-benzoic acid methyl ester | 3-(Chloromethyl)-benzoyl chloride | p-Methoxybenzaldehyde | N,N-Diethyl-N'-methyl-ethylenediamine |
| Compound 864 | 2-Amino-5-piperidine-1-yl-benzoic acid methyl ester | 3-(Chloromethyl)-benzoyl chloride | 3,4-Dimethylbenzaldehyde | 4-Piperazine-ethanol |
| Compound 865 | 2-Amino-5-piperidine-1-yl-benzoic acid methyl ester | 3-(Chloromethyl)-benzoyl chloride | p-Tolualdehyde | 4-Piperazine-ethanol |
| Compound 866 | 2-Amino-5-piperidine-1-yl-benzoic acid methyl ester | 3-(Chloromethyl)-benzoyl chloride | 4-Fluorobenzaldehyde | 4-Piperazine-ethanol |
| Compound 867 | 2-Amino-5-piperidine-1-yl-benzoic acid methyl ester | 3-(Chloromethyl)-benzoyl chloride | 3-Fluorobenzaldehyde | 4-Piperazine-ethanol |
| Compound 868 | 2-Amino-5-piperidine-1-yl-benzoic acid methyl ester | 3-(Chloromethyl)-benzoyl chloride | 4-Chloro-3-trifluoromethylbenzaldehyde | 4-Piperazine-ethanol |
| Compound 869 | 2-Amino-5-piperidine-1-yl-benzoic acid methyl ester | 3-(Chloromethyl)-benzoyl chloride | p-Methoxybenzaldehyde | 4-Piperazine-ethanol |
| Compound 870 | 2-Amino-5-piperidine-1-yl-benzoic acid methyl ester | 3-(Chloromethyl)-benzoyl chloride | 3,4-Dimethylbenzaldehyde | 4-Hydroxypiperidine |
| Compound 871 | 2-Amino-5-piperidine-1-yl-benzoic acid methyl ester | 3-(Chloromethyl)-benzoyl chloride | p-Tolualdehyde | 4-Hydroxypiperidine |
| Compound 872 | 2-Amino-5-piperidine-1-yl-benzoic acid methyl ester | 3-(Chloromethyl)-benzoyl chloride | 4-Fluorobenzaldehyde | 4-Hydroxypiperidine |
| Compound 873 | 2-Amino-5-piperidine-1-yl-benzoic acid methyl ester | 3-(Chloromethyl)-benzoyl chloride | 3-Fluorobenzaldehyde | 4-Hydroxypiperidine |
| Compound 874 | 2-Amino-5-piperidine-1-yl-benzoic acid methyl ester | 3-(Chloromethyl)-benzoyl chloride | 4-Chloro-3-trifluoromethylbenzaldehyde | 4-Hydroxypiperidine |
| Compound 875 | 2-Amino-5-piperidine-1-yl-benzoic acid methyl ester | 3-(Chloromethyl)-benzoyl chloride | p-Methoxybenzaldehyde | 4-Hydroxypiperidine |
| Compound 876 | 2-Amino-5-piperidine-1-yl-benzoic acid methyl ester | 3-(Chloromethyl)-benzoyl chloride | 3,4-Dimethylbenzaldehyde | 2-(Diethylamino)-ethanethiol |
| Compound 877 | 2-Amino-5-piperidine-1-yl-benzoic acid methyl ester | 3-(Chloromethyl)-benzoyl chloride | 4-Fluorobenzaldehyde | 2-(Diethylamino)-ethanethiol |
| Compound 878 | 2-Amino-5-piperidine-1-yl-benzoic acid methyl ester | 3-(Chloromethyl)-benzoyl chloride | 4-Chloro-3-trifluoromethylbenzaldehyde | 2-(Diethylamino)-ethanethiol |
| Compound 879 | 2-Amino-5-piperidine-1-yl-benzoic acid methyl ester | 3-(Chloromethyl)-benzoyl chloride | p-Methoxybenzaldehyde | 2-(Diethylamino)-ethanethiol |

TABLE 1-continued

| | A | B | C | B' |
|---|---|---|---|---|
| Compound 880 | 2-Amino-5-piperidine-1-yl-benzoic acid methyl ester | 3-(Chloromethyl)-benzoyl chloride | 3,4-Dimethylbenzaldehyde | 2-Mercapto-ethanol |
| Compound 881 | 2-Amino-5-piperidine-1-yl-benzoic acid methyl ester | 3-(Chloromethyl)-benzoyl chloride | p-Tolualdehyde | 2-Mercapto-ethanol |
| Compound 882 | 2-Amino-5-piperidine-1-yl-benzoic acid methyl ester | 3-(Chloromethyl)-benzoyl chloride | 4-Fluorobenzaldehyde | 2-Mercapto-ethanol |
| Compound 883 | 2-Amino-5-piperidine-1-yl-benzoic acid methyl ester | 3-(Chloromethyl)-benzoyl chloride | 4-Fluorobenzaldehyde | 2-Mercapto-ethanol |
| Compound 884 | 2-Amino-5-piperidine-1-yl-benzoic acid methyl ester | 3-(Chloromethyl)-benzoyl chloride | 4-Chloro-3-trifluoromethylbenzaldehyde | 2-Mercapto-ethanol |
| Compound 885 | 2-Amino-5-piperidine-1-yl-benzoic acid methyl ester | 3-(Chloromethyl)-benzoyl chloride | p-Methoxybenzaldehyde | 2-Mercapto-ethanol |
| Compound 886 | 2-Amino-5-piperidine-1-yl-benzoic acid methyl ester | 3-(Chloromethyl)-benzoyl chloride | 3,4-Dimethylbenzaldehyde | 3-Mercapto-propionic acid |
| Compound 887 | 2-Amino-5-piperidine-1-yl-benzoic acid methyl ester | 3-(Chloromethyl)-benzoyl chloride | p-Tolualdehyde | 3-Mercapto-propionic acid |
| Compound 888 | 2-Amino-5-piperidine-1-yl-benzoic acid methyl ester | 3-(Chloromethyl)-benzoyl chloride | 4-Fluorobenzaldehyde | 3-Mercapto-propionic acid |
| Compound 889 | 2-Amino-5-piperidine-1-yl-benzoic acid methyl ester | 3-(Chloromethyl)-benzoyl chloride | 4-Chloro-3-trifluoromethylbenzaldehyde | 3-Mercapto-propionic acid |
| Compound 890 | 2-Amino-5-piperidine-1-yl-benzoic acid methyl ester | 3-(Chloromethyl)-benzoyl chloride | p-Methoxybenzaldehyde | 3-Mercapto-propionic acid |
| Compound 891 | 2-Amino-5-piperidine-1-yl-benzoic acid methyl ester | 3-(Chloromethyl)-benzoyl chloride | 4-Chloro-3-trifluoromethylbenzaldehyde | Mercapto-acetic acid |
| Compound 892 | 2-Amino-5-piperidine-1-yl-benzoic acid methyl ester | 3-(Chloromethyl)-benzoyl chloride | p-Methoxybenzaldehyde | Mercapto-acetic acid |
| Compound 893 | 2-Amino-5-piperidine-1-yl-benzoic acid methyl ester | 3-(Chloromethyl)-benzoyl chloride | 3,4-Dimethylbenzaldehyde | 1,2,3,4-Tetra-hydropyrido-[4,3-b][1,8]-naphthyridine |
| Compound 894 | 2-Amino-5-piperidine-1-yl-benzoic acid methyl ester | 3-(Chloromethyl)-benzoyl chloride | p-Tolualdehyde | 1,2,3,4-Tetra-hydropyrido-[4,3-b][1,8]-naphthyridine |
| Compound 895 | 2-Amino-5-piperidine-1-yl-benzoic acid methyl ester | 3-(Chloromethyl)-benzoyl chloride | 4-Fluorobenzaldehyde | 1,2,3,4-Tetra-hydropyrido-[4,3-b][1,8]-naphthyridine |
| Compound 896 | 2-Amino-5-piperidine-1-yl-benzoic acid methyl ester | 3-(Chloromethyl)-benzoyl chloride | 3-Fluorobenzaldehyde | 1,2,3,4-Tetra-hydropyrido-[4,3-b][1,8]-naphthyridine |
| Compound 897 | 2-Amino-5-piperidine-1-yl-benzoic acid methyl ester | 3-(Chloromethyl)-benzoyl chloride | 4-Chloro-3-trifluoromethylbenzaldehyde | 1,2,3,4-Tetra-hydropyrido-[4,3-b][1,8]-naphthyridine |
| Compound 898 | 2-Amino-5-piperidine-1-yl-benzoic acid methyl ester | 3-(Chloromethyl)-benzoyl chloride | p-Methoxybenzaldehyde | 1,2,3,4-Tetra-hydropyrido-[4,3-b][1,8]-naphthyridine |

TABLE 1-continued

| | A | B | C | B' |
|---|---|---|---|---|
| Compound 899 | 2-Amino-5-piperidine-1-yl-benzoic acid methyl ester | 3-(Chloromethyl)-benzoyl chloride | 3,4-Dimethylbenzaldehyde | 3-Mercapto-1,2-propane-diol |
| Compound 900 | 2-Amino-5-piperidine-1-yl-benzoic acid methyl ester | 3-(Chloromethyl)-benzoyl chloride | p-Tolualdehyde | 3-Mercapto-1,2-propane-diol |
| Compound 901 | 2-Amino-5-piperidine-1-yl-benzoic acid methyl ester | 3-(Chloromethyl)-benzoyl chloride | 4-Fluorobenzaldehyde | 3-Mercapto-1,2-propane-diol |
| Compound 902 | 2-Amino-5-piperidine-1-yl-benzoic acid methyl ester | 3-(Chloromethyl)-benzoyl chloride | 4-Fluorobenzaldehyde | 3-Mercapto-1,2-propane-diol |
| Compound 903 | 2-Amino-5-piperidine-1-yl-benzoic acid methyl ester | 3-(Chloromethyl)-benzoyl chloride | 4-Chloro-3-trifluoromethylbenzaldehyde | 3-Mercapto-1,2-propane-diol |
| Compound 904 | 2-Amino-5-piperidine-1-yl-benzoic acid methyl ester | 3-(Chloromethyl)-benzoyl chloride | p-Methoxybenzaldehyde | 3-Mercapto-1,2-propane-diol |
| Compound 905 | 2-Amino-5-piperidine-1-yl-benzoic acid methyl ester | 3-(Chloromethyl)-benzoyl chloride | 3,4-Dimethylbenzaldehyde | 1,1,7,7-Tetraethyl-diethylene-triamine |
| Compound 906 | 2-Amino-5-piperidine-1-yl-benzoic acid methyl ester | 3-(Chloromethyl)-benzoyl chloride | p-Tolualdehyde | 1,1,7,7-Tetraethyl-diethylene-triamine |
| Compound 907 | 2-Amino-5-piperidine-1-yl-benzoic acid methyl ester | 3-(Chloromethyl)-benzoyl chloride | 4-Fluorobenzaldehyde | 1,1,7,7-Tetraethyl-diethylene-triamine |
| Compound 908 | 2-Amino-5-piperidine-1-yl-benzoic acid methyl ester | 3-(Chloromethyl)-benzoyl chloride | 3-Fluorobenzaldehyde | 1,1,7,7-Tetraethyl-diethylene-triamine |
| Compound 909 | 2-Amino-5-piperidine-1-yl-benzoic acid methyl ester | 3-(Chloromethyl)-benzoyl chloride | 4-Chloro-3-trifluoromethylbenzaldehyde | 1,1,7,7-Tetraethyl-diethylene-triamine |
| Compound 910 | 2-Amino-5-piperidine-1-yl-benzoic acid methyl ester | 3-(Chloromethyl)-benzoyl chloride | p-Methoxybenzaldehyde | 1,1,7,7-Tetraethyl-diethylene-triamine |
| Compound 911 | 2-Amino-5-dipropylamino-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 912 | 2-Amino-5-dipropylamino-benzoic acid methyl ester | 3-(Chloromethyl)-benzoyl chloride | p-Methoxybenzaldehyde | N,N-Diethyl-N'-methyl-ethylenediamine |
| Compound 913 | 2-Amino-5-piperidine-1-yl-benzoic acid methyl ester | 3-(Chloromethyl)-benzoyl chloride | 3,4-Dimethylbenzaldehyde | N,N-bis(2-hydroxyethyl)-ethylenediamine |
| Compound 914 | 2-Amino-5-piperidine-1-yl-benzoic acid methyl ester | 3-(Chloromethyl)-benzoyl chloride | 4-Chloro-3-trifluoromethylbenzaldehyde | N,N-bis(2-hydroxyethyl)-ethylenediamine |
| Compound 915 | 2-Amino-5-piperidine-1-yl-benzoic acid methyl ester | 3-(Chloromethyl)-benzoyl chloride | p-Methoxybenzaldehyde | N,N-bis(2-hydroxyethyl)-ethylenediamine |
| Compound 916 | 2-Amino-5-pyrrolidine-1-yl-benzoic acid methyl ester | 3-(Chloromethyl)-benzoyl chloride | 3,4-Dimethylbenzaldehyde | N,N-Diethyl-N'-methyl-ethylenediamine |
| Compound 917 | 2-Amino-5-pyrrolidine-1-yl-benzoic acid methyl ester | 3-(Chloromethyl)-benzoyl chloride | 4-Chloro-3-trifluoromethylbenzaldehyde | N,N-Diethyl-N'-methyl-ethylenediamine |

TABLE 1-continued

| | A | B | C | B' |
|---|---|---|---|---|
| Compound 918 | 2-Amino-5-pyrrolidine-1-yl-benzoic acid methyl ester | 3-(Chloromethyl)-benzoyl chloride | p-Methoxybenzaldehyde | N,N-Diethyl-N'-methyl-ethylenediamine |
| Compound 919 | 2-Amino-5-pyrrolidine-1-yl-benzoic acid methyl ester | 3-(Chloromethyl)-benzoyl chloride | 3,4-Dimethylbenzaldehyde | 2-Mercapto-ethanol |
| Compound 920 | 2-Amino-5-pyrrolidine-1-yl-benzoic acid methyl ester | 3-(Chloromethyl)-benzoyl chloride | 4-Chloro-3-trifluoromethylbenzaldehyde | 2-Mercapto-ethanol |
| Compound 921 | 2-Amino-5-pyrrolidine-1-yl-benzoic acid methyl ester | 3-(Chloromethyl)-benzoyl chloride | p-Methoxybenzaldehyde | 2-Mercapto-ethanol |
| Compound 922 | 2-Amino-5-(4-methyl-[1,4]diazepin-1-yl)-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 923 | 2-Amino-5-[4-(2-hydroxy-ethyl)-piperazine-1-yl]-benzoic acid methyl ester | 3-(Chloromethyl)-benzoyl chloride | 4-Chloro-3-trifluoromethylbenzaldehyde | 2-Mercapto-ethanol |
| Compound 924 | 2-Amino-5-[4-(2-hydroxy-ethyl)-piperazine-1-yl]-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 925 | 1-(4-Amino-3-methoxycarbonylphenyl)-piperidine-3-carboxylic acid | 3-(Chloromethyl)-benzoyl chloride | 4-Chloro-3-trifluoromethylbenzaldehyde | 2-Mercapto-ethanol |
| Compound 926 | 2-Amino-5-thiomorpholine-4-yl-benzoic acid methyl ester | 3-(Chloromethyl)-benzoyl chloride | 3,4-Dimethylbenzaldehyde | 2-Mercapto-ethanol |
| Compound 927 | 2-Amino-5-thiomorpholine-4-yl-benzoic acid methyl ester | 3-(Chloromethyl)-benzoyl chloride | 4-Chloro-3-trifluoromethylbenzaldehyde | 2-Mercapto-ethanol |
| Compound 928 | 2-Amino-5-thiomorpholine-4-yl-benzoic acid methyl ester | 3-(Chloromethyl)-benzoyl chloride | p-Methoxybenzaldehyde | 2-Mercapto-ethanol |
| Compound 929 | 2-Amino-5-thiomorpholine-4-yl-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 930 | Methyl 2-aminothiophene-3-carboxylate | 3-(Chloromethyl)-benzoyl chloride | p-Methoxybenzaldehyde | Dimethyl-amine hydrochloride |
| Compound 931 | 2-Amino-5-(4-methyl-[1,4]diazepin-1-yl)-benzoic acid methyl ester | 3-(Chloromethyl)-benzoyl chloride | p-Methoxybenzaldehyde | N,N-Diethyl-N'-methyl-ethylenediamine |
| Compound 932 | 2-Amino-5-(4-methyl-[1,4]diazepin-1-yl)-benzoic acid methyl ester | 3-(Chloromethyl)-benzoyl chloride | 4-Chloro-3-trifluoromethylbenzaldehyde | 2-Mercapto-ethanol |
| Compound 933 | 2-Amino-5-(4-methyl-[1,4]diazepin-1-yl)-benzoic acid methyl ester | 3-(Chloromethyl)-benzoyl chloride | p-Methoxybenzaldehyde | N,N-Diethyl-N'-methyl-ethylenediamine |
| Compound 934 | 1-(4-Amino-3-methoxycarbonylphenyl)-piperidine-3-carboxylic acid | 3-(Chloromethyl)-benzoyl chloride | 3,4-Dimethylbenzaldehyde | 2-Mercapto-ethanol |
| Compound 935 | 2-Amino-5-piperidine-1-yl-benzoic acid ethyl ester | 3,4-Dimethoxybenzoyl chloride | 3,4-Dimethylbenzaldehyde | |

TABLE 1-continued

| | A | B | C | B' |
|---|---|---|---|---|
| Compound 936 | 2-Amino-5-piperidine-1-yl-benzoic acid ethyl ester | 3,4-Dimethoxybenzoyl chloride | Nicotinaldehyde | |
| Compound 937 | 2-Amino-5-piperidine-1-yl-benzoic acid ethyl ester | 3,4-Dimethoxybenzoyl chloride | Imidazole-2-carboxaldehyde | |
| Compound 938 | 2-Amino-5-piperidine-1-yl-benzoic acid ethyl ester | 3,4-Dimethoxybenzoyl chloride | Vanillin | |
| Compound 939 | 2-Amino-5-morpholine-4-yl-benzoic acid ethyl ester | 3,4-Dimethoxybenzoyl chloride | 3,4-Dimethylbenzaldehyde | |
| Compound 940 | 2-Amino-5-morpholine-4-yl-benzoic acid ethyl ester | 3,4-Dimethoxybenzoyl chloride | Vanillin | |
| Compound 941 | 2-Amino-5-morpholine-4-yl-benzoic acid ethyl ester | 3,4-Dimethoxybenzoyl chloride | p-Methoxybenzaldehyde | |
| Compound 942 | 2-Amino-5-piperidine-1-yl-benzoic acid ethyl ester | 3-(Chloromethyl)-benzoyl chloride | 4-Chloro-3-trifluoromethylbenzaldehyde | Diisopropanolamine |
| Compound 943 | 2-Amino-5-hydroxy-benzoic acid methyl ester | 3-(Chloromethyl)-benzoyl chloride | 3,4-Dimethylbenzaldehyde | Diisopropanolamine |
| Compound 944 | 2-Amino-5-(2-oxo-pyrrolidine-1-yl)-benzoic acid methyl ester | 3-(Chloromethyl)-benzoyl chloride | 3,4-Dimethylbenzaldehyde | Diisopropanolamine |
| Compound 945 | 2-Amino-5-(2-oxo-pyrrolidine-1-yl)-benzoic acid methyl ester | 3-(Chloromethyl)-benzoyl chloride | 4-Chloro-3-trifluoromethylbenzaldehyde | Diisopropanolamine |
| Compound 946 | 2-Amino-5-(2-oxo-pyrrolidine-1-yl)-benzoic acid methyl ester | 3-(Chloromethyl)-benzoyl chloride | p-Methoxybenzaldehyde | Diisopropanolamine |
| Compound 947 | 2-Amino-5-(2-oxo-pyrrolidine-1-yl)-benzoic acid methyl ester | 3-(Chloromethyl)-benzoyl chloride | 4-Fluorobenzaldehyde | Diisopropanolamine |
| Compound 948 | 2-Amino-5-(2-oxo-pyrrolidine-1-yl)-benzoic acid methyl ester | 3-(Chloromethyl)-benzoyl chloride | p-Tolualdehyde | Diisopropanolamine |
| Compound 949 | 2-Amino-5-hydroxy-benzoic acid methyl ester | 3-(Chloromethyl)-benzoyl chloride | 3,4-Dimethylbenzaldehyde | Diisopropanolamine |
| Compound 950 | 2-Amino-5-hydroxy-benzoic acid methyl ester | 3-(Chloromethyl)-benzoyl chloride | 4-Chloro-3-trifluoromethylbenzaldehyde | Diisopropanolamine |
| Compound 951 | 2-Amino-5-hydroxy-benzoic acid methyl ester | 3-(Chloromethyl)-benzoyl chloride | 3,4-Dimethylbenzaldehyde | Diisopropanolamine |
| Compound 952 | 2-Amino-5-hydroxy-benzoic acid methyl ester | 3-(Chloromethyl)-benzoyl chloride | 4-Chloro-3-trifluoromethylbenzaldehyde | Diisopropanolamine |
| Compound 953 | 2-Amino-5-hydroxy-benzoic acid methyl ester | 3-(Chloromethyl)-benzoyl chloride | 3,4-Dimethylbenzaldehyde | Diisopropanolamine |
| Compound 954 | 2-Amino-5-hydroxy-benzoic acid methyl ester | 3-(Chloromethyl)-benzoyl chloride | 4-Chloro-3-trifluoromethylbenzaldehyde | Diisopropanolamine |
| Compound 955 | Methyl 2-aminothiophene-3-carboxylate | 3,4-Dimethoxybenzoyl chloride | 4-Chloro-3-trifluoromethylbenzaldehyde | |
| Compound 956 | Ethyl 2-amino-4-methylthiophene-3-carboxylate | 3-(Chloromethyl)-benzoyl chloride | 4-Chloro-3-trifluoromethylbenzaldehyde | Diethylamine |

TABLE 1-continued

| | A | B | C | B' |
|---|---|---|---|---|
| Compound 957 | Ethyl 2-amino-4-methylthiophene-3-carboxylate | 3-(Chloromethyl)-benzoyl chloride | p-Methoxybenzaldehyde | Diethylamine |
| Compound 958 | 2-Amino-5-piperidine-1-yl-benzoic acid ethyl ester | 3-(Chloromethyl)-benzoyl chloride | p-Methoxybenzaldehyde | Diisopropanolamine |
| Compound 959 | 3-Amino-naphthalene-2-carboxylic acid methyl ester | 3-(Chloromethyl)-benzoyl chloride | 3-Fluorobenzaldehyde | Diisopropanolamine |
| Compound 960 | 3-Amino-naphthalene-2-carboxylic acid methyl ester | 3-(Chloromethyl)-benzoyl chloride | p-Tolualdehyde | Diisopropanolamine |
| Compound 961 | 3-Amino-naphthalene-2-carboxylic acid methyl ester | 3-(Chloromethyl)-benzoyl chloride | 3,4-Dimethylbenzaldehyde | Diisopropanolamine |
| Compound 962 | 3-Amino-naphthalene-2-carboxylic acid methyl ester | 3-(Chloromethyl)-benzoyl chloride | 4-Chloro-3-trifluoromethylbenzaldehyde | Diisopropanolamine |
| Compound 963 | 3-Amino-naphthalene-2-carboxylic acid methyl ester | 3-(Chloromethyl)-benzoyl chloride | p-Methoxybenzaldehyde | Diisopropanolamine |
| Compound 964 | 2-Amino-nicotinoic acid methyl ester | 3-(Chloromethyl)-benzoyl chloride | 3-Fluorobenzaldehyde | Diisopropanolamine |
| Compound 965 | 2-Amino-nicotinoic acid methyl ester | 3-(Chloromethyl)-benzoyl chloride | p-Tolualdehyde | Diisopropanolamine |
| Compound 966 | 2-Amino-nicotinoic acid methyl ester | 3-(Chloromethyl)-benzoyl chloride | 3,4-Dimethylbenzaldehyde | Diisopropanolamine |
| Compound 967 | 2-Amino-nicotinoic acid methyl ester | 3-(Chloromethyl)-benzoyl chloride | 4-Chloro-3-trifluoromethylbenzaldehyde | Diisopropanolamine |
| Compound 968 | 2-Amino-nicotinoic acid methyl ester | 3-(Chloromethyl)-benzoyl chloride | p-Methoxybenzaldehyde | Diisopropanolamine |
| Compound 969 | 3-Amino-naphthalene-2-carboxylic acid methyl ester | 3-(Chloromethyl)-benzoyl chloride | 3-Fluorobenzaldehyde | 1-(2-Hydroxyethyl)-piperazine |
| Compound 970 | 3-Amino-naphthalene-2-carboxylic acid methyl ester | 3-(Chloromethyl)-benzoyl chloride | p-Tolualdehyde | 1-(2-Hydroxyethyl)-piperazine |
| Compound 971 | 3-Amino-naphthalene-2-carboxylic acid methyl ester | 3-(Chloromethyl)-benzoyl chloride | 3,4-Dimethylbenzaldehyde | 1-(2-Hydroxyethyl)-piperazine |
| Compound 972 | 3-Amino-naphthalene-2-carboxylic acid methyl ester | 3-(Chloromethyl)-benzoyl chloride | 4-Chloro-3-trifluoromethylbenzaldehyde | 1-(2-Hydroxyethyl)-piperazine |
| Compound 973 | 3-Amino-naphthalene-2-carboxylic acid methyl ester | 3-(Chloromethyl)-benzoyl chloride | p-Methoxybenzaldehyde | 1-(2-Hydroxyethyl)-piperazine |
| Compound 974 | 4-Amino-thiophene-3-carboxylic acid methyl ester | 3-(Chloromethyl)-benzoyl chloride | 3-Fluorobenzaldehyde | Diisopropanolamine |
| Compound 975 | 4-Amino-thiophene-3-carboxylic acid methyl ester | 3-(Chloromethyl)-benzoyl chloride | m-Tolualdehyde | Diisopropanolamine |
| Compound 976 | 4-Amino-thiophene-3-carboxylic acid methyl ester | 3-(Chloromethyl)-benzoyl chloride | p-Tolualdehyde | Diisopropanolamine |
| Compound 977 | 4-Amino-thiophene-3-carboxylic acid methyl ester | 3-(Chloromethyl)-benzoyl chloride | 3,4-Dimethylbenzaldehyde | Diisopropanolamine |
| Compound 978 | 4-Amino-thiophene-3-carboxylic acid methyl ester | 3-(Chloromethyl)-benzoyl chloride | 4-Chloro-3-trifluoromethylbenzaldehyde | Diisopropanolamine |
| Compound 979 | 4-Amino-thiophene-3-carboxylic acid methyl ester | 3-(Chloromethyl)-benzoyl chloride | p-Methoxybenzaldehyde | Diisopropanolamine |

TABLE 1-continued

| | A | B | C | B' |
|---|---|---|---|---|
| Compound 980 | 4-Amino-thiophene-3-carboxylic acid methyl ester | 3-(Chloromethyl)-benzoyl chloride | 3-Fluorobenzaldehyde | 1-(2-Hydroxyethyl)-piperazine |
| Compound 981 | 4-Amino-thiophene-3-carboxylic acid methyl ester | 3-(Chloromethyl)-benzoyl chloride | p-Tolualdehyde | 1-(2-Hydroxyethyl)-piperazine |
| Compound 982 | 4-Amino-thiophene-3-carboxylic acid methyl ester | 3-(Chloromethyl)-benzoyl chloride | 3,4-Dimethylbenzaldehyde | 1-(2-Hydroxyethyl)-piperazine |
| Compound 983 | 4-Amino-thiophene-3-carboxylic acid methyl ester | 3-(Chloromethyl)-benzoyl chloride | 4-Chloro-3-trifluoromethylbenzaldehyde | 1-(2-Hydroxyethyl)-piperazine |
| Compound 984 | 4-Amino-thiophene-3-carboxylic acid methyl ester | 3-(Chloromethyl)-benzoyl chloride | p-Methoxybenzaldehyde | 1-(2-Hydroxyethyl)-piperazine |
| Compound 985 | 2-Amino-5-fluorobenzoic acid methyl ester | 3-(Chloromethyl)-benzoyl chloride | 3,4-Dimethylbenzaldehyde | Diisopropanolamine |
| Compound 986 | 2-Amino-5-fluorobenzoic acid methyl ester | 3-(Chloromethyl)-benzoyl chloride | 3,4-Dimethylbenzaldehyde | Diisopropanolamine |
| Compound 987 | 2-Amino-5-fluorobenzoic acid methyl ester | 3-(Chloromethyl)-benzoyl chloride | 3-Fluorobenzaldehyde | Diisopropanolamine |
| Compound 988 | 2-Amino-5-fluorobenzoic acid methyl ester | 3-(Chloromethyl)-benzoyl chloride | 3-Fluorobenzaldehyde | Diisopropanolamine |
| Compound 989 | 2-Amino-5-fluorobenzoic acid methyl ester | 3-(Chloromethyl)-benzoyl chloride | p-Tolualdehyde | Diisopropanolamine |
| Compound 990 | 2-Amino-5-fluorobenzoic acid methyl ester | 3-(Chloromethyl)-benzoyl chloride | p-Methoxybenzaldehyde | Diisopropanolamine |
| Compound 991 | 3-Amino-5-tert-butyl-thiophene-2-carboxylic acid methyl ester | 3-(Chloromethyl)-benzoyl chloride | 3,4-Dimethylbenzaldehyde | 1-(2-Hydroxyethyl)-piperazine |
| Compound 992 | 3-Amino-thiophene-2-carboxylic acid methyl ester | 3-(Chloromethyl)-benzoyl chloride | 3-Fluorobenzaldehyde | Diisopropanolamine |
| Compound 993 | 3-Amino-thiophene-2-carboxylic acid methyl ester | 3-(Chloromethyl)-benzoyl chloride | 4-Chloro-3-trifluoromethylbenzaldehyde | Diisopropanolamine |
| Compound 995 | 3-Amino-thiophene-2-carboxylic acid methyl ester | 3-(Chloromethyl)-benzoyl chloride | 3-Fluorobenzaldehyde | Diethylamine |
| Compound 996 | Methyl 2-amino-5-bromobenzoate | 3-(Chloromethyl)-benzoyl chloride | 3-Fluoroacetophenone | Diisopropanolamine |
| Compound 997 | Methyl 2-amino-5-bromobenzoate | 3-(Chloromethyl)-benzoyl chloride | p-Methoxy acetophenone | Diisopropanolamine |
| Compound 998 | Methyl 2-amino-5-chlorobenzoate | 3-(Chloromethyl)-benzoyl chloride | 4-(3-Dimethyl-amino-propoxy)-benzaldehyde | Diisopropanolamine |
| Compound 999 | Methyl 2-amino-5-chlorobenzoate | 3-(Chloromethyl)-benzoyl chloride | 4-(3-Dimethyl-amino-propoxy)-benzaldehyde | N,N-Diethyl-N'-methylethylenediamine |
| Compound 1000 | Methyl 2-amino-5-chlorobenzoate | 3-(Chloromethyl)-benzoyl chloride | (4-Formyl-phenoxy)-acetic acid | N,N-Diethyl-N'-methylethylenediamine |
| Compound 1001 | 2-Amino-4,5,6,7-tetrahydro-benzothiophene-3-carboxylic acid | 3-(Chloromethyl)-benzoyl chloride | 4-Trifluoromethoxybenzaldehyde | N,N-Diethyl-N'-methylethylenediamine |
| Compound 1002 | 2-Amino-4,5,6,7-tetrahydro-benzothiophene-3-carboxylic acid | 3-(Chloromethyl)-benzoyl chloride | 4-(2-Hydroxy-ethoxy)-benzaldehyde | N,N-Diethyl-N'-methylethylenediamine |
| Compound 1003 | 2-Amino-4,5,6,7-tetrahydro-benzothiophene-3-carboxylic acid | 3-(Chloromethyl)-benzoyl chloride | 3-Fluoro-acetophenone | N,N-Diethyl-N'-methylethylenediamine |
| Compound 1004 | Methyl 2-amino-5-chlorobenzoate | Quinoxaline-2-carbonyl chloride | 3-Fluorobenzaldehyde | |
| Compound 1005 | Methyl 2-amino-5-chlorobenzoate | Quinoxaline-2-carbonyl chloride | 3,4-Dimethylbenzaldehyde | |
| Compound 1006 | Methyl 2-amino-5-chlorobenzoate | Quinoxaline-2-carbonyl chloride | 4-Chloro-3-trifluoromethylbenzaldehyde | |

TABLE 1-continued

| | A | B | C | B' |
|---|---|---|---|---|
| Compound 1007 | Methyl 2-amino-5-chlorobenzoate | 3-(Chloromethyl)-benzoyl chloride | 3-Fluorobenzaldehyde | 3-Mercapto-propane-1,2-diol |
| Compound 1008 | Methyl 2-amino-5-chlorobenzoate | 3-(Chloromethyl)-benzoyl chloride | p-Tolualdehyde | 3-Mercapto-propane-1,2-diol |
| Compound 1009 | Methyl 2-amino-5-chlorobenzoate | 3-(Chloromethyl)-benzoyl chloride | 3,4-Dimethylbenzaldehyde | 3-Mercapto-propane-1,2-diol |
| Compound 1010 | Methyl 2-amino-5-chlorobenzoate | 3-(Chloromethyl)-benzoyl chloride | 4-Chloro-3-trifluoromethylbenzaldehyde | 3-Mercapto-propane-1,2-diol |
| Compound 1011 | Methyl 2-amino-5-chlorobenzoate | 3-(Chloromethyl)-benzoyl chloride | p-Methoxybenzaldehyde | 3-Mercapto-propane-1,2-diol |
| Compound 1012 | Methyl 2-amino-5-chlorobenzoate | 3-(Chloromethyl)-benzoyl chloride | 4-Trifluoromethoxybenzaldehyde | 3-Mercapto-propane-1,2-diol |
| Compound 1013 | 2-Amino-4,5-bis-(2-methoxy-ethoxy)-benzoic acid ethyl ester | 3-(Chloromethyl)-benzoyl chloride | 3-Fluorobenzaldehyde | 3-Mercapto-propane-1,2-diol |
| Compound 1014 | 2-Amino-4,5-bis-(2-methoxy-ethoxy)-benzoic acid ethyl ester | 3-(Chloromethyl)-benzoyl chloride | p-Tolualdehyde | 3-Mercapto-propane-1,2-diol |
| Compound 1015 | 2-Amino-4,5-bis-(2-methoxy-ethoxy)-benzoic acid ethyl ester | 3-(Chloromethyl)-benzoyl chloride | 3,4-Dimethylbenzaldehyde | 3-Mercapto-propane-1,2-diol |
| Compound 1016 | 2-Amino-4,5-bis-(2-methoxy-ethoxy)-benzoic acid ethyl ester | 3-(Chloromethyl)-benzoyl chloride | 4-Chloro-3-trifluoromethylbenzaldehyde | 3-Mercapto-propane-1,2-diol |
| Compound 1017 | 2-Amino-5-methoxy-benzoic acid methyl ester | 3-(Chloromethyl)-benzoyl chloride | 3-Fluorobenzaldehyde | 3-Mercapto-propane-1,2-diol |
| Compound 1018 | 2-Amino-5-methoxy-benzoic acid methyl ester | 3-(Chloromethyl)-benzoyl chloride | p-Tolualdehyde | 3-Mercapto-propane-1,2-diol |
| Compound 1019 | 2-Amino-5-methoxy-benzoic acid methyl ester | 3-(Chloromethyl)-benzoyl chloride | 3,4-Dimethylbenzaldehyde | 3-Mercapto-propane-1,2-diol |
| Compound 1020 | 2-Amino-5-methoxy-benzoic acid methyl ester | 3-(Chloromethyl)-benzoyl chloride | 4-Chloro-3-trifluoromethylbenzaldehyde | 3-Mercapto-propane-1,2-diol |
| Compound 1021 | 2-Amino-5-methoxy-benzoic acid methyl ester | 3-(Chloromethyl)-benzoyl chloride | p-Methoxybenzaldehyde- | 3-Mercapto-propane-1,2-diol |
| Compound 1022 | 2-Amino-5-methoxy-benzoic acid methyl ester | 3-(Chloromethyl)-benzoyl chloride | 3-Fluorobenzaldehyde | N,N-Diethyl-N'-methylethylenediamine |
| Compound 1023 | 2-Amino-5-methoxy-benzoic acid methyl ester | 3-(Chloromethyl)-benzoyl chloride | 4-Chloro-3-trifluoromethylbenzaldehyde | N,N-Diethyl-N'-methylethylenediamine |
| Compound 1024 | 2-Amino-5-methoxy-benzoic acid methyl ester | 3-(Chloromethyl)-benzoyl chloride | p-Methoxybenzaldehyde | N,N-Diethyl-N'-methylethylenediamine |
| Compound 1025 | 2-Amino-5-methoxy-ethoxy-benzoic acid methyl ester | 3-(Chloromethyl)-benzoyl chloride | 3-Fluorobenzaldehyde | N,N-Diethyl-N'-methylethylenediamine |
| Compound 1026 | 2-Amino-5-methoxy-ethoxy-benzoic acid methyl ester | 3-(Chloromethyl)-benzoyl chloride | p-Tolualdehyde | N,N-Diethyl-N'-methyl-ethylenediamine |
| Compound 1027 | 2-Amino-5-methoxy-ethoxy-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 1028 | 2-Amino-4,5-bis-(2-methoxy-ethoxy)-benzoic acid ethyl ester | 3-(Chloromethyl)-benzoyl chloride | 3-Fluorobenzaldehyde | N,N-Diethyl-N'-methyl-ethylenediamine |
| Compound 1029 | 2-Amino-4,5-bis-(2-methoxy-ethoxy)-benzoic acid ethyl ester | 3-(Chloromethyl)-benzoyl chloride | p-Tolualdehyde | N,N-Diethyl-N'-methyl-ethylenediamine |

TABLE 1-continued

| | A | B | C | B' |
|---|---|---|---|---|
| Compound 1030 | 2-Amino-4,5-bis-(2-methoxy-ethoxy)-benzoic acid ethyl ester | 3-(Chloromethyl)-benzoyl chloride | 3,4-Dimethylbenzaldehyde | N,N-Diethyl-N'-methyl-ethylenediamine |
| Compound 1031 | 2-Amino-4,5-bis-(2-methoxy-ethoxy)-benzoic acid ethyl ester | 3-(Chloromethyl)-benzoyl chloride | 4-Chloro-3-trifluoromethylbenzaldehyde | N,N-Diethyl-N'-methyl-ethylenediamine |
| Compound 1032 | 2-Amino-4,5-bis-(2-methoxy-ethoxy)-benzoic acid ethyl ester | 3-(Chloromethyl)-benzoyl chloride | p-Methoxybenzaldehyde | N,N-Diethyl-N'-methyl-ethylenediamine |
| Compound 1033 | 2-Amino-5-[2-(2-methoxy-ethoxy)-ethoxy]-benzoic acid methyl ester | 3-(Chloromethyl)-benzoyl chloride | 3-Fluorobenzaldehyde | N,N-Diethyl-N'-methyl-ethylenediamine |
| Compound 1034 | 2-Amino-5-[2-(2-methoxy-ethoxy)-ethoxy]-benzoic acid methyl ester | 3-(Chloromethyl)-benzoyl chloride | p-Tolualdehyde | N,N-Diethyl-N'-methyl-ethylenediamine |
| Compound 1035 | 2-Amino-5-[2-(2-methoxy-ethoxy)-ethoxy]-benzoic acid methyl ester | 3-(Chloromethyl)-benzoyl chloride | 3,4-Dimethylbenzaldehyde | N,N-Diethyl-N'-methyl-ethylenediamine |
| Compound 1036 | 2-Amino-5-[2-(2-methoxy-ethoxy)-ethoxy]-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 1037 | 2-Amino-5-[2-(2-methoxy-ethoxy)-ethoxy]-benzoic acid methyl ester | 3-(Chloromethyl)-benzoyl chloride | p-Methoxybenzaldehyde | N,N-Diethyl-N'-methyl-ethylenediamine |
| Compound 1038 | 2-Amino-5-(3-piperidine-1-yl-propoxy)-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 1039 | 2-Amino-5-(3-piperidine-1-yl-propoxy)-benzoic acid methyl ester | 3-(Chloromethyl)-benzoyl chloride | 4-Chloro-3-trifluoromethylbenzaldehyde | 2-Mercapto-ethanol |
| Compound 1040 | 2-Amino-5-(3-piperidine-1-yl-propoxy)-benzoic acid methyl ester | 3-(Chloromethyl)-benzoyl chloride | p-Methoxybenzaldehyde | 2-Mercapto-ethanol |
| Compound 1041 | 2-Amino-5-(3-piperidine-1-yl-propoxy)-benzoic acid methyl ester | 3-(Chloromethyl)-benzoyl chloride | 3,4-Dimethylbenzaldehyde | 2-Mercapto-ethanol |
| Compound 1042 | 2-Amino-5-(2-piperidine-1-yl-ethoxy)-benzoic acid methyl ester | 3-(Chloromethyl)-benzoyl chloride | p-Tolualdehyde | 2-Mercapto-ethanol |
| Compound 1043 | 2-Amino-5-(2-piperidine-1-yl-ethoxy)-benzoic acid methyl ester | 3-(Chloromethyl)-benzoyl chloride | 3,4-Dimethylbenzaldehyde | 2-Mercapto-ethanol |
| Compound 1044 | 2-Amino-5-(2-piperidine-1-yl-ethoxy)-benzoic acid methyl ester | 3-(Chloromethyl)-benzoyl chloride | 4-Chloro-3-trifluoromethylbenzaldehyde | 2-Mercapto-ethanol |
| Compound 1045 | 2-Amino-5-(2-piperidine-1-yl-ethoxy)-benzoic acid methyl ester | 3-(Chloromethyl)-benzoyl chloride | p-Methoxybenzaldehyde | 2-Mercapto-ethanol |
| Compound 1046 | 2-Amino-5-cyclohexylmethoxy-benzoic acid methyl ester | 3-(Chloromethyl)-benzoyl chloride | 3-Fluorobenzaldehyde | N,N-Diethyl-N'-methyl-ethylenediamine |
| Compound 1047 | 2-Amino-5-cyclohexylmethoxy-benzoic acid methyl ester | 3-(Chloromethyl)-benzoyl chloride | p-Tolualdehyde | N,N-Diethyl-N'-methyl-ethylenediamine |
| Compound 1048 | 2-Amino-5-cyclohexylmethoxy-benzoic acid methyl ester | 3-(Chloromethyl)-benzoyl chloride | 3,4-Dimethylbenzaldehyde | N,N-Diethyl-N'-methyl-ethylenediamine |

TABLE 1-continued

| | A | B | C | B' |
|---|---|---|---|---|
| Compound 1049 | 2-Amino-5-cyclohexylmethoxy-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 1050 | 2-Amino-5-cyclohexylmethoxy-benzoic acid methyl ester | 3-(Chloromethyl)-benzoyl chloride | p-Methoxybenzaldehyde | N,N-Diethyl-N'-methyl-ethylenediamine |
| Compound 1051 | 2-Amino-5-(4-fluoro-butoxy)-benzoic acid methyl ester | 3-(Chloromethyl)-benzoyl chloride | 3-Fluorobenzaldehyde | 2-Mercapto-ethanol |
| Compound 1052 | 2-Amino-5-(4-fluoro-butoxy)-benzoic acid methyl ester | 3-(Chloromethyl)-benzoyl chloride | p-Tolualdehyde | 2-Mercapto-ethanol |
| Compound 1053 | 2-Amino-5-(4-fluoro-butoxy)-benzoic acid methyl ester | 3-(Chloromethyl)-benzoyl chloride | 3,4-Dimethylbenzaldehyde | 2-Mercapto-ethanol |
| Compound 1054 | 2-Amino-5-(4-fluoro-butoxy)-benzoic acid methyl ester | 3-(Chloromethyl)-benzoyl chloride | 4-Chloro-3-trifluoromethylbenzaldehyde | 2-Mercapto-ethanol |
| Compound 1055 | 2-Amino-5-(4-fluoro-butoxy)-benzoic acid methyl ester | 3-(Chloromethyl)-benzoyl chloride | p-Methoxybenzaldehyde | 2-Mercapto-ethanol |
| Compound 1056 | Ethyl 2-amino-4,5,6,7-tetrahydrobenzo(B)-thiophene-3-carboxylate | 3-(Chloromethyl)-benzoyl chloride | p-Tolualdehyde | 1,1,7,7-Tetraethyl-diethylene-triamine |
| Compound 1057 | 2-Amino-5-(4-fluoro-butoxy)-benzoic acid methyl ester | 3-(Chloromethyl)-benzoyl chloride | 3-Fluorobenzaldehyde | N,N-Diethyl-N'-methyl-ethylenediamine |
| Compound 1058 | 2-Amino-5-(4-fluoro-butoxy)-benzoic acid methyl ester | 3-(Chloromethyl)-benzoyl chloride | p-Tolualdehyde | N,N-Diethyl-N'-methyl-ethylenediamine |
| Compound 1059 | 2-Amino-5-(4-fluoro-butoxy)-benzoic acid methyl ester | 3-(Chloromethyl)-benzoyl chloride | 3,4-Dimethylbenzaldehyde | N,N-Diethyl-N'-methyl-ethylenediamine |
| Compound 1060 | 2-Amino-5-(4-fluoro-butoxy)-benzoic acid methyl ester | 3-(Chloromethyl)-benzoyl chloride | 4-Chloro-3-trifluoromethylbenzaldehyde | N,N-Diethyl-N'-methyl-ethylenediamine |
| Compound 1061 | 2-Amino-5-(4-fluoro-butoxy)-benzoic acid methyl ester | 3-(Chloromethyl)-benzoyl chloride | p-Methoxybenzaldehyde | N,N-Diethyl-N'-methyl-ethylenediamine |
| Compound 1062 | 2-Amino-5-(4-Hydroxypiperidine-1-yl)-benzoic acid methyl ester | 3-(Chloromethyl)-benzoyl chloride | 3-Trifluoro-methyl-4-chlorobenzaldehyde | 2-Mercapto-ethanol |
| Compound 1063 | 2-Amino-5-(4-hydroxymethyl-piperidine-1-yl)-benzoic acid methyl ester | 3-(Chloromethyl)-benzoyl chloride | 3-Trifluoro-methyl-4-chlorobenzaldehyde | 2-Mercapto-ethanol |
| Compound 1064 | 2-Amino-5-morpholine-4-yl-benzoic acid methyl ester | 3-(Chloromethyl)-benzoyl chloride | 3,4-Dimethylbenzaldehyde | 2-Mercapto-ethanol |
| Compound 1065 | 2-Amino-5-morpholine-4-yl-benzoic acid methyl ester | 3-(Chloromethyl)-benzoyl chloride | 3-Trifluoro-methyl-4-chlorobenzaldehyde | 2-Mercapto-ethanol |
| Compound 1066 | 2-Amino-5-morpholine-4-yl-benzoic acid methyl ester | 3-(Chloromethyl)-benzoyl chloride | p-Methoxybenzaldehyde | 2-Mercapto-ethanol |
| Compound 1067 | 2-Amino-5-[1,4']bipiperidinyl-1'-yl-benzoic acid methyl ester | 3-(Chloromethyl)-benzoyl chloride | 3-Trifluoro-methyl-4-chlorobenzaldehyde | 2-Mercapto-ethanol |

TABLE 1-continued

| | A | B | C | B' |
|---|---|---|---|---|
| Compound 1068 | 2-Amino-5-[1,4']bipiperidinyl-1'-yl-benzoic acid methyl ester | 3-(Chloromethyl)-benzoyl chloride | p-Methoxybenzaldehyde | 2-Mercapto-ethanol |
| Compound 1069 | 2-Amino-5-(4-methyl-piperidine-1-yl)-benzoic acid methyl ester | 3-(Chloromethyl)-benzoyl chloride | 3,4-Dimethylbenzaldehyde | 2-Mercapto-ethanol |
| Compound 1070 | 2-Amino-5-(4-methyl-piperidine-1-yl)-benzoic acid methyl ester | 3-(Chloromethyl)-benzoyl chloride | 3-Trifluoro-methyl-4-chlorobenzaldehyde | 2-Mercapto-ethanol |
| Compound 1071 | 2-Amino-5-(4-methyl-piperidine-1-yl)-benzoic acid methyl ester | 3-(Chloromethyl)-benzoyl chloride | p-Methoxybenzaldehyde | 2-Mercapto-ethanol |
| Compound 1072 | 2-Amino-5-(4-methyl-piperazine-1-yl)-benzoic acid methyl ester | 3-(Chloromethyl)-benzoyl chloride | 3-Trifluoro-methyl-4-chlorobenzaldehyde | 2-Mercapto-ethanol |
| Compound 1073 | 2-Amino-5-(4-methyl-piperazine-1-yl)-benzoic acid methyl ester | 3-(Chloromethyl)-benzoyl chloride | p-Methoxybenzaldehyde | 2-Mercapto-ethanol |
| Compound 1074 | 2-Amino-5-morpholine-4-yl-benzoic acid methyl ester | 3-(Chloromethyl)-benzoyl chloride | 3,4-Dimethylbenzaldehyde | N,N-Diethyl-N'-methyl-ethylenediamine |
| Compound 1075 | 2-Amino-5-morpholine-4-yl-benzoic acid methyl ester | 3-(Chloromethyl)-benzoyl chloride | 3-Trifluoro-methyl-4-chlorobenzaldehyde | N,N-Diethyl-N'-methyl-ethylenediamine |
| Compound 1076 | 2-Amino-5-morpholine-4-yl-benzoic acid methyl ester | 3-(Chloromethyl)-benzoyl chloride | p-Methoxybenzaldehyde | N,N-Diethyl-N'-methyl-ethylenediamine |

Starting compounds and reaction paths used in the synthesis of compounds corresponding to compounds A in synthesizing compounds 853, 854, 857 to 929, 931 to 942, 944 to 948, 958 to 973, 985 to 990, 1013 to 1055, and 1057 to 1076 are shown in Table 2. In the table, compounds A, D, and E correspond to compounds described in Examples and schemes A to H.

TABLE 2

| | A' | D | E | Reaction path |
|---|---|---|---|---|
| Compound 853 | 2-Amino-5-fluorobenzoic acid | | | Scheme G |
| Compound 854 | 2-Amino-5-fluorobenzoic acid | | | Scheme G |
| Compound 857 | 2-Amino-5-fluorobenzoic acid | | | Scheme G |
| Compound 858 | 5-Chloro-2-nitro-benzoic acid | Piperidine | | Scheme A |
| Compound 859 | 5-Chloro-2-nitro-benzoic acid | Piperidine | | Scheme A |
| Compound 860 | 5-Chloro-2-nitro-benzoic acid | Piperidine | | Scheme A |
| Compound 861 | 5-Chloro-2-nitro-benzoic acid | Piperidine | | Scheme A |
| Compound 862 | 5-Chloro-2-nitro-benzoic acid | Piperidine | | Scheme A |
| Compound 863 | 5-Chloro-2-nitro-benzoic acid | Piperidine | | Scheme A |
| Compound 864 | 5-Chloro-2-nitro-benzoic acid | Piperidine | | Scheme A |
| Compound 865 | 5-Chloro-2-nitro-benzoic acid | Piperidine | | Scheme A |
| Compound 866 | 5-Chloro-2-nitro-benzoic acid | Piperidine | | Scheme A |

TABLE 2-continued

| | A' | D | E | Reaction path |
|---|---|---|---|---|
| Compound 867 | 5-Chloro-2-nitro-benzoic acid | Piperidine | | Scheme A |
| Compound 868 | 5-Chloro-2-nitro-benzoic acid | Piperidine | | Scheme A |
| Compound 869 | 5-Chloro-2-nitro-benzoic acid | Piperidine | | Scheme A |
| Compound 870 | 5-Chloro-2-nitro-benzoic acid | Piperidine | | Scheme A |
| Compound 871 | 5-Chloro-2-nitro-benzoic acid | Piperidine | | Scheme A |
| Compound 872 | 5-Chloro-2-nitro-benzoic acid | Piperidine | | Scheme A |
| Compound 873 | 5-Chloro-2-nitro-benzoic acid | Piperidine | | Scheme A |
| Compound 874 | 5-Chloro-2-nitro-benzoic acid | Piperidine | | Scheme A |
| Compound 875 | 5-Chloro-2-nitro-benzoic acid | Piperidine | | Scheme A |
| Compound 876 | 5-Chloro-2-nitro-benzoic acid | Piperidine | | Scheme A |
| Compound 877 | 5-Chloro-2-nitro-benzoic acid | Piperidine | | Scheme A |
| Compound 878 | 5-Chloro-2-nitro-benzoic acid | Piperidine | | Scheme A |
| Compound 879 | 5-Chloro-2-nitro-benzoic acid | Piperidine | | Scheme A |
| Compound 880 | 5-Chloro-2-nitro-benzoic acid | Piperidine | | Scheme A |
| Compound 881 | 5-Chloro-2-nitro-benzoic acid | Piperidine | | Scheme A |
| Compound 882 | 5-Chloro-2-nitro-benzoic acid | Piperidine | | Scheme A |
| Compound 883 | 5-Chloro-2-nitro-benzoic acid | Piperidine | | Scheme A |
| Compound 884 | 5-Chloro-2-nitro-benzoic acid | Piperidine | | Scheme A |
| Compound 885 | 5-Chloro-2-nitro-benzoic acid | Piperidine | | Scheme A |
| Compound 886 | 5-Chloro-2-nitro-benzoic acid | Piperidine | | Scheme A |
| Compound 887 | 5-Chloro-2-nitro-benzoic acid | Piperidine | | Scheme A |
| Compound 888 | 5-Chloro-2-nitro-benzoic acid | Piperidine | | Scheme A |
| Compound 889 | 5-Chloro-2-nitro-benzoic acid | Piperidine | | Scheme A |
| Compound 890 | 5-Chloro-2-nitro-benzoic acid | Piperidine | | Scheme A |
| Compound 891 | 5-Chloro-2-nitro-benzoic acid | Piperidine | | Scheme A |
| Compound 892 | 5-Chloro-2-nitro-benzoic acid | Piperidine | | Scheme A |
| Compound 893 | 5-Chloro-2-nitro-benzoic acid | Piperidine | | Scheme A |
| Compound 894 | 5-Chloro-2-nitro-benzoic acid | Piperidine | | Scheme A |
| Compound 895 | 5-Chloro-2-nitro-benzoic acid | Piperidine | | Scheme A |
| Compound 896 | 5-Chloro-2-nitro-benzoic acid | Piperidine | | Scheme A |
| Compound 897 | 5-Chloro-2-nitro-benzoic acid | Piperidine | | Scheme A |
| Compound 898 | 5-Chloro-2-nitro-benzoic acid | Piperidine | | Scheme A |
| Compound 899 | 5-Chloro-2-nitro-benzoic acid | Piperidine | | Scheme A |
| Compound 900 | 5-Chloro-2-nitro-benzoic acid | Piperidine | | Scheme A |
| Compound 901 | 5-Chloro-2-nitro-benzoic acid | Piperidine | | Scheme A |
| Compound 902 | 5-Chloro-2-nitro-benzoic acid | Piperidine | | Scheme A |
| Compound 903 | 5-Chloro-2-nitro-benzoic acid | Piperidine | | Scheme A |
| Compound 904 | 5-Chloro-2-nitro-benzoic acid | Piperidine | | Scheme A |
| Compound 905 | 5-Chloro-2-nitro-benzoic acid | Piperidine | | Scheme A |

TABLE 2-continued

|  | A' | D | E | Reaction path |
|---|---|---|---|---|
| Compound 906 | 5-Chloro-2-nitro-benzoic acid | Piperidine | | Scheme A |
| Compound 907 | 5-Chloro-2-nitro-benzoic acid | Piperidine | | Scheme A |
| Compound 908 | 5-Chloro-2-nitro-benzoic acid | Piperidine | | Scheme A |
| Compound 909 | 5-Chloro-2-nitro-benzoic acid | Piperidine | | Scheme A |
| Compound 910 | 5-Chloro-2-nitro-benzoic acid | Piperidine | | Scheme A |
| Compound 911 | 5-Amino-2-nitro-benzoic acid methyl ester | Propionaldehyde | | Scheme H |
| Compound 912 | 5-Amino-2-nitro-benzoic acid methyl ester | Propionaldehyde | | Scheme H |
| Compound 913 | 5-Chloro-2-nitro-benzoic acid | Piperidine | | Scheme A |
| Compound 914 | 5-Chloro-2-nitro-benzoic acid | Piperidine | | Scheme A |
| Compound 915 | 5-Chloro-2-nitro-benzoic acid | Piperidine | | Scheme A |
| Compound 916 | 5-Chloro-2-nitro-benzoic acid | Pyrrolidine | | Scheme A |
| Compound 917 | 5-Chloro-2-nitro-benzoic acid | Pyrrolidine | | Scheme A |
| Compound 918 | 5-Chloro-2-nitro-benzoic acid | Pyrrolidine | | Scheme A |
| Compound 919 | 5-Chloro-2-nitro-benzoic acid | Pyrrolidine | | Scheme A |
| Compound 920 | 5-Chloro-2-nitro-benzoic acid | Pyrrolidine | | Scheme A |
| Compound 921 | 5-Chloro-2-nitro-benzoic acid | Pyrrolidine | | Scheme A |
| Compound 922 | 5-Chloro-2-nitro-benzoic acid | 1-Methyl-homopiperazine | | Scheme A |
| Compound 923 | 5-Chloro-2-nitro-benzoic acid | 1-Piperazineethanol | | Scheme A |
| Compound 924 | 5-Chloro-2-nitro-benzoic acid | 1-Piperazineethanol | | Scheme A |
| Compound 925 | 5-Chloro-2-nitro-benzoic acid | 3-Piperidine-carboxylic acid | | Scheme A |
| Compound 926 | 5-Chloro-2-nitro-benzoic acid | Thiomorpholine | | Scheme A |
| Compound 927 | 5-Chloro-2-nitro-benzoic acid | Thiomorpholine | | Scheme A |
| Compound 928 | 5-Chloro-2-nitro-benzoic acid | Thiomorpholine | | Scheme A |
| Compound 929 | 5-Chloro-2-nitro-benzoic acid | Thiomorpholine | | Scheme A |
| Compound 931 | 5-Chloro-2-nitro-benzoic acid | 1-Methyl-homopiperazine | | Scheme A |
| Compound 932 | 5-Chloro-2-nitro-benzoic acid | 1-Methyl-homopiperazine | | Scheme A |
| Compound 933 | 5-Chloro-2-nitro-benzoic acid | 1-Methyl-homopiperazine | | Scheme A |
| Compound 934 | 5-Chloro-2-nitro-benzoic acid | 3-Piperidine-carboxylic acid | | Scheme A |
| Compound 935 | 5-Chloro-2-nitro-benzoic acid | Piperidine | | Scheme A |
| Compound 936 | 5-Chloro-2-nitro-benzoic acid | Piperidine | | Scheme A |
| Compound 937 | 5-Chloro-2-nitro-benzoic acid | Piperidine | | Scheme A |
| Compound 938 | 5-Chloro-2-nitro-benzoic acid | Piperidine | | Scheme A |
| Compound 939 | 5-Chloro-2-nitro-benzoic acid | Morpholine | | Scheme A |
| Compound 940 | 5-Chloro-2-nitro-benzoic acid | Morpholine | | Scheme A |
| Compound 941 | 5-Chloro-2-nitro-benzoic acid | Morpholine | | Scheme A |
| Compound 942 | 5-Chloro-2-nitro-benzoic acid | Piperidine | | Scheme A |
| Compound 944 | 5-Amino-2-nitro-benzoic acid | 4-Chloro-butyryl chloride | | Scheme D |
| Compound 945 | 5-Amino-2-nitro-benzoic acid | 4-Chloro-butyryl chloride | | Scheme D |

TABLE 2-continued

| | A' | D | E | Reaction path |
|---|---|---|---|---|
| Compound 946 | 5-Amino-2-nitro-benzoic acid | 4-Chloro-butyryl chloride | | Scheme D |
| Compound 947 | 5-Amino-2-nitro-benzoic acid | 4-Chloro-butyryl chloride | | Scheme D |
| Compound 948 | 5-Amino-2-nitro-benzoic acid | 4-Chloro-butyryl chloride | | Scheme D |
| Compound 958 | 5-Chloro-2-nitro-benzoic acid | Piperidine | | Scheme A |
| Compound 959 | 3-Amino-naphthalene-2-carboxylic acid | | | Scheme G |
| Compound 960 | 3-Amino-naphthalene-2-carboxylic acid | | | Scheme G |
| Compound 961 | 3-Amino-naphthalene-2-carboxylic acid | | | Scheme G |
| Compound 962 | 3-Amino-naphthalene-2-carboxylic acid | | | Scheme G |
| Compound 963 | 3-Amino-naphthalene-2-carboxylic acid | | | Scheme G |
| Compound 964 | 2-Amino-nicotinoic acid | | | Scheme G |
| Compound 965 | 2-Amino-nicotinoic acid | | | Scheme G |
| Compound 966 | 2-Amino-nicotinoic acid | | | Scheme G |
| Compound 967 | 2-Amino-nicotinoic acid | | | Scheme G |
| Compound 968 | 2-Amino-nicotinoic acid | | | Scheme G |
| Compound 969 | 3-Amino-naphthalene-2-carboxylic acid | | | Scheme G |
| Compound 970 | 3-Amino-naphthalene-2-carboxylic acid | | | Scheme G |
| Compound 971 | 3-Amino-naphthalene-2-carboxylic acid | | | Scheme G |
| Compound 972 | 3-Amino-naphthalene-2-carboxylic acid | | | Scheme G |
| Compound 973 | 3-Amino-naphthalene-2-carboxylic acid | | | Scheme G |
| Compound 985 | 2-Amino-5-fluorobenzoic acid | | | Scheme G |
| Compound 986 | 2-Amino-5-fluorobenzoic acid | | | Scheme G |
| Compound 987 | 2-Amino-5-fluorobenzoic acid | | | Scheme G |
| Compound 988 | 2-Amino-5-fluorobenzoic acid | | | Scheme G |
| Compound 989 | 2-Amino-5-fluorobenzoic acid | | | Scheme G |
| Compound 990 | 2-Amino-5-fluorobenzoic acid | | | Scheme G |
| Compound 1013 | 3,4-Dihydroxy-benzoic acid ethyl ester | 1-Bromo-2-methoxy-ethane | | Scheme F |
| Compound 1014 | 3,4-Dihydroxy-benzoic acid ethyl ester | 1-Bromo-2-methoxy-ethane | | Scheme F |
| Compound 1015 | 3,4-Dihydroxy-benzoic acid ethyl ester | 1-Bromo-2-methoxy-ethane | | Scheme F |
| Compound 1016 | 3,4-Dihydroxy-benzoic acid ethyl ester | 1-Bromo-2-methoxy-ethane | | Scheme F |
| Compound 1017 | 5-Methoxy-2-nitro-benzoic acid | | | Scheme E |
| Compound 1018 | 5-Methoxy-2-nitro-benzoic acid | | | Scheme E |
| Compound 1019 | 5-Methoxy-2-nitro-benzoic acid | | | Scheme E |

TABLE 2-continued

| | A' | D | E | Reaction path |
|---|---|---|---|---|
| Compound 1020 | 5-Methoxy-2-nitro-benzoic acid | | | Scheme E |
| Compound 1021 | 5-Methoxy-2-nitro-benzoic acid | | | Scheme E |
| Compound 1022 | 5-Methoxy-2-nitro-benzoic acid | | | Scheme E |
| Compound 1023 | 5-Methoxy-2-nitro-benzoic acid | | | Scheme E |
| Compound 1024 | 5-Methoxy-2-nitro-benzoic acid | | | Scheme E |
| Compound 1025 | 5-Hydroxy-2-nitro-benzoic acid | 1-Bromo-2-methoxy-ethane | | Scheme B |
| Compound 1026 | 5-Hydroxy-2-nitro-benzoic acid | 1-Bromo-2-methoxy-ethane | | Scheme B |
| Compound 1027 | 5-Hydroxy-2-nitro-benzoic acid | 1-Bromo-2-methoxy-ethane | | Scheme B |
| Compound 1028 | 3,4-Dihydroxy-benzoic acid ethyl ester | 1-Bromo-2-methoxy-ethane | | Scheme F |
| Compound 1029 | 3,4-Dihydroxy-benzoic acid ethyl ester | 1-Bromo-2-methoxy-ethane | | Scheme F |
| Compound 1030 | 3,4-Dihydroxy-benzoic acid ethyl ester | 1-Bromo-2-methoxy-ethane | | Scheme F |
| Compound 1031 | 3,4-Dihydroxy-benzoic acid ethyl ester | 1-Bromo-2-methoxy-ethane | | Scheme F |
| Compound 1032 | 3,4-Dihydroxy-benzoic acid ethyl ester | 1-Bromo-2-methoxy-ethane | | Scheme F |
| Compound 1033 | 5-Hydroxy-2-nitro-benzoic acid | 1-Bromo-2-(2-methoxy-ethoxy)-ethane | | Scheme B |
| Compound 1034 | 5-Hydroxy-2-nitro-benzoic acid | 1-Bromo-2-(2-methoxy-ethoxy)-ethane | | Scheme B |
| Compound 1035 | 5-Hydroxy-2-nitro-benzoic acid | 1-Bromo-2-(2-methoxy-ethoxy)-ethane | | Scheme B |
| Compound 1036 | 5-Hydroxy-2-nitro-benzoic acid | 1-Bromo-2-(2-methoxy-ethoxy)-ethane | | Scheme B |
| Compound 1037 | 5-Hydroxy-2-nitro-benzoic acid | 1-Bromo-2-(2-methoxy-ethoxy)-ethane | | Scheme B |
| Compound 1038 | 5-Hydroxy-2-nitro-benzoic acid | 1-Bromo-3-chloropropane | Piperidine | Scheme C |
| Compound 1039 | 5-Hydroxy-2-nitro-benzoic acid | 1-Bromo-3-chloropropane | Piperidine | Scheme C |
| Compound 1040 | 5-Hydroxy-2-nitro-benzoic acid | 1-Bromo-3-chloropropane | Piperidine | Scheme C |
| Compound 1041 | 5-Hydroxy-2-nitro-benzoic acid | 1-Bromo-3-chloropropane | Piperidine | Scheme C |
| Compound 1042 | 5-Hydroxy-2-nitro-benzoic acid | 1-Bromo-2-chloroethane | Piperidine | Scheme C |
| Compound 1043 | 5-Hydroxy-2-nitro-benzoic acid | 1-Bromo-2-chloroethane | Piperidine | Scheme C |
| Compound 1044 | 5-Hydroxy-2-nitro-benzoic acid | 1-Bromo-2-chloroethane | Piperidine | Scheme C |
| Compound 1045 | 5-Hydroxy-2-nitro-benzoic acid | 1-Bromo-2-chloroethane | Piperidine | Scheme C |
| Compound 1046 | 5-Hydroxy-2-nitro-benzoic acid | Bromomethyl-cyclohexane | | Scheme B |
| Compound 1047 | 5-Hydroxy-2-nitro-benzoic acid | Bromomethyl-cyclohexane | | Scheme B |
| Compound 1048 | 5-Hydroxy-2-nitro-benzoic acid | Bromomethyl-cyclohexane | | Scheme B |
| Compound 1049 | 5-Hydroxy-2-nitro-benzoic acid | Bromomethyl-cyclohexane | | Scheme B |
| Compound 1050 | 5-Hydroxy-2-nitro-benzoic acid | Bromomethyl-cyclohexane | | Scheme B |
| Compound 1051 | 5-Hydroxy-2-nitro-benzoic acid | 1-Bromo-4-fluoro-butane | | Scheme B |
| Compound 1052 | 5-Hydroxy-2-nitro-benzoic acid | 1-Bromo-4-fluoro-butane | | Scheme B |
| Compound 1053 | 5-Hydroxy-2-nitro-benzoic acid | 1-Bromo-4-fluoro-butane | | Scheme B |

TABLE 2-continued

| | A' | D | E | Reaction path |
|---|---|---|---|---|
| Compound 1054 | 5-Hydroxy-2-nitro-benzoic acid | 1-Bromo-4-fluoro-butane | | Scheme B |
| Compound 1055 | 5-Hydroxy-2-nitro-benzoic acid | 1-Bromo-4-fluoro-butane | | Scheme B |
| Compound 1057 | 5-Hydroxy-2-nitro-benzoic acid | 1-Bromo-4-fluoro-butane | | Scheme B |
| Compound 1058 | 5-Hydroxy-2-nitro-benzoic acid | 1-Bromo-4-fluoro-butane | | Scheme B |
| Compound 1059 | 5-Hydroxy-2-nitro-benzoic acid | 1-Bromo-4-fluoro-butane | | Scheme B |
| Compound 1060 | 5-Hydroxy-2-nitro-benzoic acid | 1-Bromo-4-fluoro-butane | | Scheme B |
| Compound 1061 | 5-Hydroxy-2-nitro-benzoic acid | 1-Bromo-4-fluoro-butane | | Scheme B |
| Compound 1062 | 5-Chloro-2-nitro-benzoic acid | 4-Hydroxy-piperidine | | Scheme A |
| Compound 1063 | 5-Chloro-2-nitro-benzoic acid | 4-Piperidine-methanol | | Scheme A |
| Compound 1064 | 5-Chloro-2-nitro-benzoic acid | Morpholine | | Scheme A |
| Compound 1065 | 5-Chloro-2-nitro-benzoic acid | Morpholine | | Scheme A |
| Compound 1066 | 5-Chloro-2-nitro-benzoic acid | Morpholine | | Scheme A |
| Compound 1067 | 5-Chloro-2-nitro-benzoic acid | 4-Piperidino-piperidine | | Scheme A |
| Compound 1068 | 5-Chloro-2-nitro-benzoic acid | 4-Piperidino-piperidine | | Scheme A |
| Compound 1069 | 5-Chloro-2-nitro-benzoic acid | 4-Methylpiperidine | | Scheme A |
| Compound 1070 | 5-Chloro-2-nitro-benzoic acid | 4-Methylpiperidine | | Scheme A |
| Compound 1071 | 5-Chloro-2-nitro-benzoic acid | 4-Methylpiperidine | | Scheme A |
| Compound 1072 | 5-Chloro-2-nitro-benzoic acid | 4-Methylpiperazine | | Scheme A |
| Compound 1073 | 5-Chloro-2-nitro-benzoic acid | 4-Methylpiperazine | | Scheme A |
| Compound 1074 | 5-Chloro-2-nitro-benzoic acid | Morpholine | | Scheme A |
| Compound 1075 | 5-Chloro-2-nitro-benzoic acid | Morpholine | | Scheme A |
| Compound 1076 | 5-Chloro-2-nitro-benzoic acid | Morpholine | | Scheme A |
| Compound 935 | 5-Chloro-2-nitro-benzoic acid | Piperidine | | Scheme A |
| Compound 936 | 5-Chloro-2-nitro-benzoic acid | Piperidine | | Scheme A |
| Compound 937 | 5-Chloro-2-nitro-benzoic acid | Piperidine | | Scheme A |
| Compound 938 | 5-Chloro-2-nitro-benzoic acid | Piperidine | | Scheme A |
| Compound 939 | 5-Chloro-2-nitro-benzoic acid | Morpholine | | Scheme A |
| Compound 940 | 5-Chloro-2-nitro-benzoic acid | Morpholine | | Scheme A |
| Compound 941 | 5-Chloro-2-nitro-benzoic acid | Morpholine | | Scheme A |
| Compound 942 | 5-Chloro-2-nitro-benzoic acid | Piperidine | | Scheme A |
| Compound 944 | 5-Amino-2-nitro-benzoic acid | 4-Chloro-butyryl chloride | | Scheme D |
| Compound 945 | 5-Amino-2-nitro-benzoic acid | 4-Chloro-butyryl chloride | | Scheme D |
| Compound 946 | 5-Amino-2-nitro-benzoic acid | 4-Chloro-butyryl chloride | | Scheme D |
| Compound 947 | 5-Amino-2-nitro-benzoic acid | 4-Chloro-butyryl chloride | | Scheme D |
| Compound 948 | 5-Amino-2-nitro-benzoic acid | 4-Chloro-butyryl chloride | | Scheme D |
| Compound 958 | 5-Chloro-2-nitro-benzoic acid | Piperidine | | Scheme A |
| Compound 959 | 3-Amino-naphthalene-2-carboxylic acid | | | Scheme G |
| Compound 960 | 3-Amino-naphthalene-2-carboxylic acid | | | Scheme G |

TABLE 2-continued

|  | A' | D | E | Reaction path |
|---|---|---|---|---|
| Compound 961 | 3-Amino-naphthalene-2-carboxylic acid |  |  | Scheme G |
| Compound 962 | 3-Amino-naphthalene-2-carboxylic acid |  |  | Scheme G |
| Compound 963 | 3-Amino-naphthalene-2-carboxylic acid |  |  | Scheme G |
| Compound 964 | 2-Almino-nicotinoic acid |  |  | Scheme G |
| Compound 965 | 2-Almino-nicotinoic acid |  |  | Scheme G |
| Compound 966 | 2-Amino-nicotinoic acid |  |  | Scheme G |
| Compound 967 | 2-Amino-nicotinoic acid |  |  | Scheme G |
| Compound 968 | 2-Amino-nicotinoic acid |  |  | Scheme G |
| Compound 969 | 3-Amino-naphthalene-2-carboxylic acid |  |  | Scheme G |
| Compound 970 | 3-Amino-naphthalene-2-carboxylic acid |  |  | Scheme G |
| Compound 971 | 3-Amino-naphthalene-2-carboxylic acid |  |  | Scheme G |
| Compound 972 | 3-Amino-naphthalene-2-carboxylic acid |  |  | Scheme G |
| Compound 973 | 3-Amino-naphthalene-2-carboxylic acid |  |  | Scheme G |
| Compound 985 | 2-Amino-5-fluoro-benzoic acid |  |  | Scheme G |
| Compound 986 | 2-Amino-5-fluoro-benzoic acid |  |  | Scheme G |
| Compound 987 | 2-Amino-5-fluoro-benzoic acid |  |  | Scheme G |
| Compound 988 | 2-Amino-5-fluoro-benzoic acid |  |  | Scheme G |
| Compound 989 | 2-Amino-5-fluoro-benzoic acid |  |  | Scheme G |
| Compound 990 | 2-Amino-5-fluoro-benzoic acid |  |  | Scheme G |
| Compound 1013 | 3,4-Dihydroxy-benzoic acid ethyl ester | 1-Bromo-2-methoxy-ethane |  | Scheme F |
| Compound 1014 | 3,4-Dihydroxy-benzoic acid ethyl ester | 1-Bromo-2-methoxy-ethane |  | Scheme F |
| Compound 1015 | 3,4-Dihydroxy-benzoic acid ethyl ester | 1-Bromo-2-methoxy-ethane |  | Scheme F |
| Compound 1016 | 3,4-Dihydroxy-benzoic acid ethyl ester | 1-Bromo-2-methoxy-ethane |  | Scheme F |
| Compound 1017 | 5-Methoxy-2-nitro-benzoic acid |  |  | Scheme E |
| Compound 1018 | 5-Methoxy-2-nitro-benzoic acid |  |  | Scheme E |
| Compound 1019 | 5-Methoxy-2-nitro-benzoic acid |  |  | Scheme E |
| Compound 1020 | 5-Methoxy-2-nitro-benzoic acid |  |  | Scheme E |
| Compound 1021 | 5-Methoxy-2-nitro-benzoic acid |  |  | Scheme E |
| Compound 1022 | 5-Methoxy-2-nitro-benzoic acid |  |  | Scheme E |
| Compound 1023 | 5-Methoxy-2-nitro-benzoic acid |  |  | Scheme E |
| Compound 1024 | 5-Methoxy-2-nitro-benzoic acid |  |  | Scheme E |
| Compound 1025 | 5-Hydroxy-2-nitro-benzoic acid | 1-Bromo-2-methoxy-ethane |  | Scheme B |
| Compound 1026 | 5-Hydroxy-2-nitro-benzoic acid | 1-Bromo-2-methoxy-ethane |  | Scheme B |

TABLE 2-continued

| | A' | D | E | Reaction path |
|---|---|---|---|---|
| Compound 1027 | 5-Hydroxy-2-nitro-benzoic acid | 1-Bromo-2-methoxy-ethane | | Scheme B |
| Compound 1028 | 3,4-Dihydroxy-benzoic acid ethyl ester | 1-Bromo-2-methoxy-ethane | | Scheme F |
| Compound 1029 | 3,4-Dihydroxy-benzoic acid ethyl ester | 1-Bromo-2-methoxy-ethane | | Scheme F |
| Compound 1030 | 3,4-Dihydroxy-benzoic acid ethyl ester | 1-Bromo-2-methoxy-ethane | | Scheme F |
| Compound 1031 | 3,4-Dihydroxy-benzoic acid ethyl ester | 1-Bromo-2-methoxy-ethane | | Scheme F |
| Compound 1032 | 3,4-Dihydroxy-benzoic acid ethyl ester | 1-Bromo-2-methoxy-ethane | | Scheme F |
| Compound 1033 | 5-Hydroxy-2-nitro-benzoic acid | 1-Bromo-2-(2-methoxy-ethoxy)-ethane | | Scheme B |
| Compound 1034 | 5-Hydroxy-2-nitro-benzoic acid | 1-Bromo-2-(2-methoxy-ethoxy)-ethane | | Scheme B |
| Compound 1035 | 5-Hydroxy-2-nitro-benzoic acid | 1-Bromo-2-(2-methoxy-ethoxy)-ethane | | Scheme B |
| Compound 1036 | 5-Hydroxy-2-nitro-benzoic acid | 1-Bromo-2-(2-methoxy-ethoxy)-ethane | | Scheme B |
| Compound 1037 | 5-Hydroxy-2-nitro-benzoic acid | 1-Bromo-2-(2-methoxy-ethoxy)-ethane | | Scheme B |
| Compound 1038 | 5-Hydroxy-2-nitro-benzoic acid | 1-Bromo-3-chloropropane | Piperidine | Scheme C |
| Compound 1039 | 5-Hydroxy-2-nitro-benzoic acid | 1-Bromo-3-chloropropane | Piperidine | Scheme C |
| Compound 1040 | 5-Hydroxy-2-nitro-benzoic acid | 1-Bromo-3-chloropropane | Piperidine | Scheme C |
| Compound 1041 | 5-Hydroxy-2-nitro-benzoic acid | 1-Bromo-3-chloropropane | Piperidine | Scheme C |
| Compound 1042 | 5-Hydroxy-2-nitro-benzoic acid | 1-Bromo-2-chloroethane | Piperidine | Scheme C |
| Compound 1043 | 5-Hydroxy-2-nitro-benzoic acid | 1-Bromo-2-chloroethane | Piperidine | Scheme C |
| Compound 1044 | 5-Hydroxy-2-nitro-benzoic acid | 1-Bromo-2-chloroethane | Piperidine | Scheme C |
| Compound 1045 | 5-Hydroxy-2-nitro-benzoic acid | 1-Bromo-2-chloroethane | Piperidine | Scheme C |
| Compound 1046 | 5-Hydroxy-2-nitro-benzoic acid | Bromomethyl-cyclohexane | | Scheme B |
| Compound 1047 | 5-Hydroxy-2-nitro-benzoic acid | Bromomethyl-cyclohexane | | Scheme B |
| Compound 1048 | 5-Hydroxy-2-nitro-benzoic acid | Bromomethyl-cyclohexane | | Scheme B |
| Compound 1049 | 5-Hydroxy-2-nitro-benzoic acid | Bromomethyl-cyclohexane | | Scheme B |
| Compound 1050 | 5-Hydroxy-2-nitro-benzoic acid | Bromomethyl-cyclohexane | | Scheme B |
| Compound 1051 | 5-Hydroxy-2-nitro-benzoic acid | 1-Bromo-4-fluoro-butane | | Scheme B |
| Compound 1052 | 5-Hydroxy-2-nitro-benzoic acid | 1-Bromo-4-fluoro-butane | | Scheme B |
| Compound 1053 | 5-Hydroxy-2-nitro-benzoic acid | 1-Bromo-4-fluoro-butane | | Scheme B |
| Compound 1054 | 5-Hydroxy-2-nitro-benzoic acid | 1-Bromo-4-fluoro-butane | | Scheme B |
| Compound 1055 | 5-Hydroxy-2-nitro-benzoic acid | 1-Bromo-4-fluoro-butane | | Scheme B |
| Compound 1057 | 5-Hydroxy-2-nitro-benzoic acid | 1-Bromo-4-fluoro-butane | | Scheme B |
| Compound 1058 | 5-Hydroxy-2-nitro-benzoic acid | 1-Bromo-4-fluoro-butane | | Scheme B |
| Compound 1059 | 5-Hydroxy-2-nitro-benzoic acid | 1-Bromo-4-fluoro-butane | | Scheme B |
| Compound 1060 | 5-Hydroxy-2-nitro-benzoic acid | 1-Bromo-4-fluoro-butane | | Scheme B |
| Compound 1061 | 5-Hydroxy-2-nitro-benzoic acid | 1-Bromo-4-fluoro-butane | | Scheme B |

TABLE 2-continued

| | A' | D | E | Reaction path |
|---|---|---|---|---|
| Compound 1062 | 5-Chloro-2-nitro-benzoic acid | 4-Hydroxy-piperidine | | Scheme A |
| Compound 1063 | 5-Chloro-2-nitro-benzoic acid | 4-Piperidine-methanol | | Scheme A |
| Compound 1064 | 5-Chloro-2-nitro-benzoic acid | Morpholine | | Scheme A |
| Compound 1065 | 5-Chloro-2-nitro-benzoic acid | Morpholine | | Scheme A |
| Compound 1066 | 5-Chloro-2-nitro-benzoic acid | Morpholine | | Scheme A |
| Compound 1067 | 5-Chloro-2-nitro-benzoic acid | 4-Piperidino-piperidine | | Scheme A |
| Compound 1068 | 5-Chloro-2-nitro-benzoic acid | 4-Piperidino-piperidine | | Scheme A |
| Compound 1069 | 5-Chloro-2-nitro-benzoic acid | 4-Methylpiperidine | | Scheme A |
| Compound 1070 | 5-Chloro-2-nitro-benzoic acid | 4-Methylpiperidine | | Scheme A |
| Compound 1071 | 5-Chloro-2-nitro-benzoic acid | 4-Methylpiperidine | | Scheme A |
| Compound 1072 | 5-Chloro-2-nitro-benzoic acid | 4-Methylpiperazine | | Scheme A |
| Compound 1073 | 5-Chloro-2-nitro-benzoic acid | 4-Methylpiperazine | | Scheme A |
| Compound 1074 | 5-Chloro-2-nitro-benzoic acid | Morpholine | | Scheme A |
| Compound 1075 | 5-Chloro-2-nitro-benzoic acid | Morpholine | | Scheme A |
| Compound 1076 | 5-Chloro-2-nitro-benzoic acid | Morpholine | | Scheme A |

TABLE 3

Structures of compounds 1 to 1077 are shown in Table 3.

| Compound No. | Chemical structural formula |
|---|---|
| Compound 1 | 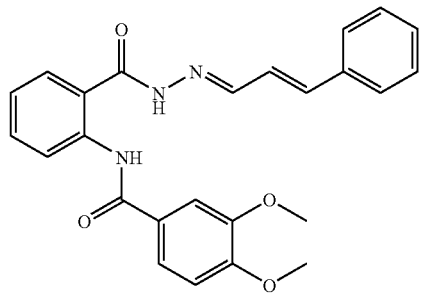 |
| Compound 2 | 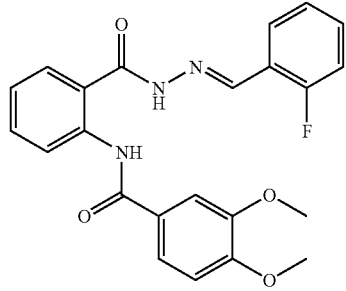 |

TABLE 3-continued
Structures of compounds 1 to 1077 are shown in Table 3.
| Compound No. | Chemical structural formula |
|---|---|
| Compound 3 | 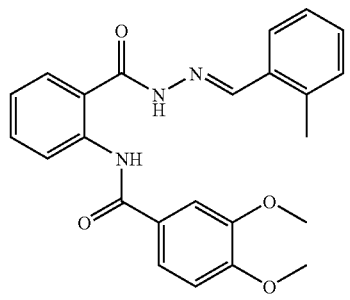 |
| Compound 4 | 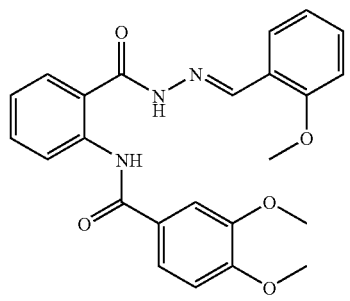 |
| Compound 5 | 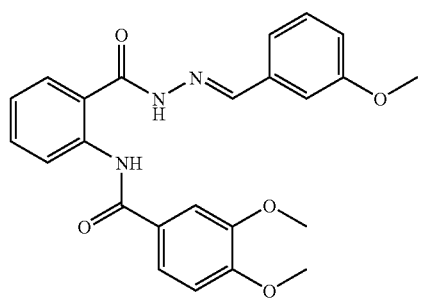 |
| Compound 6 | 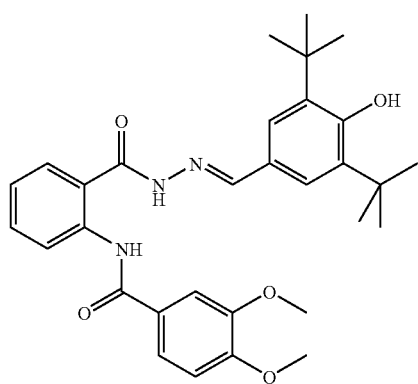 |

TABLE 3-continued
Structures of compounds 1 to 1077 are shown in Table 3.
| Compound No. | Chemical structural formula |
| --- | --- |
| Compound 7 | 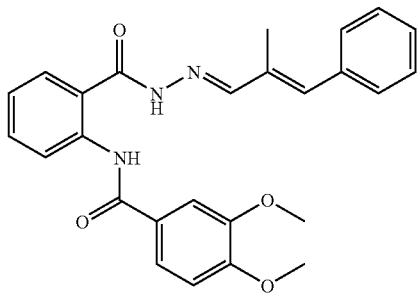 |
| Compound 8 | 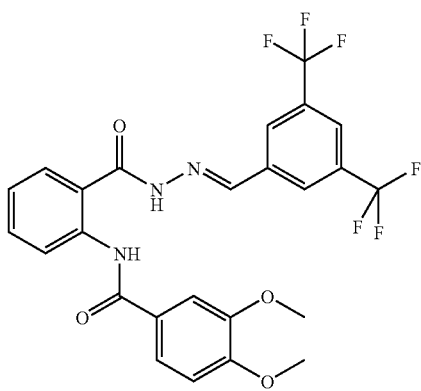 |
| Compound 9 | 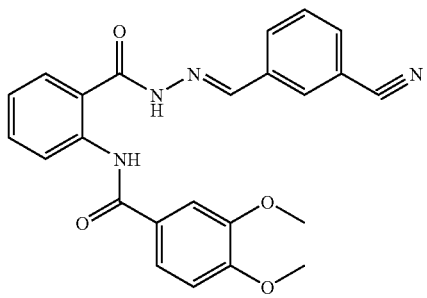 |
| Compound 10 | 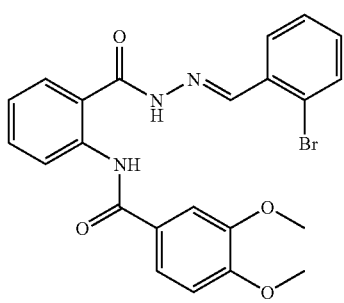 |

TABLE 3-continued
Structures of compounds 1 to 1077 are shown in Table 3.
| Compound No. | Chemical structural formula |
|---|---|
| Compound 11 | 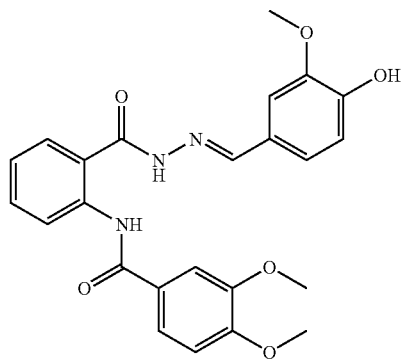 |
| Compound 12 | 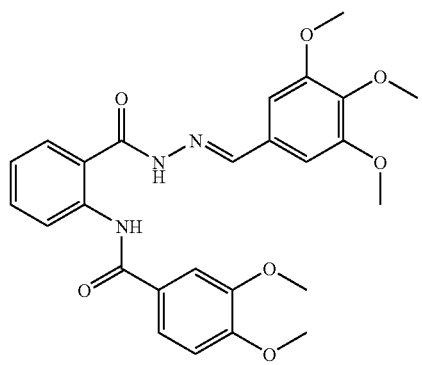 |
| Compound 13 | 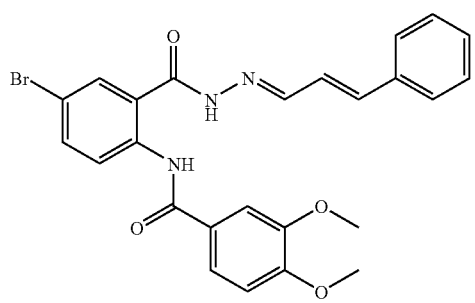 |
| Compound 14 | 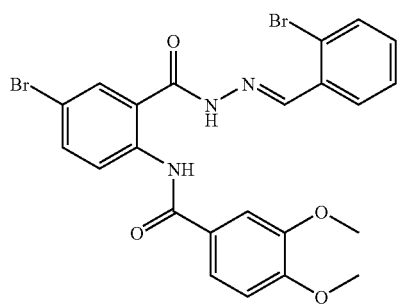 |

TABLE 3-continued

Structures of compounds 1 to 1077 are shown in Table 3.

| Compound No. | Chemical structural formula |
| --- | --- |
| Compound 15 | |
| Compound 16 | |
| Compound 17 | |
| Compound 18 | |
| Compound 19 | |

TABLE 3-continued
Structures of compounds 1 to 1077 are shown in Table 3.
| Compound No. | Chemical structural formula |
|---|---|
| Compound 20 | 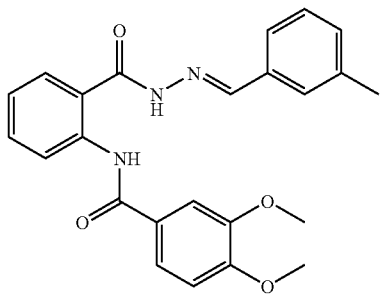 |
| Compound 21 | 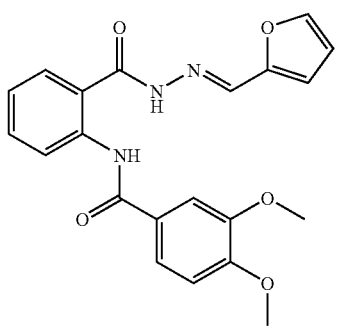 |
| Compound 22 | 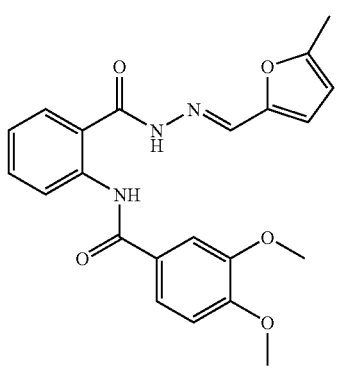 |
| Compound 23 | 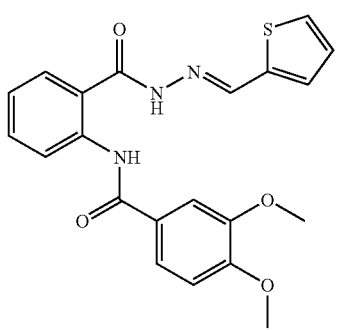 |

TABLE 3-continued
Structures of compounds 1 to 1077 are shown in Table 3.
| Compound No. | Chemical structural formula |
| --- | --- |
| Compound 24 | 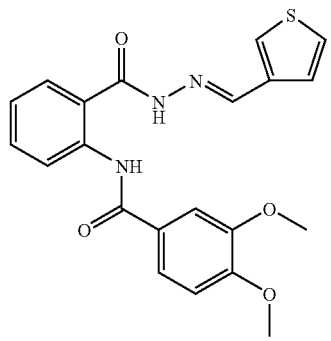 |
| Compound 25 | 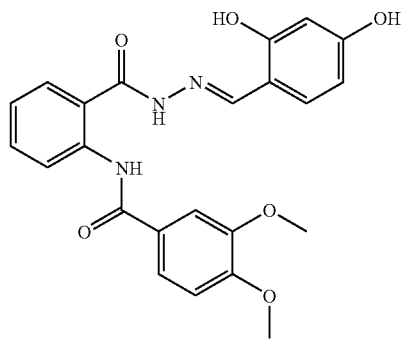 |
| Compound 26 |  |
| Compound 27 | 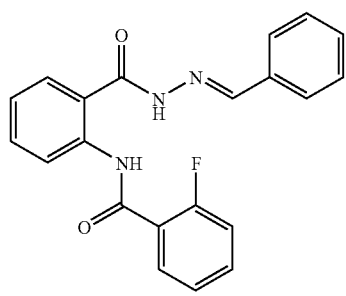 |

TABLE 3-continued
Structures of compounds 1 to 1077 are shown in Table 3.
| Compound No. | Chemical structural formula |
|---|---|
| Compound 28 | 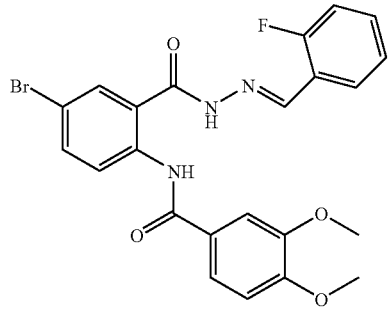 |
| Compound 29 | 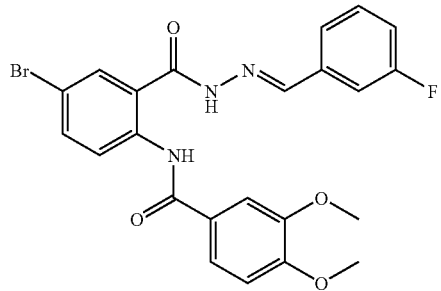 |
| Compound 30 | 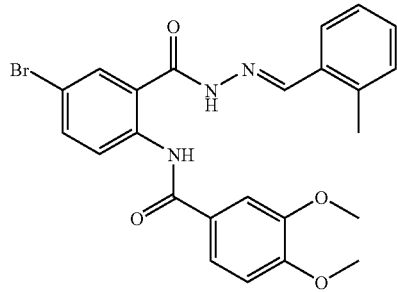 |
| Compound 31 | 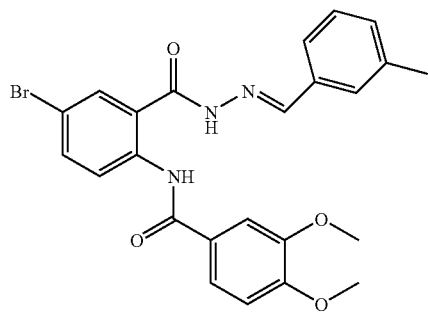 |

TABLE 3-continued
Structures of compounds 1 to 1077 are shown in Table 3.
| Compound No. | Chemical structural formula |
|---|---|
| Compound 32 | 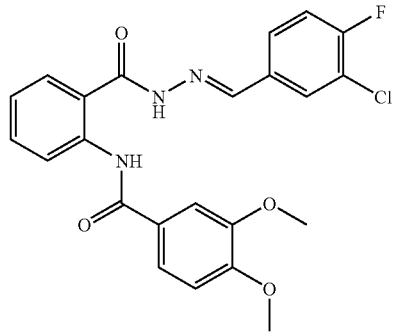 |
| Compound 33 | 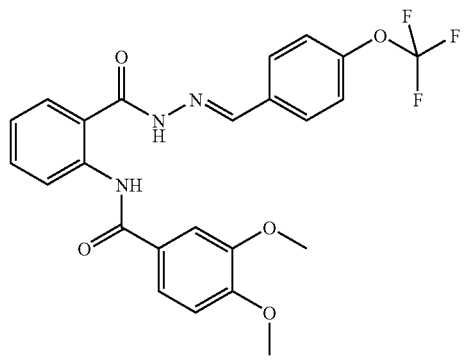 |
| Compound 34 | 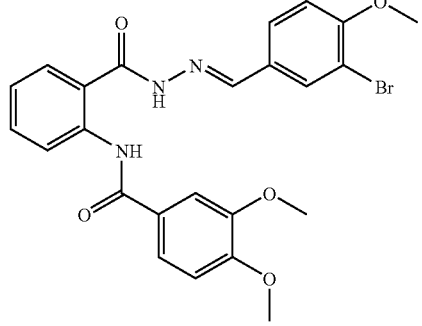 |
| Compound 35 | 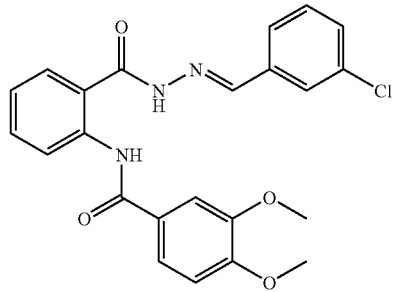 |

TABLE 3-continued
Structures of compounds 1 to 1077 are shown in Table 3.
| Compound No. | Chemical structural formula |
| --- | --- |
| Compound 36 | 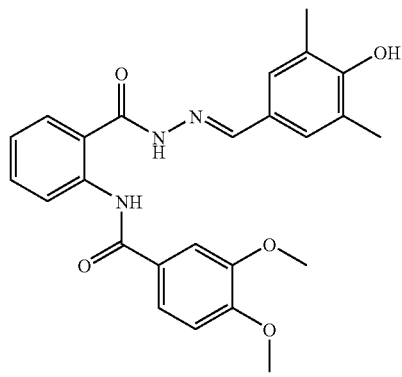 |
| Compound 37 | 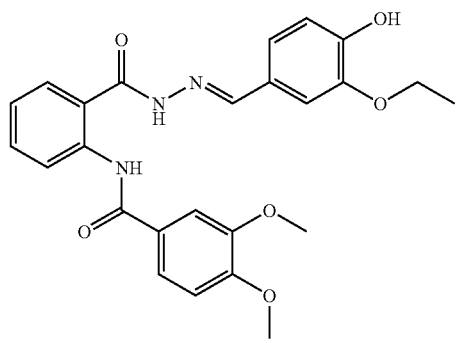 |
| Compound 38 | 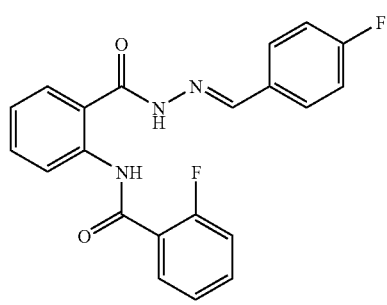 |
| Compound 39 | 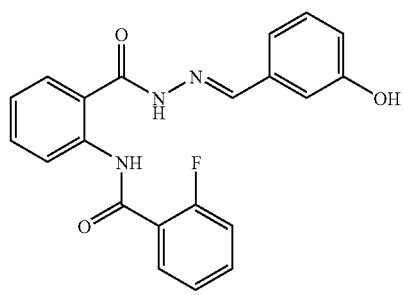 |

TABLE 3-continued
Structures of compounds 1 to 1077 are shown in Table 3.
| Compound No. | Chemical structural formula |
|---|---|
| Compound 40 | 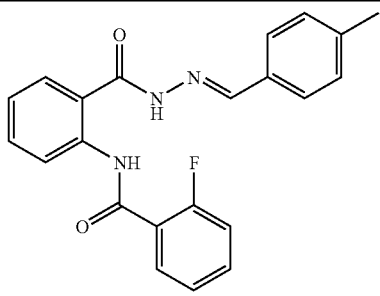 |
| Compound 41 | 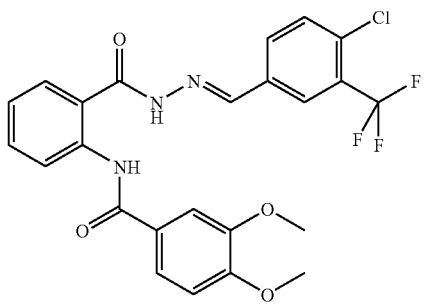 |
| Compound 42 | 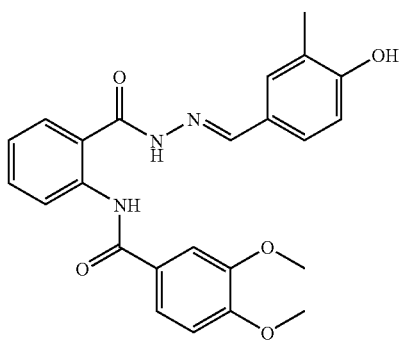 |
| Compound 43 | 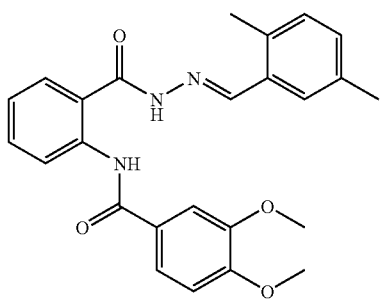 |
| Compound 44 | 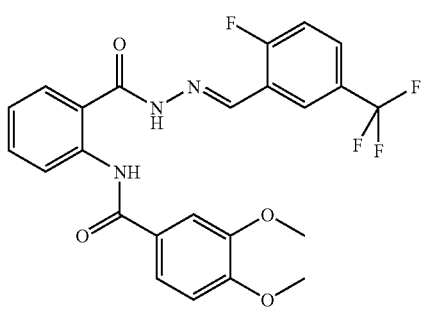 |

TABLE 3-continued
Structures of compounds 1 to 1077 are shown in Table 3.
| Compound No. | Chemical structural formula |
|---|---|
| Compound 45 | 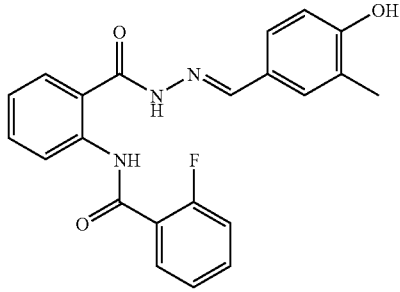 |
| Compound 46 | 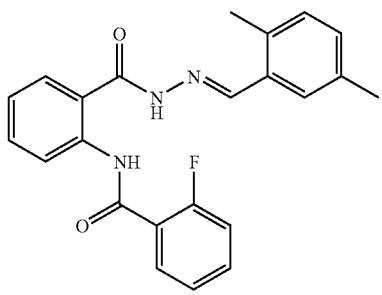 |
| Compound 47 | 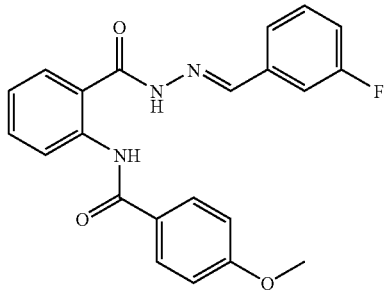 |
| Compound 48 | 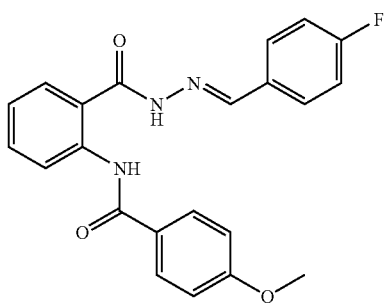 |
| Compound 49 | 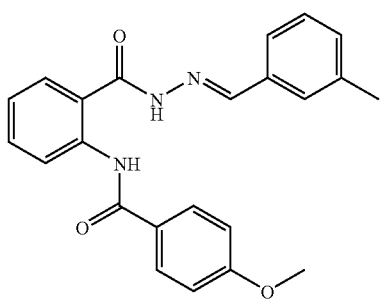 |

TABLE 3-continued

Structures of compounds 1 to 1077 are shown in Table 3.

| Compound No. | Chemical structural formula |
|---|---|
| Compound 50 | |
| Compound 51 | |
| Compound 52 | |
| Compound 53 | |
| Compound 54 | |

TABLE 3-continued
Structures of compounds 1 to 1077 are shown in Table 3.
| Compound No. | Chemical structural formula |
|---|---|
| Compound 55 | 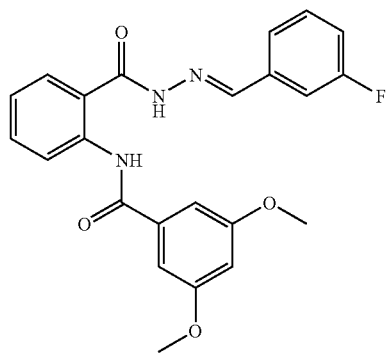 |
| Compound 56 | 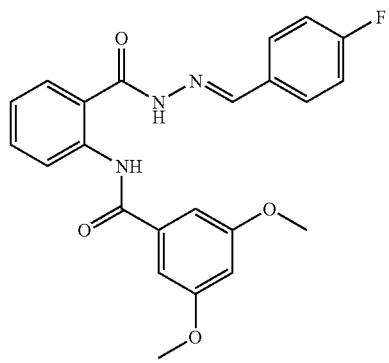 |
| Compound 57 | 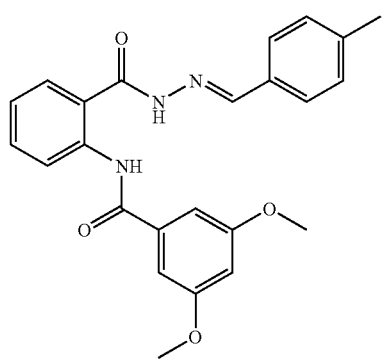 |
| Compound 58 | 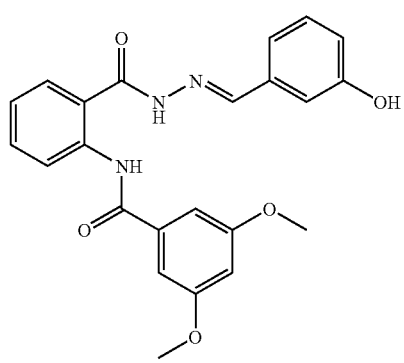 |

TABLE 3-continued
Structures of compounds 1 to 1077 are shown in Table 3.
| Compound No. | Chemical structural formula |
|---|---|
| Compound 59 | 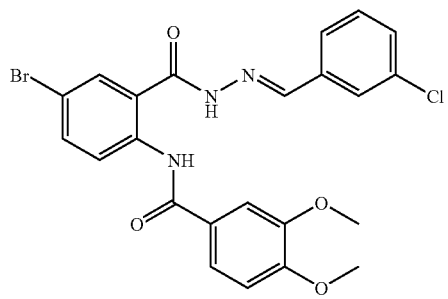 |
| Compound 60 | 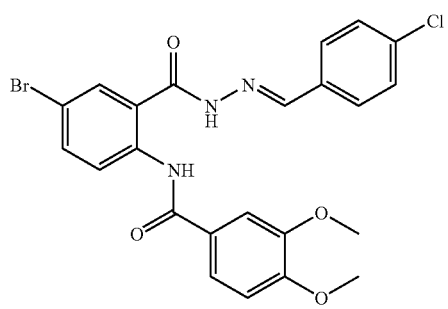 |
| Compound 61 | 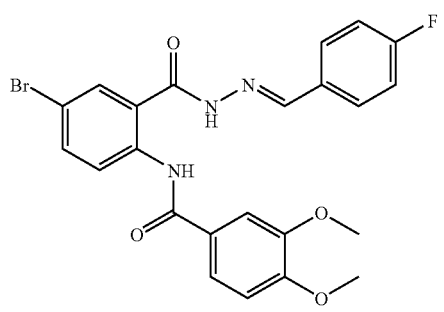 |
| Compound 62 | 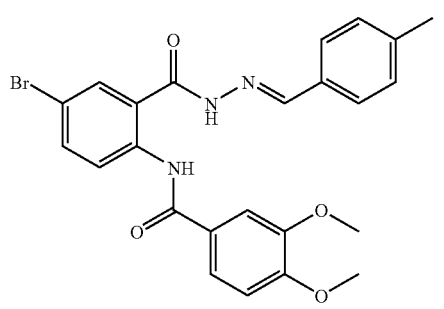 |
| Compound 63 | 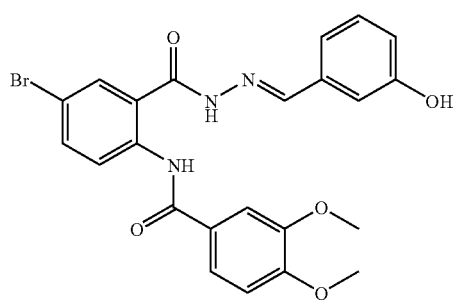 |

TABLE 3-continued
Structures of compounds 1 to 1077 are shown in Table 3.
| Compound No. | Chemical structural formula |
|---|---|
| Compound 64 | 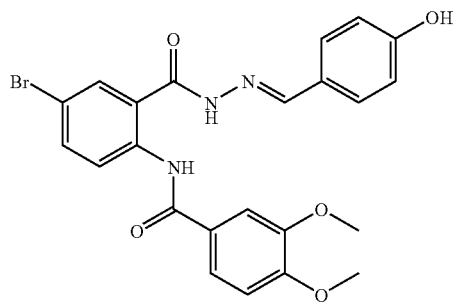 |
| Compound 65 | 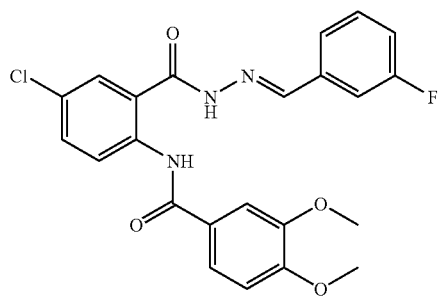 |
| Compound 66 | 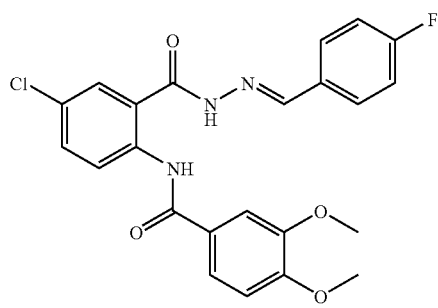 |
| Compound 67 | 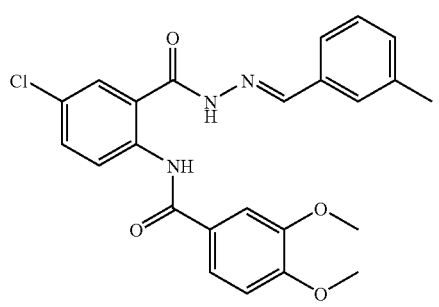 |
| Compound 68 | 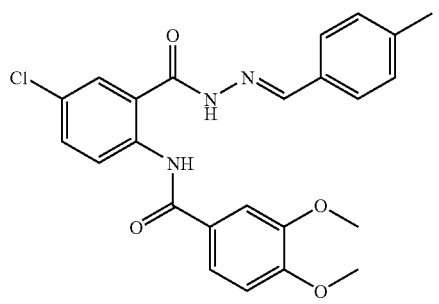 |

TABLE 3-continued
Structures of compounds 1 to 1077 are shown in Table 3.
| Compound No. | Chemical structural formula |
| --- | --- |
| Compound 69 | 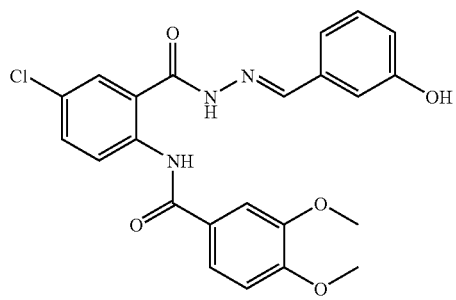 |
| Compound 70 | 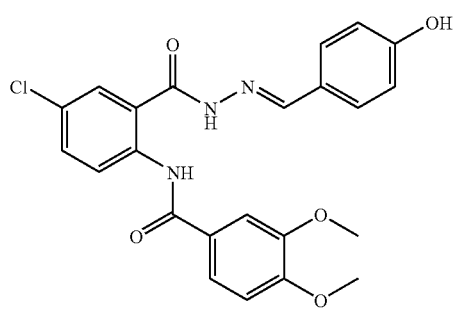 |
| Compound 71 | 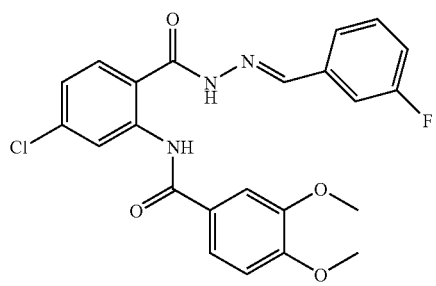 |
| Compound 72 | 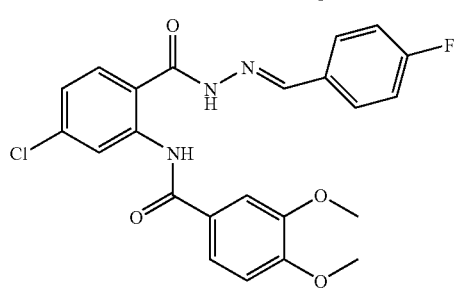 |
| Compound 73 | 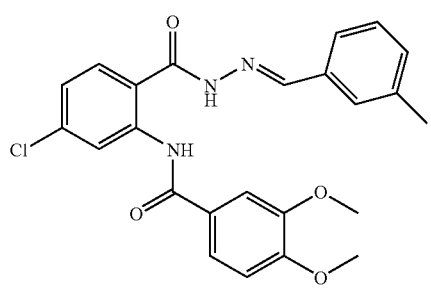 |

TABLE 3-continued
Structures of compounds 1 to 1077 are shown in Table 3.
| Compound No. | Chemical structural formula |
|---|---|
| Compound 74 | 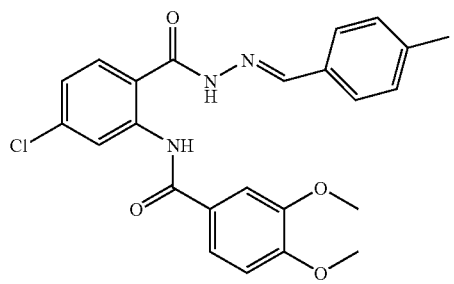 |
| Compound 75 | 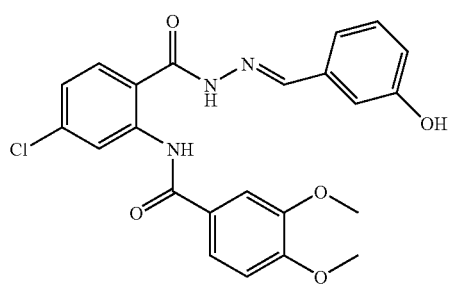 |
| Compound 76 | 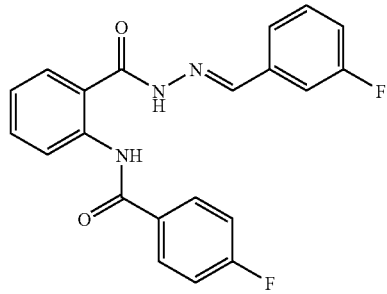 |
| Compound 77 | 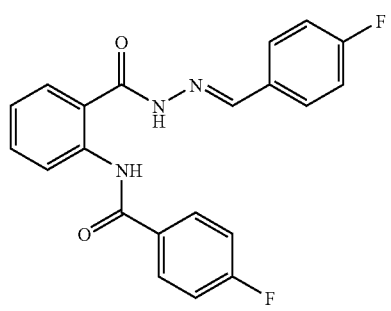 |
| Compound 78 | 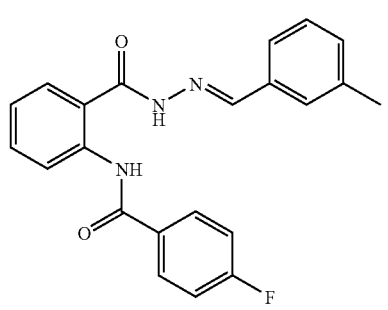 |

TABLE 3-continued
Structures of compounds 1 to 1077 are shown in Table 3.
| Compound No. | Chemical structural formula |
|---|---|
| Compound 79 | 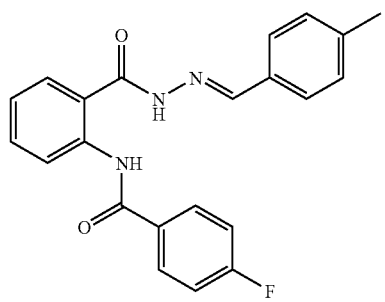 |
| Compound 80 | 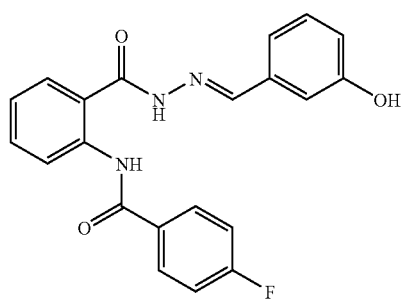 |
| Compound 81 | 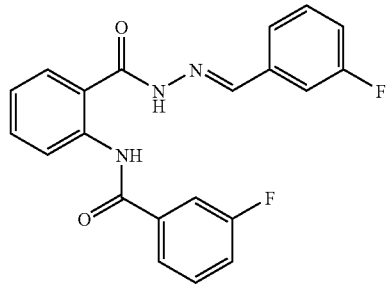 |
| Compound 82 | 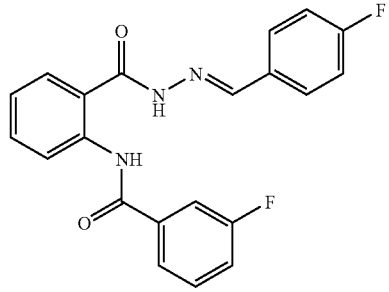 |
| Compound 83 | 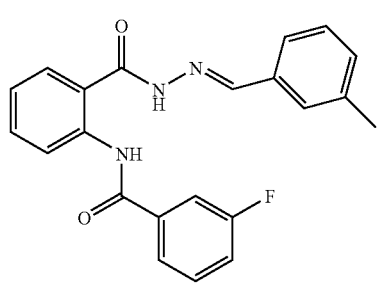 |

TABLE 3-continued
Structures of compounds 1 to 1077 are shown in Table 3.
| Compound No. | Chemical structural formula |
| --- | --- |
| Compound 84 | 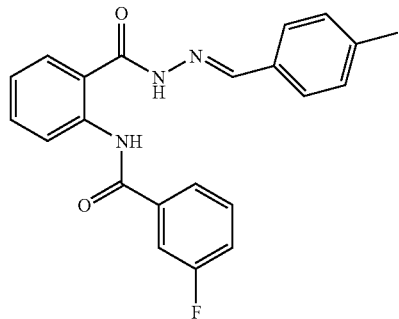 |
| Compound 85 | 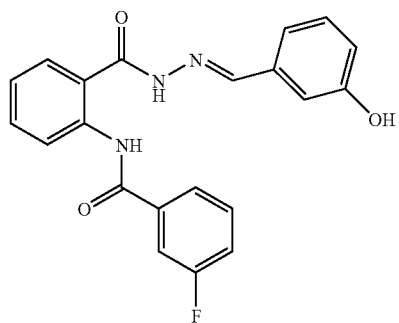 |
| Compound 86 | 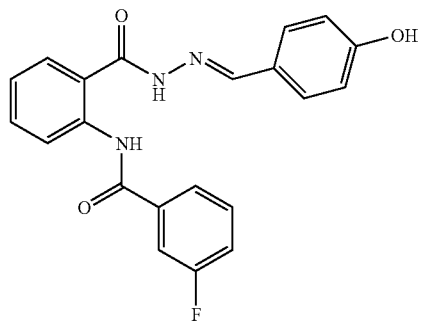 |
| Compound 87 | 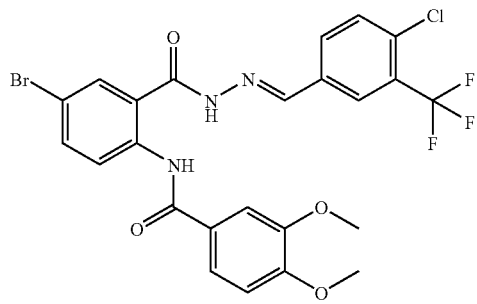 |
| Compound 88 | 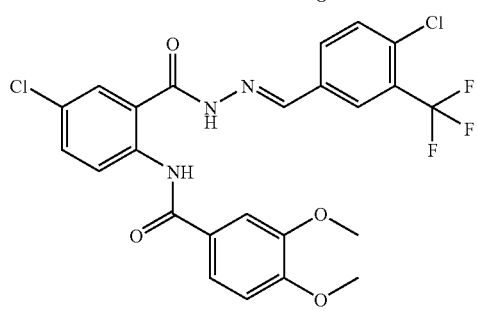 |

TABLE 3-continued
Structures of compounds 1 to 1077 are shown in Table 3.
| Compound No. | Chemical structural formula |
|---|---|
| Compound 89 | 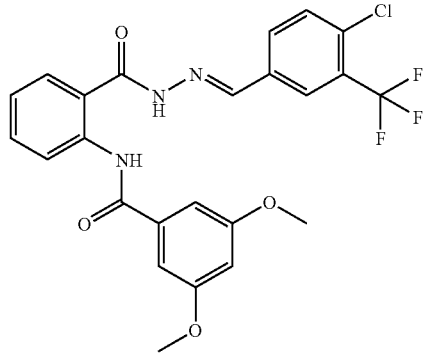 |
| Compound 90 | 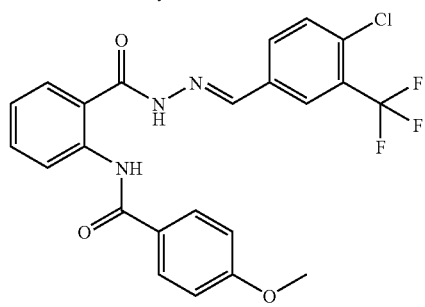 |
| Compound 91 | 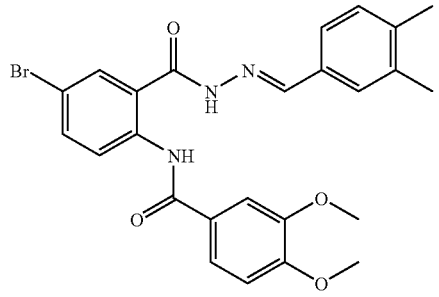 |
| Compound 92 |  |
| Compound 93 | 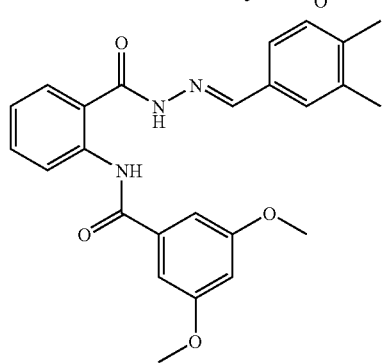 |

TABLE 3-continued
Structures of compounds 1 to 1077 are shown in Table 3.
| Compound No. | Chemical structural formula |
|---|---|
| Compound 94 | 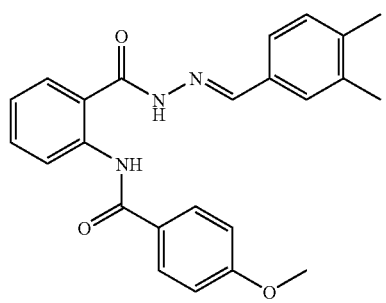 |
| Compound 95 | 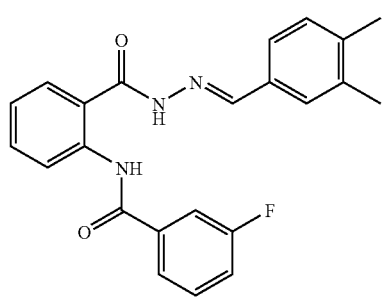 |
| Compound 96 | 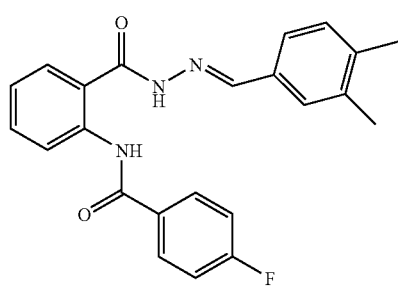 |
| Compound 97 | 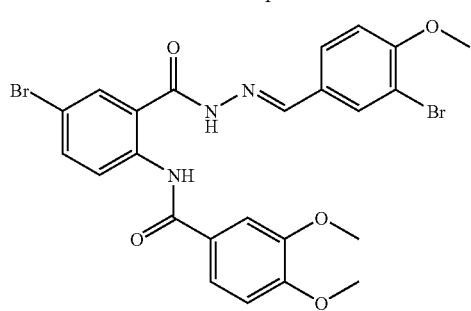 |
| Compound 98 | 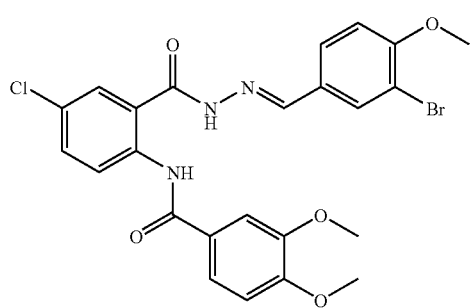 |

TABLE 3-continued
Structures of compounds 1 to 1077 are shown in Table 3.
| Compound No. | Chemical structural formula |
|---|---|
| Compound 99 | 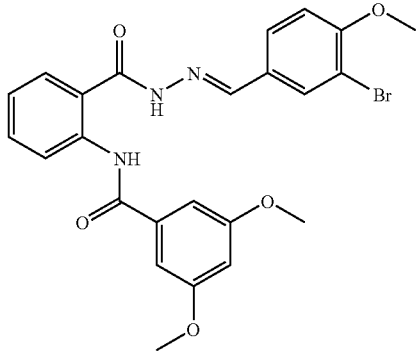 |
| Compound 100 | 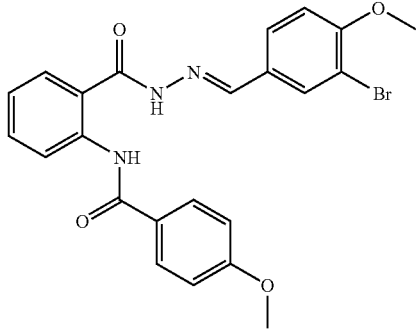 |
| Compound 101 | 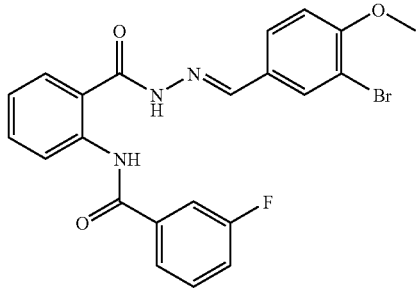 |
| Compound 102 | 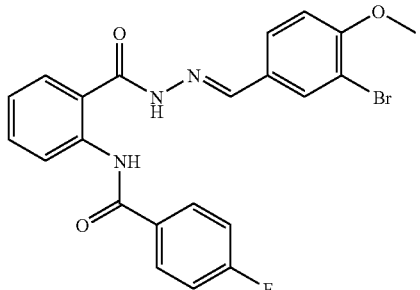 |
| Compound 103 | 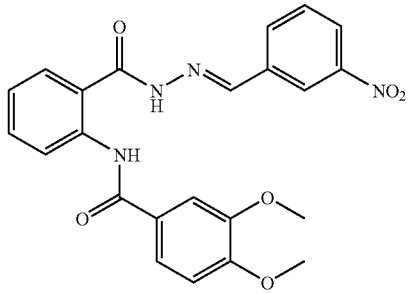 |

TABLE 3-continued
Structures of compounds 1 to 1077 are shown in Table 3.
| Compound No. | Chemical structural formula |
|---|---|
| Compound 104 | 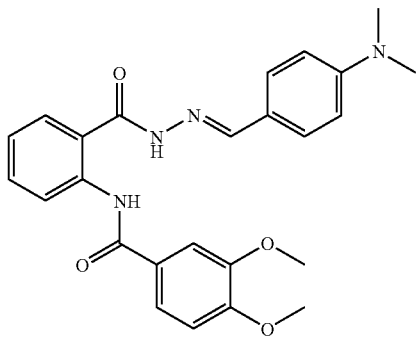 |
| Compound 105 | 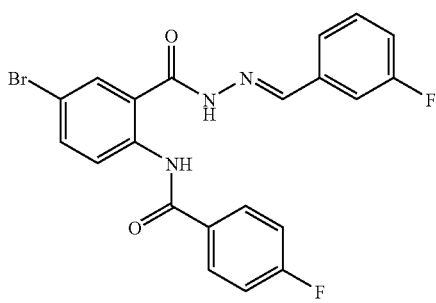 |
| Compound 106 | 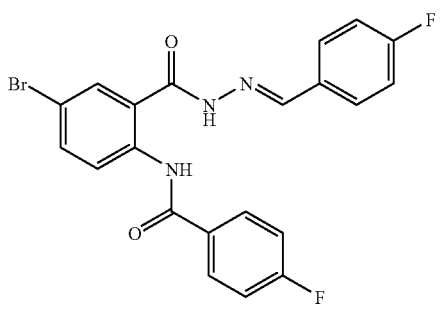 |
| Compound 107 | 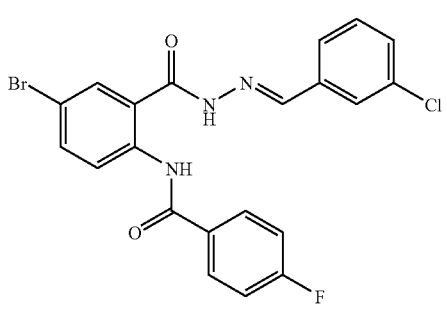 |
| Compound 108 | 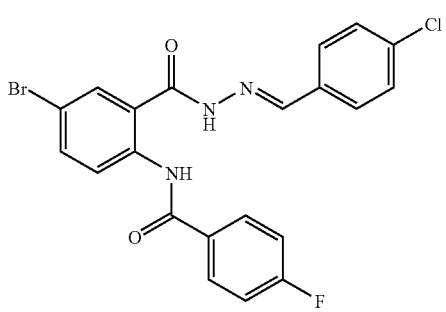 |

413 414
TABLE 3-continued
Structures of compounds 1 to 1077 are shown in Table 3.
| Compound No. | Chemical structural formula |
|---|---|
| Compound 109 | 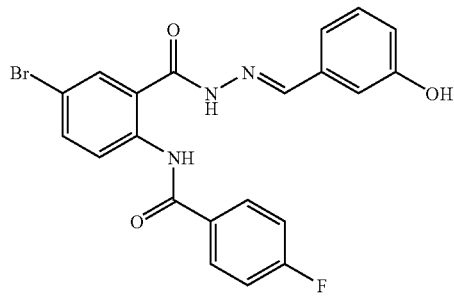 |
| Compound 110 | 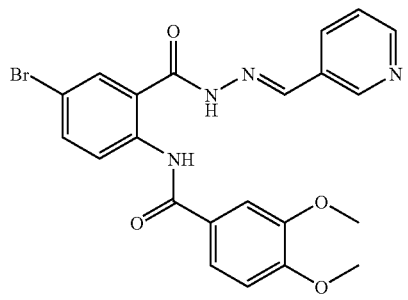 |
| Compound 111 | 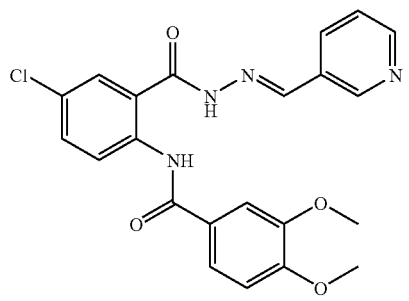 |
| Compound 112 | 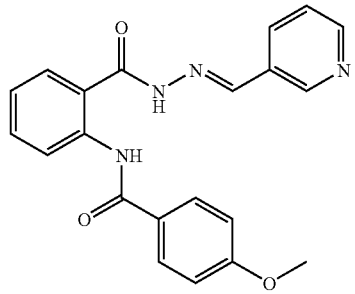 |
| Compound 113 | 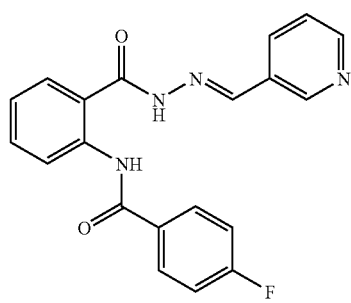 |

TABLE 3-continued
Structures of compounds 1 to 1077 are shown in Table 3.
| Compound No. | Chemical structural formula |
|---|---|
| Compound 114 | 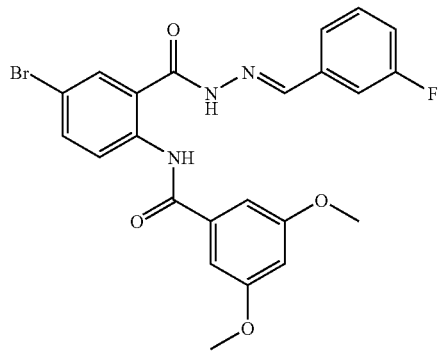 |
| Compound 115 | 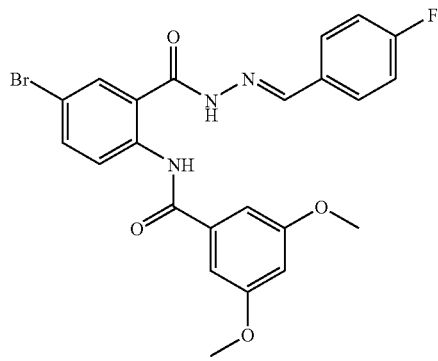 |
| Compound 116 | 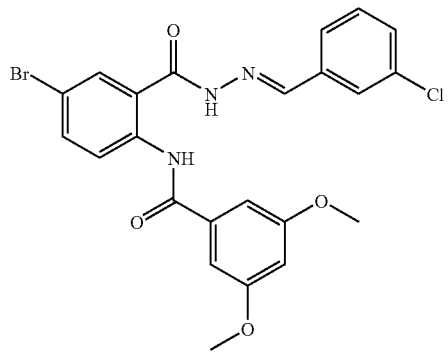 |
| Compound 117 | 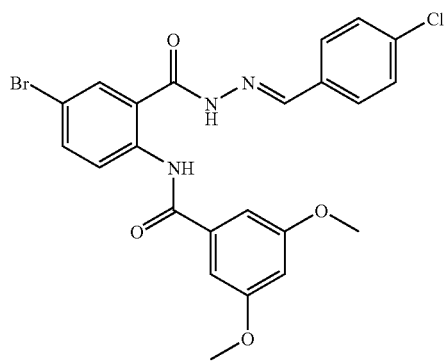 |

TABLE 3-continued
Structures of compounds 1 to 1077 are shown in Table 3.
| Compound No. | Chemical structural formula |
| --- | --- |
| Compound 118 | 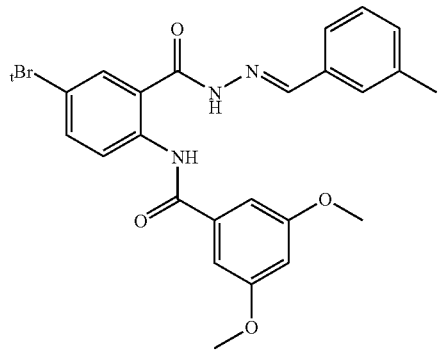 |
| Compound 119 | 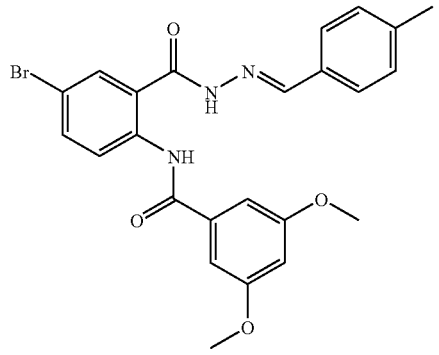 |
| Compound 120 | 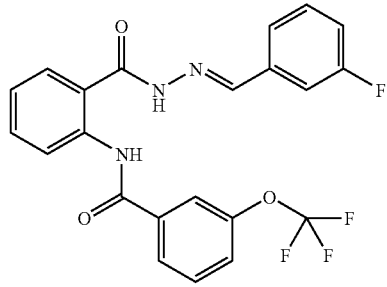 |
| Compound 121 | 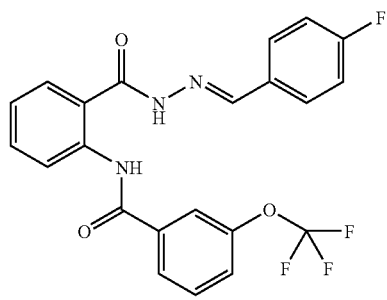 |
| Compound 122 | 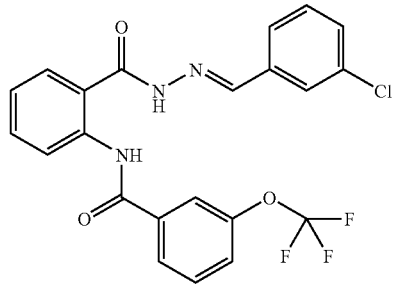 |

US 8,134,015 B2
419                                                                 420
TABLE 3-continued
Structures of compounds 1 to 1077 are shown in Table 3.
| Compound No. | Chemical structural formula |
|---|---|
| Compound 123 | 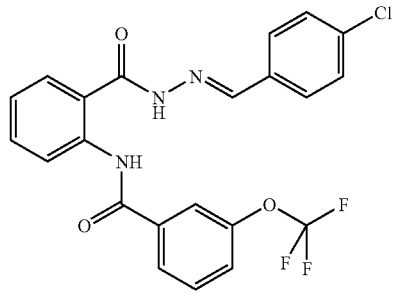 |
| Compound 124 | 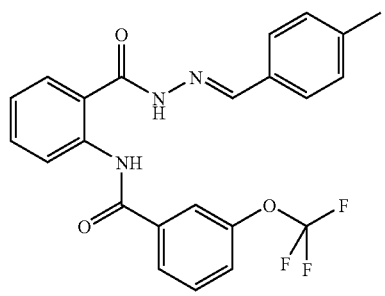 |
| Compound 125 | 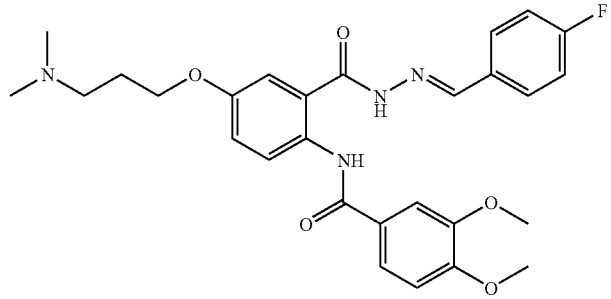 |
| Compound 126 | 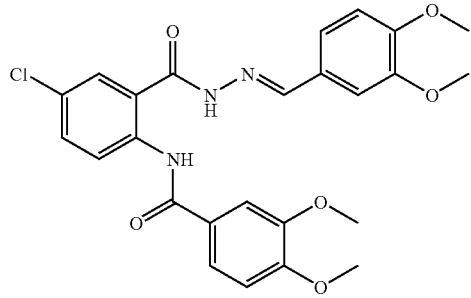 |
| Compound 127 | 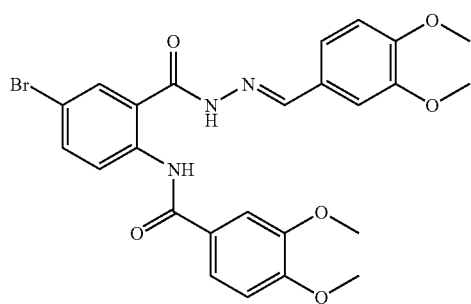 |

TABLE 3-continued
Structures of compounds 1 to 1077 are shown in Table 3.
| Compound No. | Chemical structural formula |
| --- | --- |
| Compound 128 | 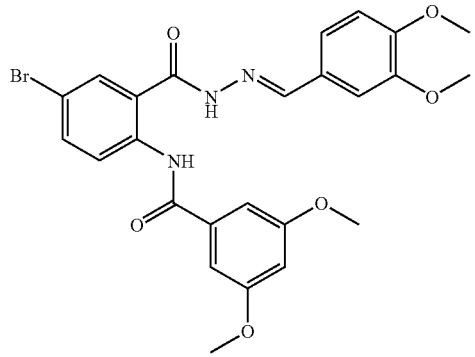 |
| Compound 129 | 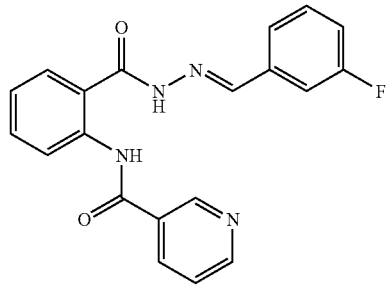 |
| Compound 130 | 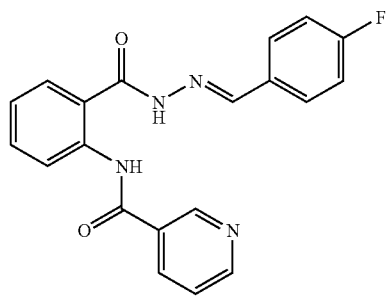 |
| Compound 131 | 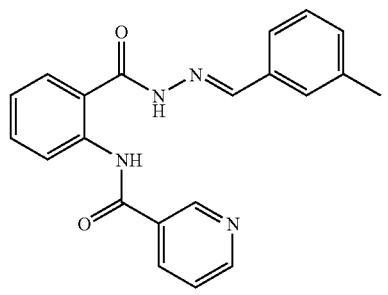 |
| Compound 132 | 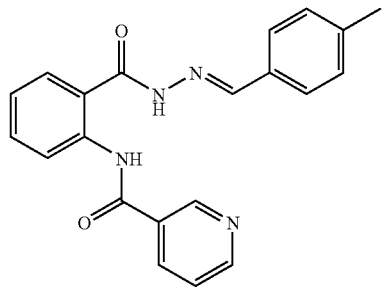 |

TABLE 3-continued
Structures of compounds 1 to 1077 are shown in Table 3.
| Compound No. | Chemical structural formula |
| --- | --- |
| Compound 133 | 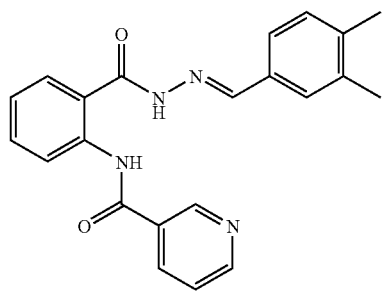 |
| Compound 134 | 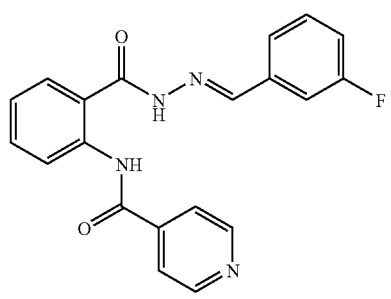 |
| Compound 135 | 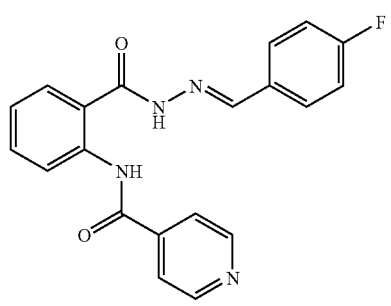 |
| Compound 136 | 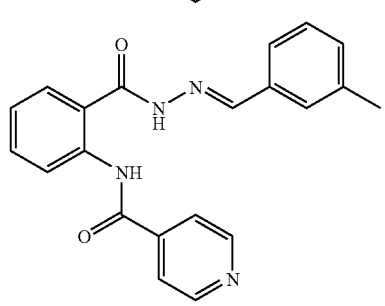 |
| Compound 137 | 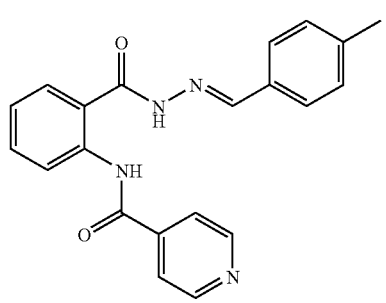 |

TABLE 3-continued
Structures of compounds 1 to 1077 are shown in Table 3.
| Compound No. | Chemical structural formula |
|---|---|
| Compound 138 | 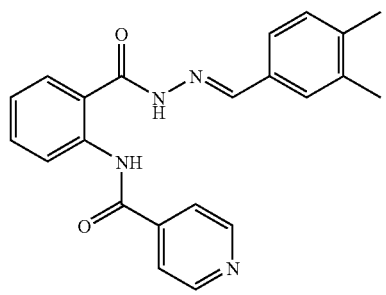 |
| Compound 139 | 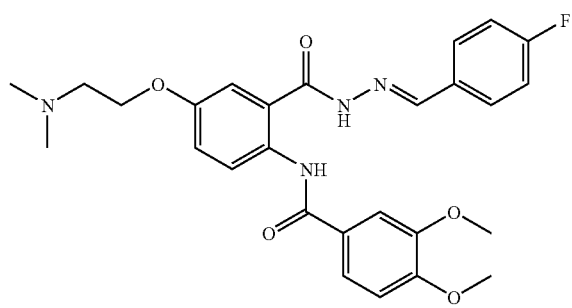 |
| Compound 140 | 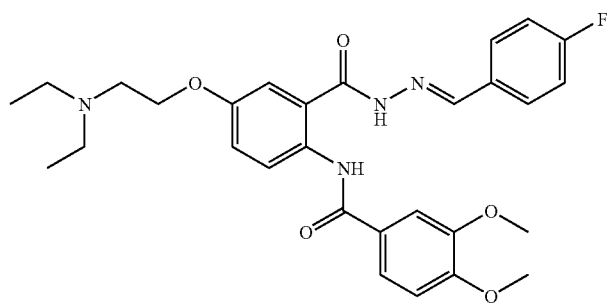 |
| Compound 141 | 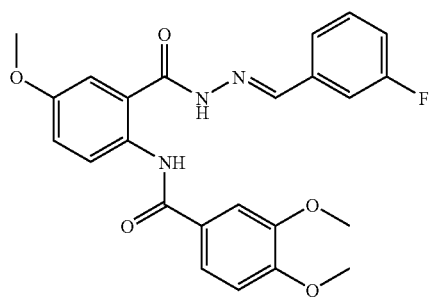 |
| Compound 142 | 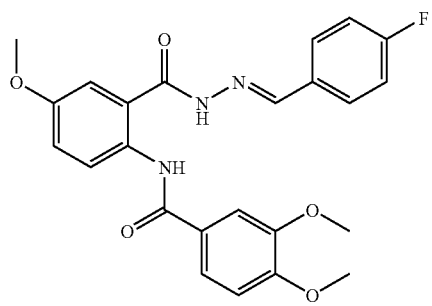 |

TABLE 3-continued
Structures of compounds 1 to 1077 are shown in Table 3.
| Compound No. | Chemical structural formula |
|---|---|
| Compound 143 | 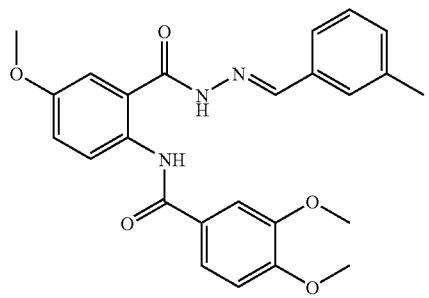 |
| Compound 144 | 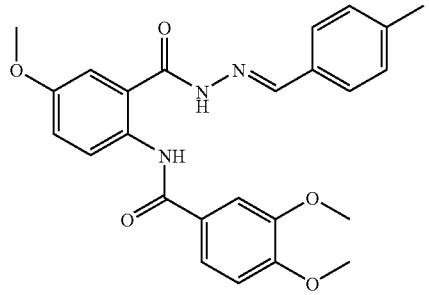 |
| Compound 145 | 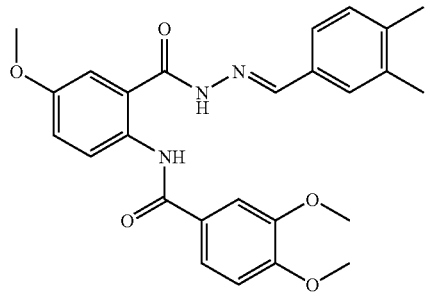 |
| Compound 146 | 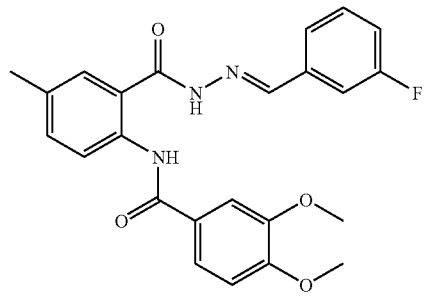 |
| Compound 147 | 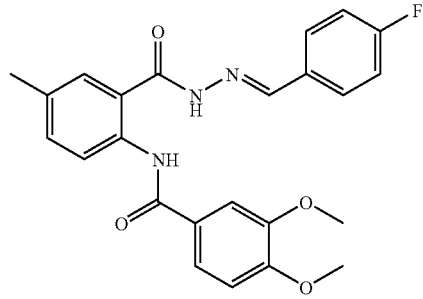 |

TABLE 3-continued
Structures of compounds 1 to 1077 are shown in Table 3.
| Compound No. | Chemical structural formula |
|---|---|
| Compound 148 | 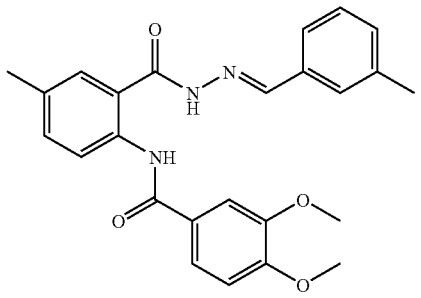 |
| Compound 149 | 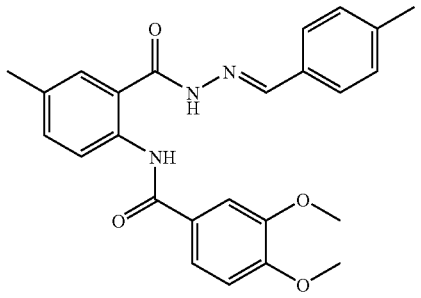 |
| Compound 150 | 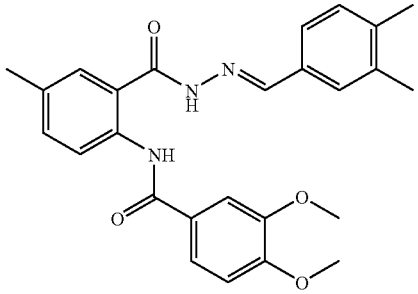 |
| Compound 151 | 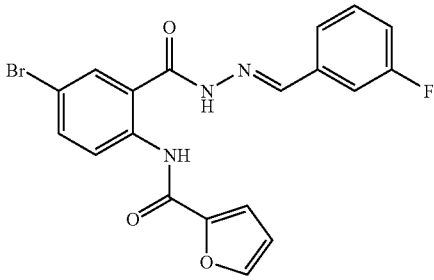 |
| Compound 152 | 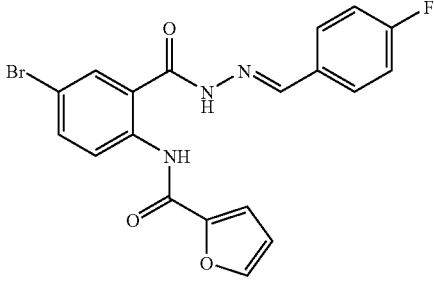 |

TABLE 3-continued
Structures of compounds 1 to 1077 are shown in Table 3.
| Compound No. | Chemical structural formula |
| --- | --- |
| Compound 153 | 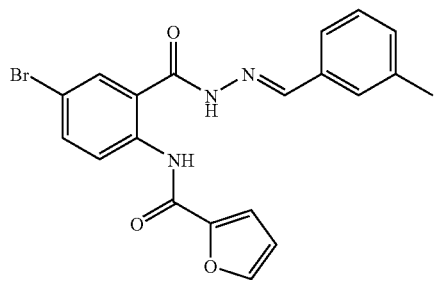 |
| Compound 154 | 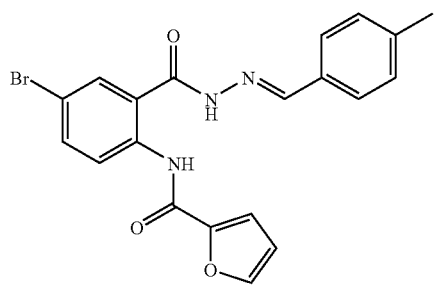 |
| Compound 155 | 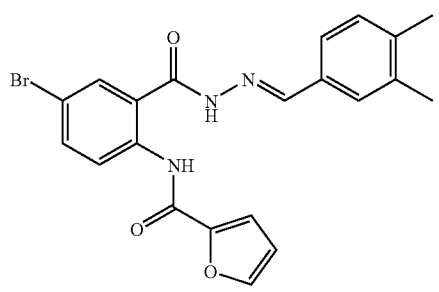 |
| Compound 156 | 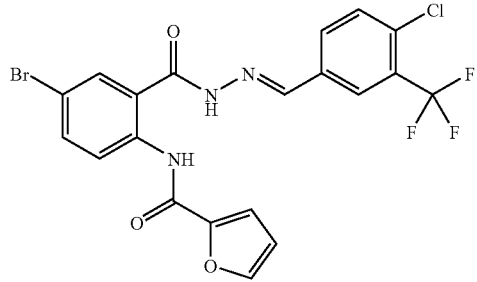 |
| Compound 157 | 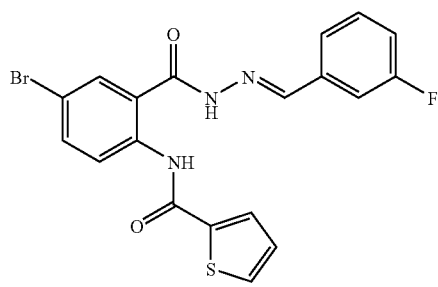 |

TABLE 3-continued
Structures of compounds 1 to 1077 are shown in Table 3.
| Compound No. | Chemical structural formula |
| --- | --- |
| Compound 158 | 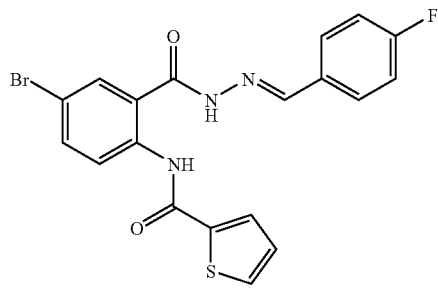 |
| Compound 159 | 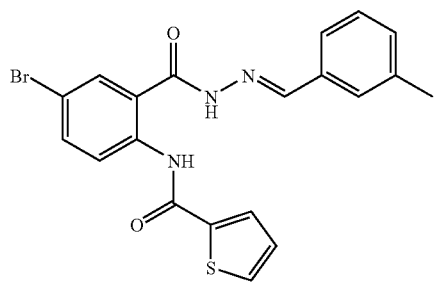 |
| Compound 160 | 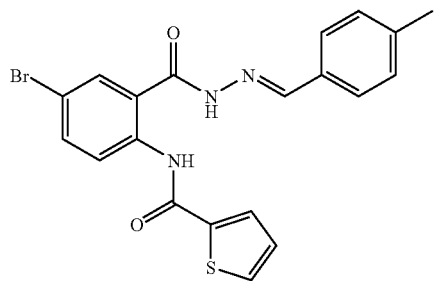 |
| Compound 161 | 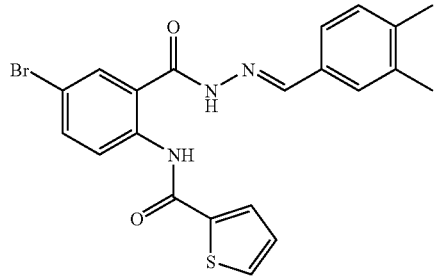 |
| Compound 162 | 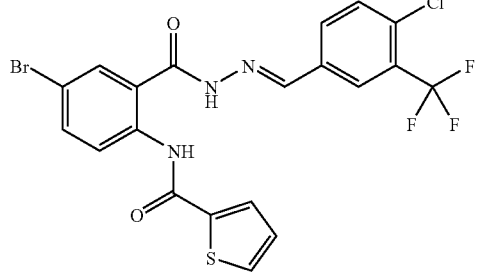 |

TABLE 3-continued
Structures of compounds 1 to 1077 are shown in Table 3.
| Compound No. | Chemical structural formula |
| --- | --- |
| Compound 163 | 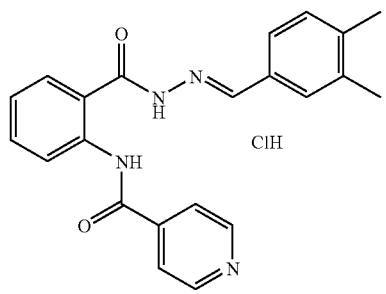 |
| Compound 164 | 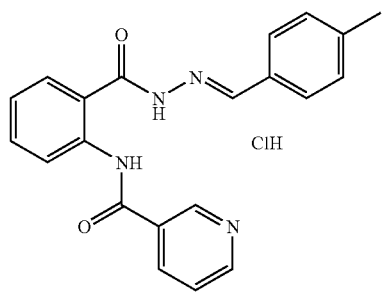 |
| Compound 165 | 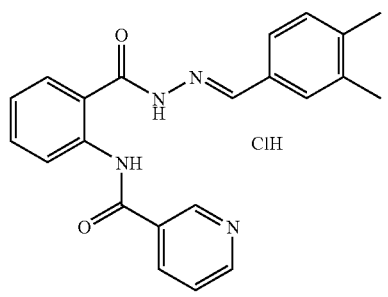 |
| Compound 166 | 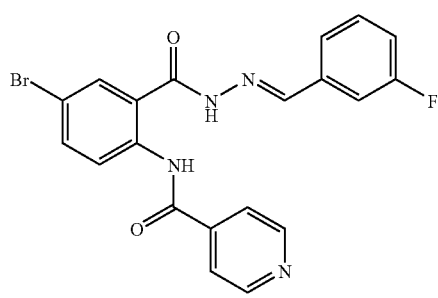 |
| Compound 167 | 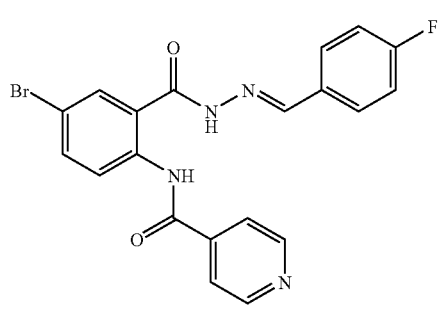 |

TABLE 3-continued

Structures of compounds 1 to 1077 are shown in Table 3.

| Compound No. | Chemical structural formula |
|---|---|
| Compound 168 | |
| Compound 169 | |
| Compound 170 | |
| Compound 171 | |
| Compound 172 | |

TABLE 3-continued

Structures of compounds 1 to 1077 are shown in Table 3.

| Compound No. | Chemical structural formula |
| --- | --- |
| Compound 173 | |
| Compound 174 | |
| Compound 175 | |
| Compound 176 | |
| Compound 177 | |

US 8,134,015 B2
441                                                                      442
TABLE 3-continued
Structures of compounds 1 to 1077 are shown in Table 3.
| Compound No. | Chemical structural formula |
|---|---|
| Compound 178 | 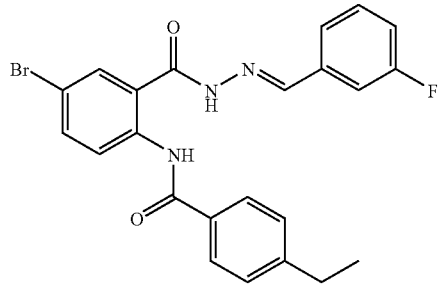 |
| Compound 179 | 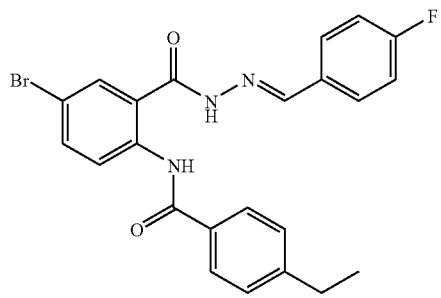 |
| Compound 180 | 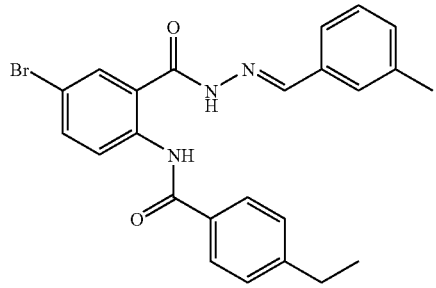 |
| Compound 181 | 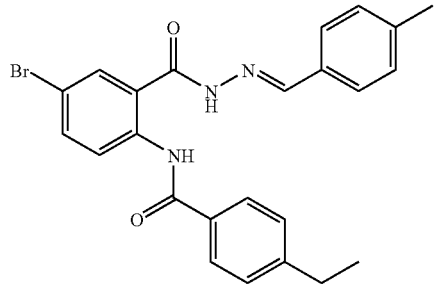 |
| Compound 182 | 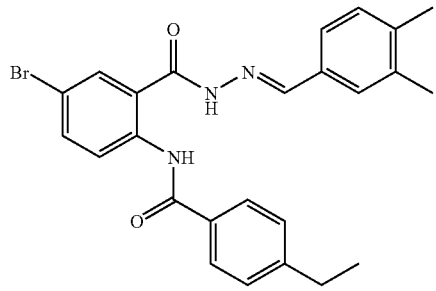 |

TABLE 3-continued
Structures of compounds 1 to 1077 are shown in Table 3.
| Compound No. | Chemical structural formula |
|---|---|
| Compound 183 | 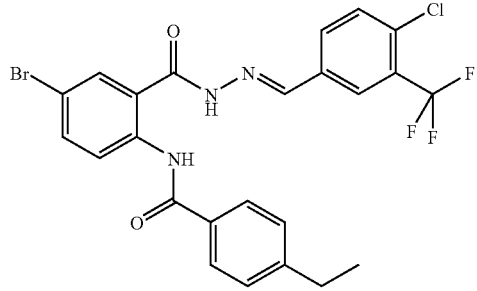 |
| Compound 184 | 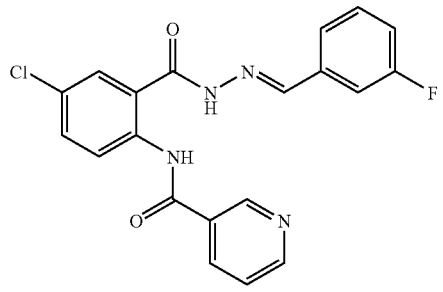 |
| Compound 185 | 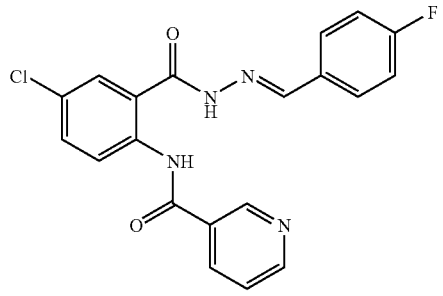 |
| Compound 186 | 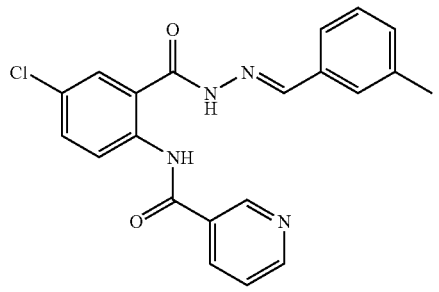 |
| Compound 187 | 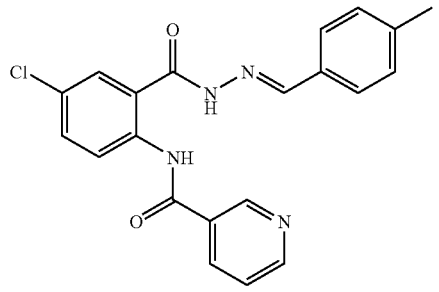 |

TABLE 3-continued
Structures of compounds 1 to 1077 are shown in Table 3.
| Compound No. | Chemical structural formula |
|---|---|
| Compound 188 | 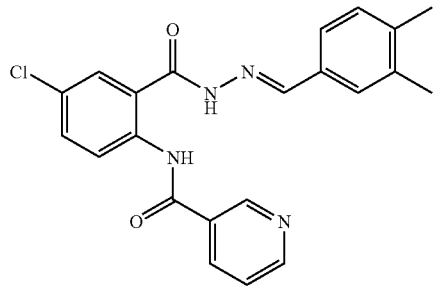 |
| Compound 189 | 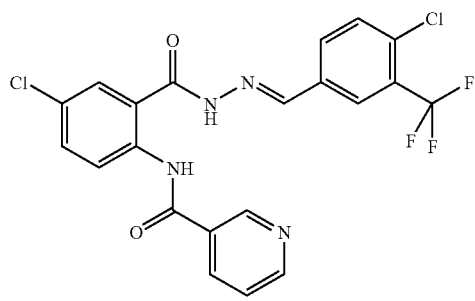 |
| Compound 190 | 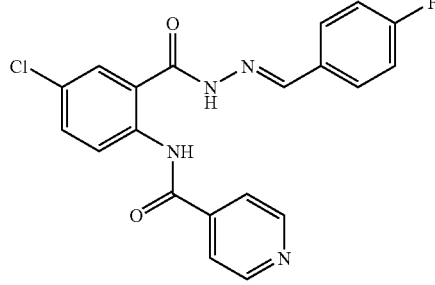 |
| Compound 191 | 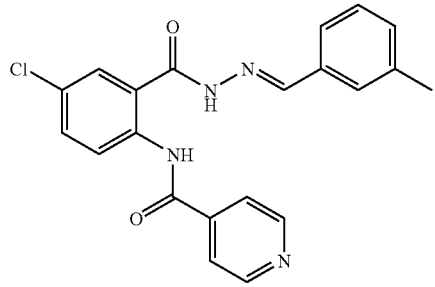 |
| Compound 192 | 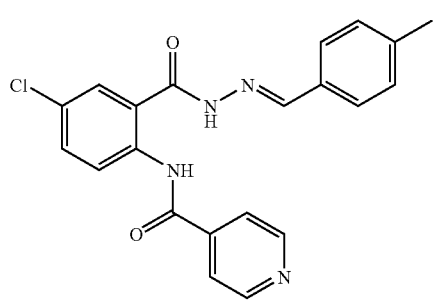 |

TABLE 3-continued
Structures of compounds 1 to 1077 are shown in Table 3.
| Compound No. | Chemical structural formula |
|---|---|
| Compound 193 |  |
| Compound 194 | 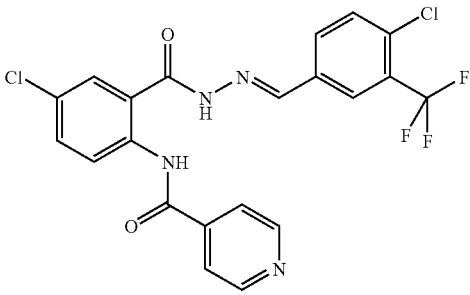 |
| Compound 195 | 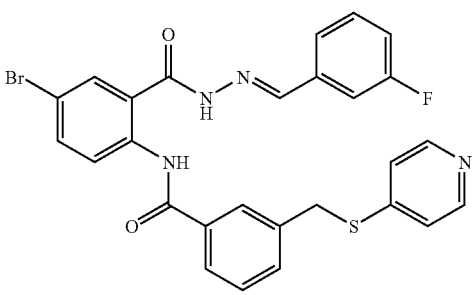 |
| Compound 196 | 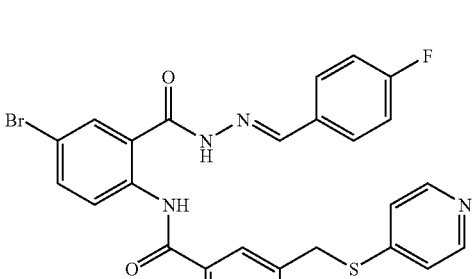 |
| Compound 197 | 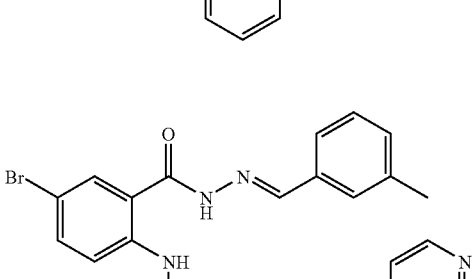 |

TABLE 3-continued
Structures of compounds 1 to 1077 are shown in Table 3.
| Compound No. | Chemical structural formula |
| --- | --- |
| Compound 198 | 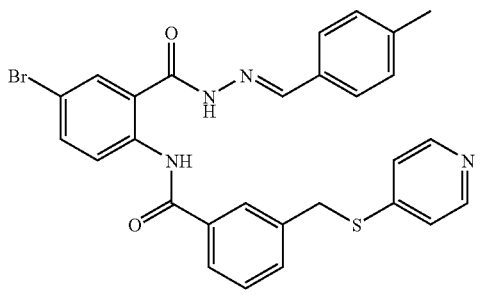 |
| Compound 199 | 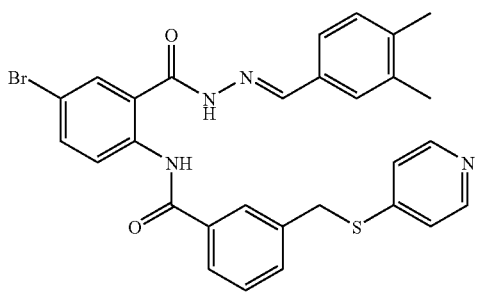 |
| Compound 200 | 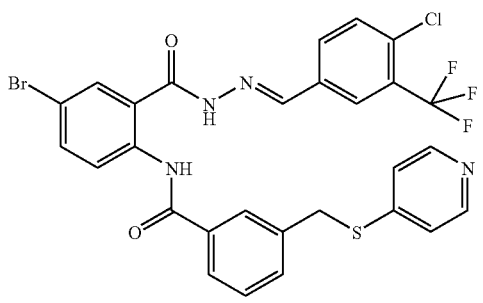 |
| Compound 201 | 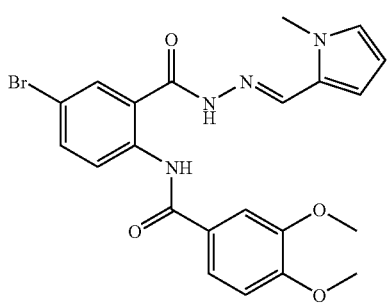 |
| Compound 202 | 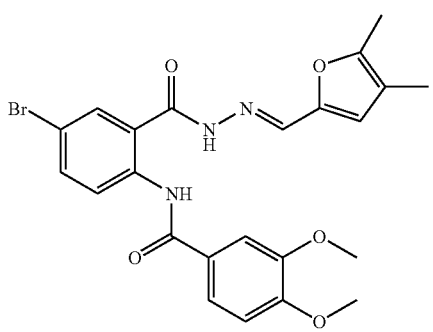 |

TABLE 3-continued
Structures of compounds 1 to 1077 are shown in Table 3.
| Compound No. | Chemical structural formula |
|---|---|
| Compound 203 | 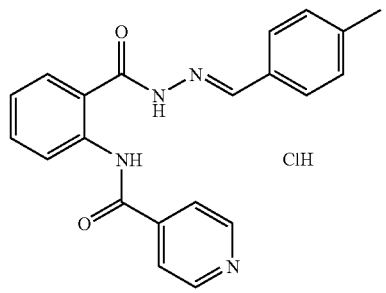 ClH |
| Compound 204 | 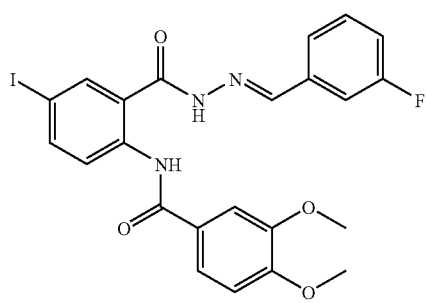 |
| Compound 205 | 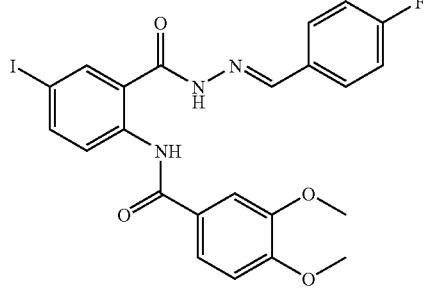 |
| Compound 206 | 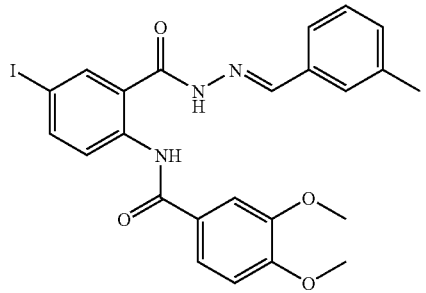 |
| Compound 207 | 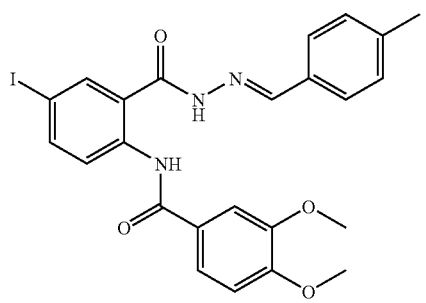 |

TABLE 3-continued
Structures of compounds 1 to 1077 are shown in Table 3.
| Compound No. | Chemical structural formula |
|---|---|
| Compound 208 | 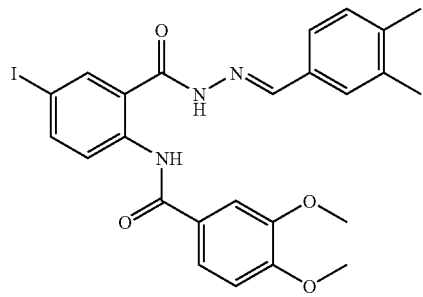 |
| Compound 209 | 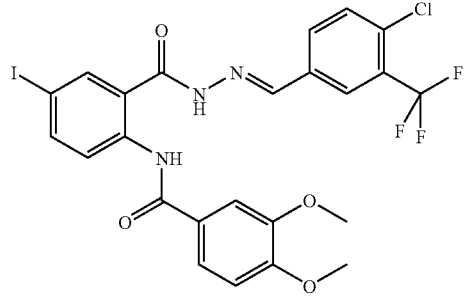 |
| Compound 210 | 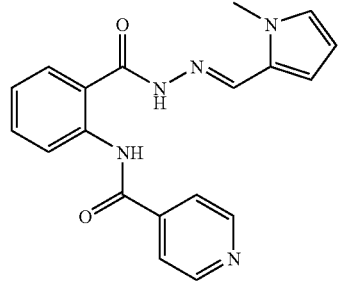 |
| Compound 211 | 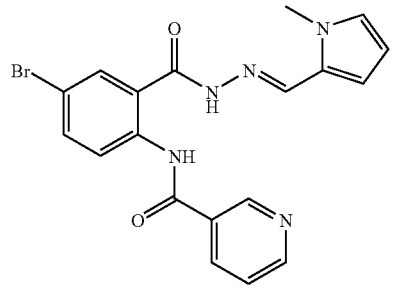 |
| Compound 212 | 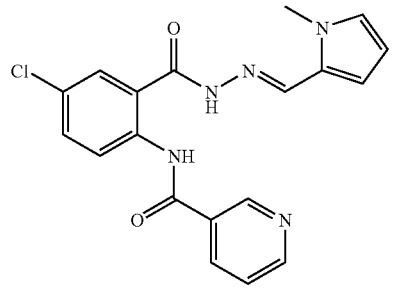 |

TABLE 3-continued
Structures of compounds 1 to 1077 are shown in Table 3.
| Compound No. | Chemical structural formula |
| --- | --- |
| Compound 213 | 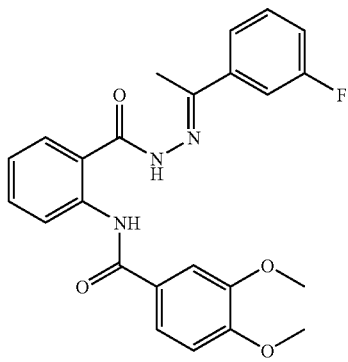 |
| Compound 214 | 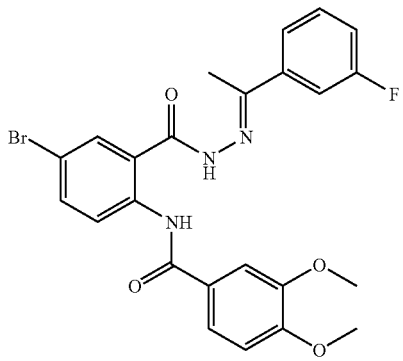 |
| Compound 215 | 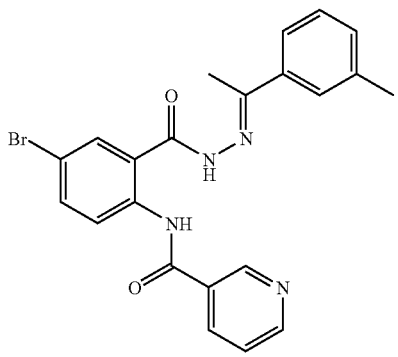 |
| Compound 216 | 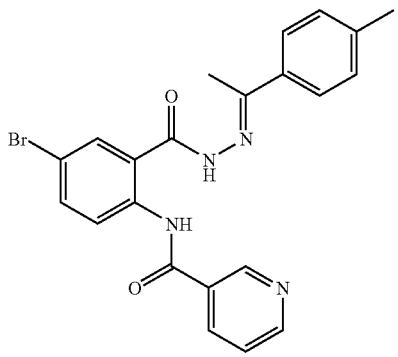 |

TABLE 3-continued
Structures of compounds 1 to 1077 are shown in Table 3.
| Compound No. | Chemical structural formula |
| --- | --- |
| Compound 217 | 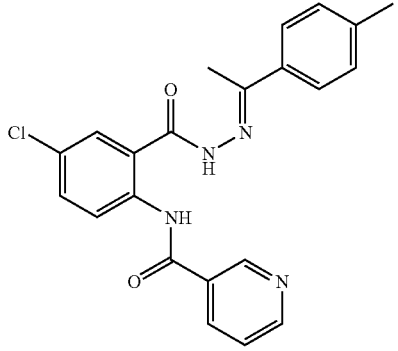 |
| Compound 218 | 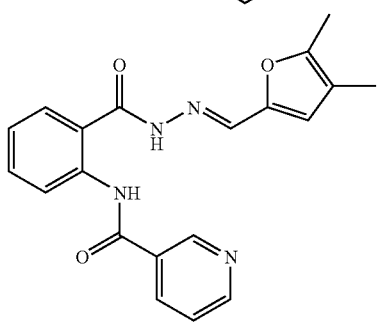 |
| Compound 219 | 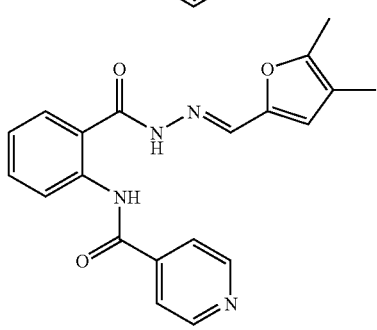 |
| Compound 220 | 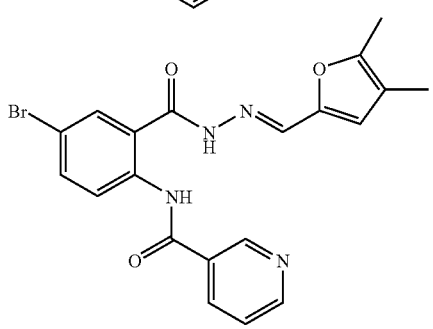 |
| Compound 221 | 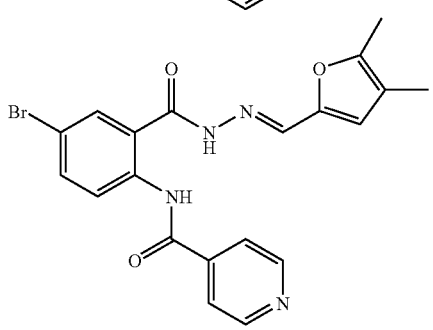 |

TABLE 3-continued
Structures of compounds 1 to 1077 are shown in Table 3.
| Compound No. | Chemical structural formula |
|---|---|
| Compound 222 | 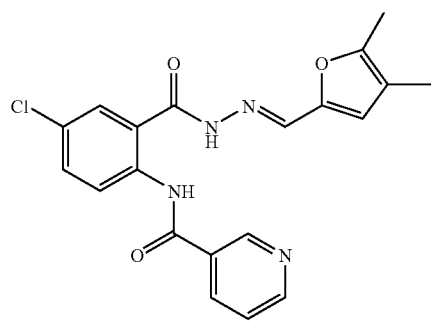 |
| Compound 223 | 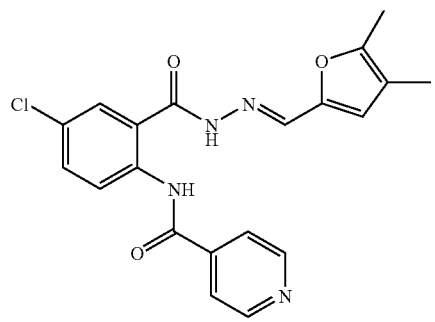 |
| Compound 224 | 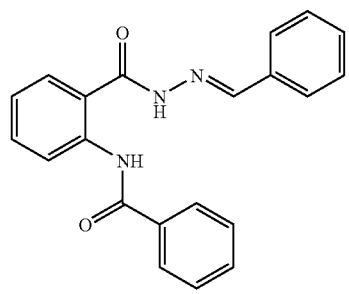 |
| Compound 225 | 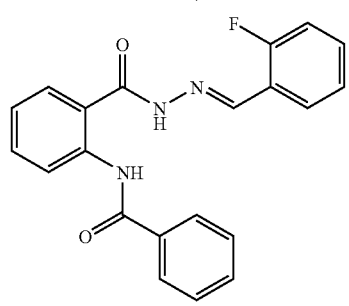 |
| Compound 226 | 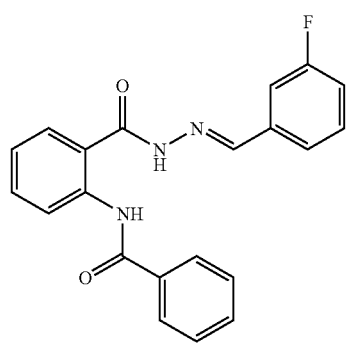 |

TABLE 3-continued
Structures of compounds 1 to 1077 are shown in Table 3.
| Compound No. | Chemical structural formula |
|---|---|
| Compound 227 | 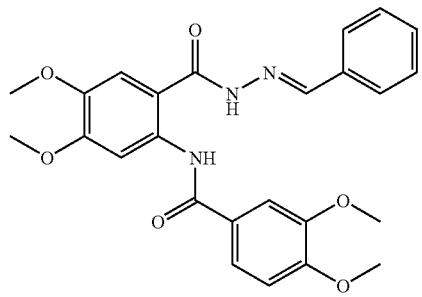 |
| Compound 228 | 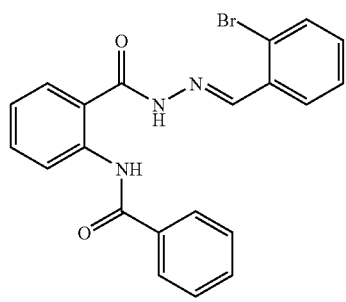 |
| Compound 229 | 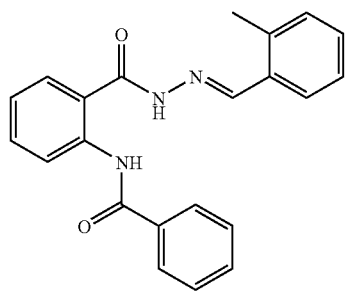 |
| Compound 230 | 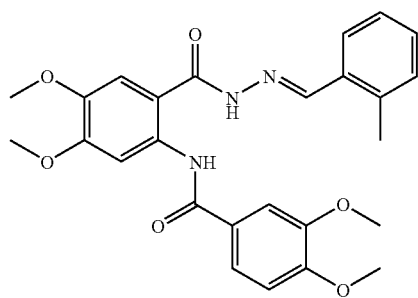 |
| Compound 231 | 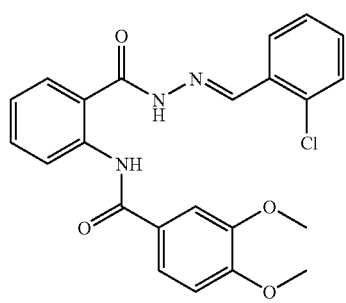 |

| Compound No. | Chemical structural formula |
|---|---|
| Compound 232 | 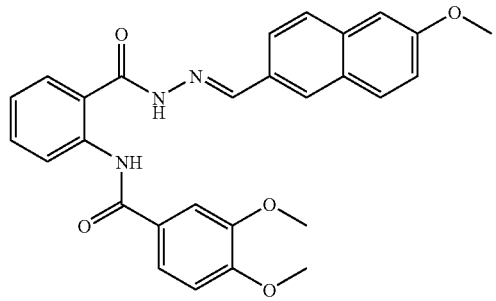 |
| Compound 233 | 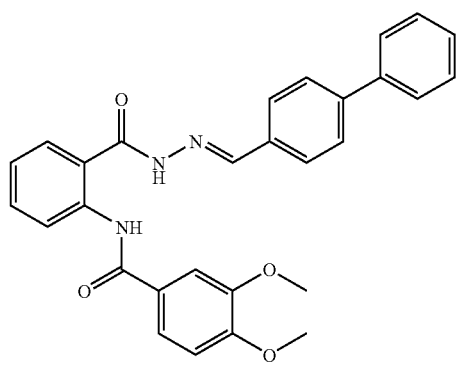 |
| Compound 234 | 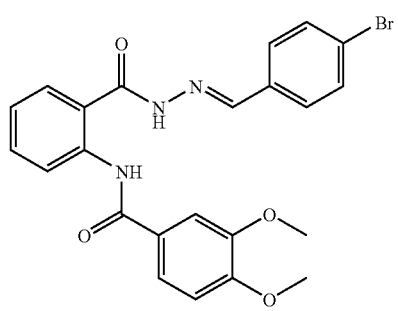 |
| Compound 235 | 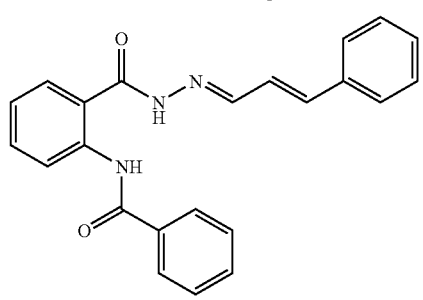 |
| Compound 236 | 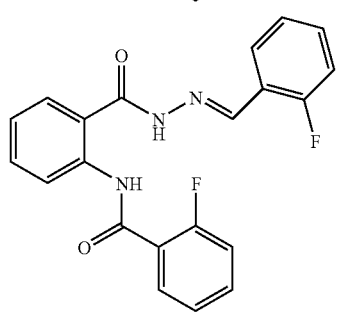 |

TABLE 3-continued
Structures of compounds 1 to 1077 are shown in Table 3.
| Compound No. | Chemical structural formula |
|---|---|
| Compound 237 | 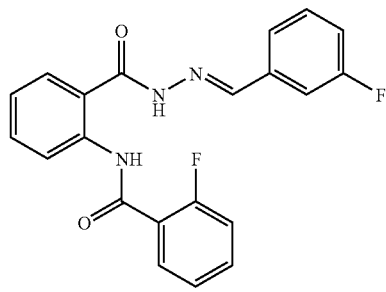 |
| Compound 238 | 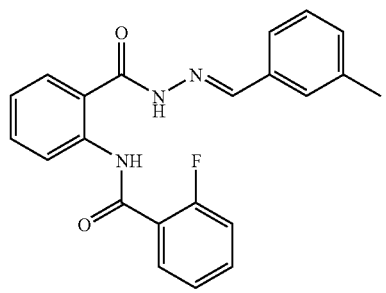 |
| Compound 239 | 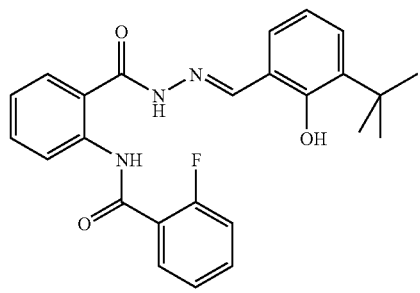 |
| Compound 240 | 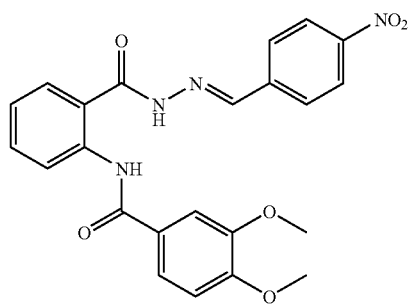 |
| Compound 241 | 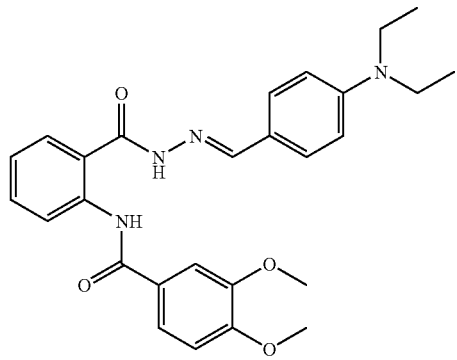 |

TABLE 3-continued
Structures of compounds 1 to 1077 are shown in Table 3.
| Compound No. | Chemical structural formula |
| --- | --- |
| Compound 242 | 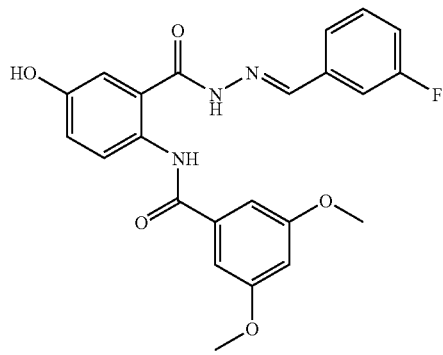 |
| Compound 243 | 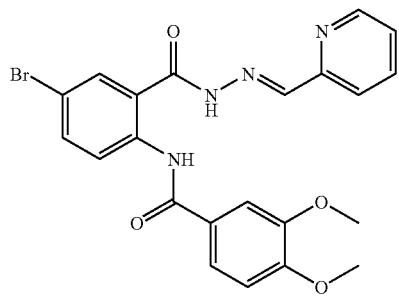 |
| Compound 244 | 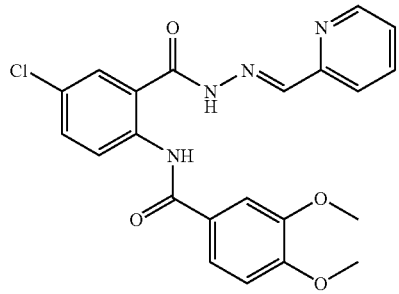 |
| Compound 245 | 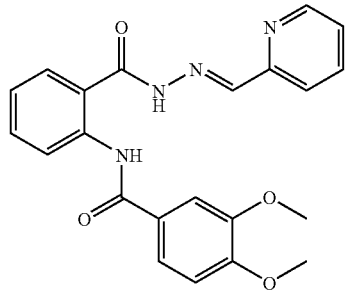 |
| Compound 246 | 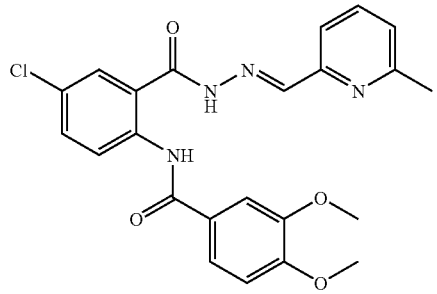 |

TABLE 3-continued
Structures of compounds 1 to 1077 are shown in Table 3.
| Compound No. | Chemical structural formula |
|---|---|
| Compound 247 | 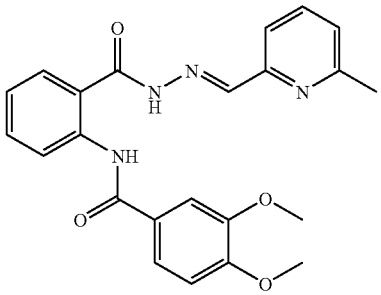 |
| Compound 248 | 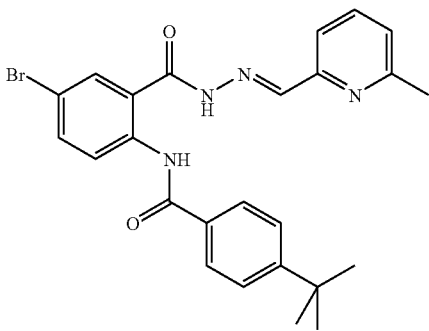 |
| Compound 249 | 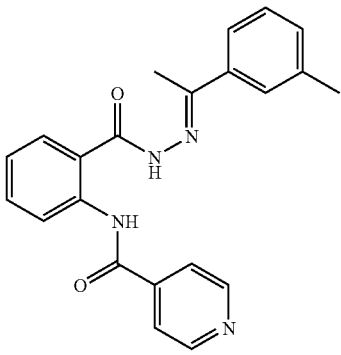 |
| Compound 250 | 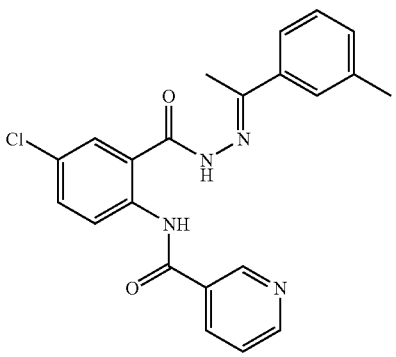 |

TABLE 3-continued
Structures of compounds 1 to 1077 are shown in Table 3.
| Compound No. | Chemical structural formula |
|---|---|
| Compound 251 | 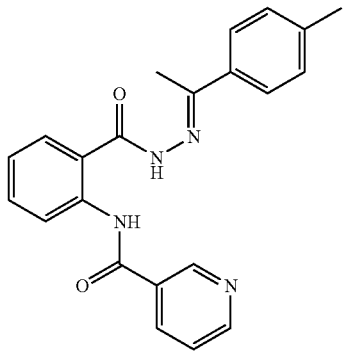 |
| Compound 252 | 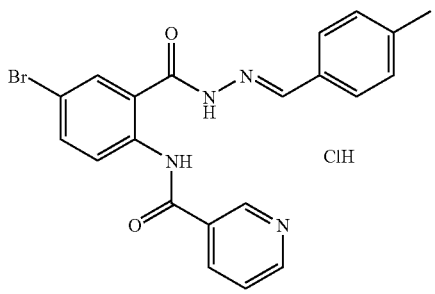 |
| Compound 253 | 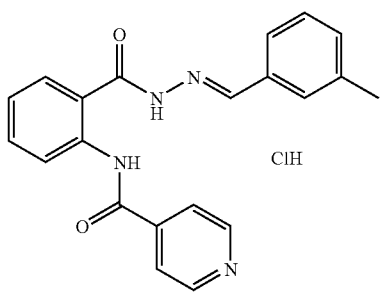 |
| Compound 255 | 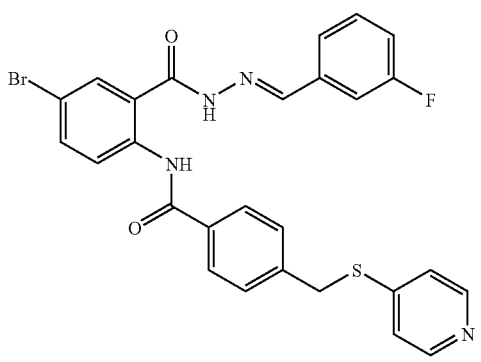 |

473
474
TABLE 3-continued
Structures of compounds 1 to 1077 are shown in Table 3.
| Compound No. | Chemical structural formula |
| --- | --- |
| Compound 256 | 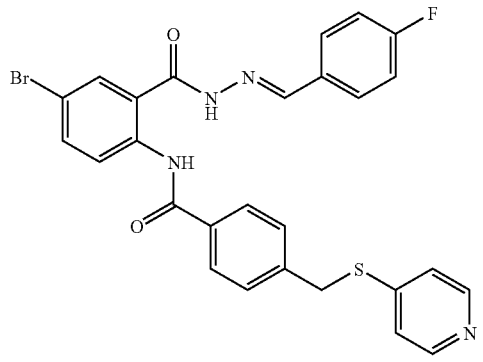 |
| Compound 257 | 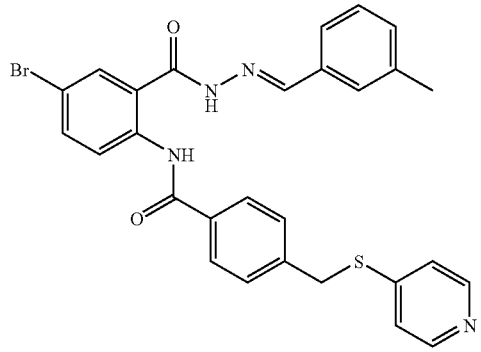 |
| Compound 258 | 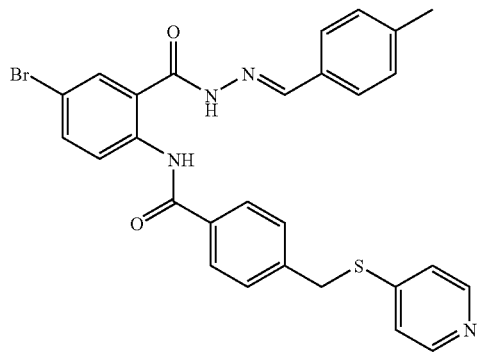 |
| Compound 259 | 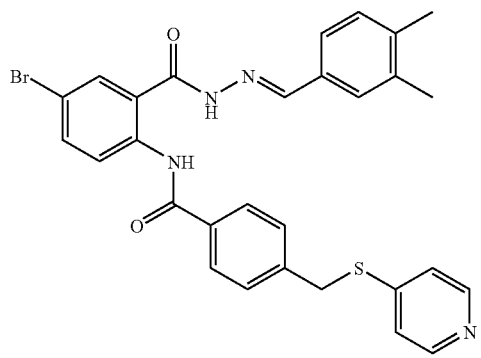 |

TABLE 3-continued
Structures of compounds 1 to 1077 are shown in Table 3.
| Compound No. | Chemical structural formula |
|---|---|
| Compound 260 | 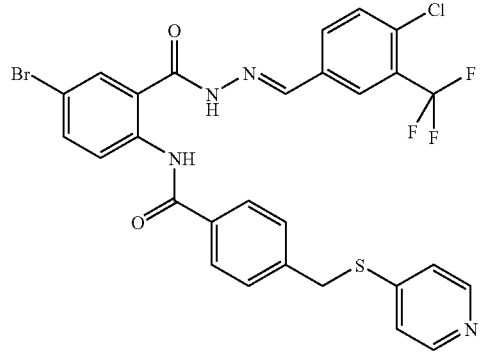 |
| Compound 261 | 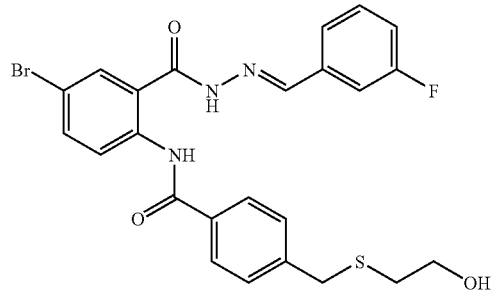 |
| Compound 262 | 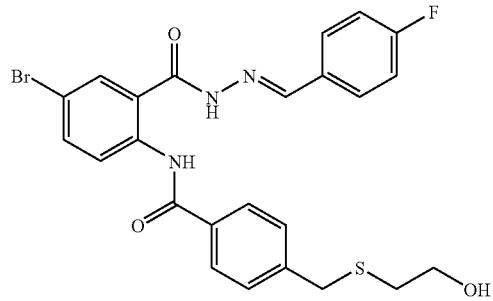 |
| Compound 263 | 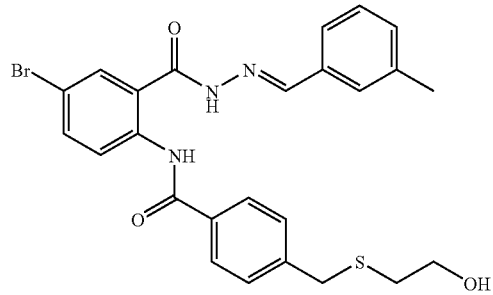 |
| Compound 264 | 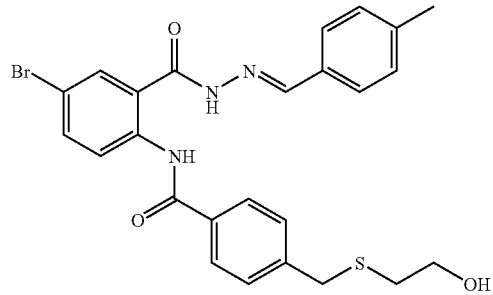 |

TABLE 3-continued
Structures of compounds 1 to 1077 are shown in Table 3.
| Compound No. | Chemical structural formula |
|---|---|
| Compound 265 | 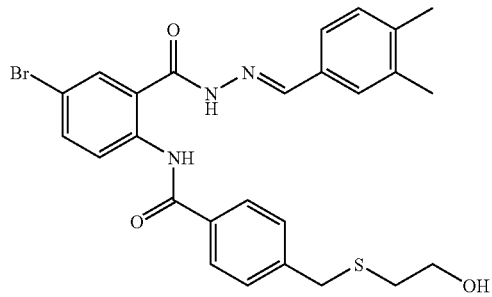 |
| Compound 266 | 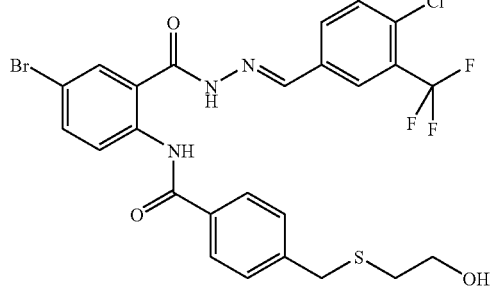 |
| Compound 267 | 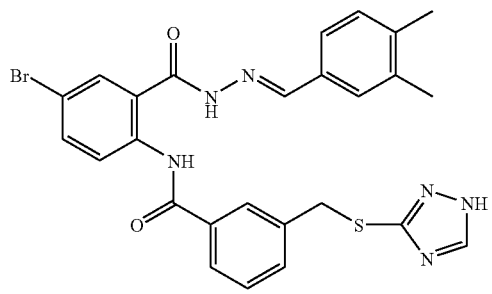 |
| Compound 268 | 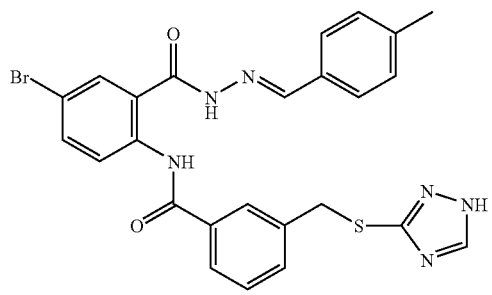 |
| Compound 269 | 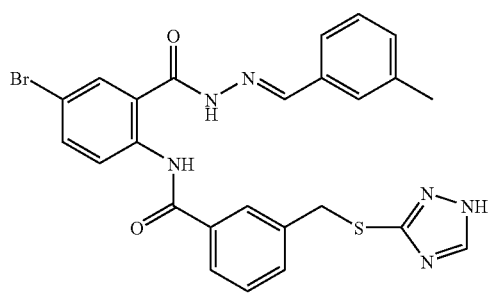 |

TABLE 3-continued
Structures of compounds 1 to 1077 are shown in Table 3.
| Compound No. | Chemical structural formula |
| --- | --- |
| Compound 270 | 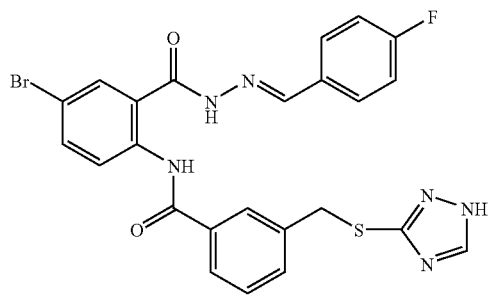 |
| Compound 271 | 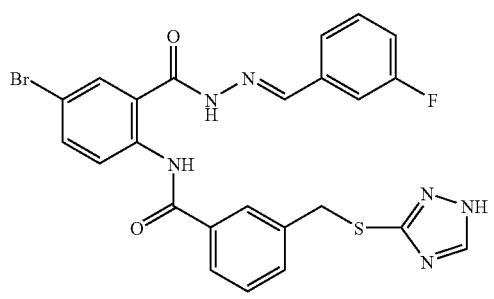 |
| Compound 272 | 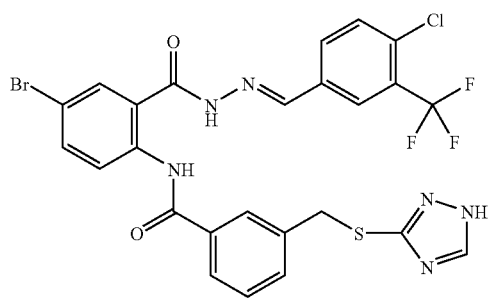 |
| Compound 273 | 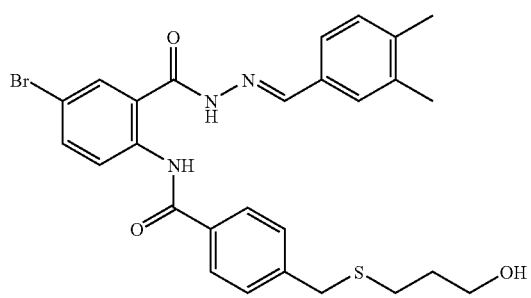 |
| Compound 274 | 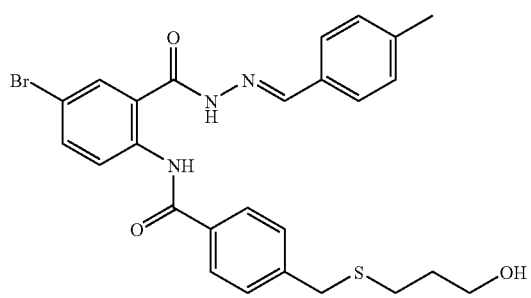 |

TABLE 3-continued
Structures of compounds 1 to 1077 are shown in Table 3.
| Compound No. | Chemical structural formula |
| --- | --- |
| Compound 275 | 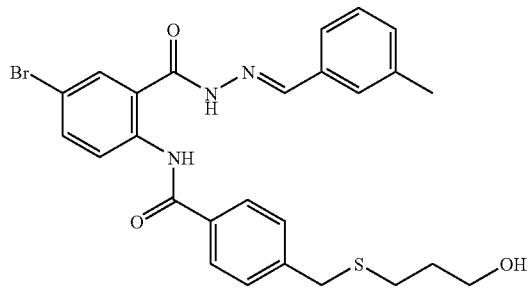 |
| Compound 276 | 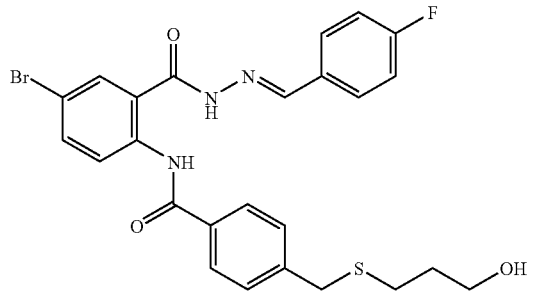 |
| Compound 277 | 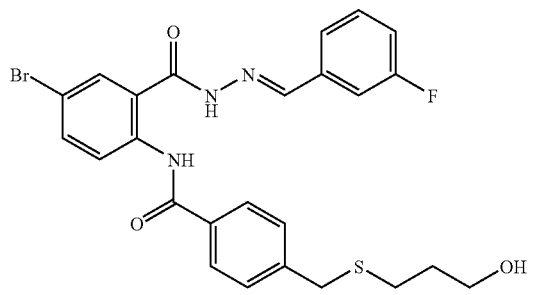 |
| Compound 278 |  |
| Compound 279 | 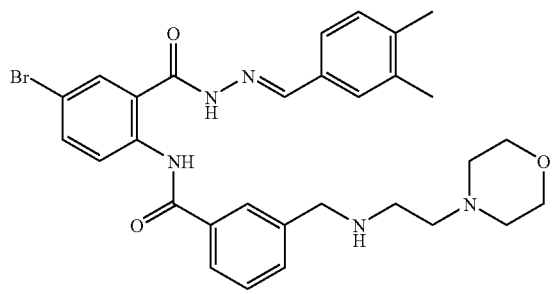 |

TABLE 3-continued
Structures of compounds 1 to 1077 are shown in Table 3.
| Compound No. | Chemical structural formula |
|---|---|
| Compound 280 | 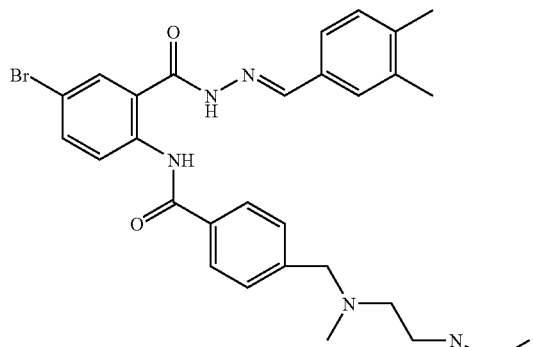 |
| Compound 281 | 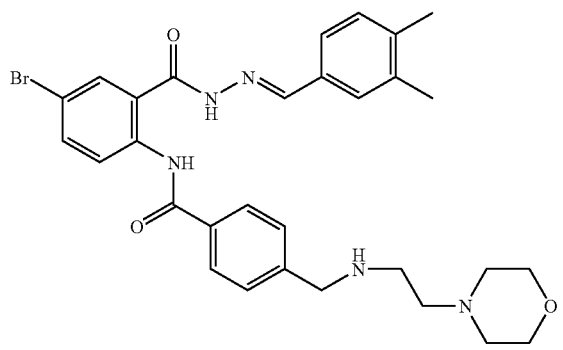 |
| Compound 282 | 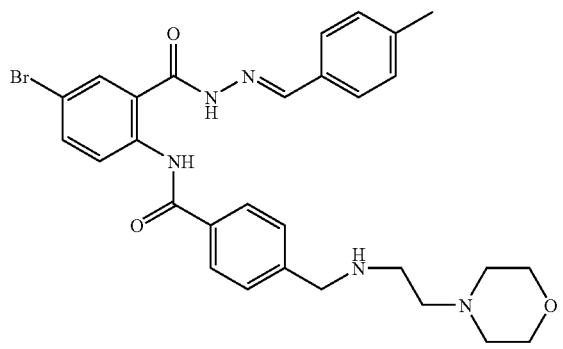 |
| Compound 283 | 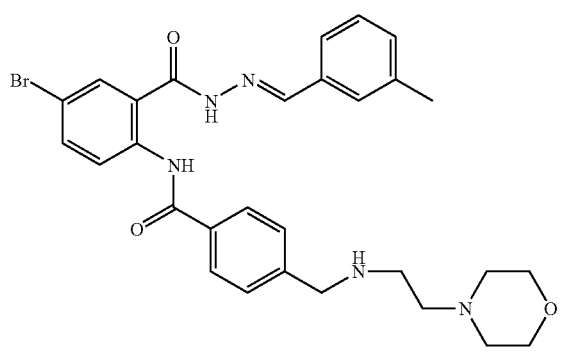 |

485 486
TABLE 3-continued
Structures of compounds 1 to 1077 are shown in Table 3.
| Compound No. | Chemical structural formula |
|---|---|
| Compound 284 | 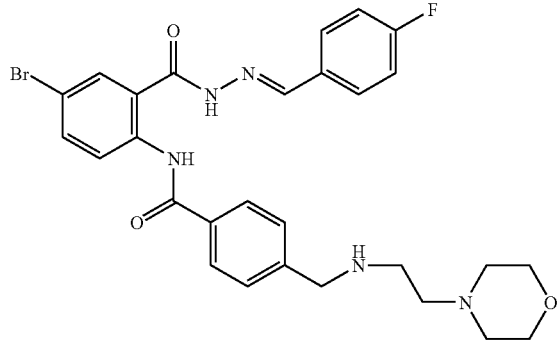 |
| Compound 285 | 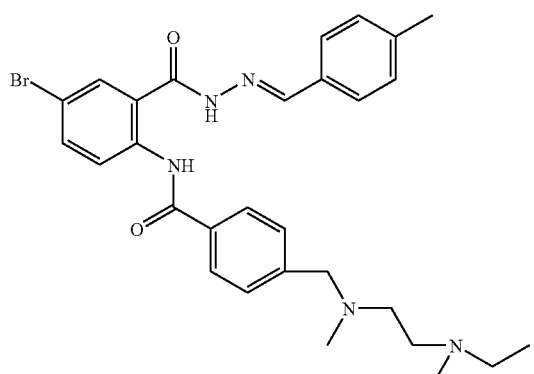 |
| Compound 286 | 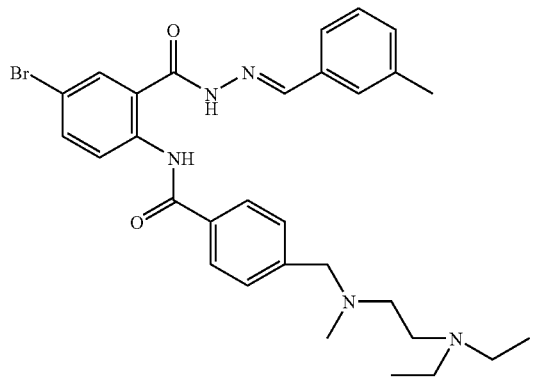 |
| Compound 287 | 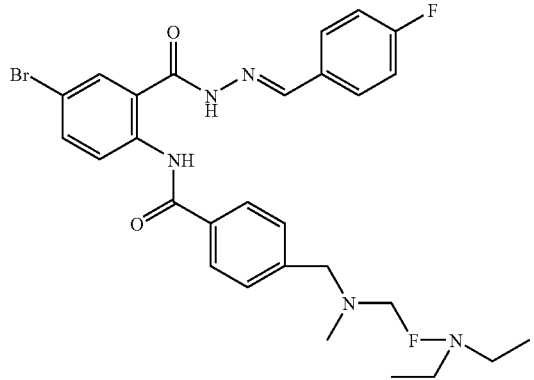 |

TABLE 3-continued
Structures of compounds 1 to 1077 are shown in Table 3.
| Compound No. | Chemical structural formula |
|---|---|
| Compound 288 | 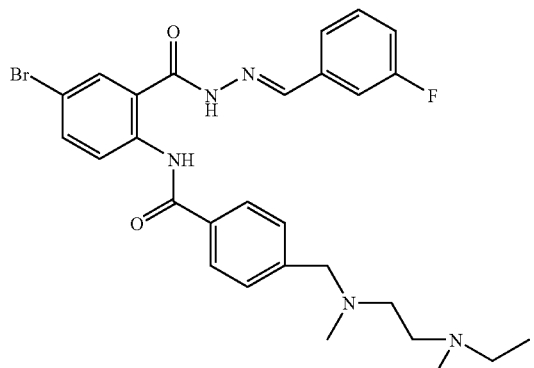 |
| Compound 289 | 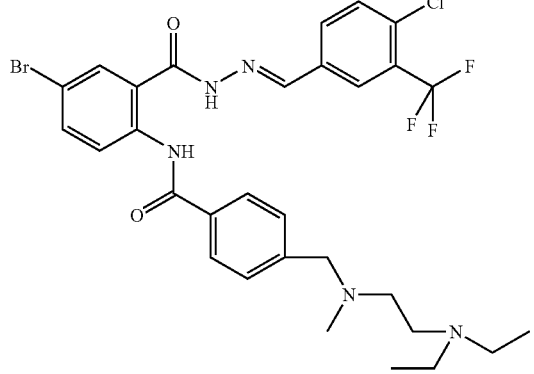 |
| Compound 290 | 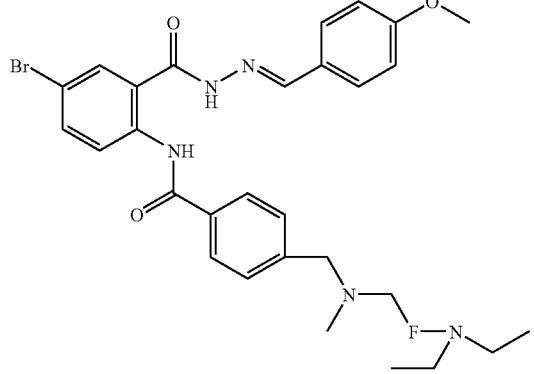 |
| Compound 291 | 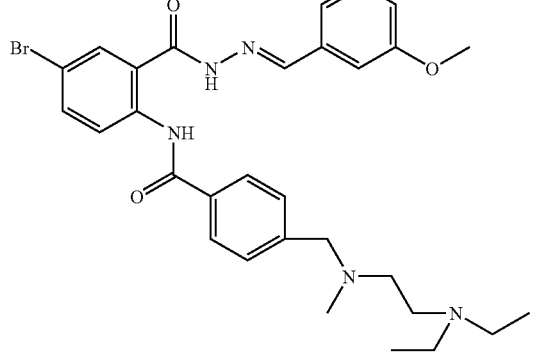 |

TABLE 3-continued
Structures of compounds 1 to 1077 are shown in Table 3.
| Compound No. | Chemical structural formula |
|---|---|
| Compound 292 |  |
| Compound 293 | 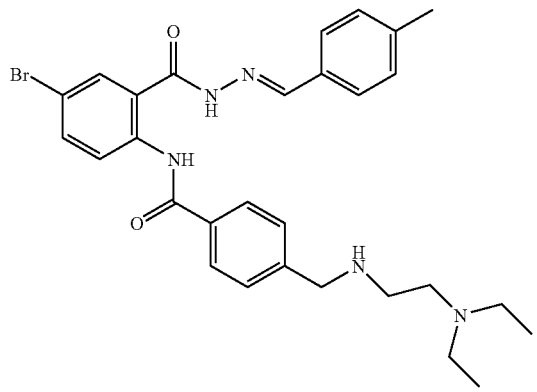 |
| Compound 294 | 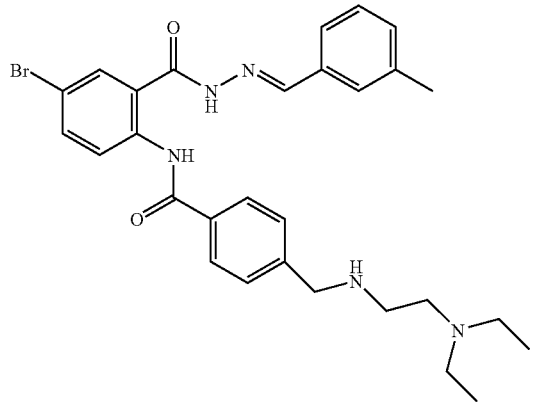 |
| Compound 295 | 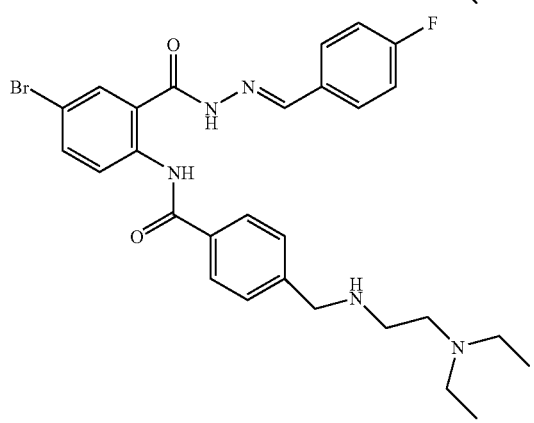 |

TABLE 3-continued
Structures of compounds 1 to 1077 are shown in Table 3.
| Compound No. | Chemical structural formula |
|---|---|
| Compound 296 | 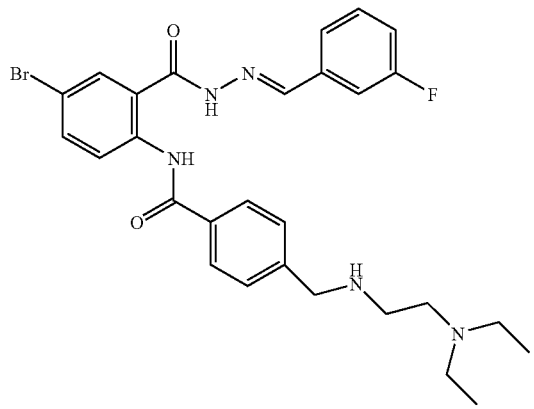 |
| Compound 297 | 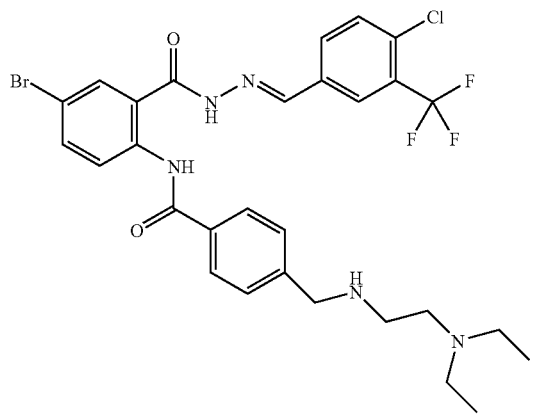 |
| Compound 298 | 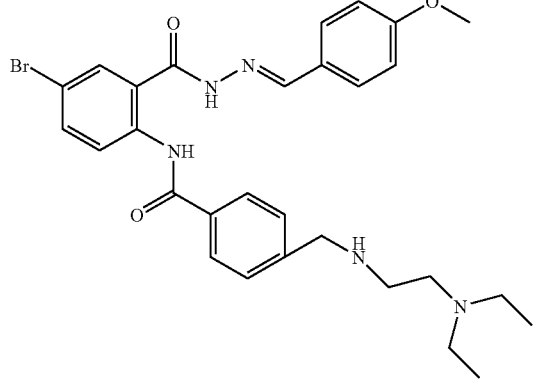 |
| Compound 299 | 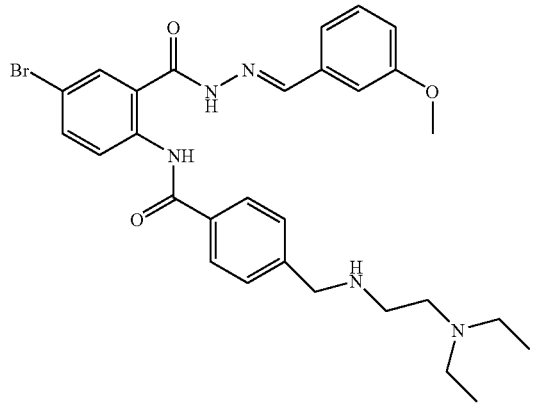 |

TABLE 3-continued
Structures of compounds 1 to 1077 are shown in Table 3.
| Compound No. | Chemical structural formula |
|---|---|
| Compound 300 | 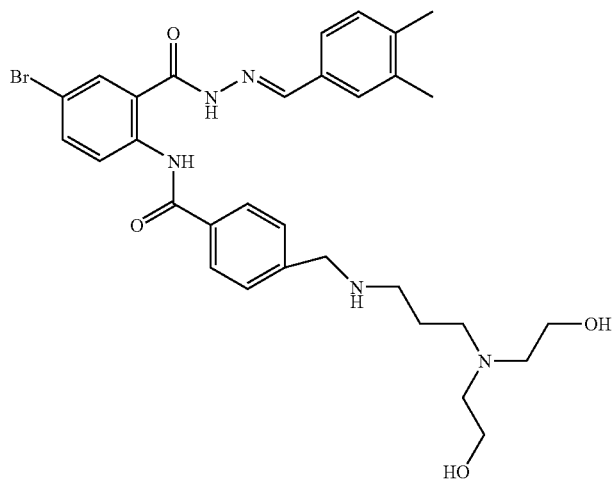 |
| Compound 301 | 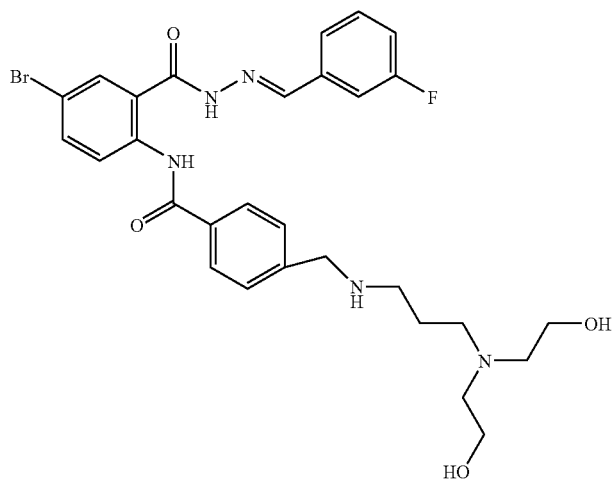 |
| Compound 302 | 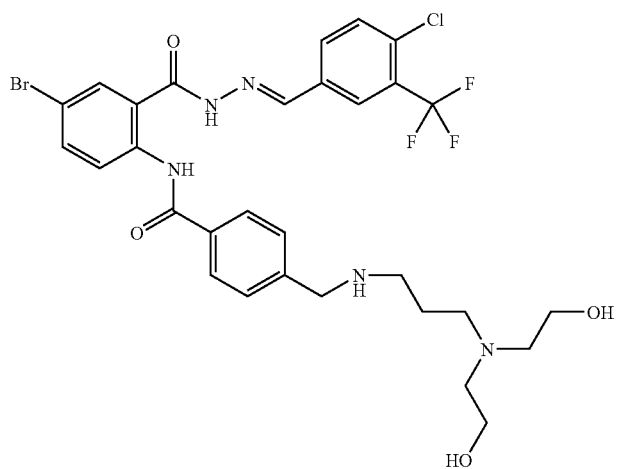 |

TABLE 3-continued
Structures of compounds 1 to 1077 are shown in Table 3.
| Compound No. | Chemical structural formula |
|---|---|
| Compound 303 | 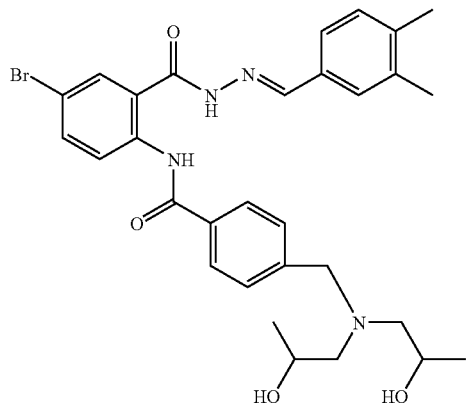 |
| Compound 304 | 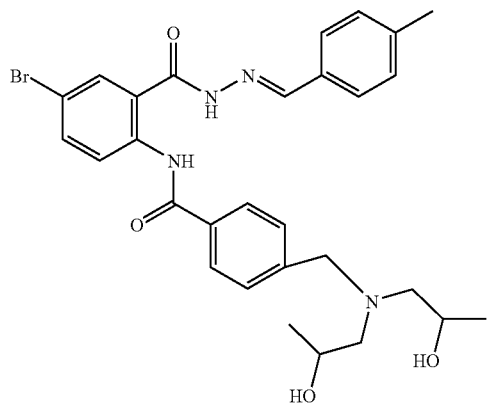 |
| Compound 305 | 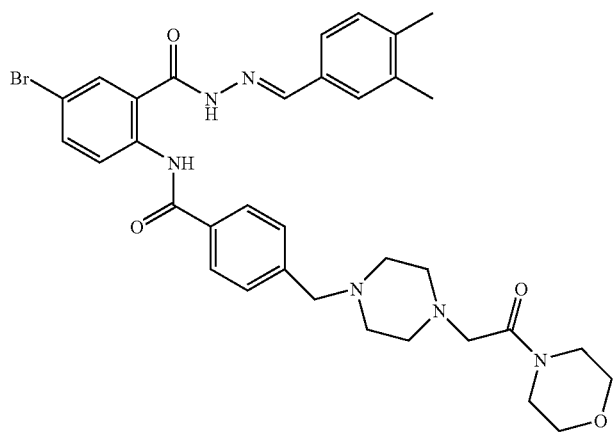 |

TABLE 3-continued
Structures of compounds 1 to 1077 are shown in Table 3.
| Compound No. | Chemical structural formula |
|---|---|
| Compound 306 | 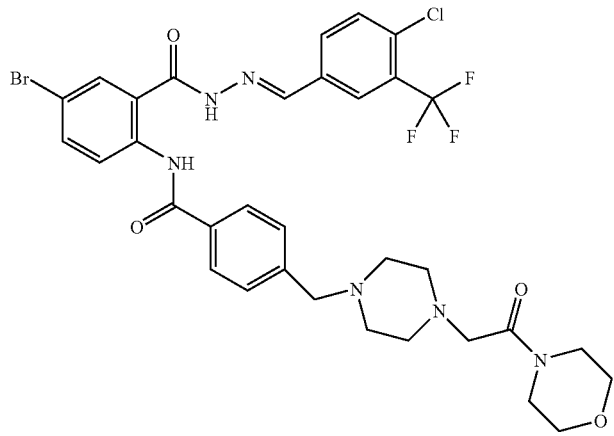 |
| Compound 307 | 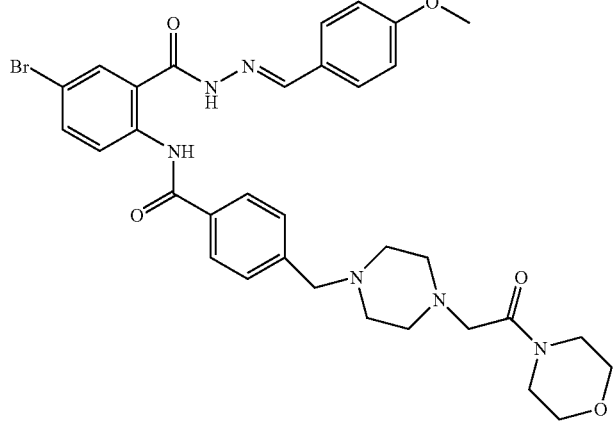 |
| Compound 308 | 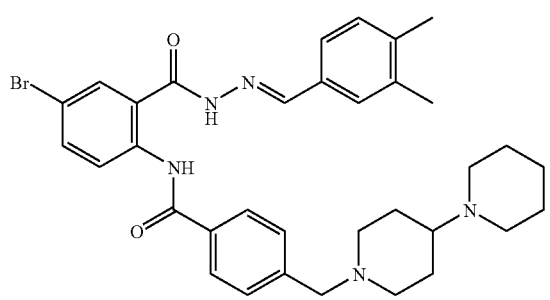 |
| Compound 309 | 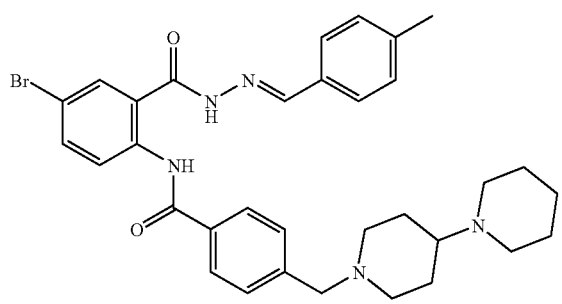 |

TABLE 3-continued

Structures of compounds 1 to 1077 are shown in Table 3.

| Compound No. | Chemical structural formula |
| --- | --- |
| Compound 310 | |
| Compound 311 | |
| Compound 312 | |
| Compound 313 | |

TABLE 3-continued
Structures of compounds 1 to 1077 are shown in Table 3.
| Compound No. | Chemical structural formula |
|---|---|
| Compound 314 | 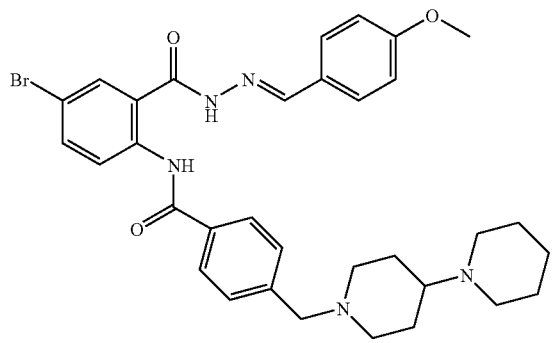 |
| Compound 315 | 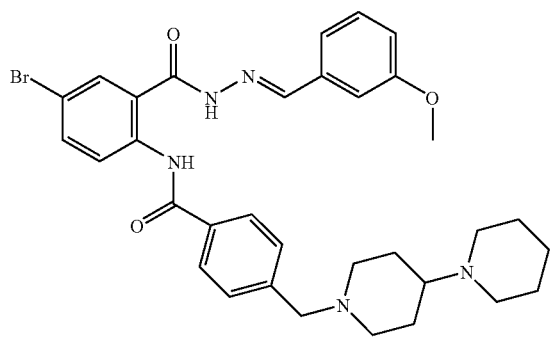 |
| Compound 316 | 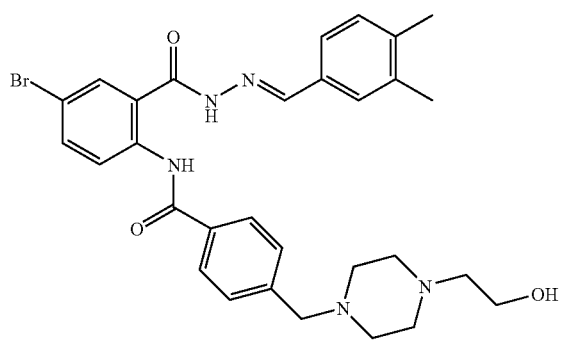 |
| Compound 317 |  |

TABLE 3-continued
Structures of compounds 1 to 1077 are shown in Table 3.
| Compound No. | Chemical structural formula |
| --- | --- |
| Compound 318 | 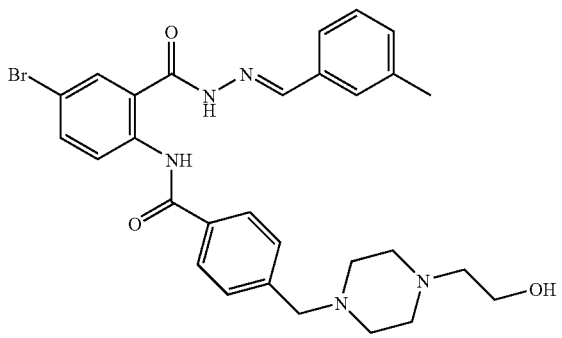 |
| Compound 319 | 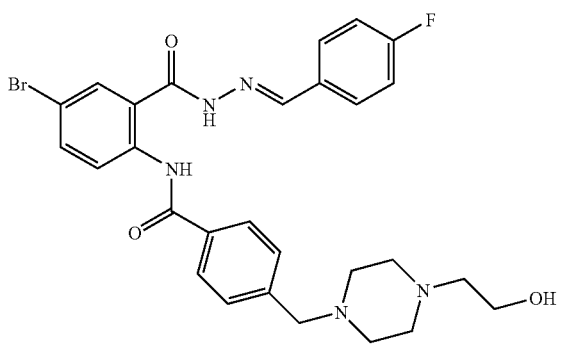 |
| Compound 320 | 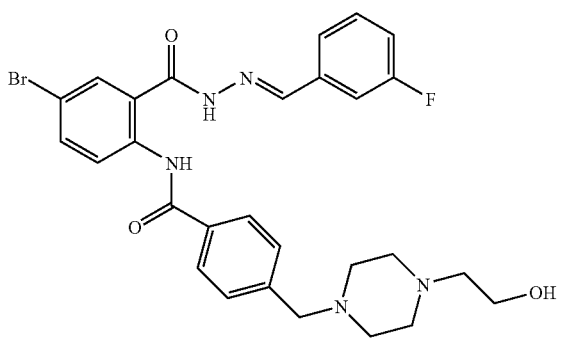 |
| Compound 321 | 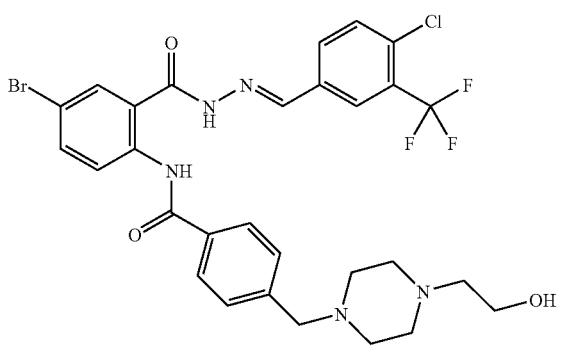 |

TABLE 3-continued
Structures of compounds 1 to 1077 are shown in Table 3.
| Compound No. | Chemical structural formula |
|---|---|
| Compound 322 | 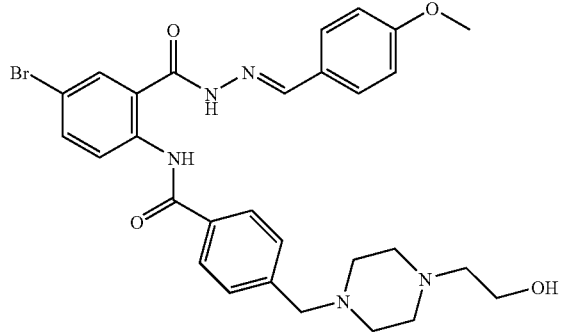 |
| Compound 323 | 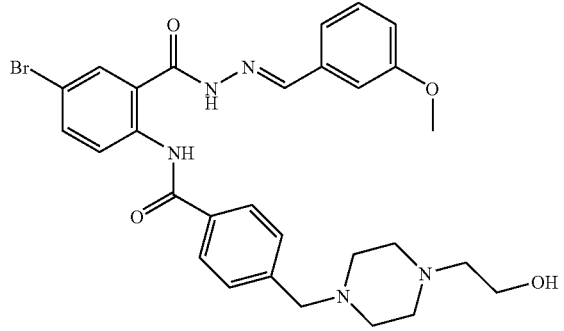 |
| Compound 324 | 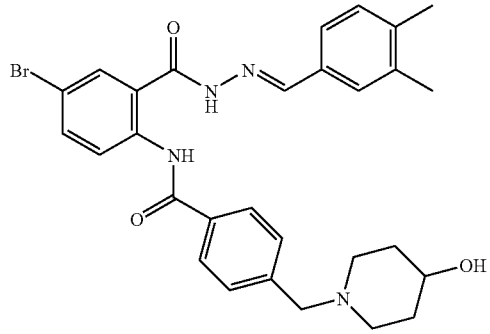 |
| Compound 325 | 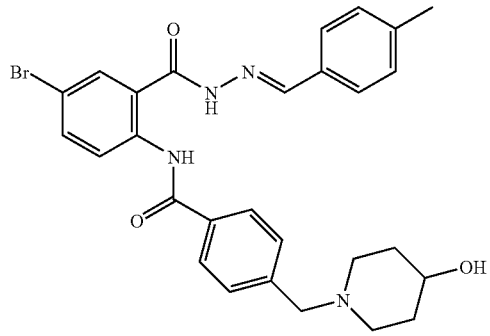 |

TABLE 3-continued

Structures of compounds 1 to 1077 are shown in Table 3.

| Compound No. | Chemical structural formula |
|---|---|
| Compound 326 | |
| Compound 327 | |
| Compound 328 | |
| Compound 329 | |

TABLE 3-continued
Structures of compounds 1 to 1077 are shown in Table 3.
| Compound No. | Chemical structural formula |
| --- | --- |
| Compound 330 | 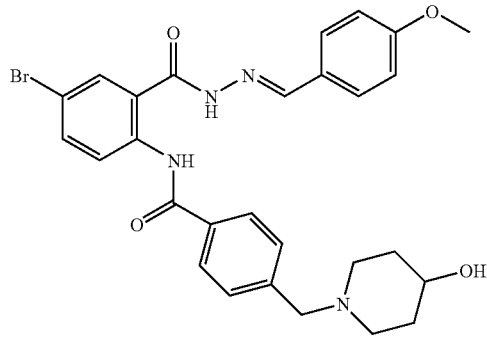 |
| Compound 331 | 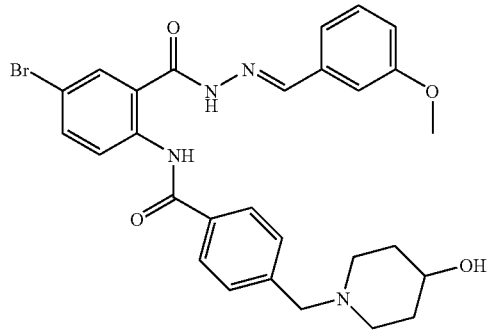 |
| Compound 332 | 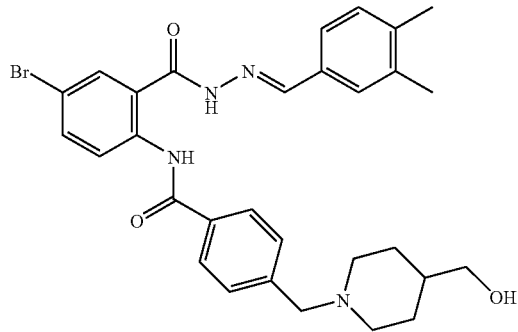 |
| Compound 333 | 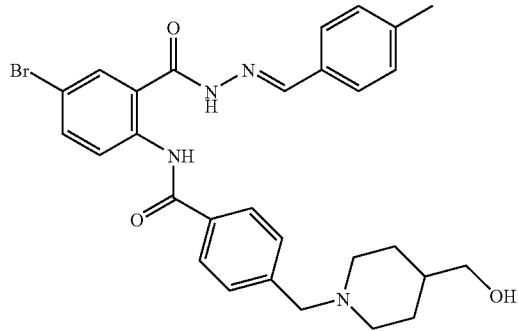 |

TABLE 3-continued
Structures of compounds 1 to 1077 are shown in Table 3.
| Compound No. | Chemical structural formula |
| --- | --- |
| Compound 334 | 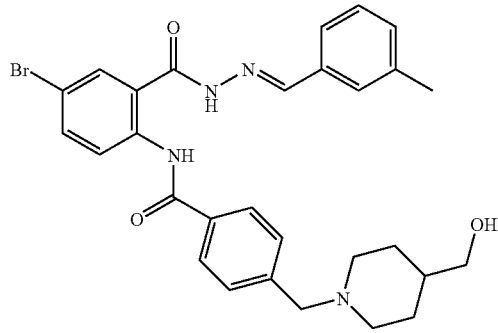 |
| Compound 335 | 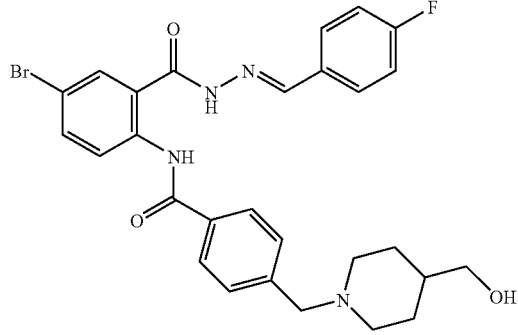 |
| Compound 336 | 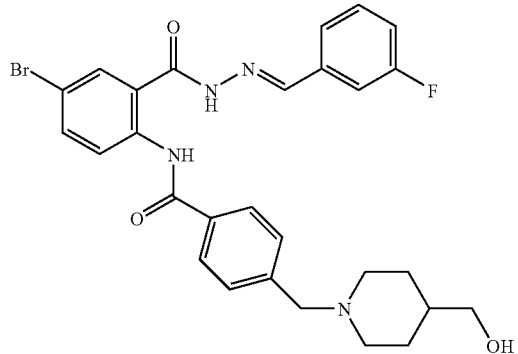 |
| Compound 337 | 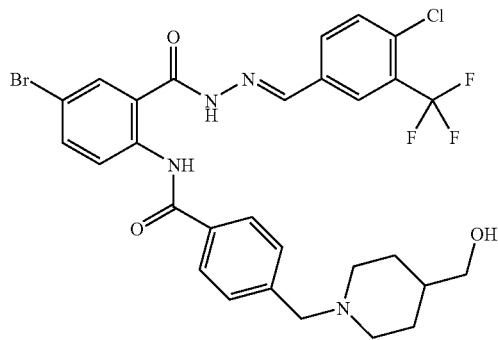 |

TABLE 3-continued
Structures of compounds 1 to 1077 are shown in Table 3.
| Compound No. | Chemical structural formula |
|---|---|
| Compound 338 | 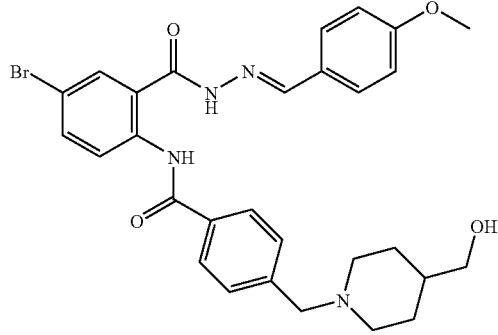 |
| Compound 339 | 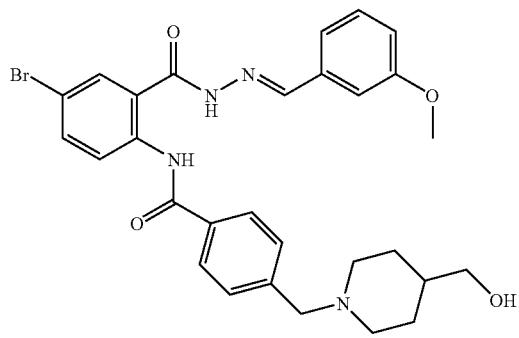 |
| Compound 340 | 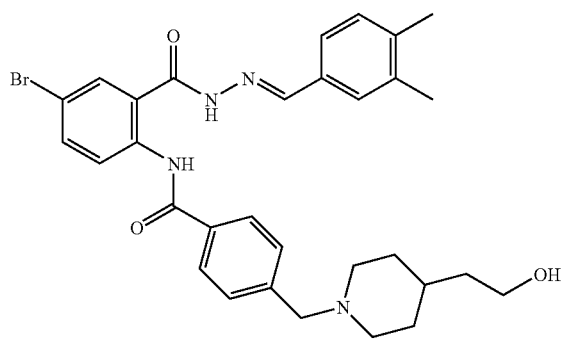 |
| Compound 341 | 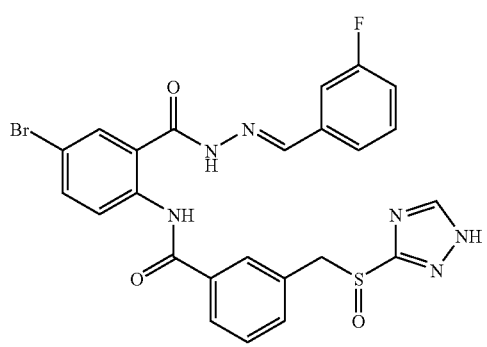 |

TABLE 3-continued
Structures of compounds 1 to 1077 are shown in Table 3.
| Compound No. | Chemical structural formula |
|---|---|
| Compound 342 | 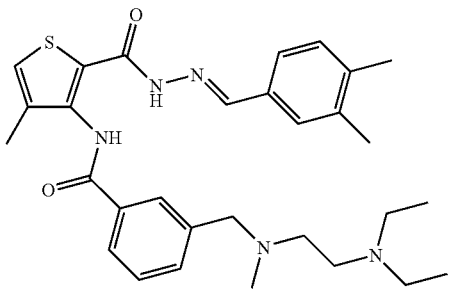 |
| Compound 343 | 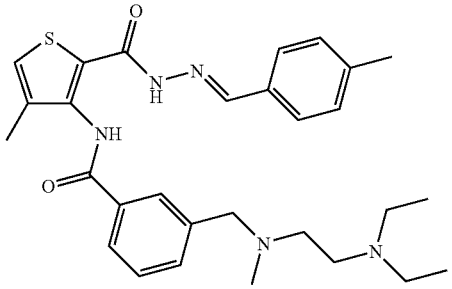 |
| Compound 344 | 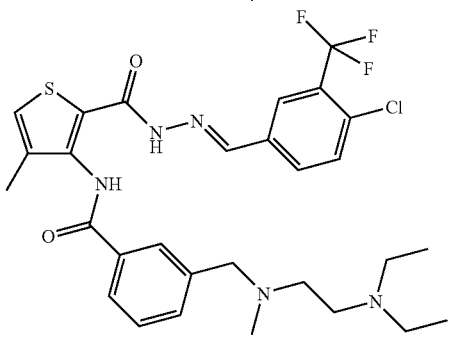 |
| Compound 345 | 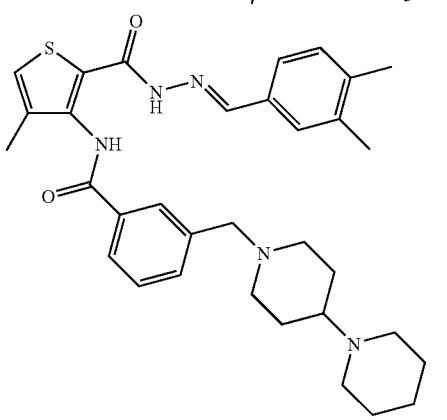 |
| Compound 346 | 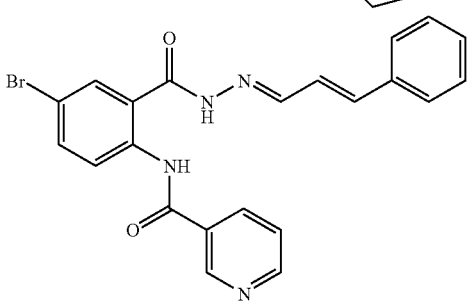 |

TABLE 3-continued
Structures of compounds 1 to 1077 are shown in Table 3.
| Compound No. | Chemical structural formula |
|---|---|
| Compound 347 | 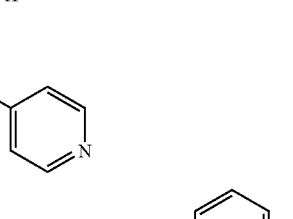 |
| Compound 348 | 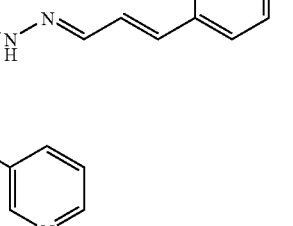 |
| Compound 349 | 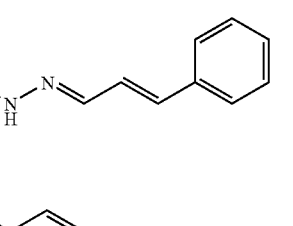 |
| Compound 350 | 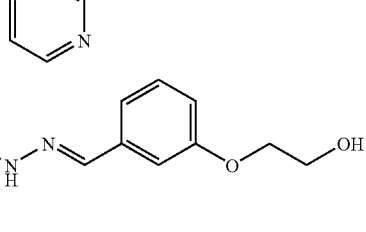 |
| Compound 351 | 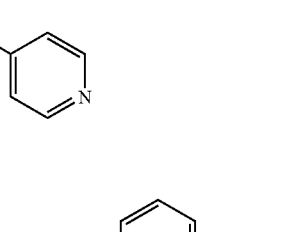 |

TABLE 3-continued
Structures of compounds 1 to 1077 are shown in Table 3.
| Compound No. | Chemical structural formula |
|---|---|
| Compound 352 | 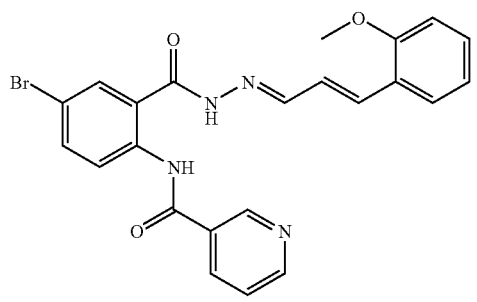 |
| Compound 353 | 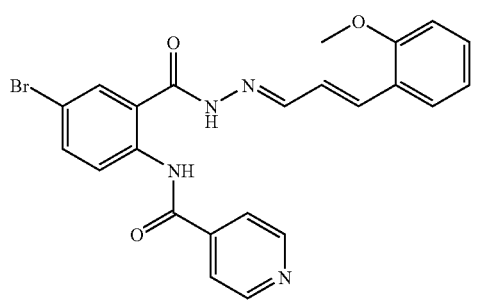 |
| Compound 354 | 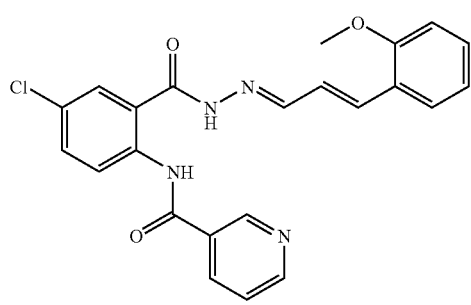 |
| Compound 355 | 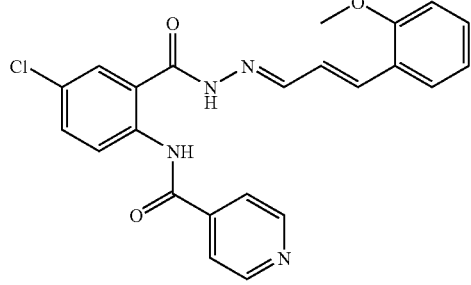 |
| Compound 356 | 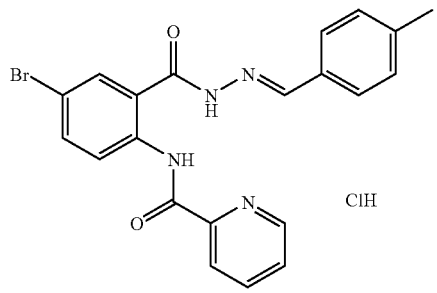 |

TABLE 3-continued
Structures of compounds 1 to 1077 are shown in Table 3.
| Compound No. | Chemical structural formula |
| --- | --- |
| Compound 357 | 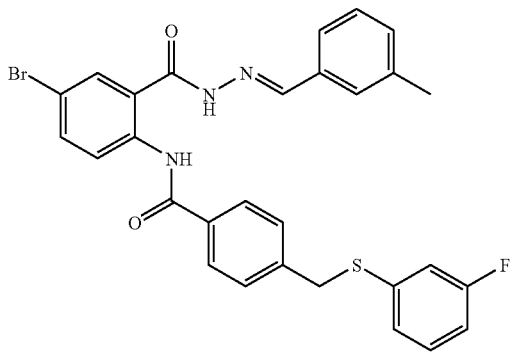 |
| Compound 358 | 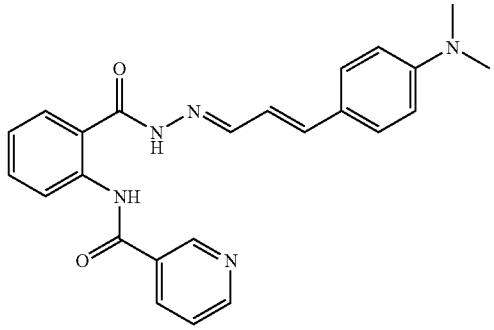 |
| Compound 359 | 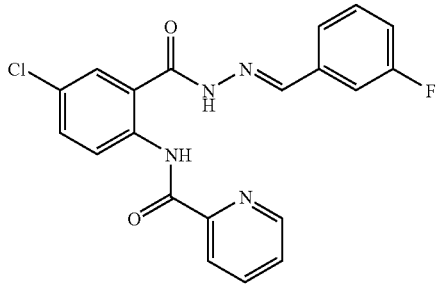 |
| Compound 360 | 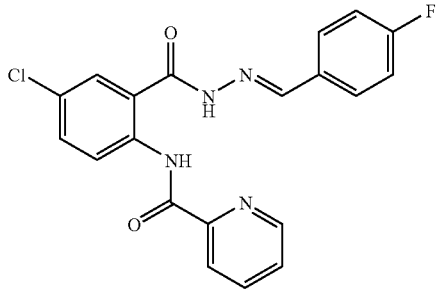 |
| Compound 361 | 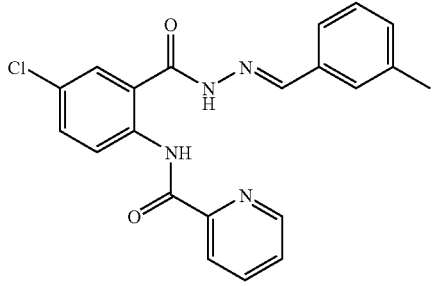 |

US 8,134,015 B2
523                                                                                  524
TABLE 3-continued
Structures of compounds 1 to 1077 are shown in Table 3.
| Compound No. | Chemical structural formula |
| --- | --- |
| Compound 362 | 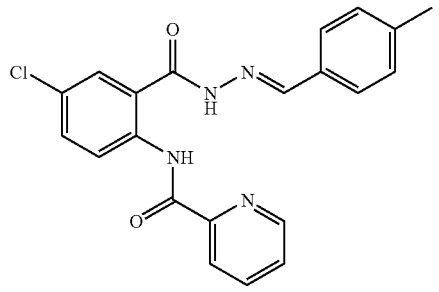 |
| Compound 363 | 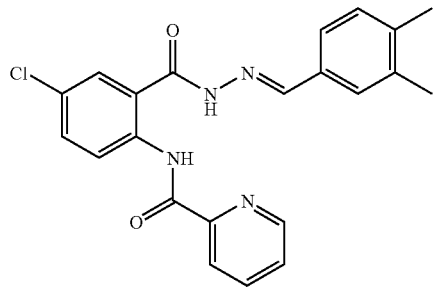 |
| Compound 364 | 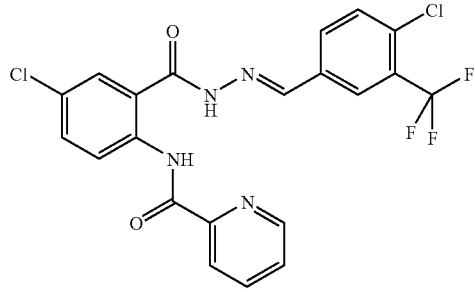 |
| Compound 366 | 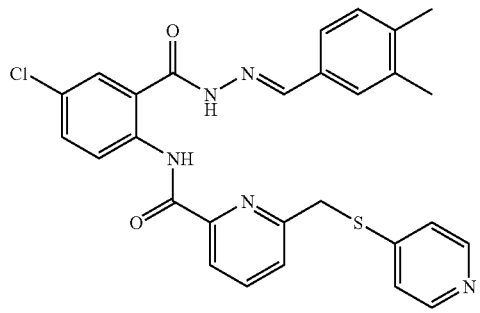 |
| Compound 367 | 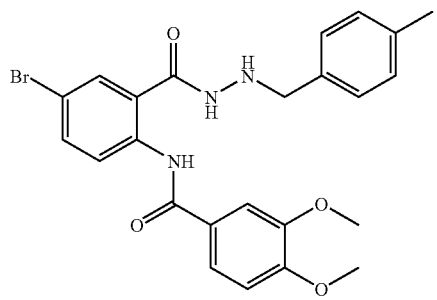 |

TABLE 3-continued
Structures of compounds 1 to 1077 are shown in Table 3.
| Compound No. | Chemical structural formula |
|---|---|
| Compound 368 | 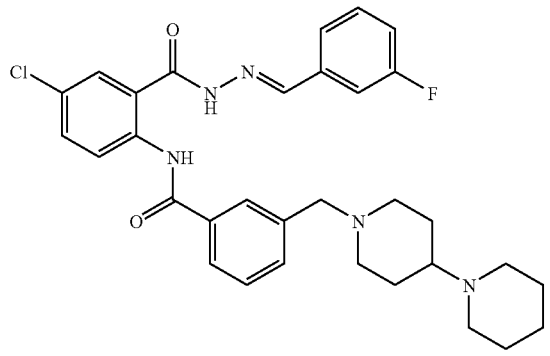 |
| Compound 369 | 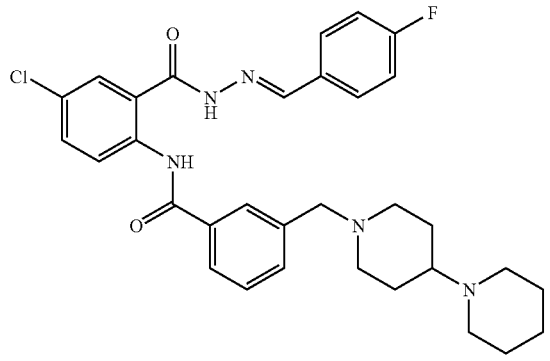 |
| Compound 370 | 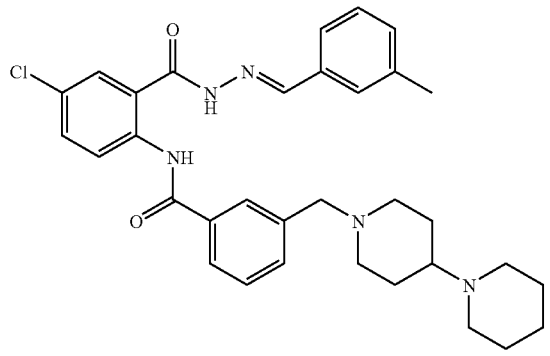 |
| Compound 371 | 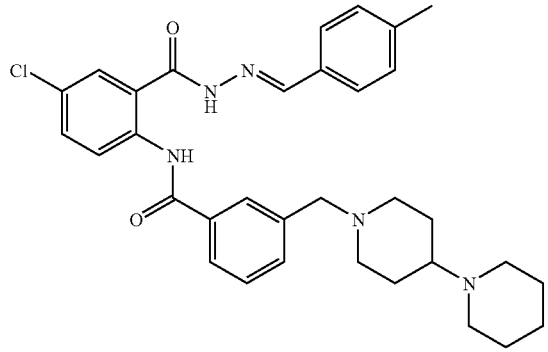 |

TABLE 3-continued
Structures of compounds 1 to 1077 are shown in Table 3.
| Compound No. | Chemical structural formula |
|---|---|
| Compound 372 | 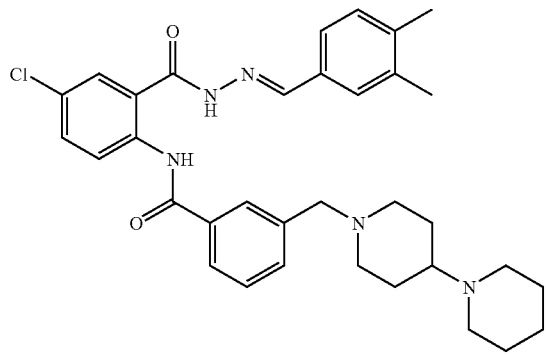 |
| Compound 373 | 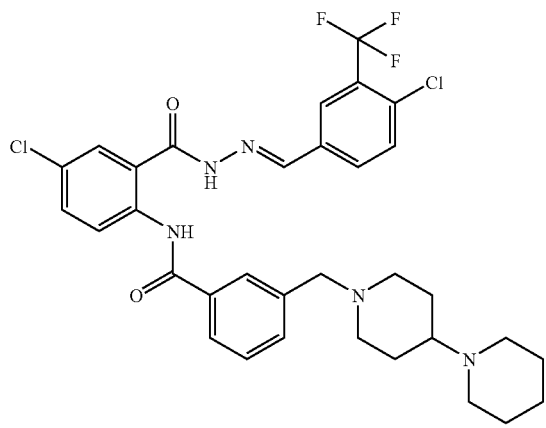 |
| Compound 374 | 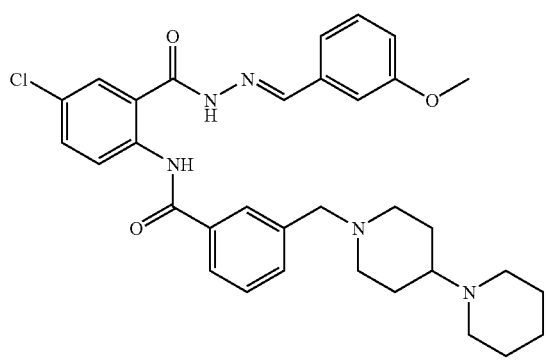 |
| Compound 375 | 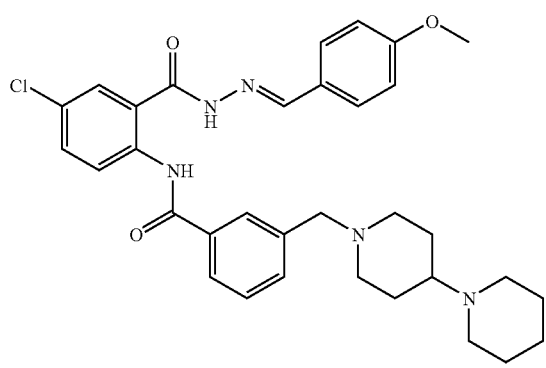 |

TABLE 3-continued

Structures of compounds 1 to 1077 are shown in Table 3.

| Compound No. | Chemical structural formula |
| --- | --- |
| Compound 376 | |
| Compound 377 | |
| Compound 378 | |
| Compound 379 | |
| Compound 380 | |

TABLE 3-continued
Structures of compounds 1 to 1077 are shown in Table 3.
| Compound No. | Chemical structural formula |
|---|---|
| Compound 381 | 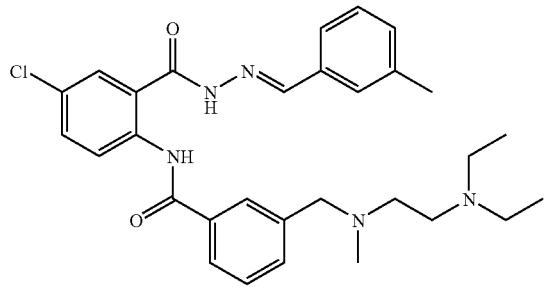 |
| Compound 382 | 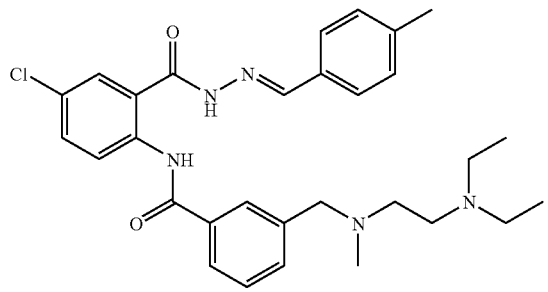 |
| Compound 383 | 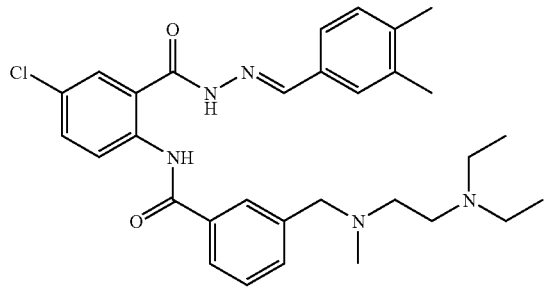 |
| Compound 384 | 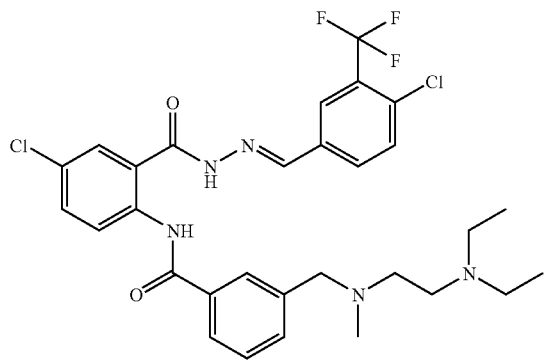 |
| Compound 385 | 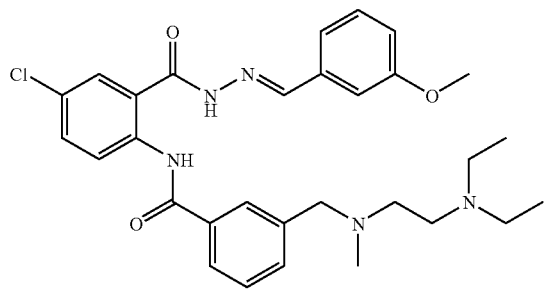 |

TABLE 3-continued
Structures of compounds 1 to 1077 are shown in Table 3.
| Compound No. | Chemical structural formula |
| --- | --- |
| Compound 386 | 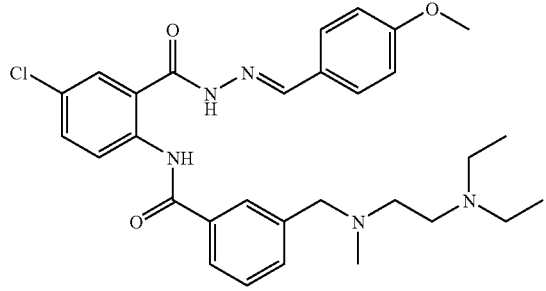 |
| Compound 387 | 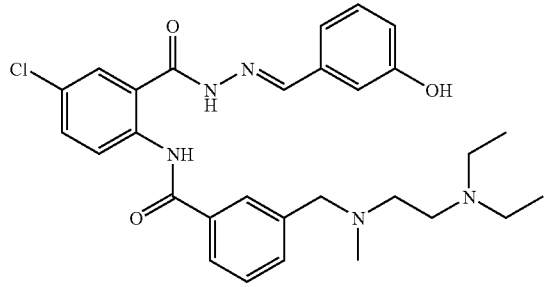 |
| Compound 388 | 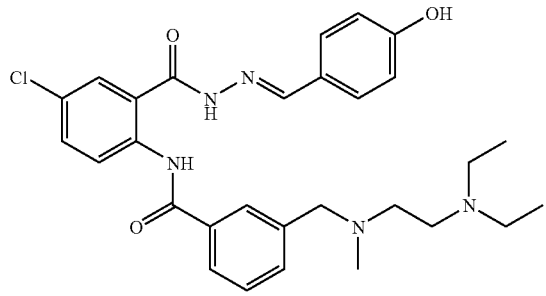 |
| Compound 389 | 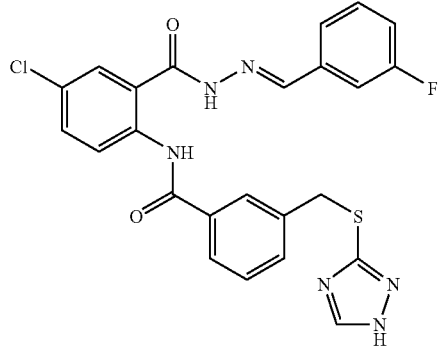 |
| Compound 390 | 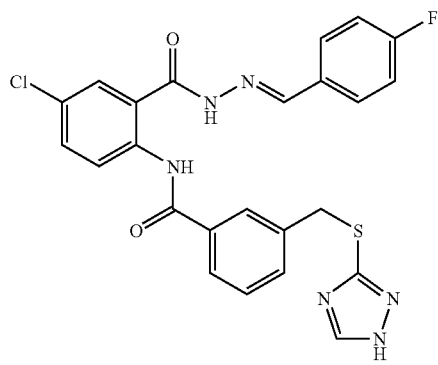 |

TABLE 3-continued
Structures of compounds 1 to 1077 are shown in Table 3.
| Compound No. | Chemical structural formula |
| --- | --- |
| Compound 391 | 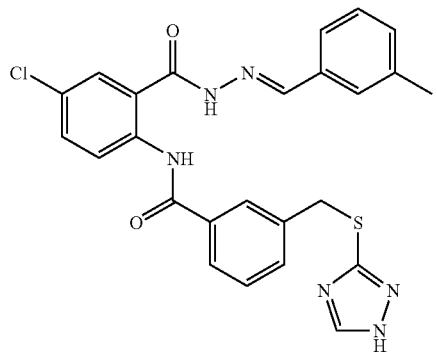 |
| Compound 392 | 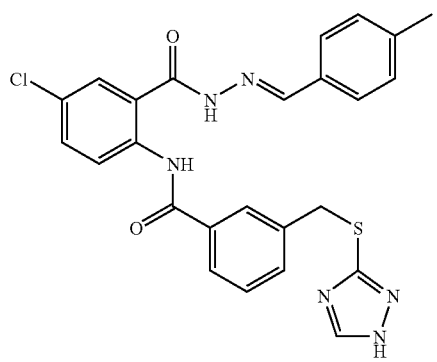 |
| Compound 393 | 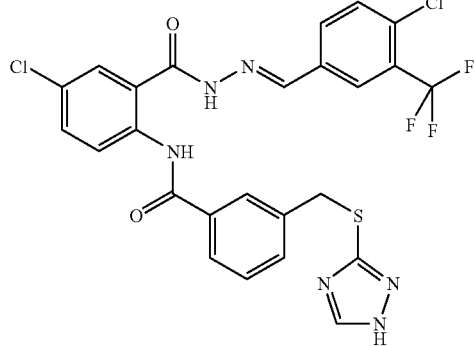 |
| Compound 394 | 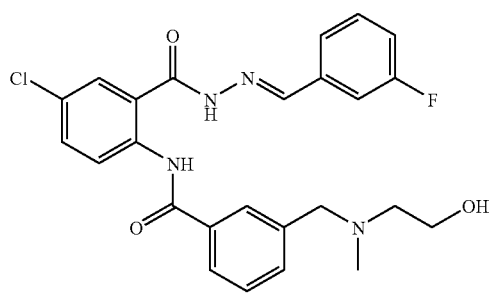 |

TABLE 3-continued
Structures of compounds 1 to 1077 are shown in Table 3.
| Compound No. | Chemical structural formula |
| --- | --- |
| Compound 395 | 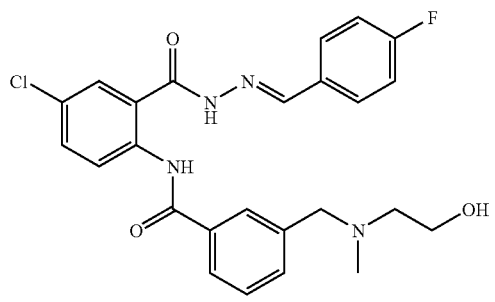 |
| Compound 396 | 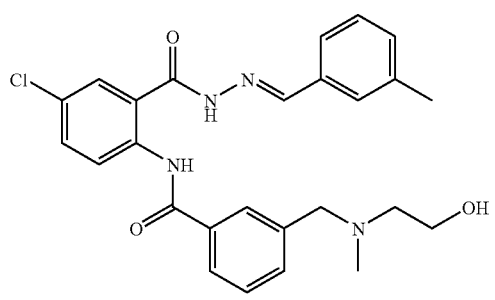 |
| Compound 397 | 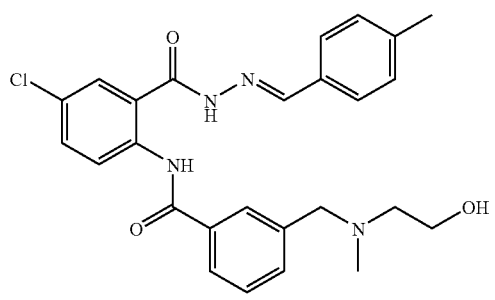 |
| Compound 398 | 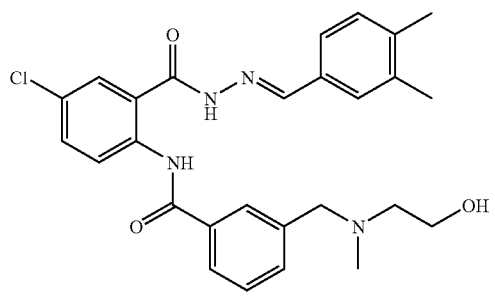 |
| Compound 399 | 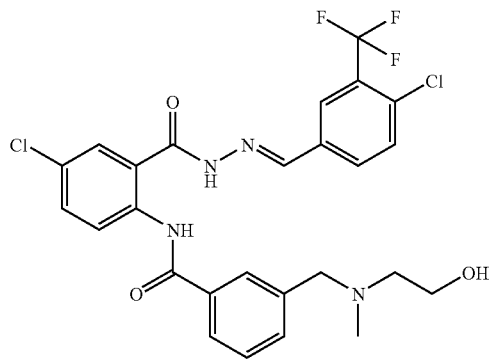 |

TABLE 3-continued
Structures of compounds 1 to 1077 are shown in Table 3.
| Compound No. | Chemical structural formula |
|---|---|
| Compound 400 | 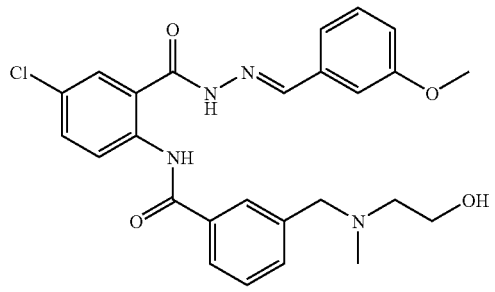 |
| Compound 401 | 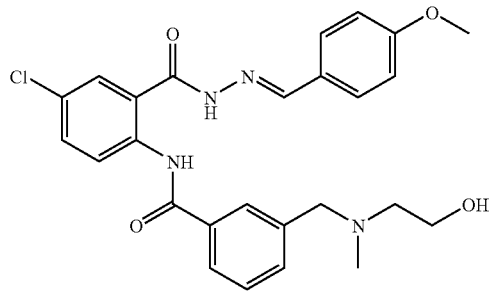 |
| Compound 402 | 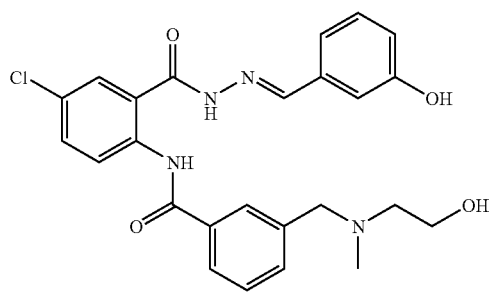 |
| Compound 403 | 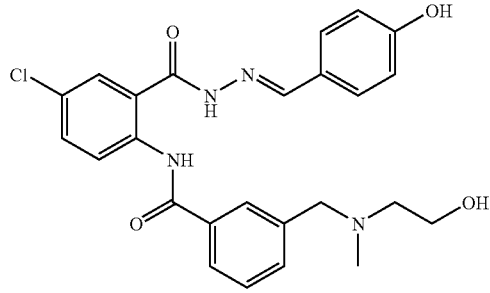 |
| Compound 404 | 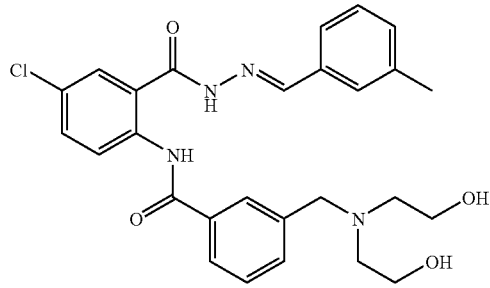 |

TABLE 3-continued
Structures of compounds 1 to 1077 are shown in Table 3.
| Compound No. | Chemical structural formula |
| --- | --- |
| Compound 405 | 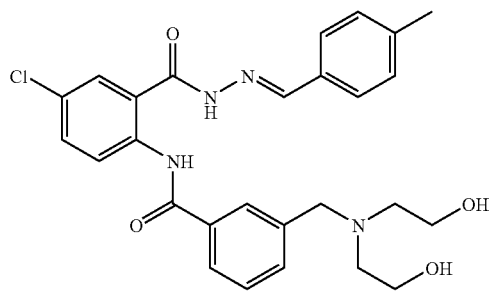 |
| Compound 406 | 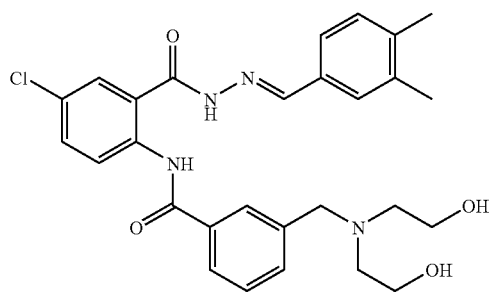 |
| Compound 407 | 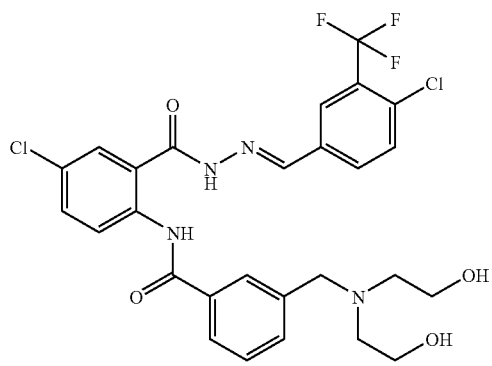 |
| Compound 408 | 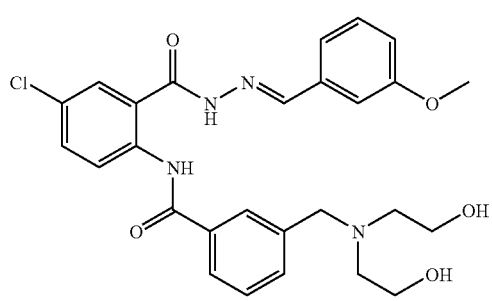 |
| Compound 409 | 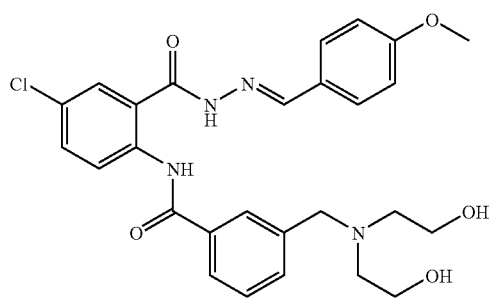 |

TABLE 3-continued
Structures of compounds 1 to 1077 are shown in Table 3.
| Compound No. | Chemical structural formula |
|---|---|
| Compound 410 | 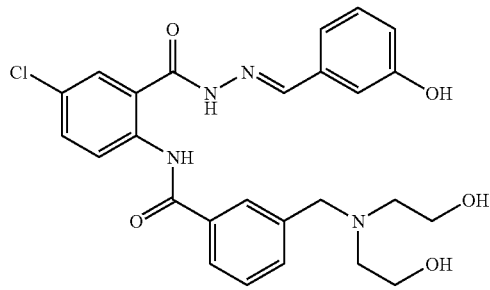 |
| Compound 411 | 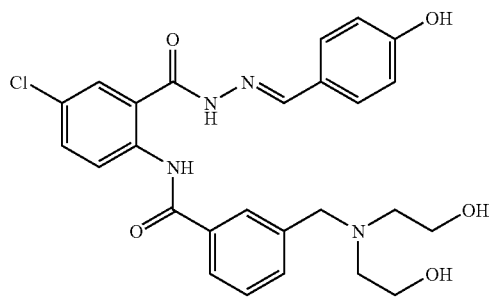 |
| Compound 412 | 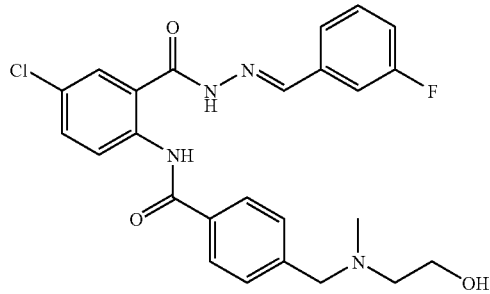 |
| Compound 413 | 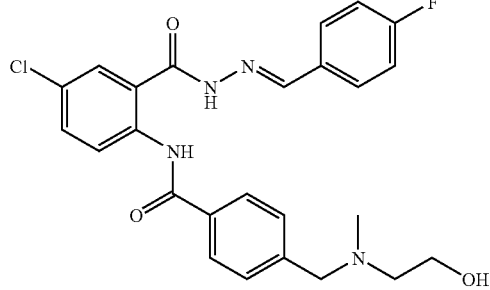 |
| Compound 414 | 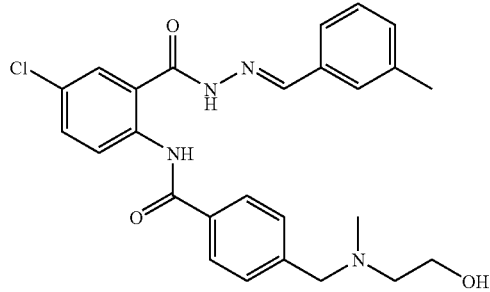 |

TABLE 3-continued
Structures of compounds 1 to 1077 are shown in Table 3.
| Compound No. | Chemical structural formula |
|---|---|
| Compound 415 | 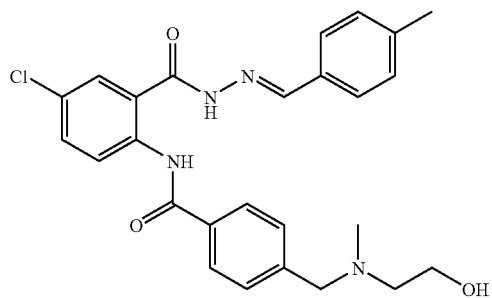 |
| Compound 416 | 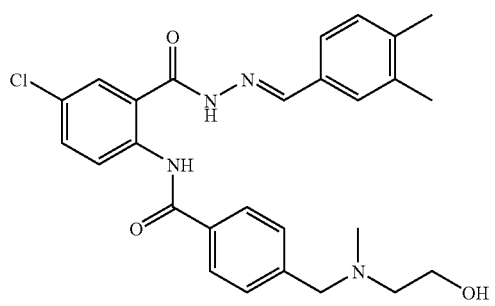 |
| Compound 417 | 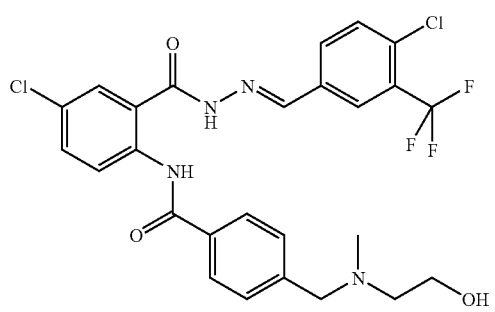 |
| Compound 418 | 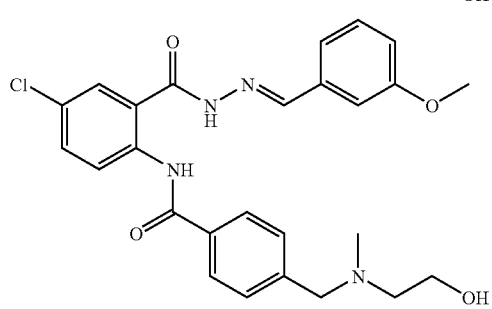 |
| Compound 419 | 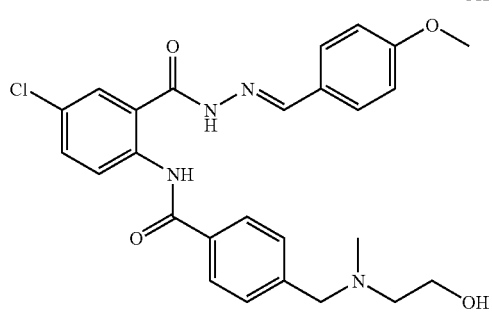 |

TABLE 3-continued
Structures of compounds 1 to 1077 are shown in Table 3.
| Compound No. | Chemical structural formula |
|---|---|
| Compound 420 | 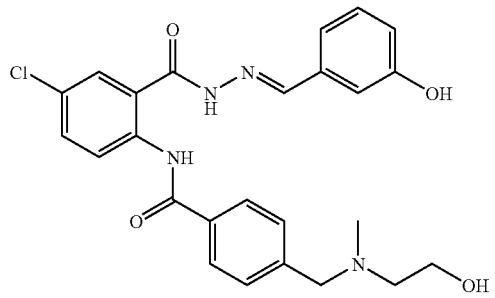 |
| Compound 421 | 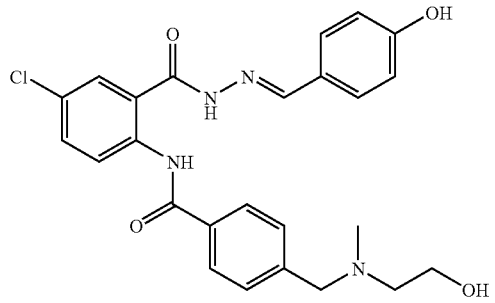 |
| Compound 422 | 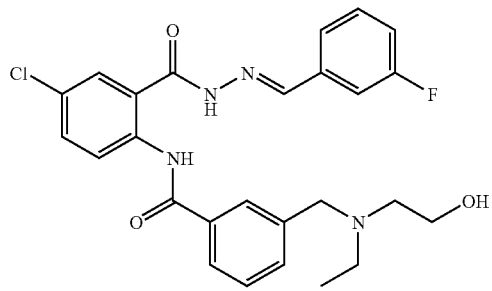 |
| Compound 423 | 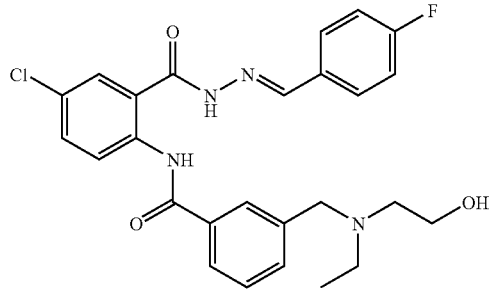 |
| Compound 424 | 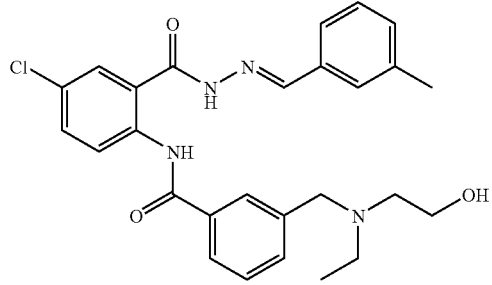 |

TABLE 3-continued
Structures of compounds 1 to 1077 are shown in Table 3.
| Compound No. | Chemical structural formula |
|---|---|
| Compound 425 | 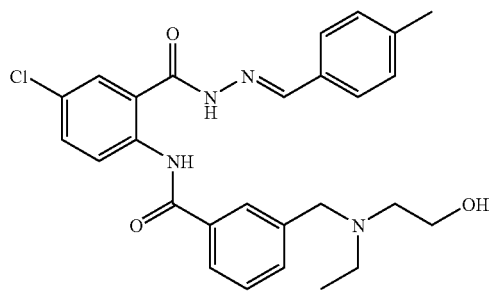 |
| Compound 426 | 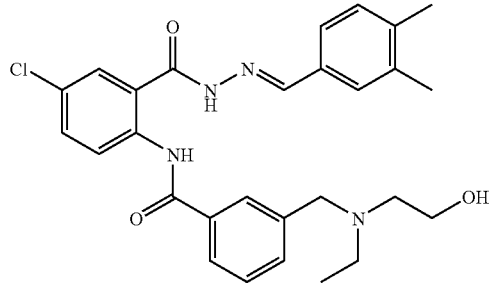 |
| Compound 427 | 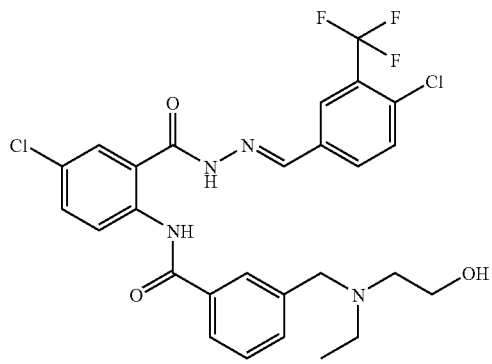 |
| Compound 428 | 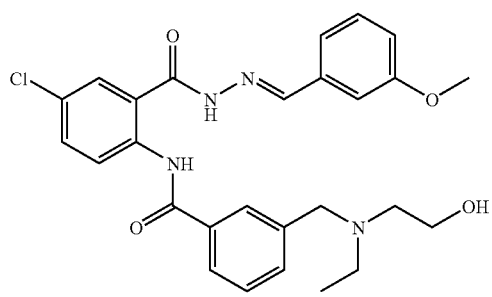 |
| Compound 429 | 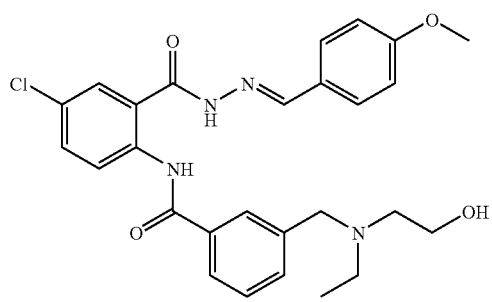 |

TABLE 3-continued
Structures of compounds 1 to 1077 are shown in Table 3.
| Compound No. | Chemical structural formula |
|---|---|
| Compound 430 | 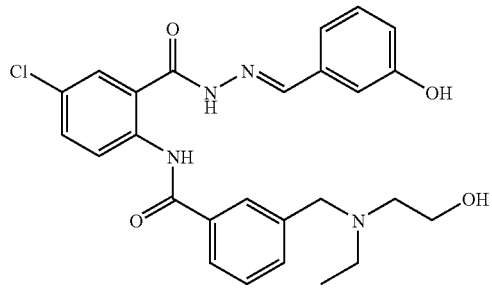 |
| Compound 431 | 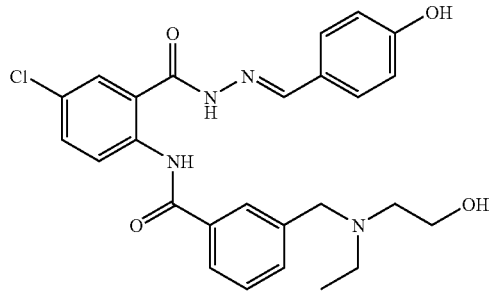 |
| Compound 432 | 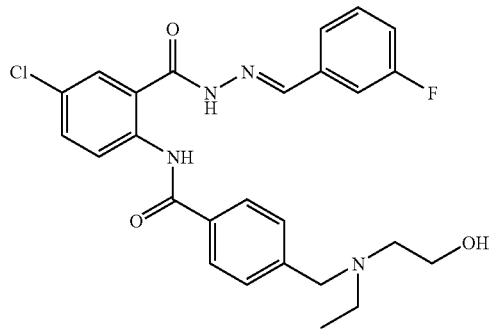 |
| Compound 433 | 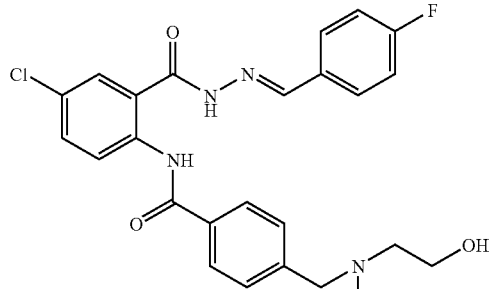 |
| Compound 434 | 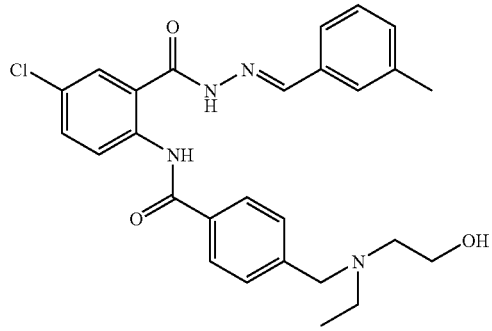 |

TABLE 3-continued
Structures of compounds 1 to 1077 are shown in Table 3.
| Compound No. | Chemical structural formula |
|---|---|
| Compound 435 | 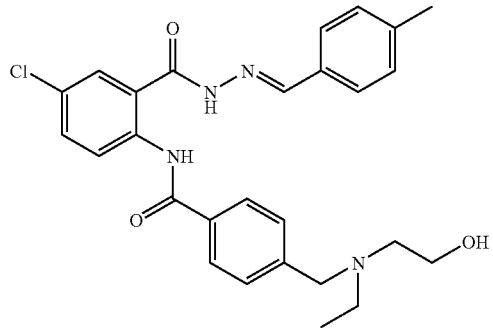 |
| Compound 436 | 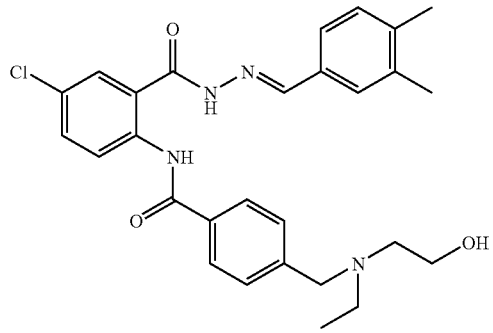 |
| Compound 437 | 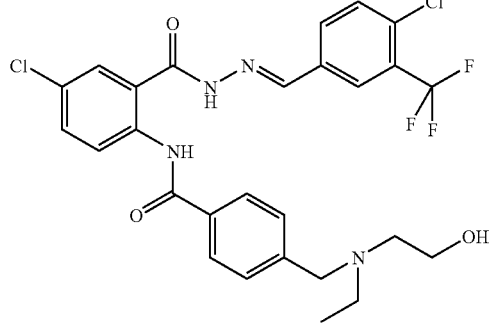 |
| Compound 438 | 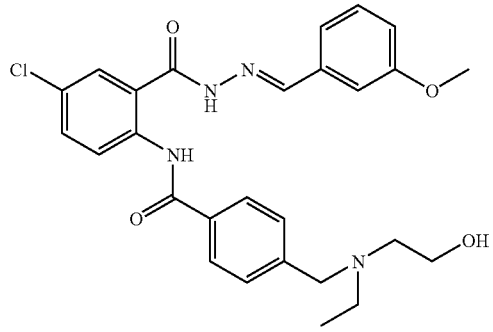 |

TABLE 3-continued
Structures of compounds 1 to 1077 are shown in Table 3.
| Compound No. | Chemical structural formula |
|---|---|
| Compound 439 | 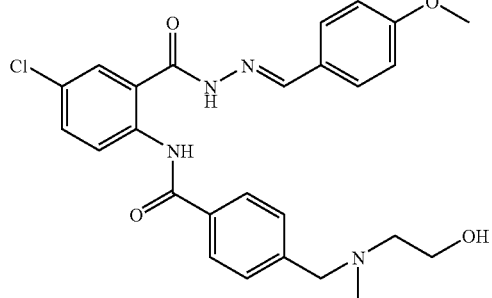 |
| Compound 440 | 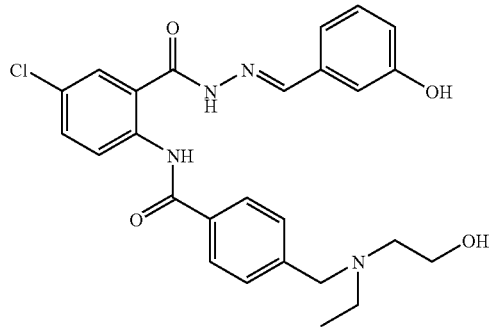 |
| Compound 441 | 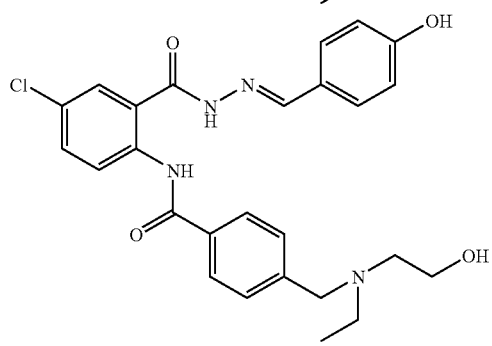 |
| Compound 442 | 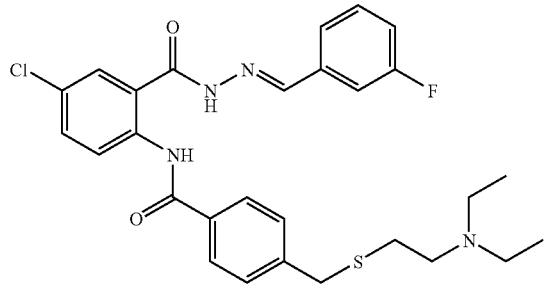 |
| Compound 443 | 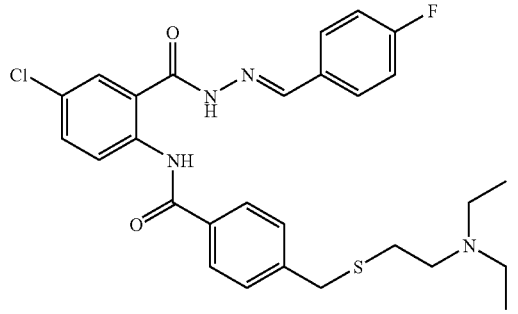 |

TABLE 3-continued
Structures of compounds 1 to 1077 are shown in Table 3.
| Compound No. | Chemical structural formula |
|---|---|
| Compound 444 | 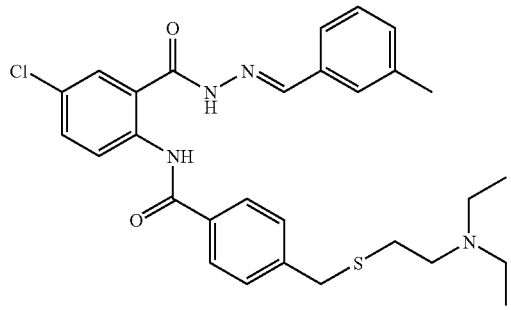 |
| Compound 445 | 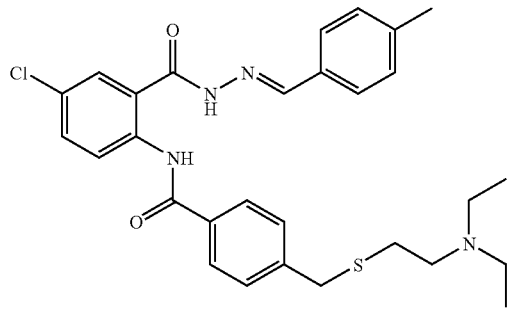 |
| Compound 446 | 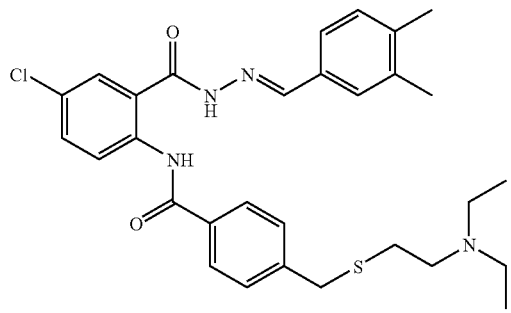 |
| Compound 447 | 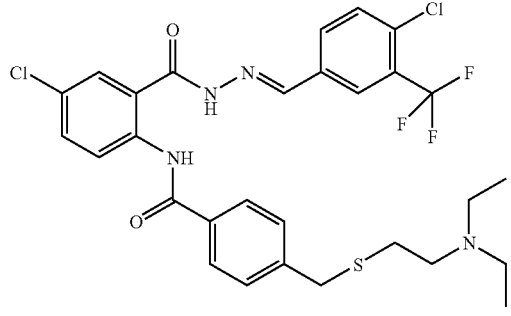 |
| Compound 448 | 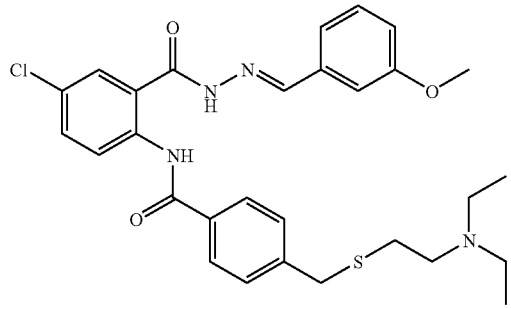 |

TABLE 3-continued
Structures of compounds 1 to 1077 are shown in Table 3.
| Compound No. | Chemical structural formula |
|---|---|
| Compound 449 | 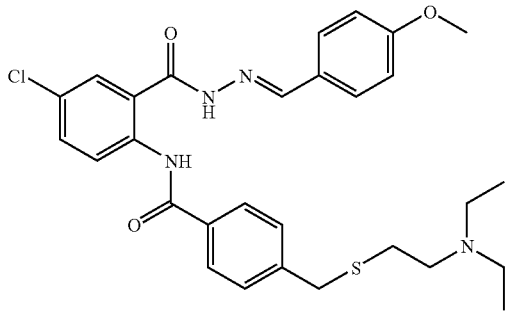 |
| Compound 450 | 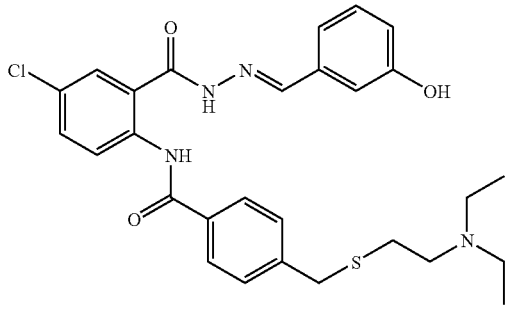 |
| Compound 451 | 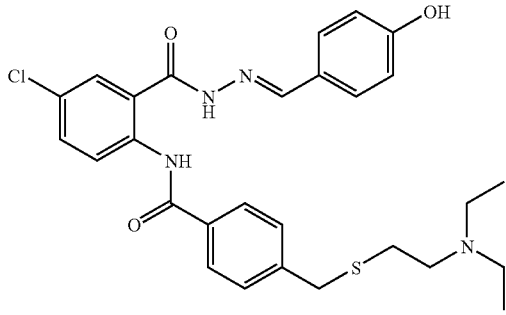 |
| Compound 452 | 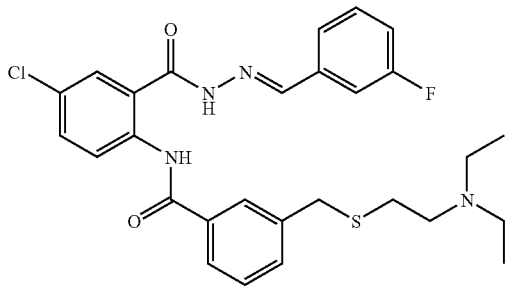 |
| Compound 453 | 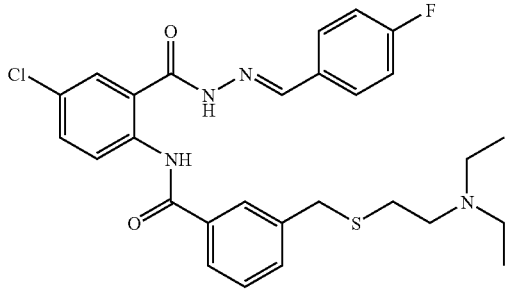 |

TABLE 3-continued
Structures of compounds 1 to 1077 are shown in Table 3.
| Compound No. | Chemical structural formula |
|---|---|
| Compound 454 | 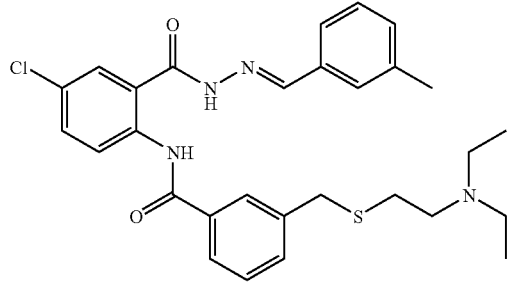 |
| Compound 455 | 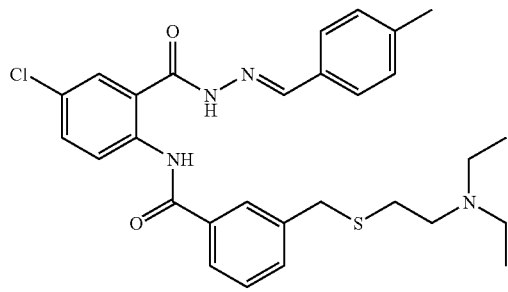 |
| Compound 456 | 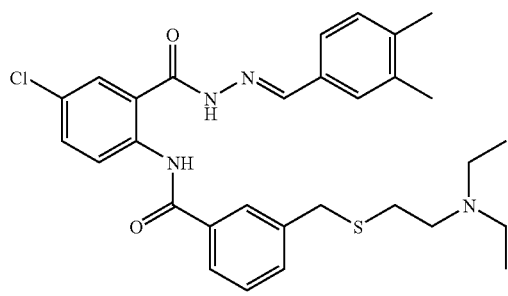 |
| Compound 457 | 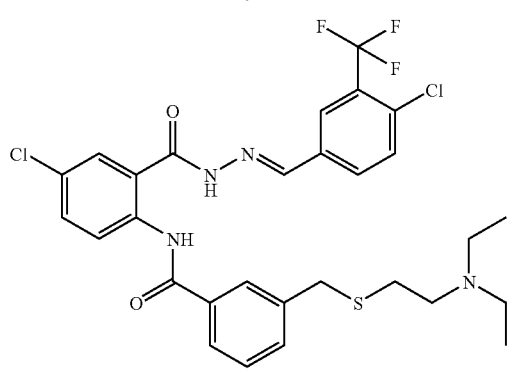 |
| Compound 458 | 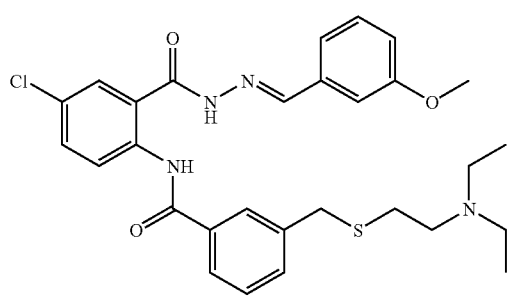 |

TABLE 3-continued
Structures of compounds 1 to 1077 are shown in Table 3.
| Compound No. | Chemical structural formula |
|---|---|
| Compound 459 | 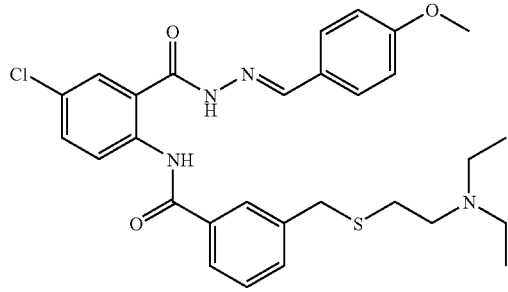 |
| Compound 460 | 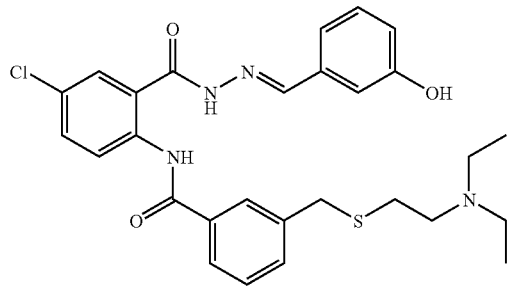 |
| Compound 461 | 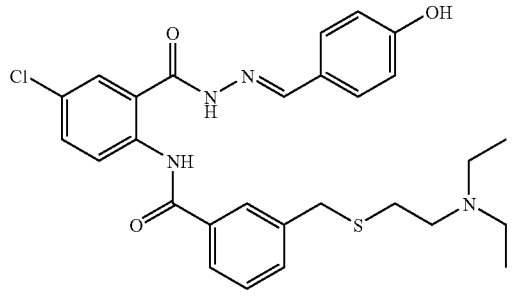 |
| Compound 462 | 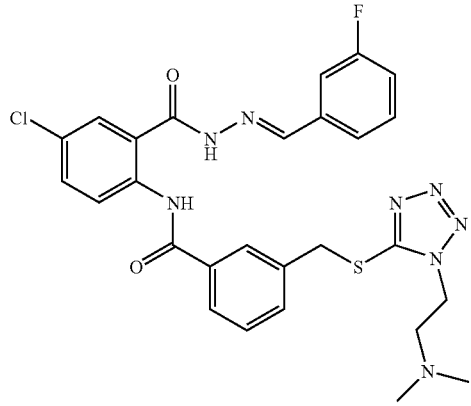 |

TABLE 3-continued
Structures of compounds 1 to 1077 are shown in Table 3.
| Compound No. | Chemical structural formula |
|---|---|
| Compound 463 | 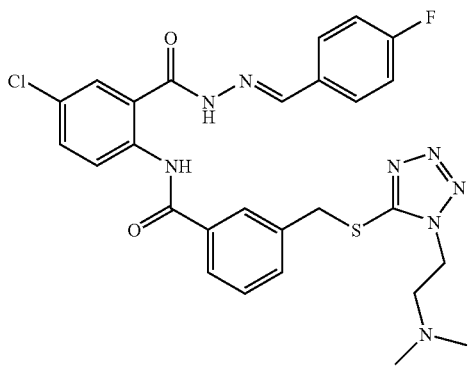 |
| Compound 464 | 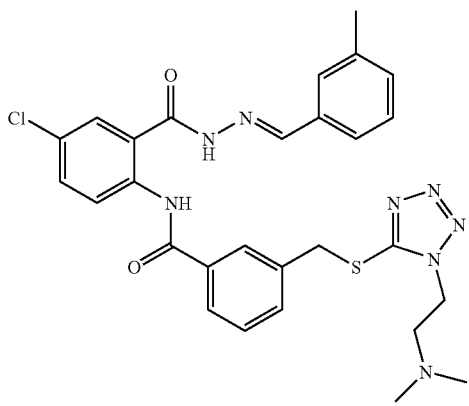 |
| Compound 465 | 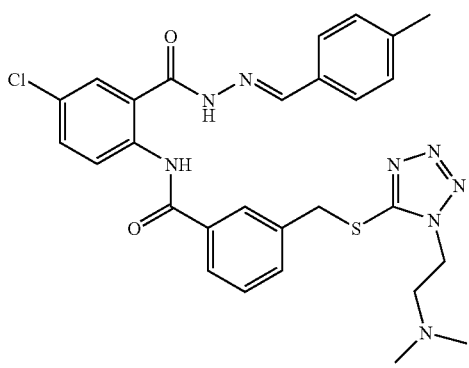 |
| Compound 466 | 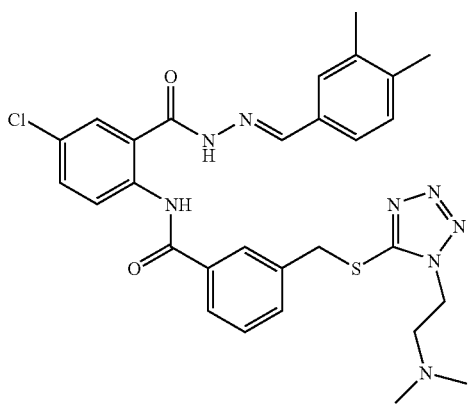 |

TABLE 3-continued
Structures of compounds 1 to 1077 are shown in Table 3.
| Compound No. | Chemical structural formula |
|---|---|
| Compound 467 | 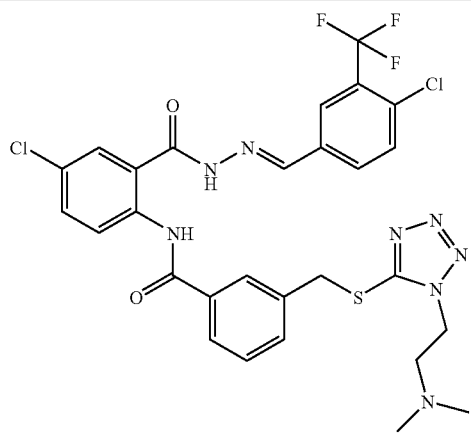 |
| Compound 468 | 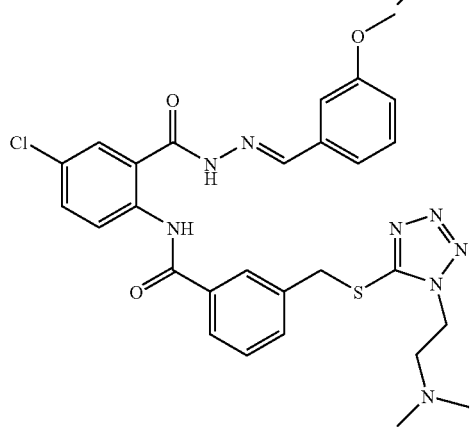 |
| Compound 469 | 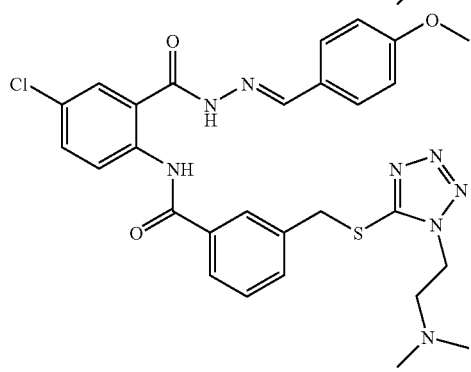 |
| Compound 470 | 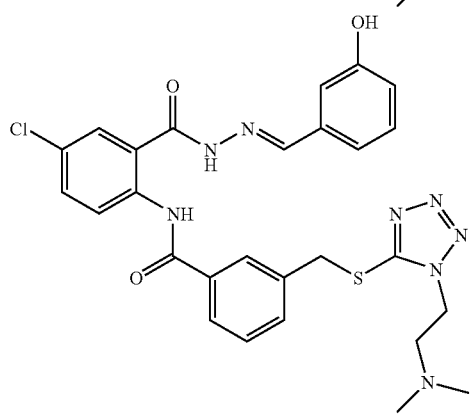 |

TABLE 3-continued
Structures of compounds 1 to 1077 are shown in Table 3.
| Compound No. | Chemical structural formula |
|---|---|
| Compound 471 | 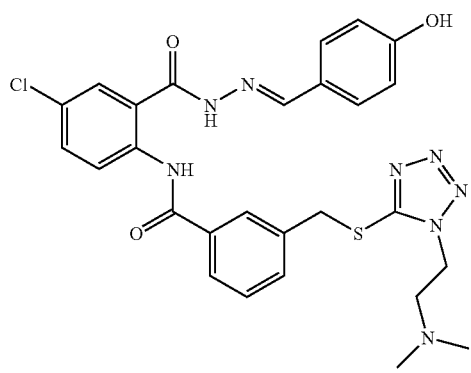 |
| Compound 472 | 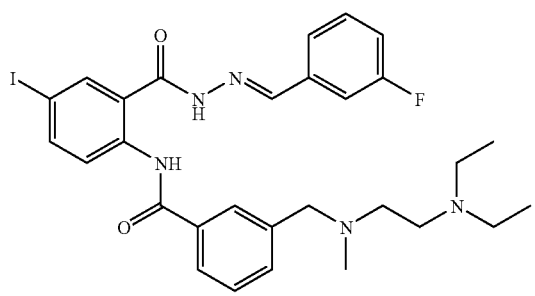 |
| Compound 473 | 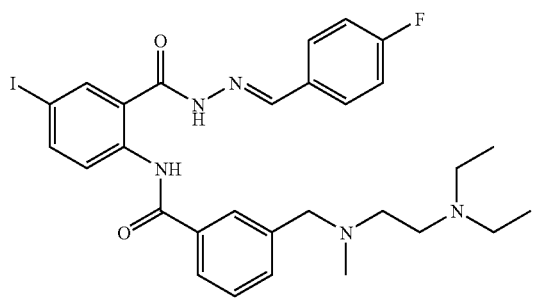 |
| Compound 474 | 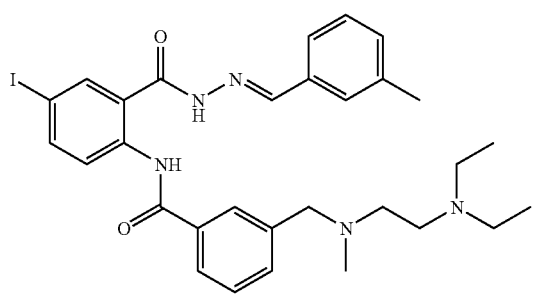 |
| Compound 475 | 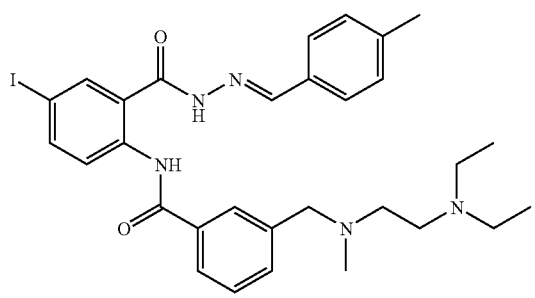 |

TABLE 3-continued
Structures of compounds 1 to 1077 are shown in Table 3.
| Compound No. | Chemical structural formula |
|---|---|
| Compound 476 | 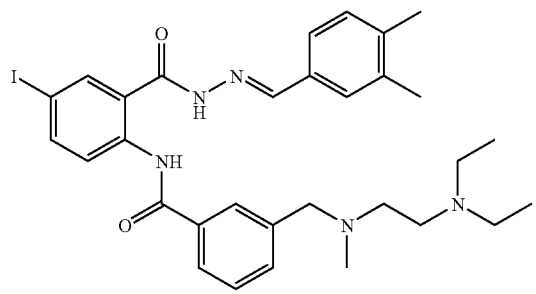 |
| Compound 477 | 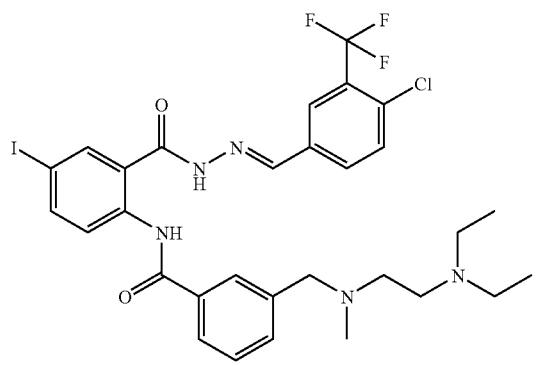 |
| Compound 478 | 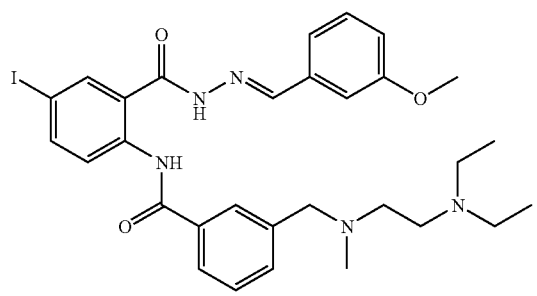 |
| Compound 479 | 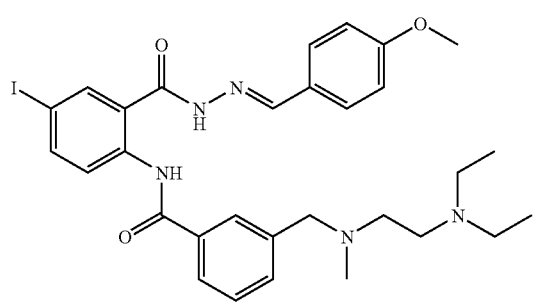 |
| Compound 480 | 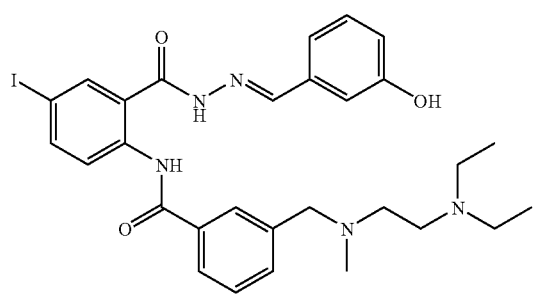 |

TABLE 3-continued
Structures of compounds 1 to 1077 are shown in Table 3.
| Compound No. | Chemical structural formula |
|---|---|
| Compound 481 | 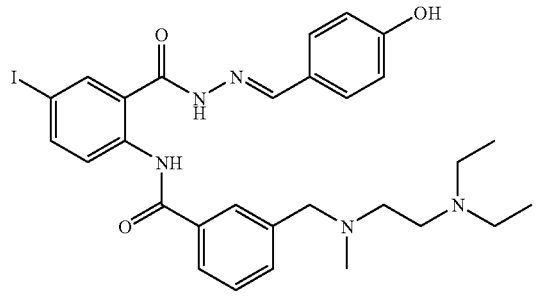 |
| Compound 482 | 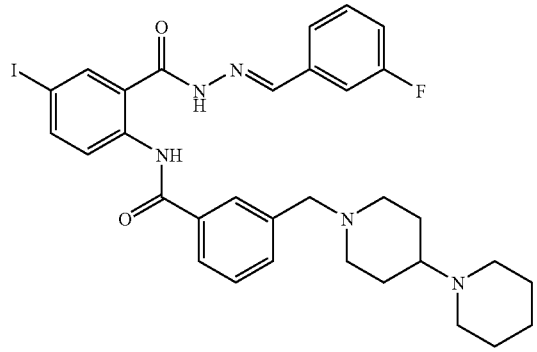 |
| Compound 483 | 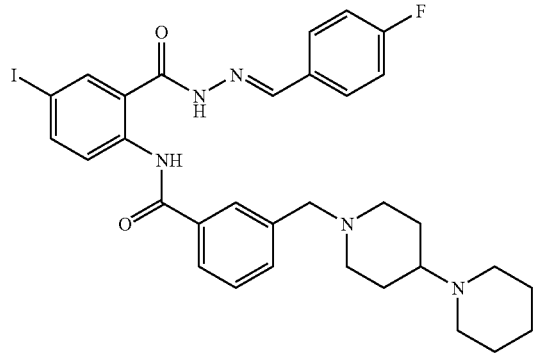 |
| Compound 484 | 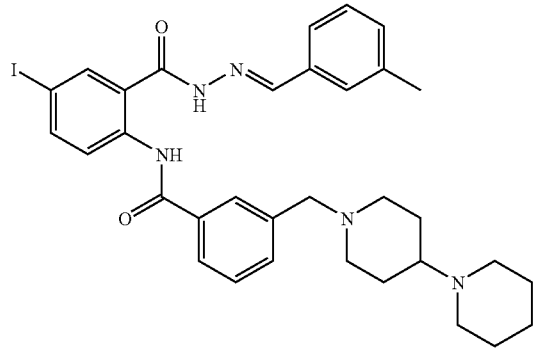 |

TABLE 3-continued

Structures of compounds 1 to 1077 are shown in Table 3.

| Compound No. | Chemical structural formula |
|---|---|
| Compound 485 | |
| Compound 486 | |
| Compound 487 | |
| Compound 488 | |

TABLE 3-continued
Structures of compounds 1 to 1077 are shown in Table 3.
| Compound No. | Chemical structural formula |
|---|---|
| Compound 489 | 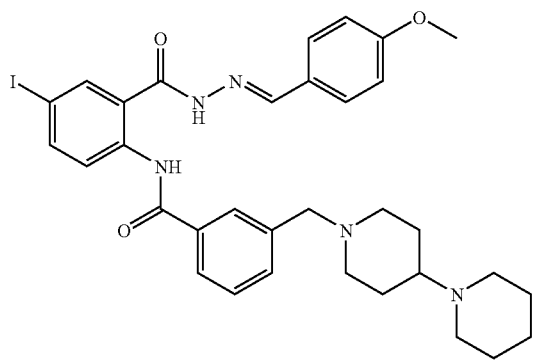 |
| Compound 490 | 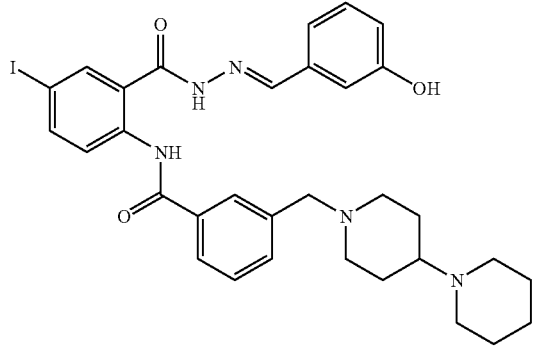 |
| Compound 491 | 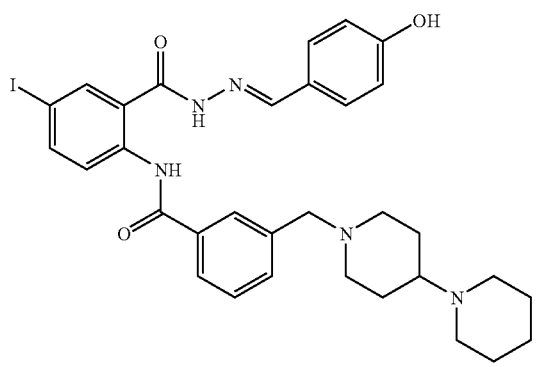 |
| Compound 492 | 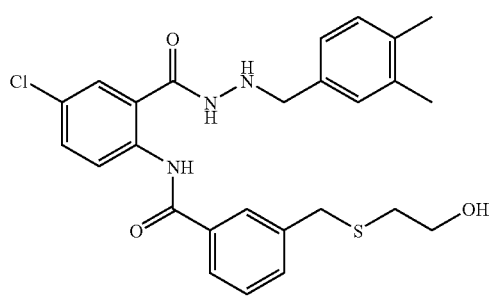 |

TABLE 3-continued
Structures of compounds 1 to 1077 are shown in Table 3.
| Compound No. | Chemical structural formula |
|---|---|
| Compound 493 | 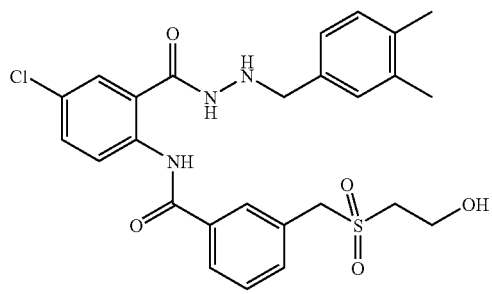 |
| Compound 494 | 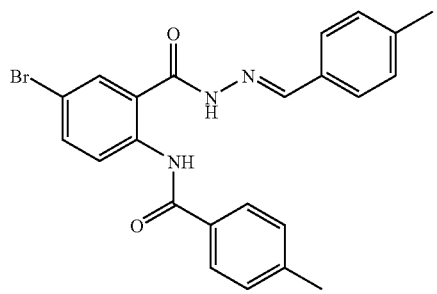 |
| Compound 495 | 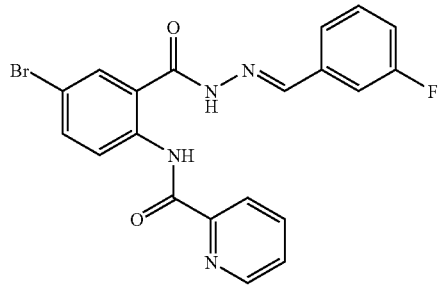 |
| Compound 496 | 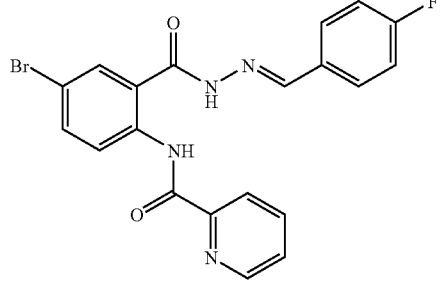 |
| Compound 497 | 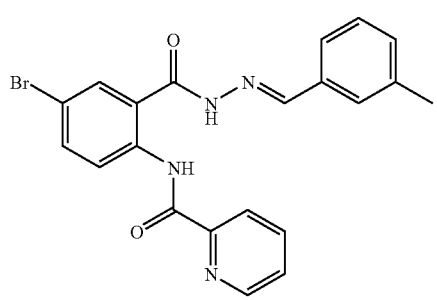 |

TABLE 3-continued
Structures of compounds 1 to 1077 are shown in Table 3.
| Compound No. | Chemical structural formula |
|---|---|
| Compound 498 | 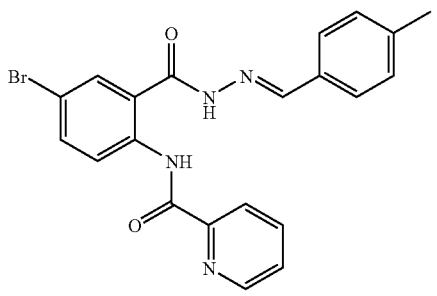 |
| Compound 499 | 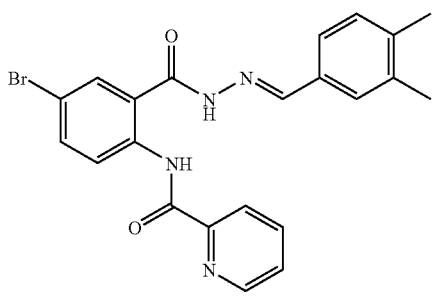 |
| Compound 500 | 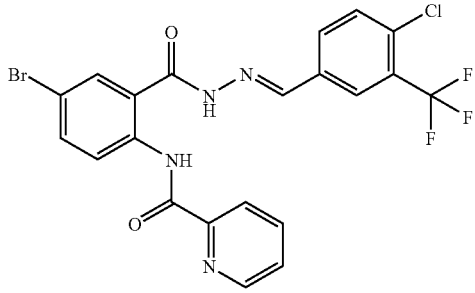 |
| Compound 501 | 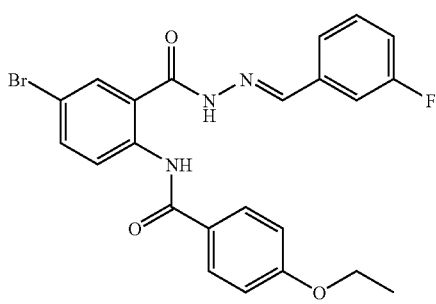 |
| Compound 502 | 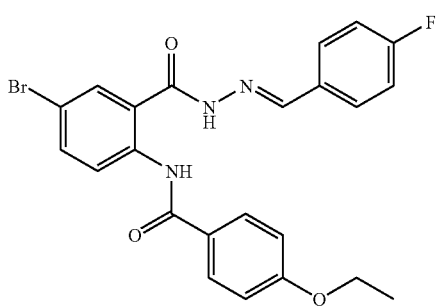 |

TABLE 3-continued
Structures of compounds 1 to 1077 are shown in Table 3.
| Compound No. | Chemical structural formula |
|---|---|
| Compound 503 | 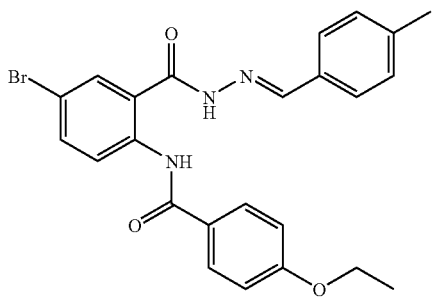 |
| Compound 504 | 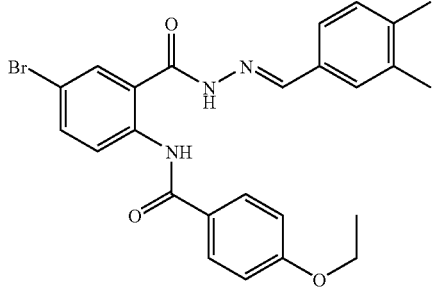 |
| Compound 505 | 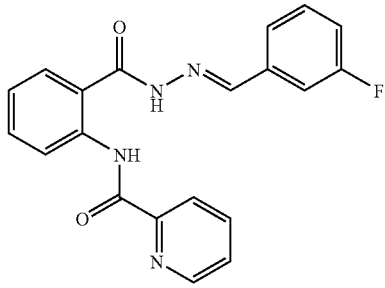 |
| Compound 506 | 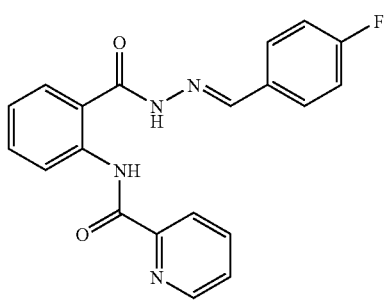 |
| Compound 507 | 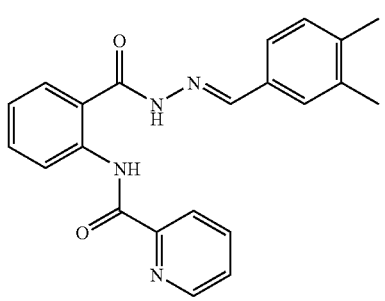 |

TABLE 3-continued
Structures of compounds 1 to 1077 are shown in Table 3.
| Compound No. | Chemical structural formula |
|---|---|
| Compound 508 | 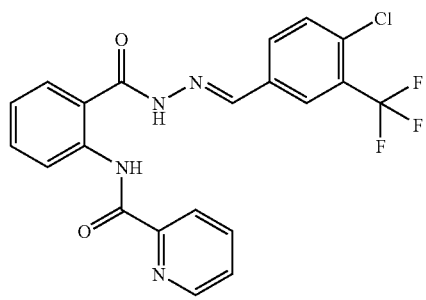 |
| Compound 509 | 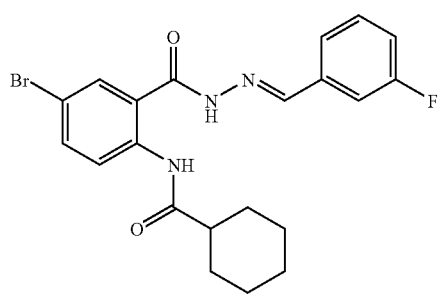 |
| Compound 510 | 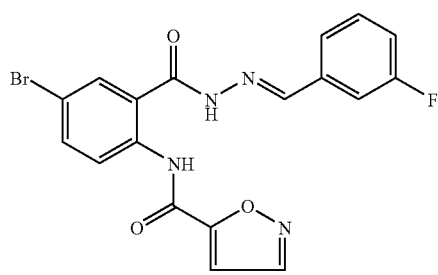 |
| Compound 511 | 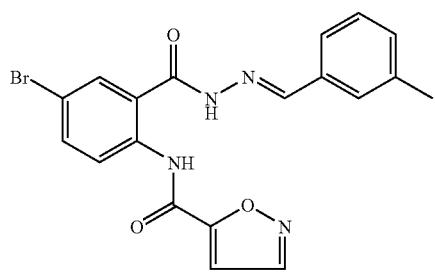 |
| Compound 512 | 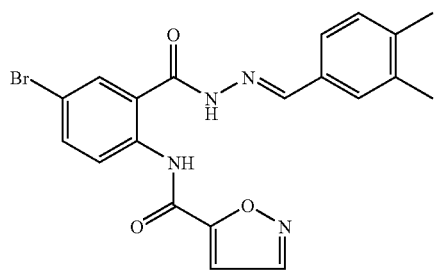 |

TABLE 3-continued

Structures of compounds 1 to 1077 are shown in Table 3.

| Compound No. | Chemical structural formula |
| --- | --- |
| Compound 513 | |
| Compound 514 | |
| Compound 515 | |
| Compound 516 | |
| Compound 517 | |

TABLE 3-continued
Structures of compounds 1 to 1077 are shown in Table 3.
| Compound No. | Chemical structural formula |
| --- | --- |
| Compound 518 | 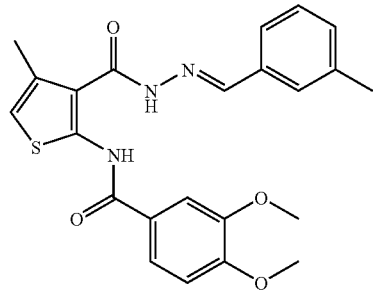 |
| Compound 519 | 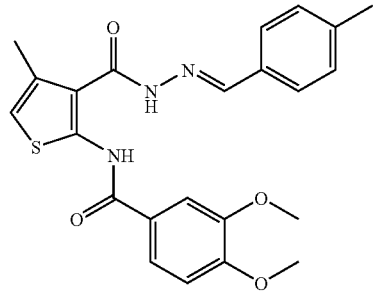 |
| Compound 521 | 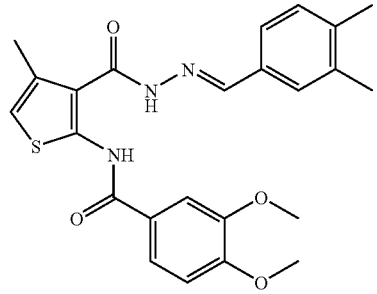 |
| Compound 522 | 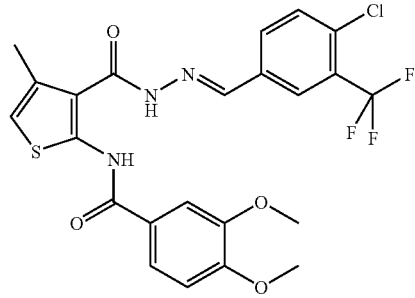 |
| Compound 523 | 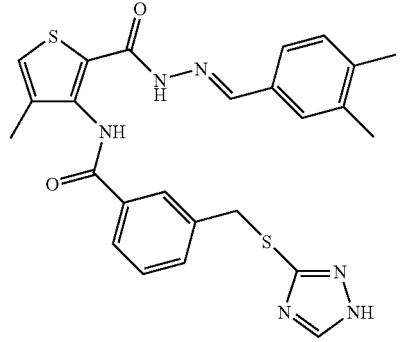 |

TABLE 3-continued
Structures of compounds 1 to 1077 are shown in Table 3.
| Compound No. | Chemical structural formula |
|---|---|
| Compound 524 | 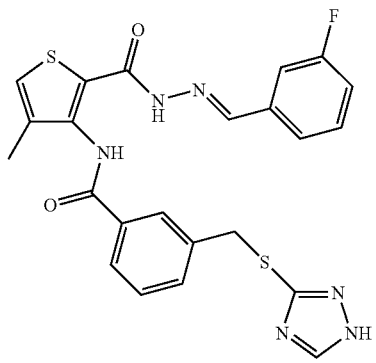 |
| Compound 525 | 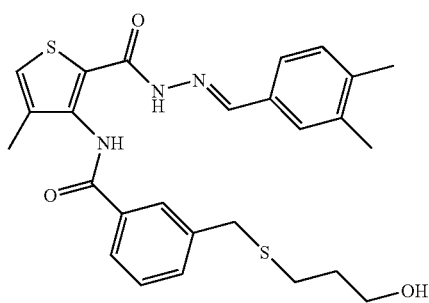 |
| Compound 526 | 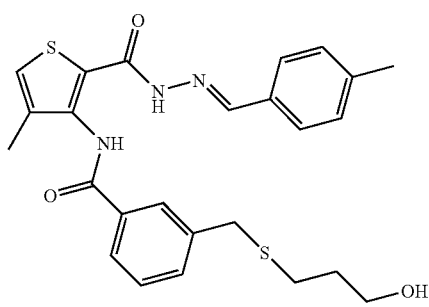 |
| Compound 527 | 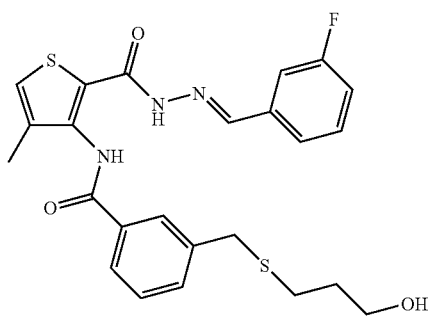 |
| Compound 528 | 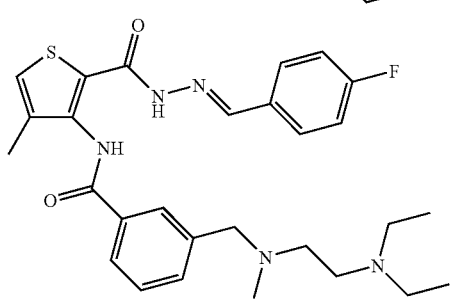 |

TABLE 3-continued
Structures of compounds 1 to 1077 are shown in Table 3.
| Compound No. | Chemical structural formula |
| --- | --- |
| Compound 529 | 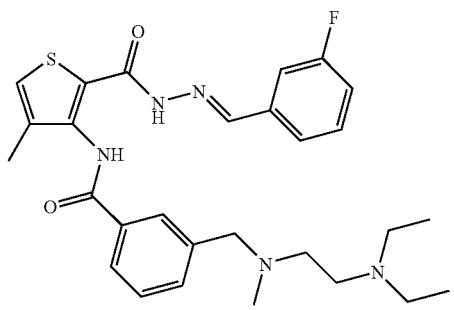 |
| Compound 530 | 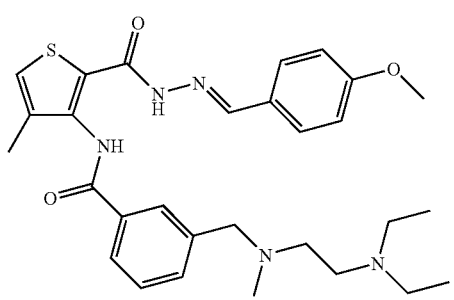 |
| Compound 531 | 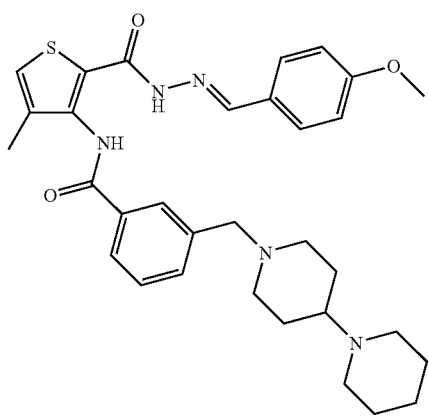 |
| Compound 532 | 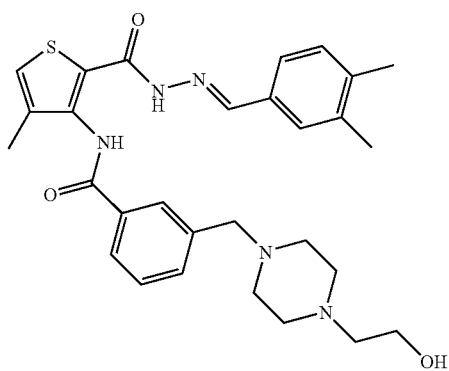 |

TABLE 3-continued
Structures of compounds 1 to 1077 are shown in Table 3.
| Compound No. | Chemical structural formula |
| --- | --- |
| Compound 533 | 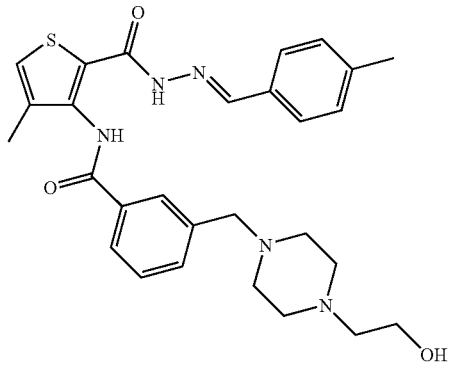 |
| Compound 534 | 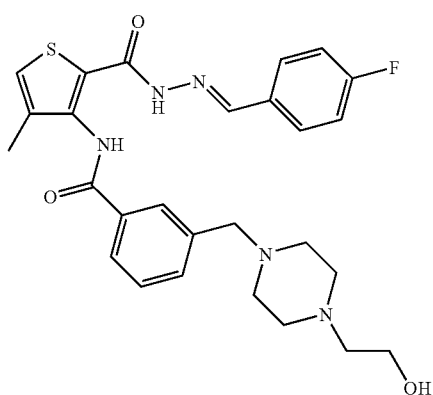 |
| Compound 535 | 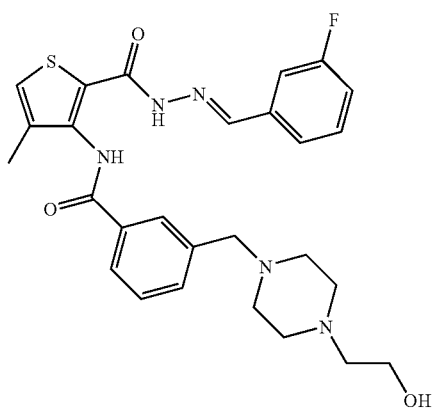 |
| Compound 536 | 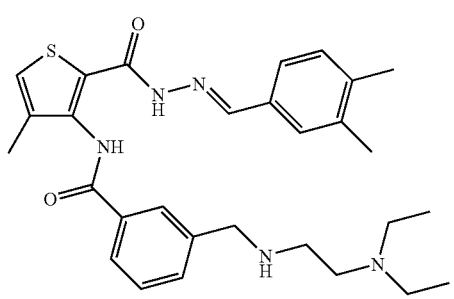 |

TABLE 3-continued
Structures of compounds 1 to 1077 are shown in Table 3.
| Compound No. | Chemical structural formula |
| --- | --- |
| Compound 537 | 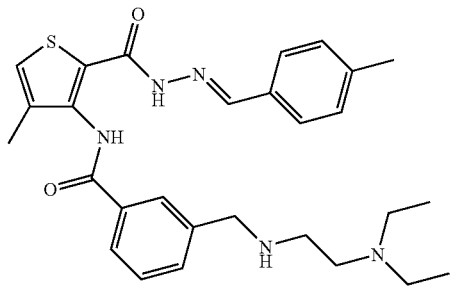 |
| Compound 538 | 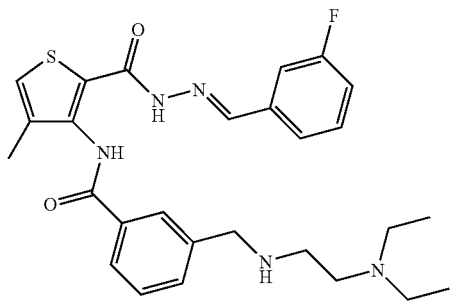 |
| Compound 539 | 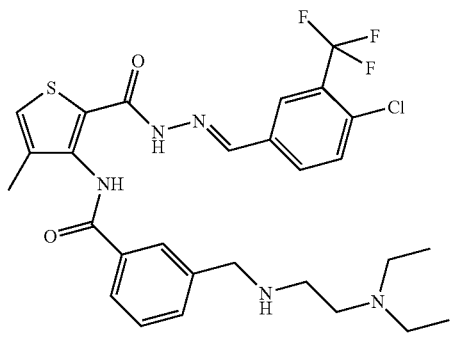 |
| Compound 540 | 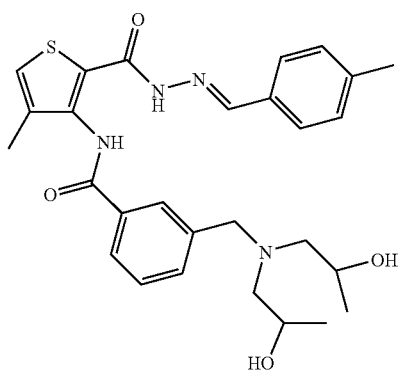 |

TABLE 3-continued
Structures of compounds 1 to 1077 are shown in Table 3.
| Compound No. | Chemical structural formula |
|---|---|
| Compound 541 | 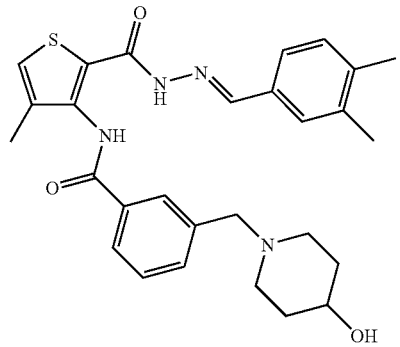 |
| Compound 542 | 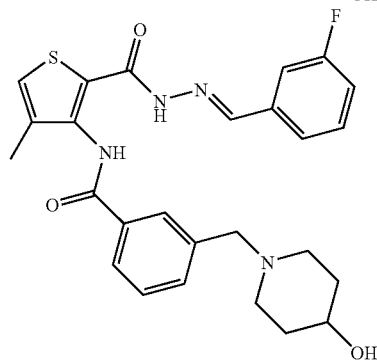 |
| Compound 543 | 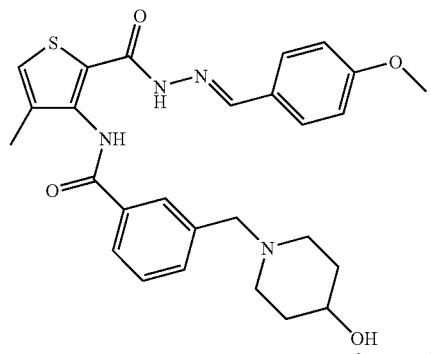 |
| Compound 544 | 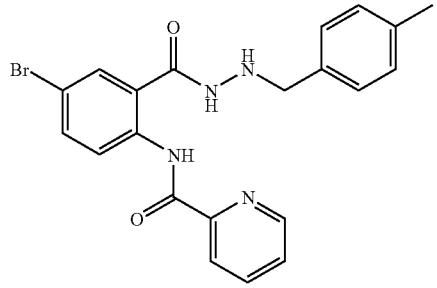 |
| Compound 545 | 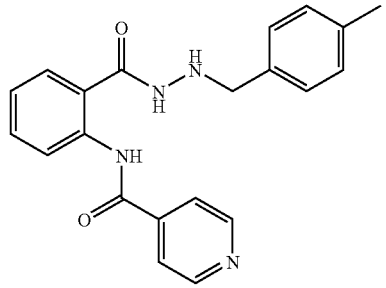 |

TABLE 3-continued
Structures of compounds 1 to 1077 are shown in Table 3.
| Compound No. | Chemical structural formula |
|---|---|
| Compound 546 | 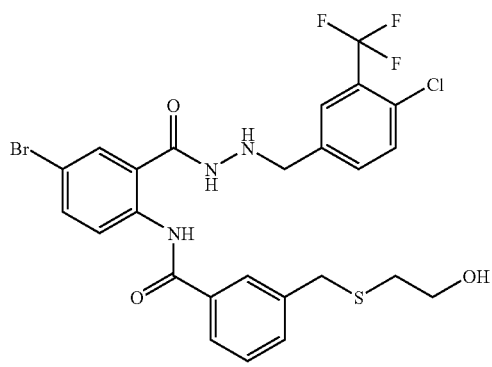 |
| Compound 547 | 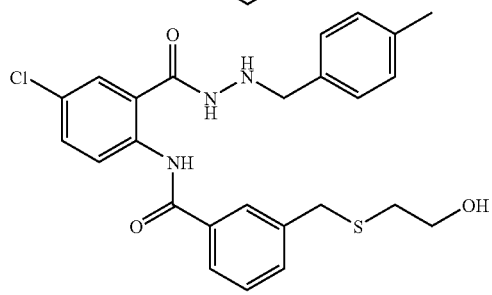 |
| Compound 548 | 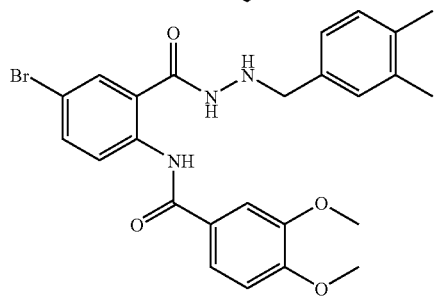 |
| Compound 549 | 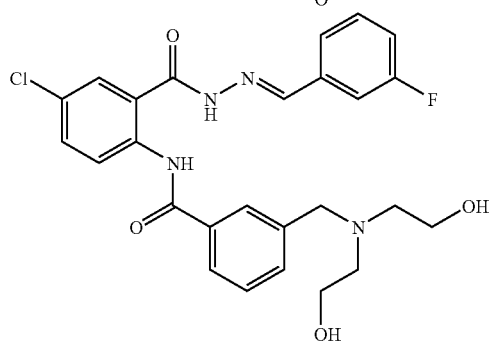 |
| Compound 550 | 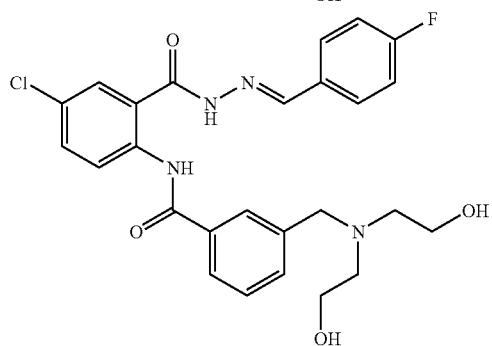 |

TABLE 3-continued

Structures of compounds 1 to 1077 are shown in Table 3.

| Compound No. | Chemical structural formula |
|---|---|
| Compound 551 | |
| Compound 552 | |
| Compound 553 | |
| Compound 554 | |

TABLE 3-continued
Structures of compounds 1 to 1077 are shown in Table 3.
Compound No.   Chemical structural formula
Compound 555
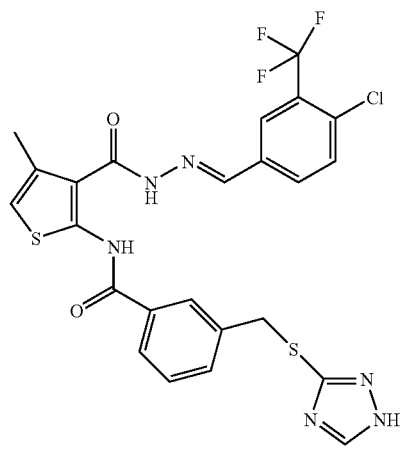
Compound 556
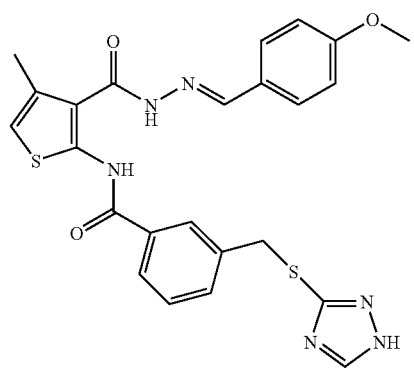
Compound 557
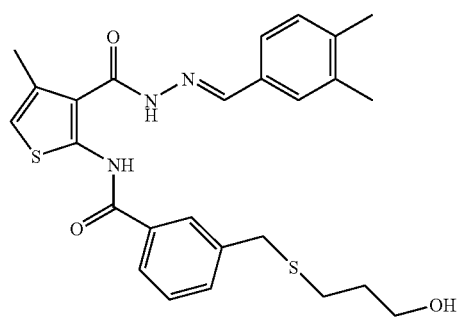
Compound 558
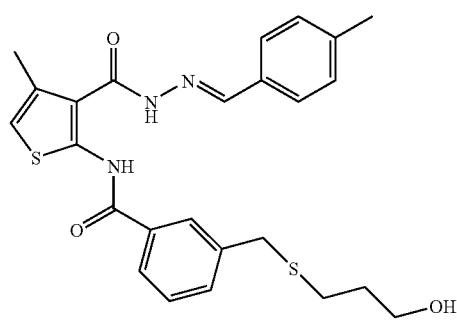

TABLE 3-continued
Structures of compounds 1 to 1077 are shown in Table 3.
| Compound No. | Chemical structural formula |
|---|---|
| Compound 559 | 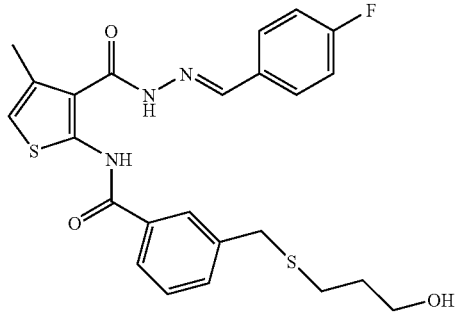 |
| Compound 560 | 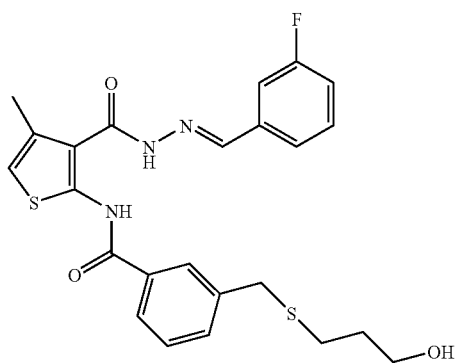 |
| Compound 561 | 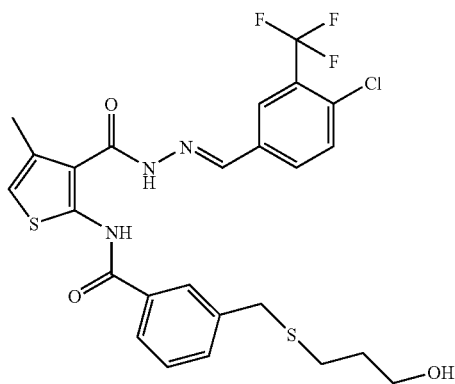 |
| Compound 562 | 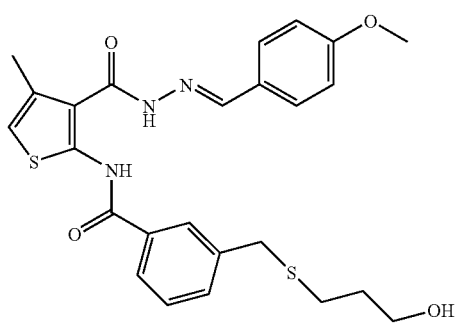 |

TABLE 3-continued
Structures of compounds 1 to 1077 are shown in Table 3.
| Compound No. | Chemical structural formula |
| --- | --- |
| Compound 563 | 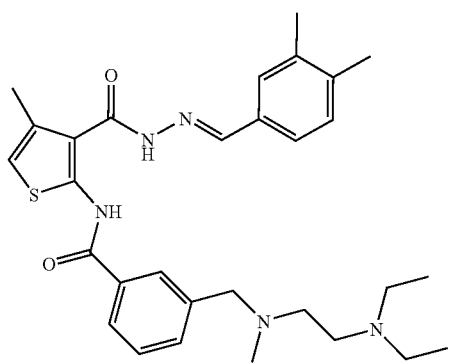 |
| Compound 564 | 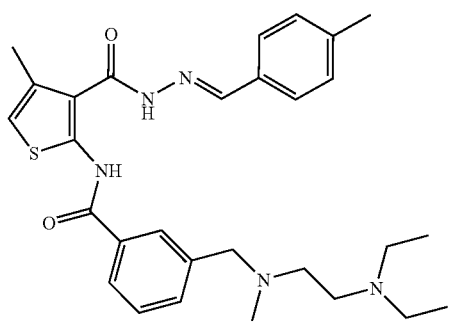 |
| Compound 565 | 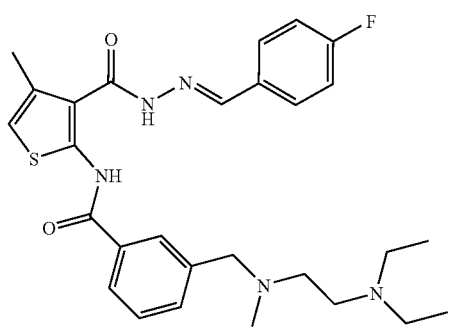 |
| Compound 566 | 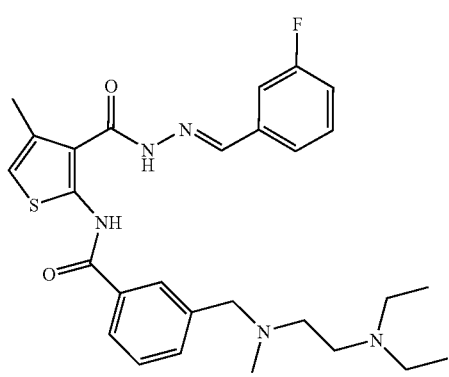 |

TABLE 3-continued
Structures of compounds 1 to 1077 are shown in Table 3.
| Compound No. | Chemical structural formula |
| --- | --- |
| Compound 567 | 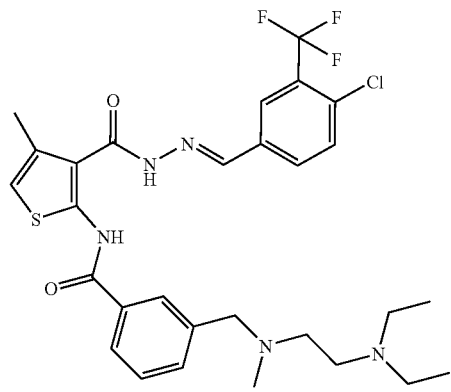 |
| Compound 568 | 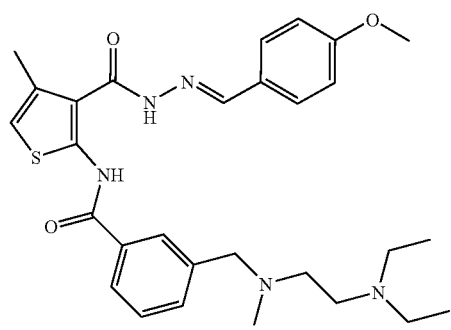 |
| Compound 569 | 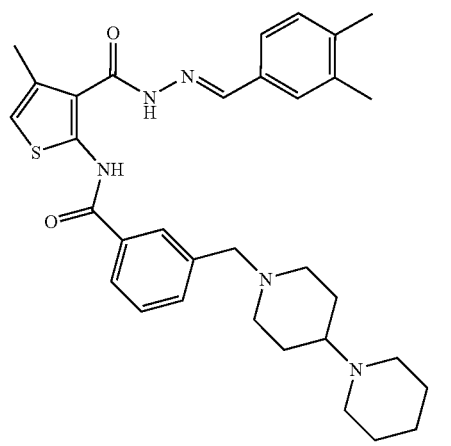 |
| Compound 570 | 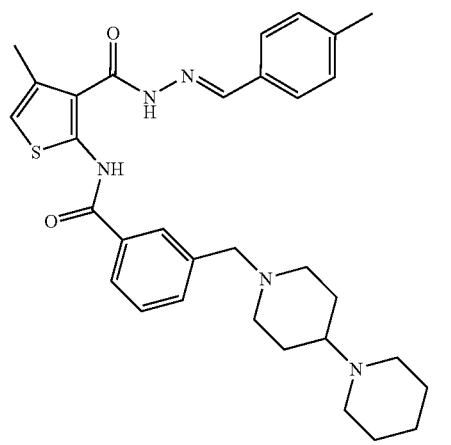 |

TABLE 3-continued
Structures of compounds 1 to 1077 are shown in Table 3.
Compound No. Chemical structural formula
Compound 571
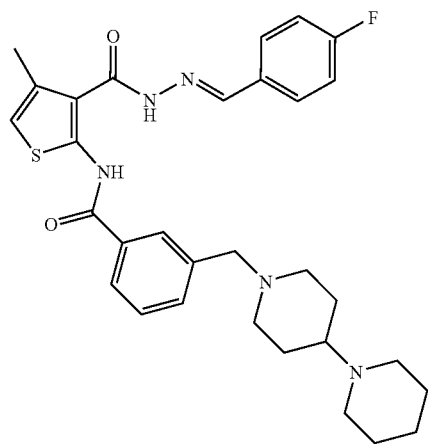
Compound 572
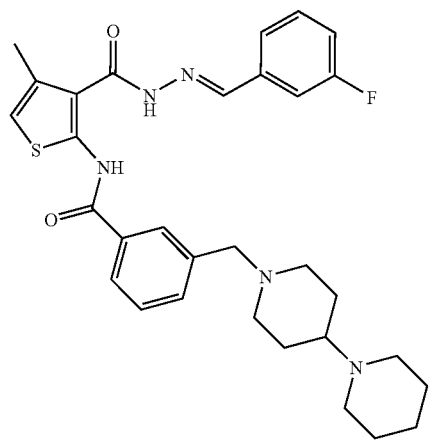
Compound 573
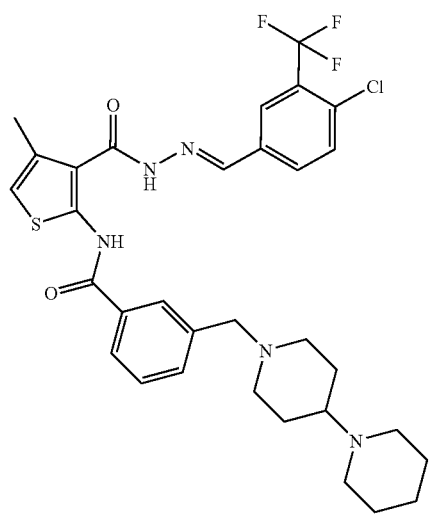

US 8,134,015 B2
TABLE 3-continued
Structures of compounds 1 to 1077 are shown in Table 3.
| Compound No. | Chemical structural formula |
|---|---|
| Compound 574 | 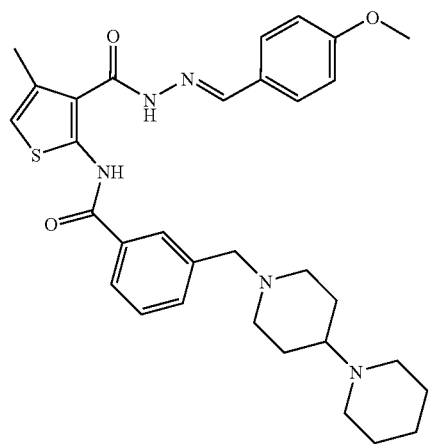 |
| Compound 575 | 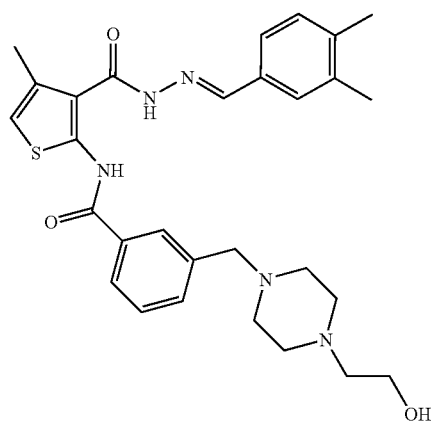 |
| Compound 576 | 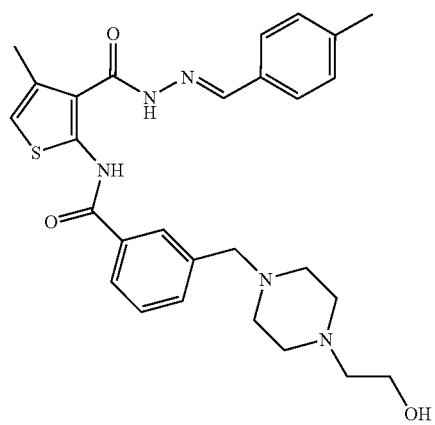 |

TABLE 3-continued
Structures of compounds 1 to 1077 are shown in Table 3.
| Compound No. | Chemical structural formula |
| --- | --- |
| Compound 577 | 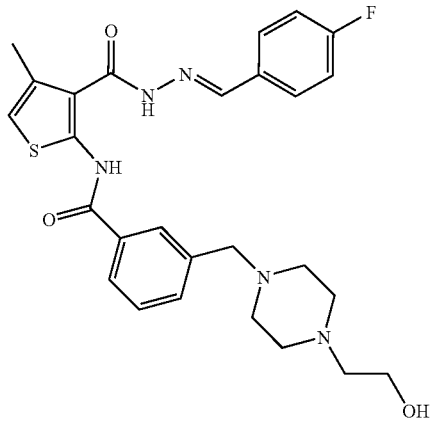 |
| Compound 578 | 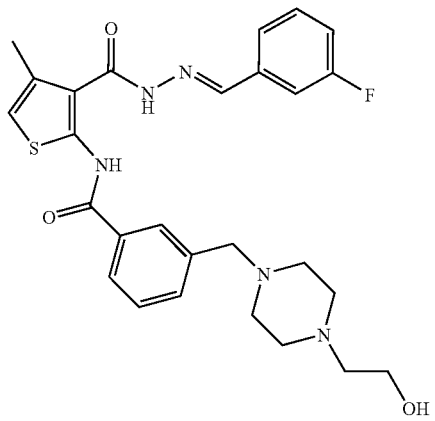 |
| Compound 579 | 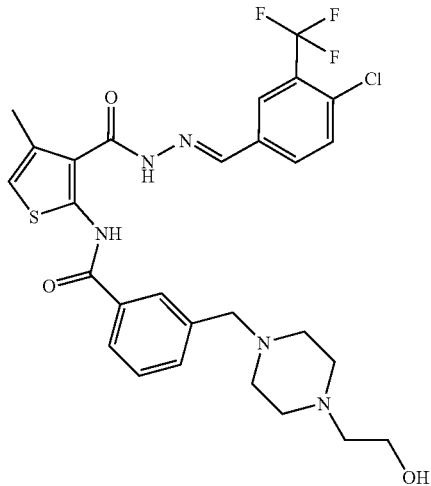 |

US 8,134,015 B2
619                                                                                                    620
TABLE 3-continued
Structures of compounds 1 to 1077 are shown in Table 3.
| Compound No. | Chemical structural formula |
|---|---|
| Compound 580 | 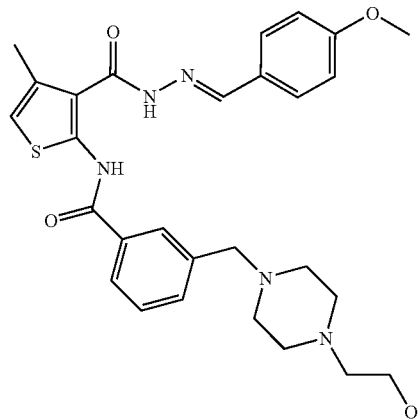 |
| Compound 581 | 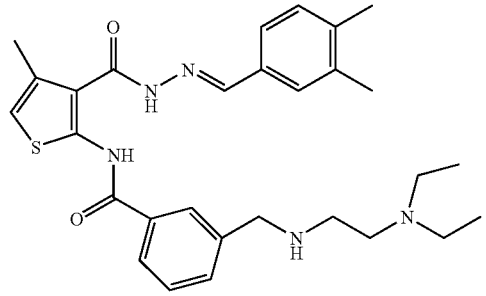 |
| Compound 582 | 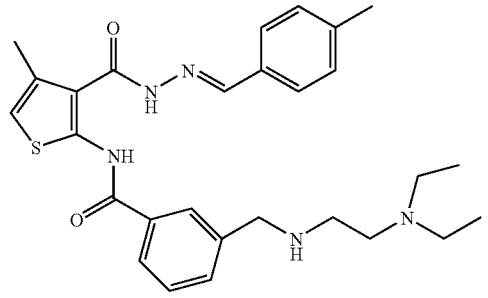 |
| Compound 583 | 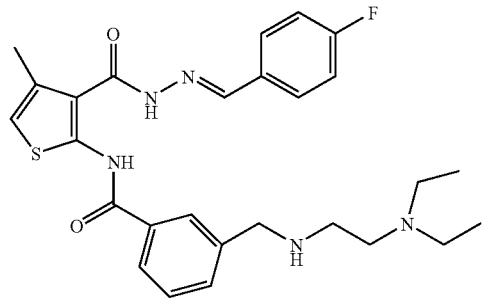 |
| Compound 584 | 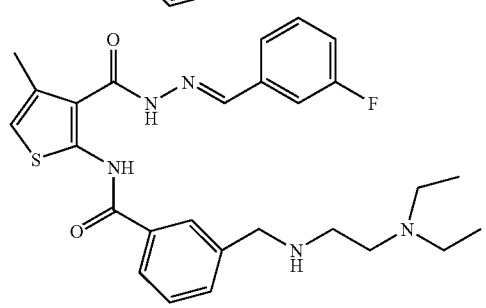 |

TABLE 3-continued
Structures of compounds 1 to 1077 are shown in Table 3.
| Compound No. | Chemical structural formula |
|---|---|
| Compound 585 | 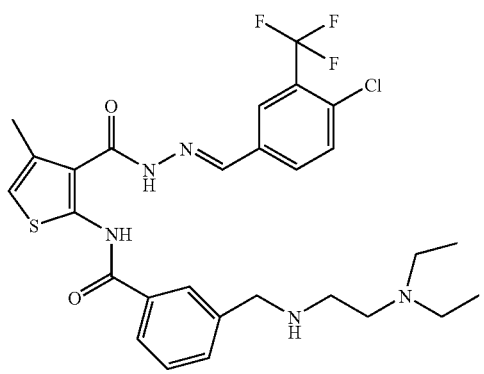 |
| Compound 586 | 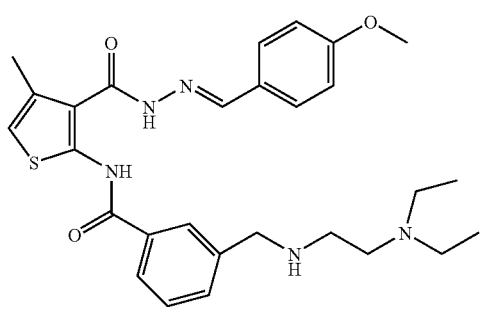 |
| Compound 587 | 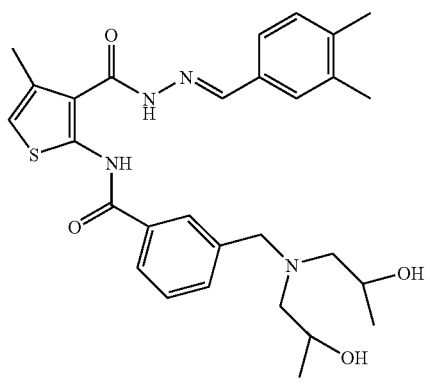 |
| Compound 588 | 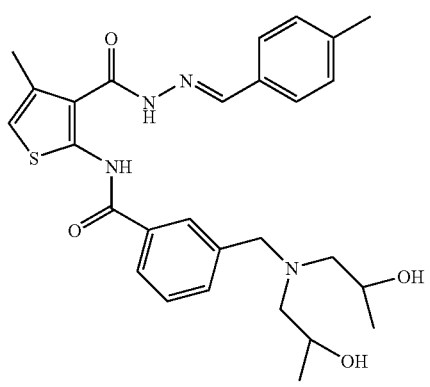 |

TABLE 3-continued

Structures of compounds 1 to 1077 are shown in Table 3.

| Compound No. | Chemical structural formula |
| --- | --- |
| Compound 589 | |
| Compound 590 | |
| Compound 591 | |
| Compound 592 | |

TABLE 3-continued
Structures of compounds 1 to 1077 are shown in Table 3.
| Compound No. | Chemical structural formula |
| --- | --- |
| Compound 593 | 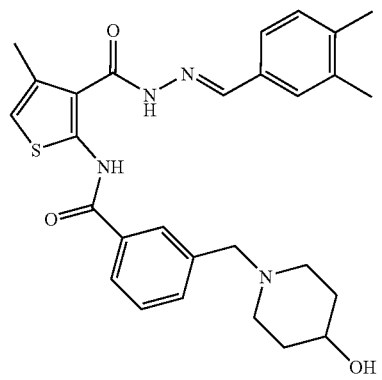 |
| Compound 594 | 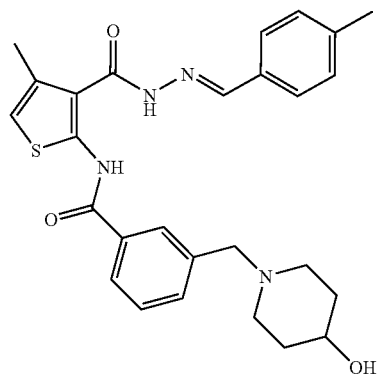 |
| Compound 595 | 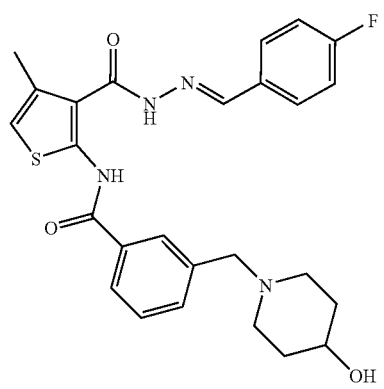 |
| Compound 596 | 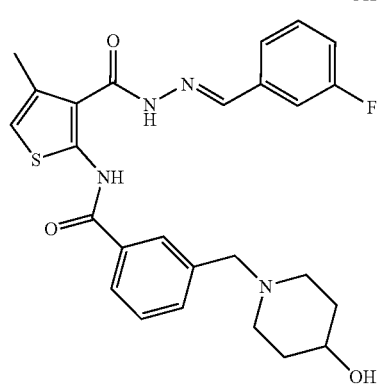 |

TABLE 3-continued
Structures of compounds 1 to 1077 are shown in Table 3.
| Compound No. | Chemical structural formula |
|---|---|
| Compound 597 | 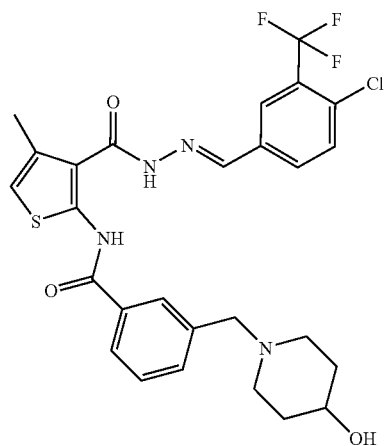 |
| Compound 598 | 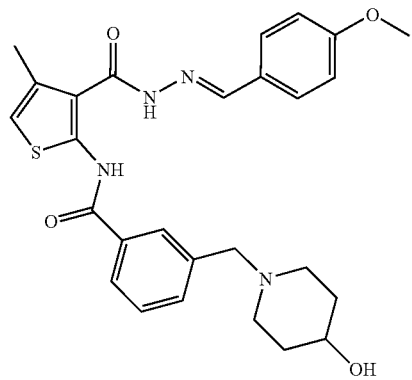 |
| Compound 599 | 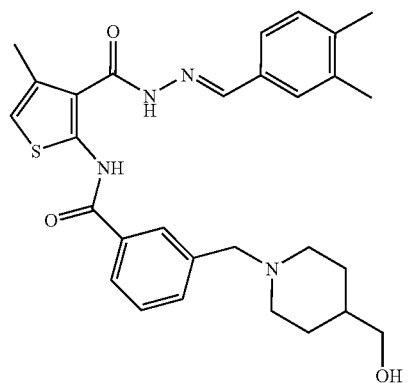 |
| Compound 600 | 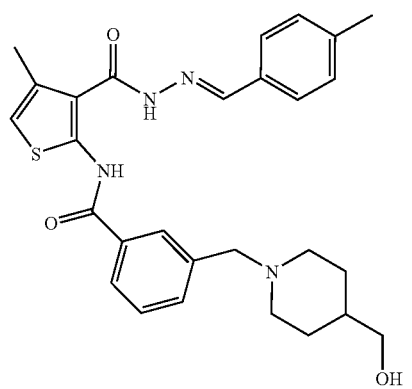 |

TABLE 3-continued

Structures of compounds 1 to 1077 are shown in Table 3.

| Compound No. | Chemical structural formula |
|---|---|
| Compound 601 | |
| Compound 602 | |
| Compound 603 | |
| Compound 604 | |

TABLE 3-continued
Structures of compounds 1 to 1077 are shown in Table 3.
| Compound No. | Chemical structural formula |
|---|---|
| Compound 605 | 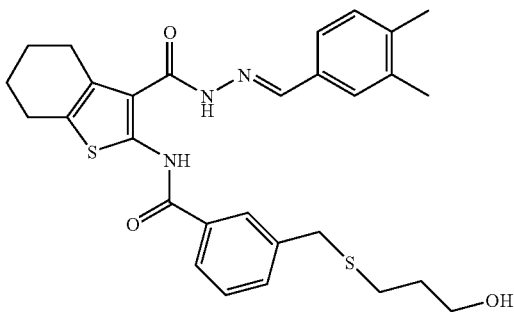 |
| Compound 606 | 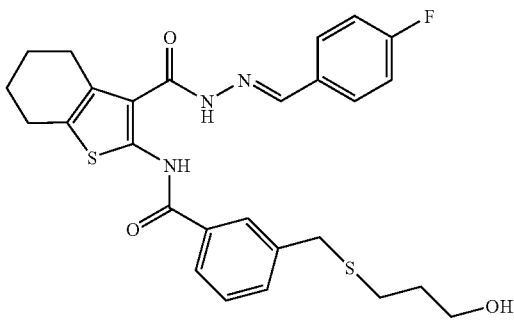 |
| Compound 607 | 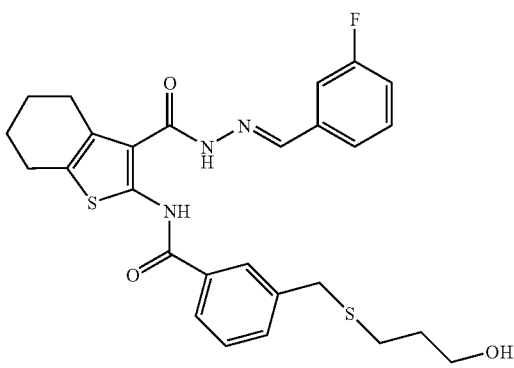 |
| Compound 608 | 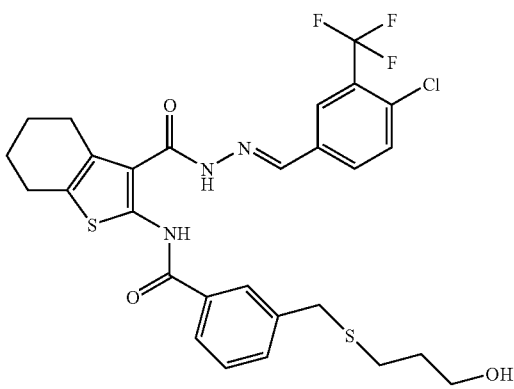 |

TABLE 3-continued
Structures of compounds 1 to 1077 are shown in Table 3.
| Compound No. | Chemical structural formula |
|---|---|
| Compound 609 | 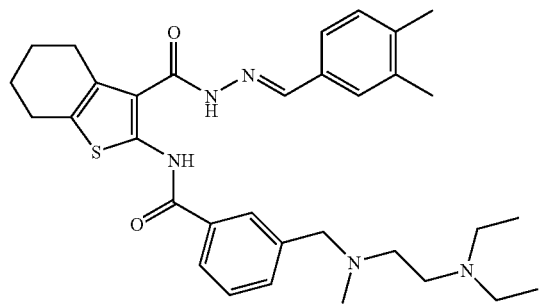 |
| Compound 610 | 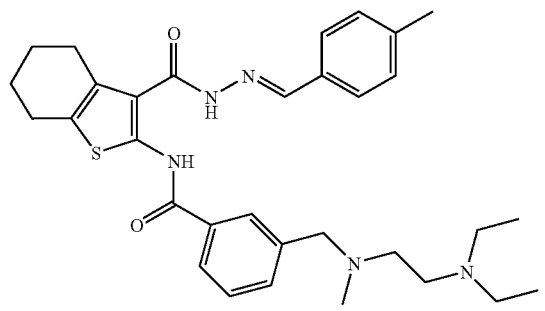 |
| Compound 611 | 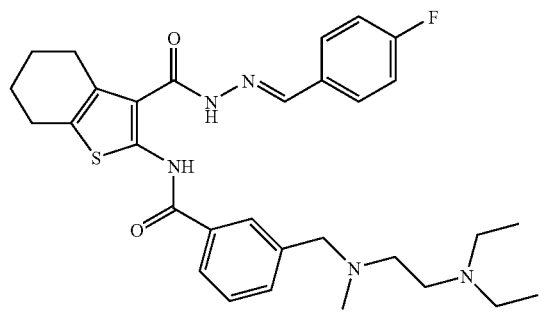 |
| Compound 612 | 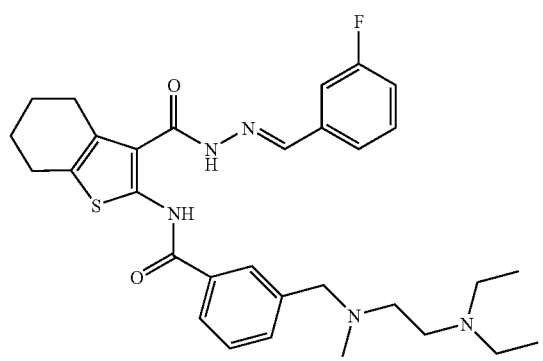 |

TABLE 3-continued
Structures of compounds 1 to 1077 are shown in Table 3.
| Compound No. | Chemical structural formula |
|---|---|
| Compound 613 | 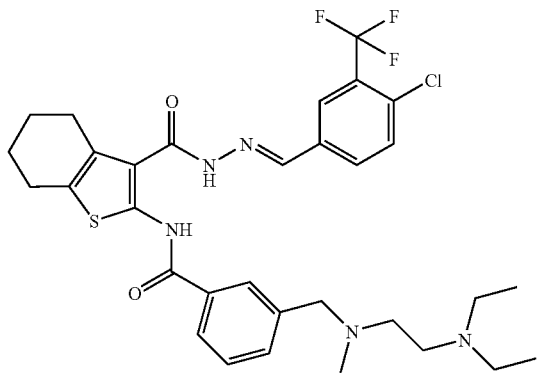 |
| Compound 614 | 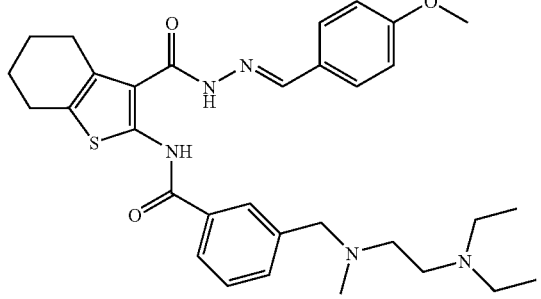 |
| Compound 615 | 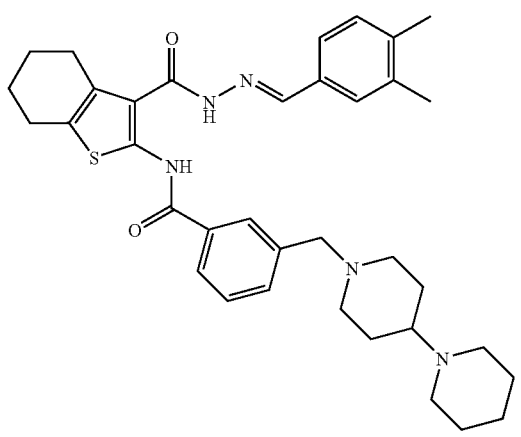 |
| Compound 616 | 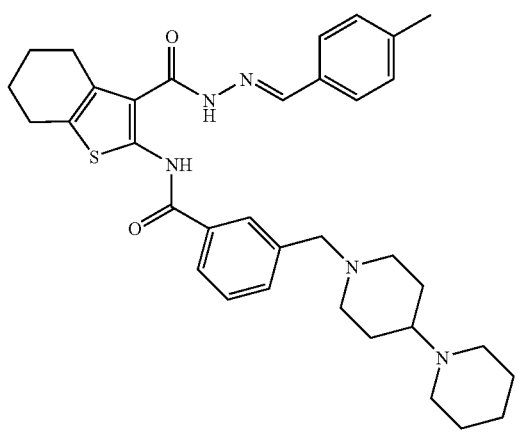 |

TABLE 3-continued
Structures of compounds 1 to 1077 are shown in Table 3.
| Compound No. | Chemical structural formula |
| --- | --- |
| Compound 617 | 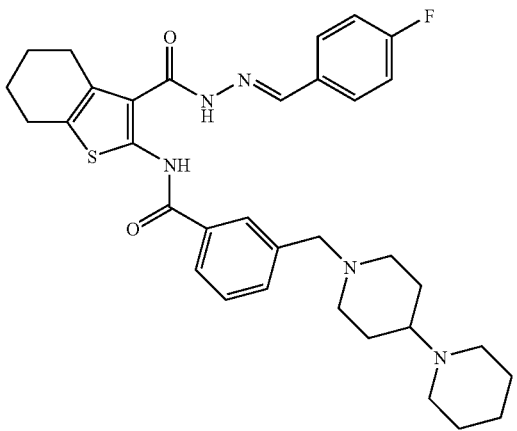 |
| Compound 618 | 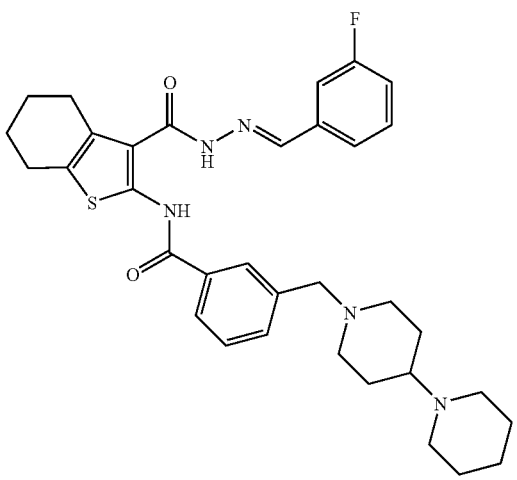 |
| Compound 619 | 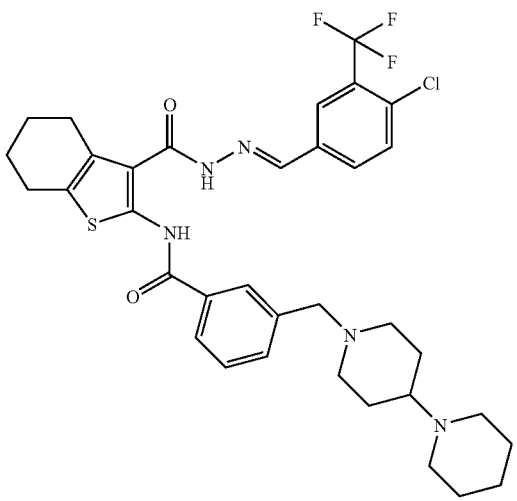 |

TABLE 3-continued
Structures of compounds 1 to 1077 are shown in Table 3.
| Compound No. | Chemical structural formula |
| --- | --- |
| Compound 620 | 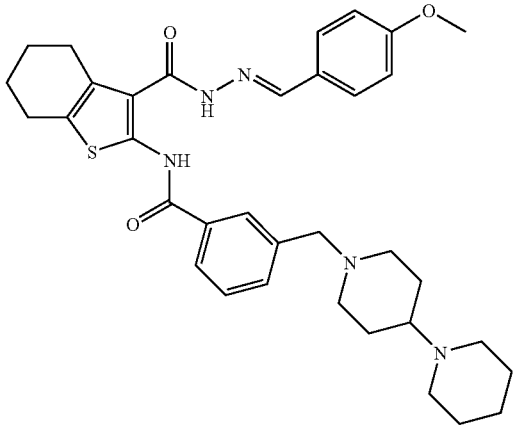 |
| Compound 621 | 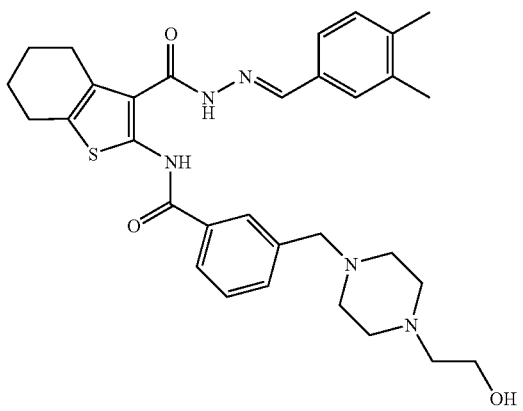 |
| Compound 622 | 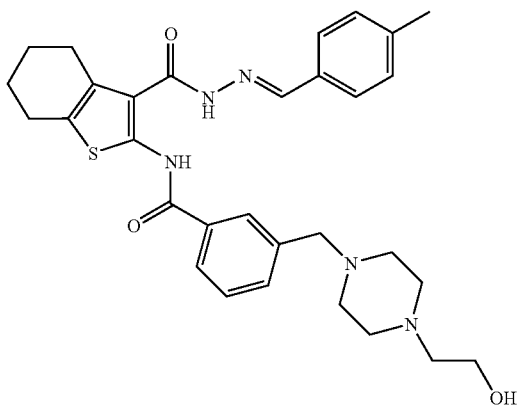 |

TABLE 3-continued
Structures of compounds 1 to 1077 are shown in Table 3.
| Compound No. | Chemical structural formula |
|---|---|
| Compound 623 | 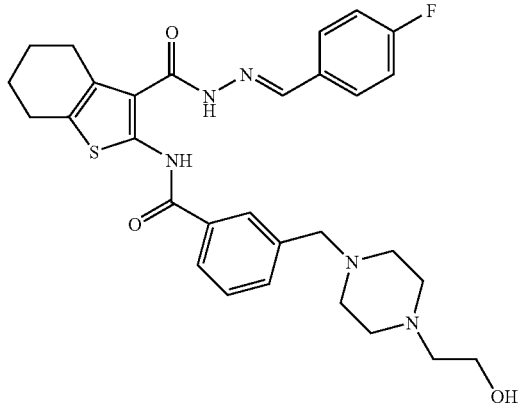 |
| Compound 624 | 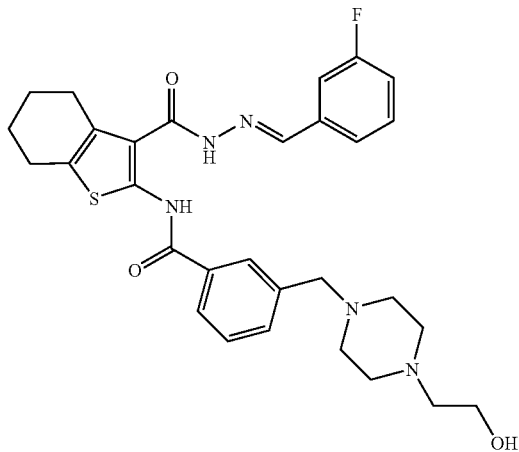 |
| Compound 625 | 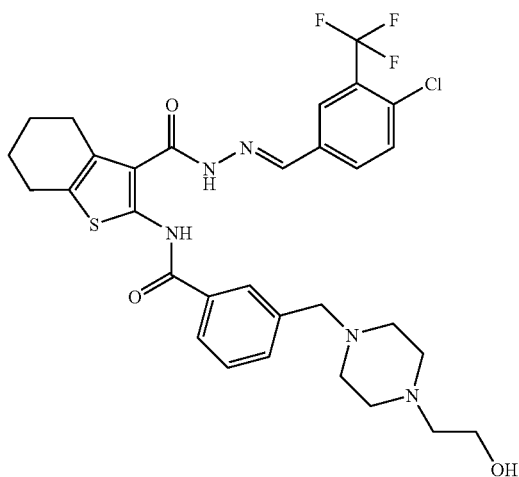 |

TABLE 3-continued
Structures of compounds 1 to 1077 are shown in Table 3.
| Compound No. | Chemical structural formula |
|---|---|
| Compound 626 | 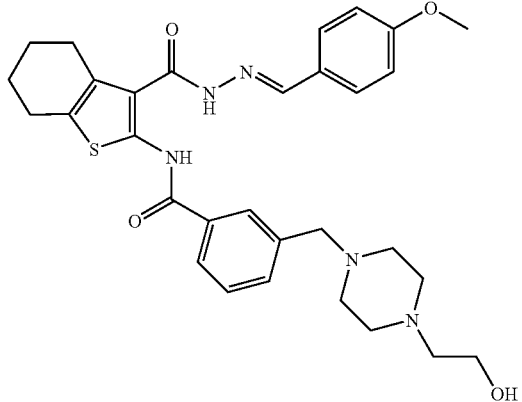 |
| Compound 627 | 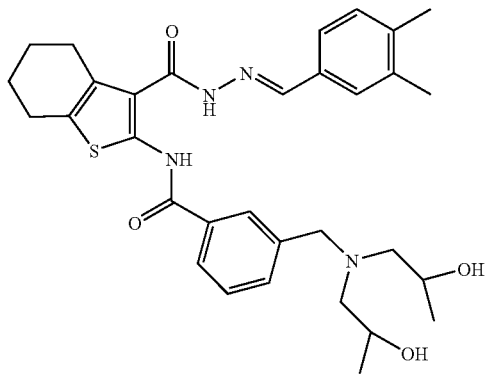 |
| Compound 628 | 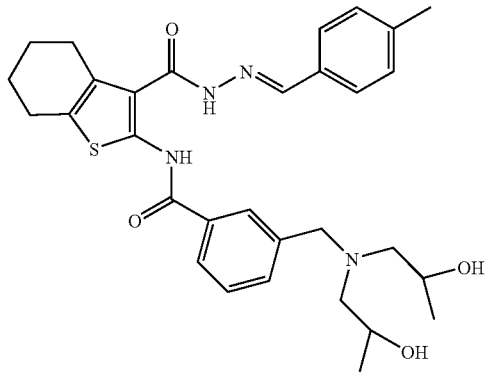 |
| Compound 629 | 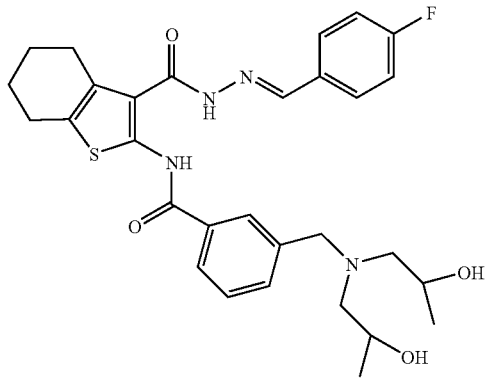 |

TABLE 3-continued
Structures of compounds 1 to 1077 are shown in Table 3.
| Compound No. | Chemical structural formula |
|---|---|
| Compound 630 | 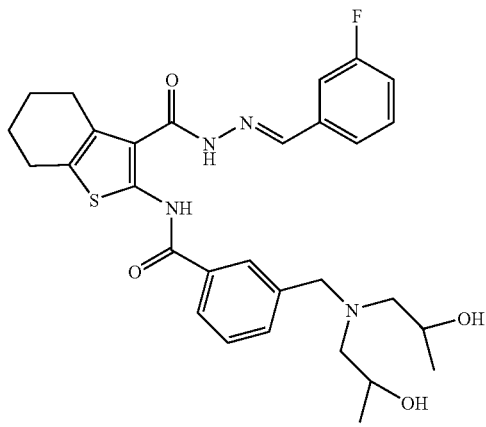 |
| Compound 631 | 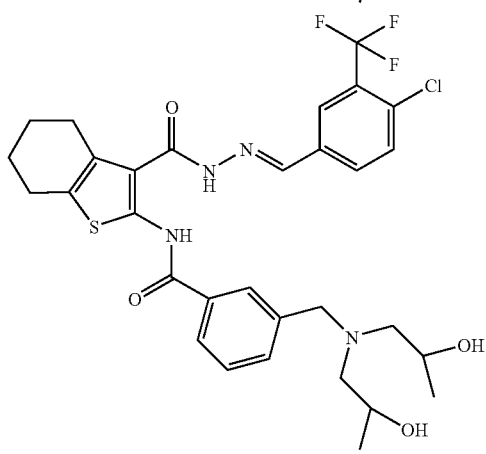 |
| Compound 632 | 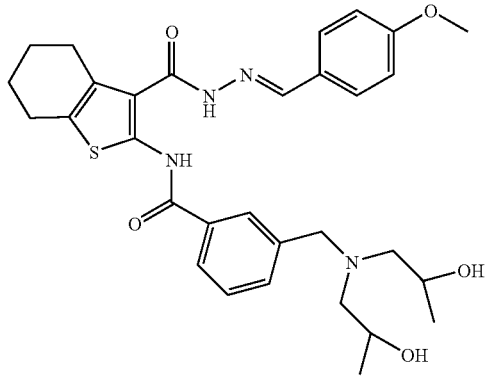 |
| Compound 633 | 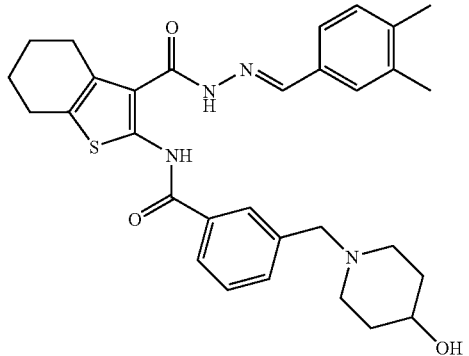 |

TABLE 3-continued
Structures of compounds 1 to 1077 are shown in Table 3.
| Compound No. | Chemical structural formula |
|---|---|
| Compound 634 | 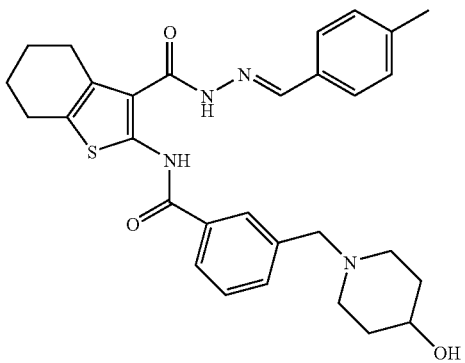 |
| Compound 635 | 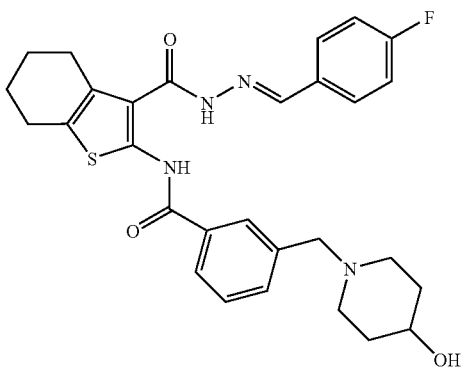 |
| Compound 636 | 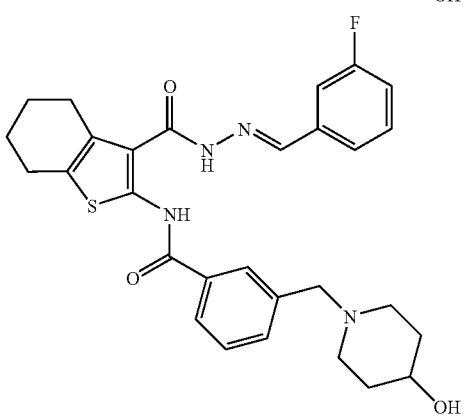 |
| Compound 637 | 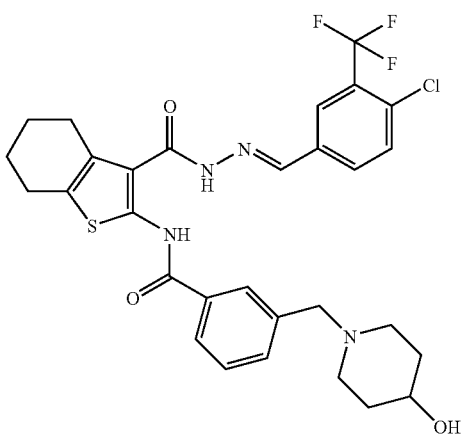 |

TABLE 3-continued
Structures of compounds 1 to 1077 are shown in Table 3.
| Compound No. | Chemical structural formula |
|---|---|
| Compound 638 | 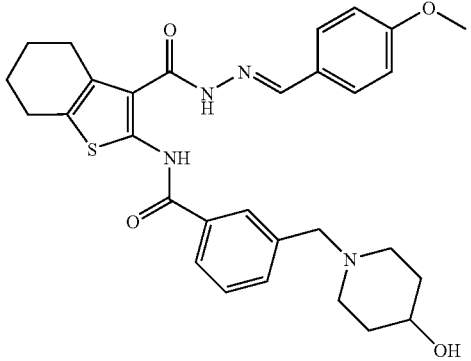 |
| Compound 639 | 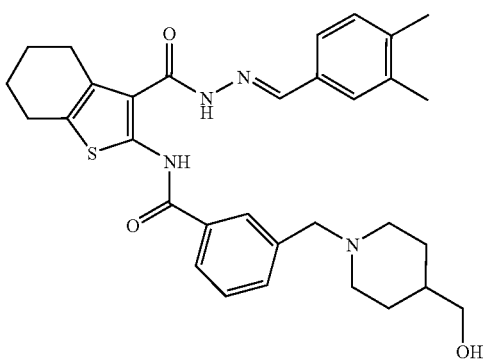 |
| Compound 640 | 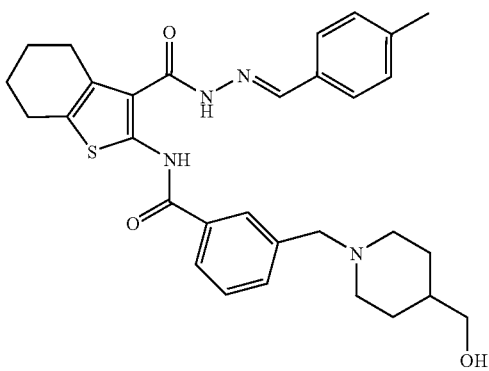 |
| Compound 641 | 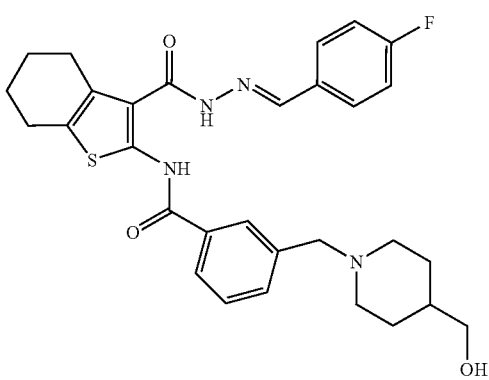 |

TABLE 3-continued
Structures of compounds 1 to 1077 are shown in Table 3.
| Compound No. | Chemical structural formula |
|---|---|
| Compound 642 | 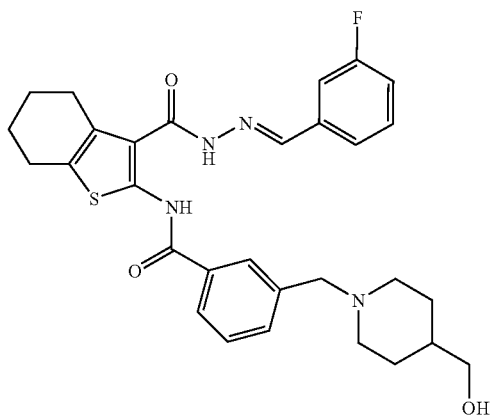 |
| Compound 643 | 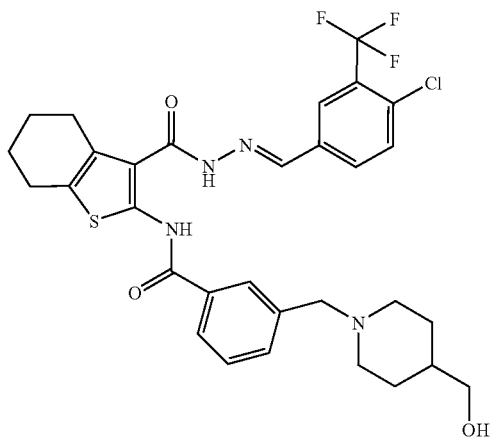 |
| Compound 644 | 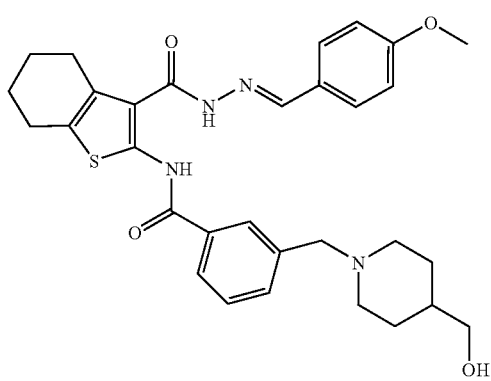 |
| Compound 645 | 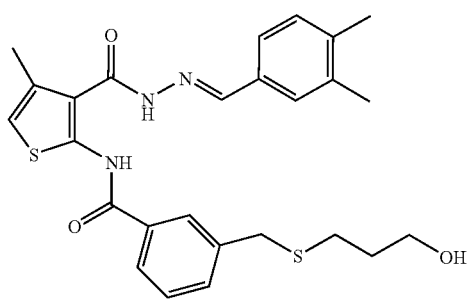 |

TABLE 3-continued
Structures of compounds 1 to 1077 are shown in Table 3.
| Compound No. | Chemical structural formula |
|---|---|
| Compound 646 | 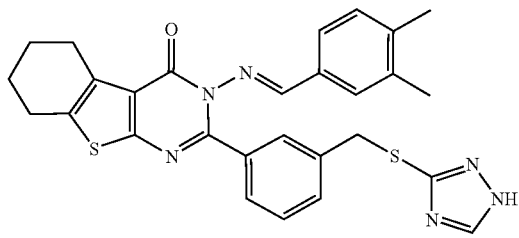 |
| Compound 647 | 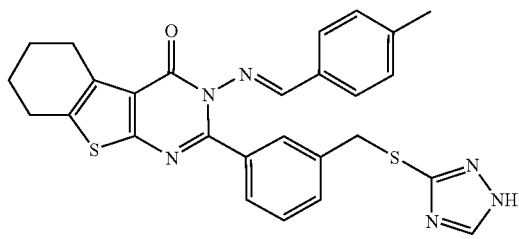 |
| Compound 648 | 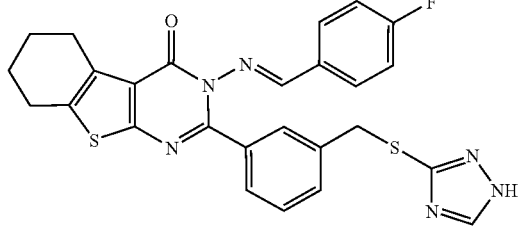 |
| Compound 649 | 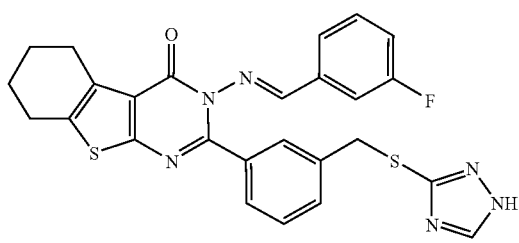 |
| Compound 650 | 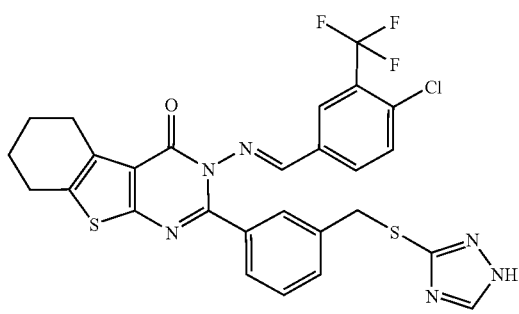 |
| Compound 651 | 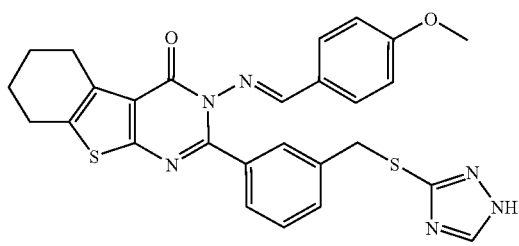 |

TABLE 3-continued
Structures of compounds 1 to 1077 are shown in Table 3.
Compound No.   Chemical structural formula
Compound 652
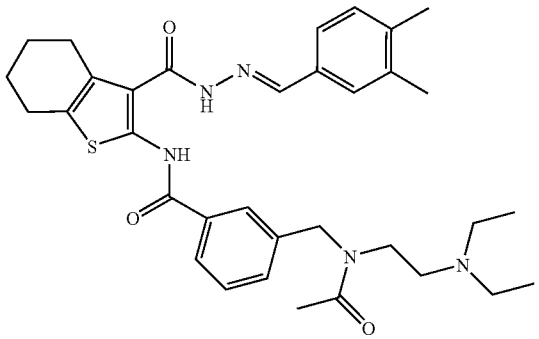
Compound 653
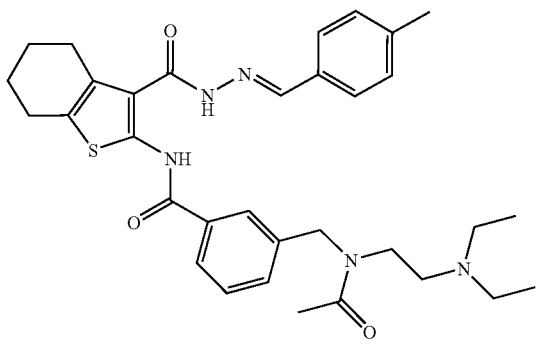
Compound 654
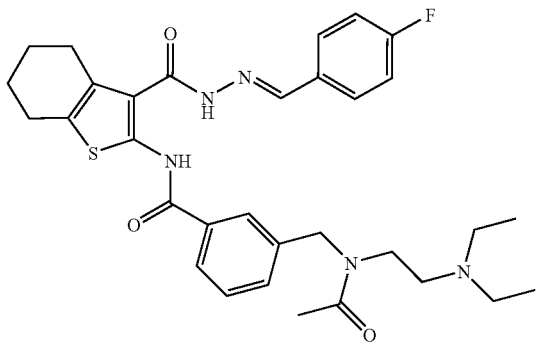
Compound 655
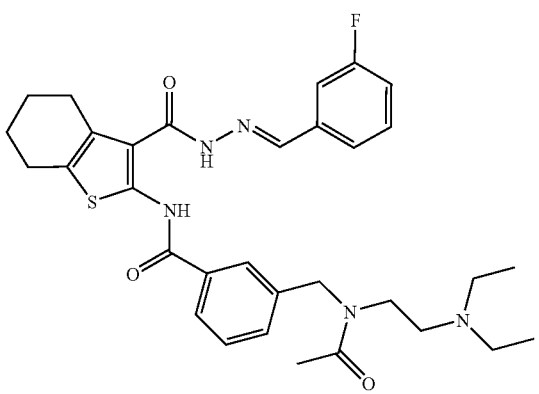

TABLE 3-continued
Structures of compounds 1 to 1077 are shown in Table 3.
| Compound No. | Chemical structural formula |
|---|---|
| Compound 656 | 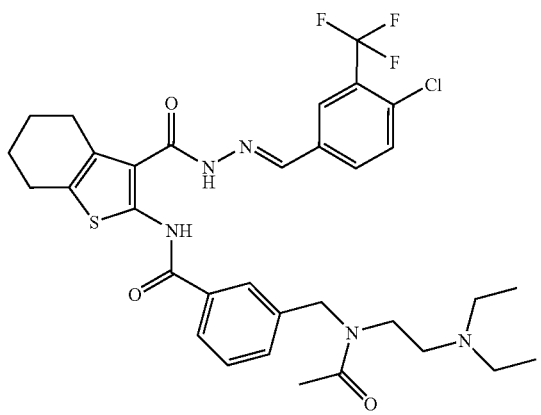 |
| Compound 657 | 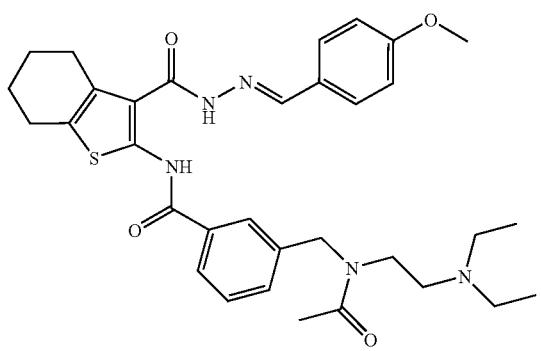 |
| Compound 658 | 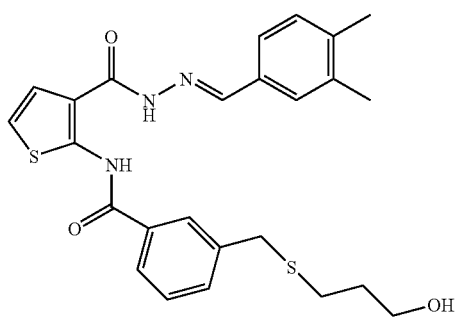 |
| Compound 659 | 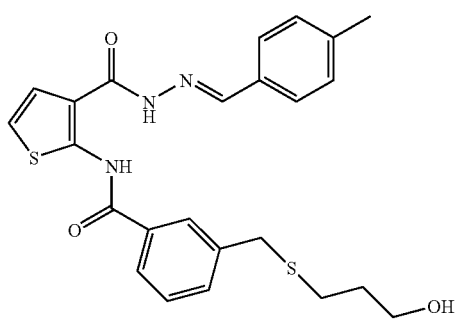 |

TABLE 3-continued
Structures of compounds 1 to 1077 are shown in Table 3.
| Compound No. | Chemical structural formula |
|---|---|
| Compound 660 | 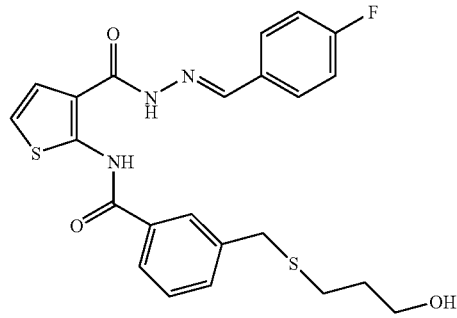 |
| Compound 661 | 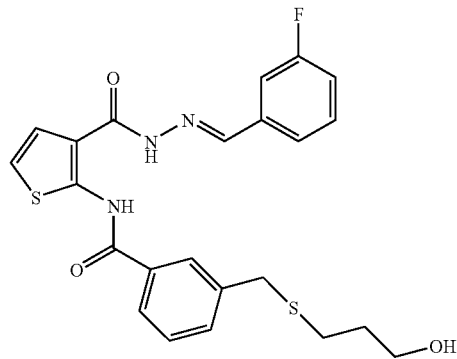 |
| Compound 662 | 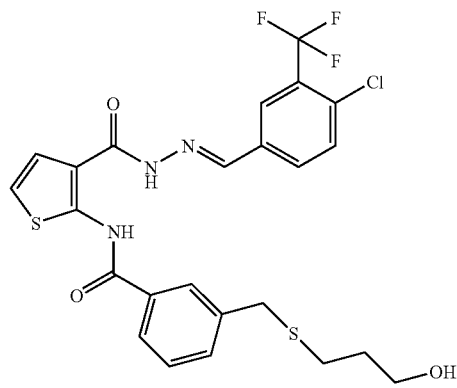 |
| Compound 663 | 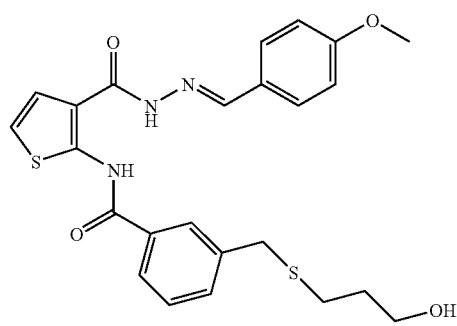 |

TABLE 3-continued
Structures of compounds 1 to 1077 are shown in Table 3.
| Compound No. | Chemical structural formula |
|---|---|
| Compound 664 | 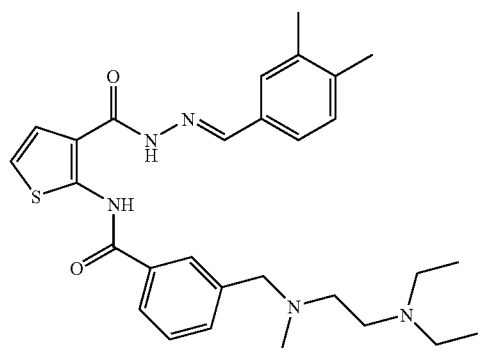 |
| Compound 665 | 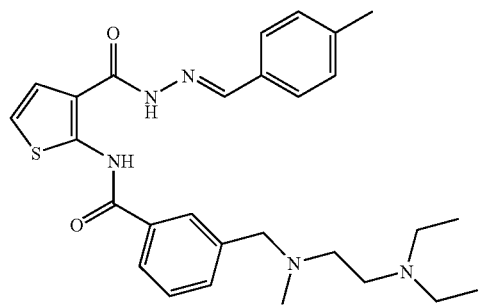 |
| Compound 666 | 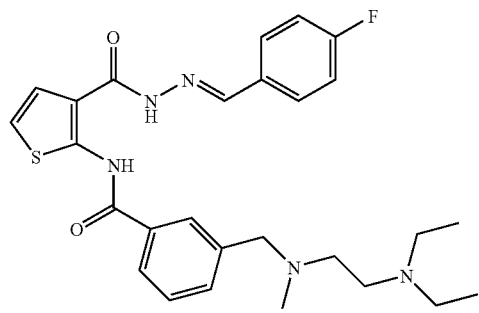 |
| Compound 667 | 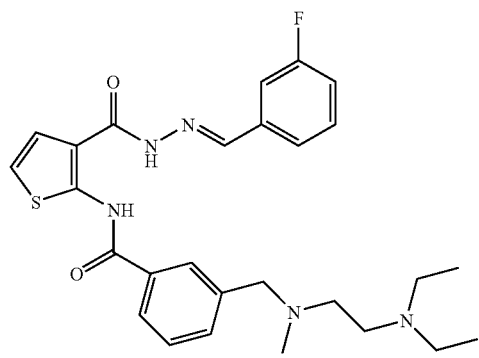 |

TABLE 3-continued
Structures of compounds 1 to 1077 are shown in Table 3.
| Compound No. | Chemical structural formula |
|---|---|
| Compound 668 | 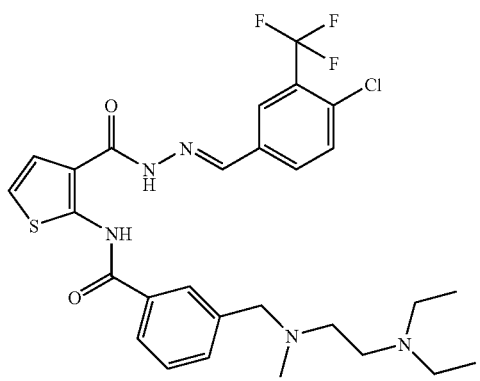 |
| Compound 669 | 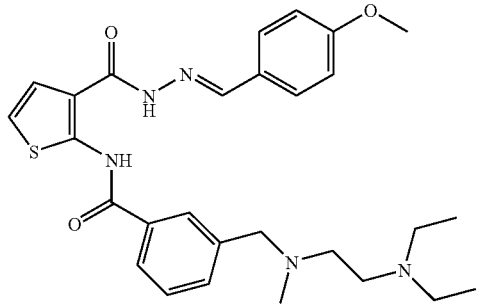 |
| Compound 670 | 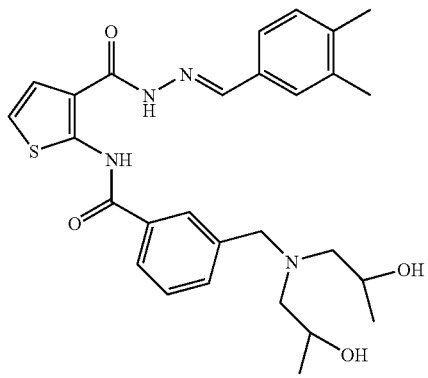 |
| Compound 671 | 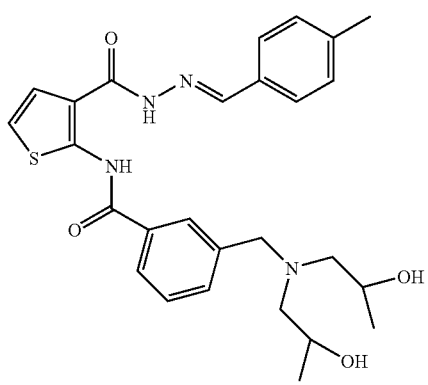 |

TABLE 3-continued
Structures of compounds 1 to 1077 are shown in Table 3.
| Compound No. | Chemical structural formula |
|---|---|
| Compound 672 | 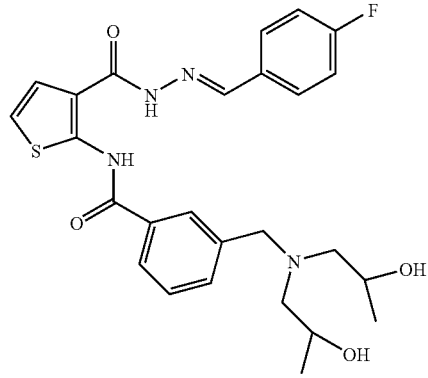 |
| Compound 673 | 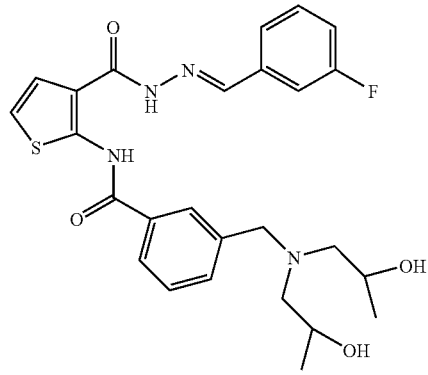 |
| Compound 674 | 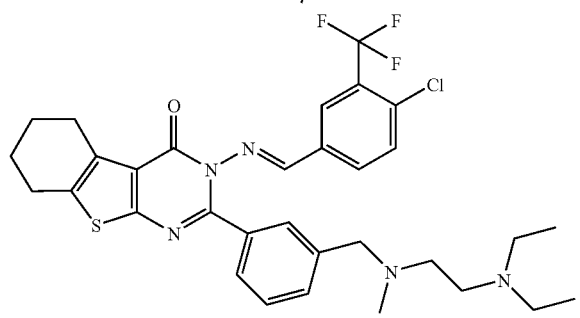 |
| Compound 675 | 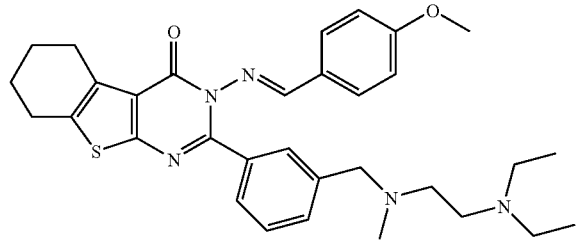 |
| Compound 676 | 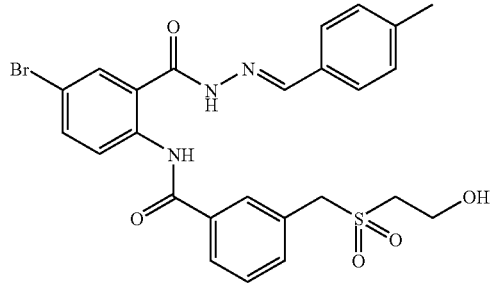 |

TABLE 3-continued

Structures of compounds 1 to 1077 are shown in Table 3.

| Compound No. | Chemical structural formula |
| --- | --- |
| Compound 677 | |
| Compound 678 | |
| Compound 679 | |
| Compound 680 | |
| Compound 681 | |

TABLE 3-continued
Structures of compounds 1 to 1077 are shown in Table 3.
Compound No. Chemical structural formula
Compound 682
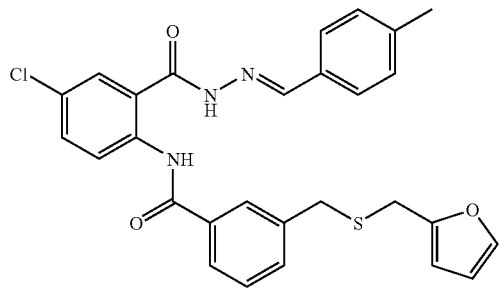
Compound 683
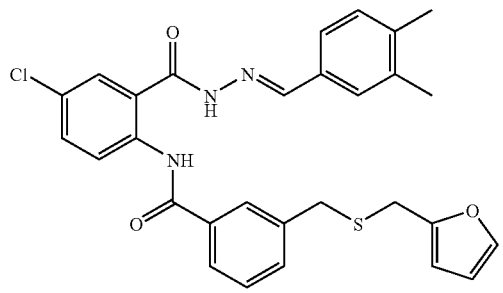
Compound 684
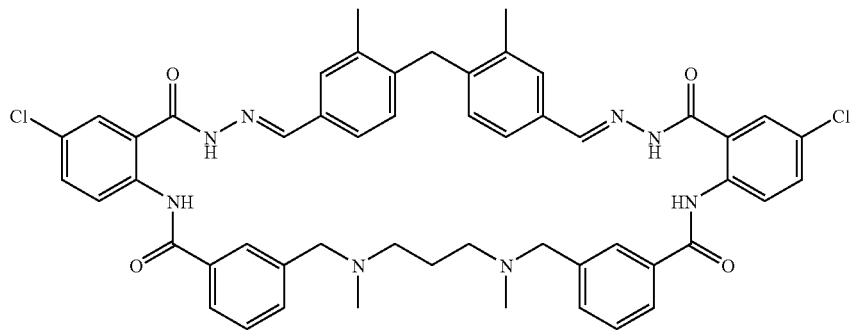
Compound 685
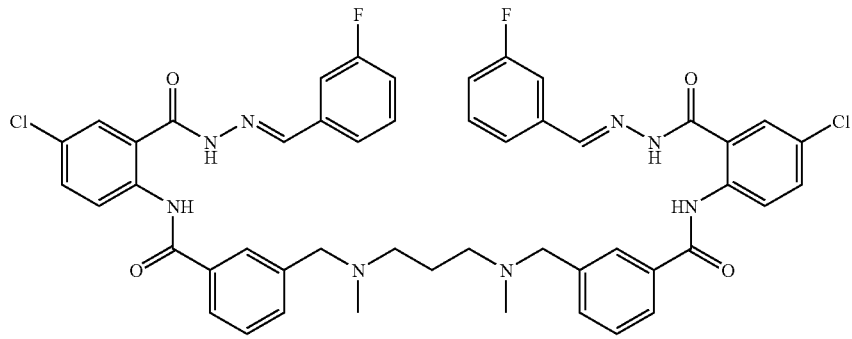
Compound 686
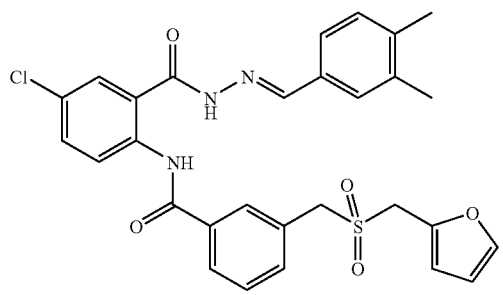

TABLE 3-continued
Structures of compounds 1 to 1077 are shown in Table 3.
| Compound No. | Chemical structural formula |
|---|---|
| Compound 687 | 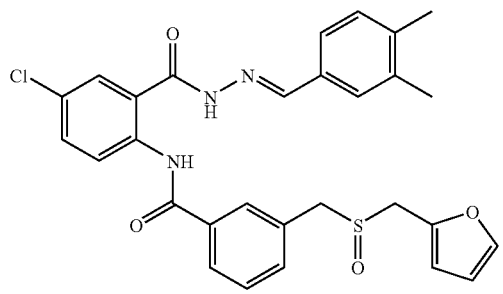 |
| Compound 688 | 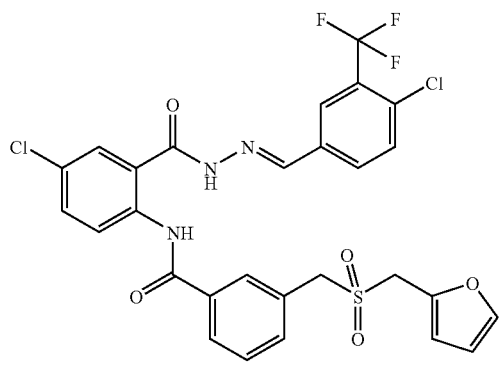 |
| Compound 689 | 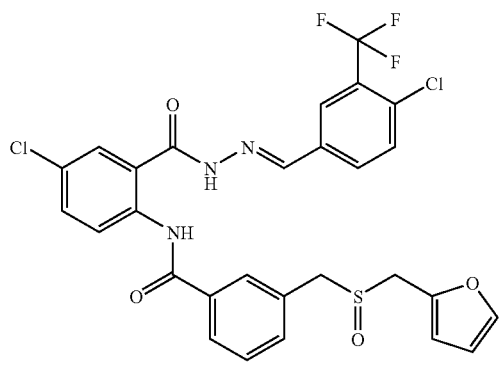 |
| Compound 690 | 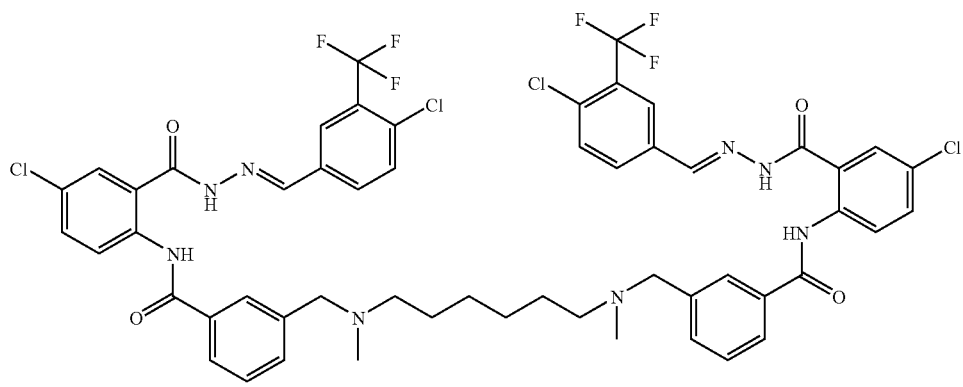 |

TABLE 3-continued
Structures of compounds 1 to 1077 are shown in Table 3.
| Compound No. | Chemical structural formula |
|---|---|
| Compound 691 | 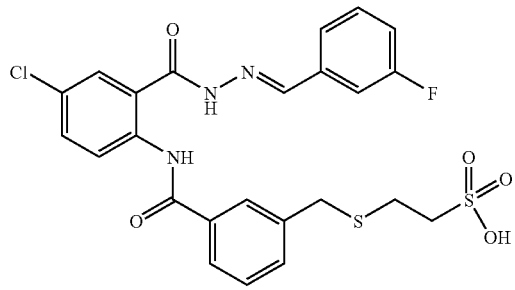 |
| Compound 692 | 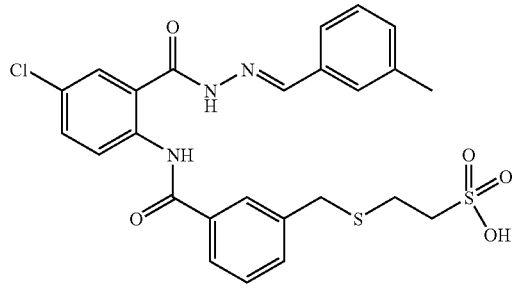 |
| Compound 693 | 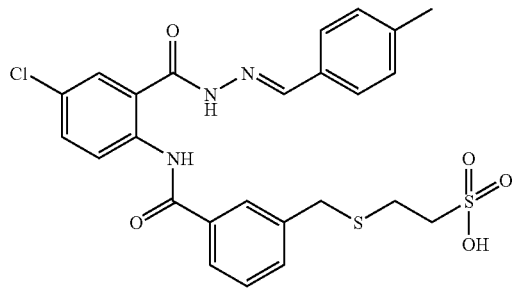 |
| Compound 694 | 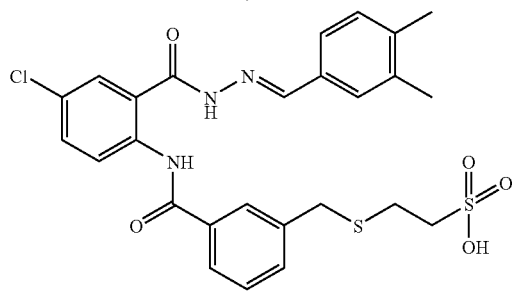 |
| Compound 695 | 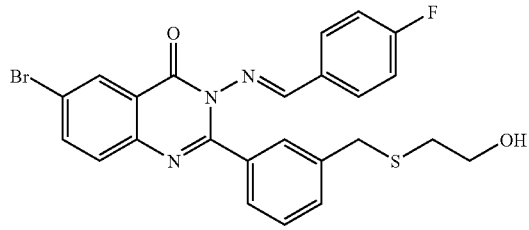 |
| Compound 696 | 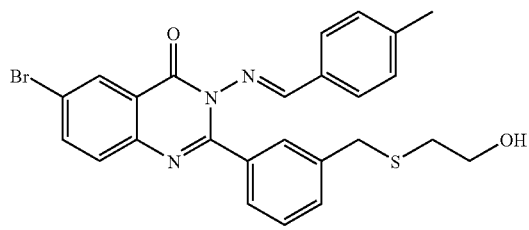 |

TABLE 3-continued

Structures of compounds 1 to 1077 are shown in Table 3.

| Compound No. | Chemical structural formula |
|---|---|
| Compound 697 | |
| Compound 698 | |
| Compound 699 | |
| Compound 700 | |
| Compound 701 | |

TABLE 3-continued

Structures of compounds 1 to 1077 are shown in Table 3.

| Compound No. | Chemical structural formula |
|---|---|
| Compound 702 | |
| Compound 703 | |
| Compound 704 | |
| Compound 705 | |
| Compound 706 | |

TABLE 3-continued
Structures of compounds 1 to 1077 are shown in Table 3.
| Compound No. | Chemical structural formula |
|---|---|
| Compound 707 | 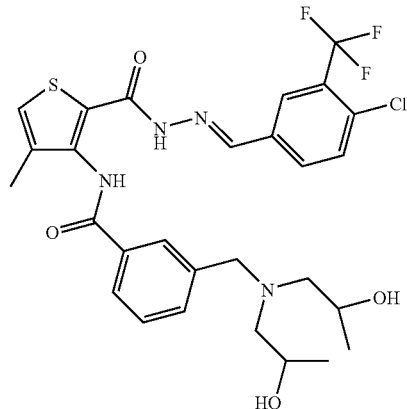 |
| Compound 708 | 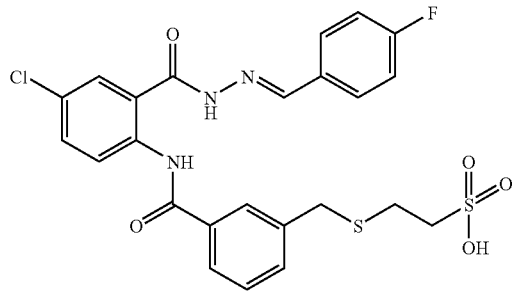 |
| Compound 709 | 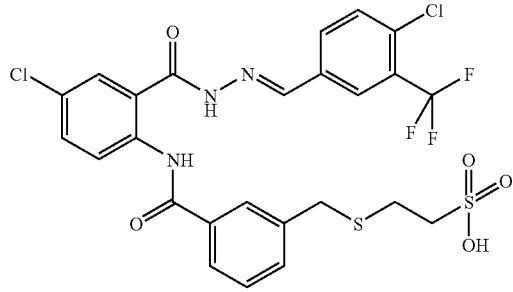 |
| Compound 710 | 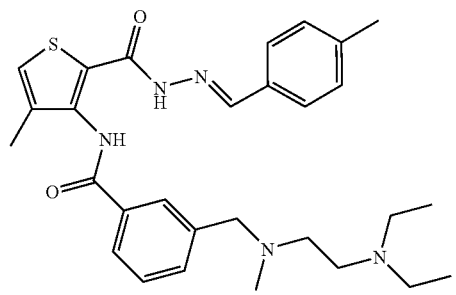 |
| Compound 711 | 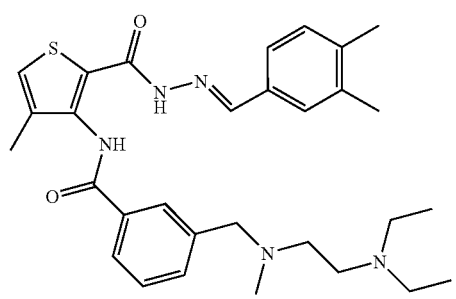 |

TABLE 3-continued
Structures of compounds 1 to 1077 are shown in Table 3.
| Compound No. | Chemical structural formula |
| --- | --- |
| Compound 712 | 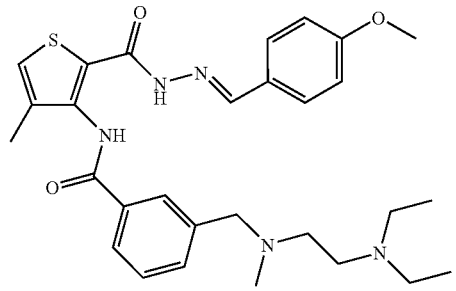 |
| Compound 713 | 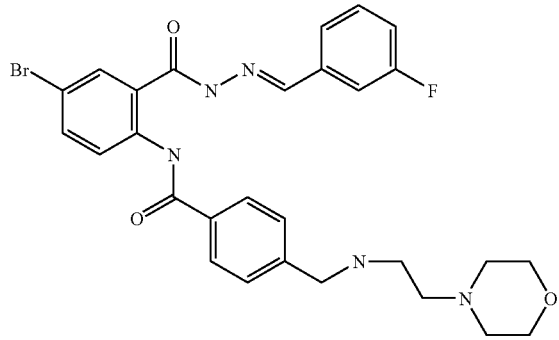 |
| Compound 714 | 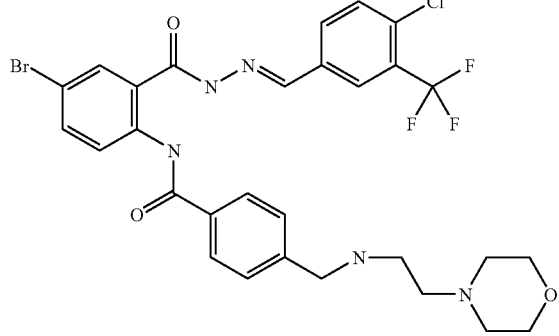 |
| Compound 715 |  |

TABLE 3-continued
Structures of compounds 1 to 1077 are shown in Table 3.
| Compound No. | Chemical structural formula |
|---|---|
| Compound 716 | 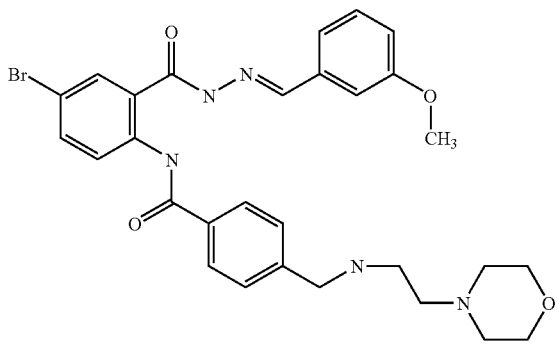 |
| Compound 717 | 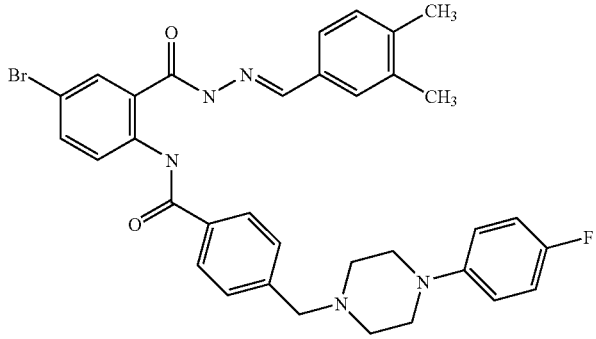 |
| Compound 718 | 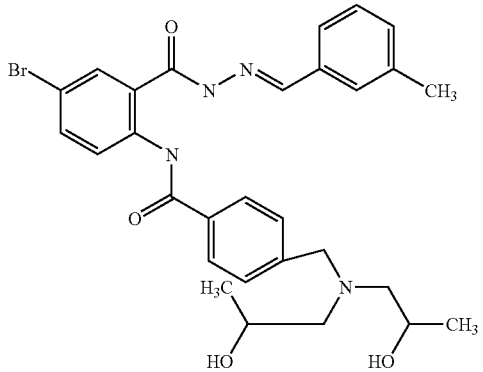 |
| Compound 719 | 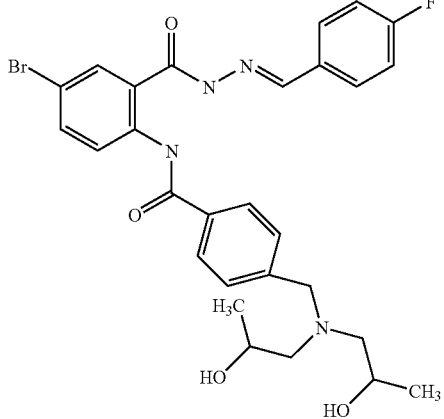 |

685 686
TABLE 3-continued
Structures of compounds 1 to 1077 are shown in Table 3.
Compound No. Chemical structural formula
Compound 720
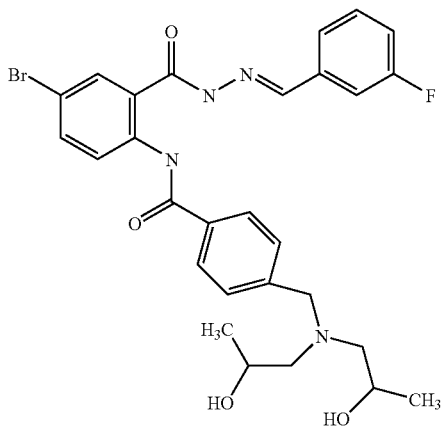
Compound 721
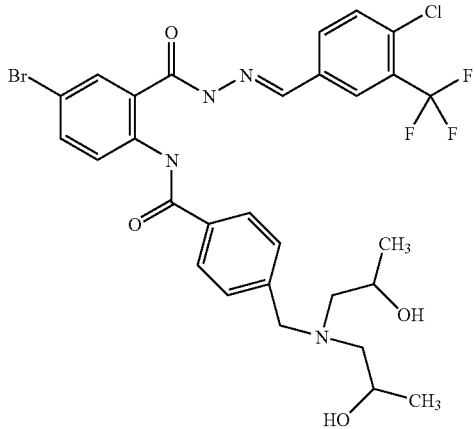
Compound 722
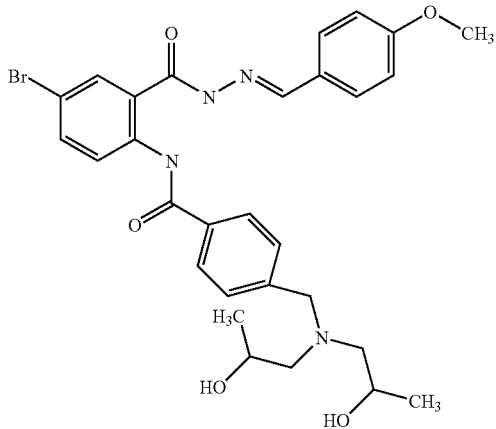

TABLE 3-continued
Structures of compounds 1 to 1077 are shown in Table 3.
| Compound No. | Chemical structural formula |
|---|---|
| Compound 723 | 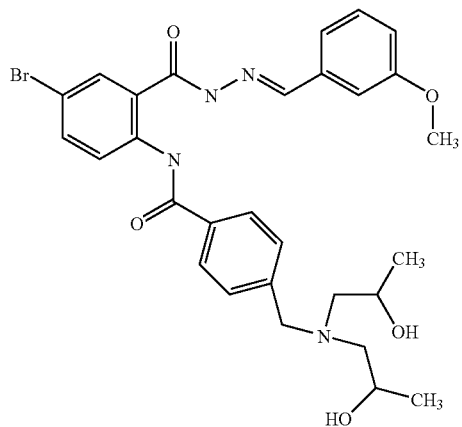 |
| Compound 724 | 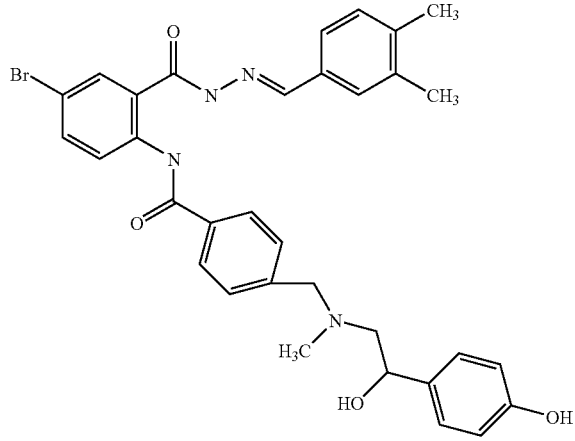 |
| Compound 725 | 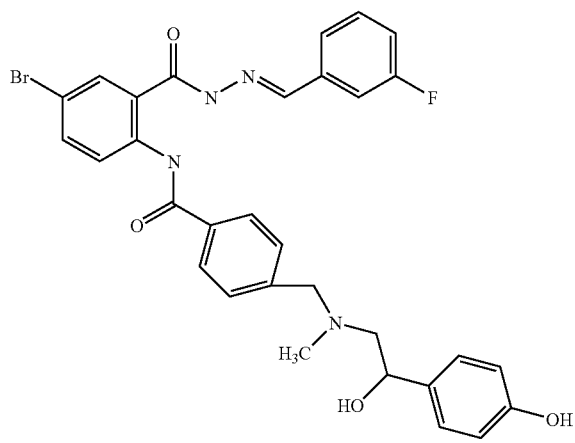 |

TABLE 3-continued
Structures of compounds 1 to 1077 are shown in Table 3.
| Compound No. | Chemical structural formula |
|---|---|
| Compound 726 |  |
| Compound 727 | 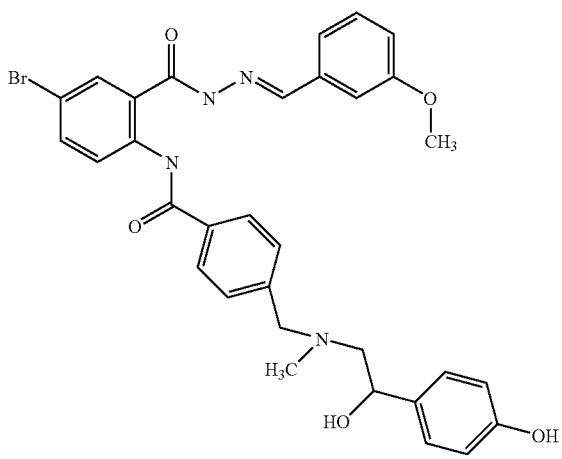 |
| Compound 728 | 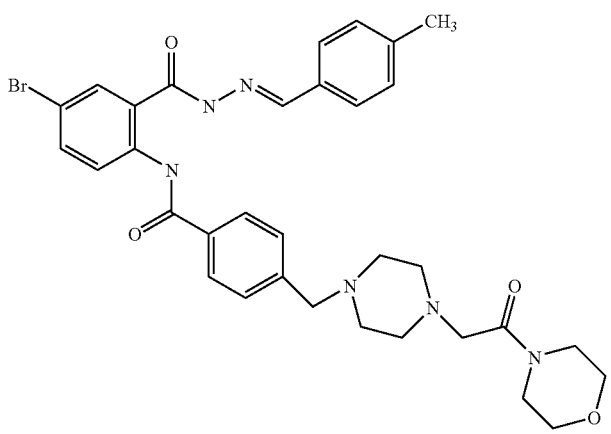 |

TABLE 3-continued

Structures of compounds 1 to 1077 are shown in Table 3.

| Compound No. | Chemical structural formula |
|---|---|
| Compound 729 | |
| Compound 730 | |
| Compound 731 | |

TABLE 3-continued
Structures of compounds 1 to 1077 are shown in Table 3.
Compound No.   Chemical structural formula
Compound 732
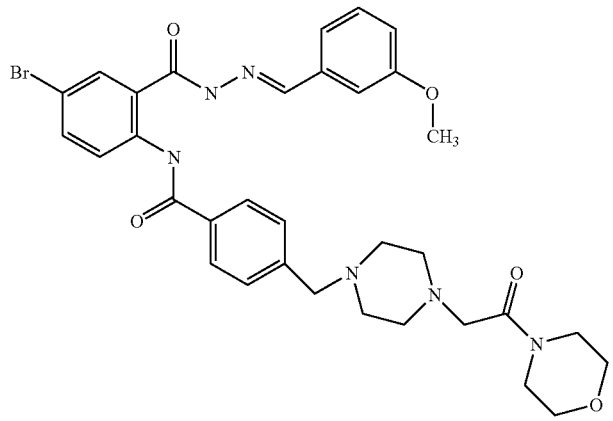
Compound 733
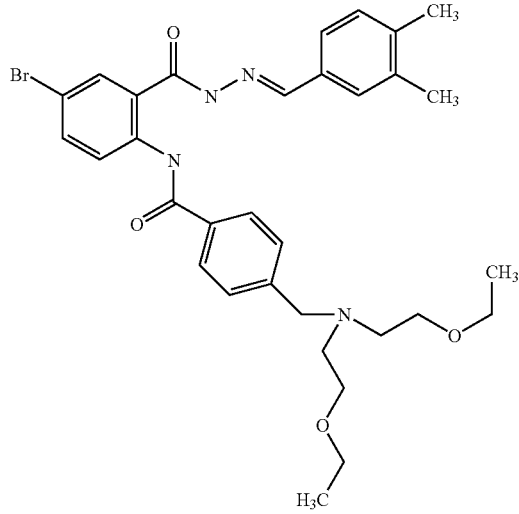
Compound 734
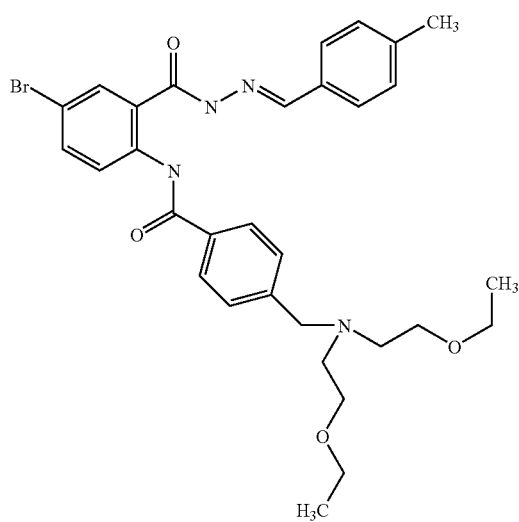

TABLE 3-continued
Structures of compounds 1 to 1077 are shown in Table 3.
| Compound No. | Chemical structural formula |
| --- | --- |
| Compound 735 | 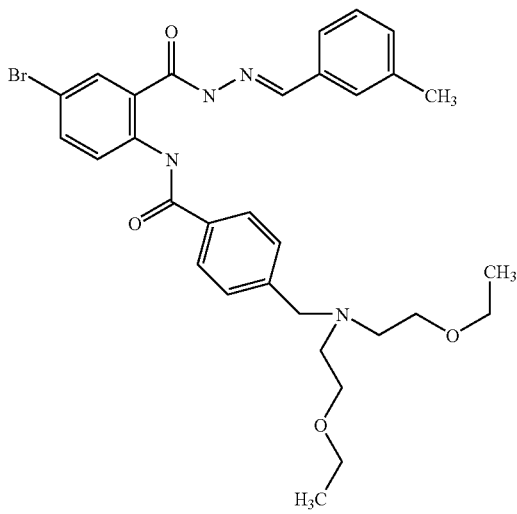 |
| Compound 736 | 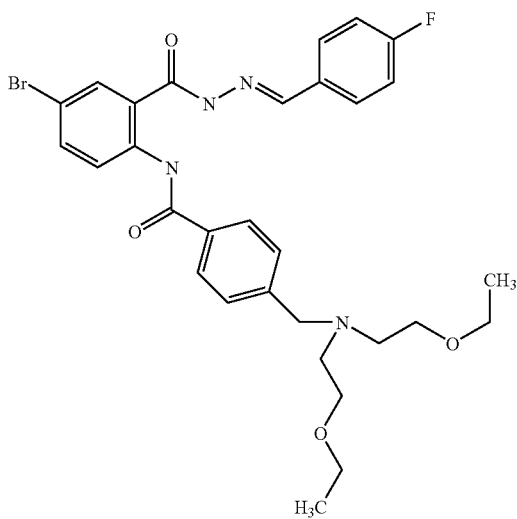 |
| Compound 737 | 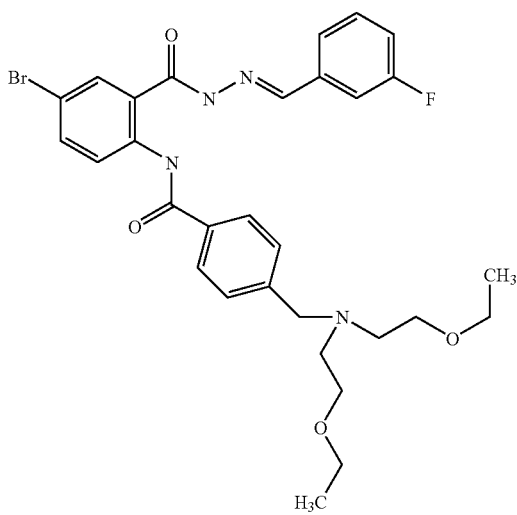 |

TABLE 3-continued
Structures of compounds 1 to 1077 are shown in Table 3.
| Compound No. | Chemical structural formula |
|---|---|
| Compound 738 | 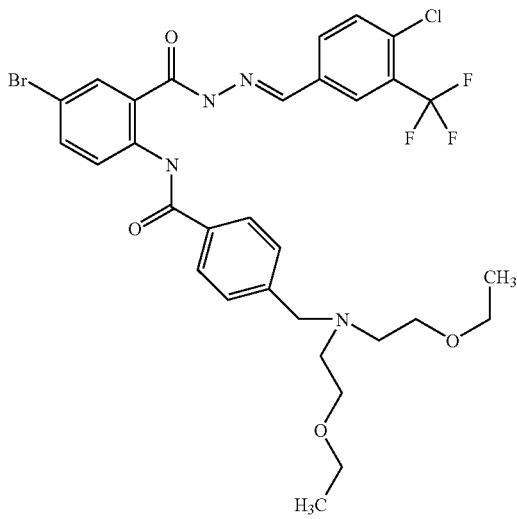 |
| Compound 739 | 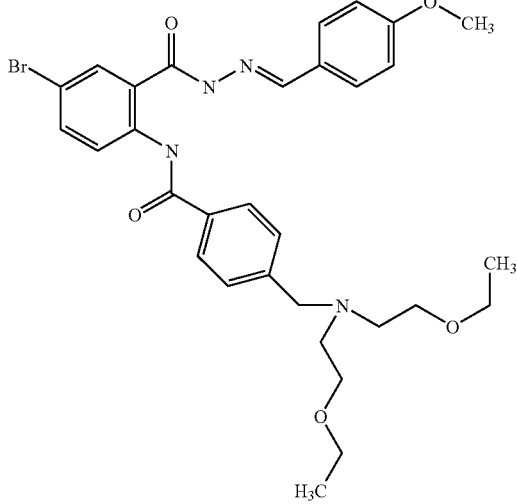 |
| Compound 740 | 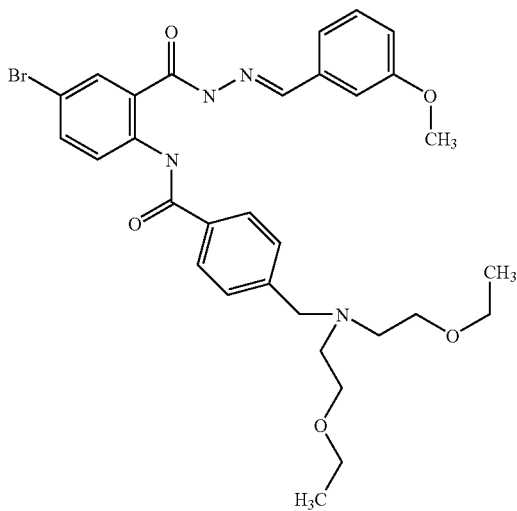 |

TABLE 3-continued
Structures of compounds 1 to 1077 are shown in Table 3.
| Compound No. | Chemical structural formula |
| --- | --- |
| Compound 741 | 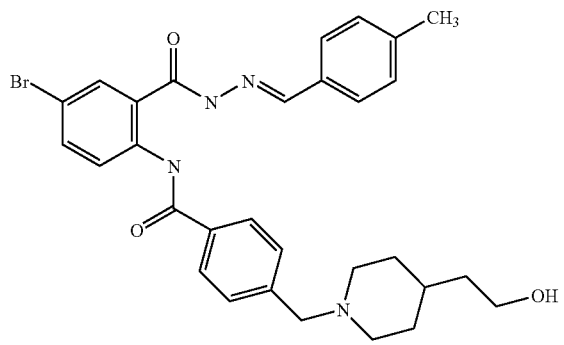 |
| Compound 742 | 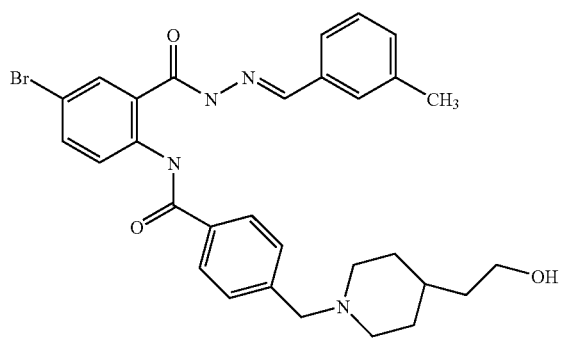 |
| Compound 743 | 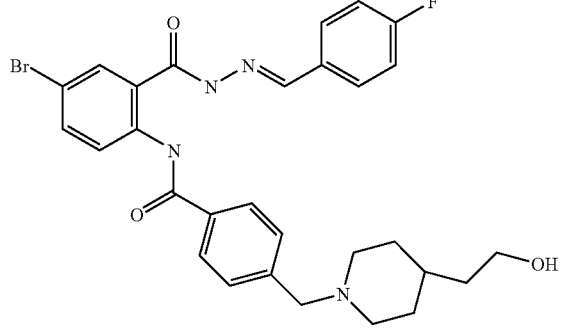 |
| Compound 744 | 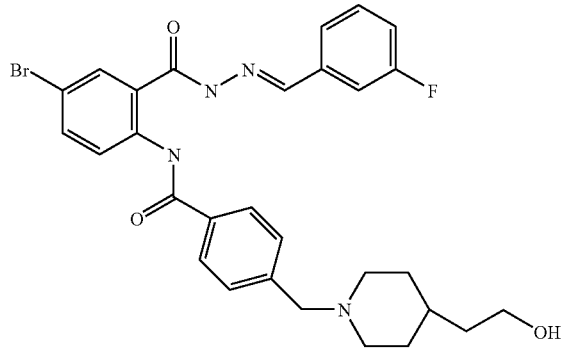 |

TABLE 3-continued
Structures of compounds 1 to 1077 are shown in Table 3.
| Compound No. | Chemical structural formula |
|---|---|
| Compound 745 | 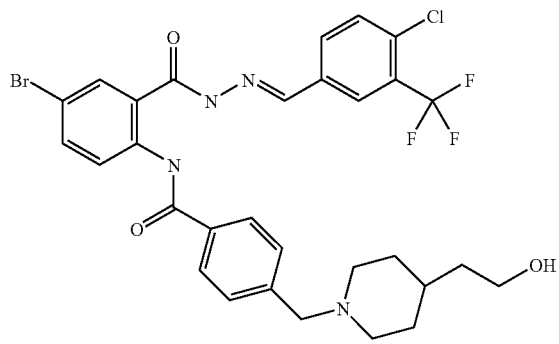 |
| Compound 746 | 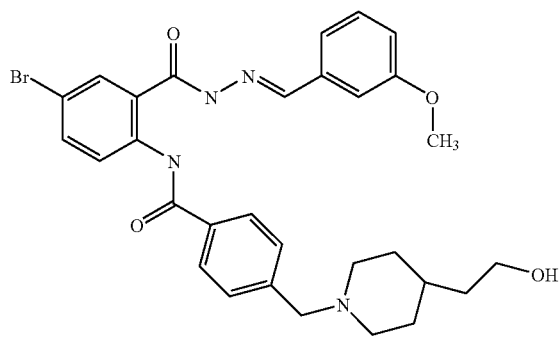 |
| Compound 747 | 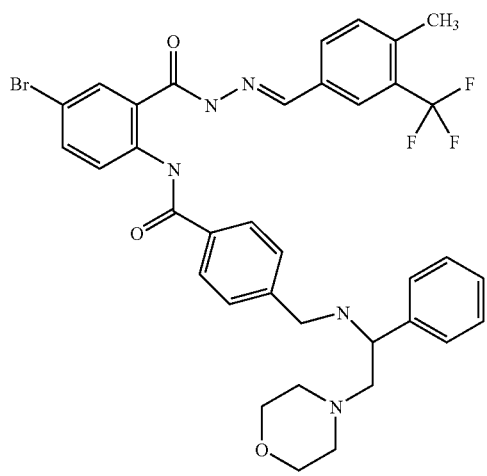 |

TABLE 3-continued
Structures of compounds 1 to 1077 are shown in Table 3.
| Compound No. | Chemical structural formula |
|---|---|
| Compound 748 | 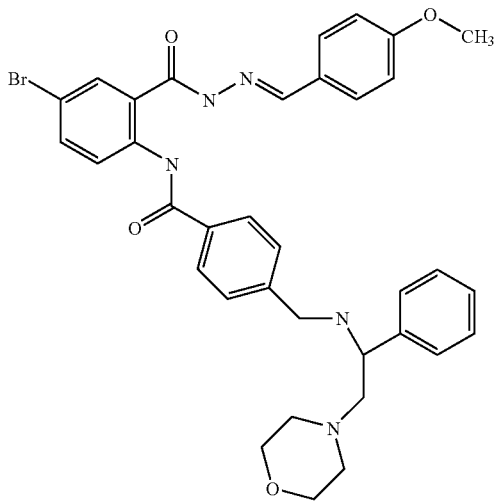 |
| Compound 749 | 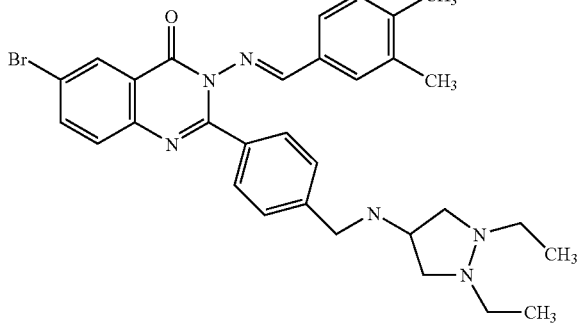 |
| Compound 750 | 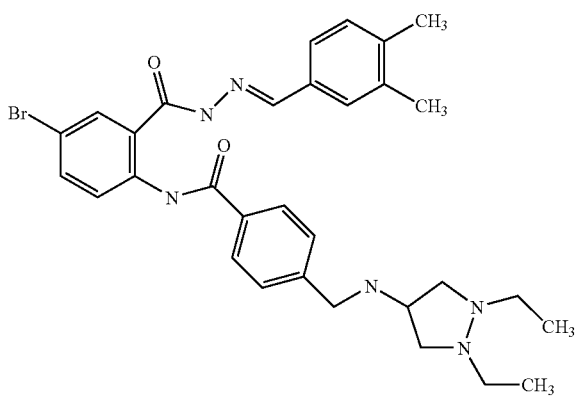 |
| Compound 751 | 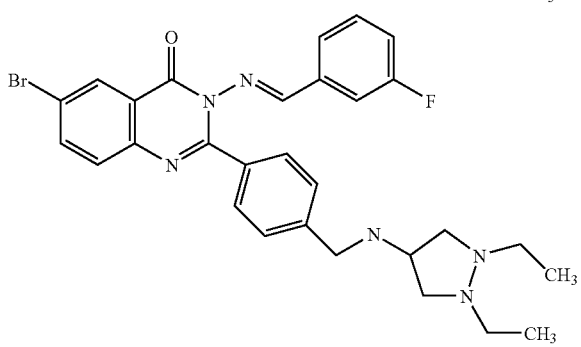 |

TABLE 3-continued
Structures of compounds 1 to 1077 are shown in Table 3.
| Compound No. | Chemical structural formula |
|---|---|
| Compound 752 | 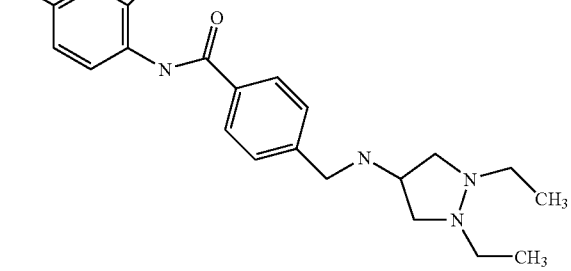 |
| Compound 753 | 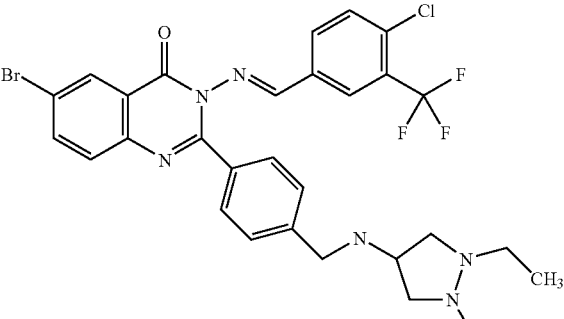 |
| Compound 754 | 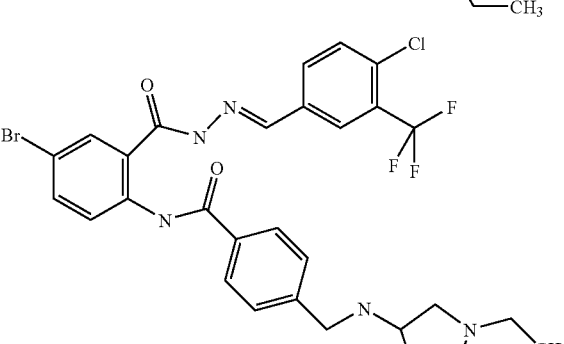 |
| Compound 755 | 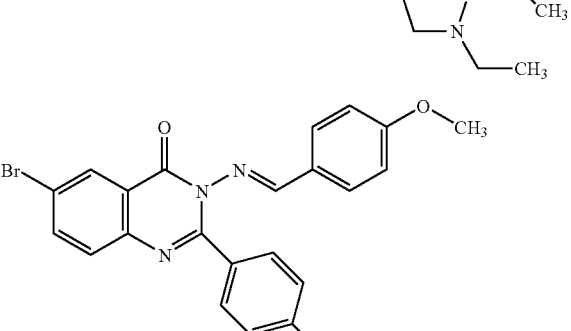 |

TABLE 3-continued
Structures of compounds 1 to 1077 are shown in Table 3.
| Compound No. | Chemical structural formula |
|---|---|
| Compound 756 | 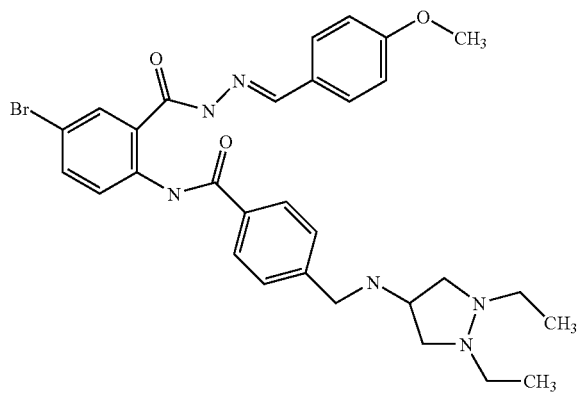 |
| Compound 757 | 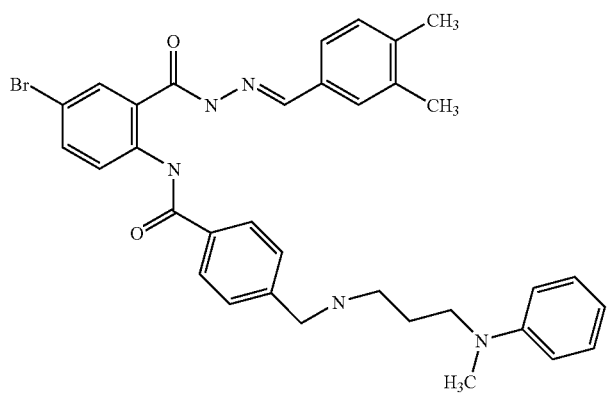 |
| Compound 758 | 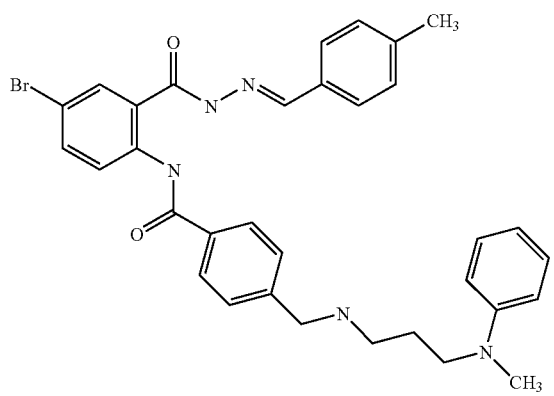 |
| Compound 759 | 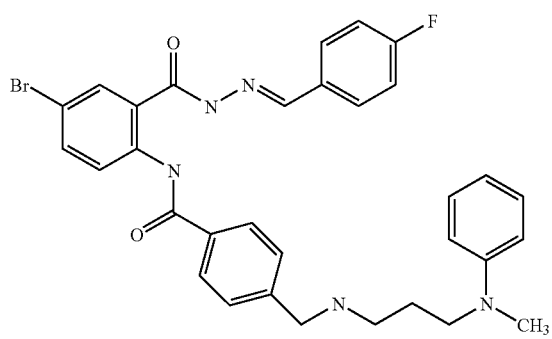 |

TABLE 3-continued

Structures of compounds 1 to 1077 are shown in Table 3.

| Compound No. | Chemical structural formula |
| --- | --- |
| Compound 760 | |
| Compound 761 | |
| Compound 762 | |
| Compound 763 | |

TABLE 3-continued
Structures of compounds 1 to 1077 are shown in Table 3.
| Compound No. | Chemical structural formula |
|---|---|
| Compound 764 | 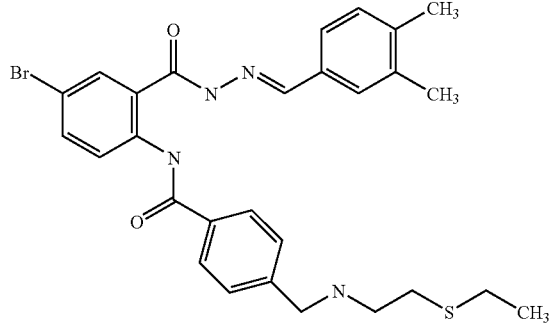 |
| Compound 765 | 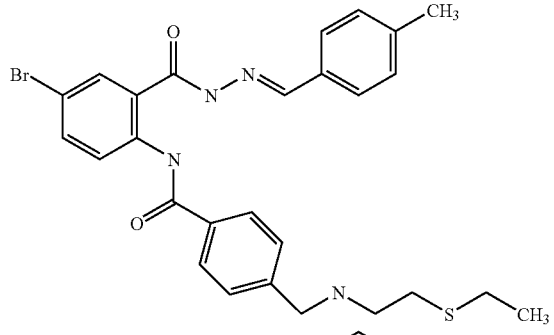 |
| Compound 766 | 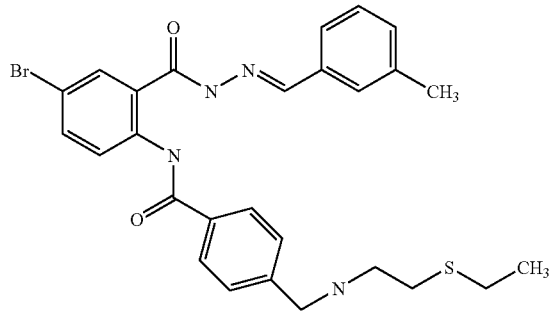 |
| Compound 767 | 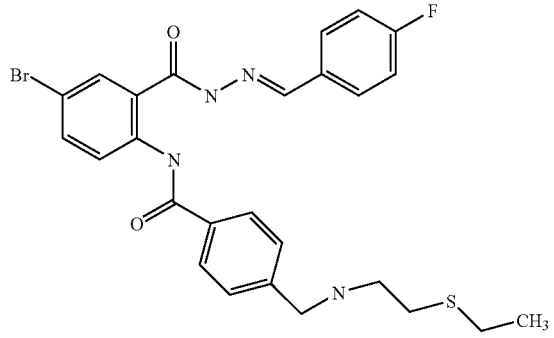 |
| Compound 768 | 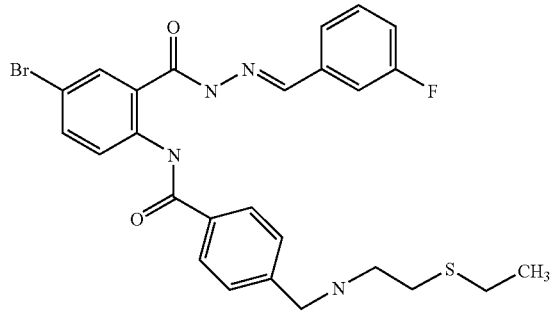 |

TABLE 3-continued
Structures of compounds 1 to 1077 are shown in Table 3.
| Compound No. | Chemical structural formula |
|---|---|
| Compound 769 | 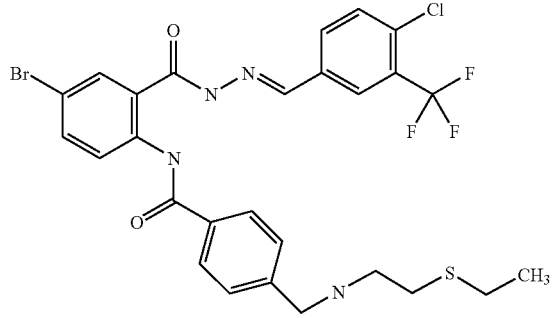 |
| Compound 770 | 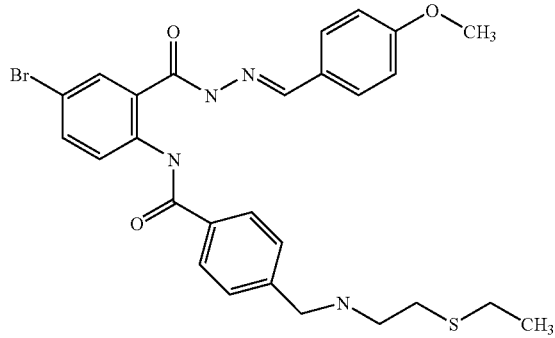 |
| Compound 771 | 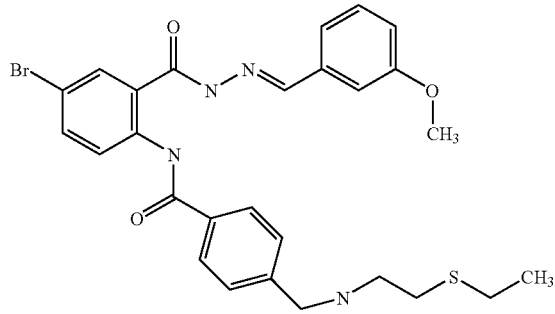 |
| Compound 772 | 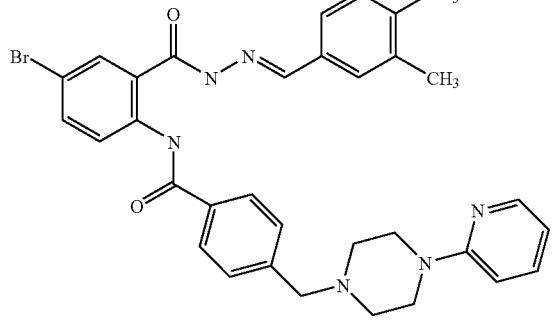 |

TABLE 3-continued

Structures of compounds 1 to 1077 are shown in Table 3.

| Compound No. | Chemical structural formula |
| --- | --- |
| Compound 773 | |
| Compound 774 | |
| Compound 775 | |
| Compound 776 | |

TABLE 3-continued
Structures of compounds 1 to 1077 are shown in Table 3.
| Compound No. | Chemical structural formula |
| --- | --- |
| Compound 777 | 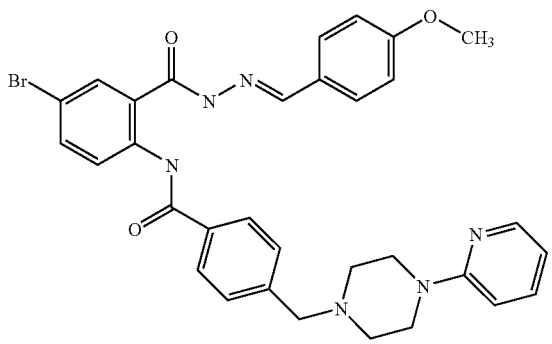 |
| Compound 778 | 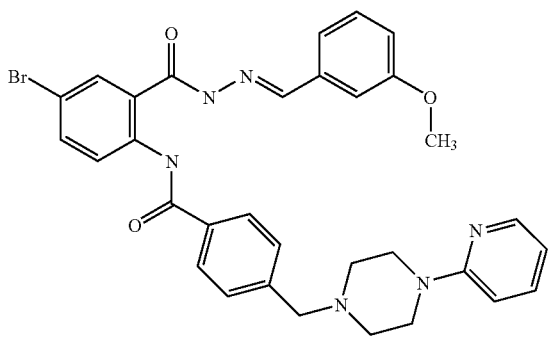 |
| Compound 779 | 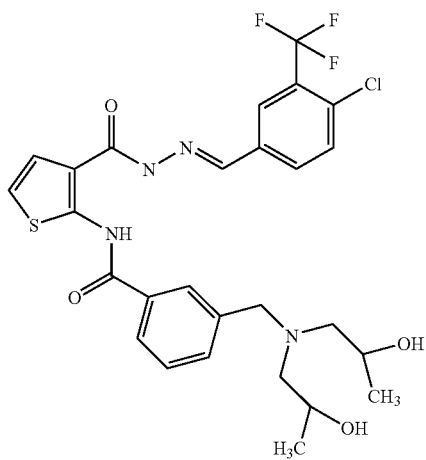 |
| Compound 780 | 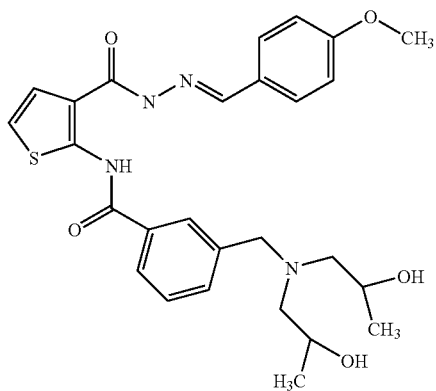 |

TABLE 3-continued
Structures of compounds 1 to 1077 are shown in Table 3.
| Compound No. | Chemical structural formula |
|---|---|
| Compound 781 | 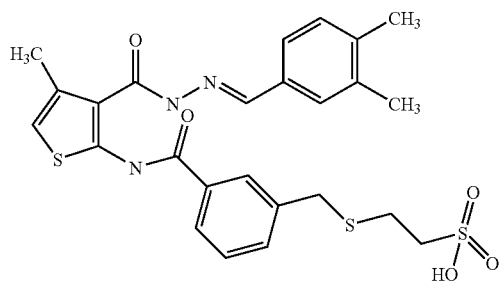 |
| Compound 782 | 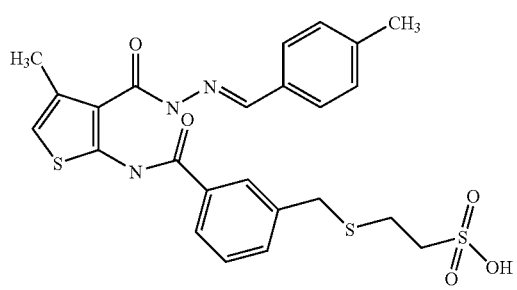 |
| Compound 783 | 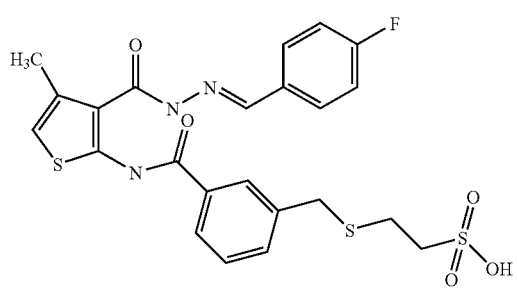 |
| Compound 784 | 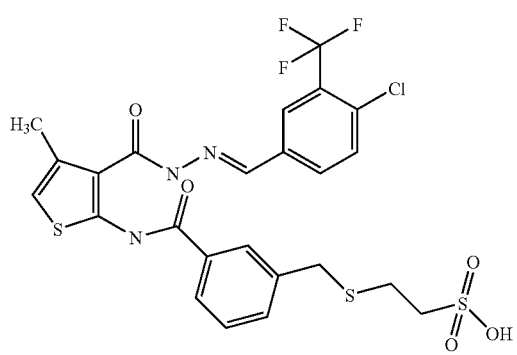 |
| Compound 785 | 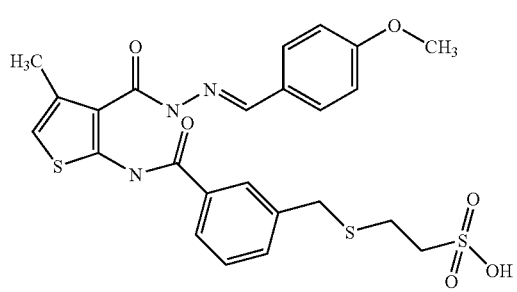 |

TABLE 3-continued
Structures of compounds 1 to 1077 are shown in Table 3.
| Compound No. | Chemical structural formula |
|---|---|
| Compound 786 | 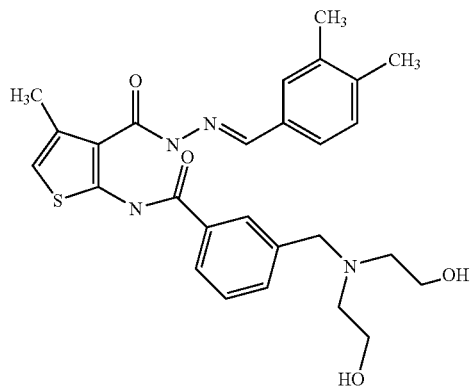 |
| Compound 787 | 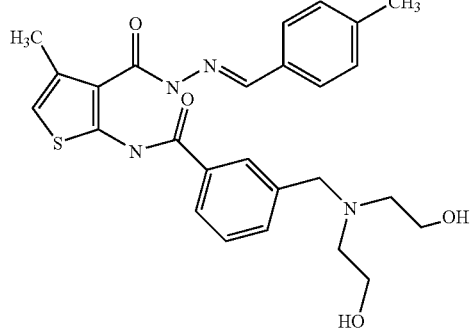 |
| Compound 788 | 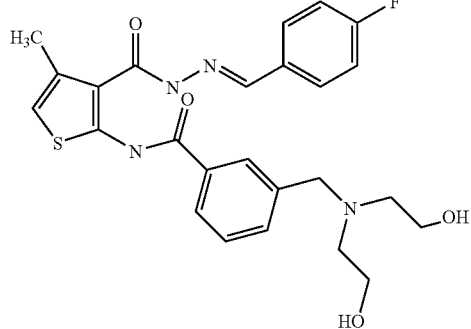 |
| Compound 789 | 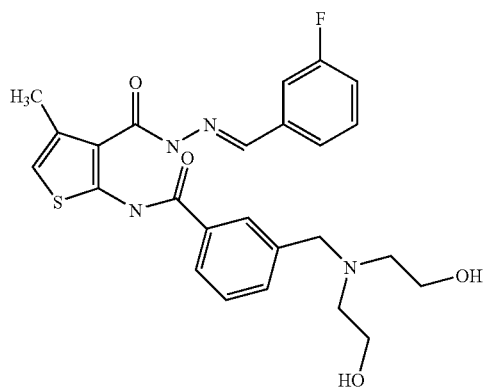 |

TABLE 3-continued
Structures of compounds 1 to 1077 are shown in Table 3.
| Compound No. | Chemical structural formula |
| --- | --- |
| Compound 790 | 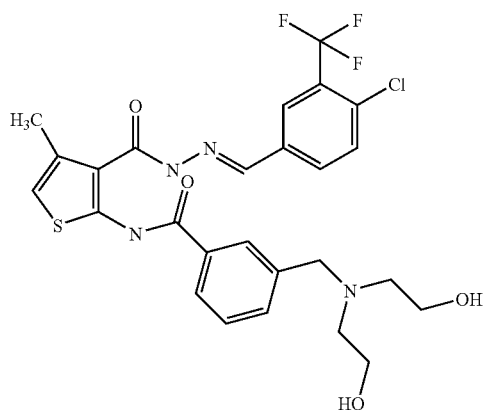 |
| Compound 791 | 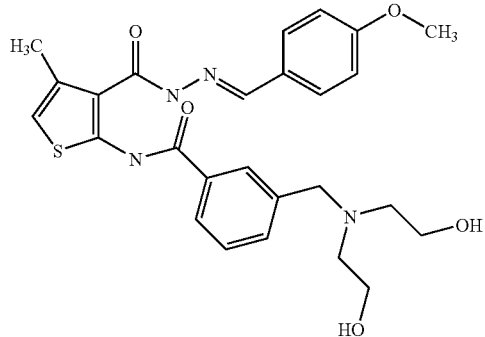 |
| Compound 792 | 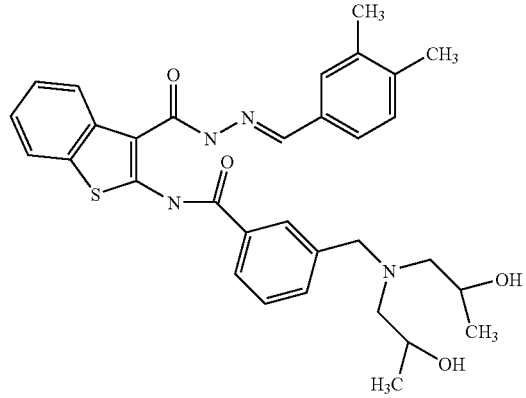 |
| Compound 793 | 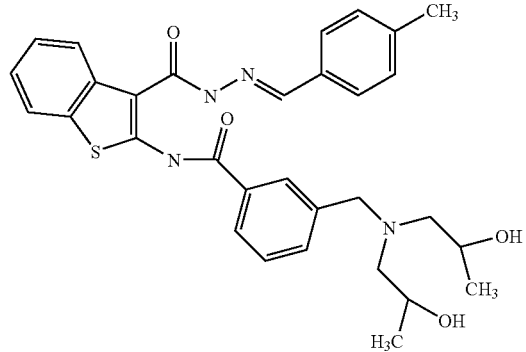 |

TABLE 3-continued
Structures of compounds 1 to 1077 are shown in Table 3.
| Compound No. | Chemical structural formula |
|---|---|
| Compound 794 | 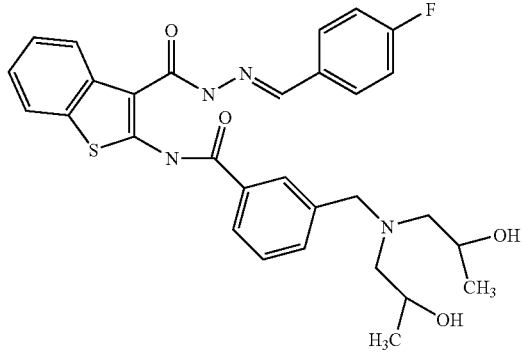 |
| Compound 795 | 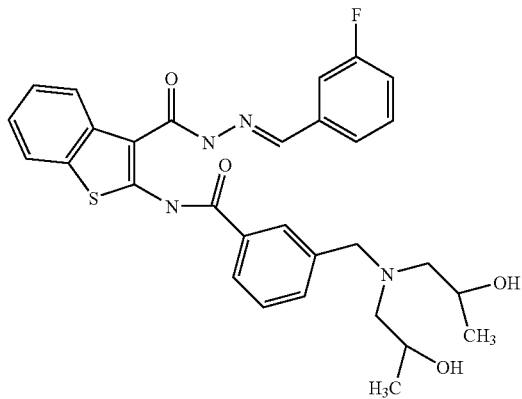 |
| Compound 796 | 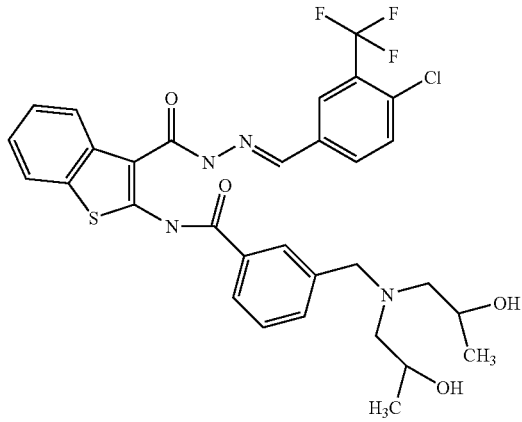 |
| Compound 797 | 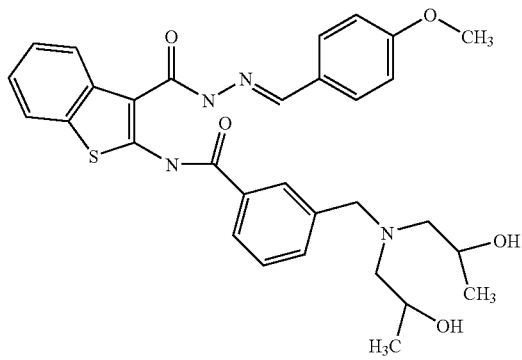 |

TABLE 3-continued
Structures of compounds 1 to 1077 are shown in Table 3.
| Compound No. | Chemical structural formula |
|---|---|
| Compound 798 | 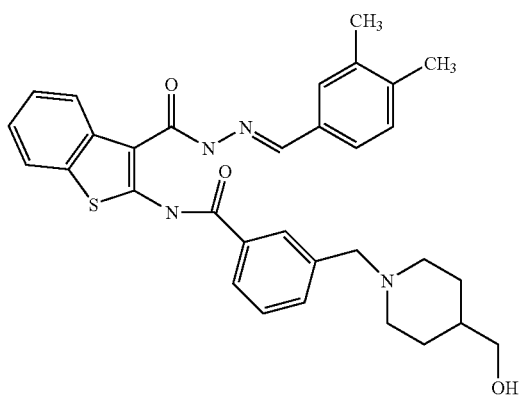 |
| Compound 799 | 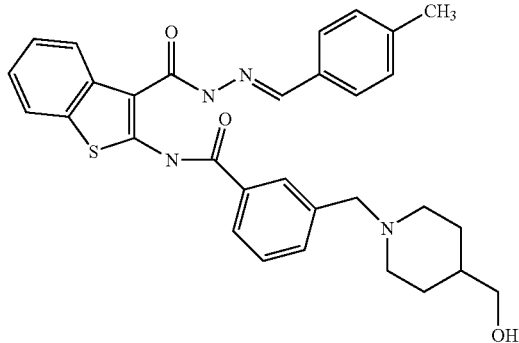 |
| Compound 800 | 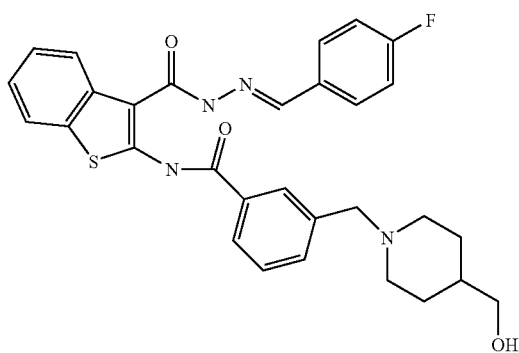 |
| Compound 801 | 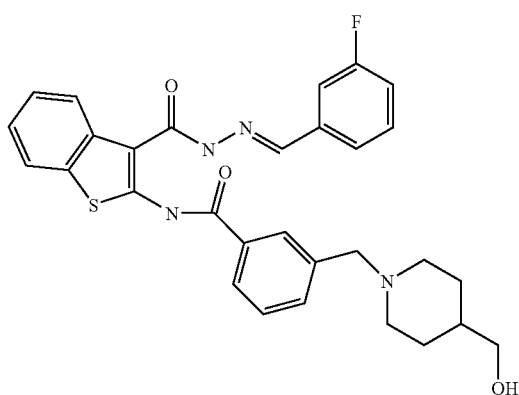 |

TABLE 3-continued
Structures of compounds 1 to 1077 are shown in Table 3.
| Compound No. | Chemical structural formula |
|---|---|
| Compound 802 | 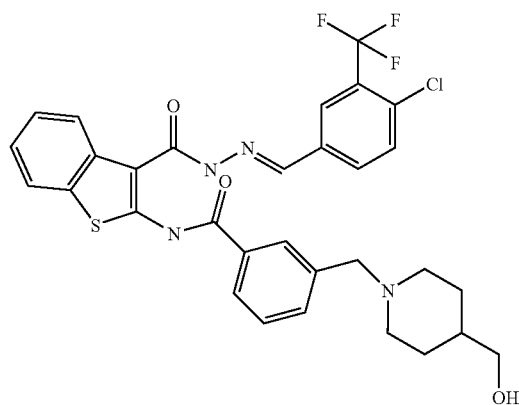 |
| Compound 803 | 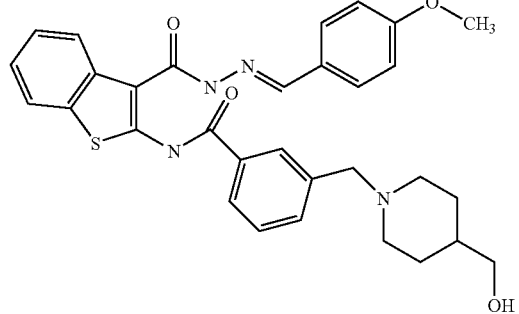 |
| Compound 804 | 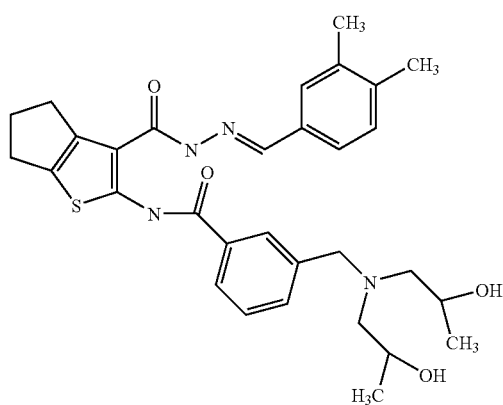 |
| Compound 805 | 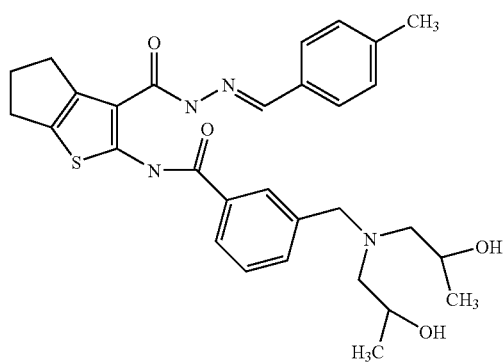 |

TABLE 3-continued
Structures of compounds 1 to 1077 are shown in Table 3.
| Compound No. | Chemical structural formula |
| --- | --- |
| Compound 806 | 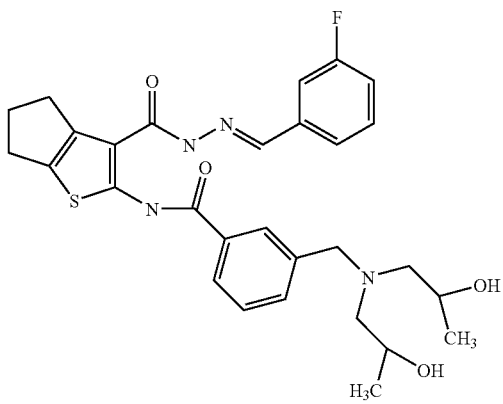 |
| Compound 807 | 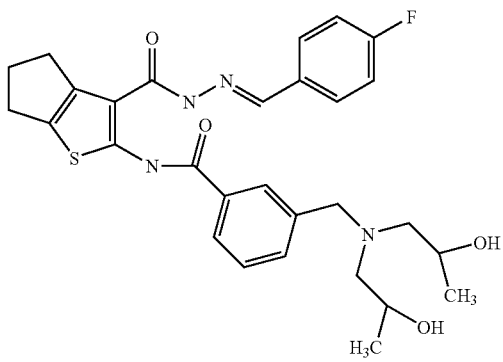 |
| Compound 808 | 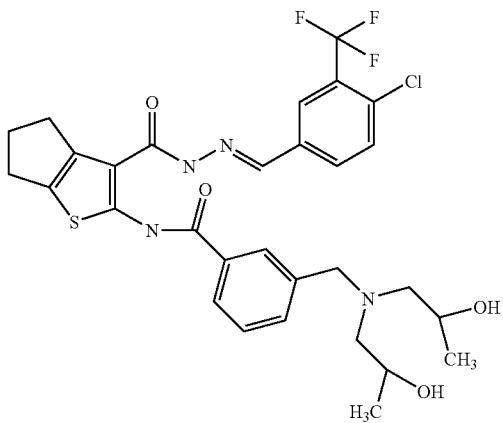 |
| Compound 809 | 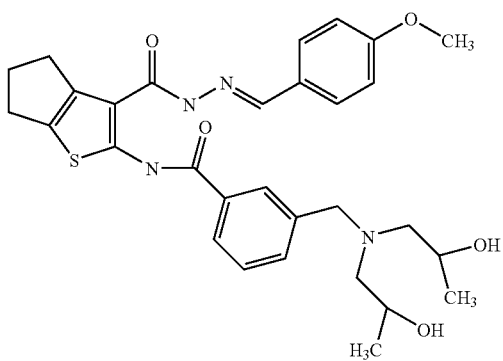 |

TABLE 3-continued
Structures of compounds 1 to 1077 are shown in Table 3.
| Compound No. | Chemical structural formula |
|---|---|
| Compound 810 | 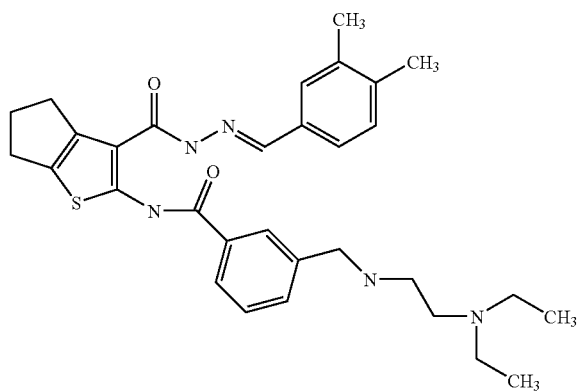 |
| Compound 811 | 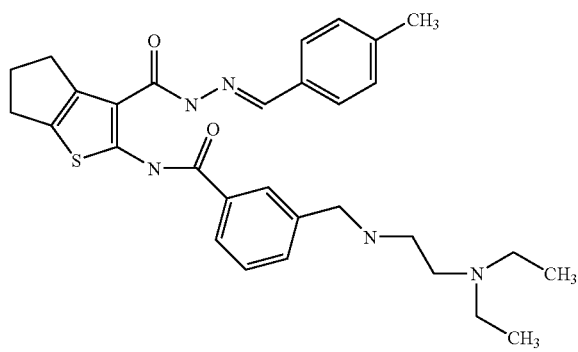 |
| Compound 812 | 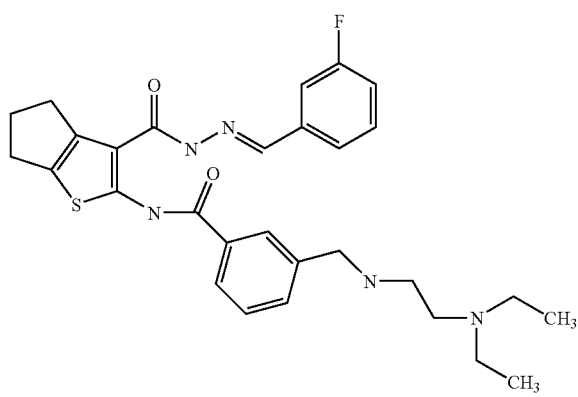 |
| Compound 813 | 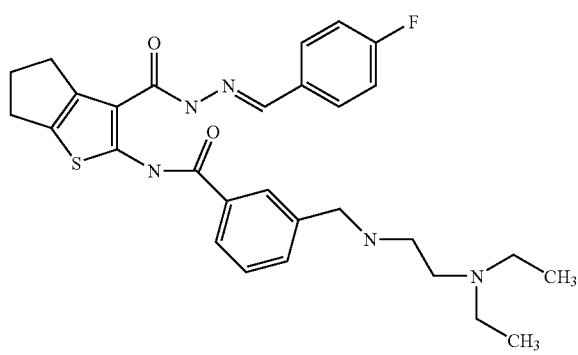 |

TABLE 3-continued
Structures of compounds 1 to 1077 are shown in Table 3.
| Compound No. | Chemical structural formula |
|---|---|
| Compound 814 | 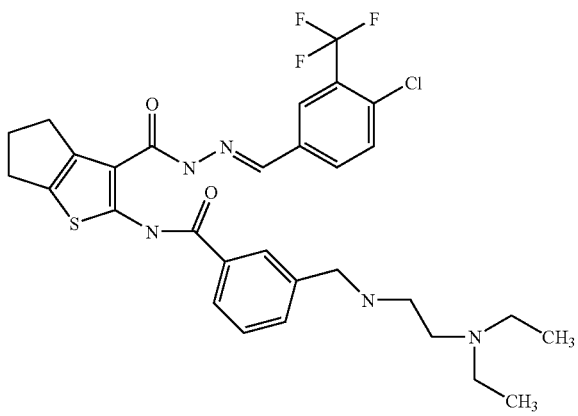 |
| Compound 815 | 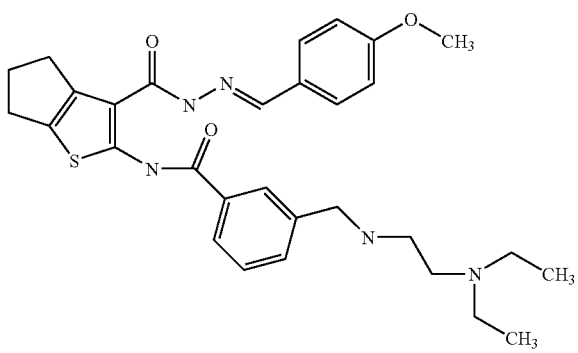 |
| Compound 816 | 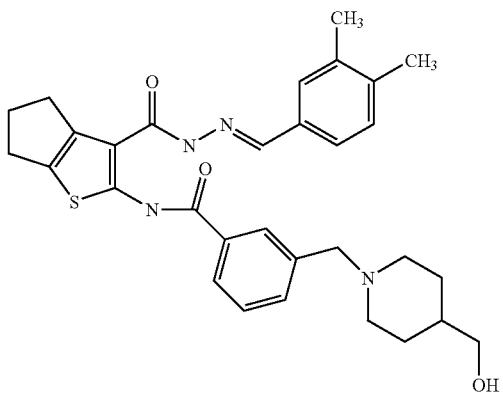 |
| Compound 817 | 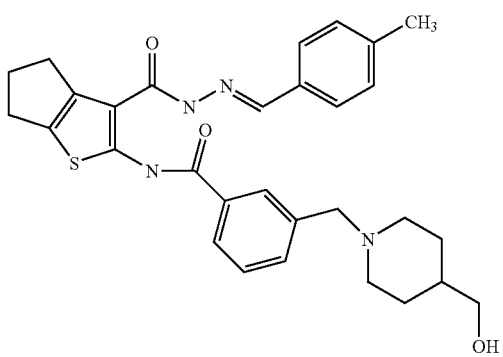 |

TABLE 3-continued
Structures of compounds 1 to 1077 are shown in Table 3.
| Compound No. | Chemical structural formula |
|---|---|
| Compound 818 | 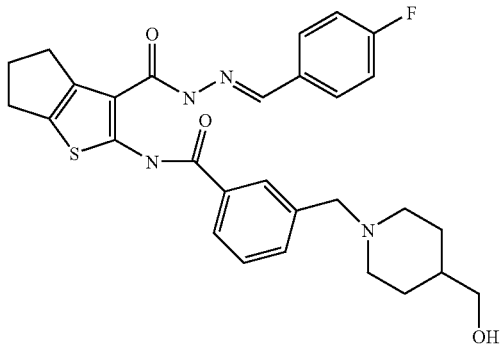 |
| Compound 819 | 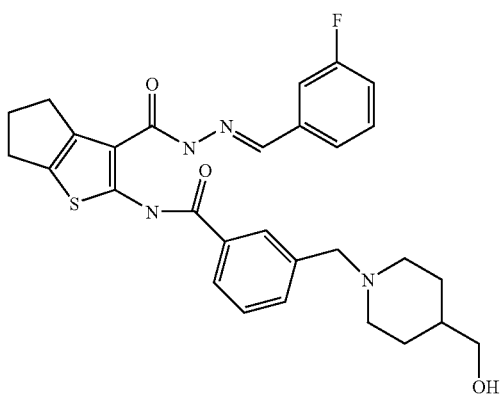 |
| Compound 820 | 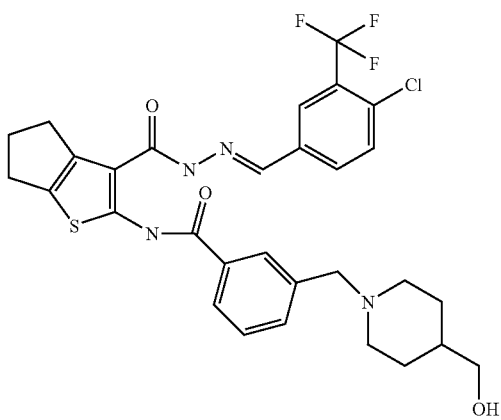 |
| Compound 821 | 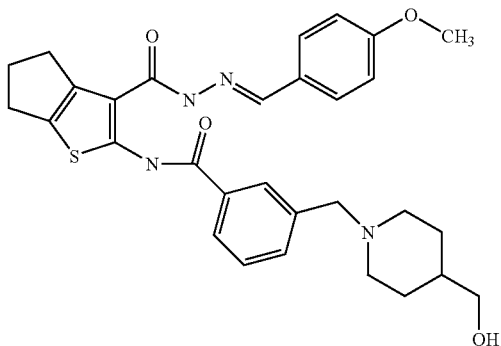 |

TABLE 3-continued
Structures of compounds 1 to 1077 are shown in Table 3.
| Compound No. | Chemical structural formula |
|---|---|
| Compound 822 | 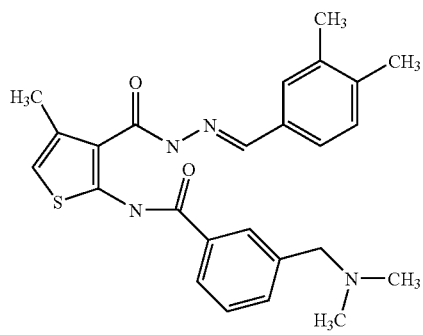 |
| Compound 823 | 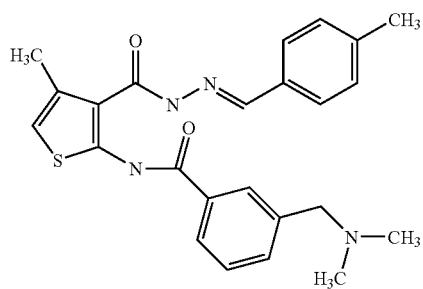 |
| Compound 824 | 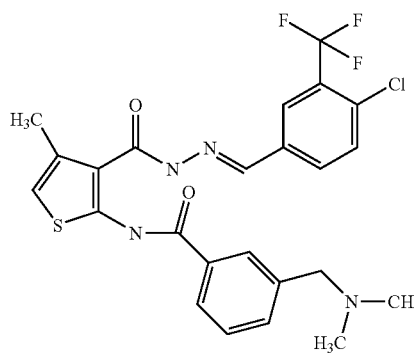 |
| Compound 825 | 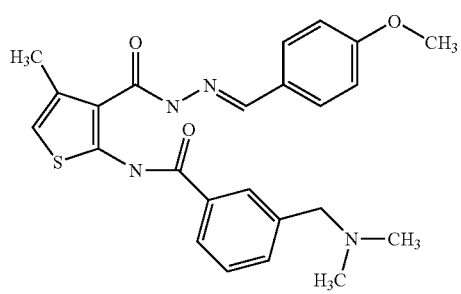 |

TABLE 3-continued
Structures of compounds 1 to 1077 are shown in Table 3.
| Compound No. | Chemical structural formula |
|---|---|
| Compound 826 | 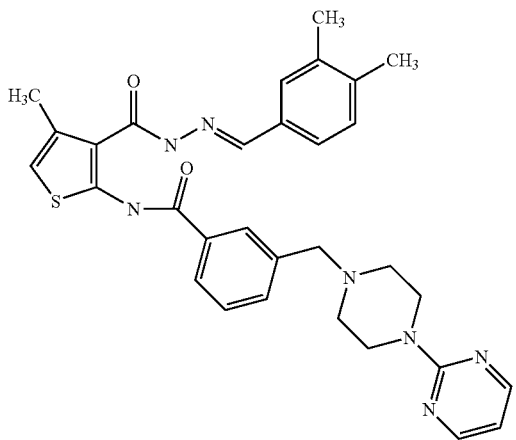 |
| Compound 827 | 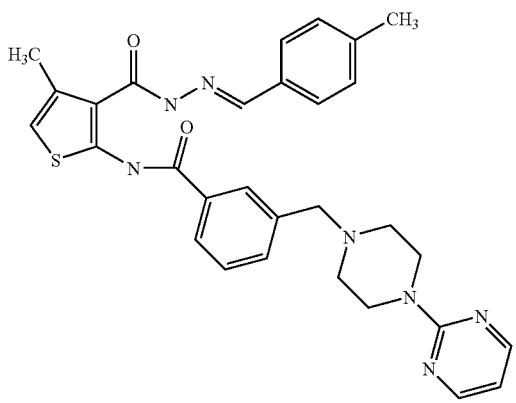 |
| Compound 828 | 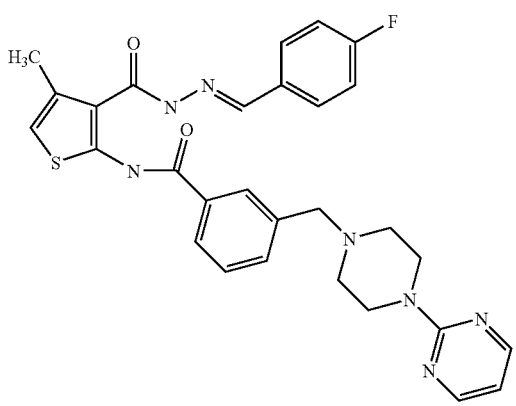 |

TABLE 3-continued
Structures of compounds 1 to 1077 are shown in Table 3.
| Compound No. | Chemical structural formula |
| --- | --- |
Compound 829
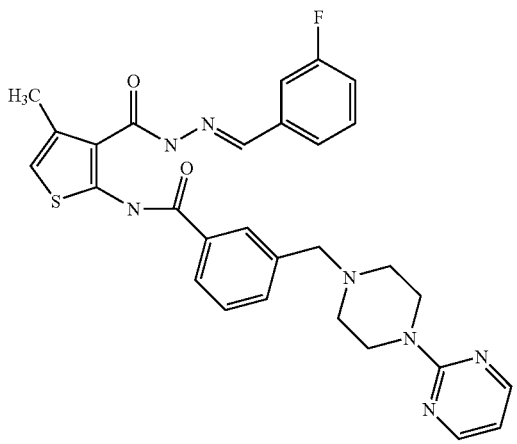
Compound 830
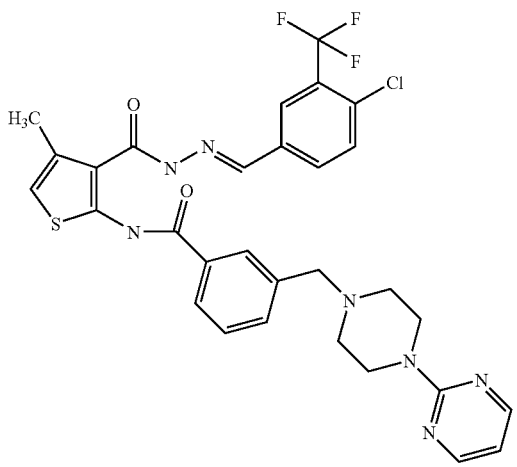
Compound 831
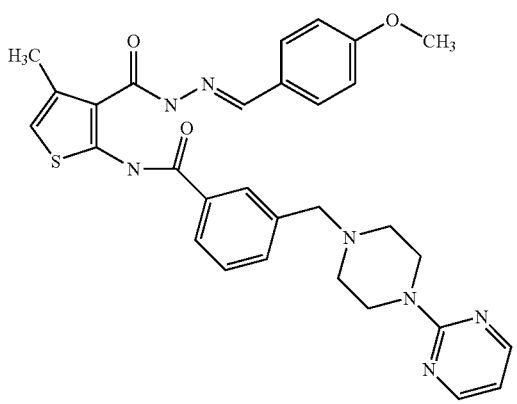

TABLE 3-continued
Structures of compounds 1 to 1077 are shown in Table 3.
| Compound No. | Chemical structural formula |
|---|---|
| Compound 832 | 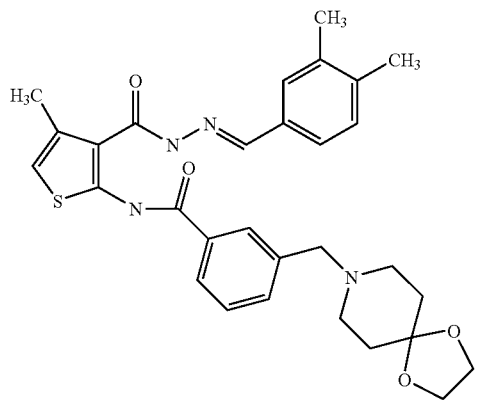 |
| Compound 833 | 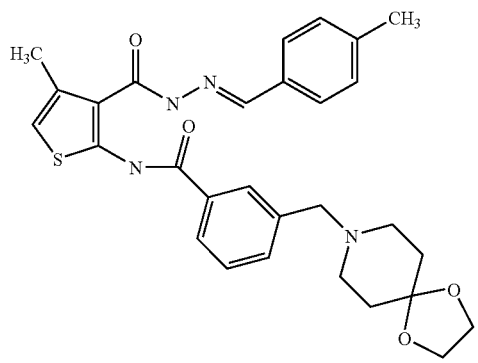 |
| Compound 834 | 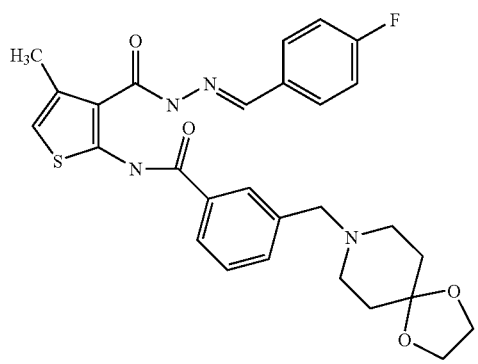 |
| Compound 835 | 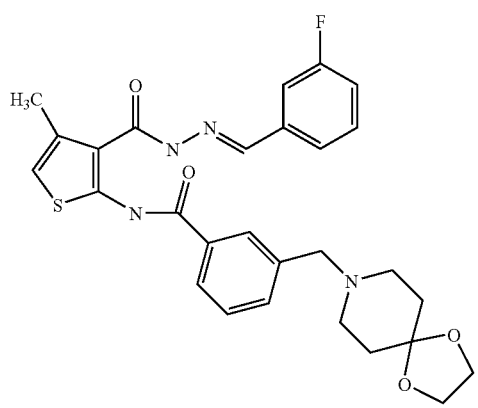 |

TABLE 3-continued
Structures of compounds 1 to 1077 are shown in Table 3.
| Compound No. | Chemical structural formula |
| --- | --- |
| Compound 836 | 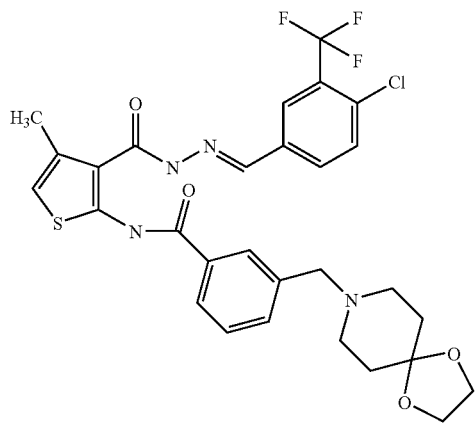 |
| Compound 837 | 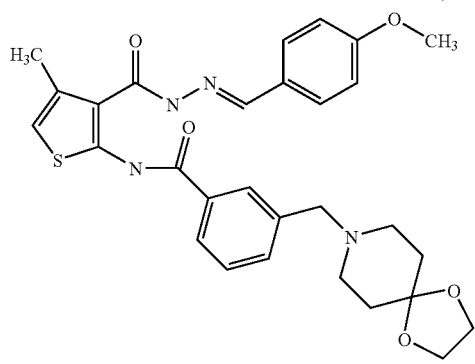 |
| Compound 838 | 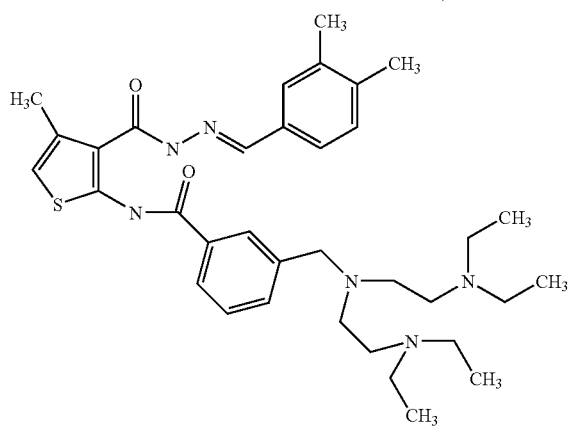 |
| Compound 839 | 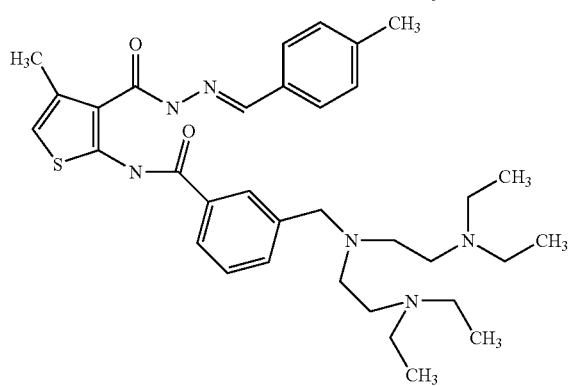 |

TABLE 3-continued
Structures of compounds 1 to 1077 are shown in Table 3.
| Compound No. | Chemical structural formula |
|---|---|
| Compound 840 | 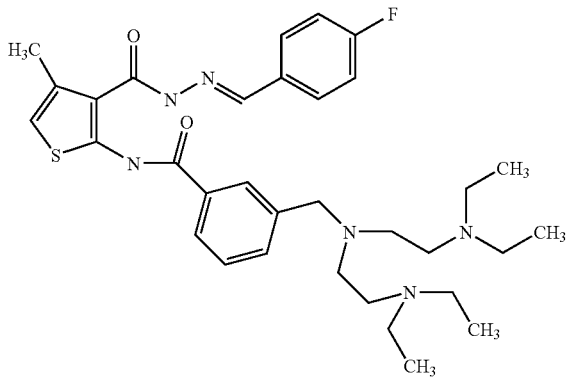 |
| Compound 841 | 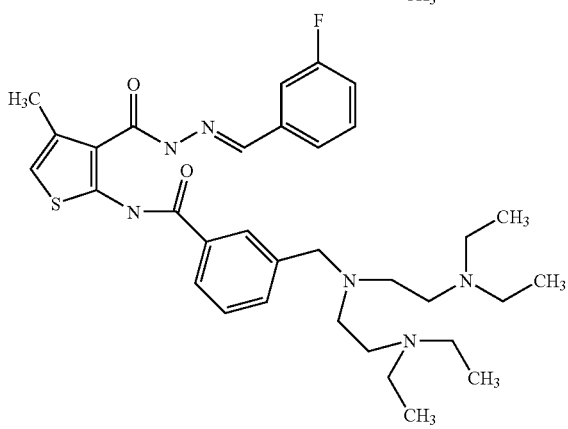 |
| Compound 842 | 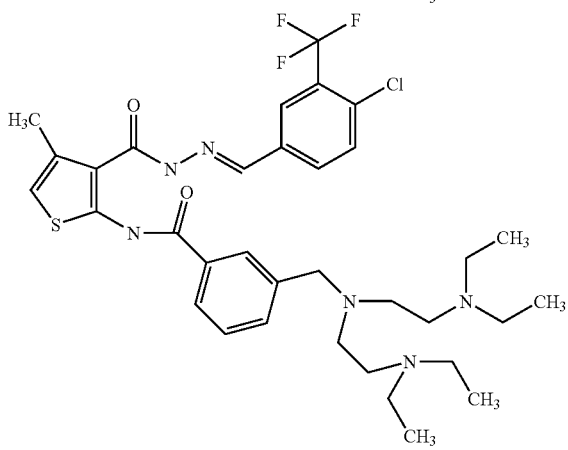 |
| Compound 843 | 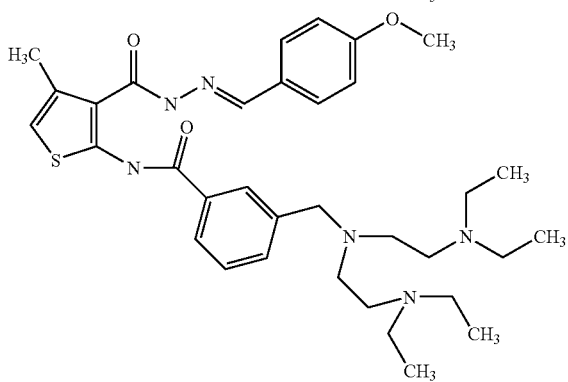 |

TABLE 3-continued
Structures of compounds 1 to 1077 are shown in Table 3.
| Compound No. | Chemical structural formula |
|---|---|
| Compound 844 | 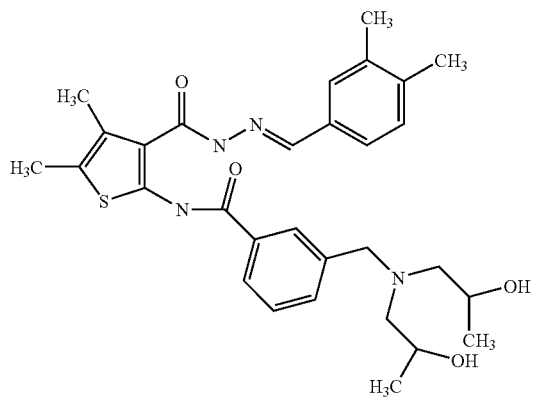 |
| Compound 845 | 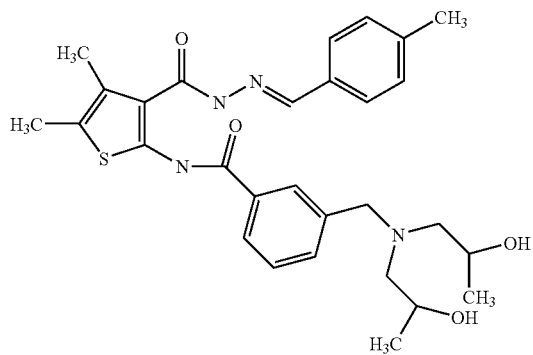 |
| Compound 846 | 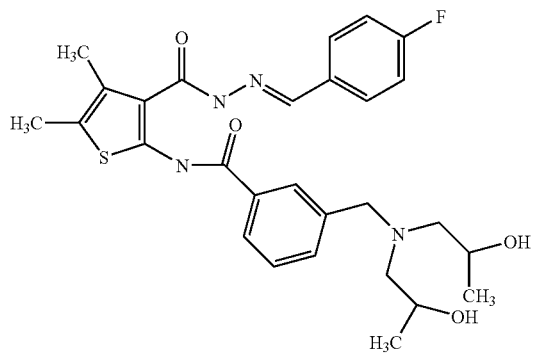 |
| Compound 847 | 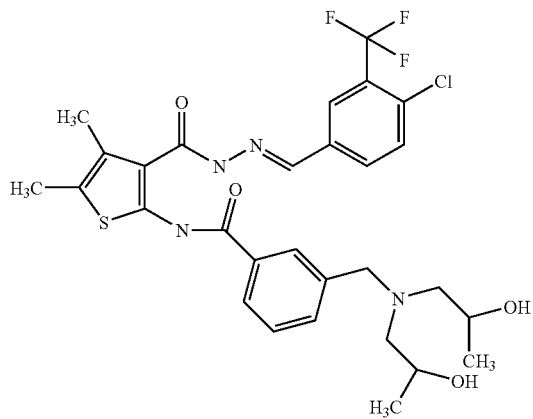 |

TABLE 3-continued
Structures of compounds 1 to 1077 are shown in Table 3.
Compound No.    Chemical structural formula
Compound 848
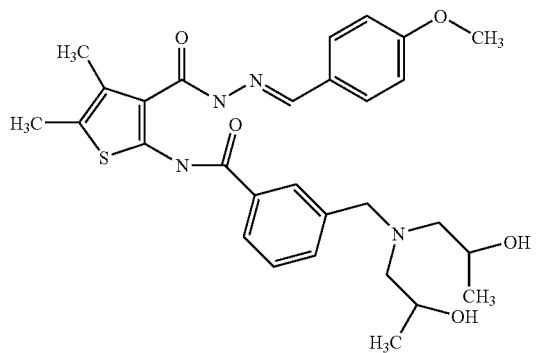
Compound 849
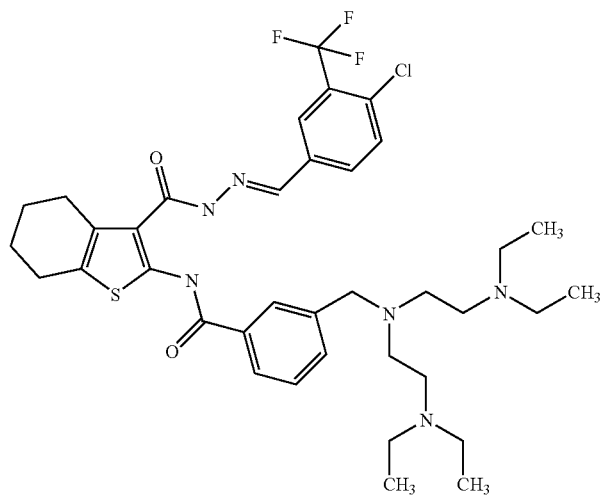
Compound 850
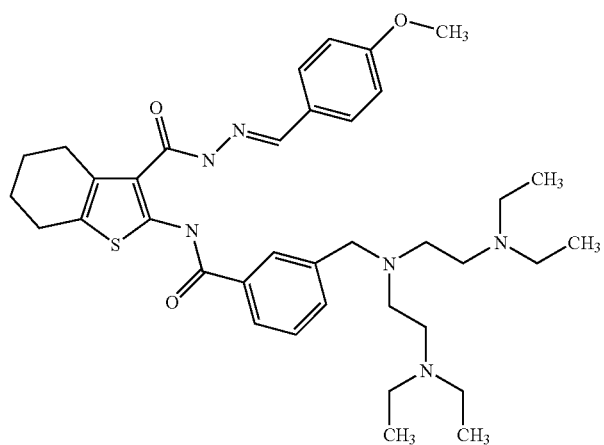

TABLE 3-continued
Structures of compounds 1 to 1077 are shown in Table 3.
| Compound No. | Chemical structural formula |
|---|---|
| Compound 851 | 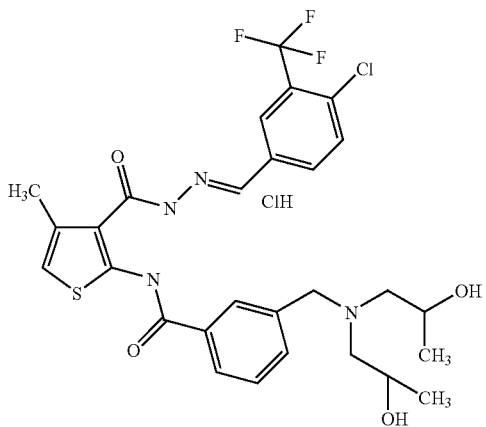 |
| Compound 852 | 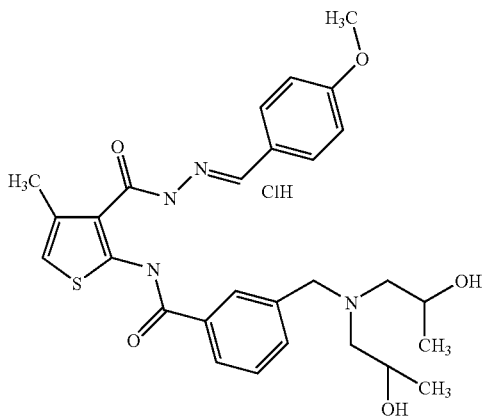 |
| Compound 853 | 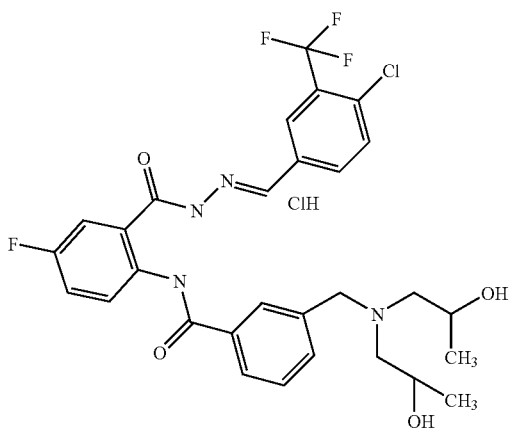 |

TABLE 3-continued
Structures of compounds 1 to 1077 are shown in Table 3.
| Compound No. | Chemical structural formula |
|---|---|
| Compound 854 | 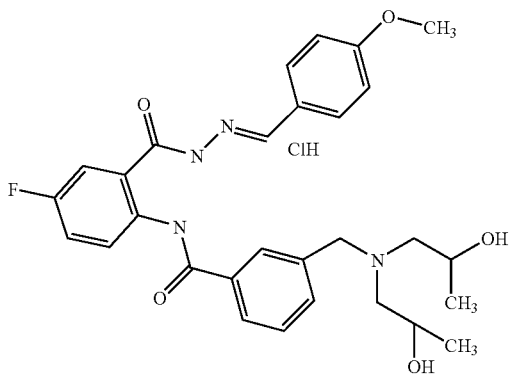 |
| Compound 855 | 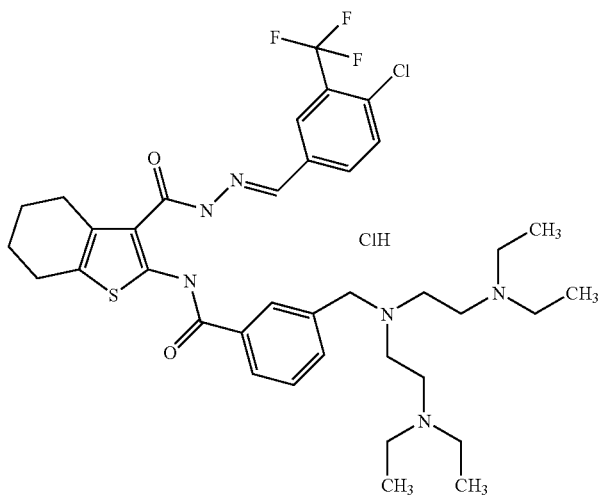 |
| Compound 856 | 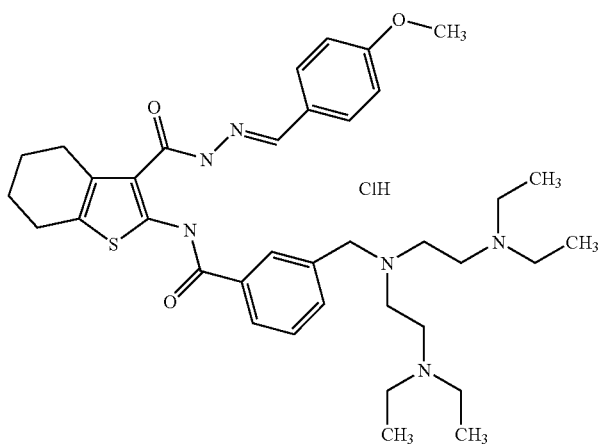 |

TABLE 3-continued
Structures of compounds 1 to 1077 are shown in Table 3.
Compound No.   Chemical structural formula
Compound 857
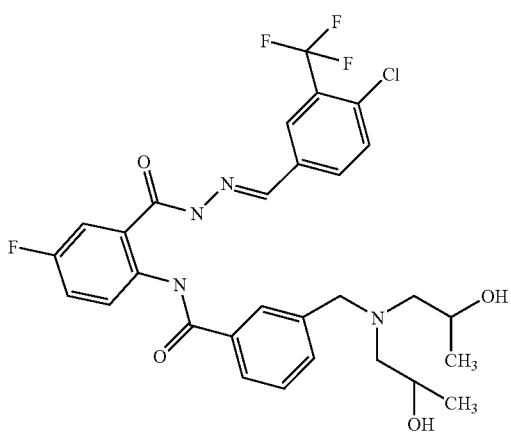
Compound 858
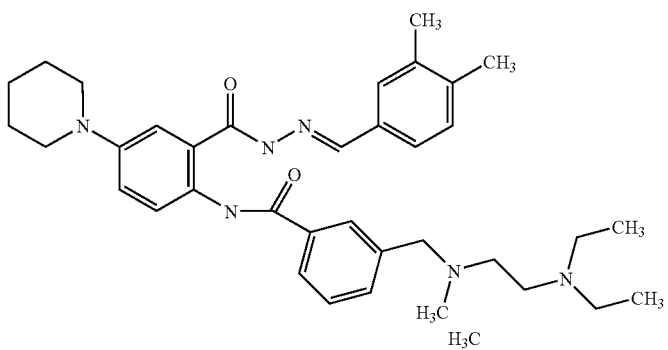
Compound 859
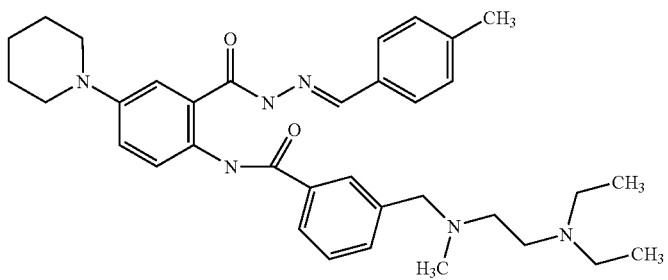
Compound 860
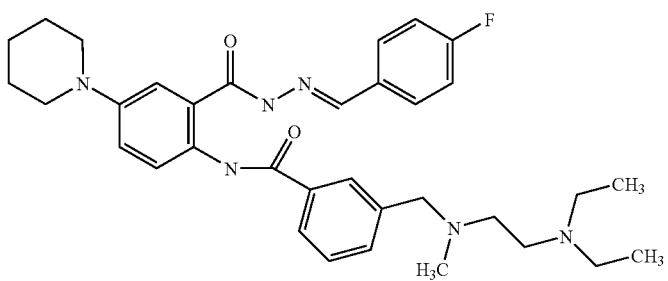

TABLE 3-continued
Structures of compounds 1 to 1077 are shown in Table 3.
| Compound No. | Chemical structural formula |
| --- | --- |
| Compound 861 | 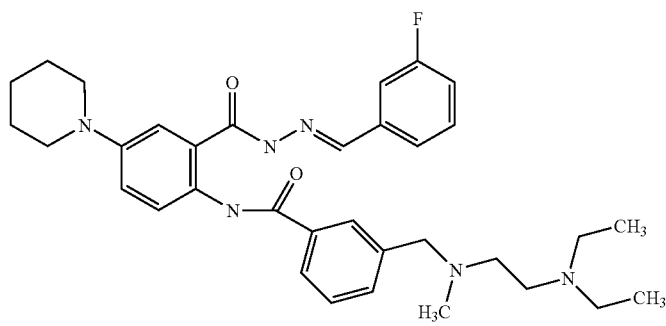 |
| Compound 862 | 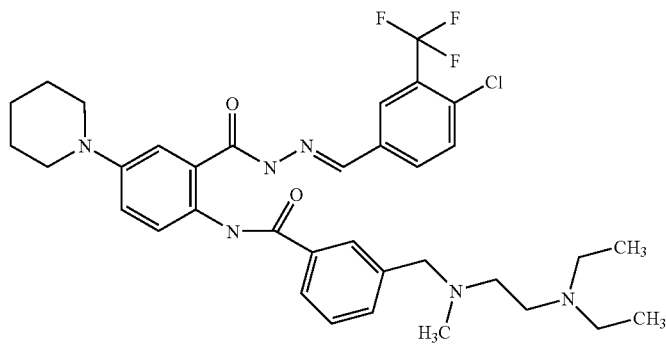 |
| Compound 863 | 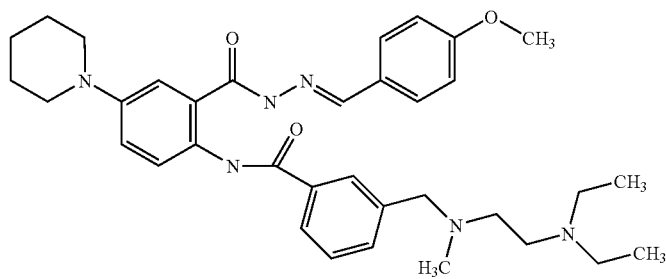 |
| Compound 864 | 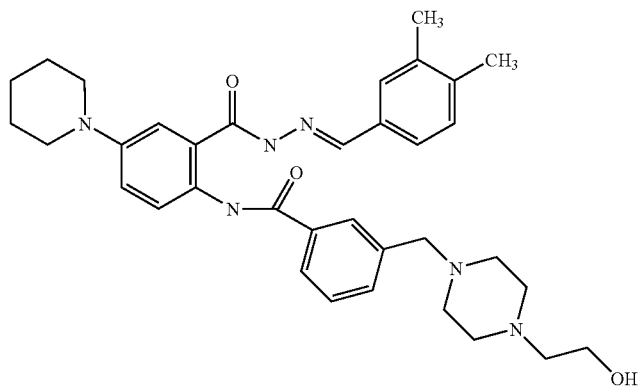 |

TABLE 3-continued
Structures of compounds 1 to 1077 are shown in Table 3.
| Compound No. | Chemical structural formula |
|---|---|
| Compound 865 | 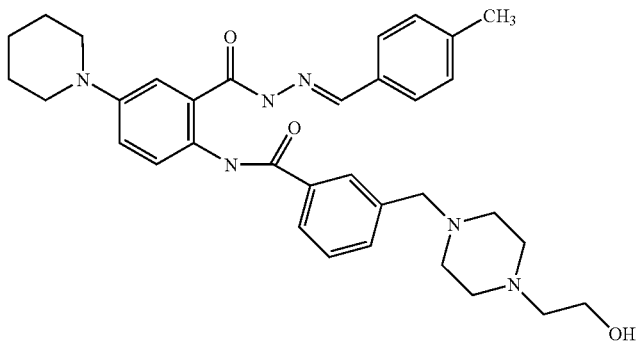 |
| Compound 866 | 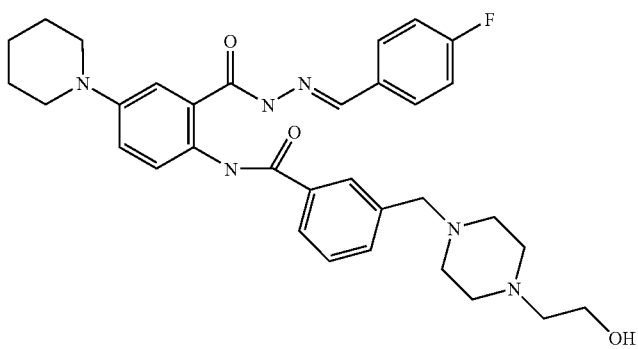 |
| Compound 867 | 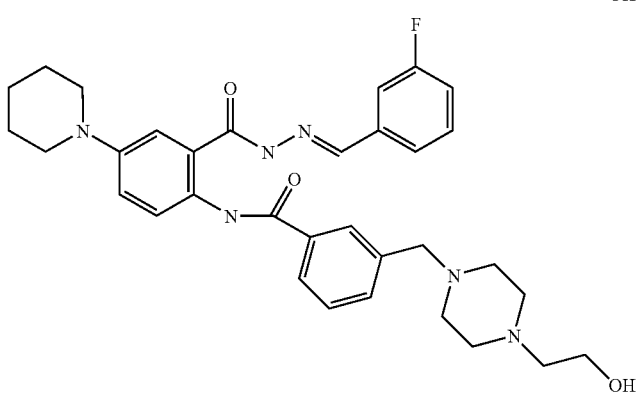 |
| Compound 868 | 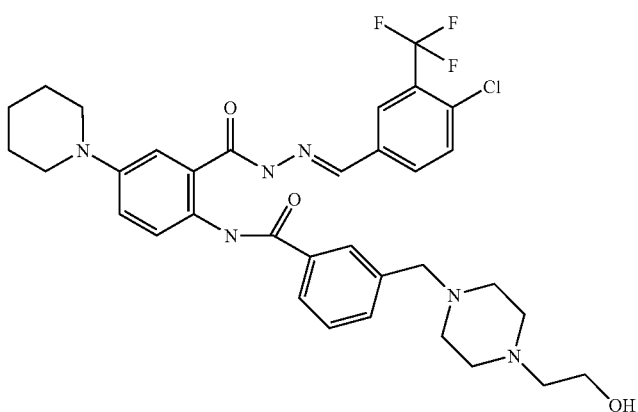 |

TABLE 3-continued
Structures of compounds 1 to 1077 are shown in Table 3.
| Compound No. | Chemical structural formula |
|---|---|
| Compound 869 | 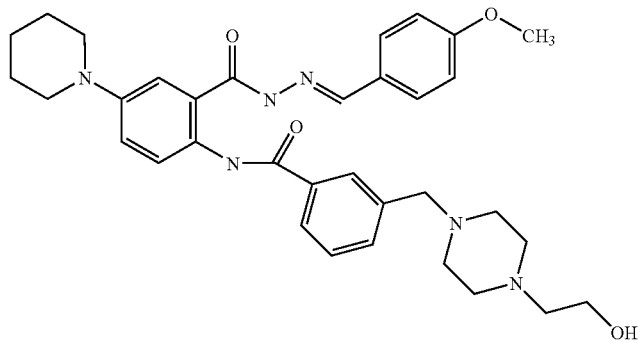 |
| Compound 870 | 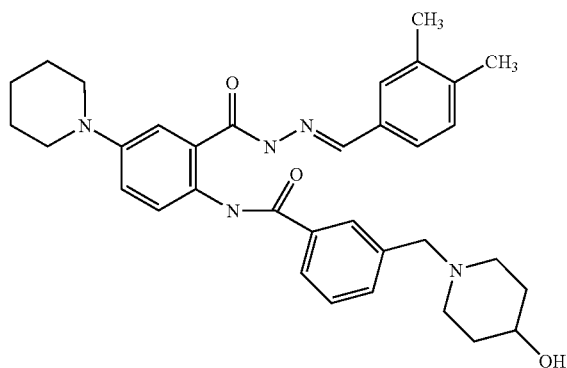 |
| Compound 871 | 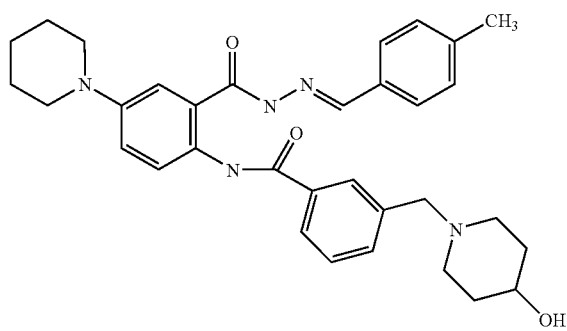 |
| Compound 872 | 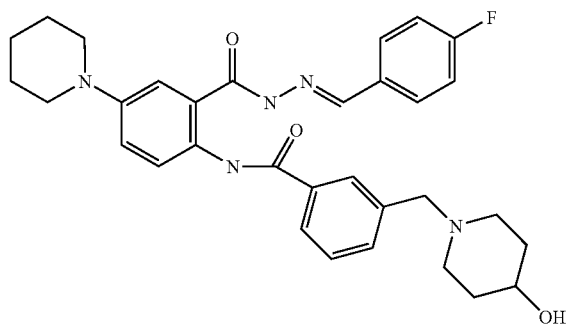 |

TABLE 3-continued
Structures of compounds 1 to 1077 are shown in Table 3.
Compound No.   Chemical structural formula
Compound 873
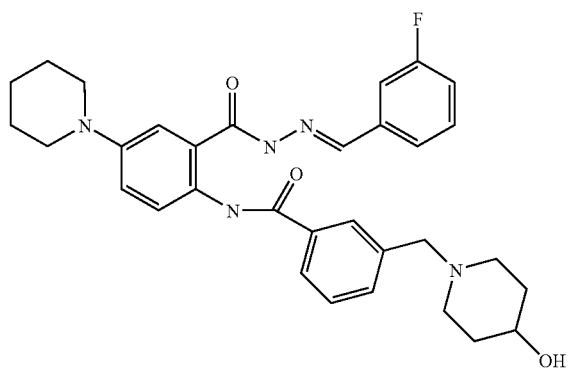
Compound 874
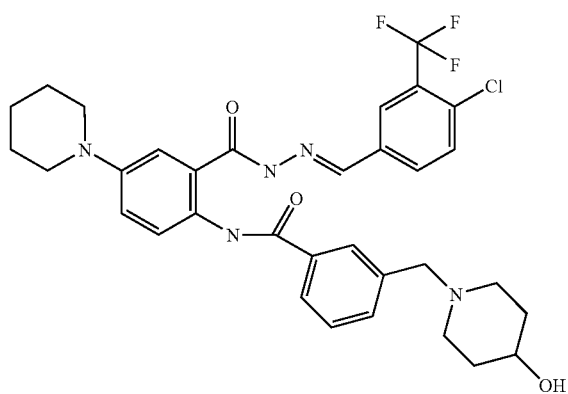
Compound 875
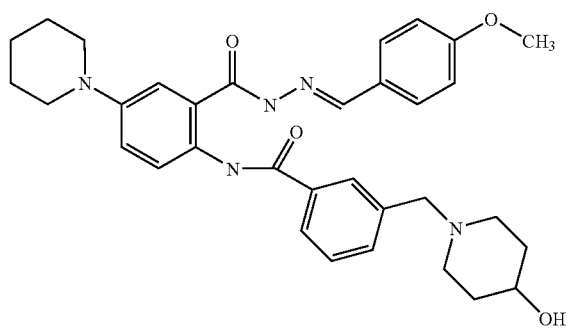
Compound 876
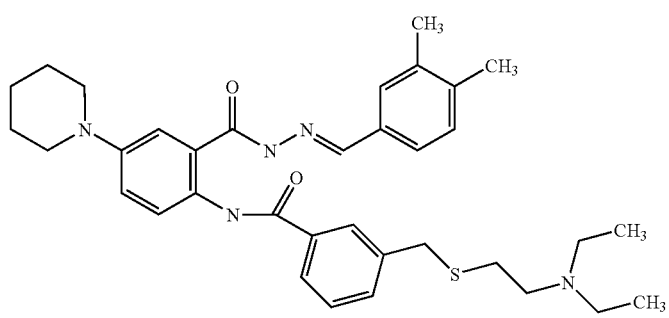

TABLE 3-continued
Structures of compounds 1 to 1077 are shown in Table 3.
| Compound No. | Chemical structural formula |
|---|---|
| Compound 877 | 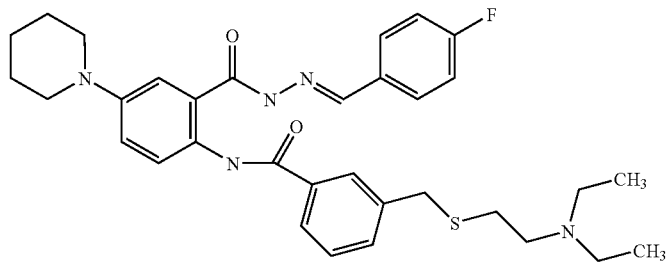 |
| Compound 878 | 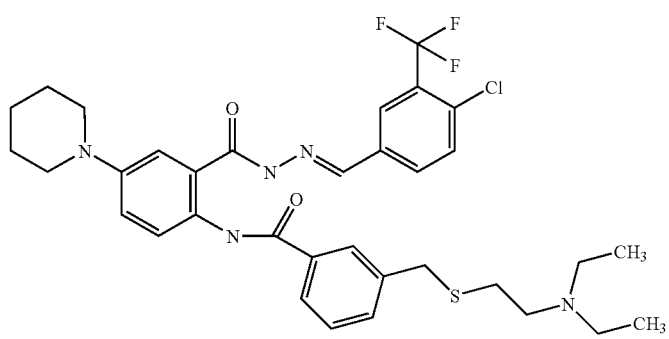 |
| Compound 879 | 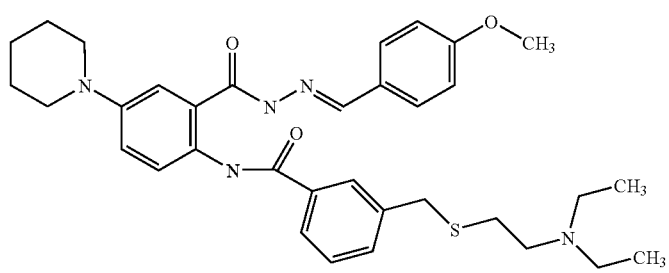 |
| Compound 880 | 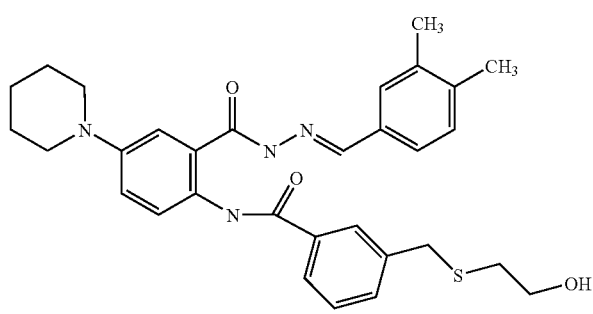 |
| Compound 881 | 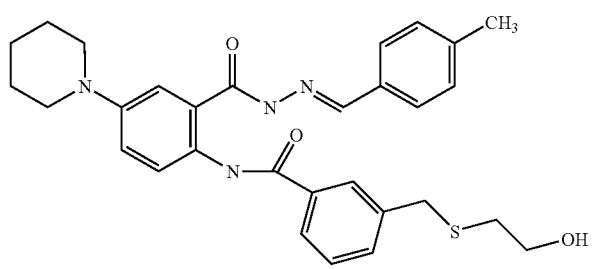 |

TABLE 3-continued
Structures of compounds 1 to 1077 are shown in Table 3.
| Compound No. | Chemical structural formula |
|---|---|
| Compound 882 | 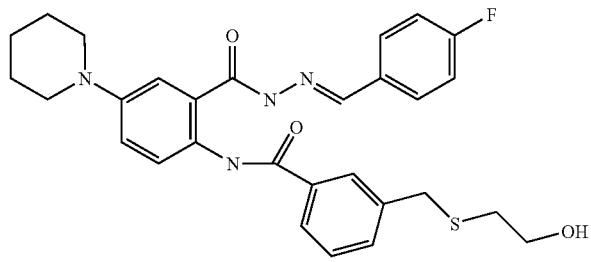 |
| Compound 883 | 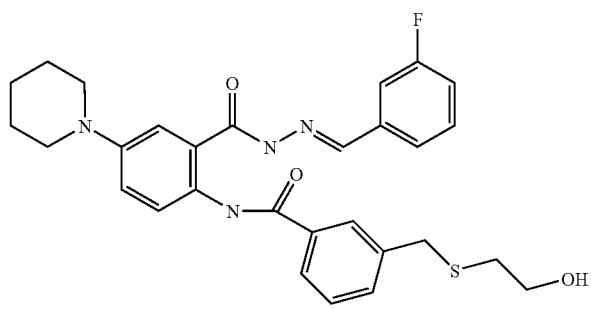 |
| Compound 884 | 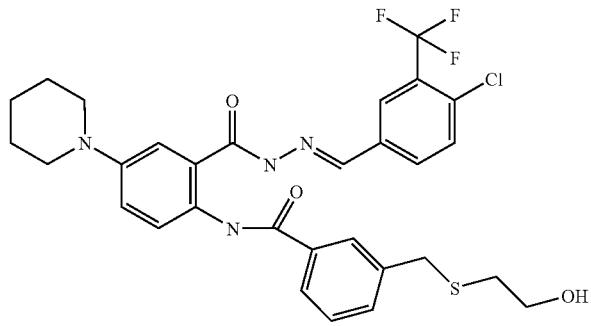 |
| Compound 885 | 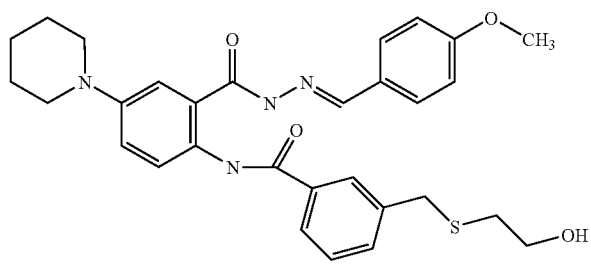 |
| Compound 886 | 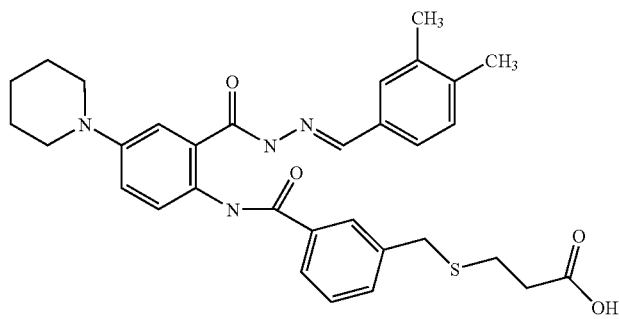 |

TABLE 3-continued
Structures of compounds 1 to 1077 are shown in Table 3.
| Compound No. | Chemical structural formula |
|---|---|
| Compound 887 | 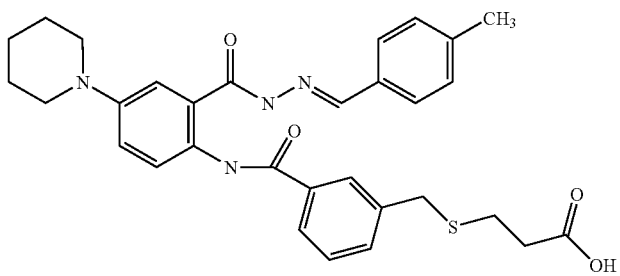 |
| Compound 888 | 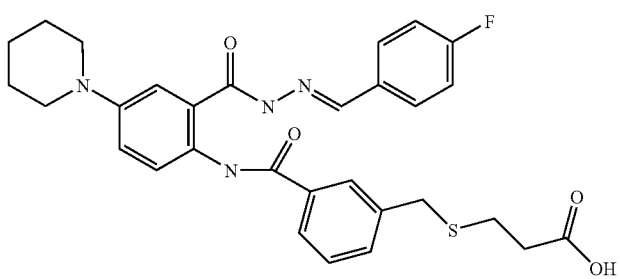 |
| Compound 889 | 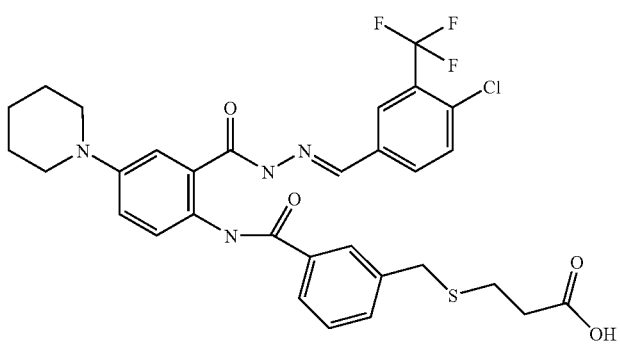 |
| Compound 890 | 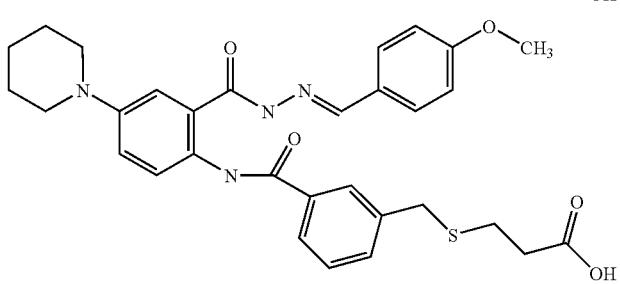 |
| Compound 891 | 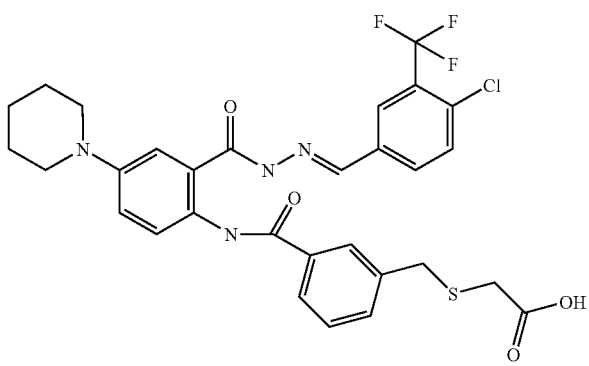 |

TABLE 3-continued

Structures of compounds 1 to 1077 are shown in Table 3.

| Compound No. | Chemical structural formula |
|---|---|
| Compound 892 | |
| Compound 893 | |
| Compound 894 | |
| Compound 895 | |

TABLE 3-continued

Structures of compounds 1 to 1077 are shown in Table 3.

| Compound No. | Chemical structural formula |
|---|---|
| Compound 896 | |
| Compound 897 | |
| Compound 898 | |
| Compound 899 | |

TABLE 3-continued
Structures of compounds 1 to 1077 are shown in Table 3.
| Compound No. | Chemical structural formula |
|---|---|
| Compound 900 | 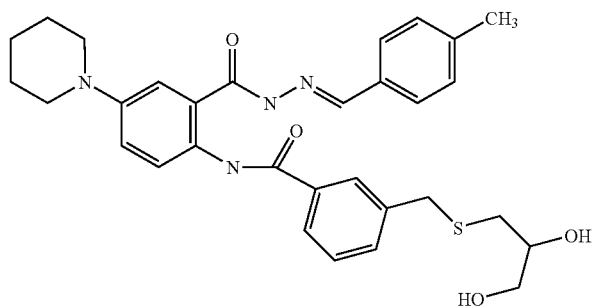 |
| Compound 901 | 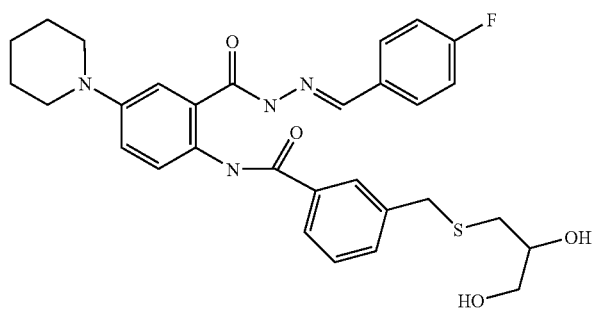 |
| Compound 902 | 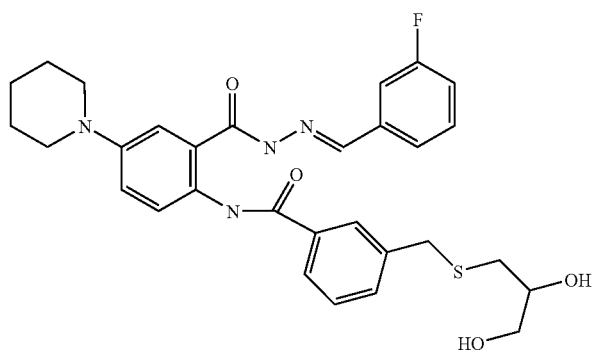 |
| Compound 903 | 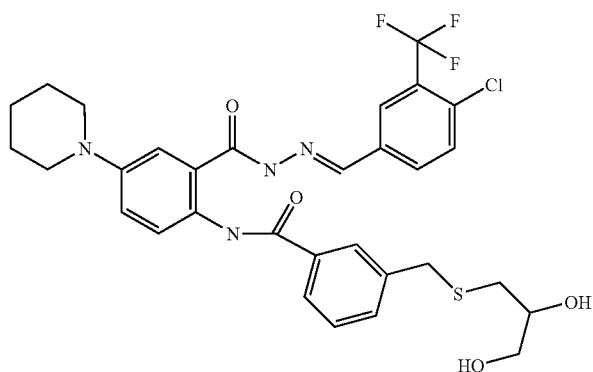 |

TABLE 3-continued
Structures of compounds 1 to 1077 are shown in Table 3.
| Compound No. | Chemical structural formula |
|---|---|
| Compound 904 | 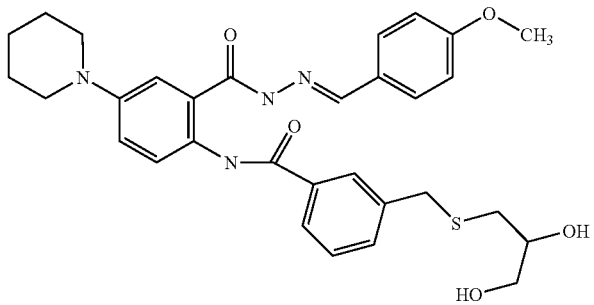 |
| Compound 905 | 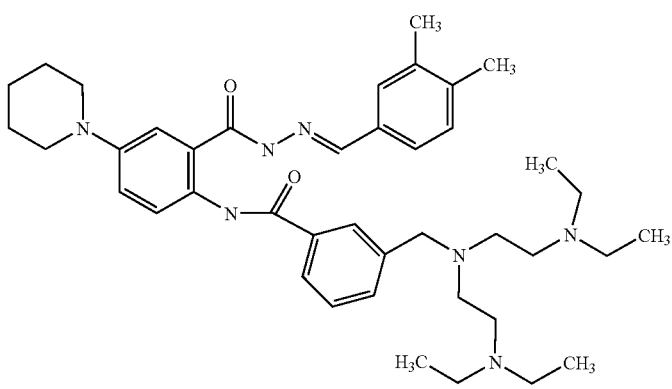 |
| Compound 906 | 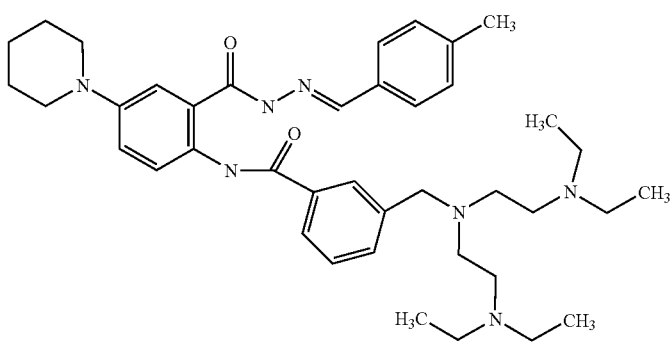 |
| Compound 907 | 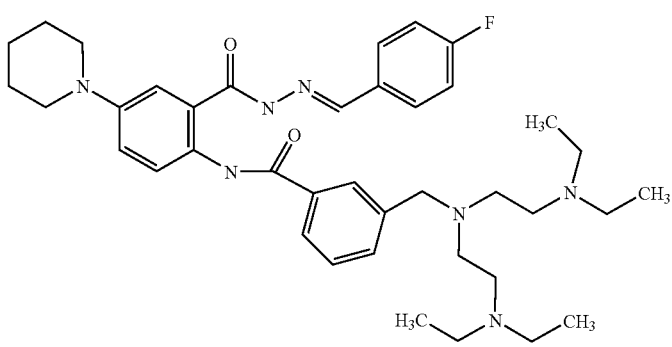 |

TABLE 3-continued
Structures of compounds 1 to 1077 are shown in Table 3.
| Compound No. | Chemical structural formula |
|---|---|
| Compound 908 | 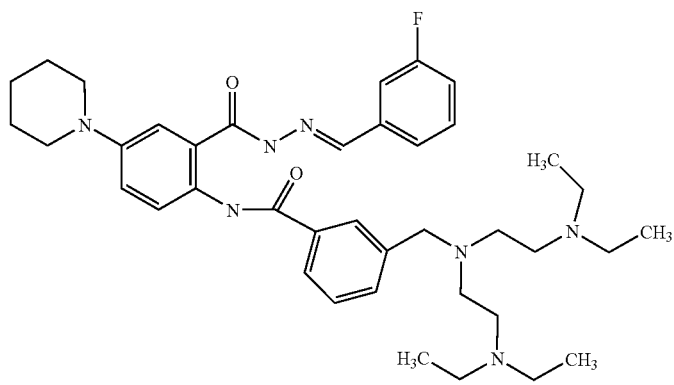 |
| Compound 909 | 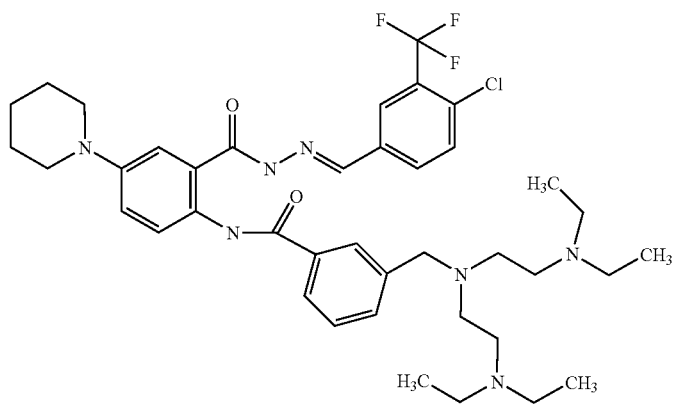 |
| Compound 910 | 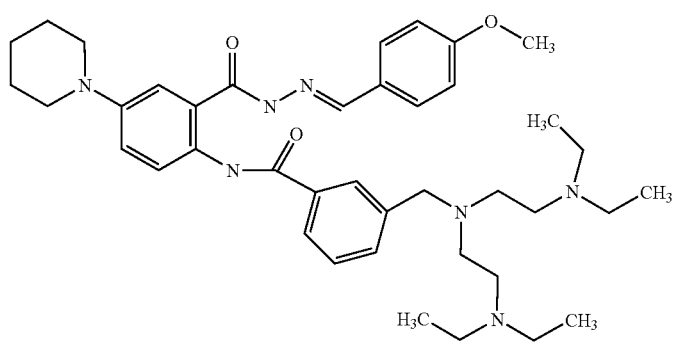 |
| Compound 911 | 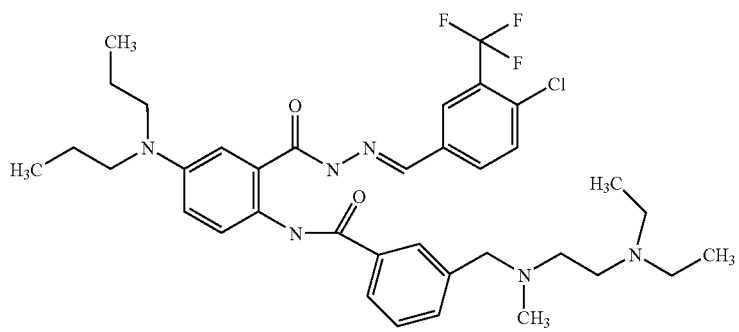 |

US 8,134,015 B2
785
786
TABLE 3-continued
Structures of compounds 1 to 1077 are shown in Table 3.
| Compound No. | Chemical structural formula |
| --- | --- |
| Compound 912 | 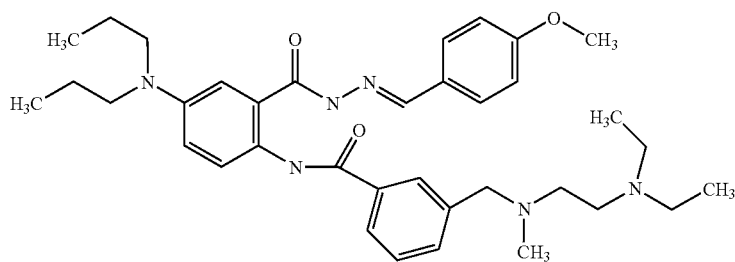 |
| Compound 913 | 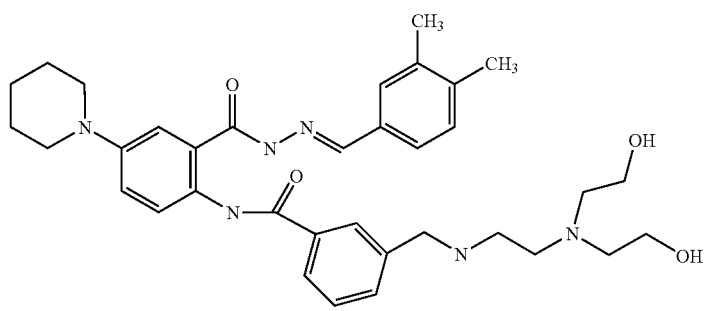 |
| Compound 914 | 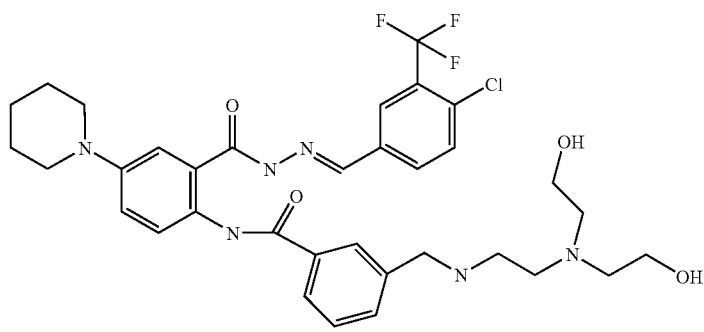 |
| Compound 915 | 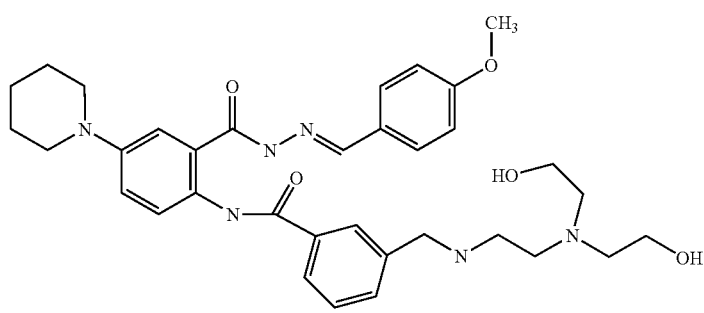 |
| Compound 916 | 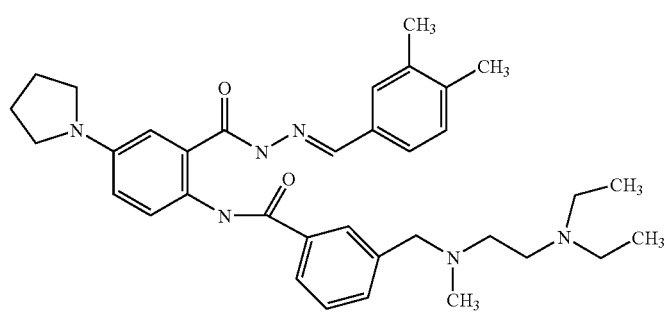 |

TABLE 3-continued
Structures of compounds 1 to 1077 are shown in Table 3.
| Compound No. | Chemical structural formula |
|---|---|
| Compound 917 | 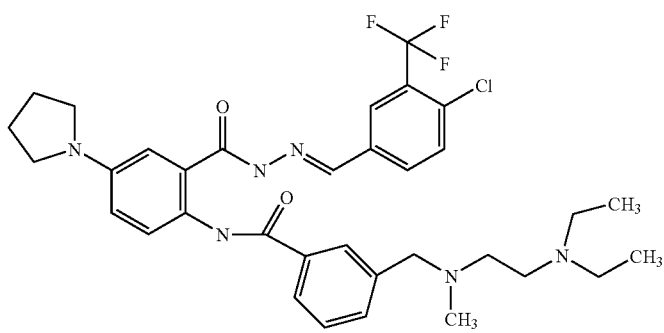 |
| Compound 918 | 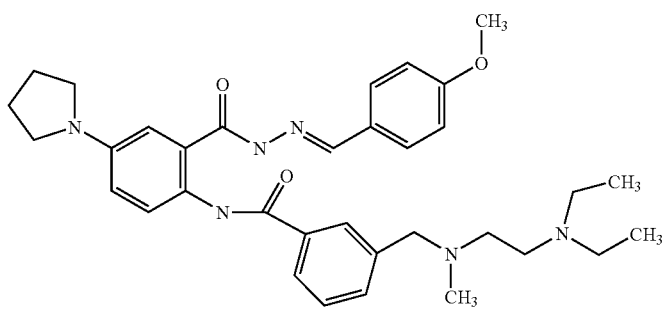 |
| Compound 919 | 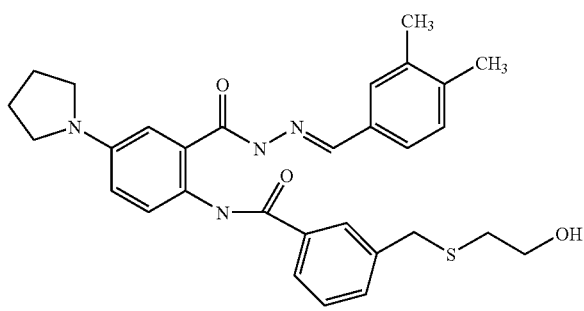 |
| Compound 920 | 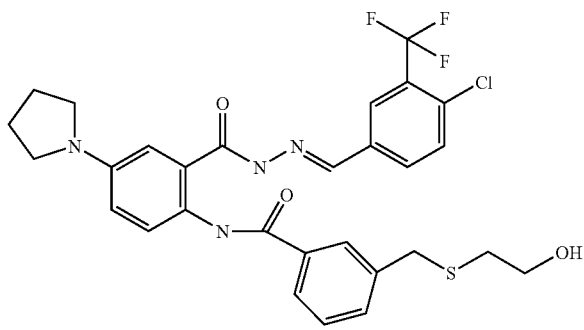 |
| Compound 921 | 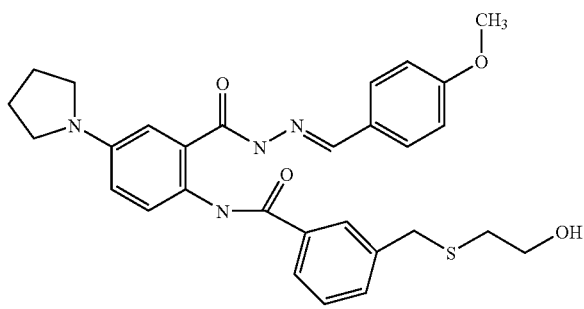 |

TABLE 3-continued
Structures of compounds 1 to 1077 are shown in Table 3.
| Compound No. | Chemical structural formula |
|---|---|
| Compound 922 | 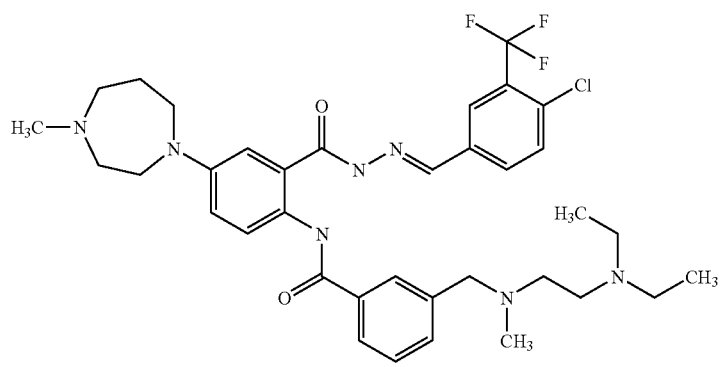 |
| Compound 923 | 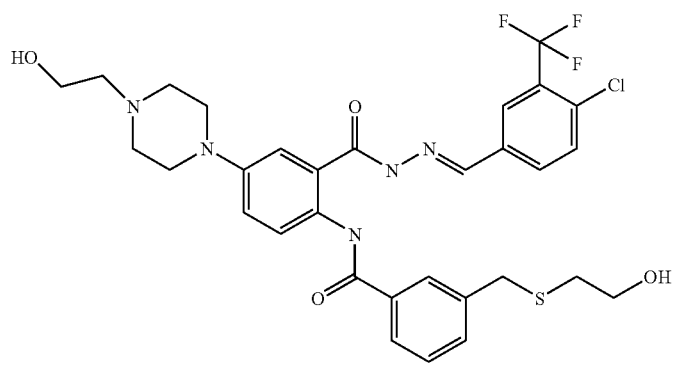 |
| Compound 924 | 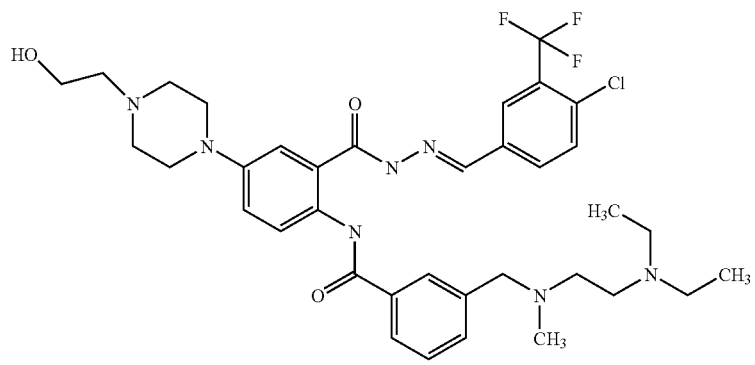 |
| Compound 925 | 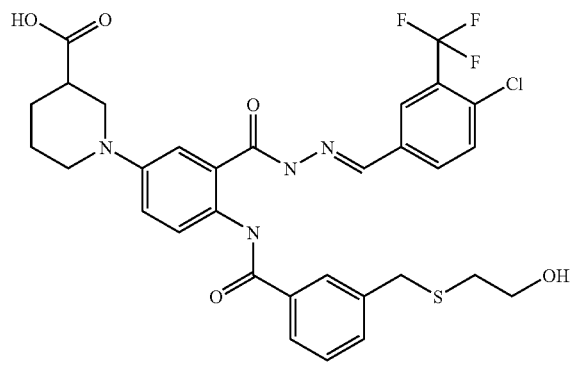 |

| Compound No. | Chemical structural formula |
|---|---|
| Compound 926 | 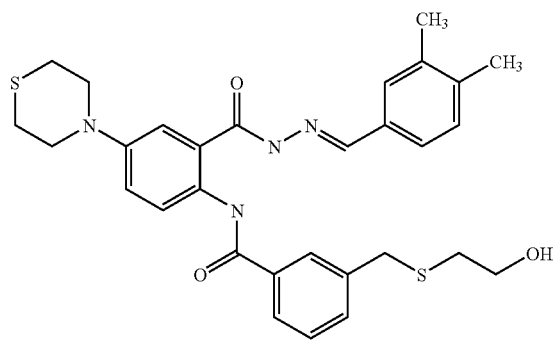 |
| Compound 927 | 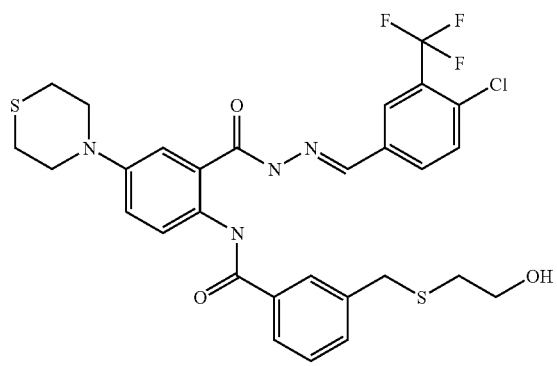 |
| Compound 928 | 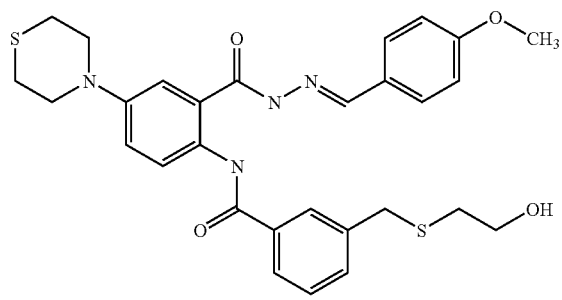 |
| Compound 929 | 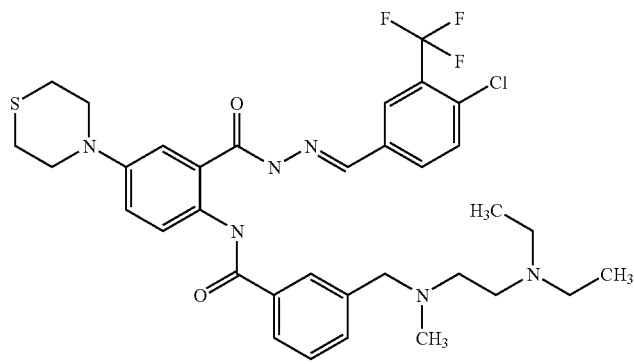 |

TABLE 3-continued
Structures of compounds 1 to 1077 are shown in Table 3.
Compound No. Chemical structural formula
Compound 930
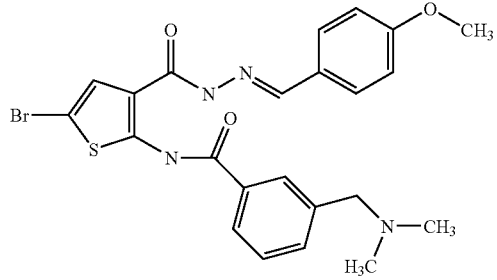
Compound 931
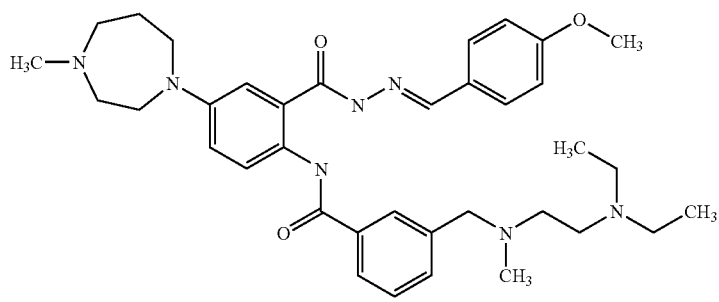
Compound 932
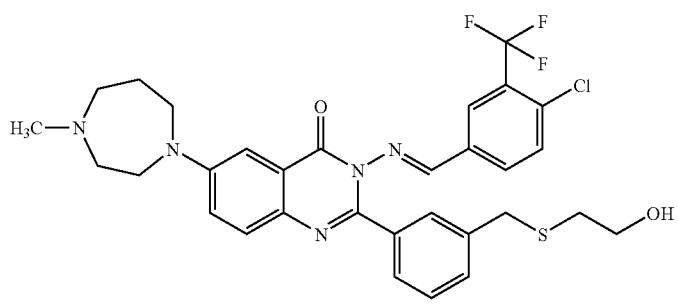
Compound 933
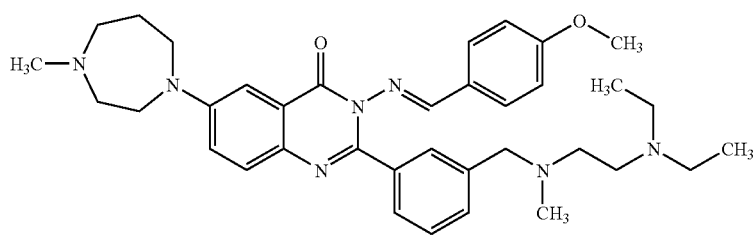
Compound 934
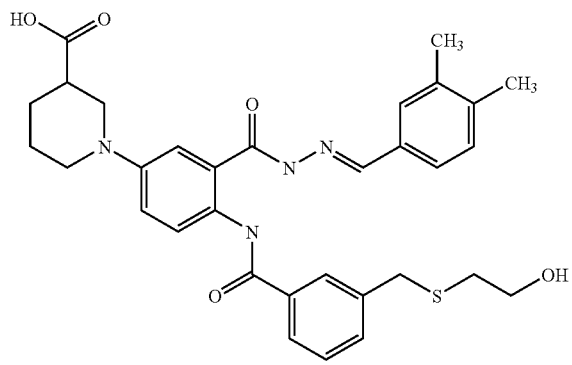

TABLE 3-continued
Structures of compounds 1 to 1077 are shown in Table 3.
| Compound No. | Chemical structural formula |
|---|---|
| Compound 935 | 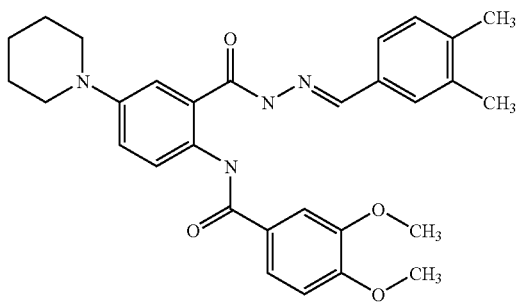 |
| Compound 936 | 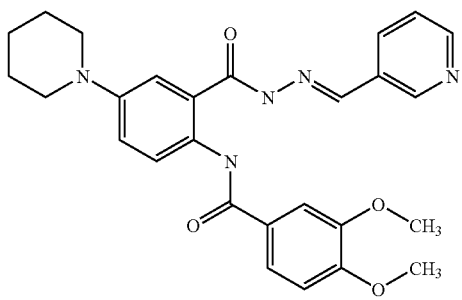 |
| Compound 937 | 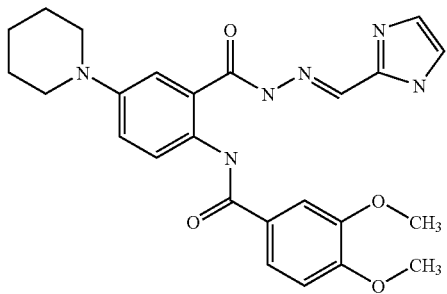 |
| Compound 938 | 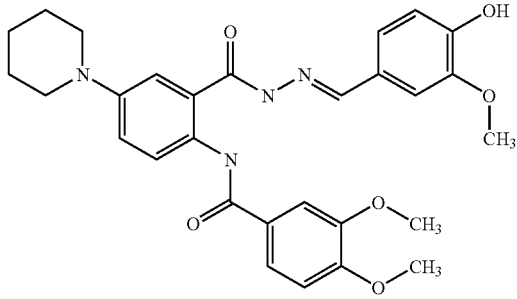 |
| Compound 939 | 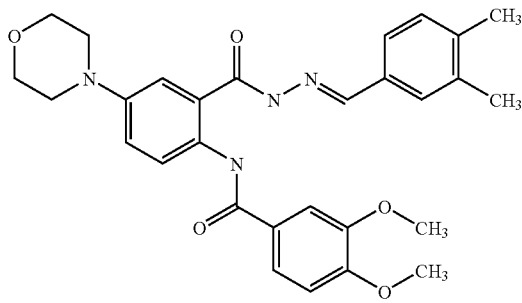 |

TABLE 3-continued
Structures of compounds 1 to 1077 are shown in Table 3.
| Compound No. | Chemical structural formula |
| --- | --- |
| Compound 940 | 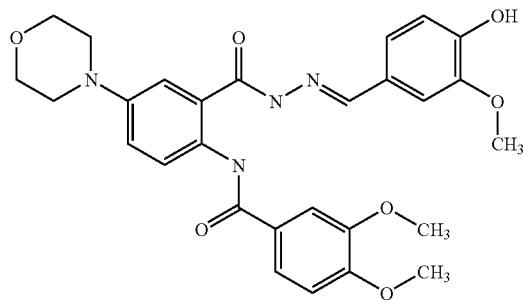 |
| Compound 941 | 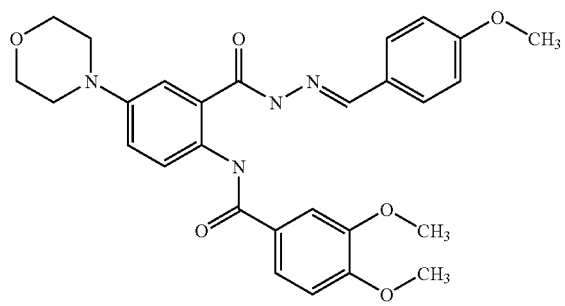 |
| Compound 942 | 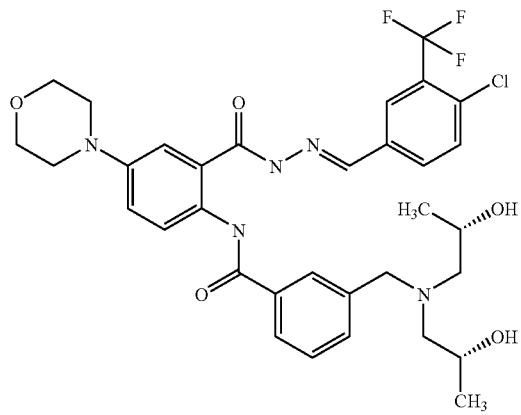 |
| Compound 943 | 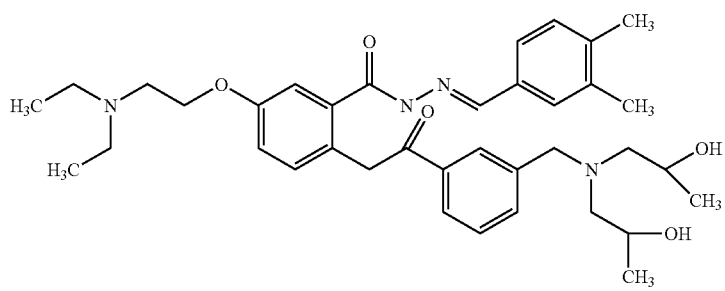 |

TABLE 3-continued
Structures of compounds 1 to 1077 are shown in Table 3.
Compound No.   Chemical structural formula
Compound 944
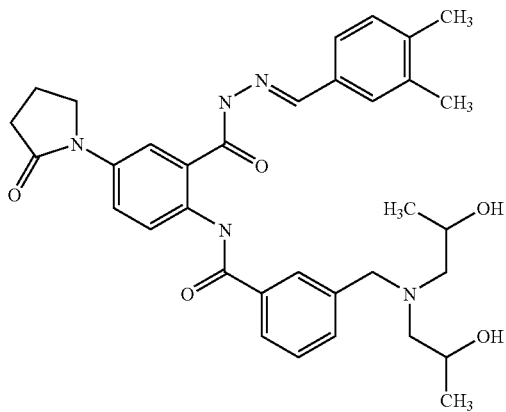
Compound 945
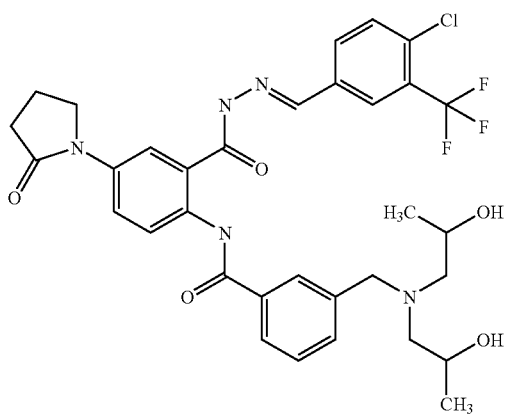
Compound 946
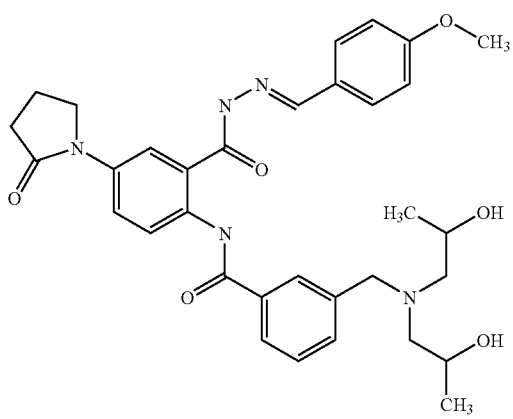

TABLE 3-continued
Structures of compounds 1 to 1077 are shown in Table 3.
Compound No.   Chemical structural formula
Compound 947
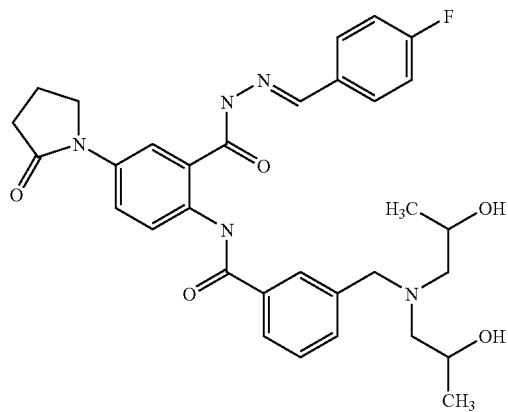
Compound 948
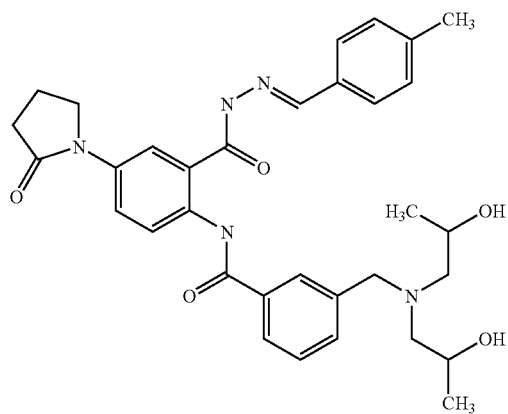
Compound 949
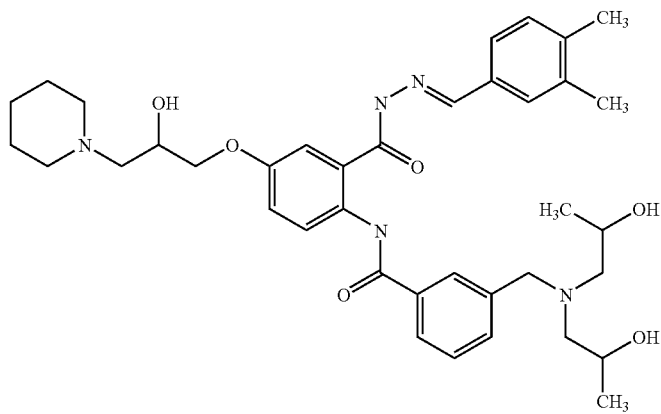

US 8,134,015 B2
803                                                                                                    804
TABLE 3-continued
Structures of compounds 1 to 1077 are shown in Table 3.
| Compound No. | Chemical structural formula |
|---|---|
Compound 950
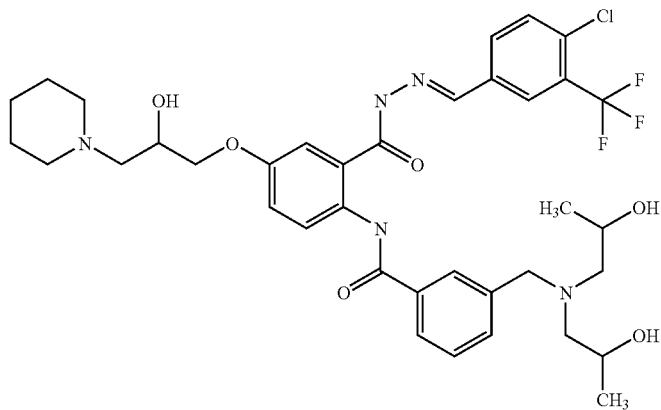
Compound 951
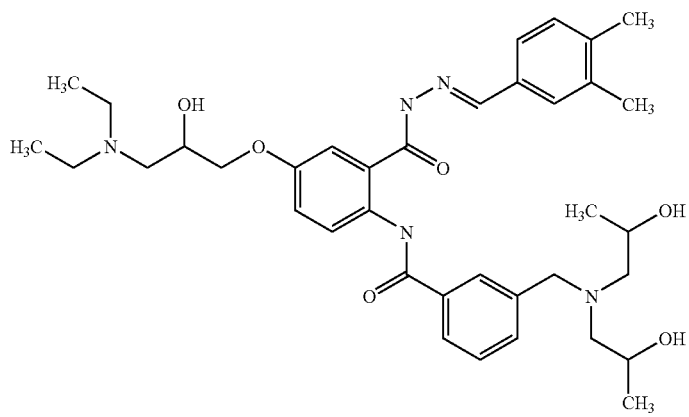
Compound 952
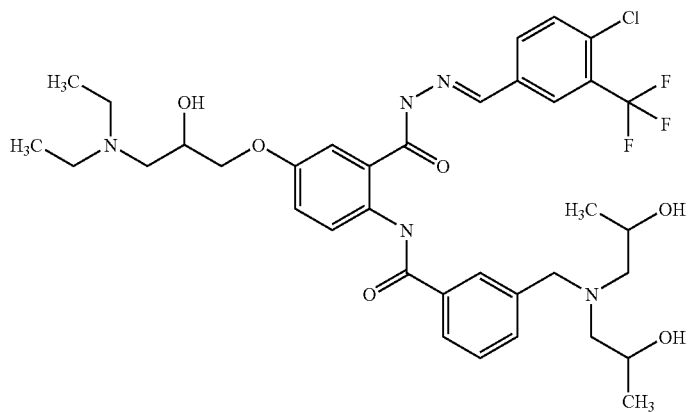

TABLE 3-continued
Structures of compounds 1 to 1077 are shown in Table 3.
| Compound No. | Chemical structural formula |
|---|---|
| Compound 953 | 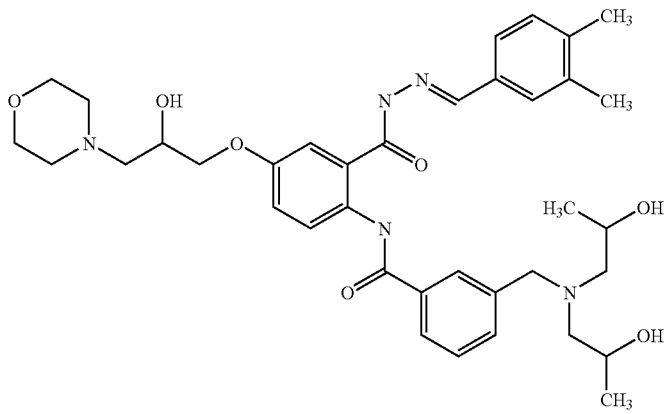 |
| Compound 954 | 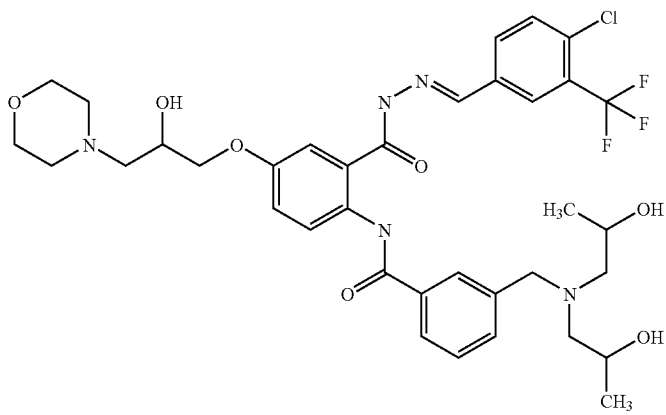 |
| Compound 955 | 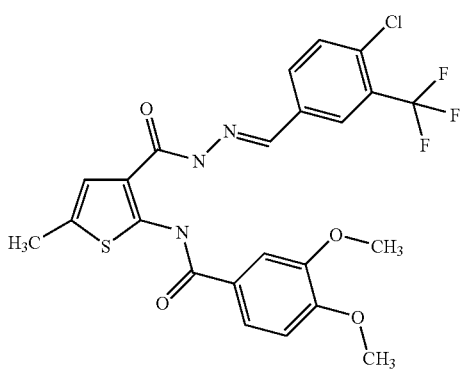 |
| Compound 956 | 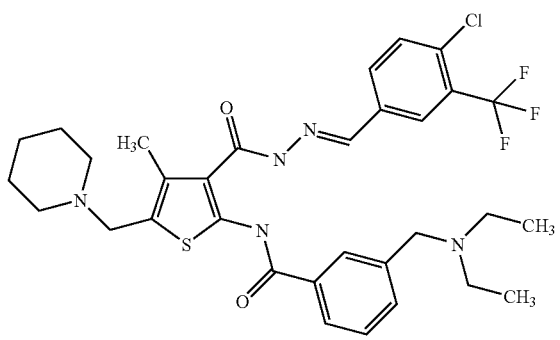 |

TABLE 3-continued
Structures of compounds 1 to 1077 are shown in Table 3.
| Compound No. | Chemical structural formula |
|---|---|
| Compound 957 | 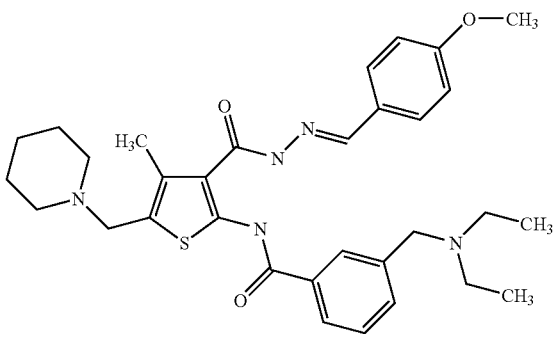 |
| Compound 958 | 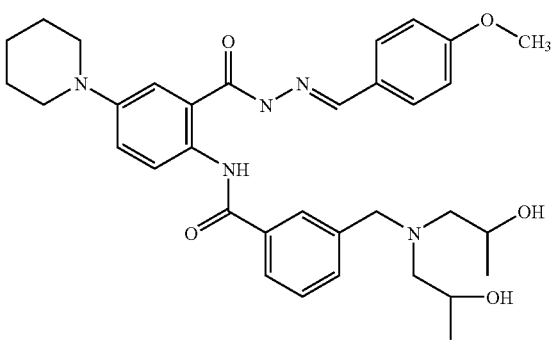 |
| Compound 959 | 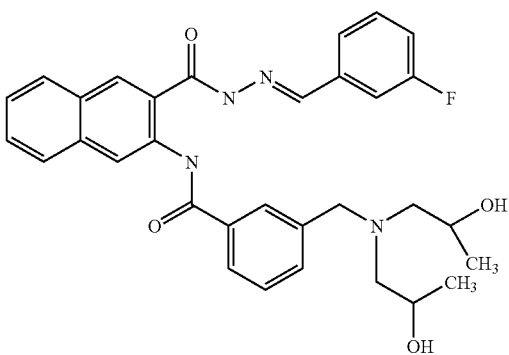 |
| Compound 960 | 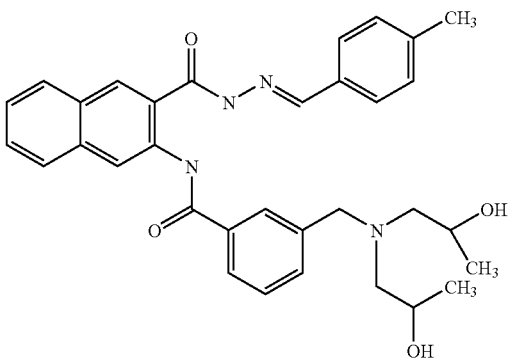 |

US 8,134,015 B2
TABLE 3-continued
Structures of compounds 1 to 1077 are shown in Table 3.
| Compound No. | Chemical structural formula |
|---|---|
| Compound 961 | 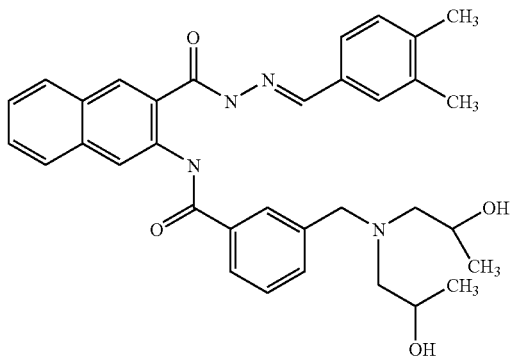 |
| Compound 962 | 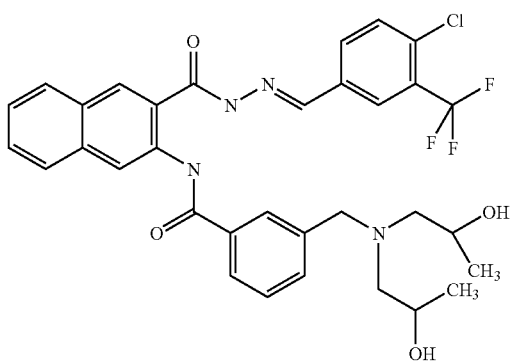 |
| Compound 963 | 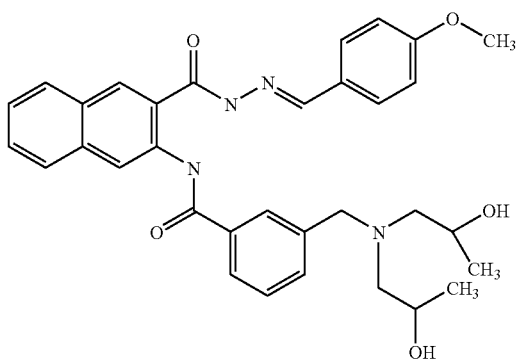 |
| Compound 964 | 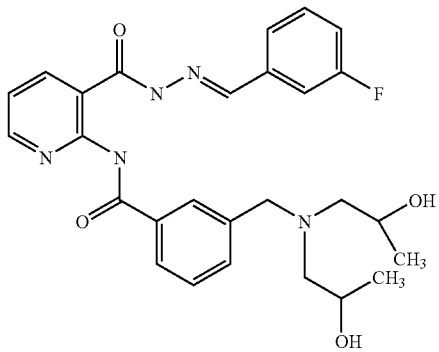 |

TABLE 3-continued
Structures of compounds 1 to 1077 are shown in Table 3.
| Compound No. | Chemical structural formula |
|---|---|
| Compound 965 | 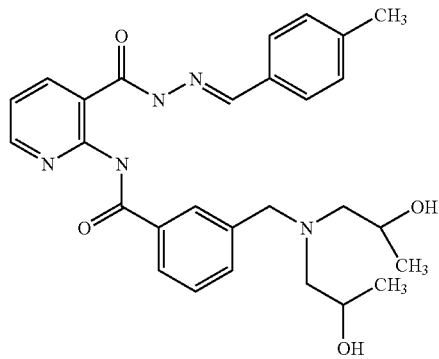 |
| Compound 966 | 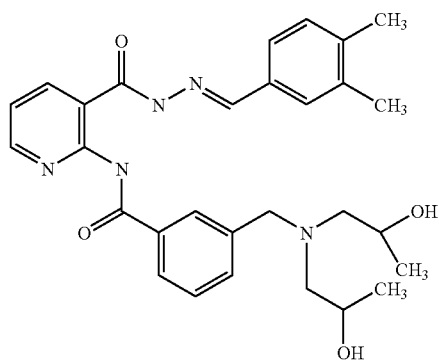 |
| Compound 967 | 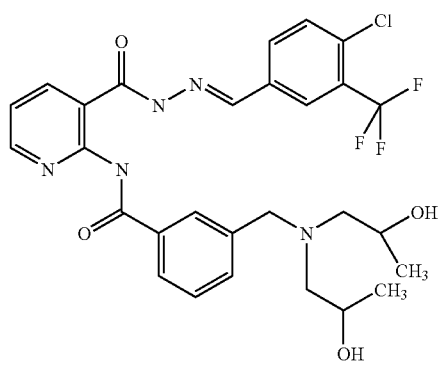 |
| Compound 968 | 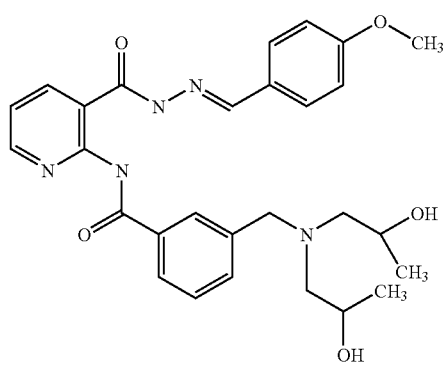 |

ND TABLE 3-continued
Structures of compounds 1 to 1077 are shown in Table 3.
| Compound No. | Chemical structural formula |
|---|---|
| Compound 969 | 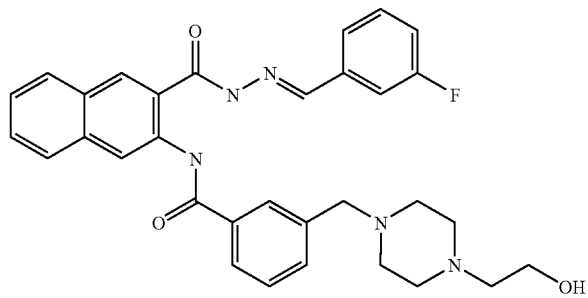 |
| Compound 970 | 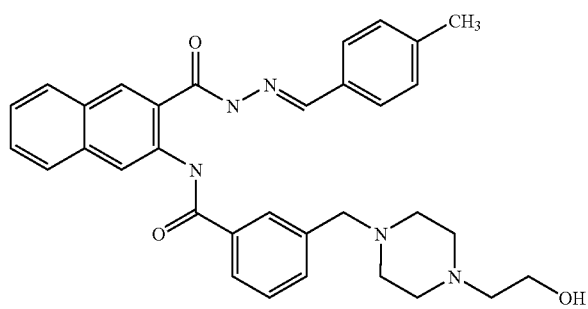 |
| Compound 971 | 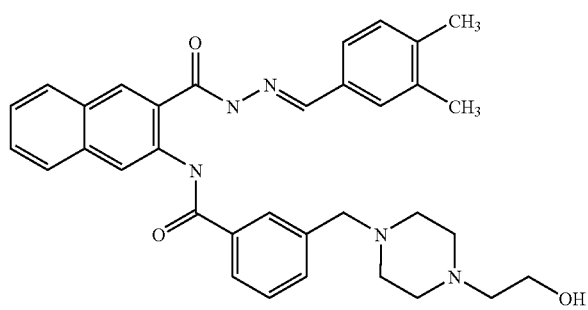 |
| Compound 972 | 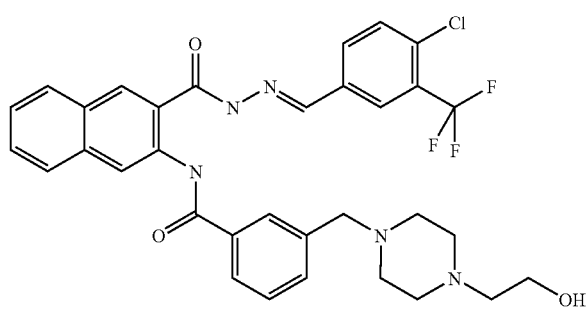 |
| Compound 973 | 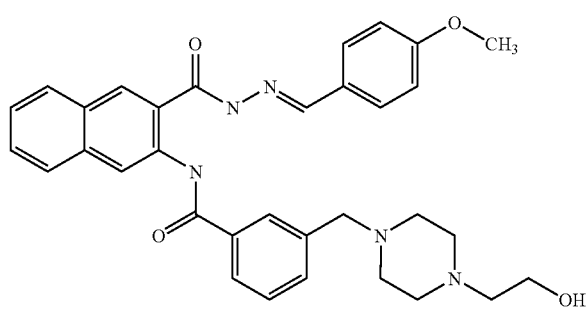 |

TABLE 3-continued
Structures of compounds 1 to 1077 are shown in Table 3.
| Compound No. | Chemical structural formula |
|---|---|
| Compound 974 | 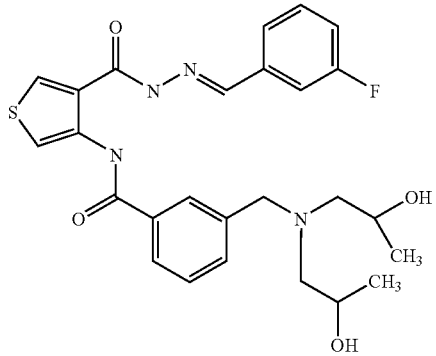 |
| Compound 975 | 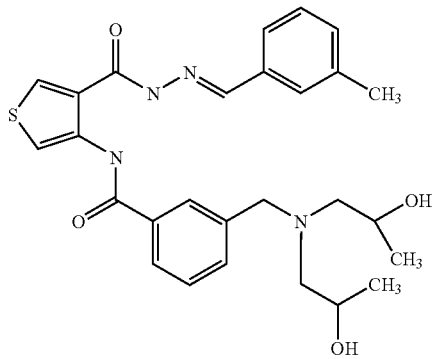 |
| Compound 976 | 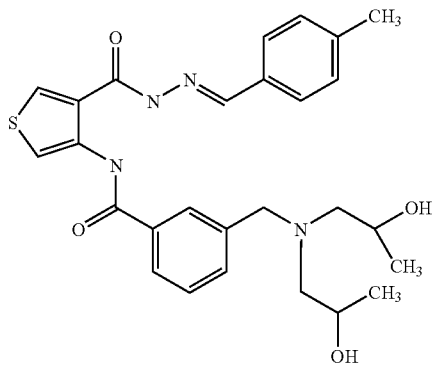 |
| Compound 977 | 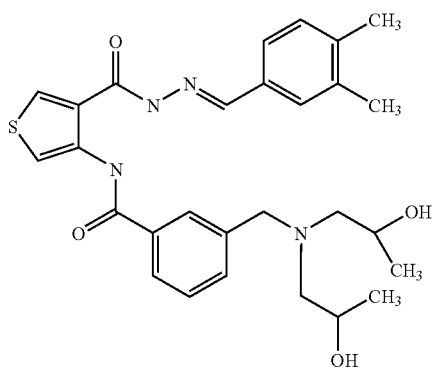 |

TABLE 3-continued
Structures of compounds 1 to 1077 are shown in Table 3.
| Compound No. | Chemical structural formula |
|---|---|
| Compound 978 | 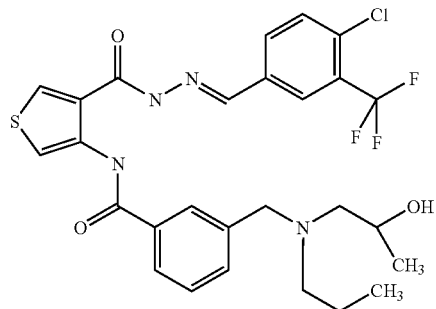 |
| Compound 979 | 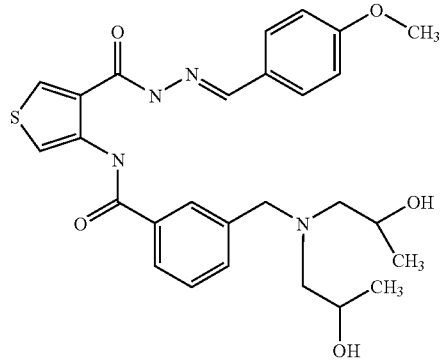 |
| Compound 980 | 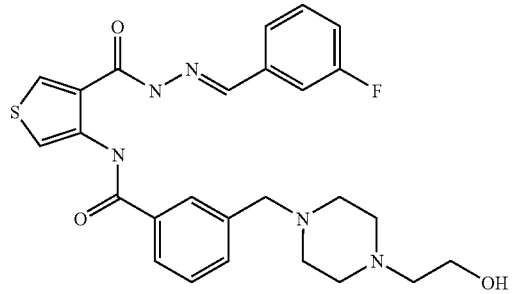 |
| Compound 981 | 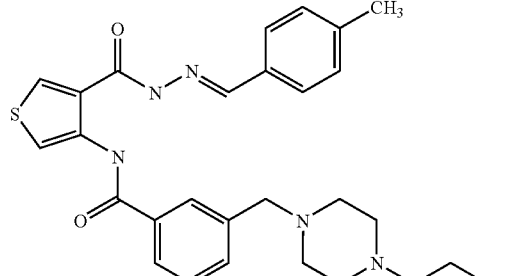 |
| Compound 982 | 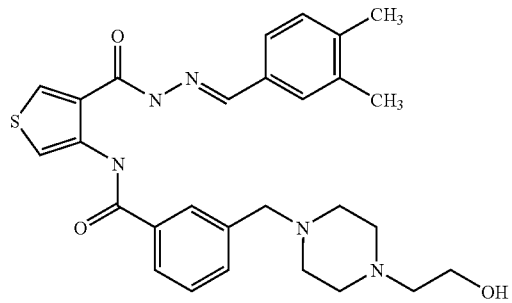 |

TABLE 3-continued
Structures of compounds 1 to 1077 are shown in Table 3.
| Compound No. | Chemical structural formula |
|---|---|
| Compound 983 | 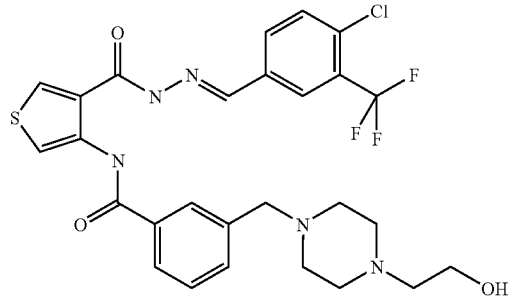 |
| Compound 984 | 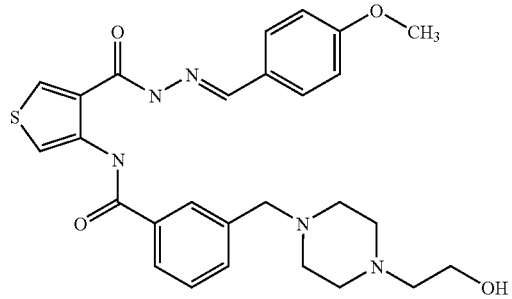 |
| Compound 985 | 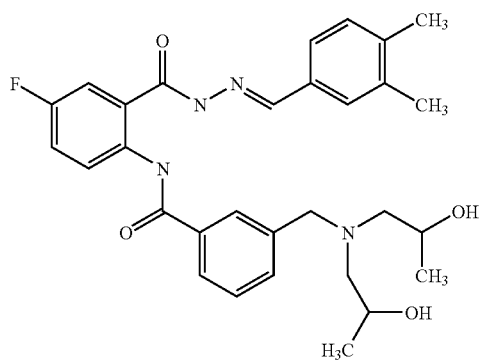 |
| Compound 986 | 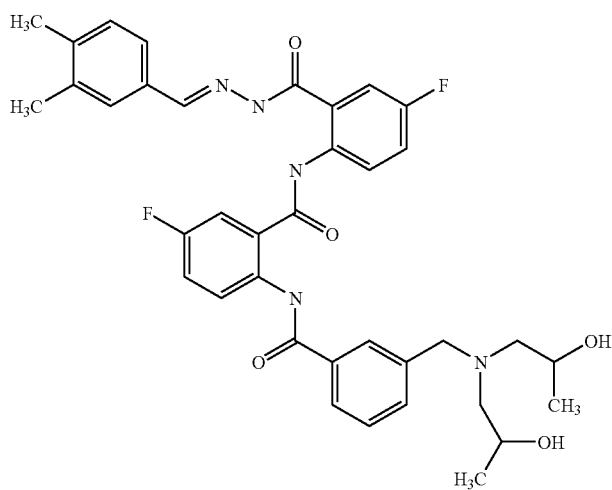 |

TABLE 3-continued
Structures of compounds 1 to 1077 are shown in Table 3.
| Compound No. | Chemical structural formula |
| --- | --- |
| Compound 987 | 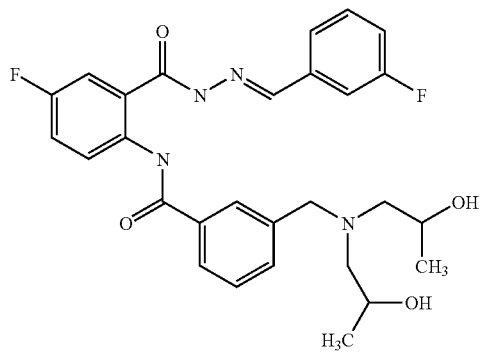 |
| Compound 988 | 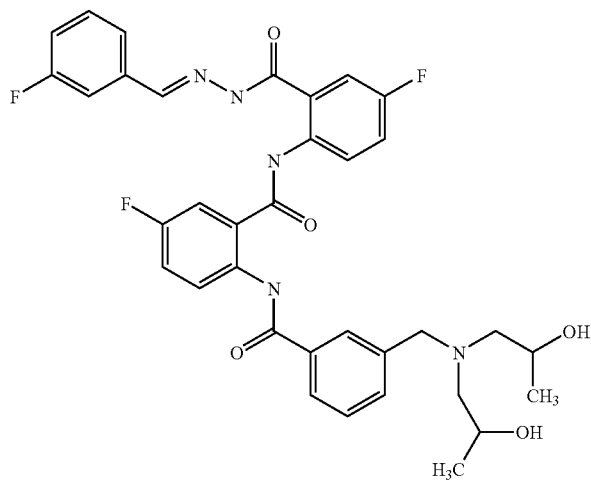 |
| Compound 989 | 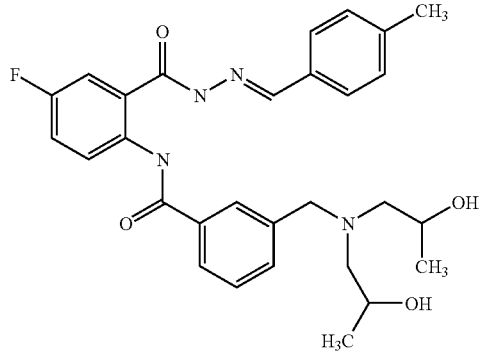 |
| Compound 990 | 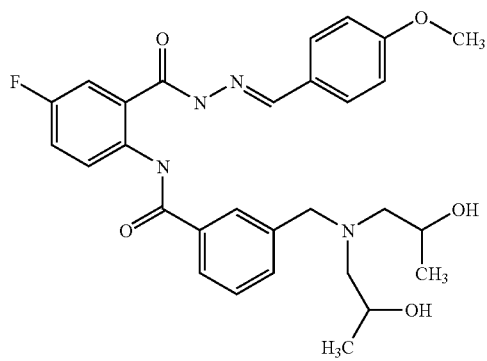 |

TABLE 3-continued
Structures of compounds 1 to 1077 are shown in Table 3.
| Compound No. | Chemical structural formula |
|---|---|
| Compound 991 | 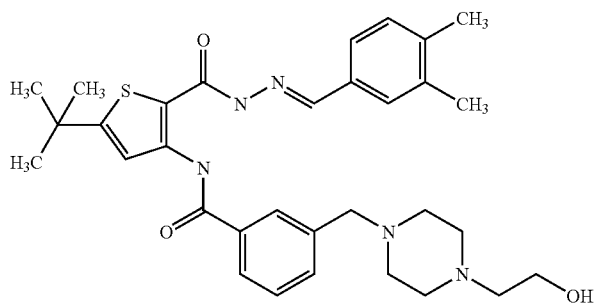 |
| Compound 992 | 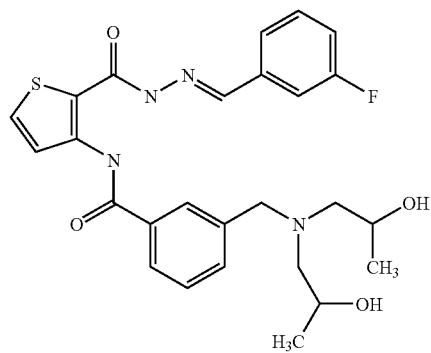 |
| Compound 993 | 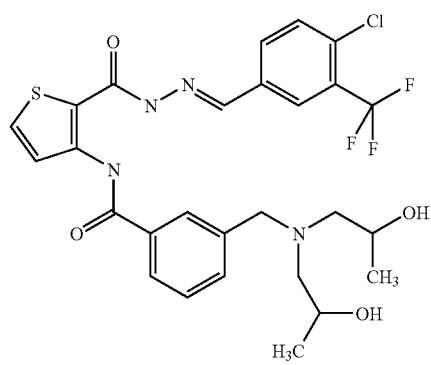 |
| Compound 995 | 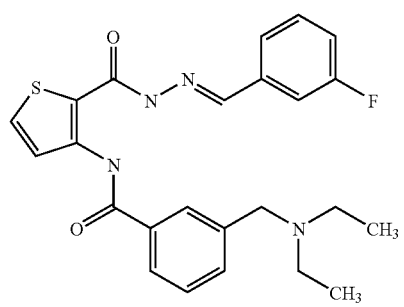 |

TABLE 3-continued
Structures of compounds 1 to 1077 are shown in Table 3.
| Compound No. | Chemical structural formula |
| --- | --- |
| Compound 996 | 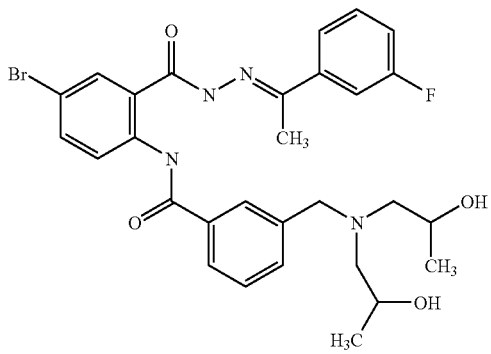 |
| Compound 997 | 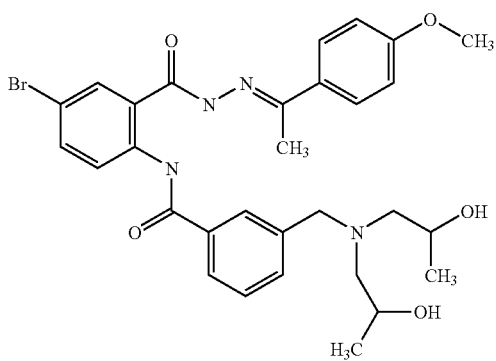 |
| Compound 998 | 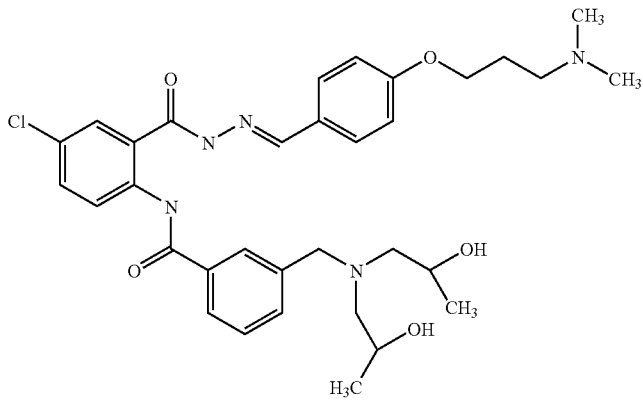 |
| Compound 999 | 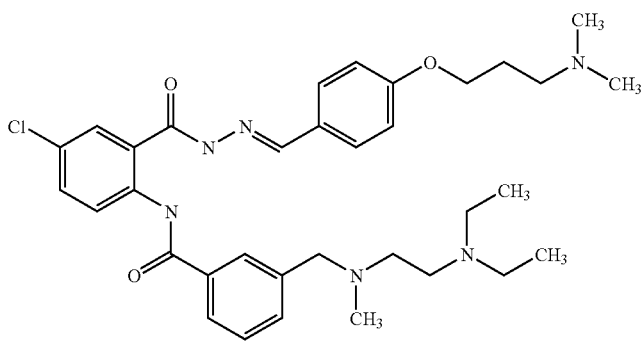 |

TABLE 3-continued
Structures of compounds 1 to 1077 are shown in Table 3.
| Compound No. | Chemical structural formula |
|---|---|
| Compound 1000 | 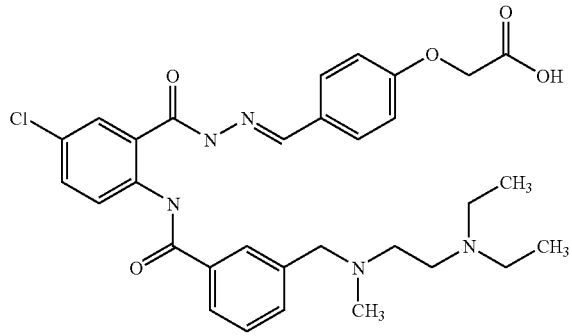 |
| Compound 1001 | 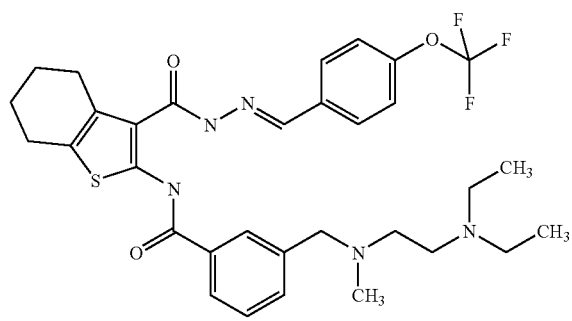 |
| Compound 1002 | 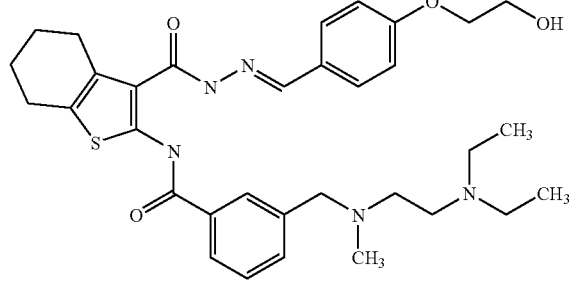 |
| Compound 1003 | 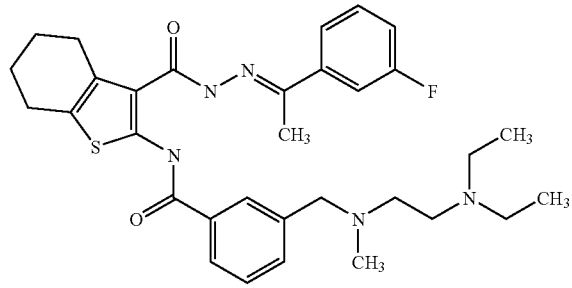 |
| Compound 1004 | 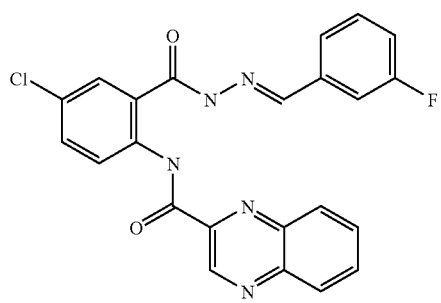 |

TABLE 3-continued
Structures of compounds 1 to 1077 are shown in Table 3.
| Compound No. | Chemical structural formula |
|---|---|
| Compound 1005 | 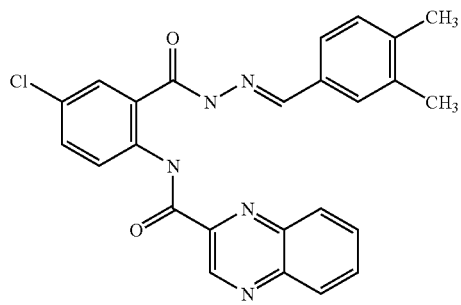 |
| Compound 1006 | 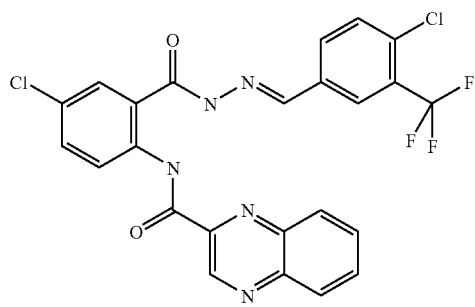 |
| Compound 1007 | 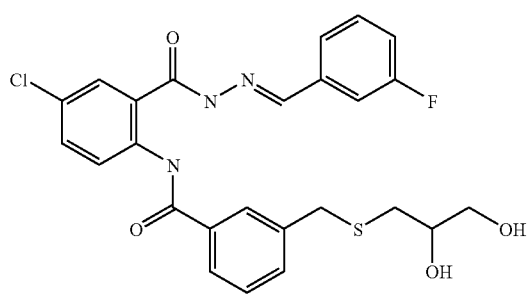 |
| Compound 1008 | 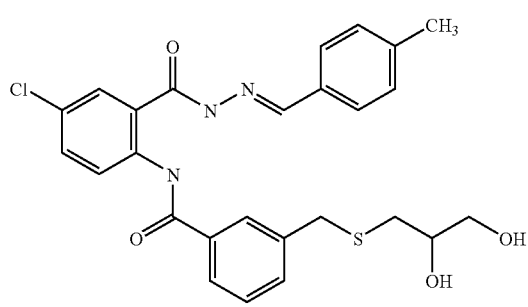 |
| Compound 1009 | 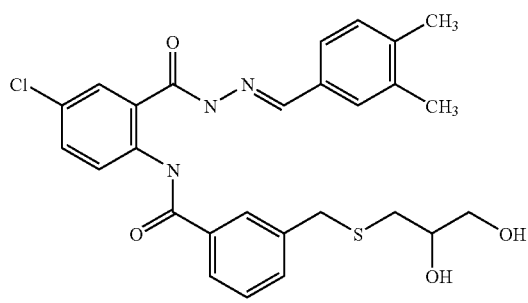 |

TABLE 3-continued
Structures of compounds 1 to 1077 are shown in Table 3.
| Compound No. | Chemical structural formula |
|---|---|
| Compound 1010 | 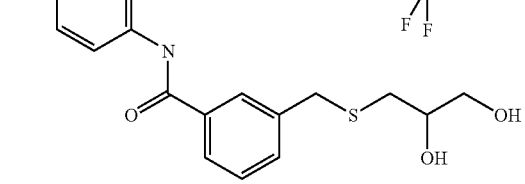 |
| Compound 1011 | 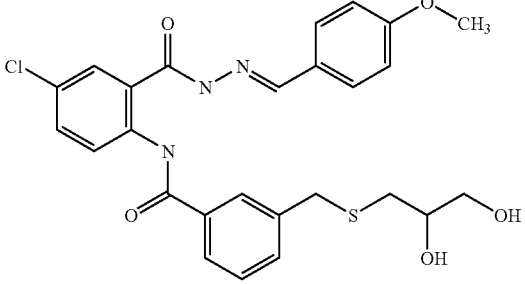 |
| Compound 1012 | 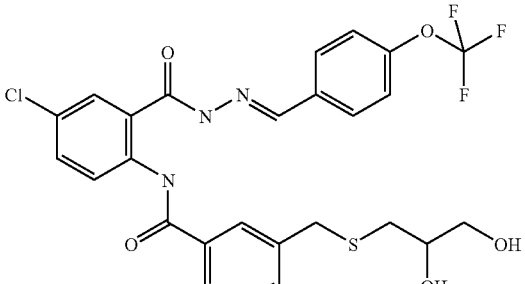 |
| Compound 1013 | 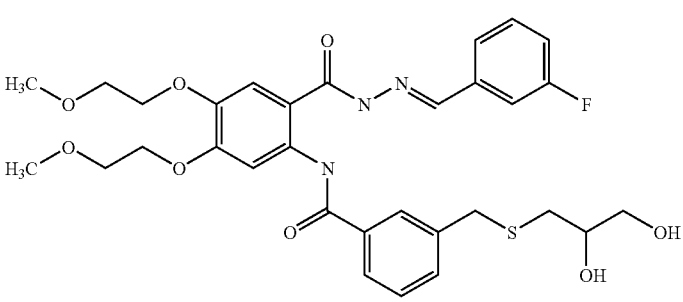 |
| Compound 1014 | 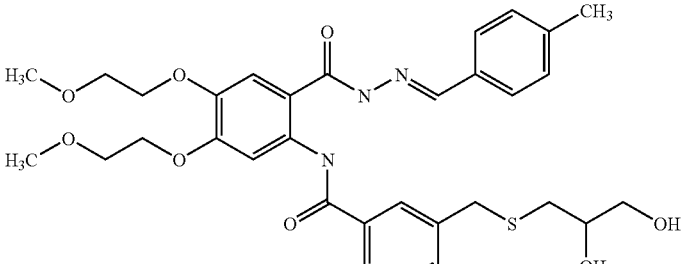 |

TABLE 3-continued
Structures of compounds 1 to 1077 are shown in Table 3.
| Compound No. | Chemical structural formula |
|---|---|
| Compound 1015 | 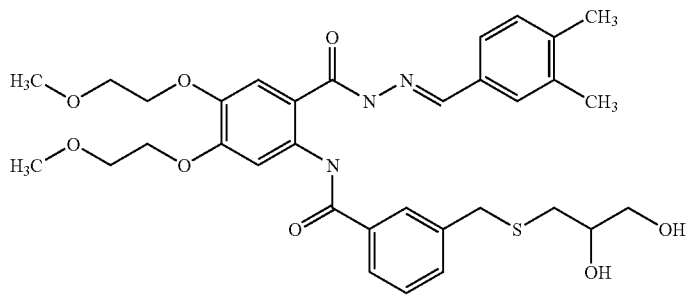 |
| Compound 1016 | 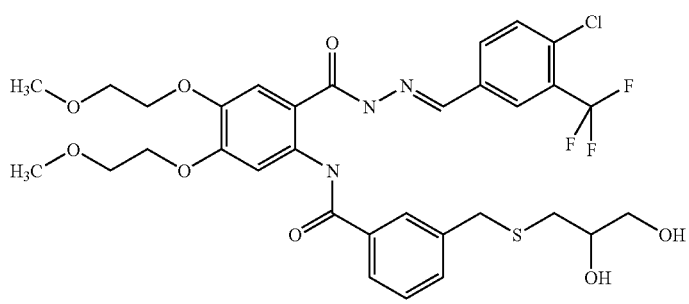 |
| Compound 1017 | 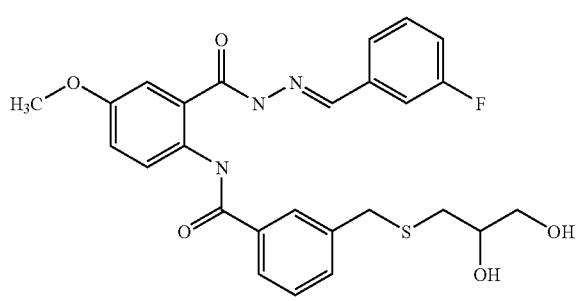 |
| Compound 1018 | 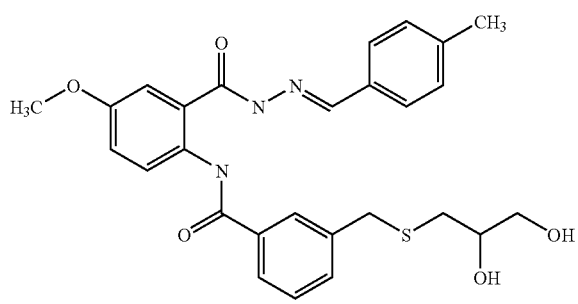 |
| Compound 1019 | 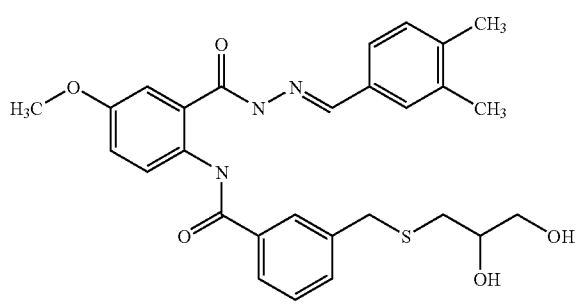 |

TABLE 3-continued
Structures of compounds 1 to 1077 are shown in Table 3.
| Compound No. | Chemical structural formula |
|---|---|
| Compound 1020 | 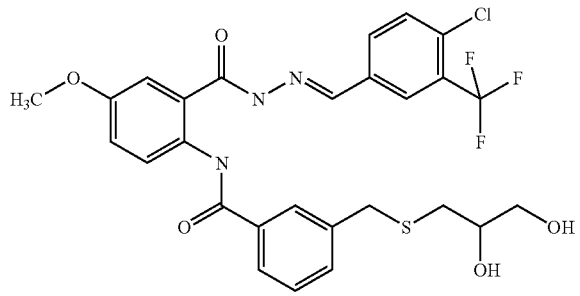 |
| Compound 1021 | 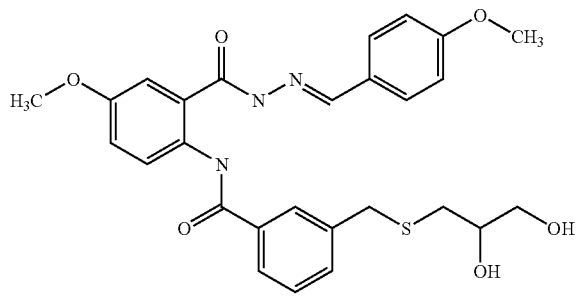 |
| Compound 1022 | 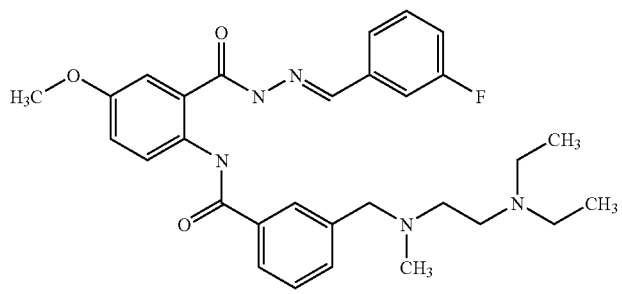 |
| Compound 1023 | 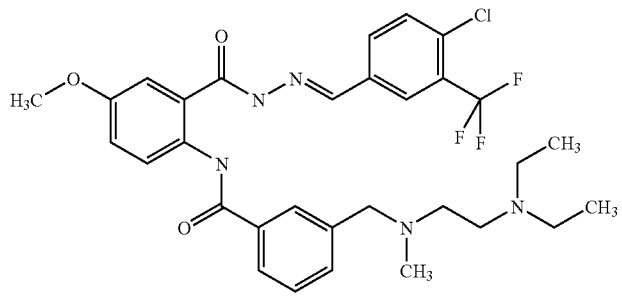 |
| Compound 1024 | 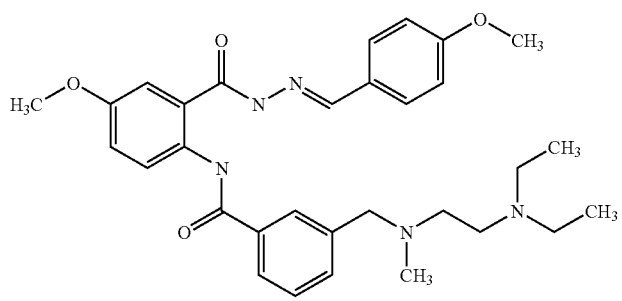 |

TABLE 3-continued
Structures of compounds 1 to 1077 are shown in Table 3.
| Compound No. | Chemical structural formula |
| --- | --- |
| Compound 1025 | 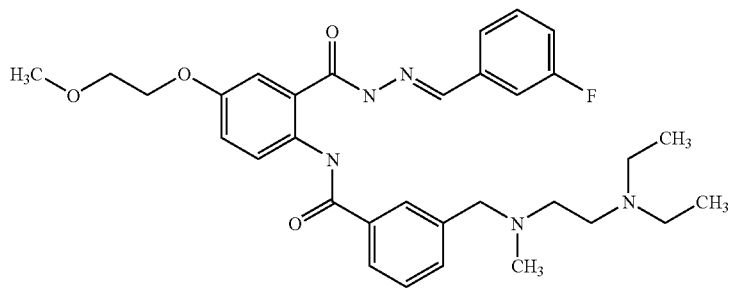 |
| Compound 1026 | 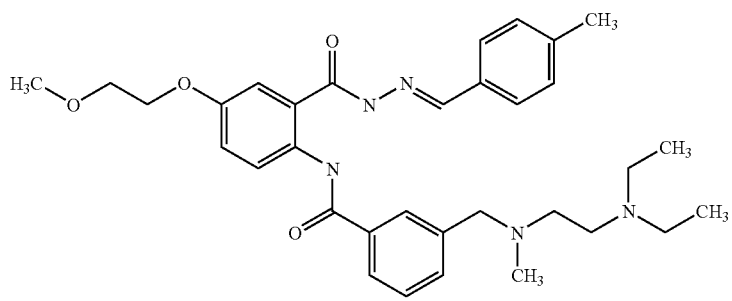 |
| Compound 1027 | 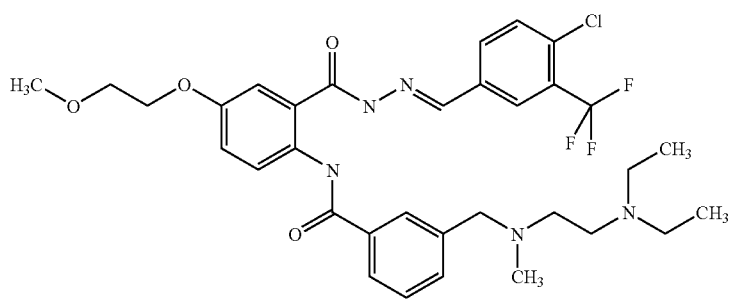 |
| Compound 1028 | 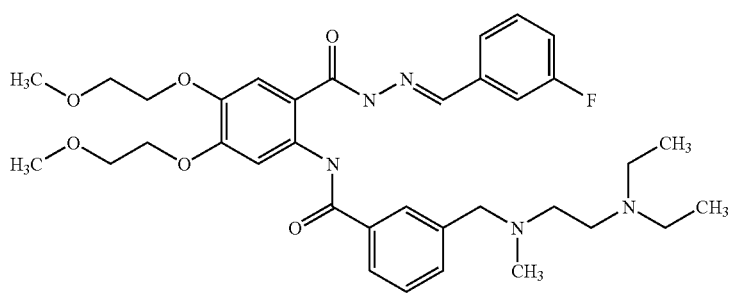 |
| Compound 1029 | 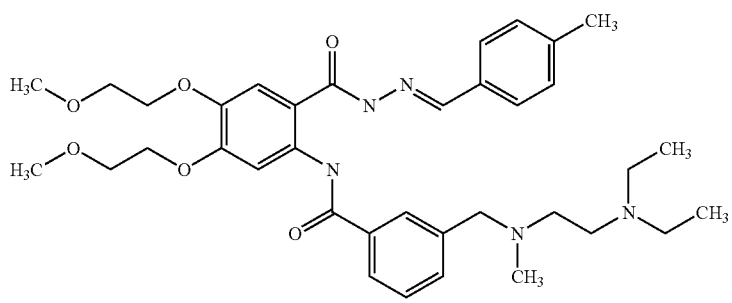 |

//
| Compound No. | Chemical structural formula |
|---|---|
| Compound 1030 | 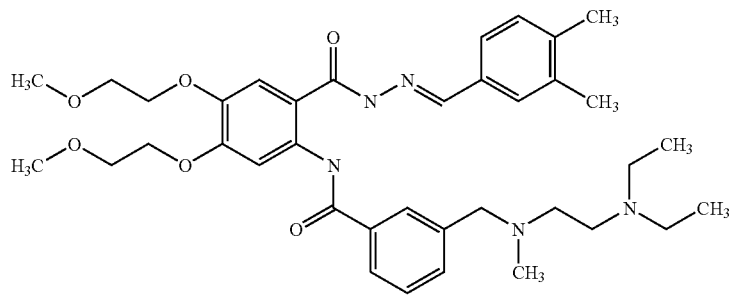 |
| Compound 1031 | 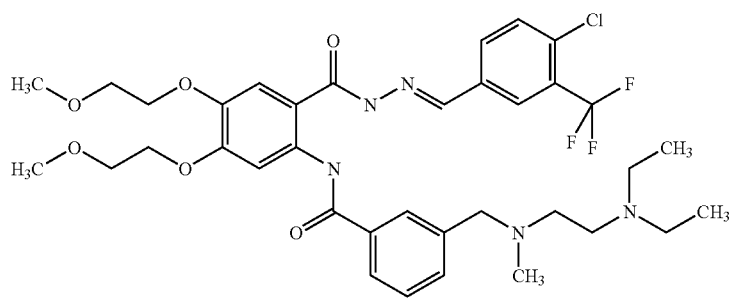 |
| Compound 1032 | 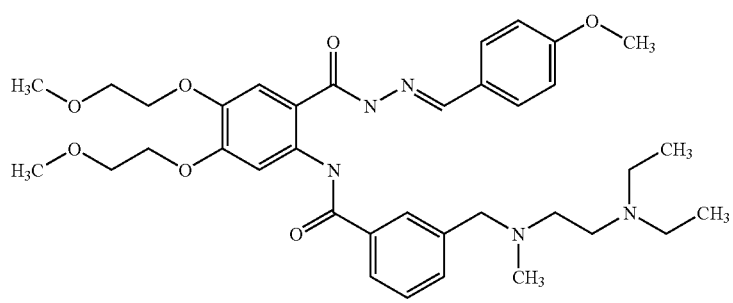 |
| Compound 1033 | 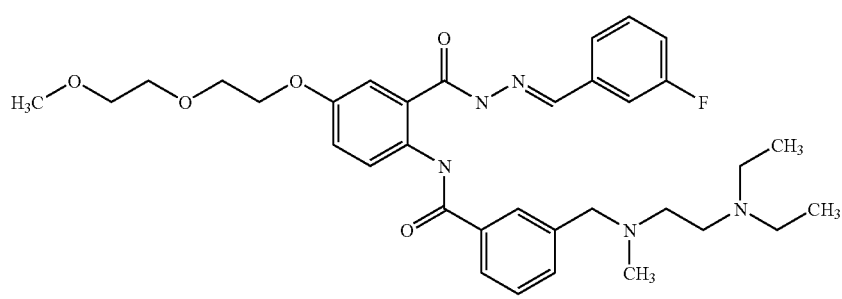 |
| Compound 1034 | 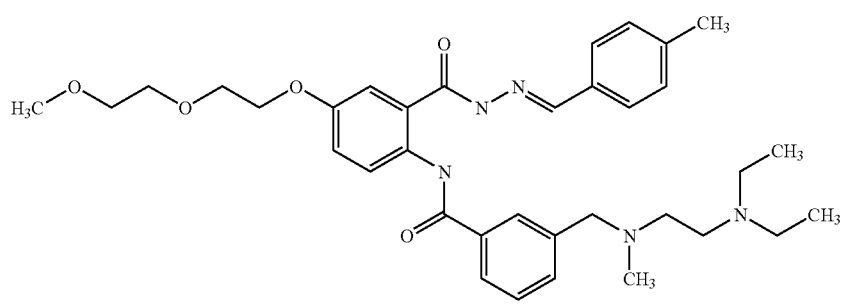 |

TABLE 3-continued
Structures of compounds 1 to 1077 are shown in Table 3.
| Compound No. | Chemical structural formula |
| --- | --- |
| Compound 1035 | 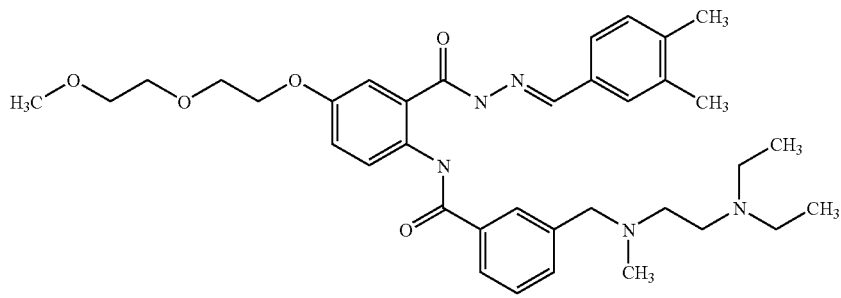 |
| Compound 1036 | 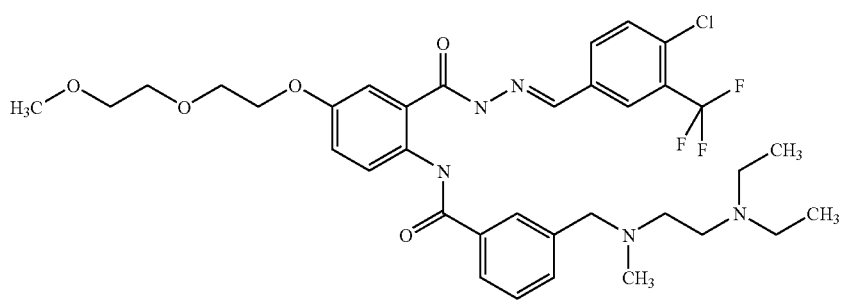 |
| Compound 1037 | 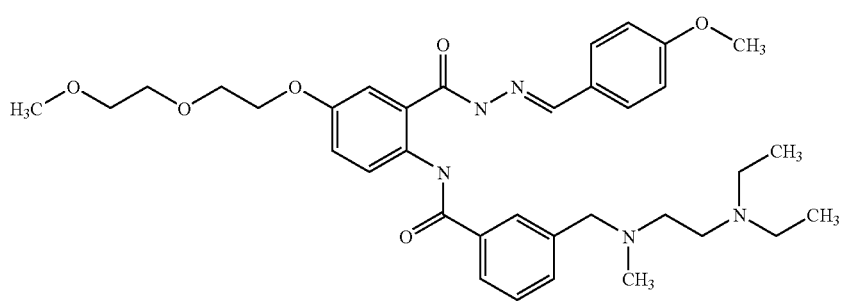 |
| Compound 1038 | 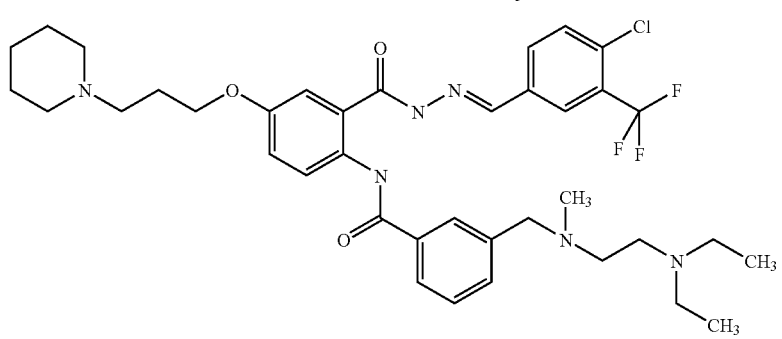 |
| Compound 1039 | 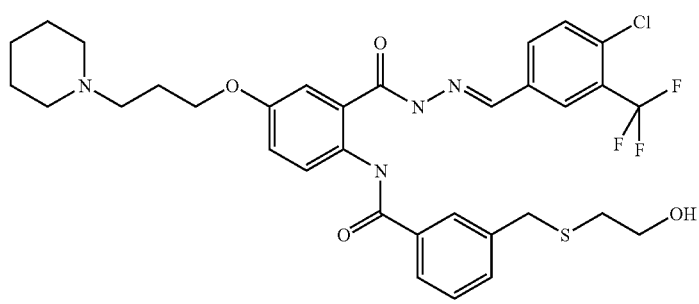 |

TABLE 3-continued
Structures of compounds 1 to 1077 are shown in Table 3.
| Compound No. | Chemical structural formula |
|---|---|
| Compound 1040 | 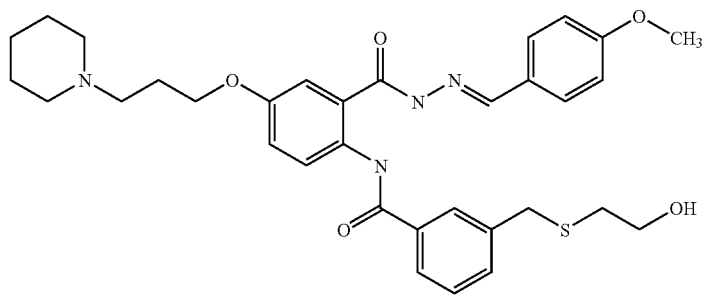 |
| Compound 1041 | 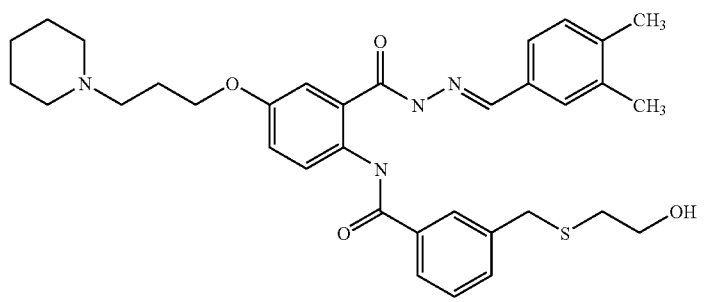 |
| Compound 1042 | 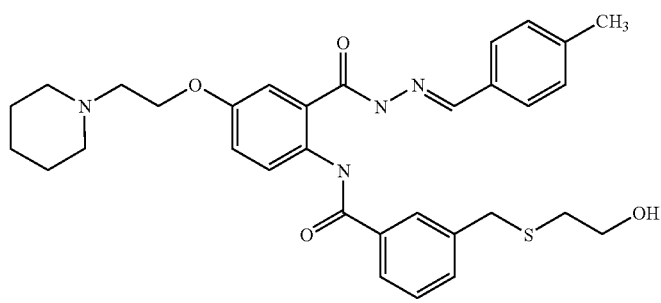 |
| Compound 1043 | 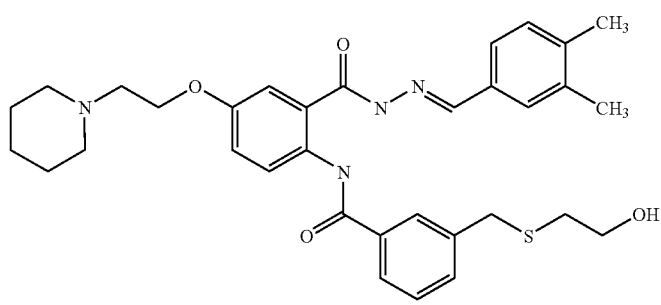 |
| Compound 1044 | 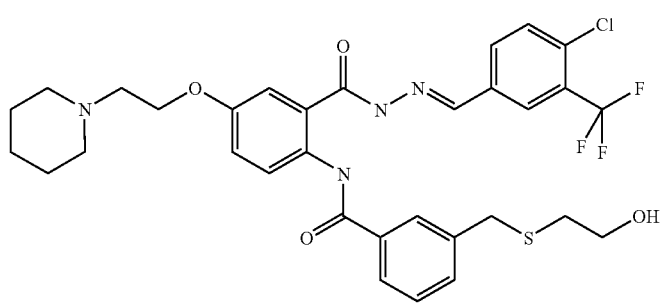 |

TABLE 3-continued

Structures of compounds 1 to 1077 are shown in Table 3.

| Compound No. | Chemical structural formula |
|---|---|
| Compound 1045 | |
| Compound 1046 | |
| Compound 1047 | |
| Compound 1048 | |
| Compound 1049 | |

848
TABLE 3-continued
Structures of compounds 1 to 1077 are shown in Table 3.
| Compound No. | Chemical structural formula |
| --- | --- |
| Compound 1050 | 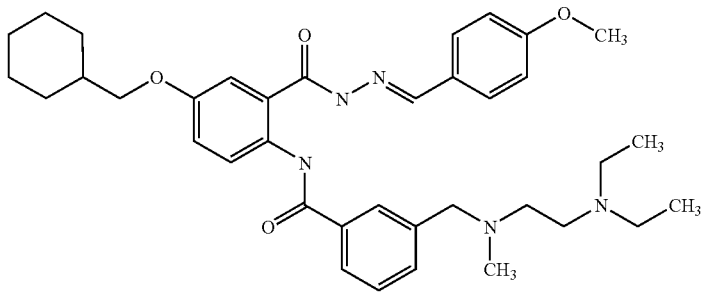 |
| Compound 1051 | 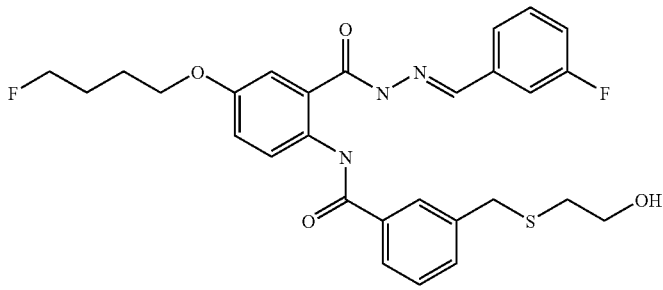 |
| Compound 1052 | 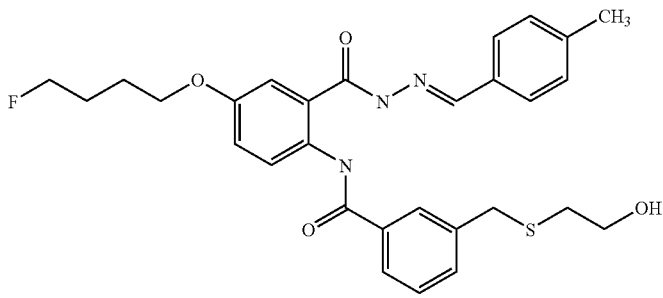 |
| Compound 1053 | 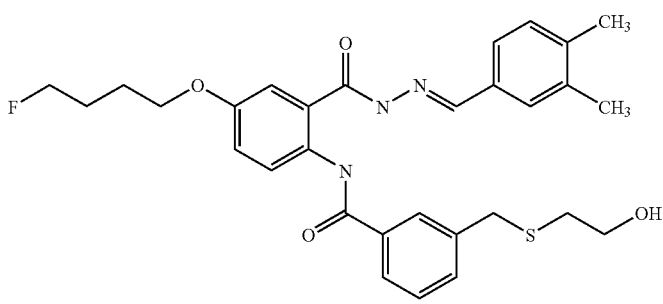 |
| Compound 1054 | 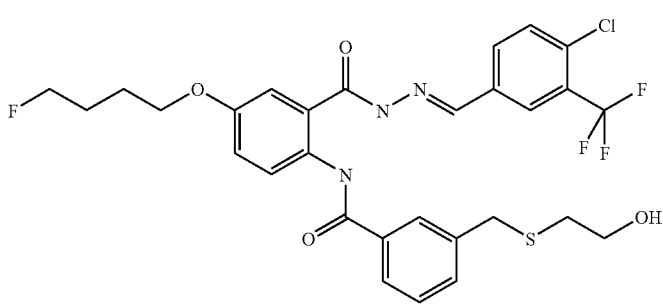 |

TABLE 3-continued
Structures of compounds 1 to 1077 are shown in Table 3.
| Compound No. | Chemical structural formula |
|---|---|
| Compound 1055 | 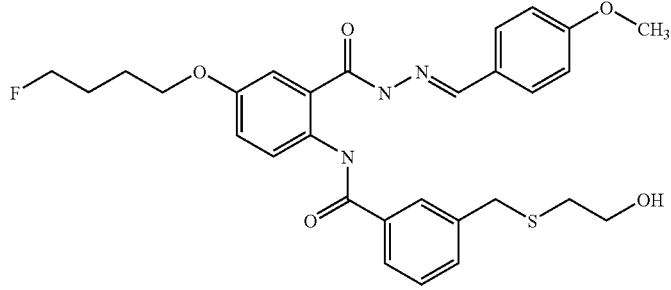 |
| Compound 1056 | 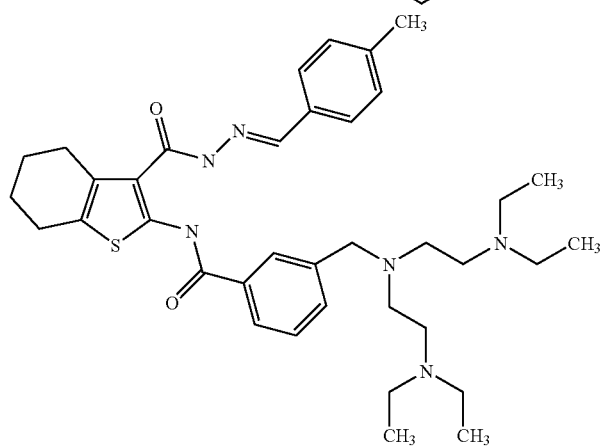 |
| Compound 1057 | 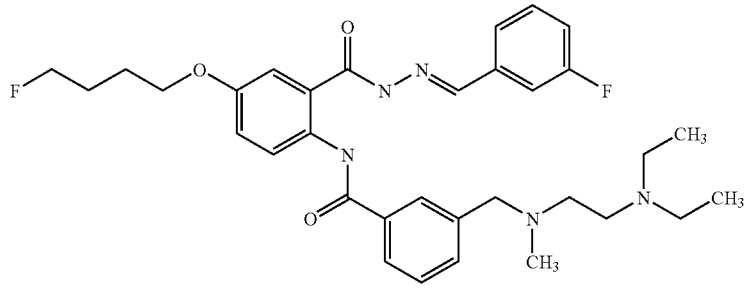 |
| Compound 1058 | 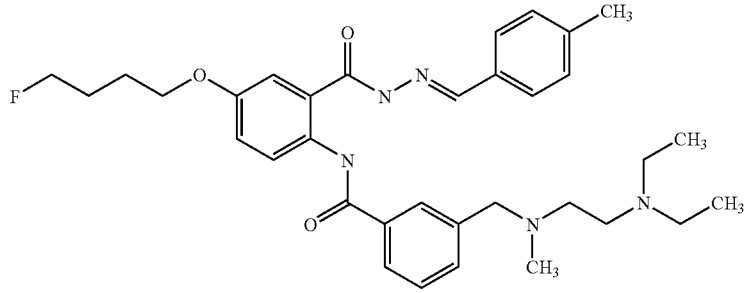 |
| Compound 1059 | 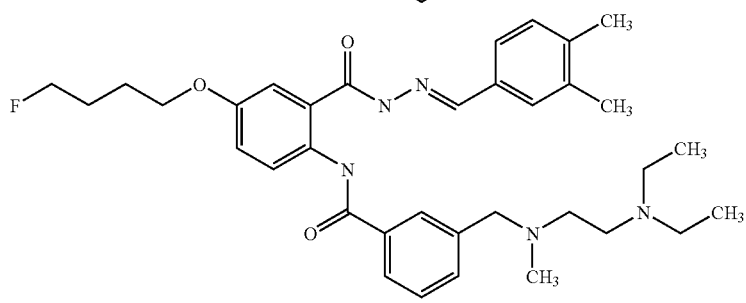 |

TABLE 3-continued
Structures of compounds 1 to 1077 are shown in Table 3.
Compound No.  Chemical structural formula
Compound 1060
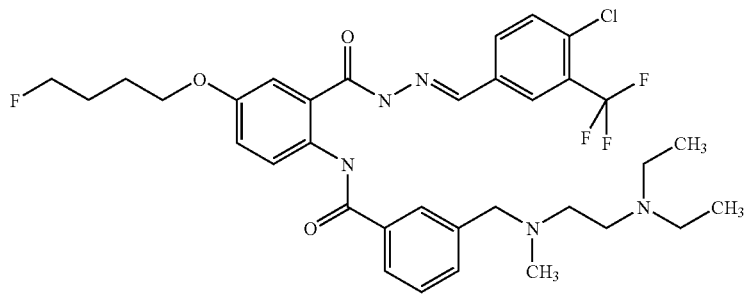
Compound 1061
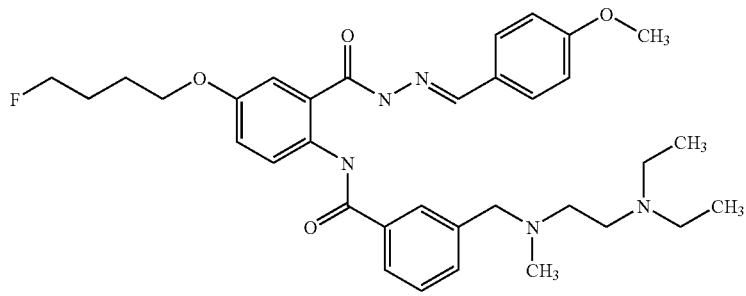
Compound 1062
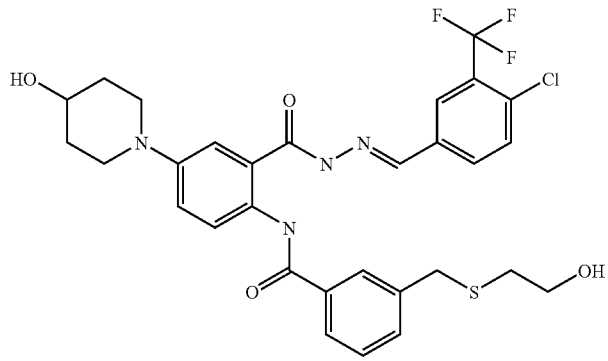
Compound 1063
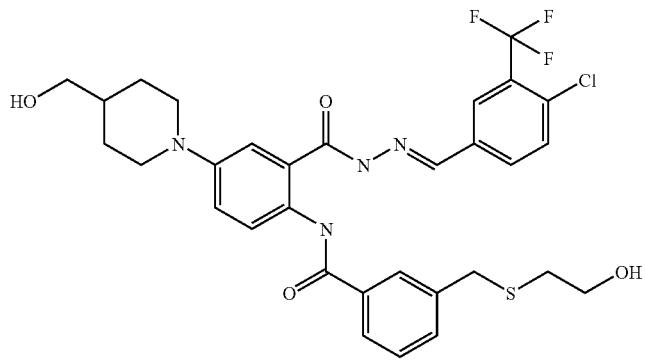

TABLE 3-continued

Structures of compounds 1 to 1077 are shown in Table 3.

| Compound No. | Chemical structural formula |
| --- | --- |
| Compound 1064 | |
| Compound 1065 | |
| Compound 1066 | |
| Compound 1067 | |

TABLE 3-continued
Structures of compounds 1 to 1077 are shown in Table 3.
| Compound No. | Chemical structural formula |
|---|---|
| Compound 1068 | 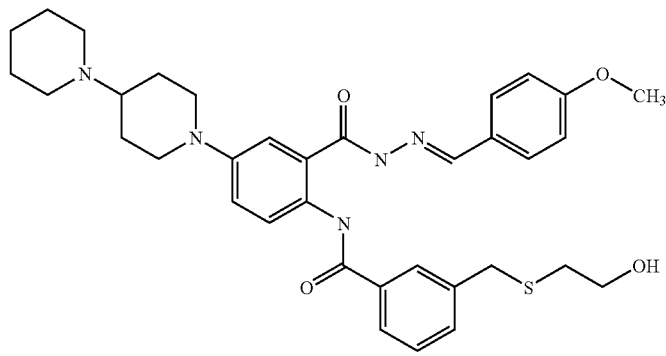 |
| Compound 1069 | 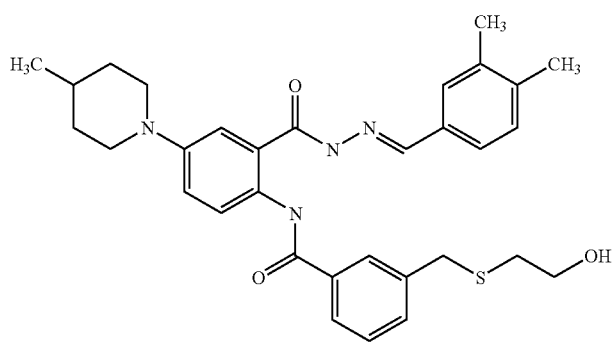 |
| Compound 1070 | 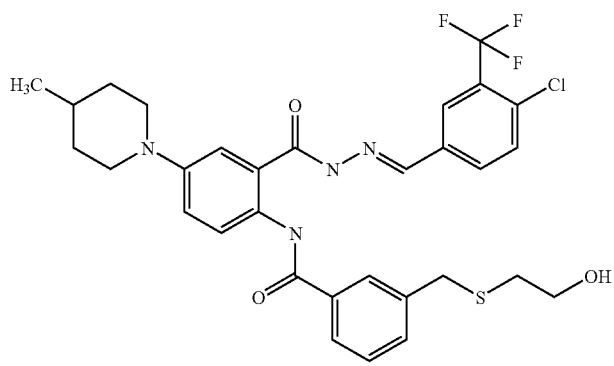 |
| Compound 1071 | 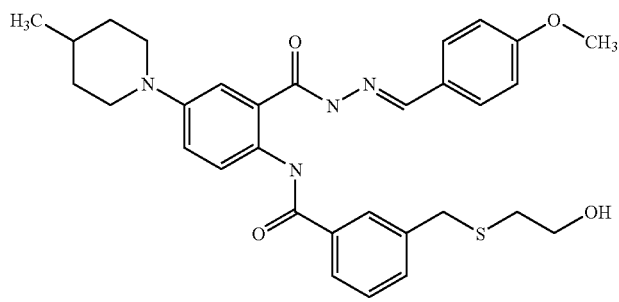 |

TABLE 3-continued
Structures of compounds 1 to 1077 are shown in Table 3.
| Compound No. | Chemical structural formula |
|---|---|
| Compound 1072 | 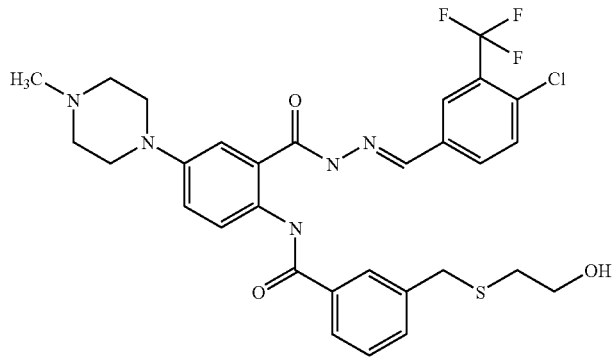 |
| Compound 1073 | 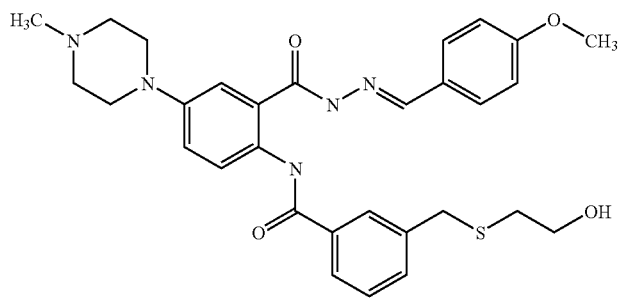 |
| Compound 1074 | 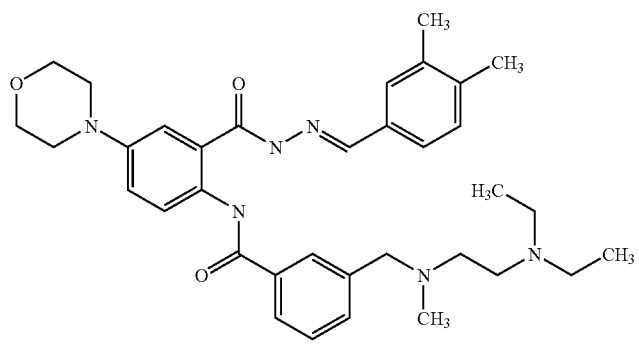 |
| Compound 1075 | 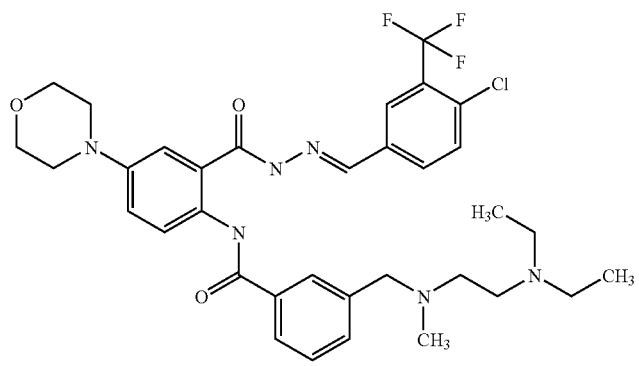 |

TABLE 3-continued

Structures of compounds 1 to 1077 are shown in Table 3.

| Compound No. | Chemical structural formula |
|---|---|
| Compound 1076 | |
| Compound 1077 | |

Pharmacological Test Example 1

Experiment of Sodium-Dependent Phosphate Uptake of *Xenopus oocytes* which Expressed NaPi-2b Degenerate primers were prepared from sequences of mouse NaPi-2b disclosed in Hilfiker H. et al., Pro Natl Acad Sci USA, 95 (24): 14564-14569, 1988 and sequences of human and rat NaPi-2a disclosed in Magagnin S. et al., Proc Natl Aca Sci USA, 90 (13): 5979-5983, 1993. RNA was extracted from the rat small intestine using ISOGEN; manufactured by NIPPON GENE CO., LTD (Japan). 400 bp gene fragments were obtained by PCR using, as a template, a cDNA library prepared with a cDNA synthesis kit (manufactured by STRATAGENE (US)). Thereafter, the above rat small intestine cDNA library was screened using the gene fragment as a probe, and the whole gene sequence of rat NaPi-2b was cloned. cRNA was synthesized from the cloned rat NaPi-2b cDNA with a cRNA synthesis kit (manufactured by Ambion (US)). The synthesized cRNA was injected into *Xenopus oocytes* (obtained from COPACETIC (Japan)) with a liquid microinjector (manufactured by Drummond (US)) and was cultured for 2 days to express rat NaPi-2b. Thereafter, for a group of derivatives, phosphate uptake inhibitory activity were measured using the *Xenopus oocytes* with $^{32}P$ radioactive phosphorus (manufactured by Daiichi Kagaku Inc. (Japan)). As a result, it was found that these compounds had inhibitory activity with $IC_{50}$ values as shown in Table 4. $IC_{50}$ values were determined by determining an inhibition curve by an approximation formula using the least square from inhibitory activity values obtained from five concentration levels of the compound and determining the concentration of the compound which exhibits 50% of the maximum inhibitory activity. The inhibitory activity for 300 µM and 100 µM was determined from the same inhibition curve and expressed in percentage inhibition (%) in Table 5.

TABLE 4

| Compound No. | IC50 (µM) |
|---|---|
| Compound 1 | 9.11 |
| Compound 3 | 7.15 |
| Compound 4 | 79.93 |
| Compound 5 | 3.31 |
| Compound 6 | 5.38 |
| Compound 7 | 7.15 |
| Compound 8 | 1.72 |
| Compound 9 | 4.26 |
| Compound 10 | 26.12 |
| Compound 11 | 8.21 |
| Compound 12 | 4.51 |
| Compound 13 | 9.22 |
| Compound 14 | 12.10 |
| Compound 15 | 1.41 |
| Compound 16 | 2.30 |
| Compound 17 | 3.59 |
| Compound 18 | 4.03 |
| Compound 19 | 8.16 |
| Compound 20 | 2.83 |
| Compound 21 | 21.53 |
| Compound 22 | 26.67 |
| Compound 23 | 9.88 |
| Compound 24 | 20.92 |
| Compound 25 | 23.91 |
| Compound 26 | 25.37 |
| Compound 27 | 3.63 |
| Compound 28 | 5.12 |
| Compound 29 | 0.55 |
| Compound 30 | 7.86 |
| Compound 31 | 0.58 |
| Compound 32 | 1.95 |
| Compound 33 | 15.02 |
| Compound 34 | 1.50 |
| Compound 35 | 3.23 |
| Compound 36 | 4.04 |
| Compound 37 | 13.47 |
| Compound 38 | 5.64 |
| Compound 39 | 9.24 |
| Compound 40 | 2.03 |
| Compound 41 | 2.43 |
| Compound 42 | 8.21 |

TABLE 4-continued

| Compound No. | IC50 (μM) |
|---|---|
| Compound 43 | 20.66 |
| Compound 44 | 4.71 |
| Compound 45 | 26.14 |
| Compound 46 | 7.41 |
| Compound 47 | 4.38 |
| Compound 48 | 2.07 |
| Compound 49 | 3.37 |
| Compound 50 | 19.48 |
| Compound 51 | 4.60 |
| Compound 52 | 10.39 |
| Compound 53 | 4.05 |
| Compound 54 | 6.45 |
| Compound 55 | 0.86 |
| Compound 56 | 0.89 |
| Compound 57 | 1.02 |
| Compound 58 | 7.67 |
| Compound 59 | 1.22 |
| Compound 60 | 1.58 |
| Compound 61 | 0.31 |
| Compound 62 | 0.90 |
| Compound 63 | 5.97 |
| Compound 64 | 3.77 |
| Compound 65 | 1.29 |
| Compound 66 | 0.89 |
| Compound 67 | 0.65 |
| Compound 68 | 0.36 |
| Compound 69 | 3.93 |
| Compound 70 | 9.51 |
| Compound 71 | 12.33 |
| Compound 72 | 10.41 |
| Compound 73 | 1.75 |
| Compound 74 | 2.15 |
| Compound 75 | 12.77 |
| Compound 76 | 13.17 |
| Compound 77 | 3.01 |
| Compound 78 | 7.17 |
| Compound 79 | 2.87 |
| Compound 80 | 10.87 |
| Compound 81 | 5.65 |
| Compound 82 | 6.03 |
| Compound 83 | 2.98 |
| Compound 84 | 8.42 |
| Compound 85 | 2.00 |
| Compound 86 | 11.4 |
| Compound 87 | 0.29 |
| Compound 88 | 0.22 |
| Compound 89 | 1.11 |
| Compound 90 | 3.42 |
| Compound 91 | 0.22 |
| Compound 92 | 0.26 |
| Compound 93 | 10.98 |
| Compound 94 | 5.63 |
| Compound 95 | 1.27 |
| Compound 96 | 5.94 |
| Compound 97 | 0.51 |
| Compound 98 | 0.62 |
| Compound 99 | 3.03 |
| Compound 100 | 0.64 |
| Compound 101 | 0.75 |
| Compound 102 | 5.58 |
| Compound 103 | 5.73 |
| Compound 104 | 11.34 |
| Compound 105 | 7.29 |
| Compound 106 | 5.11 |
| Compound 107 | 1.08 |
| Compound 108 | 3.83 |
| Compound 109 | 6.18 |
| Compound 110 | 7.70 |
| Compound 111 | 9.12 |
| Compound 112 | 41.98 |
| Compound 113 | 17.91 |
| Compound 114 | 2.55 |
| Compound 115 | 5.48 |
| Compound 116 | 7.01 |
| Compound 117 | 0.58 |
| Compound 118 | 6.07 |
| Compound 119 | 0.74 |
| Compound 120 | 2.55 |
| Compound 121 | 4.06 |
| Compound 122 | <3.00 |
| Compound 123 | 3.77 |
| Compound 124 | 3.15 |
| Compound 125 | 136.43 |
| Compound 126 | 6.43 |
| Compound 127 | 11.59 |
| Compound 128 | 11.61 |
| Compound 129 | 13.70 |
| Compound 130 | 11.42 |
| Compound 132 | 0.75 |
| Compound 133 | 0.88 |
| Compound 134 | 7.82 |
| Compound 135 | 3.74 |
| Compound 136 | 4.52 |
| Compound 137 | 3.00 |
| Compound 138 | 4.47 |
| Compound 139 | 55.50 |
| Compound 140 | 74.24 |
| Compound 141 | 5.78 |
| Compound 142 | 9.20 |
| Compound 143 | 5.88 |
| Compound 144 | 5.02 |
| Compound 145 | 3.82 |
| Compound 146 | 1.99 |
| Compound 147 | 7.68 |
| Compound 148 | 15.63 |
| Compound 149 | 5.51 |
| Compound 150 | 1.09 |
| Compound 151 | 3.07 |
| Compound 152 | 1.48 |
| Compound 153 | 3.50 |
| Compound 154 | 2.37 |
| Compound 155 | 0.32 |
| Compound 156 | 0.46 |
| Compound 157 | 7.19 |
| Compound 158 | 3.28 |
| Compound 159 | 4.35 |
| Compound 160 | 0.93 |
| Compound 161 | 0.96 |
| Compound 162 | 3.11 |
| Compound 163 | 1.60 |
| Compound 164 | 4.76 |
| Compound 165 | 2.43 |
| Compound 166 | 27.85 |
| Compound 167 | 30.20 |
| Compound 168 | 4.84 |
| Compound 169 | 4.24 |
| Compound 170 | 5.34 |
| Compound 171 | 5.12 |
| Compound 172 | 2.74 |
| Compound 173 | 7.40 |
| Compound 174 | 12.54 |
| Compound 175 | 3.57 |
| Compound 176 | 4.10 |
| Compound 177 | 26.01 |
| Compound 178 | 7.54 |
| Compound 179 | 18.69 |
| Compound 180 | <3.00 |
| Compound 181 | 3.16 |
| Compound 182 | 10.24 |
| Compound 183 | <3.00 |
| Compound 184 | 4.01 |
| Compound 185 | 2.02 |
| Compound 186 | 10.1 |
| Compound 187 | 7.87 |
| Compound 188 | 19.43 |
| Compound 189 | 1.47 |
| Compound 190 | 20.32 |
| Compound 191 | 12.12 |
| Compound 192 | 23.09 |
| Compound 193 | 4.21 |
| Compound 194 | 7.36 |
| Compound 195 | 0.98 |
| Compound 196 | 0.61 |
| Compound 197 | 4.87 |
| Compound 198 | 2.71 |
| Compound 199 | 1.82 |

TABLE 4-continued

| Compound No. | IC50 (μM) |
|---|---|
| Compound 200 | 0.39 |
| Compound 201 | 11.10 |
| Compound 202 | 3.14 |
| Compound 203 | <3.00 |
| Compound 204 | <3.00 |
| Compound 205 | <3.00 |
| Compound 206 | <3.00 |
| Compound 207 | <1.00 |
| Compound 208 | <0.30 |
| Compound 209 | <1.00 |
| Compound 210 | 34.96 |
| Compound 211 | 69.07 |
| Compound 212 | 71.27 |
| Compound 213 | 16.64 |
| Compound 214 | 3.95 |
| Compound 215 | <3.00 |
| Compound 216 | 21.82 |
| Compound 217 | 11.21 |
| Compound 218 | 4.05 |
| Compound 219 | 9.07 |
| Compound 220 | 9.42 |
| Compound 221 | 9.51 |
| Compound 222 | 8.86 |
| Compound 223 | 11.30 |
| Compound 224 | 19.99 |
| Compound 225 | 60.98 |
| Compound 226 | 1.69 |
| Compound 227 | 7.40 |
| Compound 228 | 22.48 |
| Compound 229 | 6.32 |
| Compound 252 | 1.49 |
| Compound 253 | 3.47 |
| Compound 255 | 3.54 |
| Compound 256 | <10.00 |
| Compound 257 | <3.00 |
| Compound 258 | <3.00 |
| Compound 259 | <3.00 |
| Compound 260 | <3.00 |
| Compound 261 | <3.00 |
| Compound 262 | 1.10 |
| Compound 263 | <1.00 |
| Compound 264 | <1.00 |
| Compound 265 | <1.00 |
| Compound 266 | <1.00 |
| Compound 267 | 0.43 |
| Compound 268 | 1.02 |
| Compound 269 | 2.19 |
| Compound 270 | 5.04 |
| Compound 271 | 0.21 |
| Compound 272 | 0.47 |
| Compound 273 | 0.15 |
| Compound 274 | 1.04 |
| Compound 275 | 1.73 |
| Compound 276 | 6.20 |
| Compound 277 | 1.60 |
| Compound 278 | 0.16 |
| Compound 279 | 2.31 |
| Compound 280 | 0.78 |
| Compound 281 | 4.60 |
| Compound 282 | 6.71 |
| Compound 283 | 22.44 |
| Compound 284 | 26.94 |
| Compound 285 | 0.90 |
| Compound 286 | 0.57 |
| Compound 287 | 0.11 |
| Compound 288 | 1.31 |
| Compound 289 | 2.89 |
| Compound 290 | 3.25 |
| Compound 291 | 1.16 |
| Compound 292 | 3.50 |
| Compound 293 | 5.59 |
| Compound 294 | 7.80 |
| Compound 295 | 7.58 |
| Compound 296 | 1.45 |
| Compound 297 | 0.96 |
| Compound 298 | 9.22 |
| Compound 299 | 3.91 |
| Compound 300 | 1.92 |

TABLE 4-continued

| Compound No. | IC50 (μM) |
|---|---|
| Compound 301 | 15.17 |
| Compound 302 | 1.12 |
| Compound 303 | 1.13 |
| Compound 304 | 1.23 |
| Compound 305 | 2.47 |
| Compound 306 | 2.13 |
| Compound 307 | 41.17 |
| Compound 308 | 2.76 |
| Compound 309 | 15.12 |
| Compound 310 | 7.82 |
| Compound 311 | 7.78 |
| Compound 312 | 3.31 |
| Compound 313 | 1.24 |
| Compound 314 | 3.39 |
| Compound 315 | 9.02 |
| Compound 316 | 4.71 |
| Compound 317 | 5.02 |
| Compound 318 | 2.49 |
| Compound 319 | 9.76 |
| Compound 320 | 4.09 |
| Compound 321 | 2.66 |
| Compound 322 | 5.93 |
| Compound 323 | 4.69 |
| Compound 324 | 4.43 |
| Compound 325 | 2.56 |
| Compound 326 | 2.10 |
| Compound 327 | 5.12 |
| Compound 328 | 1.15 |
| Compound 329 | 5.63 |
| Compound 330 | 10.69 |
| Compound 331 | 15.76 |
| Compound 332 | 2.87 |
| Compound 333 | 17.18 |
| Compound 334 | 7.69 |
| Compound 335 | 5.86 |
| Compound 336 | 16.63 |
| Compound 337 | 1.39 |
| Compound 338 | 18.97 |
| Compound 339 | 12.77 |
| Compound 340 | 8.41 |
| Compound 341 | <3.00 |
| Compound 342 | 32.60 |
| Compound 343 | 124.10 |
| Compound 344 | 30.99 |
| Compound 345 | 129.95 |
| Compound 346 | 4.46 |
| Compound 347 | 4.91 |
| Compound 348 | 16.59 |
| Compound 349 | 8.78 |
| Compound 350 | 25.32 |
| Compound 351 | 8.96 |
| Compound 352 | 13.00 |
| Compound 353 | 8.85 |
| Compound 354 | 1.54 |
| Compound 356 | 0.17 |
| Compound 358 | 54.07 |
| Compound 359 | 7.10 |
| Compound 360 | 0.63 |
| Compound 361 | <1.00 |
| Compound 362 | <1.00 |
| Compound 363 | <1.00 |
| Compound 364 | <1.00 |
| Compound 367 | 6.88 |
| Compound 368 | 1.37 |
| Compound 369 | 1.45 |
| Compound 370 | 1.86 |
| Compound 371 | 2.54 |
| Compound 372 | 0.80 |
| Compound 373 | 1.68 |
| Compound 374 | 9.25 |
| Compound 375 | 24.71 |
| Compound 376 | 21.00 |
| Compound 377 | 9.65 |
| Compound 378 | 4.35 |
| Compound 379 | 0.97 |
| Compound 380 | 0.35 |
| Compound 381 | 1.00 |
| Compound 382 | 1.04 |

TABLE 4-continued

| Compound No. | IC50 (μM) |
|---|---|
| Compound 383 | 1.98 |
| Compound 384 | 0.25 |
| Compound 385 | 0.31 |
| Compound 386 | <3.00 |
| Compound 387 | 6.45 |
| Compound 388 | 19.67 |
| Compound 389 | 1.09 |
| Compound 390 | 0.45 |
| Compound 391 | 1.02 |
| Compound 392 | 1.42 |
| Compound 393 | 0.52 |
| Compound 394 | 0.95 |
| Compound 395 | 8.55 |
| Compound 396 | 8.19 |
| Compound 397 | 9.25 |
| Compound 398 | <0.30 |
| Compound 399 | 3.67 |
| Compound 400 | <0.30 |
| Compound 401 | 6.13 |
| Compound 402 | 14.12 |
| Compound 403 | 26.73 |
| Compound 404 | 2.18 |
| Compound 405 | 1.90 |
| Compound 406 | 0.88 |
| Compound 407 | 0.57 |
| Compound 408 | 0.69 |
| Compound 409 | 2.52 |
| Compound 410 | 4.05 |
| Compound 411 | 10.08 |
| Compound 412 | 7.96 |
| Compound 413 | <3.00 |
| Compound 414 | <3.00 |
| Compound 415 | <3.00 |
| Compound 416 | 3.25 |
| Compound 417 | <3.00 |
| Compound 418 | 9.38 |
| Compound 419 | 9.20 |
| Compound 420 | 27.14 |
| Compound 421 | 29.56 |
| Compound 422 | 1.15 |
| Compound 423 | <3.00 |
| Compound 424 | 1.79 |
| Compound 425 | <3.00 |
| Compound 426 | 1.89 |
| Compound 427 | <3.00 |
| Compound 428 | 1.82 |
| Compound 429 | 5.88 |
| Compound 430 | 4.53 |
| Compound 431 | 5.57 |
| Compound 432 | 22.22 |
| Compound 433 | 14.34 |
| Compound 434 | 7.78 |
| Compound 435 | 7.65 |
| Compound 436 | 8.36 |
| Compound 437 | <3.00 |
| Compound 438 | 26.27 |
| Compound 439 | 28.74 |
| Compound 440 | 32.35 |
| Compound 441 | 40.14 |
| Compound 442 | 3.15 |
| Compound 443 | 11.05 |
| Compound 444 | <3.00 |
| Compound 445 | 10.33 |
| Compound 446 | 1.54 |
| Compound 447 | 2.16 |
| Compound 448 | 9.41 |
| Compound 449 | 21.73 |
| Compound 450 | 16.94 |
| Compound 451 | 37.84 |
| Compound 452 | <3.00 |
| Compound 453 | <3.00 |
| Compound 454 | <3.00 |
| Compound 455 | <3.00 |
| Compound 456 | <3.00 |
| Compound 457 | <3.00 |
| Compound 458 | <3.00 |
| Compound 459 | <3.00 |
| Compound 460 | <3.00 |
| Compound 461 | 3.59 |
| Compound 462 | <3.00 |
| Compound 463 | 4.44 |
| Compound 464 | 5.00 |
| Compound 465 | 7.43 |
| Compound 466 | <3.00 |
| Compound 467 | 7.94 |
| Compound 468 | 22.45 |
| Compound 469 | 33.16 |
| Compound 470 | 23.54 |
| Compound 472 | <3.00 |
| Compound 473 | <3.00 |
| Compound 474 | <3.00 |
| Compound 475 | <3.00 |
| Compound 476 | <3.00 |
| Compound 477 | <3.00 |
| Compound 478 | <3.00 |
| Compound 479 | <3.00 |
| Compound 480 | <3.00 |
| Compound 481 | 12.10 |
| Compound 482 | <3.00 |
| Compound 483 | <3.00 |
| Compound 484 | <3.00 |
| Compound 485 | <3.00 |
| Compound 486 | <3.00 |
| Compound 487 | <3.00 |
| Compound 488 | <3.00 |
| Compound 489 | <3.00 |
| Compound 490 | <3.00 |
| Compound 491 | <3.00 |
| Compound 492 | <3.00 |
| Compound 493 | <3.00 |
| Compound 494 | 2.07 |
| Compound 495 | 0.35 |
| Compound 496 | 0.64 |
| Compound 497 | 0.51 |
| Compound 498 | 0.60 |
| Compound 499 | 0.98 |
| Compound 500 | 0.35 |
| Compound 501 | 23.13 |
| Compound 502 | 15.68 |
| Compound 503 | 10.35 |
| Compound 504 | 18.93 |
| Compound 505 | 1.21 |
| Compound 506 | 19.5 |
| Compound 507 | 1.86 |
| Compound 508 | 0.48 |
| Compound 509 | 13.59 |
| Compound 510 | 1.48 |
| Compound 511 | 2.16 |
| Compound 512 | 28.30 |
| Compound 513 | 15.96 |
| Compound 514 | 2.15 |
| Compound 515 | 1.90 |
| Compound 516 | 2.13 |
| Compound 517 | 1.71 |
| Compound 518 | 1.52 |
| Compound 519 | 1.72 |
| Compound 521 | 1.24 |
| Compound 522 | 1.09 |
| Compound 551 | 0.47 |
| Compound 552 | 2.63 |
| Compound 553 | 2.80 |
| Compound 554 | 1.46 |
| Compound 555 | <3.00 |
| Compound 556 | <3.00 |
| Compound 557 | <0.30 |
| Compound 558 | 1.07 |
| Compound 559 | 1.26 |
| Compound 560 | 1.09 |
| Compound 561 | 0.31 |
| Compound 562 | <1.00 |
| Compound 563 | <1.00 |
| Compound 564 | 11.57 |
| Compound 565 | 12.98 |
| Compound 566 | 14.58 |
| Compound 567 | <1.00 |
| Compound 568 | 4.32 |

TABLE 4-continued

| Compound No. | IC50 (μM) |
|---|---|
| Compound 569 | <3.00 |
| Compound 570 | 6.04 |
| Compound 571 | 5.27 |
| Compound 572 | 4.12 |
| Compound 573 | 1.75 |
| Compound 574 | 6.93 |
| Compound 575 | <3.00 |
| Compound 576 | <3.00 |
| Compound 577 | <3.00 |
| Compound 578 | <3.00 |
| Compound 579 | <3.00 |
| Compound 580 | <3.00 |
| Compound 581 | <3.00 |
| Compound 582 | <3.00 |
| Compound 583 | <3.00 |
| Compound 584 | <3.00 |
| Compound 585 | <3.00 |
| Compound 586 | <3.00 |
| Compound 587 | <3.00 |
| Compound 588 | 9.33 |
| Compound 589 | <3.00 |
| Compound 590 | 6.18 |
| Compound 591 | 1.01 |
| Compound 592 | 11.94 |
| Compound 593 | <3.00 |
| Compound 594 | 3.60 |
| Compound 595 | 3.87 |
| Compound 596 | 5.47 |
| Compound 597 | 1.47 |
| Compound 598 | 53.04 |
| Compound 599 | <3.00 |
| Compound 600 | 3.84 |
| Compound 601 | <3.00 |
| Compound 602 | 3.98 |
| Compound 603 | <3.00 |
| Compound 604 | 9.23 |
| Compound 605 | 0.95 |
| Compound 606 | 1.01 |
| Compound 607 | 0.43 |
| Compound 608 | <0.30 |
| Compound 609 | <0.30 |
| Compound 610 | 1.82 |
| Compound 611 | 2.16 |
| Compound 612 | 2.34 |
| Compound 613 | 1.41 |
| Compound 614 | 3.29 |
| Compound 615 | 2.08 |
| Compound 616 | 13.86 |
| Compound 617 | 3.68 |
| Compound 618 | 4.25 |
| Compound 619 | <3.00 |
| Compound 620 | 3.58 |
| Compound 621 | <3.00 |
| Compound 622 | <3.00 |
| Compound 623 | <3.00 |
| Compound 624 | <3.00 |
| Compound 625 | <3.00 |
| Compound 626 | <3.00 |
| Compound 627 | <1.00 |
| Compound 628 | 1.29 |
| Compound 629 | 3.01 |
| Compound 630 | <1.00 |
| Compound 631 | <1.00 |
| Compound 632 | <1.00 |
| Compound 633 | 1.19 |
| Compound 634 | 1.74 |
| Compound 635 | 1.56 |
| Compound 636 | 3.89 |
| Compound 637 | <1.00 |
| Compound 638 | 3.15 |
| Compound 639 | 1.84 |
| Compound 640 | 1.61 |
| Compound 641 | 2.92 |
| Compound 642 | 2.14 |
| Compound 643 | 3.68 |
| Compound 644 | 5.91 |
| Compound 645 | <3.00 |
| Compound 646 | 1.77 |
| Compound 647 | 5.62 |
| Compound 648 | 2.04 |
| Compound 649 | 2.69 |
| Compound 650 | 0.95 |
| Compound 651 | 262.90 |
| Compound 652 | 0.72 |
| Compound 653 | 1.10 |
| Compound 654 | 2.03 |
| Compound 655 | 1.58 |
| Compound 656 | 2.98 |
| Compound 657 | 2.63 |
| Compound 658 | <3.00 |
| Compound 659 | 12.45 |
| Compound 660 | 18.70 |
| Compound 661 | <10.00 |
| Compound 662 | 3.20 |
| Compound 663 | 136.67 |
| Compound 664 | 15.08 |
| Compound 666 | 31.23 |
| Compound 667 | 30.49 |
| Compound 668 | 9.13 |
| Compound 669 | 15.29 |
| Compound 671 | <3.00 |
| Compound 672 | 31.18 |
| Compound 673 | 10.13 |
| Compound 675 | <3.00 |
| Compound 676 | <3.00 |
| Compound 677 | <3.00 |
| Compound 678 | <3.00 |
| Compound 679 | <3.00 |
| Compound 680 | 4.04 |
| Compound 681 | 25.90 |
| Compound 682 | 12.50 |
| Compound 683 | <3.00 |
| Compound 684 | 54.25 |
| Compound 685 | 36.43 |
| Compound 686 | <3.00 |
| Compound 687 | <3.00 |
| Compound 688 | <3.00 |
| Compound 689 | <3.00 |
| Compound 690 | 87.97 |
| Compound 691 | 97.03 |
| Compound 692 | 99.40 |
| Compound 693 | 70.18 |
| Compound 694 | 38.77 |
| Compound 695 | 6.76 |
| Compound 696 | 4.47 |
| Compound 697 | <3.00 |
| Compound 698 | <3.00 |
| Compound 713 | 15.49 |
| Compound 714 | 3.52 |
| Compound 718 | 6.91 |
| Compound 719 | 9.59 |
| Compound 720 | 3.51 |
| Compound 721 | 22.34 |
| Compound 722 | 12.84 |
| Compound 723 | 18.03 |
| Compound 724 | 17.08 |
| Compound 725 | 69.40 |
| Compound 726 | <3.00 |
| Compound 728 | 20.33 |
| Compound 729 | 27.33 |
| Compound 730 | 15.66 |
| Compound 731 | 19.18 |
| Compound 732 | 29.35 |
| Compound 733 | <10.00 |
| Compound 735 | 18.34 |
| Compound 737 | 4.24 |
| Compound 738 | 7.55 |
| Compound 743 | 14.40 |
| Compound 745 | 6.12 |
| Compound 746 | 16.77 |
| Compound 747 | 11.93 |
| Compound 749 | 9.05 |
| Compound 750 | <3.00 |
| Compound 751 | 13.11 |
| Compound 752 | <3.00 |
| Compound 753 | 12.36 |

TABLE 4-continued

| Compound No. | IC50 (μM) |
|---|---|
| Compound 754 | <3.00 |
| Compound 756 | 10.33 |
| Compound 757 | 18.84 |
| Compound 763 | 11.18 |
| Compound 764 | 5.92 |
| Compound 765 | 6.88 |
| Compound 768 | 10.62 |
| Compound 769 | 4.44 |
| Compound 770 | 16.49 |
| Compound 786 | 1.33 |
| Compound 787 | 1.69 |
| Compound 788 | 2.04 |
| Compound 789 | 1.16 |
| Compound 790 | 4.32 |
| Compound 791 | 5.50 |
| Compound 792 | 1.26 |
| Compound 793 | 1.41 |
| Compound 794 | 0.97 |
| Compound 795 | 1.92 |
| Compound 796 | 0.35 |
| Compound 797 | 3.39 |
| Compound 798 | 3.62 |
| Compound 799 | 3.72 |
| Compound 800 | 9.24 |
| Compound 801 | 4.70 |
| Compound 802 | 1.20 |
| Compound 803 | 4.92 |
| Compound 804 | 1.23 |
| Compound 805 | 4.76 |
| Compound 806 | 3.90 |
| Compound 807 | <1.00 |
| Compound 808 | 1.97 |
| Compound 809 | 5.22 |
| Compound 810 | 6.68 |
| Compound 811 | 9.11 |
| Compound 812 | 5.58 |
| Compound 813 | 6.25 |
| Compound 814 | <3.00 |
| Compound 815 | 16.74 |
| Compound 816 | 14.77 |
| Compound 817 | 36.14 |
| Compound 818 | 7.38 |
| Compound 819 | 5.95 |
| Compound 820 | 17.86 |
| Compound 821 | 17.86 |
| Compound 822 | 5.90 |
| Compound 823 | 6.93 |
| Compound 824 | 3.22 |
| Compound 825 | 4.52 |
| Compound 826 | 4.44 |
| Compound 827 | 3.50 |
| Compound 828 | 9.33 |
| Compound 829 | 3.91 |
| Compound 830 | 4.81 |
| Compound 831 | 3.88 |
| Compound 832 | 4.97 |
| Compound 833 | 7.89 |
| Compound 834 | 19.02 |
| Compound 835 | 6.46 |
| Compound 836 | 0.77 |
| Compound 837 | 12.91 |
| Compound 838 | <3.00 |
| Compound 839 | 5.04 |
| Compound 840 | 6.95 |
| Compound 841 | <3.00 |
| Compound 842 | 3.22 |
| Compound 843 | 4.19 |
| Compound 844 | <3.00 |
| Compound 845 | <3.00 |
| Compound 846 | <3.00 |
| Compound 847 | <3.00 |
| Compound 848 | 2.20 |
| Compound 849 | <3.00 |
| Compound 850 | 3.10 |
| Compound 851 | 1.36 |
| Compound 852 | <1.00 |
| Compound 853 | 2.14 |
| Compound 854 | 1.33 |
| Compound 855 | 1.75 |
| Compound 856 | 1.77 |
| Compound 857 | 1.18 |
| Compound 858 | 0.46 |
| Compound 859 | 0.39 |
| Compound 860 | 0.65 |
| Compound 861 | 0.52 |
| Compound 862 | 0.35 |
| Compound 863 | 1.22 |
| Compound 864 | 0.74 |
| Compound 865 | 1.49 |
| Compound 866 | 1.92 |
| Compound 867 | 2.24 |
| Compound 868 | <0.30 |
| Compound 869 | 6.68 |
| Compound 870 | 0.53 |
| Compound 871 | 1.00 |
| Compound 872 | <3.00 |
| Compound 873 | 0.66 |
| Compound 874 | <0.30 |
| Compound 875 | 5.20 |
| Compound 876 | <3.00 |
| Compound 877 | <0.30 |
| Compound 878 | <0.30 |
| Compound 879 | 3.72 |
| Compound 880 | 0.08 |
| Compound 881 | 0.18 |
| Compound 882 | 0.33 |
| Compound 883 | 0.04 |
| Compound 884 | 0.95 |
| Compound 885 | 1.24 |
| Compound 886 | 0.81 |
| Compound 887 | 1.75 |
| Compound 888 | 2.55 |
| Compound 889 | 0.33 |
| Compound 890 | 3.91 |
| Compound 891 | 1.47 |
| Compound 892 | 14.84 |
| Compound 893 | <0.30 |
| Compound 894 | 0.50 |
| Compound 895 | <0.30 |
| Compound 896 | <0.30 |
| Compound 897 | <0.30 |
| Compound 898 | <0.30 |
| Compound 899 | <1.00 |
| Compound 900 | <1.00 |
| Compound 901 | <1.00 |
| Compound 902 | <1.00 |
| Compound 903 | <1.00 |
| Compound 904 | 1.71 |
| Compound 905 | 1.18 |
| Compound 906 | 1.83 |
| Compound 907 | 6.75 |
| Compound 908 | 13.16 |
| Compound 909 | 1.02 |
| Compound 910 | 7.81 |
| Compound 911 | <1.00 |
| Compound 912 | 1.04 |
| Compound 913 | 1.65 |
| Compound 914 | 1.75 |
| Compound 915 | 8.15 |
| Compound 916 | 5.22 |
| Compound 917 | 1.25 |
| Compound 918 | 1.55 |
| Compound 919 | 0.31 |
| Compound 920 | <1.00 |
| Compound 921 | 1.22 |
| Compound 922 | 2.89 |
| Compound 923 | 18.79 |
| Compound 924 | 40.16 |
| Compound 925 | 25.50 |
| Compound 926 | <1.00 |
| Compound 927 | <1.00 |
| Compound 928 | <1.00 |
| Compound 929 | <1.00 |
| Compound 935 | 0.17 |
| Compound 936 | 5.59 |
| Compound 937 | 137.00 |

TABLE 4-continued

| Compound No. | IC50 (µM) |
|---|---|
| Compound 938 | 1.41 |
| Compound 939 | <3.00 |
| Compound 940 | 30.63 |
| Compound 941 | 8.72 |
| Compound 942 | 0.20 |
| Compound 943 | 10.58 |
| Compound 944 | 12.04 |
| Compound 945 | 19.38 |
| Compound 947 | 30.19 |
| Compound 948 | 11.62 |
| Compound 950 | 9.08 |
| Compound 952 | 19.24 |
| Compound 954 | 60.51 |
| Compound 956 | 29.85 |
| Compound 958 | <1.00 |
| Compound 959 | <1.00 |
| Compound 960 | 1.12 |
| Compound 961 | <1.00 |
| Compound 962 | <1.00 |
| Compound 963 | <1.00 |
| Compound 965 | 27.22 |
| Compound 966 | 16.04 |
| Compound 967 | 6.57 |
| Compound 969 | <3.00 |
| Compound 970 | <3.00 |
| Compound 971 | <3.00 |
| Compound 972 | <3.00 |
| Compound 973 | <3.00 |
| Compound 974 | 12.56 |
| Compound 975 | 17.36 |
| Compound 976 | 10.73 |
| Compound 977 | 10.15 |
| Compound 980 | 13.80 |
| Compound 981 | 12.17 |
| Compound 982 | 8.05 |
| Compound 983 | 8.31 |
| Compound 984 | 22.12 |
| Compound 985 | <3.00 |
| Compound 986 | 28.95 |
| Compound 987 | <3.00 |
| Compound 988 | 3.88 |
| Compound 989 | <3.00 |
| Compound 990 | <3.00 |
| Compound 996 | 2.66 |
| Compound 997 | 7.88 |
| Compound 998 | 16.57 |
| Compound 999 | 58.16 |
| Compound 1001 | <3.00 |
| Compound 1002 | 2.58 |
| Compound 1003 | 9.12 |
| Compound 1006 | 6.31 |
| Compound 1007 | 0.40 |
| Compound 1008 | 0.30 |
| Compound 1009 | 0.10 |
| Compound 1010 | 0.24 |
| Compound 1011 | 1.28 |
| Compound 1012 | 1.89 |
| Compound 1013 | 8.89 |
| Compound 1015 | 11.07 |
| Compound 1016 | 9.23 |
| Compound 1017 | 0.87 |
| Compound 1018 | 0.92 |
| Compound 1019 | 0.41 |
| Compound 1020 | 0.39 |
| Compound 1021 | 5.57 |
| Compound 1022 | 3.23 |
| Compound 1023 | 0.99 |
| Compound 1024 | 3.94 |
| Compound 1025 | 5.71 |
| Compound 1026 | 3.86 |
| Compound 1027 | 1.20 |
| Compound 1028 | 29.07 |
| Compound 1029 | 34.73 |
| Compound 1030 | 14.16 |
| Compound 1033 | 18.66 |
| Compound 1034 | 17.21 |
| Compound 1035 | 3.70 |
| Compound 1036 | 1.50 |
| Compound 1037 | 38.51 |
| Compound 1038 | 3.35 |
| Compound 1039 | 2.76 |
| Compound 1040 | 52.16 |
| Compound 1041 | 10.25 |
| Compound 1042 | 14.74 |
| Compound 1043 | 8.26 |
| Compound 1044 | 2.13 |
| Compound 1045 | 13.11 |
| Compound 1046 | <1.00 |
| Compound 1047 | <1.00 |
| Compound 1048 | <1.00 |
| Compound 1049 | <1.00 |
| Compound 1050 | 1.42 |
| Compound 1051 | 1.16 |
| Compound 1052 | 1.33 |
| Compound 1053 | <1.00 |
| Compound 1054 | <1.00 |
| Compound 1055 | 1.96 |
| Compound 1056 | 1.88 |
| Compound 1057 | 1.26 |
| Compound 1058 | 1.07 |
| Compound 1059 | 0.43 |
| Compound 1060 | 0.44 |
| Compound 1061 | 1.99 |
| Compound 1062 | 6.76 |
| Compound 1064 | <1.00 |
| Compound 1065 | 1.21 |
| Compound 1066 | 2.69 |
| Compound 1067 | 2.79 |
| Compound 1069 | <1.00 |
| Compound 1070 | <1.00 |
| Compound 1071 | <1.00 |
| Compound 1072 | 3.88 |
| Compound 1073 | 20.36 |
| Compound 1074 | 1.54 |
| Compound 1075 | 1.34 |
| Compound 1076 | 2.57 |

TABLE 5

| Compound No. | Inhibition (%) (300 µM) |
|---|---|
| Compound 2 | 77.30 |
| Compound 131 | 32.40 |
| Compound 230 | 50.42 |
| Compound 231 | 32.76 |
| Compound 232 | 44.92 |
| Compound 233 | 33.62 |
| Compound 234 | 37.88 |
| Compound 235 | 47.92 |
| Compound 236 | 49.42 |
| Compound 237 | 33.12 |
| Compound 238 | 30.58 |
| Compound 239 | 59.08 |
| Compound 240 | 37.92 |
| Compound 241 | 46.94 |
| Compound 242 | 37.61 |
| Compound 243 | 50.17 |
| Compound 244 | 30.72 |
| Compound 245 | 31.68 |
| Compound 246 | 32.62 |
| Compound 247 | 34.81 |
| Compound 248 | 30.30 |
| Compound 249 | 41.59 |
| Compound 250 | 37.86 |
| Compound 251 | 31.22 |
| Compound 357 | 65.82 |
| Compound 366 | 69.87 |
| Compound 471 | 50.99 |
| Compound 523 | 50.09 |
| Compound 524 | 42.75 |
| Compound 525 | 38.89 |

TABLE 5-continued

| Compound No. | |
|---|---|
| Compound 526 | 40.24 |
| Compound 527 | 40.94 |
| Compound 528 | 58.38 |
| Compound 529 | 80.96 |
| Compound 530 | 38.16 |
| Compound 531 | 35.68 |
| Compound 532 | 76.00 |
| Compound 533 | 36.87 |
| Compound 534 | 43.82 |
| Compound 535 | 52.98 |
| Compound 536 | 88.25 |
| Compound 537 | 82.05 |
| Compound 538 | 30.31 |
| Compound 539 | 88.39 |
| Compound 540 | 38.41 |
| Compound 541 | 32.16 |
| Compound 542 | 41.11 |
| Compound 543 | 30.2 |
| Compound 544 | 60.05 |
| Compound 545 | 88.81 |
| Compound 546 | 85.19 |
| Compound 547 | 66.61 |
| Compound 548 | 85.72 |
| Compound 549 | 85.10 |
| Compound 550 | 78.88 |
| Compound 665 | 82.34 |
| Compound 670 | 70.17 |
| Compound 674 | 85.12 |
| Compound 699 | 58.35 |
| Compound 700 | 40.28 |
| Compound 701 | 53.98 |
| Compound 702 | 49.17 |
| Compound 703 | 57.92 |
| Compound 704 | 46.62 |
| Compound 705 | 44.68 |
| Compound 706 | 47.79 |
| Compound 707 | 41.22 |
| Compound 708 | 42.04 |
| Compound 709 | 59.36 |
| Compound 710 | 83.13 |
| Compound 711 | 81.04 |
| Compound 712 | 48.73 |
| Compound 715 | 84.11 |
| Compound 716 | 85.77 |
| Compound 717 | 53.54 |
| Compound 727 | 67.74 |
| Compound 734 | 64.91 |
| Compound 736 | 61.49 |
| Compound 739 | 58.89 |
| Compound 740 | 58.55 |
| Compound 741 | 50.93 |
| Compound 742 | 77.57 |
| Compound 744 | 83.71 |
| Compound 748 | 56.45 |
| Compound 755 | 67.27 |
| Compound 758 | 58.21 |
| Compound 759 | 63.85 |
| Compound 760 | 73.34 |
| Compound 761 | 46.24 |
| Compound 762 | 52.08 |
| Compound 766 | 81.89 |
| Compound 767 | 81.83 |
| Compound 771 | 85.12 |
| Compound 772 | 67.72 |
| Compound 773 | 53.91 |
| Compound 774 | 58.85 |
| Compound 775 | 44.62 |
| Compound 776 | 49.19 |
| Compound 777 | 34.17 |
| Compound 778 | 39.12 |
| Compound 779 | 51.64 |
| Compound 780 | 47.74 |
| Compound 781 | 51.18 |
| Compound 782 | 86.76 |
| Compound 783 | 88.84 |
| Compound 784 | 88.49 |
| Compound 785 | 39.53 |
| Compound 930 | 40.20 |
| Compound 931 | 31.22 |
| Compound 932 | 36.09 |
| Compound 933 | 37.62 |
| Compound 934 | 39.27 |
| Compound 946 | 45.00 |
| Compound 949 | 72.60 |
| Compound 951 | 68.51 |
| Compound 953 | 67.80 |
| Compound 955 | 57.67 |
| Compound 957 | 54.91 |
| Compound 964 | 67.50 |
| Compound 968 | 52.70 |
| Compound 978 | 74.08 |
| Compound 979 | 73.73 |
| Compound 991 | 30.11 |
| Compound 992 | 31.92 |
| Compound 993 | 39.71 |
| Compound 995 | 42.10 |
| Compound 1000 | 32.14 |
| Compound 1004 | 34.20 |
| Compound 1005 | 59.07 |
| Compound 1014 | 55.20 |
| Compound 1031 | 58.77 |
| Compound 1032 | 39.98 |
| Compound 1077 | 40.18 |
| Inhibition (%) (100 μM) | |
| Compound 1063 | 63.94 |
| Compound 1068 | 74.42 |

Pharmacological Test Example 2

Experiment of Sodium-Dependent Phosphate Uptake of Rabbit Jejunal Brush Border Membrane Vesicles Jejunal epithelium was obtained from New Zealand white male rabbits (7 weeks old, obtained from KITAYAMA LABES Co., Ltd. (Japan)), and brush border membrane vesicles were isolated by the calcium precipitation method described in Kanako Katai et al., J. Biochem. 121, 50-55, 1997, and Peerce, B. E. et al., Biochemistry 26, 4272-4279, 1987. Thereafter, for compound 29 and compound 68, the phosphate uptake inhibitory activity was measured using the same samples with $^{32}P$ radioactive phosphorus (manufactured by Daiichi Kagaku Inc. (Japan)) by the rapid filtration method described in Kanako Katai et al., J. Biochem. 121, 50-55, 1997. As a result, these compounds had concentration-dependent inhibitory activity (FIG. 1). Further, in the same experiment, nonspective inhibitory activity against glucose absorption was determined using 14C-glucose (manufactured by Moravek Biochemical Inc. (US)). As a result, these compounds did not have the inhibitory activity (FIG. 2). In both the experiments, a group with the addition of potassium chloride was used as a negative control for nonspecific uptake. All the test results given below were expressed in terms of average value±standard error. Student's t-test was used for a significant test of the control group and the test compound group.

Pharmacological Test Example 3

Experiment of Sodium-Dependent Phosphate Uptake of *Xenopus oocytes* which Expressed NaPi-2a cDNA of human NaPi-2a described in Magagnin S. et al., Proc Natl Aca Sci USA, 90 (13): 5979-5983, 1993 was cloned by PCR. In the same manner as in Pharmacological Test Example 1, NaPi-2a was expressed in *Xenopus oocytes*, and the phosphate uptake inhibitory activity was measured with $^{32}P$ radioactive phosphorus. As a result, compound 1 had concentration-dependent inhibitory activity against NaPi-2a (FIG. 3). Compound 29 had inhibitory activity against not only NaPi-2b but also NaPi-2a (FIG. 4). In the test, a group with the addition of choline chloride (Choline Cl) was used as a negative control for nonspecific uptake, and PFA (phosphonoformic acid) was used as a positive control for phosphate transport inhibition.

Further, the compounds according to the present invention had inhibitory activity with $IC_{50}$ values shown in Table 6. $IC_{50}$ values were determined by determining an inhibition curve by an approximation formula using the least square from inhibitory activity values obtained from five concentration levels of the compound and determining the concentration of the compound which exhibits 50% of the maximum inhibitory activity.

TABLE 6

| | IC50 (μM) |
|---|---|
| Compound 260 | <3.00 |
| Compound 262 | 4.42 |
| Compound 264 | 4.36 |
| Compound 591 | 4.04 |
| Compound 592 | 9.51 |
| Compound 627 | 3.53 |
| Compound 628 | 3.59 |
| Compound 629 | 12.94 |
| Compound 630 | 3.50 |
| Compound 631 | 2.43 |
| Compound 632 | 28.66 |
| Compound 633 | 13.46 |
| Compound 634 | 16.87 |
| Compound 635 | 1.34 |
| Compound 636 | 5.30 |
| Compound 637 | 0.95 |
| Compound 638 | 4.22 |
| Compound 639 | 11.15 |
| Compound 640 | 15.59 |
| Compound 641 | 7.53 |
| Compound 642 | 13.30 |
| Compound 786 | <3.00 |
| Compound 787 | <3.00 |
| Compound 788 | 6.64 |
| Compound 789 | 9.28 |
| Compound 791 | 6.70 |
| Compound 793 | 8.46 |
| Compound 794 | 9.57 |
| Compound 795 | 8.52 |
| Compound 800 | 10.05 |
| Compound 801 | 3.72 |
| Compound 802 | 5.96 |
| Compound 806 | 12.14 |
| Compound 807 | 9.07 |
| Compound 810 | 23.81 |
| Compound 811 | 37.22 |
| Compound 813 | 35.59 |
| Compound 814 | 18.34 |
| Compound 818 | 31.43 |
| Compound 822 | 18.01 |
| Compound 824 | 8.19 |
| Compound 827 | 24.37 |
| Compound 828 | 10.02 |
| Compound 829 | <3.00 |
| Compound 830 | 10.73 |
| Compound 831 | 28.83 |
| Compound 832 | 6.40 |
| Compound 833 | 38.11 |
| Compound 834 | 52.10 |
| Compound 835 | 10.98 |
| Compound 836 | 10.18 |
| Compound 838 | 10.17 |
| Compound 839 | 23.15 |
| Compound 840 | 34.06 |
| Compound 841 | 19.85 |
| Compound 845 | <3.00 |
| Compound 846 | <3.00 |
| Compound 858 | <1.00 |
| Compound 859 | 1.60 |
| Compound 860 | <1.00 |
| Compound 861 | <1.00 |
| Compound 862 | 1.65 |
| Compound 863 | 6.90 |
| Compound 864 | 1.94 |
| Compound 865 | 4.34 |
| Compound 878 | 7.22 |
| Compound 880 | 1.30 |
| Compound 881 | 2.67 |
| Compound 882 | 4.45 |
| Compound 883 | 1.98 |
| Compound 884 | 35.90 |
| Compound 886 | 2.93 |
| Compound 887 | 15.06 |
| Compound 889 | 1.41 |
| Compound 890 | 1.33 |
| Compound 891 | 13.86 |
| Compound 893 | 5.11 |
| Compound 894 | 3.61 |
| Compound 895 | 5.52 |
| Compound 896 | 7.40 |
| Compound 899 | <1.00 |
| Compound 900 | 2.53 |
| Compound 901 | <1.00 |
| Compound 902 | <1.00 |
| Compound 903 | <1.00 |
| Compound 904 | 1.69 |
| Compound 914 | 3.13 |
| Compound 935 | 9.68 |
| Compound 936 | 30.05 |
| Compound 985 | <3.00 |
| Compound 987 | 16.31 |
| Compound 989 | 7.84 |
| Compound 990 | 7.14 |
| Compound 1007 | 1.00 |
| Compound 1008 | 2.30 |
| Compound 1009 | 1.41 |
| Compound 1020 | 2.25 |
| Compound 1027 | 1.58 |

Pharmacological Test Example 4

Inhibitory Activity Against $^{32}P$ Absorption from Intestinal Tract

SD rats (6 to 7 weeks old, obtained from Charles River Japan, Inc. (Japan)) were raised with low-phosphorus diet (phosphorus content 0.1%, manufactured by Oriental Yeast Co., Ltd. (Japan)) for 3 to 4 days and then fasted for about 24 hr for experiment. $^{32}P$ was diluted with purified water or liquid feed (CLEA JAPAN INC. (Japan)) to 0.7 to 3.5 MBq/ml and was forcibly orally administered at a dose of 5 ml/kg (administered into the gaster through an oral probe). The compounds or media were forcibly orally administered at a dose of 5 ml/kg (divided dose of twice), 30 min before the administration of $^{32}P$ and simultaneously with the administration of $^{32}P$. Blood was collected from caudal artery 30 min, 45 min, or 60 min after $^{32}P$ administration, and blood $^{32}P$ radioactivity was measured with a liquid scintillation counter. Inhibition of an increase in blood radioactivity was used as a measure of inhibition of phosphate absorption from the intestinal tract.

The results are expressed in terms of the percentage inhibition determined by the following equation.

(Blood radioactivity for group with the administration of medium−Blood radioactivity for group with the administration of compound)/(Blood radioactivity for group with the administration of medium)×100 t-Test was used for a significant test of the average value difference of blood radioactivity.

The results are shown in Table 7. As is apparent from the table, the compounds significantly inhibited phosphate absorption from the intestinal tract.

TABLE 7

Inhibitory activity against $^{32}$P absorption from intestinal tract

| Compound | Dose, mg/kg | Blood radioactivity inhibition, % |
|---|---|---|
| 91 | 320 | 28.3 |
| 92 | 160 | 25.5 |
| 88 | 400 | 29.1 |
| 163 | 360 | 57.8 |
| 130 | 270 | 22.8 |
| 157 | 320 | 20.7 |
| 164 | 400 | 55.0 |
| 165 | 400 | 27.6 |
| 252 | 400 | 29.2 |
| 253 | 400 | 39.0 |
| 254 | 400 | 68.4 |
| 315 | 100 | 42.4 |
| 372 | 100 | 63.7 |
| 285 | 80 | 60.3 |

For all the compounds, a significant difference was observed as compared with the group with the administration of medium at p<0.05.

The invention claimed is:

1. A compound represented by formula (I-1), or a pharmaceutically acceptable salt thereof:

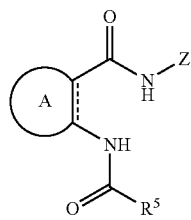

(I-1)

wherein

A represents a five- to nine-membered unsaturated heterocyclic moiety, and selected from the group consisting of formula (IIb), formula (IIc), and formula (IId):

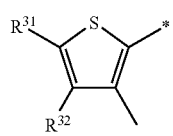

(IIb)

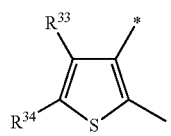

(IIc)

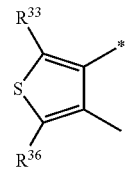

(IId)

wherein in formula (IIb)

$R^{31}$ and $R^{32}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, when $R^{31}$ and $R^{32}$ represent $C_{1-6}$ alkyl or $C_{2-6}$ alkenyl, the alkyl or the alkenyl groups together with the carbon atoms to which they are respectively attached may form an unsaturated five- to seven-membered carbocyclic ring, wherein in formula (IIc)

$R^{33}$ and $R^{34}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, when $R^{33}$ and $R^{34}$ represent $C_{1-6}$ alkyl or $C_{2-6}$ alkenyl, alkyl or the alkenyl groups together with the carbon atoms to which they are respectively attached may form an unsaturated five- to seven-membered carbocyclic ring, wherein in formula (IId)

$R^{35}$ and $R^{36}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, and wherein in formula (IIb), formula (IIc), and formula (IId) * represents a bond to —C(=O)—NH(—Z)

═══ represents a single bond or a double bond, $R^5$ represents $C_{1-6}$ alkyl, aryl, $C_{1-6}$ alkoxy, aryloxy, $C_{1-6}$ alkylamino, arylamino, $C_{1-6}$ alkylthio, arylthio, $C_{3-7}$ cycloalkyl, or a heterocyclic group, and the $C_{1-6}$ alkyl, the aryl, the $C_{1-6}$ alkoxy, the aryloxy $C_{1-6}$ the alkylamino, the arylamino, the $C_{1-6}$ alkylthio, the arylthio, the $C_{3-7}$ cycloalkyl, or the heterocyclic group represented by $R^5$ is optionally substituted by (I) a halogen atom;
(II) $C_{1-6}$ alkyl optionally containing a substituent selected from the group consisting of (1) hydroxyl, (2) thiol, (3) amino, (4) $C_{1-6}$ alkoxy, (5) $C_{1-6}$ alkylthio, (6) $C_{1-6}$ alkylsulfinyl, (7) $C_{1-6}$ alkylsulfonyl, (8) mono- or di $C_{1-6}$ alkylamino, (8') amino substituted by a heterocyclic group optionally substituted by $C_{1-6}$ alkyl, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-5}$ alkylamino- or arylaminocarbonyloxy, (21) carboxyl, (22) nitro, (23) a heterocyclic group, (23') Het-S(=O)j wherein the Het represents a heterocyclic group, j is 0, 1, or 2, and the Het is optionally substituted by alkyl optionally substituted by mono- or di-$C_{1-6}$ alkylamino in which the di-$C_{1-6}$ alkylamino group may form cyclic amino optionally containing 1 to 3 heteroatoms and one or two alkyl groups on the amino group and the cyclic amino moiety are optionally substituted by hydroxyl, (24) cyano, and (25) a halogen atom, wherein the alkyl moiety in (4) the $C_{1-6}$ alkoxy group, (5) the $C_{1-6}$ alkylthio group, (6) the $C_{1-6}$ alkylsulfinyl group, and (7) the $C_{1-6}$ alkylsulfonyl group is optionally substituted by a halogen atom; $C_{1-6}$ alkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms; aryloxy; arylthio; hydroxyl; carboxyl; —S(=O)$_2$(—OH); $C_{1-6}$ alkoxy- or aryloxy-carbonyl; $C_{1-6}$ alkylcarbonyl; aryl; or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxy, and in (8) the mono- or di-$C_{1-6}$ alkylamino group, the di-$C_{1-6}$ alkylamino group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl;

$C_{1-6}$ alkylcarbonyl; aryl optionally substituted by a halogen atom or hydroxyl; or a heterocyclic group, and, when one carbon atom in the cyclic amino moiety is substituted by two $C_{1-6}$ alkoxy groups which may be the same or different, the two alkoxy groups together may form group —O—(CH$_2$)$_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

(III) $C_{1-6}$ alkoxy optionally substituted by a halogen atom;
(IV) $C_{1-6}$ alkylthio optionally substituted by a halogen atom;
(V) $C_{3-7}$ cycloalkyl;
(VI) aryl;
(VII) aryloxy;
(VIII) $C_{1-6}$ alkylcarbonylamino;
(VIX) $C_{1-6}$ alkylcarbonyloxy;
(X) hydroxyl;
(XI) nitro;
(XII) cyano;
(XIII) amino;
(XIV) mono or di-$C_{1-6}$ alkylamino in which the di-$C_{1-6}$ alkylamino group may form cyclic amino optionally containing 1 to 3 heteroatoms;
(XV) arylamino;
(XVI) $C_{1-6}$ alkyl- or aryl-sulfonylamino;
(XVII) $C_{1-6}$ alkyl- or aryl-ureido;
(XVIII) $C_{1-6}$ alkoxy- or aryloxy-carbonylamino;
(XIX) $C_{1-6}$ alkylamino- or arylamino-carbonyloxy;
(XX) $C_{1-6}$ alkoxy- or aryloxy-carbonyl;
(XXI) acyl;
(XXII) carboxyl;
(XXIII) carbamoyl;
(XXIV) mono- or di-alkylcarbamoyl;
(XXV) a heterocyclic group;
(XXVI) alkyl- or aryl-sulfonyl;
(XXVII) $C_{2-6}$ alkenyloxy group; or
(XXVIII) $C_{2-6}$ alkenyloxy, Z represents group (A):

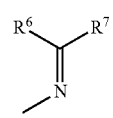

(A)

wherein
$R^6$ and $R^7$, which may be the same or different, represent a hydrogen atom, $C_{1-6}$ alkyl, $C_{2-6}$ alkenyl, $C_{2-6}$ alkenyl, aryl, aryl $C_{1-6}$ alkyl, aryl $C_{2-6}$ alkenyl, or a heterocyclic group, and the $C_{1-6}$ alkyl, the aryl, the aryl $C_{1-6}$ alkyl, the aryl $C_{2-6}$ alkenyl, and the heterocyclic groups, which may be the same or different, are optionally substituted by;

(I) a halogen atom;
(II) $C_{1-6}$ alkyl optionally having one or more substituents selected from a group consisting of (1) hydroxyl, (2) thiol, (3) amino, (4) $C_{1-6}$ alkoxy, (5) $C_{1-6}$ alkylthio optionally substituted by hydroxyl, (6) $C_{1-6}$ alkylsulfinyl, (7) $C_{1-6}$ alkylsulfonyl, (8) mono- or di-$C_{1-6}$ alkylamino in which the di-$C_{1-6}$ alkylamino group may form cyclic amino optionally containing 1 to 3 heteroatoms, (9) $C_{1-6}$ alkylcarbonyloxy, (10) $C_{1-6}$ alkylcarbonylthio, (11) $C_{1-6}$ alkylcarbonylamino, (12) aryloxy, (13)

arylthio, (14) arylsulfinyl, (15) arylsulfonyl, (16) arylamino, (17) $C_{1-8}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S— wherein the Het represents a heterocyclic group, (24) cyano, (25) a halogen atom, and (26) $C_{1-6}$ alkyl- or aryl-oxycarbonyl;

(III) $C_{1-6}$ alkoxy optionally having one or more substituents selected from the group consisting of (1) hydroxyl, (2) thiol, (3) amino, (4) $C_{1-6}$ alkoxy, (5) $C_{1-6}$ alkylthio optionally substituted by hydroxyl, (6) $C_{1-6}$ alkylsulfinyl, (7) $C_{1-6}$ alkylsulfonyl, (8) mono- or di-$C_{1-6}$ alkylamino in which the di-$C_{1-6}$ alkylamino group may form cyclic amino optionally containing 1 to 3 heteroatoms, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-8}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S— wherein the Het represents a heterocyclic group, (24) cyano, (25) a halogen atom, and (26) $C_{1-6}$ alkyl- or aryl-oxycarbonyl;

(IV) $C_{1-6}$ alkylthio optionally substituted by a halogen atom;
(V) $C_{3-7}$ cycloalkyl;
(VI) aryl;
(VII) aryloxy;
(VIII) $C_{1-6}$ alkylcarbonylamino;
(VIX) $C_{1-6}$ alkylcarbonyloxy;
(X) hydroxyl;
(XI) nitro;
(XII) cyano;
(XIII) amino;
(XIV) mono- or di-$C_{1-6}$ alkylamino in which the di-$C_{1-6}$ alkylamino may form cyclic amino optionally containing 1 to 3 heteroatoms;
(XV) arylamino;
(XVI) $C_{1-6}$ alkyl- or aryl-sulfonylamino;
(XVII) $C_{1-6}$ alkyl- or aryl-ureido;
(XVIII) $C_{1-6}$ alkoxy- or aryloxy-carbonylamino;
(XIX) $C_{1-6}$ alkylamino- or arylamino-carbonyloxy;
(XX) $C_{1-6}$ alkoxy- or aryloxy-carbonyl;
(XXI) aryl;
(XXII) carboxyl;
(XXIII) carbamoyl;
(XXIV) mono- or di-alkylcarbamoyl;
(XXV) a heterocyclic group;
(XXVI) alkyl- or aryl-sulfonyl;
(XXVII) $C_{2-6}$ alkenyloxy; or
(XXVIII) $C_{2-6}$ alkynyloxy.

2. The compound according to claim 1, wherein A represents formula (IIb):

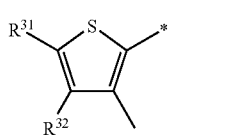

(IIb)

wherein $R^{31}$ and $R^{32}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, when $R^{31}$ and $R^{32}$ represent $C_{1-6}$ alkyl or $C_{2-6}$ alkenyl, the alkyl or the alkenyl groups together with the carbon atoms to which they are respectively attached may form an unsaturated five- to seven-membered carbocyclic ring, and

* represents a bond to —C(=O)—NH(—Z)
$R^5$ represents $C_{5-7}$ cycloalkyl, aryl, or saturated or unsaturated five- or six-membered heterocyclic group, and the $C_{5-7}$ cycloalkyl, aryl, or saturated or unsaturated five- or six-membered heterocyclic group represented by $R^5$ is optionally substituted by (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), or (XXVII), Z represents group (A):

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

3. The compound according to claim 1, wherein A represents formula (IIc):

(IIc)

wherein $R^{33}$ and $R^{34}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (8) aryloxy, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, when $R^{33}$ and $R^{34}$ represent $C_{1-6}$ alkyl or $C_{2-6}$ alkenyl, the alkyl or the alkenyl groups together with the carbon atoms to which they are respectively attached may form an unsaturated five- to seven-membered carbocyclic ring, and \* represents a bond to —C(=O)—NH(—Z)

$R^5$ represents $C_{5-7}$ cycloalkyl, aryl, or saturated or unsaturated five- or six-membered heterocyclic group, and the $C_{5-7}$ cycloalkyl, aryl, or saturated or unsaturated five- or six-membered heterocyclic group represented by $R^5$ is optionally substituted by (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), or (XXVII), Z represents group (A):

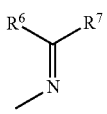

(A)

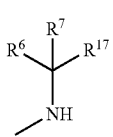

(B)

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

4. The compound according to claim 1, wherein A represents formula (IId):

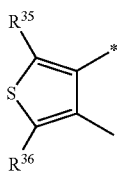

(IId)

wherein $R^{35}$ and $R^{36}$, which may be the same or different, represent a hydrogen atom; a halogen atom; or $C_{1-6}$ alkyl in which the alkyl group is optionally substituted by (1) hydroxyl, (2) thiol, (3) amino, (4) $C_{1-6}$ alkoxy, (5) $C_{1-6}$ alkylthio, (6) $C_{1-6}$ alkylsulfonyl, (7) mono- or di-$C_{1-6}$ alkylamino in which the di-$C_{1-6}$ alkylamino may form cyclic amino optionally containing 1 to 3 heteroatoms, (9) arylthio, (10) arylsulfonyl, (11) aryl, (12) a heterocyclic group, (13) a halogen atom, or (14) arylamino in which the amino group is optionally substituted by $C_{1-6}$ alkyl, and the aryl group is optionally substituted by a halogen, $C_{1-6}$ alkyl, $C_{1-6}$ alkoxy, or $C_{1-6}$ alkylamino; or $C_{2-6}$ alkenyl, and \* represents a bond to —C(=O)—NH(—Z)

$R^5$ represents $C_{5-7}$ cycloalkyl, aryl, or saturated or unsaturated five- or six-membered heterocyclic group, and the $C_{5-7}$ cycloalkyl, aryl, or saturated or unsaturated five- or six-membered heterocyclic group represented by $R^5$ is optionally substituted by (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), or (XXVII), Z represents group (A):

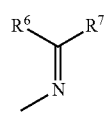

(A)

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group, and $R^{17}$ represents a hydrogen atom.

5. The compound according to claim 1, wherein $R^5$ represents formula (IIIa), formula (IIIb), or formula (IIIc)

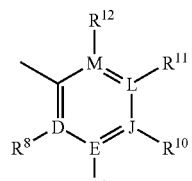

(IIIa)

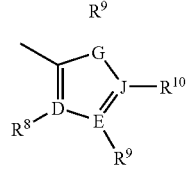

(IIIb)

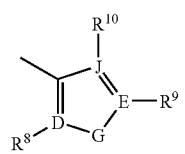

(IIIc)

wherein

D, E, J, L, and M, which may be the same or different, represent a carbon or nitrogen atom, G represents an oxygen or sulfur atom, $R^8$, $R^9$, $R^{10}$, $R^{11}$, and $R^{12}$, which may be the same or different, represent (I) a halogen atom;

(II) $C_{1-6}$ alkyl optionally containing a substituent selected from the group consisting of (1) hydroxyl, (2) thiol, (3) amino, (4) $C_{1-6}$ alkoxy, (5) $C_{1-6}$ alkylthio, (6) $C_{1-6}$ alkylsulfinyl, (7) $C_{1-6}$ alkylsulfonyl, (8) mono- or di-$C_{1-6}$ alkylamino, (8') amino substituted by a heterocyclic group optionally substituted by $C_{1-6}$ alkyl, (9) $C_{1-6}$ alkylcarbonyloxy, (10) $C_{1-6}$ alkylcarbonylthio, (11) $C_{1-6}$ alkylcarbonylamino, (12) aryloxy, (13) arylthio, (14) arylsulfinyl, (15) arylsulfonyl, (16) arylamino, (17) $C_{1-6}$ alkyl- or aryl-sulfonylamino, (18) $C_{1-6}$ alkyl- or aryl-ureido, (19) $C_{1-6}$ alkoxy- or aryloxy-carbonylamino, (20) $C_{1-6}$ alkylamino- or arylamino-carbonyloxy, (21) carboxyl, (22) nitro, (23) a heterocyclic group, (23') Het-S(=O)j- wherein the Het represents a heterocyclic group, j is 0, 1, or 2, and the Het is optionally substituted by alkyl optionally substituted by mono- or di-$C_{1-6}$ alkylamino in which the di-$C_{1-6}$ alkylamino group may form cyclic amino optionally containing 1 to 3 heteroatoms and one or two alkyl groups on the amino group and the cyclic amino moiety are optionally substituted by hydroxyl, (24) cyano, and (25) a halogen atom, wherein the alkyl moiety in (4) the $C_{1-6}$ alkoxy group, (5) the $C_{1-6}$ alkylthio group, (6) the $C_{1-6}$ alkylsulfinyl group, and (7) the $C_{1-6}$ alkylsulfonyl group is optionally substituted by a hydrogen atom; a halogen atom; $C_{1-6}$ alkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms; aryloxy; arylthio; hydroxyl; carboxyl; —S(=O)$_2$(—OH); $C_{1-6}$ alkoxy- or aryloxy-carbonyl; $C_{1-6}$ alkylcarbonyl; aryl; or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxy, and in (8) the mono- or di-$C_{1-6}$ alkylamino group, the di-$C_{1-6}$ alkylamino group may form cyclic amino optionally containing 1 to 3 heteroatoms, and one or two alkyl groups on the amino group and the cyclic amino moiety are optionally substituted by a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, and, when one carbon atom in the cyclic amino moiety is substituted by two $C_{1-6}$ alkoxy groups which may be the same or different, the two alkoxy groups together may form group —O—(CH$_2$)$_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

(III) $C_{1-6}$ alkoxy optionally substituted by a halogen atom;
(IV) $C_{1-6}$ alkylthio optionally substituted by a halogen atom;
(V) $C_{3-7}$ cycloalkyl;
(VI) aryl;
(VII) aryloxy;
(VIII) $C_{1-6}$ alkylcarbonylamino;
(VIX) $C_{1-6}$ alkylcarbonyloxy;
(X) hydroxyl;
(XI) nitro;
(XII) cyano;
(XIII) amino;
(XIV) mono- or di-$C_{1-6}$ alkylamino in which the di-$C_{1-6}$ alkylamino group may form cyclic amino optionally containing 1 to 3 heteroatoms;
(XV) arylamino;
(XVI) $C_{1-6}$ alkyl- or aryl-sulfonylamino;
(XVII) $C_{1-6}$ alkyl- or aryl-ureido;
(XVIII) $C_{1-6}$ alkoxy- or aryloxy-carbonylamino;
(XIX) $C_{1-6}$ alkylamino- or arylamino-carbonyloxy;
(XX) $C_{1-6}$ alkoxy- or aryloxy-carbonyl;
(XXI) acyl;
(XXII) carboxyl;
(XXIII) carbamoyl;
(XXIV) mono- or di-alkylcarbamoyl;
(XXV) a heterocyclic group;
(XXVI) alkyl- or aryl-sulfonyl;
(XXVII) $C_{2-6}$ alkenyloxy;
(XXVIII) $C_{2-6}$ alkynyloxy; or
(XXIX) a hydrogen atom, and when D, E, J, L, or M represents a nitrogen atom, $R^8$, $R^9$, $R^{10}$, $R^{11}$, and $R^{12}$ each are absent, or otherwise may combine with a nitrogen atom to form N-oxide (N→O).

6. The compound according to claim 1, wherein A represents formula (IIb)

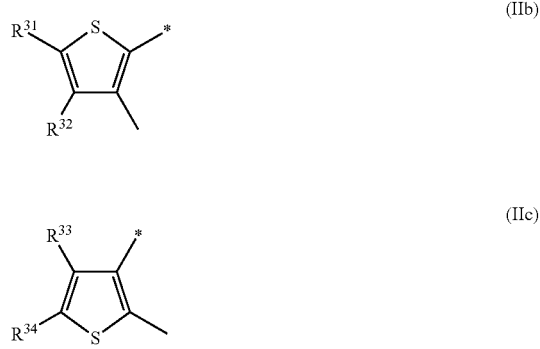

wherein (i) $R^{31}$ and $R^{32}$ represent a hydrogen atom, (ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms, (iii) $R^{31}$ and $R^{32}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or (iv) $R^{31}$ and $R^{32}$ together with the carbon atoms to which they are respectively attached form an unsaturated five- to seven-membered carbocyclic ring, and

* represents a bond to —C(=O)—NH(—Z)

$R^5$ represents formula (IIIa)

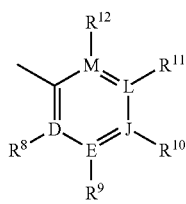
(IIIa)

wherein
(i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom,
(ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom,
(iii) D, E, J, L, and M represent a carbon atom, $R^8$, $R^9$, and $R^{12}$ represent a hydrogen atom, any one of $R^{10}$ and $R^{11}$ represents a group of formula (IV)

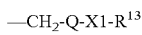
—CH$_2$-Q-X1-R$^{13}$ (IV)

wherein
Q represents an oxygen atom, a sulfur atom, sulfinyl, or sulfonyl,
X1 represents a bond or straight chain or branched chain alkylene having 1 to 5 carbon atoms,
$R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;
or a group of formula (V)

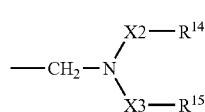
(V)

wherein
X2 represents a bond or straight chain or branched chain alkylene having 1 to 5 carbon atoms,
X3 represents a bond or straight chain or branched chain alkylene having 1 to 5 carbon atoms, $R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or
$R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—(CH$_2$)$_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;
and the other represents a hydrogen atom,
(iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV)

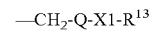
—CH$_2$-Q-X1-R$^{13}$ (IV)

wherein
Q represents an oxygen atom, a sulfur atom, sulfinyl, or sulfonyl,
X1 represents a bond or straight chain or branched chain alkylene having 1 to 5 carbon atoms,
$R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

(V)

wherein
X2 represents a bond or straight chain or branched chain alkylene having 1 to 5 carbon atoms,
X3 represents a bond or straight chain or branched chain alkylene having 1 to 5 carbon atoms,
$R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or
$R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—(CH$_2$)$_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;
and the other represents a hydrogen atom,
Z represents group (A):

(A)

wherein
$R^6$ represents a hydrogen atom or $C_{1-6}$ alkyl,
$R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

7. The compound according to claim 1, wherein A represents formula (IIb)

(IIb)

wherein
(i) $R^{31}$ and $R^{32}$ represent a hydrogen atom,
(ii) any one of $R^{31}$ and $R^{32}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{31}$ and $R^{32}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or (iv) $R^{31}$ and $R^{32}$ together with the carbon atoms to which they are respectively attached form an unsaturated five- to seven-membered carbocyclic ring, and

* represents a bond to —C(=O)—NH(—Z)

$R^5$ represents formula (IIIb) or formula (IIIc)

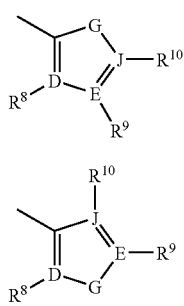

wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or (ii) D, E, and J represent a carbon atom, G represents an oxygen or sulfur atom, one of $R^8$, $R^9$, and $R^{10}$ represents a group of formula (IV)

  —$CH_2$-Q-X1-$R^{13}$       (IV)

wherein
Q represents an oxygen atom, a sulfur atom, sulfinyl, or sulfonyl,

X1 represents a bond or straight chain or branched chain alkylene having 1 to 5 carbon atoms, $R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

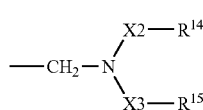

wherein
X2 represents a bond or straight chain or branched chain alkylene having 1 to 5 carbon atoms, X3 represents a bond or straight chain or branched chain alkylene having 1 to 5 carbon atoms, $R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—($CH_2$)$_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the others represent a hydrogen atom,

Z represents group (A):

wherein

R⁶ represents a hydrogen atom or $C_{1-6}$ alkyl,

R⁷ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

8. The compound according to claim 1, wherein A represents formula (IIc)

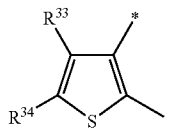

(IIc)

wherein (i) $R^{33}$ and $R^{34}$ represent a hydrogen atom, (ii) any one of $R^{33}$ and $R^{34}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms, (iii) $R^{33}$ and $R^{34}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or (iv) $R^{33}$ and $R^{34}$ together with the carbon atoms to which they are respectively attached form an unsaturated five- to seven-membered carbocyclic ring, and

* represents a bond to —C(=O)—NH(—Z)

R⁵ represents formula (IIIc)

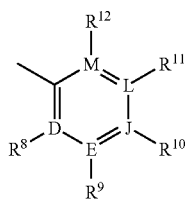

(IIIa)

wherein (i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom, (iii) D, E, J, L, and M represent a carbon atom, $R^8$, $R^9$, and $R^{12}$ represent a hydrogen atom, any one of $R^{10}$ and $R^{11}$ represents a group of formula (IV)

—CH₂-Q-X1-R¹³  (IV)

wherein

Q represents an oxygen atom, a sulfur atom, sulfinyl, or sulfonyl,

X1 represents a bond or straight chain or branched chain alkylene having 1 to 5 carbon atoms, $R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)₂(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

(V)

wherein

X2 represents a bond or straight chain or branched chain alkylene having 1 to 5 carbon atoms, X3 represents a bond or straight chain or branched chain alkylene having 1 to 5 carbon atoms, $R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—$(CH_2)_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the other represents a hydrogen atom, (iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV)

$$—CH_2\text{-}Q\text{-}X1\text{-}R^{13} \quad (IV)$$

wherein
Q represents an oxygen atom, a sulfur atom, sulfinyl, or sulfonyl,
X1 represents a bond or straight chain or branched chain alkylene having 1 to 5 carbon atoms,
$R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

wherein
X2 represents a bond or straight chain or branched chain alkylene having 1 to 5 carbon atoms,
X3 represents a bond or straight chain or branched chain alkylene having 1 to 5 carbon atoms,
$R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—$(CH_2)_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the other represents a hydrogen atom,
Z represents group (A):

wherein

R⁶ represents a hydrogen atom or $C_{1-6}$ alkyl,

R⁷ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

9. The compound according to claim 1, wherein A represents formula (IIc)

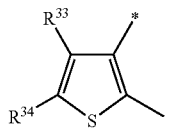

(IIc)

wherein
(i) $R^{33}$ and $R^{34}$ represent a hydrogen atom,
(ii) any one of $R^{33}$ and $R^{34}$ represents a hydrogen atom, and the other represents $C_{1-6}$ alkyl optionally substituted by mono- or di-$C_{1-6}$ alkylamino, which may form cyclic amino, or a halogen atom, and the cyclic amino group may contain 1 to 3 heteroatoms,
(iii) $R^{33}$ and $R^{34}$, which may be the same or different, represent $C_{1-6}$ alkyl optionally substituted by mono- or di-$C_{1-6}$ alkylamino, which may form cyclic amino, or a halogen atom, and the cyclic amino group may contain 1 to 3 heteroatoms, or
(iv) $R^{33}$ and $R^{34}$ together with the carbon atoms to which they are respectively attached form an unsaturated five- to seven-membered carbocyclic ring, and
* represents a bond to —C(=O)—NH(—Z)

R⁵ represents formula (IIIb) or formula (IIIc)

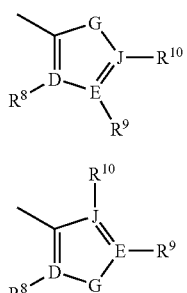

(IIIb)

(IIIc)

wherein
(i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, or
(ii) D, E, and J represent a carbon atom, G represents an oxygen or sulfur atom, one of $R^8$, $R^9$, and $R^{10}$ represents a group of formula (IV)

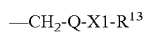
—CH₂-Q-X1-R¹³ (IV)

wherein
Q represents an oxygen atom, a sulfur atom, sulfinyl, or sulfonyl,
X1 represents a bond or straight chain or branched chain alkylene having 1 to 5 carbon atoms, R¹³ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)₂(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

(V)

wherein
X2 represents a bond or straight chain or branched chain alkylene having 1 to 5 carbon atoms,
X3 represents a bond or straight chain or branched chain alkylene having 1 to 5 carbon atoms,
$R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—$(CH_2)_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the others represent a hydrogen atom,

Z represents group (A):

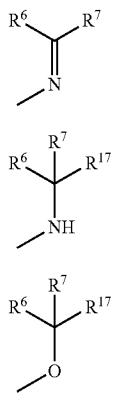

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

10. The compound according to claim 1, wherein A represents formula (IId)

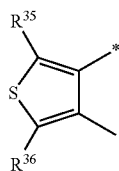

wherein $R^{35}$ and $R^{36}$ represent a hydrogen atom, or any one of $R^{35}$ and $R^{36}$ represents a hydrogen atom and the other represents $C_{1-6}$ alkyl optionally substituted by a halogen atom, and \* represents a bond to —C(=O)—NH(—Z)

$R^5$ represents formula (Ma)

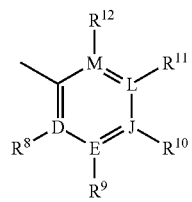

wherein (i) D, E, J, L, and M represent a carbon atom, any one or two of $R^8$, $R^9$, $R^{10}$, $R^{11}$, and $R^{12}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) any one or two of D, E, J, L, and M represent a nitrogen atom, and the others represent a carbon atom, any one or two of $R^8$, $R^9$, $R^{10}$, $R^{11}$, and $R^{12}$ may be the same or different and represent a halogen atom; hydroxymethyl; $C_{1-6}$ alkyl optionally substituted by a halogen atom, or $C_{1-6}$ alkoxy optionally substituted by a halogen atom, and the others represent a hydrogen atom, (iii) D, E, J, L, and M represent a carbon atom, $R^8$, $R^9$, and $R^{12}$ represent a hydrogen atom, any one of $R^{10}$ and $R^{11}$ represents a group of formula (IV)

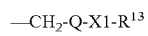

wherein

Q represents an oxygen atom, a sulfur atom, sulfinyl, or sulfonyl,

X1 represents a bond or straight chain or branched chain alkylene having 1 to 5 carbon atoms, $R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

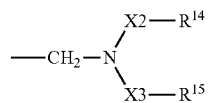

wherein

X2 represents a bond or straight chain or branched chain alkylene having 1 to 5 carbon atoms, X3 represents a bond or straight chain or branched chain alkylene having 1 to 5 carbon atoms, $R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—$(CH_2)_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the other represents a hydrogen atom, or (iv) any one or two of D, E, J, L, and M represent a nitrogen atom, and the others represent a carbon atom, $R^8$, $R^9$, and $R^{12}$ represent a hydrogen atom, and one of $R^{10}$ and $R^{11}$ represents a group of formula (IV)

—$CH_2$-Q-X1-$R^{13}$ (IV)

wherein

Q represents an oxygen atom, a sulfur atom, sulfinyl, or sulfonyl,

X1 represents a bond or straight chain or branched chain alkylene having 1 to 5 carbon atoms, $R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

(V)

wherein

X2 represents a bond or straight chain or branched chain alkylene having 1 to 5 carbon atoms, X3 represents a bond or straight chain or branched chain alkylene having 1 to 5 carbon atoms, $R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom (=O), and, when one carbon atom in the cyclic amino moiety is substituted by two $C_{1-6}$ alkoxy groups which may be the same or different, the two alkoxy groups together may form group —O—$(CH_2)_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the other represents a hydrogen atom,

Z represents group (A):

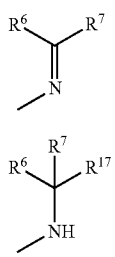

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

11. The compound according to claim 1, wherein A represents formula (IId)

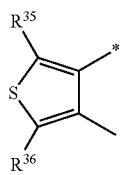

wherein $R^{35}$ and $R^{36}$ represent a hydrogen atom, or any one of $R^{35}$ and $R^{36}$ represents a hydrogen atom and the other represents $C_{1-6}$ alkyl optionally substituted by a halogen atom, and

* represents a bond to —C(=O)—NH(—Z)

$R^5$ represents formula (IIIb) or formula (IIIc)

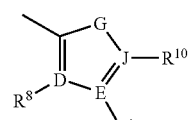

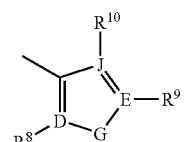

wherein (i) D, E, and J represent a carbon atom, G represents an oxygen or sulfur atom, any one or two of $R^8$, $R^9$, and $R^{10}$, which may be the same or different, represent a halogen atom; hydroxymethyl; $C_{1-6}$ alkyl optionally substituted by a halogen atom; or $C_{1-6}$ alkoxy optionally substituted by a halogen atom, and the others represent a hydrogen atom, (ii) D, E, and J represent a carbon atom, G represents an oxygen or sulfur atom, one of $R^8$, $R^9$, and $R^{10}$ represents a group of formula (IV)

—CH$_2$-Q-X1-R$^{13}$ (IV)

wherein

Q represents an oxygen atom, a sulfur atom, sulfinyl, or sulfonyl,

X1 represents a bond or straight chain or branched chain alkylene having 1 to 5 carbon atoms, $R^{13}$ represents a hydrogen atom, a halogen atom, $C_{1-6}$ alkyl, $C_{1-6}$ alkoxy, $C_{1-6}$ alkylthio, mono- or di-$C_{1-6}$ alkylamino in which the di-$C_{1-6}$ alkylamino group may form cyclic amino optionally containing 1 to 3 heteroatoms, aryloxy, arylthio, hydroxyl, carboxyl, —S(=O)$_2$(—OH), $C_{1-6}$ alkoxy- or aryloxy-carbonyl, $C_{1-6}$ alkylcarbonyl, aryl, or a heterocyclic group optionally substituted by alkyl optionally substituted by mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl;

or a group of formula (V)

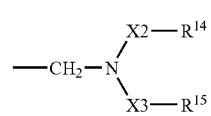

wherein

X2 represents a bond or straight chain or branched chain alkylene having 1 to 5 carbon atoms, X3 represents a bond or straight chain or branched chain alkylene having 1 to 5 carbon atoms, $R^{14}$ and $R^{15}$, which may be the same or different, represent a hydrogen atom; a halogen atom; $C_{1-6}$ alkyl optionally substituted by hydroxyl, a halogen atom, aryl optionally substituted by a halogen atom, $C_{1-6}$ alkyl, or $C_{1-6}$ alkyloxy, a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; $C_{1-6}$ alkoxy; $C_{1-6}$ alkylthio; mono- or di-$C_{1-6}$ alkylamino in which the di-$C_{1-6}$ alkylamino group may form cyclic amino optionally containing 1 to 3 heteroatoms, and one or two alkyl groups on the amino group and the cyclic amino moiety are optionally substituted by hydroxyl; arylamino in which the amino group is optionally substituted by $C_{1-6}$ alkyl; mono- or di-$C_{1-6}$ alkylcarbamoylmethyl in which the di-$C_{1-6}$ alkylamino may form cyclic amino optionally containing 1 to 3 heteroatoms, and one or two alkyl groups on the amino group and the cyclic amino moiety are optionally substituted by hydroxyl; aryloxy; arylthio; an oxygen atom (=O); hydroxyl; carboxyl; $C_{1-6}$ alkoxy- or aryloxy-carbonyl; $C_{1-6}$ alkylcarbonyl; aryl optionally substituted by a halogen atom or hydroxyl; or a heterocyclic group, provided that, when X2 represents a bond, $R^{14}$ represents a hydrogen atom, or when X3 represents a bond, $R^{15}$ represents a hydrogen atom, or $R^{14}$ and $R^{15}$ together with a nitrogen atom to which they are respectively attached to may form a heterocyclic group that may contain 1 to 3 heteroatoms in addition to the nitrogen atom, to which $R^{14}$ and $R^{15}$ are attached, and is optionally substituted by hydroxyl; $C_{1-6}$ alkyl optionally substituted by hydroxyl, a halogen atom, aryl optionally substituted by a halogen atom, $C_{1-6}$ alkyl, or $C_{1-6}$ alkyloxy, or a heterocyclic group optionally substituted by a halogen atom, $C_{1-6}$ alkyl, or $C_{1-6}$ alkyloxy, and, when one or two alkyl groups on the amino group and the cyclic amino moiety are substituted by two $C_{1-6}$ alkyl groups, they together may form $C_{3-7}$ cycloalkyl; mono- or di-$C_{1-6}$ alkylamino in which the di-$C_{1-6}$ alkylamino may form cyclic amino optionally containing 1 to 3 heteroatoms, and one or two alkyl groups on the amino group and the cyclic amino moiety are optionally substituted by hydroxyl; a saturated or unsaturated five- or six-membered heterocyclic group; mono- or di-$C_{1-6}$ alkylcarbamoylmethyl in which the di-$C_{1-6}$ alkylamino group may form cyclic amino optionally containing 1 to 3 heteroatoms, and one or two alkyl groups on the amino group and the cyclic amino moiety are optionally substituted by hydroxyl; phenyl; or an oxygen atom and, when one carbon atom in the cyclic amino moiety is substituted by two $C_{1-6}$ alkoxy groups which may be the same or different, the two alkoxy groups together may form group —O—$(CH_2)_p$—O— wherein p is an integer of 2 to 4, and the cyclic amino group may condense with a monocyclic or bicyclic aromatic carbocyclic ring or a monocyclic or bicyclic aromatic heterocyclic ring to represent a bicyclic or tricyclic heterocyclic group;

and the others represent a hydrogen atom,

Z represents group (A):

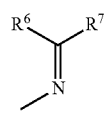

(A)

wherein $R^6$ represents a hydrogen atom or $C_{1-6}$ alkyl, $R^7$ represents optionally substituted aryl, optionally substituted aryl $C_{1-6}$ alkyl, optionally substituted aryl $C_{2-6}$ alkenyl, or optionally substituted saturated or unsaturated five- or six-membered heterocyclic group.

12. A pharmaceutical composition comprising as an active ingredient a compound according to claim 1 or a pharmaceutically acceptable salt thereof.

* * * * *